United States Patent
Ellermann et al.

(10) Patent No.: US 10,118,930 B2
(45) Date of Patent: Nov. 6, 2018

(54) PIPERIDINYLPYRAZOLOPYRIMIDINONES AND THEIR USE

(71) Applicant: BAYER PHARMA AKTIENGESELLSCHAFT, Berlin (DE)

(72) Inventors: Manuel Ellermann, Berlin (DE); Gaelle Valot, Wuppertal (DE); Yolanda Cancho Grande, Leverkusen (DE); Jorma Haßfeld, Düsseldorf (DE); Tom Kinzel, Beijing (CN); Johannes Köbberling, Neuss (DE); Kristin Beyer, Düsseldorf (DE); Susanne Röhrig, Hilden (DE); Michael Sperzel, Kierspe (DE); Jan Stampfuß, Düsseldorf (DE); Imke Meyer, Haan (DE); Maria Köllnberger, Velbert (DE); Nils Burkhardt, Velbert (DE); Karl-Heinz Schlemmer, Wuppertal (DE); Christian Stegmann, Berlin (DE); Joachim Schuhmacher, Kirchseeon (DE); Matthias Werner, Feldkirchen-Westerham (DE); Jörg Heiermann, Wesel (DE); Willem Jan Hengeveld, Arnhem (NL)

(73) Assignee: BAYER PHARMA AKTIENGESELLSCHAFT, Berlin (DE)

( * ) Notice: Subject to any disclaimer, the term of this patent is extended or adjusted under 35 U.S.C. 154(b) by 0 days.

(21) Appl. No.: 15/523,954

(22) PCT Filed: Oct. 30, 2015

(86) PCT No.: PCT/EP2015/075208
§ 371 (c)(1),
(2) Date: May 3, 2017

(87) PCT Pub. No.: WO2016/071216
PCT Pub. Date: May 12, 2016

(65) Prior Publication Data
US 2017/0334917 A1    Nov. 23, 2017

(30) Foreign Application Priority Data
Apr. 30, 2015    (EP) .................................... 15165918

(51) Int. Cl.
| A01N 43/90 | (2006.01) |
| A61K 31/519 | (2006.01) |
| C07D 487/04 | (2006.01) |
| C07D 471/04 | (2006.01) |
| C07D 211/06 | (2006.01) |
| C07D 403/14 | (2006.01) |
| C07D 231/00 | (2006.01) |
| C07D 247/02 | (2006.01) |
| C07D 271/06 | (2006.01) |
| C07D 271/10 | (2006.01) |

(52) U.S. Cl.
CPC .......... *C07D 487/04* (2013.01); *A61K 31/519* (2013.01); *C07D 211/06* (2013.01); *C07D 231/00* (2013.01); *C07D 247/02* (2013.01); *C07D 271/06* (2013.01); *C07D 271/10* (2013.01); *C07D 403/14* (2013.01); *C07D 471/04* (2013.01)

(58) Field of Classification Search
CPC ........................... A61K 31/519; C07D 487/04
USPC ....................................... 514/259.3; 544/281
See application file for complete search history.

(56) References Cited

FOREIGN PATENT DOCUMENTS

| WO | 1998/03510 | 1/1998 |
| WO | 2004/052315 | 6/2004 |
| WO | 2006/023000 | 3/2006 |
| WO | 2008/008539 | 1/2008 |
| WO | 2008/011560 | 1/2008 |
| WO | 2009/017954 | 2/2009 |
| WO | 2009/023179 | 2/2009 |
| WO | 2009/070567 | 6/2009 |
| WO | 2010/117323 | 10/2010 |
| WO | 2011/140333 | 11/2011 |
| WO | 2012/047156 | 4/2012 |
| WO | 2012/078855 | 6/2012 |
| WO | 2014/012964 | 1/2014 |
| WO | 2014/173289 | 10/2014 |

OTHER PUBLICATIONS

International Search Report for PCT/EP2015/075208, dated Dec. 18, 2015, three pages.

(Continued)

*Primary Examiner* — Jeffrey H Murray
(74) *Attorney, Agent, or Firm* — Nixon & Vanderhe P.C.

(57) ABSTRACT

The present application relates to novel substituted piperidinylpyrazolopyrimidinones, to processes for their preparation, the compounds for use alone or in combinations in a method for the treatment and/or prophylaxis of diseases, in particular for the treatment and/or prophylaxis of acute and recurrent bleeding in patients with or without underlying hereditary or acquired hemostatic disorders, wherein the bleeding is associated with a disease or medical intervention selected from the group consisting of heavy menstrual bleeding, postpartum hemorrhage, hemorrhagic shock, hemorrhagic cystitis, gastrointestinal hemorrhage, trauma, surgery, transplantation, stroke, liver diseases, hereditary angioedema, nosebleed, and synovitis and cartilage damage following hemarthrosis.

19 Claims, No Drawings

(56) References Cited

OTHER PUBLICATIONS

Written Opinion of the ISA for PCT/EP2015/075208, dated Dec. 18, 2015, five pages.
Cesarman-Maus et al. "Molecular mechanisms of fibrinolysis" Br. J. Haematol. 129:307-321 (2005).
Day et al. "Direct comparison of binding equilibrium, thermodynamic, and rate constants determined by surface and solution-based biophysical methods" Protein Sci. 11:1017-1025 (2002).
Dunn et al. "Tranexamic Acid: A Review of its use in surgery and other indications" Drugs 57:1005-1032 (1999).
El-Hemaidi et al. "Menorrhagia and bleeding disorders" Curr. Opin. Obstet. Gynecol. 19:513-520 (2007).
Flemmig et al. "Serine-proteases as plasminogen activators in terms of fibrinolysis" J. Pharm. Pharmacol. 64:1025-1039 (2012).
Fraser et al. "Health-related quality of life and economic burden of abnormal uterine bleeding" Expert Rev. Obstet. Gynecol. 4:179-189 (2009).
Hallberg et al. "Menstrual blood loss—A population study: Variation at different ages and attempts to define normality" Acta Obstet. Gynecol. Scand. 45:320-351 (1966).
Hallberg et al. "Determination of menstrual blood loss" Scand. J. Clin. Lab. Invest. 16:244-248 (1964).
Hurskainen et al. "Diagnosis and treatment of menorrhagia" Acta Obstetricia et Gynecologica 86:749-757 (2007).
Johnsson et al. "Immobilization of proteins to a carboxymethyldextran-modified gold surface for biospecific interaction analysis in surface plasmon resonance sensors" Anal. Biochem. 198:268-277 (1991).
Jönsson et al. "Introducing a biosensor based technology for real-time biospecific interaction analysis" Ann. Biol. Clin. 51:19-26 (1993).
Kadir et al. "Hemostatic disorders in women" J. Thromb. Haemost. 11 (suppl. 1):170-179 (2013).
Levy "Antifibrinolytic therapy: New data and new concepts" Lancet 376:3-4 (2010).
Menhart et al. "Construction, expression, and purification of recombinant kringle 1 of human plasminogen and analysis of its interaction with ω-amino acids" Biochem. 30:1948-1957 (1991).
Myszka et al. "Analysis of small-molecule interactions using Biacore S51 technology" Anal. Biochem. 329:316-323 (2004).
Nieuwenhuizen et al. "Antiplasmin, but not amiloride, prevents synovitis and cartilage damage following hemarthrosis in hemophilic mice" J. Thromb. Haemost. 12:237-245 (2013).
O'Flynn et al. "Menorrhagia in general practice—disease or illness" Soc. Sci. Med. 50:651-661 (2000).
Shapley et al. "An epidemiological survey of symptoms of menstrual loss in the community" Br. J. Gen. Pract. 54, 359-363 (2004).
Sperzel et al. "Evaluation of aprotinin and tranexamic acid in different in vitro and in vivo models of fibrinolysis, coagulation and thrombus formation" J. Thromb. Haemost. 5:2113-2118 (2007).
Wellington et al. "Tranexamic acid: A review of its use in the management of menorrhagia" Drugs 63:1417-1433 (2003).

PIPERIDINYLPYRAZOLOPYRIMIDINONES AND THEIR USE

This application is the U.S. national phase of International Application No. PCT/EP2015/075208 filed 30 Oct. 2015, which designated the U.S. and claims priority to Patent Application Nos. EP 14191410.1, filed 3 Nov. 2014, and EP 15165918.2, filed 30 Apr. 2015; the entire contents of each of which are hereby incorporated by reference.

The present application relates to novel substituted piperidinylpyrazolopyrimidinones, to processes for their preparation, the compounds for use alone or in combinations in a method for the treatment and/or prophylaxis of diseases, in particular for the treatment and/or prophylaxis of acute and recurrent bleeding in patients with or without underlying hereditary or acquired hemostatic disorders. The present invention also relates to medicaments comprising the compounds according to the invention for the treatment and/or prophylaxis of acute and recurrent bleeding in patients with or without underlying hereditary or acquired hemostatic disorders, wherein the bleeding is associated with a disease or medical intervention selected from the group consisting of heavy menstrual bleeding (HMB), postpartum hemorrhage, hemorrhagic shock, trauma, surgery, transplantation, stroke, liver diseases, hereditary angioedema, nosebleed, and synovitis and cartilage damage following hemarthrosis.

Bleeding is the common clinical hallmark in hereditary and acquired hemostatic disorders, trauma, surgery, stroke, heavy menstrual bleeding (HMB) (also termed menorrhagia), postpartum hemorrhage, and liver diseases. When tissue is damaged, vessels can rupture, immediately triggering the hemostatic mechanism, resulting in a stable fibrin network. The fibrinolytic system is activated by the deposition of fibrin and assists in the maintenance of an open lumen in damaged blood vessels. A balance between the formation and lysis of fibrin is required to maintain and remold the hemostatic seal during several days in which the injured vessel wall is repaired.

Fibrinolysis is the physiological mechanism that dissolves clots. The fibrinolytic system comprises plasminogen, the circulating inactive precursor of plasmin, a potent serine protease involved in the dissolution of fibrin blood clots. Tissue-type plasminogen activator (tPA) and urokinase-type plasminogen activator (uPA) are the two major plasminogen activators expressed in many cell types and tissues (Levi J H, Lancet 2010, 376, 9734, 3-4). Plasminogen binds to lysine residues on the surface of fibrin and is converted to plasmin by an activator released from endothelial cells—tPA—that simultaneously binds to fibrin. As part of the hemostatic balance, plasmin generation and activity are also modulated by multiple inhibitors that include plasminogen activator inhibitor (PAI-1), thrombin-activatable fibrinolysis inhibitor (TAFI) and aa-antiplasmin (Cesarman-Maus G, Hajjar K A, Br J Haematol 2005; 129: 307-21).

Activators of fibrinolysis can be therapeutically used to dissolve blood clots in thrombotic conditions like myocardial infarction or ischemic stroke, to avoid degradation of the surrounding tissue (Flemming M, Melzig M F, J Pharm Pharmacol. 2012, 64(8):1025-39). On the other hand inhibition of fibrinolysis can be, and is successfully and safely used in the management of bleeding. After extensive tissue injury that occurs with trauma or surgery, the equilibrium is shifted and fibrinolysis is considered to be an important contributor to bleeding and coagulopathy. In surgical patients, many studies reported the use of antifibrinolytic agents to decrease bleeding and need for allogeneic transfusions. The most commonly used are the lysine analogues, ε-aminocaproic acid and tranexamic acid that interfere with the binding of plasminogen to fibrin, which are necessary for activating plasmin (Levi J H, Lancet 2010, 376, 9734, 3-4).

Antifibrinolytics are a safe and effective proven concept for reducing blood loss and rebleeding, without increased risk for thrombotic events, for example in the management of hemostatic disorders like haemophilia and von Willebrand's disease, in heavy menstrual bleeding (HMB) (menorrhagia) and in different surgical conditions.

Bleeding due to platelet disorders/dysfunctions like Glantzmann's thrombasthenia and thrombocytopenia as well as anticoagulant-induced bleeding and PAI-1 deficiency might be potential areas of use. Patients with acute promyelocytic leukaemia who frequently develop severe bleeding might also benefit from antifibrinolytics therapy. In addition, it has been suggested that blocking fibrinolysis could potentially be useful to block plasmin-induced proteolysis which may be of biological relevance during athero-thrombosis and inflammatory states, cancer and other diseases.

Further, it has been described that antiplasmin may be used for treating synovitis and cartilage damage following hemarthrosis in patients with underlying hemostatic disorders including hemophilia and von Willebrand's disease (L. Nieuwenhuizen L, Roosendaal G, Masterbergen S C, Coeleveld K, Biesma D H, Lafeber F P J G, and Schuthens, R E G, J Thrombosis and Haemostasis 2013, 12: 237-245).

A further potential area of use of antifibrinolytics is the treatment of nosebleed caused by trauma and other causes, also coupled with underlying hemostatic disorders including hemophilia and von Willebrand's disease.

Antifibrinolytics have also been successfully applied to the treatment of hereditary angioedema, where a reduction in the number and severity of attacks of edema in patients treated with tranexamic acid could be demonstrated (Dunn C J, Goa K L, Drugs 1999, 57(6): 1005-1032).

Abnormal uterine bleeding (AUB) may be diagnosed when a woman experiences a change in her menstrual blood loss (MBL), or the degree of MBL or vaginal bleeding pattern differs from that experienced by the age-matched general female population (National Collaborating Centre for Women's and Children's Health (NCCWCH): National Institute for Clinical Excellence (NICE) guidelines. CG44 Heavy Menstrual Bleeding: full guideline. 24 Jan. 2007). Normal menstruation occurs at a cycle of 28±7 days, lasting 4±2 days with a mean MBL of 40±20 mL. AUB presents a spectrum of abnormal menstrual bleeding patterns that includes irregular, heavy or prolonged menstrual bleeding or an altered bleeding pattern. AUB may be associated with ovulatory or anovulatory cycles. Terms in use are dysfunctional uterine bleeding (DUB), heavy menstrual bleeding (HMB) (abnormally heavy menstrual bleeding at regular intervals which may also be prolonged), metrorrhagia (uterine bleeding at irregular intervals, particularly between the expected menstrual periods), and metromenorrhagia (combination of both).

AUB is one of the most frequent gynecological disorders observed by general practitioners and gynecologists. AUB is an exclusion diagnosis; an organic cause should always be ruled out. Organic causes of AUB include benign uterine neoplasia, especially cervical and endometrial polyps and myoma's, adenomyosis, and malignancies of the cervix and endometrium.

Heavy menstrual bleeding, HMB (Menorrhagia) is widely defined in the medical literature as blood loss (MBL) of 80 mL or more per menstrual period (Hallberg L, Nilsson L. Determination of menstrual blood loss. Scandinav J Clin Lab Invest 1964; 16:244-8, Hallberg L, Hogdahl A M, Nilsson L, Rybo G. Menstrual blood loss—a population study. Variation at different ages and attempts to define normality. Acta Obstet Gynecol Scand 1966; 45(3): 320-51, O'Flynn N, Britten N. Menorrhagia in general practice disease or illness. Soc Sci Med 2000; 50(5): 651-61). Within the meaning of the present invention, heavy menstrual bleeding is defined as menstrual blood loss of 60 ml or more per cycle, for example 60 to 80 ml per cycle, in particular more than 80 ml per cycle. According to NICE, heavy menstrual bleeding should be defined for clinical purposes as excessive menstrual blood loss which interferes with the woman's physical, emotional, social and material quality of life, and which can occur alone or in combination with other symptoms. Any interventions should aim to improve quality of life measures. The global prevalence rate of heavy menstrual bleeding, based on 18 epidemiological studies, ranges from 4% to 52% (Fraser I S, Langham S, Uhl-Hochgraeber K. Health-related quality of life and economic burden of abnormal uterine bleeding. Expert Rev Obstet Gynecol 2009; 4(2): 179-89). The wide variation can be accounted for by different methods of assessment and population samples used by each study. Prevalence rates in studies that use subjective assessments have been found to be consistently higher, compared to 9-11% in studies that directly measured MBL. However an estimated 30% of women suffering from heavy menstrual bleeding appears to be more representative (Hurskainen R, Grenman S, Komi I, Kujansuu E, Luoto R, Orrainen M, et al. Diagnosis and treatment of menorrhagia. Acta Obstet Gynecol Scand 2007; 86(6): 749-57, El-Hemaidi I, Gharaibeh A, Shehata H. Menorrhagia and bleeding disorders. Curr Opin Obstet Gynecol 2007; 19(6): 513-20). Heavy menstrual bleeding is more prevalent among women at the extreme ends of the reproductive age spectrum (i.e., adolescent girls and women approaching or going through menopause) (Shapley M, Jordan K, Croft P R. An epidemiological survey of symptoms of menstrual loss in the community. Br J Gen Pract 2004; 54(502): 359-63).

Underlying hemostatic disorders, for example hereditary or acquired hemostatic disorders, such as hemophilia and von Willebrand's disease, platelet disorders/dysfunctions like Glantzmann's thrombasthenia and thrombocytopenia as well as PAI-1 deficiency, are potential causes of heavy menstrual bleeding. Menstruation and ovulation are unique hemostatic challenges that occur monthly in women of reproductive age. Integral hemostatic systems are required to control excessive bleeding during these events. While men with mild hereditary hemostatic disorders are often asymptomatic, women suffer a significant morbidity and impaired quality of life mainly with menstrual-related bleedings. Heavy menstrual bleeding is often the presenting symptom of an underlying hemostatic disorder and can be the only bleeding symptom in women. Heavy menstrual bleeding was recognized as a valuable predictor for diagnosis of hemostatic disorders. A prospective study of 150 women presenting with heavy menstrual bleeding found the frequency of undiagnosed hemostatic disorders of 17% and von Willebrand's disease was the most common with an incidence of 13%. Subsequently, a systematic review of literature confirmed an overall incidence of 13% (95% CI 11%, 15.6%) of von Willebrand's disease among 988 women in 11 studies. Mild platelet function defects are also a frequently found hereditary hemostatic disorder in women with heavy menstrual bleeding. However, disorders of platelet function are more likely to remain undiagnosed due to the complex and specialized testing that requires fresh specimens. There are only a few studies in the literature that assess the incidence of platelet function disorders in women with heavy menstrual bleeding. These studies reported platelet function defects to be more common than von Willebrand's disease and were found in approximately 50% of women presenting with heavy menstrual bleeding. Thus, the association of heavy menstrual bleeding in women and hereditary hemostatic disorders is well established (Kadir R A, Davies J. Hemostatic disorders in women. J Thromb Haemost 2013, 11 (Suppl. 1): 170-9).

Tranexamic acid is approved for the treatment of heavy menstrual bleeding and a variety of surgical hemorrhagic conditions. Very high, multiple doses of tranexamic acid are required and the most commonly reported drug-related adverse events after oral administration are gastrointestinal, like nausea, vomiting, diarrhea and dyspepsia (Wellington K, Wagstaff A J, Drugs 2003, 63 (13): 1417-1433), (Dunn C J, Goa K L, Drugs 1999, 57(6): 1005-1032). WO 2006/023000 A1 pertains to modified release oral tranexamic acid formulations and methods of treatment herewith.

WO 2010/117323 A1 and WO 2012/047156 A1 pertain to isoxazol-3(2H)-one analogs as plasminogen inhibitors and their use in the treatment of fibrinolysis related diseases, including inherited hemostatic disorders, stroke, heavy menstrual bleeding and liver diseases. EP 1671962 A1 pertains to fused heterocyclic compounds having kinase (especially c-Jun N-terminalkinase) inhibitory activity and an inhibitory activity of a function of AP-1 as a transcription factor useful as preventive and/or therapeutic agent of e.g. metabolic or inflammatory diseases. WO 2009/017954 A1 pertains to fused heterocyclic compounds having Jak2 kinase inhibitory activity. WO 2011/140333 A1 pertains to the identification of stabilizers of multimeric proteins, the stabilizers comprising structurally diverse compounds. WO 2012/078855 A1 pertains inter alia to substituted pyrazolopyrimidines and dihydropyrazolopyrimidines and related compounds, and methods of use of these compounds in treating lysosomal storage disorders such as Gaucher disease.

WO 2009/023179 A2 pertains to nitrogen containing bicyclic chemical entities for treating viral infections. WO 2009/070567 A1 pertains to pyrazolo[1,5-a] pyrimidine compounds useful as protein kinase inhibitors, and inter alia pharmaceutical compositions to treat diseases such as, for example, cancer, inflammation, arthritis, viral diseases, neurodegenerative diseases such as Alzheimer's disease, cardiovascular diseases, and fungal diseases. WO 2008/011560 A2 pertains to benzothiophene compounds and compositions and their application as pharmaceuticals for the treatment of disease and to methods of inhibition on Rho kinase activity for the treatment of diseases such as Ophthalmologic diseases. WO 2008/008539 A2 pertains to fused heterocyclic derivatives and methods of use thereof in particular for treating cancer. WO 2004/052315 A2 pertains to tyrosine kinase inhibitors and methods of using them to treat tyrosine kinase-dependent diseases and conditions, such as angiogenesis, cancer, tumor growth, atherosclerosis, age related macular degeneration, diabetic retinopathy, and inflammatory diseases. WO 98/03510 A1 pertains to [1,5-a]-pyrazolo-1,3,5-triazines, [1,5-a]-1,2,3-triazolo-1,3,5-triazines, [1,5-a]-pyrazolo-pyrimidines and [1,5-a]-1,2,3-triazolo-pyrimidineazolotriazines for the treatment of psychiatric disorders and neurological diseases.

It was an object of the present invention to provide novel substances which act as inhibitors of fibrinolysis and, as such, are suitable for the treatment and/or prophylaxis of diseases.

The present invention provides compounds of the formula (I-A)

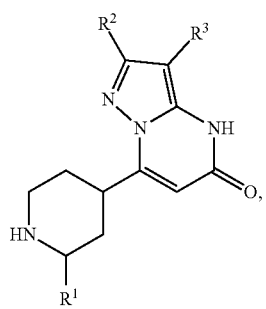

in which
R¹ is selected from hydrogen and $C_1$-$C_5$ alkyl;
R² is selected from hydrogen, $C_1$-$C_4$ alkyl, $C_3$-$C_6$ cycloalkyl, $C_1$-$C_4$ haloalkyl, carboxyl, $C_1$-$C_4$ alkylester, $C_1$-$C_4$ alkoxy-$C_1$-$C_4$ alkyl, phenyl,
the phenyl being optionally substituted with halogen,
5-6 membered heteroaryl, amino, $C_1$-$C_4$ alkyl-amide, and $C_1$-$C_4$ alkyl-sulfonamide;
R³ is selected from hydrogen, halogen, cyano, $C_1$-$C_4$ alkyl, $C_1$-$C_4$ alkylester, carboxyl, carboxamide, benzylester, —NH—CO-phenyl, —CS—NH₂,
phenylsulfonyl, the phenylsulfonyl being optionally substituted with one, two, or three substituents selected from halogen;
phenyl,
the phenyl being optionally substituted with one, two or three substituents selected from halogen and $C_1$-$C_4$ alkoxy, where two adjacent methoxy groups may optionally form a dioxane ring,
or the phenyl being optionally substituted with one or two substituents selected from $C_1$-$C_4$ alkyl, $C_1$-$C_4$ haloalkyl, $C_1$-$C_4$ haloalkoxy, cyano, benzyloxy, methylsulfonyl, and phenyl,
the phenyl being optionally substituted with $C_1$-$C_4$ haloalkyl;
5-6 membered heterocyclyl;
5-6 membered heteroaryl, the 5-6 membered heteroaryl being optionally substituted with one, two or three substituents selected from
$C_1$-$C_6$ alkyl, $C_1$-$C_6$ haloalkyl, $C_1$-$C_4$ aminoalkyl, $C_1$-$C_4$ alkylester, $C_1$-$C_4$ alkoxy, $C_1$-$C_4$ alkoxy-$C_1$-$C_4$ alkyl, cyano, hydroxyl, carboxyl, $C_1$-$C_4$ alkyl-SO₂—$C_1$-$C_4$ alkyl, and —CO—NH₂,
or the 5-6 membered heteroaryl being optionally substituted with one $C_3$-$C_6$ cycloalkyl substituent,
the $C_3$-$C_6$ cycloalkyl optionally being substituted with phenyl, the phenyl being optionally substituted with $C_1$-$C_4$ alkoxy or halogen
or the 5-6 membered heteroaryl being optionally substituted with one substituent selected from
fused or bridged $C_5$-$C_{12}$ bi- or tricycloalkyl;
$C_3$-$C_6$ cycloalkyl-$C_1$-$C_4$ alkyl;
phenyl,
the phenyl optionally being substituted with one, two or three substituents selected from $C_1$-$C_4$ alkyl, halogen, $C_1$-$C_4$ haloalkyl, $C_1$-$C_4$ alkoxy, $C_1$-$C_4$ haloalkoxy, $C_1$-$C_4$-alkylester, nitro, amino, di-$C_1$-$C_4$ alkylamine, and cyano;
phenyl-$C_1$-$C_4$ alkyl,
the phenyl moiety optionally being substituted with one, two or three substituents selected from halogen, $C_1$-$C_4$ alkyl, $C_1$-$C_4$ haloalkyl, $C_1$-$C_4$ alkoxy, $C_1$-$C_4$ haloalkoxy;
the alkyl moiety optionally being substituted with one or two substituents selected from $C_1$-$C_4$ alkyl and hydroxyl;
5-6 membered heterocycloalkyl, the 5-6 membered heterocycloalkyl being optionally substituted with $C_3$-$C_6$ cycloalkyl or $C_1$-$C_4$ alkyl;
5-6 membered heterocycloalkyl-$C_1$-$C_4$ alkyl,
the 5-6 membered heterocycloalkyl moiety being optionally substituted with $C_1$-$C_4$ alkyl or oxo;
the $C_1$-$C_4$ alkyl moiety being optionally substituted with $C_1$-$C_4$ alkyl,
5-6 membered heteroaryl, the 5-6 membered heteroaryl being optionally substituted with one, two or three substituents selected from halogen, $C_1$-$C_4$ alkyl, and $C_1$-$C_4$ haloalkyl;
and
5-6 membered heteroaryl-$C_1$-$C_4$ alkyl,
the 5-6 membered heteroaryl-moiety being optionally substituted with one or two substituents selected from $C_1$-$C_4$ alkoxy and $C_1$-$C_4$ alkyl,
the $C_1$-$C_4$ alkyl-moiety being optionally substituted with one or two methyl substituents;
CO—R⁴, with
R⁴ being selected from the group of the compounds of the formulae

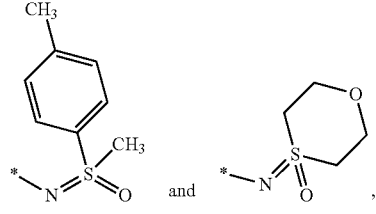 [SMILES: *N=S(C)(=O)c1ccc(C)cc1 ; *N=S1(=O)CCOCC1]

wherein "*" does not represent a carbon atom or a CH₂ group but forms part of the bond to the atom which is designated in each case and to which R⁴ is attached;
and
CO—N(R⁵R⁷), with
R⁵ being selected from hydrogen, and $C_1$-$C_4$ alkyl;
R⁷ being selected from hydrogen, $C_1$-$C_6$ alkyl, $C_1$-$C_6$ haloalkyl, $C_1$-$C_4$-alkoxy-$C_1$-$C_4$ alkyl, amino-oxo-$C_1$-$C_4$ alkyl, naphthyl;
$C_3$-$C_6$ cycloalkyl, the $C_3$-$C_6$ cycloalkyl being optionally substituted with one, or two substituents selected from $C_1$-$C_4$ alkyl;
$C_3$-$C_6$ cycloalkyl-$C_1$-$C_4$ alkyl, 5-6 membered heterocyclyl, oxazolidinyl-$C_1$-$C_4$ alkyl;
benzyl, the benzyl being optionally substituted with one, two or three substituents selected from $C_1$-$C_4$ alkyl, halogen, and $C_1$-$C_4$-alkoxy;
benzyl-$C_3$-$C_6$ cycloalkyl;
imidazolyl-$C_1$-$C_4$ alkyl, the imidazolyl-$C_1$-$C_4$ alkyl being optionally substituted with one, two or three substituents selected from $C_1$-$C_4$ alkyl;
oxazolidinone-$C_1$-$C_4$ alkyl;
and
phenyl, the phenyl being optionally substituted with one, two or three substituents selected from $C_1$-$C_4$ alkyl, halogen, and $C_1$-$C_4$ alkoxy;

Or
—N(R⁵R⁷) being selected from the group of 5-7 membered cyclic amines which contain one or two ring nitrogen atoms and zero or one ring oxygen atom and are attached via a ring nitrogen atom, the 5 to 7 membered cyclic amines being optionally substituted with one, two or three substituents selected from $C_1$-$C_4$ alkoxy, oxo, hydroxyl, halogen, and $C_1$-$C_4$ alkyl;
or
R² and R³ together form a $C_5$-$C_6$ cycloalkyl ring;
and its salts, solvates, and solvates of the salts.

The present invention also provides compounds of the formula (I-B)

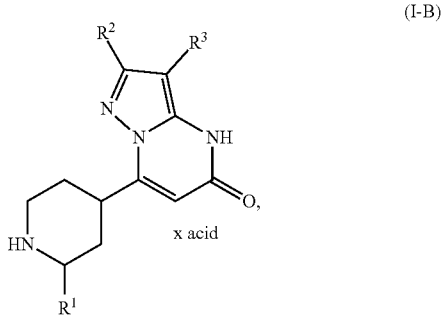

in which R¹, R², and R³ are as defined above.

Compounds according to the invention are the compounds of the formulae (I-A) or (I-B) and their salts, solvates and solvates of the salts, the compounds included in the formulae (I-A) or (I-B) of the formulae mentioned in the following and their salts, solvates and solvates of the salts, and the compounds included in the formulae (I-A) or (I-B) and mentioned in the following as embodiment examples and their salts, solvates and solvates of the salts, where the compounds included in the formulae (I-A) or (I-B) and mentioned in the following are not already salts, solvates and solvates of the salts.

Within the meaning of the present invention, the term "x acid" in any of the formulae does not indicate any defined stoichiometric ratio of acid and the respective compound. Thus, depending e.g. on the alkalinity of the respective compound, the term "x acid" denotes different ratios of the compound to the acid, such as 10:1 to 1:10, 8:1 to 1:8, 7:1 to 1:7, 5:1 to 1:5, 4.5:1 to 1:4.5, 4:1 to 1:4, 3.5:1 to 1:3.5, 3:1 to 1:3, 2.5:1 to 1:2.5, 2:1 to 1:2, 1.5:1 to 1:1.5, and 1:1.

Preferred salts in the context of the present invention are physiologically acceptable salts of the compounds of formula (I-A) or (I-B) according to the invention. Salts which are not themselves suitable for pharmaceutical uses but can be used, for example, for isolation or purification of the compounds of formula (I-A) or (I-B) according to the invention are also included.

Physiologically acceptable salts of the compounds of formula (I-A) or (I-B) according to the invention include acid addition salts of mineral acids, carboxylic acids and sulphonic acids, e.g. salts of hydrochloric acid, hydrobromic acid, sulphuric acid, phosphoric acid, methanesulphonic acid, ethanesulphonic acid, toluenesulphonic acid, benzenesulphonic acid, naphthalenedisulphonic acid, formic acid, acetic acid, trifluoroacetic acid, propionic acid, lactic acid, tartaric acid, malic acid, citric acid, fumaric acid, maleic acid, benzoic acid, oxalic acid, ascorbic acid, and salicylic acid.

Physiologically acceptable salts of the compounds of formula (I-A) or (I-B) according to the invention also include salts of conventional bases, such as, by way of example and preferably, alkali metal salts (e.g. sodium and potassium salts), alkaline earth metal salts (e.g. calcium and magnesium salts) and ammonium salts derived from ammonia or organic amines having 1 to 16 carbon atoms, such as, by way of example and preferably, ethylamine, diethylamine, triethylamine, ethyldiisopropylamine, mono-ethanolamine, diethanolamine, triethanolamine, dicyclohexylamine, dimethylaminoethanol, procaine, dibenzylamine, N-methylmorpholine, arginine, lysine, ethylenediamine, and N-methylpiperidine.

According to an embodiment of the invention, physiologically acceptable salts of the compounds of formula (I-A) or (I-B) according to the invention include salts of hydrochloric acid, sulphuric acid, maleic acid, acetic acid, trifluoroacetic acid, phosphoric acid, tartaric acid, citric acid, fumaric acid, oxalic acid, ascorbic acid, salicylic acid, and lysine.

According to an embodiment of the invention, physiologically acceptable salts of the compounds of formula (I-A) or (I-B) according to the invention include salts of hydrochloric acid, sulphuric acid, maleic acid, acetic acid, trifluoroacetic acid, tartaric acid, ascorbic acid, and salicylic acid.

According to an embodiment of the invention, physiologically acceptable salts of the compounds of formula (I-A) or (I-B) according to the invention include salts of hydrochloric acid, and trifluoroacetic acid.

According to an embodiment of the invention, the physiologically acceptable salts of the compounds of formula (I-A) or (I-B) according to the invention are the salts of hydrochloric acid.

Solvates in the context of the invention are designated as those forms of the compounds of formula (I-A) or (I-B) according to the invention which form a complex in the solid or liquid state by coordination with solvent molecules. Hydrates are a specific form of solvates, in which the coordination takes place with water. Hydrates are preferred solvates in the context of the present invention.

The compounds of formula (I-A) or (I-B) according to the invention can exist in different stereoisomeric forms depending on their structure, i.e. in the form of configuration isomers or optionally also as conformation isomers (enantiomers and/or diastereomers, including those in the case of atropisomers). The present invention therefore includes the enantiomers and diastereomers and their particular mixtures. The stereoisomerically uniform constituents can be isolated from such mixtures of enantiomers and/or diastereomers in a known manner; chromatography processes are preferably used for this, in particular HPLC chromatography on an achiral or chiral phase.

Where the compounds of formula (I-A), (I-B), or (IV) according to the invention can occur in tautomeric forms, the present invention includes all the tautomeric forms.

Examples of stereoisomeric forms of the compounds of formula (I-A) or (I-B) or (IV) according to the invention are compounds of the formulae (I-A) or (I-B) as defined above, and compounds of the formula (IV) as defined below, wherein the substituent R¹ has the meaning of $C_1$-$C_4$ alkyl.

Formula (I-A), wherein the substituent R¹ has the meaning of $C_1$-$C_4$ alkyl, comprises the following transisomers:

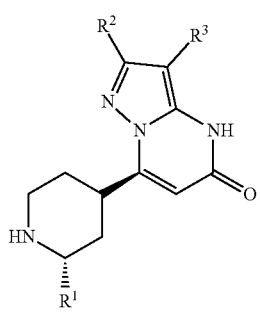 (I-A)

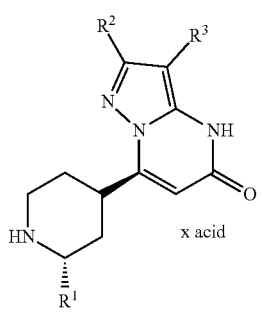 (I-B)

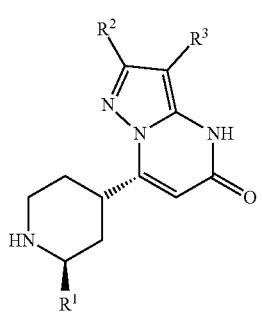 (I-A)

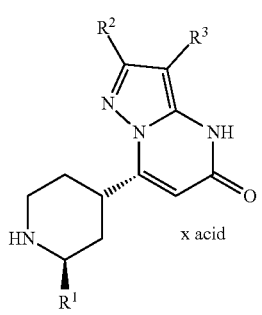 (I-B)

Formula (I-A), wherein the substituent $R^1$ has the meaning of $C_1$-$C_4$ alkyl, further comprises the following cis-isomers:

Formula (I-B), wherein the substituent $R^1$ has the meaning of $C_1$-$C_4$ alkyl, further comprises the following cis-isomers:

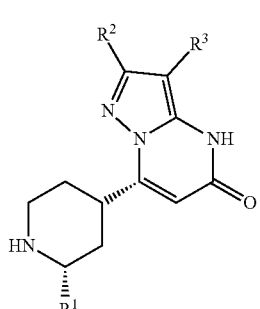 (I-A)

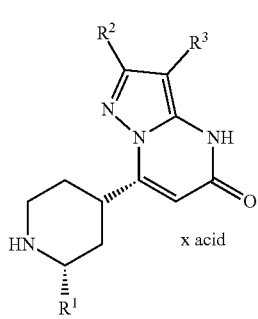 (I-B)

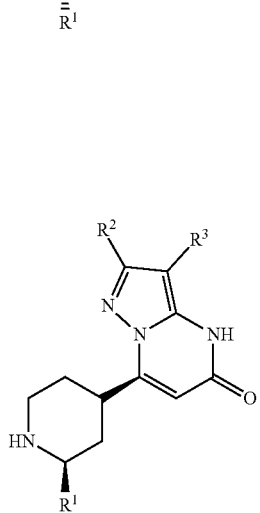 (I-A)

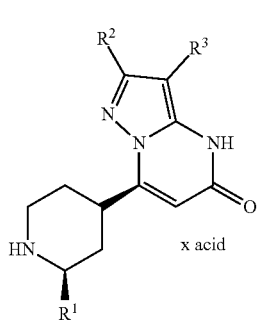 (I-B)

Formula (I-B), wherein the substituent $R^1$ has the meaning of $C_1$-$C_4$ alkyl, comprises the following transisomers:

Formula (IV), wherein the substituent $R^1$ has the meaning of $C_1$-$C_4$ alkyl, comprises the following transisomers:

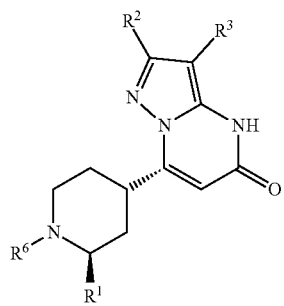

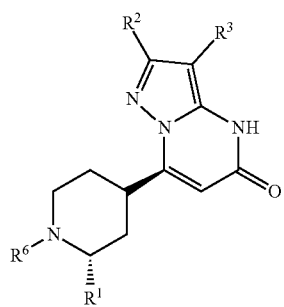

Formula (IV), wherein the substituent $R^1$ has the meaning of $C_1$-$C_4$ alkyl, further comprises the following cis-isomers:

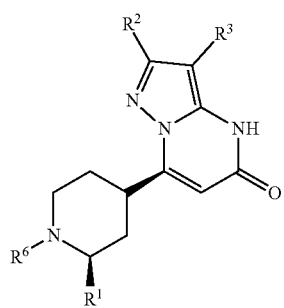

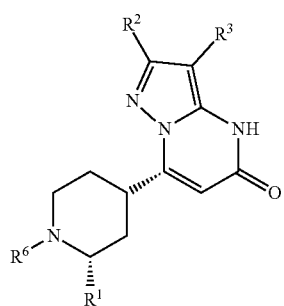

The present invention comprises all possible stereoisomeric forms, also in cases where no stereoisomerism is indicated.

According to an embodiment of the invention, the compounds of formulae (I-A), (I-B), and (IV), wherein the substituent $R^1$ has the meaning of $C_1$-$C_4$ alkyl, are present as mixtures of cis- and transisomers.

According to an embodiment of the invention, the compounds of formulae (I-A), (I-B), and (IV), wherein the substituent $R^1$ has the meaning of $C_1$-$C_4$ alkyl, are present as mixtures of cis- and transisomers, wherein more than 50%, more than 55%, more than 60%, more than 65%, more than 70%, more than 75%, more than 80%, more than 85%, more than 90%, more than 95%, more than 97%, more than 98%, or more than 99%, of the compounds of formulae (I-A), (I-B), and (IV) are present as trans-isomer.

According to an embodiment of the invention, the compounds of formulae (I-A), (I-B), and (IV), wherein the substituent $R^1$ has the meaning of $C_1$-$C_4$ alkyl, are present as the enantiomerically pure transisomers.

The present invention also encompasses all suitable isotopic variants of the compounds of formula (I-A) or (I-B) according to the invention. An isotopic variant of a compound according to the invention is understood here to mean a compound in which at least one atom within the compound according to the invention has been exchanged for another atom of the same atomic number, but with a different atomic mass than the atomic mass which usually or predominantly occurs in nature. Examples of isotopes which can be incorporated into a compound according to the invention are those of hydrogen, carbon, nitrogen, oxygen, phosphorus, sulphur, fluorine, chlorine, bromine and iodine, such as $^2H$ (deuterium), $^3H$ (tritium), $^{13}C$, $^{14}C$, $^{15}N$, $^{17}O$, $^{18}O$, $^{32}P$, $^{33}P$, $^{33}S$, $^{34}S$, $^{35}S$, $^{36}S$, $^{18}F$, $^{36}Cl$, $^{82}Br$, $^{123}I$, $^{124}I$, $^{129}I$ and $^{131}I$. Particular isotopic variants of a compound according to the invention, especially those in which one or more radioactive isotopes have been incorporated, may be beneficial, for example, for the examination of the mechanism of action or of the active compound distribution in the body; due to comparatively easy preparability and detectability, especially compounds labelled with $^3H$ or $^{14}C$ isotopes are suitable for this purpose. In addition, the incorporation of isotopes, for example of deuterium, can lead to particular therapeutic benefits as a consequence of greater metabolic stability of the compound, for example an extension of the half-life in the body or a reduction in the active dose required; such modifications of the compounds of formula (I-A) or (I-B) according to the invention may therefore in some cases also constitute a preferred embodiment of the present invention. Isotopic variants of the compounds of formula (I-A) or (I-B) according to the invention can be prepared by processes known to those skilled in the art, for example by the methods described below and the methods described in the working examples, by using corresponding isotopic modifications of the particular reagents and/or starting compounds therein.

The present invention moreover also includes prodrugs of the compounds of formula (I-A) or (I-B) according to the invention. The term "prodrugs" here designates compounds which themselves can be biologically active or inactive, but are converted (for example metabolically or hydrolytically) into compounds of formula (I-A) or (I-B) according to the invention during their dwell time in the body.

In the context of the present invention, the substituents have the following meaning, unless specified otherwise:

Alkyl in the context of the invention represents a straight-chain or branched alkyl radical having the number of carbon atoms stated in each case. The following may be mentioned by way of example and by way of preference: methyl, ethyl, n-propyl, isopropyl, n-butyl, isobutyl, 1-methylpropyl, tert-butyl, n-pentyl, isopentyl, 1-ethylpropyl, 1-methylbutyl, 2-methylbutyl, 3-methylbutyl, n-hexyl, 1-methylpentyl, 2-methylpentyl, 3-methylpentyl, 4-methylpentyl, 3,3-dimethylbutyl, 1-ethylbutyl, 2-ethylbutyl, 3-methyl-3-ethylpropyl.

Haloalkyl in the context of the invention represents an alkyl radical as defined above being mono- or polyhalogenated up to the maximum possible number of substituents.

In the case of polyhalogenation, the halogen atoms can be identical or different. Here, halogen represents fluorine, chlorine, bromine or iodine, in particular fluorine, chlorine or bromine. The following may be mentioned by way of example and by way of preference: fluoromethyl, difluoromethyl, trifluoromethyl, fluoroethyl, difluoroethyl, trifluoroethyl, pentafluoroethyl, chloromethyl, dichloromethyl, trichloromethyl, chloroethyl, dichloroethyl, 3-methyl-3-fluorethyl-1-fluorpropyl.

Fluoroalkyl in the context of the invention represents an alkyl radical as defined above being mono- or polyfluorinated up to the maximum possible number of fluorine substituents Cycloalkyl or carbocycle in the context of the invention represents a monocyclic saturated alkyl radical having the number of ring carbon atoms stated in each case. The following may be mentioned by way of example and by way of preference: cyclopropyl, cyclobutyl, cyclopentyl, cyclohexyl and cycloheptyl.

Cycloalkylalkyl in the context of the invention represents a monocyclic saturated cycloalkyl radical being as defined above, attached to an alkyl group, being as defined above. The following may be mentioned by way of example and by way of preference: cyclopropyl-methyl, cyclopropyl-ethyl, cyclopropyl-propyl, cyclopropyl-isopropyl, cyclopropyl-butyl, cyclopropyl-isobutyl, cyclopropyl-1-methylpropyl, cyclopropyl-tert-butyl, cyclobutyl-methyl, cyclobutyl-ethyl, cyclobutyl-propyl, cyclobutyl-isopropyl, cyclobutyl-butyl, cyclobutyl-isobutyl, cyclobutyl-1-methylpropyl, cyclobutyl-tert-butyl, cyclopentyl-methyl, cyclopentyl-ethyl, cyclopentyl-propyl, cyclopentyl-isopropyl cyclopentyl-butyl, cyclopentyl-isobutyl, cyclopentyl-1-methylpentyl, cyclopentyl-tert-butyl, cyclohexylmethyl, cyclohexyl-ethyl, cyclohexyl-propyl, cyclohexyl-isopropyl cyclohexyl-butyl, cyclohexyl-isobutyl, cyclohexyl-1-methylhexyl, and cyclohexyl-tert-butyl.

Bridged bi- and tri-cycloalkyl in the context of the invention include $C_5$-$C_{12}$, or $C_7$-$C_{12}$, or $C_8$, groups. Bicyclic and tricyclic groups may be fused or bridged. Examples include: bicyclo-[2,2,1]-heptyl, methylbicyclo-[2,2,1]-octyl, bicyclo-[3,3,0]-octyl, bicyclo-[2,2,2]-octyl, bicyclo-[3,2,1]-octyl, bicyclo-[4,3,0]-nonyl, and bicyclo-[3,3,1]-nonyl.

Bicyclic azaspiro compounds in the context of the invention include bicyclic [2.2], [2.3], [2.4], [2.5], [2.6], [3.3], [3.4], [3.5], [3.6], [4.4], [4.5], [4.6], [5.5], [5.6], and [6.6] azaspiro compounds, the azaspiro compounds being optionally substituted with oxo. Examples include azaspiro[2.5]oct-5-yl and azaspiro[3.5] non-1-yl, the azaspiro compounds being optionally substituted with oxo.

3- to 6-membered heterocycloalkyl in the context of the invention represents a monocyclic saturated heterocycloalkyl radical which has a total of 3 to 6 ring atoms, which contains one or two ring heteroatoms from the group consisting of N, O, S, SO and $SO_2$ and which is attached via a ring carbon atom or, if appropriate, a ring nitrogen atom. The following may be mentioned by way of example: azetidinyl, oxetanyl, oxythianyl, oxoimidazolidinyl, oxazolidinyl, pyrrolidinyl, pyrazolidinyl, tetrahydrofuranyl, thiolanyl, piperidinyl, piperazinyl, tetrahydropyranyl, tetrahydrothiopyranyl, morpholinyl, thiomorpholinyl, hexahydroazepinyl, diazepanyl, and hexahydro-1,4-diazepinyl. Preference is given to oxythianyl, oxoimidazolidinyl, oxazolidinyl, piperidinyl, piperazinyl, morpholinyl, and diazepanyl.

3- to 6-membered heterocycloalkyl-alkyl in the context of the invention represents a heterocycloalkyl radical being as defined above, attached to an alkyl group, being as defined above. The following may be mentioned by way of example and by way of preference: azetidinylmethyl, oxetanylmethyl, oxythianylmethyl, oxoimidazolidinylmethyl, oxazolidinylmethyl, pyrrolidinylmethyl, pyrazolidinylmethyl, tetrahydrofuranylmethyl, thiolanylmethyl, piperidinylmethyl, piperazinylmethyl, tetrahydropyranylmethyl, tetrahydrothiopyranylmethyl, morpholinylmethyl, thiomorpholinylmethyl, hexahydroazepinylmethyl, diazepanylmethyl, hexahydro-1methyl,4-diazepinyl, azetidinylethyl, oxetanylethyl, oxythianylethyl, oxoimidazolidinylethyl, oxazolidinylethyl, pyrrolidinylethyl, pyrazolidinylethyl, tetrahydrofuranylethyl, thiolanylethyl, piperidinylethyl, piperazinylethyl, tetrahydro-pyranylethyl, tetrahydrothiopyranylethyl, morpholinylethyl, thiomorpholinylethyl, hexahydroazepinylethyl, diazepanylethyl, hexahydro-1 ethyl,4-diazepinyl. Preference is given to oxythianylmethyl, oxoimidazolidinylmethyl, oxazolidinylmethyl, piperidinylmethyl, piperazinylmethyl, morpholinylmethyl, diazepanyl, oxythianylethyl, oxoimidazolidinylethyl, oxazolidinylethyl, piperidinylethyl, piperazinylethyl, morpholinylethyl, diazepanyl.

A cyclic amine in the context of the invention represents a 5 to 7 membered heterocycle which contains one or two ring nitrogen atoms and zero or one ring oxygen atom and is attached via a ring nitrogen atom. The following may be mentioned by way of example: morpholinyl, piperidinyl, piperazinyl, diazepanyl, pyrrolidinyl, aziridinyl, and azetidinyl.

Alkenyl in the context of the invention represents a straight-chain or branched alkenyl radical having 2 to 6 carbon atoms and one or two double bonds. Preference is given to a straight-chain or branched alkenyl radical having 2 to 4 carbon atoms and one double bond. The following may be mentioned by way of example and by way of preference: vinyl, allyl, isopropenyl and n-but-2-en-1-yl.

Alkoxy in the context of the invention represents a straight-chain or branched alkoxy radical having 1 to 4 carbon atoms. The following may be mentioned by way of example and by way of preference: methoxy, ethoxy, n-propoxy, isopropoxy, 1-methylpropoxy, n-butoxy, isobutoxy and tert-butoxy.

Haloalkoxy in the context of the invention represents an alkoxy radical as defined above being mono- or polyhalogenated up to the maximum possible number of substituents. In the case of polyhalogenation, the halogen atoms can be identical or different. Here, halogen represents fluorine, chlorine, bromine or iodine, in particular fluorine, chlorine or bromine.

Fluoroalkoxy in the context of the invention represents an alkoxy radical as defined above being mono- or polyfluorinated up to the maximum possible number of fluorine substituents.

Alkoxyalkyl in the context of the invention represents a straight-chain or branched alkoxy radical having 1 to 4 carbon atoms as defined above, attached to an alkyl group, being as defined above. The following may be mentioned by way of example and by way of preference: methoxy-methyl, methoxyethyl, methoxy-propyl, methoxy-isopropyl, methoxy-butyl, methoxy-isobutyl, methoxy-1-methylpropyl, methoxy-tert-butyl, ethoxy-methyl, ethoxy-ethyl, ethoxy-propyl, ethoxy-isopropyl, ethoxy-butyl, ethoxy-isobutyl, ethoxy-1-ethylpropyl, ethoxy-tert-butyl, n-propoxy-methyl, n-propoxy-ethyl, n-propoxy-propyl, n-propoxy-isopropyl, n-propoxy-butyl, n-propoxy-isobutyl, n-propoxy-1-ethylpropyl, n-propoxy-tert-butyl, isopropoxymethyl, isopropoxy-ethyl, isopropoxy-propyl, isopropoxy-isopropyl, isopropoxy-butyl, isopropoxy-isobutyl, isopropoxy-1-ethylpropyl, isopropoxy-tert-butyl, 1-methylpropoxy-methyl, 1-methylpropoxy-ethyl, 1-methylpropoxy-propyl, 1-methylpropoxy-isopropyl, 1-methylpropoxy-butyl, 1-methylpropoxy-isobutyl, 1-methylpropoxy-1-ethylpropyl, 1-methylpropoxy-tert-butyln-butoxy-methyl, n-butoxy-ethyl, n-butoxy-propyl, n-butoxy-isopropyl, n-butoxy-butyl, n-butoxy-isobutyl, n-butoxy-1-ethylpropyl, n-butoxy-tert-butyl, isobutoxy-methyl, isobutoxy-ethyl, isobutoxy-propyl, isobutoxy-isopropyl, isobutoxy-butyl, isobutoxy-isobutyl, isobutoxy-1-ethylpropyl, isobutoxy-tert-butyl, tert-butoxy-methyl, tert-butoxy-ethyl, tert-butoxy-propyl, tert-butoxy-isopropyl, tert-butoxy-butyl, tert-butoxy-isobutyl, tert-butoxy-1-ethylpropyl, and tert-butoxy-tert-butyl.

Alkylester in the context of the invention represents a straight-chain or branched alkyl radical having 1 to 4 carbon atoms as defined above, which is attached to a carboxy group.

Alkylamino in the context of the invention includes mono- and dialkylamino and represents an amino group wherein one or two hydrogen atoms are substituted with alkyl radicals.

A 5 to 6-membered Heteroaryl in the context of the invention represents a monocyclic aromatic heterocycle (heteroaromatic) which has a total of 5 or 6 ring atoms, which contains up to three identical or different ring heteroatoms from the group consisting of N, O and S and is attached via a ring carbon atom or, if appropriate, a ring nitrogen atom. The following may be mentioned by way of example and by way of preference: furanyl, pyrrolyl, thiophenyl, pyrazolyl, imidazolyl, thiazolyl, including 1,3 thiazolyl, isothiazolyl, oxazolyl, including 1,2 oxadiazolyl, isoxazolyl, isothiazolyl, triazolyl, including 1,2,4- and 1,2,3-triazolyl, oxadiazolyl, including 1,2,4-oxadiazol-5-yl, 1,2,4-oxadiazol-3-yl, and 1,3,4-oxadiazol-5-yl, thiadiazolyl, including 1,2,3-, 1,2,4-, 1,2,5-, and 1,3,4-, thiadiazolyl, pyridinyl, pyrimidinyl, pyridazinyl, pyrazinyl and triazinyl, including 1,2,3-, 1,2,4-, and 1,3,5-triazinyl.

Halogen in the context of the invention includes fluorine, chlorine, bromine and iodine. Preference is given to chlorine, bromine, or fluorine.

If radicals in the compounds of formula (I-A) or (I-B) according to the invention are substituted, the radicals may, unless specified otherwise, be mono- or polysubstituted. In the context of the present invention, all radicals which occur more than once are defined independently of one another. Substitution by one, two or three identical or different substituents is preferred.

In the context of the present invention, the term "treatment" or "treat" includes the inhibition, delay, arrest, amelioration, attenuation, limitation, reduction, suppression, reversal or cure of a disease, a condition, a disorder, an injury and a health impairment, of the development, course or the progression of such states and/or the symptoms of such states. Here, the term "therapy" is understood to be synonymous with the term "treatment".

In the context of the present invention, the terms "prevention", "prophylaxis" or "precaution" are used synonymously and refer to the avoidance or reduction of the risk to get, to contract, to suffer from or to have a disease, a condition, a disorder, an injury or a health impairment, a development or a progression of such states and/or the symptoms of such states.

The treatment or the prevention of a disease, a condition, a disorder, an injury or a health impairment may take place partially or completely.

According to an embodiment of the present invention, the compounds of the formulae (I-A) or (I-B) are defined as follows:
$R^1$ is selected from hydrogen and $C_1$-$C_5$ alkyl;
$R^2$ is selected from hydrogen, $C_1$-$C_4$ alkyl, $C_3$-$C_6$ cycloalkyl, $C_1$-$C_4$ haloalkyl, carboxyl, $C_1$-$C_4$ alkylester, $C_1$-$C_4$ alkoxy-$C_1$-$C_4$ alkyl, halogen, methylsulfanyl, phenyl,
the phenyl being optionally substituted with halogen, and
5 membered heteroaryl,
$R^3$ is selected from hydrogen, halogen, cyano, $C_1$-$C_4$ alkyl,
the alkyl being optionally substituted with di-$C_1$-$C_4$ alkylamino, $C_1$-$C_4$ alkenyl, $C_1$-$C_4$ alkylester, the $C_1$-$C_4$ alkylester being optionally substituted with one, two, three, four, or five halogen substituents, $C_3$-$C_4$ cycloalkylester, $C_3$-$C_4$ cycloalkyl, carboxyl, carboxamide, benzylester, —NH—CO-phenyl, —CS—$NH_2$, phenylsulfonyl, the phenylsulfonyl being optionally substituted with one, two, or three substituents selected from halogen,
phenyl,
 the phenyl being optionally substituted with one, two or three substituents selected from halogen and $C_1$-$C_4$ alkoxy, where two adjacent methoxy groups may optionally form a dioxane ring,
 or the phenyl being optionally substituted with one or two substituents selected from $C_1$-$C_4$ alkyl, $C_1$-$C_4$ haloalkyl, $C_1$-$C_4$ haloalkoxy, cyano, benzyloxy, methylsulfonyl, and phenyl,
 the phenyl being optionally substituted with $C_1$-$C_4$ haloalkyl,
5-6 membered heterocyclyl-$C_1$-$C_4$ alkyl, the 5-6 membered heterocyclyl-moiety being optionally substituted with one, two or three substituents selected from $C_1$-$C_4$ alkyl and oxo;
5-6 membered heteroaryl, the 5-6 membered heteroaryl being optionally substituted with one, two or three substituents selected from
 $C_1$-$C_6$ alkyl, $C_2$-$C_6$ alkenyl, $C_1$-$C_6$ haloalkyl, $C_1$-$C_4$ aminoalkyl, $C_1$-$C_4$ alkylester, $C_1$-$C_4$ alkoxy, $C_1$-$C_4$ haloalkoxy, $C_1$-$C_4$ alkoxy-$C_1$-$C_4$ alkyl, cyano, hydroxyl, carboxyl, $C_1$-$C_4$ alkyl-$SO_2$—$C_1$-$C_4$ alkyl, and —CO—$NH_2$,
 or the 5-6 membered heteroaryl being optionally substituted with one $C_3$-$C_6$ cycloalkyl substituent, the $C_3$-$C_6$ cycloalkyl optionally being substituted with one, two, or three halogen or methyl substituents, or with phenyl, the phenyl being optionally substituted with $C_1$-$C_4$ alkoxy or halogen,
 or the 5-6 membered heteroaryl being optionally substituted with one substituent selected from
 fused or bridged $C_5$-$C_{12}$ bi- or tricycloalkyl,
 $C_3$-$C_6$ cycloalkyl-$C_1$-$C_4$ alkyl, $C_3$-$C_6$ cycloalkyl-$C_1$-$C_4$ alkenyl
 phenyl,
  the phenyl optionally being substituted with one, two or three substituents selected from $C_1$-$C_4$ alkyl, halogen, $C_1$-$C_4$ haloalkyl, $C_1$-$C_4$ alkoxy, $C_1$-$C_4$ haloalkoxy, $C_1$-$C_4$-alkylester, nitro, amino, di-$C_1$-$C_4$ alkylamine, and cyano,
 phenyl-$C_1$-$C_4$ alkyl,
  the phenyl moiety optionally being substituted with one, two or three substituents selected from halogen, $C_1$-$C_4$ alkyl, $C_1$-$C_4$ haloalkyl, $C_1$-$C_4$ alkoxy, $C_1$-$C_4$ haloalkoxy, and hydroxyl, the alkyl moiety optionally being substituted with one or two substituents selected from $C_1$-$C_4$ alkyl and hydroxyl, 5-6 membered heterocycloalkyl, the 5-6 membered heterocycloalkyl being optionally substituted with $C_3$-$C_6$ cycloalkyl or $C_1$-$C_4$ alkyl, 5-6 membered heterocycloalkyl-$C_1$-$C_4$ alkyl,
the 5-6 membered heterocycloalkyl moiety being optionally substituted with $C_1$-$C_4$ alkyl or oxo,
the $C_1$-$C_4$ alkyl moiety being optionally substituted with $C_1$-$C_4$ alkyl, 5-6 membered heteroaryl, the 5-6 membered heteroaryl being optionally substituted with one, two or three substituents selected from halogen, $C_1$-$C_4$ alkyl, and $C_1$-$C_4$ haloalkyl,
and 5-6 membered heteroaryl-$C_1$-$C_4$ alkyl,
the 5-6 membered heteroaryl-moiety being optionally substituted with one or two substituents selected from $C_1$-$C_4$ alkoxy and $C_1$-$C_4$ alkyl,
the $C_1$-$C_4$ alkyl-moiety being optionally substituted with one or two methyl substituents;
—CO—$R^4$, with
$R^4$ being selected from the group of $C_1$-$C_4$ alkyl, wherein the $C_1$-$C_4$ alkyl is optionally substituted with 1 or 2 methyl, and $C_3$-$C_6$ cycloalkyl;
—CO—N($R^5R^7$), with
$R^5$ being selected from hydrogen, and $C_1$-$C_4$ alkyl;
$R^7$ being selected from hydrogen, $C_1$-$C_6$ alkyl, $C_1$-$C_6$ haloalkyl, $C_1$-$C_4$-alkoxy-$C_1$-$C_4$ alkyl, amino-oxo-$C_1$-$C_4$ alkyl, naphthyl,
$C_3$-$C_6$ cycloalkyl, the $C_3$-$C_6$ cycloalkyl being optionally substituted with one, or two substituents selected from $C_1$-$C_4$ alkyl,
$C_3$-$C_6$ cycloalkyl-$C_1$-$C_4$ alkyl, 5-6 membered heterocyclyl, oxazolidinyl-$C_1$-$C_4$ alkyl,
benzyl, the phenyl moiety of the benzyl being optionally substituted with one, two or three substituents selected from $C_1$-$C_4$ alkyl, the methyl moiety of the benzyl optionally being substituted with $C_1$-$C_4$ alkyl;
benzyl-$C_3$-$C_6$ cycloalkyl,
imidazolyl-$C_1$-$C_4$ alkyl, the imidazolyl-$C_1$-$C_4$ alkyl being optionally substituted with one, two or three substituents selected from $C_1$-$C_4$ alkyl,
oxazolyl-$C_1$-$C_4$ alkyl, the oxazolyl-$C_1$-$C_4$ alkyl being optionally substituted with one, two or three substituents selected from $C_1$-$C_4$ alkyl,
oxazolidinone-$C_1$-$C_4$ alkyl,
pyridinyl-$C_1$-$C_4$ alkyl,
and
phenyl, the phenyl being optionally substituted with one, two or three substituents selected from $C_1$-$C_4$ alkyl, halogen, and $C_1$-$C_4$ alkoxy;
or
—N($R^5R^7$) being selected from the group of 5-7 membered cyclic amines which contain one or two ring nitrogen atoms, zero or one ring oxygen atom, and zero or one ring sulfur atom, and are attached via a ring nitrogen atom, the 5 to 7 membered cyclic amines being optionally substituted with one, two or three substituents selected from $C_1$-$C_4$ alkoxy, $C_1$-$C_4$ alkoxy $C_1$-$C_4$ alkyl, oxo, hydroxyl, halogen, and $C_1$-$C_4$ alkyl;
or
—N($R^5R^7$) being selected from the group of two annelated, aromatic, partially saturated or saturated rings which are each 5-7 membered and each contain one or two ring nitrogen atoms and are attached via a ring nitrogen atom;
and
—N($R^5R^7$) being selected from bicyclic azaspiro compounds, the azaspiro compounds being optionally substituted with oxo;
or
$R^2$ and $R^3$ together form a $C_5$-$C_6$ cycloalkyl ring;
and its salts, solvates, and solvates of the salts. According to an embodiment of the present invention, the compounds of the formulae (I-A) or (I-B) are defined as follows:
$R^1$ is selected from hydrogen and $C_1$-$C_5$ alkyl;
$R^2$ is selected from hydrogen, $C_1$-$C_2$ alkyl, $C_3$-$C_5$ cycloalkyl, $C_1$-$C_2$ haloalkyl, carboxyl, $C_1$-$C_2$ alkylester, $C_1$-$C_2$ alkoxy-$C_1$-$C_2$ alkyl, phenyl,
the phenyl being optionally substituted with a substituent selected from fluorine and chlorine,
and 5-6 membered heteroaryl;
$R^3$ is selected from hydrogen, bromine, chlorine, cyano, methyl, ethyl, $C_1$-$C_2$ alkylester, carboxyl, carboxamide, benzylester, —NH—CO-phenyl, —CS—$NH_2$;
phenylsulfonyl, the phenylsulfonyl being optionally substituted with one or two substituents selected from chlorine and fluorine;
phenyl,
the phenyl being optionally substituted with one, two or three substituents selected from bromine, chlorine, fluorine, ethoxy and methoxy, where two adjacent methoxy groups may optionally form a dioxane ring,
or the phenyl being optionally substituted with one or two substituents selected from $C_1$-$C_2$ alkyl, $C_1$-$C_2$ fluoroalkyl, $C_1$-$C_2$ fluoroalkoxy, and cyano,
or the phenyl being optionally substituted with one substituent selected from benzyloxy, methylsulfonyl, and phenyl,
the phenyl being optionally substituted with $C_1$-$C_2$ haloalkyl;
5-6 membered heterocyclyl;
5-6 membered heteroaryl, the 5-6 membered heteroaryl being optionally substituted with one or two substituents selected from
$C_1$-$C_6$ alkyl, $C_1$-$C_4$ haloalkyl, $C_1$-$C_2$ aminoalkyl, $C_1$-$C_2$ alkylester, $C_1$-$C_2$ alkoxy, $C_1$-$C_2$ alkoxy-$C_1$-$C_4$ alkyl, cyano, hydroxyl, carboxyl, $C_1$-$C_2$ alkyl-$SO_2$—$C_1$-$C_2$ alkyl, and —CO—$NH_2$,
or the 5-6 membered heteroaryl being optionally substituted with one or two substituents selected from $C_3$-$C_6$ cycloalkyl,
the $C_3$-$C_6$ cycloalkyl optionally being substituted with phenyl, the phenyl being optionally substituted with $C_1$-$C_2$ alkoxy, chlorine or fluorine bridged bi- or tricycloalkyl
$C_3$-$C_6$ cycloalkyl-$C_1$-$C_2$ alkyl;
phenyl, the phenyl optionally being substituted with one, two or three substituents selected from $C_1$-$C_4$ alkyl, halogen, $C_1$-$C_2$ haloalkyl, $C_1$-$C_2$ alkoxy, $C_1$-$C_2$ haloalkoxy, $C_1$-$C_2$-alkylester, nitro, amino, di-$C_1$-$C_2$ alkylamino, and cyano;
phenyl-$C_1$-$C_2$ alkyl,
the phenyl moiety optionally being substituted with one, two or three substituents selected from fluorine, chlorine, $C_1$-$C_2$ alkyl, $C_1$-$C_2$ fluoroalkyl, $C_1$-$C_2$ alkoxy, $C_1$-$C_2$ fluoroalkoxy;
the alkyl moiety optionally being substituted with one or two substituents selected from $C_1$-$C_2$ alkyl and hydroxyl;

5-6 membered heterocycloalkyl, the 5-6 membered heterocycloalkyl being optionally substituted with $C_3$-$C_5$ cycloalkyl or $C_1$-$C_3$ alkyl;

5-6 membered heterocycloalkyl-$C_1$-$C_4$ alkyl,
the 5-6 membered heterocycloalkyl moiety being optionally substituted with $C_1$-$C_2$ alkyl or oxo;
the $C_1$-$C_4$ alkyl moiety being optionally substituted with $C_1$-$C_4$ alkyl, 5-6 membered heteroaryl, the 5-6 membered heteroaryl being optionally substituted with one, two or three substituents selected from halogen, $C_1$-$C_2$ alkyl, and $C_1$-$C_2$ haloalkyl;
and 5-6 membered heteroaryl-$C_1$-$C_4$ alkyl,
the 5-6 membered heteroaryl-moiety being optionally substituted with one or two substituents selected from $C_1$-$C_2$ alkoxy and $C_1$-$C_2$ alkyl,
the $C_1$-$C_2$ alkyl-moiety being optionally substituted with one or two methyl substituents;

CO—$R^4$, with
$R^4$ being selected from the group of the compounds of the formulae

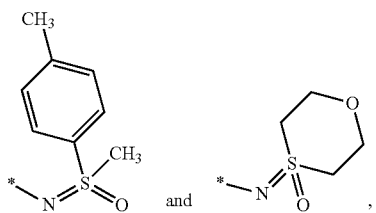 [SMILES: *N=S(C)(=O)c1ccc(C)cc1 ; *N=S1(=O)CCOCC1]

wherein "*" does not represent a carbon atom or a $CH_2$ group but forms part of the bond to the atom which is designated in each case and to which $R^4$ is attached;
and CO—$N(R^5R^7)$, with
$R^5$ being selected from hydrogen, and $C_1$-$C_4$ alkyl;
$R^7$ being selected from hydrogen, $C_1$-$C_6$ alkyl, $C_1$-$C_6$ haloalkyl, $C_1$-$C_4$-alkoxy-$C_1$-$C_4$ alkyl, amino-oxo-$C_1$-$C_4$ alkyl, naphthyl;
$C_3$-$C_6$ cycloalkyl, the $C_3$-$C_6$ cycloalkyl being optionally substituted with one, or two substituents selected from $C_1$-$C_4$ alkyl, 1;
$C_3$-$C_6$ cycloalkyl-$C_1$-$C_4$ alkyl, 5-6 membered heterocyclyl, oxazolidinyl-$C_1$-$C_4$ alkyl;
benzyl, the benzyl being optionally substituted with one, two or three substituents selected from $C_1$-$C_4$ alkyl, halogen, and $C_1$-$C_4$-alkoxy;
benzyl-$C_3$-$C_6$ cycloalkyl;
imidazolyl-$C_1$-$C_4$ alkyl, the imidazolyl-$C_1$-$C_4$ alkyl being optionally substituted with one, two or three substituents selected from $C_1$-$C_4$ alkyl;
oxazolidinone-$C_1$-$C_4$ alkyl;
and
phenyl, the phenyl being optionally substituted with one, two or three substituents selected from $C_1$-$C_4$ alkyl, halogen, and $C_1$-$C_4$ alkoxy;
or
—$N(R^5R^7)$ being selected from the group of 5 to 7 membered cyclic amines which contain one or two ring nitrogen atoms and zero or one ring oxygen atom and are attached via a ring nitrogen atom, the 5 to 7 membered cyclic amines being optionally substituted with one, two or three substituents selected from $C_1$-$C_4$ alkoxy, oxo, hydroxyl, halogen, and $C_1$-$C_4$ alkyl;
or
$R^2$ and $R^3$ together form a $C_5$-$C_6$ cycloalkyl ring;
and its salts, solvates, and solvates of the salts.

According to an embodiment of the present invention, the compounds of the formulae (I-A) or (I-B) are defined as follows:

$R^1$ is selected from hydrogen and $C_1$-$C_5$ alkyl;
$R^2$ is selected from hydrogen, methyl, cyclopropyl, trifluoromethyl, carboxyl, methylester, methoxy-methyl, phenyl,
the phenyl being optionally substituted with fluorine,
and thiophen-yl;
$R^3$ is selected from hydrogen, bromine, chlorine, cyano, methyl, ethyl, ethylester, carboxyl, carboxamide, benzylester, —NH—CO-phenyl, —CS—$NH_2$,
phenylsulfonyl, the phenylsulfonyl being optionally substituted with one or two substituents selected from chlorine and fluorine;
phenyl,
the phenyl being optionally substituted with one or two substituents selected from bromine, chlorine, fluorine, and methoxy, where two adjacent methoxy groups may optionally form a dioxane ring,
or the phenyl being optionally substituted with one or two substituents selected from methyl, trifluoromethyl, trifluoromethoxy, and cyano,
or the phenyl being optionally substituted with one substituent selected from benzyloxy, methylsulfonyl, and phenyl,
the phenyl being optionally substituted with trifluoromethyl;
oxanyl;
1,2,4 oxadiazol-5-yl of the formula

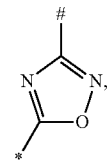

or 1,3,4 oxadiazol-5-yl of the formula

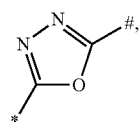

or 1,2,4 oxadiazol-3-yl

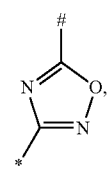

wherein * indicates the position of binding to the pyrazolopyrimidone and # denotes the binding to a further substituent, the oxadiazolyl being substituted with a substituent selected from C₁-C₆ alkyl, C₁-C₄ haloalkyl, aminomethyl, ethylester, methoxy-C₁-C₄ alkyl, tert-butoxy-ethyl, hydroxyl, carboxyl, isopropylsulfonylmethyl, methylsulfonylmethyl, CO—NH₂, C₃-C₆ cycloalkyl,
  the C₃-C₆ cycloalkyl optionally being substituted with phenyl, the phenyl optionally being substituted with chlorine or methoxy;
bicyclo[2.2.2]octyl;
cyclohexylmethyl;
phenyl-C₁-C₂ alkyl,
  the phenyl moiety optionally being substituted with one, two or three substituents selected from chlorine, fluorine, methyl, trifluoromethyl, methoxy, isopropyl-oxy, difluoromethoxy, trifluoromethoxy;
  the alkyl moiety optionally being substituted with one or two substituents selected from methyl, ethyl, and hydroxyl;
oxanyl;
oxopyrrolidinyl-methyl piperidinyl, the piperidinyl being substituted with cyclopropyl or iso-propyl;
piperidinylmethyl, the piperidinylmethyl being optionally substituted with methyl;
morpholinyl-ethyl, the ethyl moiety being optionally substituted with methyl;
tetrahydrofuranyl,
1,2,4 triazolyl-methyl, the methyl moiety being substituted with two methyl substituents;
phenyl, the phenyl optionally being substituted with one, two or three substituents selected from
  C₁-C₄ alkyl, halogen, trifluoromethyl, methoxy, trifluoromethoxy, methylester, nitro, amino, di-methylamino, and cyano;
thiophenyl, the thiophenyl being optionally substituted with fluorine;
furanyl;
imidazolyl, the imidazolyl being substituted with methyl;
thiazolyl-methyl, the thiazolyl-methyl being substituted with methyl;
pyridinyl, the pyridinyl being optionally substituted with one or two substituents selected from methyl, trifluoromethyl, fluorine, and chlorine;
and
pyridinylmethyl, the pyridinylmethyl being optionally substituted with methoxy;
1,2 oxazolyl, the 1,2 oxazolyl being substituted with phenyl
pyridinyl, the pyridinyl being optionally substituted with methoxy;
thiophen-yl, the thiophen-yl being optionally substituted with a substituent selected from methyl and cyano;
and
1,3 thiazolyl,
  the 1,3 thiazolyl being substituted with one substituent selected from C₁-C₆ alkyl, C₁-C₄ haloalkyl, cyclopropyl and phenyl,
    the phenyl being optionally substituted with one or two substituents selected from fluorine, chlorine, methyl, and trifluoromethyl
  or the thiazolyl being substituted with two substituents selected from methyl, ethyl, and
    iso-propyl substituents, or the thiazolyl being optionally substituted with phenyl and methyl;
or
R² and R³ together form a C₅-C₆ cycloalkyl ring;
and its salts, solvates, and solvates of the salts.

According to an embodiment of the present invention, the compounds of the formulae (I-A) or (I-B) are defined as follows:
R¹ is hydrogen;
R² is hydrogen;
R³ is selected from
  1,2,4 oxadiazol-5-yl of the formula

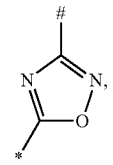

or 1,3,4 oxadiazol-5-yl of the formula

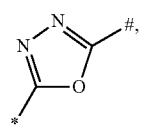

or 1,2,4 oxadiazol-3-yl of the formula

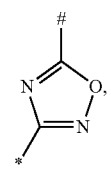

wherein * indicates the position of binding to the pyrazolopyrimidone and # denotes the optional binding to a further substituent, the oxadiazolyl being substituted with a substituent selected from
  C₁-C₆ alkyl, C₁-C₄ fluoroalkyl, methoxy-C₁-C₄ alkyl, tert-butoxy-ethyl, C₃-C₆ cycloalkyl,
    the C₃-C₆ cycloalkyl optionally being substituted with phenyl, the phenyl optionally being substituted with chlorine or methoxy;
  oxanyl;
  oxopyrrolidinyl-methyl
  piperidinyl, the piperidinyl being substituted with cyclopropyl or iso-propyl;
  piperidinyl-methyl, the piperidinylmethyl being optionally substituted with methyl;
  morpholinyl-ethyl, the ethyl moiety being optionally substituted with methyl;
  tetrahydrofuranyl;
  phenyl, the phenyl optionally being substituted with one, two or three substituents selected from
    C₁-C₄ alkyl, fluorine, chlorine, trifluoromethyl, methoxy, trifluoromethoxy, methylester, nitro, amino, di-methylamino, and cyano;
  and
  benzyl,
    the phenyl moiety of the benzyl being optionally substituted with one or two fluorine and one methoxy substituent,
    or the phenyl moiety of the benzyl being optionally substituted with one or two substituents selected from fluorine, chlorine, and methoxy, or the phenyl moiety being optionally substituted with one substituent selected from fluorine, chlorine, methyl, trifluoromethyl, methoxy, isopropyloxy, trifluoromethoxy, and difluoromethoxy, the methyl moiety of the benzyl being optionally substituted with hydroxyl, ethyl, or one or two methyl substituents;

1,2 oxazolyl, the 1,2 oxazolyl being substituted with phenyl thiophen-yl, the thiophen-yl being optionally substituted with a substituent selected from methyl and cyano;

and 1,3 thiazolyl, the 1,3 thiazolyl being optionally substituted with one substituent selected from $C_1$-$C_5$ alkyl, $C_1$-$C_4$ haloalkyl, cyclopropyl and phenyl, the phenyl being optionally substituted with one of two substituents selected from fluorine, chlorine, methyl, and trifluoromethyl or the 1,3 thiazolyl being optionally substituted with two substituents selected from methyl, ethyl, and iso-propyl substituents, or the 1,3 thiazolyl being optionally substituted with phenyl and methyl;

and its salts, solvates, and solvates of the salts.

According to an embodiment of the present invention, the compounds of the formulae (I-A) or (I-B) are defined as follows:

$R^1$ is hydrogen;

$R^2$ is hydrogen;

$R^3$ is selected from 1,2,4 oxadiazol-5-yl of the formula

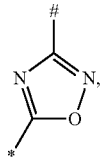

wherein * indicates the position of binding to the pyrazolopyrimidone and # denotes the optional binding to a further substituent, the oxadiazolyl being substituted with a substituent selected from $C_1$-$C_6$ alkyl, $C_1$-$C_4$ fluoroalkyl, methoxy-$C_1$-$C_4$ alkyl, tert-butoxy-ethyl, $C_3$-$C_6$ cycloalkyl, the $C_3$-$C_6$ cycloalkyl optionally being substituted with phenyl, the phenyl optionally being substituted with methoxy;

oxanyl;

piperidinyl, the piperidinyl being substituted with cyclopropyl;

piperidinyl-methyl, the piperidinylmethyl being optionally substituted with methyl;

tetrahydrofuranyl;

phenyl, the phenyl optionally being substituted with one, two or three substituents selected from $C_1$-$C_4$ alkyl, fluorine, chlorine, trifluoromethyl, methoxy, trifluoromethoxy, methylester, nitro, amino, and di-methylamino;

and benzyl, the phenyl moiety of the benzyl being optionally substituted with one or two fluorine and one methoxy substituent, or the phenyl moiety of the benzyl being optionally substituted with one or two substituents selected from fluorine, chlorine, and methoxy, or the phenyl moiety being optionally substituted with one substituent selected from fluorine, chlorine, methyl, trifluoromethyl, methoxy, isopropyloxy, trifluoromethoxy, and difluoromethoxy, the methyl moiety of the benzyl being optionally substituted with hydroxyl, ethyl, or one or two methyl substituents;

1,3,4 oxadiazol-5-yl of the formula

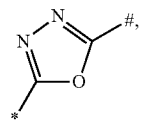

wherein * indicates the position of binding to the pyrazolopyrimidone and # denotes the optional binding to a further substituent, the oxadiazolyl being substituted with a substituent selected from $C_1$-$C_4$ alkyl, $C_1$-$C_2$ fluoroalkyl, methoxy-$C_1$-$C_4$ alkyl, tert-butoxy-ethyl, $C_3$-$C_6$ cycloalkyl, the $C_3$-$C_6$ cycloalkyl optionally being substituted with phenyl, the phenyl optionally being substituted with chlorine or methoxy;

oxopyrrolidinyl-methyl piperidinyl-methyl;

morpholinyl-ethyl, the ethyl moiety being optionally substituted with methyl;

phenyl, the phenyl optionally being substituted with one or two substituents selected from $C_1$-$C_4$ alkyl, fluorine, chlorine, trifluoromethyl, methoxy, and cyano;

and benzyl, the phenyl moiety of the benzyl being optionally substituted with one or two substituents selected from fluorine, chlorine, methoxy, trifluoromethoxy, and difluoromethoxy;

1,2,4 oxadiazol-3-yl of the formula

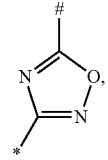

wherein * indicates the position of binding to the pyrazolopyrimidone and # denotes the optional binding to a further substituent, the oxadiazolyl being substituted with a substituent selected from $C_1$-$C_4$ alkyl, phenyl, the phenyl optionally being substituted with one or two substituents selected from $C_1$-$C_2$ alkyl, fluorine, chlorine, trifluoromethyl, methoxy, and trifluoromethoxy;

and benzyl, the phenyl moiety of the benzyl being optionally substituted with one or two chlorine substituents;

1,2 oxazolyl, the 1,2 oxazolyl being substituted with phenyl
thiophen-yl, the thiophen-yl being optionally substituted with a substituent selected from methyl and cyano;
1,3 thiazolyl,
the 1,3 thiazolyl being optionally substituted with one substituent selected from $C_1$-$C_4$ alkyl, $C_1$-$C_4$ haloalkyl, cyclopropyl and phenyl,
the phenyl being optionally substituted with one or two substituents selected from fluorine, chlorine, methyl, and trifluoromethyl
or the 1,3 thiazolyl being optionally substituted with two substituents selected from methyl, ethyl, and iso-propyl substituents, or the 1,3 thiazolyl being optionally substituted with phenyl and methyl;
and its salts, solvates, and solvates of the salts.

According to an embodiment of the present invention, the compounds of the formulae (I-A) or (I-B) are defined as follows:
$R^1$ is hydrogen
$R^2$ and $R^3$ are as defined above
and its salts, solvates, and solvates of the salts.

According to an embodiment of the present invention, the compounds of the formulae (I-A) or (I-B) are defined as follows:
$R^1$ is hydrogen
$R^2$ is hydrogen or methyl
$R^3$ is as defined above
and its salts, solvates, and solvates of the salts.

According to an embodiment of the present invention, the compounds of the formulae (I-A) or (I-B) are defined as follows:
$R^1$ is hydrogen
$R^2$ is hydrogen or methyl
$R^3$ is selected from
1,2,4 oxadiazol-5-yl of the formula

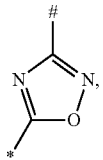

wherein * indicates the position of binding to the pyrazolopyrimidone and # denotes the optional binding to a further substituent, the oxadiazolyl being substituted with a substituent selected from
$C_1$-$C_6$ alkyl, $C_1$-$C_4$ fluoroalkyl, methoxy-$C_1$-$C_4$ alkyl, tert-butoxy-ethyl, $C_3$-$C_6$ cycloalkyl,
the $C_3$-$C_6$ cycloalkyl optionally being substituted with phenyl, the phenyl optionally being substituted with methoxy;
oxanyl;
piperidinyl, the piperidinyl being substituted with cyclopropyl;
piperidinyl-methyl, the piperidinylmethyl being optionally substituted with methyl;
tetrahydrofuranyl;
phenyl, the phenyl optionally being substituted with one, two or three substituents selected from
$C_1$-$C_4$ alkyl, fluorine, chlorine, trifluoromethyl, methoxy, trifluoromethoxy, methylester, nitro, amino, and di-methylamino; and
benzyl, the phenyl moiety of the benzyl being optionally substituted with one or two fluorine and one methoxy substituent, or
the phenyl moiety of the benzyl being optionally substituted with one or two substituents selected from fluorine, chlorine, and methoxy,
or the phenyl moiety being optionally substituted with one substituent selected from fluorine, chlorine, methyl, trifluoromethyl, methoxy, isopropyloxy, trifluoromethoxy, and difluoromethoxy,
the methyl moiety of the benzyl being optionally substituted with hydroxyl, ethyl, or one or two methyl substituents
and its salts, solvates, and solvates of the salts.

According to an embodiment of the present invention, the compounds of the formulae (I-A) or (I-B) are defined as follows:
$R^1$ is hydrogen
$R^2$ is hydrogen or methyl
$R^3$ is selected from
1,3,4 oxadiazol-5-yl of the formula

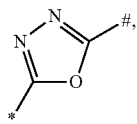

wherein * indicates the position of binding to the pyrazolopyrimidone and # denotes the optional binding to a further substituent, the oxadiazolyl being substituted with a substituent selected from
$C_1$-$C_4$ alkyl, $C_1$-$C_2$ fluoroalkyl, methoxy-$C_1$-$C_4$ alkyl, tert-butoxy-ethyl, $C_3$-$C_6$ cycloalkyl,
the $C_3$-$C_6$ cycloalkyl optionally being substituted with phenyl, the phenyl optionally being substituted with chlorine or methoxy;
oxopyrrolidinyl-methyl
piperidinyl-methyl;
morpholinyl-ethyl, the ethyl moiety being optionally substituted with methyl;
phenyl, the phenyl optionally being substituted with one or two substituents selected from
$C_1$-$C_4$ alkyl, fluorine, chlorine, trifluoromethyl, methoxy, and cyano; and
benzyl,
the phenyl moiety of the benzyl being optionally substituted with one or two substituents selected from fluorine, chlorine, methoxy, trifluoromethoxy, and difluoromethoxy.

According to an embodiment of the present invention, the compounds of the formulae (I-A) or (I-B) are defined as follows:
$R^1$ is hydrogen
$R^2$ is hydrogen or methyl
$R^3$ is selected from
1,2,4 oxadiazol-3-yl of the formula

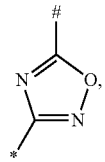

wherein * indicates the position of binding to the pyrazolopyrimidone and # denotes the optional binding to a further substituent, the oxadiazolyl being substituted with a substituent selected from
$C_1$-$C_4$ alkyl,
phenyl, the phenyl optionally being substituted with one or two substituents selected from
$C_1$-$C_2$ alkyl, fluorine, chlorine, trifluoromethyl, methoxy, and trifluoromethoxy; and
benzyl,
the phenyl moiety of the benzyl being optionally substituted with one or two chlorine substituents
and its salts, solvates, and solvates of the salts.

According to an embodiment of the present invention, the compounds of the formulae (I-A) or (I-B) are defined as follows:
$R^1$ is hydrogen
$R^2$ is hydrogen or methyl
$R^3$ is selected from
1,3 thiazolyl,
the 1,3 thiazolyl being substituted with one substituent selected from $C_1$-$C_5$ alkyl, $C_1$-$C_4$ haloalkyl, cyclopropyl and phenyl,
the phenyl being optionally substituted with one or two substituents selected from fluorine, chlorine, methyl, and trifluoromethyl
or the 1,3 thiazolyl being substituted with two substituents selected from methyl, ethyl, and iso-propyl substituents, or the thiazolyl being optionally substituted with phenyl and methyl;
and its salts, solvates, and solvates of the salts.

The present invention provides compounds of the general formula (I-A)

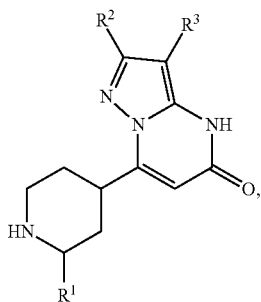

(I-A)

in which
$R^1$ is selected from hydrogen and $C_1$-$C_4$ alkyl;
$R^2$ is selected from hydrogen, $C_1$-$C_4$ alkyl, $C_3$-$C_6$ cycloalkyl, $C_1$-$C_4$ haloalkyl, carboxyl, $C_1$-$C_4$ alkylester, $C_1$-$C_4$ alkoxy-$C_1$-$C_4$ alkyl, phenyl, the phenyl being optionally substituted with halogen, 5-6 membered heteroaryl, amino, $C_1$-$C_4$ alkyl-amide, and $C_1$-$C_4$ alkyl-sulfonamide;
$R^3$ is selected from hydrogen, halogen, cyano, $C_1$-$C_4$ alkylester, carboxyl, carboxamide, benzylester;
phenylsulfonyl, the phenylsulfonyl being optionally substituted with one, two, or three substituents selected from halogen;
phenyl, the phenyl being optionally substituted with one, two or three substituents selected from
halogen, $C_1$-$C_4$ alkyl, $C_1$-$C_4$ haloalkyl, $C_1$-$C_4$ alkoxy, where two adjacent methoxy groups may optionally form a dioxane ring, $C_1$-$C_4$ haloalkoxy, benzyloxy, cyano, methylsulfonyl, and phenyl, the phenyl being optionally substituted with $C_1$-$C_4$ haloalkyl;
5-6 membered heteroaryl, the 5-6 membered heteroaryl being optionally substituted with one, two or three substituents selected from
$C_1$-$C_4$ alkyl, $C_1$-$C_4$ haloalkyl, $C_1$-$C_4$ alkoxy, $C_1$-$C_4$ alkoxy-$C_1$-$C_4$ alkyl, cyano, $C_1$-$C_4$ alkyl-$SO_2$—$C_1$-$C_4$ alkyl, CO—$NH_2$, $C_3$-$C_6$ cycloalkyl, $C_3$-$C_6$ cycloalkyl-$C_1$-$C_4$ alkyl;
benzyl, the benzyl optionally being substituted with one, two or three substituents selected from $C_1$-$C_4$ alkyl, $C_1$-$C_4$ alkoxy, and halogen;
5- to 6-membered heterocycloalkyl, the 5- to 6-membered heterocycloalkyl being optionally substituted with $C_3$-$C_6$ cycloalkyl;
5- to 6-membered heterocycloalkyl-$C_1$-$C_4$ alkyl, the 5- to 6-membered heterocycloalkyl being optionally substituted with $C_1$-$C_4$ alkyl;
phenyl, the phenyl optionally being substituted with one, two or three substituents selected from $C_1$-$C_4$ alkyl, halogen, $C_1$-$C_4$ haloalkyl, $C_1$-$C_4$ alkoxy, $C_1$-$C_4$ haloalkoxy, CO—O—$C_1$-$C_4$-alkyl, $NO_2$, $NH_2$, di-$C_1$-$C_4$ alkylamine, and cyano; and
5 to 6 membered heteroaryl, the 5 to 6 membered heteroaryl being optionally substituted with one, two or three substituents selected from halogen, $C_1$-$C_4$ alkyl, and $C_1$-$C_4$ haloalkyl;
CO—$R^4$, with
$R^4$ being selected from the group of the compounds of the formulae

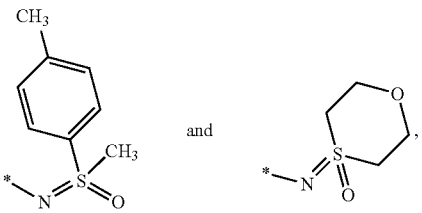 [SMILES: *N=S(C)(=O)c1ccc(C)cc1 ; *N=S1(=O)CCOCC1]

wherein "*" does not represent a carbon atom or a $CH_2$ group but forms part of the bond to the atom which is designated in each case and to which $R^4$ is attached;
and
CO—$N(R^5R^7)$, with
$R^5$ being selected from hydrogen, and $C_1$-$C_4$ alkyl;
$R^7$ being selected from hydrogen, $C_1$-$C_6$ alkyl, $C_1$-$C_6$ haloalkyl, $C_1$-$C_4$-alkoxy-$C_1$-$C_4$ alkyl, amino-oxo-$C_1$-$C_4$ alkyl, naphthyl;
$C_3$-$C_6$ cycloalkyl, the $C_3$-$C_6$ cycloalkyl being optionally substituted with one, two or three substituents selected from $C_1$-$C_4$ alkyl;
$C_3$-$C_6$ cycloalkyl-$C_1$-$C_4$ alkyl, $C_3$-$C_6$ heterocyclyl, oxazolidinyl-$C_1$-$C_4$ alkyl;
benzyl, the benzyl being optionally substituted with one, two or three substituents selected from $C_1$-$C_4$ alkyl, halogen, and $C_1$-$C_4$-alkoxy;
benzyl-$C_3$-$C_6$ cycloalkyl;
imidazolyl-$C_1$-$C_4$ alkyl, the imidazolyl-$C_1$-$C_4$ alkyl being optionally substituted with one, two or three substituents selected from $C_1$-$C_4$ alkyl;
oxazolidinone-$C_1$-$C_4$ alkyl;
and
phenyl, the phenyl being optionally substituted with one, two or three substituents selected from $C_1$-$C_4$ alkyl, halogen, and $C_1$-$C_4$ alkoxy;

or
—N($R^5R^7$) being selected from the group of 5 to 7 membered cyclic amines which contain one or two ring nitrogen atoms and zero or one ring oxygen atom and are attached via a ring nitrogen atom, the 5 to 7 membered cyclic amines being optionally substituted with one, two or three substituents selected from $C_1$-$C_4$ alkoxy, oxo, halogen, and $C_1$-$C_4$ alkyl;
or
$R^2$ and $R^3$ together form a $C_5$-$C_6$ cycloalkyl ring;
and its salts, solvates, and solvates of the salts.

The present invention also provides compounds of the formula (I-B)

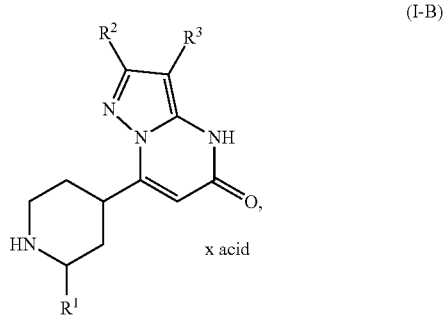

(I-B)

in which $R^1$, $R^2$, and $R^3$ are as defined above.

According to an embodiment of the present invention, the compounds of the formulae (I-A) or (I-B) are defined as follows:
$R^1$ is selected from hydrogen and $C_1$ alkyl;
$R^2$ is selected from hydrogen, $C_1$-$C_4$ alkyl, $C_3$-$C_6$ cycloalkyl, $C_1$-$C_4$ haloalkyl, carboxyl, $C_1$-$C_4$ alkylester, $C_1$-$C_4$ alkoxy-$C_1$-$C_4$ alkyl, phenyl, the phenyl being optionally substituted with halogen, 5-6 membered heteroaryl;
$R^3$ is selected from hydrogen, halogen, cyano, $C_1$-$C_4$ alkylester, carboxyl, carboxamide, benzylester;
phenylsulfonyl, the phenylsulfonyl being optionally substituted with one, two, or three substituents selected from halogen;
phenyl, the phenyl being optionally substituted with one, two or three substituents selected from
halogen, $C_1$-$C_4$ alkyl, $C_1$-$C_4$ haloalkyl, $C_1$-$C_4$ alkoxy, where two adjacent methoxy groups may optionally form a dioxane ring, $C_1$-$C_4$ haloalkoxy, benzyloxy, cyano, methylsulfonyl, and
phenyl, the phenyl being optionally substituted with $C_1$-$C_4$ haloalkyl;
5-6 membered heteroaryl, the 5-6 membered heteroaryl being optionally substituted with one, two or three substituents selected from
$C_1$-$C_4$ alkyl, $C_1$-$C_4$ haloalkyl, $C_1$-$C_4$ alkoxy, $C_1$-$C_4$ alkoxy-$C_1$-$C_4$ alkyl, cyano, $C_1$-$C_4$ alkyl-$SO_2$—$C_1$-$C_4$ alkyl, CO—$NH_2$, $C_3$-$C_6$ cycloalkyl, $C_3$-$C_6$ cycloalkyl-$C_1$-$C_4$ alkyl;
benzyl, the benzyl optionally being substituted with one, two or three substituents selected from $C_1$-$C_4$ alkyl, $C_1$-$C_4$ alkoxy, and halogen;
5- to 6-membered heterocycloalkyl, the 5- to 6-membered heterocycloalkyl being optionally substituted with $C_3$-$C_6$ cycloalkyl;
5- to 6-membered heterocycloalkyl-$C_1$-$C_4$ alkyl, the 5- to 6-membered heterocycloalkyl being optionally substituted with $C_1$-$C_4$ alkyl;
phenyl, the phenyl optionally being substituted with one, two or three substituents selected from $C_1$-$C_4$ alkyl, halogen, $C_1$-$C_4$ haloalkyl, $C_1$-$C_4$ alkoxy, and $C_1$-$C_4$ haloalkoxy, CO—O—$C_1$-$C_4$-alkyl, $NO_2$, $NH_2$, di-$C_1$-$C_4$ alkylamine, and cyano; and
5 to 6 membered heteroaryl, the 5 to 6 membered heteroaryl being optionally substituted with one, two or three substituents selected from halogen, $C_1$-$C_4$ alkyl, and $C_1$-$C_4$ haloalkyl;
or
$R^2$ and $R^3$ together form a $C_5$-$C_6$ cycloalkyl ring;
and its salts, solvates, and solvates of the salts.

According to an embodiment of the present invention, the compounds of the formulae (I-A) or (I-B) are defined as follows:
$R^1$ is selected from hydrogen and $C_1$ alkyl;
$R^2$ is hydrogen;
$R^3$ is selected from hydrogen;
phenyl, the phenyl being optionally substituted with one, two or three substituents selected from
halogen, $C_1$-$C_4$ alkyl, $C_1$-$C_4$ haloalkyl, $C_1$-$C_4$ alkoxy, where two adjacent methoxy groups may optionally form a dioxane ring, $C_1$-$C_4$ haloalkoxy, benzyloxy, cyano, methylsulfonyl, and
phenyl, the phenyl being optionally substituted with $C_1$-$C_4$ haloalkyl;
5-6 membered heteroaryl, the 5-6 membered heteroaryl being optionally substituted with one, two or three substituents selected from
$C_1$-$C_4$ alkyl, $C_1$-$C_4$ haloalkyl, $C_1$-$C_4$ alkoxy, $C_1$-$C_4$ alkoxy-$C_1$-$C_4$ alkyl, cyano, $C_1$-$C_4$ alkyl-$SO_2$—$C_1$-$C_4$ alkyl, CO—$NH_2$, $C_3$-$C_6$ cycloalkyl, $C_3$-$C_6$ cycloalkyl-$C_1$-$C_4$ alkyl;
benzyl, the benzyl optionally being substituted with one, two or three substituents selected from $C_1$-$C_4$ alkyl, $C_1$-$C_4$ alkoxy, and halogen;
5- to 6-membered heterocycloalkyl, the 5- to 6-membered heterocycloalkyl being optionally substituted with $C_3$-$C_6$ cycloalkyl;
5- to 6-membered heterocycloalkyl-$C_1$-$C_4$ alkyl, the 5- to 6-membered heterocycloalkyl being optionally substituted with $C_1$-$C_4$ alkyl;
phenyl, the phenyl optionally being substituted with one, two or three substituents selected from
$C_1$-$C_4$ alkyl, halogen, $C_1$-$C_4$ haloalkyl, $C_1$-$C_4$ alkoxy, and $C_1$-$C_4$ haloalkoxy, CO—O—$C_1$-$C_4$-alkyl, $NO_2$, $NH_2$, di-$C_1$-$C_4$ alkylamine, and cyano; and
5 to 6 membered heteroaryl, the 5 to 6 membered heteroaryl being optionally substituted with one, two or three substituents selected from halogen, $C_1$-$C_4$ alkyl, and $C_1$-$C_4$ haloalkyl;
and its salts, solvates, and solvates of the salts.

According to an embodiment of the present invention, the compounds of the formulae (I-A) or (I-B) are defined as follows:
$R^1$ is hydrogen;
$R^2$ is hydrogen;
$R^3$ is selected from
phenyl, the phenyl being optionally substituted with one, two or three substituents selected from
halogen, methyl, trifluoromethyl, methoxy, where two adjacent methoxy groups may optionally form a dioxane ring, trifluoromethoxy, benzyloxy, cyano, methylsulfonyl, and
phenyl, optionally substituted with trifluoromethyl;

oxadiazolyl of the formula

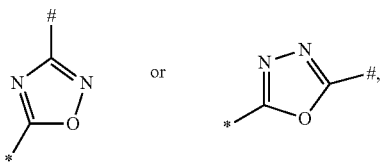

wherein * indicates the position of binding to the pyrazolopyrimidone and # denotes the optional binding to a further substituent, the oxadiazolyl being optionally substituted with a substituent selected from
$C_1$-$C_4$ alkyl, $C_1$-$C_4$ haloalkyl, methoxy-$C_1$-$C_4$ alkyl, $C_1$-$C_3$-alkylsulfonylmethyl, sulfonyl-$C_1$-$C_3$-alkyl, CO—$NH_2$, $C_3$-$C_6$ cycloalkyl, $C_3$-$C_6$ cycloalkyl-$C_1$ alkyl;
benzyl, the benzyl optionally being substituted with one, two or three substituents selected from methyl, methoxy, and halogen;
piperidinyl, the piperidinyl being optionally substituted with cyclopropyl;
piperidinylmethyl, the piperidinylmethyl being optionally substituted with methyl;
phenyl, the phenyl optionally being substituted with one, two or three substituents selected from
$C_1$-$C_4$ alkyl, halogen, trifluoromethyl, methoxy, trifluoromethoxy, CO—O—$CH_3$, $NO_2$, $NH_2$, di-methylamine, and cyano;
thiophenyl, the thiophenyl being optionally substituted with halogen;
furanyl;
imidazolyl, the imidazolyl optionally being substituted with methyl;
and
pyridinyl, the pyridinyl being optionally substituted with one, two or three substituents selected from methyl, trifluoromethyl, and halogen;
pyridinyl, the pyridinyl being optionally substituted with methoxy;
thiophenyl, the thiophenyl being optionally substituted with a substituent selected from methyl and cyano; and
thiazolyl, the thiazolyl being optionally substituted with one, two or three substituents selected from methyl and phenyl, the phenyl being optionally substituted with a substituent selected from halogen and trifluoromethyl;
and its salts, solvates, and solvates of the salts.

According to an embodiment of the present invention, the compounds of the formulae (I-A) or (I-B) are defined as follows:
$R^1$ and $R^2$ are as defined above;
$R^3$ is selected from
phenyl, the phenyl being optionally substituted with one, two or three substituents selected from
halogen, methyl, trifluoromethyl, methoxy, where two adjacent methoxy groups may optionally form a dioxane ring, trifluoromethoxy, benzyloxy, cyano, methylsulfonyl, and
phenyl, optionally substituted with trifluoromethyl;
and its salts, solvates, and solvates of the salts.

According to an embodiment of the present invention, the compounds of the formulae (I-A) or (I-B) are defined as follows:
$R^1$ is hydrogen;
$R^2$ is hydrogen;
$R^3$ is selected from
phenyl, the phenyl being optionally substituted with one, two or three substituents selected from
halogen, methyl, trifluoromethyl, methoxy, where two adjacent methoxy groups may optionally form a dioxane ring, trifluoromethoxy, benzyloxy, cyano, methylsulfonyl, and
phenyl, optionally substituted with trifluoromethyl;
and its salts, solvates, and solvates of the salts.

According to an embodiment of the present invention, the compounds of the formulae (I-A) or (I-B) are defined as follows:
$R^1$ and $R^2$ are as defined above;
$R^3$ is selected from
oxadiazolyl of the formula

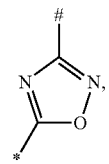

wherein * indicates the position of binding to the pyrazolopyrimidone and # denotes the optional binding to a further substituent, the oxadiazolyl being optionally substituted with a substituent selected from
$C_1$-$C_4$ alkyl, $C_1$-$C_4$ haloalkyl, methoxy-$C_1$-$C_4$ alkyl, $C_3$-$C_6$ cycloalkyl, $C_3$-$C_6$ cycloalkyl-$C_1$ alkyl;
benzyl, the benzyl optionally being substituted with one, two or three substituents selected from methyl, methoxy, and halogen;
phenyl, the phenyl optionally being substituted with one, two or three substituents selected from
$C_1$-$C_4$ alkyl, halogen, trifluoromethyl, methoxy, trifluoromethoxy, CO—O—$CH_3$, $NO_2$, $NH_2$, di-methylamine, and cyano; and
thiophenyl, the thiophenyl being optionally substituted with halogen;
furanyl;
imidazolyl, the imidazolyl optionally being substituted with methyl;
and
pyridinyl, the pyridinyl being optionally substituted with one, two or three substituents selected from methyl, trifluoromethyl, and halogen;
and its salts, solvates, and solvates of the salts.

According to an embodiment of the present invention, the compounds of the formulae (I-A) or (I-B) are defined as follows:
$R^1$ is hydrogen;
$R^2$ is hydrogen;
$R^3$ is selected from
oxadiazolyl of the formula

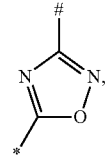

wherein * indicates the position of binding to the pyrazolopyrimidone and # denotes the optional binding to a further substituent, the oxadiazolyl being optionally substituted with a substituent selected from C$_1$-C$_4$ alkyl, C$_1$-C$_4$ haloalkyl, methoxy-C$_1$-C$_4$ alkyl, C$_3$-C$_6$ cycloalkyl, C$_3$-C$_6$ cycloalkyl-C$_1$ alkyl;

benzyl, the benzyl optionally being substituted with one, two or three substituents selected from methyl, methoxy, and halogen;

phenyl, the phenyl optionally being substituted with one, two or three substituents selected from C$_1$-C$_4$ alkyl, halogen, trifluoromethyl, methoxy, trifluoromethoxy, CO—O—CH$_3$, NO$_2$, NH$_2$, di-methylamine, and cyano; and thiophenyl, the thiophenyl being optionally substituted with halogen, furanyl, imidazolyl, the imidazolyl optionally being substituted with methyl, and pyridinyl, the pyridinyl being optionally substituted with one, two or three substituents selected from methyl, trifluoromethyl, and halogen;

and its salts, solvates, and solvates of the salts.

According to an embodiment of the present invention, the compounds of the formulae (I-A) or (I-B) are defined as follows:

R$^1$ and R$^2$ are as defined above;
R$^3$ is selected from
oxadiazolyl of the formula

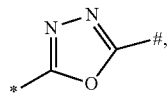

wherein * indicates the position of binding to the pyrazolopyrimidone and # denotes the optional binding to a further substituent, the oxadiazolyl being optionally substituted with a substituent selected from C$_1$-C$_4$ alkyl, C$_1$-C$_4$ haloalkyl, methoxy-C$_1$-C$_4$ alkyl, C$_3$-C$_6$ cycloalkyl, C$_3$-C$_6$ cycloalkyl-C$_1$ alkyl;

benzyl, the benzyl optionally being substituted with one, two or three substituents selected from methyl, methoxy, and halogen;

phenyl, the phenyl optionally being substituted with one, two or three substituents selected from C$_1$-C$_4$ alkyl, halogen, trifluoromethyl, methoxy, trifluoromethoxy; and thiophenyl, the thiophenyl being optionally substituted with halogen;

furanyl;

imidazolyl, the imidazolyl optionally being substituted with methyl;

and pyridinyl, the pyridinyl being optionally substituted with one, two or three substituents selected from methyl, trifluoromethyl, and halogen;

and its salts, solvates, and solvates of the salts.

According to an embodiment of the present invention, the compounds of the formulae (I-A) or (I-B) are defined as follows:

R$^1$ is hydrogen;
R$^2$ is hydrogen;
R$^3$ is selected from
oxadiazolyl of the formula

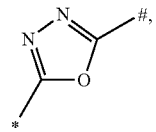

wherein * indicates the position of binding to the pyrazolopyrimidone and # denotes the optional binding to a further substituent, the oxadiazolyl being optionally substituted with a substituent selected from C$_1$-C$_4$ alkyl, C$_1$-C$_4$ haloalkyl, methoxy-C$_1$-C$_4$ alkyl, C$_3$-C$_6$ cycloalkyl, C$_3$-C$_6$ cycloalkyl-C$_1$ alkyl;

benzyl, the benzyl optionally being substituted with one, two or three substituents selected from methyl, methoxy, and halogen;

phenyl, the phenyl optionally being substituted with one, two or three substituents selected from C$_1$-C$_4$ alkyl, halogen, trifluoromethyl, methoxy, trifluoromethoxy; and thiophenyl, the thiophenyl being optionally substituted with halogen;

furanyl;

imidazolyl, the imidazolyl optionally being substituted with methyl;

and pyridinyl, the pyridinyl being optionally substituted with one, two or three substituents selected from methyl, trifluoromethyl, and halogen;

and its salts, solvates, and solvates of the salts.

According to an embodiment of the present invention, the compounds of the formulae (I-A) or (I-B) are defined as follows:

R$^1$ and R$^2$ are as defined above;
R$^3$ is selected from
oxadiazolyl of the formula

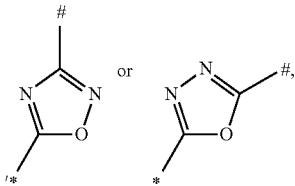

wherein * indicates the position of binding to the pyrazolopyrimidone and # denotes the optional binding to a further substituent, the oxadiazolyl being optionally substituted with a substituent selected from phenyl, the phenyl optionally being substituted with one, two or three substituents selected from C$_1$-C$_4$ alkyl, halogen, trifluoromethyl, methoxy, trifluoromethoxy, CO—O—CH$_3$, NO$_2$, NH$_2$, di-methylamine, and cyano; and and its salts, solvates, and solvates of the salts.

According to an embodiment of the present invention, the compounds of the formulae (I-A) or (I-B) are defined as follows:

$R^1$ is hydrogen;
$R^2$ is hydrogen;
$R^3$ is selected from
    oxadiazolyl of the formula

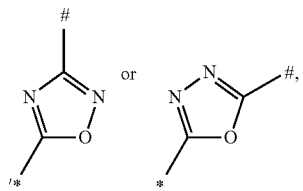

wherein * indicates the position of binding to the pyrazolopyrimidone and # denotes the optional binding to a further substituent, the oxadiazolyl being optionally substituted with a substituent selected from phenyl, the phenyl optionally being substituted with one, two or three substituents selected from
      $C_1$-$C_4$ alkyl, halogen, trifluoromethyl, methoxy, trifluoromethoxy, CO—O—$CH_3$, $NO_2$, $NH_2$, di-methylamine, and cyano; and and its salts, solvates, and solvates of the salts.

According to an embodiment of the present invention, the compounds of the formulae (I-A) or (I-B) are defined as follows:
$R^1$ and $R^2$ are as defined above;
$R^3$ is selected from
    pyridinyl, the pyridinyl being optionally substituted with methoxy,
    thiophenyl, the thiophenyl being optionally substituted with a substituent selected from methyl and cyano,
    thiazolyl, the thiazolyl being optionally substituted with one, two or three substituents selected from methyl and phenyl, the phenyl being optionally substituted with a substituent selected from halogen and trifluoromethyl,
and its salts, solvates, and solvates of the salts.

According to an embodiment of the present invention, the compounds of the formulae (I-A) or (I-B) are defined as follows:
$R^1$ is hydrogen;
$R^2$ is hydrogen;
$R^3$ is selected from
    pyridinyl, the pyridinyl being optionally substituted with methoxy, thiophenyl, the thiophenyl being optionally substituted with a substituent selected from methyl and cyano,
    thiazolyl, the thiazolyl being optionally substituted with one, two or three substituents selected from methyl and phenyl, the phenyl being optionally substituted with a substituent selected from halogen and trifluoromethyl,
and its salts, solvates, and solvates of the salts.

According to an embodiment of the present invention, the compounds of the formulae (I-A) or (I-B) are defined as follows:
$R^1$ and $R^2$ are as defined above;
$R^3$ is oxadiazolyl of the formula

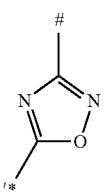

wherein * indicates the position of binding to the pyrazolopyrimidone and # denotes the binding to a further substituent, the oxadiazolyl being substituted with a phenyl substituent, the phenyl substituent being substituted with 4-trifluoromethyl;
and its salts, solvates, and solvates of the salts.

According to an embodiment of the present invention, the compounds of the formulae (I-A) or (I-B) are defined as follows:
$R^1$ is hydrogen;
$R^2$ is hydrogen;
$R^3$ is oxadiazolyl of the formula

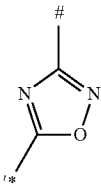

wherein * indicates the position of binding to the pyrazolopyrimidone and # denotes the binding to a further substituent, the oxadiazolyl being substituted with a phenyl substituent, the phenyl substituent being substituted with 4-trifluoromethyl;
and its salts, solvates, and solvates of the salts.

According to an embodiment of the present invention, the compounds of the formulae (I-A) or (I-B) are defined as follows:
$R^1$ and $R^2$ are as defined above;
$R^3$ is oxadiazolyl of the formula

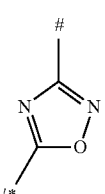

wherein * indicates the position of binding to the pyrazolopyrimidone and # denotes the binding to a further substituent, the oxadiazolyl being substituted with a phenyl substituent, the phenyl substituent being substituted with 3-chloro;
and its salts, solvates, and solvates of the salts.

According to an embodiment of the present invention, the compounds of the formulae (I-A) or (I-B) are defined as follows:
$R^1$ is hydrogen;
$R^2$ is hydrogen;
$R^3$ is oxadiazolyl of the formula

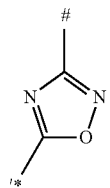

wherein * indicates the position of binding to the pyrazolopyrimidone and # denotes the binding to a further substituent, the oxadiazolyl being substituted with a phenyl substituent, the phenyl substituent being substituted with 3-chloro;
and its salts, solvates, and solvates of the salts.

According to an embodiment of the present invention, the compounds of the formulae (I-A) or (I-B) are defined as follows:
$R^1$ is hydrogen;
and $R^2$ and $R^3$ each have the meaning as defined above.

According to an embodiment of the present invention, the compounds of the formulae (I-A) or (I-B) are defined as follows.
$R^2$ is hydrogen;
and $R^1$ and $R^3$ each have the meaning as defined above.

The present invention also provides compounds of the general formula (I-A)

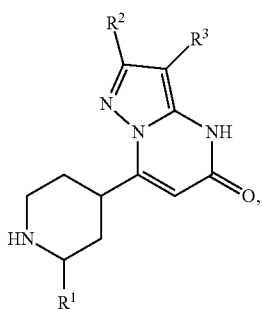

in which
$R^1$ is selected from hydrogen and $C_1$-$C_4$ alkyl;
$R^2$ is selected from hydrogen, $C_1$-$C_4$ alkyl, $C_3$-$C_6$ cycloalkyl, $C_1$-$C_4$ haloalkyl, carboxyl, $C_1$-$C_4$ alkylester, $C_1$-$C_4$ alkoxy-$C_1$-$C_4$ alkyl, phenyl, the phenyl being optionally substituted with halogen, 5-6 membered heteroaryl, amino, $C_1$-$C_4$ alkyl-amide, and $C_1$-$C_4$ alkyl sulfonamide;
$R^3$ is selected from hydrogen, halogen, cyano, $C_1$-$C_4$ alkylester, carboxyl, carboxamide, benzylester,
phenylsulfonyl, the phenylsulfonyl being optionally substituted with one, two, or three substituents selected from halogen,
phenyl, the phenyl being optionally substituted with one, two or three substituents selected from halogen, $C_1$-$C_4$ alkyl, $C_1$-$C_4$ haloalkyl, $C_1$-$C_4$ alkoxy, where two adjacent methoxy groups may optionally form a dioxane ring, $C_1$-$C_4$ haloalkoxy, benzyloxy, cyano, and methylsulfonyl,
5-6 membered heteroaryl, the 5-6 membered heteroaryl being optionally substituted with one, two or three substituents selected from $C_1$-$C_4$ alkyl, $C_1$-$C_4$ alkoxy, $C_1$-$C_4$ alkoxy $C_1$-$C_4$ alkyl, cyano, benzyl, $C_3$-$C_6$ cycloalkyl, phenyl, the phenyl optionally being substituted with $C_1$-$C_4$ alkyl, halogen, $C_1$-$C_4$ haloalkyl, $C_1$-$C_4$ haloalkoxy, and 5 to 6 membered heteroaryl, the 5 to 6 membered heteroaryl being optionally substituted with one, two or three halogen substituents,
CO—$R^4$, with
$R^4$ being selected from the group of the compounds of the formulae

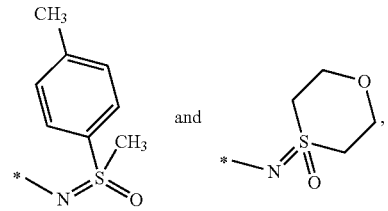

wherein "*" does not represent a carbon atom or a $CH_2$ group but forms part of the bond to the atom which is designated in each case and to which $R^4$ is attached;
and
CO—N($R^5R^7$), with
$R^5$ being selected from hydrogen, and $C_1$-$C_4$ alkyl,
$R^7$ being selected from hydrogen, $C_1$-$C_6$ alkyl, $C_1$-$C_6$ haloalkyl, $C_1$-$C_4$-alkoxy-$C_1$-$C_4$ alkyl, amino-oxo-$C_1$-$C_4$ alkyl, naphthyl,
$C_3$-$C_6$ cycloalkyl, the $C_3$-$C_6$ cycloalkyl being optionally substituted with one, two or three substituents selected from $C_1$-$C_4$ alkyl,
$C_3$-$C_6$ cycloalkyl-$C_1$-$C_4$ alkyl, $C_3$-$C_6$ heterocyclyl, oxazolidinyl-$C_1$-$C_4$ alkyl,
benzyl, the benzyl being optionally substituted with one, two or three substituents selected from $C_1$-$C_4$ alkyl, halogen, and $C_1$-$C_4$-alkoxy
benzyl-$C_3$-$C_6$ cycloalkyl,
imidazolyl-$C_1$-$C_4$ alkyl, the imidazolyl-$C_1$-$C_4$ alkyl being optionally substituted with one, two or three substituents selected from $C_1$-$C_4$ alkyl,
oxazolidinone-$C_1$-$C_4$ alkyl,
and
phenyl, the phenyl being optionally substituted with one, two or three substituents selected from $C_1$-$C_4$ alkyl, halogen, and $C_1$-$C_4$ alkoxy;
or
—N($R^5R^7$) being selected from the group of 5 to 7 membered cyclic amines which contain one or two ring nitrogen atoms and zero or one ring oxygen atom and are attached via a ring nitrogen atom, the 5 to 7 membered cyclic amines being optionally substituted with one, two or three substituents selected from $C_1$-$C_4$ alkoxy, oxo, halogen, and $C_1$-$C_4$ alkyl;
or
$R^2$ and $R^3$ together form a $C_5$-$C_6$ cycloalkyl ring;
and its salts, solvates, and solvates of the salts.

According to an embodiment of the present invention, the compounds of the formulae (I-A) or (I-B) are defined as follows:

R$^1$ is selected from hydrogen and C$_1$-C$_4$ alkyl;
R$^2$ is selected from hydrogen, C$_1$-C$_4$ alkyl, C$_3$-C$_6$ cycloalkyl, C$_1$-C$_4$ haloalkyl, carboxyl, C$_1$-C$_4$ alkylester, C$_1$-C$_4$ alkoxy-C$_1$-C$_4$ alkyl, phenyl, the phenyl being optionally substituted with halogen, 5-6 membered heteroaryl;
R$^3$ is selected from hydrogen, halogen, cyano, C$_1$-C$_4$ alkylester, carboxyl, carboxamide, benzylester, phenylsulfonyl, the phenylsulfonyl being optionally substituted with one, two, or three substituents selected from halogen,
  C$_5$ aryl, the C$_5$ aryl being optionally substituted with one, two or three substituents selected from halogen, C$_1$-C$_4$ alkyl, C$_1$-C$_4$ haloalkyl, C$_1$-C$_4$ alkoxy, where two adjacent methoxy groups may optionally form a dioxane ring, C$_1$-C$_4$ haloalkoxy, benzyloxy, cyano, and methylsulfonyl,
  5-6 membered heteroaryl, the 5-6 membered heteroaryl being optionally substituted with one, two or three substituents selected from C$_1$-C$_4$ alkyl, C$_1$-C$_4$ alkoxy, C$_1$-C$_4$ alkoxy C$_1$-C$_4$ alkyl, cyano, benzyl, C$_3$-C$_6$ cycloalkyl, phenyl, the phenyl optionally being substituted with C$_1$-C$_4$ alkyl, and 5 to 6 membered heteroaryl, the 5 to 6 membered heteroaryl being optionally substituted with one, two or three halogen substituents,
  CO—R$^4$, with
    R$^4$ being selected from the group of the compounds of the formulae

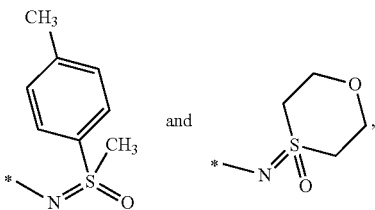

wherein "*" does not represent a carbon atom or a CH$_2$ group but forms part of the bond to the atom which is designated in each case and to which R$^4$ is attached;
and
  CO—N(R$^5$R$^7$), with
    R$^5$ being selected from hydrogen, and C$_1$-C$_4$ alkyl,
    R$^7$ being selected from hydrogen, C$_1$-C$_6$ alkyl, C$_1$-C$_6$ haloalkyl, C$_1$-C$_4$-alkoxy-C$_1$-C$_4$ alkyl, amino-oxo-C$_1$-C$_4$ alkyl, naphthyl,
      C$_3$-C$_6$ cycloalkyl, the C$_3$-C$_6$ cycloalkyl being optionally substituted with one, two or three substituents selected from C$_1$-C$_4$ alkyl, C$_3$-C$_6$ cycloalkyl-C$_1$-C$_4$ alkyl, C$_3$-C$_6$ heterocyclyl, oxazolidinyl-C$_1$-C$_4$ alkyl,
      benzyl, the benzyl being optionally substituted with one, two or three substituents selected from C$_1$-C$_4$ alkyl, benzyl-C$_3$-C$_6$ cycloalkyl, imidazolyl-C$_1$-C$_4$ alkyl, the imidazolyl-C$_1$-C$_4$ alkyl being optionally substituted with one, two or three substituents selected from C$_1$-C$_4$ alkyl, oxazolidinone-C$_1$-C$_4$ alkyl,
      and
      phenyl, the phenyl being optionally substituted with one, two or three substituents selected from C$_1$-C$_4$ alkyl, halogen, and C$_1$-C$_4$ alkoxy;
    or
    —N(R$^5$R$^7$) being selected from the group of 5 to 7 membered cyclic amines which contain one or two ring nitrogen atoms and zero or one ring oxygen atom and are attached via a ring nitrogen atom, being optionally substituted with one, two or three substituents selected from C$_1$-C$_4$ alkoxy, oxo, halogen, and C$_1$-C$_4$ alkyl;
or
R$^2$ and R$^3$ together form a C$_5$-C$_6$ cycloalkyl ring;
and its salts, solvates, and solvates of the salts.

According to an embodiment of the present invention, the compounds of the formulae (I-A) or (I-B) are defined as follows:
R$^1$ is selected from hydrogen and C$_1$-C$_4$ alkyl;
R$^2$ is selected from hydrogen, C$_1$-C$_4$ alkyl, C$_3$-C$_6$ cycloalkyl, C$_1$-C$_4$ haloalkyl, carboxyl, C$_1$-C$_4$ alkylester, C$_1$-C$_4$ alkoxy-C$_1$-C$_4$ alkyl, phenyl, the phenyl being optionally substituted with halogen, 5-6 membered heteroaryl;
R$^3$ is selected from hydrogen, halogen, cyano, C$_1$-C$_4$ alkylester, carboxyl, carboxamide, benzylester, phenylsulfonyl, the phenylsulfonyl being optionally substituted with one, two, or three substituents selected from halogen, phenyl,
  the phenyl being optionally substituted with one, two or three substituents selected from halogen, C$_1$-C$_4$ alkyl, C$_1$-C$_4$ haloalkyl, C$_1$-C$_4$ alkoxy, where two adjacent methoxy groups may optionally form a dioxane ring, C$_1$-C$_4$ haloalkoxy, benzyloxy, cyano, and methylsulfonyl,
  5-6 membered heteroaryl,
    the 5-6 membered heteroaryl being optionally substituted with one, two or three substituents selected from C$_1$-C$_4$ alkyl, C$_1$-C$_4$ alkoxy, C$_1$-C$_4$ alkoxy C$_1$-C$_4$ alkyl, cyano, benzyl, C$_3$-C$_6$ cycloalkyl, phenyl, the phenyl optionally being substituted with C$_1$-C$_4$ alkyl, and 5 to 6 membered heteroaryl, the 5 to 6 membered heteroaryl being optionally substituted with one, two or three halogen substituents,
  CO—R$^4$, with
    R$^4$ being selected from the group of the compounds of the formulae

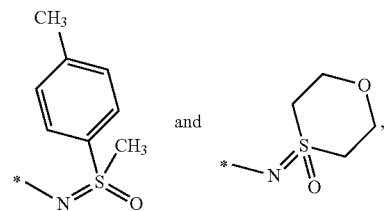

wherein "*" does not represent a carbon atom or a CH$_2$ group but forms part of the bond to the atom which is designated in each case and to which R$^4$ is attached;
and
  CO—N(R$^5$R$^7$), with
    R$^5$ being selected from hydrogen, and C$_1$-C$_4$ alkyl,
    R$^7$ being selected from hydrogen, C$_1$-C$_6$ alkyl, C$_1$-C$_6$ haloalkyl, C$_1$-C$_4$-alkoxy-C$_1$-C$_4$ alkyl, amino-oxo-C$_1$-C$_4$ alkyl, naphthyl,
      C$_3$-C$_6$ cycloalkyl, the C$_3$-C$_6$ cycloalkyl being optionally substituted with one, two or three substituents selected from C$_1$-C$_4$ alkyl, C$_3$-C$_6$ cycloalkyl-C$_1$-C$_4$ alkyl, C$_3$-C$_6$ heterocyclyl, oxazolidinyl-C$_1$-C$_4$ alkyl,
      benzyl, the benzyl being optionally substituted with one, two or three substituents selected from C$_1$-C$_4$ alkyl, benzyl-C$_3$-C$_6$ cycloalkyl, imidazolyl-C$_1$-C$_4$ alkyl, the imidazolyl-C$_1$-C$_4$ alkyl being optionally substituted with one, two or three substituents selected from $C_1$-$C_4$ alkyl, oxazolidinone-$C_1$-$C_4$ alkyl, and phenyl, the phenyl being optionally substituted with one, two or three substituents selected from $C_1$-$C_4$ alkyl, halogen, and $C_1$-$C_4$ alkoxy;

or

—N($R^5R^7$) being selected from morpholinyl, piperidinyl, piperazinyl, diazepanyl, and pyrrolidinyl, the morpholinyl, piperidinyl, piperazinyl, diazepanyl, and pyrrolidinyl being optionally substituted with one, two or three substituents selected from $C_1$-$C_4$ alkoxy, oxo, halogen, and $C_1$-$C_4$ alkyl;

or $R^2$ and $R^3$ together form a $C_5$-$C_6$ cycloalkyl ring;

and its salts, solvates, and solvates of the salts.

According to an embodiment of the present invention, the compounds of the formulae (I-A) or (I-B) are defined as follows:

$R^1$ is selected from hydrogen and methyl;

$R^2$ is selected from hydrogen, methyl, cyclopropyl, trifluoromethyl, carboxyl, methylester, methoxy-methyl, phenyl, the phenyl being optionally substituted with halogen, and thienyl;

$R^3$ is selected from hydrogen, halogen, cyano, ethylester, carboxyl, carboxamide, benzylester, phenylsulfonyl, the phenylsulfonyl being optionally substituted with one, two, or three substituents selected from halogen, phenyl, the phenyl being optionally substituted with one, two or three substituents selected from halogen, methyl, trifluoromethyl, methoxy, where two adjacent methoxy groups may optionally form a dioxane ring, trifluoromethoxy, benzyloxy, cyano, and methylsulfonyl, oxadiazolyl, the oxadiazolyl being optionally substituted with one, two or three substituents selected from methyl, ethyl, methoxyisobutyl, cyclobutyl, benzyl, thienyl, the thienyl being optionally substituted by halogen, and furanyl, pyridinyl, the pyridinyl being optionally substituted with methoxy, thienyl, the thienyl being optionally substituted with a substituent selected from methyl and cyano, CO—$R^4$, with $R^4$ being selected from the group of the compounds of the formulae

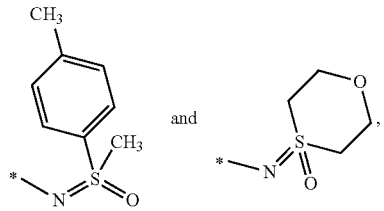

wherein "*" does not represent a carbon atom or a $CH_2$ group but forms part of the bond to the atom which is designated in each case and to which $R^4$ is attached;

and

CO—N($R^5R^7$), with $R^5$ being selected from hydrogen, methyl, and ethyl, $R^7$ being selected from hydrogen, propyl, isopentyl, trifluoroethyl, methoxypropyl, amino-oxo-ethyl, naphthyl, cyclobutyl, the cyclobutyl being optionally substituted with methyl, cyclopropyl-methyl, cyclopentyl-methyl, cyclopentyl-ethyl, tetrahydrofuranyl, oxazolidinyl-ethyl, benzyl, the benzyl being optionally substituted with one, two or three methyl substituents, benzyl-cyclopropyl, imidazolyl-methyl, the imidazolyl-methyl being optionally substituted with propyl, oxazolidinone-ethyl, phenyl, the phenyl being optionally substituted with one, two or three substituents selected from methyl, ethyl, halogen, methoxy;

or

—N($R^5R^7$) being selected from morpholinyl, piperidinyl, piperazinyl, diazepanyl, and pyrrolidinyl, the morpholinyl, piperidinyl, piperazinyl, diazepanyl, and pyrrolidinyl being optionally substituted with one, two or three substituents selected from $C_1$-$C_2$ alkoxy, oxo, halogen, and methyl;

or $R^2$ and $R^3$ together form a cyclopentyl ring;

and its salts, solvates, and solvates of the salts.

According to an embodiment of the present invention, the compounds of the formulae (I-A) or (I-B) are defined as follows.

$R^1$ is hydrogen;

$R^2$ is hydrogen;

$R^3$ is selected from hydrogen, halogen, cyano, carboxyl, carboxamide, phenyl, the phenyl being optionally substituted with one, two or three substituents selected from halogen, methyl, trifluoromethyl, methoxy, where two adjacent methoxy groups may optionally form a dioxane ring, trifluoromethoxy, benzyloxy, cyano, and methylsulfonyl, oxadiazolyl, the oxadiazolyl being optionally substituted with one, two or three substituents selected from methyl, ethyl, methoxyisobutyl, cyclobutyl, benzyl, thienyl, the thienyl being optionally substituted with halogen, and furanyl, pyridinyl, the pyridinyl being optionally substituted with methoxy, thienyl, the thienyl being optionally substituted with a substituent selected from methyl and cyano, CO—N($R^5R^7$), with $R^5$ being hydrogen, $R^7$ being selected from hydrogen, propyl, isopentyl, trifluoroethyl, methoxypropyl, amino-oxo-ethyl, naphthyl, cyclobutyl, the cyclobutyl being optionally substituted with methyl, cyclopropyl-methyl, cyclopentyl-methyl, cyclopentyl-ethyl, tetrahydrofuranyl, oxazolidinyl-ethyl, benzyl, the benzyl being optionally substituted with one, two or three methyl substituents, benzyl-cyclopropyl, imidazolyl-methyl, the imidazolyl-methyl being optionally substituted with propyl, oxazolidinone-ethyl, phenyl, the phenyl being optionally substituted with one, two or three substituents selected from methyl, ethyl, halogen, methoxy;

or

—N($R^5R^7$) being selected from morpholinyl, piperidinyl, piperazinyl, diazepanyl, and pyrrolidinyl, the morpholinyl, piperidinyl, piperazinyl, diazepanyl, and pyrrolidinyl being optionally substituted with one, two or three substituents selected from $C_1$-$C_2$ alkoxy, oxo, halogen, and methyl;

or $R^2$ and $R^3$ together form a cyclopentyl ring;

and its salts, solvates, and solvates of the salts.

According to an embodiment of the present invention, the compounds of the formulae (I-A) or (I-B) are defined as follows:

$R^1$ is hydrogen;
$R^2$ is hydrogen;
$R^3$ is oxadiazolyl, the oxadiazolyl being optionally substituted with one, two or three substituents selected from methyl, ethyl, methoxyisobutyl, cyclobutyl, benzyl, thienyl, the thienyl being optionally substituted with halogen, and furanyl, pyridinyl, the pyridinyl being optionally substituted with methoxy, thienyl, the thienyl being optionally substituted with a substituent selected from methyl and cyano.

According to an embodiment of the present invention, the compounds of the formulae (I-A) or (I-B) are defined as follows:

$R^1$ is selected from hydrogen and $C_1$-$C_5$ alkyl;
$R^2$ is selected from hydrogen, $C_1$-$C_2$ alkyl, $C_3$-$C_4$ cycloalkyl, $C_1$-$C_2$ haloalkyl, carboxyl, $C_1$-$C_2$ alkylester, $C_1$-$C_2$ alkoxy-$C_1$-$C_2$ alkyl, halogen, methylsulfanyl, phenyl,
   the phenyl being optionally substituted with a substituent selected from fluorine and chlorine,
   and 5-6 membered heteroaryl;
$R^3$ is selected from hydrogen, bromine, chlorine, cyano, methyl, the methyl being optionally substituted with di-$C_1$-$C_4$ alkylamino, ethyl, $C_1$-$C_4$ alkenyl, $C_1$-$C_4$ alkylester, the $C_1$-$C_4$ alkylester being optionally substituted with one, two, or three fluorine substituents, $C_3$-$C_4$ cycloalkylester, $C_3$-$C_4$ cycloalkyl, carboxyl, carboxamide, benzylester, —NH—CO-phenyl, —CS—NH$_2$,
   phenylsulfonyl, the phenylsulfonyl being optionally substituted with one or two substituents selected from chlorine and fluorine,
   phenyl,
      the phenyl being optionally substituted with one, two or three substituents selected from bromine, chlorine, fluorine, ethoxy and methoxy, where two adjacent methoxy groups may optionally form a dioxane ring,
      or the phenyl being optionally substituted with one or two substituents selected from $C_1$-$C_2$ alkyl, $C_1$-$C_2$ fluoroalkyl, $C_1$-$C_2$ fluoroalkoxy, and cyano,
      or the phenyl being optionally substituted with one substituent selected from benzyloxy, methylsulfonyl, and phenyl,
         the phenyl being optionally substituted with $C_1$-$C_2$ fluoroalkyl,
   5-6 membered heterocyclyl-$C_1$-$C_2$ alkyl, the 5-6 membered heterocyclyl-moiety being optionally substituted with one, two or three substituents selected from $C_1$-$C_2$ alkyl and oxo;
   5-6 membered heteroaryl, the 5-6 membered heteroaryl being optionally substituted with one or two substituents selected from
      $C_1$-$C_6$ alkyl, $C_2$-$C_6$ alkenyl, $C_1$-$C_4$ haloalkyl, $C_1$-$C_2$ aminoalkyl, $C_1$-$C_2$ alkylester, $C_1$-$C_2$ alkoxy, $C_1$-$C_2$ haloalkoxy, $C_1$-$C_2$ alkoxy-$C_1$-$C_4$ alkyl, cyano, hydroxyl, carboxyl, $C_1$-$C_2$ alkyl-SO$_2$—$C_1$-$C_2$ alkyl, and —CO—NH$_2$,
      or the 5-6 membered heteroaryl being optionally substituted with one $C_3$-$C_6$ cycloalkyl substituent,
         the $C_3$-$C_6$ cycloalkyl optionally being substituted with one, two, or three chlorine, fluorine, or methyl substituents, or with phenyl, the phenyl being optionally substituted with $C_1$-$C_2$ alkoxy, chlorine or fluorine
   bridged bi- or tricycloalkyl $C_3$-$C_6$ cycloalkyl-$C_1$-$C_2$ alkyl, $C_3$-$C_6$ cycloalkyl-$C_1$-$C_4$ alkenyl
   phenyl, the phenyl optionally being substituted with one, two or three substituents selected from $C_1$-$C_4$ alkyl, chlorine, fluorine, $C_1$-$C_2$ fluoroalkyl, $C_1$-$C_2$ alkoxy, $C_1$-$C_2$ fluoroalkoxy, $C_1$-$C_2$-alkylester, nitro, amino, di-$C_1$-$C_2$ alkylamino, and cyano,
   phenyl-$C_1$-$C_2$ alkyl,
      the phenyl moiety optionally being substituted with one, two or three substituents selected from fluorine, chlorine, $C_1$-$C_2$ alkyl, $C_1$-$C_2$ fluoroalkyl, $C_1$-$C_2$ alkoxy, $C_1$-$C_2$ fluoroalkoxy, and hydroxyl,
      the alkyl moiety optionally being substituted with one or two substituents selected from $C_1$-$C_2$ alkyl and hydroxyl,
   5-6 membered heterocycloalkyl, the 5-6 membered heterocycloalkyl being optionally substituted with $C_3$-$C_5$ cycloalkyl or $C_1$-$C_3$ alkyl,
   5-6 membered heterocycloalkyl-$C_1$-$C_2$ alkyl,
      the 5-6 membered heterocycloalkyl moiety being optionally substituted with $C_1$-$C_2$ alkyl or oxo,
      the $C_1$-$C_2$ alkyl moiety being optionally substituted with $C_1$-$C_2$ alkyl,
   5-6 membered heteroaryl, the 5-6 membered heteroaryl being optionally substituted with one, two or three substituents selected from fluorine, chlorine, $C_1$-$C_3$ alkyl, and $C_1$-$C_2$ fluoroalkyl,
   and
   5-6 membered heteroaryl-$C_1$-$C_4$ alkyl,
      the 5-6 membered heteroaryl-moiety being optionally substituted with one or two substituents selected from $C_1$-$C_2$ alkoxy and $C_1$-$C_2$ alkyl,
      the $C_1$-$C_2$ alkyl-moiety being optionally substituted with one or two methyl substituents;

CO—$R^4$, with
   $R^4$ being selected from the group of $C_1$-$C_4$ alkyl, wherein the $C_1$-$C_4$ alkyl is optionally substituted with 1 or 2 methyl substituents, and $C_3$-$C_6$ cycloalkyl;
and
CO—N($R^5R^7$), with
   $R^5$ being selected from hydrogen, and $C_1$-$C_4$ alkyl;
   $R^7$ being selected from $C_1$-$C_4$ alkyl, $C_1$-$C_4$ haloalkyl, $C_1$-$C_2$-alkoxy-$C_1$-$C_4$ alkyl, amino-oxo-$C_1$-$C_4$ alkyl, naphthyl,
      $C_3$-$C_6$ cycloalkyl, the $C_3$-$C_6$ cycloalkyl being optionally substituted with one, or two substituents selected from $C_1$-$C_2$ alkyl,
      $C_3$-$C_6$ cycloalkyl-$C_1$-$C_2$ alkyl, 5-6 membered heterocyclyl, oxazolidinyl-$C_1$-$C_2$ alkyl,
      benzyl, the phenyl moiety of the benzyl being optionally substituted with one, two or three substituents selected from $C_1$-$C_2$ alkyl, the methyl moiety of the benzyl being optionally substituted with $C_1$-$C_2$ alkyl;
      benzyl-$C_3$-$C_4$ cycloalkyl,
      imidazolyl-$C_1$-$C_2$ alkyl, the imidazolyl-$C_1$-$C_2$ alkyl being optionally substituted with one, two or three substituents selected from $C_1$-$C_2$ alkyl,
      oxazolyl-$C_1$-$C_2$ alkyl, the oxazolyl-$C_1$-$C_2$ alkyl being optionally substituted with one, two or three substituents selected from $C_1$-$C_2$ alkyl,
      oxazolidinone-$C_1$-$C_2$ alkyl,
      pyridinyl-$C_1$-$C_2$ alkyl, and
phenyl, the phenyl being optionally substituted with one, two or three substituents selected from $C_1$-$C_2$ alkyl, halogen, and $C_1$-$C_2$ alkoxy;
or
—$N(R^5R^7)$ being selected from the group of 5 to 7 membered cyclic amines which contain one or two ring nitrogen atoms, zero or one ring oxygen atom, and zero or one ring sulfur atom, and are attached via a ring nitrogen atom, the 5 to 7 membered cyclic amines being optionally substituted with one, two or three substituents selected from $C_1$-$C_4$ alkoxy, $C_1$-$C_2$ alkoxy $C_1$-$C_2$ alkyl, oxo, hydroxyl, halogen, and $C_1$-$C_3$ alkyl;
or
—$N(R^5R^7)$ being selected from the group of two annelated, aromatic, partially saturated or saturated rings which are each 5-7 membered and each contain one or two ring nitrogen atoms and are attached via a ring nitrogen atom,
or
—$N(R^5R^7)$ being selected from azaspiro[2.5] oct-5-yl and oxa-azaspiro[3.5] non-1-yl, the azaspiro compounds being optionally substituted with oxo;
or
$R^2$ and $R^3$ together form a $C_5$-$C_6$ cycloalkyl ring;
and its salts, solvates, and solvates of the salts.

According to an embodiment of the present invention, the compounds of the formulae (I-A) or (I-B) are defined as follows:
$R^1$ is selected from hydrogen and $C_1$-$C_5$ alkyl;
$R^2$ is selected from hydrogen, methyl, ethyl, trifluoromethyl, and methylsulfanyl;
$R^3$ is selected from $C_1$-$C_4$ alkylester, the $C_1$-$C_4$ alkylester being optionally substituted with one, two,
  or three fluorine substituents, $C_3$-$C_4$ cycloalkylester, $C_3$-$C_4$ cycloalkyl,
5 membered heteroaryl, the 5 membered heteroaryl being optionally substituted with one or two substituents selected from
    $C_1$-$C_6$ alkyl, $C_2$-$C_6$ alkenyl, $C_1$-$C_4$ haloalkyl, $C_1$-$C_2$ aminoalkyl, $C_1$-$C_2$ alkylester, $C_1$-$C_2$ alkoxy, $C_1$-$C_2$ haloalkoxy, $C_1$-$C_2$ alkoxy-$C_1$-$C_4$ alkyl, cyano, hydroxyl, carboxyl, $C_1$-$C_2$ alkyl-$SO_2$—$C_1$-$C_2$ alkyl, and —CO—$NH_2$,
  or the 5 membered heteroaryl being optionally substituted with one $C_3$-$C_6$ cycloalkyl substituent,
    the $C_3$-$C_6$ cycloalkyl optionally being substituted with one, two, or three chlorine, fluorine, or methyl substituents, or one or two methyl substituents, or with phenyl, the phenyl being optionally substituted with $C_1$-$C_2$ alkoxy, chlorine or fluorine
bridged bi- or tricycloalkyl
$C_3$-$C_6$ cycloalkyl-$C_1$-$C_2$ alkyl, $C_3$-$C_6$ cycloalkyl-$C_1$-$C_4$ alkenyl
phenyl, the phenyl optionally being substituted with one, two or three substituents selected from $C_1$-$C_4$ alkyl, chlorine, fluorine, $C_1$-$C_2$ fluoroalkyl, $C_1$-$C_2$ alkoxy, $C_1$-$C_2$ fluoroalkoxy, $C_1$-$C_2$-alkylester, nitro, amino, di-$C_1$-$C_2$ alkylamino, and cyano,
phenyl-$C_1$-$C_2$ alkyl,
  the phenyl moiety optionally being substituted with one, two or three substituents selected from fluorine, chlorine, $C_1$-$C_2$ alkyl, $C_1$-$C_2$ fluoroalkyl, $C_1$-$C_2$ alkoxy, $C_1$-$C_2$ fluoroalkoxy, and hydroxyl,
  the alkyl moiety optionally being substituted with one or two substituents selected from $C_1$-$C_2$ alkyl and hydroxyl,
5-6 membered heterocycloalkyl, the 5-6 membered heterocycloalkyl being optionally substituted with $C_3$-$C_5$ cycloalkyl or $C_1$-$C_3$ alkyl,
5-6 membered heterocycloalkyl-$C_1$-$C_2$ alkyl,
  the 5-6 membered heterocycloalkyl moiety being optionally substituted with $C_1$-$C_2$ alkyl or oxo,
  the $C_1$-$C_2$ alkyl moiety being optionally substituted with $C_1$-$C_2$ alkyl,
5-6 membered heteroaryl, the 5-6 membered heteroaryl being optionally substituted with one, two or three substituents selected from fluorine, chlorine, $C_1$-$C_3$ alkyl, and $C_1$-$C_2$ fluoroalkyl,
and
  5-6 membered heteroaryl-$C_1$-$C_4$ alkyl, the 5-6 membered heteroaryl-moiety being optionally substituted with one or two substituents selected from $C_1$-$C_2$ alkoxy and $C_1$-$C_2$ alkyl,
  the $C_1$-$C_2$ alkyl-moiety being optionally substituted with one or two methyl substituents;
or
$R^2$ and $R^3$ together form a $C_5$-$C_6$ cycloalkyl ring;
and its salts, solvates, and solvates of the salts.

According to an embodiment of the present invention, the compounds of the formulae (I-A) or (I-B) are defined as follows:
$R^1$ is hydrogen;
$R^2$ is hydrogen;
$R^3$ is selected from
  1,2,4 oxadiazol-5-yl of the formula

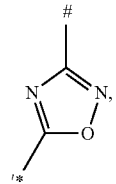

or 1,3,4 oxadiazol-5-yl of the formula

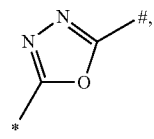

or 1,2,4 oxadiazol-3-yl of the formula

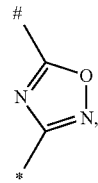

wherein * indicates the position of binding to the pyrazolopyrimidone and # denotes the optional binding to a further substituent, the oxadiazolyl being substituted with a substituent selected from $C_1$-$C_6$ alkyl, $C_2$-$C_6$ alkenyl, $C_1$-$C_4$ fluoroalkyl, $C_1$-$C_2$ fluoroalkoxy, methoxy-$C_1$-$C_4$ alkyl, tert-butoxy-ethyl, $C_1$-$C_2$ alkylester, $C_3$-$C_6$ cycloalkyl, the $C_3$-$C_6$ cycloalkyl optionally being substituted with chlorine, fluorine, methyl, or phenyl, the phenyl optionally being substituted with chlorine or methoxy, oxanyl, oxopyrrolidinyl-methyl, piperidinyl, the piperidinyl being substituted with cyclopropyl or iso-propyl, piperidinyl-methyl, the piperidinylmethyl being optionally substituted with methyl, morpholinyl-ethyl, the ethyl moiety being optionally substituted with methyl, tetrahydrofuranyl, phenyl, the phenyl optionally being substituted with one, two or three substituents selected from $C_1$-$C_4$ alkyl, fluorine, chlorine, trifluoromethyl, methoxy, trifluoromethoxy, methylester, nitro, amino, di-methylamino, and cyano, and benzyl, the phenyl moiety of the benzyl being optionally substituted with one or two fluorine and one methoxy substituent, or the phenyl moiety of the benzyl being optionally substituted with one or two substituents selected from fluorine, chlorine, methoxy, and hydroxyl, or the phenyl moiety being optionally substituted with one substituent selected from fluorine, chlorine, methyl, trifluoromethyl, methoxy, isopropyloxy, trifluoromethoxy, and difluoromethoxy, the methyl moiety of the benzyl being optionally substituted with hydroxyl, ethyl, or one or two methyl substituents, 1,2 oxazolyl, the 1,2 oxazolyl being substituted with phenyl, thiophen-yl, the thiophen-yl being optionally substituted with a substituent selected from methyl and cyano, 1,3 thiazolyl, the 1,3 thiazolyl being optionally substituted with one substituent selected from $C_1$-$C_5$ alkyl, $C_1$-$C_4$ haloalkyl, cyclopropyl and phenyl, the phenyl being optionally substituted with one of two substituents selected from fluorine, chlorine, methyl, and trifluoromethyl or the 1,3 thiazolyl being optionally substituted with two substituents selected from methyl, ethyl, and iso-propyl substituents, or the thiazolyl being optionally substituted with phenyl and methyl;

pyridinyl, the pyridinyl being optionally substituted with one or two substituents selected from fluorine, chlorine, methyl, and trifluoromethyl, and its salts, solvates, and solvates of the salts.

According to an embodiment of the present invention, the compounds of the formulae (I-A) or (I-B) are defined as follows:

$R^1$ is hydrogen;

$R^2$ is hydrogen;

$R^3$ is selected from 1,2,4 oxadiazol-5-yl of the formula

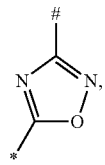

or 1,3,4 oxadiazol-5-yl of the formula

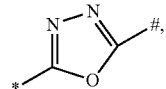

or 1,2,4 oxadiazol-3-yl of the formula

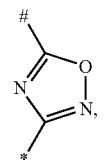

wherein * indicates the position of binding to the pyrazolopyrimidone and # denotes the optional binding to a further substituent, the oxadiazolyl being optionally substituted with one substituent selected from methyl, ethyl, propyl, isopropyl, tert-butyl, hexyl, trifluoromethyl, trifluoroethyl, trifluorobutyl, methoxymethyl, methoxypropyl, methoxyisobutyl, ethylester, $C_3$-$C_6$ cycloalkyl, benzyl, the phenyl moiety of the benzyl being optionally substituted with one or two substituents selected from methyl, methoxy, isopropyloxy, fluorine, chlorine, trifluoromethyl, trifluoromethoxy, and difluoromethoxy, or pyridinyl, the pyridinyl being optionally substituted with chlorine, fluorine, methyl, or trifluoromethyl, and its salts, solvates, and solvates of the salts.

According to an embodiment of the present invention, the compounds of the formulae (I-A) or (I-B) are defined as follows:

$R^1$ is hydrogen;

$R^2$ is hydrogen;

$R^3$ is 1,2,4-oxadiazol-5-yl of the formula

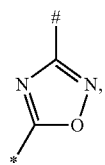

wherein * indicates the position of binding to the pyrazolopyrimidone and # denotes the optional binding to a further substituent, the oxadiazolyl being substituted with tert-butyl, and its salts, solvates, and solvates of the salts.

According to an embodiment of the present invention, the compounds of the formulae (I-A) or (I-B) are defined as follows:

$R^1$ is hydrogen;

$R^2$ is methyl;

$R^3$ is selected from 1,2,4 oxadiazol-5-yl of the formula

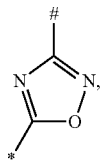

or 1,3,4 oxadiazol-5-yl of the formula

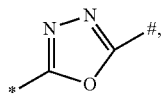

or 1,2,4 oxadiazol-3-yl of the formula

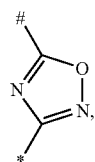

wherein * indicates the position of binding to the pyrazolopyrimidone and # denotes the optional binding to a further substituent, the oxadiazolyl being optionally substituted with one substituent selected from
methyl, ethyl, isopropyl, tert-butyl, trifluoromethyl, methoxyethyl, tert-butoxyethyl, $C_3$-$C_6$ cycloalkyl,
  the $C_3$-$C_6$ cycloalkyl being optionally substituted with one or two methyl substituents, cyclobutyl, benzyl,
  the phenyl moiety of the benzyl being optionally substituted with a substituent selected from fluorine, chlorine, and hydroxyl,
phenyl,
  the phenyl being optionally substituted with a substituent selected from methyl, fluorine, chlorine, methoxy, trifluoromethyl, and trifluoromethoxy
and its salts, solvates, and solvates of the salts.

According to an embodiment of the present invention, the compounds of the formulae (I-A) or (I-B) are defined as follows:
$R^1$ is hydrogen;
$R^2$ is hydrogen;
$R^3$ is selected from methylester, ethylester, propylester, isopropylester, the ethylester and the propylester being optionally substituted with one, two, or three fluorine substituents, and cyclobutylester,
and its salts, solvates, and solvates of the salts.

According to an embodiment of the present invention, the compounds of the formulae (I-A) or (I-B) are defined as follows:
$R^1$ is hydrogen;
$R^2$ is methyl;
$R^3$ is selected from ethylester, propylester, isopropylester, tert-butylester, the ethylester and the propylester being optionally substituted with one, two, or three fluorine substituents, and cyclobutylester,
and its salts, solvates, and solvates of the salts.

According to an embodiment of the present invention, the compounds of the formulae (I-A) or (I-B) are defined as follows:
$R^1$ is hydrogen;
$R^2$ is methyl;
$R^3$ is ethylester,
and its salts, solvates, and solvates of the salts.

According to an embodiment of the present invention, the compounds of the formulae (I-A) or (I-B) are defined as follows:
$R^1$ is hydrogen;
$R^2$ is selected from trifluoromethyl, ethyl and methylsulfanyl
$R^3$ is selected from $C_1$-$C_4$ alkylester, the $C_1$-$C_4$ alkylester being optionally substituted with one, two, or three fluorine substituents, and $C_3$-$C_4$ cycloalkylester,
and its salts, solvates, and solvates of the salts.

The definitions of radicals indicated specifically in the respective combinations of radicals are replaced as desired irrespective of the particular combinations indicated for the radicals also by definitions of radicals of other combinations.

According to an embodiment of the invention, two or more of the embodiments mentioned above are combined.

The invention furthermore provides a process for preparing the compounds of the formula (IV)

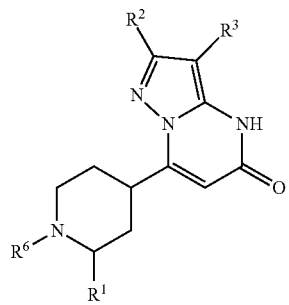

(IV)

in which $R^1$, $R^2$, and $R^3$ each have the meaning as defined above and $R^6$ represents an amino protective group, wherein
[A] a compound of the formula (II-A)

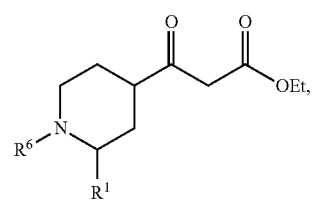

(II-A)

in which $R^1$ and $R^6$ have the meaning given above, is reacted with a compound of the formula (III)

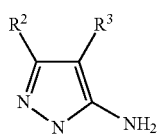

(III)

in which $R^2$ and $R^3$ each have the meaning given above in an inert solvent, optionally in the presence of a base, to give a compound of the formula (IV)

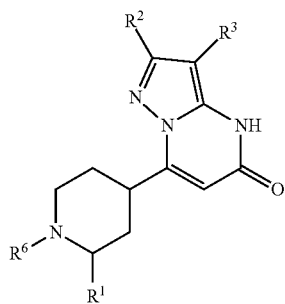

(IV)

in which $R^1$, $R^2$, $R^3$, and $R^6$ each have the meaning given above, or

[B] a compound of the formula (II-B)

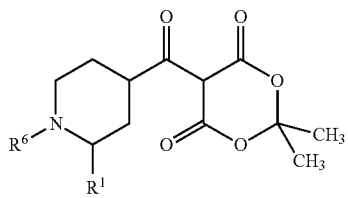

(II-B)

in which $R^1$ has the meaning given above and $R^6$ represents an amino protective group, is reacted with a compound of the formula (III)

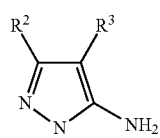

(III)

in which $R^2$ and $R^3$ each have the meaning given above in an inert solvent optionally in the presence of a base, to give a compound of the formula (IV)

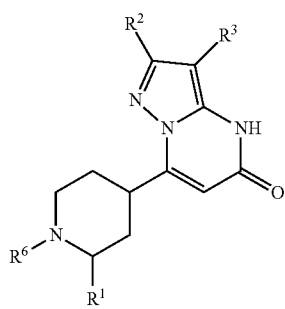

(IV)

in which $R^1$, $R^2$, $R^3$, and $R^6$ each have the meaning given above.

The invention furthermore provides a process for preparing the compounds of the formula (IV)

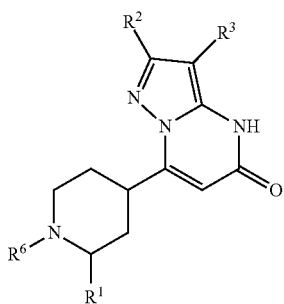

(IV)

in which $R^1$, $R^2$, and $R^3$ each have the meaning as defined above and $R^6$ represents an amino protective group, wherein

[B] a compound of the formula (II-B)

(II-B)

in which $R^1$ has the meaning given above and $R^6$ represents an amino protective group, is reacted with a compound of the formula (III)

(III)

in which $R^2$ and $R^3$ each have the meaning given above in an inert solvent optionally in the presence of a base, to give a compound of the formula (IV)

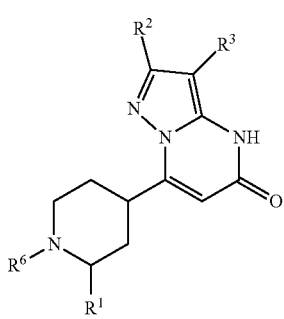

(IV)

in which $R^1$, $R^2$, and $R^3$ each have the meaning given above and $R^6$ represents an amino protective group.

The invention furthermore provides a regioselective process for preparing the compounds of the formula (IV)

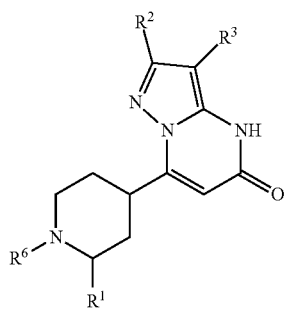

in which $R^1$, $R^2$, and $R^3$ each have the meaning as defined above and $R^6$ represents an amino protective group, wherein [B] a compound of the formula (II-B)

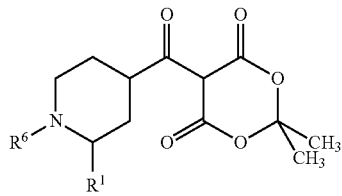

in which $R^1$ has the meaning given above and $R^6$ stands for an amino protective group, is reacted with a compound of the formula (III)

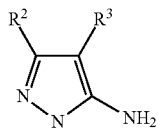

in which $R^2$ and $R^3$ each have the meaning given above in an inert solvent optionally in the presence of a base, to give a compound of the formula (IV)

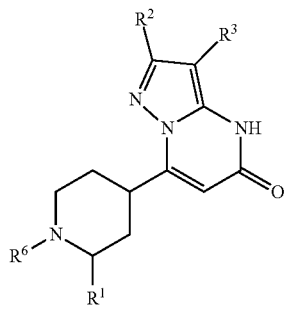

in which $R^1$, $R^2$, and $R^3$ each have the meaning given above and $R^6$ represents an amino protective group.

The term "regioselective process" within the meaning of the invention is defined as a process that yields a compound of formula (IV) wherein less than 20%, less than 15%, less than 10%, less than 5%, less than 3%, less than 2%, less than 1%, less than 0.5%, less than 0.1% or 0% of the compound of formula (IV) is present as the regioisomer of the compound of formula IV shown below

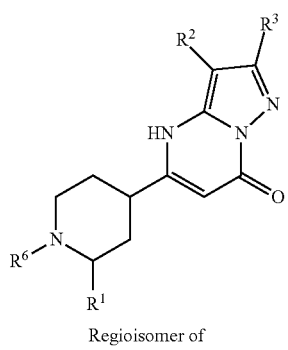

Regioisomer of

According to an embodiment of the invention, $R^6$ is an acid cleavable amino protective group, such as tert-butoxycarbonyl (Boc), and the compound of the formula (IV)

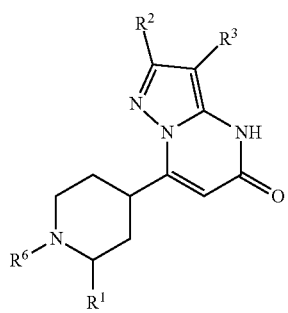

obtained in reaction [A] or [B] is reacted to the compound of the formula (I-B) by addition of an acid

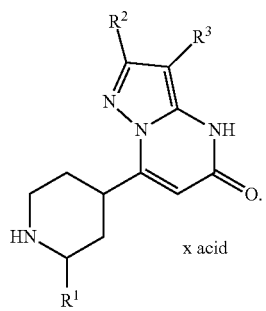

x acid

According to an embodiment of the invention, the compound of the formula (I-A) is obtained by treating the compound of formula (I-B) with a base.

According to an embodiment of the invention, the compound of the formula (I-A) is obtained by treating the compound of formula (I-B) with a suitable chromatographic method by using a basic eluent.

According to an embodiment of the invention, $R^6$ is not cleavable by an acid and the compound of the formula (I-A) is obtained from the compound of formula (IV) by cleaving the amino protective group of the compound of formula (IV)

for example by hydrogenation. Examples for this reaction are the cleavage of the amino protective groups benzyloxycarbonyl (Cbz), and of optionally substituted benzyl.

According to an embodiment of the invention, the compound of the formula (I-B) is obtained by treating the compound of formula (I-A) with an acid.

The resulting compounds of the formulae (I-A) or (I-B) are optionally converted with the appropriate (i) solvents and/or (ii) acids or bases into their solvates, salts and/or solvates of the salts.

The present invention also provides compounds of the general formula (IV)

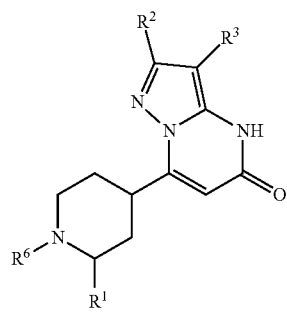
(IV)

in which $R^1$, $R^2$, $R^3$, and $R^6$ each have the meaning given above.

The present invention also provides a compound of the general formula (II-B)

(II-B)

wherein
$R^1$ is selected from hydrogen and $C_1$-$C_4$ alkyl and
$R^6$ is an amino protective group.

The present invention also provides a compound of the general formula (II-B)

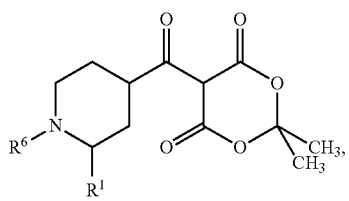
(II-B)

wherein
$R^1$ is selected from hydrogen and methyl and
$R^6$ is selected from tert-butoxycarbonyl (Boc), and benzyloxycarbonyl (Cbz).

The present invention also provides a compound of the general formula (II-B)

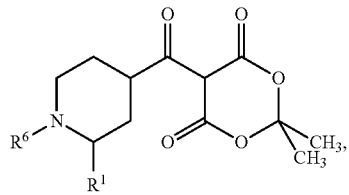
(II-B)

wherein
$R^1$ is selected from hydrogen and $C_1$-$C_4$ alkyl and
$R^6$ is tert-butoxycarbonyl (Boc).

The invention furthermore provides a process for preparing the compounds of formula (VI)

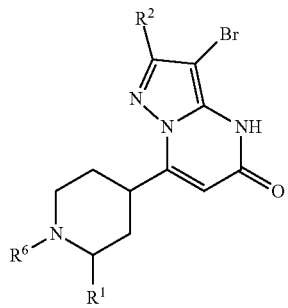
(VI)

in which $R^1$, $R^2$, and $R^6$ are as defined above, wherein a compound of formula (II-B)

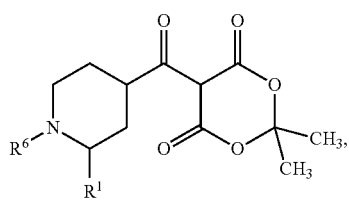
(II-B)

is reacted with a compound of formula (III)

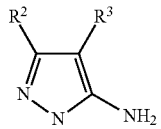
(III)

wherein $R^3$ is bromine, in an inert solvent optionally in the presence of a base to give a compound of formula (VI).

The invention furthermore provides a process for preparing the compounds of formula (VII)

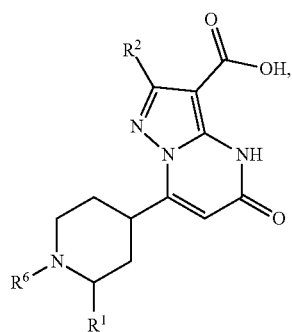
(VII)

in which $R^1$, $R^2$ and $R^6$ are as defined above, wherein a compound of formula (II-B)

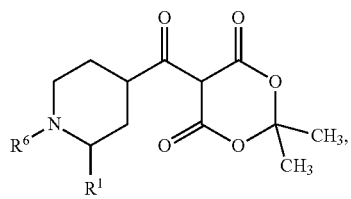
(II-B)

is reacted with a compound of formula (III)

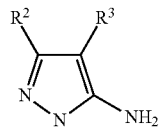
(III)

wherein $R^3$ is $C_1$-$C_4$ alkylester, in an inert solvent optionally in the presence of a base to give a compound of formula (VIII)

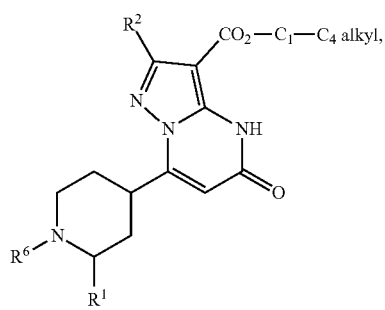
(VIII)

then a compound of formula (VIII) is reacted in an inert solvent and in the presence of a base to give a compound of formula (VII).

The invention furthermore provides a process for preparing the compounds of formula (IX),

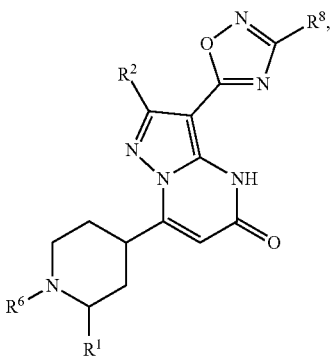
(IX)

in which $R^1$, $R^2$ and $R^6$ are as defined above and $R^8$ is as defined above as substituent of 1,2,4 oxadiazol-5-yl, wherein the 1,2,4 oxadiazol-5-yl together with $R^8$ forms $R^3$, wherein a compound of the formula (VII)

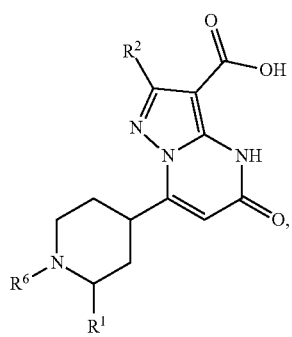
(VII)

is reacted in an inert solvent, optionally in the presence of a dehydrating reagent, and optionally in the presence of a base, and in the presence of an amidoxime of formula (XXVIII)

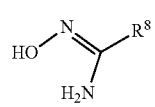
(XXVIII)

to give a compound of formula (IX).

The invention furthermore provides a process for preparing the compounds of formula (X),

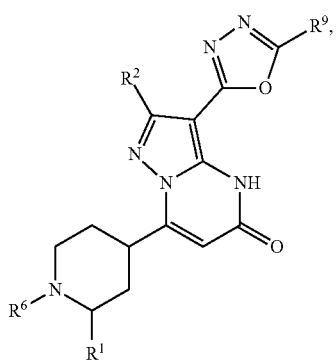
(X)

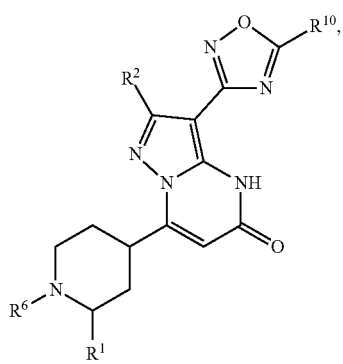
(XII)

in which $R^1$, $R^2$ and $R^6$ are as defined above and $R^9$ is as defined above as substituent of 1,3,4 oxadiazol-5-yl, wherein the 1,3,4 oxadiazol-5-yl together with $R^9$ forms $R^3$, wherein a compound of the formula (VII)

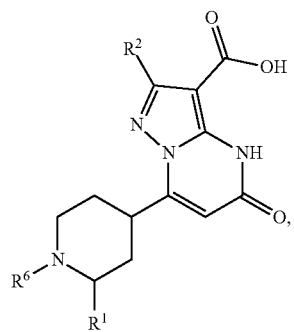
(VII)

is reacted with $H_2N$—$NH$—$COR^9$ in an inert solvent, in the presence of a dehydration reagent, and optionally in the presence of a base, to give a compound of formula (XI)

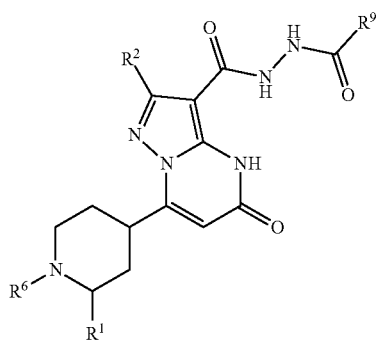
(XI)

and the compound of formula (XI) is then reacted with a dehydrating reagent, in an inert solvent, to give a compound of formula (X).

The invention furthermore provides a process for preparing the compounds of formula (XII)

in which $R^1$, $R^2$ and $R^6$ are as defined above and $R^{10}$ is as defined above as substituent of 1,2,4 oxadiazol-3-yl, wherein the 1,2,4 oxadiazol-3-yl together with $R^{10}$ forms $R^3$, wherein a compound of the formula

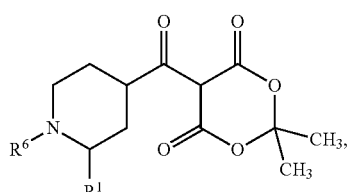
(II-B)

is reacted with a compound of formula (XIII)

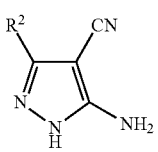
(XIII)

in the presence of an inert solvent, optionally in the presence of a base, to give a compound of formula (XIV)

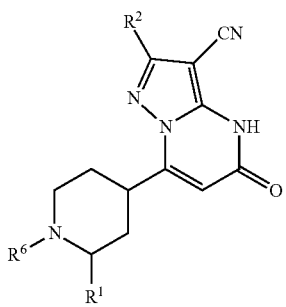
(XIV)

then the compound of formula (XIV) is reacted with hydroxylamine or its salt, in an inert solvent, optionally in the presence of a base to give a compound of formula (XV)

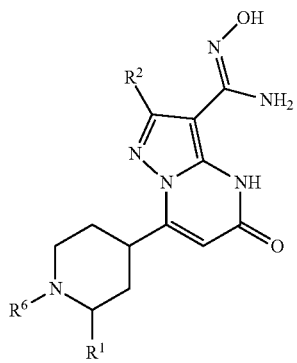

(XV)

and then the compound of formula (XV) is reacted with a compound of formula (XVI)

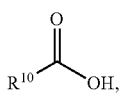

(XVI)

in an inert solvent, in the presence of an amide coupling agent and optionally in the presence of a base to give the compound of formula (XII).

The invention furthermore provides a process for preparing the compounds of formula (XVII)

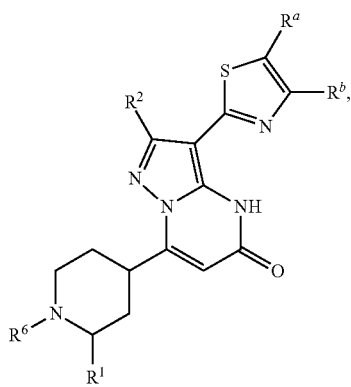

(XVII)

in which $R^1$, $R^2$ and $R^6$ are as defined above and $R^a/R^b$ are as defined above as substituents of 1,3 thiazolyl, wherein the 1,3, thiazolyl together with $R^a/R^b$ forms $R^3$, wherein a compound of formula (II-B)

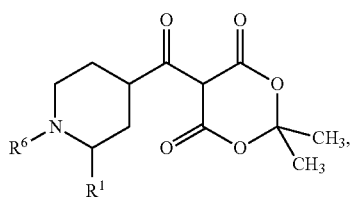

(II-B)

is reacted with a compound of formula (XVIII)

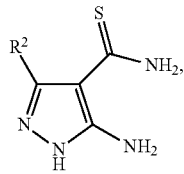

(XVIII)

in an inert solvent, optionally in the presence of a base, to give a compound of formula (XIX)

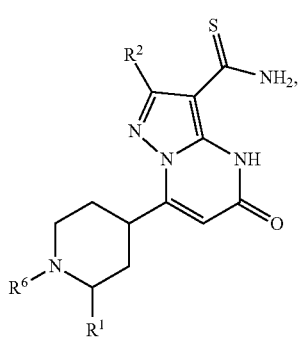

(XIX)

and then the compound of formula (XIX) is reacted with a compound of formula (XX)

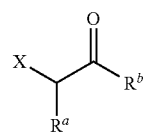

(XX)

in which X is Cl or Br, in an inert solvent, optionally in the presence of a base, to give a compound of formula (XVII).

The invention furthermore provides a process for preparing the compounds of formula (XXI)

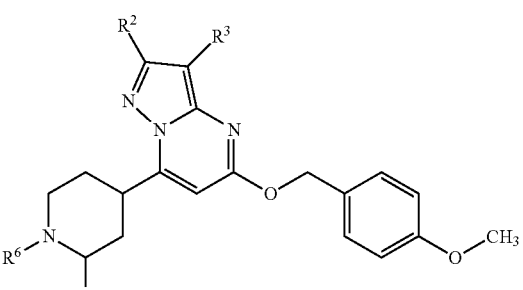

(XXI)

in which $R^1$, $R^2$, $R^3$, and $R^6$ are as defined above, wherein a compound of formula (VI)

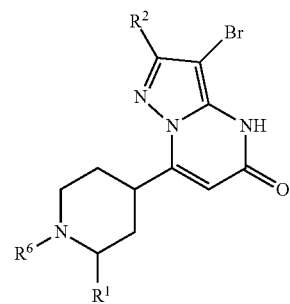

(VI)

is reacted with 1-(halomethyl)-4-methoxybenzene in an inert solvent and optionally in the presence of a base to give a compound of formula (XXIII)

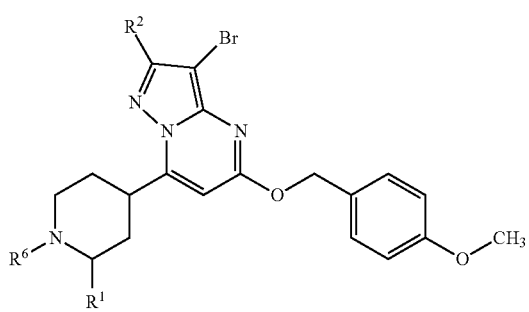

(XXIII)

and then the compound of formula (XXIII) is reacted with a compound of formula (XXIV)

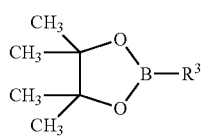

(XXIV)

in an inert solvent and in the presence of a palladium catalyst, optionally in the presence of a ligand, and optionally in the presence of a base to give a compound of formula (XXI).

The invention furthermore provides a process for preparing the compounds of formula (XXV)

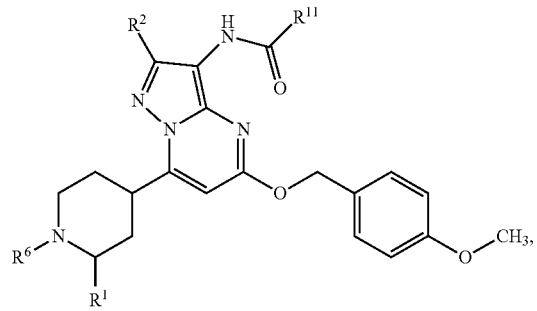

(XXV)

in which $R^1$, $R^2$, $R^3$, and $R^6$ are as defined above and R" is R" is selected from optionally substituted phenyl, alkyl, and cycloalkyl, wherein a compound of formula (XXVI)

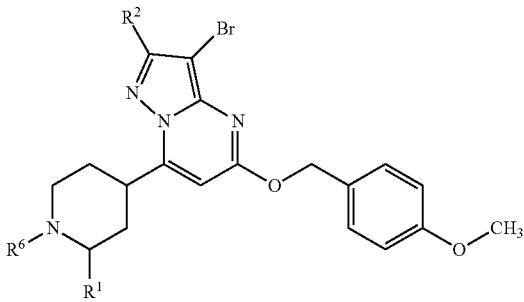

(XXIII)

is reacted with a compound of formula (XXVI)

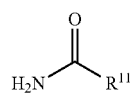

(XXVII)

in an inert solvent in the presence of a catalyst, optionally in the presence of a ligand, and optionally in the presence of a base to give a compound of formula (XXV).

The invention furthermore provides a process for preparing a compound of formula (XXXIX)

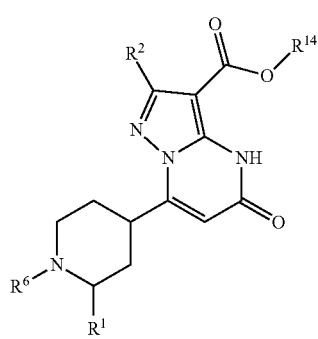

(XXXIX)

in which $R^1$, $R^2$, and $R^6$ are as defined above and $R^{14}$ is selected from $C_1$-$C_4$ alkyl, the $C_1$-$C_4$ alkyl being optionally substituted with one, two, or three halogen substituents, $C_3$-$C_4$ cycloalkyl, and benzyl, wherein

[A] a compound of formula (VII)

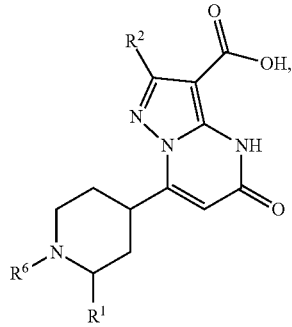

(VII)

is reacted with $R^{14}$-2,2,2-trichloroethanimidate, in the presence of a lewis acid, in an inert solvent, at a temperature from 0° C. to the reflux temperature of the solvent to give a compound of formula (XXXIX)

or

[B] a compound of formula (VII) is reacted in a first step in an inert solvent, in the presence of carbodiimidazole as a dehydrating reagent, and, in the case that the dehydrating reagent used is not carbodiimidazole, also in the presence of imidazole, optionally in the presence of a base, at a temperature from 0° C. to the reflux temperature of the solvent to give a compound of formula (XXXVIII),

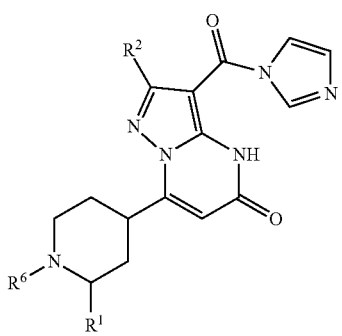

(XXXVIII)

and then the compound of formula (XXXVIII) is reacted in a second step with $R^{14}$OH, optionally in an inert solvent, optionally in the presence of a base, at a temperature from 0° C. to the reflux temperature of the solvent to give a compound of formula (XXXIX), wherein the first and second step of [B] can also be conducted as one step without isolation of (XXXVIII).

The present invention also provides a compound of the general formula (VII)

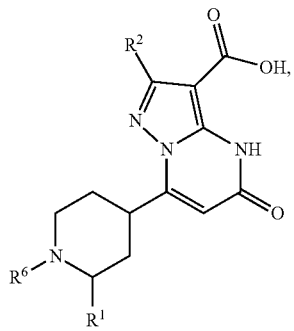

(VII)

in which $R^1$, $R^2$, and $R^6$ are as defined above.

The present invention also provides a compound of the general formula (XV)

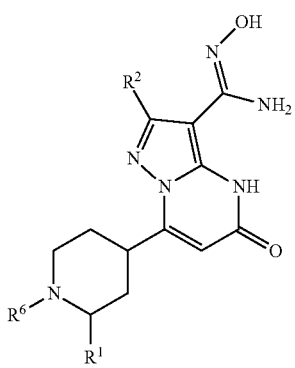

(XV)

in which $R^1$, $R^2$, and $R^6$ are as defined above.

The present invention also provides a compound of the general formula (XIX)

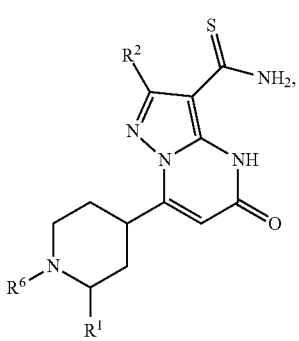

(XIX)

in which $R^1$, $R^2$, and $R^6$ are as defined above.

The present invention also provides a compound of the general formula (VI)

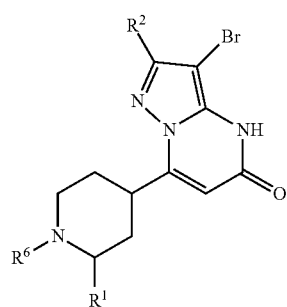

(VI)

in which $R^1$, $R^2$, and $R^6$ are as defined above.

The present invention also provides a compound of the general formula (XXIII)

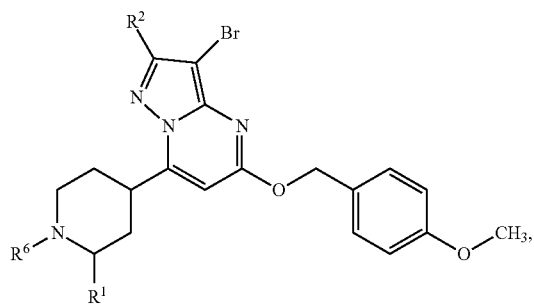

(XXIII)

in which $R^1$, $R^2$, and $R^6$ are as defined above.

The present invention also provides a compound of the general formula (VIII)

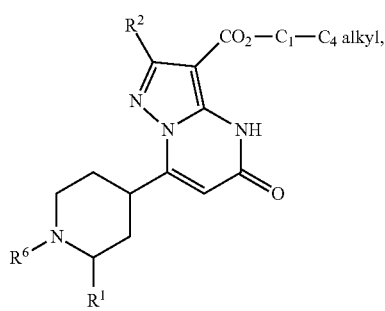

(VIII)

in which $R^1$, $R^2$, and $R^6$ are as defined above.

The present invention also provides a compound of the general formula (XIV)

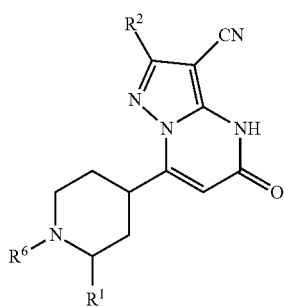

(XIV)

in which $R^1$, $R^2$, and $R^6$ are as defined above.

The present invention also provides a compound of the general formula (XXXVIII)

(XXXVIII)

in which $R^1$, $R^2$, and $R^6$ are as defined above.

Further compounds of formula (I-A) or (I-B) according to the invention can optionally also be prepared by converting functional groups of individual substituents, starting with the compounds of the formula (I-A) and (I-B) obtained by the above processes. These conversions are carried out by customary methods known to the person skilled in the art and include, for example, reactions such as nucleophilic and electrophilic substitutions, oxidations, reductions, hydrogenations, transition metal-catalyzed coupling reactions, eliminations, alkylation, amination, esterification, ester cleavage, etherification, ether cleavage, formation of carboxamides, and also the introduction and removal of temporary protective groups.

The preparation processes described can be illustrated in an exemplary manner by the synthesis schemes below (Schemes 1 and 2).

Scheme 1: Synthesis of pyrazolopyrimidinones via the piperidinyl-beta-ketoester

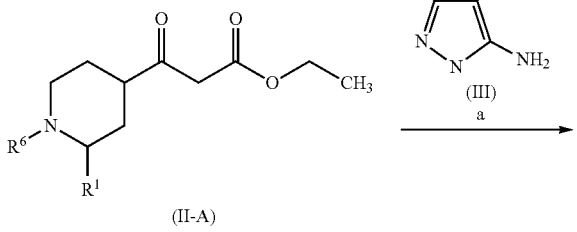

(II-A)    (III)    a

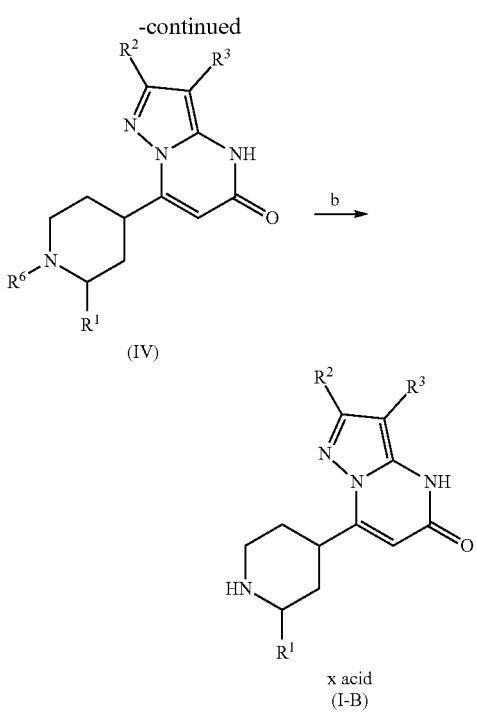

a) Aminopyrazole, 1-methoxy-2-propanol, potassium phosphate, microwave, 15 minutes, 180° C., b) HCl 4N in dioxane, RT or TFA, dichloromethane, RT Suitable amino protecting groups (substituent $R^6$) in formulae (II-A), (II-B), and (IV) are tert-butoxycarbonyl (Boc), removed by a concentrated strong acid, benzyloxycarbonyl (Cbz), removed by hydrogenolysis, methyl or ethylcarbamate, removed by TMSI in $CHCl_3$ or HBr in AcOH, Trimethylsilylethyl carbamate (Teoc), removed by fluoride, p-Methoxybenzyl carbamate (Moz or MeOZ), removed by hydrogenolysis, 9-Fluorenylmethyl carbamate (F-moc), removed by a base, and optionally substituted benzyl or benzylamine, removed by hydrogenolysis. Preferred for use as amino protective group is tert-butoxycarbonyl (Boc).

According to an embodiment of the invention, the amino protective group $R^6$ is selected from tert-butoxycarbonyl (Boc), and benzyloxycarbonyl (Cbz). Preferred for use as amino protective group is tert-butoxycarbonyl (Boc).

The reaction can also be carried out without protecting the amino group. In this case, $R^6$ is hydrogen.

According to an embodiment of the invention, the reaction is carried out without protecting the amino group. In this embodiment, $R^6$ is hydrogen.

The invention furthermore provides a process for preparing the compounds of the formula (IV)

Scheme 2: Synthesis of pyrazolopyrimidinones via the piperidinyl Meldrum's acid derivative

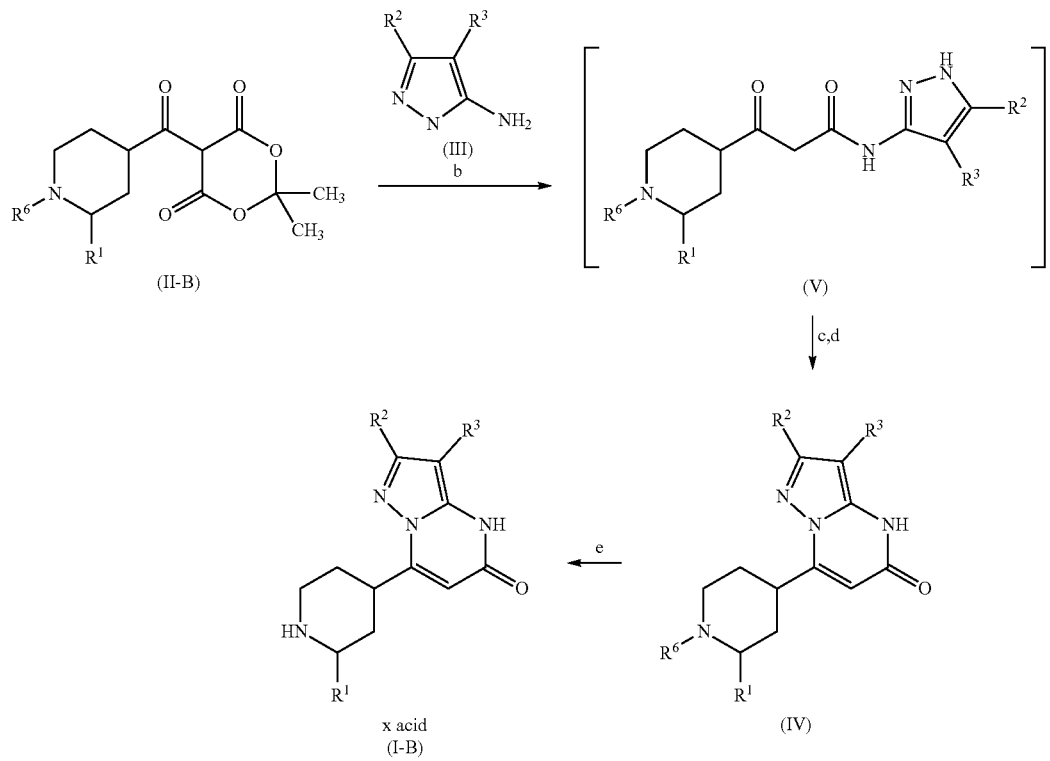

b) acetonitrile, 60° C.; c) evaporation of the solvent, d) 1-methoxy-2-propanol, tripotassium phosphate, 110° C., e) HCl 4N in dioxane, RT or TFA, dichloromethane, RT.

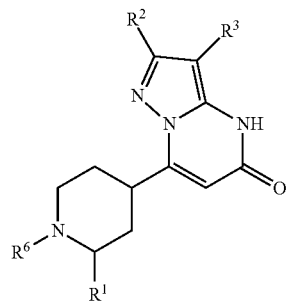

(IV)

in which $R^1$, $R^2$, and $R^3$ each have the meaning as defined above and $R^6$ is hydrogen, wherein

[A] a compound of the formula (II-A)

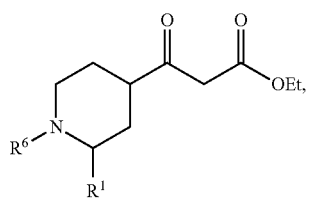

(II-A)

in which $R^1$ has the meaning given above and $R^6$ is hydrogen, is reacted with a compound of the formula (III)

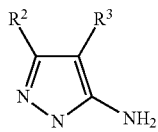

(III)

in which $R^2$ and $R^3$ each have the meaning given above in an inert solvent, optionally in the presence of a base, to give a compound of the formula (IV)

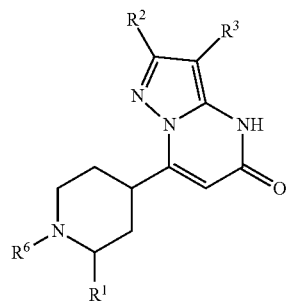

(IV)

in which $R^1$, $R^2$, and $R^3$ each have the meaning given above and $R^6$ is hydrogen, or

[B] a compound of the formula (II-B)

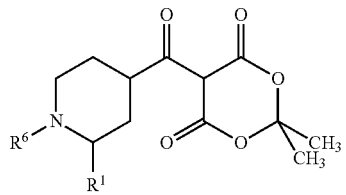

(II-B)

in which $R^1$ has the meaning given above and $R^6$ is hydrogen, is reacted with a compound of the formula (III)

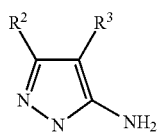

(III)

in which $R^2$ and $R^3$ each have the meaning given above in an inert solvent optionally in the presence of a base, to give a compound of the formula (IV)

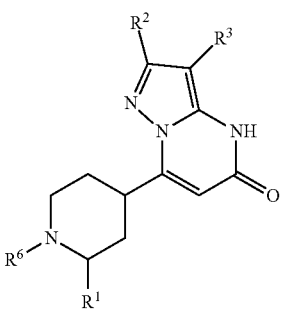

(IV)

in which $R^1$, $R^2$, and $R^3$ each have the meaning given above and $R^6$ is hydrogen.

Suitable solvents for the process steps (II-A)+(III)→(IV) are inert solvents, for example, aliphatic alcohols such as methanol, ethanol, iso-propanol, 1-methoxy-2-propanol or tert-butanol, ethers such as diethyl ether, dioxane, tetrahydrofuran, glycol dimethyl ether or diethylene glycol dimethyl ether, hydrocarbons such as benzene, toluene, xylene, hexane, cyclohexane or mineral oil fractions, halogenated hydrocarbons such as dichloromethane, trichloromethane, carbon tetrachloride, 1,2-dichloroethane, trichloroethylene or chlorobenzene, or other solvents such as acetone, ethyl acetate, acetonitrile, pyridine, dimethyl sulphoxide, N,N-dimethylformamide, N,N-dimethylacetamide, N,N'-dimethylpropyleneurea (DMPU) or N-methylpyrrolidone (NMP). It is also possible to use mixtures of the solvents mentioned. Preference is given to polar solvents with high boiling points, such as toluene, 1-methoxy-2-propanol, and dioxane, or mixtures of these solvents.

The condensation process (II-A)+(III)→(IV) may proceed in the absence of a base, in the presence of organic bases such as triethylamine or diisopropylethylamine, or in the presence of inorganic bases. Inorganic bases include alkali metal or alkali earth metal phosphates and carbonates such as potassium phosphate, potassium carbonate, cesium carbonate, sodium phosphate, or calcium carbonate. Preference is given to the presence of potassium phosphate.

According to an embodiment of the invention, the compounds of formulae (II-A) and (III) are reacted in the presence of a base, in particular in the presence of an inorganic base, preferably in the presence of potassium phosphate.

The condensation process (II-A)+(III)→(IV) is generally carried out in a temperature range from 50° C. to 250° C., preferably within 100° C. to 200° C. Heating options include conventional heating below the boiling point of the solvent, under reflux, or above the boiling point of the solvent in a closed vial, or in a closed vial with the aid of a microwave reactor. Preference is given to heating the reaction in a microwave vial from 160° C. to 200° C.

According to an embodiment of the invention, the compounds of formulae (II-A) and (III) are reacted at a temperature of 50° C. to 250° C., preferably at a temperature of 100° C. to 200° C.

The condensation process (II-A)+(III)→(IV) can be carried out at atmospheric, elevated or reduced pressure (for example from 0.5 to 25 bar). In general, the reactions are in each case carried out at atmospheric pressure to 15 bar.

According to an embodiment of the invention, the compounds of formulae (II-A) and (III) are reacted at a pressure between atmospheric pressure and 15 bar.

Typically, the condensation process (II-A)+(III)→(IV) yields mixtures of regioisomers. The desired regioisomer is isolated by a suitable chromatographic method such as chromatography on silica gel, reverse-phase high-performance liquid chromatography, or preparative thin-layer chromatography. Inert solvents used as liquid phase include ethyl acetate, cyclohexane, dichloromethane, methanol, supercritical carbon dioxide, water, acetonitrile, and mixtures thereof. The desired regioisomer can further be isolated by crystallisation.

According to an embodiment of the invention, the compound of formula (IV) is isolated from the mixture of regioisomers.

The condensation process (II-B)+(III)→[(V)]→(IV) can be carried out in one single step without isolation of the intermediate (V), in two separate steps by changing the reaction conditions for the formation of (V) from (II-B) and (III) and the formation of (IV) from (V) but without purification of the intermediate (V), or in two separate steps involving the purification of intermediate (V). Preference is given to a procedure with two separate steps without purification of the intermediate.

According to an embodiment of the invention, the compounds of formulae (II-B) and (III) are reacted in a first step to a compound of formula (V). The compound of formula (V) is reacted in a second step to the compound of formula (IV) without separation and purification of the intermediate (V). According to a further embodiment of the invention, the solvent is changed between the first and the second step.

Suitable solvents for the process steps (II-B)+(III)→(V) are, for example, aliphatic alcohols such as methanol, ethanol, iso-propanol, 1-methoxy-2-propanol or tert-butanol, ethers such as diethyl ether, dioxane, tetrahydrofuran, glycol dimethyl ether or diethylene glycol dimethyl ether, hydrocarbons such as benzene, toluene, xylene, hexane, cyclohexane or mineral oil fractions, halogenated hydrocarbons such as dichloromethane, trichloromethane, carbon tetrachloride, 1,2-dichloroethane, trichloroethylene or chlorobenzene, or other solvents such as acetone, ethyl acetate, acetonitrile, pyridine, dimethyl sulphoxide, N,N-dimethylformamide, N,N-dimethylacetamide, N,N'-dimethylpropyleneurea (DMPU) or N-methylpyrrolidone (NMP). It is also possible to use mixtures of the solvents mentioned. Preference is given to using acetonitrile or toluene as solvents, or mixtures of these solvents.

Suitable solvents for the process steps (V)→(IV) are, for example, aliphatic alcohols such as methanol, ethanol, iso-propanol, 1-methoxy-2-propanol or tert-butanol, ethers such as diethyl ether, dioxane, tetrahydrofuran, glycol dimethyl ether or diethylene glycol dimethyl ether, hydrocarbons such as benzene, toluene, xylene, hexane, cyclohexane or mineral oil fractions, halogenated hydrocarbons such as dichloromethane, trichloromethane, carbon tetrachloride, 1,2-dichloroethane, trichloroethylene or chlorobenzene, or other solvents such as acetone, ethyl acetate, acetonitrile, pyridine, dimethyl sulphoxide, N,N-dimethylformamide, N,N-dimethylacetamide, N,N'-dimethylpropyleneurea (DMPU) or N-methylpyrrolidone (NMP). It is also possible to use mixtures of the solvents mentioned. Preference is given to using 1-methoxy-2-propanol or toluene as solvents, or mixtures of these solvents.

The process (II-B)+(III)→(V) may proceed in the absence of a base, in the presence of organic bases such as triethylamine or diisopropylethylamine, or in the presence of inorganic bases. Inorganic bases include alkali metal or alkali earth metal phosphates and carbonates such as potassium phosphate, potassium carbonate, cesium carbonate, sodium phosphate, or calcium carbonate. Preference is given to reacting the compounds of formulae (II-B) and (III) in the absence of a base.

According to an embodiment of the invention, the compounds of formulae (II-B) and (III) are reacted in the absence of a base.

The condensation process (V)→(IV) may proceed in the absence of a base, in the presence of organic bases such as triethylamine or diisopropylethylamine, or in the presence of inorganic bases. Inorganic bases include alkali metal or alkali earth metal phosphates and carbonates such as potassium phosphate, potassium carbonate, cesium carbonate, sodium phosphate, or calcium carbonate. Preference is given to reacting the compound of formula (V) to the compound of formula (IV) in the presence of potassium phosphate.

According to an embodiment of the invention, the compound of formula (V) is reacted to the compound of formula (IV) in the presence of a base, in particular in the presence of potassium phosphate.

According to an embodiment of the invention, wherein the compounds of formulae (II-B) and (III) are reacted to the compound of formula (V) and the compound of formula (V) is reacted to the compound of formula (IV) in one single step without isolation of the intermediate (V), the reaction is carried out in the presence of a base.

The process (II-B)+(III)→(V) is generally carried out in a temperature range of 0° C. to 100° C., preferably from 40° C. to 80° C.

According to an embodiment of the invention, the compounds of formulae (II-B) and (III) are reacted at a temperature of 0° C. to 100° C., preferably of 40° C. to 80° C.

The process (V)→(IV) is generally carried out in a temperature range of 0° C. to 150° C., preferably from 60° C. to 130° C.

According to an embodiment of the invention, the compound of formula (V) is reacted to a compound of formula (IV) at a temperature of 0° C. to 150° C., preferably of 60° C. to 130° C.

According to an embodiment of the invention, wherein $R^6$ is an acid cleavable amino protective group, such as tert-butoxycarbonyl, the compound of the formula (IV) obtained in reaction [A] or [B] is reacted to the compound of the formula (I-B) by addition of an acid. This reaction is carried out in a suitable solvent, e.g. dioxane.

Generally, the salts of formula (I-B) may be transformed to the respective free bases of formula (I-A) by any way known to the person skilled in art.

The compound of formula (I-B) may be reacted to the compound of formula (I-A) by treating the compound of formula (I-B) with a base. Preferred bases are ammonia, sodium hydroxide, NaHCO$_3$, and Na$_2$CO$_3$. This may also be achieved by a suitable chromatographic method by using a basic eluent.

According to an embodiment of the invention, the acid used to obtain the compound of the formula (I-B) from the compound of the formula (IV) is selected from hydrochloric acid, trifluoroacetic acid, acetic acid, sulphuric acid, maleic acid, tartaric acid, ascorbic acid, and salicylic acid.

According to an embodiment of the invention, wherein $R^6$ is not cleaved by an acid, the compound of the formula (I-A) is obtained from the compound of formula (IV) by cleaving the amino protection group of the compound of formula (IV) for example by hydrogenation. Examples for this reaction are the cleavage of benzyloxycarbonyl (Cbz), and of optionally substituted benzyl.

The compounds of the formulae (II-A), (III) and (II-B) are commercially available, known from the literature or can be prepared analogously to processes known from the literature. The synthesis of compounds of the formula (II-B) is described in scheme 3 below. Schemes 4 to 6 below describe the preparation of certain compounds of the formulae (I-A) or (I-B).

Scheme 4: Preparation of 3-(hetero)arylpyrazolopyrimidinones via the bromo derivative

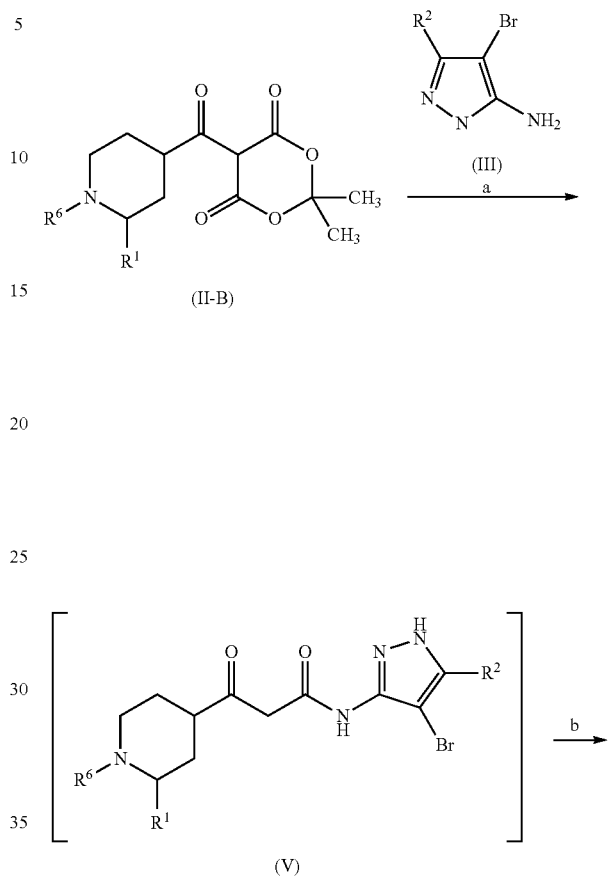

Scheme 3: Synthesis of the methylpiperidinyl Meldrum's acid derivative

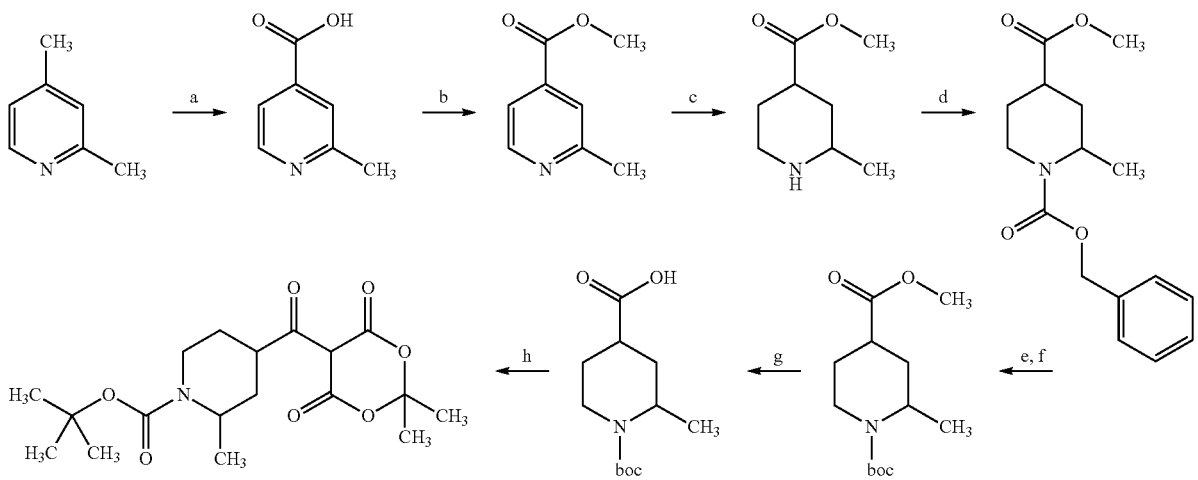

a) 2,4-lutidine, KMnO$_4$, water, 80° C.; b) thionyl chloride, methanol, reflux; c) AcOH, platinum(IV)oxide, 20 bar, RT; d) benzyl chloroformate, diisopropylethylamine, dichloromethane, RT, then separation of the stereoisomers by chromatography on chiral phase;
e) Pd/C, H$_2$, ethanol, RT; f) di-tert-butyl dicarbonate, tetrahydrofurane, RT; g) lithium hydroxide, tetrahydrofuran/water, RT; h) 2,2-dimethyl-1,3-dioxane-4,6-dione, DMAP, EDCI, dichloromethane, RT.

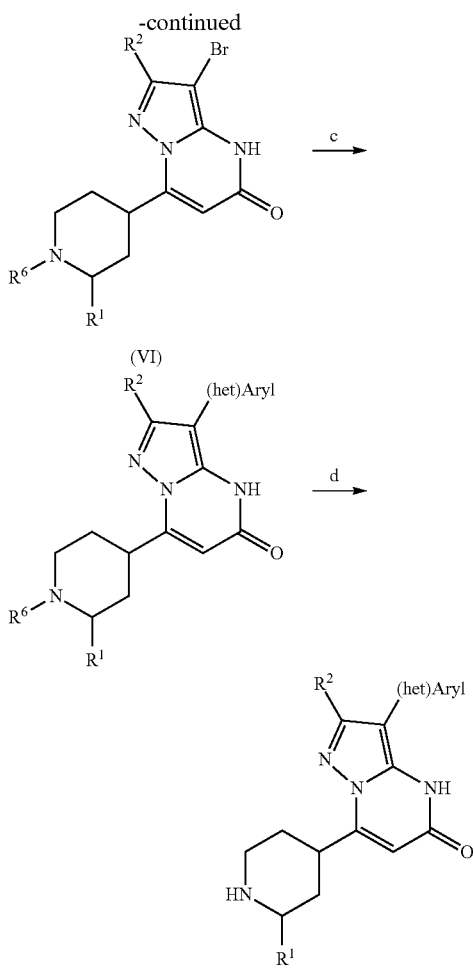

a) acetonitrile, 60° C.; b) 1-methoxy-2-propanol, tripotassium phosphate, 110° C., c) (2-Dicyclohexylphosphino-2',4',6'-triisopropyl-1,1'-biphenyl)[2-(2'-amino-1,1'-biphenyl)]palladium(II) methanesulfonate (=Xphos precatalyst), tetrahydrofuran, 1M aqueous tripotassium phosphate-solution, 40° C.; d) HCl 4N in dioxane, RT or TFA, dichloromethane, RT.

The condensation process (II-B)+(III)→[(V)]→(VI) can be carried out in one single step without isolation of the intermediate (V), in two separate steps by changing the reaction conditions for the formation of (V) from (II-B) and (III) and the formation of (VI) from (V) but without purification of the intermediate (V), or in two separate steps involving the purification of intermediate (V). Preference is given to a procedure with two separate steps without purification of the intermediate.

According to an embodiment of the invention, the compounds of formulae (II-B) and (III) are reacted in a first step to a compound of formula (V). The compound of formula (V) is reacted in a second step to the compound of formula (VI) without separation and purification of the intermediate (V). According to a further embodiment of the invention, the solvent is changed between the first and the second step.

Suitable solvents for the process steps (II-B)+(III)→(V) are, for example, aliphatic alcohols such as methanol, ethanol, iso-propanol, 1-methoxy-2-propanol or tert-butanol, ethers such as diethyl ether, dioxane, tetrahydrofuran, glycol dimethyl ether or diethylene glycol dimethyl ether, hydrocarbons such as benzene, toluene, xylene, hexane, cyclohexane or mineral oil fractions, halogenated hydrocarbons such as dichloromethane, trichloromethane, carbon tetrachloride, 1,2-dichloroethane, trichloroethylene or chlorobenzene, or other solvents such as acetone, ethyl acetate, acetonitrile, pyridine, dimethyl sulphoxide, N,N-dimethylformamide, N,N-dimethylacetamide, N,N'-dimethylpropyleneurea (DMPU) or N-methylpyrrolidone (NMP). It is also possible to use mixtures of the solvents mentioned. Preference is given to using acetonitrile or toluene as solvents, or mixtures of these solvents.

Suitable solvents for the process steps (V)→(VI) are, for example, aliphatic alcohols such as methanol, ethanol, iso-propanol, 1-methoxy-2-propanol or tert-butanol, ethers such as diethyl ether, dioxane, tetrahydrofuran, glycol dimethyl ether or diethylene glycol dimethyl ether, hydrocarbons such as benzene, toluene, xylene, hexane, cyclohexane or mineral oil fractions, halogenated hydrocarbons such as dichloromethane, trichloromethane, carbon tetrachloride, 1,2-dichloroethane, trichloroethylene or chlorobenzene, or other solvents such as acetone, ethyl acetate, acetonitrile, pyridine, dimethyl sulphoxide, N,N-dimethylformamide, N,N-dimethylacetamide, N,N'-dimethylpropyleneurea (DMPU) or N-methylpyrrolidone (NMP). It is also possible to use mixtures of the solvents mentioned. Preference is given to using 1-methoxy-2-propanol or toluene or acetonitrile as solvents, or mixtures of these solvents.

The process (II)+(III)→(V) may proceed in the absence of a base, in the presence of organic bases such as triethylamine or diisopropylethylamine, or in the presence of inorganic bases. Inorganic bases include alkali metal or alkali earth metal phosphates and carbonates such as potassium phosphate, potassium carbonate, cesium carbonate, sodium phosphate, or calcium carbonate. Preference is given to reacting the compounds of formulae (II-B) and (III) in the absence of a base.

According to an embodiment of the invention, the compounds of formulae (II-B) and (III) are reacted in the absence of a base.

The condensation process (V)→(VI) may proceed in the absence of a base, in the presence of organic bases such as triethylamine or diisopropylethylamine, or in the presence of inorganic bases. Inorganic bases include alkali metal or alkali earth metal phosphates and carbonates such as potassium phosphate, potassium carbonate, cesium carbonate, sodium phosphate, or calcium carbonate. Preference is given to reacting the compound of formula (V) to the compound of formula (VI) in the presence of potassium phosphate.

According to an embodiment of the invention, the compound of formula (V) is reacted to the compound of formula (VI) in the presence of a base, in particular in the presence of potassium phosphate.

According to an embodiment of the invention, wherein the compounds of formulae (II-B) and (III) are reacted to the compound of formula (V) and the compound of formula (V) is reacted to the compound of formula (VI) in one single step without isolation of the intermediate (V), the reaction is carried out in the presence of a base.

The process (II-B)+(III)→(V) is generally carried out in a temperature range of 0° C. to 100° C., preferably from 40° C. to 80° C.

According to an embodiment of the invention, the compounds of formulae (II-B) and (III) are reacted at a temperature of 0° C. to 100° C., preferably of 40° C. to 80° C.

The process (V)→(VI) is generally carried out in a temperature range of 0° C. to 150° C., preferably from 60° C. to 130° C.

According to an embodiment of the invention, the compound of formula (V) is reacted to a compound of formula (VI) at a temperature of 0° C. to 150° C., preferably of 60° C. to 130° C.

According to an embodiment of the invention, wherein $R^6$ is an acid cleavable amino protective group, such as tert-butoxycarbonyl, the compound of the formula (VI) obtained in reaction [A] or [B] is reacted to the compound of the formula (I-B) by addition of an acid. This reaction is carried out in a suitable solvent, e.g. dioxane.

Generally, the salts of formula (I-B) may be transformed to the respective free bases of formula (I-A) by any way known to the person skilled in art.

The compound of formula (I-B) may be reacted to the compound of formula (I-A) by treating the compound of formula (I-B) with a base. Preferred bases are ammonia, sodium hydroxide, $NaHCO_3$, and $Na_2CO_3$. This may also be achieved by a suitable chromatographic method by using a basic eluent.

According to an embodiment of the invention, the acid used to obtain the compound of the formula (I-B) from the compound of the formula (VI) is selected from hydrochloric acid, trifluoroacetic acid, acetic acid, sulphuric acid, maleic acid, tartaric acid, ascorbic acid, and salicylic acid.

According to an embodiment of the invention, wherein $R^6$ is not cleaved by an acid, the compound of the formula (I-A) is obtained from the compound of formula (VI) by cleaving the amino protection group of the compound of formula (VI) for example by hydrogenation. Examples for this reaction are the cleavage of benzyloxycarbonyl (Cbz), and of optionally substituted benzyl.

The compounds of the formulae (III) and (II-B) are commercially available, known from the literature or can be prepared analogously to processes known from the literature.

Scheme 5: Preparation of 3-amidopyrazolopyrimidinones via the $C_1$—$C_4$ alkyl ester derivative

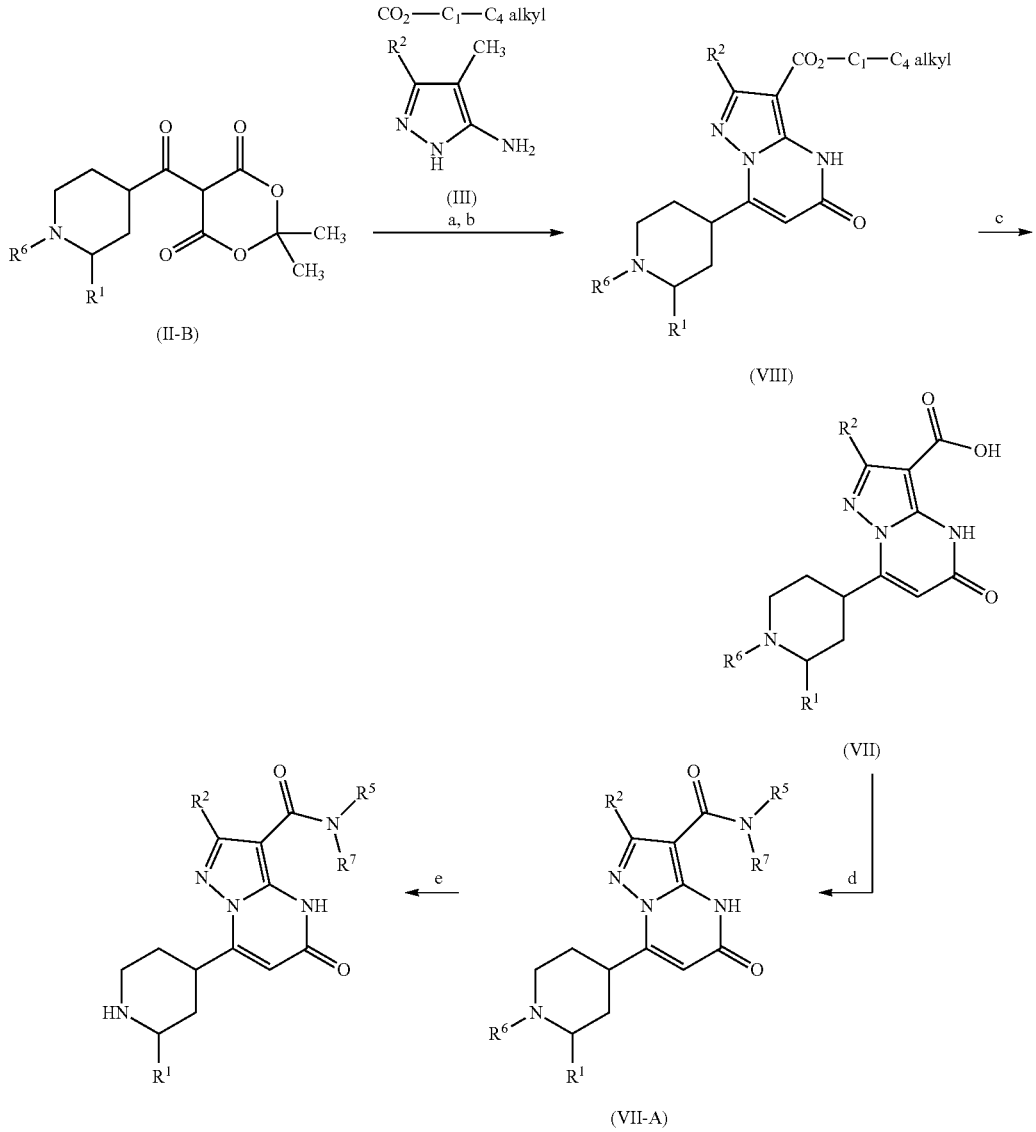

a) $C_1$-$C_4$-alkyl 5-amino-1H-pyrazole-4-carboxylate (III), acetonitrile, 60° C.;
b) 1-methoxy-2-propanol, tripotassium phosphate, 110° C., c) LiOH, THF/water 60° C.; d) $HNR^5R^7$; HOBt, EDCI, HCl, DMF, RT; e) HCl 4N in dioxane, RT or TFA, dichloromethane, RT.

The condensation process (II-B)+(III)→[(V)]→(VIII) can be carried out in one single step without isolation of the intermediate (V), in two separate steps by changing the reaction conditions for the formation of (V) from (II-B) and (III) and the formation of (VIII) from (V) but without purification of the intermediate (V), or in two separate steps involving the purification of intermediate (V). Preference is given to a procedure with two separate steps without purification of the intermediate.

According to an embodiment of the invention, the compounds of formulae (II-B) and (III) are reacted in a first step to a compound of formula (V). The compound of formula (V) is reacted in a second step to the compound of formula (VIII) without separation and purification of the intermediate (V). According to a further embodiment of the invention, the solvent is changed between the first and the second step.

Suitable solvents for the process steps (II-B)+(III)→(V) are, for example, aliphatic alcohols such as methanol, ethanol, iso-propanol, 1-methoxy-2-propanol or tert-butanol, ethers such as diethyl ether, dioxane, tetrahydrofuran, glycol dimethyl ether or diethylene glycol dimethyl ether, hydrocarbons such as benzene, toluene, xylene, hexane, cyclohexane or mineral oil fractions, halogenated hydrocarbons such as dichloromethane, trichloromethane, carbon tetrachloride, 1,2-dichloroethane, trichloroethylene or chlorobenzene, or other solvents such as acetone, ethyl acetate, acetonitrile, pyridine, dimethyl sulphoxide, N,N-dimethylformamide, N,N-dimethylacetamide, N,N'-dimethylpropyleneurea (DMPU) or N-methylpyrrolidone (NMP). It is also possible to use mixtures of the solvents mentioned. Preference is given to using acetonitrile or toluene as solvents, or mixtures of these solvents.

Suitable solvents for the process steps (V)→(VIII) are, for example, aliphatic alcohols such as methanol, ethanol, iso-propanol, 1-methoxy-2-propanol or tert-butanol, ethers such as diethyl ether, dioxane, tetrahydrofuran, glycol dimethyl ether or diethylene glycol dimethyl ether, hydrocarbons such as benzene, toluene, xylene, hexane, cyclohexane or mineral oil fractions, halogenated hydrocarbons such as dichloromethane, trichloromethane, carbon tetrachloride, 1,2-dichloroethane, trichloroethylene or chlorobenzene, or other solvents such as acetone, ethyl acetate, acetonitrile, pyridine, dimethyl sulphoxide, N,N-dimethylformamide, N,N-dimethylacetamide, N,N'-dimethylpropyleneurea (DMPU) or N-methylpyrrolidone (NMP). It is also possible to use mixtures of the solvents mentioned. Preference is given to using 1-methoxy-2-propanol or toluene or acetonitrile as solvents, or mixtures of these solvents.

The process (II)+(III)→(V) may proceed in the absence of a base, in the presence of organic bases such as triethylamine or diisopropylethylamine, or in the presence of inorganic bases. Inorganic bases include alkali metal or alkali earth metal phosphates and carbonates such as potassium phosphate, potassium carbonate, cesium carbonate, sodium phosphate, or calcium carbonate. Preference is given to reacting the compounds of formulae (II-B) and (III) in the absence of a base.

According to an embodiment of the invention, the compounds of formulae (II-B) and (III) are reacted in the absence of a base.

The condensation process (V)→(VIII) may proceed in the absence of a base, in the presence of organic bases such as triethylamine or diisopropylethylamine, or in the presence of inorganic bases. Inorganic bases include alkali metal or alkali earth metal phosphates and carbonates such as potassium phosphate, potassium carbonate, cesium carbonate, sodium phosphate, or calcium carbonate. Preference is given to reacting the compound of formula (V) to the compound of formula (VIII) in the presence of potassium phosphate.

According to an embodiment of the invention, the compound of formula (V) is reacted to the compound of formula (VIII) in the presence of a base, in particular in the presence of potassium phosphate.

According to an embodiment of the invention, wherein the compounds of formulae (II-B) and (III) are reacted to the compound of formula (V) and the compound of formula (V) is reacted to the compound of formula (VIII) in one single step without isolation of the intermediate (V), the reaction is carried out in the presence of a base.

The process (II-B)+(III)→(V) is generally carried out in a temperature range of 0° C. to 100° C., preferably from 40° C. to 80° C.

According to an embodiment of the invention, the compounds of formulae (II-B) and (III) are reacted at a temperature of 0° C. to 100° C., preferably of 40° C. to 80° C.

The process (V)→(VIII) is generally carried out in a temperature range of 0° C. to 150° C., preferably from 60° C. to 130° C.

According to an embodiment of the invention, the compound of formula (V) is reacted to a compound of formula (VIII) at a temperature of 0° C. to 150° C., preferably of 60° C. to 130° C.

According to an embodiment of the invention, wherein $R^6$ is an acid cleavable amino protective group, such as tert-butoxycarbonyl, the compound of the formula (VIII) obtained in reaction [A] or [B] is reacted to the compound of the formula (I-B) by addition of an acid. This reaction is carried out in a suitable solvent, e.g. dioxane.

Generally, the salts of formula (I-B) may be transformed to the respective free bases of formula (I-A) by any way known to the person skilled in art.

The compound of formula (I-B) may be reacted to the compound of formula (I-A) by treating the compound of formula (I-B) with a base. Preferred bases are ammonia, sodium hydroxide, $NaHCO_3$, and $Na_2CO_3$. This may also be achieved by a suitable chromatographic method by using a basic eluent.

According to an embodiment of the invention, the acid used to obtain the compound of the formula (I-B) from the compound of the formula (VIII) is selected from hydrochloric acid, trifluoroacetic acid, acetic acid, sulphuric acid, maleic acid, tartaric acid, ascorbic acid, and salicylic acid.

According to an embodiment of the invention, wherein $R^6$ is not cleaved by an acid, the compound of the formula (I-A) is obtained from the compound of formula (VIII) by cleaving the amino protection group of the compound of formula (VIII) for example by hydrogenation. Examples for this reaction are the cleavage of benzyloxycarbonyl (Cbz), and of optionally substituted benzyl.

The compounds of the formulae (III) and (II-B) are commercially available, known from the literature or can be prepared analogously to processes known from the literature.

The reaction in process (VIII)→(VII) is generally effected in solvents, in the presence of a base, preferably within a temperature range from 0° C. to the reflux of the solvents at standard pressure.

Suitable solvents for the process step are, for example, water, or aliphatic alcohols such as methanol, ethanol, iso-propanol, 1-methoxy-2-propanol or tert-butanol, ethers such as diethyl ether, dioxane, tetrahydrofuran, glycol dimethyl ether or diethylene glycol dimethyl ether, hydrocarbons such as benzene, toluene, xylene, hexane, cyclohexane or mineral oil fractions, halogenated hydrocarbons such as carbon tetrachloride, trichloroethylene or chlorobenzene, or other solvents such as acetonitrile, pyridine, dimethyl sulphoxide, N,N-dimethylformamide, N,N-dimethylacetamide, N,N'-dimethylpropyleneurea (DMPU) or N-methylpyrrolidone (NMP). It is also possible to use mixtures of the solvents mentioned. Preference is given to using water or water in combination with tetrahydrofuran.

Bases are alkali hydroxides, such as lithium hydroxide or sodium hydroxide or potassium hydroxide or caesium hydroxide. Bases can also be used as solutions in water. Preference is given to lithium hydroxide.

The reaction in process (VII)→(VII-A) is generally effected in inert solvents, optionally in the presence of a dehydrating reagent, optionally in the presence of a base, preferably within a temperature range from 0° C. to the reflux of the solvents at standard pressure.

Suitable dehydrating reagents here are, for example, carbodiimides, for example N,N'-diethyl-, N,N'-dipropyl-, N,N'-diisopropyl- and N,N'-dicyclohexylcarbodiimide, N-(3-dimethylaminoisopropyl)-N'-ethylcarbodiimide hydrochloride (EDC) (optionally in the presence of pentafluorophenol (PFP)), N-cyclohexylcarbodiimide-N'-propyloxymethyl-polystyrene (PS-carbodiimide) or carbonyl compounds such as 1,1'-carbonyldiimidazole, or 1,2-oxazolium compounds such as 2-ethyl-5-phenyl-1,2-oxazolium 3-sulphate or 2-tert-butyl-5-methyl-isoxazolium perchlorate, or acylamino compounds such as 2-ethoxy-1-ethoxycarbonyl-1,2-dihydroquinoline, or propanephosphonic anhydride, or isobutyl chloroformate, or bis-(2-oxo-3-oxazolidinyl)phosphoryl chloride or benzotriazolyloxytri(dimethylamino)phosphonium hexafluorophosphate, or O-(benzotriazol-1-yl)-N,N,N',N'-tetramethyluronium hexafluorophosphate (HBTU), 2-(2-oxo-1-(2H)-pyridinyl)-1,1,3,3-tetramethyluronium tetrafluoroborate (TPTU), (benzotriazol-1-yloxy)bisdimethylaminomethylium fluoroborate (TBTU) or O-(7-azabenzotriazol-1-yl)-N,N,N',N'-tetramethyluronium hexafluorophosphate (HATU), or 1-hydroxybenzotriazole (HOBt), or benzotriazol-1-yloxytris(dimethylamino)phosphonium hexafluorophosphate (BOP), or ethyl cyano(hydroxyimino) acetate (Oxyma), or (1-cyano-2-ethoxy-2-oxoethylideneaminooxy)dimethylamino-morpholino-carbenium hexafluorophosphate (COMU), or N-[(dimethylamino)(3H-[1,2,3]triazolo[4,5-b]pyridin-3-yloxy)methylidene]-N-methylmethanaminium hexafluorophosphate, or 2,4,6-tripropyl-1,3,5,2,4,6-trioxatriphosphinane 2,4,6-trioxide (T3P), or mixtures of these, preference being given to N-(3-dimethylaminoisopropyl)-N'-ethylcarbodiimide hydrochloride or N-(3-dimethylaminoisopropyl)-N'-ethylcarbodiimide hydrochloride in combination with 1-hydroxybenzotriazole.

Bases are, for example, alkali metal carbonates, for example sodium carbonate or potassium carbonate, or sodium hydrogencarbonate or potassium hydrogencarbonate, or organic bases such as trialkylamines, for example triethylamine, N-methylmorpholine, N-methylpiperidine, 4-dimethylaminopyridine or diisopropylethylamine, preference being given to diisopropylethylamine.

Inert solvents are, for example, halogenated hydrocarbons such as dichloromethane or trichloromethane, hydrocarbons such as benzene, or other solvents such as nitromethane, tetrahydrofuran, dioxane, dimethylformamide, dimethyl sulphoxide, acetonitrile or pyridine, or mixtures of the solvents, preference being given to dimethylformamide.

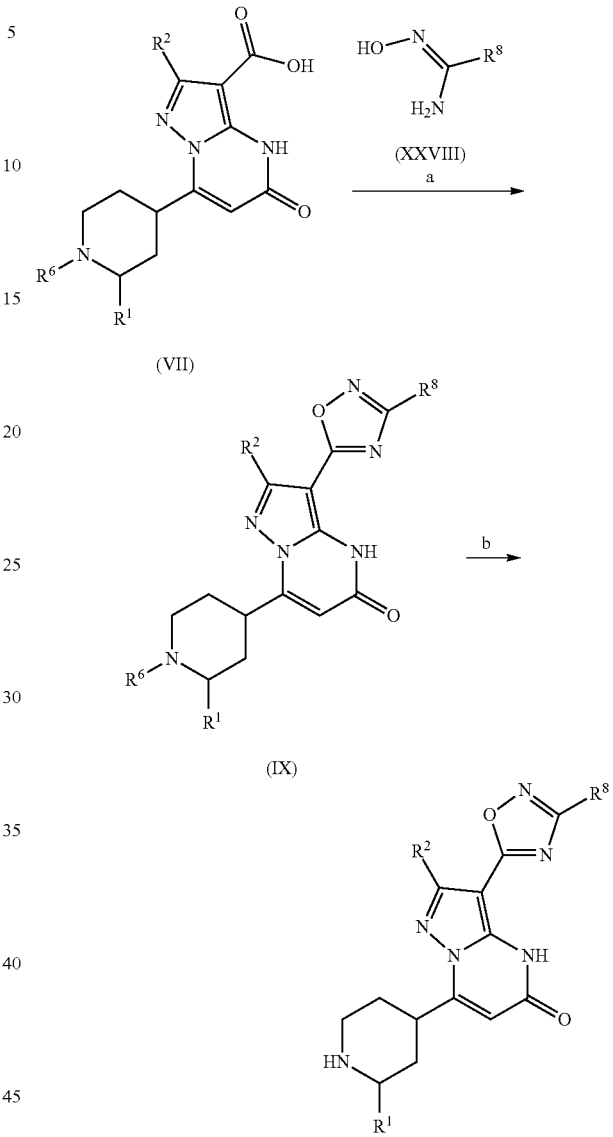

Scheme 6: Preparation of 1,2,4 oxadiazol-5-yl pyrazolopyrimidinones via the carboxylic acid derivative a) i. CDI, diisopropylethylamine, DMF, 60-90° C. ii. amidoxime of formula (XXVIII), 120° C.; b) HCl 4N in dioxane, RT or TFA, dichloromethane, RT. $R^8$ is as defined above as substituent of 1,2,4 oxadiazol-5-yl, wherein the 1,2,4 oxadiazol-5-yl together with $R^8$ forms $R^3$.

The reaction in process (VII)→(IX) is generally effected in inert solvents, optionally in the presence of a dehydrating reagent, optionally in the presence of a base, preferably within a temperature range from 0° C. to the reflux of the solvents at standard pressure.

Suitable dehydrating reagents here are, for example, carbodiimides, for example N,N'-diethyl-, N,N'-dipropyl-, N,N'-diisopropyl- and N,N'-dicyclohexylcarbodiimide, N-(3-dimethylaminoisopropyl)-N'-ethylcarbodiimide hydrochloride (EDC) (optionally in the presence of pentafluorophenol (PFP)), N-cyclohexylcarbodiimide-N'-propyloxymethyl-polystyrene (PS-carbodiimide) or carbonyl compounds such as 1,1-carbonyldiimidazole (CDI), or 1,2-oxazolium compounds such as 2-ethyl-5-phenyl-1,2-oxazolium 3-sulphate or 2-tert-butyl-5-methyl-isoxazolium perchlorate, or acylamino compounds such as 2-ethoxy-1-ethoxycarbonyl-1,2-dihydroquinoline, or propanephosphonic anhydride, or isobutyl chloroformate, or bis-(2-oxo-3-oxazolidinyl)phosphoryl chloride or benzotriazolyloxytri(dimethylamino)phosphonium hexafluorophosphate, or O-(benzotriazol-1-yl)-N,N,N', N'-tetramethyluronium hexafluorophosphate (HBTU), 2-(2-oxo-1-(2H)-pyridinyl)-1,1,3,3-tetramethyluronium tetrafluoroborate (TPTU), (benzotriazol-1-yloxy)bisdimethylaminomethylium fluoroborate (TBTU) or O-(7-azabenzotriazol-1-yl)-N,N,N',N'-tetramethyluronium hexafluorophosphate (HATU), or 1-hydroxybenzotriazole (HOBt), or benzotriazol-1-yloxytris(dimethylamino)phosphonium hexafluorophosphate (BOP), or ethyl cyano(hydroxyimino)acetate (Oxyma), or (1-cyano-2-ethoxy-2-oxoethylideneaminooxy) dimethylaminomorpholinocarbenium hexafluorophosphate (COMU), or N-[(dimethylamino)(3H-[1,2,3]triazolo[4,5-b]pyridin-3-yloxy)methylidene]-N-methylmethanaminium hexafluorophosphate, or 2,4,6-tripropyl-1,3,5,2,4,6-trioxatriphosphinane 2,4,6-trioxide (T3P), or mixtures of these, preference being given to 1,1'-carbonyldiimidazole.

Bases are, for example, alkali metal carbonates, for example sodium carbonate or potassium carbonate, or sodium hydrogencarbonate or potassium hydrogencarbonate, or organic bases such as trialkylamines, for example triethylamine, N-methylmorpholine, N-methylpiperidine, 4-dimethylaminopyridine or diisopropylethylamine, preference being given to diisopropylethylamine.

Inert solvents are, for example, halogenated hydrocarbons such as dichloromethane or trichloromethane, hydrocarbons such as benzene, or other solvents such as nitromethane, tetrahydrofuran, dioxane, dimethylformamide, dimethyl sulphoxide, acetonitrile or pyridine, or mixtures of the solvents, preference being given to dimethylformamide.

Scheme 7: Preparation of 1,3,4 oxadiazol-5-yl-pyrazolopyrimidinones via Burgess reagent

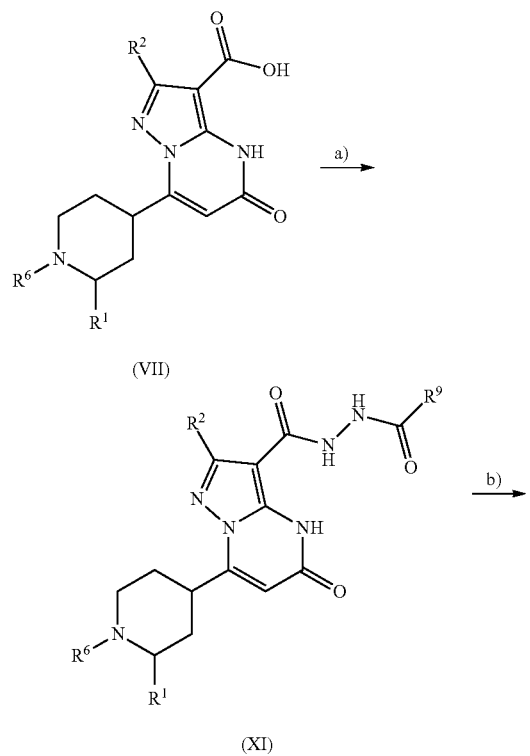

a) hydrazide-R⁹, N,N-Diisopropylethylamin, N-[(Dimethylamino)(3H-[1,2,3]triazolo[4,5-b]pyridin-3-yloxy)methyliden]-N-methyl-methanaminium-hexafluorophosphate (HATU), N,N-Dimethylformamide, RT; b) Methyl N-(triethylammoniosulfonyl)carbamate (Burgess reagent), THF, RT; c), HCl 4N in 1,4 dioxane, 1,4 dioxane, RT. $R^9$ is as defined above as substituent of 1,3,4 oxadiazol-5-yl, wherein the 1,3,4 oxadiazol-5-yl together with $R^9$ forms $R^3$.

The reaction in process (VII)→(XI) is generally effected in inert solvents, optionally in the presence of a base, optionally in the presence of a dehydrating reagent, preferably within a temperature range from 0° C. to the reflux of the solvents at standard pressure.

Suitable dehydrating reagents here are, for example, carbodiimides, for example N,N'-diethyl-, N,N'-dipropyl-, N,N'-diisopropyl- and N,N'-dicyclohexylcarbodiimide, N-(3-dimethylaminoisopropyl)-N'-ethylcarbodiimide hydrochloride (EDC) (optionally in the presence of pentafluorophenol (PFP)), N-cyclohexylcarbodiimide-N'-propyloxymethyl-polystyrene (PS-carbodiimide) or carbonyl compounds such as 1,1'-carbonyldiimidazole, or 1,2-oxazolium compounds such as 2-ethyl-5-phenyl-1,2-oxazolium 3-sulphate or 2-tert-butyl-5-methyl-isoxazolium perchlorate, or acylamino compounds such as 2-ethoxy-1-ethoxycarbonyl-1,2-dihydroquinoline, or propanephosphonic anhydride, or isobutyl chloroformate, or bis-(2-oxo-3-oxazolidinyl)phosphoryl chloride or benzotriazolyloxytri(dimethylamino)phosphonium hexafluorophosphate, or O-(benzotriazol-1-yl)-N,N,N',N'-tetramethyluronium hexafluorophosphate (HBTU), 2-(2-oxo-1-(2H)-pyridinyl)-1,1,3,3-tetramethyluronium tetrafluoroborate (TPTU), (benzotriazol-1-yloxy)bisdimethylaminomethylium fluoroborate (TBTU) or O-(7-azabenzotriazol-1-yl)-N,N,N',N'-tetramethyluronium hexafluorophosphate (HATU), or 1-hydroxybenzotriazole (HOBt), or benzotriazol-1-yloxytris(dimethylamino)phosphonium hexafluorophosphate (BOP), or ethyl cyano(hydroxyimino)acetate (Oxyma), or (1-cyano-2- ethoxy-2-oxoethylideneaminooxy) dimethylaminomorpholinocarbenium hexafluorophosphate (COMU), or N-[(dimethylamino)(3H-[1,2,3]triazolo[4,5-b]pyridin-3-yloxy)methylidene]-N-methylmethanaminium hexafluorophosphate, or 2,4,6-tripropyl-1,3,5,2,4,6-trioxatriphosphinane 2,4,6-trioxide (T3P), or mixtures of these, preference being given to O-(7-azabenzotriazol-1-yl)-N,N,N',N'-tetramethyluronium hexafluorophosphate (HATU).

Bases are, for example, alkali metal carbonates, for example sodium carbonate or potassium carbonate, or sodium hydrogencarbonate or potassium hydrogencarbonate, or organic bases such as trialkylamines, for example triethylamine, N-methylmorpholine, N-methylpiperidine, 4-dimethylaminopyridine or diisopropylethylamine, preference being given to diisopropylethylamine.

Inert solvents are, for example, halogenated hydrocarbons such as dichloromethane or trichloromethane, hydrocarbons such as benzene, or other solvents such as nitromethane, tetrahydrofuran, dioxane, dimethylformamide, dimethyl sulphoxide, acetonitrile or pyridine, or mixtures of the solvents, preference being given to dimethylformamide.

The reaction in process (XI)→(X) is generally effected in inert solvents, in the presence of a dehydrating reagent, preferably within a temperature range from 0° C. to the reflux of the solvents at standard pressure.

Suitable dehydrating reagents here are, for example, methyl N-(triethylammoniosulfonyl)carbamate (Burgess reagent), carbodiimides, for example N,N'-diethyl-, N,N'-dipropyl-, N,N'-diisopropyl- and N,N'-dicyclohexylcarbodiimide, N-(3-dimethylaminoisopropyl)-N'-ethylcarbodiimide hydrochloride (EDC) (optionally in the presence of pentafluorophenol (PFP)), N-cyclohexylcarbodiimide-N'-propyloxymethyl-polystyrene (PS-carbodiimide) or carbonyl compounds such as 1,1'-carbonyldiimidazole, or 1,2-oxazolium compounds such as 2-ethyl-5-phenyl-1,2-oxazolium 3-sulphate or 2-tert-butyl-5-methyl-isoxazolium perchlorate, or acylamino compounds such as 2-ethoxy-1-ethoxycarbonyl-1,2-dihydroquinoline, or propanephosphonic anhydride, or isobutyl chloroformate, or bis-(2-oxo-3-oxazolidinyl)phosphoryl chloride or benzotriazolyloxytri(dimethylamino)phosphonium hexafluorophosphate, or O-(benzotriazol-1-yl)-N,N,N',N'-tetramethyluronium hexafluorophosphate (HBTU), 2-(2-oxo-1-(2H)-pyridinyl)-1,1,3,3-tetramethyluronium tetrafluoroborate (TPTU), (benzotriazol-1-yloxy)bisdimethylaminomethylium fluoroborate (TBTU) or O-(7-azabenzotriazol-1-yl)-N,N,N',N'-tetramethyluronium hexafluorophosphate (HATU), or benzotriazol-1-yloxytris (dimethylamino)phosphonium hexafluorophosphate (BOP), or ethyl cyano(hydroxyimino)acetate (Oxyma), or (1-cyano-2-ethoxy-2-oxoethylideneaminooxy) dimethylaminomorpholinocarbenium hexafluorophosphate (COMU), or N-[(dimethylamino)(3H-[1,2,3]triazolo[4,5-b]pyridin-3-yloxy)methylidene]-N-methylmethanaminium hexafluorophosphate, or 2,4,6-tripropyl-1,3,5,2,4,6-trioxatriphosphinane 2,4,6-trioxide (T3P), or mixtures of these, preference being given to methyl N-(triethylammoniosulfonyl)carbamate.

Inert solvents are, for example, halogenated hydrocarbons such as dichloromethane or trichloromethane, hydrocarbons such as benzene, or other solvents such as nitromethane, tetrahydrofuran, dioxane, dimethylformamide, dimethyl sulphoxide, acetonitrile or pyridine, or mixtures of the solvents, preference being given to tetrahydrofuran.

Scheme 8: Preparation of 1,2,4 oxadiazol-3-yl-pryazolopyrimidinones via the nitrile derivative

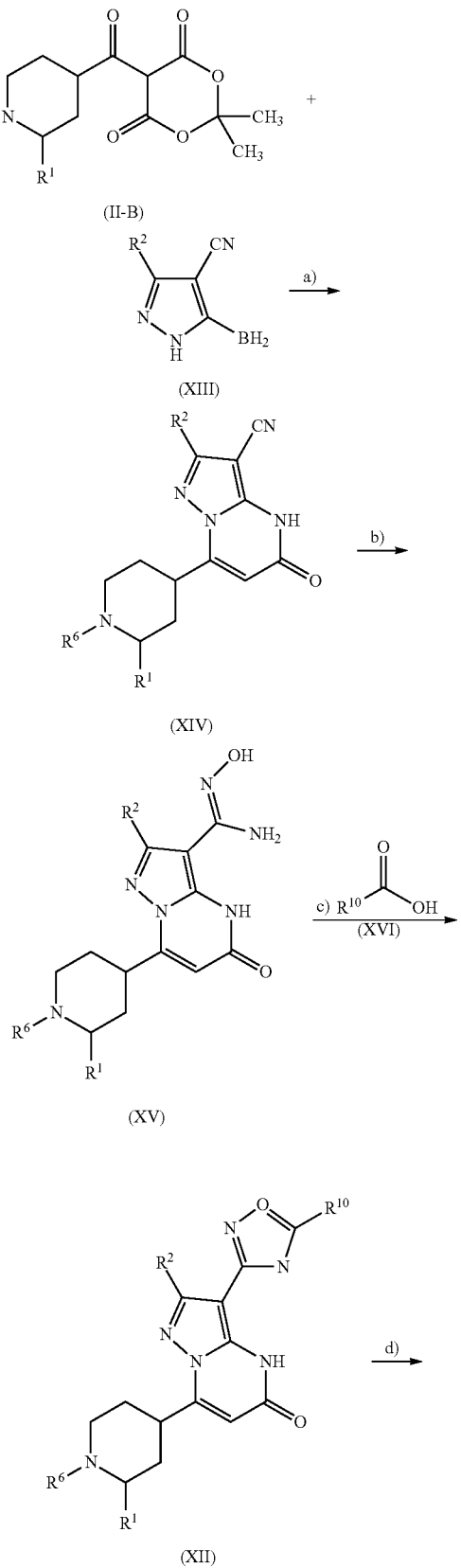

-continued

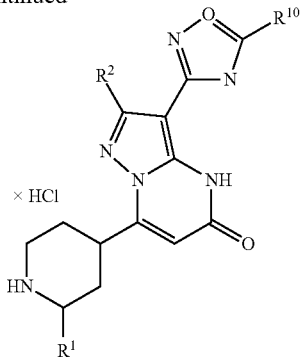

a) i. acetonitrile, 60° C., ii. 1-methoxy-2-propanol, tripotassium phosphate,
120° C.; b) hydroxylamine hydrochloride, triethylamine, ethanol,
50° C.; c) i. carboxylic acid (XVI), (benzotriazol-1-yloxy)tripyrrolidinophosphonium
hexafluorophosphate, ethyldiisopropylamine,
N,N-dimethylformamide, RT, ii. (XV) 110° C., d) HCl 4N in 1,4-dioxan,
1,4-dioxan, RT. $R^{10}$ is as defined above as substituent of 1,2,4 oxadiazol-3-yl, wherein
the 1,2,4 oxadiazol-3-yl together with $R^{10}$ forms $R^3$.

The condensation process (II-B)+(XIII)→[(V)]→(XIV) can be carried out in one single step without isolation of the intermediate (V), in two separate steps by changing the reaction conditions for the formation of (V) from (II-B) and (XIII) and the formation of (XIV) from (V) but without purification of the intermediate (V), or in two separate steps involving the purification of intermediate (V). Preference is given to a procedure with two separate steps without purification of the intermediate.

According to an embodiment of the invention, the compounds of formulae (II-B) and (XIII) are reacted in a first step to a compound of formula (V). The compound of formula (V) is reacted in a second step to the compound of formula (XIV) without separation and purification of the intermediate (V). According to a further embodiment of the invention, the solvent is changed between the first and the second step.

Suitable solvents for the process steps (II-B)+(XIII)→(V) are, for example, aliphatic alcohols such as methanol, ethanol, iso-propanol, 1-methoxy-2-propanol or tert-butanol, ethers such as diethyl ether, dioxane, tetrahydrofuran, glycol dimethyl ether or diethylene glycol dimethyl ether, hydrocarbons such as benzene, toluene, xylene, hexane, cyclohexane or mineral oil fractions, halogenated hydrocarbons such as dichloromethane, trichloromethane, carbon tetrachloride, 1,2-dichloroethane, trichloroethylene or chlorobenzene, or other solvents such as acetone, ethyl acetate, acetonitrile, pyridine, dimethyl sulphoxide, N,N-dimethylformamide, N,N-dimethylacetamide, N,N'-dimethylpropyleneurea (DMPU) or N-methylpyrrolidone (NMP). It is also possible to use mixtures of the solvents mentioned. Preference is given to using acetonitrile or toluene as solvents, or mixtures of these solvents.

Suitable solvents for the process steps (V)→(XIV) are, for example, aliphatic alcohols such as methanol, ethanol, iso-propanol, 1-methoxy-2-propanol or tert-butanol, ethers such as diethyl ether, dioxane, tetrahydrofuran, glycol dimethyl ether or diethylene glycol dimethyl ether, hydrocarbons such as benzene, toluene, xylene, hexane, cyclohexane or mineral oil fractions, halogenated hydrocarbons such as dichloromethane, trichloromethane, carbon tetrachloride, 1,2-dichloroethane, trichloroethylene or chlorobenzene, or other solvents such as acetone, ethyl acetate, acetonitrile, pyridine, dimethyl sulphoxide, N,N-dimethylformamide, N,N-dimethylacetamide, N,N'-dimethylpropyleneurea (DMPU) or N-methylpyrrolidone (NMP). It is also possible to use mixtures of the solvents mentioned. Preference is given to using 1-methoxy-2-propanol or toluene or acetonitrile as solvents, or mixtures of these solvents.

The process (II)+(XIII)→(V) may proceed in the absence of a base, in the presence of organic bases such as triethylamine or diisopropylethylamine, or in the presence of inorganic bases. Inorganic bases include alkali metal or alkali earth metal phosphates and carbonates such as potassium phosphate, potassium carbonate, cesium carbonate, sodium phosphate, or calcium carbonate. Preference is given to reacting the compounds of formulae (II-B) and (XIII) in the absence of a base.

According to an embodiment of the invention, the compounds of formulae (II-B) and (XIII) are reacted in the absence of a base.

The condensation process (V)→(XIV) may proceed in the absence of a base, in the presence of organic bases such as triethylamine or diisopropylethylamine, or in the presence of inorganic bases. Inorganic bases include alkali metal or alkali earth metal phosphates and carbonates such as potassium phosphate, potassium carbonate, cesium carbonate, sodium phosphate, or calcium carbonate. Preference is given to reacting the compound of formula (V) to the compound of formula (XIV) in the presence of potassium phosphate.

According to an embodiment of the invention, the compound of formula (V) is reacted to the compound of formula (XIV) in the presence of a base, in particular in the presence of potassium phosphate.

According to an embodiment of the invention, wherein the compounds of formulae (II-B) and (XIII) are reacted to the compound of formula (V) and the compound of formula (V) is reacted to the compound of formula (XIV) in one single step without isolation of the intermediate (V), the reaction is carried out in the presence of a base.

The process (II-B)+(XIII)→(V) is generally carried out in a temperature range of 0° C. to 100° C., preferably from 40° C. to 80° C.

According to an embodiment of the invention, the compounds of formulae (II-B) and (XIII) are reacted at a temperature of 0° C. to 100° C., preferably of 40° C. to 80° C.

The process (V)→(XIV) is generally carried out in a temperature range of 0° C. to 150° C., preferably from 60° C. to 130° C.

According to an embodiment of the invention, the compound of formula (V) is reacted to a compound of formula (XIV) at a temperature of 0° C. to 150° C., preferably of 60° C. to 130° C.

According to an embodiment of the invention, wherein $R^6$ is an acid cleavable amino protective group, such as tert-butoxycarbonyl, the compound of the formula (XIV) obtained in reaction [A] or [B] is reacted to the compound of the formula (I-B) by addition of an acid. This reaction is carried out in a suitable solvent, e.g. dioxane.

Generally, the salts of formula (I-B) may be transformed to the respective free bases of formula (I-A) by any way known to the person skilled in art.

The compound of formula (I-B) may be reacted to the compound of formula (I-A) by treating the compound of formula (I-B) with a base. Preferred bases are ammonia, sodium hydroxide, $NaHCO_3$, and $Na_2CO_3$. This may also be achieved by a suitable chromatographic method by using a basic eluent.

According to an embodiment of the invention, the acid used to obtain the compound of the formula (I-B) from the compound of the formula (XIV) is selected from hydrochloric acid, trifluoroacetic acid, acetic acid, sulphuric acid, maleic acid, tartaric acid, ascorbic acid, and salicylic acid.

According to an embodiment of the invention, wherein $R^6$ is not cleaved by an acid, the compound of the formula (I-A) is obtained from the compound of formula (XIV) by cleaving the amino protection group of the compound of formula (XIV) for example by hydrogenation. Examples for this reaction are the cleavage of benzyloxycarbonyl (Cbz), and of optionally substituted benzyl.

The compounds of the formulae (XIII) and (II-B) are commercially available, known from the literature or can be prepared analogously to processes known from the literature.

The reaction in process (XIV)→(XV) is generally effected in the presence of hydroxylamine or its salt, in inert solvents, optionally in the presence of a base, preferably within a temperature range from 0° C. to the reflux of the solvents at standard pressure.

The reaction in process (XIV)→(XV) is effected in the presence of hydroxylamine or one of its salts like hydroxylamine hydrochloride or hydroxylamine acetate. Preference is given to hydroxylamine hydrochloride.

The reactions in process (XIV)→(XV) may proceed in the absence of a base, or in the presence of organic bases such as metal alcoholates, such as sodium tert-butoxide, potassium tert-butoxide, and metal amides, or amines such as triethylamine or diisopropylethylamine, or in the presence of inorganic bases. Inorganic bases include alkali metal or alkali earth metal phosphates and carbonates such as potassium phosphate, potassium carbonate, cesium carbonate, sodium phosphate, or calcium carbonate. Preference is given to using triethylamine.

Suitable solvents for reactions in process (XIV)→(XV) are, for example, aliphatic alcohols such as methanol, ethanol, iso-propanol, 1-methoxy-2-propanol, 2-methyl-2-butanol or tert-butanol, ethers such as diethyl ether, dioxane, tetrahydrofuran, glycol dimethyl ether or diethylene glycol dimethyl ether, hydrocarbons such as benzene, toluene, xylene, hexane, cyclohexane or mineral oil fractions, halogenated hydrocarbons such as dichloromethane, trichloromethane, carbon tetrachloride, 1,2-dichloroethane, trichloroethylene or chlorobenzene, or other solvents such as acetone, ethyl acetate, acetonitrile, pyridine, dimethyl sulphoxide, N,N-dimethylformamide, N,N-dimethylacetamide, N,N'-dimethylpropyleneurea (DMPU) or N-methylpyrrolidone (NMP). It is also possible to use mixtures of the solvents mentioned. Preference is given to using ethanol.

The reactions in process (XIV)→(XV) are generally carried out in a temperature range from 0° C. to 200° C. Heating options include conventional heating below the boiling point of the solvent, under reflux, or above the boiling point of the solvent in a closed vial, or in a closed vial with the aid of a microwave reactor. Preference is given to heating the reaction to 50° C.

The reactions in process (XIV)→(XV) can be carried out at atmospheric, elevated or reduced pressure (for example from 0.5 to 25 bar). In general, the reactions are carried out at atmospheric pressure.

The reaction in process (XV)+(XVI)→(XII) is generally effected in inert solvents, optionally in the presence of a dehydrating reagent, optionally in the presence of a base, preferably within a temperature range from 0° C. to the reflux of the solvents at standard pressure.

Suitable dehydrating reagents here are, for example, carbodiimides, for example N,N'-diethyl-, N,N'-dipropyl-, N,N'-diisopropyl- and N,N'-dicyclohexylcarbodiimide, N-(3-dimethylaminoisopropyl)-N'-ethylcarbodiimide hydrochloride (EDC) (optionally in the presence of pentafluorophenol (PFP)), N-cyclohexylcarbodiimide-N'-propyloxymethyl-polystyrene (PS-carbodiimide) or carbonyl compounds such as 1,1'-Carbonyldiimidazole (CDI), or 1,2-oxazolium compounds such as 2-ethyl-5-phenyl-1,2-oxazolium 3-sulphate or 2-tert-butyl-5-methyl-isoxazolium perchlorate, or acylamino compounds such as 2-ethoxy-1-ethoxycarbonyl-1,2-dihydroquinoline, N-isopropoxycarbonyl-2-isopropoxy-1,2-dihydroquinoline, or propanephosphonic anhydride, or isobutyl chloroformate, or bis-(2-oxo-3-oxazolidinyl)phosphoryl chloride or benzotriazolyloxytri(dimethylamino)phosphonium hexafluorophosphate, or O-(benzotriazol-1-yl)-N,N,N',N'-tetramethyluronium hexafluorophosphate (HBTU), 2-(2-oxo-1-(2H)-pyridinyl)-1,1,3,3-tetramethyluronium tetrafluoroborate (TPTU), (benzotriazol-1-yloxy)bisdimethylaminomethylium fluoroborate (TBTU) or O-(7-azabenzotriazol-1-yl)-N,N,N',N'-tetramethyluronium hexafluorophosphate (HATU), O-benzotriazole-N,N,N',N'-tetramethyl-uronium-hexafluorophosphate (HBTU), or 1-hydroxybenzotriazole (HOBt), or benzotriazol-1-yloxytris(dimethylamino)phosphonium hexafluorophosphate (BOP), or benzotriazol-1-yl-oxy-tris-pyrrolidino-phosphonium hexafluorophosphate (commercially available as PyBOP), or ethyl cyano(hydroxyimino) acetate (Oxyma), or (1-cyano-2-ethoxy-2-oxoethylideneaminooxy) dimethylaminomorpholinocarbenium hexafluorophosphate (COMU), or N-[(dimethylamino)(3H-[1,2,3]triazolo[4,5-b]pyridin-3-yloxy)methylidene]-N-methylmethanaminium hexafluorophosphate, or 2,4,6-tripropyl-1,3,5,2,4,6-trioxatriphosphinane 2,4,6-trioxide (T3P), or mixtures of these, preference being given to benzotriazol-1-yl-oxy-tris-pyrrolidino-phosphonium hexafluorophosphate (commercially available as PyBOP).

Bases are, for example, alkali metal carbonates, for example sodium carbonate or potassium carbonate, or sodium hydrogencarbonate or potassium hydrogencarbonate, or organic bases such as trialkylamines, for example triethylamine, N-methylmorpholine, N-methylpiperidine, 4-dimethylaminopyridine or diisopropylethylamine, preference being given to diisopropylethylamine.

Inert solvents are, for example, halogenated hydrocarbons such as dichloromethane or trichloromethane, hydrocarbons such as benzene, or other solvents such as nitromethane, tetrahydrofuran, dioxane, dimethylformamide, dimethyl sulphoxide, acetonitrile or pyridine, or mixtures of the solvents, preference being given to dimethylformamide.

The reactions in process (XV)+(XVI)→(XII) are generally carried out in a temperature range from 0° C. to 200° C. Heating options include conventional heating below the boiling point of the solvent, under reflux, or above the boiling point of the solvent in a closed vial, or in a closed vial with the aid of a microwave reactor. Preference is given to heating the reaction to 20-110° C.

The reactions in process (XV)+(XVI)→(XII) can be carried out at atmospheric, elevated or reduced pressure (for example from 0.5 to 25 bar). In general, the reactions are carried out at atmospheric pressure.

Scheme 9: Preparation of 3-(1,3-thiazol-2-yl)-pyrazolopyrimidinones via the thioamide derivative

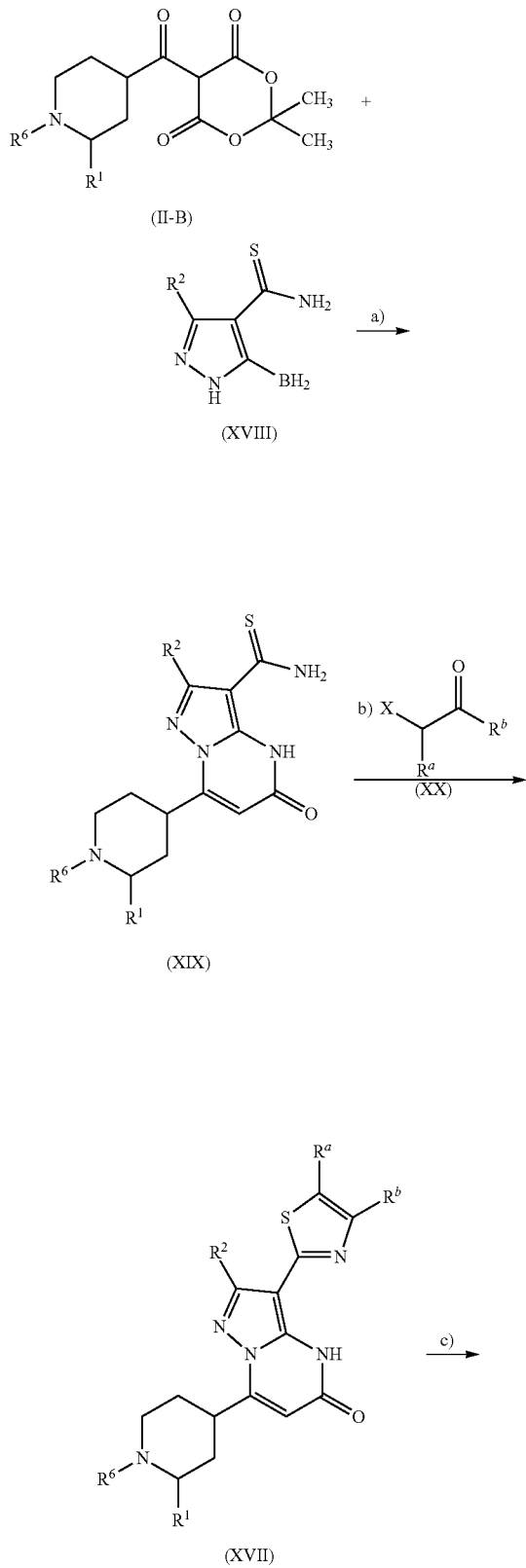

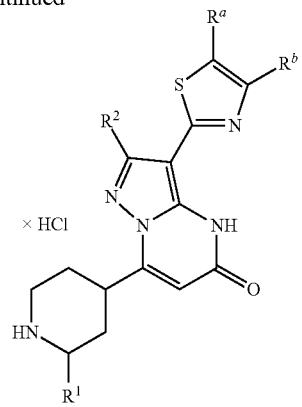

a) i. acetonitrile, 60° C., ii. 1-methoxy-2-propanol, tripotassium phosphate, 100° C.; b) alpha-halo-ketone (XX), N,N-Diisopropylethylamin, ethanol, 70° C.; c) HCl 4N in 1,4-dioxan, 1,4-dioxan, RT, overnight. X = Cl, Br, $R^a/R^b$ are as defined above as substituents of 1,3 thiazolyl, wherein the 1,3 thiazolyl together with $R^a/R^b$ form $R^3$.

The condensation process (II-B)+(XVIII)→[(V)]→(XIX) can be carried out in one single step without isolation of the intermediate (V), in two separate steps by changing the reaction conditions for the formation of (V) from (II-B) and (XVIII) and the formation of (XIX) from (V) but without purification of the intermediate (V), or in two separate steps involving the purification of intermediate (V). Preference is given to a procedure with two separate steps without purification of the intermediate.

According to an embodiment of the invention, the compounds of formulae (II-B) and (XVIII) are reacted in a first step to a compound of formula (V). The compound of formula (V) is reacted in a second step to the compound of formula (XIX) without separation and purification of the intermediate (V). According to a further embodiment of the invention, the solvent is changed between the first and the second step.

Suitable solvents for the process steps (II-B)+(XVIII)→(V) are, for example, aliphatic alcohols such as methanol, ethanol, iso-propanol, 1-methoxy-2-propanol or tert-butanol, ethers such as diethyl ether, dioxane, tetrahydrofuran, glycol dimethyl ether or diethylene glycol dimethyl ether, hydrocarbons such as benzene, toluene, xylene, hexane, cyclohexane or mineral oil fractions, halogenated hydrocarbons such as dichloromethane, trichloromethane, carbon tetrachloride, 1,2-dichloroethane, trichloroethylene or chlorobenzene, or other solvents such as acetone, ethyl acetate, acetonitrile, pyridine, dimethyl sulphoxide, N,N-dimethylformamide, N,N-dimethylacetamide, N,N'-dimethylpropyleneurea (DMPU) or N-methylpyrrolidone (NMP). It is also possible to use mixtures of the solvents mentioned. Preference is given to using acetonitrile or toluene as solvents, or mixtures of these solvents.

Suitable solvents for the process steps (V)→(XIX) are, for example, aliphatic alcohols such as methanol, ethanol, iso-propanol, 1-methoxy-2-propanol or tert-butanol, ethers such as diethyl ether, dioxane, tetrahydrofuran, glycol dimethyl ether or diethylene glycol dimethyl ether, hydrocarbons such as benzene, toluene, xylene, hexane, cyclohexane or mineral oil fractions, halogenated hydrocarbons such as dichloromethane, trichloromethane, carbon tetrachloride, 1,2-dichloroethane, trichloroethylene or chlorobenzene, or other solvents such as acetone, ethyl acetate, acetonitrile, pyridine, dimethyl sulphoxide, N,N-dimethylformamide, N,N-dimethylacetamide, N,N'-dimethylpropyleneurea (DMPU) or N-methylpyrrolidone (NMP). It is also possible to use mixtures of the solvents mentioned. Preference is given to using 1-methoxy-2-propanol or toluene or acetonitrile as solvents, or mixtures of these solvents.

The process (II-B)+(XVIII)→(V) may proceed in the absence of a base, in the presence of organic bases such as triethylamine or diisopropylethylamine, or in the presence of inorganic bases. Inorganic bases include alkali metal or alkali earth metal phosphates and carbonates such as potassium phosphate, potassium carbonate, cesium carbonate, sodium phosphate, or calcium carbonate. Preference is given to reacting the compounds of formulae (II-B) and (XVIII) in the absence of a base.

According to an embodiment of the invention, the compounds of formulae (II-B) and (XVIII) are reacted in the absence of a base.

The condensation process (V)→(XIX) may proceed in the absence of a base, in the presence of organic bases such as triethylamine or diisopropylethylamine, or in the presence of inorganic bases. Inorganic bases include alkali metal or alkali earth metal phosphates and carbonates such as potassium phosphate, potassium carbonate, cesium carbonate, sodium phosphate, or calcium carbonate. Preference is given to reacting the compound of formula (V) to the compound of formula (XIX) in the presence of potassium phosphate.

According to an embodiment of the invention, the compound of formula (V) is reacted to the compound of formula (XIX) in the presence of a base, in particular in the presence of potassium phosphate.

According to an embodiment of the invention, wherein the compounds of formulae (II-B) and (XVIII) are reacted to the compound of formula (V) and the compound of formula (V) is reacted to the compound of formula (XIX) in one single step without isolation of the intermediate (V), the reaction is carried out in the presence of a base.

The process (II-B)+(XVIII)→(V) is generally carried out in a temperature range of 0° C. to 100° C., preferably from 40° C. to 100° C.

According to an embodiment of the invention, the compounds of formulae (II-B) and (XVIII) are reacted at a temperature of 0° C. to 100° C., preferably of 40° C. to 80° C.

The process (V)→(XIX) is generally carried out in a temperature range of 0° C. to 150° C., preferably from 60° C. to 130° C.

According to an embodiment of the invention, the compound of formula (V) is reacted to a compound of formula (XIX) at a temperature of 0° C. to 150° C., preferably of 60° C. to 130° C.

According to an embodiment of the invention, wherein $R^6$ is an acid cleavable amino protective group, such as tert-butoxycarbonyl, the compound of the formula (XIX) obtained in reaction [A] or [B] is reacted to the compound of the formula (I-B) by addition of an acid. This reaction is carried out in a suitable solvent, e.g. dioxane.

Generally, the salts of formula (I-B) may be transformed to the respective free bases of formula (I-A) by any way known to the person skilled in art.

The compound of formula (I-B) may be reacted to the compound of formula (I-A) by treating the compound of formula (I-B) with a base. Preferred bases are ammonia, sodium hydroxide, $NaHCO_3$, and $Na_2CO_3$. This may also be achieved by a suitable chromatographic method by using a basic eluent.

According to an embodiment of the invention, the acid used to obtain the compound of the formula (I-B) from the compound of the formula (XIX) is selected from hydrochloric acid, trifluoroacetic acid, acetic acid, sulphuric acid, maleic acid, tartaric acid, ascorbic acid, and salicylic acid.

According to an embodiment of the invention, wherein $R^6$ is not cleaved by an acid, the compound of the formula (I-A) is obtained from the compound of formula (XIX) by cleaving the amino protection group of the compound of formula (XIX) for example by hydrogenation. Examples for this reaction are the cleavage of benzyloxycarbonyl (Cbz), and of optionally substituted benzyl.

The compounds of the formulae (XVIII) and (II-B) are commercially available, known from the literature or can be prepared analogously to processes known from the literature.

The reaction in process (XIX)+(XX)→(XVII) is generally effected in inert solvents, optionally in the presence of a base, optionally in the presence of a dehydrating reagent, preferably within a temperature range from 0° C. to the reflux of the solvents at standard pressure.

Suitable dehydrating reagents here are, for example, methyl N-(triethylammoniosulfonyl)carbamate (Burgess reagent), carbodiimides, for example N,N'-diethyl-, N,N'-dipropyl-, N,N'-diisopropyl- and N,N'-dicyclohexylcarbodiimide, N-(3-dimethylaminoisopropyl)-N'-ethylcarbodiimide hydrochloride (EDC) (optionally in the presence of pentafluorophenol (PFP)), N-cyclohexylcarbodiimide-N'-propyloxymethyl-polystyrene (PS-carbodiimide) or carbonyl compounds such as 1,1'-carbonyldiimidazole, or 1,2-oxazolium compounds such as 2-ethyl-5-phenyl-1,2-oxazolium 3-sulphate or 2-tert-butyl-5-methyl-isoxazolium perchlorate, or acylamino compounds such as 2-ethoxy-1-ethoxycarbonyl-1,2-dihydroquinoline, or propanephosphonic anhydride, or isobutyl chloroformate, or bis-(2-oxo-3-oxazolidinyl)phosphoryl chloride or benzotriazolyloxytri(dimethylamino)phosphonium hexafluorophosphate, or O-(benzotriazol-1-yl)-N,N,N',N'-tetramethyluronium hexafluorophosphate (HBTU), 2-(2-oxo-1-(2H)-pyridinyl)-1,1,3,3-tetramethyluronium tetrafluoroborate (TPTU), (benzotriazol-1-yloxy)bisdimethylaminomethylium fluoroborate (TBTU) or O-(7-azabenzotriazol-1-yl)-N,N,N',N'-tetramethyluronium hexafluorophosphate (HATU), or benzotriazol-1-yloxytris (dimethylamino)phosphonium hexafluorophosphate (BOP), or ethyl cyano(hydroxyimino)acetate (Oxyma), or (1-cyano-2-ethoxy-2-oxoethylideneaminooxy) dimethylaminomorpholinocarbenium hexafluorophosphate (COMU), or N-[(dimethylamino)(3H-[1,2,3]triazolo[4,5-b] pyridin-3-yloxy)methylidene]-N-methylmethanaminium hexafluorophosphate, or 2,4,6-tripropyl-1,3,5,2,4,6-trioxatriphosphinane 2,4,6-trioxide (T3P), or mixtures of these, preference being given to methyl N-(triethylammoniosulfonyl)carbamate.

Bases are, for example, alkali metal carbonates, for example sodium carbonate or potassium carbonate, or sodium hydrogencarbonate or potassium hydrogencarbonate, or organic bases such as trialkylamines, for example triethylamine, N-methylmorpholine, N-methylpiperidine, 4-dimethylaminopyridine or N,N-Diisopropylethylamine, preference being given to N,N-Diisopropylethylamine.

Inert solvents are, for example, alcohols, such as aliphatic alcohols such as methanol, ethanol, iso-propanol, 1-methoxy-2-propanol or tert-butanol, ethers such as diethyl ether, dioxane, tetrahydrofuran, glycol dimethyl ether or diethylene glycol dimethyl ether, hydrocarbons such as benzene, toluene, xylene, hexane, cyclohexane or mineral oil fractions, halogenated hydrocarbons such as dichloromethane, trichloromethane, carbon tetrachloride, 1,2-dichloroethane, trichloroethylene or chlorobenzene, or other solvents such as acetone, ethyl acetate, acetonitrile, pyridine, dimethyl sulphoxide, N,N-dimethylformamide, N,N-dimethylacetamide, N,N'-dimethylpropyleneurea (DMPU) or N-methylpyrrolidone (NMP). It is also possible to use mixtures of the solvents mentioned. Preference being given to ethanol.

such as metal alcoholates, such as sodium tert-butoxide, potassium tert-butoxide, and metal amides, such as Lithium diisopropylamide or Lithium bis(trimethylsylyl)amide, or amines such as triethylamine or diisopropylethylamine, or in the presence of inorganic bases. Inorganic bases include alkali metal or alkali earth metal phosphates and carbonates Scheme 10: Suzuki coupling with the PMB-protected pyridone bromopyrazolopyrimidinone derivative

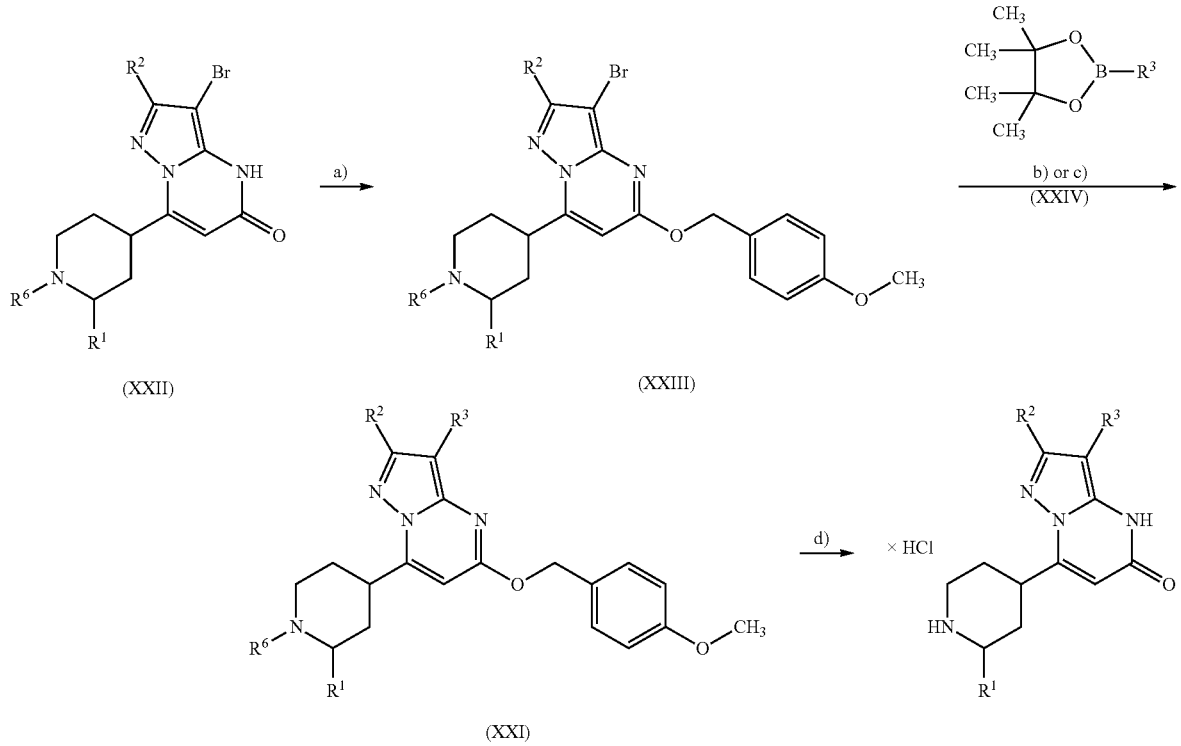

a) 1-(chloromethyl)-4-methoxybenzene, potassium carbonate, N,N-dimethylformamide, 45° C.; b) [1,1'-Bis(diphenylphosphino)ferrocene]dichloropalladium(II), tricyclohexylphosphine, tripotassium phosphate, 1,4-dioxan, microwave, 140° C. c) (2-Dicyclohexylphosphino-2',4',6'-triisopropyl-1,1'-biphenyl)[2-(2'-amino-1,1'-biphenyl)]palladium(II), tripotassium phosphate, 1,4-dioxan, 70° C. → 110° C.; d) HCl 4N in 1,4-dioxan, 1,4-dioxan, RT.

The reaction in process (XXII)→(XXIII) is generally effected in inert solvents, in the presence of a base and 1-(halomethyl)-4-methoxybenzene, preferably within a temperature range from 0° C. to the reflux of the solvents at standard pressure.

Suitable solvents for reactions in process (XXII)→(XXIII) are, for example, aliphatic alcohols such as methanol, ethanol, iso-propanol, 1-methoxy-2-propanol, 2-methyl-2-butanol or tert-butanol, ethers such as diethyl ether, dioxane, tetrahydrofuran, glycol dimethyl ether or diethylene glycol dimethyl ether, hydrocarbons such as benzene, toluene, xylene, hexane, cyclohexane or mineral oil fractions, halogenated hydrocarbons such as dichloromethane, trichloromethane, carbon tetrachloride, 1,2-dichloroethane, trichloroethylene or chlorobenzene, or other solvents such as acetone, ethyl acetate, acetonitrile, pyridine, dimethyl sulphoxide, N,N-dimethylformamide, N,N-dimethylacetamide, N,N'-dimethylpropyleneurea (DMPU) or N-methylpyrrolidone (NMP). It is also possible to use mixtures of the solvents mentioned. Preference is given to using N,N-dimethylformamide.

The reactions in process (XXII)→(XXIII) may proceed in the absence of a base, or in the presence of organic bases such as potassium phosphate, potassium carbonate, cesium carbonate, sodium phosphate, or calcium carbonate. Preference is given to using potassium carbonate.

The reactions in process (XXII)→(XXIII) are generally carried out in a temperature range from 0° C. to 200° C. Heating options include conventional heating below the boiling point of the solvent, under reflux, or above the boiling point of the solvent in a closed vial, or in a closed vial with the aid of a microwave reactor. Preference is given to heating the reaction to 45° C.

The reactions in process (XXII)→(XXIII) can be carried out at atmospheric, elevated or reduced pressure (for example from 0.5 to 25 bar). In general, the reactions are carried out at atmospheric pressure.

The reactions in process (XXII)→(XXIII) may proceed in the presence of 1-(chloromethyl)-4-methoxybenzene, 1-(bromomethyl)-4-methoxybenzene, 1-(iodomethyl)-4-methoxybenzene, 4-methoxybenzyl methanesulfonate, 4-methoxybenzyl 4-methylbenzenesulfonate. Preference is given to using 1-(chloromethyl)-4-methoxybenzene.

The reaction in process (XXIII)+(XXIV)→(XXI) is generally effected in inert solvents, in the presence of a catalyst and a base, optionally in the presence of ligand, optionally in a microwave, preferably within a temperature range from room temperature to 150° C. at standard pressure to 3 bar.

Catalysts are, for example, palladium catalysts customary for Suzuki reaction conditions, preference being given to catalysts such as dichlorobis(triphenylphosphine)palladium, tetrakistriphenylphosphinepalladium(0), palladium(II) acetate/triscyclohexylphosphine, tris(dibenzylideneacetone) dipalladium, bis(diphenylphosphineferrocenyl)palladium (II) chloride, 1,3-bis(2,6-diisopropylphenyl)imidazol-2-ylidene(1,4-naphthoquinone)palladium dimer, allyl(chloro) (1,3-dimesityl-1,3-dihydro-2H-imidazol-2-ylidene) palladium, palladium(II) acetate/dicyclohexyl(2',4',6'-triisopropyl-biphenyl-2-yl)phosphine, [1,1-bis(diphenylphosphino)ferrocene]palladium(II) chloride monodichloromethane adduct, [1,1'-Bis(diphenylphosphino)ferrocene]dichloropalladium(II) or (2-Dicyclohexylphosphino-2',4',6'-triisopropyl-1,1'-biphenyl) [2-(2'-amino-1,1'-biphenyl)]palladium(II), preference being given to [1,1'-Bis(diphenylphosphino)ferrocene]dichloropalladium (II) or (2-Dicyclohexylphosphino-2',4',6'-triisopropyl-1,1'-biphenyl) [2-(2'-amino-1,1'-biphenyl)]palladium(II).

Suitable ligands for the reactions in process (XXIII)+(XXIV)→(XXI) are usually phosphor ligands, for example, tricyclohexylphosphine, 2-(Dicyclohexylphosphino)3,6-dimethoxy-2',4',6'-triisopropyl-1,1'-biphenyl (BrettPhos), 2-(Di-tert-butylphosphino)-2',4',6'-triisopropyl-3,6-dimethoxy-1,1'-biphenyl (tBuBrettPhos), 2-Dicyclohexylphosphino-2',6'-bis(N,N-dimethylamino)biphenyl (CPhos), 2-Dicyclohexylphosphino-2'-(N,N-dimethylamino)biphenyl (DavePhos), 2-{Bis[3,5-bis(trifluoromethyl)phenyl]phosphino}-3,6-dimethoxy-2',4',6'-triisopropyl-1,1'-biphenyl (JackiePhos), (2-Biphenyl)di-tert-butylphosphine (JohnPhos), 2-Dicyclohexylphosphino-2'-methylbiphenyl (MePhos), 2-Di(tert-butyl)phosphino-2',4',6'-triisopropyl-3-methoxy-6-methylbiphenyl (RockPhos), 2-Dicyclohexylphosphino-2',6'-diisopropoxybiphenyl (RuPhos), 2-Dicyclohexylphosphino-2',6'-dimethoxybiphenyl (SPhos), rac-2-(Di-tert-butylphosphino)-1,1'-binaphthyl (TrixiePhos), 2-Dicyclohexylphosphino-2',4',6'-triisopropylbiphenyl (XPhos), 4,5-Bis(diphenylphosphino)-9,9-dimethylxanthene (XantPhos), 2-Di-tert-butylphosphino-2',4', 6'-triisopropylbiphenyl (tBuXPhos), 2,2'-Bis (diphenylphosphino)-1,1'-binaphthyl (BINAP). Preference is given to using tricyclohexylphosphine or no ligand.

Suitable solvents for reactions in process (XXIII)+(XXIV)→(XXI) are, for example, aliphatic alcohols such as methanol, ethanol, iso-propanol, 1-methoxy-2-propanol, 2-methyl-2-butanol or tert-butanol, ethers such as diethyl ether, dioxane, tetrahydrofuran, glycol dimethyl ether or diethylene glycol dimethyl ether, hydrocarbons such as benzene, toluene, xylene, hexane, cyclohexane or mineral oil fractions, halogenated hydrocarbons such as dichloromethane, trichloromethane, carbon tetrachloride, 1,2-dichloroethane, trichloroethylene or chlorobenzene, or other solvents such as acetone, ethyl acetate, acetonitrile, pyridine, dimethyl sulphoxide, N,N-dimethylformamide, N,N-dimethylacetamide, N,N'-dimethylpropyleneurea (DMPU) or N-methylpyrrolidone (NMP). It is also possible to use mixtures of the solvents mentioned. Preference is given to using 1,4-dioxan.

The reactions in process (XXIII)+(XXIV)→(XXI) may proceed in the absence of a base, or in the presence of organic bases such as metal alcoholates, such as sodium tert-butoxide, potassium tert-butoxide, and metal amides, such as Lithium diisopropylamide or Lithium bis(trimethylsylyl)amide, or amines such as triethylamine or diisopropylethylamine, or in the presence of inorganic bases. Inorganic bases include alkali metal or alkali earth metal phosphates and carbonates such as potassium phosphate, potassium carbonate, cesium carbonate, sodium phosphate, or calcium carbonate. Preference is given to using tripotassium phosphate.

The reactions in process (XXIII)+(XXIV)→(XXI) are generally carried out in a temperature range from 0° C. to 200° C. Heating options include conventional heating below the boiling point of the solvent, under reflux, or above the boiling point of the solvent in a closed vial, or in a closed vial with the aid of a microwave reactor. Preference is given to heating the reaction to 70-140° C., optionally in a microwave.

The reactions in process (XXII)→(XXIII) can be carried out at atmospheric, elevated or reduced pressure (for example from 0.5 to 25 bar). In general, the reactions are carried out at atmospheric pressure to 3 bar.

Scheme 11: Coupling for compounds with $R^3$ being an amide

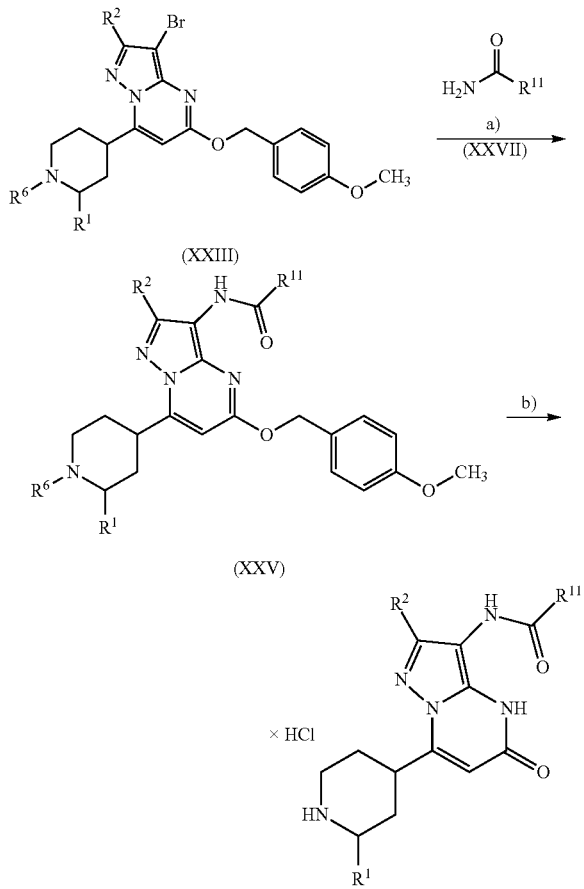

a) [(2-di-tert-butylphosphino-3,6-dimethoxy-2',4',6'-triisopropyl-1,1'-biphenyl)-2-(2'-amino-1,1'-biphenyl)]palladium(II) methanesulfonate, 2-(di-tert-butylphosphino)-2',4',6'-triisopropyl-3,6-dimethoxy-1,1'-biphenyl, tripotassium phosphate, tert-butanol, 110° C.,; b) HCl 4N in 1,4-dioxan, 1,4-dioxan, RT,. $R^{11}$ is selected from optionally substituted phenyl, alkyl, and cycloalkyl.

The reaction in process (XXIII)+(XXVII)→(XXV) is generally effected in inert solvents, in the presence of a base and a catalyst, optionally in the presence of a ligand, preferably within a temperature range from 20° C. to the reflux of the solvents at standard pressure.

Suitable solvents for reactions in process (XXIII)+(XXVII)→(XXV) are, for example, aliphatic alcohols such as methanol, ethanol, iso-propanol, 1-methoxy-2-propanol, 2-methyl-2-butanol or tert-butanol, ethers such as diethyl ether, dioxane, tetrahydrofuran, glycol dimethyl ether or diethylene glycol dimethyl ether, hydrocarbons such as benzene, toluene, xylene, hexane, cyclohexane or mineral oil fractions, halogenated hydrocarbons such as dichloromethane, trichloromethane, carbon tetrachloride, 1,2-dichloroethane, trichloroethylene or chlorobenzene, or other solvents such as acetone, ethyl acetate, acetonitrile, pyridine, dimethyl sulphoxide, N,N-dimethylformamide, N,N-dimethylacetamide, N,N'-dimethylpropyleneurea (DMPU) or N-methylpyrrolidone (NMP). It is also possible to use mixtures of the solvents mentioned. Preference is given to using tert-butanol.

The reactions in process (XXIII)+(XXVII)→(XXV) may proceed in the absence of a base, or in the presence of organic bases such as metal alcoholates, such as sodium tert-butoxide, potassium tert-butoxide, and metal amides, such as Lithium diisopropylamide or Lithium bis(trimethylsylyl)amide, or amines such as triethylamine or diisopropylethylamine, or in the presence of inorganic bases. Inorganic bases include alkali metal or alkali earth metal phosphates and carbonates such as potassium phosphate, potassium carbonate, cesium carbonate, sodium phosphate, or calcium carbonate. Preference is given to using tripotassium phosphate.

The reactions in process (XXIII)+(XXVII)→(XXV) are generally carried out in a temperature range from 0° C. to 200° C. Heating options include conventional heating below the boiling point of the solvent, under reflux, or above the boiling point of the solvent in a closed vial, or in a closed vial with the aid of a microwave reactor. Preference is given to heating the reaction to 110° C.

The reactions in process (XXIII)+(XXVII)→(XXV) can be carried out at atmospheric, elevated or reduced pressure (for example from 0.5 to 25 bar). In general, the reactions are carried out at atmospheric pressure.

Suitable catalysts for reactions in process (XXIII)+(XXVII)→(XXV) are usually palladium catalyst, for example, Palladium(II) acetate, Bis(dibenzylideneacetone)palladium(0), Tris(dibenzylideneacetone)dipalladium(0), Tetrakis(triphenylphosphine)palladium(0), Bis(triphenylphosphine)palladium(II) dichloride, [1,1'-Bis(diphenylphosphino)ferrocene]dichloropalladium(II), 1,3-Bis(2,6-diisopropylphenyl)imidazol-2-ylidene (1,4-naphthoquinone) palladium(0) dimer, Methanesulfonato[2-(di-1-adamantylphosphino)-3,6-dimethoxy-2',4',6'-tri-i-propyl-1,1'-biphenyl](2'-amino-1,1'-biphenyl-2-yl)palladium(II) (AdBrettPhos Pd G3), Methanesulfonato{[4-(N,N-dimethylamino)phenyl]di-t-butylphosphino}(2'-amino-1,1'-biphenyl-2-yl)palladium(II) (Amphos Pd G3), [(2-Di-cyclohexylphosphino-3,6-dimethoxy-2',4',6'-triisopropyl-1,1'-biphenyl)-2-(2'-amino-1,1'-biphenyl)]palladium(II) methanesulfonate (BrettPhos Pd G3), [(2-di-tert-butylphosphino-3,6-dimethoxy-2',4',6'-triisopropyl-1,1'-biphenyl)-2-(2'-amino-1,1'-biphenyl)]palladium(II) methanesulfonate (tBuBrettPhos Pd G3), Methanesulfonato[2-(dicyclohexylphosphino)-2'-(N,N-dimethylamino)-1,1'-biphenyl](2'-amino-1,1'-biphenyl-2-yl)palladium(II) (DavePhos Pd G3), Methanesulfonato {(R)-(−)-1-[(S)-2-(dicyclohexylphosphino)ferrocenyl]ethyldi-t-butylphosphine}(2'-amino-1,1'-biphenyl-2-yl)palladium(II) (JosiPhos Pd G3), Methanesulfonato(tri-t-butylphosphino)(2'-methylamino-1,1'-biphenyl-2-yl)palladium(II) (P(t-Bu)3 Pd G4), Methanesulfonato (tricyclohexylphosphine)(2'-amino-1,1'-biphenyl-2-yl)palladium(II) (PCy3 Pd G3), Methanesulfonato(2-(di-t-butylphosphino)-3-methoxy-6-methyl-2',4',6'-tri-i-propyl-1, 1'-biphenyl)(2'-amino-1,1'-biphenyl-2-yl)palladium(II) (RockPhos Pd G3), Methanesulfonato(2-dicyclohexylphosphino-2',6'-di-i-propoxy-1,1'-biphenyl)(2'-amino-1,1'-biphenyl-2-yl)palladium(II) (RuPhos Pd G3), Methanesulfonato(2-dicyclohexylphosphino-2',6'-dimethoxy-1,1'-biphenyl)(2'-amino-1,1'-biphenyl-2-yl)palladium(II) (SPhos Pd G3), (2-Dicyclohexylphosphino-2',4',6'-triisopropyl-1,1'-biphenyl)[2-(2'-amino-1,1'-biphenyl)]palladium(II) methanesulfonate (XPhos Pd G3), Methanesulfonato(2-di-t-butylphosphino-2',4',6'-tri-i-propyl-1,1'-biphenyl) (2'-amino-1, 1'-biphenyl-2-yl)palladium(II) (tBuXPhos Pd G3), Methanesulfonato[9,9-dimethyl-4,5-bis(diphenylphosphino)xanthene][2'-amino-1,1'-biphenyl]palladium(II) (XantPhos Pd G3), Methanesulfonato[2-bis(3,5-di(trifluoromethyl)phenylphosphino)-3,6-dimethoxy-2',4',6'-tri-i-propyl-1,1'-biphenyl](2'-amino-1,1'-biphenyl-2-yl)palladium(II) (JackiePhos Pd G3). Preference is given to using [(2-di-tert-butylphosphino-3,6-dimethoxy-2',4',6'-triisopropyl-1,1'-biphenyl)-2-(2'-amino-1,1'-biphenyl)]palladium(II) methanesulfonate.

Suitable ligands for the reactions in process (XXIII)+(XXVII)→(XXV) are usually phosphor ligands, for example, 2-(Di-1-adamantylphosphino)-3,6-dimethoxy-2',4',6'-tri-i-propyl-1,1'-biphenyl (AdBrettPhos), 2-(Dicyclohexylphosphino)3,6-dimethoxy-2',4',6'-triisopropyl-1,1'-biphenyl (BrettPhos), 2-(Di-tert-butylphosphino)-2',4',6'-triisopropyl-3,6-dimethoxy-1,1'-biphenyl (tBuBrettPhos), 2-Dicyclohexylphosphino-2',6'-bis(N,N-dimethylamino)biphenyl (CPhos), 2-Dicyclohexylphosphino-2'-(N,N-dimethylamino)biphenyl (DavePhos), 2'-(Di-tert-butylphosphino)-N,N-dimethylbiphenyl-2-amine (tBuDavePhos), 2'-(Diphenylphosphino)-N,N'-dimethyl-(1,1'-biphenyl)-2-amine (PhDavePhos), 2-{Bis[3,5-bis(trifluoromethyl)phenyl]phosphino}-3,6-dimethoxy-2',4',6'-triisopropyl-1,1'-biphenyl (JackiePhos), (2-Biphenyl)di-tert-butylphosphine (JohnPhos), (2-Biphenyl)dicyclohexylphosphine (CyJohnPhos), 2-Dicyclohexylphosphino-2'-methylbiphenyl (MePhos), 2-Di-tert-butylphosphino-2'-methylbiphenyl (tBuMePhos), 2-Di(tert-butyl)phosphino-2',4',6'-triisopropyl-3-methoxy-6-methylbiphenyl (RockPhos), 2-Dicyclohexylphosphino-2',6'-diisopropoxybiphenyl (RuPhos), 2-Dicyclohexylphosphino-2',6'-dimethoxybiphenyl (SPhos), rac-2-(Di-tert-butylphosphino)-1,1'-binaphthyl (TrixiePhos), 2-Dicyclohexylphosphino-2',4',6'-triisopropylbiphenyl (XPhos), 4,5-Bis(diphenylphosphino)-9,9-dimethylxanthene (XantPhos), 2-Di-tert-butylphosphino-2',4',6'-triisopropylbiphenyl (tBuXPhos), 2-Di-tert-butylphosphino-3,4,5,6-tetramethyl-2',4',6'-triisopropyl-1, 1'-biphenyl (tetramethyl tBuXPhos), 2-Di-t-butylphosphino-4-methoxy-3,5,6-trimethyl-2',4',6'-tri-i-propylbiphenyl (Me$_3$(OMe)tBuXPhos), 2,2'-Bis(diphenylphosphino)-1,1'-binaphthyl (BINAP).

Preference is given to using 22-(di-tert-butylphosphino)-2',4',6'-triisopropyl-3,6-dimethoxy-1,1'-biphenyl.

Scheme 12: Preparation of ethyl ketone-substituted pyrazolopyrimidinones via Weinreb amide

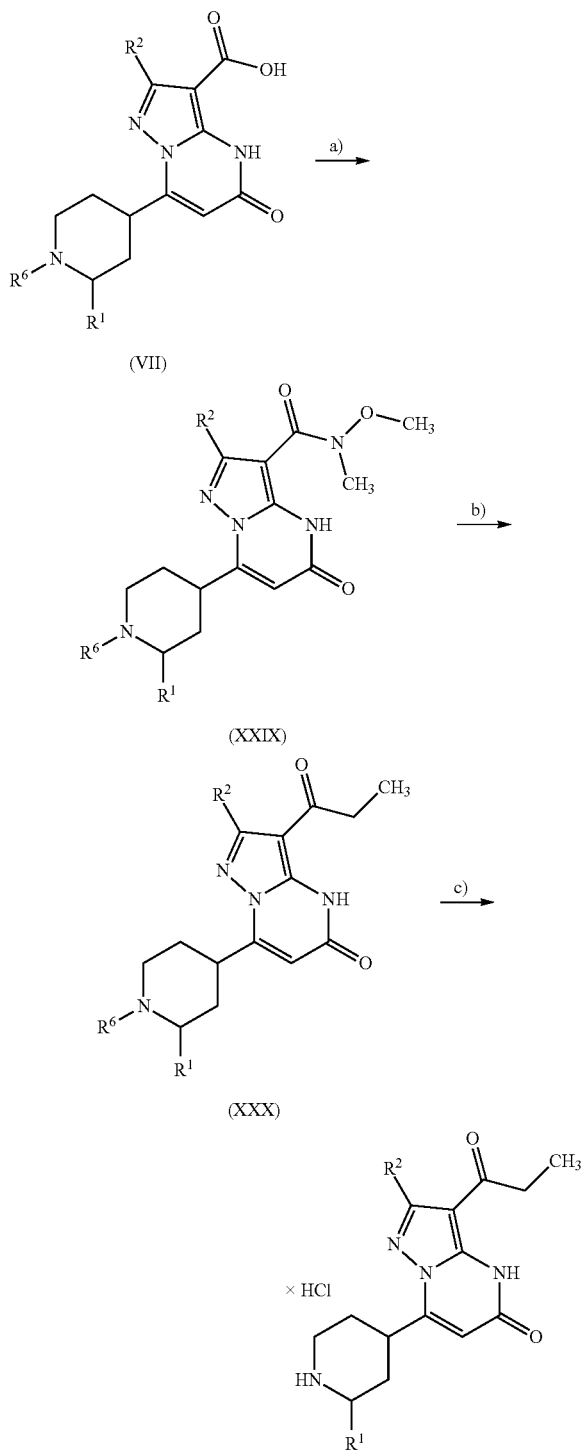

a) 4-dimethylaminopyridine, 1-hydroxybenzotriazole hydrate, 1-(3-dimethylaminopropyl)-3-ethylcarbodiimide hydrochloride, N-methoxymethanamine hydrochloride, ethyldiisopropylamine, acetonitrile, room temperature; b) bromo(ethyl)magnesium (1.0M in tetrahydrofuran), tetrahydrofuran, 0° C.-room temperature; c) hydrochloric acid (4N solution in 1,4-dioxan), room temperature.

The reaction sequence can be applied analogously with bromo(methyl)magnesium to yield the methylester derivative.

The reaction in process (VII)→(XXIX) is generally effected in inert solvents, optionally in the presence of a dehydrating reagent, optionally in the presence of a catalyst, optionally in the presence of a base, preferably within a temperature range from 0° C. to the reflux of the solvents at standard pressure.

Suitable dehydrating reagents here are, for example, carbodiimides, for example N,N'-diethyl-, N,N'-dipropyl-, N,N'-diisopropyl- and N,N'-dicyclohexylcarbodiimide, 1-(3-dimethylaminopropyl)-3-ethylcarbodiimide hydrochloride (EDC) (optionally in the presence of pentafluorophenol (PFP)), N-cyclohexylcarbodiimide-N'-propyloxymethyl-polystyrene (PS-carbodiimide) or carbonyl compounds such as 1,1'-carbonyldiimidazole, or 1,2-oxazolium compounds such as 2-ethyl-5-phenyl-1,2-oxazolium 3-sulphate or 2-tert-butyl-5-methyl-isoxazolium perchlorate, or acylamino compounds such as 2-ethoxy-1-ethoxycarbonyl-1,2-dihydroquinoline, or propanephosphonic anhydride, or isobutyl chloroformate, or bis-(2-oxo-3-oxazolidinyl)phosphoryl chloride or benzotriazolyloxytri(dimethylamino)phosphonium hexafluorophosphate, or O-(benzotriazol-1-yl)-N,N,N',N'-tetramethyluronium hexafluorophosphate (HBTU), 2-(2-oxo-1-(2H)-pyridinyl)-1,1,3,3-tetramethyluronium tetrafluoroborate (TPTU), (benzotriazol-1-yloxy)bisdimethylaminomethylium fluoroborate (TBTU) or O-(7-azabenzotriazol-1-yl)-N,N,N',N'-tetramethyluronium hexafluorophosphate (HATU), or 1-hydroxybenzotriazole (HOBt), or benzotriazol-1-yloxytris(dimethylamino)phosphonium hexafluorophosphate (BOP), or ethyl cyano(hydroxyimino)acetate (Oxyma), or (1-cyano-2-ethoxy-2-oxoethylideneaminooxy)dimethylamino-morpholino-carbenium hexafluorophosphate (COMU), or N-[(dimethylamino)(3H-[1,2,3]triazolo[4,5-b]pyridin-3-yloxy)methylidene]-N-methylmethanaminium hexafluorophosphate, or 2,4,6-tripropyl-1,3,5,2,4,6-trioxatriphosphinane 2,4,6-trioxide (T3P), or mixtures of these, optionally in the presence of 4-dimethylaminopyridine as catalyst. Preference is given to 1-(3-dimethylaminopropyl)-3-ethylcarbodiimide hydrochloride in combination with 1-hydroxybenzotriazole and 4-dimethylaminopyridine.

Bases are, for example, alkali metal carbonates, for example sodium carbonate or potassium carbonate, or sodium hydrogencarbonate or potassium hydrogencarbonate, or organic bases such as trialkylamines, for example triethylamine, N-methylmorpholine, N-methylpiperidine, 4-dimethylaminopyridine or diisopropylethylamine, preference being given to diisopropylethylamine.

Inert solvents are, for example, halogenated hydrocarbons such as dichloromethane or trichloromethane, hydrocarbons such as benzene, or other solvents such as nitromethane, tetrahydrofuran, dioxane, dimethylformamide, dimethyl sulphoxide, acetonitrile or pyridine, or mixtures of the solvents, preference being given to acetonitrile.

The reactions in process (VII)→(XXIX) are generally carried out in a temperature range from 0° C. to 200° C. Heating options include conventional heating below the boiling point of the solvent, under reflux, or above the boiling point of the solvent in a closed vial, or in a closed vial with the aid of a microwave reactor. Preference is given to room temperature.

The reactions in process (VII)→(XXIX) can be carried out at atmospheric, elevated or reduced pressure (for example from 0.5 to 25 bar). In general, the reactions are carried out at atmospheric pressure.

The reaction in process (XXIX)→(XXX) is generally effected in inert solvents, in the presence of an organometallic alkyl halide reagent, preferably within a temperature range from −80° C. to the reflux of the solvents at standard pressure.

The reactions in process (XXIX)→(XXX) are generally carried out in the presence of organometallic alkyl halide reagents, where the metallic component can be magnesium, lithium, copper or zinc. Preference is given to the alkyl magnesium bromide or alkyl magnesium chloride.

The reactions in process (XXIX)→(XXX) are generally carried out in an inert organic solvent, for example benzene, toluene, xylene, petroleum ether, hexane, heptane, tetrahydrofuran, diethylether, isopropylether, di-n-butylether, methyl-tert-butyl ether, ethylene glycol dimethyl ether, 1,4-dioxane or a mixture of those, preference being given to tetrahydrofuran.

The reactions in process (XXIX)→(XXX) are generally carried out in a temperature range from −80° C. to 200° C. Heating options include conventional heating below the boiling point of the solvent, under reflux, or above the boiling point of the solvent in a closed vial, or in a closed vial with the aid of a microwave reactor. Preference is given to room temperature.

The reactions in process (XXIX)→(XXX) can be carried out at atmospheric, elevated or reduced pressure (for example from 0.5 to 25 bar). In general, the reactions are carried out at atmospheric pressure.

Scheme 13: Preparation of methyl ketone-substituted pyrazolopyrimidinones

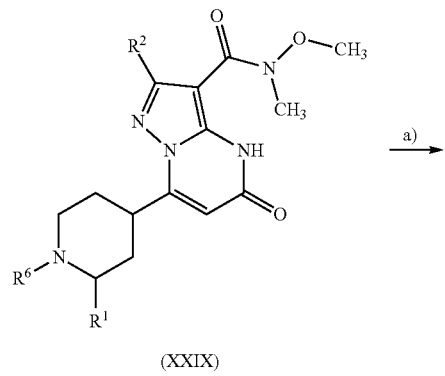

(XXIX)

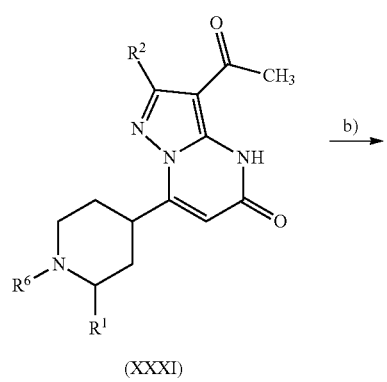

(XXXI)

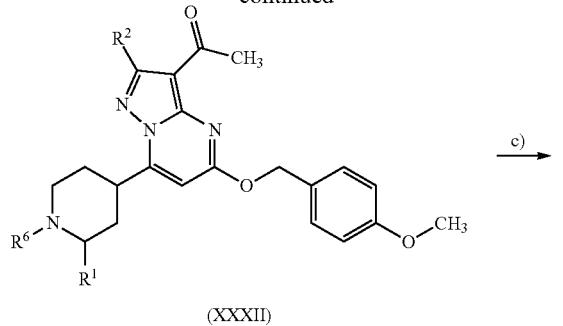

(XXXII)

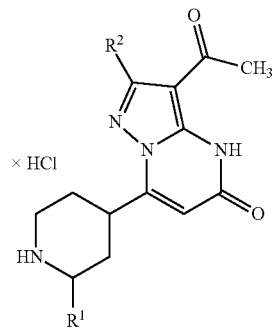

a) bromo(methyl)magnesium (3.0M in diethyl ether), tetrahydrofuran, 0° C.-room temperature; b) potassium carbonate, 1-(chloromethyl)-4-methoxybenzene, N,N-Dimethylformamide, room temperature; c) hydrochloric acid (4N solution in 1,4-dioxan), room temperature.

The reaction in process (XXIX)→(XXXI) is generally effected in inert solvents, in the presence of an organometallic alkyl halide reagent, preferably within a temperature range from −80° C. to the reflux of the solvents at standard pressure.

The reactions in process (XXIX)→(XXXI) are generally carried out in the presence of organometallic alkyl halide reagents, where the metallic component can be magnesium, lithium, copper or zinc. Preference is given to the alkyl magnesium bromide or alkyl magnesium chloride.

The reactions in process (XXIX)→(XXXI) are generally carried out in an inert organic solvent, for example benzene, toluene, xylene, petroleum ether, hexane, heptane, tetrahydrofuran, diethylether, isopropylether, di-n-butylether, methyl-tert-butyl ether, ethylene glycol dimethyl ether, 1,4-dioxane or a mixture of those, preference being given to tetrahydrofuran.

The reactions in process (XXIX)→(XXXI) are generally carried out in a temperature range from −80° C. to 200° C. Heating options include conventional heating below the boiling point of the solvent, under reflux, or above the boiling point of the solvent in a closed vial, or in a closed vial with the aid of a microwave reactor. Preference is given to room temperature.

The reactions in process (XXIX)→(XXXI) can be carried out at atmospheric, elevated or reduced pressure (for example from 0.5 to 25 bar). In general, the reactions are carried out at atmospheric pressure.

The reaction in process (XXXI)→(XXXII) is generally effected in inert solvents, in the presence of a base and 1-(halomethyl)-4-methoxybenzene, preferably within a temperature range from 0° C. to the reflux of the solvents at standard pressure.

Suitable solvents for reactions in process (XXXI)→(XXXII) are, for example, aliphatic alcohols such as methanol, ethanol, iso-propanol, 1-methoxy-2-propanol, 2-methyl-2-butanol or tert-butanol, ethers such as diethyl ether, dioxane, tetrahydrofuran, glycol dimethyl ether or diethylene glycol dimethyl ether, hydrocarbons such as benzene, toluene, xylene, hexane, cyclohexane or mineral oil fractions, halogenated hydrocarbons such as dichloromethane, trichloromethane, carbon tetrachloride, 1,2-dichloroethane, trichloroethylene or chlorobenzene, or other solvents such as acetone, ethyl acetate, acetonitrile, pyridine, dimethyl sulphoxide, N,N-dimethylformamide, N,N-dimethylacetamide, N,N'-dimethylpropyleneurea (DMPU) or N-methylpyrrolidone (NMP). It is also possible to use mixtures of the solvents mentioned. Preference is given to using N,N-dimethylformamide.

The reactions in process (XXXI)→(XXXII) may proceed in the absence of a base, or in the presence of organic bases such as metal alcoholates, such as sodium tert-butoxide, potassium tert-butoxide, and metal amides, such as Lithium diisopropylamide or Lithium bis(trimethylsylyl)amide, or amines such as triethylamine or diisopropylethylamine, or in the presence of inorganic bases. Inorganic bases include alkali metal or alkali earth metal phosphates and carbonates such as potassium phosphate, potassium carbonate, cesium carbonate, sodium phosphate, or calcium carbonate. Preference is given to using potassium carbonate.

The reactions in process (XXXI)→(XXXII) are generally carried out in a temperature range from 0° C. to 200° C. Heating options include conventional heating below the boiling point of the solvent, under reflux, or above the boiling point of the solvent in a closed vial, or in a closed vial with the aid of a microwave reactor. Preference is given to room temperature.

The reactions in process (XXXI)→(XXXII) can be carried out at atmospheric, elevated or reduced pressure (for example from 0.5 to 25 bar). In general, the reactions are carried out at atmospheric pressure.

The reactions in process (XXXI)→(XXXII) may proceed in the presence of 1-(chloromethyl)-4-methoxybenzene, 1-(bromomethyl)-4-methoxybenzene, 1-(iodomethyl)-4-methoxybenzene, 4-methoxybenzyl methanesulfonate, 4-methoxybenzyl 4-methylbenzenesulfonate. Preference is given to using 1-(chloromethyl)-4-methoxybenzene.

Scheme 14: Preparation of alkyl ketone-substituted pyrazolopyrimidinones from the nitrile

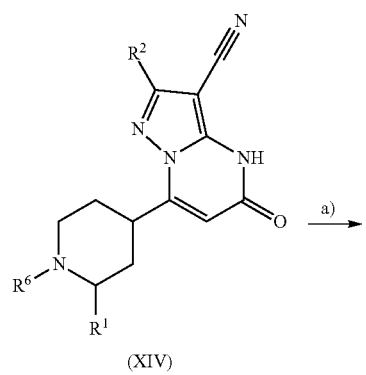

(XIV)

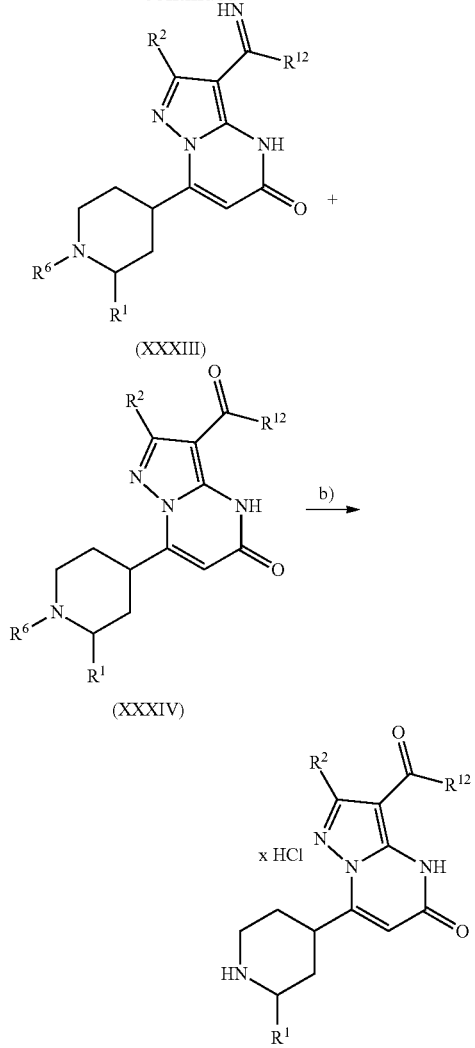

a) $R^{12}$-magnesium bromide or chloride, tetrahydrofuran, room temperature-60° C.;
b) hydrochloric acid (1N solution in water), acetonitrile, 40° C. $R^{12}$ is selected from $C_1$-$C_5$ alkyl and $C_3$-$C_6$ cycloalkyl. The reactioon in process (XIV) → (XXXIII) is generally effected in inert solvents, in the presence of an organometallic alkyl or cycloalkyl halide reagent, preferably within a temperature range from -80° C. to the reflux of the solvents at standard pressure.

The reactions in process (XIV)→(XXXIII) are generally carried out in the presence of organometallic alkyl or cycloalkyl halide reagents, where the metallic component can be magnesium, lithium, copper or zinc. Preference is given to the alkyl and cycloalkyl magnesium bromide, or alkyl and cycloalkyl magnesium chloride.

The reactions in process (XIV)→(XXXIII) are generally carried out in an inert organic solvent, for example benzene, toluene, xylene, petroleum ether, hexane, heptane, tetrahydrofuran, diethylether, isopropylether, di-n-butylether, methyl-tert-butyl ether, ethylene glycol dimethyl ether, 1,4-dioxane or a mixture of those, preference being given to tetrahydrofuran.

The reactions in process (XIV)→(XXXIII) are generally carried out in a temperature range from −80° C. to 200° C. Heating options include conventional heating below the boiling point of the solvent, under reflux, or above the boiling point of the solvent in a closed vial, or in a closed vial with the aid of a microwave reactor. Preference is given to 60° C.

The reactions in process (XIV)→(XXXIII) can be carried out at atmospheric, elevated or reduced pressure (for example from 0.5 to 25 bar). In general, the reactions are carried out at atmospheric pressure.

Scheme 15: Preparation of propenyl-substituted pyrazolopyrimidinones

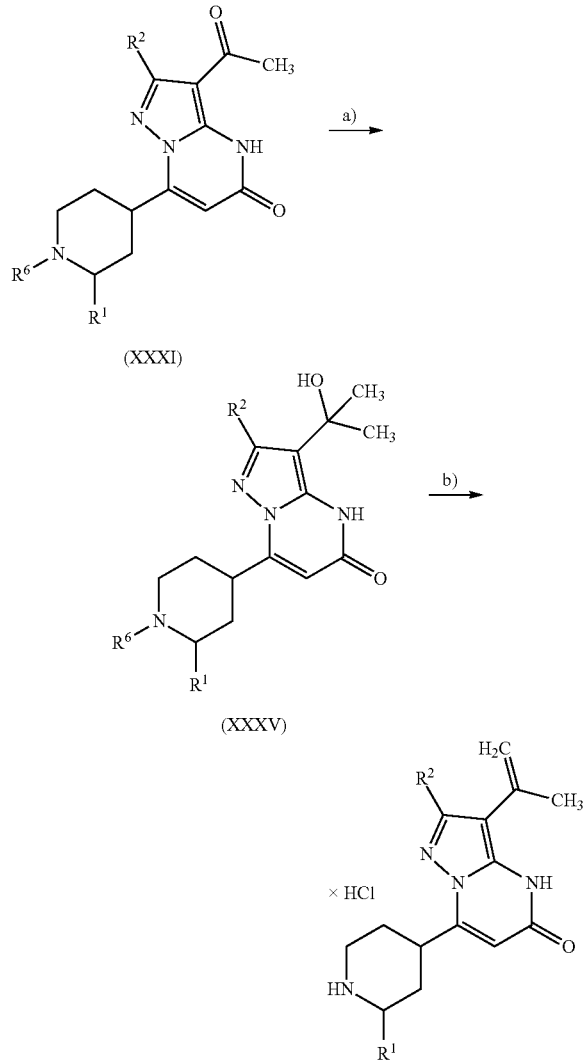

a) bromo(methyl)magnesium (1.0M in diethyl ether), tetrahydrofuran, 0° C.-room temperature; b) hydrochloric acid (4N solution in 1,4-dioxan), room temperature. The reaction in process (XXXI) → (XXXV) is generally effected in inert solvents, in the presence of an organometallic alkyl halide reagent, preferably within a temperature range from -80° C. to the reflux of the solvents at standard pressure.

The reactions in process (XXXI)→(XXXV) are generally carried out in the presence of organometallic alkyl halide reagents, where the metallic component can be magnesium, lithium, copper or zinc. Preference is given to the alkyl magnesium bromide or alkyl magnesium chloride.

The reactions in process (XXXI)→(XXXV) are generally carried out in an inert organic solvent, for example benzene, toluene, xylene, petroleum ether, hexane, heptane, tetrahydrofuran, diethylether, isopropylether, di-n-butylether, methyl-tert-butyl ether, ethylene glycol dimethyl ether, 1,4-dioxane or a mixture of those, preference being given to tetrahydrofuran.

The reactions in process (XXXI)→(XXXV) are generally carried out in a temperature range from -80° C. to 200° C.

Heating options include conventional heating below the boiling point of the solvent, under reflux, or above the boiling point of the solvent in a closed vial, or in a closed vial with the aid of a microwave reactor. Preference is given to room temperature.

The reactions in process (XXXI)→(XXXV) can be carried out at atmospheric, elevated or reduced pressure (for example from 0.5 to 25 bar). In general, the reactions are carried out at atmospheric pressure.

Scheme 16: Preparation of thiazole-substituted pyrazolopyrimidinones

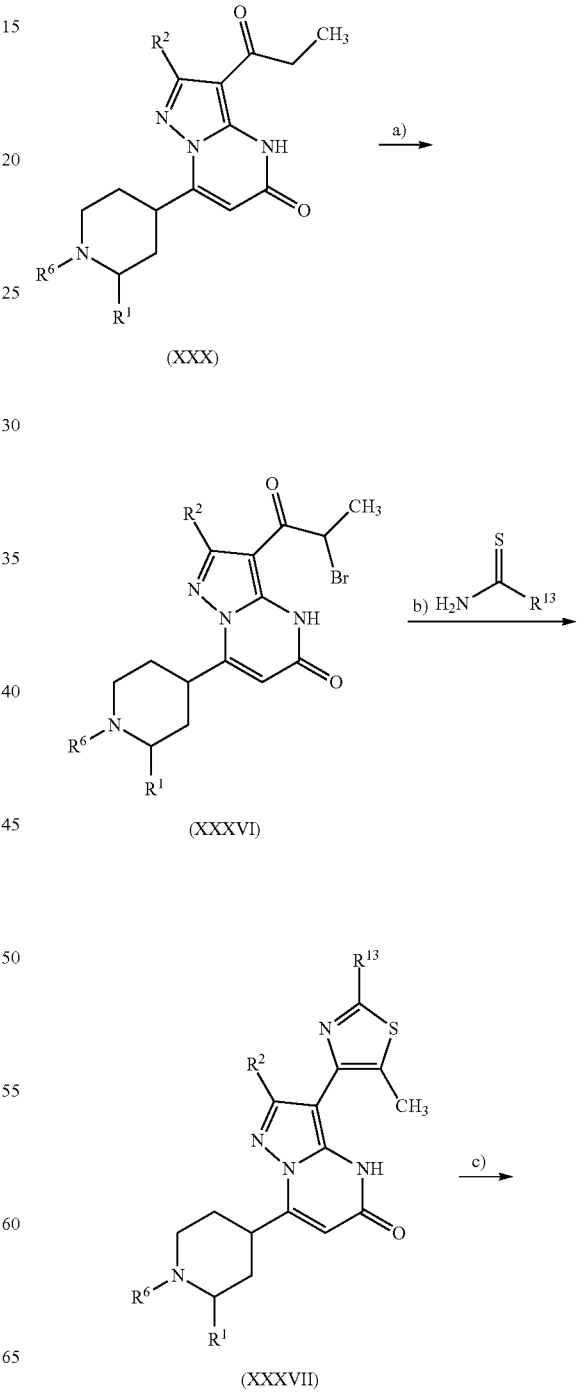

-continued

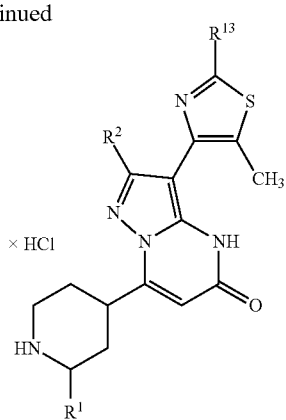

a) pyridinium tribromide, tetrahydrofuran, room temperature; b) ethyldiisopropylamine, ethanol, 70° C.; c) hydrochloric acid (4N solution in 1,4-dioxan), room temperature. $R^{13}$ is selected from phenyl, the phenyl being optionally substituted with fluorine, chlorine, trifluoromethyl, methoxy, or ethoxy, phenoxymethyl, the phenoxymethyl being optionally substituted with chlorine, benzyl, the benzyl being optionally substituted with methoxy, pyridinyl, the pyridinyl being optionally substituted with ethyl, pyrazinyl, pyrazolyl, the pyrazolyl being optionally substituted with one or two methyl, imidazolylethyl, oxazole, the oxazole being optionally substituted with methyl, oxadiazole, $C_3$-$C_6$ cycloalkyl, oxanyl, cyano-methyl, $C_1$-$C_4$ alkyl, and trifluoromethyl.

The reaction in process (XXX)→(XXXVI) is generally effected in inert solvents, optionally in the presence of a base or an acid, in the presence of a brominating reagent, preferably within a temperature range from −80° C. to the reflux of the solvents at standard pressure.

Brominating agents are, for example, bromine (optionally in the presence of phosphorus tribromide, magnesium sulfate, aluminum bromide or aluminum chloride), bromotrimethylsilane, sodium bromate, 1,4-diazabicyclo[2.2.2]octane hydrobromide, sodium bromide, copper(II) bromide optionally in the presence of lithium bromide, copper bomide, bromosuccinimide, 1,3-dibromo-5,5-dimethylhydantoin, hydrogen bromide optionally in the presence of hydrogen peroxide, 1-butyl-3-methylimidazolium tribromide, tetrabutylammonium tribromide, pyridinium tribromide, pyridine hydrobromide, trimethylphenylammonium tribromide, dioxane dibromide, pyrrolidin-2-one-bromine (3:1) hydrobromide in the presence of pyrrolidin-2-one, 1,2-phenylene phosphorobromidite, tetrabutylammonium bromide, preference being given to pyridinium tribromide.

Bases are, for example, lithium diisopropylamide, disodium carbonate, potassium carbonate, sodium hydroxide, sodium hydrogen carbonate, lithium bis(trimethylsilyl)amide, pyridine. Preference is given to use no base.

Acids are, for example, sulfuric acid, acetic acid, methanesulfonic acid, p-toluenesulfonic acid, sodium bisulfate, hydrochloric acid. Preference is given to use no acid.

Solvents are, for example, dimethyl sulfoxide, acetonitrile, water, chloroform, methanol, ethanol, diethylether, diisopropyl ether, tert-butyl methyl ether, ethyl acetate, carbon tetrachloride, carbon tetrabromide, dichloromethane, 1,2-dichloroethane, benzene, toluene, tetrahydrofuran, 1,2-dimethoxyethane, 1,4 dioxane, acetone, hexane, cyclohexane, or a mixture of those. Preference is given to tetrahydrofuran.

The reactions in process (XXX)→(XXXVI) are generally carried out in a temperature range from −80° C. to 200° C. Heating options include conventional heating below the boiling point of the solvent, under reflux, or above the boiling point of the solvent in a closed vial, or in a closed vial with the aid of a microwave reactor. Preference is given to room temperature.

The reactions in process (XXX)→(XXXVI) can be carried out at atmospheric, elevated or reduced pressure (for example from 0.5 to 25 bar). In general, the reactions are carried out at atmospheric pressure.

The reaction in process (XXXVI)→(XXXVII) is generally effected in inert solvents, optionally in the presence of a base, optionally in the presence of a dehydrating reagent, preferably within a temperature range from 0° C. to the reflux of the solvents at standard pressure.

Suitable dehydrating reagents here are, for example, methyl N-(triethylammoniosulfonyl)carbamate (Burgess reagent), carbodiimides, for example N,N'-diethyl-, N,N'-dipropyl-, N,N'-diisopropyl- and N,N'-dicyclohexylcarbodiimide, N-(3-dimethylaminoisopropyl)-N'-ethylcarbodiimide hydrochloride (EDC) (optionally in the presence of pentafluorophenol (PFP)), N-cyclohexylcarbodiimide-N'-propyloxymethyl-polystyrene (PS-carbodiimide) or carbonyl compounds such as 1,1'-carbonyldiimidazole, or 1,2-oxazolium compounds such as 2-ethyl-5-phenyl-1,2-oxazolium 3-sulphate or 2-tert-butyl-5-methyl-isoxazolium perchlorate, or acylamino compounds such as 2-ethoxy-1-ethoxycarbonyl-1,2-dihydroquinoline, or propanephosphonic anhydride, or isobutyl chloroformate, or bis-(2-oxo-3-oxazolidinyl)phosphoryl chloride or benzotriazolyloxytri(dimethylamino)phosphonium hexafluorophosphate, or O-(benzotriazol-1-yl)-N,N,N',N'-tetramethyluronium hexafluorophosphate (HBTU), 2-(2-oxo-1-(2H)-pyridinyl)-1,1,3,3-tetramethyluronium tetrafluoroborate (TPTU), (benzotriazol-1-yloxy)bisdimethylaminomethylium fluoroborate (TBTU) or O-(7-azabenzotriazol-1-yl)-N,N,N',N'-tetramethyluronium hexafluorophosphate (HATU), or benzotriazol-1-yloxytris (dimethylamino)phosphonium hexafluorophosphate (BOP), or ethyl cyano(hydroxyimino)acetate (Oxyma), or (1-cyano-2-ethoxy-2-oxoethylideneaminooxy) dimethylamino morpholinocarbenium hexafluorophosphate (COMU), or N-[(dimethylamino)(3H-[1,2,3]triazolo[4,5-b]pyridin-3-yloxy)methylidene]-N-methylmethanaminium hexafluorophosphate, or 2,4,6-tripropyl-1,3,5,2,4,6-trioxatriphosphinane 2,4,6-trioxide (T3P), or mixtures of these, preference being given to methyl N-(triethylammoniosulfonyl)carbamate.

Bases are, for example, alkali metal carbonates, for example sodium carbonate or potassium carbonate, or sodium hydrogencarbonate or potassium hydrogencarbonate, or organic bases such as trialkylamines, for example triethylamine, N-methylmorpholine, N-methylpiperidine, 4-dimethylaminopyridine or N,N-Diisopropylethylamine, preference being given to N,N-Diisopropylethylamine.

Inert solvents are, for example, alcohols, such as aliphatic alcohols such as methanol, ethanol, iso-propanol, 1-methoxy-2-propanol or tert-butanol, ethers such as diethyl ether, dioxane, tetrahydrofuran, glycol dimethyl ether or diethylene glycol dimethyl ether, hydrocarbons such as benzene, toluene, xylene, hexane, cyclohexane or mineral oil fractions, halogenated hydrocarbons such as dichloromethane, trichloromethane, carbon tetrachloride, 1,2-dichloroethane, trichloroethylene or chlorobenzene, or other solvents such as acetone, ethyl acetate, acetonitrile, pyridine, dimethyl sulphoxide, N,N-dimethylformamide, N,N-dimethylacetamide, N,N'-dimethylpropyleneurea (DMPU) or N-methylpyrrolidone (NMP). It is also possible to use mixtures of the solvents mentioned. Preference being given to ethanol.

The reactions in process (XXXVI)→(XXXVII) are generally carried out in a temperature range from 0° C. to 200° C. Heating options include conventional heating below the boiling point of the solvent, under reflux, or above the boiling point of the solvent in a closed vial, or in a closed vial with the aid of a microwave reactor. Preference is given to 70° C.

The reactions in process (XXXVI)→(XXXVII) can be carried out at atmospheric, elevated or reduced pressure (for example from 0.5 to 25 bar). In general, the reactions are carried out at atmospheric pressure.

Scheme 17: Preparation of compound of the formula (XXXIX) via the carboxylic acid derivative

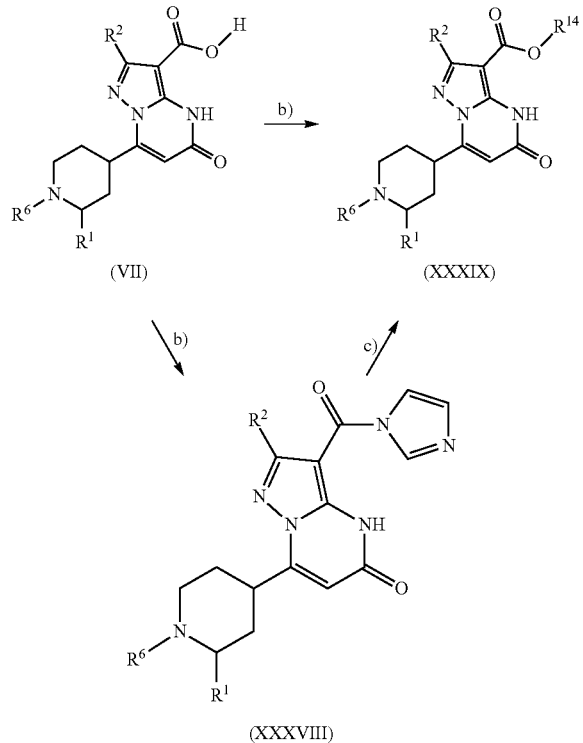

(VII)   (XXXIX)

(XXXVIII)

a) $R^{14}$-2,2,2-trichloroethanimidate, $BF_3 \cdot OEt_2$, THF; b) Carbodiimidazole, THF, reflux; c) $R^{14}OH$, NaH, THF, reflux; or $R^{14}OH$, THF, reflux. Step b) and c) can also be conducted as one step without isolation of (XXXVIII). $R^{14}$ is selected from $C_1$-$C_4$ alkyl, the $C_1$-$C_4$ alkyl being optionally substituted with one, two, or three halogen substituents, $C_3$-$C_4$ cycloalkyl, and benzyl.

The reaction in process (VII)→(XXXIX) is generally effected in inert solvents, optionally in the presence of a lewis acid, preferably within a temperature range from 0° C. to the reflux of the solvents at standard pressure.

Lewis acids are, for example, $BF_3 \cdot OEt_2$, $BCl_3$, $SnCl_4$, TMSTf, $AlCl_3$, preference being given to $BF_3 \cdot OEt_2$.

Inert solvents are, for example, halogenated hydrocarbons such as dichloromethane or trichloromethane, hydrocarbons such as benzene, or other solvents such as nitromethane, tetrahydrofuran, dioxane, dimethylformamide, dimethyl sulphoxide, acetonitrile or pyridine, or mixtures of the solvents, preference being given to tetrahydrofuran.

Alternatively, the reaction in process (VII)→(XXXIX) can be effected by alcohols of the formula $R^{14}OH$ as reactive solvents, together with a dehydrating agent, optionally in the presence of a base, optionally in the presence of inert solvents, preferably within a temperature range from 0° C. to the reflux of the solvents at standard or elevated pressure. $R^{14}$ being selected from $C_1$-$C_4$ alkyl, the $C_1$-$C_4$ alkyl being optionally substituted with one, two, or three halogen substituents, $C_3$-$C_4$ cycloalkyl, and benzyl as defined above. Suitable dehydrating reagents here are, for example, carbodiimides, for example N,N'-diethyl-, N,N'-dipropyl-, N,N'-diisopropyl- and N,N'-dicyclohexylcarbodiimide, N-(3-dimethylaminoisopropyl)-N'-ethylcarbodiimide hydrochloride (EDC) (optionally in the presence of pentafluorophenol (PFP)), N-cyclohexylcarbodiimide-N'-propyloxymethyl-polystyrene (PS-carbodiimide) or carbonyl compounds such as 1,1'-carbonyldiimidazole, or 1,2-oxazolium compounds such as 2-ethyl-5-phenyl-1,2-oxazolium 3-sulphate or 2-tert-butyl-5-methyl-isoxazolium perchlorate, or acylamino compounds such as 2-ethoxy-1-ethoxycarbonyl-1,2-dihydroquinoline, or propanephosphonic anhydride, or isobutyl chloroformate, or bis-(2-oxo-3-oxazolidinyl)phosphoryl chloride or benzotriazolyloxytri(dimethylamino)phosphonium hexafluorophosphate, or O-(benzotriazol-1-yl)-N,N,N',N'-tetramethyluronium hexafluorophosphate (HBTU), 2-(2-oxo-1-(2H)-pyridinyl)-1,1,3,3-tetramethyluronium tetrafluoroborate (TPTU), (benzotriazol-1-yloxy)bisdimethylaminomethylium fluoroborate (TBTU) or O-(7-azabenzotriazol-1-yl)-N,N,N',N'-tetramethyluronium hexafluorophosphate (HATU), or 1-hydroxybenzotriazole (HOBt), or benzotriazol-1-yloxytris(dimethylamino)phosphonium hexafluorophosphate (BOP), or ethyl cyano(hydroxyimino)acetate (Oxyma), or (1-cyano-2-ethoxy-2-oxoethylideneaminooxy) dimethylaminomorpholinocarbenium hexafluorophosphate (COMU), or N-[(dimethylamino)(3H-[1,2,3]triazolo[4,5-b]pyridin-3-yloxy)methylidene]-N-methylmethanaminium hexafluorophosphate, Burgess reagent, or 2,4,6-tripropyl-1,3,5,2,4,6-trioxatriphosphinane 2,4,6-trioxide (T3P), acetic acid anhydride, or carbodiimidazole (CDI), or mixtures of these, preference being given to carbodiimidazole (CDI).

Bases are, for example, alkali metal carbonates, such as sodium carbonate or potassium carbonate, or sodium hydrogencarbonate or potassium hydrogencarbonate, or organic bases for example pyridine, trialkylamines, such as triethylamine, N-methylmorpholine, N-methylpiperidine, 4-dimethylaminopyridine or diisopropylethylamine, or combinations of these. Preference is given to 4-dimethylaminopyridine.

Inert solvents are, for example, halogenated hydrocarbons such as dichloromethane or trichloromethane, hydrocarbons such as benzene, toluene, or other solvents such as nitromethane, tetrahydrofuran, dioxane, dimethylformamide, dimethyl sulphoxide, acetonitrile or pyridine, or mixtures of the solvents.

Alternatively, the reaction in process (VII)→(XXXIX) can be effected by $R^{14}$ halides, in the presence of a base, in an inert solvent, preferably within a temperature range from 0° C. to the reflux of the solvent at standard or elevated pressure.

$R^{14}$ halides are, for example, $R^{14}Cl$, $R^{14}Br$, and $R^{14}I$, wherein $R^{14}$ is selected from $C_1$-$C_4$ alkyl, the $C_1$-$C_4$ alkyl being optionally substituted with one, two, or three halogen substituents, $C_3$-$C_4$ cycloalkyl, and benzyl as defined above.

Bases are, for example, alkali metal carbonates, such as sodium carbonate, potassium carbonate, or caesium carbonate, or sodium hydrogencarbonate or potassium hydrogencarbonate, or organic bases for example pyridine, trialkylamines, for example triethylamine, N-methylmorpholine, N-methylpiperidine, 4-dimethylaminopyridine or diisopropylethylamine, or combinations of these. Preference is given to potassium carbonate or triethylamine.

Inert solvents are, for example, halogenated hydrocarbons such as dichloromethane or trichloromethane, hydrocarbons such as benzene, toluene, or other solvents such as tetrahydrofuran, dioxane, dimethylformamide, dimethyl sulphoxide, acetonitrile or pyridine, or mixtures of these solvents.

Alternatively, the reaction in process (VII)→(XXXIX) can be effected by alcohols of the formula $R^{14}OH$, in the presence of an alkyl azodicarboxylate and a phosphine, in inert solvents, preferably within a temperature range from 0° C. to the reflux of the solvents at standard pressure, wherein $R^{14}$ is selected from $C_1$-$C_4$ alkyl, the $C_1$-$C_4$ alkyl being optionally substituted with one, two, or three halogen substituents, $C_3$-$C_4$ cycloalkyl, and benzyl as defined above.

Alkyl azodicarboxylates are, for example, diethyl azodicarboxylate (DEAD), diisopropyl azodicarboxylate (DIAD), 1,1'-(Azodicarbonyl)dipiperidine, 1,1'-Azobis(N,N-dimethylformamide). Preference is given to diisopropyl azodicarboxylate (DIAD).

Phosphines are, for example, triphenylphosphine, 4-(Dimethylamino)phenyldiphenylphosphine, 4-(Dimethylamino)phenyldiphenylphosphine, Dicyclohexylphenylphosphine, Diphenyl-2-pyridylphosphine, 4-Diphenylphosphinomethyl Polystyrene Resin, preference is given to triphenylphosphine.

Inert solvents are, for example, halogenated hydrocarbons such as dichloromethane or trichloromethane, hydrocarbons such as benzene, toluene, or other solvents such as tetrahydrofuran, dioxane, dimethylformamide, dimethyl sulphoxide, acetonitrile or pyridine, or mixtures of these solvents.

The reaction in process (VII)→(XXXVIII) is generally effected with CDI, or with a dehydrating reagent different from CDI in combination with imidazole, in an inert solvent, optionally in the presence of a base, preferably within a temperature range from 0° C. to the reflux of the solvents at standard pressure.

Suitable dehydrating reagents different from CDI here are, for example, carbodiimides, for example N,N'-diethyl-, N,N'-dipropyl-, N,N'-diisopropyl- and N,N'-dicyclohexylcarbodiimide, N-(3-dimethylaminoisopropyl)-N'-ethylcarbodiimide hydrochloride (EDC) (optionally in the presence of pentafluorophenol (PFP)), N-cyclohexylcarbodiimide-N'-propyloxymethyl-polystyrene (PS-carbodiimide) or carbonyl compounds such as 1,1'-carbonyldiimidazole, or 1,2-oxazolium compounds such as 2-ethyl-5-phenyl-1,2-oxazolium 3-sulphate or 2-tert-butyl-5-methyl-isoxazolium perchlorate, or acylamino compounds such as 2-ethoxy-1-ethoxycarbonyl-1,2-dihydroquinoline, or propanephosphonic anhydride, or isobutyl chloroformate, or bis-(2-oxo-3-oxazolidinyl)phosphoryl chloride or benzotriazolyloxytri(dimethylamino)phosphonium hexafluorophosphate, or O-(benzotriazol-1-yl)-N,N,N',N'-tetramethyluronium hexafluorophosphate (HBTU), 2-(2-oxo-1-(2H)-pyridinyl)-1,1,3,3-tetramethyluronium tetrafluoroborate (TPTU), (benzotriazol-1-yloxy)bisdimethylaminomethylium fluoroborate (TBTU) or O-(7-azabenzotriazol-1-yl)-N,N,N',N'-tetramethyluronium hexafluorophosphate (HATU), or 1-hydroxybenzotriazole (HOBt), or benzotriazol-1-yloxytris(dimethylamino)phosphonium hexafluorophosphate (BOP), or ethyl cyano(hydroxyimino)acetate (Oxyma), or (1-cyano-2-ethoxy-2-oxoethylideneaminooxy) dimethylaminomorpholinocarbenium hexafluorophosphate (COMU), or N-[(dimethylamino)(3H-[1,2,3]triazolo[4,5-b]pyridin-3-yloxy)methylidene]-N-methylmethanaminium hexafluorophosphate, or 2,4,6-tripropyl-1,3,5,2,4,6-trioxatriphosphinane 2,4,6-trioxide (T3P), or mixtures of these, preference being given to N-(3-dimethylaminoisopropyl)-N'-ethylcarbodiimide hydrochloride (EDC) or N,N'-dicyclohexylcarbodiimide. If any of these dehydrating reagents different from CDI is used in the reaction, then a mixture of the dehydrating reagent with imidazole is necessary.

Bases are, for example, alkali metal carbonates, for example sodium carbonate or potassium carbonate, or sodium hydrogencarbonate or potassium hydrogencarbonate, or organic bases such as trialkylamines, for example triethylamine, N-methylmorpholine, N-methylpiperidine, 4-dimethylaminopyridine or diisopropylethylamine, preference being given to diisopropylethylamine.

Inert solvents are, for example, halogenated hydrocarbons such as dichloromethane or trichloromethane, hydrocarbons such as benzene, or other solvents such as nitromethane, tetrahydrofuran, dioxane, dimethylformamide, dimethyl sulphoxide, acetonitrile or pyridine, or mixtures of the solvents, preference being given to tetrahydrofuran.

The reaction in process (XXXVIII)→(XXXIX) is generally effected in inert solvents, optionally in the presence of a base, preferably within a temperature range from 0° C. to the reflux of the solvents at standard pressure.

Bases are, for example, alkali metal carbonates, for example sodium carbonate or potassium carbonate, or sodium hydrogencarbonate or potassium hydrogencarbonate, alkali metal hydrides, such as sodium hydride, potassium hydride, or organic bases such as trialkylamines, for example triethylamine, N-methylmorpholine, N-methylpiperidine, 4-dimethylaminopyridine or diisopropylethylamine, preference being given to sodium hydride.

Inert solvents are, for example, halogenated hydrocarbons such as dichloromethane or trichloromethane, hydrocarbons such as benzene, or other solvents such as nitromethane, tetrahydrofuran, dioxane, dimethylformamide, dimethyl sulphoxide, acetonitrile or pyridine, alcohols, such as the corresponding $R^{14}OH$, or mixtures of the solvents, preference being given to $R^{14}OH$.

Scheme 18: Preparation of a compound of the formula (XXXXI) via the ester derivative

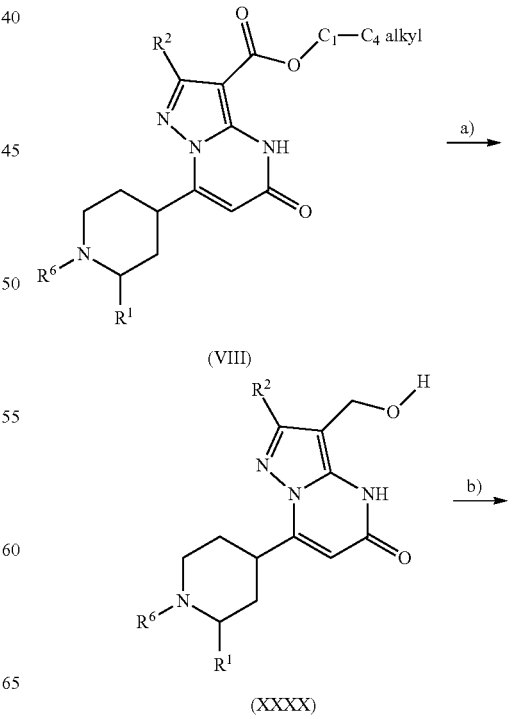

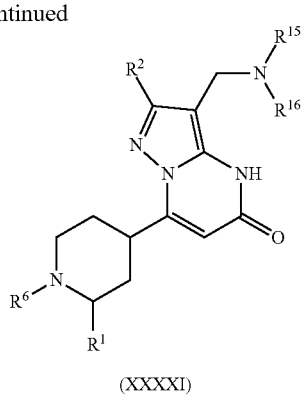

(XXXXI)

a) LiAlH₄, THF; b) triphenylphosphine, NBS, THF, -18° C., then HNR¹⁵R¹⁶, reflux. R¹⁵ and R¹⁶ are selected from $C_1$-$C_4$ alkyl, N, $R^{15}$, and $R^{16}$ together form a 5-6 membered heterocyclyl, the 5-6 membered heterocyclyl-moiety being optionally substituted with one, two or three substituents selected from $C_1$-$C_4$ alkyl and oxo.

The reaction in process (VIII)→(XXXX) is generally effected in inert solvents, preferably within a temperature range from the freezing point of the solvent to c.a. 40° C. at standard pressure.

Inert solvents are, for example, ethereal solvents selected from the group consisting of tetrahydrofuran, t-butyl methyl ether, diethylether, 2-methyl-tetrahydrofuran, 1,2-dimethoxyethane, diethoxymethane, or mixtures of the solvents, preference being given to tetrahydrofuran.

The reaction in process (XXXX)→(XXXXI) is generally effected in inert solvents, preferably within a temperature range from the freezing point of the solvent to reflux of the solvent at standard pressure.

Inert solvents are, for example, ethereal solvents selected from the group consisting of tetrahydrofuran, diethylether, t-butyl methyl ether, 2-methyl-tetrahydrofuran, 1,2-dimethoxyethane, diethoxymethane, or mixtures of the solvents, preference being given to tetrahydrofuran.

The compounds of formula (I-A) or (I-B) according to the invention have useful pharmacological properties and can be employed for the prevention and treatment of disorders in humans and animals.

The compounds of formula (I-A) or (I-B) according to the invention open up a further treatment alternative and are therefore an enrichment of pharmacy.

The compounds of formula (I-A) or (I-B) according to the invention bring about an inhibition of clot lysis (fibrinolysis), lead to an increase in clot stability (clot firmness) and thereby to a reduction of bleeding, re-bleeding and blood loss. These effects are due to direct inhibition of plasminogen, the central precursor of plasmin, a potent serine protease involved in the dissolution of fibrin blood clots.

The compounds of formula (I-A) or (I-B) according to the invention are suitable for the treatment and/or prophylaxis of acute and recurrent bleeding in patients with or without underlying hereditary or acquired hemostatic disorders. The compounds of formula (I-A) or (I-B) according to the invention are also suitable for the treatment and/or prophylaxis of acute and recurrent bleeding in patients with or without underlying hereditary or acquired hemostatic disorders. The compounds of formula (I-A) or (I-B) according to the invention are also suitable for the treatment and/or prophylaxis of acute and recurrent bleeding in patients with or without underlying hereditary rare hemostatic disorders. The compounds of formula (I-A) or (I-B) according to the invention are also suitable for the treatment and/or prophylaxis of hereditary or acquired hemostatic disorders, hereditary or acquired hemostatic disorders, and rare hemostatic disorders. Within the meaning of the present invention, the term underlying hereditary or acquired hemostatic disorders comprises von Willebrand's disease, platelet disorders/dysfunctions like Glantzmann's thrombasthenia and thrombocytopenia, and vitamin K deficiency, PAI-1 deficiency, mild and moderate hemophilia, including hemophilia A (factor VIII deficiency), hemophilia B (factor IX deficiency), and hemophilia C (factor XI deficiency), symptomatic carriers of hemophilia and other hereditary hemostatic disorders, autoimmune disorders that lead to the formation of antibodies against the coagulation factor, blood cancers, bone marrow diseases, infections, kidney failure, liver disease, medications, medications, including heparin, low molecular weight heparin, and coumarin derivatives, like warfarin, accidental injuries and surgical interventions leading to massive blood loss and resulting in a critical reduction in the level of coagulation factors which can lead to additional non-surgical bleeding complications (e.g. coagulopathic bleeding), acquired von Willebrand syndrome (AVWS), characterized by structural or functional defects of von Willebrand factor (VWF) that are secondary to autoimmune, lymphoproliferative or myeloproliferative, malignant, cardiovascular, or other disorders.

Within the meaning of the present invention, the term mild hemophilia is defined as a level of clotting factor activity of the respective deficient factor of 5% to 50% of the normal level, the term moderate hemophilia is defined as a level of clotting factor activity of the respective deficient factor of 1% to 5% of the normal level.

Within the meaning of the present invention, the term underlying hereditary or acquired hemostatic disorders is defined as pathological processes involving the integrity of blood circulation.

Within the meaning of this invention, the terms "underlying hereditary or acquired bleeding disorders" and "underlying hereditary or acquired hemostatic disorders" are interchangeable.

Within the meaning of the present invention, the term underlying hereditary rare hemostatic disorders (RBD) is defined as hemostatic disorders caused by less common hereditary disorders, including deficiency of fibrinogen, prothrombin, factors V, combined V+VIII, VII, X, XI and XIII.

The compounds of formula (I-A) or (I-B) according to the invention can be used in a wide range of hemorrhagic conditions like upper gastrointestinal bleeding, hemorrhages caused by antifibrinolytics, and gynecological bleeding indications including heavy menstrual bleeding (menorrhagia), placental bleeding, postpartum hemorrhage and conisation of the cervix.

Within the meaning of the present invention, heavy menstrual bleeding (menorrhagia) is defined as menstrual blood loss of 60 ml or more per cycle, for example 60 to 80 ml per cycle, in particular more than 80 ml per cycle. Also within the meaning of the present invention and according to National Institute for Clinical Excellence (NICE) guidelines, heavy menstrual bleeding is defined for clinical purposes as excessive menstrual blood loss which interferes with the woman's physical, emotional, social and material quality of life, and which can occur alone or in combination with other symptoms.

Within the meaning of this invention, the terms "heavy menstrual bleeding (HMB)" and "menorrhagia" are interchangeable.

In particular, the compounds of formula (I-A) or (I-B) according to the invention can be used in heavy menstrual bleeding (menorrhagia) caused by underlying hemostatic disorders, for example hereditary or acquired hemostatic disorders, such as von Willebrand's disease, platelet disorders/dysfunctions like Glantzmann's thrombasthenia and thrombocytopenia, and vitamin K deficiency, PAI-1 deficiency, mild and moderate hemophilia, including hemophilia A (factor VIII deficiency), hemophilia B (factor IX deficiency), and hemophilia C (factor XI deficiency), symptomatic carriers of hemophilia and other hereditary hemostatic disorders, such as deficiency of fibrinogen, of prothrombin, of factors V, and combined factor V+VIII, VII, X, XI and XIII deficiencies, autoimmune disorders, blood cancers, bone marrow diseases, infections, kidney failure, liver disease, medications, including heparin, low molecular weight heparin, and coumarin derivatives, like warfarin, accidental injuries and surgical interventions leading to massive blood loss and resulting in a critical reduction in the level of coagulation factors, and acquired von Willebrand syndrome (AVWS).

The compounds of formula (I-A) or (I-B) according to the invention can also be used for reducing peri- and postoperative blood loss and rebleeding during and after different surgical interventions, including cardiovascular surgery, including coronary artery bypass surgery, spinal surgery, trauma surgery, transplantation, including orthotopic liver transplantation, and hysterectomy, as well as transfusion requirements in patients with or without underlying hemostatic disorders. Moreover, the compounds of formula (I-A) or (I-B) according to the invention can be used for the prevention of recurrence of bleeding in patients after elective minor surgery like prostatic surgery including prostatectomy and transurethral prostatic surgery, urinary surgery, otolaryngological (ENT) surgery including tonsillectomy, and adenoidectomy, oral surgery, and dental surgery, in patients with or without underlying hemostatic disorders.

In the context of the present invention, the term "medical intervention" includes medical interventions associated with bleeding, such as surgery, transplantation, and procedures. The definition of the term "medical intervention" also includes minor medical interventions that may cause bleeding, such as tooth extractions, periodontal (gum) surgery, dental implant placement, biopsies, e.g. dental, prostatic, and urinary biopsies, and the removal of urinary stones.

The compounds of formula (I-A) or (I-B) according to the invention can also be used for treatment and/or prophylaxis of acute and recurrent bleeding in patients with liver diseases, including patients with end-stage liver diseases in patients with or without underlying hemostatic disorders.

The compounds of formula (I-A) or (I-B) according to the invention can also be used for treatment and/or prophylaxis of acute and recurrent bleeding in patients with trauma and/or traumatic hyphaema, hemorrhagic stroke, acute promyelocytic leukaemia and to block plasmin-induced proteolysis which may be of biological relevance during atherothrombosis and inflammatory states, cancer and other diseases in patients with or without underlying hemostatic disorders.

The compounds of formula (I-A) or (I-B) according to the invention can also be used for the treatment and/or prophylaxis of hereditary or acquired hemostatic disorders in patients including von Willebrand's disease, platelet disorders/dysfunctions like Glantzmann's thrombasthenia and thrombocytopenia, and vitamin K deficiency, PAI-1 deficiency, mild and moderate hemophilia, including hemophilia A (factor VIII deficiency), hemophilia B (factor IX deficiency), and hemophilia C (factor XI deficiency), symptomatic carriers of hemophilia and other hereditary hemostatic disorders, such as deficiency of fibrinogen, of prothrombin, of factors V, and combined factor V+VIII, VII, X, XI and XIII deficiencies, autoimmune disorders, blood cancers, bone marrow diseases, infections, kidney failure, liver disease, medications, medications, including heparin, low molecular weight heparin, and coumarin derivatives, like warfarin, accidental injuries and surgical interventions leading to massive blood loss and resulting in a critical reduction in the level of coagulation factors, and acquired von Willebrand syndrome (AVWS).

The compounds of the present invention can be used either alone as monotherapy or in combination with other therapies to address a hemostatic disorder. For instance, co-administration of one or more compounds of the invention with a plasma-derived or recombinant coagulation factor such as factor VIIa, factor VIII, factor IX or desmopressin is believed useful for treating hemophilia.

The compounds of formula (I-A) or (I-B) according to the invention can also be used for treating synovitis, wherein the synovitis may be associated with cartilage damage and is associated with hemarthrosis in patients with or without underlying hereditary or acquired hemostatic disorders.

The compounds of formula (I-A) or (I-B) according to the invention can also be used for the treatment of nosebleed (epistaxis) caused by trauma or other causes in patients with or without underlying hereditary or acquired hemostatic disorders.

The compounds of formula (I-A) or (I-B) according to the invention can also be used for the treatment and/or prophylaxis of hereditary or acquired hemostatic disorders in patients.

The present invention further relates to the use of the compounds of formula (I-A) or (I-B) according to the invention for the treatment and/or prophylaxis of diseases, in particular the aforementioned diseases.

An embodiment of the present invention is also a compound of formula (I-A) or (I-B) according to the invention for use in a method for the treatment and/or prophylaxis of diseases.

An embodiment of the present invention is also a compound of formula (I-A) or (I-B) according to the invention for use in a method for the treatment and/or prophylaxis of acute and recurrent bleeding in patients with or without underlying hereditary or acquired bleeding disorders.

An embodiment of the present invention is also a compound of formula (I-A) or (I-B) according to the invention for use in a method for the treatment and/or prophylaxis of acute and recurrent bleeding in patients with underlying hereditary or acquired hemostatic disorders.

An embodiment of the present invention is also a compound of formula (I-A) or (I-B) according to the invention for use in a method for the treatment and/or prophylaxis of acute and recurrent bleeding in patients with or without underlying hereditary or acquired hemostatic disorders, wherein the bleeding is associated with a disease or medical intervention selected from the group consisting of heavy menstrual bleeding, postpartum hemorrhage, hemorrhagic shock, trauma, surgery, otolaryngological surgery, dental surgery, urinary surgery, prostatic surgery, gynecological surgery, cardiovascular surgery, spinal surgery, liver or lung transplantation, stroke, liver diseases, hereditary angioedema, nosebleed, and synovitis and cartilage damage following hemarthrosis.

An embodiment of the present invention is also a compound of formula (I-A) or (I-B) according to the invention for use in a method for the treatment and/or prophylaxis of acute and recurrent bleeding in patients with underlying hereditary or acquired hemostatic disorders, wherein the bleeding is associated with a disease or medical intervention selected from the group consisting of heavy menstrual bleeding, postpartum hemorrhage, hemorrhagic shock, trauma, surgery, otolaryngological surgery, dental surgery, urinary surgery, prostatic surgery, gynecological surgery, cardiovascular surgery, spinal surgery, liver or lung transplantation, stroke, liver diseases, hereditary angioedema, nosebleed, and synovitis and cartilage damage following hemarthrosis.

An embodiment of the present invention is also a compound of formula (I-A) or (I-B) according to the invention for use in a method for the treatment and/or prophylaxis of acute and recurrent bleeding in patients with or without underlying hereditary or acquired hemostatic disorders, wherein the bleeding is associated with a disease or medical intervention selected from the group consisting of heavy menstrual bleeding, postpartum hemorrhage, hemorrhagic shock, hemorrhagic cystitis, gastrointestinal hemorrhage, trauma, surgery, otolaryngological surgery, dental surgery, orthopaedic surgery, urinary surgery, prostatic surgery, gynecological surgery, cardiovascular surgery, spinal surgery, liver or lung transplantation, stroke, liver diseases, hereditary angioedema, nosebleed, and synovitis and cartilage damage following hemarthrosis.

An embodiment of the present invention is also a compound of formula (I-A) or (I-B) according to the invention for use in a method for the treatment and/or prophylaxis of acute and recurrent bleeding in patients with underlying hereditary or acquired hemostatic disorders, wherein the bleeding is associated with a disease or medical intervention selected from the group consisting of heavy menstrual bleeding, postpartum hemorrhage, hemorrhagic shock, hemorrhagic cystitis, gastrointestinal hemorrhage, trauma, surgery, otolaryngological surgery, dental surgery, orthopaedic surgery, urinary surgery, prostatic surgery, gynecological surgery, cardiovascular surgery, spinal surgery, liver or lung transplantation, stroke, liver diseases, hereditary angioedema, nosebleed, and synovitis and cartilage damage following hemarthrosis.

The present invention further relates to the use of the compounds of formula (I-A) or (I-B) according to the invention for producing a medicament for the treatment and/or prophylaxis of diseases, in particular the aforementioned diseases.

The present invention further relates to the use of the compounds of formula (I-A) or (I-B) according to the invention for producing a medicament for the treatment and/or prophylaxis of acute and recurrent bleeding in patients with or without underlying hereditary or acquired hemostatic disorders, wherein the bleeding is associated with a disease or medical intervention selected from the group consisting of heavy menstrual bleeding, postpartum hemorrhage, hemorrhagic shock, hemorrhagic cystitis, gastrointestinal hemorrhage, trauma, surgery, otolaryngological surgery, dental surgery, orthopaedic surgery, urinary surgery, prostatic surgery, gynecological surgery, cardiovascular surgery, spinal surgery, liver or lung transplantation, stroke, liver diseases, hereditary angioedema, nosebleed, and synovitis and cartilage damage following hemarthrosis.

The present invention further relates to the use of the compounds of formula (I-A) or (I-B) according to the invention for producing a medicament for the treatment and/or prophylaxis of acute and recurrent bleeding in patients with underlying hereditary or acquired hemostatic disorders, wherein the bleeding is associated with a disease or medical intervention selected from the group consisting of heavy menstrual bleeding, postpartum hemorrhage, hemorrhagic shock, hemorrhagic cystitis, gastrointestinal hemorrhage, trauma, surgery, otolaryngological surgery, dental surgery, orthopaedic surgery, urinary surgery, prostatic surgery, gynecological surgery, cardiovascular surgery, spinal surgery, liver or lung transplantation, stroke, liver diseases, hereditary angioedema, nosebleed, and synovitis and cartilage damage following hemarthrosis.

An embodiment of the present invention is also a medicament comprising a compound of the formula (I-A) or (I-B) according to the invention in combination with an inert, non-toxic, pharmaceutically suitable auxiliary.

An embodiment of the present invention is also a medicament comprising a compound of the formula (I-A) or (I-B) according to the invention in combination with a further active compound selected from the group consisting of Factor VIII, Factor IX, Factor VIIa, activated prothrombin complex concentrates (aPCC) or prothrombin complex concentrates (PCCs), ε-aminocaproic acid, ethamsylate, paraaminobutyl benzoic acid, tranexamic acid, desmopressin, danazol, combined oral contraceptive pills (COCPs), progestin intrauterine system, glucocorticoid receptor agonists, analgesics, and nonsteroidal anti-inflammatory drugs (NSAIDs).

An embodiment of the present invention is also a medicament comprising a compound of the formula (I-A) or (I-B) according to the invention as described above for the treatment and/or prophylaxis of acute and recurrent bleeding in patients with or without underlying hereditary or acquired hemostatic disorders.

An embodiment of the present invention is also a medicament comprising a compound of the formula (I-A) or (I-B) according to the invention as described above for the treatment and/or prophylaxis of acute and recurrent bleeding in patients with or without underlying hereditary or acquired bleeding disorders.

An embodiment of the present invention is also a medicament comprising a compound of the formula (I-A) or (I-B) according to the invention as described above for the treatment and/or prophylaxis of acute and recurrent bleeding in patients with underlying hereditary or acquired hemostatic disorders.

An embodiment of the present invention is also a medicament comprising a compound of the formula (I-A) or (I-B) according to the invention as described above for the treatment and/or prophylaxis of acute and recurrent bleeding in patients with underlying hereditary or acquired bleeding disorders.

An embodiment of the present invention is also a medicament comprising a compound of the formula (I-A) or (I-B) according to the invention as defined above for the treatment and/or prophylaxis of acute and recurrent bleeding in patients with or without underlying hereditary or acquired hemostatic disorders, wherein the bleeding is associated with a disease or medical intervention selected from the group consisting of heavy menstrual bleeding, postpartum hemorrhage, hemorrhagic shock, hemorrhagic cystitis, gastrointestinal hemorrhage, trauma, surgery, otolaryngological surgery, dental surgery, orthopaedic surgery, urinary surgery, prostatic surgery, gynecological surgery, cardiovascular surgery, spinal surgery, liver or lung transplantation, stroke, liver diseases, hereditary angioedema, nosebleed, and synovitis and cartilage damage following hemarthrosis.

An embodiment of the present invention is also a medicament comprising a compound of the formula (I-A) or (I-B)

according to the invention as defined above for the treatment and/or prophylaxis of acute and recurrent bleeding in patients with underlying hereditary or acquired hemostatic disorders, wherein the bleeding is associated with a disease or medical intervention selected from the group consisting of heavy menstrual bleeding, postpartum hemorrhage, hemorrhagic shock, hemorrhagic cystitis, gastrointestinal hemorrhage, trauma, surgery, otolaryngological surgery, dental surgery, orthopaedic surgery, urinary surgery, prostatic surgery, cardiovascular surgery, spinal surgery, liver or lung transplantation, stroke, liver diseases, hereditary angioedema, nosebleed, and synovitis and cartilage damage following hemarthrosis.

An embodiment of the present invention is also a method for the treatment and/or prophylaxis of acute and recurrent bleeding in patients with or without underlying hereditary or acquired hemostatic disorders in humans and animals using an effective amount of at least one compound of the formula (I-A) or (I-B) according to the invention or a medicament comprising a compound of the formula (I-A) or (I-B) according to the invention as defined above.

An embodiment of the present invention is also a method for the treatment and/or prophylaxis of acute and recurrent bleeding in patients with underlying hereditary or acquired hemostatic disorders in humans and animals using an effective amount of at least one compound of the formula (I-A) or (I-B) according to the invention or a medicament comprising a compound of the formula (I-A) or (I-B) according to the invention as defined above.

An embodiment of the present invention is also a method for the treatment and/or prophylaxis of acute and recurrent bleeding in patients with or without underlying hereditary or acquired hemostatic disorders in humans and animals using an effective amount of at least one compound of the formula (I-A) or (I-B) according to the invention or a medicament comprising a compound of the formula (I-A) or (I-B) according to the invention as defined above, wherein the bleeding is associated with a disease or medical intervention selected from the group consisting of heavy menstrual bleeding, postpartum hemorrhage, hemorrhagic shock, hemorrhagic cystitis, gastrointestinal hemorrhage, trauma, surgery, otolaryngological surgery, dental surgery, orthopaedic surgery, urinary surgery, prostatic surgery, cardiovascular surgery, spinal surgery, liver or lung transplantation, stroke, liver diseases, hereditary angioedema, nosebleed, and synovitis and cartilage damage following hemarthrosis.

An embodiment of the present invention is also a method for the treatment and/or prophylaxis of acute and recurrent bleeding in patients with or without underlying hereditary or acquired bleeding disorders in humans and animals using an effective amount of at least one compound of the formula (I-A) or (I-B) according to the invention or a medicament comprising a compound of the formula (I-A) or (I-B) according to the invention as defined above, wherein the bleeding is associated with a disease or medical intervention selected from the group consisting of heavy menstrual bleeding, postpartum hemorrhage, hemorrhagic shock, hemorrhagic cystitis, gastrointestinal hemorrhage, trauma, surgery, otolaryngological surgery, dental surgery, orthopaedic surgery, urinary surgery, prostatic surgery, cardiovascular surgery, spinal surgery, liver or lung transplantation, stroke, liver diseases, hereditary angioedema, nosebleed, and synovitis and cartilage damage following hemarthrosis.

An embodiment of the present invention is also a method for the treatment and/or prophylaxis of acute and recurrent bleeding in patients with underlying hereditary or acquired hemostatic disorders in humans and animals using an effective amount of at least one compound of the formula (I-A) or (I-B) according to the invention or a medicament comprising a compound of the formula (I-A) or (I-B) according to the invention as defined above, wherein the bleeding is associated with a disease or medical intervention selected from the group consisting of heavy menstrual bleeding, postpartum hemorrhage, hemorrhagic shock, hemorrhagic cystitis, gastrointestinal hemorrhage, trauma, surgery, otolaryngological surgery, dental surgery, orthopaedic surgery, urinary surgery, prostatic surgery, cardiovascular surgery, spinal surgery, liver or lung transplantation, stroke, liver diseases, hereditary angioedema, nosebleed, and synovitis and cartilage damage following hemarthrosis.

An embodiment of the present invention is also a method for the treatment and/or prophylaxis of acute and recurrent bleeding in patients with underlying hereditary or acquired bleeding disorders in humans and animals using an effective amount of at least one compound of the formula (I-A) or (I-B) according to the invention or a medicament comprising a compound of the formula (I-A) or (I-B) according to the invention as defined above, wherein the bleeding is associated with a disease or medical intervention selected from the group consisting of heavy menstrual bleeding, postpartum hemorrhage, hemorrhagic shock, hemorrhagic cystitis, gastrointestinal hemorrhage, trauma, surgery, otolaryngological surgery, dental surgery, orthopaedic surgery, urinary surgery, prostatic surgery, cardiovascular surgery, spinal surgery, liver or lung transplantation, stroke, liver diseases, hereditary angioedema, nosebleed, and synovitis and cartilage damage following hemarthrosis.

The efficacy of the compounds of formula (I-A) and (I-B) according of the invention for the treatment and/or prophylaxis of hereditary or acquired hemostatic disorders, and of acute and recurrent bleeding in patients with or without underlying hereditary or acquired hemostatic disorders, wherein the bleeding is associated with a disease or medical intervention selected from the group consisting of heavy menstrual bleeding, postpartum hemorrhage, hemorrhagic shock, hemorrhagic cystitis, gastrointestinal hemorrhage, trauma, surgery, otolaryngological surgery, dental surgery, orthopaedic surgery, urinary surgery, prostatic surgery, cardiovascular surgery, spinal surgery, liver or lung transplantation, stroke, liver diseases, hereditary angioedema, nosebleed, and synovitis and cartilage damage following hemarthrosis, can be demonstrated for example by a reduction in blood loss (quantitative and laboratory values), by a shortened duration of bleeding, by an increased clot firmness, by a lower incidence of recurrent bleeding, by an improved quality of life, which may in the case of heavy menstrual bleeding be determined by the Menorrhagia Impact Questionnaire, the number of medical visits, and/or by improved compliance due to less frequent dosing as compared to e.g. lysine analogs, including tranexamic acid and ε-aminocaproic acid.

The compound of formula (I-A) or (I-B) need not be, but is optionally administered with one or more agents currently used to prevent or treat the disorder in question. The effective amount of such other agents depends on the amount of compound of the invention present, the type of disorder or treatment. These are generally used in the same dosages and with administration routes as used hereinbefore or about from 1 to 99% of the heretofore employed dosages. The present invention further relates to medicaments containing at least one of the compounds of formula (I-A) or (I-B) according to the invention and one or more further active substances, in particular for the treatment and/or prophylaxis of the aforementioned diseases. As suitable combination active substances, we may mention for example and preferably:

Factor VIII, Factor IX, Factor VIIa, activated prothrombin complex concentrates (aPCC) or prothrombin complex concentrates (PCCs), ε-aminocaproic acid, ethamsylate, paraaminobutyl benzoic acid, tranexamic acid, desmopressin, danazol, combined oral contraceptive pills (COCPs), progestin intrauterine systems, glucocorticoid receptor agonists, analgesics, and nonsteroidal anti-inflammatory drugs (NSAIDs).

In an embodiment of the invention, the compounds of formula (I-A) or (I-B) according to the invention are administered in a combination with the coagulation factor commonly known as Factor VIII, any derivatives, fragments, muteins or conjugates thereof.

In an embodiment of the invention, the compounds of formula (I-A) or (I-B) according to the invention are administered in a combination with the coagulation factor commonly known as Factor IX, any derivatives, fragments, muteins or conjugates thereof.

In an embodiment of the invention, the compounds of formula (I-A) or (I-B) according to the invention are administered in a combination with the coagulation factor commonly known as Factor VIIa, any derivatives, fragments, muteins or conjugates thereof.

In an embodiment of the invention, the compounds of formula (I-A) or (I-B) according to the invention are administered in a combination with activated prothrombin complex concentrates (aPCCs) or prothrombin complex concentrates (PCCs).

In an embodiment of the invention, the compounds of formula (I-A) or (I-B) according to the invention are administered in a combination with antifibrinolytic agents such as, by way of example and preferably, ε-aminocaproic acid, ethamsylate, paraaminobutyl benzoic acid, and tranexamic acid.

In an embodiment of the invention, the compounds of formula (I-A) or (I-B) according to the invention are administered in a combination with desmopressin.

In an embodiment of the invention, the compounds of formula (I-A) or (I-B) according to the invention are administered in a combination with danazol.

In an embodiment of the invention, the compounds of formula (I-A) or (I-B) according to the invention are administered in combination with combined oral contraceptive pills (COCPs) such as, by way of example and preferably, combinations of an estrogen, for example the synthetic estrogen ethinylestradiol or the natural estrogens estradiol and estradiolderivatives, preferably estradiolester, such as estradiolvalerate and estradiolhydrate, and a gestagen for example progesterone, trimegestone, medroxyprogesterone acetate, megestrol acetate, cyproterone acetate, chlormadinone acetate, nestorone, levonorgestrel, norgestimate, desogestrel, ethonogestrel (3-Ketodesogestrel), nomegestrol acetate (NOMAC), norethisterone acetate (NETA), drospirenone, gestodene, dienogest, norethindrone acetate, danazole, norgestrel, and tanaproget.

In an embodiment of the invention, the compounds of formula (I-A) or (I-B) according to the invention are administered in combination with intrauterine devices, including progestine impregnated intrauterine devices, e.g. LNG-IUS levonorgestrel intrauterine system.

In an embodiment of the invention, the compounds of formula (I-A) or (I-B) according to the invention are administered in combination with a glucocorticoid receptor agonist, such as, by way of example and preferably, cortisol, cortisone, hydrocortisone, prednisone, methyl-prednisolone, prednylidene, deflazacort, fluocortolone, triamcinolone, dexamethasone or betamethasone.

In an embodiment of the invention, the compounds of formula (I-A) or (I-B) according to the invention are administered in combination with nonsteroidal anti-inflammatory drugs (NSAIDs), such as by way of example and preferably acetylsalicylic acid, diclofenac, flurbiprofen, ibuprofen, indomethacin, mefenamic acid, meclofenamic acid, and naproxen.

In an embodiment of the invention, the compounds of formula (I-A) or (I-B) according to the invention are administered in combination with analgesics, such as by way of example and preferably, acetaminophen, acetanilide, aminobenzoic acid, antipyrine, calcium or choline salicylate, codeine, phenatecin, phenyltoloxamine citrate, salicylamide, sodium salicylate, and sodium para-aminobenzoate.

An embodiment of the invention is also a medicament, comprising a compound of the formula (I-A) or (I-B) as defined above in combination with a further active compound selected from the group consisting of Factor VIII, Factor IX, Factor VIIa, activated prothrombin complex concentrates (aPCC) or prothrombin complex concentrates (PCCs), ε-aminocaproic acid, ethamsylate, paraaminobutyl benzoic acid, tranexamic acid, desmopressin, danazol, hormonal treatments, including combined oral contraceptive pills (COCPs), progestin intrauterine system, glucocorticoid receptor agonists, analgesics, and nonsteroidal anti-inflammatory drugs (NSAIDs).

An embodiment of the invention is also a medicament as defined above for the treatment and/or prophylaxis of genetic or acquired hemostatic disorders, trauma, surgery, stroke, heavy menstrual bleeding (HMB), including heavy menstrual bleeding in women with underlying hemostatic disorders, postpartum hemorrhage, liver diseases, and hereditary angioedema.

An embodiment of the invention is also a method for the treatment and/or prophylaxis of genetic or acquired hemostatic disorders, trauma, surgery, stroke, heavy menstrual bleeding, including heavy menstrual bleeding in women with underlying hemostatic disorders, postpartum hemorrhage, liver diseases, and hereditary angioedema in humans and animals using an effective amount of at least one compound of the formula (I-A) or (I-B) as defined above or a medicament as defined above.

The present invention further relates to medicaments that contain at least one compound of formula (I-A) or (I-B) according to the invention, usually together with one or more inert, non-toxic, pharmaceutically suitable auxiliaries, and use thereof for the aforementioned purposes.

The compounds of formula (I-A) or (I-B) according to the invention may be effective after systemic and/or local administration. For this purpose they can be applied in a suitable way, e.g. by oral, parenteral, pulmonary, nasal, sublingual, lingual, buccal, rectal, dermal, transdermal, conjunctival, or otic administration or as implant or stent.

For these routes of application, the compounds of formula (I-A) or (I-B) according to the invention can be administered in suitable dosage forms.

Dosage forms functioning according to the prior art, for rapid and/or modified release of the compounds according to the invention, which contain the compounds of formula (I-A) or (I-B) according to the invention in crystalline and/or amorphized and/or dissolved form, e.g. tablets (uncoated or coated tablets, for example with enteric coatings or coatings with delayed dissolution or insoluble coatings, which control the release of the compound formula (I-A) or (I-B)

according to the invention), tablets or films/wafers that disintegrate rapidly in the oral cavity, films/lyophilizates, capsules (for example hard or soft gelatin capsules), sugar-coated pills, granules, pellets, powders, emulsions, suspensions, aerosols or solutions, are suitable for oral administration.

Parenteral administration can take place avoiding an absorption step (e.g. intravenous, intraarterial, intracardiac, intraspinal or intralumbar) or including absorption (e.g. intramuscular, subcutaneous, intracutaneous, percutaneous or intraperitoneal). Injection and infusion preparations in the form of solutions, suspensions, emulsions, lyophilizates or sterile powders are suitable, among others, as dosage forms for parenteral application. Intravenous administration can take place for example by bolus administration or by continuous infusion.

Inhaled pharmaceutical forms (including powder inhalers, nebulizers), nasal drops, nasal solutions or nasal sprays, tablets, films/wafers or capsules for lingual, sublingual or buccal application, suppositories, ear or eye preparations, vaginal capsules, aqueous suspensions (lotions, shaking mixtures), lipophilic suspensions, ointments, creams, transdermal therapeutic systems (e.g. patches), milk, pastes, foams, dusting powders, implants or stents for example are suitable for other routes of administration.

In one embodiment, the compounds of formula (I-A) or (I-B) according to the invention can be administered in the form of nasal drops, nasal solutions or nasal sprays for the treatment and/or prophylaxis of acute and recurrent nosebleed in patients, in particular in patients with underlying hereditary or acquired hemostatic disorders.

In one embodiment, the compounds of formula (I-A) or (I-B) according to the invention can be administered in the form of patches soaked with the compounds of formula (I-A) or (I-B) according to the invention and applied to the wound for the treatment and/or prophylaxis of acute and recurrent bleeding in patients, in particular in patients with underlying hereditary or acquired hemostatic disorders. In one embodiment, the compounds of formula (I-A) or (I-B) according to the invention are administered intra-muscular, rectal or transvaginal for the treatment and/or prophylaxis of acute and recurrent bleeding in patients with trauma and other forms of acute bleeding, in particular in patients with underlying hereditary or acquired hemostatic disorders.

In one embodiment, the compounds of formula (I-A) or (I-B) according to the invention are administered in form of a swish and swallow or a lozenge for the treatment and/or prophylaxis of acute and recurrent mouth bleeding in patients, in particular in patients with underlying hereditary or acquired hemostatic disorders. A swish and swallow route of administration is defined as the administration of a liquid substance to the oral mucosa by swishing the drug inside the mouth for a certain amount of time then allowed to be swallowed. The drug action is both topical and systemic.

The compounds of formula (I-A) or (I-B) according to the invention can also be used in vitro or ex vivo to inhibit fibrinolysis, for example for in vitro/ex vivo assays, to inhibit fibrinolysis in blood and plasma products, to pretreat catheters and other medicinal devices and equipment, for surface coatings or in biological samples.

The compounds of formula (I-A) or (I-B) according to the invention can be transformed to the aforementioned dosage forms. This can take place in a manner known per se by mixing with inert, non-toxic, pharmaceutically suitable auxiliaries. These auxiliaries include inter alia carriers (for example microcrystalline cellulose, lactose, mannitol), solvents (e.g. liquid polyethylene glycols), emulsifiers and dispersants or wetting agents (for example sodium dodecyl sulphate, polyoxysorbitan oleate), binders (for example polyvinylpyrrolidone), synthetic and natural polymers (for example albumin), stabilizers (e.g. antioxidants such as ascorbic acid), colorants (e.g. inorganic pigments, for example iron oxides) and taste and/or odour correctants.

An embodiment of the invention are pharmaceutical compositions comprising at least one compound of formula (I-A) or (I-B) according to the invention, preferably together with at least one inert, non-toxic, pharmaceutically suitable auxiliary, and the use of these pharmaceutical compositions for the above cited purposes.

For the prevention or treatment of disease, the appropriate dosage of a compound of the invention (when used alone or in combination with other agents) will depend on the type of disease to be treated, the type of compound, the severity and course of the disease, whether the compound is administered for preventive or therapeutic purposes, previous therapy, the patient's clinical history and response to the compound, and the discretion of the attending physician. The compound is suitably administered to the patient at one time or over a series of treatments. Depending on the type and severity of disease, about 0.1 µg/kg to 100 mg/kg of the compound is an initial candidate dosage for administration to the patient, whether for example, by one or more separate administrations, or by continuous infusion. A typical daily dosage might range from about 0.1 µg/kg to 100 mg/kg or more, depending on the factors mentioned above. For repeated administrations over several days or longer, depending on the condition, the treatment is sustained until a desired suppression of disease symptoms occurs. An initial higher loading dose, followed by one or more lower doses may be administered. However, other dosing regimen may be useful. The progress of this therapy is easily monitored by conventional techniques and assays.

In general, it has proved advantageous, in the case of oral or parenteral administration, to administer amounts in a range of from 0.1 to 300 or from 0.5 to 50 or from 1 to 50 or from 2 to 10 mg/kg body weight every 24 hours to achieve effective results.

According to a further embodiment, it has proved advantageous, in the case of oral administration of an immediate release tablet, to administer amounts in a range of from 5 to 15 or from 7 to 12 or from 9 to 11 or of 10 mg/kg body weight twice a day (b.i.d.). In the case of oral administration of a modified release tablet it has proved advantageous to administer amounts up to 2-fold lower than that in the case of oral administration of an immediate release tablet.

Nevertheless, it may optionally be necessary to deviate from the stated amounts, namely depending on body weight, route of administration, individual response to the active substance, type of preparation and time point or interval when application takes place. Thus, in some cases it may be sufficient to use less than the aforementioned minimum amount, whereas in other cases the stated upper limit must be exceeded. When applying larger amounts, it may be advisable to distribute these in several individual doses throughout the day.

According to a further embodiment, the compounds of formula (I-A) or (I-B) according to the invention are administered orally once or twice or three times a day. According to a further embodiment, the compounds of formula (I-A) or (I-B) according to the invention are administered orally once or twice a day. According to a further embodiment, the compounds of formula (I-A) or (I-B) according to the invention are administered orally once a day. For the oral administration, a rapid release or a modified release dosage form may be used.

According to a further embodiment, the compounds of formula (I-A) or (I-B) according to the invention are administered orally once or twice or three times a day on 1 or 2 or 3 or 4 or 5 or 6 or 7 or 8 or 9 or 10 days per month. According to a further embodiment, the compounds of formula (I-A) or (I-B) according to the invention are administered orally once or twice or three times a day on 2 or 3 or 4 or 5 or 6 or 7 or 8 or 9 or 10 consecutive days per month. According to a further embodiment, the compounds of formula (I-A) or (I-B) according to the invention are administered orally once or twice or three times a day on 3 or 4 or 5 or 6 or 7 days per month. According to a further embodiment, the compounds of formula (I-A) or (I-B) according to the invention are administered orally once or twice or three times a day on 3 or 4 or 5 or 6 or 7 consecutive days per month.

The following practical examples explain the invention. The invention is not limited to the examples.

The percentages in the following tests and examples are percentages by weight, unless stated otherwise; parts are parts by weight. Proportions of solvents, dilution ratios and concentrations for liquid/liquid solutions refer in each case to the volume.

A. EXAMPLES

Abbreviations and Acronyms

| | |
|---|---|
| [α] | specific rotation value |
| AcOH | acetic acid |
| Boc | tert-butoxycarbonyl |
| br. | broad signal (NMR coupling pattern) |
| Burgess Reagent | N-(triethylammoniosulfonyl)carbamate |
| CDI | 1,1'-carbonyldiimidazole |
| COMU | (1-Cyano-2-ethoxy-2-oxoethylidenaminooxy)dimethylamino-morpholino-carbenium hexafluorophosphate |
| Conc. | Concentrated |
| CPhos | 2-dicyclohexylphosphino-2',6'-bis(N,N-dimethylamino)-1,1'-biphenyl |
| δ | NMR shift in ppm |
| d | doublet (NMR coupling pattern) |
| DAD | diode array detector |
| DCM | dichloromethane |
| DIPEA | diisopropyl ethyl amine |
| DMAP | 4-N,N-dimethylaminopyridine |
| DMF | N,N-dimethylformamide |
| DMSO | dimethylsulfoxide |
| EDCI | N-ethyl-N'-(3-dimethylaminopropyl)carbodiimide hydrochloride |
| ELSD | evaporative light scattering detector |
| ESI | electrospray ionisation (MS) |
| GC-MS | gas chromatography coupled to mass spectrometry |
| h | hour(s) |
| HATU | 1-[Bis(dimethylamino)methylene]-1H-1,2,3-triazolo[4,5-b]pyridinium 3-oxid hexafluorophosphate |
| HCl | Hydrochloric acid |
| HOBt | 1-Hydroxybenzotriazole hydrate |
| HPLC | high performance liquid chromatography |
| LC-MS | liquid chromatography-coupled to mass spectrometry |
| M | Molar |
| m | multiplet (NMR coupling pattern) |
| min | minute(s) |
| MS | mass spectrometry |
| MTBE | tert-butyl methyl ether |
| NMR | nuclear magnetic resonance |
| PMB | p-methoxybenzyl |
| q | quartet (NMR coupling pattern) |
| $R_t$ | retention time |
| RT | room temperature |
| s | singlet (NMR coupling pattern) |
| t | triplet (NMR coupling pattern) |
| TFA | trifluoroacetic acid |
| THF | tetrahydrofurane |
| TLC | thin layer chromatography |
| UV | ultraviolet |
| WL | wavelength |
| XPhos | 2-dicyclohexylphosphino-2',4',6'-triisopropylbiphenyl |
| XPhos precatalyst | (2-dicyclohexylphosphino-2',4',6'-triisopropyl-1,1'-biphenyl) [2-(2'-amino-1,1'-biphenyl]palladium(II)methansulfonate |

Preparative HPLC

Method 1A

Column: Chromatorex C18 48 µm 100×30 5 µm, Flow: 50 mL/min, Eluent: A: acetonitrile B: water/0.1% formic acid, Gradient 20% A→90% A Method 2A Column: Xbridge 100×30 5 µm, Flow: 50 mL/min, Eluent: A: acetonitrile B: water/0.2% ammonia, Gradient 10% A→95% A Method 3A Instrument MS: Waters, Instrument HPLC: Waters (column Phenomenex Luna 5µ C18(2) 100A, AXIA Tech. 50×21.2 mm, Eluent A: water+0.05% formic acid, Eluent B: acetonitrile or methanol (ULC)+0.05% formic acid, gradient elution; flow: 40 ml/min; UV-Detection: DAD; 210-400 nm).

Method 4A

Instrument MS: Waters, Instrument HPLC: Waters (column Waters X-Bridge C18, 18 mm×50 mm, 5 µm, Eluent A: water+0.05% triethylamine, Eluent B: acetonitrile or methanol (ULC)+0.05% triethylamine, gradient elution; flow: 40 ml/min; UV-Detection: DAD; 210-400 nm).

Method 5A

Instrument MS: Waters, Instrument HPLC: Waters (column: Phenomenex Synergie polar 4 µm 80A, AXIA Tech. 50×21.2 mm, Solvent A: Water+0.375% Formic acid, Solvent B: Acetonitrile (ULC)+0.375% Formic acid, gradient; Flow: 40 ml/min; UV-Detection: DAD; 210-400 nm).

LC-MS-Methods

Method 1B

Instrument: Waters ACQUITY SQD UPLC system; column: Waters Acquity UPLC HSS T3 1.8µ 50×1 mm; eluent A: 1 l water+0.25 ml 99% HCOOH, eluent B: 1 l acetonitrile+0.25 ml 99% HCOOH; gradient: 0.0 min 90% A→1.2 min 5% A→2.0 min 5% A; oven: 50° C.; flow: 0.40 ml/min; UV-detection: 208-400 nm.

Method 2B

Instrument MS: Waters (Micromass) QM; Instrument HPLC: Agilent 1100 series; column: Agilent ZORBAX Extend-C18 3.0×50 mm 3.5 µm; Eluent A: 1 l water+0.01 mol ammonium carbonate, eluent B: 1 l acetonitrile; gradient: 0.0 min 98% A→0.2 min 98% A→3.0 min 5% A→4.5 min 5% A; Oven: 40° C.; Flow: 1.75 ml/min; UV-detection: 210 nm Method 3B Instrument: Micromass Quattro Premier with Waters UPLC Acquity; Column: Thermo Hypersil GOLD 1.9µ 50×1 mm; Eluent A: 1 l Wasser+0.5 ml 50% formic acid, Eluent B: 1 l Acetonitril+0.5 ml 50% formix acid; Gradient: 0.0 min 97% A→0.5 min 97% A→3.2 min 5% A→4.0 min 5% A Oven: 50° C.; Flow: 0.3 ml/min; UV-detection: 210 nm.

Method 4B

Instrument MS: Waters SQD; Instrument HPLC: Waters UPLC; column: Zorbax SB-Aq (Agilent), 50 mm×2.1 mm, 1.8 μm; Eluent A: water+0.025% formic acid, Eluent B: acetonitrile (ULC)+0.025% formic acid; gradient: 0.0 min 98% A-0.9 min 25% A-1.0 min 5% A-1.4 min 5% A-1.41 min 98% A-1.5 min 98% A; oven: 40° C.; flow: 0.600 ml/min; UV-detection: DAD; 210 nm.

Method 5B

Instrument: Waters ACQUITY SQD UPLC system; column: Waters Acquity UPLC HSS T3 1.8μ 30×2 mm; eluent A: 1 l water+0.25 ml 99% formic acid, eluent B: 1 l acetonitrile+0.25 ml 99% formic acid; gradient: 0.0 min 90% A→1.2 min 5% A→2.0 min 5% A oven: 50° C.; flow: 0.60 ml/min; UV-detection: 208-400 nm.

Method 6B

Instrument: Waters ACQUITY SQD UPLC system; column: Waters Acquity UPLC HSS T3 1.8μ 50×1 mm; eluent A: 1 l water+0.25 ml 99% formic acid, eluent B: 1 l acetonitrile+0.25 ml 99% formic acid; gradient: 0.0 min 95% A→6.0 min 5% A→7.5 min 5% A oven: 50° C.; flow: 0.35 ml/min; UV-detection: 210-400 nm.

Method 7B

Instrument MS: Waters (Micromass) QM; Instrument HPLC: Agilent 1100 Series; Column: Agilent ZORBAX Extend-C18 3.0×50 mm 3.5-Micron; Eluent A: 1 L water+0.01 mol ammonium carbonate, Eluent B: 1 L acetonitrile; Gradient: 0.0 min 98% A→0.2 min 98% A→3.0 min 5% A→4.5 min 5% A; Oven: 40° C.; Flow: 1.75 ml/min; UV-detection: 210 nm.

Method 8B

Instrument: Agilent MS Quad 6150; HPLC: Agilent 1290; Column: Waters Acquity UPLC HSS T3 1.8μ 50×2.1 mm; Eluent A: 1 l water+0.25 ml 99% formic acid, Eluent B: 1 l acetonitrile+0.25 ml 99% formic acid; Gradient: 0.0 min 90% A→0.3 min 90% A→1.7 min 5% A→3.0 min 5% A Oven: 50° C.; Flow: 1.20 ml/min; UV-Detection: 205-305 nm.

Method 9B

Instrument MS: ThermoFisherScientific LTQ-Orbitrap-XL; Instrument HPLC: Agilent 1200SL; Column: Agilent, POROSHELL 120, 3×150 mm, SB—C18 2.7 μm; Eluent A: 1 l water+0.1% trifluoroacetic acid; Eluent B: 1 l acetonitrile+0.1% trifluoroacetic acid; Gradient: 0.0 min 2% B→0.3 min 2% B→5.0 min 95% B→10.0 min 95% B; Oven: 40° C.; Flow: 0.75 ml/min; UV-Detection: 210 nm.

Method 10B

Instrument MS: Waters (Micromass) Quattro Micro; Instrument Waters UPLC Acquity; column: Waters BEH C18 1.7μ 50×2.1 mm; solvent A: 1 l water+0.01 mol Ammonium formate, solvent B: 1 l Acetonitrile; gradient: 0.0 min 95% A→0.1 min 95% A→2.0 min 15% A→2.5 min 15% A→2.51 min 10% A→3.0 min 10% A; oven: 40° C.; flows: 0.5 ml/min; UV-detection: 210 nm Method 11B Instrument MS: Thermo Scientific FT-MS; Instrument UHPLC+: Thermo Scientific UltiMate 3000; column: Waters, HSST3, 2.1×75 mm, C18 1.8 μm; solvent A: 1 l water+0.01% formic acid; solvent B: 1 l Acetonitrile+0.01% formic acid; gradient: 0.0 min 10% B→2.5 min 95% B→3.5 min 95% B; oven: 50° C.; flow: 0.90 ml/min; UV-detection: 210 nm/Optimum Integration Path 210-300 nm Method 12B Instrument MS: Waters SQD; Instrument HPLC: Waters UPLC; column: Zorbax SB-Aq (Agilent), 50 mm×2.1 mm, 1.8 μm; eluent A: water+0.025% formic acid, eluent B: acetonitrile (ULC)+0.025% formic acid; gradient: 0.0 min 98% A-0.9 min 25% A-1.0 min 5% A-1.4 min 5% A-1.41 min 98% A-1.5 min 98% A; oven: 40° C.; flow: 0.600 ml/min; UV-detection: DAD; 210 nm.

Method 13B

MS instrument type: Agilent Technologies 6130 Quadrupole LC-MS; HPLC instrument type: Agilent Technologies 1260 Infinity; column: Waters XSelect (C18, 30×2.1 mm, 3.5μ); flow: 1 ml/min; column temp: 35° C.; eluent A: 0.1% formic acid in acetonitrile; eluent B: 0.1% formic acid in water; lin. gradient: t=0 min 5% A, t=1.6 min 98% A, t=3 min 98% A; detection: DAD (220-320 nm); detection: MSD (ESI pos/neg) mass range: 100-800; detection: ELSD (PL-ELS 2100): gas flow 1.2 mL/min, gas temp: 70° C., neb: 50° C.

Method 14B

MS instrument type: Agilent Technologies 6130 Quadrupole LC-MS; HPLC instrument type: Agilent Technologies 1260 Infinity; column: Waters XSelect (C18, 50×2.1 mm, 3.5μ); flow: 0.8 ml/min; column temp: 35° C.; eluent A: 0.1% formic acid in acetonitrile; eluent B: 0.1% formic acid in water; lin. gradient: t=0 min 5% A, t=3.5 min 98% A, t=6 min 98% A; detection: DAD (220-320 nm); detection: MSD (ESI pos/neg) mass range: 100-800; detection: ELSD (PL-ELS 2100): gas flow 1.2 mL/min, gas temp: 70° C., neb: 50° C.

Method 15B

Instrument type: Büchi Pump Manager C-615, Büchi Pump Module C-601; columns: GraceResolv™ Silica Cartridge; 4 g cartridge, flow 5 mL/min; 12 g cartridge, flow 16 mL/min; 40 g cartridge, flow 50 mL/min; 80 g cartridge, flow 100 mL/min; 120 g cartridge, flow 160 mL/min; eluents: see experiment; detection: TLC plates, TLC Silica gel 60 F254 (Merck).

Method 16B

MS instrument type: Agilent Technologies LC/MSD SL; HPLC instrument type: Agilent Technologies 1100 Series; column: Waters XSelect (C18, 50×2.1 mm, 3.5μ; flow: 0.8 mL/min; column temp: 25° C.; eluent A: 95% acetonitrile+5% ammoniumbicarbonate in water; eluent B: 10 mmM ammoniumbicarbonate in water pH=9.0; lin. gradient: t=0 min 5% A, t=3.5 min 98% A, t=6 min 98% A; detection: DAD (220-320 nm); detection: MSD (ESI pos/neg) mass range: 100-800.

Nuclear Magnetic Resonance spectroscopy (Examples 378-395)

$^{1}$H- and $^{13}$C-NMR instrument type: Bruker DMX300 ($^{1}$H-NMR: 300 MHz; $^{13}$C-NMR: 75 MHz); internal standard: tetramethylsilane; chemical shifts (δ) are displayed in parts per million [ppm]; the following abbreviations are used: s=singlet, d=doublet, t=triplet, q=quartet, m=multiplet, b=broad; coupling constants are displayed in Hertz [Hz].

Preparative Separation of Diastereomers

Method 1C

Phase: Daicel Chiralpak AZ-H, 5 μm 250 mm×30 mm, eluent: iso-hexan/ethanol 1:1; temperature: 25° C.; flow: 40 ml/min; UV-Detection: 220 nm.

Method 2C

Phase: Daicel Chiralcel OJ-H, 5 μm 250 mm×20 mm, eluent: iso-hexan/iso-ethanol 1:1, temperature: 30° C.; flow: 15 ml/min; UV-Detection: 220 nm.

Preparative Separation of Enantiomers

Method 1D

Phase: Daicel Chiralpak IC, 5 μm 250 mm×20 mm, eluent: iso-hexan/isopropanol 7/3; temperature: 30° C.; flow: 20 ml/min; UV-Detection: 230 nm.

Analytical Separation of Diastereomers:
Method 1E
  Phase: 250 mm×4.6 mm Daicel Chiralpak AZ-H 5 µm, eluent: iso-hexan/ethanol 1/1, temperature: 30° C., flow: 1.0 ml/min; UV-Detection: 220 nm
Method 2E
  Phase: 250 mm×4.6 mm Daicel Chiralcel OJ-H 5 µm, eluent: iso-hexan/ethanol/TFA/H$_2$O 60%/40%/0.2%/1%, temperature: 30° C., flow: 1.0 ml/min; UV-Detection: 220 nm
Analytical Separation of Enantiomers
Method 1F
  Phase: 250 mm×4.6 mm Daicel Chiralpak AY-H 5 µm, eluent: iso-hexan/ethanol 9/1, temperature: 45° C., flow: 1.0 ml/min; UV-Detection: 220 nm
Other Remarks
  Microwave Instrument: Biotage Initiator
Starting Materials and Intermediates:
General Procedures:
General Procedure 1A: Condensation of Aminopyrazoles Under Standard Conditions.
  A mixture of tert-butyl 4-[(2,2-dimethyl-4,6-dioxo-1,3-dioxan-5-yl)carbonyl]piperidine-1-carboxylate (1 eq) and the corresponding aminopyrazol (1 eq) in acetonitrile was stirred at 60° C. until HPLC and/or LC-MS indicated complete consumption of the starting material. After evaporating the solvent under vacuo the crude product was dissolved in 1-methoxy-2-propanol and then potassium phosphate (2 eq) was added to the mixture. The reaction mixture was stirred at 110° C. until complete consumption of the intermediate. The work-up is described individually for each example.
General Procedure 2A: Suzuki Cross-Coupling Reaction
  A vial was equipped with a magnetic bar and charged with XPhos precatalyst (2-dicyclohexylphosphino-2',4',6'-triisopropyl-1,1'-biphenyl) [2-(2'-amino-1,1'-biphenyl]palladium(II)methansulfonate (0.1 eq), the boronic acid (1.5 eq) and tert-butyl 4-(3-bromo-5-oxo-4,5-dihydropyrazolo[1,5-a]pyrimidin-7-yl)piperidine-1-carboxylate (1 eq). The vessel was sealed with a screw-cap septum, and then degassed tetrahydrofuran and degassed 1 M aqueous K$_3$PO$_4$ solution (3 eq) were added via syringe. Then the mixture was flushed with argon during 2 minutes and after that the reaction was stirred at 80° C. for 16 h. After cooling to RT the organic phase from the mixture was separated and the aqueous phase was diluted with water and extracted with ethyl acetate. The collected organic phases were evaporated under vacuo and the crude product was purified by preparative HPLC (Method 1A).
General Procedure 3A: Preparation of Examples 75-81 in Table 1:
  36 mg (0.1 mmol) of 7-[1-(tert-butoxycarbonyl)piperidin-4-yl]-5-oxo-4,5-dihydropyrazolo[1,5-a]pyrimidine-3-carboxylic acid were dissolved in 0.3 ml DMF and added to 1 eq. of the respective amine component in a 96 deep well plate followed by a solution of 38.5 mg (0.12 mmol) of 2-(1H-benzotriazole-1-yl)-1,1,3,3-tetramethyluronium tetrafluoroborate in 0.3 ml DMF and 25.8 mg (0.2 mmol) DIPEA. The resulting mixture was shaken at RT overnight and then evaporated to dryness. The residue was treated with 0.6 ml TFA and shaken at RT overnight. The mixture was evaporated to dryness and the crude product was treated with 0.6 ml DMF, filtered off and the filtrate was purified by LC-MS with Method 3A or Method 4A. The product containing fractions were evaporated in vacuo with a centrifugal dryer, dissolved in 0.6 ml DMSO then pooled and evaporated again to give the final products.

General Procedure 4A: Preparation of Examples 82-104 in Table 2
  36 mg (0.1 mmol) of 7-[1-(tert-butoxycarbonyl)piperidin-4-yl]-5-oxo-4,5-dihydropyrazolo[1,5-a]pyrimidine-3-carboxylic acid was dissolved in 0.6 ml 1,2-dichloroethane and 17.8 mg (0.12 mmol) of 1,1'-carbonyldiimidazole were added. The mixture was heated up to 80° C. and stirred at this temperature for 2 hours and then added to 1 eq. of the respective amine component. The reaction mixture was then shaken at 80° C. up to 60 hours and then evaporated to dryness. The residue was treated with 0.6 ml DMF, filtered off and the filtrate was purified by LC-MS with Method 3A or Method 4A to isolate the protected intermediate. The intermediate containing fractions were evaporated in vacuo with a centrifugal dryer, dissolved in 0.6 ml DMSO, pooled and evaporated again. The residue was dissolved in DCM and treated with 0.4 ml (1.6 mmol) of a 4 M solution of hydrogen chloride in 1,4-dioxan. The mixture was shaken overnight and evaporated to dryness to give the final products.
General Procedure 5A: Preparation of Examples 105-110 in Table 3
  36 mg (0.1 mmol) of 7-[1-(tert-butoxycarbonyl)piperidin-4-yl]-5-oxo-4,5-dihydropyrazolo[1,5-a]pyrimidine-3-carboxylic acid was dissolved in 0.6 ml 1-methyl-2-pyrrolidone and 32.4 mg (0.2 mmol) of 1,1'-carbonyldiimidazole were added. The mixture was heated up to 60° C. and stirred at this temperature for 2 hours and then added to 1 eq. of the respective amideoxime component. The reaction mixture was then shaken at 110° C. up overnight and then evaporated to dryness. The residue was treated with 0.6 ml TFA and shaken at RT overnight. The mixture was concentrated in vacuo and the residue was dissolved in 0.6 ml DMF, filtered off and the filtrate was purified by LC-MS with Method 3A or Method 4A. The product containing fractions were evaporated in vacuo with a centrifugal dryer, dissolved in 0.6 ml DMSO then pooled and evaporated again to give the final products.

Example 1A

Tert-butyl 4-(3-ethoxy-3-oxopropanoyl)piperidine-1-carboxylate

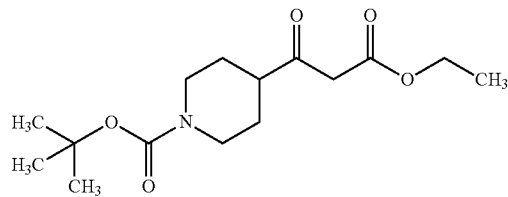 [SMILES: CCOC(=O)CC(=O)C1CCN(C(=O)OC(C)(C)C)CC1]

To a solution of boc-isonipecotic acid (150 g, 654 mmol) in tetrahydrofuran (2100 mL) was added di-1H-imidazol-1-ylmethanone (159 g, 981 mmol) and N,N-dimethylpyridin-4-amine (40.0 g, 327 mmol) at RT. The mixture was stirred at RT for 15 h (CAUTION: moderate gas evolution). In a second flask, a suspension of potassium 3-ethoxy-3-oxopropanoate (200 g, 1.18 mol) and magnesium dichloride (112 g, 1.18 mol) in tetrahydrofuran (2100 mL) was heated to 50° C. for 15 h. The resulting warm suspension was slowly added to the first flask and extensive stirring. The resulting mixture was stirred at RT for 20 h. Tetrahydrofuran was evaporated in vacuo, water (1500 mL) and ethyl acetate (1500 mL) were added. The mixture was cooled to 10° C. and 3N aqueous HCl was added until pH 1 was achieved. The organic phase was separated, the aqueous phase was extracted with ethyl acetate (1500 mL) and the combined organic phases were washed with 10% aq. NaHCO$_3$ (750 mL) and 10% aq. NaCl (750 mL), dried over magnesium sulfate, filtered and evaporated in vacuo to yield the title compound (182 g, 505 mmol) in a purity of 83% of theory.

LC-MS (Method 1B): R$_t$=1.00 min, MS (ESIPos): m/z=300 [M+H]$^+$

Example 2A

Tert-butyl 4-[(2,2-dimethyl-4,6-dioxo-1,3-dioxan-5-yl)carbonyl]piperidine-1-carboxylate

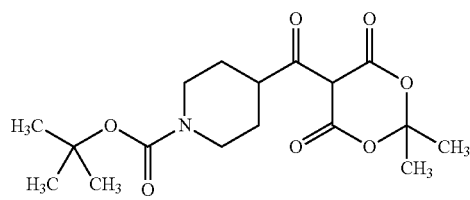 [SMILES: CC(C)(C)OC(=O)N1CCC(C(=O)C2C(=O)OC(C)(C)OC2=O)CC1]

To a solution of 1-(tert-butoxycarbonyl)piperidine-4-carboxylic acid (10 g, 43.6 mmol) and 2,2-dimethyl-1,3-dioxane-4,6-dione (6.9 g, 47.98 mmol) in 100 ml dichloromethane was added 4-dimethylaminopyridin (8.0 g, 65.42 mmol). After cooling the mixture to 0° C. 1-(3-dimethylaminopropyl)-3-ethylcarbodiimide hydrochloride (11.7 g, 61.1 mmol) was added in portions and then the reaction mixture was stirred at RT for 16 h. The mixture was treated with 50 ml of water and then the layers were separated. The organic layer was extracted with HCl 1M, dried over magnesium sulfate, filtered and evaporated under vacuo to yield the title compound (14 g, 86% of theory).

LC-MS (Method 1B): R$_t$=1.10 min, MS (ESIPos): m/z=354 [M−H]$^−$

Example 3A

2-Methylisonicotinic Acid

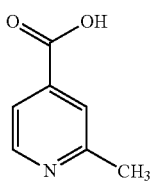

To a solution of 2,4-lutidine (280 g, 2.61 mol) in water (3.0 l) at 80° C. was added potassium permanganate (826 g, 5.23 mol) in small portions over 3 h. The reaction mixture was stirred at 80° C. overnight. The mixture was filtered through silica gel and then the filtrate was evaporated under vacuo until a volume of approximately of 20 ml was achieved. Then the solution was treated with HCl 37% (450 ml) until pH 3-4 was achieved. The solution was kept 1 h at 0° C. and then the resulting solid was filtered, washed with water at 0° C. and finally dried under vacuo overnight over phosphorus pentoxide to yield the title product (130 g, 36% of theory).

LC-MS (Method 3B): R$_t$=0.20 min, MS (ESIPos): m/z=138 [M+H]$^+$

Example 4A

Methyl 2-methylisonicotinate

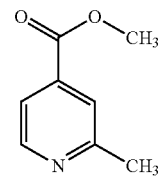

To methanol (1.54 l) at −10° C. was added slowly thionyl chloride (401 g, 3.37 mol) and the solution was stirred 10 minutes at 0° C. Then was added 2-methylisonicotinic acid (154 g, 1.20 mol) and the reaction mixture was stirred at reflux temperature overnight. The mixture was evaporated under vacuo, then diluted in ethyl acetated and finally treated with a 10% sodium hydrogen carbonate aqueous solution until pH 7 was achieved. After separation of the layers the aqueous phase was extracted with ethyl acetate. All collected organic phases were dried over magnesium sulfate, evaporated under dried under vacuo. The crude product was used in the next step without further purification (113.0 g, 48% of theory, 72% purity).

LC-MS (Method 1B): R$_t$=0.43 min, MS (ESIPos): m/z=152 [M+H]$^+$

Example 5A

Methyl 2-methylpiperidine-4-carboxylate

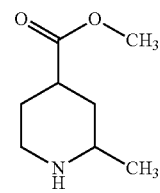

To acetic acid (700 ml) were added methyl 2-methylisonicotinate (79 g, 523 mmol) and platinum (IV) oxide (7.83 g, 34.5 mmol). The mixture was hydrogenated in the autoclave at RT and 20 bar during two days. After this time platinum (IV) oxide (5.00 g, 22.2 mmol) was added again and the mixture was hydrogenated during two days more at RT and 20 bar. After filtration of the catalyst the filtrate was evaporated under vacuo to obtain the title compound in quantitative yield.

LC-MS (Method 2B): R$_t$=1.15 min, MS (ESIPos): m/z=158 [M+H]$^+$

Example 6A (−)-Cis-1-benzyl 4-methyl 2-methylpiperidine-1,4-dicarboxylate

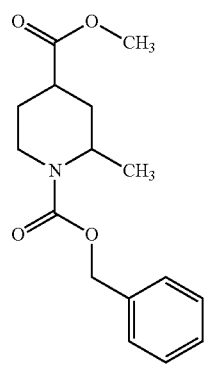 [SMILES: COC(=O)C1CCN(C(=O)OCc2ccccc2)C(C)C1]

To a solution of methyl 2-methylpiperidine-4-carboxylate (138 g, 394 mmol) in dichloromethane (620 ml) was added N,N-diisopropylethylamine (331 g, 2.56 mol). The mixture was cooled to 0° C. and then benzyl chloroformate (80.6 g, 473 mmol) was added slowly. The reaction mixture was stirred 30 min at RT and then water was added in to the mixture. After separation of the layers the aqueous phase was extracted with dichloromethane and the collected organic layers were washed with water, dried over magnesium sulfate and evaporated. The crude product was purified by silica gel chromatography with petrolether/ethyl acetate 8/2 and finally the stereoisomers were separated by chromatography on chiral phase (Method 1D) to yield the title compound (26.7 g, 23% of theory) in enantiomerically pure form.

HPLC (Method 1F): $R_f$=14.48 min $[\alpha]^{23}_D$=54.2 (c 0.9, acetonitrile)

Example 7A

Cis-methyl 2-methylpiperidine-4-carboxylate

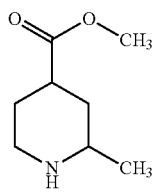

A solution of (−)-cis-1-benzyl 4-methyl 2-methylpiperidine-1,4-dicarboxylate (25.00 g, 85.8 mmol) in ethanol (250 ml) was treated with palladium on charcoal 10% (1.83 g, 1.72 mmol) under hydrogen atmosphere at normal pressure and RT for 16 h. The mixture was filtered through celite and the filtrate was evaporated and dried under vacuo to yield the title compound (13.95 g, 96% of theory).

LC-MS (Method 2B): $R_t$=1.15 min, MS (ESIPos): m/z=158[M+H]$^+$

Example 8A

Cis-1-tert-butyl 4-methyl 2-methylpiperidine-1,4-dicarboxylate

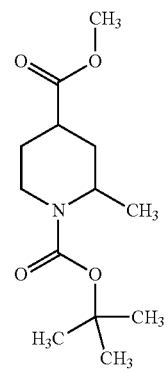

To a solution of cis-methyl 2-methylpiperidine-4-carboxylate obtained in example 7A (12.95 g, 82.34 mmol) in tetrahydrofuran (250 ml) under argon atmosphere was added di-tert-butyl dicarbonate (21.58 g, 98.88 mmol) and the reaction mixture was stirred at RT overnight. The mixture was evaporated under vacuo and the crude product was dissolved in ethyl acetate and treated with a 10% citric acid aqueous solution. After separation of the layers the organic layer was washed with 10% citric acid aqueous solution, with a saturated aqueous solution of sodium hydrogen carbonate and finally with brine. The organic phase was dried over magnesium sulfate, filtered and evaporated to yield the title compound (27.16 g, 96% of theory, 75% pure according NMR). The crude product was used in the next step without further purification.

MS (ESIPos): m/z=258[M+H]$^+$

Example 9A

Cis-1-(tert-butoxycarbonyl)-2-methylpiperidine-4-carboxylic Acid

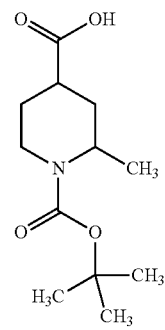

To a solution of cis-1-tert-butyl 4-methyl 2-methylpiperidine-1,4-dicarboxylate obtained in example 8A) (27.16 g, 79.16 mmol, 75% purity) in a mixture of tetrahydrofuran (250 ml) and water (125 ml) was added lithium hydroxide (10.1 g, 422 mmol) and the mixture was stirred overnight at RT. The mixture was evaporated under vacuo and was diluted in water and ethyl acetate. After separation of the layers the aqueous phase was treated with HCl 37% until pH 4 was achieved and then was extracted with ethyl acetate, dried over magnesium sulfate, filtered and evaporated under vacuo to yield the title compound (18.4 g, 95% of theory).

$^1$H-NMR (400 MHz, DMSO-$d_6$): δ=12.27 (bs, 1H), 4.07-3.99 (m, 1H), 3.67-3-61 (m, 1H), 3.06-2.98 (m, 1H), 1.89-1.76 (m, 4H), 1.62-1.53 (m, 1H), 1.39 (s, 9H), 1.04 (d, 3H).

Example 10A (−)-Cis-tert-butyl 4-[(2,2-dimethyl-4,6-dioxo-1,3-dioxan-5-yl)carbonyl]-2-methylpiperidine-1-carboxylate

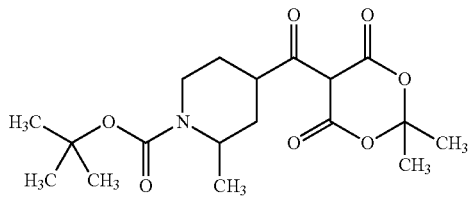 [SMILES: CC1CC(C(=O)C2C(=O)OC(C)(C)OC2=O)CCN1C(=O)OC(C)(C)C]

To a solution of cis-1-(tert-butoxycarbonyl)-2-methylpiperidine-4-carboxylic acid obtained in example 9A (17.3 g, 71.0 mmol) and 2,2-dimethyl-1,3-dioxane-4,6-dione (11.3 g, 78.0 mmol) in dichloromethane (190 ml) was added 4-dimethylaminopyridin (13.1 g, 107 mmol). After cooling the mixture at 0° C., 1-(3-dimethylaminopropyl)-3-ethylcarbodiimide hydrochloride (19.13 g, 100.0 mmol) was added in portions and then the reaction mixture was stirred at RT for 16 h. The mixture was treated with water and then the layers were separated. The organic layer was washed with HCl 1M, dried over magnesium sulfate, filtered and evaporated under vacuo to yield the title compound (20.8 g, 79% of theory).

LC-MS (Method 1B): $R_t$=1.16 min, MS (ESIPos): m/z=370 [M+H]$^+$ $[α]^{20}$=−71.36 (c. 0.625, methanol) WL=589 nm

Example 11A

Tert-butyl 4-(5-oxo-3-phenyl-4,5-dihydropyrazolo[1,5-a]pyrimidin-7-yl)piperidine-1-carboxylate

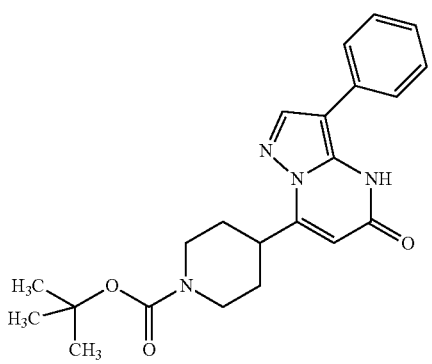 [SMILES: CC(C)(C)OC(=O)N1CCC(c2cc(=O)[nH]c3c(-c4ccccc4)cnn23)CC1]

Tert-butyl 4-(3-ethoxy-3-oxopropanoyl)piperidine-1-carboxylate (450 mg, 81% purity, 1.22 mmol), 4-phenyl-1H-pyrazol-3-amine (194 mg, 1.22 mmol, 1 eq) and potassium phosphate (517 mg, 2.43 mmol, 2 eq) were suspended in dioxane (4.3 mL) in a 20 mL microwave vial. The vial was capped and the mixture was heated in a microwave to 150° C. for 1 h. After cooling to RT, the mixture was evaporated in vacuo, diluted with water (20 mL) and extracted with ethyl acetate (2×20 mL). The combined organic layers were dried with sodium sulfate, filtered and evaporated in vacuo. The residue was purified by preparative HPLC (Method 1A). The combined product fractions were adjusted to pH 7 by addition of aqueous ammonium hydroxide. Acetonitrile was evaporated in vacuo, the remaining water was extracted with ethyl acetate, the organic layer was dried with sodium sulfate, filtered and evaporated in vacuo to give the title compound (13.5 mg, 3% of theory).

LC-MS (Method 1B): $R_t$=1.10 min, MS (ESINeg): m/z=393 [M−H]$^-$

Example 12A

Tert-butyl 4-[7-oxo-3-(pyridin-2-yl)-4,7-dihydropyrazolo[1,5-a]pyrimidin-5-yl]piperidine-1-carboxylate

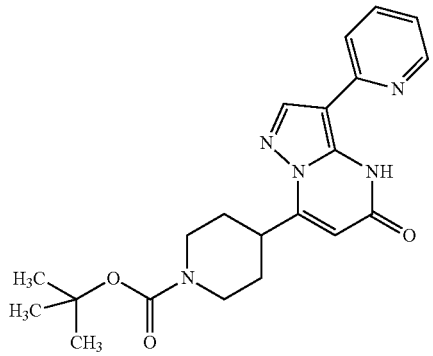 [SMILES: CC(C)(C)OC(=O)N1CCC(c2cc(=O)[nH]c3c(-c4ccccn4)cnn23)CC1]

Tert-butyl 4-(3-ethoxy-3-oxopropanoyl)piperidine-1-carboxylate (2.00 g, 6.68 mmol, 1.5 eq), 4-(pyridin-2-yl)-1H-pyrazol-3-amine (713 mg, 4.45 mmol, 1 eq) and potassium phosphate (1.89 g, 8.91 mmol, 2 eq) were suspended in 1-methoxy-2-propanol (20 mL) in two 20 mL microwave vials. The vials were capped and the mixture was heated in a microwave to 180° C. for 15 min. After cooling to RT, the suspension was diluted with water (20 mL), neutralized (pH 6) by the addition of 1N HCl and extracted with ethyl acetate (2×50 mL). The combined organic phases were dried over magnesium sulfate, filtered and evaporated in vacuo. The residue was purified by preparative HPLC (Method 1A). The combined product fractions were concentrated in vacuo to remove acetonitrile. The resulting suspension was filtered, the residue was washed with water (2 ml) and dried for 16 h at 50° C. in vacuo to give the title compound (240 mg, 14% of theory).

LC-MS (Method 1B): $R_t$=1.08 min, MS (ESIPos): m/z=396 [M+H]$^+$

Example 13A

Tert-butyl 4-[2-(methoxymethyl)-3-(4-methoxyphenyl)-5-oxo-4,5-dihydropyrazolo[1,5-a]pyrimidin-7-yl]piperidine-1-carboxylate

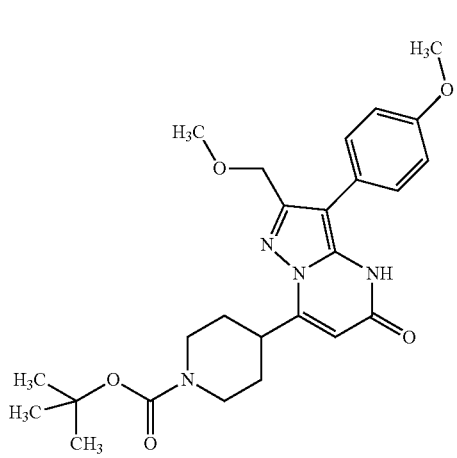 [SMILES: COCc1nn2c(C3CCN(C(=O)OC(C)(C)C)CC3)cc(=O)[nH]c2c1-c1ccc(OC)cc1]

Tert-butyl 4-(3-ethoxy-3-oxopropanoyl)piperidine-1-carboxylate (350 mg, 1.00 mmol), 5-(methoxymethyl)-4-(4-methoxyphenyl)-1H-pyrazol-3-amine (351 mg, 1.50 mmol, 1.5 eq) and potassium phosphate (425 mg, 2.00 mmol, 2 eq) were suspended in 1-methoxy-2-propanol (3 mL) in a 20 mL microwave vial. The vial was capped and the mixture was heated in a microwave to 180° C. for 15 min. After cooling to RT, the suspension was diluted with water (5 mL), neutralized (pH 6) by the addition of 1N HCl and extracted with ethyl acetate (2×20 mL). The combined organic phases were dried over magnesium sulfate, filtered and evaporated in vacuo. The residue was purified by preparative HPLC (Method 1A). The combined product fractions were adjusted to pH 7 by addition of aqueous ammonium hydroxide. Acetonitrile was evaporated in vacuo, the resulting suspension was filtered, the residue was washed with water (2 mL) and dried for 16 h at 50° C. in vacuo to give the title compound (86.6 mg, 18% of theory).

LC-MS (Method 1B): $R_t$=1.09 min, MS (ESIPos): m/z=469[M+H]$^+$

Example 14A

Tert-butyl 4-[3-(4-fluorophenyl)-7-oxo-4,7-dihydropyrazolo[1,5-a]pyrimidin-5-yl]piperidine-1-carboxylate

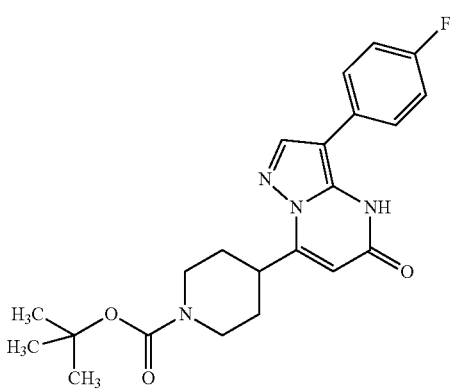 [SMILES: CC(C)(C)OC(=O)N1CCC(c2cc(=O)[nH]c3c(-c4ccc(F)cc4)cnn23)CC1]

Tert-butyl 4-(3-ethoxy-3-oxopropanoyl)piperidine-1-carboxylate (1.00 g, 3.34 mmol, 1.5 eq), 4-(4-fluorophenyl)-1H-pyrazol-3-amine (395 mg, 2.27 mmol, 1 eq) and potassium phosphate (945 mg, 4.45 mmol, 2 eq) were suspended in 1-methoxy-2-propanol (10 mL) in a 20 mL microwave vial. The vial was capped and the mixture was heated in a microwave to 180° C. for 15 min. After cooling to RT, the suspension was diluted with 20 mL dichloromethane/methanol (4:1), filtered through a short pad of silica gel with 100 mL dichloromethane/methanol (4:1) and evaporated in vacuo. The residue was purified by preparative HPLC (Method 1A). The combined product fractions were evaporated in vacuo to remove acetonitrile, the remaining water was extracted with ethyl acetate, the organic layer was dried with magnesium sulfate, filtered and evaporated in vacuo to give the title compound (64 mg, 90% purity, 6% of theory).

LC-MS (Method 1B): $R_t$=1.11 min, MS (ESIPos): m/z=413 [M+H]$^+$

Example 15A

Tert-butyl 4-[7-oxo-3-(pyridin-3-yl)-4,7-dihydropyrazolo[1,5-a]pyrimidin-5-yl]piperidine-1-carboxylate

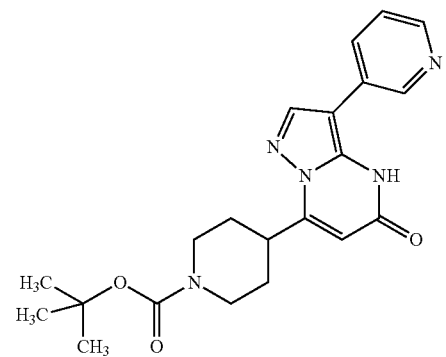 [SMILES: CC(C)(C)OC(=O)N1CCC(c2cc(=O)[nH]c3c(-c4cccnc4)cnn23)CC1]

Tert-butyl 4-(3-ethoxy-3-oxopropanoyl)piperidine-1-carboxylate (561 mg, 1.87 mmol, 1.5 eq), 4-(pyridin-3-yl)-1H- pyrazol-3-amine (200 mg, 1.25 mmol, 1 eq) and potassium phosphate (530 mg, 2.50 mmol, 2 eq) were suspended in 1-methoxy-2-propanol (4 mL) in a 20 mL microwave vial. The vial was capped and the mixture was heated in a microwave to 180° C. for 15 min. After cooling to RT, the suspension was diluted with 20 mL dichloromethane/methanol (4:1), filtered through a short pad of silica gel with 100 mL dichloromethane/methanol (4:1) and evaporated in vacuo. The residue was purified by preparative HPLC (Method 1A). The combined product fractions were evaporated in vacuo to remove acetonitrile and lyophilized to give the title compound (11.3 mg, 2% of theory).

LC-MS (Method 1B): $R_t$=0.79 min, MS (ESIPos): m/z=396 [M+H]$^+$

Example 16A

Tert-butyl 4-[3-(2-methoxyphenyl)-2-methyl-7-oxo-4,7-dihydropyrazolo[1,5-a]pyrimidin-5-yl]piperidine-1-carboxylate

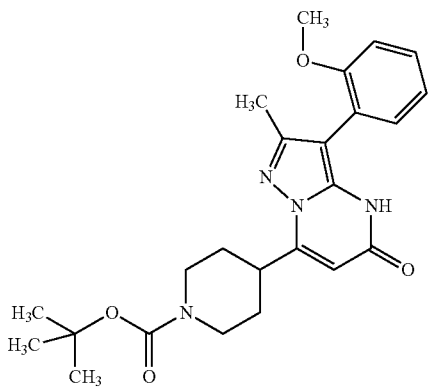 [SMILES: COc1ccccc1-c1c(C)nn2c(C3CCN(C(=O)OC(C)(C)C)CC3)cc(=O)[nH]c12]

Tert-butyl 4-(3-ethoxy-3-oxopropanoyl)piperidine-1-carboxylate (221 mg, 0.74 mmol, 1.5 eq), 4-(2-methoxyphenyl)-5-methyl-1H-pyrazol-3-amine (100 mg, 0.49 mmol, 1 eq) and potassium phosphate (209 mg, 0.98 mmol, 2 eq) were suspended in 1-methoxy-2-propanol (2 mL) in a 5 mL microwave vial. The vial was capped and the mixture was heated in a microwave to 180° C. for 15 min. After cooling to RT, the mixture was evaporated in vacuo, diluted with water (5 mL) and extracted with ethyl acetate (2×10 mL). The combined organic layers were dried with sodium sulfate, filtered and evaporated in vacuo. The residue was purified by preparative HPLC (Method 1A). The combined product fractions were adjusted to pH 7 by addition of aqueous ammonium hydroxide. Acetonitrile was evaporated in vacuo, the resulting suspension was filtered, the residue was washed with water (0.5 mL) and dried for 16 h at 50° C. in vacuo to give the title compound (4.8 mg, 2% of theory).

LC-MS (Method 1B): $R_t$=1.12 min, MS (ESIPos): m/z=439 [M+H]$^+$

Example 17A

Tert-butyl 4-{2-methyl-5-oxo-3-[3-(trifluoromethyl)phenyl]-4,5-dihydropyrazolo[1,5-a]pyrimidin-7-yl}piperidine-1-carboxylate

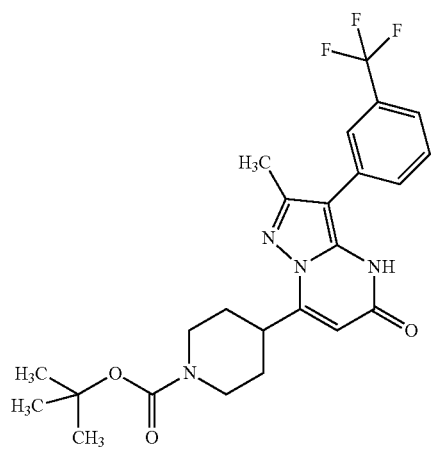 [SMILES: Cc1nn2c(C3CCN(C(=O)OC(C)(C)C)CC3)cc(=O)[nH]c2c1-c1cccc(C(F)(F)F)c1]

Tert-butyl 4-(3-ethoxy-3-oxopropanoyl)piperidine-1-carboxylate (186 mg, 0.62 mmol, 1.5 eq), 3-methyl-4-[3-(trifluoromethyl)phenyl]-1H-pyrazol-5-amine (100 mg, 0.41 mmol, 1 eq) and potassium phosphate (176 mg, 0.83 mmol, 2 eq) were suspended in 1-methoxy-2-propanol (10 mL) in a 20 mL microwave vial. The vial was capped and the mixture was heated in a microwave to 180° C. for 15 min. After cooling to RT, the mixture was evaporated in vacuo, diluted with water (5 mL) and extracted with ethyl acetate (2×10 mL). The combined organic layers were dried with sodium sulfate, filtered and evaporated in vacuo. The residue was purified by preparative HPLC (Method 1A). The combined product fractions were adjusted to pH 7 by addition of aqueous ammonium hydroxide. Acetonitrile was evaporated in vacuo, the resulting suspension was filtered, the residue was washed with water (0.5 mL) and dried for 16 h at 50° C. in vacuo to give the title compound (0.9 mg, 1% of theory).

$^1$H-NMR (400 MHz, methanol-d$_4$): δ=7.7-7.63 (m, 4H), 5.87 (s, 1H), 4.26 (d, 2H), 3.52 (t-like, 1H), 3.05-2.89 (m, 2H), 3.23 (s, 3H), 2.13 (d, 2H), 1.64 (dq-like, 2H), 1.48 (s, 9H), 1 exchangable proton not visible.

Example 18A

Tert-butyl 4-(3-cyano-2-methyl-5-oxo-4,5-dihydropyrazolo[1,5-a]pyrimidin-7-yl)piperidine-1-carboxylate

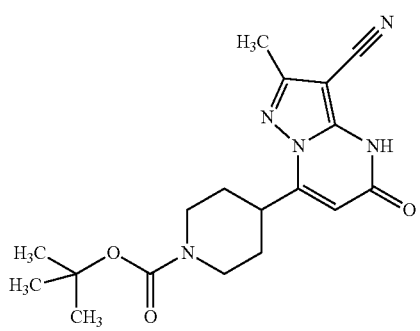 [SMILES: Cc1nn2c(C3CCN(C(=O)OC(C)(C)C)CC3)cc(=O)[nH]c2c1C#N]

Tert-butyl 4-(3-ethoxy-3-oxopropanoyl)piperidine-1-carboxylate (1.00 g, 3.34 mmol, 1.5 eq), 3-amino-5-methyl-1H-pyrazole-4-carbonitrile (272 mg, 2.27 mmol, 1 eq) and potassium phosphate (945 mg, 4.45 mmol, 2 eq) were suspended in 1-methoxy-2-propanol (6.5 mL) in a 20 mL microwave vial. The vial was capped and the mixture was heated in a microwave to 180° C. for 15 min. After cooling to RT, the mixture was evaporated in vacuo, diluted with water (5 mL), adjusted to pH 7 with 1N HCl and extracted with ethyl acetate (3×10 mL). The combined organic layers were dried with sodium sulfate, filtered and evaporated in vacuo. The residue was purified by preparative HPLC (Method 1A). The combined product fractions were adjusted to pH 7 by addition of aqueous ammonium hydroxide. Acetonitrile was evaporated in vacuo, the resulting suspension was filtered, the residue was washed with water (0.5 mL) and dried for 16 h at 50° C. in vacuo to give the title compound (62.2 mg, 8% of theory).

LC-MS (Method 1B): $R_t$=0.96 min, MS (ESINeg): m/z=356 [M-H]$^-$

Example 19A

Ethyl 7-[1-(tert-butoxycarbonyl)piperidin-4-yl]-2-methyl-5-oxo-4,5-dihydropyrazolo[1,5-a]pyrimidine-3-carboxylate

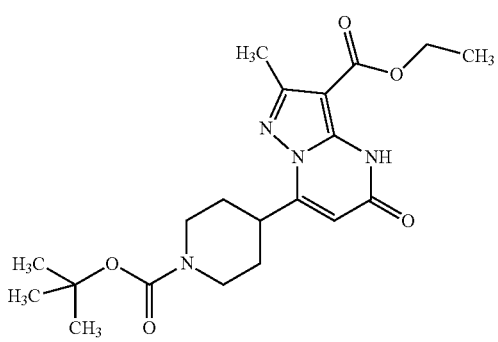 [SMILES: CCOC(=O)c1c(C)nn2c(C3CCN(C(=O)OC(C)(C)C)CC3)cc(=O)[nH]c12]

Tert-butyl 4-(3-ethoxy-3-oxopropanoyl)piperidine-1-carboxylate (1.00 g, 3.34 mmol, 1.5 eq), ethyl 5-amino-3-methyl-1H-pyrazole-4-carboxylate (377 mg, 2.27 mmol, 1 eq) and potassium phosphate (945 mg, 4.45 mmol, 2 eq) were suspended in 1-methoxy-2-propanol (10 mL) in a 20 mL microwave vial. The vial was capped and the mixture was heated in a microwave to 180° C. for 15 min. After cooling to RT, the mixture was evaporated in vacuo, diluted with water (5 mL) and extracted with ethyl acetate (3×10 mL). The combined organic layers were dried with sodium sulfate, filtered and evaporated in vacuo. The residue was purified by preparative HPLC (Method 1A). The combined product fractions were adjusted to pH 7 by addition of aqueous ammonium hydroxide. Acetonitrile was evaporated in vacuo, the resulting aqueous solution was extracted with ethyl acetate (2×20 mL), dried over sodium sulfate, filtered and evaporated in vacuo to give the title compound (31.1 mg, 3% of theory).

LC-MS (Method 1B): $R_t$=1.11 min, MS (ESINeg): m/z=403 [M-H]$^-$

Example 20A

Tert-butyl 4-(3-cyano-2-methyl-5-oxo-4,5-dihydropyrazolo[1,5-a]pyrimidin-7-yl)piperidine-1-carboxylate

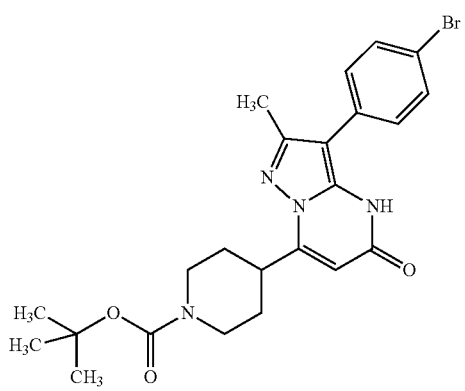 [SMILES: Cc1nn2c(C3CCN(C(=O)OC(C)(C)C)CC3)cc(=O)[nH]c2c1-c1ccc(Br)cc1]

Tert-butyl 4-(3-ethoxy-3-oxopropanoyl)piperidine-1-carboxylate (1.00 g, 3.34 mmol, 1.5 eq), 4-(4-bromophenyl)-3-methyl-1H-pyrazol-5-amine (585 mg, 2.27 mmol, 1 eq) and potassium phosphate (945 mg, 4.45 mmol, 2 eq) were suspended in 1-methoxy-2-propanol (10 mL) in a 20 mL microwave vial. The vial was capped and the mixture was heated in a microwave to 180° C. for 15 min. After cooling to RT, the mixture was evaporated in vacuo, diluted with water (5 mL) and extracted with ethyl acetate (3×10 mL). The combined organic layers were dried with sodium sulfate, filtered and evaporated in vacuo. The residue was purified by preparative HPLC (Method 1A). The combined product fractions were adjusted to pH 7 by addition of aqueous ammonium hydroxide. Acetonitrile was evaporated in vacuo, the resulting suspension was filtered, the residue was washed with water (0.5 mL) and dried for 16 h at 50° C. in vacuo to give the title compound (180 mg, 16% of theory).

LC-MS (Method 1B): $R_t$=1.23 min, MS (ESIPos): m/z=487 [M+H]$^+$

Example 21A

Tert-butyl 4-[2-(methoxymethyl)-5-oxo-3-phenyl-4,5-dihydropyrazolo[1,5-a]pyrimidin-7-yl]piperidine-1-carboxylate

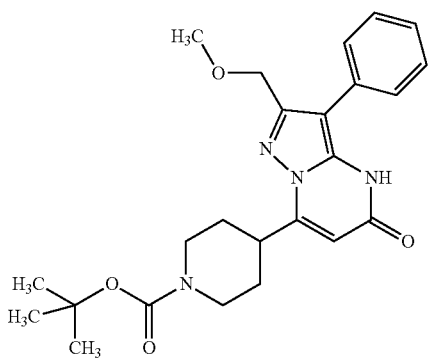 [SMILES: COCc1nn2c(C3CCN(C(=O)OC(C)(C)C)CC3)cc(=O)[nH]c2c1-c1ccccc1]

Tert-butyl 4-(3-ethoxy-3-oxopropanoyl)piperidine-1-carboxylate (1.00 g, 3.34 mmol, 1.5 eq), 5-(methoxymethyl)-4-phenyl-1H-pyrazol-3-amine (476 mg, 2.27 mmol, 1 eq) and potassium phosphate (945 mg, 4.45 mmol, 2 eq) were suspended in 1-methoxy-2-propanol (10 mL) in a 20 mL microwave vial. The vial was capped and the mixture was heated in a microwave to 180° C. for 15 min. After cooling to RT, the mixture was evaporated in vacuo, diluted with water (5 mL) and extracted with ethyl acetate (3×10 mL). The combined organic layers were dried with sodium sulfate, filtered and evaporated in vacuo. The residue was purified by preparative HPLC (Method 1A). The combined product fractions were adjusted to pH 7 by addition of aqueous ammonium hydroxide. Acetonitrile was evaporated in vacuo, the resulting suspension was filtered, the residue was washed with water (0.5 mL) and dried for 16 h at 50° C. in vacuo to give the title compound (303 mg, 30% of theory).

LC-MS (Method 1B): $R_t$=1.09 min, MS (ESIPos): m/z=439 [M+H]$^+$

Example 22A

Tert-butyl 4-{3-[3-(benzyloxy)phenyl]-5-oxo-4,5-dihydropyrazolo[1,5-a]pyrimidin-7-yl}piperidine-1-carboxylate

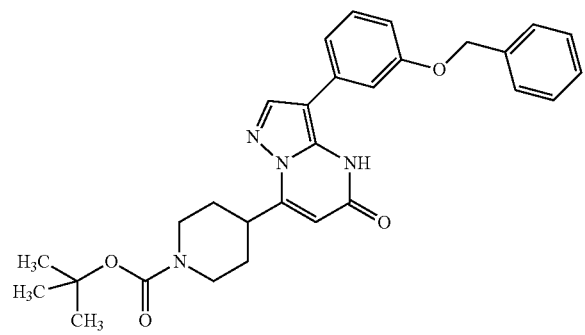 [SMILES: CC(C)(C)OC(=O)N1CCC(c2cc(=O)[nH]c3c(-c4cccc(OCc5ccccc5)c4)cnn23)CC1]

Tert-butyl 4-(3-ethoxy-3-oxopropanoyl)piperidine-1-carboxylate (950 mg, 3.17 mmol, 1.5 eq), 4-[3-(benzyloxy)phenyl]-1H-pyrazol-3-amine (591 mg, 95% purity, 2.12 mmol, 1 eq) and potassium phosphate (898 mg, 4.23 mmol, 2 eq) were suspended in 1-methoxy-2-propanol (10 mL) in a 20 mL microwave vial. The vial was capped and the mixture was heated in a microwave to 180° C. for 15 min. After cooling to RT, the mixture was evaporated in vacuo, diluted with water (5 mL) and extracted with ethyl acetate (3×10 mL). The combined organic layers were dried with sodium sulfate, filtered and evaporated in vacuo. The residue was purified by preparative HPLC (Method 1A). The combined product fractions were adjusted to pH 7 by addition of aqueous ammonium hydroxide. Acetonitrile was evaporated in vacuo, the resulting suspension was filtered, the residue was washed with water (0.5 mL) and dried for 16 h at 50° C. in vacuo to give the title compound (103 mg, 6% of theory).

LC-MS (Method 1B): $R_t$=1.29 min, MS (ESIPos): m/z=501 [M+H]$^+$

Example 23A

Tert-butyl 4-{2-methyl-5-oxo-3-[3-(trifluoromethyl)phenyl]-4,5-dihydropyrazolo[1,5-a]pyrimidin-7-yl}piperidine-1-carboxylate

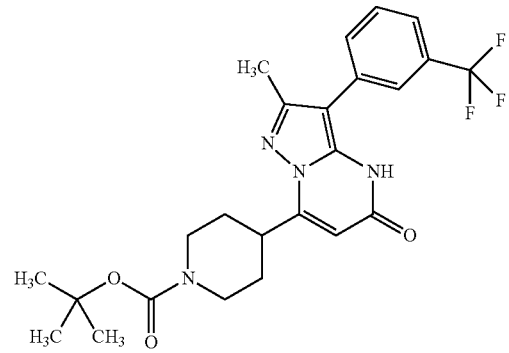 [SMILES: Cc1nn2c(C3CCN(C(=O)OC(C)(C)C)CC3)cc(=O)[nH]c2c1-c1cccc(C(F)(F)F)c1]

Tert-butyl 4-(3-ethoxy-3-oxopropanoyl)piperidine-1-carboxylate (2.41 g, 6.68 mmol), 3-methyl-4-[3-(trifluoromethyl)phenyl]-1H-pyrazol-5-amine (1.07 g, 4.45 mmol) and potassium phosphate (1.89 g, 8.91 mmol) were suspended in 1-methoxy-2-propanol (10 ml) in a 20 ml microwave vial. The vial was capped and the mixture was heated in a microwave to 180° C. for 15 min. After cooling to RT, the mixture was evaporated and the residue was diluted in water and ethyl acetate. The layers were separated and the aqueous layer was extracted with ethyl acetate. The collected organic phases were dried over magnesium sulfate, filtered and evaporated. The crude product was purified by preparative HPLC (Method 1A). The combined product fractions were neutralized with aqueous ammonium hydroxide. After the evaporation of acetonitrile a white solid was formed in the aqueous phase, which was filtered and dried under vacuo to yield the title compound (212 mg, 10% of theory).

LC-MS (Method 1B): $R_t$=1.26 min, MS (ESIPos): m/z=477[M+H]$^+$

Example 24A

Tert-butyl 4-(3-carbamoyl-5-oxo-4,5-dihydropyrazolo[1,5-a]pyrimidin-7-yl)piperidine-1-carboxylate

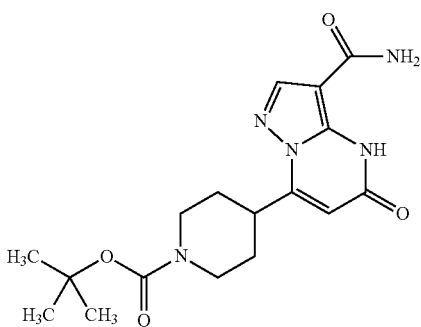 [SMILES: CC(C)(C)OC(=O)N1CCC(c2cc(=O)[nH]c3c(C(N)=O)cnn23)CC1]

Tert-butyl 4-(3-ethoxy-3-oxopropanoyl)piperidine-1-carboxylate (1.00 g, 3.34 mmol), 3-amino-1H-pyrazole-4-carboxamide (281 mg, 2.23 mmol) and potassium phosphate (945 mg, 4.45 mmol) were suspended in 1-methoxy-2-propanol (10 ml) in a 20 ml microwave vial. The vial was capped and the mixture was heated in a microwave to 180° C. for 15 min. After cooling to RT, the mixture was diluted with water, neutralized (pH 5) by the addition of 1N HCl, and extracted with ethyl acetate. The combined organic phases were washed with water and brine, dried over magnesium sulfate, filtered and evaporated. During the evaporation a white solid precipitated which was filtered off. The resulting filtrate was evaporated under vacuo. The residue was stirred in a mixture of 4 ml acetonitrile and 1 ml dimethylsulfoxide. The resulting precipitate was filtered, washed with acetonitrile and dried for 2 h at 50° C. to yield the title compound. The filtrate was purified by preparative HPLC (water/acetonitrile, 0.1% formic acid). The combined product fractions were evaporated under vacuo and lyophilized overnight to yield the title compound (64 mg, 8% of theory).

LC-MS (Method 1B): $R_t$=0.77 min, MS (ESIPos): m/z=362[M+H]$^+$

Example 25A

Tert-butyl 4-(3-cyano-5-oxo-4,5-dihydropyrazolo[1,5-a]pyrimidin-7-yl)piperidine-1-carboxylate

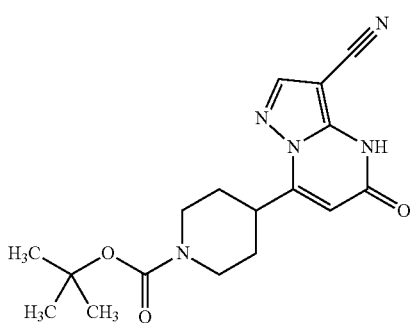 [SMILES: CC(C)(C)OC(=O)N1CCC(c2cc(=O)[nH]c3c(C#N)cnn23)CC1]

Tert-butyl 4-(3-ethoxy-3-oxopropanoyl)piperidine-1-carboxylate (1.00 g, 3.34 mmol), 3-amino-1H-pyrazole-4-carbonitrile (241 mg, 2.23 mmol) and potassium phosphate (945 mg, 4.45 mmol) were suspended in 1-methoxy-2-propanol (10 ml) in a 20 ml microwave vial. The vial was capped and the mixture was heated in a microwave to 180° C. for 15 min. After cooling to RT, the mixture was diluted with water, neutralized (pH 6) by the addition of 1N HCl, and extracted with ethyl acetate. The combined organic phases were washed with water and brine, dried over magnesium sulfate, filtered and evaporated. The crude product was purified by preparative HPLC (Method 1A). During the evaporation of the combined product fractions a white solid precipitated which was filtered and dried overnight under vacuo at 60° C. to yield the title compound (110 mg, 14% of theory).

LC-MS (Method 1B): $R_t$=0.89 min, MS (ESINeg): m/z=342 [M–H]$^-$

Example 26A

Ethyl 7-[1-(tert-butoxycarbonyl)piperidin-4-yl]-5-oxo-4,5-dihydropyrazolo[1,5-a]pyrimidine-3-carboxylate

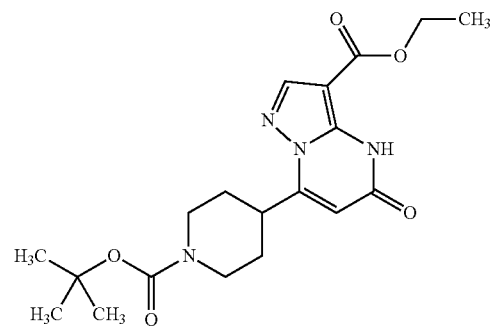 [SMILES: CCOC(=O)c1cnn2c(C3CCN(C(=O)OC(C)(C)C)CC3)cc(=O)[nH]c12]

The title compound was prepared according to General Procedure 1A starting from 1.31 g (8.44 mmol) ethyl 5-amino-1H-pyrazole-4-carboxylate and 3.0 g (8.44 mmol) tert-butyl 4-[(2,2-dimethyl-4,6-dioxo-1,3-dioxan-5-yl)carbonyl]piperidine-1-carboxylate.

Work-up: the mixture was diluted with water and treated with HCl 1N until pH 5-6 was achieved. The resulting precipitate was filtered, washed with water and dried under vacuo at 60° C. to yield the title compound (1.83 g, 54% of theory).

LC-MS (Method 1B): $R_t$=1.03 min, MS (ESIPos): m/z=391 [M+H]$^+$

Example 27A

7-[1-(tert-Butoxycarbonyl)piperidin-4-yl]-5-oxo-4,5-dihydropyrazolo[1,5-a]pyrimidine-3-carboxylic Acid

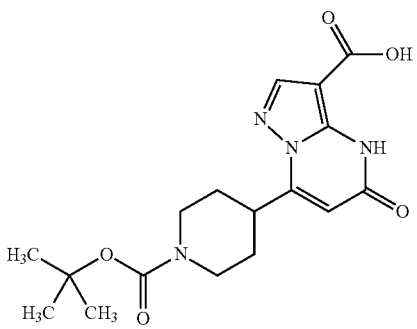 [SMILES: CC(C)(C)OC(=O)N1CCC(c2cc(=O)[nH]c3c(C(=O)O)cnn23)CC1]

To a solution of ethyl 7-[1-(tert-butoxycarbonyl)piperidin-4-yl]-5-oxo-4,5-dihydropyrazolo[1,5-a]pyrimidine-3-carboxylate (82 mg, 0.21 mmol) in a mixture of 2 ml tetrahydrofuran and 1 ml water was added lithium hydroxide (50 mg, 2.10 mmol) and the reaction mixture was stirred at 60° C. for 16 h. After that 82 mg lithium hydroxide were added into the mixture and it was still stirred at 80° C. for 10 h. After cooling to RT, the mixture was diluted with water and neutralized (pH 6) by the addition of 1N HCl. The resulting white solid was filtered and dried overnight under vacuo to yield the title compound (60 mg, 78% of theory).

LC-MS (Method 1B): $R_t$=0.84 min, MS (ESINeg): m/z=361 [M−H]⁻

Example 28A

Benzyl 7-[1-(tert-butoxycarbonyl)piperidin-4-yl]-5-oxo-4,5-dihydropyrazolo[1,5-a]pyrimidine-3-carboxylate

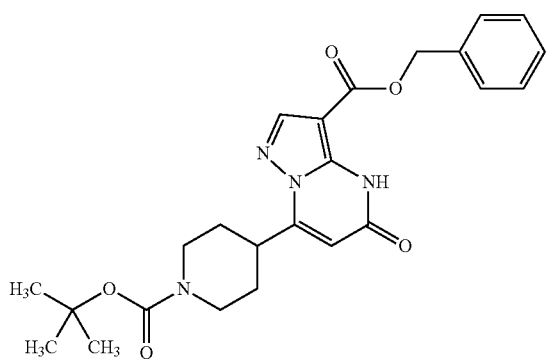 [SMILES: CC(C)(C)OC(=O)N1CCC(c2cc(=O)[nH]c3c(C(=O)OCc4ccccc4)cnn23)CC1]

Tert-butyl 4-(3-ethoxy-3-oxopropanoyl)piperidine-1-carboxylate (1.0 g, 3.34 mmol), benzyl 5-amino-1H-pyrazole-4-carboxylate (484 mg, 2.22 mmol) and potassium phosphate (945 mg, 4.45 mmol) were suspended in 1-methoxy-2-propanol (10 ml) in a 20 ml microwave vial. The vial was capped and the mixture was heated in a microwave to 180° C. for 15 min. After cooling to RT, the mixture was diluted with water and neutralized (pH 6) by the addition of 1N HCl. The resulting precipitate was filtered off and then the layers from the filtrate were separated and the aqueous layer was extracted with ethyl acetate. The collected organic fractions were washed with water, brine, dried over magnesium sulfated, filtrated and evaporated under vacuo. The residue was purified by preparative HPLC (Method 1A). During the evaporation of the combined product fractions a white solid precipitated which was collected by filtration and dried overnight under vacuo at 60° C. to yield the title compound (44 mg, 4% of theory).

LC-MS (Method 1B): $R_t$=1.16 min, MS (ESINeg): m/z=451 [M−H]⁻

Example 29A

Tert-butyl 4-[3-(ethylcarbamoyl)-5-oxo-4,5-dihydropyrazolo[1,5-a]pyrimidin-7-yl]piperidine-1-carboxylate

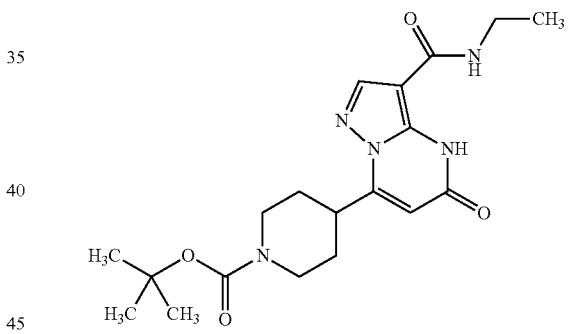

7-[1-(tert-butoxy carbonyl)piperidin-4-yl]-5-oxo-4,5-dihydropyrazolo[1,5-a]pyrimidine-3-carboxylic acid (50 mg, 0.14 mmol), 1-(3-Dimethylaminopropyl)-3-ethylcarbodiimid hydrochlorid (34 mg, 0.18 mmol) and 1-hydroxy-1H-benzotriazole hydrate (27 mg, 0.18 mmol) were dissolved in 1 ml DMF. The mixture was stirred for 10 minutes at RT and then ethylamine 2M in THF (7.4 mg, 0.17 mmol) was added. The reaction mixture was stirred at RT for 16 h. The mixture was diluted in 2 ml acetonitrile and purified by preparative HPLC (Method 1A). During the evaporation of the combined product fractions a white solid precipitated which was collected by filtration and dried overnight under vacuo to yield the title compound (11 mg, 54% of theory).

LC-MS (Method 1B): $R_t$=0.87 min, MS (ESIPos): m/z=390 [M+H]⁺

Example 30A

Tert-butyl 4-[3-(4-chlorophenyl)-5-oxo-2-(trifluoromethyl)-4,5-dihydropyrazolo[1,5-a]pyrimidin-7-yl]piperidine-1-carboxylate

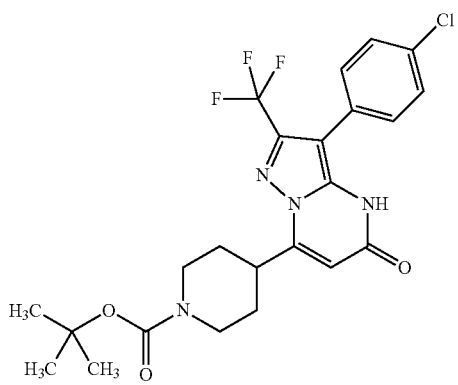 [SMILES: CC(C)(C)OC(=O)N1CCC(c2cc(=O)[nH]c3c(-c4ccc(Cl)cc4)c(C(F)(F)F)nn23)CC1]

Tert-butyl 4-(3-ethoxy-3-oxopropanoyl)piperidine-1-carboxylate (1.03 g, 2.87 mmol), 4-(4-chlorophenyl)-3-(trifluoromethyl)-1H-pyrazol-5-amine (501 mg, 1.95 mmol) and potassium phosphate (813 mg, 3.83 mmol) were suspended in 1-methoxy-2-propanol (10 ml) in a 20 ml microwave vial. The vial was capped and the mixture was heated in a microwave to 180° C. for 15 min. After cooling to RT, the mixture was evaporated under vacuo and the residue was diluted in water and extracted with ethyl acetate. The layers were separated and the aqueous layer was extracted with ethyl acetate. The collected organic fractions were washed with water and brine, dried over magnesium sulfated, filtrated and evaporated under vacuo. The crude product was purified by preparative HPLC (Method 1A). The combined product fractions were neutralized with aqueous ammonium hydroxide and acetonitrile was evaporated under vacuo. The resulting solid in the aqueous phase was filtered and dried under vacuo to yield the title compound (92 mg, 7% of theory).

LC-MS (Method 1B): $R_t$=1.32 min, MS (ESINeg): m/z=495 [M–H]⁻

Example 31A

Tert-butyl 4-[3-(isobutylcarbamoyl)-5-oxo-4,5-dihydropyrazolo[1,5-a]pyrimidin-7-yl]piperidine-1-carboxylate

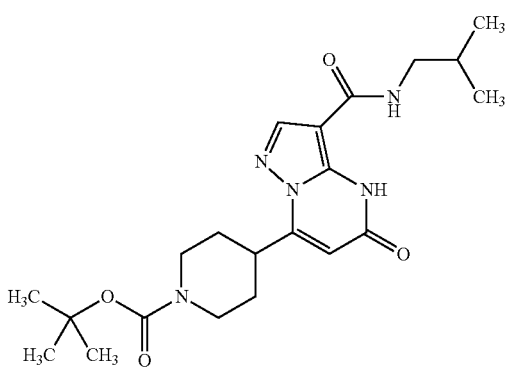 [SMILES: CC(C)CNC(=O)c1cnn2c(C3CCN(C(=O)OC(C)(C)C)CC3)cc(=O)[nH]c12]

7-[1-(tert-butoxycarbonyl)piperidin-4-yl]-5-oxo-4,5-dihydropyrazolo[1,5-a]pyrimidine-3-carboxylic acid (100 mg, 0.28 mmol), 1-(3-Dimethylaminopropyl)-3-ethylcarbodiimidhydrochlorid (158 mg, 0.83 mmol) and 1-hydroxy-1H-benzotriazole hydrate (126 mg, 0.83 mmol) were dissolved in 1 ml DMF. The mixture was stirred for 10 minutes at RT and then isobutylamine (61 mg, 0.83 mmol) was added. The reaction mixture was stirred at RT for 16 h. The mixture was diluted in 2 ml acetonitrile and purified by preparative HPLC (Method 1A). During the evaporation of the combined product fractions a white solid precipitated which was collected by filtration and dried overnight under vacuo to yield the title compound (40 mg, 35% of theory).

LC-MS (Method 1B): $R_t$=1.01 min, MS (ESIPos): m/z=418 [M+H]⁺

Example 32A

Tert-butyl 4-[3-(benzylcarbamoyl)-5-oxo-4,5-dihydropyrazolo[1,5-a]pyrimidin-7-yl]piperidine-1-carboxylate

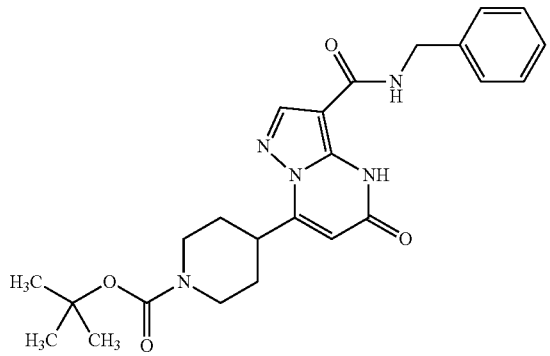 [SMILES: CC(C)(C)OC(=O)N1CCC(c2cc(=O)[nH]c3c(C(=O)NCc4ccccc4)cnn23)CC1]

7-[1-(tert-butoxycarbonyl)piperidin-4-yl]-5-oxo-4,5-dihydropyrazolo[1,5-a]pyrimidine-3-carboxylic acid (100 mg, 0.28 mmol), 1-(3-Dimethylaminopropyl)-3-ethylcarbodiimidhydrochlorid (158 mg, 0.83 mmol) and 1-hydroxy-1H-benzotriazole hydrate (126 mg, 0.83 mmol) were dissolved in 1 ml DMF. The mixture was stirred for 10 minutes at RT and then benzylamine (89 mg, 0.83 mmol) was added. The reaction mixture was stirred at RT for 16 h. The mixture was diluted in 2 ml acetonitrile and purified by preparative HPLC (Method 1A). During the evaporation of the combined product fractions a white solid precipitated which was collected by filtration and dried overnight under vacuo to yield the title compound (48 mg, 38% of theory).

LC-MS (Method 1B): $R_t$=1.03 min, MS (ESIPos): m/z=452 [M+H]⁺

Example 33A

Tert-butyl 4-[3-(morpholin-4-ylcarbonyl)-5-oxo-4,5-dihydropyrazolo[1,5-a]pyrimidin-7-yl]piperidine-1-carboxylate

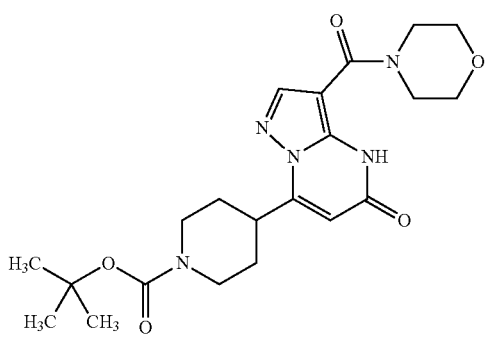 [SMILES: CC(C)(C)OC(=O)N1CCC(c2cc(=O)[nH]c3c(C(=O)N4CCOCC4)cnn23)CC1]

7-[1-(tert-butoxycarbonyl)piperidin-4-yl]-5-oxo-4,5-dihydropyrazolo[1,5-a]pyrimidine-3-carboxylic acid (100 mg, 0.28 mmol), 1-(3-Dimethylaminopropyl)-3-ethylcarbodiimidhydrochlorid (158 mg, 0.83 mmol) and 1-hydroxy-1H-benzotriazole hydrate (126 mg, 0.83 mmol) were dissolved in 1 ml DMF. The mixture was stirred for 10 minutes at RT and then morpholin (72 mg, 0.83 mmol) and N,N-diisopropylethylamine (72 mg, 0.55 mmol) were added. The reaction mixture was stirred at RT for 16 h. The mixture was diluted in 2 ml acetonitrile and purified by preparative HPLC (Method 1A). During the evaporation of the combined product fractions a white solid precipitated which was collected by filtration and dried overnight under vacuo to yield the title compound (31 mg, 26% of theory).

LC-MS (Method 1B): $R_t$=0.87 min, MS (ESIPos): m/z=432 [M+H]$^+$

Example 34A

Tert-butyl 4-[5-oxo-2-(trifluoromethyl)-4,5-dihydropyrazolo[1,5-a]pyrimidin-7-yl]piperidine-1-carboxylate

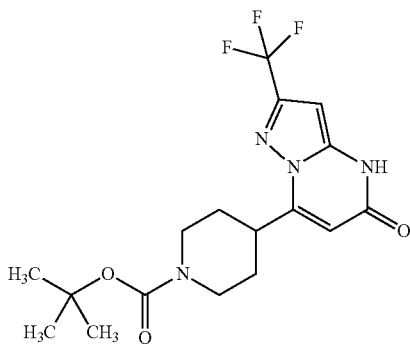 [SMILES: CC(C)(C)OC(=O)N1CCC(c2cc(=O)[nH]c3cc(C(F)(F)F)nn23)CC1]

Tert-butyl 4-(3-ethoxy-3-oxopropanoyl)piperidine-1-carboxylate (1.0 g, ca. 2.77 mmol), 3-(trifluoromethyl)-1H-pyrazol-5-amine (0.28 g, 1.85 mmol) and potassium phosphate (0.79 g, 3.70 mmol) were suspended in 1-methoxy-2-propanol (10 ml) in a 20 ml microwave vial. The vial was capped and the mixture was heated in a microwave to 180° C. for 15 min. After cooling to RT, the solvent was evaporated and the residue was treated with water and ethyl acetate. After separation of the layers the aqueous phase was neutralized by addition of HCl 4N and extracted with ethyl acetate. The collected organic layers were dried over magnesium sulfate, filtered and evaporated. The crude product was purified by preparative HPLC (Method 1A). The combined product fractions were neutralized with a 33% ammonia solution and then acetonitrile was evaporated. The aqueous phase was extracted with ethyl acetate and the collected organic fractions were dried over sodium sulfate, filtered and evaporated under vacuo to yield the title compound (132 mg, 19% of theory).

LC-MS (Method 1B): $R_t$=1.06 min, MS (ESIPos): m/z=387 [M+H]$^+$

Example 35A

Tert-butyl 4-[5-oxo-2-(2-thienyl)-4,5-dihydropyrazolo[1,5-a]pyrimidin-7-yl]piperidine-1-carboxylate

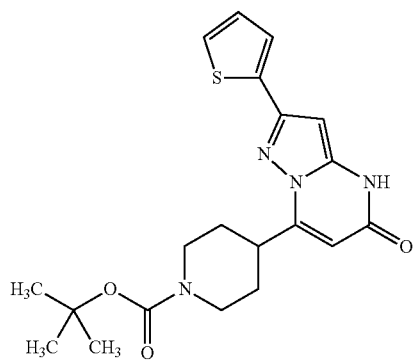 [SMILES: CC(C)(C)OC(=O)N1CCC(c2cc(=O)[nH]c3cc(-c4cccs4)nn23)CC1]

Tert-butyl 4-(3-ethoxy-3-oxopropanoyl)piperidine-1-carboxylate (1.00 g, 3.34 mmol), 3-(2-thienyl)-1H-pyrazol-5-amine (0.37 g, 2.23 mmol) and potassium phosphate (945 mg, 4.45 mmol) were suspended in 1-methoxy-2-propanol (10 ml) in a 20 ml microwave vial. The vial was capped and the mixture was heated in a microwave to 180° C. for 15 min. After cooling to RT, the mixture was diluted with water and neutralized (pH 6) by the addition of 1N HCl. The resulting precipitate was filtered off and then the layers from filtrate were separated. The aqueous layer was extracted with ethyl acetate and the collected organic layers were washed with water and brine, dried over magnesium sulfate, filtered and evaporated under vacuo. The crude product was stirred in 4 ml of a mixture acetonitrile/dimethylsulfoxide 3/1. The resulting solid was filtered, washed with acetonitrile and dried 2 h under vacuo at 60° C. to yield the title compound (53 mg, 6% of theory).

LC-MS (Method 1B): $R_t$=1.08 min, MS (ESIPos): m/z=401 [M+H]$^+$

Example 36A

Tert-butyl 4-(2-cyclopropyl-5-oxo-4,5-dihydropyrazolo[1,5-a]pyrimidin-7-yl)piperidine-1-carboxylate

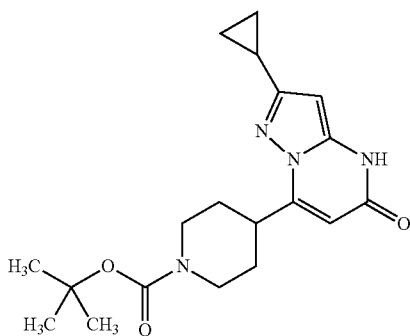 [SMILES: CC(C)(C)OC(=O)N1CCC(c2cc(=O)[nH]c3cc(C4CC4)nn23)CC1]

Tert-butyl 4-(3-ethoxy-3-oxopropanoyl)piperidine-1-carboxylate (1.00 g, 3.34 mmol), 3-cyclopropyl-1H-pyrazol-5-amine (0.27 g, 2.23 mmol) and potassium phosphate (945 mg, 4.45 mmol) were suspended in 1-methoxy-2-propanol (10 ml) in a 20 ml microwave vial. The vial was capped and the mixture was heated in a microwave to 180° C. for 15 min. After cooling to RT, the mixture was diluted with water and neutralized (pH 6) by the addition of 1N HCl. The resulting precipitate was filtered off and then the filtrate was extracted with ethyl acetate. The collected organic layers were washed with water and brine, dried over magnesium sulfate, filtered and evaporated under vacuo. The crude product was purified by preparative HPLC (Method 1A). Before complete evaporation of the combined product fractions the aqueous phase was extracted with ethyl acetate and the collected organic layers were dried over magnesium sulfate, filtered, evaporated and dried under vacuo to yield the title compound (87 mg, 11% of theory).

LC-MS (Method 1B): $R_t$=0.99 min, MS (ESIPos): m/z=359 $[M+H]^+$

Example 37A

Tert-butyl 4-[2-(4-fluorophenyl)-5-oxo-4,5-dihydropyrazolo[1,5-a]pyrimidin-7-yl]piperidine-1-carboxylate

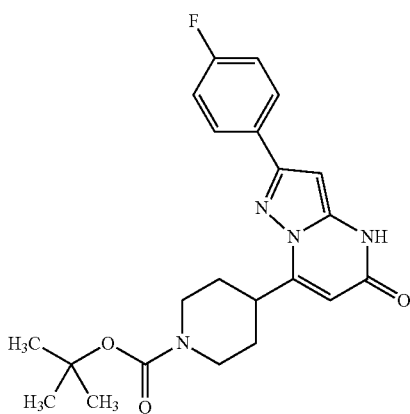 [SMILES: CC(C)(C)OC(=O)N1CCC(c2cc(=O)[nH]c3cc(-c4ccc(F)cc4)nn23)CC1]

Tert-butyl 4-(3-ethoxy-3-oxopropanoyl)piperidine-1-carboxylate (1.00 g, 3.34 mmol), 3-(4-fluorophenyl)-1H-pyrazol-5-amine (0.395 g, 2.23 mmol) and potassium phosphate (945 mg, 4.45 mmol) were suspended in 1-methoxy-2-propanol (10 ml) in a 20 ml microwave vial. The vial was capped and the mixture was heated in a microwave to 180° C. for 15 min. After cooling to RT, the mixture was diluted with water, neutralized (pH 6) by the addition of 1N HCl and extracted with ethyl acetate. The aqueous phase was evaporated under vacuo and the crude product was purified by preparative HPLC (Method 1A). During the evaporation of the combined product fractions a white solid precipitated which was collected by filtration and dried 2 h under vacuo at 60° C. to yield the title compound (119 mg, 13% of theory).

LC-MS (Method 1B): $R_t$=1.12 min, MS (ESIPos): m/z=413 $[M+H]^+$

Example 38A

Methyl 7-[1-(tert-butoxycarbonyl)piperidin-4-yl]-5-oxo-4,5-dihydropyrazolo[1,5-a]pyrimidine-2-carboxylate

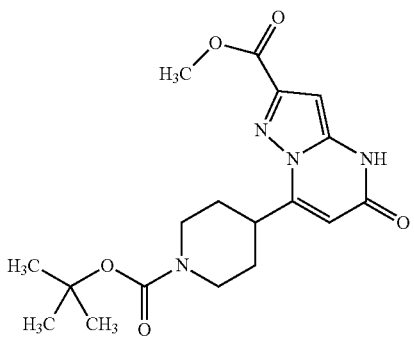 [SMILES: COC(=O)c1cc2[nH]c(=O)cc(C3CCN(C(=O)OC(C)(C)C)CC3)n2n1]

Tert-butyl 4-(3-ethoxy-3-oxopropanoyl)piperidine-1-carboxylate (0.655 mg, ca. 1.82 mmol), methyl 5-amino-1H-pyrazole-3-carboxylate hydrochloride (0.215 mg, 1.21 mmol) and potassium phosphate (0.514 g, 2.42 mmol) were suspended in 1-methoxy-2-propanol (10 ml) in a 20 ml microwave vial. The vial was capped and the mixture was heated in a microwave to 180° C. for 15 min. After cooling to RT, the solvent was evaporated and the residue was treated with water and ethyl acetate. After separation of the layers the aqueous phase was neutralized by addition of HCl 4N and extracted with ethyl acetate. The collected organic layers were dried over sodium sulfate, filtered and evaporated. The crude product was purified by preparative HPLC (Method 1A). The combined product fractions were neutralized with a 33% ammonia solution and then acetonitrile was evaporated. The resulting solid in the aqueous phase was filtered and dried under vacuo to yield the title compound (84 mg, 18% of theory).

LC-MS (Method 1B): $R_t$=0.89 min, MS (ESIPos): m/z=377 $[M+H]^+$

Example 39A

Tert-butyl 4-(3-bromo-5-oxo-2-phenyl-4,5-dihydropyrazolo[1,5-a]pyrimidin-7-yl)piperidine-1-carboxylate

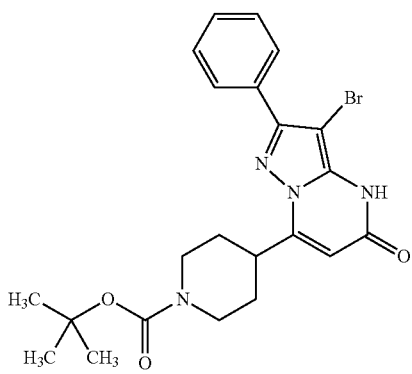 [SMILES: CC(C)(C)OC(=O)N1CCC(c2cc(=O)[nH]c3c(Br)c(-c4ccccc4)nn23)CC1]

The title compound was prepared according to General Procedure 1A starting from 200 mg (0.84 mmol) 4-bromo-3-phenyl-1H-pyrazol-5-amine and 300 mg (0.84 mmol) tert-butyl 4-[(2,2-dimethyl-4,6-dioxo-1,3-dioxan-5-yl)carbonyl]piperidine-1-carboxylate.

Work-up: the mixture was diluted with water, neutralized (pH 5-6) by addition of HCl 1N and extracted with ethyl acetate. The collected organic fractions were washed with water and brine solution, dried over sodium sulfate and concentrated under vacuo. The residue was stirred in 10 ml tert-butylmethylether and the resulting solid was filtered, washed with tert-butylmethylether and dried under vacuo for 2 h at 60° C. to yield the title compound (76 mg, 18% of theory).

LC-MS (Method 1B): $R_t$=1.22 min, MS (ESIPos): m/z=473 [M+H]$^+$

Example 40A

Tert-butyl 4-(2-oxo-1,7,8,9-tetrahydro-2H-cyclopenta[3,4]pyrazolo[1,5-a]pyrimidin-4-yl)piperidine-1-carboxylate

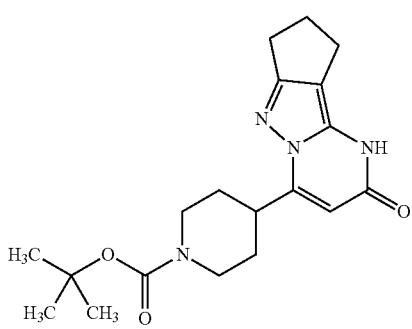 [SMILES: CC(C)(C)OC(=O)N1CCC(c2cc(=O)[nH]c3c4c(nn23)CCC4)CC1]

Tert-butyl 4-(3-ethoxy-3-oxopropanoyl)piperidine-1-carboxylate (1 g, 2.77 mmol), 2,4,5,6-tetrahydrocyclopenta[c]pyrazol-3-amine (0.228 mg, 1.85 mmol) and potassium phosphate (0.785 mg, 3.70 mmol) were suspended in 1-methoxy-2-propanol (10 ml) in a 20 ml microwave vial. The vial was capped and the mixture was heated in a microwave to 180° C. for 15 min. After cooling to RT, the solvent was evaporated and the residue was treated with water and ethyl acetate. After separation of the layers the aqueous phase was neutralized by addition of HCl 4N and extracted with ethyl acetate. The collected organic layers were dried over magnesium sulfate, filtered and evaporated. The crude product was purified by preparative HPLC (Method 1A). The combined product fractions were neutralized with a 33% ammonia solution and then acetonitrile was evaporated. The resulting solid in the aqueous phase was filtered and dried under vacuo to yield the title compound (44 mg, 6% of theory).

LC-MS (Method 2B): $R_t$=2.19 min, MS (ESIPos): m/z=359 [M+H]$^+$

Example 41A

Tert-butyl 4-(3-bromo-5-oxo-4,5-dihydropyrazolo[1,5-a]pyrimidin-7-yl)piperidine-1-carboxylate

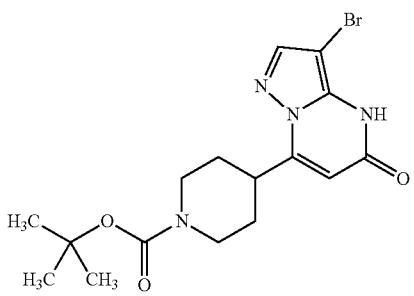 [SMILES: CC(C)(C)OC(=O)N1CCC(c2cc(=O)[nH]c3c(Br)cnn23)CC1]

The title compound was prepared according to General Procedure 1A starting from 200 mg (1.23 mmol) 4-bromo-1H-pyrazol-5-amine and 439 mg (1.23 mmol) tert-butyl 4-[(2,2-dimethyl-4,6-dioxo-1,3-dioxan-5-yl)carbonyl]piperidine-1-carboxylate.

Work-up: the mixture was diluted with water, neutralized (pH 5-6) by addition of HCl 1N and extracted with ethyl acetate. The collected organic fractions were washed with water and brine solution, dried over magnesium sulfate and concentrated under vacuo. The residue was stirred in 10 ml tert-butylmethylether and the resulting solid was filtered, washed with tert-butylmethylether and dried under vacuo for 2 h at 60° C. to yield the title compound (134 mg, 26% of theory).

LC-MS (Method 2B): $R_t$=0.96 min, MS (ESIPos): m/z=397 [M+H]$^+$

Example 42A

Tert-butyl 4-[3-(3-methyl-1,2,4-oxadiazol-5-yl)-5-oxo-4,5-dihydropyrazolo[1,5-a]pyrimidin-7-yl]piperidine-1-carboxylate

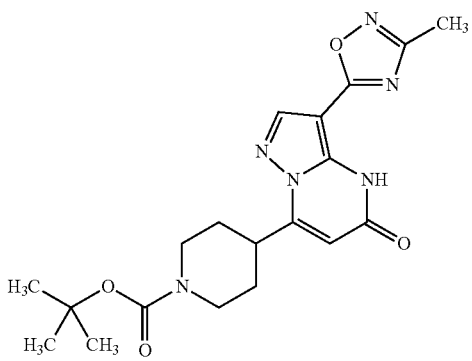 [SMILES: Cc1noc(-c2cnn3c(C4CCN(C(=O)OC(C)(C)C)CC4)cc(=O)[nH]c23)n1]

To a solution of compound 7-[1-(tert-Butoxycarbonyl)piperidin-4-yl]-5-oxo-4,5-dihydropyrazolo[1,5-a]pyrimidine-3-carboxylic acid (50 mg, 0.14 mmol) in 1 ml dimethylformamide was added 1,1'-carbonyldiimidazole (44 mg, 0.28 mmol) and N,N-diisopropylethylamine (36 mg, 0.28 mmol) and then the reaction mixture was stirred 1 h at 60° C. After this time N'-hydroxyethanimidamide (20 mg, 0.28 mmol) was added and the mixture was stirred for 4 h at 120° C. After cooling to RT, the mixture was diluted in 2 ml acetonitrile and purified by preparative HPLC (Method 1A). After evaporation of acetonitrile the aqueous fraction was lyophilized overnight to yield the title compound (10 mg, 17% of theory).

LC-MS (Method 1B): $R_t$=1.01 min, MS (ESIPos): m/z=401 $[M+H]^+$

Example 43A

Tert-butyl 4-[3-(3-isopropyl-1,2,4-oxadiazol-5-yl)-5-oxo-4,5-dihydropyrazolo[1,5-a]pyrimidin-7-yl]piperidine-1-carboxylate

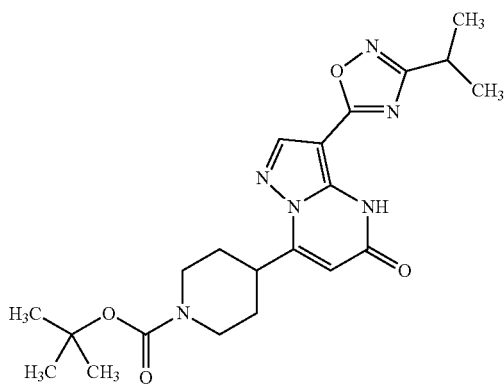 [SMILES: CC(C)c1noc(-c2cnn3c(C4CCN(C(=O)OC(C)(C)C)CC4)cc(=O)[nH]c23)n1]

To a solution of compound 7-[1-(tert-Butoxycarbonyl)piperidin-4-yl]-5-oxo-4,5-dihydropyrazolo[1,5-a]pyrimidine-3-carboxylic acid (150 mg, 0.41 mmol) in 3 ml dimethylformamide was added 1,1'-carbonyldiimidazole (134 mg, 0.83 mmol) and N,N-diisopropylethylamine (106 mg, 0.83 mmol) and then the reaction mixture was stirred 1 h at 90° C. After this time N'-hydroxy-2-methylpropanimidamide (84 mg, 0.83 mmol) was added and the mixture was stirred for 5.5 h at 110° C. After cooling to RT, the mixture was diluted with 2 ml acetonitrile and purified by preparative HPLC (Method 1A). During the evaporation of the combined product fractions a white solid precipitated which was collected by filtration and dried for 2 h at 60° C. under vacuo to yield the title compound (101 mg, 57% of theory).

LC-MS (Method 1B): $R_t$=1.14 min, MS (ESIPos): m/z=429 $[M+H]^+$

Example 44A

Tert-butyl 4-[5-oxo-3-(3-propyl-1,2,4-oxadiazol-5-yl)-4,5-dihydropyrazolo[1,5-a]pyrimidin-7-yl]piperidine-1-carboxylate

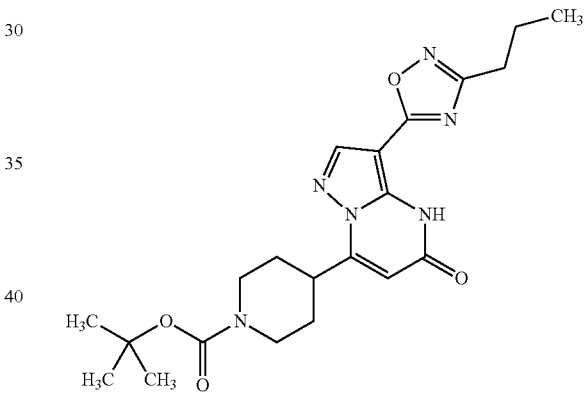

To a solution of compound 7-[1-(tert-Butoxycarbonyl)piperidin-4-yl]-5-oxo-4,5-dihydropyrazolo[1,5-a]pyrimidine-3-carboxylic acid (150 mg, 0.41 mmol) in 3 ml dimethylformamide was added 1,1'-carbonyldiimidazole (134 mg, 0.83 mmol) and N,N-diisopropylethylamine (106 mg, 0.83 mmol) and then the reaction mixture was stirred 1 h at 90° C. After this time N'-hydroxybutanimidamide (84 mg, 0.83 mmol) was added and the mixture was stirred for 5.5 h at 110° C. After cooling to RT, the mixture was diluted with 2 ml acetonitrile and purified by preparative HPLC (Method 1A). During the evaporation of the combined product fractions a white solid precipitated which was collected by filtration and dried for 2 h at 60° C. under vacuo to yield the title compound (71 mg, 40% of theory).

LC-MS (Method 1B): $R_t$=1.14 min, MS (ESIPos): m/z=429 $[M+H]^+$

Example 45A

Tert-butyl 4-[5-oxo-3-(3-phenyl-1,2,4-oxadiazol-5-yl)-4,5-dihydropyrazolo[1,5-a]pyrimidin-7-yl]piperidine-1-carboxylate

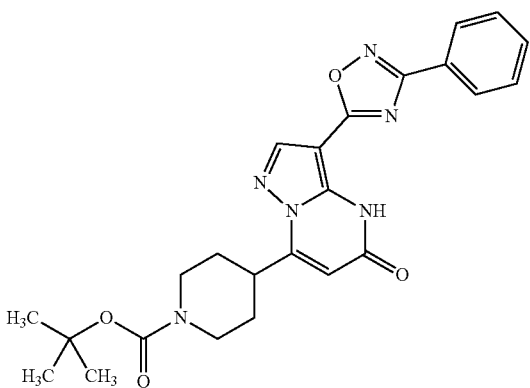 [SMILES: CC(C)(C)OC(=O)N1CCC(c2cc(=O)[nH]c3c(-c4nc(-c5ccccc5)no4)cnn23)CC1]

To a solution of compound 7-[1-(tert-Butoxycarbonyl)piperidin-4-yl]-5-oxo-4,5-dihydropyrazolo[1,5-a]pyrimidine-3-carboxylic acid (150 mg, 0.41 mmol) in 3 ml dimethylformamide was added 1,1'-carbonyldiimidazole (134 mg, 0.83 mmol) and N,N-diisopropylethylamine (106 mg, 0.83 mmol) and then the reaction mixture was stirred 1 h at 90° C. After this time N'-hydroxybenzenecarboximidamide (112 mg, 0.83 mmol) was added and the mixture was stirred for 5.5 h at 110° C. After cooling to RT, the mixture was diluted with 2 ml acetonitrile and purified by preparative HPLC (Method 1A). During the evaporation of the combined product fractions a white solid precipitated which was collected by filtration and dried for 2 h at 60° C. under vacuo to yield the title compound (115 mg, 60% of theory).

LC-MS (Method 1B): $R_t$=1.23 min, MS (ESIPos): m/z=463 [M+H]$^+$

Example 46A

Tert-butyl 4-(3-{[methyl(4-methylphenyl)oxido-lambda$^6$-sulfanylidene]carbamoyl}-5-oxo-4,5-dihydropyrazolo[1,5-a]pyrimidin-7-yl)piperidine-1-carboxylate

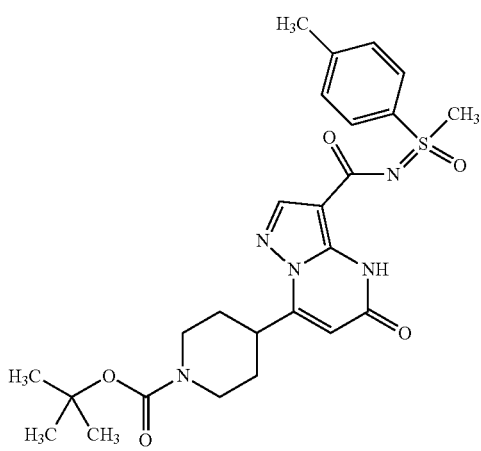 [SMILES: Cc1ccc(S(C)(=O)=NC(=O)c2cnn3c(C4CCN(C(=O)OC(C)(C)C)CC4)cc(=O)[nH]c23)cc1]

To a solution of compound 7-[1-(tert-Butoxycarbonyl)piperidin-4-yl]-5-oxo-4,5-dihydropyrazolo[1,5-a]pyrimidine-3-carboxylic acid (100 mg, 0.28 mmol) in 2 ml dichloromethane was added 1 chlor-N,N-2-trimethylpropenylamine (73 mg, 0.55 mmol) and the reaction mixture was stirred 2 h at RT. After that S-Methyl-S-(4-methylphenyl)sulfoximine (46 mg, 0.28 mmol) and triethylamine (55 mg, 0.55 mmol) were added and the mixture was stirred at RT for 16 h. After evaporating the solvent under vacuo the crude product was diluted with acetonitrile and water and purified by preparative HPLC (Method 1A). After evaporating the acetonitrile from the combined product fractions the aqueous phase was extracted with ethyl acetate. The collected organic layers were dried over magnesium sulfate, filtered, evaporated and dried under vacuo overnight to yield the title compound (16 mg, 12% of theory).

LC-MS (Method 1B): $R_t$=1.04 min, MS (ESIPos): m/z=514 [M+H]$^+$

Example 47A

Tert-butyl 4-{3-[(4-oxido-1,4lambda$^4$-oxathian-4-ylidene)carbamoyl]-5-oxo-4,5-dihydropyrazolo[1,5-a]pyrimidin-7-yl}piperidine-1-carboxylate

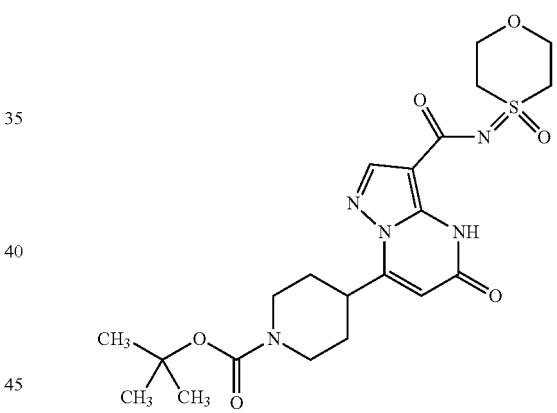

To a solution of compound 7-[1-(tert-Butoxycarbonyl)piperidin-4-yl]-5-oxo-4,5-dihydropyrazolo[1,5-a]pyrimidine-3-carboxylic acid (200 mg, 0.55 mmol) in 4 ml dichloromethane was added 1-chloro-N,N-2-trimethylpropenylamine (148 mg, 1.10 mmol) and the reaction mixture was stirred 2 h at RT. After that 1,4-oxathiane-sulfoximine (74 mg, 0.55 mmol) and triethylamine (111 mg, 1.10 mmol) were added and the mixture was stirred at RT for 16 h. After evaporating the solvent under vacuo the crude product was diluted with acetonitrile and water and purified by preparative HPLC (Method 1A). After evaporating the acetonitrile from the combined product fractions the aqueous phase was lyophilized overnight to yield the title compound (74 mg, 28% of theory).

LC-MS (Method 1B): $R_t$=0.89 min, MS (ESIPos): m/z=480 [M+H]$^+$

Example 48A

Ethyl 7-[1-(tert-butoxycarbonyl)piperidin-4-yl]-5-oxo-2-phenyl-4,5-dihydropyrazolo[1,5-a]pyrimidine-3-carboxylate

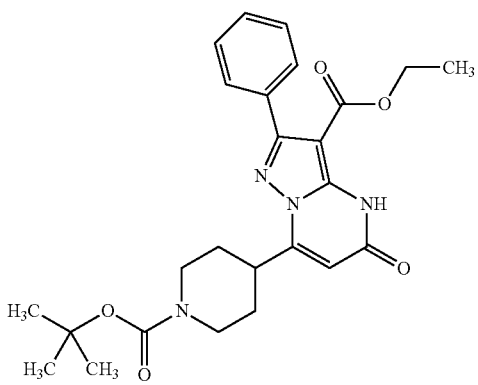 [SMILES: CCOC(=O)c1c(-c2ccccc2)nn2c(C3CCN(C(=O)OC(C)(C)C)CC3)cc(=O)[nH]c12]

The title compound was prepared according to General Procedure 1A starting from ethyl 5-amino-3-phenyl-1H-pyrazole-4-carboxylate (0.62 g, 2.64 mmol) and tert-butyl 4-[(2,2-dimethyl-4,6-dioxo-1,3-dioxan-5-yl)carbonyl]piperidine-1-carboxylate (1.00 g, 2.64 mmol).

Work-up: the mixture was evaporated under vacuo. The crude product was diluted in ethyl acetate and treated with HCl 1N. After separation of the layers the organic layer was washed with water, dried under sodium sulfate, filtrated and evaporated under vacuo. The resulting crude product was stirred in acetonitrile, filtrated and dried under vacuo to yield the title compound (0.79 g, 63% of theory).

LC-MS (Method 1B): $R_t$=1.26 min, MS (ESINeg): m/z=465 [M−H]⁻

Example 49A

Tert-butyl 4-{3-[3-(4-methylphenyl)-1,2,4-oxadiazol-5-yl]-5-oxo-4,5-dihydropyrazolo[1,5-a]pyrimidin-7-yl}piperidine-1-carboxylate

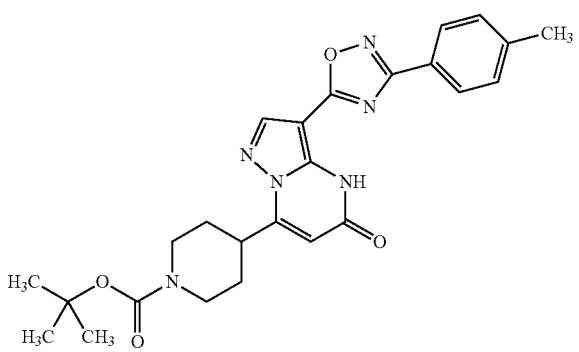 [SMILES: Cc1ccc(-c2noc(-c3cnn4c(C5CCN(C(=O)OC(C)(C)C)CC5)cc(=O)[nH]c34)n2)cc1]

To a solution of compound 7-[1-(tert-Butoxycarbonyl)piperidin-4-yl]-5-oxo-4,5-dihydropyrazolo[1,5-a]pyrimidine-3-carboxylic acid (150 mg, 0.41 mmol) in 3 ml dimethylformamide was added 1,1'-carbonyldiimidazole (134 mg, 0.83 mmol) and N,N-diisopropylethylamine (106 mg, 0.83 mmol) and then the reaction mixture was stirred 1 h at 90° C. After this time N'-hydroxy-4-methylbenzenecarboximidamide (124 mg, 0.83 mmol) was added and the mixture was stirred for 5.5 h at 110° C. After cooling to RT, the mixture was diluted with 2 ml acetonitrile and purified by preparative HPLC (Method 1A). After evaporating acetonitrile from the combined product fractions a white solid precipitated in the aqueous phase which was collected by filtration and dried for 2 h at 60° C. under vacuo to yield the title compound (92 mg, 47% of theory).

LC-MS (Method 1B): $R_t$=1.28 min, MS (ESIPos): m/z=477 [M+H]⁺

Example 50A

7-[1-(Tert-butoxycarbonyl)piperidin-4-yl]-5-oxo-2-phenyl-4,5-dihydropyrazolo[1,5-a]pyrimidine-3-carboxylic Acid

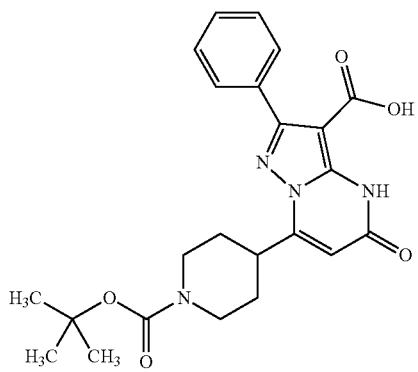 [SMILES: CC(C)(C)OC(=O)N1CCC(c2cc(=O)[nH]c3c(C(=O)O)c(-c4ccccc4)nn23)CC1]

To a suspension of compound Ethyl 7-[1-(tert-butoxycarbonyl)piperidin-4-yl]-5-oxo-2-phenyl-4,5-dihydropyrazolo[1,5-a]pyrimidine-3-carboxylate (617 mg, 1.30 mmol) in a mixture of 5.4 ml ethanol and 5.4 ml water was added lithium hydroxide monohydrate (543 mg, 12.96 mmol) and then the reaction mixture was stirred at 60° C. for 20 h. After cooling to RT ethanol was evaporated under vacuo and the aqueous suspension was treated with HCl 1N until pH=1 was achieved. The resulting white solid was filtered and dried under vacuo to yield the title compound (0.63 mg, quantitative).

LC-MS (Method 1B): $R_t$=1.03 min, MS (ESINeg): m/z=437 [M−H]⁻

Example 51A

Tert-butyl-4-(3-chloro-5-oxo-4,5-dihydropyrazolo[1,5-a]pyrimidin-7-yl)-2-methylpiperidine-1-carboxylate [enantiomerically pure trans-Isomer]

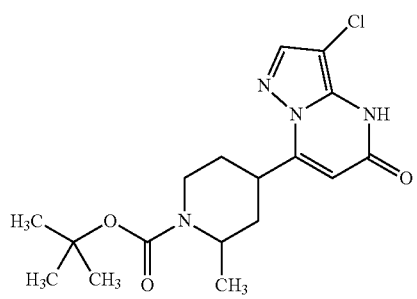 [SMILES: CC1CC(c2cc(=O)[nH]c3c(Cl)cnn23)CCN1C(=O)OC(C)(C)C]

The title compound was prepared according to General Procedure 1A starting from 0.50 g (4.25 mmol) 4-chloro-1H-pyrazol-3-amine and 1.68 g (4.25 mmol) (−)-cis-tert-butyl 4-[(2,2-dimethyl-4,6-dioxo-1,3-dioxan-5-yl)carbonyl]-2-methylpiperidine-1-carboxylate.

Work-up: the mixture was evaporated and the crude product was treated with HCl 1N and ethyl acetate. After separation of the layers the organic layer was washed with water, dried over sodium sulfate and evaporated under vacuo. The crude product was stirred in acetonitrile, filtered and dried under vacuo to yield a first fraction containing product. The filtrated was evaporated and purified by preparative HPLC (Method 1A). The combined product fractions were neutralized with a 33% ammonia solution and then acetonitrile was evaporated. In the aqueous phase precipitated a solid which was filtered and dried under vacuo to obtained a second fraction containing product. After reaction epimerization was observed obtaining a mixture of diastereomers which were separated by Method 1C to yield the title compound (385 mg, 24% of theory).

LC-MS (Method 1B): $R_t$=1.02 min, MS (ESIPos): m/z=367 [M+H]$^+$

HPLC (Method 1E): $R_t$=7.75 min

Example 52A

Tert-butyl 4-(3-carbamoyl-5-oxo-2-phenyl-4,5-dihydropyrazolo[1,5-a]pyrimidin-7-yl)piperidine-1-carboxylate

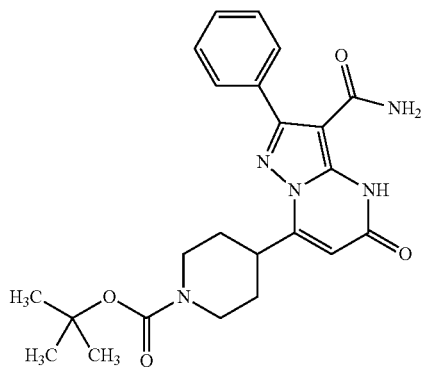 [SMILES: CC(C)(C)OC(=O)N1CCC(c2cc(=O)[nH]c3c(C(N)=O)c(-c4ccccc4)nn23)CC1]

To a solution of compound 7-[1-(tert-butoxycarbonyl)piperidin-4-yl]-5-oxo-2-phenyl-4,5-dihydropyrazolo[1,5-a]pyrimidine-3-carboxylic acid (100 mg, 0.21 mmol) in 2 ml dimethylformamide were added HATU (103 mg, 0.27 mmol) and DMAP (44 mg, 0.36 mmol). After that ammonium acetate (14 mg, 0.18 mmol) was added and then the reaction mixture was stirred at RT for 24 h and then it was left without stirring for 5 days at RT during 6 days. The mixture was diluted in DMSO and water and and purified by preparative HPLC (Method 1A). The combined product fractions were neutralized with a 33% ammonia solution and then acetonitrile was evaporated. In the aqueous phase a white solid precipitated which was filtered and dried under vacuo to yield the title compound (17 mg, 18% of theory).

LC-MS (Method 1B): $R_t$=0.98 min, MS (ESIPos): m/z=438 [M+H]$^+$

Example 53A

7-[1-(Tert-Butoxycarbonyl)piperidin-4-yl]-5-oxo-4,5-dihydropyrazolo[1,5-a]pyrimidine-2-carboxylic Acid

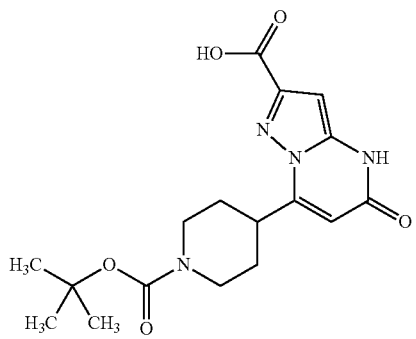 [SMILES: CC(C)(C)OC(=O)N1CCC(c2cc(=O)[nH]c3cc(C(=O)O)nn23)CC1]

To a solution of (1.95 g, aprox. 5.18 mmol) of methyl 7-[1-(tert-butoxycarbonyl)piperidin-4-yl]-5-oxo-4,5-dihydropyrazolo[1,5-a]pyrimidine-2-carboxylate in methanol (12 ml) was added a solution of lithium hydroxide (1.24 g, 51.80 mmol) in water (12 ml). The reaction mixture was stirred at 60° C. for 1 h. Methanol was evaporated under vacuo and the resulting aqueous suspension was diluted with water and extracted with ethyl acetate. Finally the aqueous phase was neutralized (pH 5) by addition of HCl 4M and the resulting precipitate was filtered, washed with water and dried at 60° C. overnight to yield the title compound (1.0 g, 52% of theory).

LC-MS (Method 3B): $R_t$=1.72 min, MS (ESINeg): m/z=361 [M−H]$^-$

Example 54A

Tert-butyl 4-[3-(benzylcarbamoyl)-5-oxo-2-phenyl-4,5-dihydropyrazolo[1,5-a]pyrimidin-7-yl]piperidine-1-carboxylate

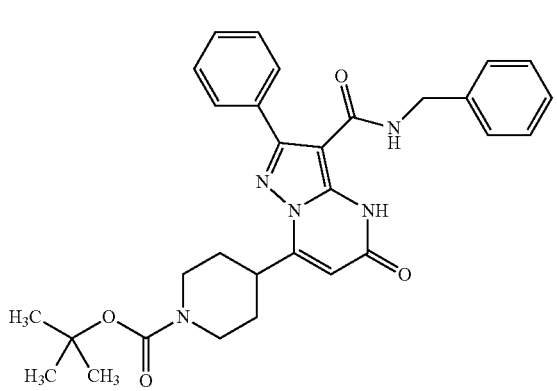 [SMILES: CC(C)(C)OC(=O)N1CCC(c2cc(=O)[nH]c3c(C(=O)NCc4ccccc4)c(-c4ccccc4)nn23)CC1]

To a solution of compound 7-[1-(tert-butoxycarbonyl)piperidin-4-yl]-5-oxo-2-phenyl-4,5-dihydropyrazolo[1,5-a]pyrimidine-3-carboxylic acid (50 mg, 0.11 mmol) in 1 ml dimethylformamide were added HATU (53 mg, 0.13 mmol) and DMAP (22 mg, 0.18 mmol). After that benzylamine (15 mg, 0.14 mmol) was added and then the reaction mixture was stirred at RT for 39 h. The mixture was diluted in DMSO and water and purified by preparative HPLC (Method 1A). The combined product fractions were neutralized with a 33% ammonia solution and then the acetonitrile was evaporated. The resulting aqueous phase was extracted with ethyl acetate and the collected organic phases were dried over sodiumsulfate, filtered and evaporated under vacuo to yield the title compound (19 mg, 34% of theory).

LC-MS (Method 1B): $R_t$=1.21 min, MS (ESIPos): m/z=528 [M+H]$^+$

Example 55A

Tert-butyl 4-[3-(morpholin-4-ylcarbonyl)-5-oxo-2-phenyl-4,5-dihydropyrazolo[1,5-a]pyrimidin-7-yl]piperidine-1-carboxylate

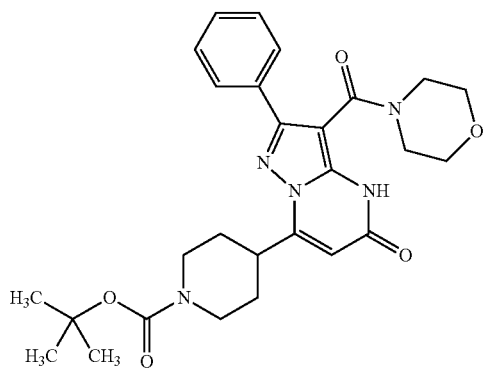 [SMILES: CC(C)(C)OC(=O)N1CCC(c2cc(=O)[nH]c3c(C(=O)N4CCOCC4)c(-c4ccccc4)nn23)CC1]

To a solution of compound 7-[1-(tert-butoxycarbonyl)piperidin-4-yl]-5-oxo-2-phenyl-4,5-dihydropyrazolo[1,5-a]pyrimidine-3-carboxylic acid (50 mg, 0.11 mmol) in 1 ml dimethylformamide were added HATU (53 mg, 0.13 mmol) and DMAP (22 mg, 0.18 mmol). After that morpholine (8 mg, 0.09 mmol) was added and then the reaction mixture was stirred at RT for 39 h. The mixture was diluted in DMSO and water and purified by preparative HPLC (Method 1A). The combined product fractions were neutralized with a 33% ammonia solution and then acetonitrile was evaporated. The resulting aqueous phase was extracted with ethyl acetate and the collected organic phases were dried over sodium sulfate, filtered and evaporated under vacuo to yield the title compound (12 mg, 22% of theory).

LC-MS (Method 1B): $R_t$=1.00 min, MS (ESIPos): m/z=508 [M+H]$^+$

Example 56A

Tert-butyl 4-[3-(isobutylcarbamoyl)-5-oxo-2-phenyl-4,5-dihydropyrazolo[1,5-a]pyrimidin-7-yl]piperidine-1-carboxylate

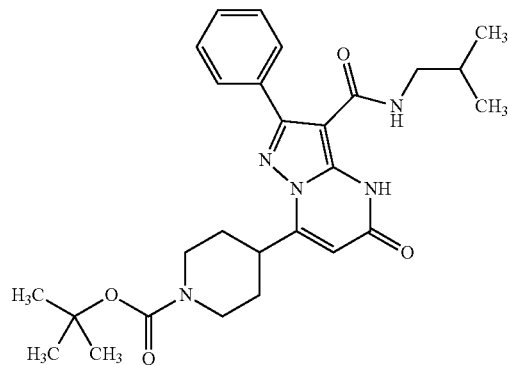 [SMILES: CC(C)CNC(=O)c1c(-c2ccccc2)nn2c(C3CCN(C(=O)OC(C)(C)C)CC3)cc(=O)[nH]c12]

To a solution of compound 7-[1-(tert-butoxycarbonyl)piperidin-4-yl]-5-oxo-2-phenyl-4,5-dihydropyrazolo[1,5-a]pyrimidine-3-carboxylic acid (50 mg, 0.11 mmol) in 1 ml dimethylformamide were added HATU (53 mg, 0.13 mmol) and DMAP (22 mg, 0.18 mmol). After that isobutylamine (10 mg, 0.13 mmol) was added and then the reaction mixture was stirred at RT for 39 h. The mixture was diluted in DMSO and water and purified by preparative HPLC (Method 1A). The combined product fractions were neutralized with a 33% ammonia solution and then acetonitrile was evaporated. The resulting aqueous phase was extracted with ethyl acetate and the collected organic phases were dried over sodium sulfate, filtered and evaporated under vacuo to yield compound (11 g, 21% of theory).

LC-MS (Method 1B): $R_t$=1.22 min, MS (ESIPos): m/z=494 [M+H]$^+$

Example 57A

Tert-butyl 4-[3-(4-methylphenyl)-5-oxo-4,5-dihydropyrazolo[1,5-a]pyrimidin-7-yl]piperidine-1-carboxylate

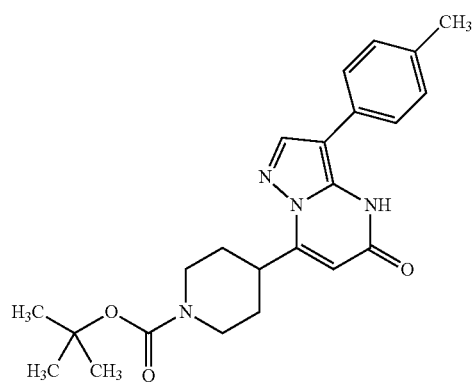 [SMILES: Cc1ccc(-c2cnn3c(C4CCN(C(=O)OC(C)(C)C)CC4)cc(=O)[nH]c23)cc1]

A vial charged with tert-butyl 4-(3-bromo-5-oxo-4,5-dihydropyrazolo[1,5-a]pyrimidin-7-yl)piperidine-1-carboxylate (150 mg, 0.38 mmol), (4-methylphenyl)boronic acid (77 mg, 0.57 mmol), tetrakis(triphenylphosphin)palladium(0) (43 mg, 0.04 mmol), lithium chloride (44 mg, 1.06 mmol) and sodium carbonate (100 mg, 0.95 mmol) was sealed with a screw-cap septum and flushed with argon for 10 minutes. Then 3 ml from a degassed solution of toluene, ethanol and water 1/1/1 were added via syringe and the reaction mixture was stirred at 100° C. for 16 h. After cooling to RT the mixture was diluted with water and extracted with ethyl acetate. The collected organic phases were washed with water, brine solution and dried over magnesium sulfate. After the evaporation of the solvent the crude product was purified by preparative HPLC (Method 1A). The acetonitrile of the combined product fractions was evaporated and the resulting aqueous phase was extracted with ethyl acetate. The collected organic phases were dried over magnesium sulfate, filtered, evaporated and dried under vacuo to yield the title compound (7 mg, 4% of theory).

LC-MS (Method 1B): $R_t$=2.56 min, MS (ESIPos): m/z=409 [M+H]$^+$

Example 58A

Methyl 7-[1-(tert-butoxy carbonyl)piperidin-4-yl]-5-oxo-4,5-dihydropyrazolo[1,5-a]pyrimidine-2-carboxylate

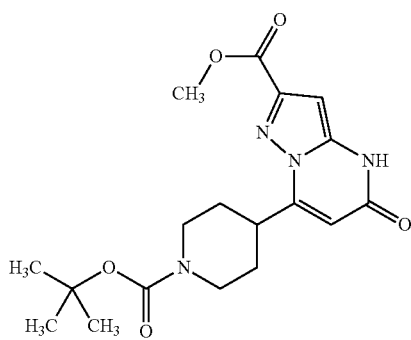 [SMILES: COC(=O)c1cc2[nH]c(=O)cc(C3CCN(C(=O)OC(C)(C)C)CC3)n2n1]

A solution of (0.78 g, 5.53 mmol) methyl 5-amino-1H-pyrazole-3-carboxylate in 20 ml water was treated with HCl 1N until pH 6 was achieved and then the solution was extracted with ethyl acetate. The combined organic phases were dried over magnesium sulfate, filtered and evaporated under vacuo. The resulting amine reacted with 1.97 g (5.53 mmol) tert-butyl 4-[(2,2-dimethyl-4,6-dioxo-1,3-dioxan-5-yl)carbonyl]piperidine-1-carboxylate according to General Procedure 1A.

Work-up: the mixture was diluted with water, neutralized (pH 5) by the addition of 1N HCl, and extracted with ethyl acetate. The combined organic phases were washed with water and brine, dried over magnesium sulfate, filtered and evaporated. The crude product was used in the next step without further purification (1.95 g, 34% of theory, 37% pure according to LC-MS).

LC-MS (Method 1B): $R_t$=0.87 min, MS (ESINeg): m/z=375 [M−H]$^-$

Example 59A

7-[1-(tert-Butoxycarbonyl)piperidin-4-yl]-5-oxo-4,5-dihydropyrazolo[1,5-a]pyrimidine-2-carboxylic Acid

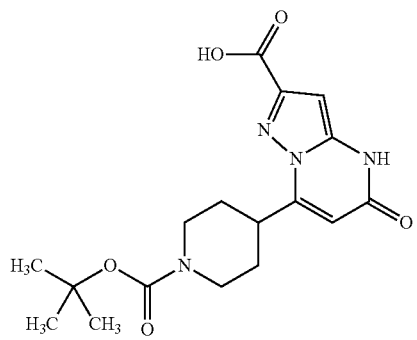 [SMILES: CC(C)(C)OC(=O)N1CCC(c2cc(=O)[nH]c3cc(C(=O)O)nn23)CC1]

To a solution of (1.95 g, aprox. 5.18 mmol) of methyl 7-[1-(tert-butoxycarbonyl)piperidin-4-yl]-5-oxo-4,5-dihydropyrazolo[1,5-a]pyrimidine-2-carboxylate in methanol (12 ml) was added a solution of lithium hydroxide (1.24 g, 51.80 mmol) in water (12 ml). The reaction mixture was stirred at 60° C. for 1 h. Methanol was evaporated under vacuo and the resulting aqueous suspension was diluted with water and extracted with ethyl acetate. Finally the aqueous phase was neutralized (pH 5) by addition of HCl 4M and the resulting precipitate was filtered, washed with water and dried at 60° C. overnight to yield the title compound (1.0 g, 52% of theory).

LC-MS (Method 3B): $R_t$=1.72 min, MS (ESINeg): m/z=361 [M−H]$^-$

Example 60A

Tert-butyl 4-[3-(4-cyanophenyl)-5-oxo-4,5-dihydropyrazolo[1,5-a]pyrimidin-7-yl]piperidine-1-carboxylate

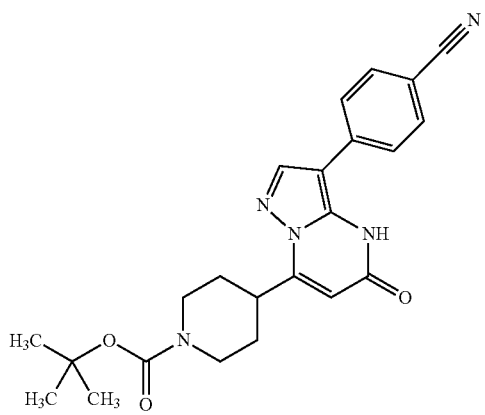 [SMILES: CC(C)(C)OC(=O)N1CCC(c2cc(=O)[nH]c3c(-c4ccc(C#N)cc4)cnn23)CC1]

Following the General Procedure 2A, a mixture of (4-cyanophenyl)boronic acid (83 mg, 0.57 mmol), tert-butyl 4-(3-bromo-5-oxo-4,5-dihydropyrazolo[1,5-a]pyrimidin-7-yl)piperidine-1-carboxylate (150 mg, 0.38 mmol), XPhos precatalyst (32 mg, 0.04 mmol), degassed THF (3 ml) and degassed aqueous 1M K$_3$PO$_4$ solution (1.1 ml) were stirred at 80° C. for 16 h. Yield: 46 mg, 30% of theory.

LC-MS (Method 1B): $R_t$=1.07 min, MS (ESINeg): m/z=418 [M−H]⁻

Example 61A

Tert-butyl 4-[3-(3-chlorophenyl)-5-oxo-4,5-dihydropyrazolo[1,5-a]pyrimidin-7-yl]piperidine-1-carboxylate

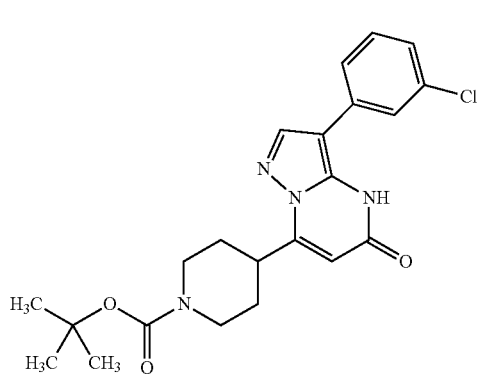 [SMILES: CC(C)(C)OC(=O)N1CCC(c2cc(=O)[nH]c3c(-c4cccc(Cl)c4)cnn23)CC1]

Following the General Procedure 2A, a mixture of 3-chlorophenyl boronic acid (89 mg, 0.57 mmol), tert-butyl 4-(3-bromo-5-oxo-4,5-dihydropyrazolo[1,5-a]pyrimidin-7-yl)piperidine-1-carboxylate (150 mg, 0.38 mmol), XPhos precatalyst (32 mg, 0.04 mmol), degassed THF (3 ml) and degassed aqueous 1M K₃PO₄ solution (1.1 ml) were stirred at 80° C. for 16 h. Yield: 39 mg, 25% of theory.

LC-MS (Method 1B): $R_t$=1.18 min, MS (ESINeg): m/z=427 [M−H]⁻

Example 62A

Tert-butyl 4-[3-(2-cyanophenyl)-5-oxo-4,5-dihydropyrazolo[1,5-a]pyrimidin-7-yl]piperidine-1-carboxylate

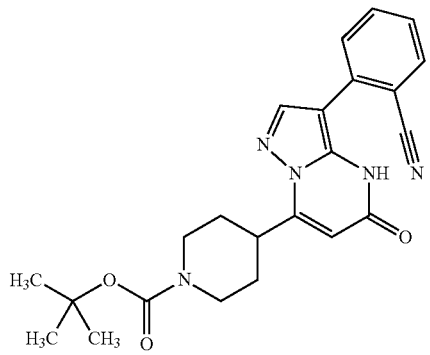 [SMILES: CC(C)(C)OC(=O)N1CCC(c2cc(=O)[nH]c3c(-c4ccccc4C#N)cnn23)CC1]

Following the General Procedure 2A, a mixture of 2-cyanophenyl boronic acid (83 mg, 0.57 mmol), tert-butyl 4-(3-bromo-5-oxo-4,5-dihydropyrazolo[1,5-a]pyrimidin-7-yl)piperidine-1-carboxylate (150 mg, 0.38 mmol), XPhos precatalyst (32 mg, 0.04 mmol), degassed THF (3 ml) and degassed aqueous 1M K₃PO₄ solution (1.1 ml) were stirred at 80° C. for 16 h. Yield: 24 mg, 15% of theory.

LC-MS (Method 1B): $R_t$=1.03 min, MS (ESINeg): m/z=418 [M−H]⁻

Example 63A

Tert-butyl 4-[3-(3-cyanophenyl)-5-oxo-4,5-dihydropyrazolo[1,5-a]pyrimidin-7-yl]piperidine-1-carboxylate

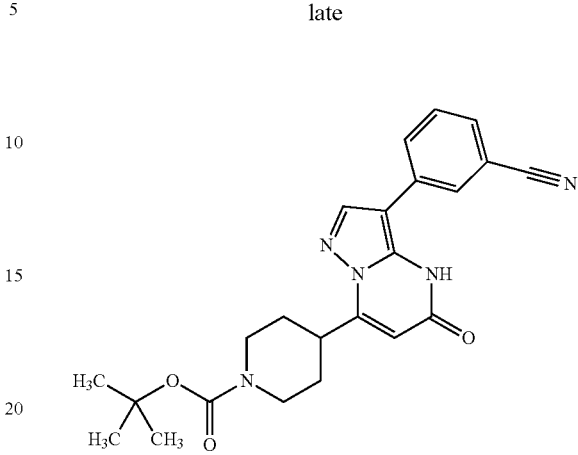

Following the General Procedure 2A, a mixture of (3-cyanophenyl)boronic acid (83 mg, 0.57 mmol), tert-butyl 4-(3-bromo-5-oxo-4,5-dihydropyrazolo[1,5-a]pyrimidin-7-yl)piperidine-1-carboxylate (150 mg, 0.38 mmol), XPhos precatalyst (32 mg, 0.04 mmol), degassed THF (3 ml) and degassed aqueous 1M K₃PO₄ solution (1.1 ml) were stirred at 80° C. for 16 h. Yield: 34 mg, 22% of theory.

LC-MS (Method 1B): $R_t$=1.08 min, MS (ESINeg): m/z=418 [M−H]⁻

Example 64A

Tert-butyl 4-(3-carbamoyl-5-oxo-4,5-dihydropyrazolo[1,5-a]pyrimidin-7-yl)-2-methylpiperidine-1-carboxylate [enantiomerically pure trans-Isomer]

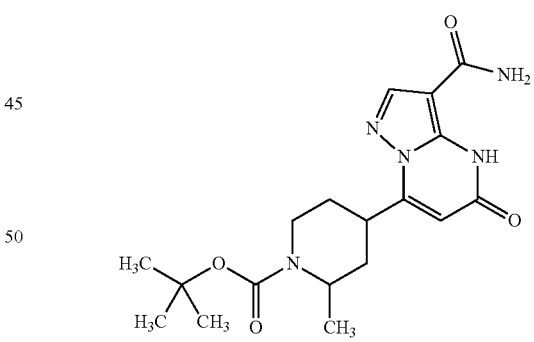

The title compound was prepared according to General Procedure 1A starting from 164 mg (1.27 mmol) 3-amino-1H-pyrazole-4-carboxamide and 500 mg (1.27 mmol) (−)-cis-tert-butyl 4-[(2,2-dimethyl-4,6-dioxo-1,3-dioxan-5-yl)carbonyl]-2-methylpiperidine-1-carboxylate.

Work-up: the mixture was evaporated and the crude product was treated with water and extracted with ethyl acetate. After separation of the phases a yellow solid precipitated in the aqueous phase which was filtered off. The aqueous phase was neutralized with HCl 1H until pH 6 was achieved and then extracted with ethyl acetate. The collected organic layers were dried over sodium sulfate, filtered, evaporated and dried under vacuo. After reaction epimerization was observed obtaining a mixture of diastereomers which were separated by Method 1C to yield the title compound (120 mg, 25% of theory).

LC-MS (Method 1B): R$_t$=0.82 min, MS (ESIPos): m/z=376 [M+H]$^+$

HPLC (Method 1E): R$_t$=8.28 min

Example 65A

Tert-butyl 4-[3-(3-fluorophenyl)-5-oxo-4,5-dihydropyrazolo[1,5-a]pyrimidin-7-yl]piperidine-1-carboxylate

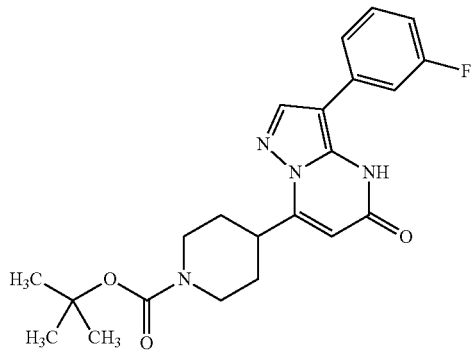 [SMILES: CC(C)(C)OC(=O)N1CCC(c2cc(=O)[nH]c3c(-c4cccc(F)c4)cnn23)CC1]

Following the General Procedure 2A, a mixture of (3-fluorophenyl) boronic acid (79 mg, 0.57 mmol), tert-butyl 4-(3-bromo-5-oxo-4,5-dihydropyrazolo[1,5-a]pyrimidin-7-yl)piperidine-1-carboxylate (150 mg, 0.38 mmol), XPhos precatalyst (32 mg, 0.04 mmol), degassed THF (3 ml) and degassed aqueous 1M K$_3$PO$_4$ solution (1.1 ml) were stirred at 80° C. for 16 h. Yield: 20 mg, 13% of theory.

LC-MS (Method 1B): R$_t$=1.09 min, MS (ESINeg): m/z=411 [M−H]$^−$

Example 66A

Tert-butyl 4-[3-(4-methoxyphenyl)-5-oxo-4,5-dihydropyrazolo[1,5-a]pyrimidin-7-yl]piperidine-1-carboxylate

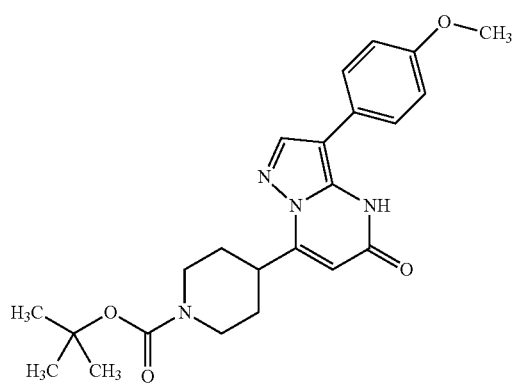 [SMILES: COc1ccc(-c2cnn3c(C4CCN(C(=O)OC(C)(C)C)CC4)cc(=O)[nH]c23)cc1]

Following the General Procedure 2A, a mixture of (4-methoxyphenyl)boronic acid (86 mg, 0.57 mmol), tert-butyl 4-(3-bromo-5-oxo-4,5-dihydropyrazolo[1,5-a]pyrimidin-7-yl)piperidine-1-carboxylate (150 mg, 0.38 mmol), XPhos precatalyst (32 mg, 0.04 mmol), degassed THF (3 ml) and degassed aqueous 1M K$_3$PO$_4$ solution (1.1 ml) were stirred at 80° C. for 16 h. Yield: 18 mg, 9% of theory.

LC-MS (Method 1B): R$_t$=1.09 min, MS (ESINeg): m/z=423 [M−H]$^−$

Example 67A

Tert-butyl 4-[3-(3,4-dimethoxyphenyl)-5-oxo-4,5-dihydropyrazolo[1,5-a]pyrimidin-7-yl]piperidine-1-carboxylate

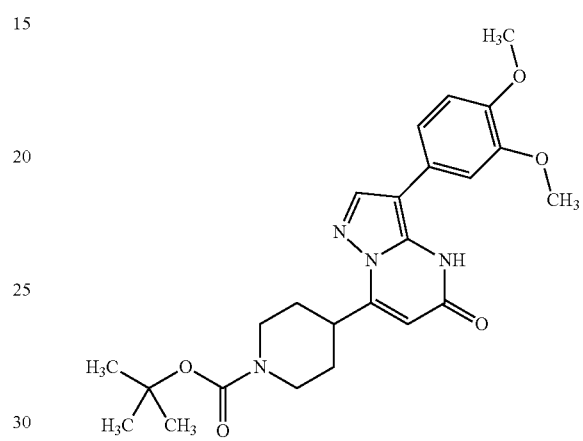

Following the General Procedure 2A, a mixture of (3,4-dimethoxyphenyl)boronic acid (103 mg, 0.57 mmol), tert-butyl 4-(3-bromo-5-oxo-4,5-dihydropyrazolo[1,5-a]pyrimidin-7-yl)piperidine-1-carboxylate (150 mg, 0.38 mmol), XPhos precatalyst (32 mg, 37.76 mmol), degassed THF (3 ml) and degassed aqueous 1M K$_3$PO$_4$ solution (1.1 ml) were stirred at 80° C. for 48 h. Yield: 30 mg, 18% of theory.

LC-MS (Method 1B): R$_t$=1.04 min, MS (ESINeg): m/z=453 [M−H]$^−$

Example 68A

Tert-butyl 4-{3-[4-(methylsulfonyl)phenyl]-5-oxo-4,5-dihydropyrazolo[1,5-a]pyrimidin-7-yl}piperidine-1-carboxylate

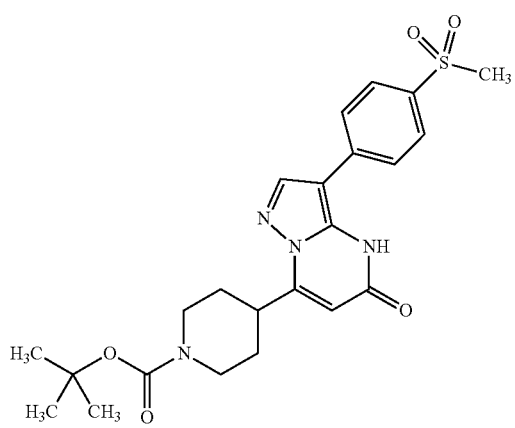 [SMILES: CC(C)(C)OC(=O)N1CCC(c2cc(=O)[nH]c3c(-c4ccc(S(C)(=O)=O)cc4)cnn23)CC1]

Following the General Procedure 2A, a mixture of 2[4-(methylsulfonyl)phenyl]boronic acid (150 mg, 0.38 mmol), tert-butyl 4-(3-bromo-5-oxo-4,5-dihydropyrazolo[1,5-a]pyrimidin-7-yl)piperidine-1-carboxylate (150 mg, 0.38 mmol), XPhos precatalyst (32 mg, 37.76 mmol), degassed THF (3 ml) and degassed aqueous 1M K₃PO₄ solution (1.1 ml) were stirred at 80° C. for 48 h. Yield: 54 mg, 22% of theory.

LC-MS (Method 1B): $R_t$=0.97 min, MS (ESINeg): m/z=471 [M–H]⁻

Example 69A

Tert-butyl 4-[3-(2-fluorophenyl)-5-oxo-4,5-dihydropyrazolo[1,5-a]pyrimidin-7-yl]piperidine-1-carboxylate

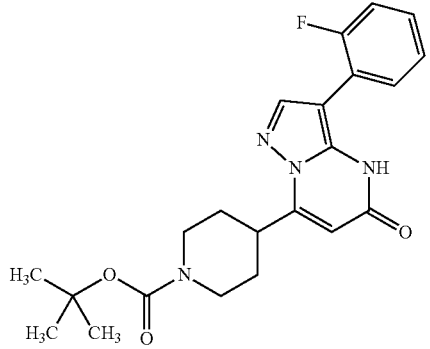 [SMILES: CC(C)(C)OC(=O)N1CCC(c2cc(=O)[nH]c3c(-c4ccccc4F)cnn23)CC1]

Following the General Procedure 2A, a mixture of (2-fluorophenyl) boronic acid (79 mg, 0.57 mmol), tert-butyl 4-(3-bromo-5-oxo-4,5-dihydropyrazolo[1,5-a]pyrimidin-7-yl)piperidine-1-carboxylate (150 mg, 0.38 mmol), XPhos precatalyst (32 mg, 0.04 mmol), degassed THF (3 ml) and degassed aqueous 1M K₃PO₄ solution (1.1 ml) were stirred at 80° C. for 16 h. Yield: 15 mg, 22% of theory.

LC-MS (Method 1B): $R_t$=1.10 min, MS (ESINeg): m/z=411 [M–H]⁻

Example 70A

Tert-butyl 4-{5-oxo-3-[3-(trifluoromethyl)phenyl]-4,5-dihydropyrazolo[1,5-a]pyrimidin-7-yl}piperidine-1-carboxylate

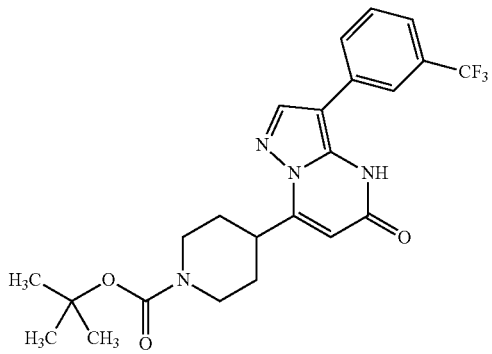 [SMILES: CC(C)(C)OC(=O)N1CCC(c2cc(=O)[nH]c3c(-c4cccc(C(F)(F)F)c4)cnn23)CC1]

Following the General Procedure 2A, a mixture of [3-(trifluoromethyl)phenyl]boronic acid (107 mg, 0.57 mmol), tert-butyl 4-(3-bromo-5-oxo-4,5-dihydropyrazolo[1,5-a]pyrimidin-7-yl)piperidine-1-carboxylate (150 mg, 0.38 mmol), XPhos precatalyst (32 mg, 0.04 mmol), degassed THF (3 ml) and degassed aqueous 1M K₃PO₄ solution (1.1 ml) were stirred at 80° C. for 16 h. Yield: 71 mg, 41% of theory.

LC-MS (Method 1B): $R_t$=1.19 min, MS (ESINeg): m/z=461 [M–H]⁻

Example 71A

Tert-butyl 4-{5-oxo-3-[4-(trifluoromethyl)phenyl]-4,5-dihydropyrazolo[1,5-a]pyrimidin-7-yl}piperidine-1-carboxylate

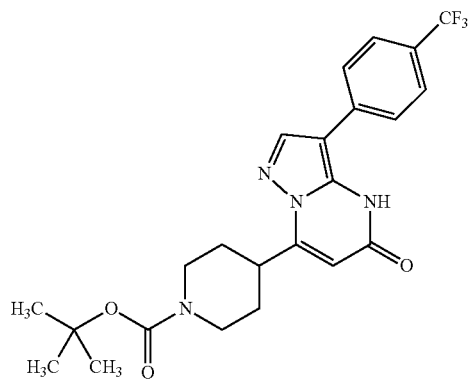 [SMILES: CC(C)(C)OC(=O)N1CCC(c2cc(=O)[nH]c3c(-c4ccc(C(F)(F)F)cc4)cnn23)CC1]

Following the General Procedure 2A, a mixture of [4-(trifluoromethyl)phenyl]boronic acid (107 mg, 0.57 mmol), tert-butyl 4-(3-bromo-5-oxo-4,5-dihydropyrazolo[1,5-a]pyrimidin-7-yl)piperidine-1-carboxylate (150 mg, 0.38 mmol), XPhos precatalyst (32 mg, 0.04 mmol), degassed THF (3 ml) and degassed aqueous 1M K₃PO₄ solution (1.1 ml) were stirred at 80° C. for 16 h. Yield: 42 mg, 22% of theory.

LC-MS (Method 1B): $R_t$=1.19 min, MS (ESINeg): m/z=461 [M–H]⁻

Example 72A

Tert-butyl 4-[5-oxo-3-(2-thienyl)-4,5-dihydropyrazolo[1,5-a]pyrimidin-7-yl]piperidine-1-carboxylate

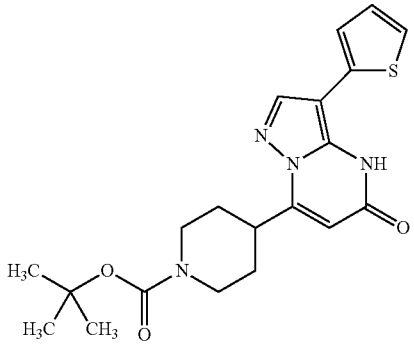 [SMILES: CC(C)(C)OC(=O)N1CCC(c2cc(=O)[nH]c3c(-c4cccs4)cnn23)CC1]

Following the General Procedure 2A, a mixture of 2-thienylboronic acid (72 mg, 0.57 mmol), tert-butyl 4-(3-bromo-5-oxo-4,5-dihydropyrazolo[1,5-a]pyrimidin-7-yl)piperidine-1-carboxylate (150 mg, 0.38 mmol), XPhos precatalyst (32 mg, 0.04 mmol), degassed THF (3 ml) and degassed aqueous 1M K₃PO₄ solution (1.1 ml) were stirred at 80° C. for 24 h. Yield: 26 mg, 15% of theory.

LC-MS (Method 1B): $R_t$=1.06 min, MS (ESIPos): m/z=401 [M+H]⁺

Example 73A

Tert-butyl 4-[3-(3-methoxyphenyl)-5-oxo-4,5-dihydropyrazolo[1,5-a]pyrimidin-7-yl]piperidine-1-carboxylate

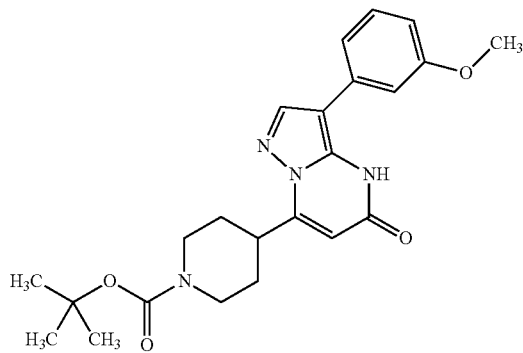 [SMILES: COc1cccc(-c2cnn3c(C4CCN(C(=O)OC(C)(C)C)CC4)cc(=O)[nH]c23)c1]

Following the General Procedure 2A, a mixture of (3-methoxyphenyl)boronic acid (86 mg, 0.57 mmol), tert-butyl 4-(3-bromo-5-oxo-4,5-dihydropyrazolo[1,5-a]pyrimidin-7-yl)piperidine-1-carboxylate (150 mg, 0.38 mmol), XPhos precatalyst (32 mg, 0.04 mmol), degassed THF (3 ml) and degassed aqueous 1M K₃PO₄ solution (1.1 ml) were stirred at 80° C. for 24 h. Yield: 40 mg, 24% of theory.

LC-MS (Method 1B): $R_t$=1.08 min, MS (ESINeg): m/z=424 [M–H]⁻

Example 74A

Tert-butyl 4-[3-(2,3-dihydro-1,4-benzodioxin-6-yl)-5-oxo-4,5-dihydropyrazolo[1,5-a]pyrimidin-7-yl]piperidine-1-carboxylate

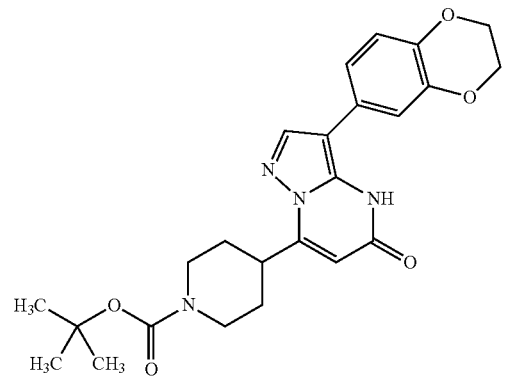 [SMILES: CC(C)(C)OC(=O)N1CCC(c2cc(=O)[nH]c3c(-c4ccc5c(c4)OCCO5)cnn23)CC1]

Following the General Procedure 2A, a mixture of 2,3-dihydro-1,4-benzodioxin-6-ylboronic acid (101 mg, 0.57 mmol), tert-butyl 4-(3-bromo-5-oxo-4,5-dihydropyrazolo[1,5-a]pyrimidin-7-yl)piperidine-1-carboxylate (150 mg, 0.38 mmol), XPhos precatalyst (32 mg, 0.04 mmol), degassed THF (3 ml) and degassed aqueous 1M K₃PO₄ solution (1.1 ml) were stirred at 80° C. for 48 h. Yield: 13 mg, 7% of theory.

LC-MS (Method 1B): $R_t$=1.08 min, MS (ESINeg): m/z=451 [M–H]⁻

Example 75A

Tert-butyl 4-[3-(2,5-dimethoxyphenyl)-5-oxo-4,5-dihydropyrazolo[1,5-a]pyrimidin-7-yl]piperidine-1-carboxylate

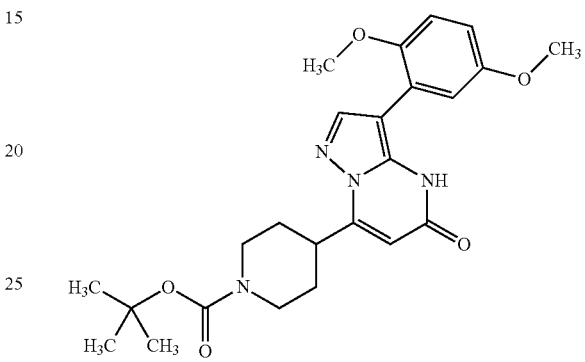

Following the General Procedure 2A, a mixture of 2 (2,5-dimethoxyphenyl)boronic acid (103 mg, 0.57 mmol), tert-butyl 4-(3-bromo-5-oxo-4,5-dihydropyrazolo[1,5-a]pyrimidin-7-yl)piperidine-1-carboxylate (150 mg, 0.38 mmol), XPhos precatalyst (32 mg, 0.04 mmol), degassed THF (3 ml) and degassed aqueous 1M K₃PO₄ solution (1.1 ml) were stirred at 80° C. for 48 h. Yield: 22 mg, 11% of theory.

LC-MS (Method 1B): $R_t$=1.12 min, MS (ESINeg): m/z=453 [M–H]⁻

Example 76A

Tert-butyl 4-{5-oxo-3-[2-(trifluoromethyl)phenyl]-4,5-dihydropyrazolo[1,5-a]pyrimidin-7-yl}piperidine-1-carboxylate

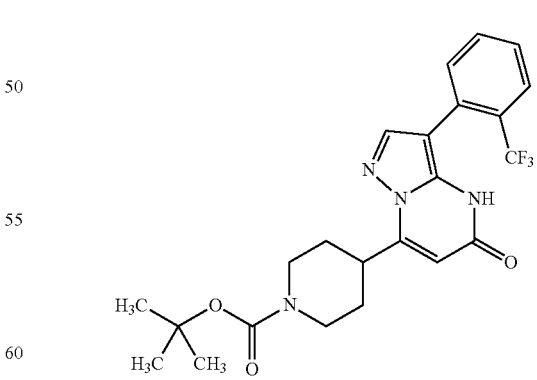

Following the General Procedure 2A, a mixture of [2-(trifluoromethyl)phenyl]boronic acid (107 mg, 0.57 mmol), tert-butyl 4-(3-bromo-5-oxo-4,5-dihydropyrazolo[1,5-a]pyrimidin-7-yl)piperidine-1-carboxylate (150 mg, 0.38 mmol), XPhos precatalyst (32 mg, 0.04 mmol), degassed THF (3 ml) and degassed aqueous 1M $K_3PO_4$ solution (1.1 ml) were stirred at 80° C. for 64 h. Yield: 16 mg, 24% of theory.

LC-MS (Method 1B): $R_t$=1.16 min, MS (ESINeg): m/z=461 [M−H]⁻

Example 77A

Tert-butyl 4-[3-(4-fluorophenyl)-5-oxo-2-phenyl-4,5-dihydropyrazolo[1,5-a]pyrimidin-7-yl]piperidine-1-carboxylate

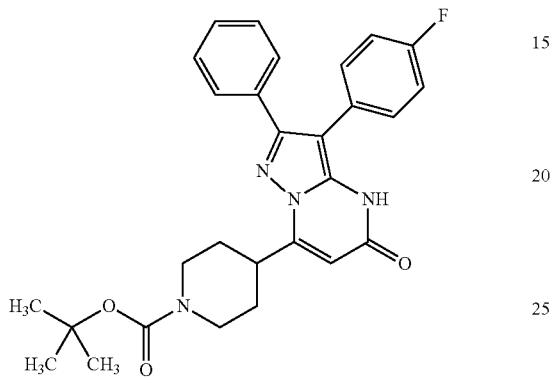

Following the General Procedure 2A, a mixture of (4-fluorophenyl)boronic acid (66 mg, 0.48 mmol), tert-butyl 4-(3-bromo-5-oxo-4,5-dihydropyrazolo[1,5-a]pyrimidin-7-yl)piperidine-1-carboxylate (150 mg, 0.38 mmol), XPhos precatalyst (26 mg, 0.03 mmol), degassed THF (2.5 ml) and degassed aqueous 1M $K_3PO_4$ solution (0.95 ml) were stirred at 80° C. for 16 h. Yield: 36 mg, 24% of theory.

LC-MS (Method 1B): $R_t$=0.70 min, MS (ESIPos): m/z=387 [M−H-boc]⁻

Example 78A

Tert-butyl 4-(3-cyano-5-oxo-4,5-dihydropyrazolo[1,5-a]pyrimidin-7-yl)-2-methylpiperidine-1-carboxylate [enantiomerically pure trans-Isomer]

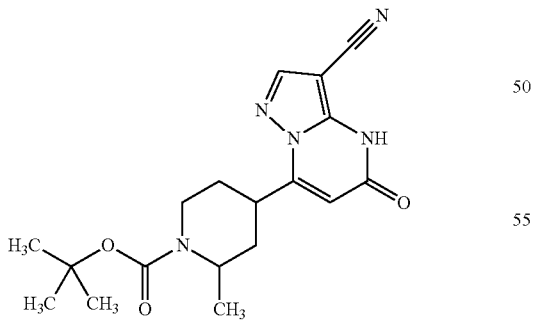

The title compound was prepared according to General Procedure 1A starting from 141 mg (1.27 mmol) 3-amino-1H-pyrazole-4-carbonitrile and 500 mg (1.27 mmol) (−)-cis-tert-butyl 4-[(2,2-dimethyl-4,6-dioxo-1,3-dioxan-5-yl)carbonyl]-2-methylpiperidine-1-carboxylate.

Work-up: the mixture was evaporated and the crude product was treated with water and extracted with ethyl acetate. The aqueous phase was neutralized with HCl 1H until pH 5 was achieved and then extracted with ethyl acetate. The collected organic layers were dried over sodium sulfate, filtered, evaporated and dried under vacuo. After reaction epimerization was observed obtaining a mixture of diastereomers which were separated by Method 2C to yield the title compound (207 mg, 46% of theory).

LC-MS (Method 1B): $R_t$=0.95 min, MS (ESINeg): m/z=356 [M−H]⁻

HPLC (Method 2E): $R_t$=8.68 min

Example 79A

Tert-butyl 4-[3-(4-methyl-2-thienyl)-5-oxo-4,5-dihydropyrazolo[1,5-a]pyrimidin-7-yl]piperidine-1-carboxylate

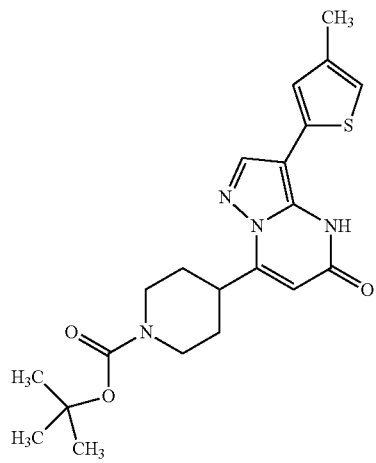 [SMILES: Cc1csc(-c2cnn3c(C4CCN(C(=O)OC(C)(C)C)CC4)cc(=O)[nH]c23)c1]

Following the General Procedure 2A, a mixture of (4-methyl-2-thienyl)boronic acid (80 mg, 0.57 mmol), tert-butyl 4-(3-bromo-5-oxo-4,5-dihydropyrazolo[1,5-a]pyrimidin-7-yl)piperidine-1-carboxylate (150 mg, 0.38 mmol), XPhos precatalyst (32 mg, 0.04 mmol), degassed THF (3.0 ml) and degassed aqueous 1M $K_3PO_4$ solution (1.13 ml) were stirred at 80° C. for 3 days. Yield: 27 mg, 17% of theory.

LC-MS (Method 1B): $R_t$=1.14 min, MS (ESIPos): m/z=415 [M+H]⁺

Example 80A

Tert-butyl 4-[3-(2-methoxyphenyl)-5-oxo-4,5-dihydropyrazolo[1,5-a]pyrimidin-7-yl]piperidine-1-carboxylate

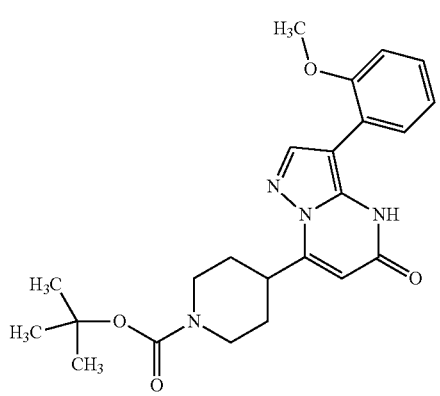 [SMILES: COc1ccccc1-c1cnn2c(C3CCN(C(=O)OC(C)(C)C)CC3)cc(=O)[nH]c12]

Following the General Procedure 2A, a mixture of (2-methoxyphenyl)boronic acid (86 mg, 0.57 mmol), tert-butyl 4-(3-bromo-5-oxo-4,5-dihydropyrazolo[1,5-a]pyrimidin-7-yl)piperidine-1-carboxylate (150 mg, 0.38 mmol), XPhos precatalyst (32 mg, 0.04 mmol), degassed THF (3.0 ml) and degassed aqueous 1M K$_3$PO$_4$ solution (1.13 ml) were stirred at 80° C. for 3 days. Yield: 46 mg, 26% of theory.

LC-MS (Method 1B): R$_t$=1.09 min, MS (ESINeg): m/z=424 [M−H]$^-$

Example 81A

Tert-butyl 4-[3-(4-cyano-2-thienyl)-5-oxo-4,5-dihydropyrazolo[1,5-a]pyrimidin-7-yl]piperidine-1-carboxylate

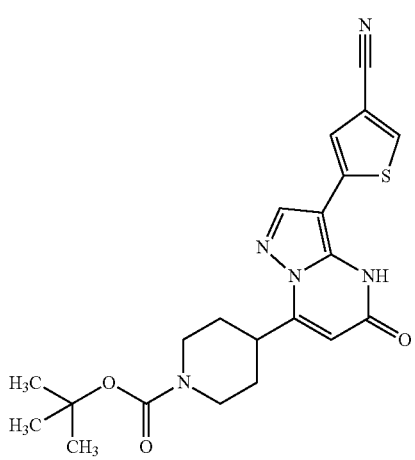 [SMILES: CC(C)(C)OC(=O)N1CCC(c2cc(=O)[nH]c3c(-c4cc(C#N)cs4)cnn23)CC1]

Following the General Procedure 2A, a mixture of (4-cyano-2-thienyl)boronic acid (86 mg, 0.57 mmol), tert-butyl 4-(3-bromo-5-oxo-4,5-dihydropyrazolo[1,5-a]pyrimidin-7-yl)piperidine-1-carboxylate (150 mg, 0.38 mmol), XPhos precatalyst (32 mg, 0.04 mmol), degassed THF (3.0 ml) and degassed aqueous 1M K$_3$PO$_4$ solution (1.13 ml) were stirred at 80° C. for 24 h. Yield: 4 mg, 3% of theory.

LC-MS (Method 1B): R$_t$=1.05 min, MS (ESINeg): m/z=424 [M−H]$^-$

Example 82A

Tert-butyl 4-[3-(6-methoxypyridin-3-yl)-5-oxo-4,5-dihydropyrazolo[1,5-a]pyrimidin-7-yl]piperidine-1-carboxylate

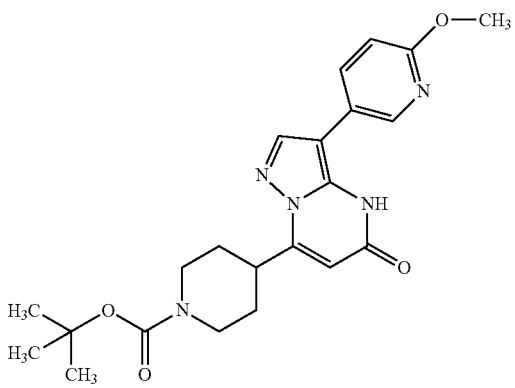 [SMILES: COc1ccc(-c2cnn3c(C4CCN(C(=O)OC(C)(C)C)CC4)cc(=O)[nH]c23)cn1]

Following the General Procedure 2A, a mixture of (6-methoxypyridin-3-yl)boronic acid (86 mg, 0.57 mmol), tert-butyl 4-(3-bromo-5-oxo-4,5-dihydropyrazolo[1,5-a]pyrimidin-7-yl)piperidine-1-carboxylate (150 mg, 0.38 mmol), XPhos precatalyst (32 mg, 0.04 mmol), degassed THF (3.0 ml) and degassed aqueous 1M K$_3$PO$_4$ solution (1.13 ml) were stirred at 80° C. for one day. Yield: 43 mg, 27% of theory.

LC-MS (Method 1B): R$_t$=0.99 min, MS (ESIPos): m/z=426 [M+H]$^+$

Example 83A

Tert-butyl 4-{5-oxo-3-[3-(trifluoromethoxy)phenyl]-4,5-dihydropyrazolo[1,5-a]pyrimidin-7-yl}piperidine-1-carboxylate

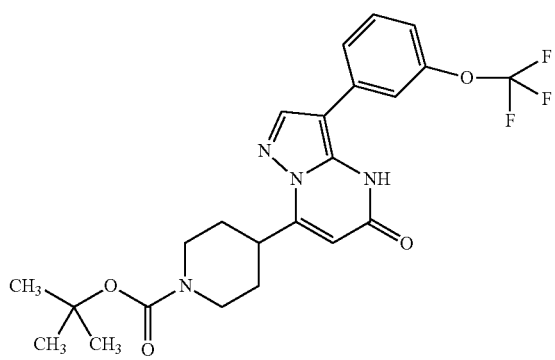 [SMILES: CC(C)(C)OC(=O)N1CCC(c2cc(=O)[nH]c3c(-c4cccc(OC(F)(F)F)c4)cnn23)CC1]

Following the General Procedure 2A, a mixture of [3-(trifluoromethoxy)phenyl]boronic acid (116 mg, 0.57 mmol), tert-butyl 4-(3-bromo-5-oxo-4,5-dihydropyrazolo[1,5-a]pyrimidin-7-yl)piperidine-1-carboxylate (150 mg, 0.38 mmol), XPhos precatalyst (32 mg, 0.04 mmol), degassed THF (3.0 ml) and degassed aqueous 1M K₃PO₄ solution (1.13 ml) were stirred at 80° C. for 16 h. Yield: 48 mg, 26% of theory.

LC-MS (Method 1B): $R_t$=1.22 min, MS (ESIPos): m/z=479 [M+H]⁺

Example 84A

Tert-butyl 4-{5-oxo-3-[2-(trifluoromethoxy)phenyl]-4,5-dihydropyrazolo[1,5-a]pyrimidin-7-yl}piperidine-1-carboxylate

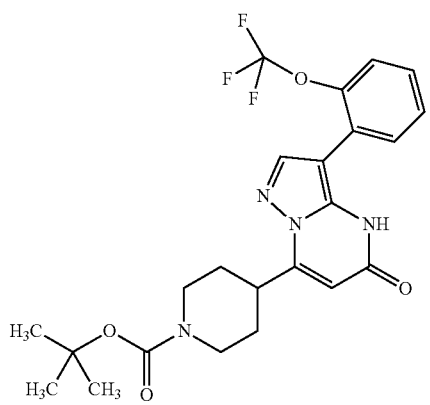 [SMILES: CC(C)(C)OC(=O)N1CCC(c2cc(=O)[nH]c3c(-c4ccccc4OC(F)(F)F)cnn23)CC1]

Following the General Procedure 2A, a mixture of [2-(trifluoromethoxy)phenyl]boronic acid (116 mg, 0.57 mmol), tert-butyl 4-(3-bromo-5-oxo-4,5-dihydropyrazolo[1,5-a]pyrimidin-7-yl)piperidine-1-carboxylate (150 mg, 0.38 mmol), XPhos precatalyst (32 mg, 0.04 mmol), degassed THF (3.0 ml) and degassed aqueous 1M K₃PO₄ solution (1.13 ml) were stirred at 80° C. for 16 h. Yield: 49 mg, 27% of theory.

LC-MS (Method 1B): $R_t$=1.17 min, MS (ESINeg): m/z=477 [M−H]⁻

Example 85A

Tert-butyl 4-[3-(3-chloro-4-fluorophenyl)-5-oxo-4,5-dihydropyrazolo[1,5-a]pyrimidin-7-yl]piperidine-1-carboxylate

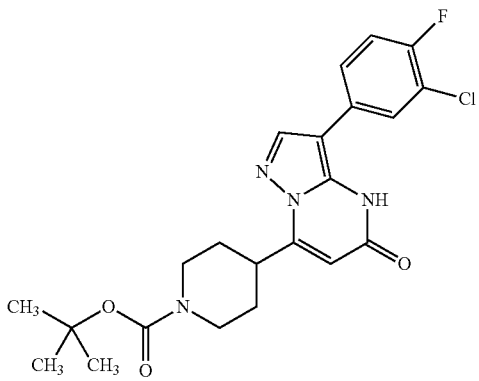 [SMILES: CC(C)(C)OC(=O)N1CCC(c2cc(=O)[nH]c3c(-c4ccc(F)c(Cl)c4)cnn23)CC1]

Following the General Procedure 2A, a mixture of (3-chloro-4-fluorophenyl)boronic acid (98 mg, 0.57 mmol), tert-butyl 4-(3-bromo-5-oxo-4,5-dihydropyrazolo[1,5-a]pyrimidin-7-yl)piperidine-1-carboxylate (150 mg, 0.38 mmol), XPhos precatalyst (32 mg, 0.04 mmol), degassed THF (3.0 ml) and degassed aqueous 1M K₃PO₄ solution (1.13 ml) were stirred overnight at 80° C. Yield: 34 mg, 20% of theory.

LC-MS (Method 1B): $R_t$=1.17 min, MS (ESINeg): m/z=445 [M−H]⁻

Example 86A 3-(Dimethylamino)-2-(phenylsulfonyl)acrylonitrile

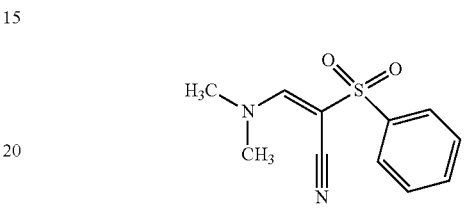

N,N-Dimethylformamide dimethyl acetal (1.84 g, 15.5 mmol) in n-hexane (8 mL) was added to (Phenylsulfonyl)acetonitrile (2.00 g, 11.0 mmol) at 0° C. and the mixture was stirred at RT for 16 h. The resulting solid was filtered, washed with n-pentane and dried to afford the title compound in 92% purity (2.49 g, 87% of theory).

LC-MS (Method 1B): $R_t$=0.73 min, MS (ESIPos): m/z=237 [M+H]⁺

Example 87A 4-(Phenylsulfonyl)-1H-pyrazol-3-amine

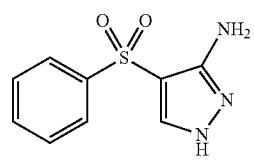 [SMILES: Nc1n[nH]cc1S(=O)(=O)c1ccccc1]

3-(Dimethylamino)-2-(phenylsulfonyl)acrylonitrile (2.48 g, 10.50 mmol) was dissolved in ethanol (20 mL) and treated with hydrazine hydrate (0.55 g, 11.0 mmol). After stirring at 50° C. for 8 h, the mixture was cooled to RT and concentrated in vacuo. The residue was dissolved in a mixture of water and ethyl acetate. The aqueous layer was extracted once more with ethyl acetate. The combined organic layers were washed twice with water, dried over magnesium sulfate, concentrated in vacuo and purified via column chromatography (ethyl acetate) to yield the title compound (1.02 g, 43% of theory).

LC-MS (Method 2B): $R_t$=0.56 min, MS (ESIPos): m/z=224 [M+H]⁺

Example 88A

Tert-butyl 4-[5-oxo-3-(phenylsulfonyl)-4,5-dihydro-pyrazolo[1,5-a]pyrimidin-7-yl]piperidine-1-carboxylate

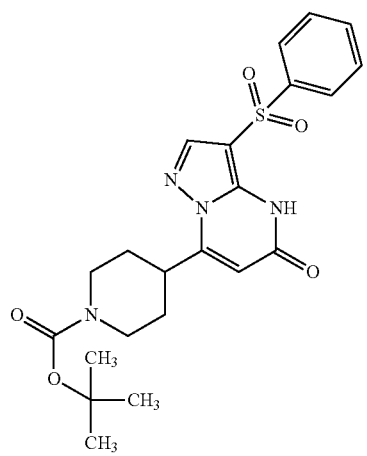 [SMILES: CC(C)(C)OC(=O)N1CCC(c2cc(=O)[nH]c3c(S(=O)(=O)c4ccccc4)cnn23)CC1]

4-(Phenylsulfonyl)-1H-pyrazol-3-amine (1.01 g, 4.52 mmol) and tert-butyl 4-[(2,2-dimethyl-4,6-dioxo-1,3-dioxan-5-yl)carbonyl]piperidine-1-carboxylate (1.61 g, 4.52 mmol) were dissolved in acetonitrile (20 mL) and refluxed for 4 h. After cooling to RT, the solvent was removed in vacuo and the residue was dissolved in 1-methoxy-2-propanol (10 mL). Potassium phosphate (1.92 g, 9.04 mmol) was added and the mixture was stirred at 80° C. for 4 h and at 100° C. for 2 h. Concentration in vacuo and purification by preparative HPLC (Method 1A) afforded the title compound (0.82 g, 39% of theory).

LC-MS (Method 1B): $R_t$=1.04 min, MS (ESINeg): m/z=457 [M−H]⁻

Example 89A

2-[(2,4-dichlorophenyl)sulfonyl]-3-(dimethylamino)acrylonitrile

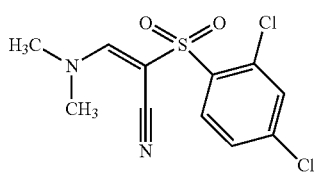 [SMILES: CN(C)/C=C(\C#N)S(=O)(=O)c1ccc(Cl)cc1Cl]

N,N-Dimethylformamide dimethyl acetal (0.67 g, 5.60 mmol) in n-hexane (5 mL) was added to [(2,4-dichlorophenyl)sulfonyl]acetonitrile (1.00 g, 4.00 mmol) at 0° C. and the mixture was stirred at RT for 16 h. The resulting solid was filtered, washed with n-pentane and dried to afford the title compound (1.15 g, 94% of theory).

LC-MS (Method 1B): $R_t$=0.96 min, MS (ESIPos): m/z=305 [M+H]⁺

Example 90A

4-[(2,4-Dichlorophenyl)sulfonyl]-1H-pyrazol-3-amine

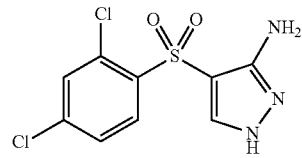 [SMILES: Nc1n[nH]cc1S(=O)(=O)c1ccc(Cl)cc1Cl]

2-[(2,4-Dichlorophenyl)sulfonyl]-3-(dimethylamino)acrylonitrile (1.15 g, 3.77 mmol) was dissolved in ethanol (10 mL) and treated with hydrazine hydrate (0.20 g, 3.96 mmol). After stirring at 50° C. for 8 h, the mixture was cooled to RT and concentrated in vacuo. The residue was dissolved in a mixture of water and ethyl acetate. The aqueous layer was extracted once more with ethyl acetate. The combined organic layers were washed twice with water, dried over magnesium sulfate, concentrated in vacuo and purified via column chromatography (ethyl acetate) to yield the title compound (0.93 g, 51% of theory) in 60% purity.

LC-MS (Method 1B): $R_t$=0.81 min, MS (ESIPos): m/z=292 [M+H]⁺

Example 91A

Tert-butyl 4-{3-[(2,4-dichlorophenyl)sulfonyl]-5-oxo-4,5-dihydropyrazolo[1,5-a]pyrimidin-7-yl}piperidine-1-carboxylate

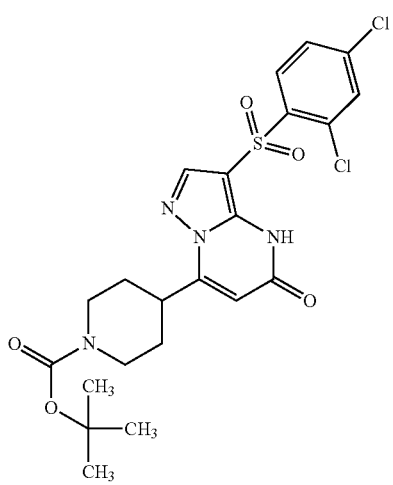 [SMILES: CC(C)(C)OC(=O)N1CCC(c2cc(=O)[nH]c3c(S(=O)(=O)c4ccc(Cl)cc4Cl)cnn23)CC1]

4-[(2,4-Dichlorophenyl)sulfonyl]-1H-pyrazol-3-amine (60% purity, 0.93 g, 3.18 mmol) and tert-butyl 4-[(2,2-dimethyl-4,6-dioxo-1,3-dioxan-5-yl)carbonyl]piperidine-1-carboxylate (1.13 g, 3.18 mmol) were dissolved in acetonitrile (15 mL) and refluxed for 4 h. After cooling to RT, the solvent was removed in vacuo and the residue was dissolved in 1-methoxy-2-propanol (10 mL). Potassium phosphate (1.63 g, 7.66 mmol) was added and the mixture was stirred at reflux for 4 h. Concentration in vacuo and purification by preparative HPLC (Method 1A) afforded the title compound (0.62 g, 31% of theory).

LC-MS (Method 1B): $R_t$=1.20 min, MS (ESINeg): m/z=525 [M−H]⁻

Example 92A

N'-hydroxy-2,4-dimethylbenzenecarboximidamide

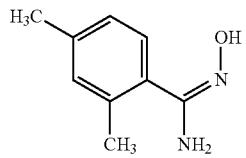

To a solution of 2,4-dimethylbenzonitrile (300 mg, 2.29 mmol) in 10 ml ethanol was added hydroxylammonium chloride (238 mg, 3.43 mmol) and triethylamine (301 mg, 2.97 mmol) and then the reaction mixture was stirred overnight at 50° C. After this time hydroxylammonium chloride (79 mg, 1.14 mmol) and triethylamine (116 mg, 1.14 mmol) were added again and the mixture was stirred 6 h at 60° C. Then the mixture was stirred at the microwave during 1.5 h at 60° C. After cooling to RT, the solvent was evaporated and the crude was solved in ethyl acetate and extracted with water and brine solution. The organic phase was dried over magnesium sulfate, filtered and evaporated under vacuum to yield the title compound (157 mg, 26% of theory, purity 60%). The compound was used without further purification.

LC-MS (method 2B): RT=1.57 min, m/z=165 (M+H)⁺

Example 93A

N'-hydroxy-4-methyl-2-(trifluoromethyl)benzenecarboximidamide

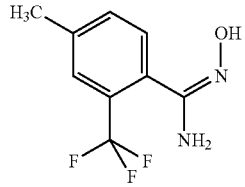

To a solution of 4-methyl-2-(trifluoromethyl)benzonitrile (300 mg, 1.62 mmol) in 10 ml ethanol was added hydroxylammonium chloride (169 mg, 2.43 mmol) and triethylamine (213 mg, 2.11 mmol) and then the reaction mixture was stirred overnight at 50° C. and then 3 h at 90° C. After cooling to RT, the solvent was evaporated and the crude was solved in ethyl acetate and extracted with water and brine solution. The organic phase was dried over magnesium sulfate, filtered and evaporated under vacuum to yield the title compound (250 mg, 46% of theory, purity 65%). The compound was used without further purification.

LC-MS (method 2B): RT=1.75 min, m/z=219 (M+H)⁺

Example 94A

2-Chloro-N'-hydroxy-4-methylbenzenecarboximidamide

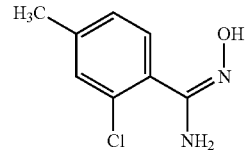

To a solution of 2-chloro-4-methylbenzonitrile (300 mg, 1.98 mmol) in 10 ml ethanol was added hydroxylammonium chloride (206 mg, 2.97 mmol) and triethylamine (260 mg, 2.57 mmol) and then the reaction mixture was stirred overnight at 50° C. After cooling to RT, the solvent was evaporated and the crude was solved in ethyl acetate and extracted with water and brine solution. The organic phase was dried over magnesium sulfate, filtered and evaporated under vacuum to yield the title compound (224 mg, 29% of theory, purity 48%). The compound was used without further purification.

LC-MS (method 2B): RT=1.64 min, m/z=185 (M+H)⁺

Example 95A

2-Fluoro-N'-hydroxy-4-methylbenzenecarboximidamide

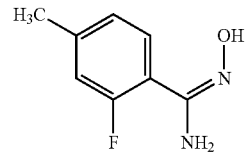

To a solution of 2-fluoro-4-methylbenzonitrile (300 mg, 2.22 mmol) in 10 ml ethanol was added hydroxylammonium chloride (231 mg, 3.33 mmol) and triethylamine (292 mg, 2.89 mmol) and then the reaction mixture was stirred overnight at 50° C. After cooling to RT, the solvent was evaporated and the crude was solved in ethyl acetate and extracted with water and brine solution. The organic phase was dried over magnesium sulfate, filtered and evaporated under vacuum to yield the title compound (268 mg, 66% of theory, purity 92%). The compound was used without further purification.

LC-MS (method 2B): RT=1.52 min, m/z=169 (M+H)⁺

Example 96A

3-Chloro-2-fluoro-N'-hydroxybenzenecarboximidamide

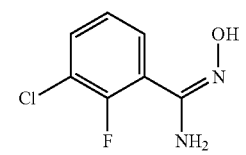

To a solution of 3-chloro-2-fluorobenzonitrile (1 g, 6.43 mmol) in 32 ml ethanol was added hydroxylammonium chloride (670 mg, 9.64 mmol) and triethylamine (846 mg, 8.36 mmol) and then the reaction mixture was stirred 3.5 h at 50° C. After cooling to RT, the solvent was evaporated and the crude was solved in ethyl acetate and extracted with water and brine solution. The organic phase was dried over magnesium sulfate, filtered and evaporated under vacuum to yield the title compound (1.29 g, 100% of theory).

LC-MS (method 2B): RT=1.65 min, m/z=189 (M+H)$^+$

Example 97A

3-Fluoro-N'-hydroxy-4-(trifluoromethyl)benzenecarboximidamide

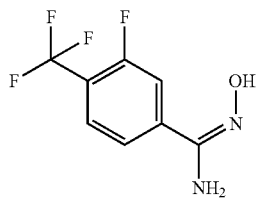

To a solution of 3-fluoro-4-(trifluoromethyl)benzonitrile (500 mg, 2.64 mmol) in 13 ml ethanol was added hydroxylammonium chloride (276 mg, 3.96 mmol) and triethylamine (348 mg, 3.44 mmol) and then the reaction mixture was stirred 3.5 h at 50° C. After cooling to RT, the solvent was evaporated and the crude was solved in ethyl acetate and extracted with water and brine solution. The organic phase was dried over magnesium sulfate, filtered and evaporated under vacuum to yield the title compound (603 mg, 93% of theory, purity 91%). The compound was used without further purification.

LC-MS (method 1B): RT=0.72 min, m/z=223 (M+H)$^+$

Example 98A

2-Fluoro-N'-hydroxy-4-(trifluoromethyl)benzenecarboximidamide

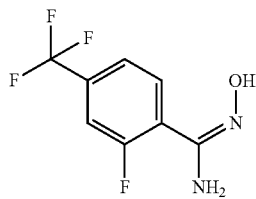

To a solution of 2-fluoro-4-(trifluoromethyl)benzonitrile (500 mg, 2.64 mmol) in 13 ml ethanol was added hydroxylammonium chloride (275 mg, 3.96 mmol) and triethylamine (348 mg, 3.44 mmol) and then the reaction mixture was stirred 13 h at 50° C. After cooling to RT, the solvent was evaporated and the crude was solved in ethyl acetate and extracted with water and brine solution. The organic phase was dried over magnesium sulfate, filtered and evaporated under vacuum to yield the title compound (525 mg, 82% of theory, purity 91%). The compound was used without further purification.

LC-MS (method 1B): RT=0.64 min, m/z=223 (M+H)$^+$

Example 99A

2-Chloro-N'-hydroxy-4-(trifluoromethyl)benzenecarboximidamide

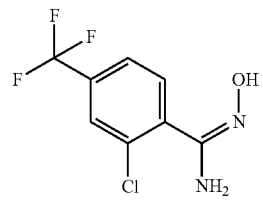 [SMILES: N/C(=N/O)c1ccc(C(F)(F)F)cc1Cl]

To a solution of 2-chloro-4-(trifluoromethyl)benzonitrile (500 mg, 2.43 mmol) in 12 ml ethanol was added hydroxylammonium chloride (253 mg, 3.65 mmol) and triethylamine (320 mg, 3.16 mmol) and then the reaction mixture was stirred 3.5 h at 50° C. After cooling to RT, the solvent was evaporated and the crude was solved in ethyl acetate and extracted with water and brine solution. The organic phase was dried over magnesium sulfate, filtered and evaporated under vacuum to yield the title compound (481 mg, 67% of theory, purity 80%). The compound was used without further purification.

LC-MS (method 3B): RT=1.49 min, m/z=239 (M+H)$^+$

Example 100A

5-Chloro-2-fluoro-N'-hydroxybenzenecarboximidamide

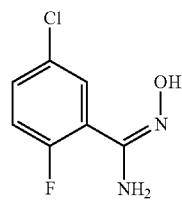

To a solution of 5-chloro-2-fluorobenzonitrile (500 mg, 3.21 mmol) in 16 ml ethanol was added hydroxylammonium chloride (335 mg, 4.82 mmol) and triethylamine (422 mg, 4.18 mmol) and then the reaction mixture was stirred 6 h at 50° C. After cooling to RT, the solvent was evaporated and the crude was solved in ethyl acetate and extracted with water and brine solution. The organic phase was dried over magnesium sulfate, filtered and evaporated under vacuum to yield the title compound (465 mg, 65% of theory, purity 85%). The compound was used without further purification.

LC-MS (method 3B): RT=0.68 min, m/z=189 (M+H)$^+$

Example 101A

3-Chloro-5-fluoro-N'-hydroxybenzenecarboximidamide

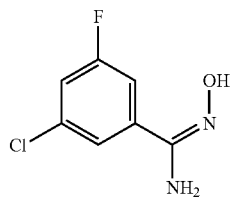

To a solution of 3-chloro-5-fluorobenzonitrile (500 mg, 3.21 mmol) in 10 ml ethanol was added hydroxylammonium chloride (335 mg, 4.82 mmol) and triethylamine (422 mg, 4.18 mmol) and then the reaction mixture was stirred 6 h at 50° C. After cooling to RT, the solvent was evaporated and the crude was solved in ethyl acetate and extracted with water and brine solution. The organic phase was dried over magnesium sulfate, filtered and evaporated under vacuum to yield the title compound (577 mg, 89% of theory, purity 94%). The compound was used without further purification.

LC-MS (method 3B): RT=1.08 min, m/z=189 (M+H)+

Example 102A

N'-hydroxy-2-methyl-4-(trifluoromethyl)benzenecarboximidamide

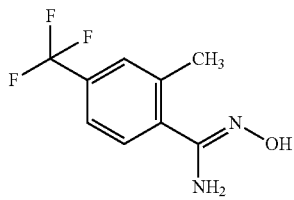

To a solution of 2-methyl-4-(trifluoromethyl)benzonitrile (500 mg, 2.70 mmol) in 10 ml ethanol was added hydroxylammonium chloride (281 mg, 4.05 mmol) and triethylamine (355 mg, 3.51 mmol) and then the reaction mixture was stirred 24 h at 50° C. After cooling to RT, the solvent was evaporated and the crude was solved in ethyl acetate and extracted with water and brine solution. The organic phase was dried over magnesium sulfate, filtered and evaporated under vacuum to yield the title compound (450 mg, 76% of theory).

LC-MS (method 2B): RT=1.69 and 1.91 min, m/z=219 (M+H)+

Example 103A

3-Chloro-N'-hydroxy-2-methylbenzenecarboximidamide

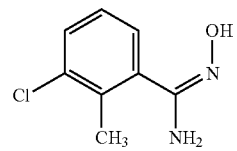

To a solution of 3-chloro-2-methylbenzonitrile (500 mg, 3.30 mmol) in 10 ml ethanol was added hydroxylammonium chloride (343 mg, 4.95 mmol) and triethylamine (434 mg, 4.29 mmol) and then the reaction mixture was stirred 12 h at 50° C. After cooling to RT, the solvent was evaporated and the crude was solved in ethyl acetate and extracted with water and brine solution. The organic phase was dried over magnesium sulfate, filtered and evaporated under vacuum to yield the title compound (484 mg, 80% of theory).

LC-MS (method 2B): RT=1.69 and 1.72 min, m/z=185 (M+H)+

Example 104A

5-Chloro-N'-hydroxy-2-methylbenzenecarboximidamide

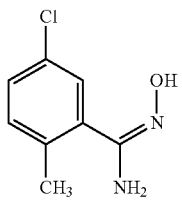

To a solution of 5-chloro-2-methylbenzonitrile (500 mg, 3.30 mmol) in 10 ml ethanol was added hydroxylammonium chloride (343 mg, 4.95 mmol) and triethylamine (434 mg, 4.29 mmol) and then the reaction mixture was stirred 18 h at 50° C. After cooling to RT, the solvent was evaporated and the crude was solved in ethyl acetate and extracted with water and brine solution. The organic phase was dried over magnesium sulfate, filtered and evaporated under vacuum to yield the title compound (330 mg, 54% of theory).

LC-MS (method 7B): RT=1.69 and 1.72 min, m/z=185 (M+H)+

Example 105A

3-Chloro-N'-hydroxy-4-methoxybenzenecarboximidamide

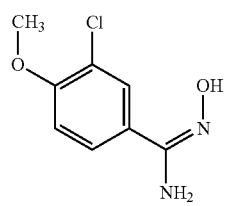

To a solution of 3-chloro-4-methoxybenzonitrile (500 mg, 3.30 mmol) in 10 ml ethanol was added hydroxylammonium chloride (311 mg, 4.0 mmol) and triethylamine (392 mg, 4.0 mmol) and then the reaction mixture was stirred 16 h at 50° C. After cooling to RT, the solvent was evaporated and the crude was solved in ethyl acetate and dichloromethane and extracted with water. The organic phase was dried over magnesium sulfate, filtered and evaporated under vacuum to yield the title compound (124 mg, 19% of theory).

LC-MS (method 3B): RT=0.79 min, m/z=201 (M+H)$^+$

Example 106A 2,3-Dichloro-N'-hydroxybenzenecarboximidamide

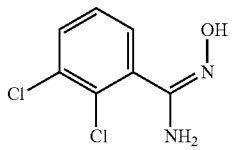

To a solution of 2,3-dichlorobenzonitrile (500 mg, 3.30 mmol) in 10 ml ethanol was added hydroxylammonium chloride (303 mg, 4.0 mmol) and triethylamine (382 mg, 4.0 mmol) and then the reaction mixture was stirred 16 h at 50° C. After cooling to RT, the solvent was evaporated and the crude was solved in ethyl acetate and dichloromethane and extracted with water. The organic phase was dried over magnesium sulfate, filtered and evaporated under vacuum to yield the title compound (225 mg, 36% of theory).

LC-MS (method 2B): RT=1.66 min, m/z=205 (M+H)$^+$

Example 107A

3-Chloro-4-fluoro-N'-hydroxybenzenecarboximidamide

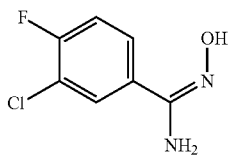 [SMILES: N/C(=N/O)c1ccc(F)c(Cl)c1]

To a solution of 3-chloro-4-fluorobenzonitrile (500 mg, 3.0 mmol) in 10 ml ethanol was added hydroxylammonium chloride (335 mg, 5.0 mmol) and triethylamine (422 mg, 4.0 mmol) and then the reaction mixture was stirred 13 h at 50° C. After cooling to RT, the solvent was evaporated and the crude was solved in dichloromethane and extracted with water. The organic phase was dried over magnesium sulfate, filtered and evaporated under vacuum to yield the title compound (451 mg, 74% of theory).

LC-MS (method 2B): RT=1.73 min, m/z=189 (M+H)$^+$

Example 108A

5-Chloro-N'-hydroxy-2-(trifluoromethyl)benzenecarboximidamide

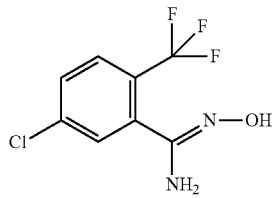 [SMILES: N/C(=N\O)c1cc(Cl)ccc1C(F)(F)F]

To a solution of 5-chloro-2-(trifluoromethyl)benzonitrile (500 mg, 2.0 mmol) in 10 ml ethanol was added hydroxylammonium chloride (253 mg, 4.0 mmol) and triethylamine (320 mg, 3.0 mmol) and then the reaction mixture was stirred 13 h at 50° C. After cooling to RT, the solvent was evaporated and the crude was solved in dichloromethane and extracted with water. The organic phase was dried over magnesium sulfate, filtered and evaporated under vacuum to yield the title compound (430 mg, 67% of theory, purity 90%). The compound was used without further purification.

LC-MS (method 2B): RT=1.87 min, m/z=239 (M+H)$^+$

Example 109A

N'-hydroxy-6-(trifluoromethyl)pyridine-2-carboximidamide

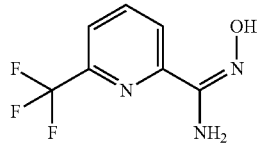

To a solution of 6-(trifluoromethyl)pyridine-2-carbonitrile (500 mg, 3.0 mmol) in 10 ml ethanol was added hydroxylammonium chloride (302 mg, 4.0 mmol) and triethylamine (382 mg, 4.0 mmol) and then the reaction mixture was stirred 13 h at 50° C. After cooling to RT, the solvent was evaporated and the crude was solved in dichloromethane and extracted with water. The organic phase was dried over magnesium sulfate, filtered and evaporated under vacuum to yield the title compound (261 mg, 44% of theory).

LC-MS (method 2B): RT=1.88 min, m/z=206 (M+H)$^+$

Example 110A

N'-hydroxy-4-(trifluoromethyl)pyridine-2-carboximidamide

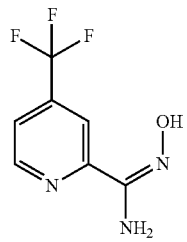

To a solution of 4-(trifluoromethyl)pyridine-2-carbonitrile (500 mg, 3.0 mmol) in 10 ml ethanol was added hydroxylammonium chloride (302 mg, 4.0 mmol) and triethylamine (382 mg, 4.0 mmol) and then the reaction mixture was stirred 13 h at 50° C. After cooling to RT, the solvent was evaporated and the crude was solved in dichloromethane and extracted with water. The organic phase was dried over magnesium sulfate, filtered and evaporated under vacuum to yield the title compound (432 mg, 65% of theory, 90% purity). The compound was used without further purification.

LC-MS (method 2B): RT=1.78 min, m/z=206 (M+H)$^+$

Example 111A

2-Chloro-N'-hydroxypyridine-3-carboximidamide

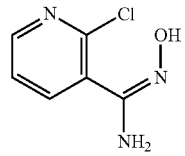

To a solution of 2-chloronicotinonitrile (500 mg, 4.0 mmol) in 10 ml ethanol was added hydroxylammonium chloride (376 mg, 5.0 mmol) and triethylamine (474 mg, 5.0 mmol) and then the reaction mixture was stirred 13 h at 50° C. After cooling to RT, the solvent was evaporated and the crude was solved in dichloromethane and extracted with water. The organic phase was dried over magnesium sulfate, filtered and evaporated under vacuum to yield the title compound (300 mg, 24% of theory, 50% purity). The compound was used without further purification.

LC-MS (method 2B): RT=0.48 min, m/z=172 (M+H)$^+$

Example 112A

3-Chloro-N'-hydroxy-4-(trifluoromethoxy)benzenecarboximidamide

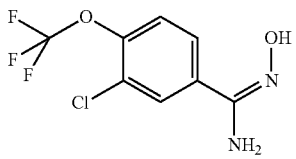 [SMILES: N/C(=N/O)c1ccc(OC(F)(F)F)c(Cl)c1]

To a solution of 3-chloro-4-(trifluoromethoxy)benzonitrile (500 mg, 2.0 mmol) in 10 ml ethanol was added hydroxylammonium chloride (235 mg, 3.0 mmol) and triethylamine (297 mg, 3.0 mmol) and then the reaction mixture was stirred 13 h at 50° C. After cooling to RT, the solvent was evaporated and the crude was solved in dichloromethane and extracted with water. The organic phase was dried over magnesium sulfate, filtered and evaporated under vacuum to yield the title compound (243 mg, 33% of theory, 77% purity). The compound was used without further purification.

LC-MS (method 2B): RT=2.16 min, m/z=255 (M+H)$^+$

Example 113A 2,6-Dichloro-N'-hydroxy-4-(trifluoromethyl)benzenecarboximidamide

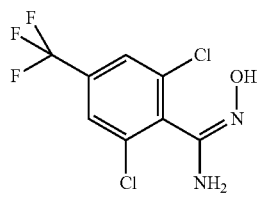

To a solution of 2,6-dichloro-4-(trifluoromethyl)benzonitrile (500 mg, 2.08 mmol) in 12 ml ethanol was added hydroxylammonium chloride (217 mg, 3.12 mmol) and triethylamine (274 mg, 2.71 mmol) and then the reaction mixture was stirred 3.5 h at 50° C. After cooling to RT, the solvent was evaporated and the crude was solved in ethyl acetate and extracted with water and brine solution. The organic phase was dried over magnesium sulfate, filtered and evaporated under vacuum to yield the title compound (399 mg, 16% of theory, 22% purity). The compound was used without further purification.

LC-MS (method 1B): RT=0.72 min, m/z=273 (M+H)$^+$

Example 114A 3,5-Dichloro-N'-hydroxybenzenecarboximidamide

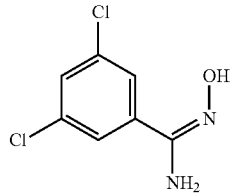

To a solution of 3,5-dichlorobenzonitrile (500 mg, 3.00 mmol) in 10 ml ethanol was added hydroxylammonium chloride (303 mg, 4.00 mmol) and triethylamine (382 mg, 4.0 mmol) and then the reaction mixture was stirred overnight at 50° C. After cooling to RT, the solvent was evaporated and the crude was solved in dichloromethane and extracted with water and brine solution. The organic phase was dried over magnesium sulfate, filtered and evaporated under vacuum to yield the title compound (108 mg, 10% of theory, 58% purity). The compound was used without further purification.

LC-MS (method 1B): RT=1.99 min, m/z=205 (M+H)$^+$

Example 115A

N'-hydroxy-2,4-bis(trifluoromethyl)benzenecarboximidamide

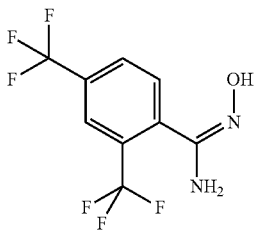 [SMILES: N/C(=N/O)c1ccc(C(F)(F)F)cc1C(F)(F)F]

To a solution of 2,4-(trifluoromethyl)benzonitrile (500 mg, 2.10 mmol) in 12 ml ethanol was added hydroxylammonium chloride (218 mg, 3.14 mmol) and triethylamine (275 mg, 2.72 mmol) and then the reaction mixture was stirred 3.5 h at 50° C. After cooling to RT, the solvent was evaporated and the crude was solved in ethyl acetate and extracted with water and brine solution. The organic phase was dried over magnesium sulfate, filtered and evaporated under vacuum to yield the title compound (397 mg, 27% of theory, 39% purity). The compound was used without further purification.

LC-MS (method 2B): RT=2.04 min, m/z=273 (M+H)$^+$

Example 116A

N'-hydroxy-4-(trifluoromethyl)benzenecarboximidamide

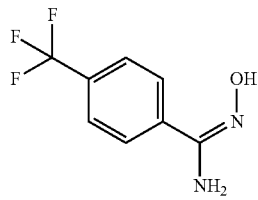 [SMILES: N/C(=N/O)c1ccc(C(F)(F)F)cc1]

To a solution of 4-(trifluoromethyl)benzonitril (5 g, 29.22 mmol) in 148 ml ethanol was added hydroxylammonium chloride (3.05 g, 43.83 mmol) and triethylamine (3.84 g, 37.98 mmol) and then the reaction mixture was 5 h at 50° C. After cooling to RT, the solvent was evaporated and the crude was solved in ethyl acetate and extracted with water and brine solution. The organic phase was dried over magnesium sulfate, filtered and evaporated under vacuum to yield the title compound (5.93 g, 99% of theory).

LC-MS (method 2B): RT=1.86 min, m/z=205 (M+H)$^+$

Example 117A

N'-hydroxy-3-methoxy-4-methylbenzenecarboximidamide

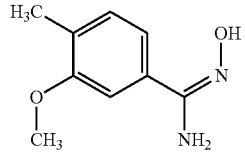

To a solution of 3-methoxy-4-methylbenzonitrile (300 mg, 2.03 mmol) in 10 ml ethanol was added hydroxylammonium chloride (212 mg, 3.06 mmol) and triethylamine (268 mg, 2.65 mmol) and then the reaction mixture was stirred overnight at 50° C. After cooling to RT, the solvent was evaporated and the crude was solved in ethyl acetate and extracted with water and brine solution. The organic phase was dried over magnesium sulfate, filtered and evaporated under vacuum to yield the title compound (274 mg, 75% of theory).

LC-MS (method 1B): RT=0.33 min, m/z=181 (M+H)$^+$

Example 118A

3-Fluoro-N'-hydroxy-4-methylbenzenecarboximidamide

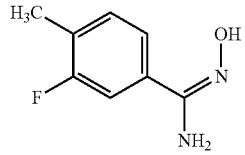

To a solution of 3-fluoro-4-methylbenzonitrile (300 mg, 2.22 mmol) in 10 ml ethanol was added hydroxylammonium chloride (231 mg, 3.33 mmol) and triethylamine (292 mg, 2.89 mmol) and then the reaction mixture was stirred overnight at 50° C. After cooling to RT, the solvent was evaporated and the crude was solved in ethyl acetate and extracted with water and brine solution. The organic phase was dried over magnesium sulfate, filtered and evaporated under vacuum to yield the title compound (331 mg, 87% of theory).

LC-MS (method 2B): RT=1.61 min, m/z=169 (M+H)⁺

Example 119A

N'-hydroxy-4-methyl-3-(trifluoromethyl)benzenecarboximidamide

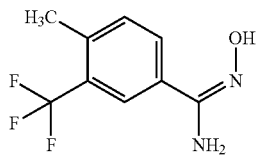

To a solution of 4-methyl-3-(trifluoromethyl)benzonitrile (300 mg, 1.62 mmol) in 10 ml ethanol was added hydroxylammonium chloride (168 mg, 2.43 mmol) and triethylamine (213 mg, 2.11 mmol) and then the reaction mixture was stirred overnight at 50° C. After cooling to RT, the solvent was evaporated and the crude was solved in ethyl acetate and extracted with water and brine solution. The organic phase was dried over magnesium sulfate, filtered and evaporated under vacuum to yield the title compound (352 mg, 100% of theory).

LC-MS (method 2B): RT=1.97 min, m/z=219 (M+H)⁺

Example 120A

3-Chloro-N'-hydroxy-4-methylbenzenecarboximidamide

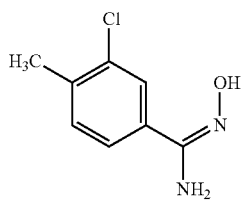

To a solution of 3-chloro-4-methylbenzonitrile (300 mg, 1.98 mmol) in 10 ml ethanol was added hydroxylammonium chloride (207 mg, 2.97 mmol) and triethylamine (260 mg, 2.58 mmol) and then the reaction mixture was stirred overnight at 50° C. After this time hydroxylammonium chloride (69 mg, 1.0 mmol) and triethylamine (100 mg, 1.0 mmol) were added again and the mixture was stirred for 2 h at 50° C. After cooling to RT, the solvent was evaporated and the crude was solved in ethyl acetate and extracted with water. The organic phase was dried over magnesium sulfate, filtered and evaporated under vacuum to yield the title compound (325 mg, 58% of theory, 65% purity). The compound was used without further purification.

LC-MS (method 1B): RT=0.46 min, m/z=185 (M+H)⁺

Example 121A

N'-hydroxy-3,4-dimethylbenzenecarboximidamide

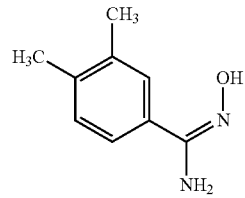

To a solution of 3,4-dimethylbenzonitrile (300 mg, 2.29 mmol) in 10 ml ethanol was added hydroxylammonium chloride (238 mg, 3.43 mmol) and triethylamine (301 mg, 2.97 mmol) and then the reaction mixture was stirred overnight at 50° C. After cooling to RT, the solvent was evaporated and the crude was solved in ethyl acetate and extracted with water. The organic phase was dried over magnesium sulfate, filtered and evaporated under vacuum to yield the title compound (282 mg, 75% of theory).

LC-MS (method 1B): RT=0.33 min, m/z=165 (M+H)⁺

Example 122A

3-Chloro-N'-hydroxybenzenecarboximidamide

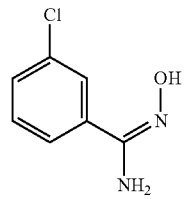 [SMILES: N/C(=N/O)c1cccc(Cl)c1]

To a solution of 3-chlorobenzonitrile (10 g, 72.7 mmol) in 367 ml ethanol was added hydroxylammonium chloride (7.58 g, 109.0 mmol) and triethylamine (9.56 g, 94.5 mmol) and then the reaction mixture was stirred overnight at 50° C. After cooling to RT, the solvent was evaporated and the crude was solved in ethyl acetate and extracted with water. The organic phase was dried over magnesium sulfate, filtered and evaporated under vacuum to yield the title compound (10.77 g, 81% of theory, 93% purity). The compound was used without further purification.

LC-MS (method 2B): RT=1.64 min, m/z=171 (M+H)⁺

Example 123A 6-chloro-N'-hydroxypyridine-2-carboximidamide

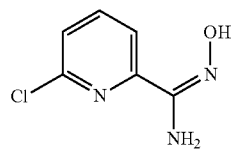 [SMILES: N/C(=N/O)c1cccc(Cl)n1]

To a solution of pyridine-2-carbonitrile (500 mg, 4.0 mmol) in 10 ml ethanol was added hydroxylammonium chloride (376 mg, 5.0 mmol) and triethylamine (474 mg, 5.0 mmol) and then the reaction mixture was stirred overnight at 50° C. After cooling to RT, the solvent was evaporated and the crude was solved in ethyl acetate and extracted with water. The organic phase was dried over magnesium sulfate, filtered and evaporated under vacuum to yield the title compound (573 mg, 81% of theory).

LC-MS (Method 7B): RT=1.58 min, m/z=172 (M+H)+

Example 124A

N'-hydroxy-2-methyl-4-(trifluoromethyl)benzenecarboximidamide

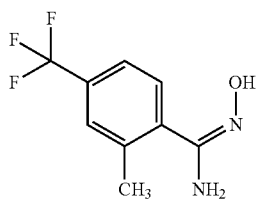

To a solution of 2-methyl-4-(trifluoromethyl)benzonitrile (500 mg, 2.70 mmol) in 14 ml ethanol was added hydroxylammonium chloride (281 mg, 4.05 mmol) and triethylamine (355 mg, 3.51 mmol) and then the reaction mixture was stirred 24 h at 50° C. After cooling to RT, the solvent was evaporated and the crude was solved in ethyl acetate and extracted with water. The organic phase was dried over magnesium sulfate, filtered and evaporated under vacuum to yield the title compound (450 mg, 76% of theory).

LC-MS (method 2B): RT=1.91 min, m/z=219 (M+H)+

Example 125A

Tert-butyl 4-(5-oxo-3-{3-[3-(trifluoromethyl)phenyl]-1,2,4-oxadiazol-5-yl}-4,5-dihydropyrazolo[1,5-a]pyrimidin-7-yl)piperidine-1-carboxylate

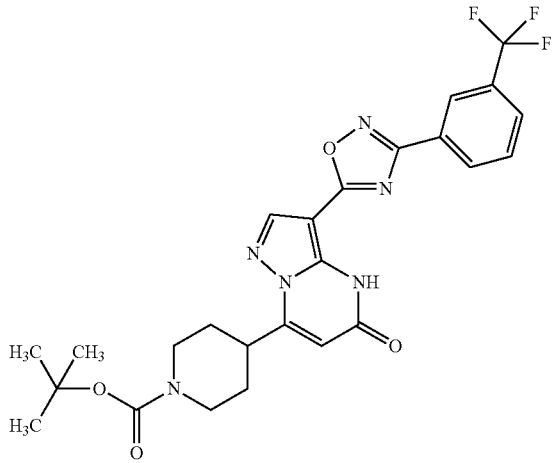 [SMILES: CC(C)(C)OC(=O)N1CCC(c2cc(=O)[nH]c3c(-c4nc(-c5cccc(C(F)(F)F)c5)no4)cnn23)CC1]

To a solution of compound 7-[1-(tert-butoxycarbonyl)piperidin-4-yl]-5-oxo-4,5-dihydropyrazolo[1,5-a]pyrimidine-3-carboxylic acid (100 mg, 0.28 mmol) in 2 ml dimethylformamide was added 1,1'-carbonyldiimidazole (89 mg, 0.55 mmol), DBU (99 mg, 0.65 mmol) and N,N-Diisopropylethylamin (71 mg, 0.55 mmol) and then the reaction mixture was stirred 1.5 h at 90° C. After this time N'-hydroxy-3-(trifluoromethyl)benzenecarboximidamide (112 mg, 0.55 mmol) was added and the mixture was stirred for 5.5 h at 110° C. After cooling to RT, the mixture was diluted in 2 ml acetonitrile and purified by preparative HPLC (water/acetonitrile, 0.1% formic acid). After evaporation of the solvent of the collected fractions a white solid was obtained to yield the title compound (63 mg, 43% of theory).

LC-MS (method 1B): RT=1.35 min, m/z=531 (M+H)+

Example 126A

Tert-butyl 4-{3-[3-(3-fluorophenyl)-1,2,4-oxadiazol-5-yl]-5-oxo-4,5-dihydropyrazolo[1,5-a]pyrimidin-7-yl}piperidine-1-carboxylate

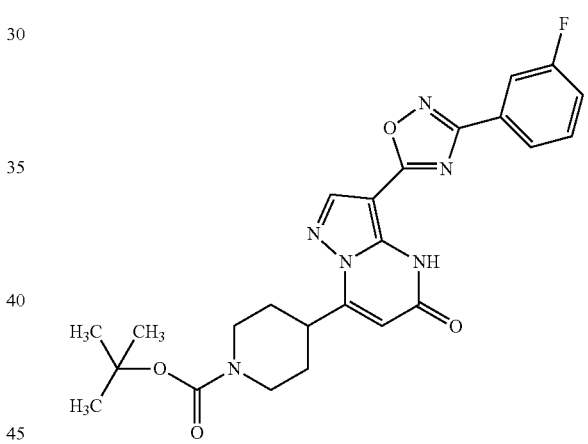

To a solution of compound 7-[1-(tert-butoxycarbonyl)piperidin-4-yl]-5-oxo-4,5-dihydropyrazolo[1,5-a]pyrimidine-3-carboxylic acid (100 mg, 0.28 mmol) in 2 ml dimethylformamide was added 1,1'-carbonyldiimidazole (89 mg, 0.55 mmol), DBU (99 mg, 0.65 mmol) and N,N-Diisopropylethylamin (71 mg, 0.55 mmol) and then the reaction mixture was stirred 1.5 h at 90° C. After this time 3-fluoro-N'-hydroxybenzenecarboximidamide (85 mg, 0.55 mmol) was added and the mixture was stirred for 5.5 h at 110° C. After cooling to RT, the mixture was diluted in 2 ml acetonitrile and purified by preparative HPLC (water/acetonitrile, 0.1% formic acid). After evaporation of the solvent of the collected fractions a white solid was obtained to yield the title compound (90 mg, 68% of theory).

LC-MS (method 1B): RT=1.27 min, m/z=479 (M−H)−

Example 127A

Tert-butyl 4-(5-oxo-3-{3-[4-(trifluoromethyl)phenyl]-1,2,4-oxadiazol-5-yl}-4,5-dihydropyrazolo[1,5-a]pyrimidin-7-yl)piperidine-1-carboxylate

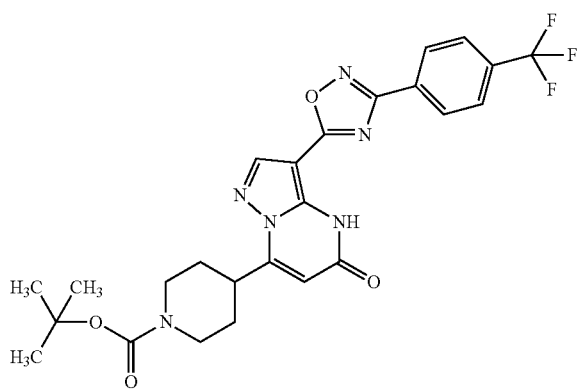 [SMILES: CC(C)(C)OC(=O)N1CCC(c2cc(=O)[nH]c3c(-c4nc(-c5ccc(C(F)(F)F)cc5)no4)cnn23)CC1]

To a solution of compound 7-[1-(tert-butoxycarbonyl)piperidin-4-yl]-5-oxo-4,5-dihydropyrazolo[1,5-a]pyrimidine-3-carboxylic acid (5.26 g, 14.52 mmol) in 105 ml dimethylformamide was added 1,1'-carbonyldiimidazole (4.71 g, 29.05 mmol), DBU (5.20 g, 34.13 mmol) and N,N-Diisopropylethylamin (3.75 g, 29.05 mmol) and then the reaction mixture was stirred 1.5 h at 90° C. After this time N'-hydroxy-4-(trifluoromethyl)benzenecarboximidamide (5.93 g, 29.05 mmol) was added and the mixture was stirred for 16 h at 110° C. After cooling to RT, the solvent was evaporated and the crude was purified by flash chromatography with silica gel (solvent: dichloromethane). After evaporation of fractions the obtained solid was crystallized in acetonitrile to yield the title compound (1.52 g, 20% of theory).

LC-MS (method 1B): RT=1.39 min, m/z=531 (M+H)$^+$

Example 128A

Tert-butyl 4-{3-[3-(4-benzylphenyl)-1,2,4-oxadiazol-5-yl]-5-oxo-4,5-dihydropyrazolo[1,5-a]pyrimidin-7-yl}piperidine-1-carboxylate

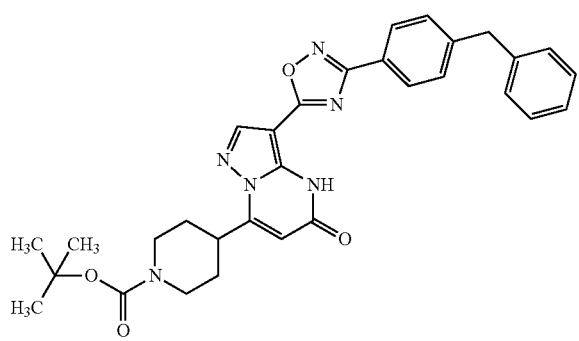 [SMILES: CC(C)(C)OC(=O)N1CCC(c2cc(=O)[nH]c3c(-c4nc(-c5ccc(Cc6ccccc6)cc5)no4)cnn23)CC1]

To a solution of compound 7-[1-(tert-butoxycarbonyl)piperidin-4-yl]-5-oxo-4,5-dihydropyrazolo[1,5-a]pyrimidine-3-carboxylic acid (150 mg, 0.41 mmol) in 3 ml dimethylformamide was added 1,1'-carbonyldiimidazole (134 mg, 0.83 mmol), DBU (148 mg, 0.97 mmol) and N,N-Diisopropylethylamin (106 mg, 0.83 mmol) and then the reaction mixture was stirred 1.5 h at 90° C. After this time 4-benzyl-N'-hydroxy-2-phenylethanimidamide (124 mg, 0.83 mmol) was added and the mixture was stirred for 5.5 h at 110° C. After cooling to RT, the mixture was diluted in 2 ml acetonitrile and purified by preparative HPLC (water/acetonitrile, 0.1% formic acid). After evaporation of the solvent of the collected fractions a white solid was obtained to yield the title compound (12 mg, 6% of theory).

LC-MS (method 1B): RT=1.11 min, m/z=477 (M+H)$^+$

Example 129A

Tert-butyl 4-(5-oxo-3-{3-[4-(trifluoromethoxy)phenyl]-1,2,4-oxadiazol-5-yl}-4,5-dihydropyrazolo[1,5-a]pyrimidin-7-yl)piperidine-1-carboxylate

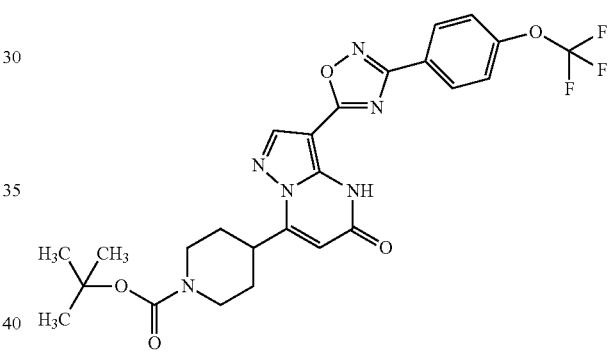

To a solution of compound 7-[1-(tert-butoxycarbonyl)piperidin-4-yl]-5-oxo-4,5-dihydropyrazolo[1,5-a]pyrimidine-3-carboxylic acid (150 mg, 0.41 mmol) in 3 ml dimethylformamide was added 1,1'-carbonyldiimidazole (134 mg, 0.83 mmol), DBU (148 mg, 0.97 mmol) and N,N-Diisopropylethylamin (106 mg, 0.83 mmol) and then the reaction mixture was stirred 1.5 h at 90° C. After this time N'-hydroxy-4-(trifluoromethoxy)benzenecarboximidamide (182 mg, 0.83 mmol) was added and the mixture was stirred for 5.5 h at 110° C. After cooling to RT, the mixture was diluted in 2 ml acetonitrile and purified by preparative HPLC (water/acetonitrile, 0.1% formic acid). After evaporation of the solvent of the collected fractions a white solid was obtained to yield the title compound (117 mg, 52% of theory).

LC-MS (method 1B): RT=1.33 min, m/z=547 (M+H)$^+$

Example 130A

Tert-butyl 4-{3-[3-(3-methoxy-4-methylphenyl)-1,2,4-oxadiazol-5-yl]-5-oxo-4,5-dihydropyrazolo[1,5-a]pyrimidin-7-yl}piperidine-1-carboxylate

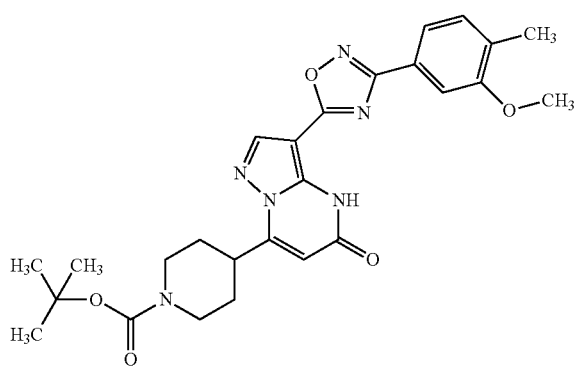 [SMILES: COc1cc(-c2noc(-c3cnn4c(C5CCN(C(=O)OC(C)(C)C)CC5)cc(=O)[nH]c34)n2)ccc1C]

To a solution of compound 7-[1-(tert-butoxycarbonyl)piperidin-4-yl]-5-oxo-4,5-dihydropyrazolo[1,5-a]pyrimidine-3-carboxylic acid (150 mg, 0.41 mmol) in 3 ml dimethylformamide was added 1,1'-carbonyldiimidazole (134 mg, 0.83 mmol), DBU (148 mg, 0.97 mmol) and N,N-Diisopropylethylamin (106 mg, 0.83 mmol) and then the reaction mixture was stirred 1.5 h at 90° C. After this time N'-hydroxy-3-methoxy-4-methylbenzenecarboximidamide (149 mg, 0.83 mmol) was added and the mixture was stirred for 5.5 h at 110° C. After cooling to RT, the mixture was diluted in 2 ml acetonitrile and purified by preparative HPLC (water/acetonitrile, 0.1% formic acid). After evaporation of the solvent of the collected fractions a white solid was obtained to yield the title compound (26 mg, 11% of theory, purity 90%).

LC-MS (method 1B): RT=1.29 min, m/z=507 (M+H)⁺

Example 131A

Tert-butyl 4-{3-[3-(3-fluoro-4-methylphenyl)-1,2,4-oxadiazol-5-yl]-5-oxo-4,5-dihydropyrazolo[1,5-a]pyrimidin-7-yl}piperidine-1-carboxylate

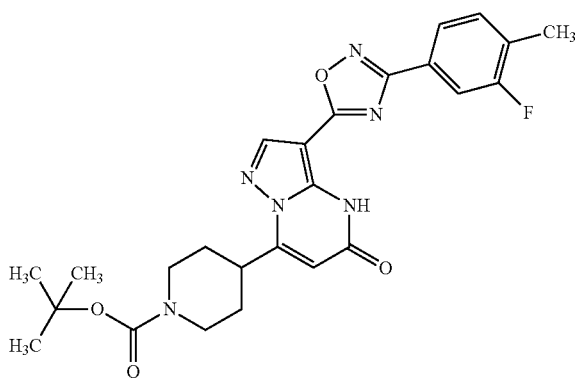 [SMILES: Cc1ccc(-c2noc(-c3cnn4c(C5CCN(C(=O)OC(C)(C)C)CC5)cc(=O)[nH]c34)n2)cc1F]

To a solution of compound 7-[1-(tert-butoxycarbonyl)piperidin-4-yl]-5-oxo-4,5-dihydropyrazolo[1,5-a]pyrimidine-3-carboxylic acid (150 mg, 0.41 mmol) in 3 ml dimethylformamide was added 1,1'-carbonyldiimidazole (134 mg, 0.83 mmol), DBU (148 mg, 0.97 mmol) and N,N-Diisopropylethylamin (106 mg, 0.83 mmol) and then the reaction mixture was stirred 1.5 h at 90° C. After this time 3-fluoro-N'-hydroxy-4-methylbenzenecarboximidamide (139 mg, 0.83 mmol) was added and the mixture was stirred for 5.5 h at 110° C. After cooling to RT, the mixture was diluted in 2 ml acetonitrile and purified by preparative HPLC (water/acetonitrile, 0.1% formic acid). After evaporation of the solvent of the collected fractions a white solid was obtained to yield the title compound (87 mg, 42% of theory).

LC-MS (method 1B): RT=1.28 min, m/z=495 (M+H)⁺

Example 132A

Tert-butyl 4-(3-{3-[4-methyl-3-(trifluoromethyl)phenyl]-1,2,4-oxadiazol-5-yl}-5-oxo-4,5-dihydropyrazolo[1,5-a]pyrimidin-7-yl)piperidine-1-carboxylate

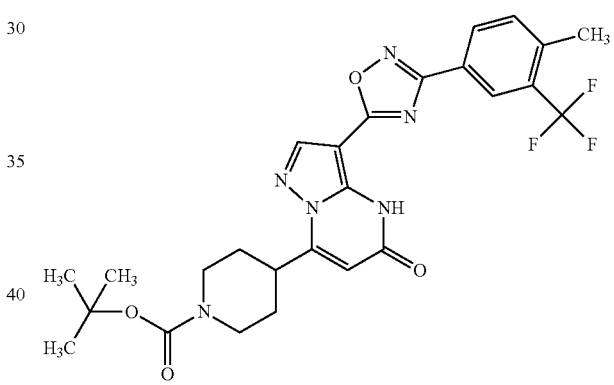

To a solution of compound 7-[1-(tert-butoxycarbonyl)piperidin-4-yl]-5-oxo-4,5-dihydropyrazolo[1,5-a]pyrimidine-3-carboxylic acid (150 mg, 0.41 mmol) in 3 ml dimethylformamide was added 1,1'-carbonyldiimidazole (134 mg, 0.83 mmol), DBU (148 mg, 0.97 mmol) and N,N-Diisopropylethylamin (106 mg, 0.83 mmol) and then the reaction mixture was stirred 1.5 h at 90° C. After this time N'-hydroxy-4-methyl-3-(trifluoromethyl)benzenecarboximidamide (180 mg, 0.83 mmol) was added and the mixture was stirred for 5.5 h at 110° C. After cooling to RT, the mixture was diluted in 2 ml acetonitrile and purified by preparative HPLC (water/acetonitrile, 0.1% formic acid). After evaporation of the solvent of the collected fractions a white solid was obtained to yield the title compound (126 mg, 43% of theory, purity 76%).

LC-MS (method 1B): RT=1.36 min, m/z=545 (M+H)⁺

Example 133A

Tert-butyl 4-{3-[3-(2-methylphenyl)-1,2,4-oxadiazol-5-yl]-5-oxo-4,5-dihydropyrazolo[1,5-a]pyrimidin-7-yl}piperidine-1-carboxylate

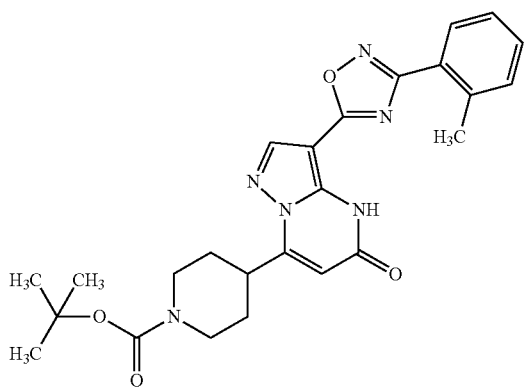 [SMILES: Cc1ccccc1-c1noc(-c2cnn3c(C4CCN(C(=O)OC(C)(C)C)CC4)cc(=O)[nH]c23)n1]

To a solution of compound 7-[1-(tert-butoxycarbonyl)piperidin-4-yl]-5-oxo-4,5-dihydropyrazolo[1,5-a]pyrimidine-3-carboxylic acid (150 mg, 0.41 mmol) in 3 ml dimethylformamide was added 1,1'-carbonyldiimidazole (134 mg, 0.83 mmol), DBU (148 mg, 0.97 mmol) and N,N-Diisopropylethylamin (106 mg, 0.83 mmol) and then the reaction mixture was stirred 1.5 h at 90° C. After this time N'-hydroxy-2-methylbenzenecarboximidamide (149 mg, 0.83 mmol) was added and the mixture was stirred for 5.5 h at 110° C. After cooling to RT, the mixture was diluted in 2 ml acetonitrile and purified by preparative HPLC (water/acetonitrile, 0.1% formic acid). After evaporation of the acetonitrile from collected fractions a white solid was formed in the aqueous phase which was filtered and dried under vacuum overnight to yield the title compound (109 mg, 55% of theory).

LC-MS (method 1B): RT=1.30 min, m/z=477 (M+H)$^+$

Example 134A

Tert-butyl 4-{3-[3-(3-methylphenyl)-1,2,4-oxadiazol-5-yl]-5-oxo-4,5-dihydropyrazolo[1,5-a]pyrimidin-7-yl}piperidine-1-carboxylate

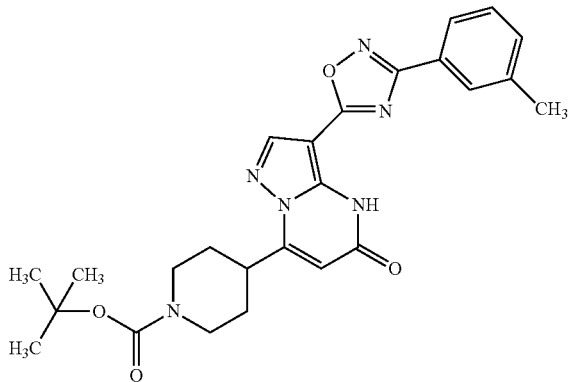 [SMILES: Cc1cccc(-c2noc(-c3cnn4c(C5CCN(C(=O)OC(C)(C)C)CC5)cc(=O)[nH]c34)n2)c1]

To a solution of compound 7-[1-(tert-butoxycarbonyl)piperidin-4-yl]-5-oxo-4,5-dihydropyrazolo[1,5-a]pyrimidine-3-carboxylic acid (150 mg, 0.41 mmol) in 3 ml dimethylformamide was added 1,1'-carbonyldiimidazole (134 mg, 0.83 mmol), DBU (148 mg, 0.97 mmol) and N,N-Diisopropylethylamin (106 mg, 0.83 mmol) and then the reaction mixture was stirred 1.5 h at 90° C. After this time N'-hydroxy-3-methylbenzenecarboximidamide (124 mg, 0.83 mmol) was added and the mixture was stirred for 5.5 h at 110° C. After cooling to RT, the mixture was diluted in 2 ml acetonitrile and purified by preparative HPLC (water/acetonitrile, 0.1% formic acid). After evaporation of the acetonitrile from collected fractions a white solid was formed in the aqueous phase which was filtered and dried under vacuum overnight to yield the title compound (67 mg, 32% of theory, purity 94%).

LC-MS (method 1B): RT=1.31 min, m/z=477 (M+H)$^+$

Example 135A

Tert-butyl 4-{3-[3-(2-chlorophenyl)-1,2,4-oxadiazol-5-yl]-5-oxo-4,5-dihydropyrazolo[1,5-a]pyrimidin-7-yl}piperidine-1-carboxylate

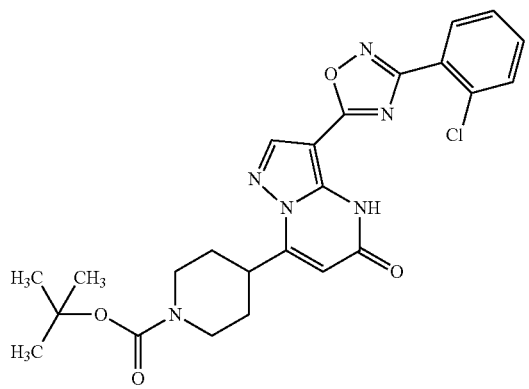 [SMILES: CC(C)(C)OC(=O)N1CCC(c2cc(=O)[nH]c3c(-c4nc(-c5ccccc5Cl)no4)cnn23)CC1]

To a solution of compound 7-[1-(tert-butoxycarbonyl)piperidin-4-yl]-5-oxo-4,5-dihydropyrazolo[1,5-a]pyrimidine-3-carboxylic acid (150 mg, 0.41 mmol) in 3 ml dimethylformamide was added 1,1'-carbonyldiimidazole (134 mg, 0.83 mmol), DBU (148 mg, 0.97 mmol) and N,N-Diisopropylethylamin (106 mg, 0.83 mmol) and then the reaction mixture was stirred 1.5 h at 90° C. After this time 2-chloro-N'-hydroxybenzenecarboximidamide (124 mg, 0.83 mmol) was added and the mixture was stirred for 5.5 h at 110° C. After cooling to RT, the mixture was diluted in 2 ml acetonitrile and purified by preparative HPLC (water/acetonitrile, 0.1% formic acid). After evaporation of the acetonitrile from collected fractions a white solid was formed in the aqueous phase which was filtered and dried under vacuum overnight to yield the title compound (107 mg, 52% of theory).

LC-MS (method 1B): RT=1.26 min, m/z=497 (M+H)$^+$

Example 136A

Tert-butyl 4-{3-[3-(3-fluoro-4-methoxyphenyl)-1,2,4-oxadiazol-5-yl]-5-oxo-4,5-dihydropyrazolo[1,5-a]pyrimidin-7-yl}piperidine-1-carboxylate

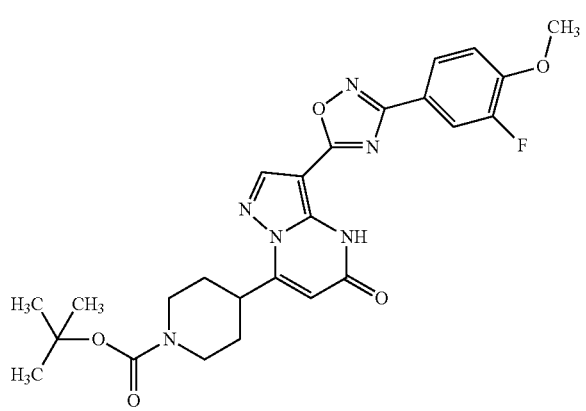 [SMILES: COc1ccc(-c2noc(-c3cnn4c(C5CCN(C(=O)OC(C)(C)C)CC5)cc(=O)[nH]c34)n2)cc1F]

To a solution of compound 7-[1-(tert-butoxycarbonyl)piperidin-4-yl]-5-oxo-4,5-dihydropyrazolo[1,5-a]pyrimidine-3-carboxylic acid (150 mg, 0.41 mmol) in 3 ml dimethylformamide was added 1,1'-carbonyldiimidazole (134 mg, 0.83 mmol), DBU (148 mg, 0.97 mmol) and N,N-Diisopropylethylamin (106 mg, 0.83 mmol) and then the reaction mixture was stirred 1.5 h at 90° C. After this time 3-fluoro-N'-hydroxy-4-methoxybenzenecarboximidamide (152 mg, 0.83 mmol) was added and the mixture was stirred for 6 h at 110° C. After cooling to RT, the mixture was diluted in 2 ml acetonitrile and purified by preparative HPLC (water/acetonitrile, 0.1% formic acid). After evaporation of the acetonitrile from collected fractions a white solid was formed in the aqueous phase which was filtered and dried under vacuum overnight to yield the title compound (85 mg, 40% of theory).

LC-MS (method 1B): RT=1.26 min, m/z=511 (M+H)$^+$

Example 137A

Tert-butyl 4-{3-[3-(3-chloro-4-methylphenyl)-1,2,4-oxadiazol-5-yl]-5-oxo-4,5-dihydropyrazolo[1,5-a]pyrimidin-7-yl}piperidine-1-carboxylate

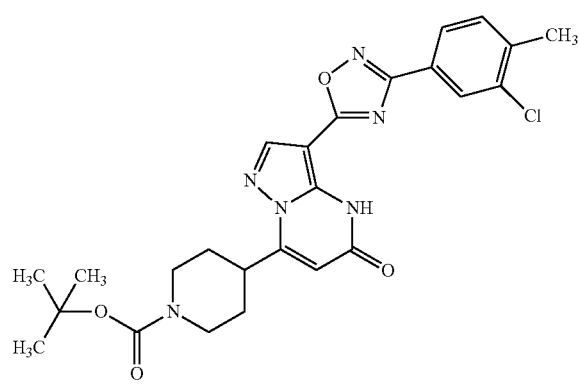

To a solution of compound 7-[1-(tert-butoxycarbonyl)piperidin-4-yl]-5-oxo-4,5-dihydropyrazolo[1,5-a]pyrimidine-3-carboxylic acid (150 mg, 0.41 mmol) in 3 ml dimethylformamide was added 1,1'-carbonyldiimidazole (134 mg, 0.83 mmol), DBU (148 mg, 0.97 mmol) and N,N-Diisopropylethylamin (106 mg, 0.83 mmol) and then the reaction mixture was stirred 1.5 h at 90° C. After this time 3-chloro-N'-hydroxy-4-methylbenzenecarboximidamide (124 mg, 0.83 mmol, 65% purity) was added and the mixture was stirred for 6 h at 110° C. After cooling to RT, the mixture was diluted in 2 ml acetonitrile and purified by preparative HPLC (water/acetonitrile, 0.1% formic acid). After evaporation of the acetonitrile from collected fractions a white solid was formed in the aqueous phase which was filtered and dried under vacuum overnight to yield the title compound (87 mg, 37% of theory, purity 90%).

LC-MS (method 1B): RT=1.34 min, m/z=511 (M+H)$^+$

Example 138A

Tert-butyl 4-(5-oxo-3-{3-[3-(trifluoromethoxy)phenyl]-1,2,4-oxadiazol-5-yl}-4,5-dihydropyrazolo[1,5-a]pyrimidin-7-yl)piperidine-1-carboxylate

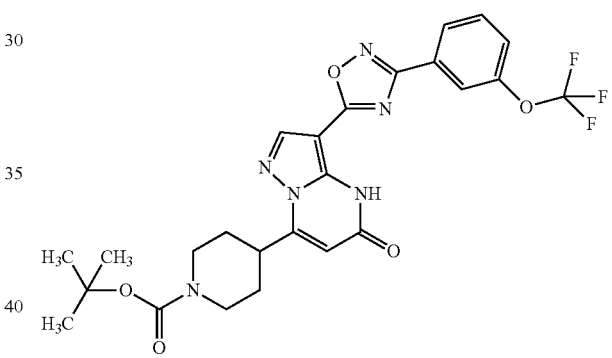

To a solution of compound 7-[1-(tert-butoxycarbonyl)piperidin-4-yl]-5-oxo-4,5-dihydropyrazolo[1,5-a]pyrimidine-3-carboxylic acid (150 mg, 0.41 mmol) in 3 ml dimethylformamide was added 1,1'-carbonyldiimidazole (134 mg, 0.83 mmol), DBU (148 mg, 0.97 mmol) and N,N-Diisopropylethylamin (106 mg, 0.83 mmol) and then the reaction mixture was stirred 1.5 h at 90° C. After this time N'-hydroxy-3-(trifluoromethoxy)benzenecarboximidamide (364 mg, 0.83 mmol, 50% purity) was added and the mixture was stirred for 5 h at 110° C. After cooling to RT, the mixture was diluted in 2 ml acetonitrile and purified by preparative HPLC (water/acetonitrile, 0.1% formic acid). After evaporation of the acetonitrile from collected fractions a white solid was formed in the aqueous phase which was filtered and dried under vacuum overnight to yield the title compound (68 mg, 29% of theory).

LC-MS (method 1B): RT=4.39 min, m/z=546 (M−H)$^−$

Example 139A

Tert-butyl 4-{3-[3-(3-methoxyphenyl)-1,2,4-oxadiazol-5-yl]-5-oxo-4,5-dihydropyrazolo[1,5-a]pyrimidin-7-yl}piperidine-1-carboxylate

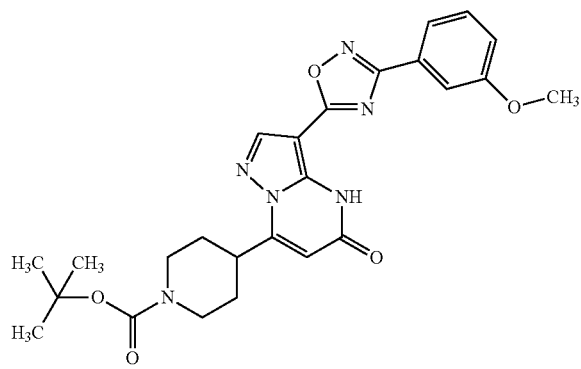 [SMILES: COc1cccc(-c2noc(-c3cnn4c(C5CCN(C(=O)OC(C)(C)C)CC5)cc(=O)[nH]c34)n2)c1]

To a solution of compound 7-[1-(tert-butoxycarbonyl)piperidin-4-yl]-5-oxo-4,5-dihydropyrazolo[1,5-a]pyrimidine-3-carboxylic acid (150 mg, 0.41 mmol) in 2.6 ml 1-methyl-2-pyrrolidone was added 1,1'-carbonyldiimidazole (134 mg, 0.83 mmol) and N,N-Diisopropylethylamin (106 mg, 0.83 mmol) and then the reaction mixture was stirred 1.5 h at 90° C. After this time N'-hydroxy-3-methoxybenzenecarboximidamide (68 mg, 0.41 mmol) was added and the mixture was stirred for 8 h at 110° C. After cooling to RT, the mixture was diluted in 2 ml acetonitrile and purified by preparative HPLC (water/acetonitrile, 0.1% formic acid). After evaporation of the acetonitrile from collected fractions a white solid was formed in the aqueous phase which was filtered and dried under vacuum overnight to yield the title compound (81 mg, 36% of theory, 90% purity).

LC-MS (method 1B): RT=1.17 min, m/z=493 (M+1)$^+$

Example 140A

Tert-butyl 4-{3-[3-(4-fluorophenyl)-1,2,4-oxadiazol-5-yl]-5-oxo-4,5-dihydropyrazolo[1,5-a]pyrimidin-7-yl}piperidine-1-carboxylate

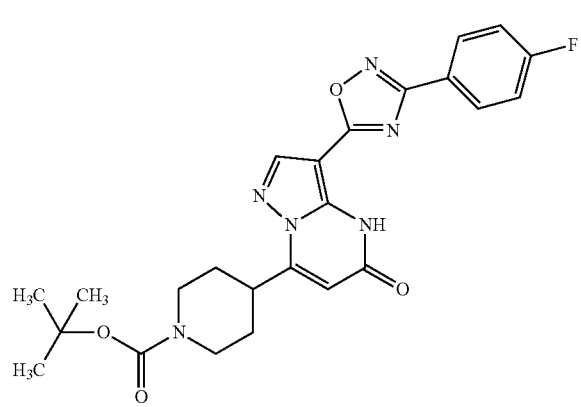 [SMILES: CC(C)(C)OC(=O)N1CCC(c2cc(=O)[nH]c3c(-c4nc(-c5ccc(F)cc5)no4)cnn23)CC1]

To a solution of compound 7-[1-(tert-butoxycarbonyl)piperidin-4-yl]-5-oxo-4,5-dihydropyrazolo[1,5-a]pyrimidine-3-carboxylic acid (150 mg, 0.41 mmol) in 3 ml dimethylformamide was added 1,1'-carbonyldiimidazole (134 mg, 0.83 mmol), DBU (148 mg, 0.97 mmol) and N,N-Diisopropylethylamin (107 mg, 0.83 mmol) and then the reaction mixture was stirred 1.5 h at 90° C. After this time 4-fluoro-N'-hydroxybenzenecarboximidamide (127 mg, 0.83 mmol) was added and the mixture was stirred for 5 h at 110° C. After cooling to RT, the mixture was diluted in 2 ml acetonitrile and purified by preparative HPLC (water/acetonitrile, 0.1% formic acid). After evaporation of acetonitrile from collected fractions the resulting solid in the aqueous fraction was filtered and dried overnight under vacuum to yield the title compound (33 mg, 16% of theory).

LC-MS (method 1B): RT=1.19 min, m/z=481 (M+H)$^+$

Example 141A

Tert-butyl 4-{3-[3-(2,4-dimethylphenyl)-1,2,4-oxadiazol-5-yl]-5-oxo-4,5-dihydropyrazolo[1,5-a]pyrimidin-7-yl}piperidine-1-carboxylate

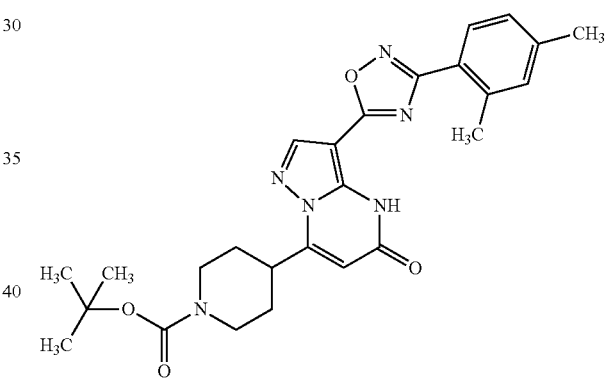

To a solution of compound 7-[1-(tert-butoxycarbonyl)piperidin-4-yl]-5-oxo-4,5-dihydropyrazolo[1,5-a]pyrimidine-3-carboxylic acid (150 mg, 0.41 mmol) in 3 ml dimethylformamide was added 1,1'-carbonyldiimidazole (134 mg, 0.83 mmol), DBU (148 mg, 0.97 mmol) and N,N-Diisopropylethylamin (107 mg, 0.83 mmol) and then the reaction mixture was stirred 1.5 h at 90° C. After this time N'-hydroxy-2,4-dimethylbenzenecarboximidamide (136 mg, 0.83 mmol) was added and the mixture was stirred for 6 h at 110° C. After cooling to RT, the mixture was diluted in 2 ml acetonitrile and purified by preparative HPLC (water/acetonitrile, 0.1% formic acid). After evaporation of acetonitrile from collected fractions the resulting solid in the aqueous fraction was filtered and dried overnight under vacuum to yield the title compound (54 mg, 27% of theory).

LC-MS (method 1B): RT=1.31 min, m/z=491 (M+H)$^+$

Example 142A

Tert-butyl 4-(3-{3-[4-methyl-2-(trifluoromethyl)phenyl]-1,2,4-oxadiazol-5-yl}-5-oxo-4,5-dihydropyrazolo[1,5-a]pyrimidin-7-yl)piperidine-1-carboxylate

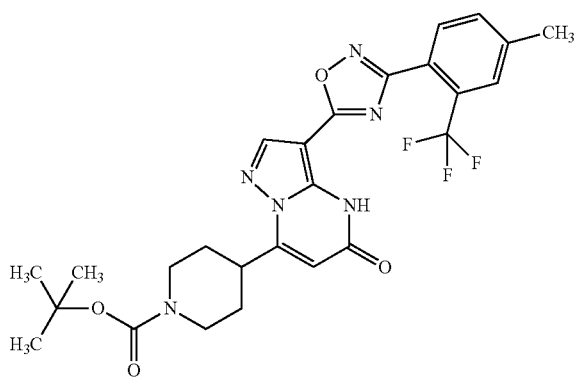 [SMILES: Cc1ccc(-c2noc(-c3cnn4c(C5CCN(C(=O)OC(C)(C)C)CC5)cc(=O)[nH]c34)n2)c(C(F)(F)F)c1]

To a solution of compound 7-[1-(tert-butoxycarbonyl)piperidin-4-yl]-5-oxo-4,5-dihydropyrazolo[1,5-a]pyrimidine-3-carboxylic acid (150 mg, 0.41 mmol) in 3 ml dimethylformamide was added 1,1'-carbonyldiimidazole (134 mg, 0.83 mmol), DBU (144 mg, 0.95 mmol) and N,N-Diisopropylethylamin (107 mg, 0.83 mmol) and then the reaction mixture was stirred 1.5 h at 90° C. After this time N'-hydroxy-4-methyl-2-(trifluoromethyl)benzenecarboximidamide (277 mg, 0.83 mmol, 65% purity) and molecular sieves were added and the mixture was stirred for 5.5 h at 110° C. After cooling to RT, the mixture was diluted in 2 ml acetonitrile and purified by preparative HPLC (water/acetonitrile, 0.1% formic acid). After evaporation of the solvent of the collected fractions a white solid was obtain to yield the title compound (63 mg, 27% of theory).

LC-MS (method 1B): RT=1.26 min, m/z=546 (M+H)+

Example 143A

Tert-butyl 4-{3-[3-(3,4-dimethylphenyl)-1,2,4-oxadiazol-5-yl]-5-oxo-4,5-dihydropyrazolo[1,5-a]pyrimidin-7-yl}piperidine-1-carboxylate

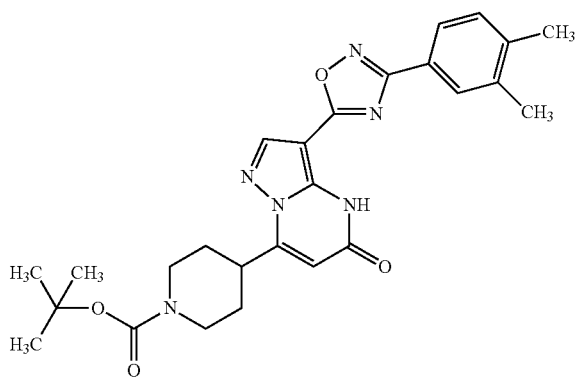

To a solution of compound 7-[1-(tert-butoxycarbonyl)piperidin-4-yl]-5-oxo-4,5-dihydropyrazolo[1,5-a]pyrimidine-3-carboxylic acid (150 mg, 0.41 mmol) in 3 ml dimethylformamide was added 1,1'-carbonyldiimidazole (134 mg, 0.83 mmol), DBU (144 mg, 0.95 mmol) and N,N-Diisopropylethylamin (107 mg, 0.83 mmol) and then the reaction mixture was stirred 1.5 h at 90° C. After this time N'-hydroxy-3,4-dimethylbenzenecarboximidamide (136 mg, 0.83 mmol) was added and the mixture was stirred for 5.5 h at 110° C. After cooling to RT, the mixture was diluted in 2 ml acetonitrile and purified by preparative HPLC (water/acetonitrile, 0.1% formic acid). After evaporation of the solvent the title compound was obtained (16 mg, 8% of theory).

LC-MS (method 1B): RT=1.36 min, m/z=491 (M+H)+

Example 144A

Tert-butyl 4-{3-[3-(2-chloro-4-methylphenyl)-1,2,4-oxadiazol-5-yl]-5-oxo-4,5-dihydropyrazolo[1,5-a]pyrimidin-7-yl}piperidine-1-carboxylate

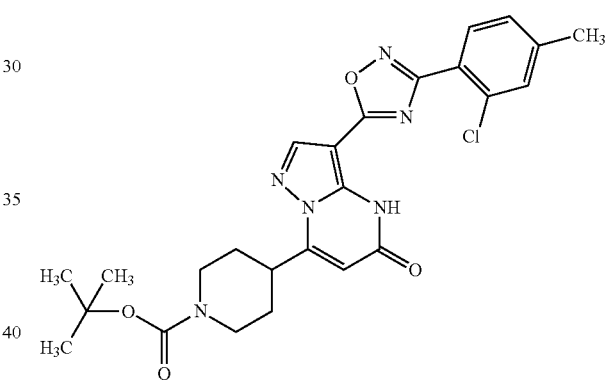

To a solution of compound 7-[1-(tert-butoxycarbonyl)piperidin-4-yl]-5-oxo-4,5-dihydropyrazolo[1,5-a]pyrimidine-3-carboxylic acid (150 mg, 0.41 mmol) in 3 ml dimethylformamide was added 1,1'-carbonyldiimidazole (134 mg, 0.83 mmol), DBU (148 mg, 0.97 mmol) and N,N-Diisopropylethylamin (107 mg, 0.83 mmol) and then the reaction mixture was stirred 1.5 h at 90° C. After this time 2-chloro-N'-hydroxy-4-methylbenzenecarboximidamide (237 mg, 0.58 mmol, 45% purity) was added and the mixture was stirred for 6 h at 110° C. After cooling to RT, the mixture was diluted in 2 ml acetonitrile and purified by preparative HPLC (water/acetonitrile, 0.1% formic acid). After evaporation of acetonitrile from collected fractions the resulting solid in the aqueous fraction was filtered and dried overnight under vacuum to yield the title compound (120 mg, 55% of theory).

LC-MS (method 1B): RT=1.32 min, m/z=511 (M+H)+

Example 145A

Tert-butyl 4-{3-[3-(2-fluoro-4-methylphenyl)-1,2,4-oxadiazol-5-yl]-5-oxo-4,5-dihydropyrazolo[1,5-a]pyrimidin-7-yl}piperidine-1-carboxylate

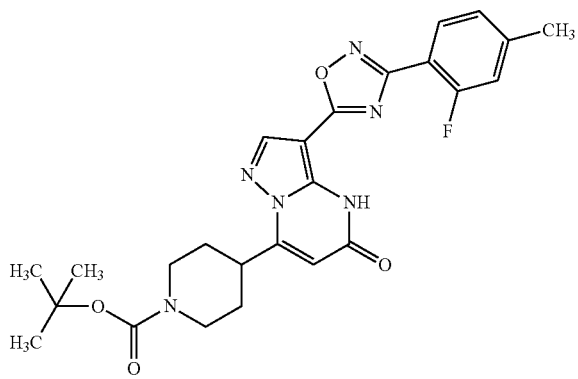 [SMILES: Cc1ccc(-c2noc(-c3cnn4c(C5CCN(C(=O)OC(C)(C)C)CC5)cc(=O)[nH]c34)n2)c(F)c1]

To a solution of compound 7-[1-(tert-butoxycarbonyl)piperidin-4-yl]-5-oxo-4,5-dihydropyrazolo[1,5-a]pyrimidine-3-carboxylic acid (150 mg, 0.41 mmol) in 3 ml dimethylformamide was added 1,1'-carbonyldiimidazole (134 mg, 0.83 mmol), DBU (148 mg, 0.97 mmol) and N,N-Diisopropylethylamin (107 mg, 0.83 mmol) and then the reaction mixture was stirred 1.5 h at 90° C. After this time 2-fluoro-N'-hydroxy-4-methylbenzenecarboximidamide (151 mg, 0.83 mmol, 92% purity) was added and the mixture was stirred for 3 h at 110° C. After cooling to RT, the mixture was diluted in 2 ml acetonitrile and purified by preparative HPLC (water/acetonitrile, 0.1% formic acid). After evaporation of acetonitrile from collected fractions the resulting solid in the aqueous fraction was filtered and dried overnight under vacuum to yield the title compound (113 mg, 53% of theory).

LC-MS (method 1B): RT=1.27 min, m/z=495 (M+H)+

Example 146A

Tert-butyl 4-{3-[3-(3-chloro-2-fluorophenyl)-1,2,4-oxadiazol-5-yl]-5-oxo-4,5-dihydropyrazolo[1,5-a]pyrimidin-7-yl}piperidine-1-carboxylate

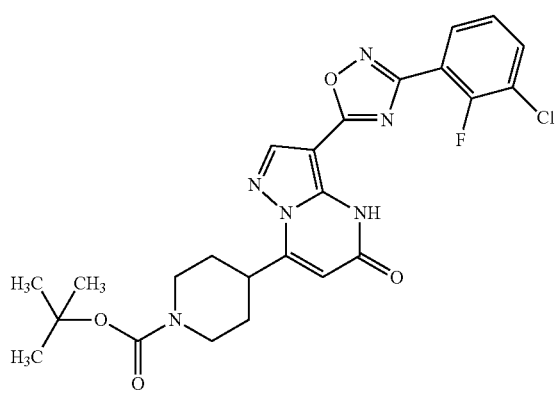 [SMILES: CC(C)(C)OC(=O)N1CCC(c2cc(=O)[nH]c3c(-c4nc(-c5cccc(Cl)c5F)no4)cnn23)CC1]

To a solution of compound 7-[1-(tert-butoxycarbonyl)piperidin-4-yl]-5-oxo-4,5-dihydropyrazolo[1,5-a]pyrimidine-3-carboxylic acid (1.23 g, 3.40 mmol) in 34 ml dimethylformamide was added 1,1'-carbonyldiimidazole (1.10 g, 6.81 mmol), DBU (1.22 mg, 8.00 mmol) and N,N-Diisopropylethylamin (880 mg, 6.81 mmol) and then the reaction mixture was stirred 2 h at 90° C. After this time 3-chloro-2-fluoro-N'-hydroxybenzenecarboximidamide (1.42 g, 6.81 mmol, 90% purity) was added and the mixture was stirred for 9 h at 110° C. After cooling to RT, the mixture was diluted in acetonitrile and purified by preparative HPLC (water/acetonitrile, 0.1% formic acid). After evaporation of the solvent product was obtained (88 mg, 5% of theory).

LC-MS (method 1B): RT=1.33 min, m/z=515 (M+H)+

Example 147A

Tert-butyl 4-{3-[3-(6-chloropyridin-2-yl)-1,2,4-oxadiazol-5-yl]-5-oxo-4,5-dihydropyrazolo[1,5-a]pyrimidin-7-yl}piperidine-1-carboxylate

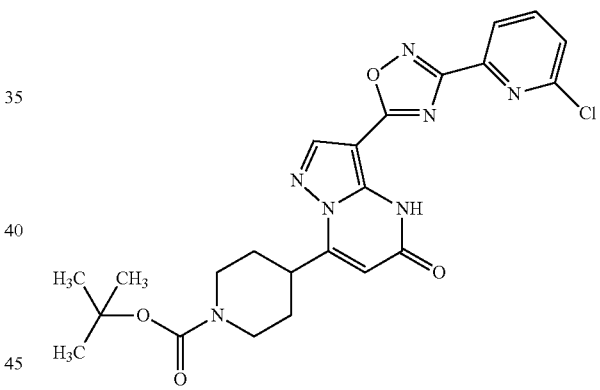

To a solution of compound 7-[1-(tert-butoxycarbonyl)piperidin-4-yl]-5-oxo-4,5-dihydropyrazolo[1,5-a]pyrimidine-3-carboxylic acid (150 mg, 0.41 mmol) in 4 ml dimethylformamide was added 1,1'-carbonyldiimidazole (134 mg, 0.83 mmol), DBU (148 mg, 0.97 mmol) and N,N-Diisopropylethylamin (107 mg, 0.83 mmol) and then the reaction mixture was stirred 3 h at 90° C. After this time 6-chloro-N'-hydroxypyridine-2-carboximidamide (142 mg, 0.83 mmol) was added and the mixture was stirred for 10 h at 110° C. After cooling to RT, the mixture was diluted in 2 ml acetonitrile and purified by preparative HPLC (water/acetonitrile, 0.1% formic acid). After evaporation of the solvent product was obtained (31 mg, 14% of theory).

LC-MS (method 1B): RT=1.10 min, m/z=498 (M+H)+

Example 148A

Tert-butyl 4-(3-{3-[3-fluoro-4-(trifluoromethyl)phenyl]-1,2,4-oxadiazol-5-yl}-5-oxo-4,5-dihydropyrazolo[1,5-a]pyrimidin-7-yl)piperidine-1-carboxylate

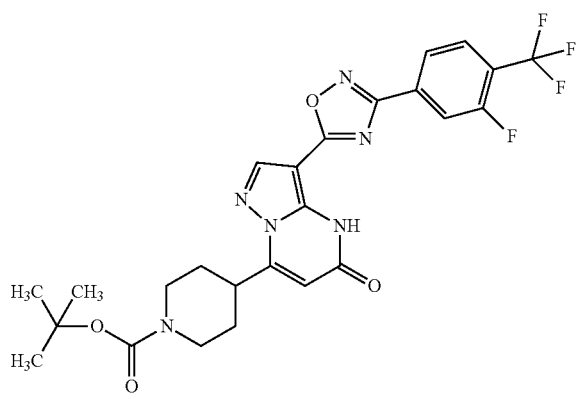 [SMILES: CC(C)(C)OC(=O)N1CCC(c2cc(=O)[nH]c3c(-c4nc(-c5ccc(C(F)(F)F)c(F)c5)no4)cnn23)CC1]

To a solution of compound 7-[1-(tert-butoxycarbonyl)piperidin-4-yl]-5-oxo-4,5-dihydropyrazolo[1,5-a]pyrimidine-3-carboxylic acid (100 mg, 0.28 mmol) in 2 ml dimethylformamide was added 1,1'-carbonyldiimidazole (89 mg, 0.55 mmol), DBU (99 mg, 0.65 mmol) and N,N-Diisopropylethylamin (71 mg, 0.55 mmol) and then the reaction mixture was stirred 1.5 h at 90° C. After this time 3-fluoro-N'-hydroxy-4-(trifluoromethyl)benzenecarboximidamide (134 mg, 0.55 mmol, 91% purity) was added and the mixture was stirred for 20 h at 110° C. After cooling to RT, the mixture was diluted in 3 ml acetonitrile and purified by preparative HPLC (water/acetonitrile, 0.1% formic acid). After evaporation of the solvent product was obtained (26 mg, 9% of theory, 50% purity).

LC-MS (method 1B): RT=1.32 min, m/z=549 (M+H)$^+$

Example 149A

Tert-butyl 4-(3-{3-[2-chloro-4-(trifluoromethyl)phenyl]-1,2,4-oxadiazol-5-yl}-5-oxo-4,5-dihydropyrazolo[1,5-a]pyrimidin-7-yl)piperidine-1-carboxylate

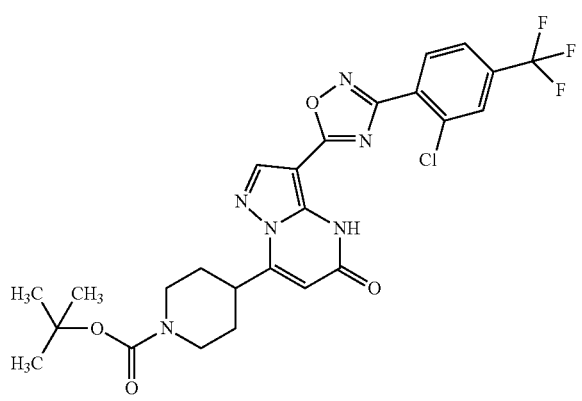 [SMILES: CC(C)(C)OC(=O)N1CCC(c2cc(=O)[nH]c3c(-c4nc(-c5ccc(C(F)(F)F)cc5Cl)no4)cnn23)CC1]

To a solution of compound 7-[1-(tert-butoxycarbonyl)piperidin-4-yl]-5-oxo-4,5-dihydropyrazolo[1,5-a]pyrimidine-3-carboxylic acid (100 mg, 0.28 mmol) in 2 ml dimethylformamide was added 1,1'-carbonyldiimidazole (89 mg, 0.55 mmol), DBU (99 mg, 0.65 mmol) and N,N-Diisopropylethylamin (71 mg, 0.55 mmol) and then the reaction mixture was stirred 1.5 h at 90° C. After this time 2-chloro-N'-hydroxy-4-(trifluoromethyl)benzenecarboximidamide (164 mg, 0.55 mmol, 80% purity) was added and the mixture was stirred for 11 h at 110° C. After cooling to RT, the mixture was diluted in 3 ml acetonitrile and purified by preparative HPLC (water/acetonitrile, 0.1% formic acid). After evaporation of the solvent product was obtained (62 mg, 40% of theory).

LC-MS (method 1B): RT=1.37 min, m/z=565 (M+H)$^+$

Example 150A

Tert-butyl 4-(3-{3-[2-fluoro-4-(trifluoromethyl)phenyl]-1,2,4-oxadiazol-5-yl}-5-oxo-4,5-dihydropyrazolo[1,5-a]pyrimidin-7-yl)piperidine-1-carboxylate

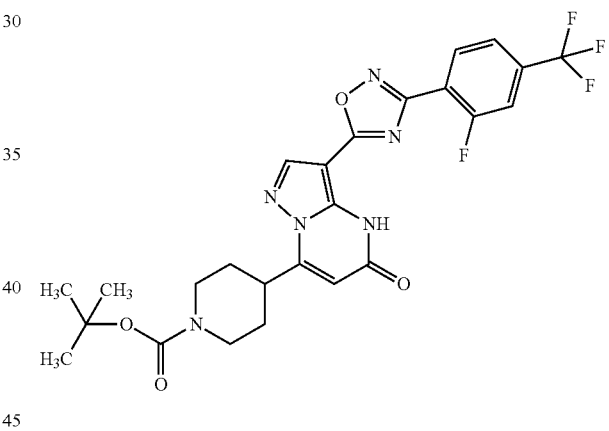

To a solution of compound 7-[1-(tert-butoxycarbonyl)piperidin-4-yl]-5-oxo-4,5-dihydropyrazolo[1,5-a]pyrimidine-3-carboxylic acid (100 mg, 0.28 mmol) in 2 ml dimethylformamide was added 1,1'-carbonyldiimidazole (89 mg, 0.55 mmol), DBU (99 mg, 0.65 mmol) and N,N-Diisopropylethylamin (71 mg, 0.55 mmol) and then the reaction mixture was stirred 1.5 h at 90° C. After this time 2-fluoro-N'-hydroxy-4-(trifluoromethyl)benzenecarboximidamide (134 mg, 0.55 mmol, 91% purity) was added and the mixture was stirred for 8 h at 110° C. After cooling to RT, the mixture was diluted in 3 ml acetonitrile and purified by preparative HPLC (water/acetonitrile, 0.1% formic acid). After evaporation of the solvent product was obtained (23 mg, 14% of theory, 91% purity).

LC-MS (method 1B): RT=1.14 min, m/z=548 (M+H)$^+$

Example 151A

Tert-butyl 4-{3-[3-(5-chloro-2-fluorophenyl)-1,2,4-oxadiazol-5-yl]-5-oxo-4,5-dihydropyrazolo[1,5-a]pyrimidin-7-yl}piperidine-1-carboxylate

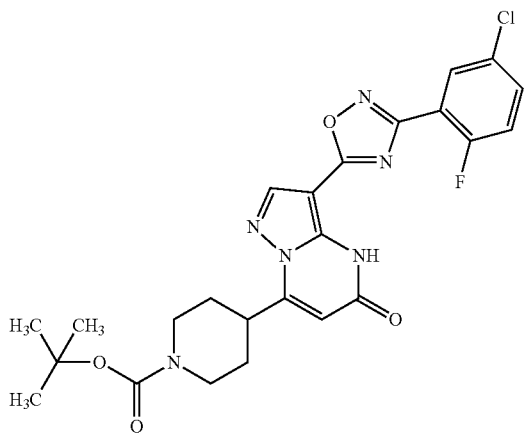 [SMILES: CC(C)(C)OC(=O)N1CCC(c2cc(=O)[nH]c3c(-c4nc(-c5cc(Cl)ccc5F)no4)cnn23)CC1]

To a solution of compound 7-[1-(tert-butoxycarbonyl)piperidin-4-yl]-5-oxo-4,5-dihydropyrazolo[1,5-a]pyrimidine-3-carboxylic acid (100 mg, 0.28 mmol) in 2 ml dimethylformamide was added 1,1'-carbonyldiimidazole (89 mg, 0.55 mmol), DBU (99 mg, 0.65 mmol) and N,N-Diisopropylethylamin (71 mg, 0.55 mmol) and then the reaction mixture was stirred 1.5 h at 90° C. After this time 5-chloro-2-fluoro-N'-hydroxybenzenecarboximidamide (122 mg, 0.55 mmol, 85% purity) was added and the mixture was stirred for 11 h at 110° C. After cooling to RT, the mixture was diluted in 2 ml acetonitrile and purified by preparative HPLC (water/acetonitrile, 0.1% formic acid). After evaporation of the solvent product was obtained (19 mg, 13% of theory).

LC-MS (method 1B): RT=1.32 min, m/z=515 (M+H)$^+$

Example 152A

Tert-butyl 4-{3-[3-(3-chloro-5-fluorophenyl)-1,2,4-oxadiazol-5-yl]-5-oxo-4,5-dihydropyrazolo[1,5-a]pyrimidin-7-yl}piperidine-1-carboxylate

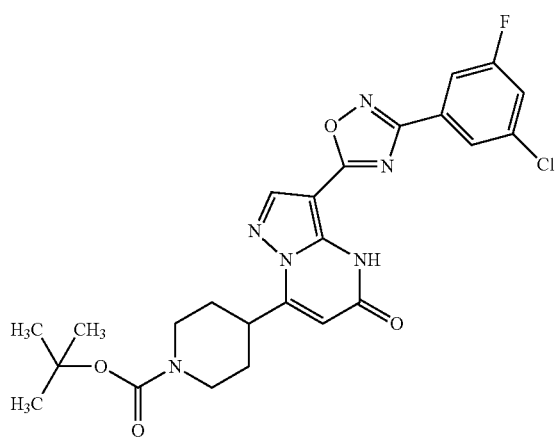 [SMILES: CC(C)(C)OC(=O)N1CCC(c2cc(=O)[nH]c3c(-c4nc(-c5cc(F)cc(Cl)c5)no4)cnn23)CC1]

To a solution of compound 7-[1-(tert-butoxycarbonyl)piperidin-4-yl]-5-oxo-4,5-dihydropyrazolo[1,5-a]pyrimidine-3-carboxylic acid (100 mg, 0.28 mmol) in 2 ml dimethylformamide was added 1,1'-carbonyldiimidazole (89 mg, 0.55 mmol), DBU (99 mg, 0.65 mmol) and N,N-Diisopropylethylamin (71 mg, 0.55 mmol) and then the reaction mixture was stirred 1.5 h at 90° C. After this time 3-chloro-5-fluoro-N'-hydroxybenzenecarboximidamide (115 mg, 0.55 mmol, 90% purity) was added and the mixture was stirred for 11 h at 110° C. After cooling to RT, the mixture was diluted in 2 ml acetonitrile and purified by preparative HPLC (water/acetonitrile, 0.1% formic acid). After evaporation of the solvent product was obtained (27 mg, 17% of theory, 93% purity).

LC-MS (method 1B): RT=1.31 min, m/z=513 (M–H)$^-$

Example 153A

Tert-butyl 4-(3-{3-[2-methyl-4-(trifluoromethyl)phenyl]-1,2,4-oxadiazol-5-yl}-5-oxo-4,5-dihydropyrazolo[1,5-a]pyrimidin-7-yl)piperidine-1-carboxylate

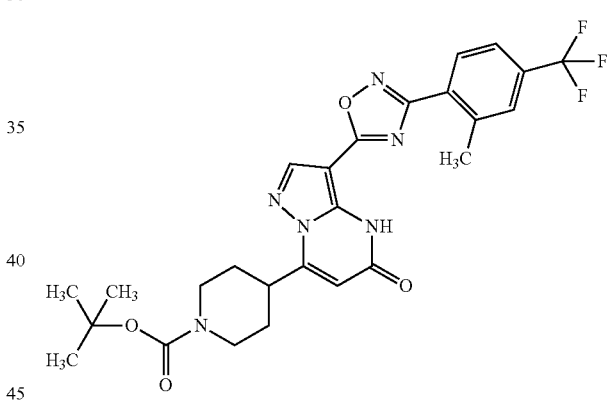

To a solution of compound 7-[1-(tert-butoxycarbonyl)piperidin-4-yl]-5-oxo-4,5-dihydropyrazolo[1,5-a]pyrimidine-3-carboxylic acid (194 mg, 0.54 mmol) in 4 ml dimethylformamide was added 1,1'-carbonyldiimidazole (174 mg, 1.07 mmol), DBU (191 mg, 1.26 mmol) and N,N-Diisopropylethylamin (138 mg, 1.07 mmol) and then the reaction mixture was stirred 4 h at 90° C. After this time N'-hydroxy-2-methyl-4-(trifluoromethyl)benzenecarboximidamide (234 mg, 1.07 mmol) was added and the mixture was stirred for 16 h at 110° C. After cooling to RT, the mixture was diluted in 2 ml acetonitrile and purified by preparative HPLC (water/acetonitrile, 0.1% formic acid). After evaporation of the solvent product was obtained (56 mg, 19% of theory).

LC-MS (method 1B): RT=1.36 min, m/z=545 (M+H)$^+$

Example 154A

Tert-butyl 4-{3-[3-(3-chloro-2-methylphenyl)-1,2,4-oxadiazol-5-yl]-5-oxo-4,5-dihydropyrazolo[1,5-a]pyrimidin-7-yl}piperidine-1-carboxylate

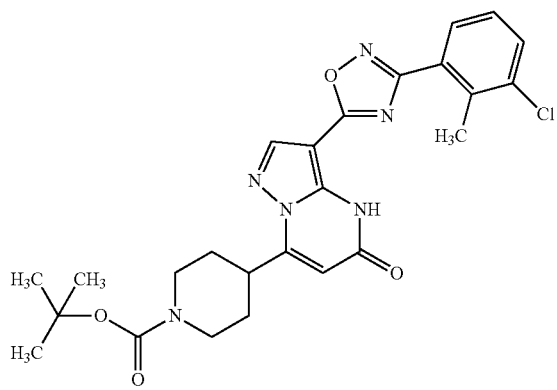 [SMILES: Cc1c(Cl)cccc1-c1noc(-c2cnn3c(C4CCN(C(=O)OC(C)(C)C)CC4)cc(=O)[nH]c23)n1]

To a solution of compound 7-[1-(tert-butoxycarbonyl)piperidin-4-yl]-5-oxo-4,5-dihydropyrazolo[1,5-a]pyrimidine-3-carboxylic acid (150 mg, 0.41 mmol) in 3 ml dimethylformamide was added 1,1'-carbonyldiimidazole (134 mg, 0.83 mmol), DBU (148 mg, 0.97 mmol) and N,N-Diisopropylethylamin (107 mg, 0.837 mmol) and then the reaction mixture was stirred 4 h at 90° C. After this time 3-chloro-N'-hydroxy-2-methylbenzenecarboximidamide (153 mg, 0.83 mmol) was added and the mixture was stirred for 16 h at 110° C. After cooling to RT, the mixture was diluted in 2 ml acetonitrile and purified by preparative HPLC (water/acetonitrile, 0.1% formic acid). After evaporation of the solvent product was obtained (101 mg, 48% of theory).

LC-MS (method 1B): RT=1.31 min, m/z=511 (M+H)$^+$

Example 155A

Tert-butyl 4-{3-[3-(5-chloro-2-methylphenyl)-1,2,4-oxadiazol-5-yl]-5-oxo-4,5-dihydropyrazolo[1,5-a]pyrimidin-7-yl}piperidine-1-carboxylate

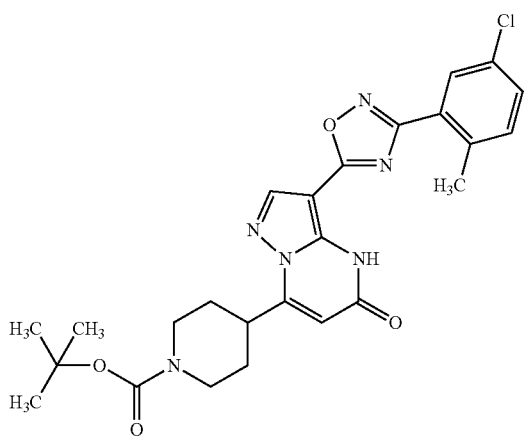 [SMILES: Cc1ccc(Cl)cc1-c1noc(-c2cnn3c(C4CCN(C(=O)OC(C)(C)C)CC4)cc(=O)[nH]c23)n1]

To a solution of compound 7-[1-(tert-butoxycarbonyl)piperidin-4-yl]-5-oxo-4,5-dihydropyrazolo[1,5-a]pyrimidine-3-carboxylic acid (170 mg, 0.47 mmol) in 3.4 ml dimethylformamide was added 1,1'-carbonyldiimidazole (152 mg, 0.94 mmol), DBU (168 mg, 1.10 mmol) and N,N-Diisopropylethylamin (121 mg, 0.94 mmol) and then the reaction mixture was stirred 4 h at 90° C. After this time 5-chloro-N'-hydroxy-2-methylbenzenecarboximidamide (173 mg, 0.94 mmol) was added and the mixture was stirred for 10 h at 110° C. After cooling to RT, the mixture was diluted in 2 ml acetonitrile and purified by preparative HPLC (water/acetonitrile, 0.1% formic acid). After evaporation of the solvent product was obtained (45 mg, 19% of theory).

LC-MS (method 1B): RT=1.33 min, m/z=511 (M+H)$^+$

Example 156A

Tert-butyl 4-{3-[3-(3-chloro-4-methoxyphenyl)-1,2,4-oxadiazol-5-yl]-5-oxo-4,5-dihydropyrazolo[1,5-a]pyrimidin-7-yl}piperidine-1-carboxylate

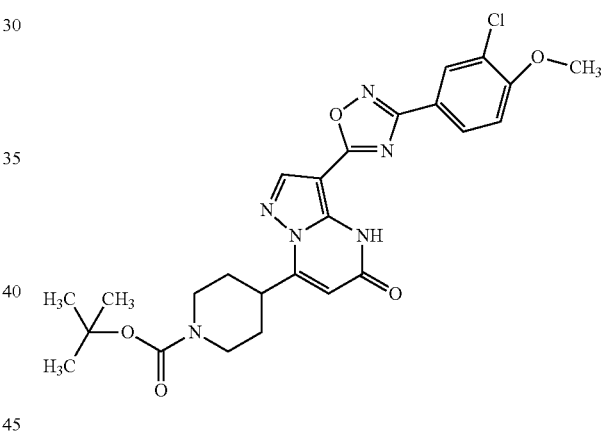

To a solution of compound 7-[1-(tert-butoxycarbonyl)piperidin-4-yl]-5-oxo-4,5-dihydropyrazolo[1,5-a]pyrimidine-3-carboxylic acid (62 mg, 0.17 mmol) in 2.4 ml dimethylformamide was added 1,1'-carbonyldiimidazole (55 mg, 0.34 mmol), DBU (61 mg, 0.40 mmol) and N,N-Diisopropylethylamin (44 mg, 0.34 mmol) and then the reaction mixture was stirred 3 h at 90° C. After this time 3-chloro-N'-hydroxy-4-methoxybenzenecarboximidamide (74 mg, 0.34 mmol, 93% purity) was added and the mixture was stirred for 10 h at 110° C. After cooling to RT, the mixture was diluted in 2 ml acetonitrile and purified by preparative HPLC (water/acetonitrile, 0.1% formic acid). After evaporation of the solvent product was obtained (37 mg, 41% of theory).

LC-MS (method 1B): RT=1.26 min, m/z=527 (M+H)$^+$

Example 157A

Tert-butyl 4-{3-[3-(2,3-dichlorophenyl)-1,2,4-oxadiazol-5-yl]-5-oxo-4,5-dihydropyrazolo[1,5-a]pyrimidin-7-yl}piperidine-1-carboxylate

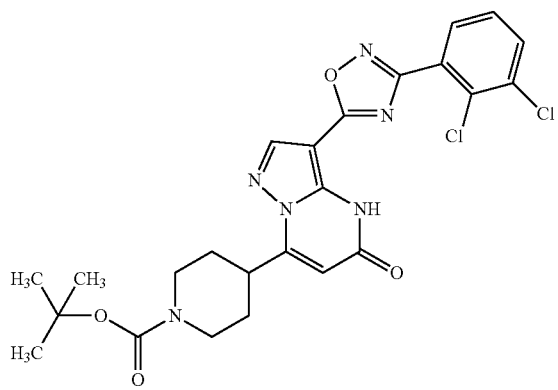 [SMILES: CC(C)(C)OC(=O)N1CCC(c2cc(=O)[nH]c3c(-c4nc(-c5cccc(Cl)c5Cl)no4)cnn23)CC1]

To a solution of compound 7-[1-(tert-butoxycarbonyl)piperidin-4-yl]-5-oxo-4,5-dihydropyrazolo[1,5-a]pyrimidine-3-carboxylic acid (100 mg, 0.28 mmol) in 2.8 ml dimethylformamide was added 1,1'-carbonyldiimidazole (89 mg, 0.55 mmol), DBU (99 mg, 0.65 mmol) and N,N-Diisopropylethylamin (71 mg, 0.55 mmol) and then the reaction mixture was stirred 3 h at 90° C. After this time 2,3-dichloro-N'-hydroxybenzenecarboximidamide (120 mg, 0.55 mmol, 95% purity) was added and the mixture was stirred for 10 h at 110° C. After cooling to RT, the solvent was evaporated and the crude purified by preparative HPLC (water/acetonitrile, 0.1% formic acid). After evaporation of the solvent product was obtained (63 mg, 43% of theory).

LC-MS (method 1B): RT=1.33 min, m/z=531 (M+H)$^+$

Example 158A

Tert-butyl 4-{3-[3-(3-chloro-4-fluorophenyl)-1,2,4-oxadiazol-5-yl]-5-oxo-4,5-dihydropyrazolo[1,5-a]pyrimidin-7-yl}piperidine-1-carboxylate

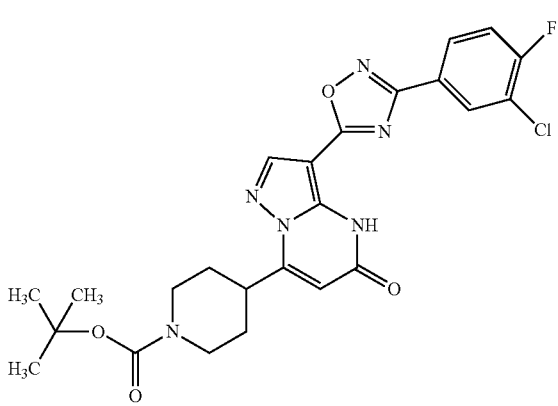 [SMILES: CC(C)(C)OC(=O)N1CCC(c2cc(=O)[nH]c3c(-c4nc(-c5ccc(F)c(Cl)c5)no4)cnn23)CC1]

To a solution of compound 7-[1-(tert-butoxycarbonyl)piperidin-4-yl]-5-oxo-4,5-dihydropyrazolo[1,5-a]pyrimidine-3-carboxylic acid (100 mg, 0.28 mmol) in 2.8 ml dimethylformamide was added 1,1'-carbonyldiimidazole (89 mg, 0.55 mmol), DBU (99 mg, 0.65 mmol) and N,N-Diisopropylethylamin (71 mg, 0.55 mmol) and then the reaction mixture was stirred 2 h at 90° C. After this time 3-chloro-4-fluoro-N'-hydroxybenzenecarboximidamide (104 mg, 0.55 mmol) was added and the mixture was stirred for 16 h at 110° C. After cooling to RT, the mixture was diluted in 2 ml acetonitrile and purified by preparative HPLC (water/acetonitrile, 0.1% formic acid). After evaporation of the solvent product was obtained (76 mg, 51% of theory).

LC-MS (method 1B): RT=1.34 min, m/z=513 (M+H)$^+$

Example 159A

Tert-butyl 4-(3-{3-[5-chloro-2-(trifluoromethyl)phenyl]-1,2,4-oxadiazol-5-yl}-5-oxo-4,5-dihydropyrazolo[1,5-a]pyrimidin-7-yl)piperidine-1-carboxylate

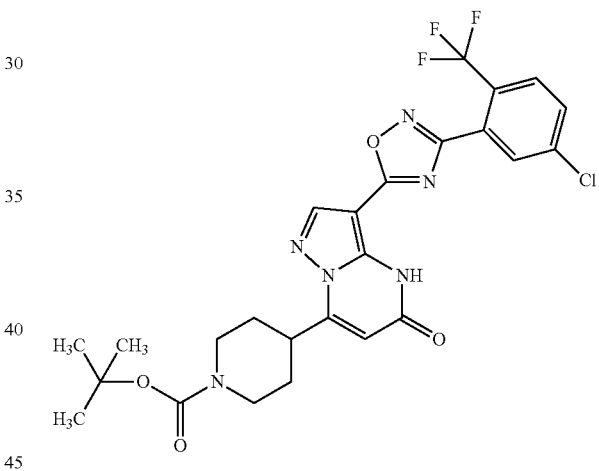

To a solution of compound 7-[1-(tert-butoxycarbonyl)piperidin-4-yl]-5-oxo-4,5-dihydropyrazolo[1,5-a]pyrimidine-3-carboxylic acid (100 mg, 0.28 mmol) in 2.8 ml dimethylformamide was added 1,1'-carbonyldiimidazole (89 mg, 0.55 mmol), DBU (99 mg, 0.65 mmol) and N,N-Diisopropylethylamin (71 mg, 0.55 mmol) and then the reaction mixture was stirred 2 h at 90° C. After this time 5-chloro-N'-hydroxy-2-(trifluoromethyl)benzenecarboximidamide (132 mg, 0.55 mmol) was added and the mixture was stirred for 16 h at 110° C. After cooling to RT, the mixture was diluted in 2 ml acetonitrile and purified by preparative HPLC (water/acetonitrile, 0.1% formic acid). After evaporation of the solvent product was obtained (54 mg, 34% of theory).

LC-MS (method 1B): RT=1.35 min, m/z=563 (M−H)$^-$

Example 160A

Tert-butyl 4-(5-oxo-3-{3-[6-(trifluoromethyl)pyridin-2-yl]-1,2,4-oxadiazol-5-yl}-4,5-dihydropyrazolo[1,5-a]pyrimidin-7-yl)piperidine-1-carboxylate

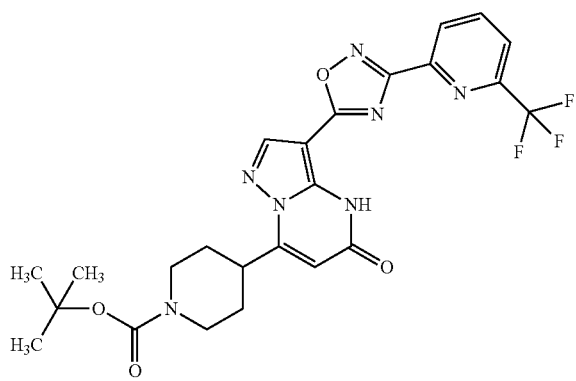 [SMILES: CC(C)(C)OC(=O)N1CCC(c2cc(=O)[nH]c3c(-c4nc(-c5cccc(C(F)(F)F)n5)no4)cnn23)CC1]

To a solution of compound 7-[1-(tert-butoxycarbonyl)piperidin-4-yl]-5-oxo-4,5-dihydropyrazolo[1,5-a]pyrimidine-3-carboxylic acid (151 mg, 0.42 mmol) in 4.2 ml dimethylformamide was added 1,1'-carbonyldiimidazole (135 mg, 0.83 mmol), DBU (149 mg, 0.98 mmol) and N,N-Diisopropylethylamin (108 mg, 0.83 mmol) and then the reaction mixture was stirred 2 h at 90° C. After this time N'-hydroxy-6-(trifluoromethyl)pyridine-2-carboximidamide (171 mg, 0.83 mmol) was added and the mixture was stirred for 16 h at 110° C. After cooling to RT, the mixture was diluted in 2 ml acetonitrile and purified by preparative HPLC (water/acetonitrile, 0.1% formic acid). After evaporation of the solvent product was obtained (111 mg, 50% of theory).

LC-MS (method 1B): RT=1.18 min, m/z=532 (M+H)$^+$

Example 161A

Tert-butyl 4-(5-oxo-3-{3-[4-(trifluoromethyl)pyridin-2-yl]-1,2,4-oxadiazol-5-yl}-4,5-dihydropyrazolo[1,5-a]pyrimidin-7-yl)piperidine-1-carboxylate

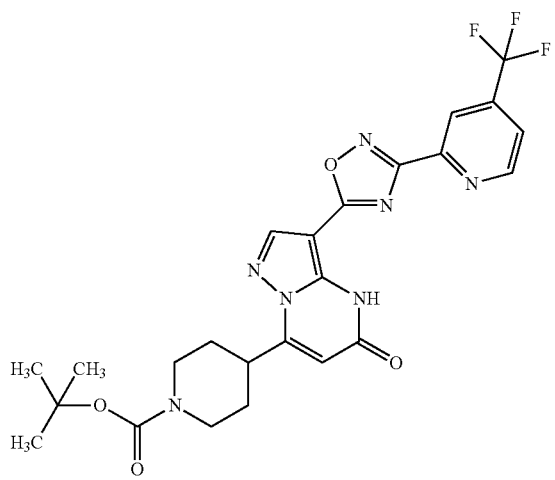 [SMILES: CC(C)(C)OC(=O)N1CCC(c2cc(=O)[nH]c3c(-c4nc(-c5cc(C(F)(F)F)ccn5)no4)cnn23)CC1]

To a solution of compound 7-[1-(tert-butoxycarbonyl)piperidin-4-yl]-5-oxo-4,5-dihydropyrazolo[1,5-a]pyrimidine-3-carboxylic acid (151 mg, 0.42 mmol) in 4.2 ml dimethylformamide was added 1,1'-carbonyldiimidazole (135 mg, 0.83 mmol), DBU (149 mg, 0.98 mmol) and N,N-Diisopropylethylamin (108 mg, 0.83 mmol) and then the reaction mixture was stirred 2 h at 90° C. After this time N'-hydroxy-4-(trifluoromethyl)pyridine-2-carboximidamide (171 mg, 0.83 mmol) was added and the mixture was stirred for 12 h at 110° C. After cooling to RT, the mixture was diluted in 2 ml acetonitrile and purified by preparative HPLC (water/acetonitrile, 0.1% formic acid). After evaporation of the solvent product was obtained (104 mg, 47% of theory).

LC-MS (method 1B): RT=1.20 min, m/z=532 (M+H)$^+$

Example 162A

Tert-butyl 4-{3-[3-(2-chloropyridin-3-yl)-1,2,4-oxadiazol-5-yl]-5-oxo-4,5-dihydropyrazolo[1,5-a]pyrimidin-7-yl}piperidine-1-carboxylate

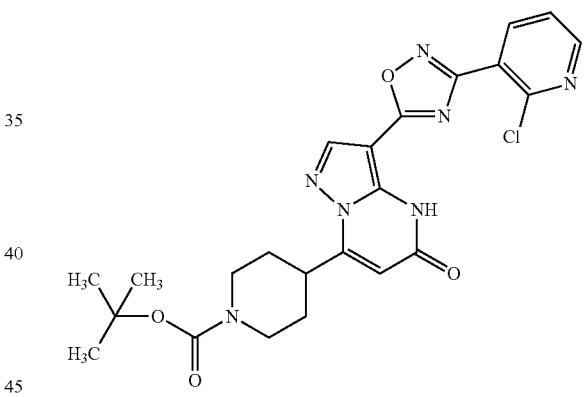

To a solution of compound 7-[1-(tert-butoxycarbonyl)piperidin-4-yl]-5-oxo-4,5-dihydropyrazolo[1,5-a]pyrimidine-3-carboxylic acid (151 mg, 0.42 mmol) in 3 ml dimethylformamide was added 1,1'-carbonyldiimidazole (135 mg, 0.83 mmol), DBU (149 mg, 0.98 mmol) and N,N-Diisopropylethylamin (108 mg, 0.83 mmol) and then the reaction mixture was stirred 1.5 h at 90° C. After this time 2-chloro-N'-hydroxypyridine-3-carboximidamide (157 mg, 0.83 mmol, 91% purity) was added and the mixture was stirred for 8 h at 110° C. After cooling to RT, the mixture was diluted in 2 ml acetonitrile and purified by preparative HPLC (water/acetonitrile, 0.1% formic acid). After evaporation of the solvent product was obtained (42 mg, 20% of theory).

LC-MS (method 1B): RT=1.10 min, m/z=498 (M+H)$^+$

Example 163A

Tert-butyl 4-(3-{3-[3-chloro-4-(trifluoromethoxy)phenyl]-1,2,4-oxadiazol-5-yl}-5-oxo-4,5-dihydropyrazolo[1,5-a]pyrimidin-7-yl)piperidine-1-carboxylate

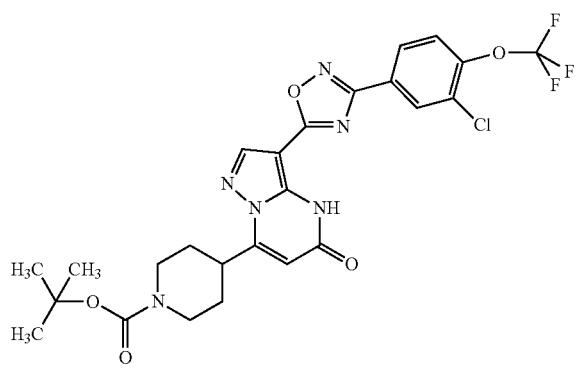 [SMILES: CC(C)(C)OC(=O)N1CCC(c2cc(=O)[nH]c3c(-c4nc(-c5ccc(OC(F)(F)F)c(Cl)c5)no4)cnn23)CC1]

To a solution of compound 7-[1-(tert-butoxycarbonyl)piperidin-4-yl]-5-oxo-4,5-dihydropyrazolo[1,5-a]pyrimidine-3-carboxylic acid (100 mg, 0.28 mmol) in 2.8 ml dimethylformamide was added 1,1'-carbonyldiimidazole (89 mg, 0.55 mmol), DBU (99 mg, 0.65 mmol) and N,N-Diisopropylethylamin (71 mg, 0.55 mmol) and then the reaction mixture was stirred 1.5 h at 90° C. After this time 3-chloro-N'-hydroxy-4-(trifluoromethoxy)benzenecarboximidamide (216 mg, 0.55 mmol, 65% purity) was added and the mixture was stirred for 21 h at 110° C. After cooling to RT, the mixture was diluted in 2 ml acetonitrile and purified by preparative HPLC (water/acetonitrile, 0.1% formic acid). After evaporation of the solvent product was obtained (61 mg, 38% of theory).

LC-MS (method 1B): RT=1.41 min, m/z=581 (M+H)$^+$

Example 164A

Tert-butyl 4-(3-{3-[2,6-dichloro-4-(trifluoromethyl)phenyl]-1,2,4-oxadiazol-5-yl}-5-oxo-4,5-dihydropyrazolo[1,5-a]pyrimidin-7-yl)piperidine-1-carboxylate

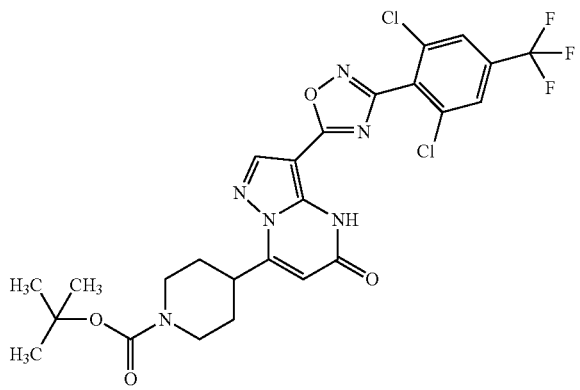 [SMILES: CC(C)(C)OC(=O)N1CCC(c2cc(=O)[nH]c3c(-c4nc(-c5c(Cl)cc(C(F)(F)F)cc5Cl)no4)cnn23)CC1]

To a solution of compound 7-[1-(tert-butoxycarbonyl)piperidin-4-yl]-5-oxo-4,5-dihydropyrazolo[1,5-a]pyrimidine-3-carboxylic acid (48 mg, 0.13 mmol) in 1.0 ml dimethylformamide was added 1,1'-carbonyldiimidazole (43 mg, 0.26 mmol), DBU (47 mg, 0.31 mmol) and N,N-Diisopropylethylamin (34 mg, 0.26 mmol) and then the reaction mixture was stirred 2.5 h at 90° C. After this time 2,6-dichloro-N'-hydroxy-4-(trifluoromethyl)benzenecarboximidamide (372 mg, 0.26 mmol, 19% purity) was added and the mixture was stirred for 16 h at 110° C. and then stayed at room temperature over the weekend. The solvent was evaporated and the crude was purified by preparative HPLC (water/acetonitrile, 0.1% formic acid). After evaporation of the solvent product was obtained (11 mg, 14% of theory).

LC-MS (method 1B): RT=1.32 min, m/z=599 (M+H)$^+$

Example 165A

Tert-butyl 4-{3-[3-(3,5-dichlorophenyl)-1,2,4-oxadiazol-5-yl]-5-oxo-4,5-dihydropyrazolo[1,5-a]pyrimidin-7-yl}piperidine-1-carboxylate

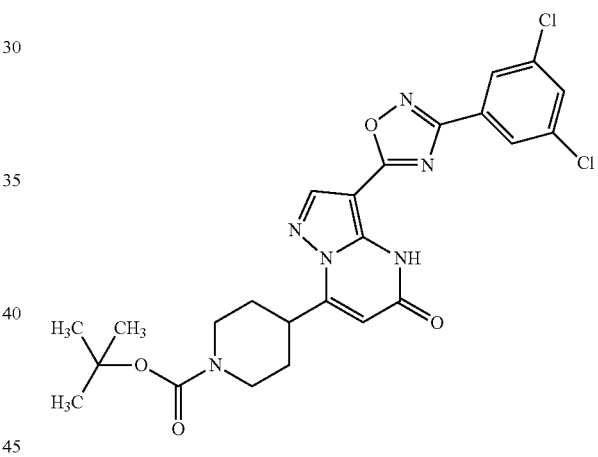

To a solution of compound 7-[1-(tert-butoxycarbonyl)piperidin-4-yl]-5-oxo-4,5-dihydropyrazolo[1,5-a]pyrimidine-3-carboxylic acid (55 mg, 0.15 mmol) in 1.5 ml dimethylformamide was added 1,1'-carbonyldiimidazole (49 mg, 0.31 mmol), DBU (55 mg, 0.36 mmol) and N,N-Diisopropylethylamin (39 mg, 0.31 mmol) and then the reaction mixture was stirred 2.5 h at 90° C. After this time 3,5-dichloro-N'-hydroxybenzenecarboximidamide (108 mg, 0.30 mmol, 58% purity) was added and the mixture was stirred for 16 h at 110° C. and then stayed at room temperature over the weekend. The solvent was evaporated and the crude was purified by preparative HPLC (water/acetonitrile, 0.1% formic acid). After evaporation of the solvent product was obtained (20 mg, 25% of theory).

LC-MS (method 3B): RT=2.91 min, m/z=531 (M+H)$^+$

Example 166A

Tert-butyl 4-(3-{3-[2,4-bis(trifluoromethyl)phenyl]-1,2,4-oxadiazol-5-yl}-5-oxo-4,5-dihydropyrazolo[1,5-a]pyrimidin-7-yl)piperidine-1-carboxylate

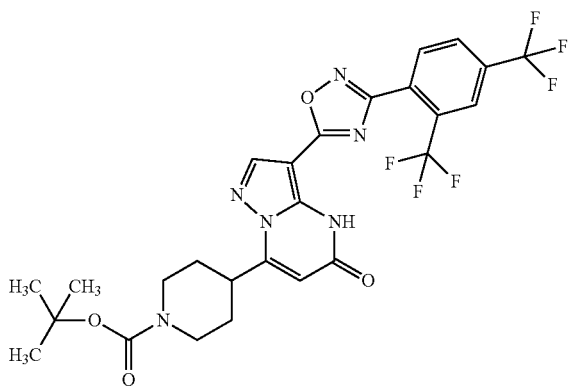 [SMILES: CC(C)(C)OC(=O)N1CCC(c2cc(=O)[nH]c3c(-c4nc(-c5ccc(C(F)(F)F)cc5C(F)(F)F)no4)cnn23)CC1]

To a solution of compound 7-[1-(tert-butoxycarbonyl)piperidin-4-yl]-5-oxo-4,5-dihydropyrazolo[1,5-a]pyrimidine-3-carboxylic acid (187 mg, 0.52 mmol) in 3.7 ml dimethylformamide was added 1,1'-carbonyldiimidazole (167 mg, 1.03 mmol), DBU (185 mg, 1.21 mmol) and N,N-Diisopropylethylamin (133 mg, 1.03 mmol) and then the reaction mixture was stirred 2.5 h at 90° C. After this time N'-hydroxy-2,4-bis(trifluoromethyl)benzenecarboximidamide (372 mg, 0.26 mmol) was added and the mixture was stirred for 16 h at 110° C. and then stayed at room temperature over the weekend. The solvent was evaporated and the crude was purified by preparative HPLC (water/acetonitrile, 0.1% formic acid). After evaporation of the solvent the product was crystallized with acetonitrile (21 mg, 7% of theory).

LC-MS (method 1B): RT=1.31 min, m/z=599 (M+H)$^+$

Example 167A

Tert-butyl 4-{3-[3-(3-chlorophenyl)-1,2,4-oxadiazol-5-yl]-5-oxo-4,5-dihydropyrazolo[1,5-a]pyrimidin-7-yl}piperidine-1-carboxylate

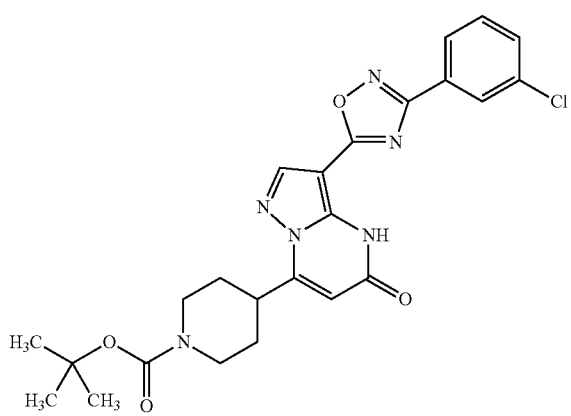 [SMILES: CC(C)(C)OC(=O)N1CCC(c2cc(=O)[nH]c3c(-c4nc(-c5cccc(Cl)c5)no4)cnn23)CC1]

To a solution of compound 7-[1-(tert-Butoxycarbonyl)piperidin-4-yl]-5-oxo-4,5-dihydropyrazolo[1,5-a]pyrimidine-3-carboxylic acid (106 mg, 0.29 mmol) in 3 ml dimethylformamide was added 1,1'-carbonyldiimidazole (95 mg, 0.59 mmol), N,N-diisopropylethylamine (76 mg, 0.59 mmol), 1,8-Diazabicyclo(5.4.0)undec-7-en (105 mg, 0.70 mmol) and then the reaction mixture was stirred 4 h at 90° C. After this time 3-chloro-N'-hydroxybenzenecarboximidamide (100 mg, 0.59 mmol) was added and the mixture was stirred for 16 h at 110° C. After cooling to RT, the mixture was diluted with 2 ml acetonitrile and purified by preparative HPLC (Method 1A) to yield the title compound (66 mg, 45% of theory).

LC-MS (Method 1B): Rt=1.34 min, MS (ESIPos): m/z=497 [M+H]$^+$

Example 168A

Tert-butyl 4-{3-[3-(4-methoxy-2-methylphenyl)-1,2,4-oxadiazol-5-yl]-5-oxo-4,5-dihydropyrazolo[1,5-a]pyrimidin-7-yl}piperidine-1-carboxylate

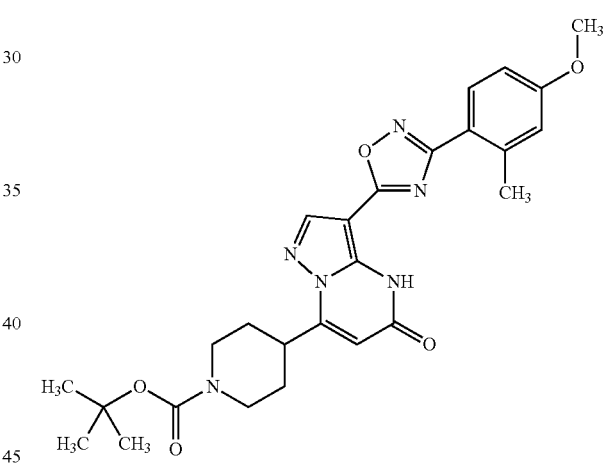

To a solution of compound 7-[1-(tert-Butoxycarbonyl)piperidin-4-yl]-5-oxo-4,5-dihydropyrazolo[1,5-a]pyrimidine-3-carboxylic acid (101 mg, 0.28 mmol) in 3 ml dimethylformamide was added 1,1'-carbonyldiimidazole (90 mg, 0.56 mmol) and N,N-diisopropylethylamine (72 mg, 0.56 mmol), 1,8-Diazabicyclo(5.4.0)undec-7-en (99 mg, 0.65 mmol) and then the reaction mixture was stirred 4 h at 90° C. After this time N'-hydroxy-4-methoxy-2-methylbenzenecarboximidamide (100 mg, 0.56 mmol) was added and the mixture was stirred for 16 h at 110° C. After cooling to RT, the mixture was diluted with 2 ml acetonitrile and purified by preparative HPLC (Method 1A) to yield the title compound (67 mg, 48% of theory).

LC-MS (Method 1B): Rt=1.17 min, MS (ESIPos): m/z=507 [M+H]$^+$

Example 169A

Tert-butyl 4-(5-oxo-3-{3-[2-(trifluoromethoxy)phenyl]-1,2,4-oxadiazol-5-yl}-4,5-dihydropyrazolo[1,5-a]pyrimidin-7-yl)piperidine-1-carboxylate

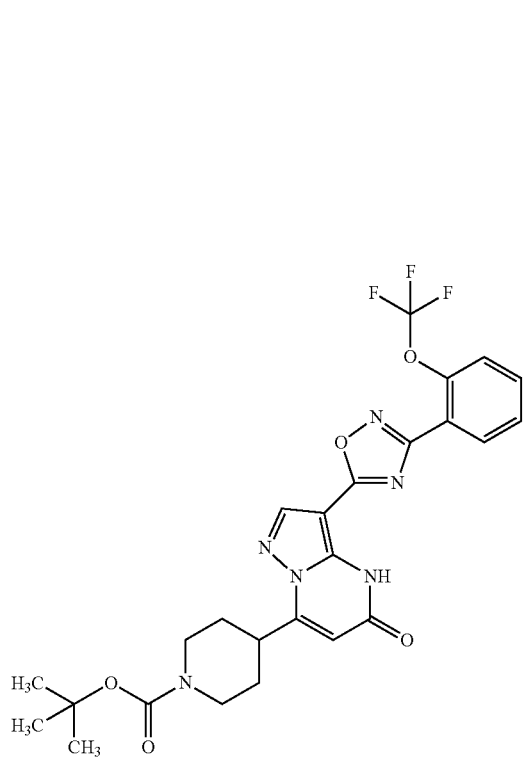 [SMILES: CC(C)(C)OC(=O)N1CCC(c2cc(=O)[nH]c3c(-c4nc(-c5ccccc5OC(F)(F)F)no4)cnn23)CC1]

To a solution of compound 7-[1-(tert-Butoxycarbonyl)piperidin-4-yl]-5-oxo-4,5-dihydropyrazolo[1,5-a]pyrimidine-3-carboxylic acid (82 mg, 0.23 mmol) in 3 ml dimethylformamide was added 1,1'-carbonyldiimidazole (74 mg, 0.45 mmol) and N,N-diisopropylethylamine (59 mg, 0.45 mmol), 1,8-Diazabicyclo(5.4.0)undec-7-en (81 mg, 0.53 mmol) and then the reaction mixture was stirred 4 h at 90° C. After this time N'-hydroxy-2-(trifluoromethoxy)benzenecarboximidamide (100 mg, 0.45 mmol) was added and the mixture was stirred for 16 h at 110° C. After cooling to RT, the mixture was diluted with 2 ml acetonitrile and purified by preparative HPLC (Method 1A) to yield the title compound (57 mg, 46% of theory).

LC-MS (Method 1B): Rt=1.33 min, MS (ESIPos): m/z=547 [M+H]$^+$

Example 170A

Tert-butyl 4-{3-[3-(4-methoxyphenyl)-1,2,4-oxadiazol-5-yl]-5-oxo-4,5-dihydropyrazolo[1,5-a]pyrimidin-7-yl}piperidine-1-carboxylate To a solution of compound 7-[1-(tert-Butoxycarbonyl)piperidin-4-yl]-5-oxo-4,5-dihydropyrazolo[1,5-a]pyrimidine-3-carboxylic acid (109 mg, 0.30 mmol) in 3 ml dimethylformamide was added 1,1'-carbonyldiimidazole (98 mg, 0.60 mmol) and N,N-diisopropylethylamine (98 mg, 0.60 mmol), 1,8-Diazabicyclo(5.4.0)undec-7-en (108 mg, 0.71 mmol) and then the reaction mixture was stirred 4 h at 90° C. After this time N'-hydroxy-4-methoxybenzenecarboximidamide (100 mg, 0.60 mmol) was added and the mixture was stirred for 16 h at 110° C. After cooling to RT, the mixture was diluted with 2 ml acetonitrile and purified by preparative HPLC (Method 1A) to yield the title compound (46 mg, 31% of theory).

LC-MS (Method 1B): Rt=1.24 min, MS (ESIPos): m/z=493 [M+H]$^+$

Example 171A

Tert-butyl 4-{3-[3-(4-chlorophenyl)-1,2,4-oxadiazol-5-yl]-5-oxo-4,5-dihydropyrazolo[1,5-a]pyrimidin-7-yl}piperidine-1-carboxylate

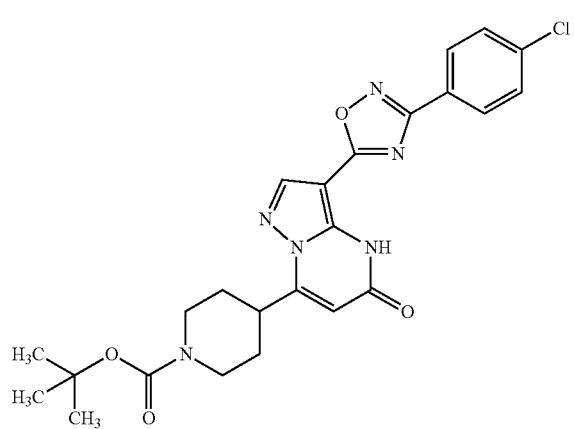 [SMILES: CC(C)(C)OC(=O)N1CCC(c2cc(=O)[nH]c3c(-c4nc(-c5ccc(Cl)cc5)no4)cnn23)CC1]

To a solution of compound 7-[1-(tert-Butoxycarbonyl) piperidin-4-yl]-5-oxo-4,5-dihydropyrazolo[1,5-a]pyrimidine-3-carboxylic acid (106 mg, 0.29 mmol) in 3 ml dimethylformamide was added 1,1'-carbonyldiimidazole (95 mg, 0.59 mmol) and N,N-diisopropylethylamine (76 mg, 0.59 mmol), 1,8-Diazabicyclo(5.4.0)undec-7-en (105 mg, 0.69 mmol) and then the reaction mixture was stirred 4 h at 90° C. After this time 4-chloro-N'-hydroxybenzenecarboximidamide (100 mg, 0.60 mmol) was added and the mixture was stirred for 16 h at 110° C. After cooling to RT, the mixture was diluted with 2 ml acetonitrile and purified by preparative HPLC (Method 1A) to yield the title compound (54 mg, 37% of theory).

LC-MS (Method 1B): Rt=1.34 min, MS (ESIPos): m/z=497 [M+H]$^+$

Example 172A

Tert-butyl 4-{3-[3-(2,4-difluorophenyl)-1,2,4-oxadiazol-5-yl]-5-oxo-4,5-dihydropyrazolo[1,5-a]pyrimidin-7-yl}piperidine-1-carboxylate

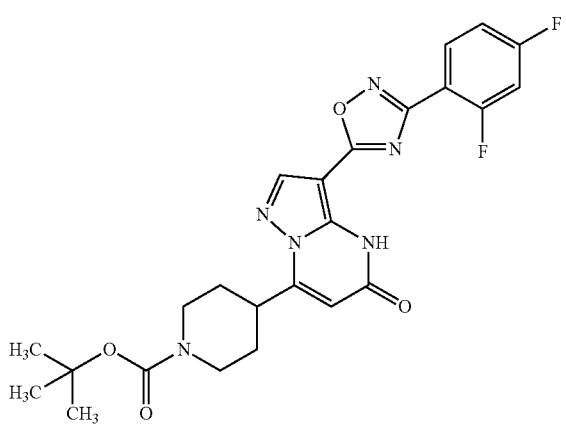 [SMILES: CC(C)(C)OC(=O)N1CCC(c2cc(=O)[nH]c3c(-c4nc(-c5ccc(F)cc5F)no4)cnn23)CC1]

To a solution of compound 7-[1-(tert-Butoxycarbonyl) piperidin-4-yl]-5-oxo-4,5-dihydropyrazolo[1,5-a]pyrimidine-3-carboxylic acid (105 mg, 0.29 mmol) in 3 ml dimethylformamide was added 1,1'-carbonyldiimidazole (94 mg, 0.58 mmol) and N,N-diisopropylethylamine (75 mg, 0.58 mmol), 1,8-Diazabicyclo(5.4.0)undec-7-en (104 mg, 0.68 mmol) and then the reaction mixture was stirred 4 h at 90° C. After this time 2,4-difluoro-N'-hydroxybenzenecarboximidamide (100 mg, 0.58 mmol) was added and the mixture was stirred for 16 h at 110° C. After cooling to RT, the mixture was diluted with 2 ml acetonitrile and purified by preparative HPLC (Method 1A) to yield the title compound (39 mg, 27% of theory).

LC-MS (Method 1B): Rt=1.24 min, MS (ESIPos): m/z=499 [M+H]$^+$

Example 173A

Tert-butyl 4-{3-[3-(2-fluorophenyl)-1,2,4-oxadiazol-5-yl]-5-oxo-4,5-dihydropyrazolo[1,5-a]pyrimidin-7-yl}piperidine-1-carboxylate

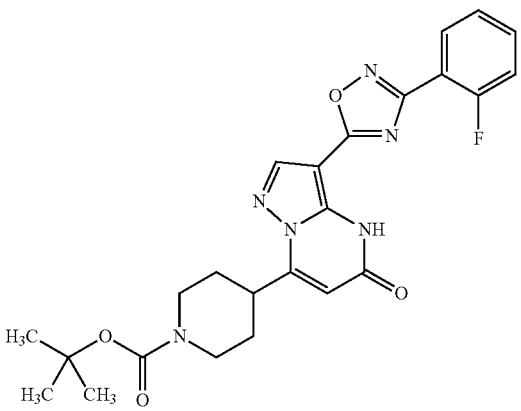 [SMILES: CC(C)(C)OC(=O)N1CCC(c2cc(=O)[nH]c3c(-c4nc(-c5ccccc5F)no4)cnn23)CC1]

To a solution of compound 7-[1-(tert-Butoxycarbonyl) piperidin-4-yl]-5-oxo-4,5-dihydropyrazolo[1,5-a]pyrimidine-3-carboxylic acid (118 mg, 0.32 mmol) in 3 ml dimethylformamide was added 1,1'-carbonyldiimidazole (105 mg, 0.65 mmol) and N,N-diisopropylethylamine (84 mg, 0.65 mmol), 1,8-Diazabicyclo(5.4.0)undec-7-en (116 mg, 0.76 mmol) and then the reaction mixture was stirred 4 h at 90° C. After this time 2-fluoro-N'-hydroxybenzenecarboximidamide (100 mg, 0.65 mmol) was added and the mixture was stirred for 16 h at 110° C. After cooling to RT, the mixture was diluted with 2 ml acetonitrile and purified by preparative HPLC (Method 1A) to yield the title compound (63 mg, 38% of theory).

LC-MS (Method 1B): Rt=1.21 min, MS (ESIPos): m/z=481 [M+H]$^+$

Example 174A

Tert-butyl 4-{3-[3-(2-methoxyphenyl)-1,2,4-oxadiazol-5-yl]-5-oxo-4,5-dihydropyrazolo[1,5-a]pyrimidin-7-yl}piperidine-1-carboxylate

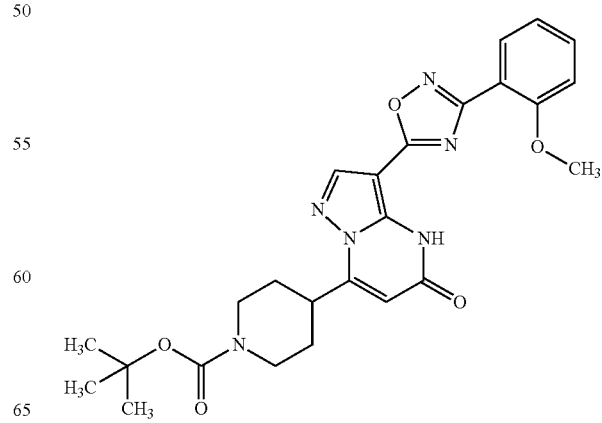

To a solution of compound 7-[1-(tert-Butoxycarbonyl)piperidin-4-yl]-5-oxo-4,5-dihydropyrazolo[1,5-a]pyrimidine-3-carboxylic acid (109 mg, 0.30 mmol) in 3 ml dimethylformamide was added 1,1'-carbonyldiimidazole (98 mg, 0.60 mmol) and N,N-diisopropylethylamine (78 mg, 0.60 mmol), 1,8-Diazabicyclo(5.4.0)undec-7-en (108 mg, 0.71 mmol) and then the reaction mixture was stirred 4 h at 90° C. After this time N'-hydroxy-2-methoxybenzenecarboximidamide (100 mg, 0.60 mmol) was added and the mixture was stirred for 16 h at 110° C. After cooling to RT, the mixture was diluted with 2 ml acetonitrile and purified by preparative HPLC (Method 1A) to yield the title compound (79 mg, 53% of theory).

LC-MS (Method 1B): Rt=1.16 min, MS (ESIPos): m/z=493 [M+H]$^+$

Example 175A

4-[4'-(trifluoromethyl)biphenyl-4-yl]-1H-pyrazol-5-amine

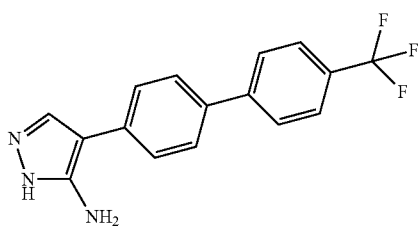 [SMILES: Nc1[nH]ncc1-c1ccc(-c2ccc(C(F)(F)F)cc2)cc1]

Following the General Procedure 2A, a mixture of [4-(trifluoromethyl)phenyl]boronic acid (324 mg, 1.70 mmol), 4-(4-chlorophenyl)-1H-pyrazol-5-amine (300 mg, 1.55 mmol), XPhos precatalyst (131 mg, 0.16 mmol), degassed dioxane (15 ml) and degassed aqueous 1M K$_3$PO$_4$ solution (5.4 ml) were stirred at 100° C. for 16 h. Preparative HPLC (Method 1A) yielded the title compound (101 mg, 22% of theory).

LC-MS (Method 1B): Rt=0.96 min, MS (ESIPos): m/z=304 [M+H]$^+$

Example 176A

Tert-butyl 4-{5-oxo-3-[4'-(trifluoromethyl)biphenyl-4-yl]-4,5-dihydropyrazolo[1,5-a]pyrimidin-7-yl}piperidine-1-carboxylate

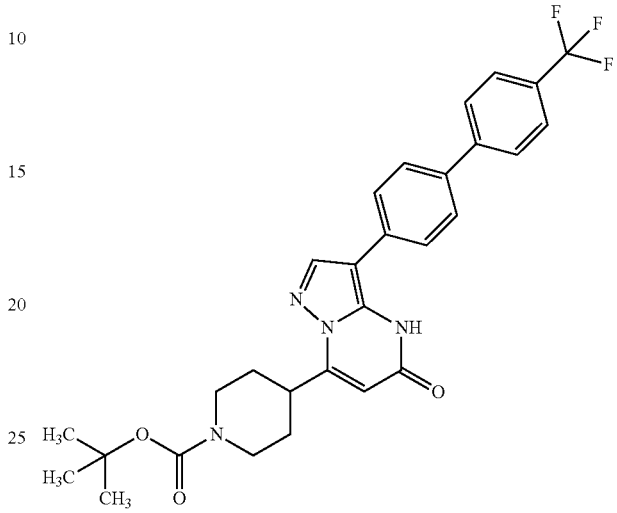

According to General Procedure 1A, tert-butyl 4-[(2,2-dimethyl-4,6-dioxo-1,3-dioxan-5-yl)carbonyl]piperidine-1-carboxylate (117 mg, 0.33 mmol) and 4-[4'-(trifluoromethyl)biphenyl-4-yl]-1H-pyrazol-5-amine (100 mg, 0.33 mmol) were reacted to yield the title compound (36 mg, 20% of theory).

LC-MS (Method 1B): Rt=1.32 min, MS (ESINeg): m/z=537 [M−H]$^-$

Example 177A

4-[4'-(trifluoromethyl)biphenyl-3-yl]-1H-pyrazol-5-amine

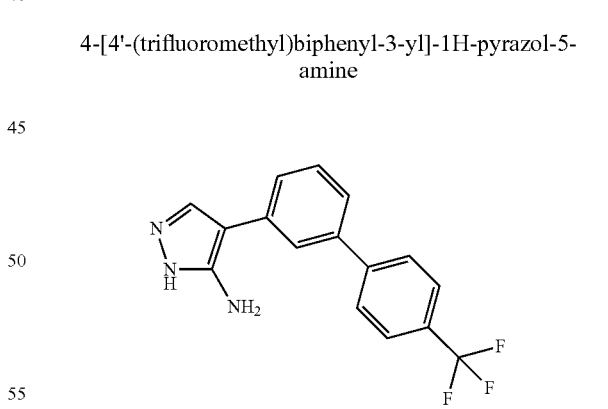

Following the General Procedure 2A, a mixture of [4-(trifluoromethyl)phenyl]boronic acid (202 mg, 1.06 mmol), 4-(3-bromophenyl)-1H-pyrazol-5-amine (230 mg, 0.97 mmol), XPhos precatalyst (82 mg, 0.10 mmol), degassed dioxane (10 ml) and degassed aqueous 1M K$_3$PO$_4$ solution (3.4 ml) were stirred at 100° C. for 16 h. Preparative HPLC (Method 1A) yielded the title compound (156 mg, 53% of theory).

LC-MS (Method 1B): Rt=0.95 min, MS (ESIPos): m/z=304 [M+H]$^+$

Example 178A

Tert-butyl 4-{5-oxo-3-[4'-(trifluoromethyl)biphenyl-3-yl]-4,5-dihydropyrazolo[1,5-a]pyrimidin-7-yl}piperidine-1-carboxylate

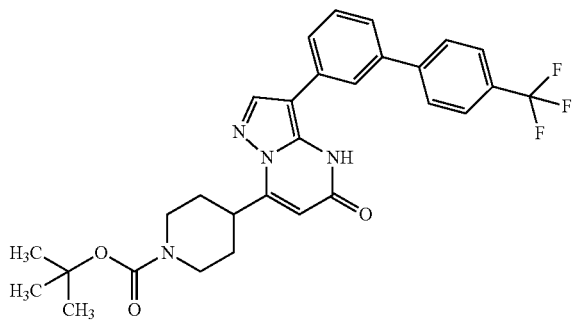 [SMILES: CC(C)(C)OC(=O)N1CCC(c2cc(=O)[nH]c3c(-c4cccc(-c5ccc(C(F)(F)F)cc5)c4)cnn23)CC1]

According to General Procedure 1A, tert-butyl 4-[(2,2-dimethyl-4,6-dioxo-1,3-dioxan-5-yl)carbonyl]piperidine-1-carboxylate (276 mg, 0.78 mmol) and 4-[4'-(trifluoromethyl)biphenyl-3-yl]-1H-pyrazol-5-amine (157 mg, 0.52 mmol) were reacted to yield the title compound (166 mg, 40% of theory).

LC-MS (Method 1B): Rt=1.32 min, MS (ESINeg): m/z=537 [M−H]−

Example 179A

4-[4-(3-chlorophenyl)-1,3-thiazol-2-yl]-1H-pyrazol-5-amine

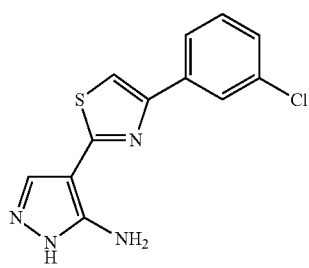 [SMILES: Nc1[nH]ncc1-c1nc(-c2cccc(Cl)c2)cs1]

5-amino-1H-pyrazole-4-carbothioamide (200 mg, 1.41 mmol) and 2-bromo-1-(3-chlorophenyl)ethanone (328 mg, 1.41 mmol) were dissolved in ethanol (4 mL) and heated under reflux for 6 h. Preparative HPLC (Method 1A) yielded the title compound (155 mg, 40% of theory).

LC-MS (Method 1B): Rt=0.92 min, MS (ESIPos): m/z=277 [M+H]+

Example 180A

Tert-butyl 4-{3-[4-(3-chlorophenyl)-1,3-thiazol-2-yl]-5-oxo-4,5-dihydropyrazolo[1,5-a]pyrimidin-7-yl}piperidine-1-carboxylate

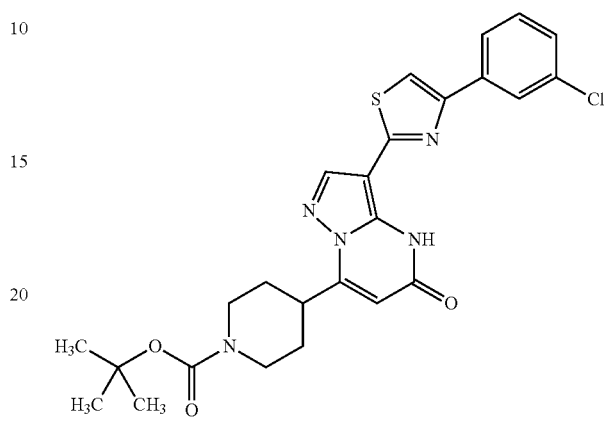

According to General Procedure 1A, tert-butyl 4-[(2,2-dimethyl-4,6-dioxo-1,3-dioxan-5-yl)carbonyl]piperidine-1-carboxylate (299 mg, 0.84 mmol) and 4-[4-(3-chlorophenyl)-1,3-thiazol-2-yl]-1H-pyrazol-5-amine (155 mg, 0.56 mmol) were reacted to yield the title compound (173 mg, 40% of theory).

LC-MS (Method 1B): Rt=1.34 min, MS (ESIPos): m/z=512 [M+H]+

Example 181A

4-{4-[4-(trifluoromethyl)phenyl]-1,3-thiazol-2-yl}-1H-pyrazol-5-amine

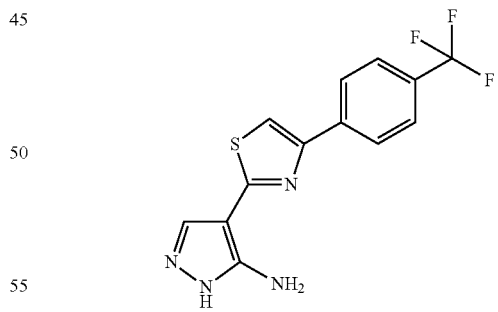

5-amino-1H-pyrazole-4-carbothioamide (200 mg, 1.41 mmol) and 2-bromo-1-[4-(trifluoromethyl)phenyl]ethanone (376 mg, 1.41 mmol) were dissolved in ethanol (4 mL) and heated under reflux for 6 h. Preparative HPLC (Method 1A) yielded the title compound (342 mg, 78% of theory).

LC-MS (Method 1B): Rt=0.97 min, MS (ESIPos): m/z=311 [M+H]+

Example 182A tert-butyl 4-(5-oxo-3-{4-[4-(trifluoromethyl)phenyl]-1,3-thiazol-2-yl}-4,5-dihydropyrazolo[1,5-a]pyrimidin-7-yl)piperidine-1-carboxylate

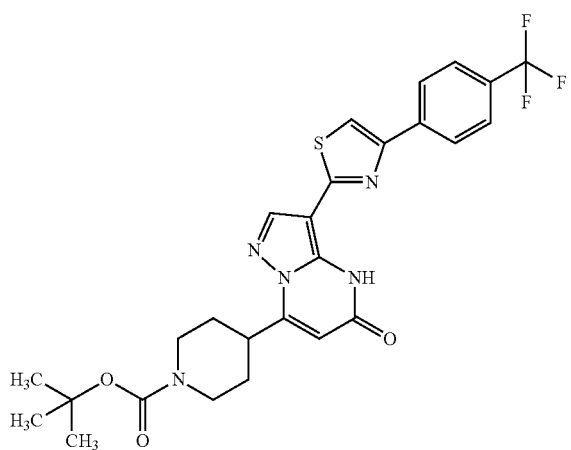 [SMILES: CC(C)(C)OC(=O)N1CCC(c2cc(=O)[nH]c3c(-c4nc(-c5ccc(C(F)(F)F)cc5)cs4)cnn23)CC1]

According to General Procedure 1A, tert-butyl 4-[(2,2-dimethyl-4,6-dioxo-1,3-dioxan-5-yl)carbonyl]piperidine-1-carboxylate (588 mg, 1.65 mmol) and 4-{4-[4-(trifluoromethyl)phenyl]-1,3-thiazol-2-yl}-1H-pyrazol-5-amine (342 mg, 1.10 mmol) were reacted to yield the title compound (88 mg, 10% of theory).

LC-MS (Method 1B): Rt=1.34 min, MS (ESIPos): m/z=546 [M+H]$^+$

Example 183A tert-butyl 4-(3-{[2-(2,2-dimethylpropanoyl)hydrazino]carbonyl}-5-oxo-4,5-dihydropyrazolo[1,5-a]pyrimidin-7-yl)piperidine-1-carboxylate

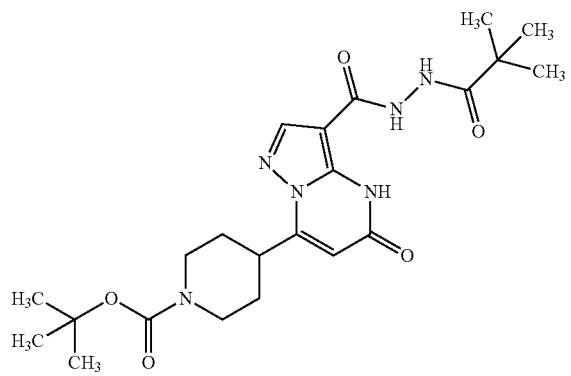 [SMILES: CC(C)(C)OC(=O)N1CCC(c2cc(=O)[nH]c3c(C(=O)NNC(=O)C(C)(C)C)cnn23)CC1]

7-[1-(tert-butoxycarbonyl)piperidin-4-yl]-5-oxo-4,5-dihydropyrazolo[1,5-a]pyrimidine-3-carboxylic acid (150 mg, 0.41 mmol) and 2,2-dimethylpropanehydrazide (72 mg, 0.6 mmol) were dissolved in N,N-Dimethylformamide (1.5 ml). N,N-Diisopropylethylamin (0.22 ml, 1.24 mmol) and N-[(Dimethylamino) (3H-[1,2,3]triazolo[4,5-b]pyridin-3-yloxy)methyliden]-N-methyl-methanaminium-hexafluorophosphate (266 mg, 0.62 mmol) were added and the mixture was stirred for 16 h at RT. The mixture was purified via reverse phase HPLC (gradient acetonitrile/water with 0.01% trifluoroacetic acid) which afforded the title compound (55.4 mg, 25% of theory).

LC-MS (Method 5B): R$_t$=0.80 min, MS (ESIPos): m/z=461.4 [M+H]$^+$

Example 184A tert-butyl 4-[3-(5-tert-butyl-1,3,4-oxadiazol-2-yl)-5-oxo-4,5-dihydropyrazolo[1,5-a]pyrimidin-7-yl]piperidine-1-carboxylate

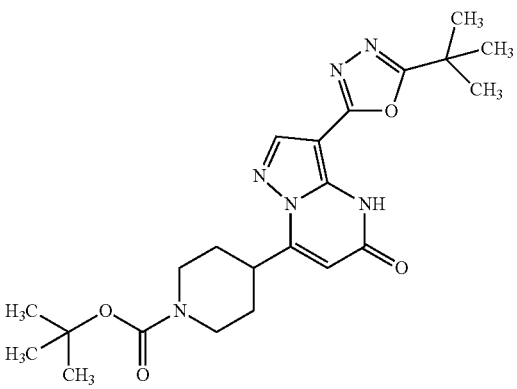 [SMILES: CC(C)(C)OC(=O)N1CCC(c2cc(=O)[nH]c3c(-c4nnc(C(C)(C)C)o4)cnn23)CC1]

tert-butyl 4-(3-{[2-(2,2-dimethylpropanoyl)hydrazino]carbonyl}-5-oxo-4,5-dihydropyrazolo[1,5-a]pyrimidin-7-yl)piperidine-1-carboxylate (147 mg, 0.32 mmol) were dissolved in tetrahydrofurane (5 ml) and treated with Methyl N-(triethylammoniosulfonyl)carbamate (92 mg, 0.4 mmol) for 16 h at RT. More Methyl N-(triethylammoniosulfonyl) carbamate (92 mg, 0.4 mmol) was added and stirred for 2 h at RT. More Methyl N-(triethylammoniosulfonyl)carbamate (Burgess reagent, 92 mg, 0.4 mmol) was added and stirred for 1 h at RT. Water was added to stop the reaction and the product was extracted with ethyl acetate. The organic phases were dried which afforded the title compound (156 mg, 89% of theory).

LC-MS (Method 5B): R$_t$=1.01 min, MS (ESIPos): m/z=443.3 [M+H]$^+$

Example 185A tert-butyl 4-[5-oxo-3-({2-[4-(trifluoromethyl)benzoyl]hydrazino}carbonyl)-4,5-dihydropyrazolo[1,5-a]pyrimidin-7-yl]piperidine-1-carboxylate

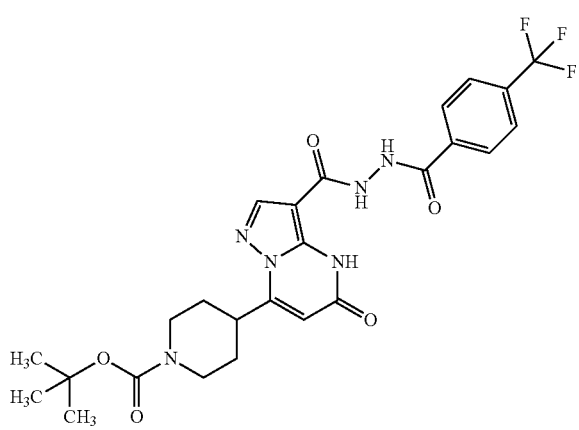 [SMILES: CC(C)(C)OC(=O)N1CCC(c2cc(=O)[nH]c3c(C(=O)NNC(=O)c4ccc(C(F)(F)F)cc4)cnn23)CC1]

7-[1-(tert-butoxycarbonyl)piperidin-4-yl]-5-oxo-4,5-dihydropyrazolo[1,5-a]pyrimidine-3-carboxylic acid (150 mg, 0.41 mmol) and 4-(trifluoromethyl)benzohydrazide (127 mg, 0.6 mmol) were dissolved in N,N-Dimethylformamide (1.5 ml). N,N-Diisopropylethylamin (0.22 ml, 1.24 mmol) and N-[(Dimethylamino)(3H-[1,2,3]triazolo[4,5-b]pyridin-3-yloxy)methyliden]-N-methyl-methanaminium-hexafluorophosphate (266 mg, 0.62 mmol) were added and the mixture was stirred for 16 h at RT. Water was added and the resulting precipitate was filtered, washed with acetonitrile, and dried to afford the title compound (144.5 mg, 49.7% of theory).

LC-MS (Method 5B): $R_t$=0.92 min, MS (ESIPos): m/z=549.3 [M+H]$^+$

Example 186A tert-butyl 4-(5-oxo-3-{5-[4-(trifluoromethyl)phenyl]-1,3,4-oxadiazol-2-yl}-4,5-dihydropyrazolo[1,5-a]pyrimidin-7-yl)piperidine-1-carboxylate

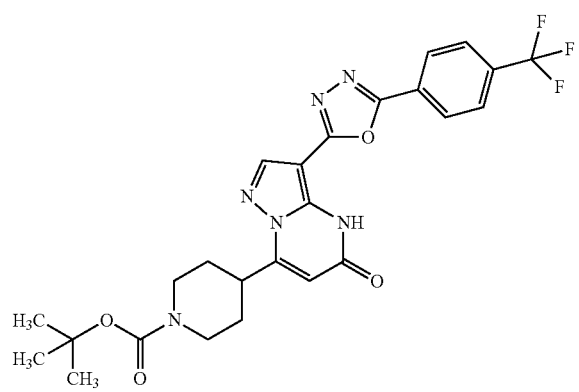 [SMILES: CC(C)(C)OC(=O)N1CCC(c2cc(=O)[nH]c3c(-c4nnc(-c5ccc(C(F)(F)F)cc5)o4)cnn23)CC1]

tert-butyl 4-[5-oxo-3-({2-[4-(trifluoromethyl)benzoyl]hydrazino}carbonyl)-4,5-dihydropyrazolo[1,5-a]pyrimidin-7-yl]piperidine-1-carboxylate (103 mg, 0.19 mmol) were dissolved in tetrahydrofurane (5 ml) and treated with Methyl N-(triethylammoniosulfonyl)carbamate (53.5 mg, 0.2 mmol) for 16 h at RT. More Methyl N-(triethylammoniosulfonyl)carbamate (92 mg, 0.4 mmol) was added and stirred for 2 h at RT. Water (2 ml) was added to stop the reaction and the product was extracted with ethyl acetate. The organic phases were dried which afforded the title compound (109.5 mg, 51% of theory).

LC-MS (Method 5B): $R_t$=1.19 min, MS (ESIPos): m/z=531.4 [M+H]$^+$

Example 187A tert-butyl 4-(3-{[2-(4-carbamoylbenzoyl)hydrazino]carbonyl}-5-oxo-4,5-dihydropyrazolo[1,5-a]pyrimidin-7-yl)piperidine-1-carboxylate

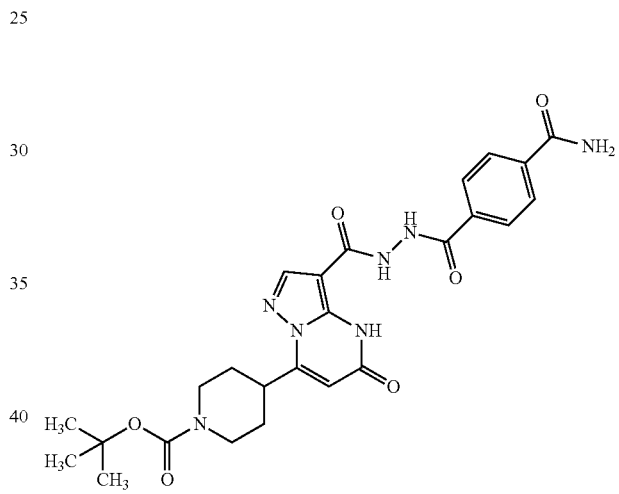

7-[1-(tert-butoxycarbonyl)piperidin-4-yl]-5-oxo-4,5-dihydropyrazolo[1,5-a]pyrimidine-3-carboxylic acid (150 mg, 0.41 mmol) and 4-(hydrazinocarbonyl)benzamide (111 mg, 0.6 mmol) were dissolved in N,N-Dimethylformamide (1.5 ml). N,N-Diisopropylethylamin (0.22 ml, 1.24 mmol) and N-[(Dimethylamino) (3H-[1,2,3]triazolo[4,5-b]pyridin-3-yloxy)methyliden]-N-methyl-methanaminium-hexafluorophosphate (266 mg, 0.62 mmol) were added and the mixture was stirred for 16 h at RT. The mixture was purified via reverse phase HPLC (gradient acetonitrile/water with 0.01% trifluoroacetic acid) which afforded the title compound (92 mg, 39% of theory).

LC-MS (Method 5B): $R_t$=0.69 min, MS (ESIPos): m/z=524.4 [M+H]$^+$

Example 188A tert-butyl 4-{3-[5-(4-cyanophenyl)-1,3,4-oxadiazol-2-yl]-5-oxo-4,5-dihydropyrazolo[1,5-a]pyrimidin-7-yl}piperidine-1-carboxylate

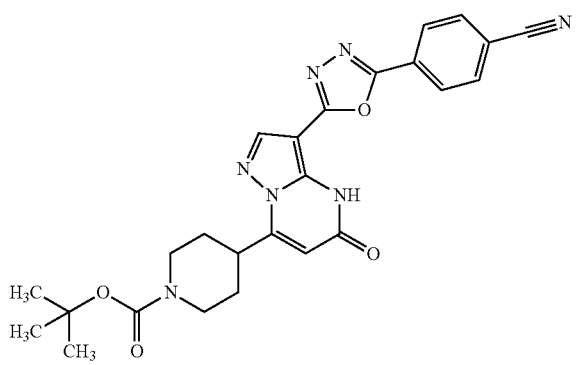 [SMILES: CC(C)(C)OC(=O)N1CCC(c2cc(=O)[nH]c3c(-c4nnc(-c5ccc(C#N)cc5)o4)cnn23)CC1]

tert-butyl 4-(3-{[2-(4-carbamoylbenzoyl)hydrazino]carbonyl}-5-oxo-4,5-dihydropyrazolo[1,5-a]pyrimidin-7-yl)piperidine-1-carboxylate (92 mg, 0.18 mmol) were dissolved in tetrahydrofurane (5 ml) and treated with Methyl N-(triethylammoniosulfonyl)carbamate (50.5 mg, 0.2 mmol) for 16 h at RT. More Methyl N-(triethylammoniosulfonyl)carbamate (50.5 mg, 0.2 mmol) was added and stirred for 2 h at RT. Water (2 ml) was added to stop the reaction and the product was extracted with ethyl acetate. The organic phases were dried which afforded the title compound (73 mg, 57% of theory).

LC-MS (Method 5B): $R_t$=1.04 min, MS (ESIPos): m/z=488.4 [M+H]$^+$

Example 189A tert-butyl 4-[3-({2-[(1-methyl-1H-imidazol-5-yl)carbonyl]hydrazino}carbonyl)-5-oxo-4,5-dihydropyrazolo[1,5-a]pyrimidin-7-yl]piperidine-1-carboxylate

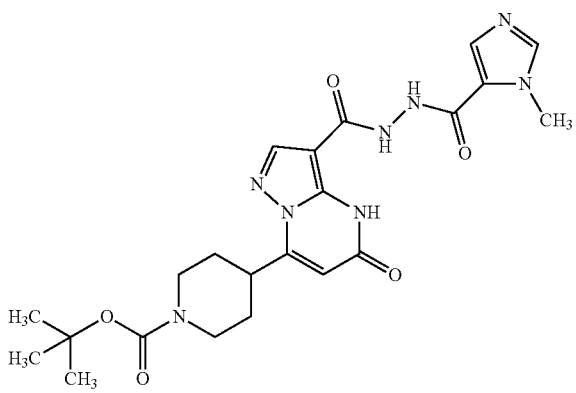 [SMILES: Cn1cncc1C(=O)NNC(=O)c1cnn2c(C3CCN(C(=O)OC(C)(C)C)CC3)cc(=O)[nH]c12]

7-[1-(tert-butoxycarbonyl)piperidin-4-yl]-5-oxo-4,5-dihydropyrazolo[1,5-a]pyrimidine-3-carboxylic acid (150 mg, 0.42 mmol) and 1-methyl-1H-imidazole-5-carbohydrazide (87 mg, 0.6 mmol) were dissolved in N,N-Dimethylformamide (1.5 ml). N,N-Diisopropylethylamin (0.22 ml, 1.24 mmol) and N-[(Dimethylamino) (3H-[1,2,3]triazolo[4,5-b]pyridin-3-yloxy)methyliden]-N-methyl-methanaminium-hexafluorophosphate (266 mg, 0.62 mmol) were added and the mixture was stirred for 16 h at RT. The mixture was purified via reverse phase HPLC (gradient acetonitrile/water with 0.01% trifluoroacetic acid) which afforded the title compound (29.8 mg, 13% of theory).

LC-MS (Method 5B): $R_t$=0.65 min, MS (ESIPos): m/z=485.3 [M+H]$^+$

Example 190A tert-butyl 4-{3-[5-(1-methyl-1H-imidazol-5-yl)-1,3,4-oxadiazol-2-yl]-5-oxo-4,5-dihydropyrazolo[1,5-a]pyrimidin-7-yl}piperidine-1-carboxylate

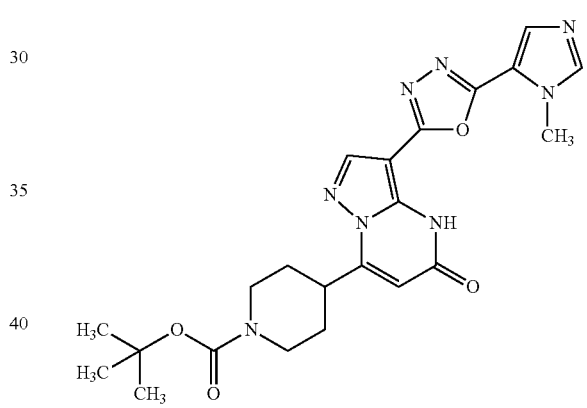

tert-butyl 4-[3-({2-[(1-methyl-1H-imidazol-5-yl)carbonyl]hydrazino}carbonyl)-5-oxo-4,5-dihydropyrazolo[1,5-a]pyrimidin-7-yl]piperidine-1-carboxylate (29.8 mg, 0.06 mmol) were dissolved in tetrahydrofurane (1.5 ml) and treated with Methyl N-(triethylammoniosulfonyl)carbamate (17.6 mg, 0.07 mmol) for 16 h at RT. More Methyl N-(triethylammoniosulfonyl)carbamate (17.6 mg, 0.07 mmol) was added and stirred for 1 h at RT. Water (2 ml) was added to stop the reaction and the product was extracted with ethyl acetate. The organic phases were dried which afforded the title compound (39 mg, 84% of theory).

LC-MS (Method 5B): $R_t$=0.76 min, MS (ESIPos): m/z=466.2 [M+H]$^+$

Example 191A tert-butyl 4-(3-{[2-(3-chlorobenzoyl)hydrazino]carbonyl}-5-oxo-4,5-dihydropyrazolo[1,5-a]pyrimidin-7-yl)piperidine-1-carboxylate

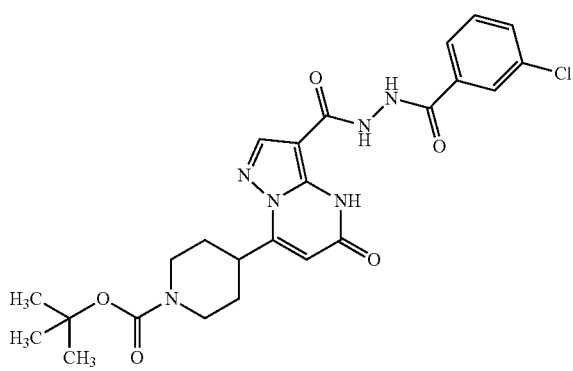 [SMILES: CC(C)(C)OC(=O)N1CCC(c2cc(=O)[nH]c3c(C(=O)NNC(=O)c4cccc(Cl)c4)cnn23)CC1]

7-[1-(tert-butoxycarbonyl)piperidin-4-yl]-5-oxo-4,5-dihydropyrazolo[1,5-a]pyrimidine-3-carboxylic acid (150 mg, 0.42 mmol) and 3-chlorobenzohydrazide (105 mg, 0.6 mmol) were dissolved in N,N-Dimethylformamide (1.5 ml). N,N-Diisopropylethylamin (0.22 ml, 1.24 mmol) and N-[(Dimethylamino) (3H-[1,2,3]triazolo[4,5-b]pyridin-3-yloxy)methyliden]-N-methyl-methanaminium-hexafluorophosphate (266 mg, 0.62 mmol) were added and the mixture was stirred for 16 h at RT. The mixture was purified via reverse phase HPLC (gradient acetonitrile/water with 0.01% trifluoroacetic acid) which afforded the title compound (97 mg, 45% of theory).

LC-MS (Method 5B): $R_t$=0.88 min, MS (ESIPos): m/z=515.4 $[M+H]^+$

Example 192A tert-butyl 4-{3-[5-(3-chlorophenyl)-1,3,4-oxadiazol-2-yl]-5-oxo-4,5-dihydropyrazolo[1,5-a]pyrimidin-7-yl}piperidine-1-carboxylate

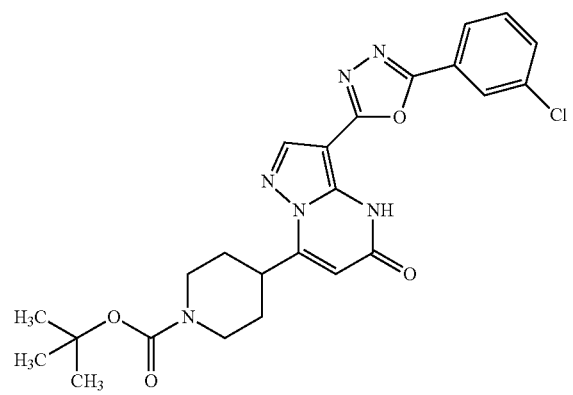 [SMILES: CC(C)(C)OC(=O)N1CCC(c2cc(=O)[nH]c3c(-c4nnc(-c5cccc(Cl)c5)o4)cnn23)CC1]

tert-butyl 4-(3-{[2-(3-chlorobenzoyl)hydrazino]carbonyl}-5-oxo-4,5-dihydropyrazolo[1,5-a]pyrimidin-7-yl)piperidine-1-carboxylate (93 mg, 0.2 mmol) were dissolved in tetrahydrofurane (2.5 ml) and treated with Methyl N-(triethylammoniosulfonyl)carbamate (60 mg, 0.25 mmol) for 16 h at RT. A solution of citric acid (10% in water) was added and the product was extracted with ethyl acetate. The organic phases were dried which afforded the title compound (159 mg, quantitative).

LC-MS (Method 5B)): $R_t$=1.17 min, MS (ESIPos): m/z=497.4 $[M+H]^+$

Example 193A tert-butyl 4-(3-{[2-(4-methylbenzoyl)hydrazino]carbonyl}-5-oxo-4,5-dihydropyrazolo[1,5-a]pyrimidin-7-yl)piperidine-1-carboxylate

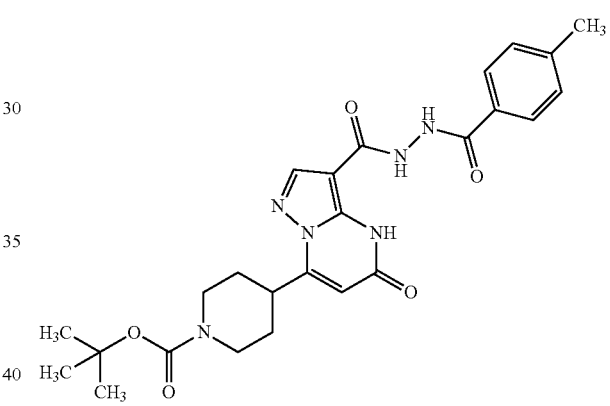

7-[1-(tert-butoxycarbonyl)piperidin-4-yl]-5-oxo-4,5-dihydropyrazolo[1,5-a]pyrimidine-3-carboxylic acid (150 mg, 0.42 mmol) and 4-methylbenzohydrazide (150 mg, 0.4 mmol) were dissolved in N,N-Dimethylformamide (1.5 ml). N,N-Diisopropylethylamin (0.22 ml, 1.24 mmol) and N-[(Dimethylamino) (3H-[1,2,3]triazolo[4,5-b]pyridin-3-yloxy)methyliden]-N-methyl-methanaminium-hexafluorophosphate (266 mg, 0.62 mmol) were added and the mixture was stirred for 16 h at RT. The mixture was purified via reverse phase HPLC (gradient acetonitrile/water with 0.01% trifluoroacetic acid) which afforded the title compound (103 mg, 47% of theory).

LC-MS (Method 5B): $R_t$=0.86 min, MS (ESIPos): m/z=495.5 $[M+H]^+$

Example 194A tert-butyl 4-(3-{[2-(2-methylbenzoyl)hydrazino]carbonyl}-5-oxo-4,5-dihydropyrazolo[1,5-a]pyrimidin-7-yl)piperidine-1-carboxylate

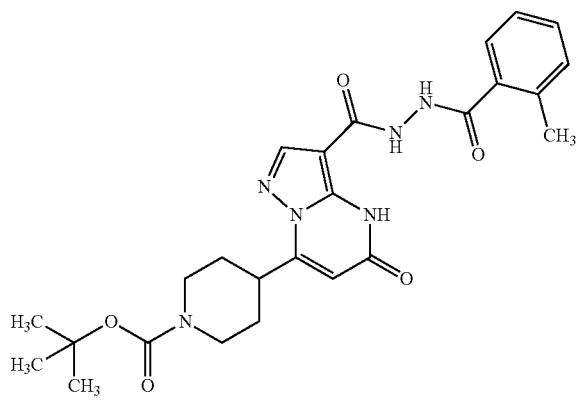 [SMILES: Cc1ccccc1C(=O)NNC(=O)c1cnn2c(C3CCN(C(=O)OC(C)(C)C)CC3)cc(=O)[nH]c12]

7-[1-(tert-butoxycarbonyl)piperidin-4-yl]-5-oxo-4,5-dihydropyrazolo[1,5-a]pyrimidine-3-carboxylic acid (150 mg, 0.42 mmol) and 2-methylbenzohydrazide (93 mg, 0.6 mmol) were dissolved in N,N-Dimethylformamide (1.5 ml). N,N-Diisopropylethylamin (0.22 ml, 1.24 mmol) and N-[(Dimethylamino)(3H-[1,2,3]triazolo[4,5-b]pyridin-3-yloxy)methyliden]-N-methyl-methanaminium-hexafluorophosphate (266 mg, 0.62 mmol) were added and the mixture was stirred for 16 h at RT. The mixture was purified via reverse phase HPLC (gradient acetonitrile/water with 0.01% trifluoroacetic acid) which afforded the title compound (117 mg, 56% of theory).

LC-MS (Method 5B): $R_t$=0.85 min, MS (ESIPos): m/z=495.4 $[M+H]^+$

Example 195A tert-butyl 4-[5-oxo-3-({2-[2-(trifluoromethyl)benzoyl]hydrazino}carbonyl)-4,5-dihydropyrazolo[1,5-a]pyrimidin-7-yl]piperidine-1-carboxylate

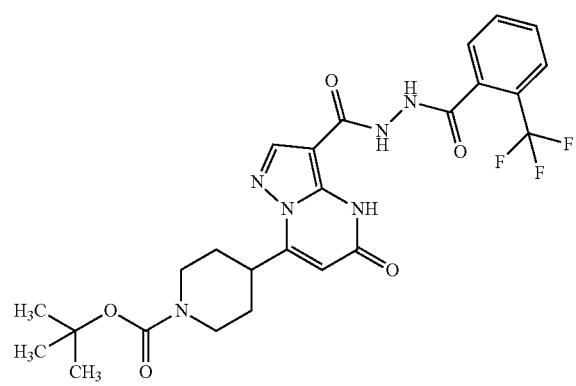 [SMILES: CC(C)(C)OC(=O)N1CCC(c2cc(=O)[nH]c3c(C(=O)NNC(=O)c4ccccc4C(F)(F)F)cnn23)CC1]

7-[1-(tert-butoxycarbonyl)piperidin-4-yl]-5-oxo-4,5-dihydropyrazolo[1,5-a]pyrimidine-3-carboxylic acid (150 mg, 0.42 mmol) and 2-methylbenzohydrazide (127 mg, 0.62 mmol) were dissolved in N,N-Dimethylformamide (1.5 ml). N,N-Diisopropylethylamin (0.22 ml, 1.24 mmol) and N-[(Dimethylamino)(3H-[1,2,3]triazolo[4,5-b]pyridin-3-yloxy)methyliden]-N-methyl-methanaminium-hexafluorophosphate (266 mg, 0.62 mmol) were added and the mixture was stirred for 16 h at RT. The mixture was purified via reverse phase HPLC (gradient acetonitrile/water with 0.01% trifluoroacetic acid) which afforded the title compound (106 mg, 44% of theory).

LC-MS (Method 5B): $R_t$=0.88 min, MS (ESIPos): m/z=549.5 $[M+H]^+$

Example 196A tert-butyl 4-(3-{[2-(methoxyacetyl)hydrazino]carbonyl}-5-oxo-4,5-dihydropyrazolo[1,5-a]pyrimidin-7-yl)piperidine-1-carboxylate

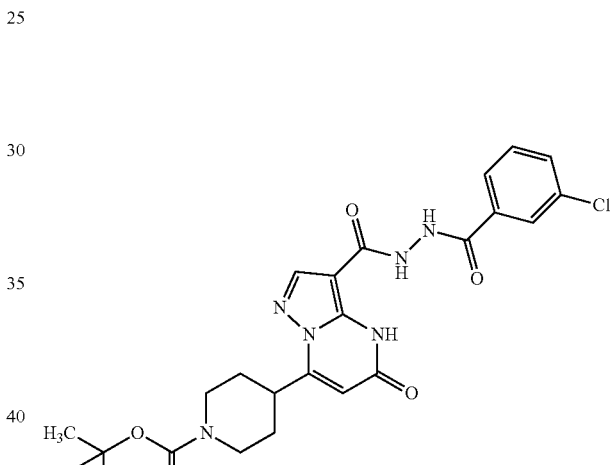

7-[1-(tert-butoxycarbonyl)piperidin-4-yl]-5-oxo-4,5-dihydropyrazolo[1,5-a]pyrimidine-3-carboxylic acid (150 mg, 0.42 mmol) and 2-methoxyacetohydrazide (150 mg, 0.4 mmol) were dissolved in N,N-Dimethylformamide (1.5 ml). N,N-Diisopropylethylamin (0.22 ml, 1.24 mmol) and N-[(Dimethylamino)(3H-[1,2,3]triazolo[4,5-b]pyridin-3-yloxy)methyliden]-N-methyl-methanaminium-hexafluorophosphate (266 mg, 0.62 mmol) were added and the mixture was stirred for 16 h at RT. The mixture was purified via reverse phase HPLC (gradient acetonitrile/water with 0.01% trifluoroacetic acid) which afforded the title compound (121 mg, 65% of theory).

LC-MS (Method 5B): $R_t$=0.69 min, MS (ESIPos): m/z=449.4 $[M+H]^+$

Example 197A tert-butyl 4-{3-[5-(methoxymethyl)-1,3,4-oxadiazol-2-yl]-5-oxo-4,5-dihydropyrazolo[1,5-a]pyrimidin-7-yl}piperidine-1-carboxylate

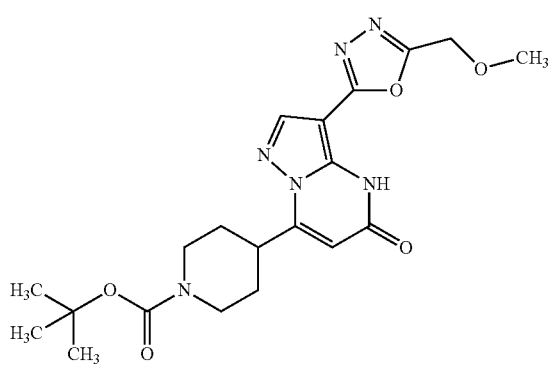 [SMILES: COCc1nnc(-c2cnn3c(C4CCN(C(=O)OC(C)(C)C)CC4)cc(=O)[nH]c23)o1]

tert-butyl 4-(3-{[2-(methoxyacetyl)hydrazino]carbonyl}-5-oxo-4,5-dihydropyrazolo[1,5-a]pyrimidin-7-yl)piperidine-1-carboxylate (121 mg, 0.27 mmol) were dissolved in tetrahydrofurane (2.5 ml) and treated with Methyl N-(triethylammoniosulfonyl)carbamate (90 mg, 0.38 mmol) for 16 h at RT. The mixture was purified via reverse phase HPLC (gradient acetonitrile/water with 0.01% formic acid). The solvents were removed in vacuo which afforded the title compound (38 mg, 33% of theory).

LC-MS (Method 5B): $R_t$=0.86 min, MS (ESIPos): m/z=431.4 [M+H]$^+$

Example 198A tert-butyl 4-(3-{[2-(cyclopropylcarbonyl)hydrazino]carbonyl}-5-oxo-4,5-dihydropyrazolo[1,5-a]pyrimidin-7-yl)piperidine-1-carboxylate

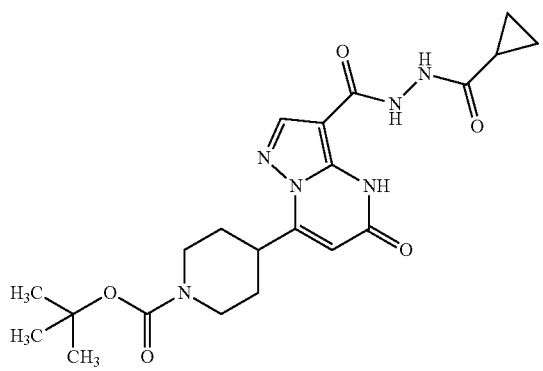 [SMILES: CC(C)(C)OC(=O)N1CCC(c2cc(=O)[nH]c3c(C(=O)NNC(=O)C4CC4)cnn23)CC1]

7-[1-(tert-butoxycarbonyl)piperidin-4-yl]-5-oxo-4,5-dihydropyrazolo[1,5-a]pyrimidine-3-carboxylic acid (150 mg, 0.42 mmol) and cyclopropanecarbohydrazide (62 mg, 0.6 mmol) were dissolved in N,N-Dimethylformamide (1.5 ml). N,N-Diisopropylethylamin (0.22 ml, 1.24 mmol) and N-[(Dimethylamino) (3H-[1,2,3]triazolo[4,5-b]pyridin-3-yloxy)methyliden]-N-methyl-methanaminium-hexafluorophosphate (266 mg, 0.62 mmol) were added and the mixture was stirred for 16 h at RT. The mixture was purified via reverse phase HPLC (gradient acetonitrile/water with 0.01% trifluoroacetic acid) which afforded the title compound (80 mg, 40% of theory).

LC-MS (Method 5B): $R_t$=0.73 min, MS (ESIPos): m/z=445.4 [M+H]$^+$

Example 199A tert-butyl 4-[3-(5-cyclopropyl-1,3,4-oxadiazol-2-yl)-5-oxo-4,5-dihydropyrazolo[1,5-a]pyrimidin-7-yl]piperidine-1-carboxylate

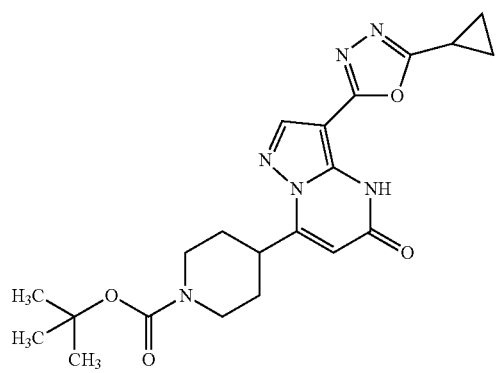 [SMILES: CC(C)(C)OC(=O)N1CCC(c2cc(=O)[nH]c3c(-c4nnc(C5CC5)o4)cnn23)CC1]

tert-butyl 4-(3-{[2-(cyclopropylcarbonyl)hydrazino]carbonyl}-5-oxo-4,5-dihydropyrazolo[1,5-a]pyrimidin-7-yl)piperidine-1-carboxylate (80 mg, 0.18 mmol) were dissolved in tetrahydrofurane (2.5 ml) and treated with Methyl N-(triethylammoniosulfonyl)carbamate (60 mg, 0.25 mmol) for 16 h at RT. The mixture was purified via reverse phase HPLC (gradient acetonitrile/water with 0.01% formic acid). The solvents were removed in vacuo which afforded the title compound (46 mg, 56% of theory).

LC-MS (Method 6B): $R_t$=2.78 min, MS (ESIPos): m/z=427.2 [M+H]$^+$

Example 200A tert-butyl 4-[5-oxo-3-({2-[3-(trifluoromethyl)benzoyl]hydrazino}carbonyl)-4,5-dihydropyrazolo[1,5-a]pyrimidin-7-yl]piperidine-1-carboxylate

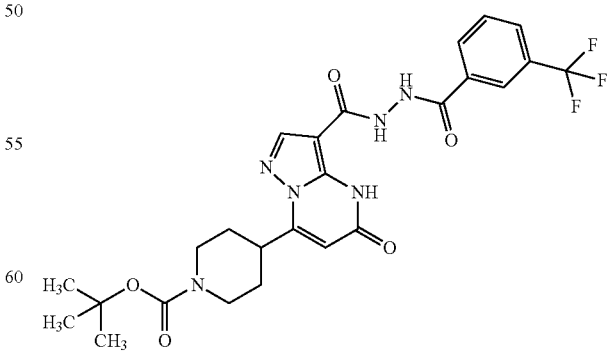

7-[1-(tert-butoxycarbonyl)piperidin-4-yl]-5-oxo-4,5-dihydropyrazolo[1,5-a]pyrimidine-3-carboxylic acid (150 mg, 0.42 mmol) and 3-(trifluoromethyl)benzohydrazide (126 mg, 0.62 mmol) were dissolved in N,N-Dimethylformamide (1.5 ml). N,N-Diisopropylethylamin (0.22 ml, 1.24 mmol) and N-[(Dimethylamino)(3H-[1,2,3]triazolo[4,5-b]pyridin-3-yloxy)methyliden]-N-methyl-methanaminium-hexafluorophosphate (266 mg, 0.62 mmol) were added and the mixture was stirred for 16 h at RT. The mixture was purified via reverse phase HPLC (gradient acetonitrile/water with 0.01% trifluoroacetic acid) which afforded the title compound (154 mg, 68% of theory).

LC-MS (Method 5B): $R_t$=0.93 min, MS (ESIPos): m/z=549.5 [M+H]$^+$

Example 201A tert-butyl 4-(5-oxo-3-{5-[3-(trifluoromethyl)phenyl]-1,3,4-oxadiazol-2-yl}-4,5-dihydropyrazolo[1,5-a]pyrimidin-7-yl)piperidine-1-carboxylate

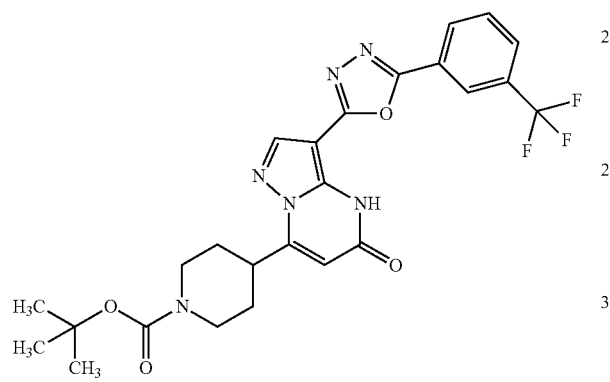

tert-butyl 4-[5-oxo-3-({2-[3-(trifluoromethyl)benzoyl]hydrazino}carbonyl)-4,5-dihydropyrazolo[1,5-a]pyrimidin-7-yl]piperidine-1-carboxylate (102 mg, 0.19 mmol) were dissolved in tetrahydrofurane (5 ml) and treated with Methyl N-(triethylammoniosulfonyl)carbamate (53 mg, 0.22 mmol) for 16 h at RT. More Methyl N-(triethylammoniosulfonyl)carbamate (53 mg, 0.22 mmol) was added and stirred for 1 h at RT. Water (2 ml) was added to stop the reaction and the product was extracted with ethyl acetate. The organic phases were dried which afforded the title compound (121 mg, quantitative).

LC-MS (Method 6B): $R_t$=1.14 min, MS (ESIPos): m/z=531.2 [M+H]$^+$

Example 202A tert-butyl 4-[3-({2-[(4-methoxyphenyl)acetyl]hydrazino}carbonyl)-5-oxo-4,5-dihydropyrazolo[1,5-a]pyrimidin-7-yl]piperidine-1-carboxylate

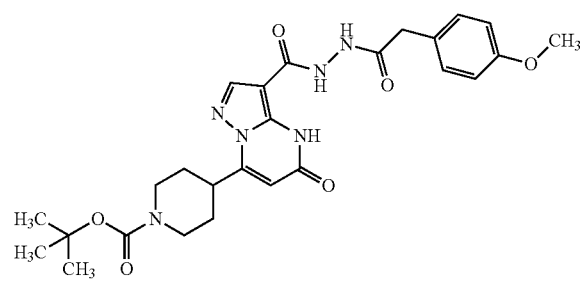 [SMILES: COc1ccc(CC(=O)NNC(=O)c2cnn3c(C4CCN(C(=O)OC(C)(C)C)CC4)cc(=O)[nH]c23)cc1]

7-[1-(tert-butoxycarbonyl)piperidin-4-yl]-5-oxo-4,5-dihydropyrazolo[1,5-a]pyrimidine-3-carboxylic acid (200 mg, 0.55 mmol) and 2-(4-methoxyphenyl)acetohydrazide (119 mg, 0.66 mmol) were dissolved in tetrahydrofurane (2 ml). N,N-Diisopropylethylamin (0.24 ml, 1.38 mmol) and (1-Cyano-2-ethoxy-2-oxoethylidenaminooxy)dimethylamino-morpholino-carbenium hexafluorophosphate (266 mg, 0.66 mmol) were added and the mixture was stirred for 2 h at RT. The mixture was purified via reverse phase HPLC (gradient acetonitrile/water with 0.01% trifluoroacetic acid) which afforded the title compound (113 mg, 37% of theory).

LC-MS (Method 5B): $R_t$=0.85 min, MS (ESIPos): m/z=525.4 [M+H]$^+$

Example 203A tert-butyl 4-{3-[5-(4-methoxybenzyl)-1,3,4-oxadiazol-2-yl]-5-oxo-4,5-dihydropyrazolo[1,5-a]pyrimidin-7-yl}piperidine-1-carboxylate

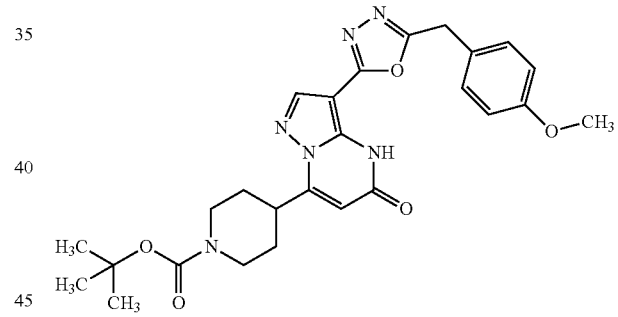

tert-butyl 4-[3-({2-[(4-methoxyphenyl)acetyl]hydrazino}carbonyl)-5-oxo-4,5-dihydropyrazolo[1,5-a]pyrimidin-7-yl]piperidine-1-carboxylate (59 mg, 0.11 mmol) were dissolved in tetrahydrofurane (2.5 ml) and treated with Methyl N-(triethylammoniosulfonyl)carbamate (37 mg, 0.16 mmol) for 16 h at RT. A solution of citric acid (10% in water) was added and the product was extracted with ethyl acetate. The organic phases were dried which afforded the title compound (195 mg, quantitative).

LC-MS (Method 6B): $R_t$=1.04 min, MS (ESIPos): m/z=507.5 [M+H]$^+$

Example 204A tert-butyl 4-(3-{[2-(cyclopentylcarbonyl)hydrazino]carbonyl}-5-oxo-4,5-dihydropyrazolo[1,5-a]pyrimidin-7-yl)piperidine-1-carboxylate

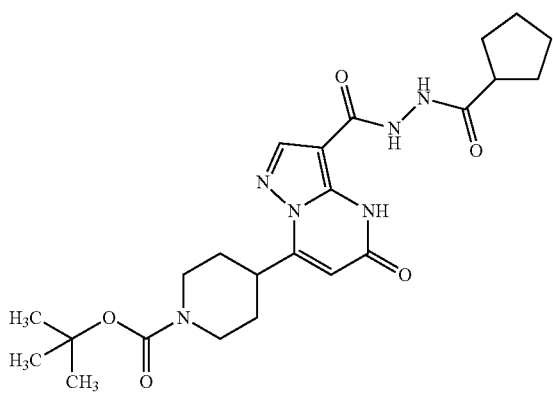 [SMILES: CC(C)(C)OC(=O)N1CCC(c2cc(=O)[nH]c3c(C(=O)NNC(=O)C4CCCC4)cnn23)CC1]

7-[1-(tert-butoxycarbonyl)piperidin-4-yl]-5-oxo-4,5-dihydropyrazolo[1,5-a]pyrimidine-3-carboxylic acid (150 mg, 0.42 mmol) and cyclopentanecarbohydrazide (79.5 mg, 0.62 mmol) were dissolved in N,N-Dimethylformamide (1.5 ml). N,N-Diisopropylethylamin (0.22 ml, 1.24 mmol) and N-[(Dimethylamino)(3H-[1,2,3]triazolo[4,5-b]pyridin-3-yloxy)methyliden]-N-methyl-methanaminium-hexafluorophosphate (266 mg, 0.62 mmol) were added and the mixture was stirred for 16 h at RT. The mixture was purified via reverse phase HPLC (gradient acetonitrile/water with 0.01% trifluoroacetic acid) which afforded the title compound (112 mg, 57% of theory).

LC-MS (Method 5B): $R_t$=0.81 min, MS (ESIPos): m/z=471.4 [M+H]$^+$

Example 205A tert-butyl 4-[3-(5-cyclopentyl-1,3,4-oxadiazol-2-yl)-5-oxo-4,5-dihydropyrazolo[1,5-a]pyrimidin-7-yl]piperidine-1-carboxylate

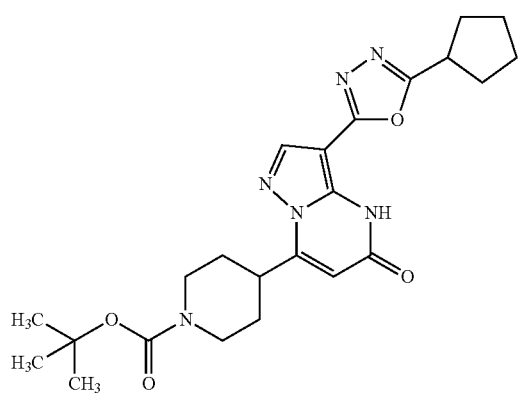 [SMILES: CC(C)(C)OC(=O)N1CCC(c2cc(=O)[nH]c3c(-c4nnc(C5CCCC5)o4)cnn23)CC1]

tert-butyl 4-(3-{[2-(cyclopentylcarbonyl)hydrazino]carbonyl}-5-oxo-4,5-dihydropyrazolo[1,5-a]pyrimidin-7-yl)piperidine-1-carboxylate (55 mg, 0.12 mmol) were dissolved in tetrahydrofurane (2.5 ml) and treated with Methyl N-(triethylammoniosulfonyl)carbamate (38.6 mg, 0.16 mmol) for 16 h at RT. A solution of citric acid (10% in water) was added and the product was extracted with ethyl acetate. The organic phases were dried which afforded the title compound (176 mg, quantitative).

LC-MS (Method 5B): $R_t$=1.07 min, MS (ESIPos): m/z=455.4 [M+H]$^+$

Example 206A tert-butyl 4-(3-{[2-(2-furoyl)hydrazino]carbonyl}-5-oxo-4,5-dihydropyrazolo[1,5-a]pyrimidin-7-yl)piperidine-1-carboxylate

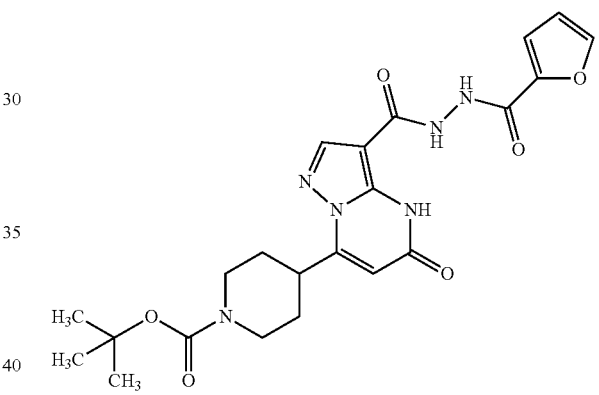

7-[1-(tert-butoxycarbonyl)piperidin-4-yl]-5-oxo-4,5-dihydropyrazolo[1,5-a]pyrimidine-3-carboxylic acid (150 mg, 0.42 mmol) and 2-furohydrazide (78.3 mg, 0.62 mmol) were dissolved in N,N-Dimethylformamide (1.5 ml). N,N-Diisopropylethylamin (0.22 ml, 1.24 mmol) and N-[(Dimethylamino)(3H-[1,2,3]triazolo[4,5-b]pyridin-3-yloxy)methyliden]-N-methyl-methanaminium-hexafluorophosphate (266 mg, 0.62 mmol) were added and the mixture was stirred for 16 h at RT. The mixture was purified via reverse phase HPLC (gradient acetonitrile/water with 0.01% trifluoroacetic acid) which afforded the title compound (65 mg, 34% of theory).

LC-MS (Method 5B): $R_t$=0.75 min, MS (ESIPos): m/z=471.4 [M+H]$^+$

Example 207A tert-butyl 4-{3-[5-(2-furyl)-1,3,4-oxadiazol-2-yl]-5-oxo-4,5-dihydropyrazolo[1,5-a]pyrimidin-7-yl}piperidine-1-carboxylate

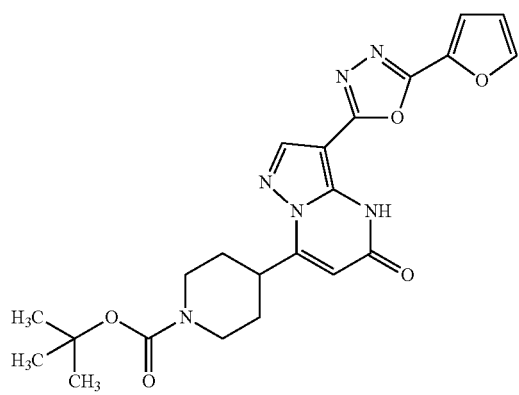

tert-butyl 4-(3-{[2-(2-furoyl)hydrazino]carbonyl}-5-oxo-4,5-dihydropyrazolo[1,5-a]pyrimidin-7-yl)piperidine-1-carboxylate (64 mg, 0.14 mmol) were dissolved in tetrahydrofurane (2.5 ml) and treated with Methyl N-(triethylammoniosulfonyl)carbamate (45 mg, 0.19 mmol) for 16 h at RT. A solution of citric acid (10% in water) was added and the product was extracted with ethyl acetate. The organic phases were dried which afforded the title compound (91 mg, quantitative).

LC-MS (Method 5B): $R_t$=0.98 min, MS (ESIPos): m/z=453.3 [M+H]$^+$

Example 208A tert-butyl 4-(3-{[2-(4-tert-butylbenzoyl)hydrazino]carbonyl}-5-oxo-4,5-dihydropyrazolo[1,5-a]pyrimidin-7-yl)piperidine-1-carboxylate

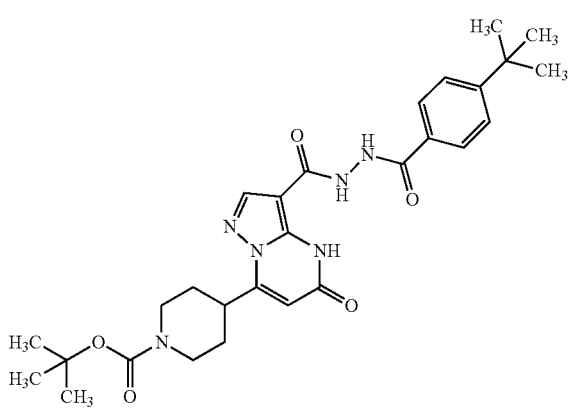 [SMILES: CC(C)(C)OC(=O)N1CCC(c2cc(=O)[nH]c3c(C(=O)NNC(=O)c4ccc(C(C)(C)C)cc4)cnn23)CC1]

7-[1-(tert-butoxycarbonyl)piperidin-4-yl]-5-oxo-4,5-dihydropyrazolo[1,5-a]pyrimidine-3-carboxylic acid (150 mg, 0.42 mmol) and 4-tert-butylbenzohydrazide (119 mg, 0.62 mmol) were dissolved in N,N-Dimethylformamide (1.5 ml). N,N-Diisopropylethylamin (0.22 ml, 1.24 mmol) and N-[(Dimethylamino)(3H-[1,2,3]triazolo[4,5-b]pyridin-3-yloxy)methyliden]-N-methyl-methanaminium-hexafluorophosphate (266 mg, 0.62 mmol) were added and the mixture was stirred for 16 h at RT. The mixture was purified via reverse phase HPLC (gradient acetonitrile/water with 0.01% trifluoroacetic acid) which afforded the title compound (119 mg, 54% of theory).

LC-MS (Method 5B): $R_t$=1.00 min, MS (ESIPos): m/z=537.5 [M+H]$^+$

Example 209A tert-butyl 4-{3-[5-(4-tert-butylphenyl)-1,3,4-oxadiazol-2-yl]-5-oxo-4,5-dihydropyrazolo[1,5-a]pyrimidin-7-yl}piperidine-1-carboxylate

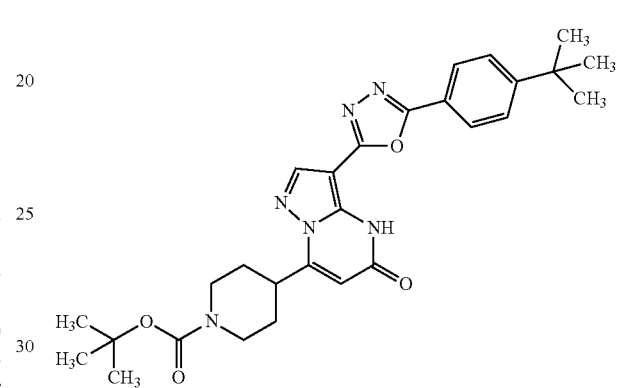

tert-butyl 4-(3-{[2-(4-tert-butylbenzoyl)hydrazino]carbonyl}-5-oxo-4,5-dihydropyrazolo[1,5-a]pyrimidin-7-yl)piperidine-1-carboxylate (119 mg, 0.22 mmol) were dissolved in tetrahydrofurane (2.5 ml) and treated with Methyl N-(triethylammoniosulfonyl)carbamate (73 mg, 0.31 mmol) for 16 h at RT. A solution of citric acid (10% in water) was added and the product was extracted with ethyl acetate. The organic phases were dried which afforded the title compound (167 mg, 89% of theory).

LC-MS (Method 5B): $R_t$=1.31 min, MS (ESIPos): m/z=519.5 [M+H]$^+$

Example 210A tert-butyl 4-(5-oxo-3-{[2-(phenylacetyl)hydrazino]carbonyl}-4,5-dihydropyrazolo[1,5-a]pyrimidin-7-yl)piperidine-1-carboxylate

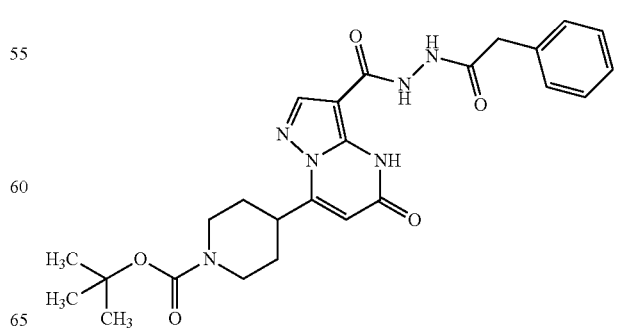

7-[1-(tert-butoxycarbonyl)piperidin-4-yl]-5-oxo-4,5-dihydropyrazolo[1,5-a]pyrimidine-3-carboxylic acid (150 mg, 0.42 mmol) and 2-phenylacetohydrazide (93 mg, 0.62 mmol) were dissolved in N,N-Dimethylformamide (1.5 ml). N,N-Diisopropylethylamin (0.22 ml, 1.24 mmol) and N-[(Dimethylamino) (3H-[1,2,3]triazolo[4,5-b]pyridin-3-yloxy)methyliden]-N-methyl-methanaminium-hexafluorophosphate (266 mg, 0.62 mmol) were added and the mixture was stirred for 16 h at RT. The mixture was purified via reverse phase HPLC (gradient acetonitrile/water with 0.01% trifluoroacetic acid) which afforded the title compound (55 mg, 27% of theory).

LC-MS (Method 5B): $R_t$=0.84 min, MS (ESIPos): m/z=495.5 [M+H]$^+$

Example 211A tert-butyl 4-[3-(5-benzyl-1,3,4-oxadiazol-2-yl)-5-oxo-4,5-dihydropyrazolo[1,5-a]pyrimidin-7-yl]piperidine-1-carboxylate

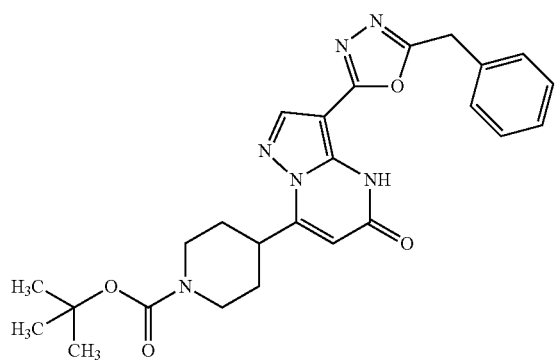 [SMILES: CC(C)(C)OC(=O)N1CCC(c2cc(=O)[nH]c3c(-c4nnc(Cc5ccccc5)o4)cnn23)CC1]

tert-butyl 4-(5-oxo-3-{[2-(phenylacetyl)hydrazino]carbonyl}-4,5-dihydropyrazolo[1,5-a]pyrimidin-7-yl)piperidine-1-carboxylate (100 mg, 0.28 mmol) were dissolved in tetrahydrofurane (2.5 ml) and treated with Methyl N-(triethylammoniosulfonyl)carbamate (67.7 mg, 0.28 mmol) for 16 h at RT. A solution of citric acid (10% in water) was added and the product was extracted with ethyl acetate. The organic phases were dried which afforded the title compound (102 mg, 83% of theory).

LC-MS (Method 5B): $R_t$=1.05 min, MS (ESIPos): m/z=477.4 [M+H]$^+$

Example 212A tert-butyl 4-(3-{[2-(4-methylbenzoyl)hydrazino]carbonyl}-5-oxo-4,5-dihydropyrazolo[1,5-a]pyrimidin-7-yl)piperidine-1-carboxylate

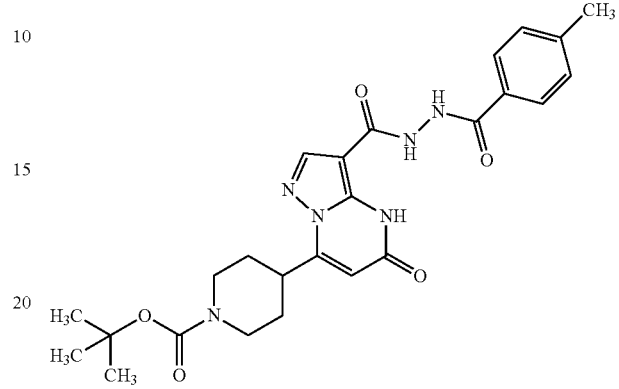

7-[1-(tert-butoxycarbonyl)piperidin-4-yl]-5-oxo-4,5-dihydropyrazolo[1,5-a]pyrimidine-3-carboxylic acid (150 mg, 0.42 mmol) and 4-methylbenzohydrazide (150 mg, 0.41 mmol) were dissolved in N,N-Dimethylformamide (1.5 ml). N,N-Diisopropylethylamin (0.22 ml, 1.24 mmol) and N-[(Dimethylamino) (3H-[1,2,3]triazolo[4,5-b]pyridin-3-yloxy)methyliden]-N-methyl-methanaminium-hexafluorophosphate (265 mg, 1.2 mmol) were added and the mixture was stirred for 16 h at rt. The mixture was purified via reverse phase HPLC (gradient acetonitrile/water with 0.01% trifluoroacetic acid) which afforded the title compound (103 mg, 47% of theory).

LC-MS (Method 5B): $R_t$=0.86 min, MS (ESIPos): m/z=495.5 [M+H]$^+$

Example 213A tert-butyl 4-(3-{[2-(4-chlorobenzoyl)hydrazino]carbonyl}-5-oxo-4,5-dihydropyrazolo[1,5-a]pyrimidin-7-yl)piperidine-1-carboxylate

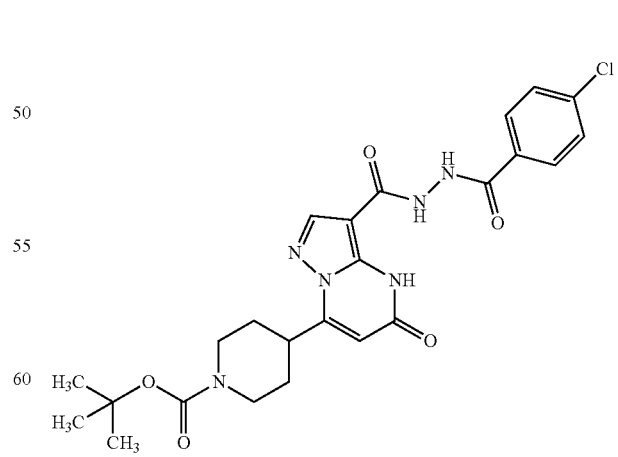

7-[1-(tert-butoxycarbonyl)piperidin-4-yl]-5-oxo-4,5-dihydropyrazolo[1,5-a]pyrimidine-3-carboxylic acid (150 mg, 0.42 mmol) and 4-chlorobenzohydrazide (116 mg, 0.62 mmol) were dissolved in N,N-Dimethylformamide (1.5 ml). N,N-Diisopropylethylamin (0.22 ml, 1.24 mmol) and N-[(Dimethylamino)(3H-[1,2,3]triazolo[4,5-b]pyridin-3-yloxy)methyliden]-N-methyl-methanaminium-hexafluorophosphate (266 mg, 0.62 mmol) were added and the mixture was stirred for 16 h at RT. The mixture was purified via reverse phase HPLC (gradient acetonitrile/water with 0.01% trifluoroacetic acid) which afforded the title compound (60 mg, 27% of theory).

LC-MS (Method 5B): $R_t$=0.88 min, MS (ESIPos): m/z=459.4 [M+H]$^+$

Example 214A tert-butyl 4-{3-[5-(4-chlorophenyl)-1,3,4-oxadiazol-2-yl]-5-oxo-4,5-dihydropyrazolo[1,5-a]pyrimidin-7-yl}piperidine-1-carboxylate

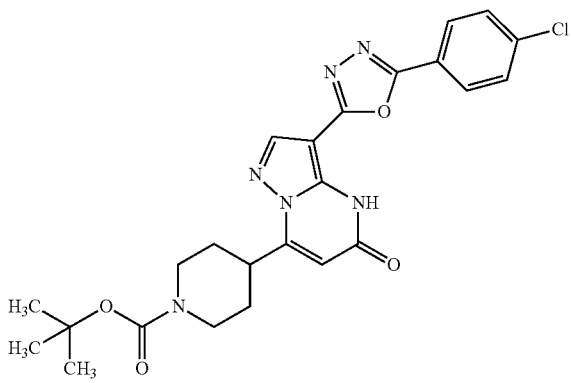 [SMILES: CC(C)(C)OC(=O)N1CCC(c2cc(=O)[nH]c3c(-c4nnc(-c5ccc(Cl)cc5)o4)cnn23)CC1]

tert-butyl 4-(3-{[2-(4-chlorobenzoyl)hydrazino]carbonyl}-5-oxo-4,5-dihydropyrazolo[1,5-a]pyrimidin-7-yl)piperidine-1-carboxylate (60 mg, 0.12 mmol) were dissolved in tetrahydrofurane (2.5 ml) and treated with Methyl N-(triethylammoniosulfonyl)carbamate (39 mg, 0.16 mmol) for 16 h at RT. A solution of citric acid (10% in water) was added and the product was extracted with ethyl acetate. The organic phases were dried which afforded the title compound (73 mg, quantitative).

LC-MS (Method 5B): $R_t$=1.17 min, MS (ESIPos): m/z=497.4 [M+H]$^+$

Example 215A tert-butyl 4-(3-{[2-(cyclohexylacetyl)hydrazino]carbonyl}-5-oxo-4,5-dihydropyrazolo[1,5-a]pyrimidin-7-yl)piperidine-1-carboxylate

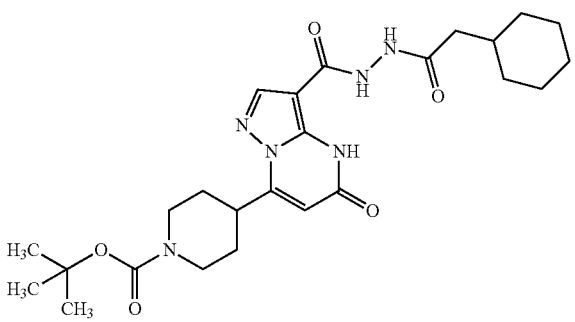

7-[1-(tert-butoxycarbonyl)piperidin-4-yl]-5-oxo-4,5-dihydropyrazolo[1,5-a]pyrimidine-3-carboxylic acid (150 mg, 0.42 mmol) and 2-cyclohexylacetohydrazide (97 mg, 0.62 mmol) were dissolved in N,N-Dimethylformamide (1.5 ml). N,N-Diisopropylethylamin (0.22 ml, 1.24 mmol) and N-[(Dimethylamino)(3H-[1,2,3]triazolo[4,5-b]pyridin-3-yloxy)methyliden]-N-methyl-methanaminium-hexafluorophosphate (266 mg, 0.62 mmol) were added and the mixture was stirred for 16 h at RT. The mixture was purified via reverse phase HPLC (gradient acetonitrile/water with 0.01% trifluoroacetic acid) which afforded the title compound (160 mg, 67% of theory).

LC-MS (Method 5B): $R_t$=0.90 min, MS (ESIPos): m/z=501.4 [M+H]$^+$

Example 216A tert-butyl 4-{3-[5-(cyclohexylmethyl)-1,3,4-oxadiazol-2-yl]-5-oxo-4,5-dihydropyrazolo[1,5-a]pyrimidin-7-yl}piperidine-1-carboxylate

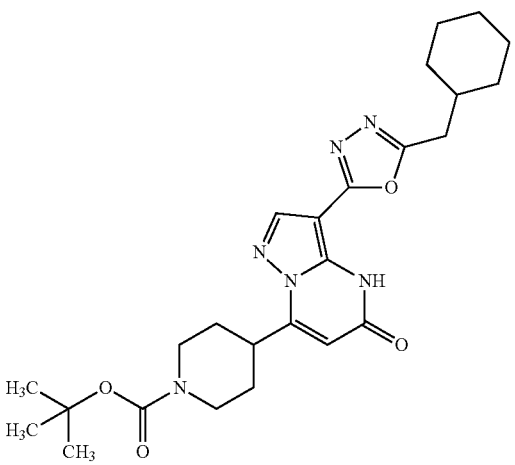 [SMILES: CC(C)(C)OC(=O)N1CCC(c2cc(=O)[nH]c3c(-c4nnc(CC5CCCCC5)o4)cnn23)CC1]

tert-butyl 4-(3-{[2-(cyclohexylacetyl)hydrazino]carbonyl}-5-oxo-4,5-dihydropyrazolo[1,5-a]pyrimidin-7-yl)piperidine-1-carboxylate (155 mg, 0.31 mmol) were dissolved in tetrahydrofurane (5 ml) and treated with Methyl N-(triethylammoniosulfonyl)carbamate (103 mg, 0.43 mmol) for 16 h at RT.

Water was added to stop the reaction and the product was extracted with ethyl acetate. The organic phases were dried which afforded the title compound (103 mg, 62% of theory).

LC-MS (Method 5B): $R_t$=1.24 min, MS (ESIPos): m/z=483.4 [M+H]$^+$

Example 217A tert-butyl 4-(3-{[2-(2-methylisonicotinoyl)hy-drazino]carbonyl}-5-oxo-4,5-dihydropyrazolo[1,5-a]pyrimidin-7-yl)piperidine-1-carboxylate

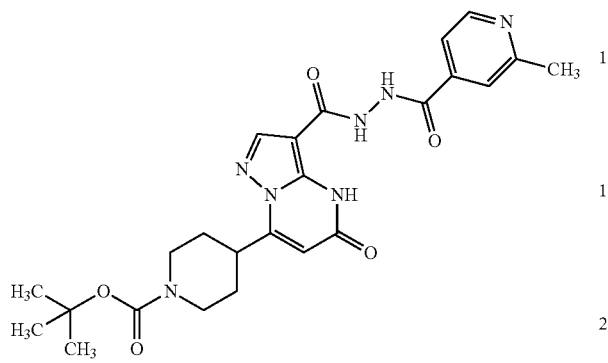

7-[1-(tert-butoxycarbonyl)piperidin-4-yl]-5-oxo-4,5-dihydropyrazolo[1,5-a]pyrimidine-3-carboxylic acid (150 mg, 0.42 mmol) and 2-methylisonicotinohydrazide (94 mg, 0.62 mmol) were dissolved in N,N-Dimethylformamide (1.5 ml). N,N-Diisopropylethylamin (0.22 ml, 1.24 mmol) and N-[(Dimethylamino) (3H-[1,2,3]triazolo[4,5-b]pyridin-3-yloxy)methyliden]-N-methyl-methanaminium-hexafluorophosphate (266 mg, 0.62 mmol) were added and the mixture was stirred for 16 h at RT. The mixture was purified via reverse phase HPLC (gradient acetonitrile/water with 0.01% trifluoroacetic acid) which afforded the title compound (24 mg, 12% of theory).

LC-MS (Method 5B): $R_t$=0.67 min, MS (ESIPos): m/z=495.2 [M+H]$^+$

Example 218A tert-butyl 4-{3-[5-(2-methylpyridin-4-yl)-1,3,4-oxadiazol-2-yl]-5-oxo-4,5-dihydropyrazolo[1,5-a]pyrimidin-7-yl}piperidine-1-carboxylate

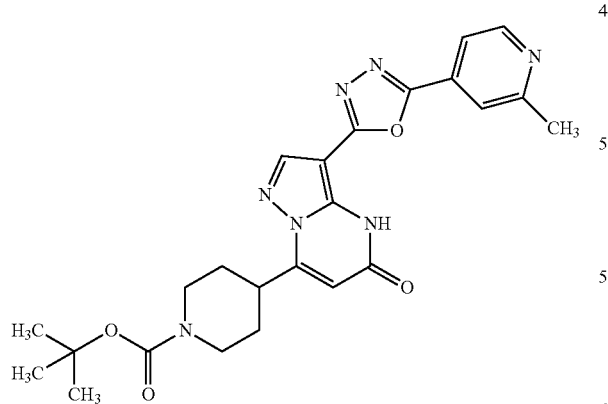

tert-butyl 4-(3-{[2-(2-methylisonicotinoyl)hydrazino]carbonyl}-5-oxo-4,5-dihydropyrazolo[1,5-a]pyrimidin-7-yl)piperidine-1-carboxylate (22 mg, 0.05 mmol) were dissolved in tetrahydrofurane (1 ml) and treated with Methyl N-(triethylammoniosulfonyl)carbamate (15 mg, 0.06 mmol) for 16 h at RT.

Water was added to stop the reaction and the product was extracted with ethyl acetate. The organic phases were dried which afforded the title compound (21 mg, 97% of theory).

LC-MS (Method 5B): $R_t$=0.92 min, MS (ESIPos): m/z=478.4 [M+H]$^+$

Example 219A tert-butyl 4-(3-{[2-(2-methoxybenzoyl)hydrazino]carbonyl}-5-oxo-4,5-dihydropyrazolo[1,5-a]pyrimidin-7-yl)piperidine-1-carboxylate

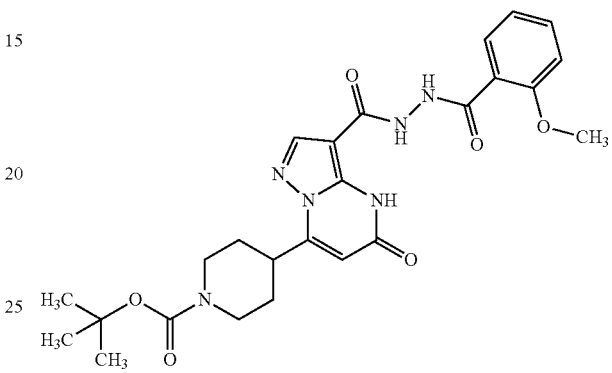

7-[1-(tert-butoxycarbonyl)piperidin-4-yl]-5-oxo-4,5-dihydropyrazolo[1,5-a]pyrimidine-3-carboxylic acid (150 mg, 0.42 mmol) and 2-methoxybenzohydrazide (103 mg, 0.62 mmol) were dissolved in N,N-Dimethylformamide (1.5 ml). N,N-Diisopropylethylamin (0.22 ml, 1.24 mmol) and N-[(Dimethylamino) (3H-[1,2,3]triazolo[4,5-b]pyridin-3-yloxy)methyliden]-N-methyl-methanaminium-hexafluorophosphate (266 mg, 0.62 mmol) were added and the mixture was stirred for 16 h at RT. The mixture was purified via reverse phase HPLC (gradient acetonitrile/water with 0.01% trifluoroacetic acid) which afforded the title compound (90 mg, 39% of theory).

LC-MS (Method 6B): $R_t$=2.61 min, MS (ESIPos): m/z=511.3 [M+H]$^+$

Example 220A tert-butyl 4-{3-[5-(2-methoxyphenyl)-1,3,4-oxadiazol-2-yl]-5-oxo-4,5-dihydropyrazolo[1,5-a]pyrimidin-7-yl}piperidine-1-carboxylate

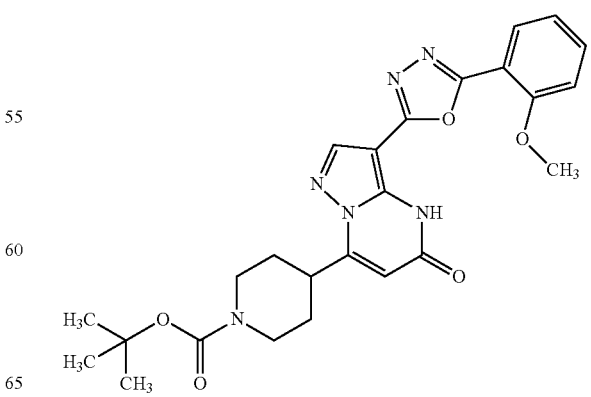

tert-butyl 4-(3-{[2-(2-methoxybenzoyl)hydrazino]carbonyl}-5-oxo-4,5-dihydropyrazolo[1,5-a]pyrimidin-7-yl)piperidine-1-carboxylate (85 mg, 0.23 mmol) were dissolved in tetrahydrofurane (2.5 ml) and treated with Methyl N-(triethylammoniosulfonyl)carbamate (55.6 mg, 0.23 mmol) for 16 h at RT. Water was added and the product was extracted with ethyl acetate. The organic phases were dried which afforded the title compound (56 mg, 68% of theory).

LC-MS (Method 5B): $R_t$=1.03 min, MS (ESIPos): m/z=493.3 [M+H]$^+$

Example 221A tert-butyl 4-{3-[(2-isonicotinoylhydrazino)carbonyl]-5-oxo-4,5-dihydropyrazolo[1,5-a]pyrimidin-7-yl}piperidine-1-carboxylate

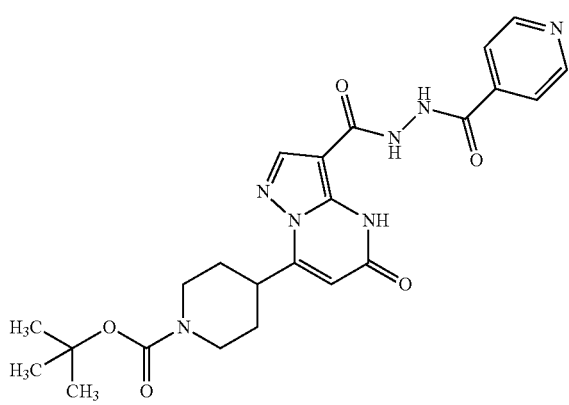 [SMILES: CC(C)(C)OC(=O)N1CCC(c2cc(=O)[nH]c3c(C(=O)NNC(=O)c4ccncc4)cnn23)CC1]

7-[1-(tert-butoxycarbonyl)piperidin-4-yl]-5-oxo-4,5-dihydropyrazolo[1,5-a]pyrimidine-3-carboxylic acid (150 mg, 0.42 mmol) and isonicotinohydrazide (85 mg, 0.62 mmol) were dissolved in N,N-Dimethylformamide (1.5 ml). N,N-Diisopropylethylamin (0.22 ml, 1.24 mmol) and N-[(Dimethylamino)(3H-[1,2,3]triazolo[4,5-b]pyridin-3-yloxy)methyliden]-N-methyl-methanaminium-hexafluorophosphate (266 mg, 0.62 mmol) were added and the mixture was stirred for 16 h at RT. The mixture was purified via reverse phase HPLC (gradient acetonitrile/water with 0.01% trifluoroacetic acid) which afforded the title compound (124 mg, 60% of theory).

LC-MS (Method 5B): $R_t$=0.69 min, MS (ESIPos): m/z=482.4 [M+H]$^+$

Example 222A tert-butyl 4-{5-oxo-3-[5-(pyridin-4-yl)-1,3,4-oxadiazol-2-yl]-4,5-dihydropyrazolo[1,5-a]pyrimidin-7-yl}piperidine-1-carboxylate

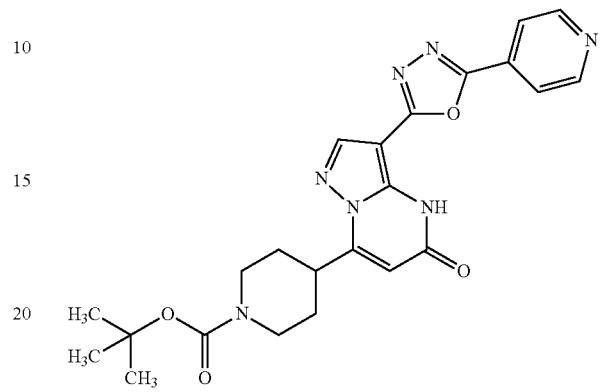

tert-butyl 4-{3-[(2-isonicotinoylhydrazino)carbonyl]-5-oxo-4,5-dihydropyrazolo[1,5-a]pyrimidin-7-yl}piperidine-1-carboxylate (121 mg, 0.25 mmol) were dissolved in tetrahydrofurane (3 ml) and treated with Methyl N-(triethylammoniosulfonyl)carbamate (83.8 mg, 0.35 mmol) for 16 h at RT. The mixture was purified via reverse phase HPLC (gradient acetonitrile/water with 0.01% formic acid). The solvents were removed in vacuo which afforded the title compound (73 mg, 53% of theory).

LC-MS (Method 5B): $R_t$=0.91 min, MS (ESIPos): m/z=464.3 [M+H]$^+$

Example 223A tert-butyl 4-(3-{[2-(2-fluorobenzoyl)hydrazino]carbonyl}-5-oxo-4,5-dihydropyrazolo[1,5-a]pyrimidin-7-yl)piperidine-1-carboxylate

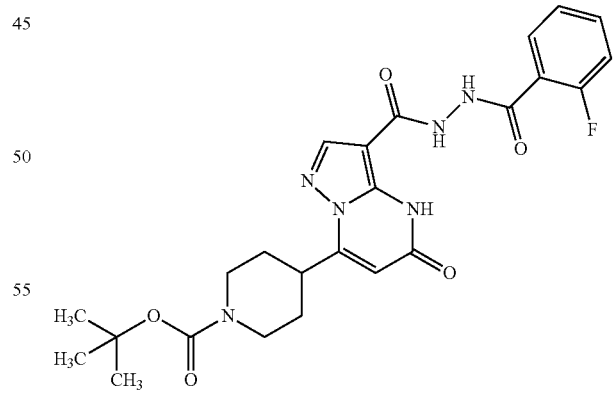

7-[1-(tert-butoxycarbonyl)piperidin-4-yl]-5-oxo-4,5-dihydropyrazolo[1,5-a]pyrimidine-3-carboxylic acid (150 mg, 0.42 mmol) and 2-fluorobenzohydrazide (96 mg, 0.62 mmol) were dissolved in N,N-Dimethylformamide (1.5 ml). N,N-Diisopropylethylamin (0.22 ml, 1.24 mmol) and N-[(Dimethylamino)(3H-[1,2,3]triazolo[4,5-b]pyridin-3-yloxy)methyliden]-N-methyl-methanaminium-hexafluorophosphate (266 mg, 0.62 mmol) were added and the mixture was stirred for 16 h at RT. The mixture was purified via reverse phase HPLC (gradient acetonitrile/water with 0.01% trifluoroacetic acid) which afforded the title compound (102 mg, 50% of theory).

LC-MS (Method 5B): $R_t$=0.81 min, MS (ESIPos): m/z=499.3 [M+H]$^+$

Example 224A tert-butyl 4-{3-[5-(2-fluorophenyl)-1,3,4-oxadiazol-2-yl]-5-oxo-4,5-dihydropyrazolo[1,5-a]pyrimidin-7-yl}piperidine-1-carboxylate

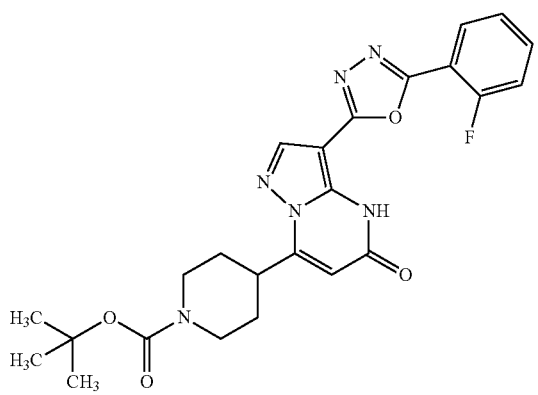 [SMILES: CC(C)(C)OC(=O)N1CCC(c2cc(=O)[nH]c3c(-c4nnc(-c5ccccc5F)o4)cnn23)CC1]

tert-butyl 4-(3-{[2-(2-fluorobenzoyl)hydrazino]carbonyl}-5-oxo-4,5-dihydropyrazolo[1,5-a]pyrimidin-7-yl)piperidine-1-carboxylate (86 mg, 0.17 mmol) were dissolved in tetrahydrofurane (2.5 ml) and treated with Methyl N-(triethylammoniosulfonyl)carbamate (57 mg, 0.24 mmol) for 16 h at RT. Water was added and the product was extracted with ethyl acetate. The organic phases were dried which afforded the title compound (80 mg, 83% of theory).

LC-MS (Method 5B): $R_t$=1.09 min, MS (ESIPos): m/z=481.3 [M+H]$^+$

Example 225A tert-butyl 4-[3-(4-methyl-2-phenyl-1,3-thiazol-5-yl)-5-oxo-4,5-dihydropyrazolo[1,5-a]pyrimidin-7-yl]piperidine-1-carboxylate

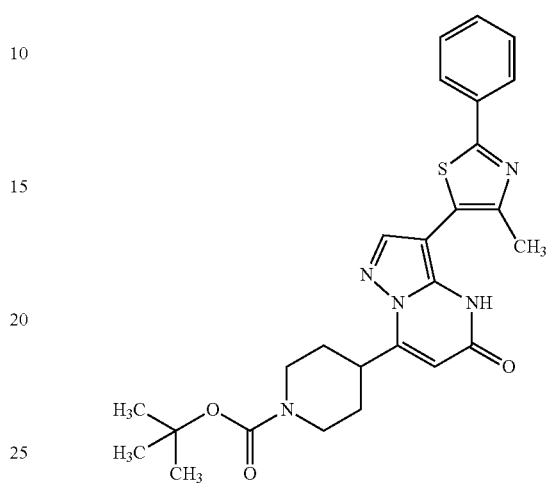

Following the General Procedure 2A, a mixture of 4-methyl-2-phenyl-5-(4,4,5,5-tetramethyl-1,3,2-dioxaborolan-2-yl)-1,3-thiazole (227 mg, 0.76 mmol), tert-butyl 4-(3-bromo-5-oxo-4,5-dihydropyrazolo[1,5-a]pyrimidin-7-yl)piperidine-1-carboxylate (200 mg, 0.50 mmol), XPhos precatalyst (85 mg, 0.10 mmol), degassed THF (10 ml) and degassed aqueous 1M $K_3PO_4$ solution (1.5 ml) were stirred at 70° C. for 24 h. Yield: 47 mg, 18% of theory.

LC-MS (Method 5B): $R_t$=1.17 min, MS (ESIPos): m/z=492.3 [M+H]$^+$

Example 226A

Tert-butyl 4-(5-oxo-3-{3-[6-(trifluoromethyl)pyridin-3-yl]-1,2,4-oxadiazol-5-yl}-4,5-dihydropyrazolo[1,5-a]pyrimidin-7-yl)piperidine-1-carboxylate

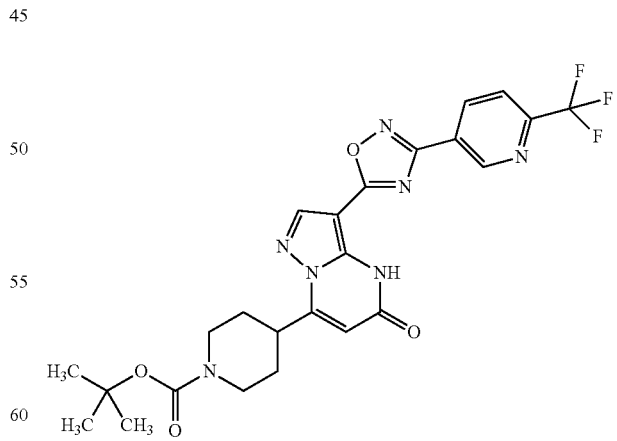

To a solution of compound 7-[1-(tert-Butoxycarbonyl)piperidin-4-yl]-5-oxo-4,5-dihydropyrazolo[1,5-a]pyrimidine-3-carboxylic acid (200 mg, 0.55 mmol) in 5 ml dimethylformamide was added 1,1'-carbonyldiimidazole (179 mg, 1.10 mmol) and N,N-diisopropylethylamine (143 mg, 1.10 mmol) and then the reaction mixture was stirred 1.5 h at 90° C. After this time N'-hydroxy-6-(trifluoromethyl)pyridine-3-carboximidamide (226 mg, 1.10 mmol) was added and the mixture was stirred overnight at 110° C. After cooling to RT, a solid came off the solution. The solid, which was filtered, washed with 2 ml acetonitrile and dried in vacuo, proved to be the expected product (165 mg, 56% of theory). The filtrate, which still contained product, was purified by preparative HPLC (gradient acetonitrile/water with 0.1% trifluoroacetic acid). Evaporation of the combined product fractions yielded some more of the title compound (37 mg, 64% purity, 8% of theory).

LC-MS (Method 8B): $R_t$=1.51 min, MS (ESINeg): m/z=530 [M−H]⁻

Example 227A

Tert-butyl 4-(5-oxo-3-{3-[4-(trifluoromethyl)pyridin-3-yl]-1,2,4-oxadiazol-5-yl}-4,5-dihydropyrazolo[1,5-a]pyrimidin-7-yl)piperidine-1-carboxylate

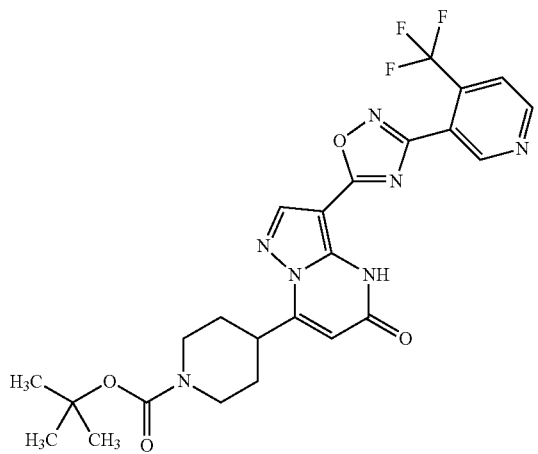 [SMILES: CC(C)(C)OC(=O)N1CCC(c2cc(=O)[nH]c3c(-c4nc(-c5cnccc5C(F)(F)F)no4)cnn23)CC1]

To a solution of compound 7-[1-(tert-Butoxycarbonyl)piperidin-4-yl]-5-oxo-4,5-dihydropyrazolo[1,5-a]pyrimidine-3-carboxylic acid (200 mg, 0.55 mmol) in 5 ml dimethylformamide was added 1,1'-carbonyldiimidazole (179 mg, 1.10 mmol) and N,N-diisopropylethylamine (143 mg, 1.10 mmol) and then the reaction mixture was stirred 1.5 h at 90° C. After this time N'-hydroxy-4-(trifluoromethyl)pyridine-3-carboximidamide (226 mg, 1.10 mmol) was added and the mixture was stirred overnight at 110° C. After cooling to RT, the mixture was purified by preparative HPLC (gradient acetonitrile/water with 0.1% trifluoroacetic acid). Evaporation of the combined product fractions yielded the title compound (119 mg, 41% of theory).

LC-MS (Method 8B): $R_t$=1.40 min, MS (ESINeg): m/z=530 [M−H]⁻

Example 228A

Tert-tert-butyl 4-{5-oxo-3-[3-(2,4,5-trifluorophenyl)-1,2,4-oxadiazol-5-yl]-4,5-dihydropyrazolo[1,5-a]pyrimidin-7-yl}piperidine-1-carboxylate

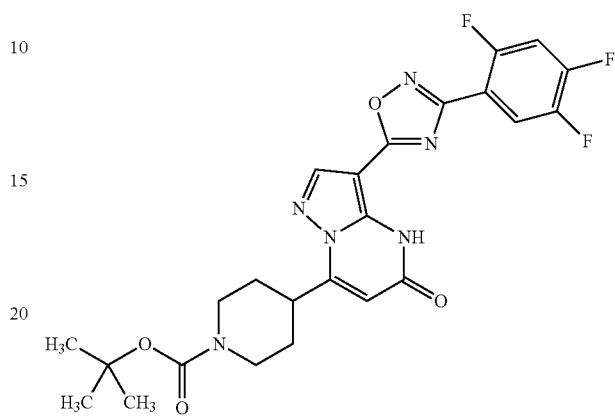

To a solution of compound 7-[1-(tert-Butoxycarbonyl)piperidin-4-yl]-5-oxo-4,5-dihydropyrazolo[1,5-a]pyrimidine-3-carboxylic acid (200 mg, 0.55 mmol) in 5 ml dimethylformamide was added 1,1'-carbonyldiimidazole (179 mg, 1.10 mmol) and N,N-diisopropylethylamine (143 mg, 1.10 mmol) and then the reaction mixture was stirred 1.5 h at 90° C. After this time 2,4,5-trifluoro-N'-hydroxybenzenecarboximidamide (210 mg, 1.10 mmol) was added and the mixture was stirred overnight at 110° C. After cooling to RT, the mixture was purified by preparative HPLC (gradient acetonitrile/water with 0.1% trifluoroacetic acid). Evaporation of the combined product fractions yielded the title compound (71 mg, 25% of theory).

LC-MS (Method 8B): $R_t$=1.51 min, MS (ESINeg): m/z=515 [M−H]⁻

Example 229A

Tert-butyl 4-(3-{3-[(methylsulfonyl)methyl]-1,2,4-oxadiazol-5-yl}-5-oxo-4,5-dihydropyrazolo[1,5-a]pyrimidin-7-yl)piperidine-1-carboxylate

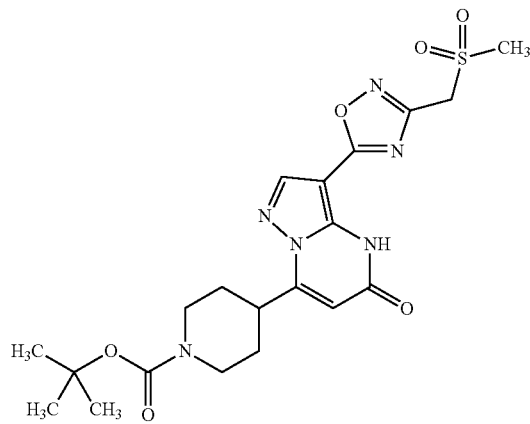 [SMILES: CC(C)(C)OC(=O)N1CCC(c2cc(=O)[nH]c3c(-c4nc(CS(C)(=O)=O)no4)cnn23)CC1]

To a solution of compound 7-[1-(tert-Butoxycarbonyl)piperidin-4-yl]-5-oxo-4,5-dihydropyrazolo[1,5-a]pyrimidine-3-carboxylic acid (200 mg, 0.55 mmol) in 5 ml dimethylformamide was added 1,1'-carbonyldiimidazole (179 mg, 1.10 mmol) and N,N-diisopropylethylamine (143 mg, 1.10 mmol) and then the reaction mixture was stirred 1.5 h at 90° C. After this time (1Z)-N'-hydroxy-2-(methylsulfonyl)ethanimidamide (168 mg, 1.10 mmol) was added and the mixture was stirred overnight at 110° C. After cooling to RT, the mixture was purified by preparative HPLC (gradient acetonitrile/water with 0.1% trifluoroacetic acid). Evaporation of the combined product fractions yielded two fractions of the title compound (47 mg, 17% of theory; and 81 mg, 28% purity, 9% of theory).

LC-MS (Method 8B): $R_t$=1.12 min, MS (ESINeg): m/z=477 [M−H]⁻

Example 230A

Tert-butyl 4-{5-oxo-3-[3-(4,4,4-trifluorobutyl)-1,2,4-oxadiazol-5-yl]-4,5-dihydropyrazolo[1,5-a]pyrimidin-7-yl}piperidine-1-carboxylate

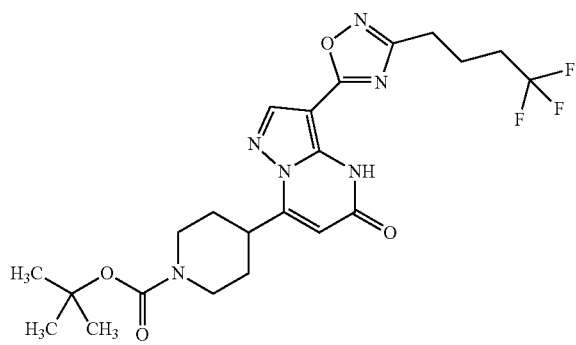 [SMILES: CC(C)(C)OC(=O)N1CCC(c2cc(=O)[nH]c3c(-c4nc(CCCC(F)(F)F)no4)cnn23)CC1]

To a solution of compound 7-[1-(tert-Butoxycarbonyl)piperidin-4-yl]-5-oxo-4,5-dihydropyrazolo[1,5-a]pyrimidine-3-carboxylic acid (200 mg, 0.55 mmol) in 5 ml dimethylformamide was added 1,1'-carbonyldiimidazole (179 mg, 1.10 mmol) and N,N-diisopropylethylamine (143 mg, 1.10 mmol) and then the reaction mixture was stirred 1.5 h at 90° C. After this time (1Z)-5,5,5-trifluoro-N'-hydroxypentanimidamide (188 mg, 1.10 mmol) was added and the mixture was stirred overnight at 110° C. After cooling to RT, the mixture was purified by preparative HPLC (gradient acetonitrile/water with 0.1% trifluoroacetic acid). Evaporation of the combined product fractions yielded the title compound (177 mg, 64% of theory).

LC-MS (Method 8B): $R_t$=1.43 min, MS (ESINeg): m/z=495 [M−H]⁻

Example 231A

Tert-butyl 4-{3-[3-(1-cyclopropylpiperidin-4-yl)-1,2,4-oxadiazol-5-yl]-5-oxo-4,5-dihydropyrazolo[1,5-a]pyrimidin-7-yl}piperidine-1-carboxylate trifluoroacetate salt

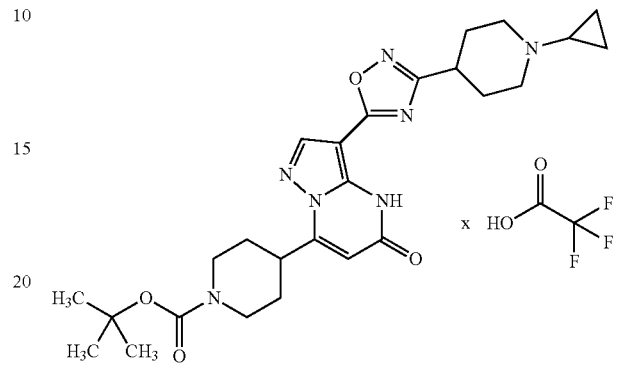

To a solution of compound 7-[1-(tert-Butoxycarbonyl)piperidin-4-yl]-5-oxo-4,5-dihydropyrazolo[1,5-a]pyrimidine-3-carboxylic acid (200 mg, 0.55 mmol) in 5 ml dimethylformamide was added 1,1'-carbonyldiimidazole (179 mg, 1.10 mmol) and N,N-diisopropylethylamine (143 mg, 1.10 mmol) and then the reaction mixture was stirred 1.5 h at 90° C. After this time 1-cyclopropyl-N'-hydroxypiperidine-4-carboximidamide (202 mg, 1.10 mmol) was added and the mixture was stirred overnight at 110° C. After cooling to RT, the mixture was purified by preparative HPLC (gradient acetonitrile/water with 0.1% trifluoroacetic acid). Evaporation of the combined product fractions yielded the title compound (155 mg, 45% of theory).

LC-MS (Method 8B): $R_t$=0.93 min, MS (ESINeg): m/z=508 [M−H]⁻

Example 232A

Tert-butyl 4-[3-(3-tert-butyl-1,2,4-oxadiazol-5-yl)-5-oxo-4,5-dihydropyrazolo[1,5-a]pyrimidin-7-yl]piperidine-1-carboxylate

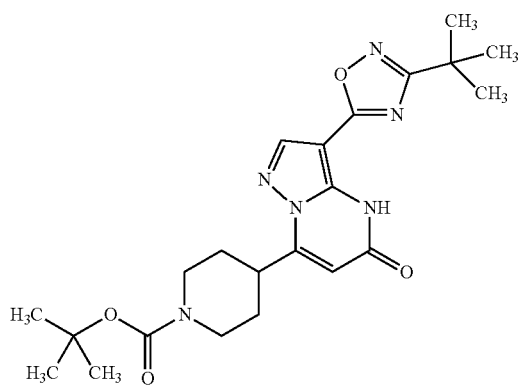 [SMILES: CC(C)(C)OC(=O)N1CCC(c2cc(=O)[nH]c3c(-c4nc(C(C)(C)C)no4)cnn23)CC1]

To a solution of compound 7-[1-(tert-Butoxycarbonyl)piperidin-4-yl]-5-oxo-4,5-dihydropyrazolo[1,5-a]pyrimidine-3-carboxylic acid (200 mg, 0.55 mmol) in 5 ml dimethylformamide was added 1,1'-carbonyldiimidazole (179 mg, 1.10 mmol) and N,N-diisopropylethylamine (143 mg, 1.10 mmol) and then the reaction mixture was stirred 1.5 h at 90° C. After this time (1Z)-N'-hydroxy-2,2-dimethylpropanimidamide (128 mg, 1.10 mmol) was added and the mixture was stirred overnight at 110° C. After cooling to RT, the mixture was purified by preparative HPLC (gradient acetonitrile/water with 0.1% trifluoroacetic acid). Evaporation of the combined product fractions yielded the title compound (179 mg, 73% of theory).

LC-MS (Method 8B): $R_t$=1.45 min, MS (ESINeg): m/z=441 [M−H]⁻

Example 233A

Tert-butyl 4-{3-[3-(2-chloro-4-fluorobenzyl)-1,2,4-oxadiazol-5-yl]-5-oxo-4,5-dihydropyrazolo[1,5-a]pyrimidin-7-yl}piperidine-1-carboxylate

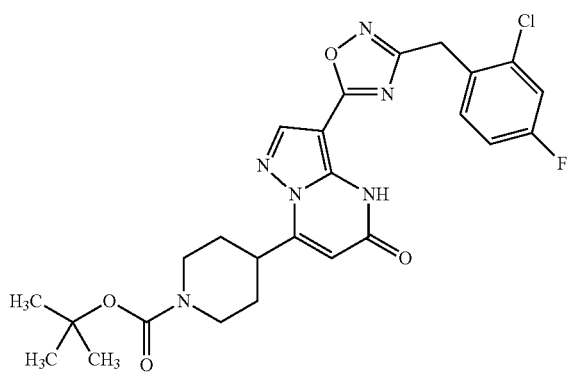 [SMILES: CC(C)(C)OC(=O)N1CCC(c2cc(=O)[nH]c3c(-c4nc(Cc5ccc(F)cc5Cl)no4)cnn23)CC1]

To a solution of compound 7-[1-(tert-Butoxycarbonyl)piperidin-4-yl]-5-oxo-4,5-dihydropyrazolo[1,5-a]pyrimidine-3-carboxylic acid (200 mg, 0.55 mmol) in 5 ml dimethylformamide was added 1,1'-carbonyldiimidazole (179 mg, 1.10 mmol) and N,N-diisopropylethylamine (143 mg, 1.10 mmol) and then the reaction mixture was stirred 1.5 h at 90° C. After this time (1Z)-2-(2-chloro-4-fluorophenyl)-N'-hydroxyethanimidamide (224 mg, 1.10 mmol) was added and the mixture was stirred overnight at 110° C. After cooling to RT, the mixture was purified by preparative HPLC (gradient acetonitrile/water with 0.1% trifluoroacetic acid). Evaporation of the combined product fractions yielded the title compound (162 mg, 55% of theory).

LC-MS (Method 8B): $R_t$=1.50 min, MS (ESINeg): m/z=527 [M−H]⁻

Example 234A

Tert-butyl 4-{3-[3-(4-tert-butylphenyl)-1,2,4-oxadiazol-5-yl]-5-oxo-4,5-dihydropyrazolo[1,5-a]pyrimidin-7-yl}piperidine-1-carboxylate

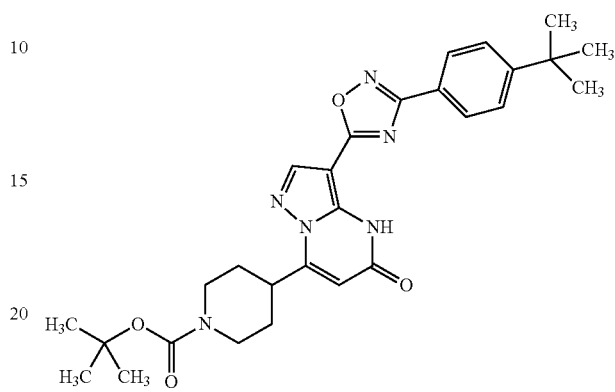

To a solution of compound 7-[1-(tert-Butoxycarbonyl)piperidin-4-yl]-5-oxo-4,5-dihydropyrazolo[1,5-a]pyrimidine-3-carboxylic acid (200 mg, 0.55 mmol) in 5 ml dimethylformamide was added 1,1'-carbonyldiimidazole (179 mg, 1.10 mmol) and N,N-diisopropylethylamine (143 mg, 1.10 mmol) and then the reaction mixture was stirred 1.5 h at 90° C. After this time 4-tert-butyl-N'-hydroxybenzenecarboximidamide (212 mg, 1.10 mmol) was added and the mixture was stirred overnight at 110° C. After cooling to RT, the suspension was filtered. The recovered solid was washed with diethyl ether and dried in vacuo to yield the title compound (115 mg, 40% of theory).

LC-MS (Method 5B): $R_t$=1.45 min, MS (ESINeg): m/z=517 [M−H]⁻

Example 235A

Tert-butyl 4-(3-{3-[4-(dimethylamino)-3-fluorophenyl]-1,2,4-oxadiazol-5-yl}-5-oxo-4,5-dihydro pyrazolo[1,5-a]pyrimidin-7-yl)piperidine-1-carboxylate

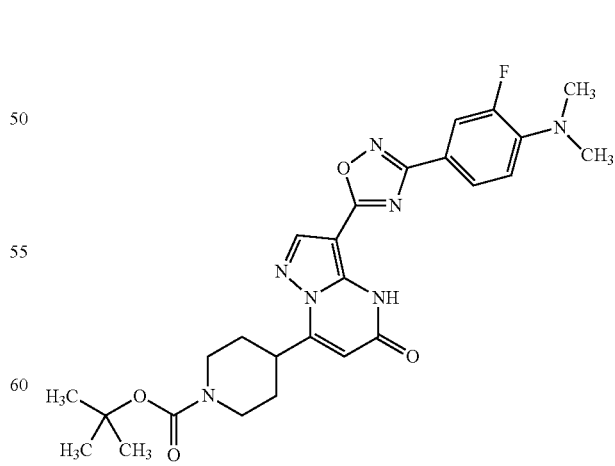

To a solution of compound 7-[1-(tert-Butoxycarbonyl)piperidin-4-yl]-5-oxo-4,5-dihydropyrazolo[1,5-a]pyrimidine-3-carboxylic acid (200 mg, 0.55 mmol) in 5 ml dimethylformamide was added 1,1'-carbonyldiimidazole (179 mg, 1.10 mmol) and N,N-diisopropylethylamine (143 mg, 1.10 mmol) and then the reaction mixture was stirred 1.5 h at 90° C. After this time 4-(dimethylamino)-3-fluoro-N'-hydroxybenzenecarboximidamide (218 mg, 1.10 mmol) was added and the mixture was stirred overnight at 110° C. After cooling to RT, the mixture was purified by preparative HPLC (gradient acetonitrile/water with 0.1% trifluoroacetic acid). Evaporation of the combined product fractions yielded the title compound (65 mg, 22% of theory).

LC-MS (Method 8B): $R_t$=1.57 min, MS (ESINeg): m/z=524 [M+H]$^+$

Example 236A

Tert-butyl 4-{3-[3-(2-methylbenzyl)-1,2,4-oxadiazol-5-yl]-5-oxo-4,5-dihydropyrazolo[1,5-a]pyrimidin-7-yl}piperidine-1-carboxylate

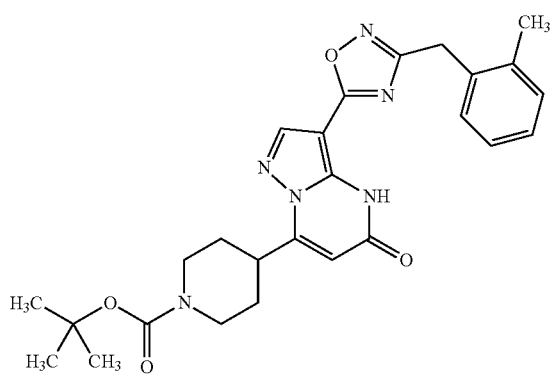 [SMILES: Cc1ccccc1Cc1noc(-c2cnn3c(C4CCN(C(=O)OC(C)(C)C)CC4)cc(=O)[nH]c23)n1]

To a solution of compound 7-[1-(tert-Butoxycarbonyl)piperidin-4-yl]-5-oxo-4,5-dihydropyrazolo[1,5-a]pyrimidine-3-carboxylic acid (200 mg, 0.55 mmol) in 5 ml dimethylformamide was added 1,1'-carbonyldiimidazole (179 mg, 1.10 mmol) and N,N-diisopropylethylamine (143 mg, 1.10 mmol) and then the reaction mixture was stirred 1.5 h at 90° C. After this time (1Z)-N'-hydroxy-2-(2-methylphenyl)ethanimidamide (181 mg, 1.10 mmol) was added and the mixture was stirred overnight at 110° C. After cooling to RT, the mixture was purified by preparative HPLC (gradient acetonitrile/water with 0.1% trifluoroacetic acid). Evaporation of the combined product fractions yielded the title compound (161 mg, 59% of theory).

LC-MS (Method 8B): $R_t$=1.48 min, MS (ESINeg): m/z=489 [M–H]$^-$

Example 237A

Tert-butyl 4-[3-(3-ethyl-1,2,4-oxadiazol-5-yl)-5-oxo-4,5-dihydropyrazolo[1,5-a]pyrimidin-7-yl]piperidine-1-carboxylate

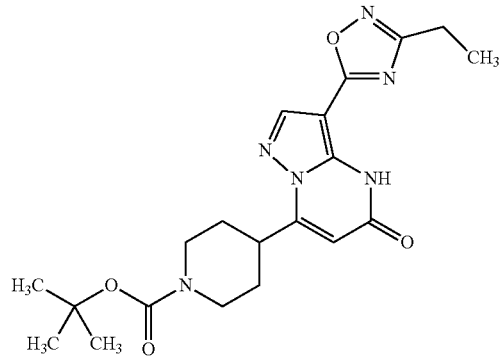 [SMILES: CCc1noc(-c2cnn3c(C4CCN(C(=O)OC(C)(C)C)CC4)cc(=O)[nH]c23)n1]

To a solution of compound 7-[1-(tert-Butoxycarbonyl)piperidin-4-yl]-5-oxo-4,5-dihydropyrazolo[1,5-a]pyrimidine-3-carboxylic acid (200 mg, 0.55 mmol) in 5 ml dimethylformamide was added 1,1'-carbonyldiimidazole (179 mg, 1.10 mmol) and N,N-diisopropylethylamine (214 mg, 1.66 mmol) and then the reaction mixture was stirred 1.5 h at 90° C. After this time (1Z)-N'-hydroxypropanimidamide hydrochloride (138 mg, 1.10 mmol) was added and the mixture was stirred overnight at 110° C. After cooling to RT, the mixture was purified by preparative HPLC (gradient acetonitrile/water with 0.1% trifluoroacetic acid). Evaporation of the combined product fractions yielded the title compound (104 mg, 45% of theory).

LC-MS (Method 8B): $R_t$=1.32 min, MS (ESINeg): m/z=413 [M–H]$^-$

Example 238A

Tert-butyl 4-[3-(3-carbamoyl-1,2,4-oxadiazol-5-yl)-5-oxo-4,5-dihydropyrazolo[1,5-a]pyrimidin-7-yl]piperidine-1-carboxylate

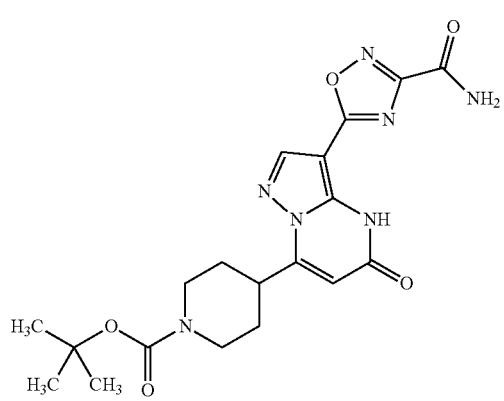 [SMILES: CC(C)(C)OC(=O)N1CCC(c2cc(=O)[nH]c3c(-c4nc(C(N)=O)no4)cnn23)CC1]

To a solution of compound 7-[1-(tert-Butoxycarbonyl)piperidin-4-yl]-5-oxo-4,5-dihydropyrazolo[1,5-a]pyrimidine-3-carboxylic acid (200 mg, 0.55 mmol) in 5 ml dimethylformamide was added 1,1'-carbonyldiimidazole (179 mg, 1.10 mmol) and N,N-diisopropylethylamine (143 mg, 1.10 mmol) and then the reaction mixture was stirred 1.5 h at 90° C. After this time (2Z)-2-amino-2-(hydroxyimino)acetamide (114 mg, 1.10 mmol) was added and the mixture was stirred overnight at 110° C. After cooling to RT, the mixture was purified by preparative HPLC (gradient acetonitrile/water with 0.1% trifluoroacetic acid). Evaporation of the combined product fractions yielded the title compound (125 mg, 94% purity, 50% of theory).

LC-MS (Method 8B): R$_t$=1.09 min, MS (ESINeg): m/z=428 [M–H]$^-$

Example 239A

Tert-butyl 4-(3-{3-[(isopropylsulfonyl)methyl]-1,2,4-oxadiazol-5-yl}-5-oxo-4,5-dihydropyrazolo[1,5-a]pyrimidin-7-yl)piperidine-1-carboxylate

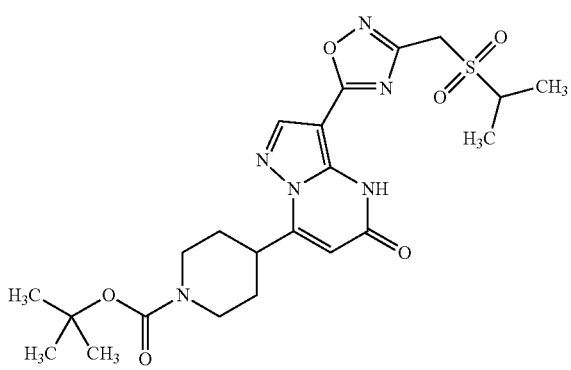 [SMILES: CC(C)S(=O)(=O)Cc1noc(-c2cnn3c(C4CCN(C(=O)OC(C)(C)C)CC4)cc(=O)[nH]c23)n1]

To a solution of compound 7-[1-(tert-Butoxycarbonyl)piperidin-4-yl]-5-oxo-4,5-dihydropyrazolo[1,5-a]pyrimidine-3-carboxylic acid (200 mg, 0.55 mmol) in 5 ml dimethylformamide was added 1,1'-carbonyldiimidazole (179 mg, 1.10 mmol) and N,N-diisopropylethylamine (143 mg, 1.10 mmol) and then the reaction mixture was stirred 1.5 h at 90° C. After this time (1Z)-N'-hydroxy-2-(isopropylsulfonyl)ethanimidamide (199 mg, 1.10 mmol) was added and the mixture was stirred overnight at 110° C. After cooling to RT, the mixture was purified by preparative HPLC (gradient acetonitrile/water with 0.1% trifluoroacetic acid). Evaporation of the combined product fractions yielded the title compound (24 mg, 93% purity, 8% of theory).

LC-MS (Method 8B): R$_t$=1.23 min, MS (ESINeg): m/z=505 [M–H]$^-$

Example 240A

Tert-butyl 4-{3-[3-(3,5-difluoropyridin-2-yl)-1,2,4-oxadiazol-5-yl]-5-oxo-4,5-dihydropyrazolo[1,5-a]pyrimidin-7-yl}piperidine-1-carboxylate

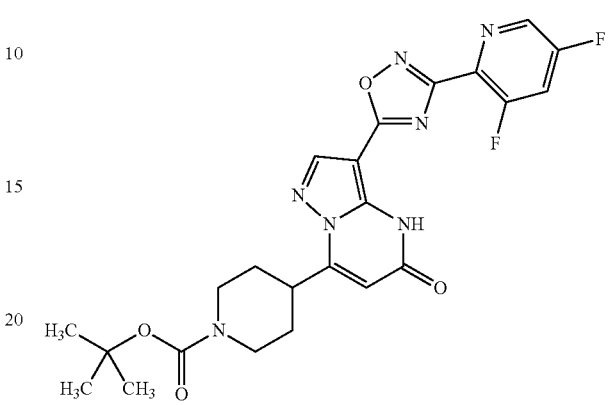

To a solution of compound 7-[1-(tert-Butoxycarbonyl)piperidin-4-yl]-5-oxo-4,5-dihydropyrazolo[1,5-a]pyrimidine-3-carboxylic acid (200 mg, 0.55 mmol) in 5 ml dimethylformamide was added 1,1'-carbonyldiimidazole (179 mg, 1.10 mmol) and N,N-diisopropylethylamine (143 mg, 1.10 mmol) and then the reaction mixture was stirred 1.5 h at 90° C. After this time 3,5-difluoro-N'-hydroxypyridine-2-carboximidamide (191 mg, 1.10 mmol) was added and the mixture was stirred overnight at 110° C. After cooling to RT, the mixture was purified by preparative HPLC (gradient acetonitrile/water with 0.1% trifluoroacetic acid). Evaporation of the combined product fractions yielded the title compound (25 mg, 9% of theory).

LC-MS (Method 8B): R$_t$=1.34 min, MS (ESINeg): m/z=498 [M–H]$^-$

Example 241A

Tert-butyl 4-(3-{3-[(1-methylpiperidin-4-yl)methyl]-1,2,4-oxadiazol-5-yl}-5-oxo-4,5-dihydropyrazolo[1,5-a]pyrimidin-7-yl)piperidine-1-carboxylate

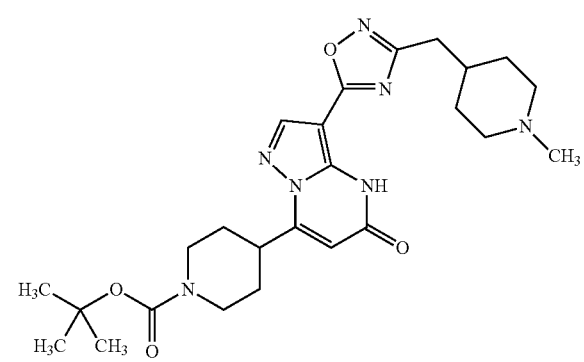 [SMILES: CN1CCC(Cc2noc(-c3cnn4c(C5CCN(C(=O)OC(C)(C)C)CC5)cc(=O)[nH]c34)n2)CC1]

To a solution of compound 7-[1-(tert-Butoxycarbonyl)piperidin-4-yl]-5-oxo-4,5-dihydropyrazolo[1,5-a]pyrimidine-3-carboxylic acid (200 mg, 0.55 mmol) in 5 ml dimethylformamide was added 1,1'-carbonyldiimidazole (179 mg, 1.10 mmol) and N,N-diisopropylethylamine (143 mg, 1.10 mmol) and then the reaction mixture was stirred 1.5 h at 90° C. After this time (1Z)-N'-hydroxy-2-(1-methylpiperidin-4-yl)ethanimidamide (189 mg, 1.10 mmol) was added and the mixture was stirred overnight at 110° C. After cooling to RT, the mixture was purified by preparative HPLC (gradient acetonitrile/water with 0.1% trifluoroacetic acid). Evaporation of the combined product fractions yielded the title compound (281 mg, 91% purity, 93% of theory).

LC-MS (Method 8B): R$_t$=0.89 min, MS (ESINeg): m/z=496 [M–H]$^-$

Example 242A

Tert-butyl 4-(3-{3-[4-(methoxycarbonyl)phenyl]-1,2,4-oxadiazol-5-yl}-5-oxo-4,5-dihydropyrazolo[1,5-a]pyrimidin-7-yl)piperidine-1-carboxylate

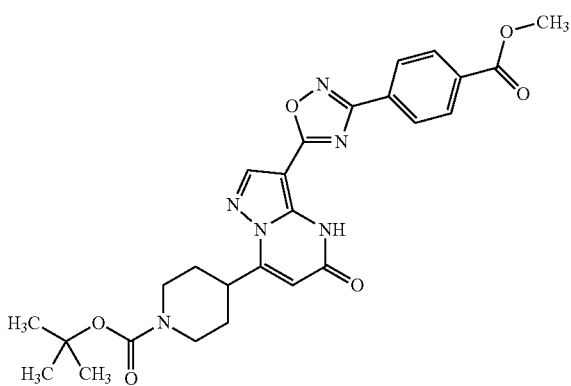 [SMILES: COC(=O)c1ccc(-c2noc(-c3cnn4c(C5CCN(C(=O)OC(C)(C)C)CC5)cc(=O)[nH]c34)n2)cc1]

To a solution of compound 7-[1-(tert-Butoxycarbonyl)piperidin-4-yl]-5-oxo-4,5-dihydropyrazolo[1,5-a]pyrimidine-3-carboxylic acid (400 mg, 1.10 mmol) in 10 ml dimethylformamide was added 1,1'-carbonyldiimidazole (358 mg, 2.21 mmol) and N,N-diisopropylethylamine (285 mg, 2.21 mmol) and then the reaction mixture was stirred 1.5 h at 90° C. After this time methyl 4-(N'-hydroxycarbamimidoyl)benzoate (429 mg, 2.21 mmol) was added and the mixture was stirred overnight at 110° C. After cooling to RT, a solid came off the solution. The solid, which was filtered and washed with 2 ml diethyl ether and dried in vacuo, proved to be the targeted product but still contained impurities. The mixture was purified by flash chromatography with silica gel (gradient dichloromethane/methanol). Evaporation of the combined product fractions yielded the title compound (41 mg, 7% of theory).

LC-MS (Method 8B): R$_t$=1.52 min, MS (ESINeg): m/z=519 [M–H]$^-$

Example 243A

Tert-butyl 4-{3-[3-(3-nitrophenyl)-1,2,4-oxadiazol-5-yl]-5-oxo-4,5-dihydropyrazolo[1,5-a]pyrimidin-7-yl}piperidine-1-carboxylate

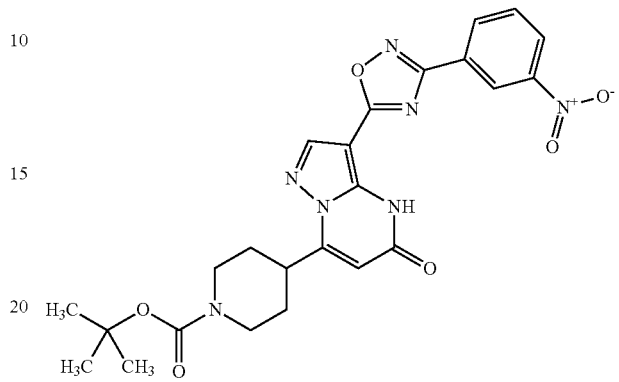

To a solution of compound 7-[1-(tert-Butoxycarbonyl)piperidin-4-yl]-5-oxo-4,5-dihydropyrazolo[1,5-a]pyrimidine-3-carboxylic acid (90 mg, 0.25 mmol) in 2.3 ml dimethylformamide was added 1,1'-carbonyldiimidazole (81 mg, 0.50 mmol) and N,N-diisopropylethylamine (64 mg, 0.50 mmol) and then the reaction mixture was stirred 1.5 h at 90° C. After this time N'-hydroxy-3-nitrobenzenecarboximidamide (90 mg, 0.50 mmol) was added and the mixture was stirred overnight at 110° C. After cooling to RT, the mixture was purified by preparative HPLC (gradient acetonitrile/water with 0.1% trifluoroacetic acid). Evaporation of the combined product fractions yielded the title compound (62 mg, 47% of theory).

LC-MS (Method 8B): R$_t$=1.50 min, MS (ESINeg): m/z=506 [M–H]$^-$

Example 244A

Tert-butyl 4-{3-[3-(2-methoxyethyl)-1,2,4-oxadiazol-5-yl]-5-oxo-4,5-dihydropyrazolo[1,5-a]pyrimidin-7-yl}piperidine-1-carboxylate

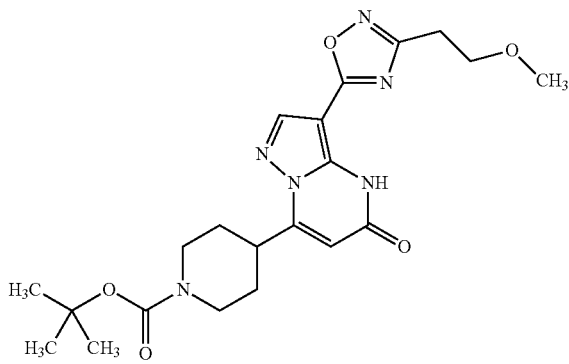 [SMILES: COCCc1noc(-c2cnn3c(C4CCN(C(=O)OC(C)(C)C)CC4)cc(=O)[nH]c23)n1]

To a solution of compound 7-[1-(tert-Butoxycarbonyl)piperidin-4-yl]-5-oxo-4,5-dihydropyrazolo[1,5-a]pyrimidine-3-carboxylic acid (200 mg, 0.55 mmol) in 5 ml dimethylformamide was added 1,1'-carbonyldiimidazole (179 mg, 1.10 mmol) and N,N-diisopropylethylamine (214 mg, 1.66 mmol) and then the reaction mixture was stirred 1.5 h at 90° C. After this time (1Z)-N'-hydroxy-3-methoxypropanimidamide (130 mg, 1.10 mmol) was added and the mixture was stirred overnight at 110° C. After cooling to RT, the mixture was purified by preparative HPLC (gradient acetonitrile/water with 0.1% trifluoroacetic acid). Evaporation of the combined product fractions yielded the title compound (103 mg, 93% purity, 39% of theory).

LC-MS (Method 8B): $R_t$=1.24 min, MS (ESINeg): m/z=443 [M−H]⁻

Example 245A

Tert-butyl 4-{5-oxo-3-[3-(pyridin-4-yl)-1,2,4-oxadiazol-5-yl]-4,5-dihydropyrazolo[1,5-a]pyrimidin-7-yl}piperidine-1-carboxylate

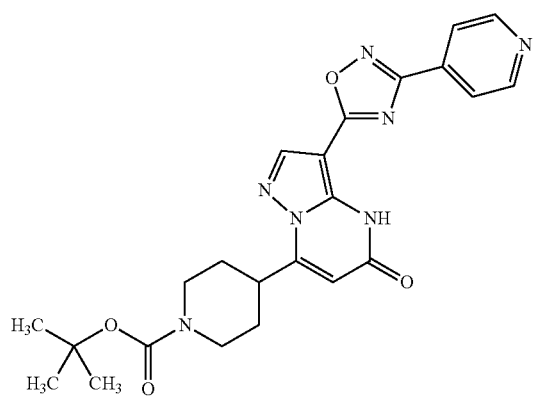 [SMILES: CC(C)(C)OC(=O)N1CCC(c2cc(=O)[nH]c3c(-c4nc(-c5ccncc5)no4)cnn23)CC1]

To a solution of compound 7-[1-(tert-Butoxycarbonyl)piperidin-4-yl]-5-oxo-4,5-dihydropyrazolo[1,5-a]pyrimidine-3-carboxylic acid (200 mg, 0.55 mmol) in 5 ml dimethylformamide was added 1,1'-carbonyldiimidazole (179 mg, 1.10 mmol) and N,N-diisopropylethylamine (214 mg, 1.66 mmol) and then the reaction mixture was stirred 1.5 h at 90° C. After this time N'-hydroxypyridine-4-carboximidamide (151 mg, 1.10 mmol) was added and the mixture was stirred overnight at 110° C. After cooling to RT, the mixture was purified by preparative HPLC (gradient acetonitrile/water with 0.1% trifluoroacetic acid). Evaporation of the combined product fractions yielded the title compound (174 mg, 65% of theory).

LC-MS (Method 8B): $R_t$=1.28 min, MS (ESINeg): m/z=462 [M−H]⁻

Example 246A

Tert-butyl 4-{3-[3-(3-aminophenyl)-1,2,4-oxadiazol-5-yl]-5-oxo-4,5-dihydropyrazolo[1,5-a]pyrimidin-7-yl}piperidine-1-carboxylate

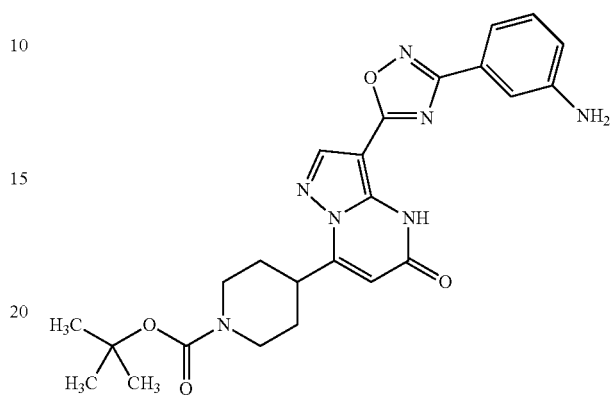

To a solution of compound 7-[1-(tert-Butoxycarbonyl)piperidin-4-yl]-5-oxo-4,5-dihydropyrazolo[1,5-a]pyrimidine-3-carboxylic acid (200 mg, 0.55 mmol) in 5 ml dimethylformamide was added 1,1'-carbonyldiimidazole (179 mg, 1.10 mmol) and N,N-diisopropylethylamine (214 mg, 1.66 mmol) and then the reaction mixture was stirred 1.5 h at 90° C. After this time 3-amino-N'-hydroxybenzenecarboximidamide (167 mg, 1.10 mmol) was added and the mixture was stirred overnight at 110° C. After cooling to RT, the mixture was purified by preparative HPLC (gradient acetonitrile/water with 0.1% trifluoroacetic acid). Evaporation of the combined product fractions yielded the title compound (178 mg, 88% purity, 59% of theory).

LC-MS (Method 8B): Rt=1.33 min, MS (ESINeg): m/z=476 [M−H]⁻

Example 247A

Tert-butyl 4-{3-bromo-5-[(4-methoxybenzyl)oxy]pyrazolo[1,5-a]pyrimidin-7-yl}piperidine-1-carboxylate

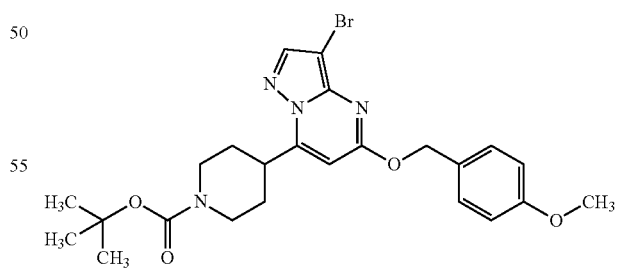

To a solution of tert-butyl 4-(3-bromo-5-oxo-4,5-dihydropyrazolo[1,5-a]pyrimidin-7-yl)piperidine-1-carboxylate (10.0 g, 25.2 mmol) in N,N-Dimethylformamide (200 ml, 1.1 mmol) under argon were added potassium carbonate (6.96 g, 50.3 mmol) and 1-(chloromethyl)-4-methoxybenzene (3.8 ml, 28 mmol). The mixture was stirred 1 h at 45° C. and was then poured onto 2 liters of water. The resulting solid, which is a 1/1 mixture of oxygen/nitrogen PMB-protected pyridone, was filtered and purified by preparative HPLC (gradient acetonitrile/water with 0.1% formic acid). Evaporation of the combined product fractions yielded the title compound.

The obtained amount was 5.46 g (100% purity, 42% of theory).

LC-MS (Method 8B): $R_t$=1.72 min.

$^1$H-NMR (400 MHz, DMSO-d6) delta [ppm]: 0.000 (2.08), 1.409 (16.00), 1.555 (0.14), 1.576 (0.36), 1.585 (0.37), 1.607 (0.40), 1.617 (0.37), 1.638 (0.16), 1.648 (0.13), 1.973 (0.49), 2.005 (0.42), 2.879 (0.17), 3.313 (1.32), 3.503 (0.16), 3.526 (0.19), 3.533 (0.31), 3.541 (0.18), 3.563 (0.15), 4.077 (0.29), 4.105 (0.28), 5.373 (2.73), 6.546 (1.69), 6.932 (0.18), 6.939 (1.44), 6.944 (0.50), 6.956 (0.53), 6.961 (1.54), 6.968 (0.18), 7.458 (0.19), 7.465 (1.45), 7.487 (1.34), 7.494 (0.16), 8.203 (1.71).

Example 248A

Tert-butyl 4-[3-(N'-hydroxycarbamimidoyl)-5-oxo-4,5-dihydropyrazolo[1,5-a]pyrimidin-7-yl]piperidine-1-carboxylate

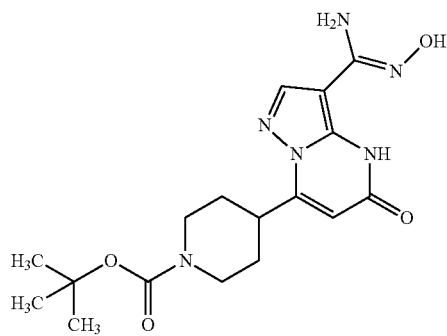 [SMILES: CC(C)(C)OC(=O)N1CCC(c2cc(=O)[nH]c3c(/C(N)=N/O)cnn23)CC1]

To a solution of tert-butyl 4-(3-cyano-5-oxo-4,5-dihydropyrazolo[1,5-a]pyrimidin-7-yl)piperidine-1-carboxylate (14.3 g, 71% purity, 29.5 mmol) in ethanol (300 ml) were added hydroxylamine hydrochloride (1:1) (3.08 g, 44.3 mmol) and triethylamine (5.3 ml, 38 mmol). The mixture was stirred overnight at 50° C. before being diluted with ethyl acetate. The organic phase was isolated, washed with water and a saturated aqueous solution of sodium chloride, dried over sodium sulfate, filtered and concentrated to yield the title compound. Despite a purity of 53%, the compound could be used in the next step without further purification.

The obtained amount was 9.83 g (53% purity, 47% of theory).

LC-MS (Method 8B): $R_t$=0.91 min; MS (ESIneg): m/z=375 [M−H]$^-$

Example 249A

Tert-butyl 4-{3-[3-(2-chlorobenzyl)-1,2,4-oxadiazol-5-yl]-5-oxo-4,5-dihydropyrazolo[1,5-a]pyrimidin-7-yl}piperidine-1-carboxylate

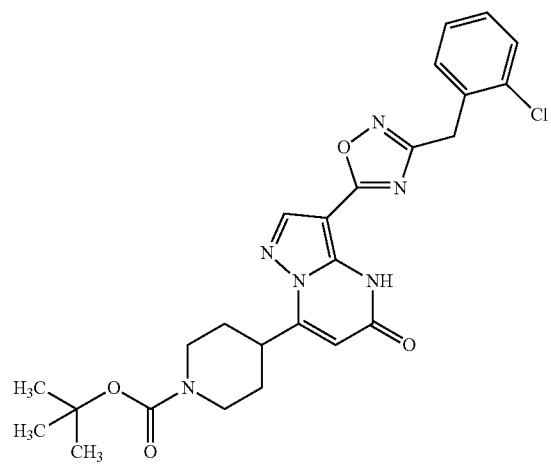 [SMILES: CC(C)(C)OC(=O)N1CCC(c2cc(=O)[nH]c3c(-c4nc(Cc5ccccc5Cl)no4)cnn23)CC1]

To a solution of 7-[1-(tert-butoxycarbonyl)piperidin-4-yl]-5-oxo-4,5-dihydropyrazolo[1,5-a]pyrimidine-3-carboxylic acid (200 mg, 552 µmol) in N,N-Dimethylformamide (5.0 ml) under argon were added 1,1'-carbonyldiimidazole (179 mg, 1.10 mmol) and Ethyldiisopropylamine (190 µl, 1.1 3 mmol). The reaction mixture was stirred 1.5 h at 90° C. After this time (1Z)-2-(2-chlorophenyl)-N'-hydroxyethanimidamide (204 mg, 1.10 mmol) was added and the mixture was stirred overnight at 110° C. After cooling to RT, the mixture was purified by preparative HPLC (gradient acetonitrile/water with 0.1% trifluoroacetic acid). Evaporation of the combined product fractions yielded the title compound.

The obtained amount was 128 mg (92% purity, 42% of theory).

LC-MS (Method 8B): $R_t$=1.51 min; MS (ESIneg): m/z=509 [M−H]$^-$

Example 250A

Tert-butyl 4-{3-[3-(4-chlorobenzyl)-1,2,4-oxadiazol-5-yl]-5-oxo-4,5-dihydropyrazolo[1,5-a]pyrimidin-7-yl}piperidine-1-carboxylate

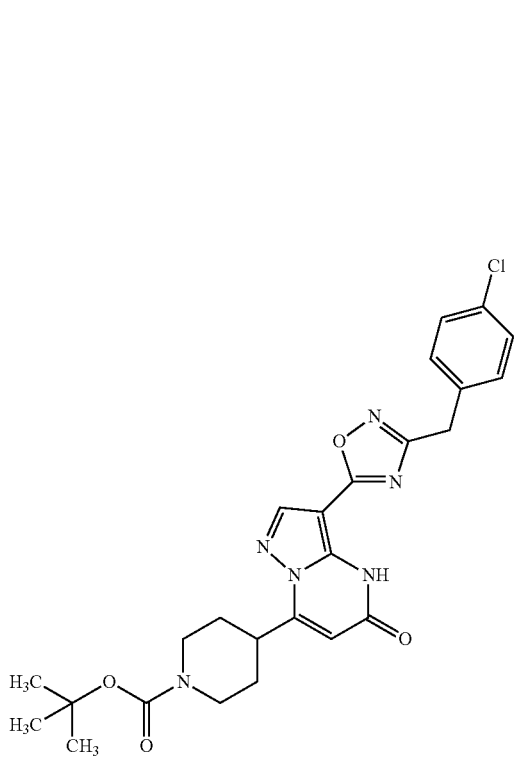

7-[1-(tert-butoxycarbonyl)piperidin-4-yl]-5-oxo-4,5-dihydropyrazolo[1,5-a]pyrimidine-3-carboxylic acid (200 mg, 552 µmol)
(1Z)-2-(4-chlorophenyl)-N'-hydroxyethanimidamide (204 mg, 1.10 mmol)
1,1'-carbonyldiimidazole (179 mg, 1.10 mmol)
Ethyldiisopropylamine (190 µl, 1.1 mmol)
N,N-Dimethylformamide (5.0 ml)

The title compound was prepared according to the same procedure as Example 249A.

The obtained amount was 117 mg (95% purity, 39% of theory).

LC-MS (Method 8B): $R_t$=1.52 min; MS (ESIneg): m/z=509 [M−H]⁻

Example 251A

Tert-butyl 4-{3-[3-(ethoxycarbonyl)-1,2,4-oxadiazol-5-yl]-5-oxo-4,5-dihydropyrazolo[1,5-a]pyrimidin-7-yl}piperidine-1-carboxylate

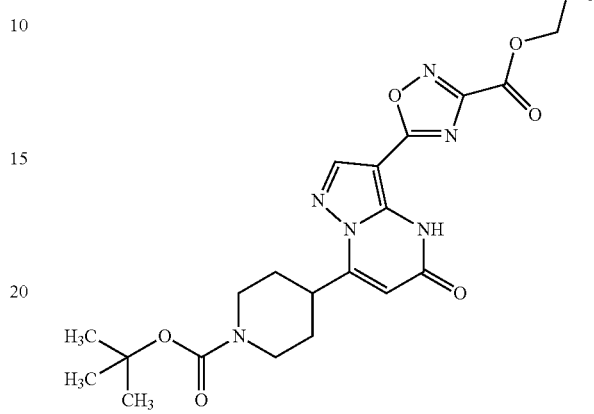

7-[1-(tert-butoxycarbonyl)piperidin-4-yl]-5-oxo-4,5-dihydropyrazolo[1,5-a]pyrimidine-3-carboxylic acid (100 mg, 276 µmol)
ethyl (2Z)-amino(hydroxyimino)ethanoate (365 mg, 2.76 mmol)
1,1'-carbonyldiimidazole (179 mg, 1.10 mmol)
Ethyldiisopropylamine (190 µl, 1.1 mmol)
N,N-Dimethylformamide (5.0 ml)

The title compound was prepared according to the same procedure as Example 249A.

The obtained amount was 40.0 mg (98% purity, 31% of theory).

LC-MS (Method 8B): $R_t$=1.31 min; MS (ESIneg): m/z=457 [M−H]⁻

Example 252A

Tert-butyl 4-[3-(3-{[(tert-butoxycarbonyl)amino]methyl}-1,2,4-oxadiazol-5-yl)-5-oxo-4,5-dihydropyrazolo[1,5-a]pyrimidin-7-yl]piperidine-1-carboxylate

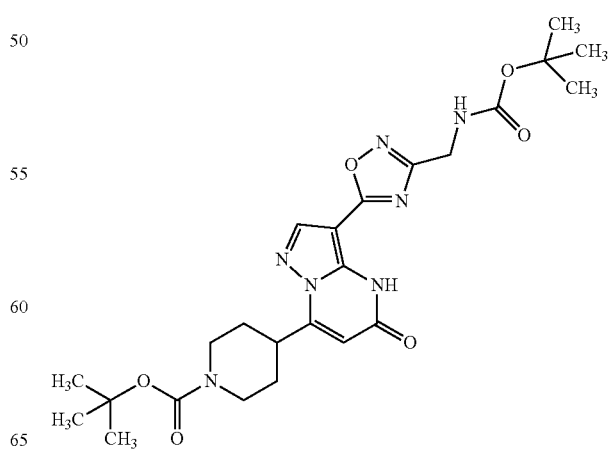

To a solution of 7-[1-(tert-butoxycarbonyl)piperidin-4-yl]-5-oxo-4,5-dihydropyrazolo[1,5-a]pyrimidine-3-carboxylic acid (286 mg, 790 µmol) in N,N-Dimethylformamide (5.0 ml) under argon was added 1,1'-carbonyldiimidazole (256 mg, 1.58 mmol) and Ethyldiisopropylamine (280 µl, 1.6 mmol). The reaction mixture was stirred 1.5 h at 90° C. After this time tert-butyl [(2Z)-2-amino-2-(hydroxyimino)ethyl]carbamate (318 mg, 94% purity, 1.58 mmol) was added and the mixture was stirred overnight at 110° C. A new portion of Ethyldiisopropylamine (140 µl, 0.8 mmol) was added, the mixture was then stirred another night at 110° C. and two days at 130° C. After cooling to RT, the mixture was purified by preparative HPLC (gradient acetonitrile/water with 0.1% trifluoroacetic acid).

Evaporation of the combined product fractions yielded the title compound.

The obtained amount was 158 mg (98% purity, 38% of theory).

LC-MS (Method 8B): $R_t$=1.34 min; MS (ESIneg): m/z=514 [M−H]⁻

Example 253A

Tert-butyl 4-{3-[3-(3,4-dichlorobenzyl)-1,2,4-oxadiazol-5-yl]-5-oxo-4,5-dihydropyrazolo[1,5-a]pyrimidin-7-yl}piperidine-1-carboxylate

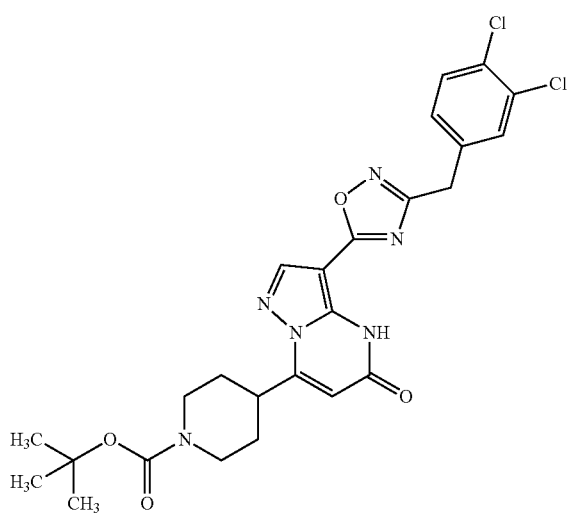 [SMILES: CC(C)(C)OC(=O)N1CCC(c2cc(=O)[nH]c3c(-c4nc(Cc5ccc(Cl)c(Cl)c5)no4)cnn23)CC1]

7-[1-(tert-butoxycarbonyl)piperidin-4-yl]-5-oxo-4,5-dihydropyrazolo[1,5-a]pyrimidine-3-carboxylic acid (300 mg, 828 µmol)

(1Z)-2-(3,4-dichlorophenyl)-N'-hydroxyethanimidamide (363 mg, 1.66 mmol)

1,1'-carbonyldiimidazole (268 mg, 1.66 mmol)

Ethyldiisopropylamine (290 µl, 1.7 mmol)

N,N-Dimethylformamide (7.5 ml)

The title compound was prepared according to the same procedure as Example 249A.

The obtained amount was 163 mg (100% purity, 36% of theory).

LC-MS (Method 8B): $R_t$=1.58 min; MS (ESIneg): m/z=543 [M−H]⁻

Example 254A

Tert-butyl 4-{3-[3-(4-methylbenzyl)-1,2,4-oxadiazol-5-yl]-5-oxo-4,5-dihydropyrazolo[1,5-a]pyrimidin-7-yl}piperidine-1-carboxylate

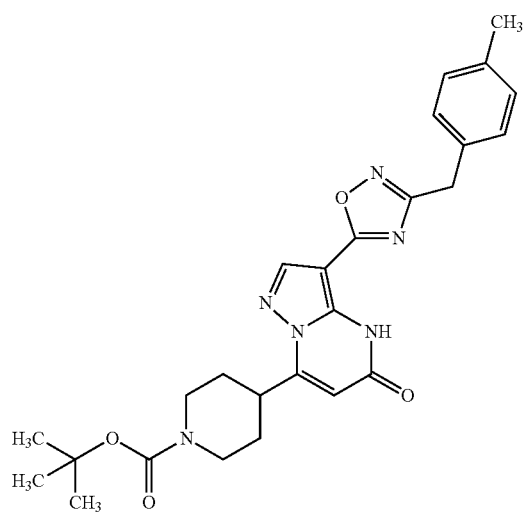 [SMILES: Cc1ccc(Cc2noc(-c3cnn4c(C5CCN(C(=O)OC(C)(C)C)CC5)cc(=O)[nH]c34)n2)cc1]

7-[1-(tert-butoxycarbonyl)piperidin-4-yl]-5-oxo-4,5-dihydropyrazolo[1,5-a]pyrimidine-3-carboxylic acid (200 mg, 552 µmol)

(1Z)-N'-hydroxy-2-(4-methylphenyl)ethanimidamide (181 mg, 1.10 mmol)

1,1'-carbonyldiimidazole (179 mg, 1.10 mmol)

Ethyldiisopropylamine (190 µl, 1.1 mmol)

N,N-Dimethylformamide (5.0 ml)

The title compound was prepared according to the same procedure as Example 249A.

The obtained amount was 130 mg (100% purity, 48% of theory).

LC-MS (Method 8B): $R_t$=1.51 min; MS (ESIneg): m/z=489 [M−H]⁻

Example 255A

Tert-butyl 4-{5-oxo-3-[3-(1-phenylethyl)-1,2,4-oxadiazol-5-yl]-4,5-dihydropyrazolo[1,5-a]pyrimidin-7-yl}piperidine-1-carboxylate

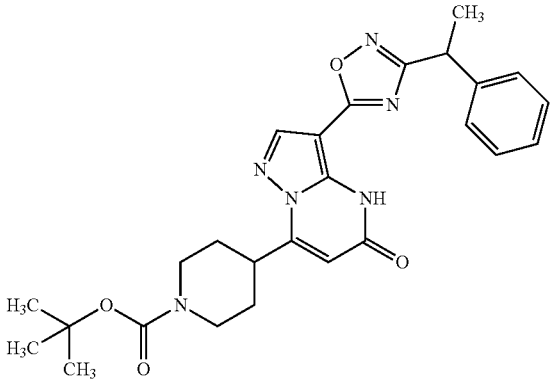 [SMILES: CC(c1ccccc1)c1noc(-c2cnn3c(C4CCN(C(=O)OC(C)(C)C)CC4)cc(=O)[nH]c23)n1]

289

7-[1-(tert-butoxycarbonyl)piperidin-4-yl]-5-oxo-4,5-dihydropyrazolo[1,5-a]pyrimidine-3-carboxylic acid (200 mg, 552 µmol)

(1Z)-N'-hydroxy-2-phenylpropanimidamide (181 mg, 1.10 mmol)

1,1'-carbonyldiimidazole (179 mg, 1.10 mmol)

Ethyldiisopropylamine (290 µl, 1.7 mmol)

N,N-Dimethylformamide (5.0 ml)

The title compound was prepared according to the same procedure as Example 249A.

The obtained amount was 56.0 mg (100% purity, 21% of theory).

LC-MS (Method 8B): R$_t$=1.51 min; MS (ESIneg): m/z=489 [M−H]⁻

Example 256A

Tert-butyl 4-{3-[5-(2-fluorophenyl)-1,2,4-oxadiazol-3-yl]-5-oxo-4,5-dihydropyrazolo[1,5-a]pyrimidin-7-yl}piperidine-1-carboxylate

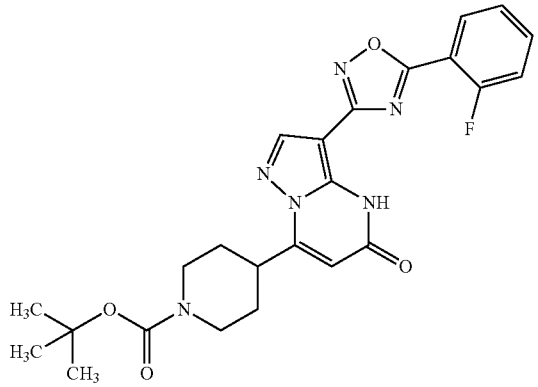 [SMILES: CC(C)(C)OC(=O)N1CCC(c2cc(=O)[nH]c3c(-c4noc(-c5ccccc5F)n4)cnn23)CC1]

To a solution of 2-fluorobenzoic acid (60.0 mg, 97% purity, 415 µmol) in N,N-Dimethylformamide (5.0 ml) under argon was added (Benzotriazol-1-yloxy)tripyrrolidinophosphonium hexafluorophosphate (262 mg, 99% purity, 498 µmol) and Ethyldiisopropylamine (85 µl, 500 µmol). The reaction mixture was stirred 1 h at room temperature. After this time tert-butyl 4-[3-(N'-hydroxycarbamimidoyl)-5-oxo-4,5-dihydropyrazolo[1,5-a]pyrimidin-7-yl]piperidine-1-carboxylate (297 mg, 58% purity, 457 µmol) was added and the mixture was stirred overnight at 110° C. After cooling to RT, the mixture was purified by flash chromatography with silica gel (gradient dichloromethane/methanol). Evaporation of the combined product fractions yielded the title compound, which proved to be still unclean and was used as such in the next step.

The obtained amount was 345 mg (53% purity, 83% of theory).

LC-MS (Method 8B): R$_t$=1.49 min; MS (ESIneg): m/z=479 [M−H]⁻

Example 257A

Tert-butyl 4-{3-[5-(3-chlorobenzyl)-1,2,4-oxadiazol-3-yl]-5-oxo-4,5-dihydropyrazolo[1,5-a]pyrimidin-7-yl}piperidine-1-carboxylate

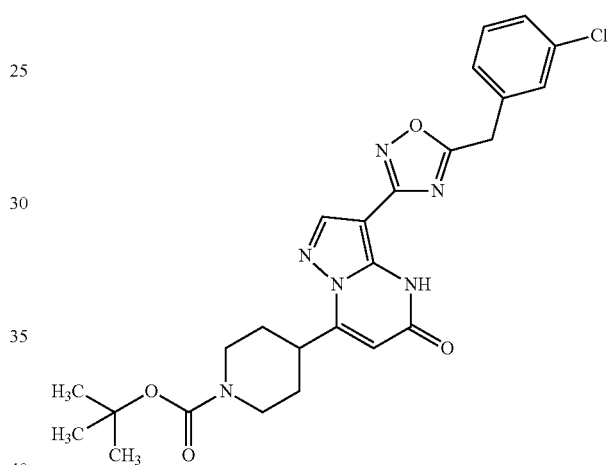

To a solution of (3-chlorophenyl)acetic acid (50.0 mg, 293 µmol) in N,N-Dimethylformamide (5.2 ml) under argon was added (Benzotriazol-1-yloxy)tripyrrolidinophosphonium hexafluorophosphate (183 mg, 352 µmol) and Ethyldiisopropylamine (61 µl, 350 µmol). The reaction mixture was stirred 1 h at room temperature. After this time tert-butyl 4-[3-(N'-hydroxycarbamimidoyl)-5-oxo-4,5-dihydropyrazolo[1,5-a]pyrimidin-7-yl]piperidine-1-carboxylate (209 mg, 58% purity, 322 µmol) was added and the mixture was stirred overnight at 110° C. After cooling to RT, the mixture was purified by preparative HPLC (gradient acetonitrile/water with 0.1% trifluoroacetic acid). Evaporation of the combined product fractions yielded the title compound.

The obtained amount was 54.0 mg (92% purity, 30% of theory).

LC-MS (Method 8B): R$_t$=1.51 min; MS (ESIneg): m/z=509 [M−H]⁻

Example 258A

Tert-butyl 4-{3-[5-(3-chloro-2-fluorophenyl)-1,2,4-oxadiazol-3-yl]-5-oxo-4,5-dihydropyrazolo[1,5-a]pyrimidin-7-yl}piperidine-1-carboxylate

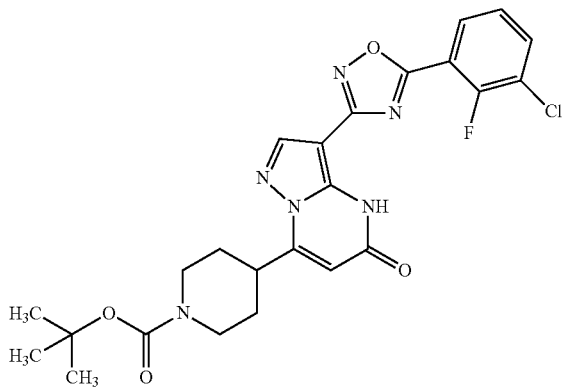 [SMILES: CC(C)(C)OC(=O)N1CCC(c2cc(=O)[nH]c3c(-c4noc(-c5cccc(Cl)c5F)n4)cnn23)CC1]

tert-butyl 4-[3-(N'-hydroxycarbamimidoyl)-5-oxo-4,5-dihydropyrazolo[1,5-a]pyrimidin-7-yl]piperidine-1-carboxylate (245 mg, 58% purity, 378 µmol)
3-chloro-2-fluorobenzoic acid (60.0 mg, 344 µmol)
(Benzotriazol-1-yloxy)tripyrrolidinophosphonium hexafluorophosphate (217 mg, 99% purity, 412 µmol)
Ethyldiisopropylamine (70 µl, 410 µmol)
N,N-Dimethylformamide (5.0 ml)
The title compound was prepared according to the same procedure as Example 257A.
The obtained amount was 82.0 mg (100% purity, 42% of theory).
LC-MS (Method 8B): $R_t$=1.57 min; MS (ESIneg): m/z=513 [M–H]⁻

Example 259A

Tert-butyl 4-{3-[5-(2-methoxyphenyl)-1,2,4-oxadiazol-3-yl]-5-oxo-4,5-dihydropyrazolo[1,5-a]pyrimidin-7-yl}piperidine-1-carboxylate

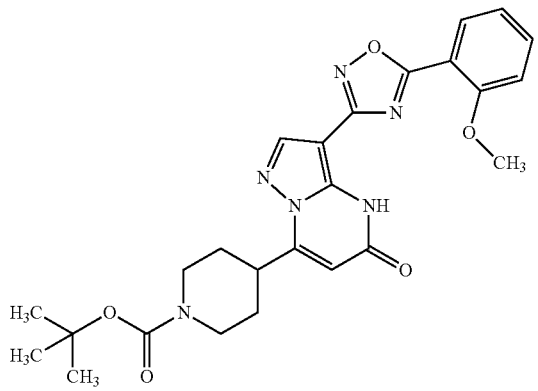 [SMILES: COc1ccccc1-c1nc(-c2cnn3c(C4CCN(C(=O)OC(C)(C)C)CC4)cc(=O)[nH]c23)no1]

tert-butyl 4-[3-(N'-hydroxycarbamimidoyl)-5-oxo-4,5-dihydropyrazolo[1,5-a]pyrimidin-7-yl]piperidine-1-carboxylate (279 mg, 58% purity, 429 µmol)
2-methoxybenzoic acid (60.0 mg, 99% purity, 390 µmol)
(Benzotriazol-1-yloxy)tripyrrolidinophosphonium hexafluorophosphate (246 mg, 99% purity, 468 µmol)
Ethyldiisopropylamine (80 µl, 470 µmol)
N,N-Dimethylformamide (5.0 ml)
The title compound was prepared according to the same procedure as Example 257A.
The obtained amount was 39.0 mg (100% purity, 18% of theory).
LC-MS (Method 8B): $R_t$=1.47 min; MS (ESIneg): m/z=491 [M–H]⁻

Example 260A

Tert-butyl 4-{3-[5-(4-methylphenyl)-1,2,4-oxadiazol-3-yl]-5-oxo-4,5-dihydropyrazolo[1,5-a]pyrimidin-7-yl}piperidine-1-carboxylate

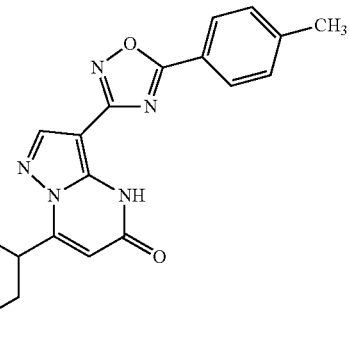

tert-butyl 4-[3-(N'-hydroxycarbamimidoyl)-5-oxo-4,5-dihydropyrazolo[1,5-a]pyrimidin-7-yl]piperidine-1-carboxylate (308 mg, 58% purity, 475 µmol)
4-methylbenzoic acid (60.0 mg, 98% purity, 432 µmol)
(Benzotriazol-1-yloxy)tripyrrolidinophosphonium hexafluorophosphate (272 mg, 99% purity, 518 µmol)
Ethyldiisopropylamine (88 µl, 520 µmol)
N,N-Dimethylformamide (5.0 ml)
The title compound was prepared according to the same procedure as Example 257A.
The obtained amount was 39.0 mg (94% purity, 16% of theory).
LC-MS (Method 8B): $R_t$=1.57 min; MS (ESIneg): m/z=475 [M–H]⁻

Example 261A

5-{7-[1-(tert-butoxycarbonyl)piperidin-4-yl]-5-oxo-4,5-dihydropyrazolo[1,5-a]pyrimidin-3-yl}-1,2,4-oxadiazole-3-carboxylic Acid

Example 262A

Tert-butyl 4-(5-oxo-3-{3-[3-(trifluoromethyl)benzyl]-1,2,4-oxadiazol-5-yl}-4,5-dihydropyrazolo[1,5-a]pyrimidin-7-yl)piperidine-1-carboxylate

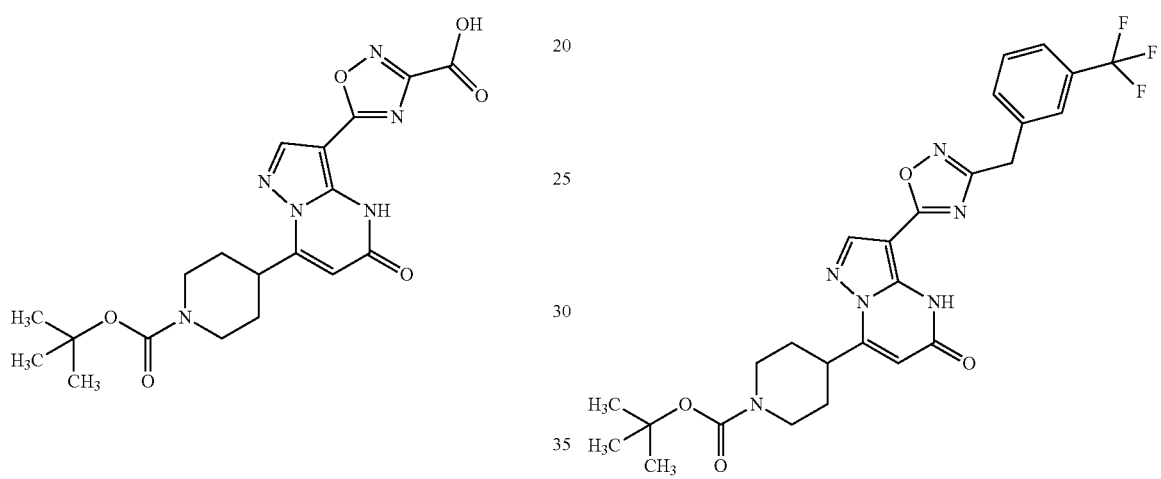

To a solution of tert-butyl 4-{3-[3-(ethoxycarbonyl)-1,2,4-oxadiazol-5-yl]-5-oxo-4,5-dihydropyrazolo[1,5-a]pyrimidin-7-yl}piperidine-1-carboxylate (50.0 mg, 97% purity, 106 μmol) in a 1/1/1 mixture of methanol/oxolane/water (1.0 mL/1.0 mL/1.0 mL) was added lithium hydroxyde (2.59 mg, 98% purity, 106 μmol). The reaction mixture was stirred for 2 h at room temperature. A second portion of lithium hydroxyde (2.59 mg, 98% purity, 106 μmol), previously dissolved in water, was added and stirring was continued for 1 h. The mixture was slightly acidified using aqueous 1.0 M hydrochloric acid and extracted three times with ethyl acetate. The organic phase was then washed with water, dried over sodium sulfate and concentrated.

The obtained amount was 36.0 mg (99% purity, 78% of theory).

LC-MS (Method 8B): $R_t$=0.95 min; MS (ESIpos): m/z=375 [M+H—(CH$_3$)$_3$]$^+$

7-[1-(tert-butoxycarbonyl)piperidin-4-yl]-5-oxo-4,5-dihydropyrazolo[1,5-a]pyrimidine-3-carboxylic acid (183 mg, 505 μmol)

(1Z)-N'-hydroxy-2-[3-(trifluoromethyl)phenyl]ethanimidamide (380 mg, 58% purity, 1.01 mmol)

1,1'-carbonyldiimidazole (164 mg, 1.01 mmol)

Ethyldiisopropylamine (260 μl, 1.5 mmol)

N,N-Dimethylformamide (5.0 ml)

The title compound was prepared according to the same procedure as Example 249A.

The obtained amount was 41.0 mg (100% purity, 15% of theory).

LC-MS (Method 8B): $R_t$=1.53 min; MS (ESIneg): m/z=543 [M−H]$^−$

Example 263A

Tert-butyl 4-{5-oxo-3-[3-(2-phenylpropan-2-yl)-1,2,4-oxadiazol-5-yl]-4,5-dihydropyrazolo[1,5-a]pyrimidin-7-yl}piperidine-1-carboxylate

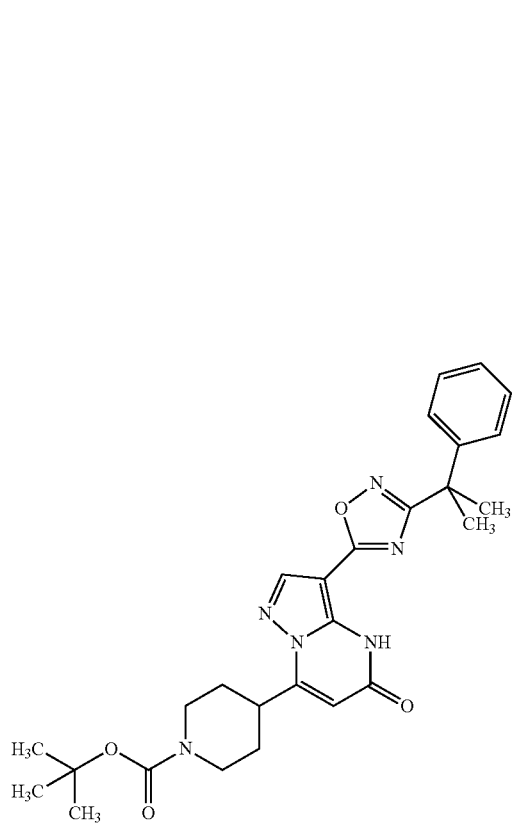 [SMILES: CC(C)(C)OC(=O)N1CCC(c2cc(=O)[nH]c3c(-c4nc(C(C)(C)c5ccccc5)no4)cnn23)CC1]

7-[1-(tert-butoxycarbonyl)piperidin-4-yl]-5-oxo-4,5-dihydropyrazolo[1,5-a]pyrimidine-3-carboxylic acid (87.4 mg, 241 µmol)
(1Z)-N'-hydroxy-2-methyl-2-phenylpropanimidamide (86.0 mg, 100% purity, 483 µmol)
1,1'-carbonyldiimidazole (78.2 mg, 483 µmol)
Ethyldiisopropylamine (130 µl, 720 µmol)
N,N-Dimethylformamide (5.0 ml)
The title compound was prepared according to the same procedure as Example 249A.
The obtained amount was 10.0 mg (100% purity, 8% of theory).
LC-MS (Method 8B): R$_t$=1.55 min; MS (ESIneg): m/z=503 [M−H]$^-$

Example 264A

Tert-butyl 4-{3-[3-(4-fluorobenzyl)-1,2,4-oxadiazol-5-yl]-5-oxo-4,5-dihydropyrazolo[1,5-a]pyrimidin-7-yl}piperidine-1-carboxylate

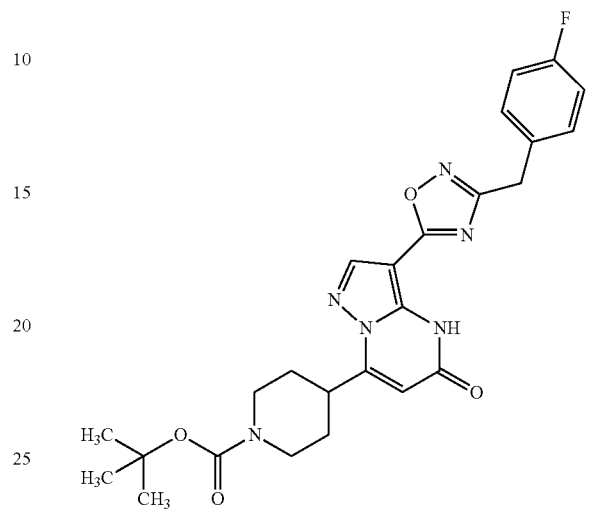

7-[1-(tert-butoxycarbonyl)piperidin-4-yl]-5-oxo-4,5-dihydropyrazolo[1,5-a]pyrimidine-3-carboxylic acid (200 mg, 552 µmol)
(1Z)-2-(4-fluorophenyl)-N'-hydroxyethanimidamide (186 mg, 1.10 mmol)
1,1'-carbonyldiimidazole (179 mg, 1.10 mmol)
Ethyldiisopropylamine (190 µl, 1.1 mmol)
N,N-Dimethylformamide (5.0 ml)
The title compound was prepared according to the same procedure as Example 249A.
The obtained amount was 96.0 mg (98% purity, 34% of theory).
LC-MS (Method 8B): R$_t$=1.45 min; MS (ESIneg): m/z=493 [M−H]$^-$

Example 265A

Tert-butyl 4-{3-[5-(2-methylphenyl)-1,2,4-oxadiazol-3-yl]-5-oxo-4,5-dihydropyrazolo[1,5-a]pyrimidin-7-yl}piperidine-1-carboxylate

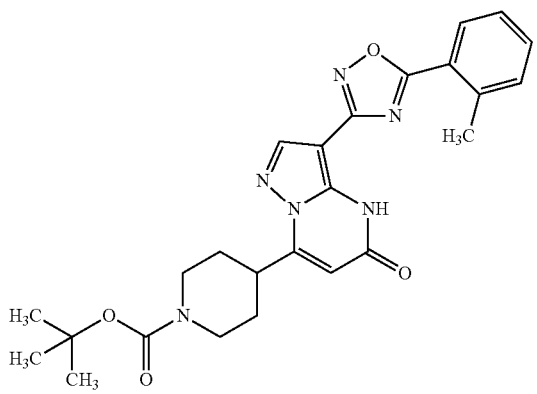 [SMILES: Cc1ccccc1-c1nc(-c2cnn3c(C4CCN(C(=O)OC(C)(C)C)CC4)cc(=O)[nH]c23)no1]

tert-butyl 4-[3-(N'-hydroxycarbamimidoyl)-5-oxo-4,5-dihydropyrazolo[1,5-a]pyrimidin-7-yl]piperidine-1-carboxylate (315 mg, 58% purity, 485 µmol)

2-methylbenzoic acid (60.0 mg, 441 µmol)

(Benzotriazol-1-yloxy)tripyrrolidinophosphonium hexafluorophosphate (278 mg, 99% purity, 529 µmol)

Ethyldiisopropylamine (90 µl, 530 µmol)

N,N-Dimethylformamide (5.0 ml)

The title compound was prepared according to the same procedure as Example 257A.

The obtained amount was 58.0 mg (100% purity, 25% of theory).

LC-MS (Method 8B): $R_t$=1.57 min; MS (ESIneg): m/z=475 [M–H]⁻

Example 266A

Tert-butyl 4-{3-[5-(3-chlorophenyl)-1,2,4-oxadiazol-3-yl]-5-oxo-4,5-dihydropyrazolo[1,5-a]pyrimidin-7-yl}piperidine-1-carboxylate

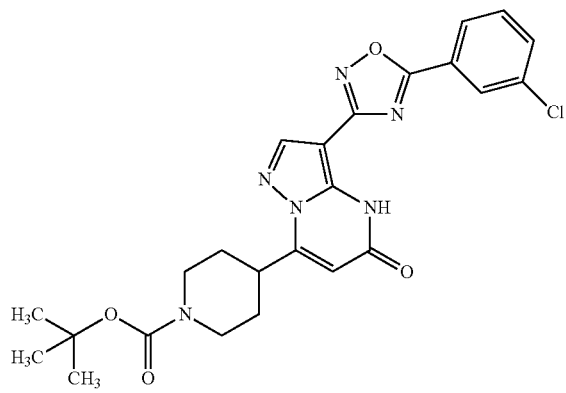 [SMILES: CC(C)(C)OC(=O)N1CCC(c2cc(=O)[nH]c3c(-c4noc(-c5cccc(Cl)c5)n4)cnn23)CC1]

To a solution of 3-chlorobenzoic acid (60.0 mg, 383 µmol) in N,N-Dimethylformamide (5.0 ml) under argon was added (Benzotriazol-1-yloxy)tripyrrolidinophosphonium hexafluorophosphate (242 mg, 99% purity, 460 µmol) and Ethyldiisopropylamine (78 µl, 460 µmol). The reaction mixture was stirred 1 h at room temperature. After this time tert-butyl 4-[3-(N'-hydroxycarbamimidoyl)-5-oxo-4,5-dihydropyrazolo[1,5-a]pyrimidin-7-yl]piperidine-1-carboxylate (274 mg, 58% purity, 422 µmol) was added and the mixture was stirred overnight at 110° C. After cooling to RT, the mixture was concentrated and used as such in the next step.

The obtained amount was 649 mg (24% purity, 74% of theory).

LC-MS (Method 8B): $R_t$=1.59 min; MS (ESIneg): m/z=495 [M–H]⁻

Example 267A

Tert-butyl 4-(5-oxo-3-{5-[3-(trifluoromethyl)phenyl]-1,2,4-oxadiazol-3-yl}-4,5-dihydropyrazolo[1,5-a]pyrimidin-7-yl)piperidine-1-carboxylate

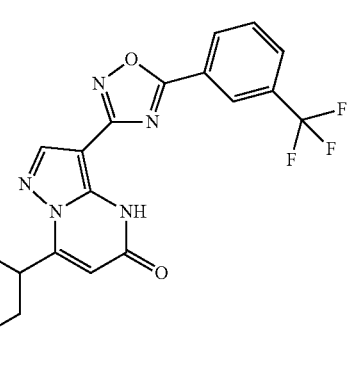

tert-butyl 4-[3-(N'-hydroxycarbamimidoyl)-5-oxo-4,5-dihydropyrazolo[1,5-a]pyrimidin-7-yl]piperidine-1-carboxylate (225 mg, 58% purity, 347 µmol)

3-(trifluoromethyl)benzoic acid (60.0 mg, 316 µmol)

(Benzotriazol-1-yloxy)tripyrrolidinophosphonium hexafluorophosphate (199 mg, 99% purity, 379 µmol)

Ethyldiisopropylamine (64 µl, 380 µmol)

N,N-Dimethylformamide (5.0 ml)

The title compound was prepared according to the same procedure as Example 257A.

The obtained amount was 53.0 mg (99% purity, 28% of theory).

LC-MS (Method 8B): $R_t$=1.60 min; MS (ESIneg): m/z=529 [M–H]⁻

Example 268A

Tert-butyl 4-[3-(5-benzyl-1,2,4-oxadiazol-3-yl)-5-oxo-4,5-dihydropyrazolo[1,5-a]pyrimidin-7-yl]piperidine-1-carboxylate

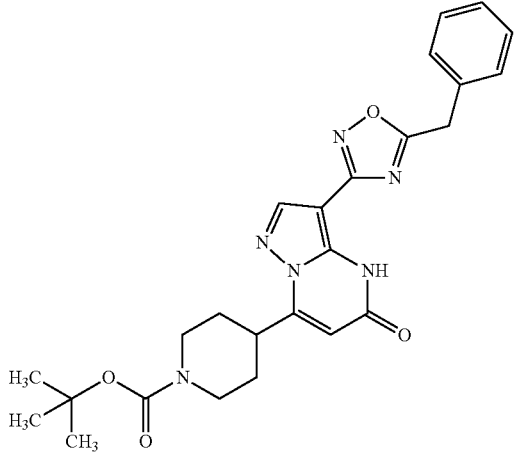 [SMILES: CC(C)(C)OC(=O)N1CCC(c2cc(=O)[nH]c3c(-c4noc(Cc5ccccc5)n4)cnn23)CC1]

tert-butyl 4-[3-(N'-hydroxycarbamimidoyl)-5-oxo-4,5-dihydropyrazolo[1,5-a]pyrimidin-7-yl]piperidine-1-carboxylate (311 mg, 58% purity, 480 µmol)

phenylacetic acid (60.0 mg, 99% purity, 436 µmol)
(Benzotriazol-1-yloxy)tripyrrolidinophosphonium hexafluorophosphate (275 mg, 99% purity, 524 µmol)
Ethyldiisopropylamine (89 µl, 520 µmol)
N,N-Dimethylformamide (5.0 ml)

The title compound was prepared according to the same procedure as Example 257A.

The obtained amount was 118 mg (86% purity, 44% of theory).

LC-MS (Method 8B): $R_t$=1.45 min; MS (ESIneg): m/z=475 [M−H]⁻

Example 269A

Tert-butyl 4-{3-[5-(3-chloro-2-methylphenyl)-1,2,4-oxadiazol-3-yl]-5-oxo-4,5-dihydropyrazolo[1,5-a]pyrimidin-7-yl}piperidine-1-carboxylate

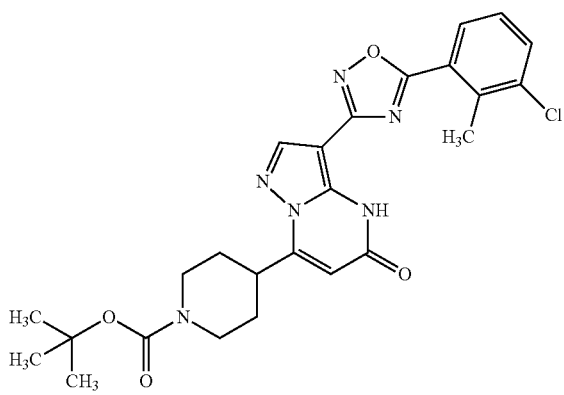 [SMILES: Cc1c(Cl)cccc1-c1nc(-c2cnn3c(C4CCN(C(=O)OC(C)(C)C)CC4)cc(=O)[nH]c23)no1]

tert-butyl 4-[3-(N'-hydroxycarbamimidoyl)-5-oxo-4,5-dihydropyrazolo[1,5-a]pyrimidin-7-yl]piperidine-1-carboxylate (251 mg, 58% purity, 387 µmol)
3-chloro-2-methylbenzoic acid (60.0 mg, 352 µmol)
(Benzotriazol-1-yloxy)tripyrrolidinophosphonium hexafluorophosphate (222 mg, 99% purity, 422 µmol)
Ethyldiisopropylamine (72 µl, 420 µmol)
N,N-Dimethylformamide (5.0 ml)

The title compound was prepared according to the same procedure as Example 257A.

The obtained amount was 36.0 mg (100% purity, 18% of theory).

LC-MS (Method 8B): $R_t$=1.65 min; MS (ESIneg): m/z=509 [M−H]⁻

Example 270A

Tert-butyl 4-{3-[5-(5-chloro-2-methylphenyl)-1,2,4-oxadiazol-3-yl]-5-oxo-4,5-dihydropyrazolo[1,5-a]pyrimidin-7-yl}piperidine-1-carboxylate

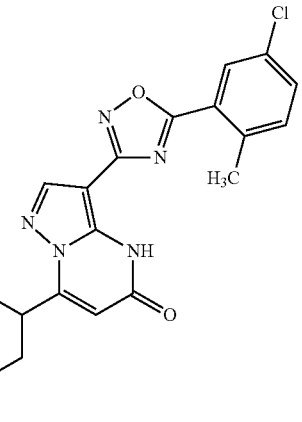

tert-butyl 4-[3-(N'-hydroxycarbamimidoyl)-5-oxo-4,5-dihydropyrazolo[1,5-a]pyrimidin-7-yl]piperidine-1-carboxylate (251 mg, 58% purity, 387 µmol)
5-chloro-2-methylbenzoic acid (60.0 mg, 352 µmol)
(Benzotriazol-1-yloxy)tripyrrolidinophosphonium hexafluorophosphate (222 mg, 99% purity, 422 µmol)
Ethyldiisopropylamine (72 µl, 420 µmol)
N,N-Dimethylformamide (5.0 ml)

The title compound was prepared according to the same procedure as Example 257A.

The obtained amount was 50.0 mg (100% purity, 25% of theory).

LC-MS (Method 8B): $R_t$=1.65 min; MS (ESIneg): m/z=509 [M−H]⁻

Example 271A

Tert-butyl 4-(5-oxo-3-{5-[4-(trifluoromethyl)phenyl]-1,2,4-oxadiazol-3-yl}-4,5-dihydropyrazolo[1,5-a]pyrimidin-7-yl)piperidine-1-carboxylate

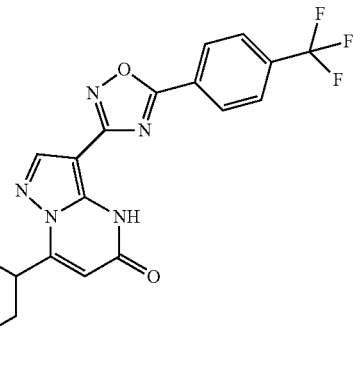

tert-butyl 4-[3-(N'-hydroxycarbamimidoyl)-5-oxo-4,5-dihydropyrazolo[1,5-a]pyrimidin-7-yl]piperidine-1-carboxylate (225 mg, 58% purity, 347 µmol)

4-(trifluoromethyl)benzoic acid (60.0 mg, 316 µmol)

(Benzotriazol-1-yloxy)tripyrrolidinophosphonium hexafluorophosphate (199 mg, 99% purity, 379 µmol)

Ethyldiisopropylamine (64 µl, 380 µmol)

N,N-Dimethylformamide (5.0 ml)

The title compound was prepared according to the same procedure as Example 257A.

The obtained amount was 57.0 mg (100% purity, 31% of theory).

LC-MS (Method 8B): $R_t$=1.60 min; MS (ESIneg): m/z=529 [M−H]⁻

Example 272A

Tert-butyl 4-(3-{5-[2-chloro-4-(trifluoromethyl)phenyl]-1,2,4-oxadiazol-3-yl}-5-oxo-4,5-dihydropyrazolo[1,5-a]pyrimidin-7-yl)piperidine-1-carboxylate

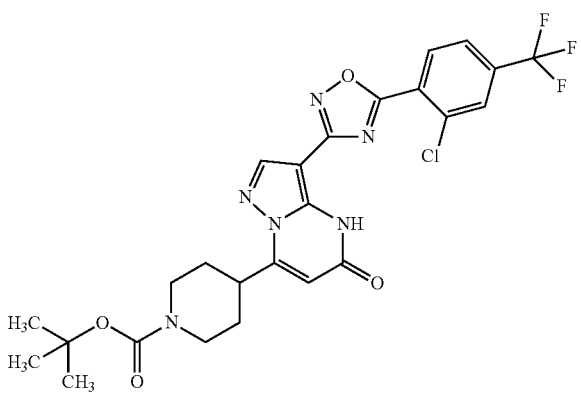 [SMILES: CC(C)(C)OC(=O)N1CCC(c2cc(=O)[nH]c3c(-c4noc(-c5ccc(C(F)(F)F)cc5Cl)n4)cnn23)CC1]

tert-butyl 4-[3-(N'-hydroxycarbamimidoyl)-5-oxo-4,5-dihydropyrazolo[1,5-a]pyrimidin-7-yl]piperidine-1-carboxylate (191 mg, 58% purity, 294 µmol)

2-chloro-4-(trifluoromethyl)benzoic acid (60.0 mg, 267 µmol)

(Benzotriazol-1-yloxy)tripyrrolidinophosphonium hexafluorophosphate (169 mg, 99% purity, 321 µmol)

Ethyldiisopropylamine (55 µl, 320 µmol)

N,N-Dimethylformamide (5.0 ml)

The title compound was prepared according to the same procedure as Example 257A.

The obtained amount was 51.0 mg (99% purity, 30% of theory).

LC-MS (Method 8B): $R_t$=1.67 min; MS (ESIneg): m/z=563 [M−H]⁻

Example 273A

Tert-butyl 4-{3-[5-(4-chlorophenyl)-1,2,4-oxadiazol-3-yl]-5-oxo-4,5-dihydropyrazolo[1,5-a]pyrimidin-7-yl}piperidine-1-carboxylate

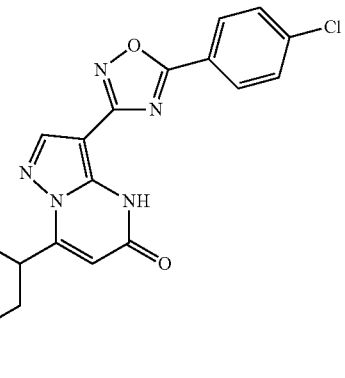

tert-butyl 4-[3-(N'-hydroxycarbamimidoyl)-5-oxo-4,5-dihydropyrazolo[1,5-a]pyrimidin-7-yl]piperidine-1-carboxylate (274 mg, 58% purity, 422 µmol)

4-chlorobenzoic acid (60.0 mg, 383 µmol)

(Benzotriazol-1-yloxy)tripyrrolidinophosphonium hexafluorophosphate (242 mg, 99% purity, 460 µmol)

Ethyldiisopropylamine (78 µl, 460 µmol)

N,N-Dimethylformamide (5.0 ml)

The title compound was prepared according to the same procedure as Example 257A.

The obtained amount was 41.0 mg (96% purity, 19% of theory).

LC-MS (Method 8B): $R_t$=1.59 min; MS (ESIneg): m/z=495 [M−H]⁻

Example 274A

Tert-butyl 4-{3-[5-(3,5-dichlorophenyl)-1,2,4-oxadiazol-3-yl]-5-oxo-4,5-dihydropyrazolo[1,5-a]pyrimidin-7-yl}piperidine-1-carboxylate

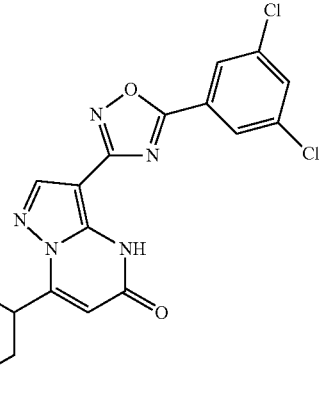

tert-butyl 4-[3-(N'-hydroxycarbamimidoyl)-5-oxo-4,5-dihydropyrazolo[1,5-a]pyrimidin-7-yl]piperidine-1-carboxylate (224 mg, 58% purity, 346 µmol)

3,5-dichlorobenzoic acid (60.0 mg, 314 µmol)

(Benzotriazol-1-yloxy)tripyrrolidinophosphonium hexafluorophosphate (198 mg, 99% purity, 377 µmol)

Ethyldiisopropylamine (64 µl, 380 µmol)

N,N-Dimethylformamide (5.0 ml)

The title compound was prepared according to the same procedure as Example 257A.

The obtained amount was 25.0 mg (77% purity, 10% of theory).

LC-MS (Method 1B): $R_t$=1.42 min; MS (ESIneg): m/z=529 [M–H]⁻

Example 275A

Tert-butyl 4-{3-[5-(5-chloro-2-fluorophenyl)-1,2,4-oxadiazol-3-yl]-5-oxo-4,5-dihydropyrazolo[1,5-a]pyrimidin-7-yl}piperidine-1-carboxylate

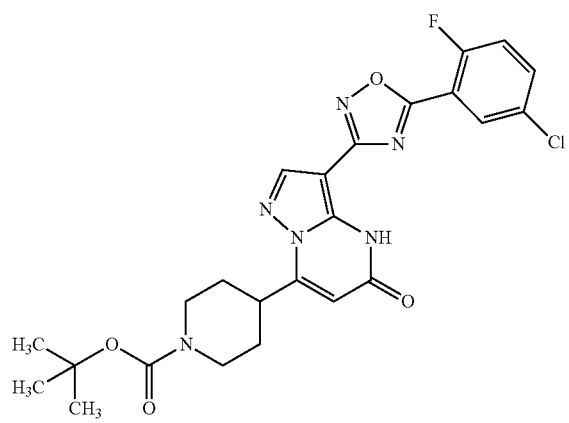 [SMILES: CC(C)(C)OC(=O)N1CCC(c2cc(=O)[nH]c3c(-c4noc(-c5cc(Cl)ccc5F)n4)cnn23)CC1]

tert-butyl 4-[3-(N'-hydroxycarbamimidoyl)-5-oxo-4,5-dihydropyrazolo[1,5-a]pyrimidin-7-yl]piperidine-1-carboxylate (198 mg, 58% purity, 306 µmol)

5-chloro-2-fluorobenzoic acid (50.0 mg, 97% purity, 278 µmol)

(Benzotriazol-1-yloxy)tripyrrolidinophosphonium hexafluorophosphate (175 mg, 99% purity, 333 µmol)

Ethyldiisopropylamine (57 µl, 330 µmol)

N,N-Dimethylformamide (5.0 ml)

The title compound was prepared according to the same procedure as Example 257A.

The obtained amount was 27.0 mg (87% purity, 15% of theory).

LC-MS (Method 8B): $R_t$=1.57 min; MS (ESIneg): m/z=513 [M–H]⁻

Example 276A

Tert-butyl 4-(5-oxo-3-{5-[2-(trifluoromethoxy)phenyl]-1,2,4-oxadiazol-3-yl}-4,5-dihydropyrazolo[1,5-a]pyrimidin-7-yl)piperidine-1-carboxylate

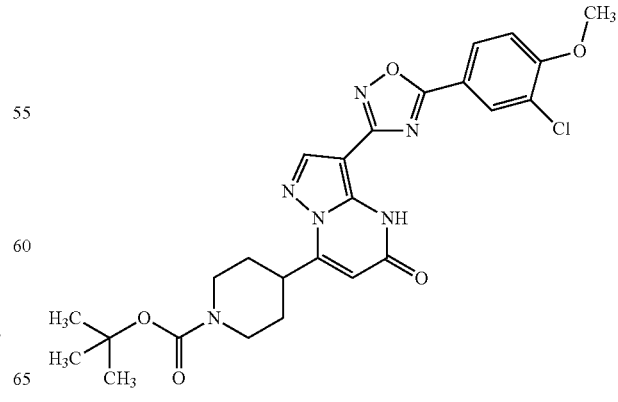

tert-butyl 4-[3-(N'-hydroxycarbamimidoyl)-5-oxo-4,5-dihydropyrazolo[1,5-a]pyrimidin-7-yl]piperidine-1-carboxylate (202 mg, 58% purity, 311 µmol)

2-(trifluoromethoxy)benzoic acid (60.0 mg, 97% purity, 282 µmol)

(Benzotriazol-1-yloxy)tripyrrolidinophosphonium hexafluorophosphate (178 mg, 99% purity, 339 µmol)

Ethyldiisopropylamine (58 µl, 340 µmol)

N,N-Dimethylformamide (5.0 ml)

The title compound was prepared according to the same procedure as Example 257A.

The obtained amount was 45.0 mg (93% purity, 25% of theory).

LC-MS (Method 8B): $R_t$=1.59 min; MS (ESIneg): m/z=545 [M–H]⁻

Example 277A

Tert-butyl 4-{3-[5-(3-chloro-4-methoxyphenyl)-1,2,4-oxadiazol-3-yl]-5-oxo-4,5-dihydropyrazolo[1,5-a]pyrimidin-7-yl}piperidine-1-carboxylate tert-butyl 4-[3-(N'-hydroxycarbamimidoyl)-5-oxo-4,5-dihydropyrazolo[1,5-a]pyrimidin-7-yl]piperidine-1-carboxylate (230 mg, 58% purity, 354 μmol)

3-chloro-4-methoxybenzoic acid (60.0 mg, 322 μmol)

(Benzotriazol-1-yloxy)tripyrrolidinophosphonium hexafluorophosphate (203 mg, 99% purity, 386 μmol)

Ethyldiisopropylamine (66 μl, 390 μmol)

N,N-Dimethylformamide (5.0 ml)

The title compound was prepared according to the same procedure as Example 257A.

The obtained amount was 10.0 mg (72% purity, 4% of theory).

LC-MS (Method 8B): $R_t$=1.57 min; MS (ESIneg): m/z=525 [M−H]⁻

Example 278A

Tert-butyl 4-(3-{3-[hydroxy(phenyl)methyl]-1,2,4-oxadiazol-5-yl}-5-oxo-4,5-dihydropyrazolo[1,5-a]pyrimidin-7-yl)piperidine-1-carboxylate

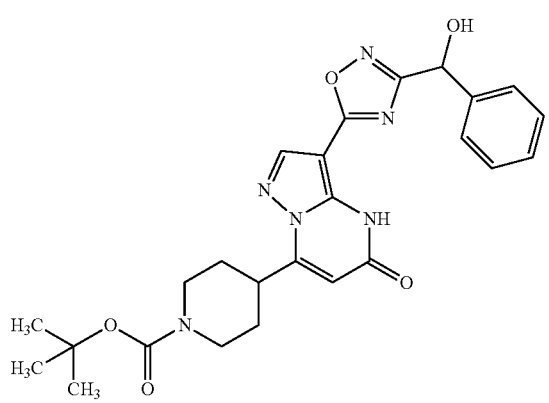 [SMILES: CC(C)(C)OC(=O)N1CCC(c2cc(=O)[nH]c3c(-c4nc(C(O)c5ccccc5)no4)cnn23)CC1]

7-[1-(tert-butoxycarbonyl)piperidin-4-yl]-5-oxo-4,5-dihydropyrazolo[1,5-a]pyrimidine-3-carboxylic acid (500 mg, 1.38 mmol)

(1Z)-N',2-dihydroxy-2-phenylethanimidamide (459 mg, 2.76 mmol)

1,1'-carbonyldiimidazole (447 mg, 2.76 mmol)

Ethyldiisopropylamine (720 μl, 4.1 mmol)

N,N-Dimethylformamide (51 ml)

The title compound was prepared according to the same procedure as Example 249A.

The obtained amount was 64.0 mg (85% purity, 8% of theory).

LC-MS (Method 8B): $R_t$=1.29 min; MS (ESIneg): m/z=491 [M−H]⁻

Example 279A

Tert-butyl 4-(5-oxo-3-{5-[4-(trifluoromethoxy)benzyl]-1,2,4-oxadiazol-3-yl}-4,5-dihydropyrazolo[1,5-a]pyrimidin-7-yl)piperidine-1-carboxylate

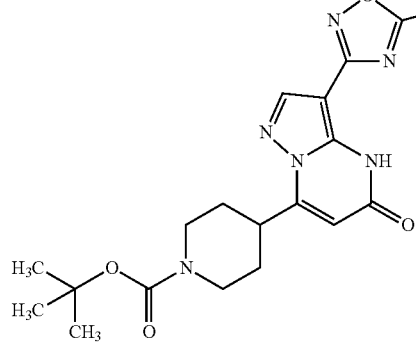

To a solution of [4-(trifluoromethoxy)phenyl]acetic acid (70.4 mg, 320 μmol) in N,N-Dimethylformamide (4.0 ml) under argon was added (Benzotriazol-1-yloxy)tripyrrolidinophosphonium hexafluorophosphate (200 mg, 384 μmol) and Ethyldiisopropylamine (67 μl, 380 μmol). The reaction mixture was stirred 1 h at room temperature. After this time tert-butyl 4-[3-(N'-hydroxycarbamimidoyl)-5-oxo-4,5-dihydropyrazolo[1,5-a]pyrimidin-7-yl]piperidine-1-carboxylate (250 mg, 53% purity, 352 μmol) was added and the mixture was stirred overnight at 110° C. After cooling to RT, the mixture was purified by preparative HPLC (gradient acetonitrile/water with 0.1% formic acid). Evaporation of the combined product fractions yielded the title compound.

The obtained amount was 66.0 mg (97% purity, 32% of theory).

LC-MS (Method 8B): $R_t$=1.54 min; MS (ESIneg): m/z=559 [M−H]⁻

Example 280A

Tert-butyl 4-{3-[5-(3,5-difluoro-4-methoxybenzyl)-1,2,4-oxadiazol-3-yl]-5-oxo-4,5-dihydropyrazolo[1,5-a]pyrimidin-7-yl}piperidine-1-carboxylate

Example 281A

Tert-butyl 4-(3-{5-[rac-1-(4-methoxyphenyl)propyl]-1,2,4-oxadiazol-3-yl}-5-oxo-4,5-dihydropyrazolo[1,5-a]pyrimidin-7-yl)piperidine-1-carboxylate

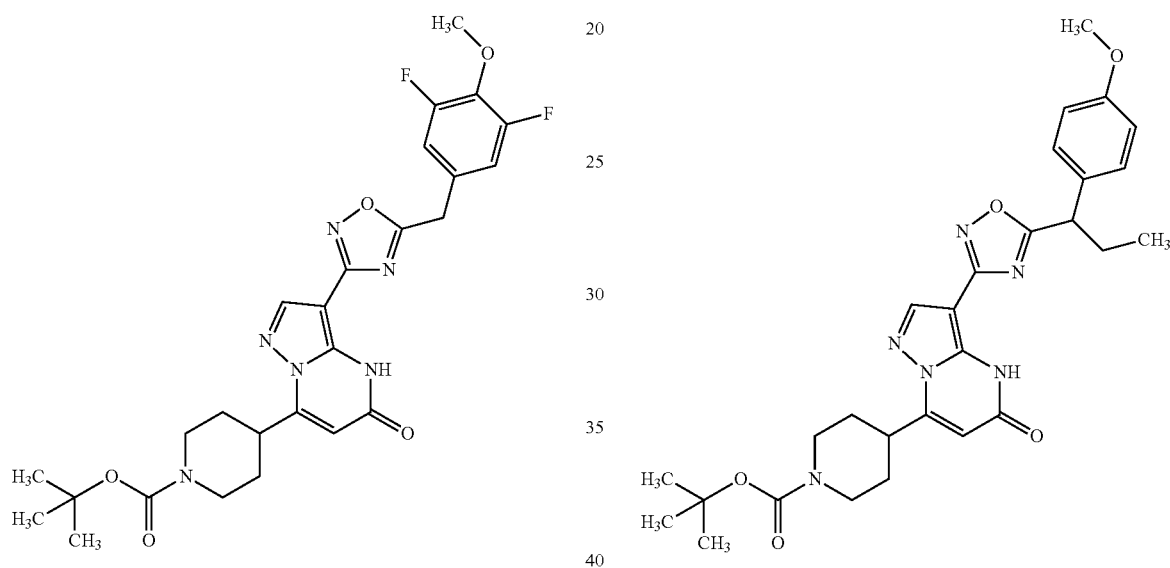

tert-butyl 4-[3-(N'-hydroxycarbamimidoyl)-5-oxo-4,5-dihydropyrazolo[1,5-a]pyrimidin-7-yl]piperidine-1-carboxylate (250 mg, 53% purity, 352 µmol)

(3,5-difluoro-4-methoxyphenyl)acetic acid (64.7 mg, 320 µmol)

(Benzotriazol-1-yloxy)tripyrrolidinophosphonium hexafluorophosphate (200 mg, 384 µmol)

Ethyldiisopropylamine (67 µl, 380 µmol)

N,N-Dimethylformamide (4.0 ml)

The title compound was prepared according to the same procedure as Example 279A.

The obtained amount was 60.0 mg (100% purity, 31% of theory).

LC-MS (Method 8B): $R_t$=1.47 min; MS (ESIneg): m/z=541 [M−H]⁻ tert-butyl 4-[3-(N'-hydroxycarbamimidoyl)-5-oxo-4,5-dihydropyrazolo[1,5-a]pyrimidin-7-yl]piperidine-1-carboxylate (250 mg, 53% purity, 352 µmol) rac-2-(4-methoxyphenyl)butanoic acid (62.2 mg, 320 µmol)

(Benzotriazol-1-yloxy)tripyrrolidinophosphonium hexafluorophosphate (200 mg, 384 µmol)

Ethyldiisopropylamine (67 µl, 380 µmol)

N,N-Dimethylformamide (4.0 ml)

The title compound was prepared according to the same procedure as Example 279A.

The obtained amount was 43.0 mg (93% purity, 21% of theory).

LC-MS (Method 8B): $R_t$=1.56 min; MS (ESIneg): m/z=533 [M−H]⁻

Example 282A

Tert-butyl 4-(3-{5-[2-(4-methoxyphenyl)propan-2-yl}-1,2,4-oxadiazol-3-yl]-5-oxo-4,5-dihydropyrazolo[1,5-a]pyrimidin-7-yl)piperidine-1-carboxylate

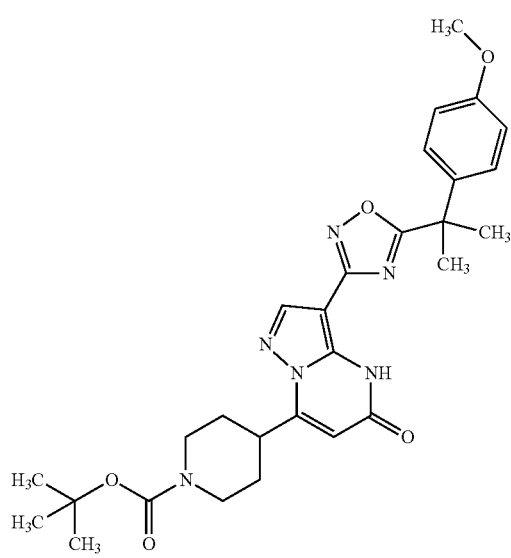 [SMILES: COc1ccc(C(C)(C)c2nc(-c3cnn4c(C5CCN(C(=O)OC(C)(C)C)CC5)cc(=O)[nH]c34)no2)cc1]

tert-butyl 4-[3-(N'-hydroxycarbamimidoyl)-5-oxo-4,5-dihydropyrazolo[1,5-a]pyrimidin-7-yl]piperidine-1-carboxylate (250 mg, 53% purity, 352 µmol)

2-(4-methoxyphenyl)-2-methylpropanoic acid (62.2 mg, 320 µmol)

(Benzotriazol-1-yloxy)tripyrrolidinophosphonium hexafluorophosphate (200 mg, 384 µmol)

Ethyldiisopropylamine (67 µl, 380 µmol)

N,N-Dimethylformamide (4.0 ml)

The title compound was prepared according to the same procedure as Example 279A.

The obtained amount was 32.0 mg (96% purity, 16% of theory).

LC-MS (Method 8B): $R_t$=1.55 min; MS (ESIneg): m/z=533 [M−H]⁻

Example 283A

Tert-butyl 4-{5-oxo-3-[5-(tetrahydro-2H-pyran-4-yl)-1,2,4-oxadiazol-3-yl]-4,5-dihydropyrazolo[1,5-a]pyrimidin-7-yl}piperidine-1-carboxylate tert-butyl 4-[3-(N'-hydroxycarbamimidoyl)-5-oxo-4,5-dihydropyrazolo[1,5-a]pyrimidin-7-yl]piperidine-1-carboxylate (250 mg, 53% purity, 352 µmol)

tetrahydro-2H-pyran-4-carboxylic acid (41.6 mg, 320 µmol)

(Benzotriazol-1-yloxy)tripyrrolidinophosphonium hexafluorophosphate (200 mg, 384 µmol)

Ethyldiisopropylamine (67 µl, 380 µmol)

N,N-Dimethylformamide (4.0 ml)

The title compound was prepared according to the same procedure as Example 279A.

The obtained amount was 60.0 mg (94% purity, 34% of theory).

LC-MS (Method 8B): $R_t$=1.28 min; MS (ESIneg): m/z=469 [M−H]⁻

Example 284A

Tert-butyl 4-(3-{5-[4-(difluoromethoxy)benzyl]-1,2,4-oxadiazol-3-yl}-5-oxo-4,5-dihydropyrazolo[1,5-a]pyrimidin-7-yl)piperidine-1-carboxylate

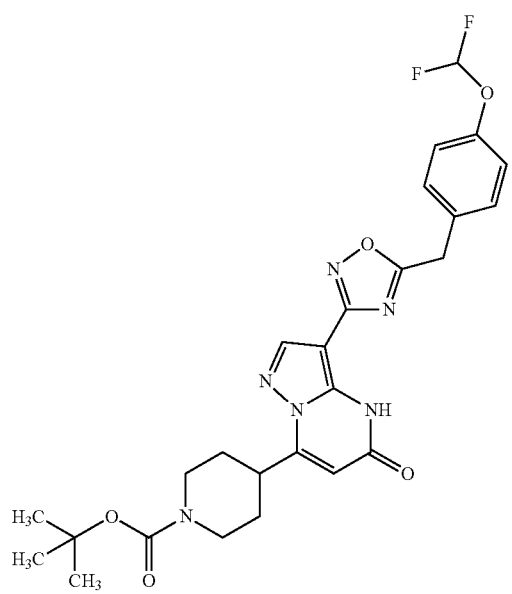 [SMILES: CC(C)(C)OC(=O)N1CCC(c2cc(=O)[nH]c3c(-c4noc(Cc5ccc(OC(F)F)cc5)n4)cnn23)CC1]

tert-butyl 4-[3-(N'-hydroxycarbamimidoyl)-5-oxo-4,5-dihydropyrazolo[1,5-a]pyrimidin-7-yl]piperidine-1-carboxylate (250 mg, 53% purity, 352 μmol) [4-(difluoromethoxy)phenyl]acetic acid (64.7 mg, 320 μmol)
(Benzotriazol-1-yloxy)tripyrrolidinophosphonium hexafluorophosphate (200 mg, 384 μmol)
Ethyldiisopropylamine (67 μl, 380 μmol)
N,N-Dimethylformamide (4.0 ml)
The title compound was prepared according to the same procedure as Example 279A.
The obtained amount was 40.0 mg (98% purity, 21% of theory).
LC-MS (Method 8B): $R_t$=1.45 min; MS (ESIneg): m/z=541 [M−H]⁻

Example 285A

Tert-butyl 4-(3-{5-[1-(4-methoxyphenyl)cyclopropyl]-1,2,4-oxadiazol-3-yl}-5-oxo-4,5-dihydropyrazolo[1,5-a]pyrimidin-7-yl)piperidine-1-carboxylate

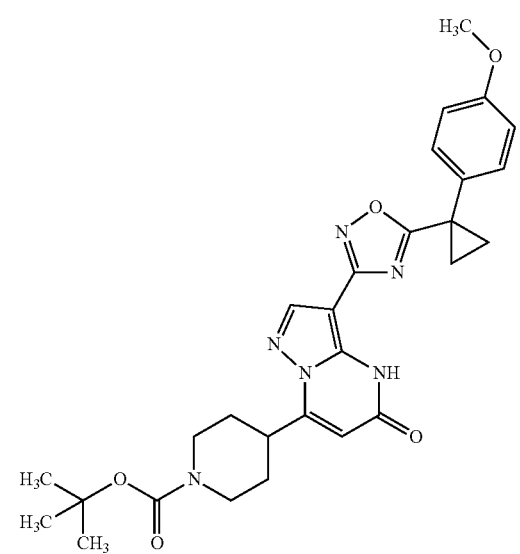 [SMILES: COc1ccc(C2(c3nc(-c4cnn5c(C6CCN(C(=O)OC(C)(C)C)CC6)cc(=O)[nH]c45)no3)CC2)cc1]

tert-butyl 4-[3-(N'-hydroxycarbamimidoyl)-5-oxo-4,5-dihydropyrazolo[1,5-a]pyrimidin-7-yl]piperidine-1-carboxylate (250 mg, 53% purity, 352 μmol)
1-(4-methoxyphenyl)cyclopropanecarboxylic acid (61.5 mg, 320 μmol)
(Benzotriazol-1-yloxy)tripyrrolidinophosphonium hexafluorophosphate (200 mg, 384 μmol)
Ethyldiisopropylamine (67 μl, 380 μmol)
N,N-Dimethylformamide (4.0 ml)
The title compound was prepared according to the same procedure as Example 279A.
The obtained amount was 43.0 mg (100% purity, 23% of theory).
LC-MS (Method 8B): $R_t$=1.53 min; MS (ESIneg): m/z=531 [M−H]⁻

Example 286A

Tert-butyl 4-{3-[5-(2-fluoro-4-methoxybenzyl)-1,2,4-oxadiazol-3-yl]-5-oxo-4,5-dihydropyrazolo[1,5-a]pyrimidin-7-yl}piperidine-1-carboxylate

Example 287A

Tert-butyl 4-{3-[5-(3-fluoro-4-methoxybenzyl)-1,2,4-oxadiazol-3-yl]-5-oxo-4,5-dihydropyrazolo[1,5-a]pyrimidin-7-yl}piperidine-1-carboxylate

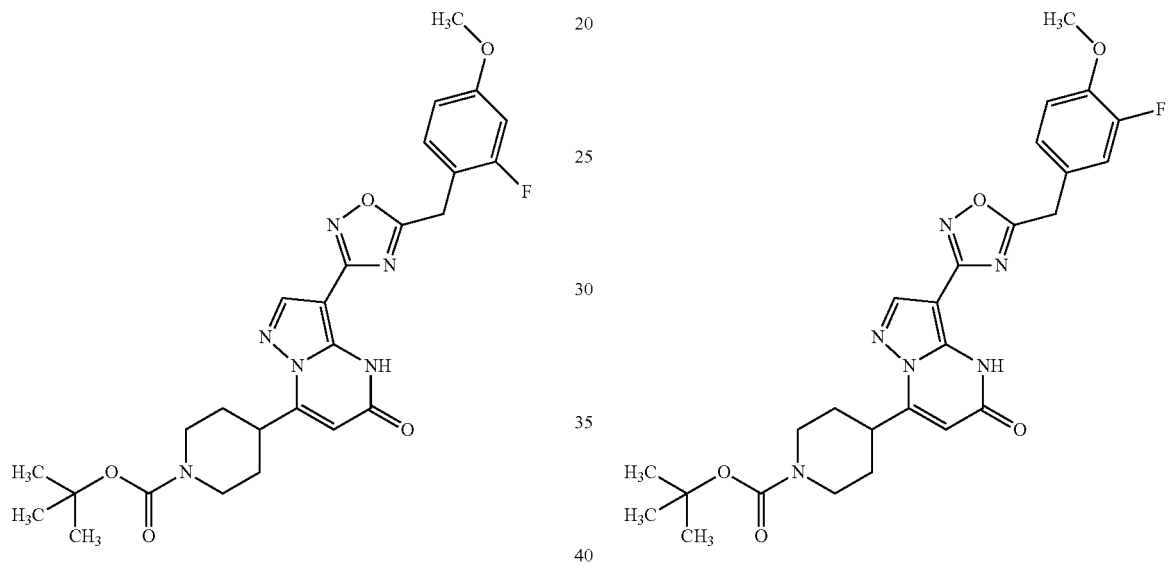

tert-butyl 4-[3-(N'-hydroxycarbamimidoyl)-5-oxo-4,5-dihydropyrazolo[1,5-a]pyrimidin-7-yl]piperidine-1-carboxylate (250 mg, 53% purity, 352 μmol)

(2-fluoro-4-methoxyphenyl)acetic acid (58.9 mg, 320 μmol)

(Benzotriazol-1-yloxy)tripyrrolidinophosphonium hexafluorophosphate (200 mg, 384 μmol)

Ethyldiisopropylamine (67 μl, 380 μmol)

N,N-Dimethylformamide (4.0 ml)

The title compound was prepared according to the same procedure as Example 279A.

The obtained amount was 65.0 mg (100% purity, 35% of theory).

LC-MS (Method 8B): $R_t$=1.45 min; MS (ESIneg): m/z=523 [M−H]⁻ tert-butyl 4-[3-(N'-hydroxycarbamimidoyl)-5-oxo-4,5-dihydropyrazolo[1,5-a]pyrimidin-7-yl]piperidine-1-carboxylate (250 mg, 53% purity, 352 μmol)

(3-fluoro-4-methoxyphenyl)acetic acid (58.9 mg, 320 μmol)

(Benzotriazol-1-yloxy)tripyrrolidinophosphonium hexafluorophosphate (200 mg, 384 μmol)

Ethyldiisopropylamine (67 μl, 380 μmol)

N,N-Dimethylformamide (4.0 ml)

The title compound was prepared according to the same procedure as Example 279A.

The obtained amount was 74.0 mg (97% purity, 39% of theory).

LC-MS (Method 8B): $R_t$=1.43 min; MS (ESIneg): m/z=523 [M−H]⁻

Example 288A

Tert-butyl 4-{3-[5-(3-chloro-4-methylphenyl)-1,2,4-oxadiazol-3-yl]-5-oxo-4,5-dihydropyrazolo[1,5-a]pyrimidin-7-yl}piperidine-1-carboxylate

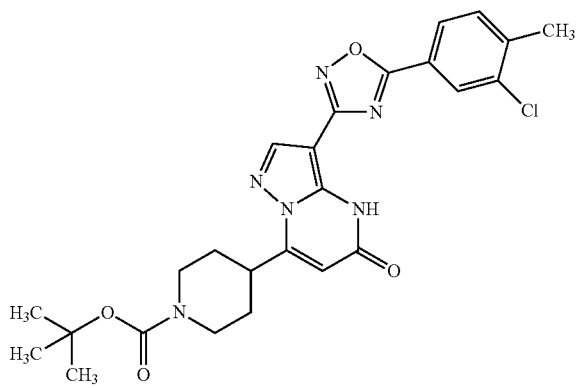 [SMILES: Cc1ccc(-c2nc(-c3cnn4c(C5CCN(C(=O)OC(C)(C)C)CC5)cc(=O)[nH]c34)no2)cc1Cl]

To a solution of 3-chloro-4-methylbenzoic acid (119 mg, 700 µmol) in N,N-Dimethylformamide (10 ml) under argon was added (Benzotriazol-1-yloxy)tripyrrolidinophosphonium hexafluorophosphate (442 mg, 99% purity, 840 µmol) and Ethyldiisopropylamine (140 µl, 840 µmol). The reaction mixture was stirred 1 h at room temperature. After this time tert-butyl 4-[3-(N'-hydroxycarbamimidoyl)-5-oxo-4,5-dihydropyrazolo[1,5-a]pyrimidin-7-yl]piperidine-1-carboxylate (500 mg, 58% purity, 770 µmol) was added and the mixture was stirred overnight at 110° C. After cooling to RT, the mixture was purified by preparative HPLC (gradient acetonitrile/water with 0.1% formic acid, then pure 2-Methoxy-2-methylpropane). Evaporation of the combined product fractions yielded the title compound.

The obtained amount was 85.0 mg (93% purity, 20% of theory).

LC-MS (Method 8B): $R_t$=1.66 min; MS (ESIneg): m/z=509 [M−H]⁻

Example 289A

Tert-butyl 4-(3-{5-[4-methyl-2-(trifluoromethyl)phenyl]-1,2,4-oxadiazol-3-yl}-5-oxo-4,5-dihydropyrazolo[1,5-a]pyrimidin-7-yl)piperidine-1-carboxylate

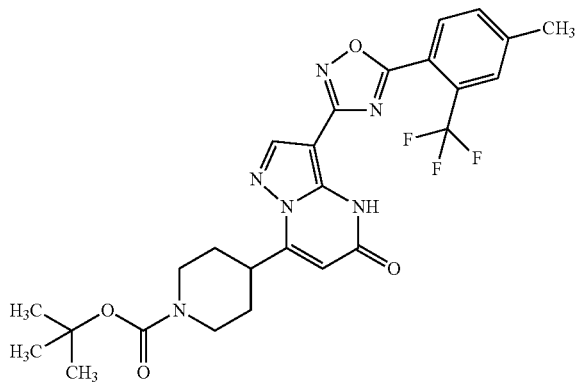 [SMILES: Cc1ccc(-c2nc(-c3cnn4c(C5CCN(C(=O)OC(C)(C)C)CC5)cc(=O)[nH]c34)no2)c(C(F)(F)F)c1]

tert-butyl 4-[3-(N'-hydroxycarbamimidoyl)-5-oxo-4,5-dihydropyrazolo[1,5-a]pyrimidin-7-yl]piperidine-1-carboxylate (1.20 g, 58% purity, 1.85 mmol)

4-methyl-2-(trifluoromethyl)benzoic acid (343 mg, 1.68 mmol)

(Benzotriazol-1-yloxy)tripyrrolidinophosphonium hexafluorophosphate (1.06 g, 99% purity, 2.02 mmol)

Ethyldiisopropylamine (340 µl, 2.0 mmol)

N,N-Dimethylformamide (30 ml)

The title compound was prepared according to the same procedure as Example 288A.

The obtained amount was 35.0 mg (98% purity, 3% of theory).

LC-MS (Method 8B): $R_t$=1.61 min; MS (ESIneg): m/z=543 [M−H]⁻

Example 290A

Tert-butyl 4-{3-(2,4-dimethyl-1,3-thiazol-5-yl)-5-[(4-methoxybenzyl)oxy]pyrazolo[1,5-a]pyrimidin-7-yl}piperidine-1-carboxylate

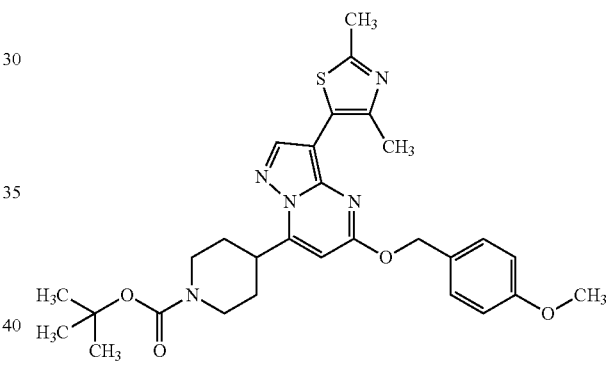

To a suspension of tert-butyl 4-{3-bromo-5-[(4-methoxybenzyl)oxy]pyrazolo[1,5-a]pyrimidin-7-yl}piperidine-1-carboxylate (50.0 mg, 96.6 µmol) in 1,4-dioxan (1.0 ml) were added 2,4-dimethyl-5-(4,4,5,5-tetramethyl-1,3,2-dioxaborolan-2-yl)-1,3-thiazole (69.3 mg, 290 µmol) and tripotassium phosphate (390 µl, 1.0 M in water, 390 µmol). The mixture was degased with argon for 10 min before [1,1'-Bis(diphenylphosphino)ferrocene]dichloropalladium(II) (10.6 mg, 14.5 µmol) and tricyclohexylphosphine (8.13 mg, 29.0 µmol) were added. The reaction was stirred for 1 h at 140° C. in the microwave. After cooling to RT, the mixture was purified by preparative HPLC (gradient acetonitrile/water with 0.1% formic acid). Evaporation of the combined product fractions yielded the title compound.

The obtained amount was 21.0 mg (98% purity, 39% of theory).

LC-MS (Method 8B): $R_t$=1.66 min; MS (ESIpos): m/z=550 [M+H]⁺

Example 291A

Tert-butyl 4-(3-{5-[(6-methoxypyridin-3-yl)methyl]-1,2,4-oxadiazol-3-yl}-5-oxo-4,5-dihydropyrazolo[1,5-a]pyrimidin-7-yl)piperidine-1-carboxylate

Example 292A

Tert-butyl 4-(5-oxo-3-{5-[4-(propan-2-yloxy)benzyl]-1,2,4-oxadiazol-3-yl}-4,5-dihydropyrazolo[1,5-a]pyrimidin-7-yl)piperidine-1-carboxylate

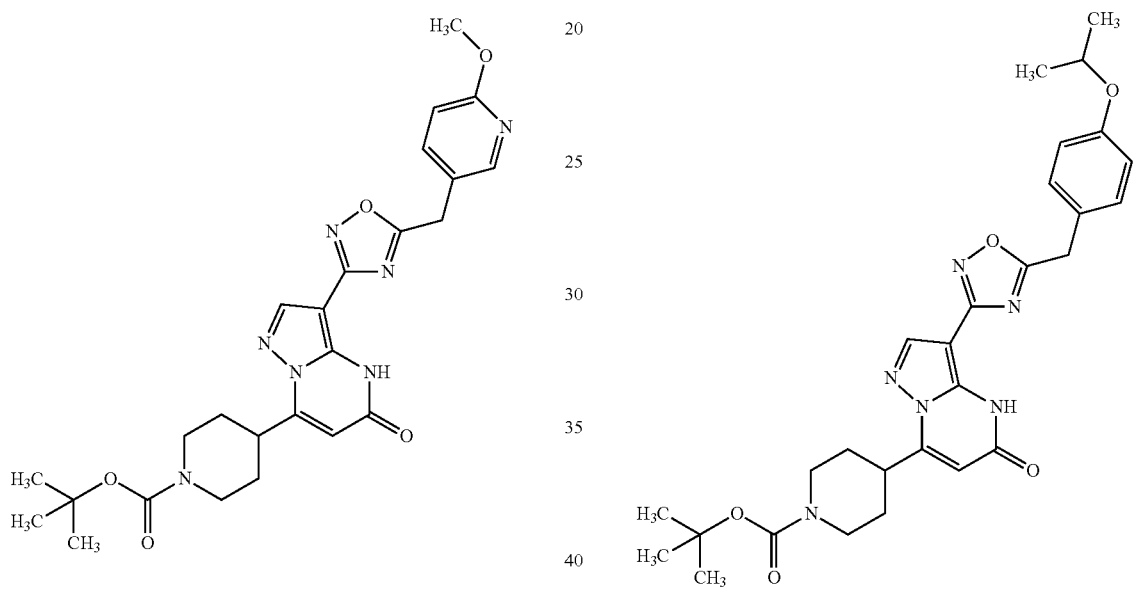

tert-butyl 4-[3-(N'-hydroxycarbamimidoyl)-5-oxo-4,5-dihydropyrazolo[1,5-a]pyrimidin-7-yl]piperidine-1-carboxylate (250 mg, 53% purity, 352 µmol)

(6-methoxypyridin-3-yl)acetic acid (53.5 mg, 320 µmol)

(Benzotriazol-1-yloxy)tripyrrolidinophosphonium hexafluorophosphate (200 mg, 384 µmol)

Ethyldiisopropylamine (67 µl, 380 µmol)

N,N-Dimethylformamide (4.0 ml)

The title compound was prepared according to the same procedure as Example 279A.

The obtained amount was 48.0 mg (100% purity, 27% of theory).

LC-MS (Method 8B): $R_t$=1.35 min; MS (ESIneg): m/z=506 [M−H]⁻ tert-butyl 4-[3-(N'-hydroxycarbamimidoyl)-5-oxo-4,5-dihydropyrazolo[1,5-a]pyrimidin-7-yl]piperidine-1-carboxylate (250 mg, 53% purity, 352 µmol) [4-(propan-2-yloxy)phenyl]acetic acid (62.2 mg, 320 µmol)

(Benzotriazol-1-yloxy)tripyrrolidinophosphonium hexafluorophosphate (200 mg, 384 µmol)

Ethyldiisopropylamine (67 µl, 380 µmol)

N,N-Dimethylformamide (4.0 ml)

The title compound was prepared according to the same procedure as Example 279A.

The obtained amount was 56.0 mg (98% purity, 29% of theory).

LC-MS (Method 8B): $R_t$=1.55 min; MS (ESIneg): m/z=533 [M−H]⁻

Example 293A

Tert-butyl 4-{5-[(4-methoxybenzyl)oxy]-3-(2-methyl-1,3-thiazol-5-yl)pyrazolo[1,5-a]pyrimidin-7-yl}piperidine-1-carboxylate

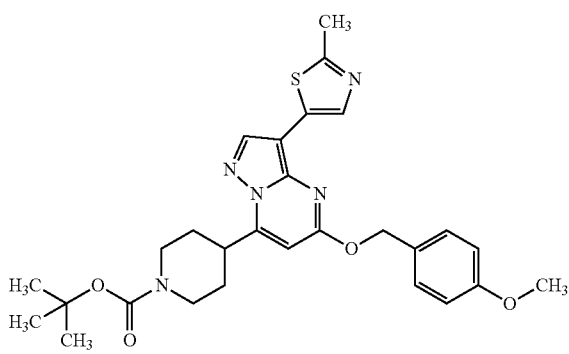 [SMILES: COc1ccc(COc2cc(C3CCN(C(=O)OC(C)(C)C)CC3)n3ncc(-c4cnc(C)s4)c3n2)cc1]

To a suspension of tert-butyl 4-{3-bromo-5-[(4-methoxybenzyl)oxy]pyrazolo[1,5-a]pyrimidin-7-yl}piperidine-1-carboxylate (150 mg, 97% purity, 281 µmol) in 1,4-dioxan (3.0 ml) were added 2-methyl-5-(4,4,5,5-tetramethyl-1,3,2-dioxaborolan-2-yl)-1,3-thiazole (190 mg, 844 µmol) and tripotassium phosphate (1.1 ml, 1.0 M in water, 1.1 mmol). The mixture was degased with argon for 10 min before [1,1'-bis(diphenylphosphino)ferrocene]dichloropalladium(II) (30.9 mg, 42.2 µmol) and tricyclohexylphosphine (23.7 mg, 84.4 µmol) were added. The reaction was stirred for 1 h at 140° C. in the microwave. After cooling to RT, the mixture was purified by preparative HPLC (gradient acetonitrile/water with 0.1% formic acid). Evaporation of the combined product fractions yielded the title compound.

The obtained amount was 36.0 mg (100% purity, 24% of theory).

LC-MS (Method 8B): $R_t$=1.65 min; MS (ESIpos): m/z=536 [M+H]$^+$

Example 294A

Tert-butyl 4-{3-(benzoylamino)-5-[(4-methoxybenzyl)oxy]pyrazolo[1,5-a]pyrimidin-7-yl}piperidine-1-carboxylate

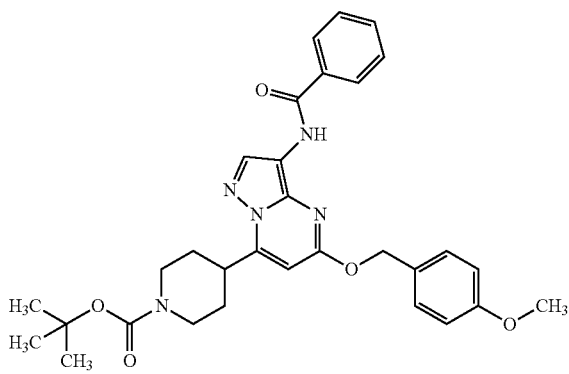 [SMILES: COc1ccc(COc2cc(C3CCN(C(=O)OC(C)(C)C)CC3)n3ncc(NC(=O)c4ccccc4)c3n2)cc1]

A mixture of tert-butyl 4-{3-bromo-5-[(4-methoxybenzyl)oxy]pyrazolo[1,5-a]pyrimidin-7-yl}piperidine-1-carboxylate (300 mg, 72% purity, 417 µmol), benzamide (126 mg, 1.04 mmol), tripotassium phosphate (124 mg, 584 µmol), [(2-di-tert-butylphosphino-3,6-dimethoxy-2',4',6'-triisopropyl-1,1'-biphenyl)-2-(2'-amino-1,1'-biphenyl)]palladium(II) methanesulfonate (=tBuBrettPhos Pd G3) (21.4 mg, 25.0 µmol), 2-(di-tert-butylphosphino)-2',4',6'-triisopropyl-3,6-dimethoxy-1,1'-biphenyl (=tBuBrettPhos) (12.1 mg, 25.0 µmol) was added to a flask and flushed with argon before being suspended in 3.0 ml of tert-butanol. The suspension was stirred overnight at 110° C. After cooling to RT, the mixture was filtered and purified by preparative HPLC (gradient acetonitrile/water with 0.1% trifluoroacetic acid). Evaporation of the combined product fractions yielded the title compound.

The obtained amount was 46.0 mg (100% purity, 17% of theory).

LC-MS (Method 8B): $R_t$=1.56 min; MS (ESIneg): m/z=556 [M−H]$^-$

Example 295A

Tert-butyl 4-(3-{3-[2-(4-fluorophenyl)propan-2-yl]-1,2,4-oxadiazol-5-yl}-5-oxo-4,5-dihydropyrazolo[1,5-a]pyrimidin-7-yl)piperidine-1-carboxylate

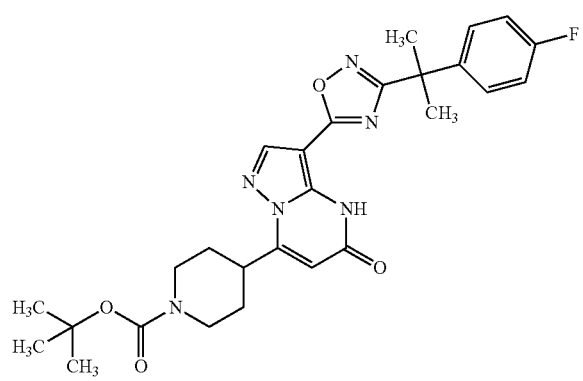 [SMILES: CC(C)(C)OC(=O)N1CCC(c2cc(=O)[nH]c3c(-c4nc(C(C)(C)c5ccc(F)cc5)no4)cnn23)CC1]

To a solution of 7-[1-(tert-butoxycarbonyl)piperidin-4-yl]-5-oxo-4,5-dihydropyrazolo[1,5-a]pyrimidine-3-carboxylic acid (865 mg, 2.39 mmol) in N,N-Dimethylformamide (23 ml) under argon were added 1,1'-carbonyldiimidazole (774 mg, 4.78 mmol) and Ethyldiisopropylamine (830 µl, 4.8 mmol). The reaction mixture was stirred 1.5 h at 90° C. After this time (1Z)-2-(4-fluorophenyl)-N'-hydroxy-2-methylpropanimidamide (956 mg, 98% purity, 4.78 mmol) was added and the mixture was stirred overnight at 110° C. After cooling to RT, the mixture was concentrated and purified by preparative HPLC (gradient acetonitrile/water with 0.1% trifluoroacetic acid). Evaporation of the combined product fractions yielded the title compound.

The obtained amount was 904 mg (94% purity, 68% of theory).

LC-MS (Method 8B): $R_t$=1.56 min; MS (ESIneg): m/z=521 [M−H]$^-$

Example 296A

Tert-butyl 4-{5-oxo-3-[5-(propan-2-yl)-1,2,4-oxadiazol-3-yl]-4,5-dihydropyrazolo[1,5-a]pyrimidin-7-yl}piperidine-1-carboxylate

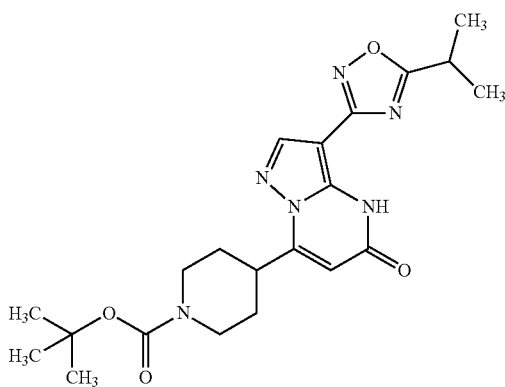 [SMILES: CC(C)c1nc(-c2cnn3c(C4CCN(C(=O)OC(C)(C)C)CC4)cc(=O)[nH]c23)no1]

To a solution of 2-methylpropanoic acid (56.4 mg, 640 µmol) in N,N-Dimethylformamide (8.0 ml) under argon was added (Benzotriazol-1-yloxy)tripyrrolidinophosphonium hexafluorophosphate (400 mg, 768 µmol) and Ethyldiisopropylamine (130 µl, 770 µmol). The reaction mixture was stirred 1 h at room temperature. After this time tert-butyl 4-[3-(N'-hydroxycarbamimidoyl)-5-oxo-4,5-dihydropyrazolo[1,5-a]pyrimidin-7-yl]piperidine-1-carboxylate (500 mg, 53% purity, 704 µmol) was added and the mixture was stirred overnight at 110° C. After cooling to RT, the mixture was purified by preparative HPLC (gradient acetonitrile/water with 0.1% formic acid). Evaporation of the combined product fractions yielded the title compound.

The obtained amount was 48.0 mg (97% purity, 15% of theory).

LC-MS (Method 1B): $R_t$=1.11 min; MS (ESIneg): m/z=427 [M−H]⁻

Example 297A

Tert-butyl 4-[3-(5-tert-butyl-1,2,4-oxadiazol-3-yl)-5-oxo-4,5-dihydropyrazolo[1,5-a]pyrimidin-7-yl]piperidine-1-carboxylate

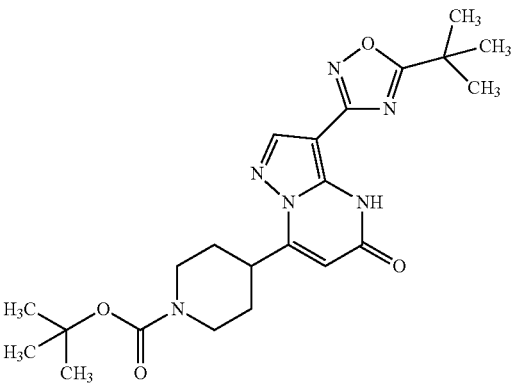 [SMILES: CC(C)(C)OC(=O)N1CCC(c2cc(=O)[nH]c3c(-c4noc(C(C)(C)C)n4)cnn23)CC1]

tert-butyl 4-[3-(N'-hydroxycarbamimidoyl)-5-oxo-4,5-dihydropyrazolo[1,5-a]pyrimidin-7-yl]piperidine-1-carboxylate (1.75 g, 64% purity, 2.98 mmol)

2,2-dimethylpropanoic acid (276 mg, 2.70 mmol)

(Benzotriazol-1-yloxy)tripyrrolidinophosphonium hexafluorophosphate (1.69 g, 3.25 mmol)

Ethyldiisopropylamine (570 µl, 3.2 mmol)

N,N-Dimethylformamide (34 ml)

The title compound was prepared according to the same procedure as Example 296A.

The obtained amount was 255 mg (100% purity, 19% of theory).

LC-MS (Method 8B): $R_t$=1.48 min; MS (ESIneg): m/z=441 [M−H]⁻

Example 298A

Tert-butyl 4-{3-(2-ethyl-4-methyl-1,3-thiazol-5-yl)-5-[(4-methoxybenzyl)oxy]pyrazolo[1,5-a]pyrimidin-7-yl}piperidine-1-carboxylate

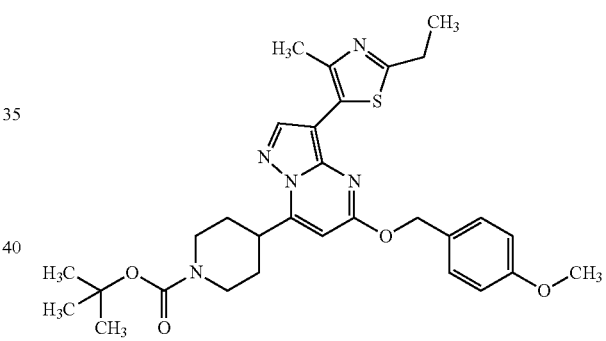

To a suspension of tert-butyl 4-{3-bromo-5-[(4-methoxybenzyl)oxy]pyrazolo[1,5-a]pyrimidin-7-yl}piperidine-1-carboxylate (75.0 mg, 145 µmol) in 1,4-dioxan (2.0 ml) were added 2-ethyl-4-methyl-5-(4,4,5,5-tetramethyl-1,3,2-dioxaborolan-2-yl)-1,3-thiazole (44.0 mg, 174 µmol), tripotassium phosphate (435 µL, 1.0 M in water, 435 µmol) and XPhos Pd G3 (3.1 mg, 4 µmol). The mixture was degased with argon for 2 min and stirred for 1 h at 110° C. After cooling to RT, the mixture was purified by preparative HPLC (gradient acetonitrile/water with 0.1% formic acid). Evaporation of the combined product fractions yielded the title compound.

The obtained amount was 57 mg (98% purity, 68% of theory).

LC-MS (Method 8B): $R_t$=1.74 min; MS (ESIpos): m/z=564 [M+H]⁺

Example 299A

Tert-butyl 4-{5-[(4-methoxybenzyl)oxy]-3-[4-methyl-2-(propan-2-yl)-1,3-thiazol-5-yl]pyrazolo[1,5-a]pyrimidin-7-yl}piperidine-1-carboxylate

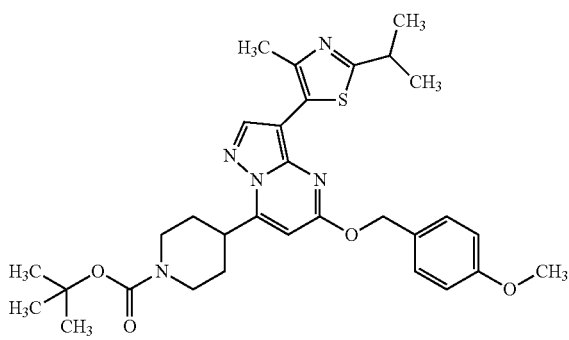 [SMILES: COc1ccc(COc2cc(C3CCN(C(=O)OC(C)(C)C)CC3)n3ncc(-c4sc(C(C)C)nc4C)c3n2)cc1]

To a suspension of tert-butyl 4-{3-bromo-5-[(4-methoxybenzyl)oxy]pyrazolo[1,5-a]pyrimidin-7-yl}piperidine-1-carboxylate (50.0 mg, 96.6 µmol) in 1,4-dioxan (1.5 ml) were added 4-methyl-2-(propan-2-yl)-5-(4,4,5,5-tetramethyl-1,3,2-dioxaborolan-2-yl)-1,3-thiazole (31.0 mg, 116 µmol), tripotassium phosphate (290 µL, 1.0 M in water, 290 µmol) and XPhos Pd G3 (2.0 mg, 2 µmol). The mixture was degased with argon for 2 min and stirred overnight at 70° C. New portions of 4-methyl-2-(propan-2-yl)-5-(4,4,5,5-tetramethyl-1,3,2-dioxaborolan-2-yl)-1,3-thiazole (31.0 mg, 116 µmol) and XPhos Pd G3 (2.0 mg, 2 µmol) were added and the stirring was continued for 1 h at 110° C.

After cooling to RT, the mixture was filtered and purified by preparative HPLC (gradient acetonitrile/water with 0.1% formic acid). Evaporation of the combined product fractions yielded the title compound.

The obtained amount was 52 mg (99% purity, 92% of theory).

LC-MS (Method 8B): $R_t$=1.80 min; MS (ESIpos): m/z=578 [M+H]$^+$

Example 300A

Tert-butyl 4-(5-oxo-3-{3-[2-(trifluoromethyl)phenyl]-1,2,4-oxadiazol-5-yl}-4,5-dihydropyrazolo[1,5-a]pyrimidin-7-yl)piperidine-1-carboxylate

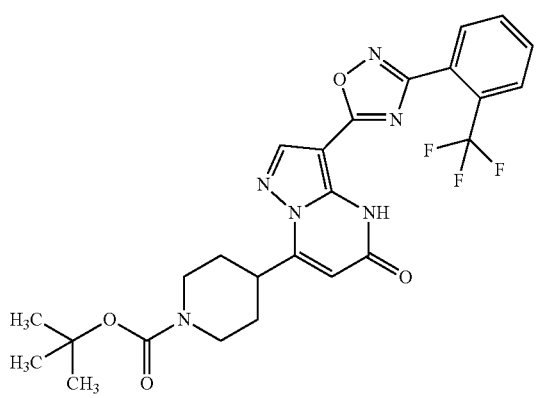 [SMILES: CC(C)(C)OC(=O)N1CCC(c2cc(=O)[nH]c3c(-c4nc(-c5ccccc5C(F)(F)F)no4)cnn23)CC1]

To a solution of 7-[1-(tert-butoxycarbonyl)piperidin-4-yl]-5-oxo-4,5-dihydropyrazolo[1,5-a]pyrimidine-3-carboxylic acid (500 mg, 1.38 mmol) in N,N-Dimethylformamide (13 ml) under argon was added 1,1'-carbonyldiimidazole (268 mg, 1.66 mmol). The reaction mixture was stirred 10 min at RT. After this time N'-hydroxy-2-(trifluoromethyl)benzenecarboximidamide (966 mg, 35% purity, 1.66 mmol) was added. The mixture was stirred for 2 h at RT, then overnight at 60° C., 3.5 h at 75° C., overnight at 110° C. and finally 4 h at 130° C. After cooling to RT, the mixture was purified by preparative HPLC (gradient acetonitrile/water with 0.1% formic acid). Evaporation of the combined product fractions yielded the title compound.

The obtained amount was 305 mg (100% purity, 42% of theory).

LC-MS (Method 8B): $R_t$=1.53 min; MS (ESIneg): m/z=529 [M−H]$^−$

Example 301A

Tert-butyl 4-{3-[5-(bicyclo[2.2.2]oct-1-yl)-1,2,4-oxadiazol-3-yl]-5-oxo-4,5-dihydropyrazolo[1,5-a]pyrimidin-7-yl}piperidine-1-carboxylate

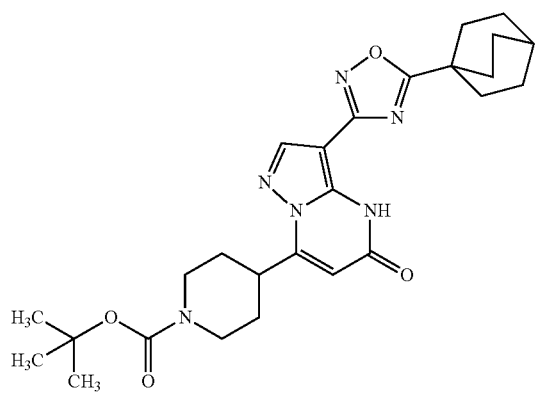 [SMILES: CC(C)(C)OC(=O)N1CCC(c2cc(=O)[nH]c3c(-c4noc(C56CCC(CC5)CC6)n4)cnn23)CC1]

To a solution of bicyclo[2.2.2]octane-1-carboxylic acid (100 mg, 648 µmol) in N,N-Dimethylformamide (11 ml) under argon was added (Benzotriazol-1-yloxy)tripyrrolidinophosphonium hexafluorophosphate (409 mg, 99% purity, 778 µmol) and Ethyldiisopropylamine (130 µl, 780 µmol). The reaction mixture was stirred 1 h at room temperature. After this time tert-butyl 4-[3-(N'-hydroxycarbamimidoyl)-5-oxo-4,5-dihydropyrazolo[1,5-a]pyrimidin-7-yl]piperidine-1-carboxylate (842 mg, 58% purity, 1.30 mmol) was added and the mixture was stirred overnight at 110° C. After cooling to RT, the mixture was purified by preparative HPLC (gradient acetonitrile/water with 0.1% formic acid). The mixture recovered after evaporation of the combined product fractions was diluted and stirred with acetonitrile. The solid that formed was filtered to yield the title compound.

The obtained amount was 30 mg (97% purity, 4% of theory).

LC-MS (Method 8B): $R_t$=1.67 min; MS (ESIneg): m/z=493 [M−H]$^−$

Example 302A

Tert-butyl 4-[3-(5-ethyl-1,2,4-oxadiazol-3-yl)-5-oxo-4,5-dihydropyrazolo[1,5-a]pyrimidin-7-yl]piperidine-1-carboxylate

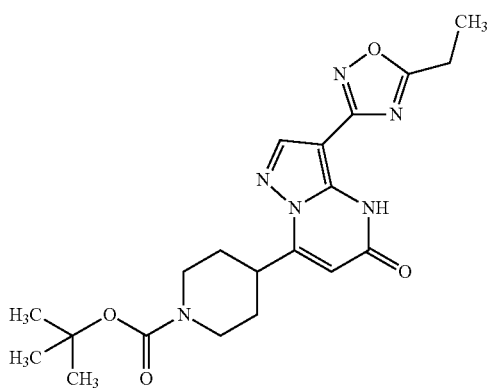 [SMILES: CCc1nc(-c2cnn3c(C4CCN(C(=O)OC(C)(C)C)CC4)cc(=O)[nH]c23)no1]

tert-butyl 4-[3-(N'-hydroxycarbamimidoyl)-5-oxo-4,5-dihydropyrazolo[1,5-a]pyrimidin-7-yl]piperidine-1-carboxylate (1.31 g, 58% purity, 2.02 mmol) propanoic acid (100 µl, 1.3 mmol)
(Benzotriazol-1-yloxy)tripyrrolidinophosphonium hexafluorophosphate (851 mg, 99% purity, 1.62 mmol)
Ethyldiisopropylamine (280 µl, 1.6 mmol)
N,N-Dimethylformamide (24 ml)

The title compound was prepared according to the same procedure as Example 296A.

The obtained amount was 180 mg (95% purity, 20% of theory).

LC-MS (Method 8B): $R_t$=1.31 min; MS (ESIneg): m/z=413 [M−H]⁻

Example 303A

Tert-butyl 4-{5-[(4-methoxybenzyl)oxy]-3-(3-phenyl-1,2-oxazol-5-yl)pyrazolo[1,5-a]pyrimidin-7-yl}piperidine-1-carboxylate

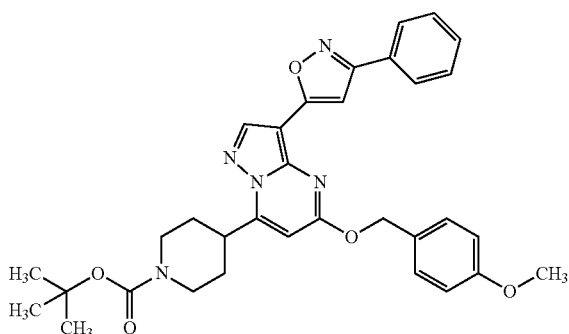

To a suspension of tert-butyl 4-{3-bromo-5-[(4-methoxybenzyl)oxy]pyrazolo[1,5-a]pyrimidin-7-yl}piperidine-1-carboxylate (100 mg, 193 µmol) in 1,4-dioxan (3.0 ml) were added 3-phenyl-5-(4,4,5,5-tetramethyl-1,3,2-dioxaborolan-2-yl)-1,2-oxazole (94.3 mg, 348 µmol), tripotassium phosphate (580 µL, 1.0 M in water, 580 µmol) and XPhos Pd G3 (4.1 mg, 5 µmol). The mixture was degased with argon for 2 min and stirred overnight at 110° C. After cooling to RT, the mixture was filtered and purified by preparative HPLC (gradient acetonitrile/water with 0.1% formic acid). Evaporation of the combined product fractions yielded the title compound.

The obtained amount was 43 mg (100% purity, 38% of theory).

LC-MS (Method 6B): $R_t$=5.09 min; MS (ESIpos): m/z=582 [M+H]⁺

Example 304A

Tert-butyl 4-(5-oxo-3-{3-[1-(propan-2-yl)piperidin-4-yl]-1,2,4-oxadiazol-5-yl}-4,5-dihydropyrazolo[1,5-a]pyrimidin-7-yl)piperidine-1-carboxylate

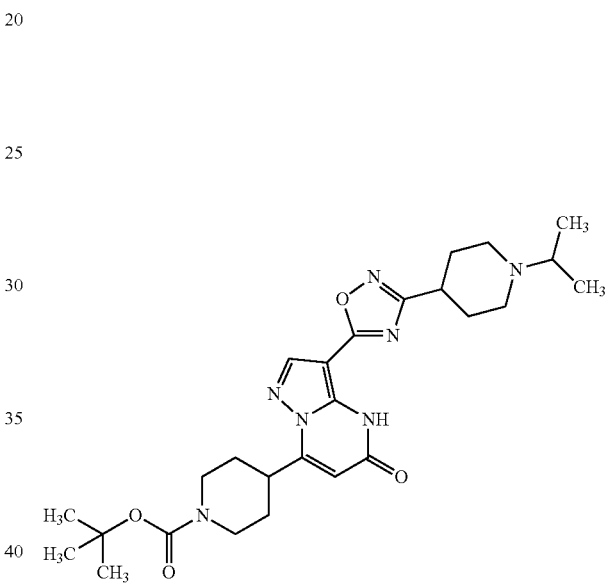

To a solution of 7-[1-(tert-butoxycarbonyl)piperidin-4-yl]-5-oxo-4,5-dihydropyrazolo[1,5-a]pyrimidine-3-carboxylic acid (200 mg, 552 µmol) in N,N-Dimethylformamide (5.0 ml) under argon were added 1,1'-carbonyldiimidazole (179 mg, 1.10 mmol) and Ethyldiisopropylamine (190 µl, 1.1 mmol). The reaction mixture was stirred 1.5 h at 90° C. After this time N'-hydroxy-1-(propan-2-yl)piperidine-4-carboximidamide (205 mg, 1.10 mmol) was added and the mixture was stirred overnight at 110° C. After cooling to RT, the mixture was purified by preparative HPLC (gradient acetonitrile/water with 0.1% trifluoroacetic acid). Evaporation of the combined product fractions yielded the title compound.

The obtained amount was 174 mg (100% purity, 62% of theory).

LC-MS (Method 8B): $R_t$=0.90 min; MS (ESIpos): m/z=512[M+H]⁺

Example 305A

Ethyl 7-[1-(tert-butoxycarbonyl)piperidin-4-yl]-2-methyl-5-oxo-4,5-dihydropyrazolo[1,5-a]pyrimidine-3-carboxylate

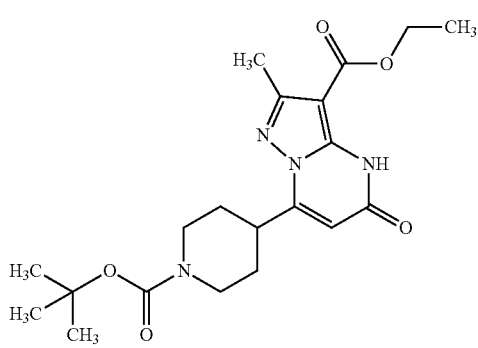 [SMILES: CCOC(=O)c1c(C)nn2c(C3CCN(C(=O)OC(C)(C)C)CC3)cc(=O)[nH]c12]

Ethyl-3-amino-5-methyl-1H-pyrazol-4-carboxylate (5 g, 30 mmol) and tert-butyl 4-[(2,2-dimethyl-4,6-dioxo-1,3-dioxan-5-yl)carbonyl]piperidine-1-carboxylate (10.5 g, 30 mmol) were heated in acetonitrile (85 ml, 1791 mmol) at 60° C. for 1.5 h. Triethylamine (12.4 ml, 69 mmol) was added and the mixture was heated at reflux for 16 h. The solvents were removed and the residue partitioned between water and ethyl acetate. The organic Phase was extracted with saturated aqueous ammonium chloride solution, water and brine. The organic phase was treated with sodium sulfate, filtered and dried in vacuo to afford the product. The obtained amount was 11.3 g (94% of theory).

LC-MS (Method 1B): $R_t$=1.03 min; MS (ESIneg): m/z=403 [M-H]⁻

Example 306A

7-[1-(tert-butoxycarbonyl)piperidin-4-yl]-2-methyl-5-oxo-4,5-dihydropyrazolo[1,5-a]pyrimidine-3-carboxylic Acid

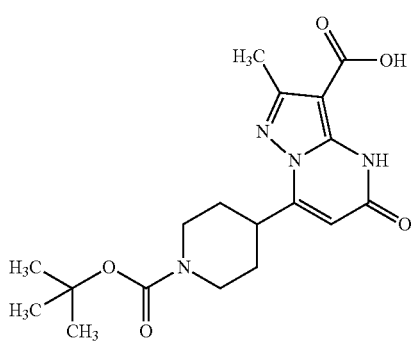 [SMILES: Cc1nn2c(C3CCN(C(=O)OC(C)(C)C)CC3)cc(=O)[nH]c2c1C(=O)O]

ethyl 7-[1-(tert-butoxycarbonyl)piperidin-4-yl]-2-methyl-5-oxo-4,5-dihydropyrazolo[1,5-a]pyrimidine-3-carboxylate (11.3 g, 28.0 mmol) and aqueous Potassium hydroxide-solution (50 ml, 2.0 M, 100 mmol) were stirred in THF (50 ml, 620 mmol) for 16 h at 65° C. Lithium hydroxide (1.34 g, 56.0 mmol) was added and the mixture was stirred for 2 h at reflux. Acetonitrile was added and the resulting participate was filtered, washed with acetonitrile and dried in vacuo. The residue was dissolved in water and diluted aqueous hydrochloric acid solution was added until pH 3 was reached. The aqueous phase was extracted three times with ethyl acetate. The combined organic phases were dried with sodium sulfate and in vacuo to afford the product. The obtained amount was 4.44 g (93% purity, 39% of theory).

LC-MS (Method 1B): $R_t$=0.81 min; MS (ESIneg): m/z=375 [M-H]⁻

1H-NMR (400 MHz, DMSO-d6) delta [ppm]: 1.389 (0.22), 1.416 (16.00), 1.490 (0.20), 1.512 (0.51), 1.520 (0.52), 1.543 (0.56), 1.551 (0.53), 1.572 (0.30), 1.934 (0.76), 1.965 (0.66), 2.407 (4.95), 2.857 (0.29), 3.310 (0.38), 3.337 (0.51), 3.368 (0.22), 4.063 (0.49), 4.092 (0.47), 5.966 (1.52), 10.699 (0.03), 12.695 (0.04).

Example 307A

Tert-butyl 2-{[4-(difluoromethoxy)phenyl]acetyl}hydrazinecarboxylate

[4-(difluoromethoxy)phenyl]acetic acid (270 mg, 1.33 mmol) and tert-butyl hydrazinecarboxylate (264 mg, 2.00 mmol) were dissolved in N,N-Dimethylformamid (2.0 ml, 26 mmol). N,N-Diisopropylethylamine (700 μl, 4.0 mmol) and HATU (760 mg, 2.00 mmol) were added and the mixture was stirred at RT for 16 h. Water and ethyl acetate were added and the organic phase was washed with saturated aqueous sodium hydrogen carbonate solution, water and aqueous citric acid solution (10%).

The organic phase was treated with sodium sulfate, filtered and dried in vacuo to afford the crude product. The obtained amount was 1114 mg.

LC-MS (Method 1B): $R_t$=0.81 min; MS (ESIneg): m/z=315 [M-H]⁻

Example 308A

Tert-butyl 2-(3-chloro-2-fluorobenzoyl)hydrazinecarboxylate 3-chloro-2-fluorobenzoic acid (270 mg, 1.54 mmol) and tert-butyl hydrazinecarboxylate (306 mg, 2.32 mmol) were dissolved in N,N-Dimethylformamid (2.3 ml, 30 mmol). N,N-Diisopropylethylamine (810 μl, 4.6 mmol) and HATU (881 mg, 2.32 mmol) were added and the mixture was stirred

Example 309A

Tert-butyl 2-{[4-(trifluoromethoxy)phenyl]acetyl}hydrazinecarboxylate

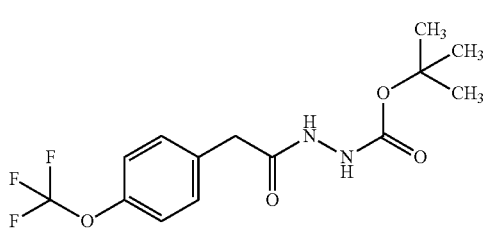 [SMILES: CC(C)(C)OC(=O)NNC(=O)Cc1ccc(OC(F)(F)F)cc1]

[4-(trifluoromethoxy)phenyl]acetic acid (250 mg, 1.14 mmol) and tert-butyl hydrazinecarboxylate (225 mg, 1.70 mmol) were dissolved in N,N-Dimethylformamid (2.0 ml, 26 mmol). N,N-Diisopropylethylamine (590 µl, 3.4 mmol) and HATU (648 mg, 1.70 mmol) were added and the mixture was stirred at RT for 16 h. Water and ethyl acetate were added and the organic phase was washed with saturated aqueous sodium hydrogen carbonate solution, water and brine. The organic phase was treated with sodium sulfate, filtered and dried in vacuo to afford the crude product. The obtained amount was 819 mg.

LC-MS (Method 1B): $R_t$=0.94 min; MS (ESIneg): m/z=333 [M−H]⁻

Example 310A

2-[4-(difluoromethoxy)phenyl]acetohydrazide hydrochloride

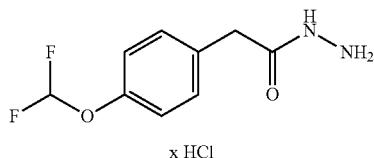 [SMILES: NNC(=O)Cc1ccc(OC(F)F)cc1]

x HCl tert-butyl 2-{[4-(difluoromethoxy)phenyl]acetyl}hydrazinecarboxylate (633 mg, 2.00 mmol) was dissolved in 1,4-dioxan (5.0 ml, 58 mmol) and treated with hydrochloric acid in 1,4-dioxan (1.0 ml, 4.0 M, 4.0 mmol) at RT for 4 h. Acetonitrile was added and the resulting participate was filtered and washed with acetonitrile. Drying in vacuo afforded the product. The obtained amount was 478 mg (95% of theory).

LC-MS (Method 1B): $R_t$=0.52 min; MS (ESIpos): m/z=217 [M+H]⁺

Example 311A 3-chloro-2-fluorobenzohydrazide hydrochloride

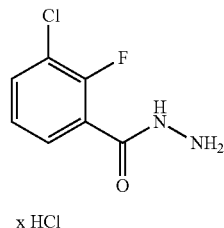 [SMILES: NNC(=O)c1cccc(Cl)c1F]

x HCl tert-butyl 2-(3-chloro-2-fluorobenzoyl)hydrazinecarboxylate (577 mg, 2.00 mmol) was dissolved in 1,4-dioxan (5.0 ml, 58 mmol) and treated with hydrochloric acid in 1,4-dioxan (1.0 ml, 4.0 M, 4.0 mmol) at RT for 4 h. Acetonitrile was added and the resulting participate was filtered and washed with acetonitrile. Drying in vacuo afforded the product. The obtained amount was 161 mg (35% of theory).

LC-MS (Method 1B): $R_t$=0.48 min; MS (ESIpos): m/z=189 [M+H]⁺

Example 312A

2-[4-(trifluoromethoxy)phenyl]acetohydrazide hydrochloride

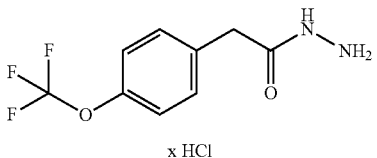 [SMILES: NNC(=O)Cc1ccc(OC(F)(F)F)cc1]

x HCl tert-butyl 2-{[4-(trifluoromethoxy)phenyl]acetyl}hydrazinecarboxylate (380 mg, 1.14 mmol) was dissolved in 1,4-dioxan (4.0 ml, 47 mmol) and treated with hydrochloric acid in 1,4-dioxan (1.0 ml, 4.0 M, 4.0 mmol) at RT for 4 h. Acetonitrile was added and the resulting participate was filtered and washed with acetonitrile. Drying in vacuo afforded the product. The obtained amount was 269 mg (87% of theory).

LC-MS (Method 10B): $R_t$=1.31 min; MS (ESIpos): m/z=235 [M+H]⁺

Example 313A

Tert-butyl 4-[3-(4-tert-butyl-1,3-thiazol-2-yl)-5-oxo-4,5-dihydropyrazolo[1,5-a]pyrimidin-7-yl]piperidine-1-carboxylate

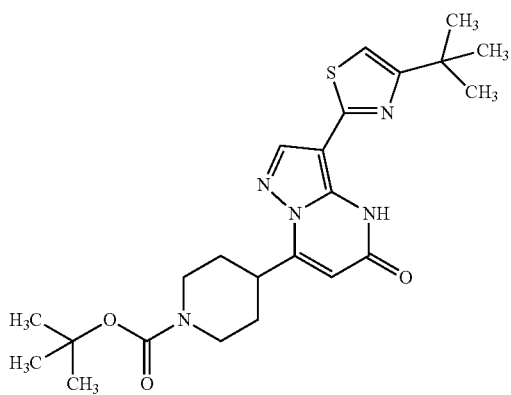 [SMILES: CC(C)(C)OC(=O)N1CCC(c2cc(=O)[nH]c3c(-c4nc(C(C)(C)C)cs4)cnn23)CC1]

tert-butyl 4-(3-carbamothioyl-5-oxo-4,5-dihydropyrazolo[1,5-a]pyrimidin-7-yl)piperidine-1-carboxylat (60.0 mg, 159 µmol)e, N,N-Diisopropylethylamine (140 µl, 790 µmol), and 1-bromo-3,3-dimethylbutan-2-one (17 µl, 130 µmol) were stirred in Ethanol (2.4 ml, 41 mmol) for 1 h at 70° C. Purification via reverse phase chromatography (Method: Reprosil C18; 10 µm; 125×30 mm/flow: 50 ml/min/solvents: A=water (0.01% formic acid), B=acetonitrile/gradient: 0.00-4.25 min=20% B, 4.50 min=30% B, 19.00-22.50 min=100% B, 22.75-25.00 min=20% B) afforded the desired product after drying in vacuo. The obtained amount was 14.8 mg (100% purity, 20% of theory).

LC-MS (Method 1B): $R_t$=1.36 min; MS (ESIpos): m/z=458 [M+H]$^+$

1H-NMR (400 MHz, DMSO-d6) delta [ppm]: 1.351 (15.01), 1.421 (16.00), 1.544 (0.15), 1.565 (0.37), 1.575 (0.42), 1.596 (0.39), 1.604 (0.36), 1.627 (0.16), 1.996 (0.45), 2.026 (0.39), 2.888 (0.21), 3.422 (0.10), 4.092 (0.36), 4.118 (0.34), 6.059 (0.07), 7.158 (0.72), 8.369 (0.10), 10.677 (0.06).

Example 314A

Tert-butyl 4-(3-ethyl-5-oxo-4,5-dihydropyrazolo[1,5-a]pyrimidin-7-yl)piperidine-1-carboxylate

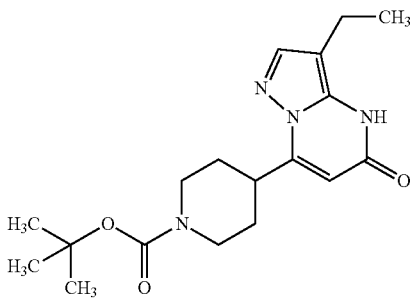 [SMILES: CCc1cnn2c(C3CCN(C(=O)OC(C)(C)C)CC3)cc(=O)[nH]c12]

tert-butyl 4-[(2,2-dimethyl-4,6-dioxo-1,3-dioxan-5-yl)carbonyl]piperidine-1-carboxylate (959 mg, 2.70 mmol) and 4-Ethyl-1H-pyrazol-3-amine (300 mg, 2.70 mmol) were stirred in Acetonitrile (10 ml, 210 mmol) form 1.5 h at 60° C. The solvent was removed. 1-Methoxy-2-propanol (10 ml, 100 mmol) and tripotassium phosphate (1.15 g, 5.40 mmol) were added and the mixture was stirred for 1.5 h at 110° C. The solvent was removed, the residue partitioned between water and ethyl acetate. The organic phase was washed with saturated aqueous ammonium chloride solution, water and brine. Drying with sodium sulfate and in vacuo afforded the product. The obtained amount was 532 mg (100% purity, 57% of theory).

LC-MS (Method 1B): $R_t$=0.92 min; MS (ESIneg): m/z=345 [M−H]$^-$

1H-NMR (400 MHz, DMSO-d6) delta [ppm]: 0.000 (0.32), 1.092 (1.43), 1.111 (2.97), 1.129 (1.48), 1.415 (16.00), 1.468 (0.19), 1.478 (0.22), 1.500 (0.55), 1.509 (0.56), 1.531 (0.60), 1.540 (0.56), 1.562 (0.26), 1.571 (0.28), 1.948 (0.77), 1.979 (0.68), 2.449 (0.49), 2.468 (1.43), 2.487 (1.40), 2.507 (1.28), 2.847 (0.28), 3.323 (0.46), 3.342 (0.48), 3.372 (0.21), 4.066 (0.47), 4.094 (0.45), 5.766 (1.24), 7.686 (1.48), 11.970 (0.57).

Example 315A

Tert-butyl 4-[5-oxo-3-(4-phenyl-1,3-thiazol-2-yl)-4,5-dihydropyrazolo[1,5-a]pyrimidin-7-yl]piperidine-1-carboxylate

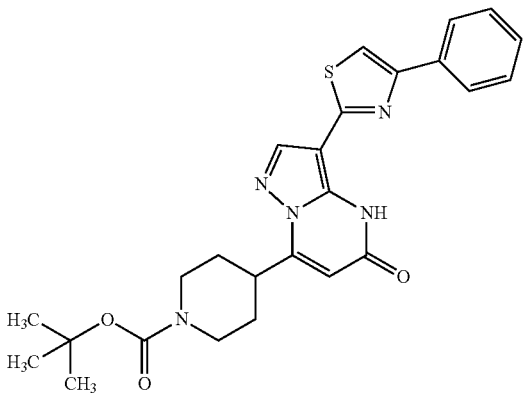 [SMILES: CC(C)(C)OC(=O)N1CCC(c2cc(=O)[nH]c3c(-c4nc(-c5ccccc5)cs4)cnn23)CC1]

tert-butyl 4-(3-carbamothioyl-5-oxo-4,5-dihydropyrazolo[1,5-a]pyrimidin-7-yl)piperidine-1-carboxylate (100 mg, 265 µmol), N,N-Diisopropylethylamine (230 µl, 1.3 mmol), and 2-bromo-1-phenylethanone (52.7 mg, 265 µmol) were stirred in ethanol (4.0 ml, 69 mmol) for 1 h at 70° C. Purification via reverse phase chromatography (Method: Reprosil C18; 10 µm; 125×30 mm/flow: 50 ml/min/solvents: A=water (0.01% formic acid), B=acetonitrile/gradient: 0.00-4.25 min=20% B, 4.50 min=30% B, 19.00-22.50 min=100% B, 22.75-25.00 min=20% B) afforded the desired product after drying in vacuo. The obtained amount was 57.6 mg (96% purity, 44% of theory).

LC-MS (Method 1B): $R_t$=1.29 min; MS (ESIpos): m/z=478 [M+H]$^+$

Example 316A

Tert-butyl 4-{3-[4-(2-fluorophenyl)-1,3-thiazol-2-yl]-5-oxo-4,5-dihydropyrazolo[1,5-a]pyrimidin-7-yl}piperidine-1-carboxylate

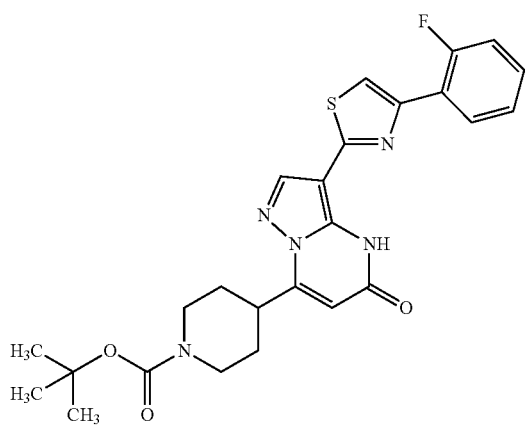 [SMILES: CC(C)(C)OC(=O)N1CCC(c2cc(=O)[nH]c3c(-c4nc(-c5ccccc5F)cs4)cnn23)CC1]

tert-butyl 4-(3-carbamothioyl-5-oxo-4,5-dihydropyrazolo[1,5-a]pyrimidin-7-yl)piperidine-1-carboxylate (80.0 mg, 212 µmol), N,N-Diisopropylethylamine (180 µl, 1.1 mmol), and 2-bromo-1-phenylethanone (29 µl, 210 µmol) were stirred in ethanol (3.2 ml, 55 mmol) for 1 h at 70° C. Purification via reverse phase chromatography (Method: Reprosil C18; 10 µm; 125×30 mm/flow: 50 ml/min/solvents: A=water (0.01% formic acid), B=acetonitrile/gradient: 0.00-4.25 min=20% B, 4.50 min=30% B, 19.00-22.50 min=100% B, 22.75-25.00 min=20% B) afforded the desired product after drying in vacuo. The obtained amount was 66.1 mg (99% purity, 62% of theory).

LC-MS (Method 1B): $R_t$=1.33 min; MS (ESIpos): m/z=496 [M+H]$^+$

1H-NMR (400 MHz, DMSO-d6) delta [ppm]: 1.426 (16.00), 1.557 (0.13), 1.566 (0.16), 1.587 (0.36), 1.596 (0.36), 1.618 (0.38), 1.627 (0.35), 1.647 (0.16), 1.658 (0.14), 2.022 (0.47), 2.051 (0.41), 2.903 (0.20), 3.489 (0.12), 4.104 (0.33), 4.132 (0.31), 6.239 (0.03), 7.323 (0.25), 7.343 (0.61), 7.362 (0.61), 7.371 (0.48), 7.380 (0.45), 7.406 (0.21), 7.410 (0.24), 7.419 (0.26), 7.424 (0.36), 7.430 (0.27), 7.436 (0.19), 7.443 (0.27), 7.457 (0.09), 7.461 (0.08), 7.911 (0.99), 7.916 (0.96), 8.328 (0.15), 8.346 (0.23), 8.365 (0.14), 11.222 (0.02).

Example 317A

Tert-butyl 4-[3-(5-methyl-4-phenyl-1,3-thiazol-2-yl)-5-oxo-4,5-dihydropyrazolo[1,5-a]pyrimidin-7-yl]piperidine-1-carboxylate

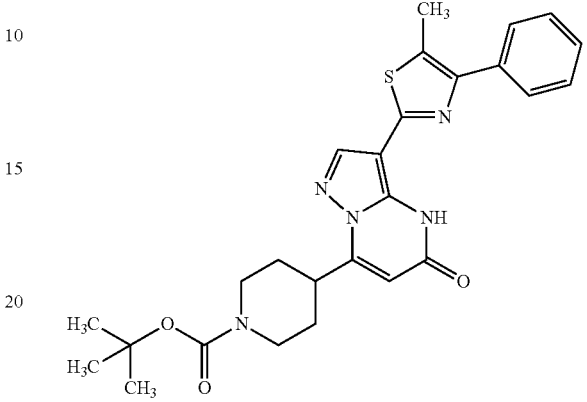

tert-butyl 4-(3-carbamothioyl-5-oxo-4,5-dihydropyrazolo[1,5-a]pyrimidin-7-yl)piperidine-1-carboxylate (60.0 mg, 159 µmol), N,N-Diisopropylethylamine (140 µl, 790 µmol), and 2-bromo-1-phenylethanone (24 µl, 160 µmol) were stirred in ethanol (2.4 ml, 41 mmol) for 1 h at 70° C. Purification via reverse phase chromatography (Method: Reprosil C18; 10 µm; 125×30 mm/flow: 50 ml/min/solvents: A=water (0.01% formic acid), B=acetonitrile/gradient: 0.00-4.25 min=20% B, 4.50 min=30% B, 19.00-22.50 min=100% B, 22.75-25.00 min=20% B) afforded the desired product after drying in vacuo. The obtained amount was 14.0 mg (100% purity, 18% of theory).

LC-MS (Method 1B): $R_t$=1.36 min; MS (ESIpos): m/z=492 [M+H]$^+$

Example 318A

Tert-butyl 4-{3-[4-(2-methylphenyl)-1,3-thiazol-2-yl]-5-oxo-4,5-dihydropyrazolo[1,5-a]pyrimidin-7-yl}piperidine-1-carboxylate

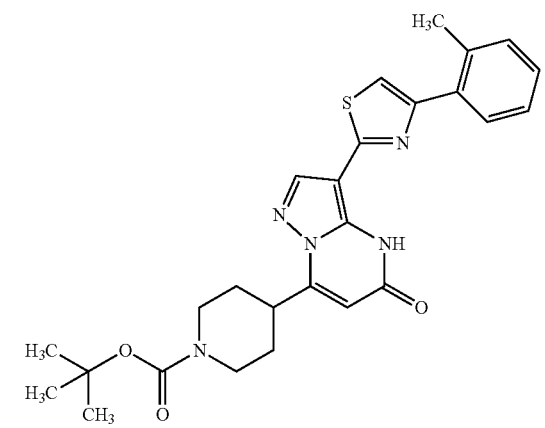 [SMILES: Cc1ccccc1-c1csc(-c2cnn3c(C4CCN(C(=O)OC(C)(C)C)CC4)cc(=O)[nH]c23)n1]

tert-butyl 4-(3-carbamothioyl-5-oxo-4,5-dihydropyrazolo[1,5-a]pyrimidin-7-yl)piperidine-1-carboxylate (40.0 mg, 106 µmol), N,N-Diisopropylethylamine (92 µl, 530 µmol), and 2-bromo-1-phenylethanone (16 µl, 110 µmol) were stirred in ethanol (1.6 ml, 27 mmol) for 1 h at 70° C. Purification via reverse phase chromatography (Method: Reprosil C18; 10 µm; 125×30 mm/flow: 50 ml/min/solvents: A=water (0.01% formic acid), B=acetonitrile/gradient: 0.00-4.25 min=20% B, 4.50 min=30% B, 19.00-22.50 min=100% B, 22.75-25.00 min=20% B) afforded the desired product after drying in vacuo. The obtained amount was 12.0 mg (96% purity, 22% of theory).

LC-MS (Method 1B): $R_t$=1.37 min; MS (ESIpos): m/z=492 [M+H]$^+$

Example 319A

Tert-butyl 4-(3-carbamothioyl-5-oxo-4,5-dihydropyrazolo[1,5-a]pyrimidin-7-yl)piperidine-1-carboxylate

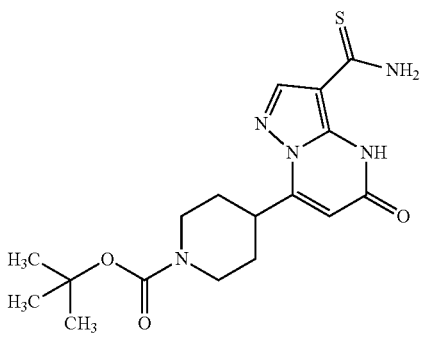 [SMILES: CC(C)(C)OC(=O)N1CCC(c2cc(=O)[nH]c3c(C(N)=S)cnn23)CC1]

3-amino-1H-pyrazole-4-carbothioamide (550 mg, 1.55 mmol) and tert-butyl 4-[(2,2-dimethyl-4,6-dioxo-1,3-dioxan-5-yl)carbonyl]piperidine-1-carboxylate (200 mg, 1.41 mmol) were heated in Acetonitrile (3.3 ml, 63 mmol) at 60° C. for 3 h. The solvents were removed and the residue dissolved in 1-Methoxy-2-propanol (3.3 ml, 34 mmol). Potassium triphosphat (597 mg, 2.81 mmol) was added and the mixture was heated at 100° C. for 2 h. The solvents were removed and the residue partitioned between aqueous citric acid solution (10%) and ethyl acetate. The aqueous solution was extracted two times with ethyl acetate. The organic phase was extracted with water and brine. The organic phase was treated with sodium sulfate, filtered and dried in vacuo to afford the product. The obtained amount was 2950 mg (95% purity, 66% of theory).

LC-MS (Method 1B): $R_t$=0.878 min; MS (ESIpos): m/z=378 [M+H]$^+$

1H-NMR (400 MHz, DMSO-d6) delta [ppm]: 1.385 (4.73), 1.414 (16.00), 1.511 (0.13), 1.518 (0.14), 1.541 (0.37), 1.550 (0.36), 1.571 (0.45), 1.580 (0.36), 1.602 (0.17), 1.612 (0.14), 1.946 (0.52), 1.977 (0.44), 2.072 (2.84), 2.108 (1.56), 2.524 (0.17), 2.858 (0.22), 4.070 (0.35), 4.099 (0.34), 6.101 (0.22), 8.448 (1.60), 9.383 (0.19), 9.467 (0.50), 11.820 (0.17).

Example 320A

Tert-butyl 4-(3-{[2-(3-chloro-2-fluorobenzoyl)hydrazinyl]carbonyl}-5-oxo-4,5-dihydropyrazolo[1,5-a]pyrimidin-7-yl)piperidine-1-carboxylate

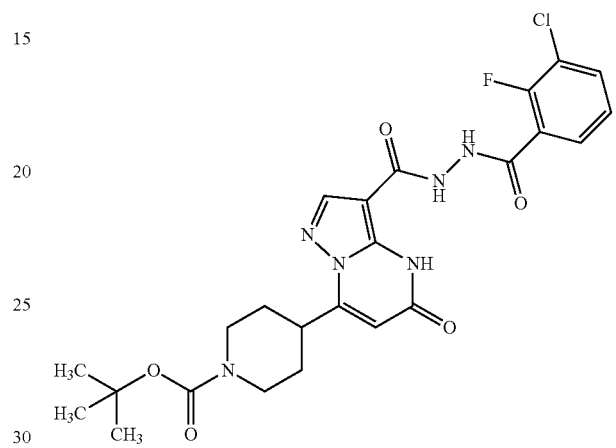

7-[1-(tert-butoxycarbonyl)piperidin-4-yl]-5-oxo-4,5-dihydropyrazolo[1,5-a]pyrimidine-3-carboxylic acid and 3-chloro-2-fluorobenzohydrazide hydrochloride (1:1) (117 mg, 621 µmol) were dissolved in N,N-Dimethylformamid (1.5 ml, 19 mmol). N,N-Diisopropylethylamine (220 µl, 1.2 mmol) and HATU (236 mg, 621 µmol) were added and the mixture was stirred at RT for 16 h. Purification via revere phase HPLC (Method: Reprosil C18; 10 µm; 125×30 mm/flow: 50 ml/min/solvents: A=water (0.01% trifluoroacetic acid), B=acetonitrile/gradient: 0.00-5.00 min=20% B, 6.50 min=40% B, 17.0-19.75 min=100% B, 19.75.00-23.00 min=40% B) afforded the desired product after drying in vacuo.

The obtained amount was 64.5 mg (100% purity, 29% of theory).

LC-MS (Method 1B): $R_t$=0.93 min; MS (ESIpos): m/z=533 [M+H]$^+$

1H-NMR (500 MHz, DMSO-d6) delta [ppm]: 1.418 (16.00), 1.526 (0.15), 1.537 (0.16), 1.544 (0.24), 1.551 (0.30), 1.556 (0.28), 1.576 (0.28), 1.600 (0.12), 1.944 (0.10), 1.975 (0.42), 2.000 (0.33), 2.863 (0.15), 3.375 (0.15), 4.089 (0.28), 6.045 (0.08), 7.359 (0.27), 7.374 (0.57), 7.390 (0.32), 7.577 (0.20), 7.580 (0.23), 7.592 (0.38), 7.605 (0.19), 7.608 (0.17), 7.770 (0.24), 7.773 (0.24), 7.787 (0.37), 7.800 (0.23), 7.804 (0.21), 8.396 (0.36), 10.458 (0.05), 10.528 (0.18), 10.918 (0.04).

Example 321A

Tert-butyl 4-{3-[(2-{[4-(difluoromethoxy)phenyl]acetyl}hydrazinyl)carbonyl-5-oxo-4,5-dihydropyrazolo[1,5-a]pyrimidin-7-yl}piperidine-1-carboxylate

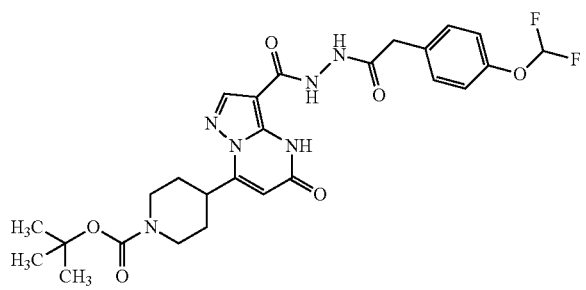 [SMILES: CC(C)(C)OC(=O)N1CCC(c2cc(=O)[nH]c3c(C(=O)NNC(=O)Cc4ccc(OC(F)F)cc4)cnn23)CC1]

7-[1-(tert-butoxycarbonyl)piperidin-4-yl]-5-oxo-4,5-dihydropyrazolo[1,5-a]pyrimidine-3-carboxylic acid (150 mg, 414 µmol) and 2-[4-(difluoromethoxy)phenyl]acetohydrazide hydrochloride (1:1) (134 mg, 621 µmol) were dissolved in N,N-Dimethylformamid (1.5 ml, 19 mmol). N,N-Diisopropylethylamine (220 µl, 1.2 mmol) and HATU (236 mg, 621 µmol) were added and the mixture was stirred at RT for 16 h. Purification via revere phase HPLC (Method: Reprosil C18; 10 µm; 125×30 mm/flow: 50 ml/min/solvents: A=water (0.01% trifluoroacetic acid), B=acetonitrile/gradient: 0.00-5.00 min=20% B, 6.50 min=40% B, 17.0-19.75 min=100% B, 19.75.00-23.00 min=40% B) afforded the desired product after drying in vacuo. The obtained amount was 93.0 mg (100% purity, 40% of theory).

LC-MS (Method 1B): $R_t$=0.89 min; MS (ESIneg): m/z=559 [M−H]⁻

1H-NMR (500 MHz, DMSO-d6) delta [ppm]: 1.413 (16.00), 1.518 (0.12), 1.538 (0.32), 1.560 (0.28), 1.582 (0.13), 1.957 (0.38), 1.981 (0.34), 2.852 (0.14), 3.537 (1.96), 4.079 (0.26), 4.096 (0.25), 6.017 (0.12), 7.127 (1.17), 7.144 (1.30), 7.196 (1.12), 7.371 (1.20), 7.388 (1.03), 8.327 (0.20), 10.192 (0.20), 10.836 (0.09).

Example 322A

Tert-butyl 4-{5-oxo-3-[(2-{[4-(trifluoromethoxy)phenyl]acetyl}hydrazinyl)carbonyl]-4,5-dihydropyrazolo[1,5-a]pyrimidin-7-yl}piperidine-1-carboxylate

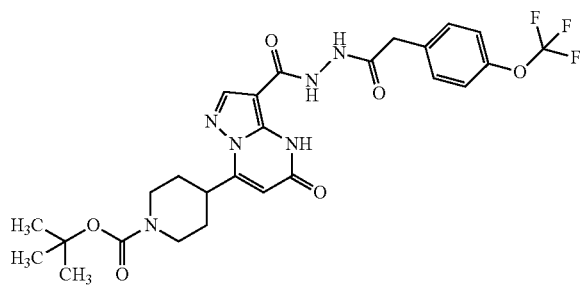 [SMILES: CC(C)(C)OC(=O)N1CCC(c2cc(=O)[nH]c3c(C(=O)NNC(=O)Cc4ccc(OC(F)(F)F)cc4)cnn23)CC1]

7-[1-(tert-butoxycarbonyl)piperidin-4-yl]-5-oxo-4,5-dihydropyrazolo[1,5-a]pyrimidine-3-carboxylic acid (150 mg, 414 µmol) and 2-[4-(trifluoromethoxy)phenyl]acetohydrazide hydrochloride (1:1) (145 mg, 621 µmol) were dissolved in N,N-Dimethylformamid (1.5 ml, 19 mmol). N,N-Diisopropylethylamine (220 µl, 1.2 mmol) and HATU (236 mg, 621 µmol) were added and the mixture was stirred at RT for 16 h. Purification via revere phase HPLC (Method: Reprosil C18; 10 µm; 125×30 mm/flow: 50 ml/min/solvents: A=water (0.01% trifluoroacetic acid), B=acetonitrile/gradient: 0.00-5.00 min=20% B, 6.50 min=40% B, 17.0-19.75 min=100% B, 19.75.00-23.00 min=40% B) afforded the desired product after drying in vacuo. The obtained amount was 199 mg (90% purity, 675% of theory).

LC-MS (Method 1B): $R_t$=0.95 min; MS (ESIpos): m/z=579 [M+H]⁺

1H-NMR (400 MHz, DMSO-d6) delta [ppm]: 1.244 (1.62), 1.258 (2.09), 1.273 (1.12), 1.413 (16.00), 1.426 (12.43), 1.510 (0.35), 1.542 (0.63), 1.563 (0.81), 1.584 (0.76), 1.617 (0.55), 1.646 (0.23), 1.794 (0.11), 1.796 (0.11), 1.954 (0.81), 1.985 (0.77), 2.002 (0.78), 2.036 (0.56), 2.889 (2.21), 3.025 (0.73), 3.586 (1.90), 3.760 (0.17), 4.075 (0.70), 4.101 (0.96), 4.129 (0.61), 7.317 (0.95), 7.338 (1.22), 7.450 (1.16), 7.471 (0.86), 7.650 (0.40), 7.661 (0.42), 7.671 (0.43), 7.682 (0.40), 7.951 (0.31), 8.327 (0.42), 8.681 (0.09), 8.712 (0.40), 8.734 (0.63), 8.755 (0.63), 8.769 (0.16), 8.833 (0.62), 8.843 (0.61), 10.239 (0.32).

Example 323A

Tert-butyl 4-[3-({2-[(3-chlorophenyl)acetyl]hydrazinyl}carbonyl)-5-oxo-4,5-dihydropyrazolo[1,5-a]pyrimidin-7-yl]piperidine-1-carboxylate

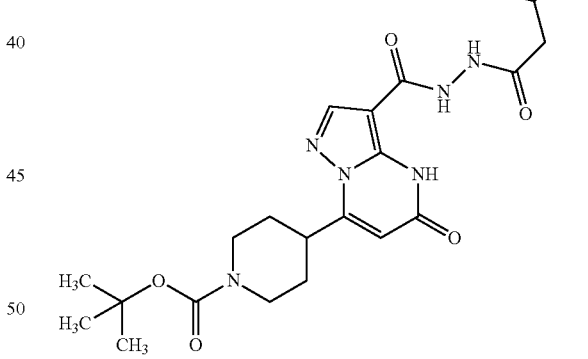

7-[1-(tert-butoxycarbonyl)piperidin-4-yl]-5-oxo-4,5-dihydropyrazolo[1,5-a]pyrimidine-3-carboxylic acid (150 mg, 414 µmol) and 2-(3-chlorophenyl)acetohydrazide (115 mg, 621 µmol) were dissolved in N,N-Dimethylformamid (1.5 ml, 19 mmol). N,N-Diisopropylethylamine (220 µl, 1.2 mmol) and HATU (266 mg, 621 µmol) were added and the mixture was stirred at RT for 16 h. Purification via revere phase HPLC (Method: Reprosil C18; 10 µm; 125×30 mm/flow: 50 ml/min/solvents: A=water (0.01% formic acid), B=acetonitrile/gradient: 0.00-5.00 min=20% B, 6.50 min=40% B, 17.0-19.75 min=100% B, 19.75.00-23.00 min=40% B) afforded the desired product after drying in vacuo. The obtained amount was 64.2 mg (100% purity, 29% of theory).

LC-MS (Method 1B): R$_f$=0.93 min; MS (ESIpos): m/z=529 [M+H]$^+$

1H-NMR (400 MHz, DMSO-d6) delta [ppm]: 1.413 (16.00), 1.508 (0.16), 1.539 (0.32), 1.569 (0.35), 1.590 (0.14), 1.955 (0.43), 1.984 (0.36), 2.855 (0.20), 3.565 (1.96), 4.070 (0.34), 4.101 (0.32), 6.016 (0.15), 7.288 (0.32), 7.306 (0.68), 7.330 (0.63), 7.346 (0.75), 7.365 (0.57), 7.384 (0.20), 7.409 (0.63), 8.326 (0.25), 10.216 (0.25), 10.848 (0.10).

Example 324A

Tert-butyl 4-[3-({2-[2-methyl-2-(1H-1,2,4-triazol-1-yl)propanoyl]hydrazinyl}carbonyl)-5-oxo-4,5-dihydropyrazolo[1,5-a]pyrimidin-7-yl]piperidine-1-carboxylate

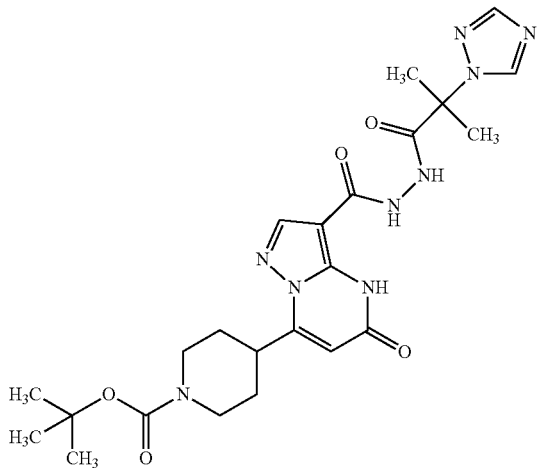 [SMILES: CC(C)(C)OC(=O)N1CCC(c2cc(=O)[nH]c3c(C(=O)NNC(=O)C(C)(C)n4cncn4)cnn23)CC1]

7-[1-(tert-butoxycarbonyl)piperidin-4-yl]-5-oxo-4,5-dihydropyrazolo[1,5-a]pyrimidine-3-carboxylic acid (150 mg, 414 μmol) and 2-methyl-2-(1H-1,2,4-triazol-1-yl)propanehydrazide (105 mg, 621 μmol) were dissolved in N,N-Dimethylformamid (1.5 ml, 19 mmol). N,N-Diisopropylethylamine (220 μl, 1.2 mmol) and HATU (266 mg, 621 μmol) were added and the mixture was stirred at RT for 16 h. Purification via revere phase HPLC (Method: Reprosil C18; 10 μm; 125×30 mm/flow: 50 ml/min/solvents: A=water (0.01% formic acid), B=acetonitrile/gradient: 0.00-5.00 min=20% B, 6.50 min=40% B, 17.0-19.75 min=100% B, 19.75.00-23.00 min=40% B) afforded the desired product after drying in vacuo. The obtained amount was 96.2 mg (100% purity, 45% of theory).

LC-MS (Method 1B): R$_f$=0.70 min; MS (ESIpos): m/z=514 [M+H]$^+$

1H-NMR (400 MHz, DMSO-d6) delta [ppm]: 1.415 (16.00), 1.507 (0.13), 1.537 (0.31), 1.569 (0.38), 1.599 (0.14), 1.837 (7.72), 1.954 (0.48), 1.983 (0.42), 2.850 (0.20), 4.072 (0.35), 4.102 (0.33), 6.014 (0.20), 8.002 (1.27), 8.338 (0.47), 8.719 (1.65), 9.881 (0.26), 10.207 (0.14), 10.901 (0.16).

Example 325A

Tert-butyl 4-[3-({2-[(2-chlorophenyl)acetyl]hydrazinyl}carbonyl)-5-oxo-4,5-dihydropyrazolo[1,5-a]pyrimidin-7-yl]piperidine-1-carboxylate

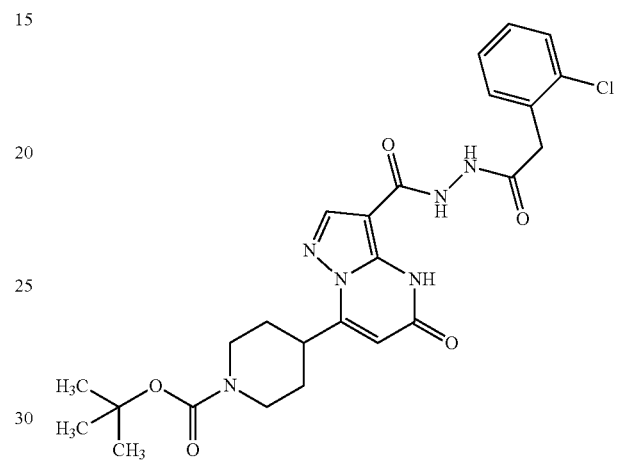

7-[1-(tert-butoxycarbonyl)piperidin-4-yl]-5-oxo-4,5-dihydropyrazolo[1,5-a]pyrimidine-3-carboxylic acid (150 mg, 414 μmol) and 2-(2-chlorophenyl)acetohydrazide (115 mg, 621 μmol) were dissolved in N,N-Dimethylformamid (1.5 ml, 19 mmol). N,N-Diisopropylethylamine (220 μl, 1.2 mmol) and HATU (266 mg, 621 μmol) were added and the mixture was stirred at RT for 16 h. Purification via revere phase HPLC (Method: Reprosil C18; 10 μm; 125×30 mm/flow: 50 ml/min/solvents: A=water (0.01% formic acid), B=acetonitrile/gradient: 0.00-5.00 min=20% B, 6.50 min=40% B, 17.0-19.75 min=100% B, 19.75.00-23.00 min=40% B) afforded the desired product after drying in vacuo. The obtained amount was 92.6 mg (88% purity, 37% of theory).

LC-MS (Method 1B): R$_f$=0.91 min; MS (ESIpos): m/z=529 [M+H]$^+$

1H-NMR (400 MHz, DMSO-d6) delta [ppm]: 1.414 (16.00), 1.508 (0.16), 1.539 (0.33), 1.570 (0.37), 1.598 (0.13), 1.958 (0.46), 1.986 (0.37), 2.855 (0.21), 3.709 (2.13), 4.071 (0.35), 4.099 (0.32), 6.018 (0.18), 7.270 (0.16), 7.276 (0.22), 7.288 (0.40), 7.294 (0.50), 7.299 (0.45), 7.305 (0.92), 7.312 (0.52), 7.317 (0.49), 7.321 (0.48), 7.336 (0.16), 7.340 (0.10), 7.429 (0.54), 7.435 (0.50), 7.447 (0.33), 7.452 (0.41), 7.464 (0.39), 7.469 (0.34), 7.481 (0.31), 7.487 (0.29), 8.349 (0.37), 10.178 (0.21), 10.839 (0.16).

Example 326A

Tert-butyl 4-[3-({2-[(5-methyl-1,3-thiazol-2-yl)acetyl]hydrazinyl}carbonyl)-5-oxo-4,5-dihydropyrazolo[1,5-a]pyrimidin-7-yl]piperidine-1-carboxylate

Example 327A

Tert-butyl 4-[3-({2-[(2-chloro-6-fluorophenyl)acetyl]hydrazinyl}carbonyl)-5-oxo-4,5-dihydropyrazolo[1,5-a]pyrimidin-7-yl]piperidine-1-carboxylate

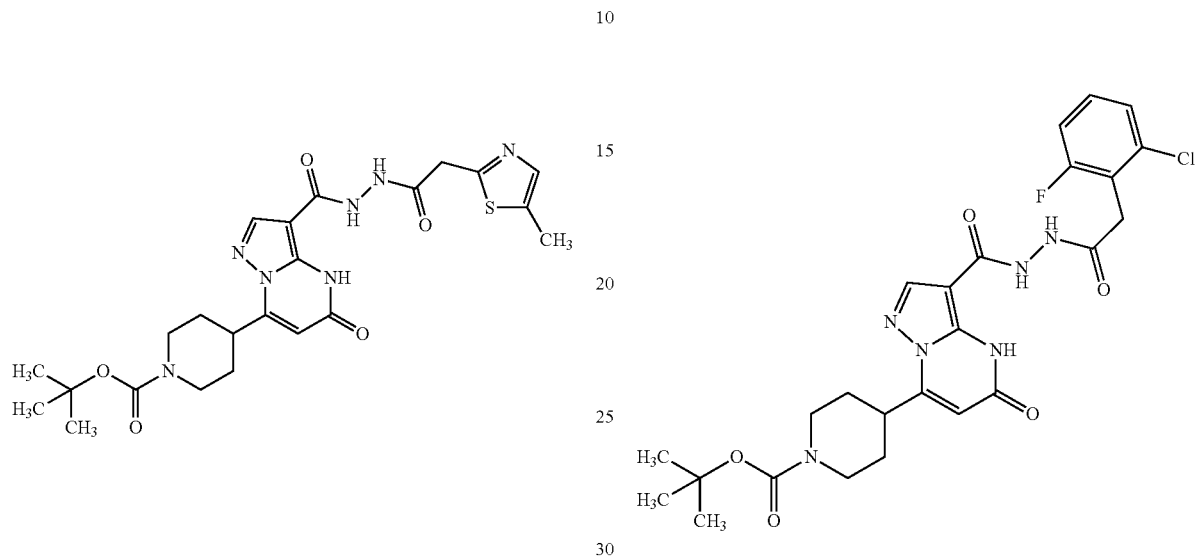

7-[1-(tert-butoxycarbonyl)piperidin-4-yl]-5-oxo-4,5-dihydropyrazolo[1,5-a]pyrimidine-3-carboxylic acid (150 mg, 414 μmol) and 2-(5-methyl-1,3-thiazol-2-yl)acetohydrazide (106 mg, 621 μmol) were dissolved in N,N-Dimethylformamid (1.5 ml, 19 mmol). N,N-Diisopropylethylamine (220 μl, 1.2 mmol) and HATU (266 mg, 621 μmol) were added and the mixture was stirred at RT for 16 h. Purification via revere phase HPLC (Method: Reprosil C18; 10 μm; 125×30 mm/flow: 50 ml/min/solvents: A=water (0.01% formic acid), B=acetonitrile/gradient: 0.00-5.00 min=20% B, 6.50 min=40% B, 17.0-19.75 min=100% B, 19.75.00-23.00 min=40% B) afforded the desired product after drying in vacuo.

The obtained amount was 161.4 mg (94% purity, 71% of theory).

LC-MS (Method 1B): $R_t$=0.81 min; MS (ESIpos): m/z=516 [M+H]$^+$

1H-NMR (400 MHz, DMSO-d6) delta [ppm]: 0.007 (0.32), 1.414 (16.00), 1.500 (0.12), 1.520 (0.20), 1.532 (0.32), 1.543 (0.30), 1.550 (0.29), 1.563 (0.35), 1.570 (0.35), 1.593 (0.16), 1.956 (0.47), 1.985 (0.42), 2.333 (3.48), 2.858 (0.21), 3.969 (1.95), 4.072 (0.35), 4.103 (0.33), 6.025 (0.20), 7.162 (0.76), 8.132 (0.29), 8.344 (0.33), 10.323 (0.16), 10.845 (0.09).

7-[1-(tert-butoxycarbonyl)piperidin-4-yl]-5-oxo-4,5-dihydropyrazolo[1,5-a]pyrimidine-3-carboxylic acid (150 mg, 414 μmol) and 2-(2-chloro-6-fluorophenyl)acetohydrazide (126 mg, 621 μmol) were dissolved in N,N-Dimethylformamid (1.5 ml, 19 mmol). N,N-Diisopropylethylamine (220 μl, 1.2 mmol) and HATU (266 mg, 621 μmol) were added and the mixture was stirred at RT for 16 h. Purification via revere phase HPLC (Method: Reprosil C18; 10 μm; 125×30 mm/flow: 50 ml/min/solvents: A=water (0.01% formic acid), B=acetonitrile/gradient: 0.00-5.00 min=20% B, 6.50 min=40% B, 17.0-19.75 min=100% B, 19.75.00-23.00 min=40% B) afforded the desired product after drying in vacuo.

The obtained amount was 53.2 mg (91% purity, 21% of theory).

LC-MS (Method 1B): $R_t$=091 min; MS (ESIpos): m/z=547 [M+H]$^+$

1H-NMR (400 MHz, DMSO-d6) delta [ppm]: 1.413 (16.00), 1.506 (0.14), 1.537 (0.30), 1.568 (0.35), 1.588 (0.14), 1.956 (0.42), 1.982 (0.36), 2.854 (0.20), 3.762 (1.30), 4.070 (0.33), 4.098 (0.32), 6.012 (0.18), 7.207 (0.18), 7.213 (0.21), 7.224 (0.24), 7.230 (0.41), 7.250 (0.24), 7.253 (0.24), 7.326 (0.28), 7.341 (1.13), 7.354 (0.40), 7.360 (0.34), 7.374 (0.33), 8.338 (0.35), 10.229 (0.22), 10.859 (0.14).

Example 328A

Tert-butyl 4-[3-({2-[(2-methoxyphenyl)acetyl]hydrazinyl}carbonyl)-5-oxo-4,5-dihydropyrazolo[1,5-a]pyrimidin-7-yl]piperidine-1-carboxylate

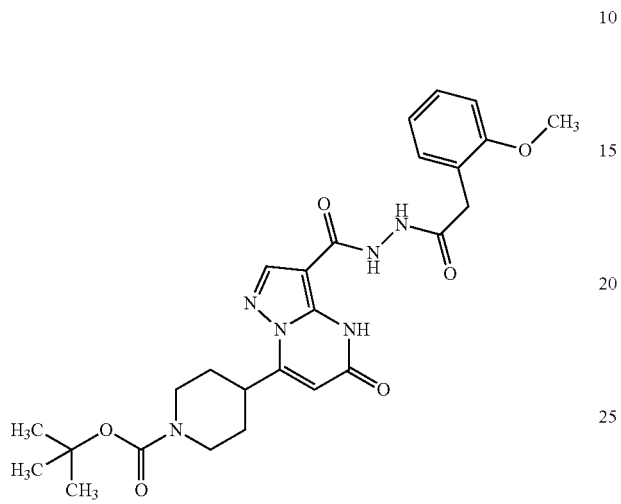

7-[1-(tert-butoxycarbonyl)piperidin-4-yl]-5-oxo-4,5-dihydropyrazolo[1,5-a]pyrimidine-3-carboxylic acid (150 mg, 414 μmol) and 2-(2-methoxyphenyl)acetohydrazide (112 mg, 621 μmol) were dissolved in N,N-Dimethylformamid (1.5 ml, 19 mmol). N,N-Diisopropylethylamine (220 μl, 1.2 mmol) and HATU (266 mg, 621 μmol) were added and the mixture was stirred at RT for 16 h. Purification via revere phase HPLC (Method: Reprosil C18; 10 μm; 125×30 mm/flow: 50 ml/min/solvents: A=water (0.01% formic acid), B=acetonitrile/gradient: 0.00-5.00 min=20% B, 6.50 min=40% B, 17.0-19.75 min=100% B, 19.75.00-23.00 min=40% B) afforded the desired product after drying in vacuo.

The obtained amount was 94.8 mg (100% purity, 44% of theory).

LC-MS (Method 1B): $R_t$=0.89 min; MS (ESIpos): m/z=525 [M+H]$^+$

1H-NMR (400 MHz, DMSO-d6) delta [ppm]: 1.410 (16.00), 1.507 (0.13), 1.537 (0.31), 1.565 (0.39), 1.591 (0.15), 1.955 (0.46), 1.984 (0.41), 2.850 (0.20), 3.504 (2.39), 3.778 (5.57), 4.069 (0.34), 4.095 (0.33), 6.011 (0.22), 6.874 (0.34), 6.893 (0.72), 6.911 (0.41), 6.954 (0.64), 6.975 (0.75), 7.213 (0.35), 7.232 (0.54), 7.258 (0.49), 7.277 (0.42), 8.341 (0.36), 9.984 (0.18), 10.173 (0.12), 10.818 (0.18).

Example 329A

Tert-butyl 4-[3-({2-[2-methyl-3-(morpholin-4-yl)propanoyl]hydrazinyl}carbonyl)-5-oxo-4,5-dihydropyrazolo[1,5-a]pyrimidin-7-yl]piperidine-1-carboxylate

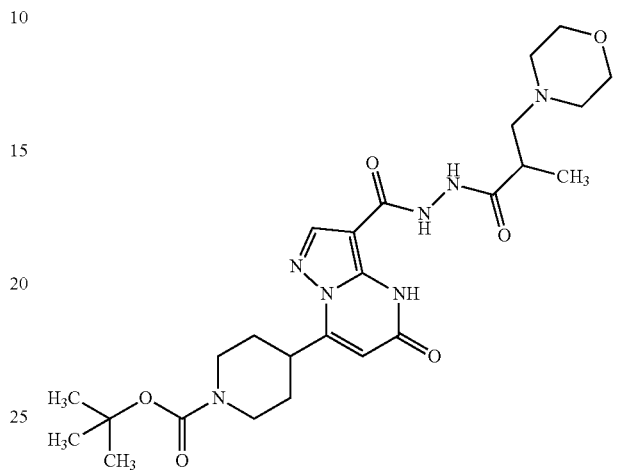

7-[1-(tert-butoxycarbonyl)piperidin-4-yl]-5-oxo-4,5-dihydropyrazolo[1,5-a]pyrimidine-3-carboxylic acid (150 mg, 414 μmol) and 2-methyl-3-(morpholin-4-yl)propanehydrazide (116 mg, 621 μmol) were dissolved in N,N-Dimethylformamid (1.5 ml, 19 mmol). N,N-Diisopropylethylamine (220 μl, 1.2 mmol) and HATU (266 mg, 621 μmol) were added and the mixture was stirred at RT for 16 h. Purification via revere phase HPLC (Method: Reprosil C18; 10 μm; 125×30 mm/flow: 50 ml/min/solvents: A=water (0.01% formic acid), B=acetonitrile/gradient: 0.00-5.00 min=20% B, 6.50 min=40% B, 17.0-19.75 min=100% B, 19.75.00-23.00 min=40% B) afforded the desired product after drying in vacuo.

The obtained amount was 119.6 mg (96% purity, 52% of theory).

LC-MS (Method 1B): $R_t$=0.61 min; MS (ESIpos): m/z=532 [M+H]$^+$

1H-NMR (400 MHz, DMSO-d6) delta [ppm]: 1.101 (0.90), 1.116 (0.86), 1.243 (7.56), 1.258 (7.24), 1.272 (4.40), 1.416 (16.00), 1.507 (0.12), 1.517 (0.14), 1.539 (0.35), 1.547 (0.36), 1.571 (0.44), 1.578 (0.38), 1.600 (0.16), 1.608 (0.14), 1.960 (0.53), 1.990 (0.46), 2.689 (2.40), 2.871 (1.07), 3.059 (0.75), 3.110 (0.27), 3.120 (0.30), 3.128 (0.67), 3.138 (0.66), 3.146 (0.67), 3.156 (0.61), 3.165 (0.28), 3.175 (0.23), 3.584 (0.47), 3.592 (0.44), 3.600 (0.58), 3.609 (0.55), 3.616 (0.67), 3.625 (0.66), 3.633 (0.57), 3.642 (0.56), 3.649 (0.41), 3.658 (0.43), 3.689 (0.44), 4.078 (0.34), 4.105 (0.32), 6.080 (0.19), 8.131 (0.76), 8.372 (1.20), 10.115 (0.18).

Example 330A

Tert-butyl 4-[3-({2-[3-(morpholin-4-yl)propanoyl]hydrazinyl}carbonyl)-5-oxo-4,5-dihydropyrazolo[1,5-a]pyrimidin-7-yl]piperidine-1-carboxylate

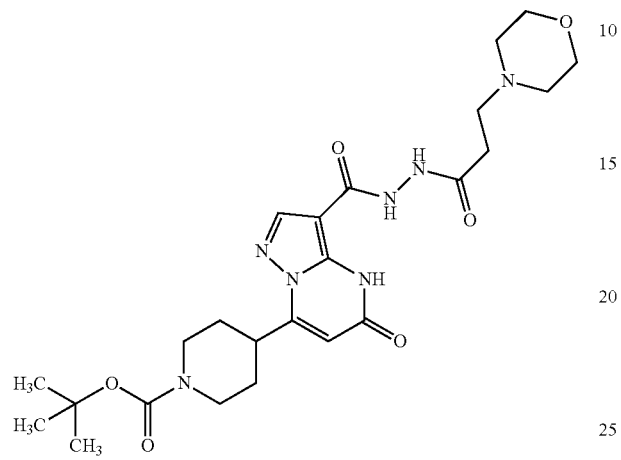

7-[1-(tert-butoxycarbonyl)piperidin-4-yl]-5-oxo-4,5-dihydropyrazolo[1,5-a]pyrimidine-3-carboxylic acid (150 mg, 414 µmol) and 3-(morpholin-4-yl)propanehydrazide (108 mg, 621 µmol) were dissolved in N,N-Dimethylformamid (1.5 ml, 19 mmol). N,N-Diisopropylethylamine (220 µl, 1.2 mmol) and HATU (266 mg, 621 µmol) were added and the mixture was stirred at RT for 16 h. Purification via revere phase HPLC (Method: Reprosil C18; 10 µm; 125×30 mm/flow: 50 ml/min/solvents: A=water (0.01% formic acid), B=acetonitrile/gradient: 0.00-5.00 min=20% B, 6.50 min=40% B, 17.0-19.75 min=100% B, 19.75.00-23.00 min=40% B) afforded the desired product after drying in vacuo.

The obtained amount was 165.1 mg (92% purity, 71% of theory).

LC-MS (Method 1B): $R_t$=0.60 min; MS (ESIpos): m/z=518 [M+H]$^+$

1H-NMR (400 MHz, DMSO-d6) delta [ppm]: 1.243 (16.00), 1.258 (15.24), 1.272 (9.70), 1.416 (14.19), 1.510 (0.10), 1.520 (0.12), 1.541 (0.29), 1.550 (0.31), 1.573 (0.36), 1.579 (0.31), 1.601 (0.13), 1.613 (0.12), 1.959 (0.41), 1.989 (0.36), 2.637 (0.30), 2.689 (4.17), 2.856 (0.33), 3.109 (0.54), 3.120 (0.61), 3.128 (1.42), 3.138 (1.42), 3.146 (1.44), 3.157 (1.36), 3.165 (0.59), 3.175 (0.52), 3.567 (0.09), 3.583 (0.36), 3.593 (0.42), 3.600 (0.85), 3.609 (0.89), 3.616 (1.14), 3.625 (1.12), 3.632 (0.91), 3.642 (0.84), 3.648 (0.45), 3.659 (0.39), 3.674 (0.17), 3.759 (0.21), 4.078 (0.28), 4.105 (0.28), 6.091 (0.13), 8.132 (0.70), 8.353 (0.88), 10.159 (0.22).

Example 331A

Tert-butyl 4-(5-oxo-3-{[2-(3-phenylpropanoyl)hydrazinyl]carbonyl}-4,5-dihydropyrazolo[1,5-a]pyrimidin-7-yl)piperidine-1-carboxylate

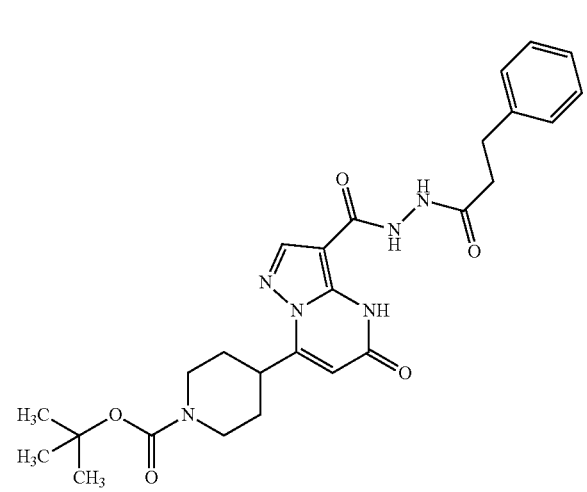 [SMILES: CC(C)(C)OC(=O)N1CCC(c2cc(=O)[nH]c3c(C(=O)NNC(=O)CCc4ccccc4)cnn23)CC1]

7-[1-(tert-butoxycarbonyl)piperidin-4-yl]-5-oxo-4,5-dihydropyrazolo[1,5-a]pyrimidine-3-carboxylic acid (150 mg, 414 µmol) and 3-phenylpropanehydrazide (102 mg, 621 µmol) were dissolved in N,N-Dimethylformamid (1.5 ml, 19 mmol). N,N-Diisopropylethylamine (220 µl, 1.2 mmol) and HATU (266 mg, 621 µmol) were added and the mixture was stirred at RT for 16 h. Purification via revere phase HPLC (Method: Reprosil C18; 10 µm; 125×30 mm/flow: 50 ml/min/solvents: A=water (0.01% formic acid), B=acetonitrile/gradient: 0.00-5.00 min=20% B, 6.50 min=40% B, 17.0-19.75 min=100% B, 19.75.00-23.00 min=40% B) afforded the desired product after drying in vacuo. The obtained amount was 73.1 mg (96% purity, 33% of theory).

LC-MS (Method 1B): $R_t$=0.90 min; MS (ESIpos): m/z=509 [M+H]$^+$

1H-NMR (400 MHz, DMSO-d6) delta [ppm]: 1.411 (16.00), 1.507 (0.17), 1.539 (0.37), 1.568 (0.42), 1.593 (0.16), 1.957 (0.51), 1.985 (0.42), 2.524 (0.87), 2.849 (0.96), 2.869 (1.27), 2.888 (0.76), 4.071 (0.39), 4.099 (0.37), 6.016 (0.20), 7.170 (0.19), 7.188 (0.53), 7.206 (0.35), 7.238 (0.63), 7.255 (1.61), 7.272 (1.27), 7.289 (1.10), 7.309 (0.34), 8.342 (0.36), 9.913 (0.21), 10.127 (0.11), 10.810 (0.17).

Example 332A

Tert-butyl 4-[3-({2-[(4-chlorophenyl)acetyl]hydrazinyl}carbonyl)-5-oxo-4,5-dihydropyrazolo[1,5-a]pyrimidin-7-yl]piperidine-1-carboxylate

Example 333A

Tert-butyl 4-(5-oxo-3-{[2-(pyridin-2-ylacetyl)hydrazinyl]carbonyl}-4,5-dihydropyrazolo[1,5-a]pyrimidin-7-yl)piperidine-1-carboxylate

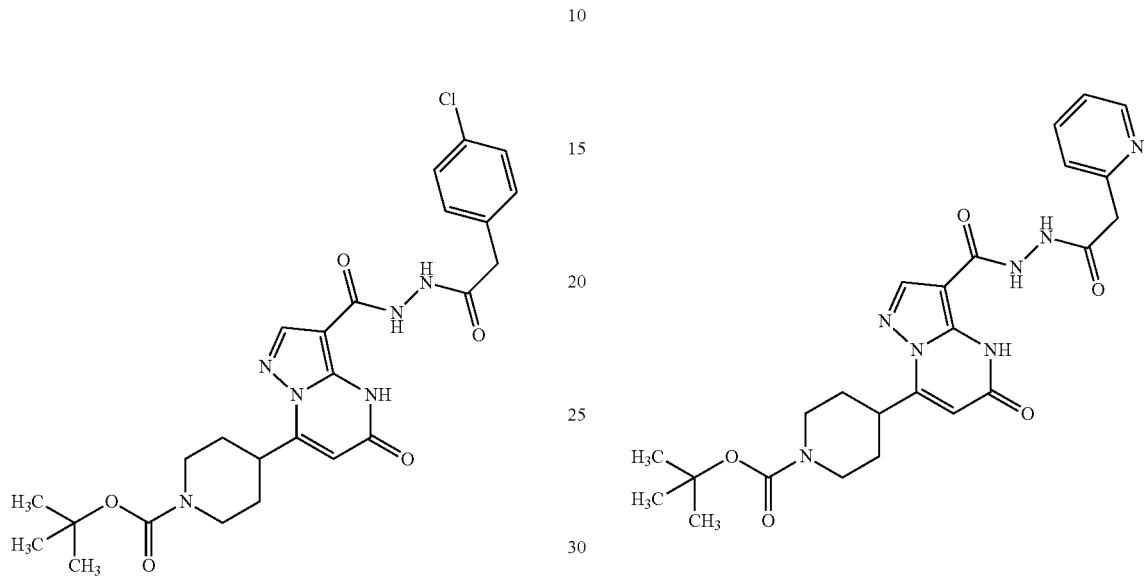

7-[1-(tert-butoxycarbonyl)piperidin-4-yl]-5-oxo-4,5-dihydropyrazolo[1,5-a]pyrimidine-3-carboxylic acid (150 mg, 414 µmol) and 2-(4-chlorophenyl)acetohydrazide (115 mg, 621 µmol) were dissolved in N,N-Dimethylformamid (1.5 ml, 19 mmol). N,N-Diisopropylethylamine (220 µl, 1.2 mmol) and HATU (266 mg, 621 µmol) were added and the mixture was stirred at RT for 16 h. Purification via revere phase HPLC (Method: Reprosil C18; 10 µm; 125×30 mm/flow: 50 ml/min/solvents: A=water (0.01% formic acid), B=acetonitrile/gradient: 0.00-5.00 min=20% B, 6.50 min=40% B, 17.0-19.75 min=100% B, 19.75.00-23.00 min=40% B) afforded the desired product after drying in vacuo. The obtained amount was 34.8 mg (90% purity, 35% of theory).

LC-MS (Method 1B): $R_t$=0.93 min; MS (ESIpos): m/z=529 [M+H]$^+$

1H-NMR (400 MHz, DMSO-d6) delta [ppm]: 1.413 (16.00), 1.511 (0.16), 1.539 (0.37), 1.569 (0.43), 1.591 (0.17), 1.954 (0.54), 1.984 (0.47), 2.853 (0.23), 3.316 (0.37), 4.072 (0.39), 4.100 (0.37), 6.017 (0.16), 7.342 (0.62), 7.363 (2.03), 7.379 (2.09), 7.401 (0.56), 8.327 (0.33), 10.201 (0.32), 10.837 (0.14).

7-[1-(tert-butoxycarbonyl)piperidin-4-yl]-5-oxo-4,5-dihydropyrazolo[1,5-a]pyrimidine-3-carboxylic acid (150 mg, 414 µmol) and 2-(pyridin-2-yl)acetohydrazide (93.9 mg, 621 µmol) were dissolved in N,N-Dimethylformamid (1.5 ml, 19 mmol). N,N-Diisopropylethylamine (220 µl, 1.2 mmol) and HATU (266 mg, 621 µmol) were added and the mixture was stirred at RT for 16 h. Purification via revere phase HPLC (Method: Reprosil C18; 10 µm; 125×30 mm/flow: 50 ml/min/solvents: A=water (0.01% formic acid), B=acetonitrile/gradient: 0.00-5.00 min=20% B, 6.50 min=40% B, 17.0-19.75 min=100% B, 19.75.00-23.00 min=40% B) afforded the desired product after drying in vacuo. The obtained amount was 78.11 mg (100% purity, 38% of theory).

LC-MS (Method 1B): $R_t$=0.66 min; MS (ESIpos): m/z=496 [M+H]$^+$

1H-NMR (400 MHz, DMSO-d6) delta [ppm]: 1.414 (16.00), 1.503 (0.11), 1.514 (0.13), 1.535 (0.31), 1.544 (0.34), 1.567 (0.38), 1.574 (0.36), 1.596 (0.16), 1.606 (0.13), 1.956 (0.48), 1.988 (0.42), 2.876 (0.28), 3.367 (0.22), 4.072 (0.33), 4.101 (0.32), 6.058 (0.08), 7.423 (0.18), 7.435 (0.24), 7.449 (0.16), 7.564 (0.28), 7.583 (0.29), 7.930 (0.16), 7.950 (0.23), 7.966 (0.12), 8.347 (0.81), 8.582 (0.37), 8.593 (0.35), 10.288 (0.26).

Example 334A

Tert-butyl 4-(3-{[2-(methoxycarbonyl)hydrazinyl]carbonyl}-5-oxo-4,5-dihydropyrazolo[1,5-a]pyrimidin-7-yl)piperidine-1-carboxylate

Example 335A

Tert-butyl 4-(5-oxo-3-{[2-(thiophen-2-ylcarbonyl)hydrazinyl]carbonyl}-4,5-dihydropyrazolo[1,5-a]pyrimidin-7-yl)piperidine-1-carboxylate

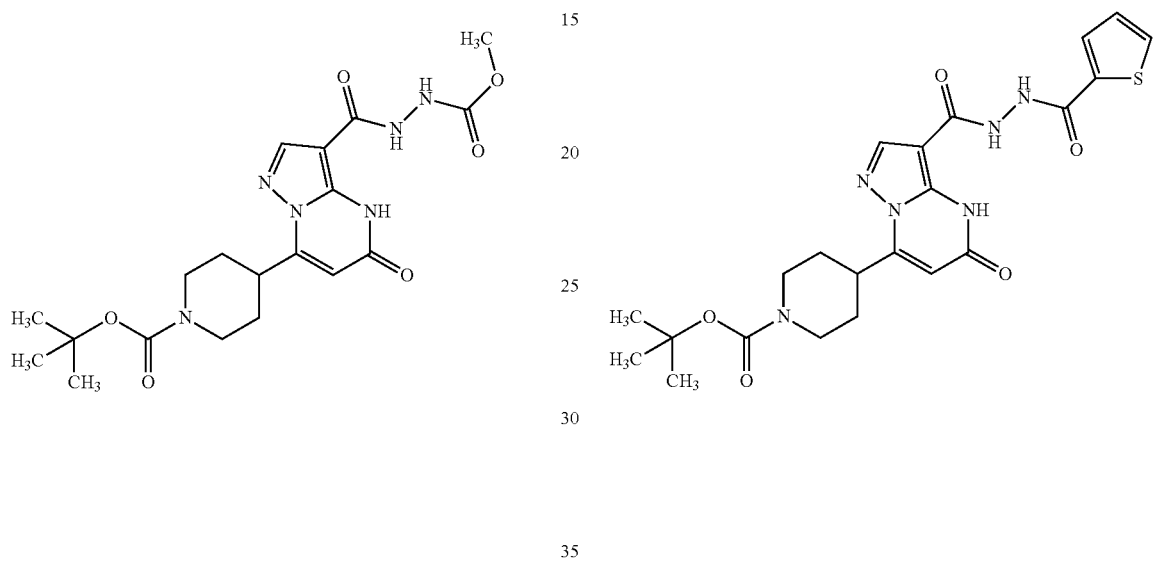

7-[1-(tert-butoxycarbonyl)piperidin-4-yl]-5-oxo-4,5-dihydropyrazolo[1,5-a]pyrimidine-3-carboxylic acid (150 mg, 414 µmol) and methyl hydrazinecarboxylate (55.9 mg, 621 µmol) were dissolved in N,N-Dimethylformamid (1.5 ml, 19 mmol). N,N-Diisopropylethylamine (220 µl, 1.2 mmol) and HATU (266 mg, 621 µmol) were added and the mixture was stirred at RT for 16 h. Purification via revere phase HPLC (Method: Reprosil C18; 10 µm; 125×30 mm/flow: 50 ml/min/solvents: A=water (0.01% formic acid), B=acetonitrile/gradient: 0.00-5.00 min=20% B, 6.50 min=40% B, 17.0-19.75 min=100% B, 19.75.00-23.00 min=40% B) afforded the desired product after drying in vacuo. The obtained amount was 156.2 mg (94% purity, 24% of theory).

LC-MS (Method 1B): $R_t$=0.73 min; MS (ESIpos): m/z=435 [M+H]$^+$

1H-NMR (400 MHz, DMSO-d6) delta [ppm]: 1.408 (16.00), 1.495 (0.11), 1.504 (0.12), 1.525 (0.32), 1.535 (0.34), 1.556 (0.36), 1.565 (0.38), 1.587 (0.15), 1.597 (0.12), 1.953 (0.46), 1.984 (0.40), 2.850 (0.17), 3.485 (0.38), 3.622 (1.21), 4.067 (0.31), 4.097 (0.30), 6.064 (0.15), 8.310 (0.39), 9.216 (0.17), 10.042 (0.04), 10.891 (0.01).

7-[1-(tert-butoxycarbonyl)piperidin-4-yl]-5-oxo-4,5-dihydropyrazolo[1,5-a]pyrimidine-3-carboxylic acid (150 mg, 414 µmol) and thiophene-2-carbohydrazide (88.3 mg, 621 µmol) were dissolved in N,N-Dimethylformamid (1.5 ml, 19 mmol). N,N-Diisopropylethylamine (220 µl, 1.2 mmol) and HATU (266 mg, 621 µmol) were added and the mixture was stirred at RT for 16 h. Purification via revere phase HPLC (Method: Reprosil C18; 10 µm; 125×30 mm/flow: 50 ml/min/solvents: A=water (0.01% formic acid), B=acetonitrile/gradient: 0.00-5.00 min=20% B, 6.50 min=40% B, 17.0-19.75 min=100% B, 19.75.00-23.00 min=40% B) afforded the desired product after drying in vacuo. The obtained amount was 64.6 mg (100% purity, 32% of theory).

LC-MS (Method 1B): $R_t$=0.84 min; MS (ESIpos): m/z=487 [M+H]$^+$

1H-NMR (500 MHz, DMSO-d6) delta [ppm]: 1.419 (16.00), 1.530 (0.11), 1.556 (0.27), 1.575 (0.28), 1.598 (0.13), 1.974 (0.38), 1.997 (0.33), 2.872 (0.14), 4.087 (0.27), 4.102 (0.25), 6.033 (0.14), 7.209 (0.47), 7.219 (0.58), 7.227 (0.48), 7.862 (0.61), 7.872 (0.60), 7.889 (0.57), 7.895 (0.56), 8.386 (0.25), 10.326 (0.09), 10.508 (0.15), 10.896 (0.10).

Example 336A

Tert-butyl 4-(5-oxo-3-{[2-(3,3,3-trifluoropropanoyl)hydrazinyl]carbonyl}-4,5-dihydropyrazolo[1,5-a]pyrimidin-7-yl)piperidine-1-carboxylate

Example 337A

Tert-butyl 4-(3-{[2-(2-chlorobenzoyl)hydrazinyl]carbonyl}-5-oxo-4,5-dihydropyrazolo[1,5-a]pyrimidin-7-yl)piperidine-1-carboxylate

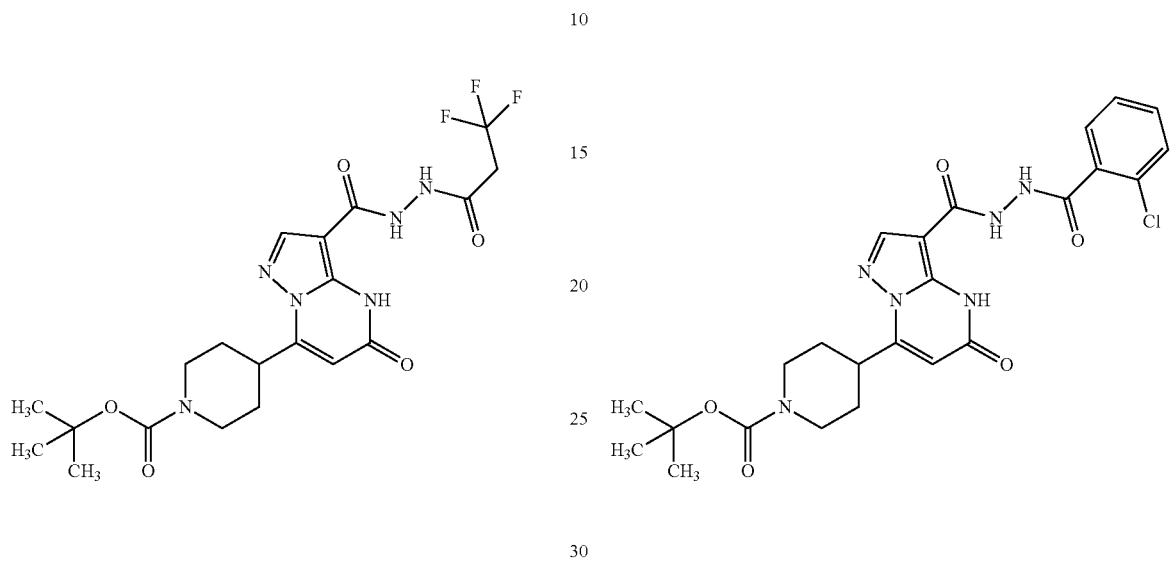

7-[1-(tert-butoxycarbonyl)piperidin-4-yl]-5-oxo-4,5-dihydropyrazolo[1,5-a]pyrimidine-3-carboxylic acid (150 mg, 414 µmol) and 3,3,3-trifluoropropanehydrazide (88.2 mg, 621 µmol) were dissolved in N,N-Dimethylformamid (1.5 ml, 19 mmol). N,N-Diisopropylethylamine (220 µl, 1.2 mmol) and HATU (266 mg, 621 µmol) were added and the mixture was stirred at RT for 16 h. More 3,3,3-trifluoropropanehydrazide (1.5 equivalents), N,N-Diisopropylethylamine (3 equivalents), and HATU (1 equivalents) were added. The mixture was stirred for 16 h at RT. Purification via revere phase HPLC (Method: Reprosil C18; 10 µm; 125×30 mm/flow: 50 ml/min/solvents: A=water (0.01% formic acid), B=acetonitrile/gradient: 0.00-5.00 min=20% B, 6.50 min=40% B, 17.0-19.75 min=100% B, 19.75.00-23.00 min=40% B) afforded the desired product after drying in vacuo. The obtained amount was 97.6 mg (60% purity, 29% of theory).

LC-MS (Method 1B): $R_t$=0.83 min; MS (ESIpos): m/z=487 [M+H]$^+$

1H-NMR (500 MHz, DMSO-d6) delta [ppm]: 1.415 (16.00), 1.524 (0.15), 1.540 (0.33), 1.546 (0.31), 1.564 (0.29), 1.570 (0.28), 1.587 (0.13), 1.961 (0.41), 1.987 (0.70), 2.857 (0.15), 3.064 (0.07), 3.393 (0.26), 3.415 (0.60), 3.437 (0.56), 3.459 (0.19), 4.082 (0.28), 4.096 (0.27), 6.023 (0.13), 8.348 (0.24), 10.347 (0.17), 10.880 (0.08).

7-[1-(tert-butoxycarbonyl)piperidin-4-yl]-5-oxo-4,5-dihydropyrazolo[1,5-a]pyrimidine-3-carboxylic acid (150 mg, 414 µmol) and 2-chlorobenzohydrazide (106 mg, 621 µmol) were dissolved in N,N-Dimethylformamid (1.5 ml, 19 mmol). N,N-Diisopropylethylamine (220 µl, 1.2 mmol) and HATU (266 mg, 621 µmol) were added and the mixture was stirred at RT for 16 h. Purification via revere phase HPLC (Method: Reprosil C18; 10 µm; 125×30 mm/flow: 50 ml/min/solvents: A=water (0.01% formic acid), B=acetonitrile/gradient: 0.00-5.00 min=20% B, 6.50 min=40% B, 17.0-19.75 min=100% B, 19.75.00-23.00 min=40% B) afforded the desired product after drying in vacuo. The obtained amount was 119.6 mg (100% purity, 56% of theory).

LC-MS (Method 1B): $R_t$=0.89 min; MS (ESIpos): m/z=515 [M+H]$^+$

1H-NMR (500 MHz, DMSO-d6) delta [ppm]: 1.420 (16.00), 1.530 (0.11), 1.546 (0.25), 1.556 (0.25), 1.576 (0.26), 1.577 (0.25), 1.598 (0.12), 1.978 (0.36), 2.001 (0.32), 2.869 (0.13), 4.088 (0.25), 4.107 (0.24), 6.033 (0.15), 7.455 (0.20), 7.458 (0.21), 7.470 (0.55), 7.473 (0.58), 7.485 (0.47), 7.487 (0.51), 7.506 (0.26), 7.509 (0.36), 7.521 (0.43), 7.525 (0.71), 7.536 (0.84), 7.540 (0.73), 7.554 (1.01), 7.556 (0.98), 7.570 (0.38), 7.572 (0.35), 8.417 (0.50), 10.416 (0.25), 10.914 (0.13).

Example 338A

Tert-butyl 4-(5-oxo-3-{[2-(piperidin-1-ylacetyl)hydrazinyl]carbonyl}-4,5-dihydropyrazolo[1,5-a]pyrimidin-7-yl)piperidine-1-carboxylate

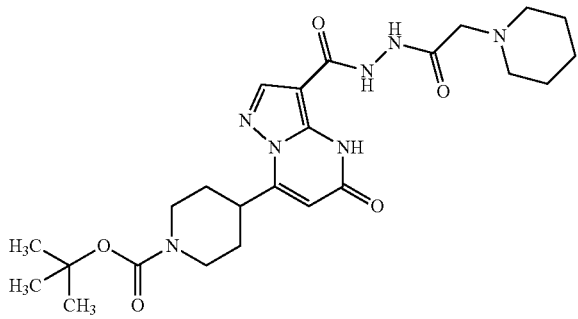 [SMILES: CC(C)(C)OC(=O)N1CCC(c2cc(=O)[nH]c3c(C(=O)NNC(=O)CN4CCCCC4)cnn23)CC1]

7-[1-(tert-butoxycarbonyl)piperidin-4-yl]-5-oxo-4,5-dihydropyrazolo[1,5-a]pyrimidine-3-carboxylic acid (150 mg, 414 μmol) and 2-(piperidin-1-yl)acetohydrazide (97.6 mg, 621 μmol) were dissolved in N,N-Dimethylformamid (1.5 ml, 19 mmol). N,N-Diisopropylethylamine (220 μl, 1.2 mmol) and HATU (266 mg, 621 μmol) were added and the mixture was stirred at RT for 16 h. Purification via revere phase HPLC (Method: Reprosil C18; 10 μm; 125×30 mm/flow: 50 ml/min/solvents: A=water (0.01% formic acid), B=acetonitrile/gradient: 0.00-5.00 min=20% B, 6.50 min=40% B, 17.0-19.75 min=100% B, 19.75.00-23.00 min=40% B) afforded the desired product after drying in vacuo. The obtained amount was 111 mg (100% purity, 53% of theory).

LC-MS (Method 1B): $R_t$=0.64 min; MS (ESIpos): m/z=502 [M+H]$^+$

1H-NMR (500 MHz, DMSO-d6) delta [ppm]: 1.416 (16.00), 1.525 (0.16), 1.532 (0.18), 1.549 (0.33), 1.556 (0.35), 1.574 (0.35), 1.580 (0.34), 1.598 (0.17), 1.605 (0.16), 1.754 (0.81), 1.962 (0.43), 1.985 (0.34), 2.855 (0.19), 2.889 (0.22), 3.057 (0.13), 3.949 (0.14), 3.986 (0.22), 4.085 (0.24), 4.104 (0.24), 6.092 (0.07), 8.351 (0.52), 10.347 (0.03), 10.524 (0.08).

Example 339A

Tert-butyl 4-[5-oxo-3-({2-[(2-oxopyrrolidin-1-yl)acetyl]hydrazinyl}carbonyl)-4,5-dihydropyrazolo[1,5-a]pyrimidin-7-yl]piperidine-1-carboxylate

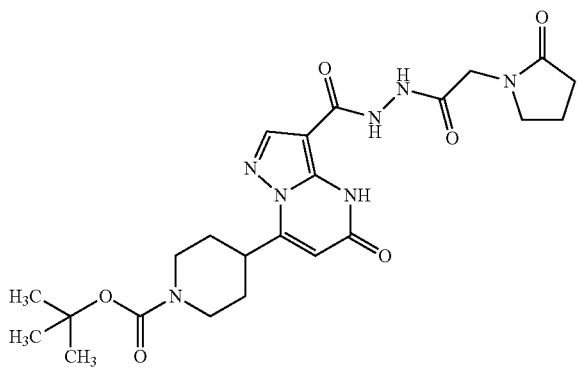 [SMILES: CC(C)(C)OC(=O)N1CCC(c2cc(=O)[nH]c3c(C(=O)NNC(=O)CN4CCCC4=O)cnn23)CC1]

7-[1-(tert-butoxycarbonyl)piperidin-4-yl]-5-oxo-4,5-dihydropyrazolo[1,5-a]pyrimidine-3-carboxylic acid (150 mg, 414 μmol) and 2-(2-oxopyrrolidin-1-yl)acetohydrazide (97.6 mg, 621 μmol) were dissolved in N,N-Dimethylformamid (1.5 ml, 19 mmol). N,N-Diisopropylethylamine (220 μl, 1.2 mmol) and HATU (266 mg, 621 μmol) were added and the mixture was stirred at RT for 16 h. Purification via revere phase HPLC (Method: Reprosil C18; 10 μm; 125×30 mm/flow: 50 ml/min/solvents: A=water (0.01% formic acid), B=acetonitrile/gradient: 0.00-5.00 min=20% B, 6.50 min=40% B, 17.0-19.75 min=100% B, 19.75.00-23.00 min=40% B) afforded the desired product after drying in vacuo. The obtained amount was 105 mg (97% purity, 49% of theory).

LC-MS (Method 1B): $R_t$=0.73 min; MS (ESIpos): m/z=502 [M+H]$^+$

1H-NMR (500 MHz, DMSO-d6) delta [ppm]: 1.415 (16.00), 1.540 (0.27), 1.565 (0.24), 1.947 (0.54), 1.962 (0.94), 1.978 (0.70), 1.991 (0.40), 2.237 (0.64), 2.253 (0.94), 2.269 (0.49), 2.874 (0.13), 3.408 (0.55), 3.422 (0.87), 3.436 (0.51), 3.952 (2.14), 4.088 (0.23), 6.020 (0.13), 8.333 (0.20), 10.042 (0.10), 10.189 (0.09), 10.852 (0.08).

Example 340A

Tert-butyl 4-(3-{[2-(cyclohexylcarbonyl)hydrazinyl]carbonyl}-5-oxo-4,5-dihydropyrazolo[1,5-a]pyrimidin-7-yl)piperidine-1-carboxylate

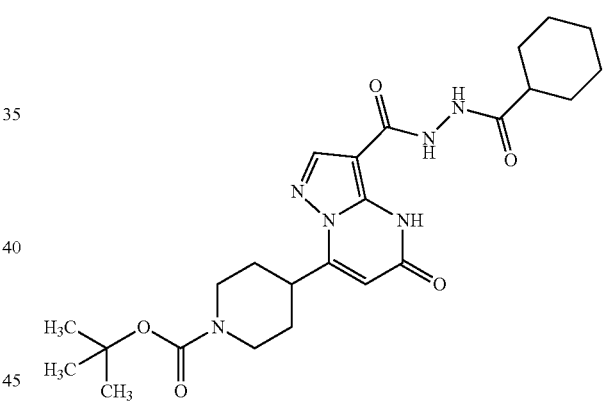

7-[1-(tert-butoxycarbonyl)piperidin-4-yl]-5-oxo-4,5-dihydropyrazolo[1,5-a]pyrimidine-3-carboxylic acid (150 mg, 414 μmol) and cyclohexanecarbohydrazide (88.3 mg, 621 μmol) were dissolved in N,N-Dimethylformamid (1.5 ml, 19 mmol). N,N-Diisopropylethylamine (220 μl, 1.2 mmol) and HATU (266 mg, 621 μmol) were added and the mixture was stirred at RT for 16 h. Purification via revere phase HPLC (Method: Reprosil C18; 10 μm; 125×30 mm/flow: 50 ml/min/solvents: A=water (0.01% formic acid), B=acetonitrile/gradient: 0.00-5.00 min=20% B, 6.50 min=40% B, 17.0-19.75 min=100% B, 19.75.00-23.00 min=40% B) afforded the desired product after drying in vacuo. The obtained amount was 128.9 mg (90% purity, 58% of theory).

LC-MS (Method 1B): $R_t$=0.90 min; MS (ESIpos): m/z=487 [M+H]$^+$

1H-NMR (500 MHz, DMSO-d6) delta [ppm]: 1.150 (0.12), 1.157 (0.16), 1.181 (0.21), 1.206 (0.19), 1.216 (0.21), 1.240 (0.38), 1.246 (0.30), 1.261 (0.26), 1.266 (0.33), 1.287 (0.17), 1.352 (0.18), 1.376 (0.39), 1.415 (16.00), 1.442

(0.23), 1.445 (0.26), 1.519 (0.13), 1.540 (0.32), 1.562 (0.26), 1.585 (0.13), 1.620 (0.21), 1.644 (0.21), 1.725 (0.87), 1.746 (0.77), 1.960 (0.36), 1.983 (0.32), 2.219 (0.09), 2.225 (0.15), 2.231 (0.10), 2.242 (0.17), 2.248 (0.28), 2.254 (0.17), 2.265 (0.10), 2.271 (0.13), 2.276 (0.08), 2.859 (0.14), 4.079 (0.26), 4.095 (0.25), 6.011 (0.16), 8.337 (0.28), 9.766 (0.13), 10.083 (0.09), 10.821 (0.13).

Example 341A

Tert-butyl 4-(3-{[2-(cyclobutylcarbonyl)hydrazinyl]carbonyl}-5-oxo-4,5-dihydropyrazolo[1,5-a]pyrimidin-7-yl)piperidine-1-carboxylate

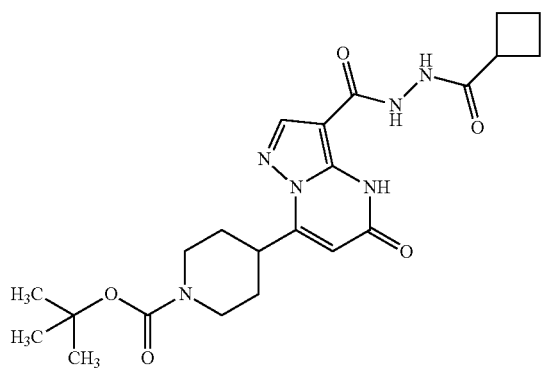 [SMILES: CC(C)(C)OC(=O)N1CCC(c2cc(=O)[nH]c3c(C(=O)NNC(=O)C4CCC4)cnn23)CC1]

7-[1-(tert-butoxycarbonyl)piperidin-4-yl]-5-oxo-4,5-dihydropyrazolo[1,5-a]pyrimidine-3-carboxylic acid (150 mg, 414 µmol) and cyclobutanecarbohydrazide (70.9 mg, 621 µmol) were dissolved in N,N-Dimethylformamid (1.5 ml, 19 mmol). N,N-Diisopropylethylamine (220 µl, 1.2 mmol) and HATU (236 mg, 621 µmol) were added and the mixture was stirred at RT for 16 h. Purification via revere phase HPLC (Method: Reprosil C18; 10 µm; 125×30 mm/flow: 50 ml/min/solvents: A=water (0.01% formic acid), B=acetonitrile/gradient: 0.00-5.00 min=20% B, 6.50 min=40% B, 17.0-19.75 min=100% B, 19.75.00-23.00 min=40% B) afforded the desired product after drying in vacuo. The obtained amount was 120.7 mg (76% purity, 48% of theory).

LC-MS (Method 1B): $R_t$=0.77 min; MS (ESIpos): m/z=459 [M+H]$^+$

1H-NMR (400 MHz, DMSO-d6) delta [ppm]: 1.415 (16.00), 1.509 (0.20), 1.518 (0.21), 1.540 (0.38), 1.571 (0.40), 1.594 (0.14), 1.759 (0.09), 1.768 (0.12), 1.791 (0.25), 1.803 (0.22), 1.816 (0.30), 1.825 (0.18), 1.839 (0.16), 1.848 (0.09), 1.882 (0.10), 1.904 (0.24), 1.926 (0.45), 1.952 (0.65), 1.959 (0.51), 1.969 (0.50), 1.987 (0.42), 1.995 (0.42), 2.048 (0.38), 2.055 (0.36), 2.069 (0.65), 2.078 (0.52), 2.084 (0.83), 2.091 (0.58), 2.099 (0.43), 2.114 (0.28), 2.121 (0.26), 2.136 (0.33), 2.141 (0.32), 2.158 (0.66), 2.179 (0.64), 2.203 (0.30), 2.208 (0.32), 2.863 (0.21), 3.094 (0.13), 3.114 (0.37), 3.135 (0.51), 3.156 (0.33), 3.176 (0.10), 4.075 (0.35), 4.100 (0.36), 6.015 (0.18), 8.332 (0.29), 9.295 (0.11), 9.297 (0.11), 9.734 (0.21), 10.084 (0.11), 10.817 (0.15).

Example 342A

Tert-butyl 4-{5-oxo-3-[(2-pentanoylhydrazinyl)carbonyl]-4,5-dihydropyrazolo[1,5-a]pyrimidin-7-yl}piperidine-1-carboxylate

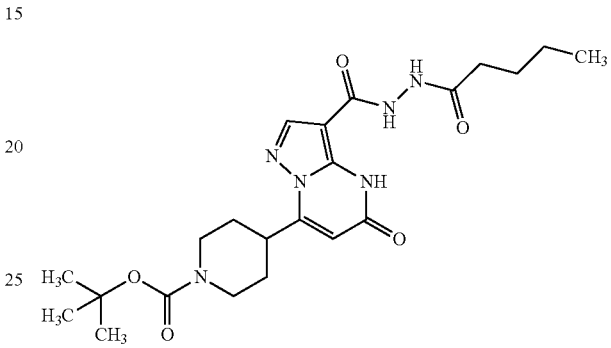

7-[1-(tert-butoxycarbonyl)piperidin-4-yl]-5-oxo-4,5-dihydropyrazolo[1,5-a]pyrimidine-3-carboxylic acid (200 mg, 552 µmol) and pentanehydrazide (96.2 mg, 828 µmol) were dissolved in N,N-Dimethylformamid (1.5 ml, 19 mmol). N,N-Diisopropylethylamine (290 µl, 1.7 mmol) and HATU (315 mg, 828 µmol) were added and the mixture was stirred at RT for 16 h. More pentanehydrazide (1.5 equivalents), N,N-Diisopropylethylamine (3 equivalents), and HATU (1 equivalents) were added. The mixture was stirred for 2 h at RT. Purification via revere phase HPLC (Method: Reprosil C18; 10 µm; 125×30 mm/flow: 50 ml/min/solvents: A=water (0.01% formic acid), B=acetonitrile/gradient: 0.00-5.00 min=20% B, 6.50 min=40% B, 17.0-19.75 min=100% B, 19.75.00-23.00 min=40% B) afforded the desired product after drying in vacuo. The obtained amount was 28.7 mg (100% purity, 15% of theory).

LC-MS (Method 1B): $R_t$=0.82 min; MS (ESIpos): m/z=461 [M+H]$^+$

1H-NMR (500 MHz, DMSO-d6) delta [ppm]: 0.874 (1.30), 0.889 (2.91), 0.904 (1.46), 1.291 (0.12), 1.306 (0.38), 1.321 (0.66), 1.336 (0.67), 1.351 (0.41), 1.365 (0.13), 1.415 (16.00), 1.501 (0.25), 1.516 (0.66), 1.531 (0.91), 1.546 (0.75), 1.561 (0.42), 1.962 (0.36), 1.986 (0.33), 2.164 (0.67), 2.178 (1.20), 2.193 (0.61), 2.857 (0.13), 4.080 (0.26), 4.099 (0.25), 6.014 (0.17), 8.341 (0.28), 9.824 (0.15), 10.811 (0.13).

Example 343A

Tert-butyl 4-{3-[5-(3-chloro-2-fluorophenyl)-1,3,4-oxadiazol-2-yl]-5-oxo-4,5-dihydropyrazolo[1,5-a]pyrimidin-7-yl}piperidine-1-carboxylate

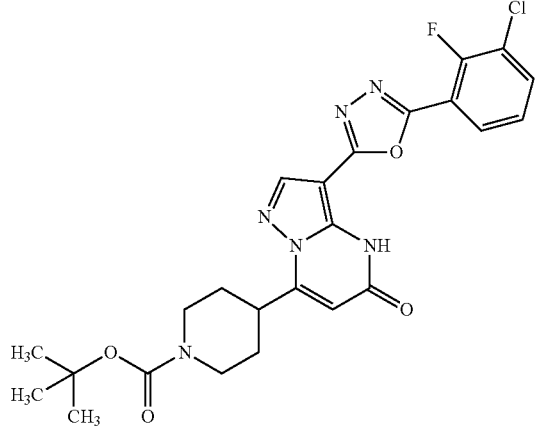 [SMILES: CC(C)(C)OC(=O)N1CCC(c2cc(=O)[nH]c3c(-c4nnc(-c5cccc(Cl)c5F)o4)cnn23)CC1]

tert-butyl 4-(3-{[2-(3-chloro-2-fluorobenzoyl)hydrazinyl]carbonyl}-5-oxo-4,5-dihydropyrazolo[1,5-a]pyrimidin-7-yl)piperidine-1-carboxylate (62.3 mg, 117 μmol) was dissolved in THF (2.0 ml, 25 mmol) and stirred with Burgess-Reagent (39.0 mg, 164 μmol) for 16 h at RT. Purification via reverse phase chromatography (Method: Reprosil C18; 10 μm; 125×30 mm/flow: 50 ml/min/solvents: A=water (0.01% formic acid), B=acetonitrile/gradient: 0.00-5.00 min=10% B, 6.50 min=20% B, 17.0-19.75 min=100% B, 19.75.00-23.00 min=90% B) afforded the desired product after drying in vacuo. The obtained amount was 32.9 mg (100% purity, 55% of theory).

LC-MS (Method 1B): $R_t$=1.19 min; MS (ESIpos): m/z=515 [M+H]$^+$

1H-NMR (400 MHz, DMSO-d6) delta [ppm]: 1.424 (16.00), 1.541 (0.11), 1.550 (0.13), 1.573 (0.33), 1.581 (0.38), 1.603 (0.36), 1.613 (0.33), 1.634 (0.15), 1.645 (0.12), 2.001 (0.45), 2.032 (0.39), 2.881 (0.17), 3.415 (0.11), 3.446 (0.18), 3.477 (0.10), 4.098 (0.28), 4.126 (0.27), 6.187 (0.09), 7.489 (0.29), 7.508 (0.62), 7.528 (0.34), 7.873 (0.24), 7.877 (0.26), 7.894 (0.44), 7.911 (0.23), 7.915 (0.22), 8.206 (0.13), 8.222 (0.22), 8.242 (0.13), 8.497 (0.29), 12.267 (0.06).

Example 344A

Tert-butyl 4-(3-{5-[4-(difluoromethoxy)benzyl]-1,3,4-oxadiazol-2-yl}-5-oxo-4,5-dihydropyrazolo[1,5-a]pyrimidin-7-yl)piperidine-1-carboxylate

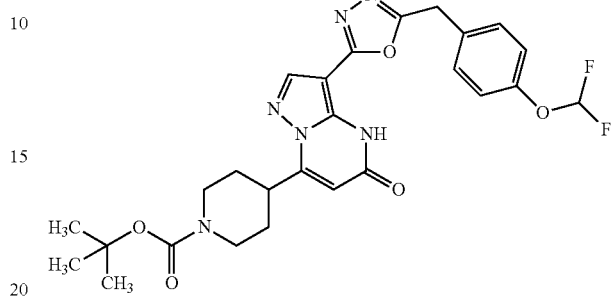

tert-butyl 4-{3-[(2-{[4-(difluoromethoxy)phenyl]acetyl}hydrazinyl)carbonyl]-5-oxo-4,5-dihydropyrazolo[1,5-a]pyrimidin-7-yl}piperidine-1-carboxylate (87.8 mg, 157 μmol) was dissolved in THF (2.0 ml, 25 mmol) and stirred with Burgess-Reagent (52.3 mg, 219 μmol) for 16 h at RT. Purification via reverse phase chromatography (Method: Reprosil C18; 10 μm; 125×30 mm/flow: 50 ml/min/solvents: A=water (0.01% formic acid), B=acetonitrile/gradient: 0.00-5.00 min=10% B, 6.50 min=20% B, 17.0-19.75 min=100% B, 19.75.00-23.00 min=90% B) afforded the desired product after drying in vacuo. The obtained amount was 50.6 mg (100% purity, 60% of theory).

LC-MS (Method 1B): $R_t$=1.11 min; MS (ESIpos): m/z=543 [M+H]$^+$

1H-NMR (400 MHz, DMSO-d6) delta [ppm]: 1.416 (16.00), 1.518 (0.10), 1.528 (0.12), 1.549 (0.29), 1.558 (0.30), 1.580 (0.33), 1.589 (0.30), 1.611 (0.14), 1.621 (0.11), 1.975 (0.41), 2.007 (0.36), 2.873 (0.16), 3.410 (0.15), 4.082 (0.27), 4.112 (0.26), 4.321 (2.30), 6.129 (0.06), 7.163 (1.12), 7.184 (1.31), 7.213 (1.11), 7.431 (1.25), 7.453 (1.07), 8.357 (0.17), 12.007 (0.07).

Example 345A

Tert-butyl 4-(5-oxo-3-{5-[4-(trifluoromethoxy)benzyl]-1,3,4-oxadiazol-2-yl}-4,5-dihydropyrazolo[1,5-a]pyrimidin-7-yl)piperidine-1-carboxylate

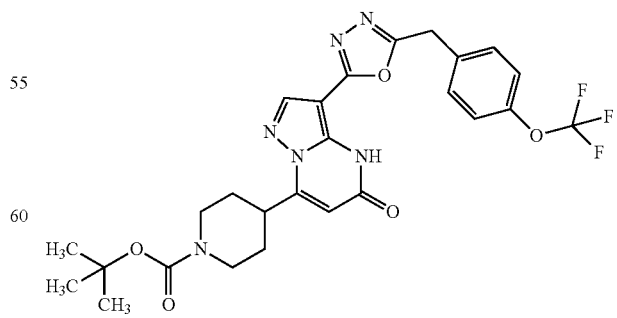

tert-butyl 4-{5-oxo-3-[(2-{[4-(trifluoromethoxy)phenyl]acetyl}hydrazinyl)carbonyl]-4,5-dihydropyrazolo[1,5-a]pyrimidin-7-yl}piperidine-1-carboxylate (179 mg, 310 µmol) was dissolved in THF (7.0 ml, 86 mmol) and stirred with Burgess-Reagent (103 mg, 434 µmol) for 16 h at RT. Purification via reverse phase chromatography (Method: Reprosil C18; 10 µm; 125×30 mm/flow: 50 ml/min/solvents: A=water (0.01% formic acid), B=acetonitrile/gradient: 0.00-5.00 min=10% B, 6.50 min=20% B, 17.0-19.75 min=100% B, 19.75.00-23.00 min=90% B) afforded the desired product after drying in vacuo. The obtained amount was 40.4 mg (87% purity, 20% of theory).

LC-MS (Method 1B): $R_t$=1.19 min; MS (ESIpos): m/z=561 [M+H]$^+$

1H-NMR (500 MHz, DMSO-d6) delta [ppm]: 1.416 (16.00), 1.441 (0.91), 1.455 (0.59), 1.530 (0.10), 1.540 (0.14), 1.554 (0.29), 1.561 (0.30), 1.578 (0.31), 1.586 (0.28), 1.603 (0.12), 1.611 (0.10), 1.978 (0.38), 2.002 (0.33), 2.872 (0.12), 3.411 (0.16), 4.088 (0.23), 4.105 (0.21), 4.373 (2.27), 6.137 (0.08), 7.361 (0.78), 7.377 (0.94), 7.389 (0.23), 7.516 (1.36), 7.534 (1.08), 8.365 (0.28).

Example 346A

Tert-butyl 4-{3-[5-(3-chlorobenzyl)-1,3,4-oxadiazol-2-yl]-5-oxo-4,5-dihydropyrazolo[1,5-a]pyrimidin-7-yl}piperidine-1-carboxylate

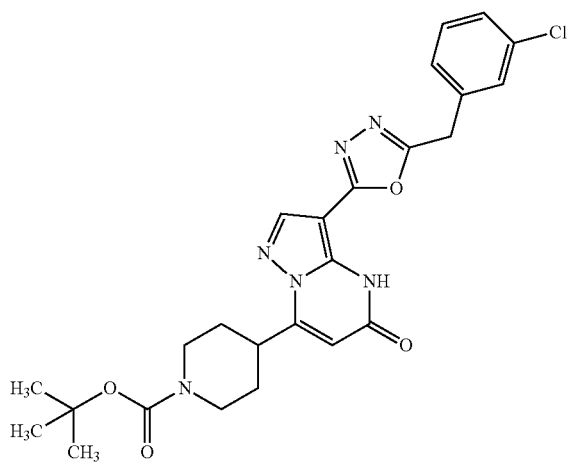 [SMILES: CC(C)(C)OC(=O)N1CCC(c2cc(=O)[nH]c3c(-c4nnc(Cc5cccc(Cl)c5)o4)cnn23)CC1]

tert-butyl 4-[3-({2-[(3-chlorophenyl)acetyl]hydrazinyl}carbonyl)-5-oxo-4,5-dihydropyrazolo[1,5-a]pyrimidin-7-yl]piperidine-1-carboxylate (64.2 mg, 121 µmol) was dissolved in THF (2.0 ml) and stirred with Burgess-Reagent (40.5 mg, 170 µmol) for 16 h at RT. 1 ml of water was added, the resulting residue was filtered, washed with water and dried in vacuo to afford the product. The obtained amount was 35.1 mg (95% purity, 54% of theory).

LC-MS (Method 1B): $R_t$=1.14 min; MS (ESIpos): m/z=511 [M+H]$^+$

1H-NMR (400 MHz, DMSO-d6) delta [ppm]: 1.413 (16.00), 1.525 (0.18), 1.546 (0.42), 1.551 (0.41), 1.555 (0.44), 1.576 (0.46), 1.586 (0.43), 1.607 (0.19), 1.974 (0.63), 2.003 (0.53), 2.862 (0.25), 3.406 (0.21), 4.079 (0.41), 4.106 (0.39), 4.347 (2.92), 6.125 (0.09), 7.342 (0.32), 7.360 (0.87), 7.375 (0.88), 7.385 (1.04), 7.402 (0.54), 7.422 (0.20), 7.492 (0.77), 8.362 (0.22), 12.022 (0.11).

Example 347A

Tert-butyl 4-(5-oxo-3-{5-[2-(1H-1,2,4-triazol-1-yl)propan-2-yl]-1,3,4-oxadiazol-2-yl}-4,5-dihydropyrazolo[1,5-a]pyrimidin-7-yl)piperidine-1-carboxylate

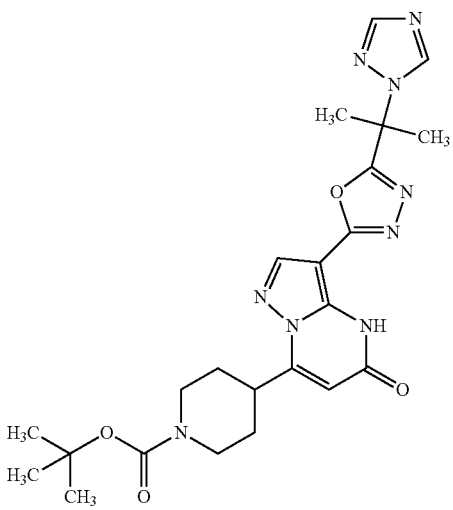 [SMILES: CC(C)(C)OC(=O)N1CCC(c2cc(=O)[nH]c3c(-c4nnc(C(C)(C)n5cncn5)o4)cnn23)CC1]

tert-butyl 4-[3-({2-[2-methyl-2-(1H-1,2,4-triazol-1-yl)propanoyl]hydrazinyl}carbonyl)-5-oxo-4,5-dihydropyrazolo[1,5-a]pyrimidin-7-yl]piperidine-1-carboxylate (96.2 mg, 187 µmol) was dissolved in THF (2.0 ml, 25 mmol) and stirred with Burgess-Reagent (62.5 mg, 262 µmol) for 16 h at RT. Water and ethyl acetate were added and the organic phase was separated and dried via a filtration through an Extrelut NT3-filter. The solvent was removed and the mixture purified via reverse phase chromatography (Method: Reprosil C18; 10 µm; 125×30 mm/flow: 50 ml/min/solvents: A=water (0.01% formic acid), B=acetonitrile/gradient: 0.00-5.00 min=10% B, 6.50 min=20% B, 17.0-19.75 min=100% B, 19.75.00-23.00 min=90% B) to obtain the product after removal of the solvents in vacuo. The obtained amount was 56 mg (100% purity, 60% of theory).

LC-MS (Method 1B): $R_t$=0.83 min; MS (ESIpos): m/z=496 [M+H]$^+$

1H-NMR (400 MHz, DMSO-d6) delta [ppm]: 1.415 (16.00), 1.508 (0.10), 1.519 (0.13), 1.540 (0.33), 1.549 (0.35), 1.571 (0.42), 1.580 (0.35), 1.602 (0.15), 1.611 (0.12), 1.968 (0.48), 1.998 (0.41), 2.113 (7.56), 2.871 (0.18), 3.378 (0.11), 3.409 (0.18), 3.433 (0.10), 4.078 (0.30), 4.106 (0.29), 6.139 (0.11), 8.018 (1.74), 8.353 (0.39), 8.874 (2.06), 12.160 (0.03).

Example 348A

Tert-butyl 4-{3-[5-(2-chlorobenzyl)-1,3,4-oxadiazol-2-yl]-5-oxo-4,5-dihydropyrazolo[1,5-a]pyrimidin-7-yl}piperidine-1-carboxylate

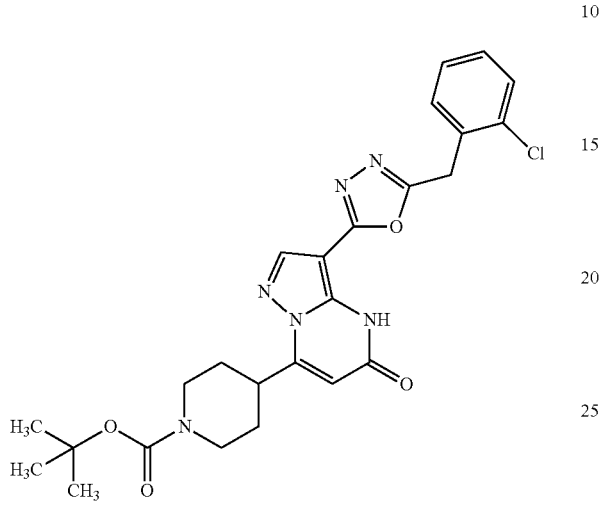

tert-butyl 4-[3-({2-[(2-chlorophenyl)acetyl]hydrazinyl}carbonyl)-5-oxo-4,5-dihydropyrazolo[1,5-a]pyrimidin-7-yl]piperidine-1-carboxylate (92.6 mg, 175 μmol) was dissolved in THF (2.0 ml, 25 mmol) and stirred with Burgess-Reagent (58.4 mg, 245 μmol) for 16 h at RT. Water and ethyl acetate were added and the organic phase was separated and dried via a filtration through an Extrelut NT3-filter. The solvent was removed and the mixture purified via reverse phase chromatography (Method: Reprosil C18; 10 μm; 125×30 mm/flow: 50 ml/min/solvents: A=water (0.01% formic acid), B=acetonitrile/gradient: 0.00-5.00 min=10% B, 6.50 min=20% B, 17.0-19.75 min=100% B, 19.75.00-23.00 min=90% B) to obtain the product after removal of the solvents in vacuo. The obtained amount was 55 mg (100% purity, 61% of theory).

LC-MS (Method 1B): $R_t$=1.09 min; MS (ESIpos): m/z=511 [M+H]$^+$

1H-NMR (400 MHz, DMSO-d6) delta [ppm]: 1.418 (16.00), 1.528 (0.14), 1.551 (0.32), 1.560 (0.35), 1.581 (0.37), 1.591 (0.35), 1.612 (0.16), 1.979 (0.48), 2.010 (0.43), 2.875 (0.20), 3.415 (0.15), 4.083 (0.33), 4.113 (0.31), 4.424 (2.93), 6.113 (0.07), 7.349 (0.15), 7.359 (1.10), 7.368 (0.96), 7.373 (0.99), 7.382 (1.43), 7.392 (0.25), 7.477 (0.10), 7.487 (0.56), 7.494 (0.46), 7.497 (0.48), 7.503 (0.87), 7.512 (0.72), 7.517 (0.50), 7.527 (0.46), 7.536 (0.09), 8.361 (0.22), 12.015 (0.08).

Example 349A

Tert-butyl 4-(3-{5-[(5-methyl-1,3-thiazol-2-yl)methyl]-1,3,4-oxadiazol-2-yl}-5-oxo-4,5-dihydropyrazolo[1,5-a]pyrimidin-7-yl)piperidine-1-carboxylate

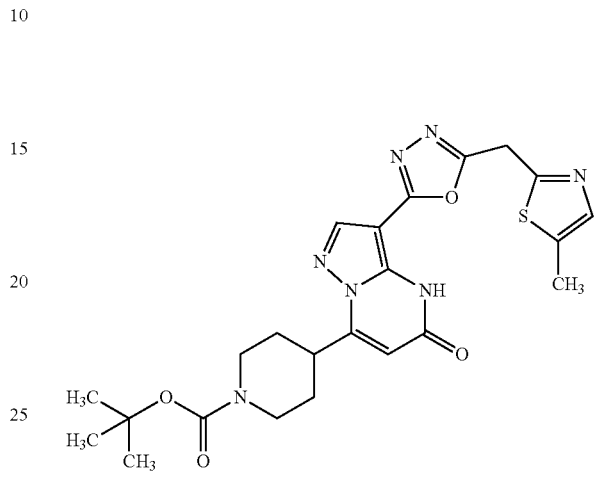

tert-butyl 4-[3-({2-[(2-chlorophenyl)acetyl]hydrazinyl}carbonyl)-5-oxo-4,5-dihydropyrazolo[1,5-a]pyrimidin-7-yl]piperidine-1-carboxylate (161 mg, 313 μmol) was dissolved in THF (3.0 ml, 37 mmol) and stirred with Burgess-Reagent (104 mg, 438 μmol) for 16 h at RT. Water and ethyl acetate were added and the organic phase was separated and dried via a filtration through an Extrelut NT3-filter. The solvent was removed and the mixture purified via reverse phase chromatography (Method: Reprosil C18; 10 μm; 125×30 mm/flow: 50 ml/min/solvents: A=water (0.01% formic acid), B=acetonitrile/gradient: 0.00-5.00 min=10% B, 6.50 min=20% B, 17.0-19.75 min=100% B, 19.75.00-23.00 min=90% B) to obtain the product after removal of the solvents in vacuo. The obtained amount was 46 mg (100% purity, 30% of theory).

LC-MS (Method 1B): $R_t$=0.92 min; MS (ESIpos): m/z=498 [M+H]$^+$

1H-NMR (400 MHz, DMSO-d6) delta [ppm]: 1.417 (16.00), 1.521 (0.11), 1.531 (0.13), 1.552 (0.32), 1.562 (0.35), 1.583 (0.37), 1.593 (0.34), 1.614 (0.15), 1.622 (0.13), 1.981 (0.48), 2.011 (0.42), 2.330 (4.02), 2.332 (4.14), 2.870 (0.19), 3.417 (0.14), 4.084 (0.32), 4.115 (0.31), 4.732 (3.17), 6.129 (0.06), 7.254 (0.65), 7.256 (0.67), 8.388 (0.14), 11.994 (0.07).

Example 350A

Tert-butyl 4-{3-[5-(2-chloro-6-fluorobenzyl)-1,3,4-oxadiazol-2-yl]-5-oxo-4,5-dihydropyrazolo[1,5-a]pyrimidin-7-yl}piperidine-1-carboxylate

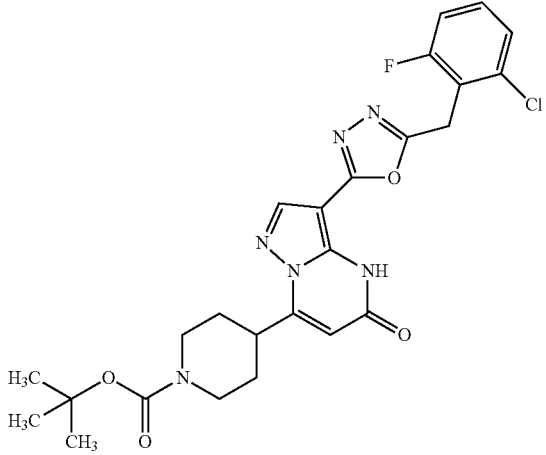 [SMILES: CC(C)(C)OC(=O)N1CCC(c2cc(=O)[nH]c3c(-c4nnc(Cc5c(F)cccc5Cl)o4)cnn23)CC1]

tert-butyl 4-[3-({2-[(2-chloro-6-fluorophenyl)acetyl]hydrazinyl}carbonyl)-5-oxo-4,5-dihydropyrazolo[1,5-a]pyrimidin-7-yl]piperidine-1-carboxylate (53.2 mg, 97.3 µmol) was dissolved in THF (2.0 ml) and stirred with Burgess-Reagent (32.4 mg, 136 µmol) for 16 h at RT. 1 ml of water was added, the resulting residue was filtered, washed with water and dried in vacuo to afford the product.

The obtained amount was 32 mg (100% purity, 61% of theory).

LC-MS (Method 1B): $R_t$=1.14 min; MS (ESIpos): m/z=529 [M+H]$^+$

1H-NMR (400 MHz, DMSO-d6) delta [ppm]: 1.419 (16.00), 1.565 (0.33), 1.589 (0.34), 1.983 (0.46), 2.009 (0.39), 2.880 (0.17), 3.400 (0.13), 4.083 (0.37), 4.112 (0.30), 4.432 (1.79), 6.043 (0.09), 7.303 (0.18), 7.310 (0.23), 7.324 (0.37), 7.328 (0.59), 7.348 (0.34), 7.352 (0.38), 7.410 (0.34), 7.414 (0.35), 7.430 (1.08), 7.435 (0.85), 7.451 (0.46), 7.456 (0.37), 7.471 (0.42), 7.492 (0.20), 8.338 (0.12), 12.021 (0.16).

Example 351A

Tert-butyl 4-{3-[5-(2-methoxybenzyl)-1,3,4-oxadiazol-2-yl]-5-oxo-4,5-dihydropyrazolo[1,5-a]pyrimidin-7-yl}piperidine-1-carboxylate

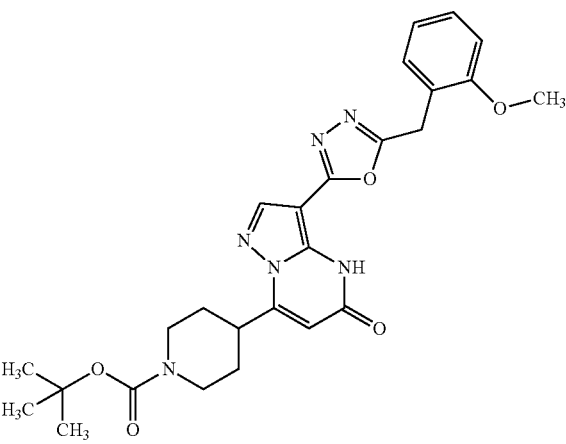 [SMILES: COc1ccccc1Cc1nnc(-c2cnn3c(C4CCN(C(=O)OC(C)(C)C)CC4)cc(=O)[nH]c23)o1]

tert-butyl 4-[3-({2-[(2-chloro-6-fluorophenyl)acetyl]hydrazinyl}carbonyl)-5-oxo-4,5-dihydropyrazolo[1,5-a]pyrimidin-7-yl]piperidine-1-carboxylate (94.8 mg, 181 µmol) was dissolved in THF (2.0 ml, 25 mmol) and stirred with Burgess-Reagent (60.3 mg, 253 µmol) for 16 h at RT. 1 ml of water was added, the resulting residue was filtered, washed with water and dried in vacuo to afford the product. The obtained amount was 77 mg (97% purity, 81% of theory).

LC-MS (Method 1B): $R_t$=1.10 min; MS (ESIpos): m/z=507 [M+H]$^+$

1H-NMR (400 MHz, DMSO-d6) delta [ppm]: 1.417 (16.00), 1.517 (0.11), 1.528 (0.14), 1.549 (0.33), 1.559 (0.34), 1.580 (0.37), 1.590 (0.34), 1.610 (0.15), 1.621 (0.12), 1.977 (0.48), 2.007 (0.41), 2.866 (0.18), 3.383 (0.12), 3.411 (0.17), 3.441 (0.10), 3.786 (6.42), 4.082 (0.31), 4.110 (0.29), 4.224 (2.62), 6.125 (0.08), 6.920 (0.32), 6.938 (0.69), 6.957 (0.41), 7.027 (0.62), 7.048 (0.74), 7.249 (0.54), 7.267 (0.48), 7.279 (0.37), 7.283 (0.30), 7.299 (0.50), 7.318 (0.27), 7.322 (0.22), 8.347 (0.27), 11.934 (0.09).

Example 352A

Tert-butyl 4-(3-{5-[1-(morpholin-4-yl)propan-2-yl]-1,3,4-oxadiazol-2-yl}-5-oxo-4,5-dihydropyrazolo[1,5-a]pyrimidin-7-yl)piperidine-1-carboxylate

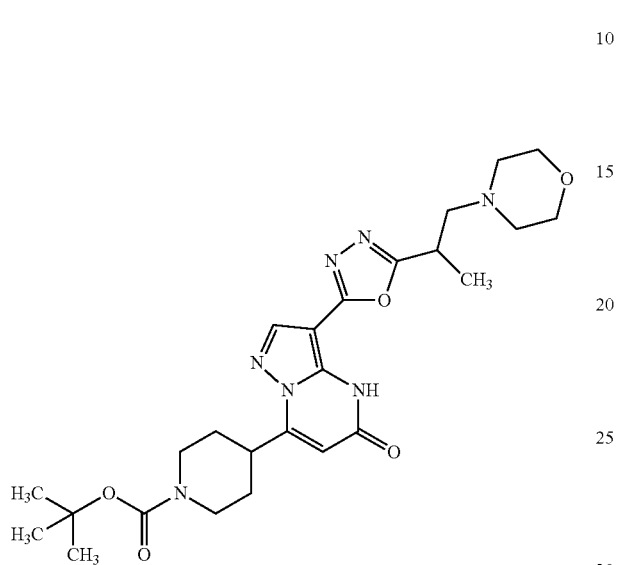

tert-butyl 4-[3-({2-[2-methyl-3-(morpholin-4-yl)propanoyl]hydrazinyl}carbonyl)-5-oxo-4,5-dihydropyrazolo[1,5-a]pyrimidin-7-yl]piperidine-1-carboxylate (114 mg, 215 μmol) was dissolved in THF (2.5 ml, 31 mmol) and stirred with Burgess-Reagent (71.6 mg, 300 μmol) for 16 h at RT. Purification via reverse phase chromatography (Method: Reprosil C18; 10 μm; 125×30 mm/flow: 50 ml/min/solvents: A=water (0.01% formic acid), B=acetonitrile/gradient: 0.00-5.00 min=10% B, 6.50 min=20% B, 17.0-19.75 min=100% B, 19.75.00-23.00 min=90% B) afforded the desired product after drying in vacuo. The obtained amount was 27 mg (66% purity, 16% of theory).

LC-MS (Method 1B): $R_t$=0.71 min; MS (ESIpos): m/z=514 [M+H]$^+$

1H-NMR (400 MHz, DMSO-d6) delta [ppm]: 1.420 (16.00), 1.542 (0.20), 1.564 (0.36), 1.573 (0.43), 1.595 (0.35), 1.603 (0.33), 1.625 (0.14), 1.983 (0.51), 2.012 (0.42), 2.877 (0.24), 3.189 (0.27), 3.215 (0.27), 3.467 (1.03), 3.512 (0.45), 3.658 (0.33), 3.741 (0.21), 3.756 (0.27), 3.771 (0.31), 3.787 (0.30), 3.802 (0.24), 3.989 (0.19), 4.092 (0.38), 4.117 (0.33), 6.153 (0.09), 8.419 (0.25), 8.462 (0.15), 9.478 (0.07).

Example 353A

Tert-butyl 4-(3-{5-[2-(morpholin-4-yl)ethyl]-1,3,4-oxadiazol-2-yl}-5-oxo-4,5-dihydropyrazolo[1,5-a]pyrimidin-7-yl)piperidine-1-carboxylate

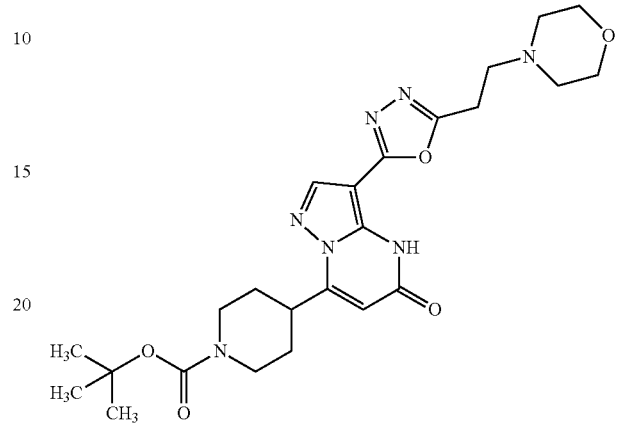

tert-butyl 4-[3-({2-[3-(morpholin-4-yl)propanoyl]hydrazinyl}carbonyl)-5-oxo-4,5-dihydropyrazolo[1,5-a]pyrimidin-7-yl]piperidine-1-carboxylate (161 mg, 311 μmol) was dissolved in THF (2.5 ml, 31 mmol) and stirred with Burgess-Reagent (104 mg, 436 μmol) for 16 h at RT. Purification via reverse phase chromatography (Method: Reprosil C18; 10 μm; 125×30 mm/flow: 50 ml/min/solvents: A=water (0.01% formic acid), B=acetonitrile/gradient: 0.00-5.00 min=10% B, 6.50 min=20% B, 17.0-19.75 min=100% B, 19.75.00-23.00 min=90% B) afforded the desired product after drying in vacuo. The obtained amount was 14.7 mg (91% purity, 8.6% of theory).

LC-MS (Method 1B): $R_t$=0.67 min; MS (ESIpos): m/z=500 [M+H]$^+$

Example 354A

Tert-butyl 4-{5-oxo-3-[5-(2-phenylethyl)-1,3,4-oxadiazol-2-yl]-4,5-dihydropyrazolo[1,5-a]pyrimidin-7-yl}piperidine-1-carboxylate

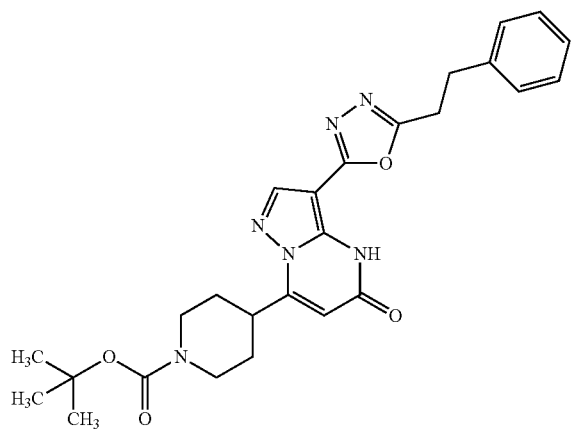 [SMILES: CC(C)(C)OC(=O)N1CCC(c2cc(=O)[nH]c3c(-c4nnc(CCc5ccccc5)o4)cnn23)CC1]

tert-butyl 4-(5-oxo-3-{[2-(3-phenylpropanoyl)hydrazinyl]carbonyl}-4,5-dihydropyrazolo[1,5-a]pyrimidin-7-yl)piperidine-1-carboxylate (70.7 mg, 139 µmol) was dissolved in THF (2.5 ml, 31 mmol) and stirred with Burgess-Reagent (46.4 mg, 195 µmol) for 16 h at RT. Purification via reverse phase chromatography (Method: Reprosil C18; 10 µm; 125×30 mm/flow: 50 ml/min/solvents: A=water (0.01% formic acid), B=acetonitrile/gradient: 0.00-5.00 min=10% B, 6.50 min=20% B, 17.0-19.75 min=100% B, 19.75.00-23.00 min=90% B) afforded the desired product after drying in vacuo.

The obtained amount was 42.8 mg (98% purity, 62% of theory).

LC-MS (Method 1B): R$_t$=1.13 min; MS (ESIpos): m/z=491 [M+H]$^+$

1H-NMR (400 MHz, DMSO-d6) delta [ppm]: 1.421 (16.00), 1.525 (0.13), 1.534 (0.16), 1.556 (0.40), 1.565 (0.42), 1.587 (0.45), 1.596 (0.42), 1.617 (0.18), 1.628 (0.15), 1.985 (0.57), 2.017 (0.50), 2.876 (0.21), 3.101 (0.39), 3.119 (1.01), 3.138 (0.95), 3.200 (0.98), 3.219 (1.04), 3.236 (0.39), 3.387 (0.16), 3.417 (0.26), 3.445 (0.13), 4.088 (0.36), 4.119 (0.34), 6.139 (0.22), 7.183 (0.08), 7.192 (0.18), 7.205 (0.35), 7.218 (0.32), 7.226 (0.23), 7.237 (0.07), 7.286 (4.41), 7.295 (1.59), 7.299 (1.61), 8.360 (0.64), 12.014 (0.09).

Example 355A

Tert-butyl 4-{3-[5-(4-chlorobenzyl)-1,3,4-oxadiazol-2-yl]-5-oxo-4,5-dihydropyrazolo[1,5-a]pyrimidin-7-yl}piperidine-1-carboxylate

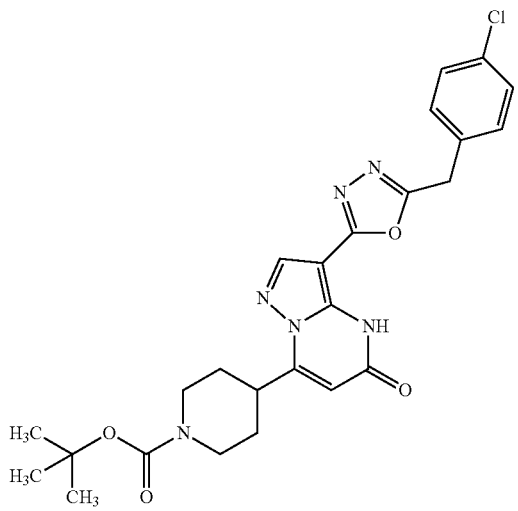 [SMILES: CC(C)(C)OC(=O)N1CCC(c2cc(=O)[nH]c3c(-c4nnc(Cc5ccc(Cl)cc5)o4)cnn23)CC1]

tert-butyl 4-[3-({2-[(4-chlorophenyl)acetyl]hydrazinyl}carbonyl)-5-oxo-4,5-dihydropyrazolo[1,5-a]pyrimidin-7-yl]piperidine-1-carboxylate (78.6 mg, 149 µmol) was dissolved in THF (2.5 ml, 31 mmol) and stirred with Burgess-Reagent (49.6 mg, 208 µmol) for 16 h at RT. Purification via reverse phase chromatography (Method: Reprosil C18; 10 µm; 125×30 mm/flow: 50 ml/min/solvents: A=water (0.01% formic acid), B=acetonitrile/gradient: 0.00-5.00 min=10% B, 6.50 min=20% B, 17.0-19.75 min=100% B, 19.75.00-23.00 min=90% B) afforded the desired product after drying in vacuo. The obtained amount was 47.8 mg (100% purity, 63% of theory).

LC-MS (Method 1B): R$_t$=1.15 min; MS (ESIpos): m/z=511 [M+H]$^+$

1H-NMR (400 MHz, DMSO-d6) delta [ppm]: 1.416 (16.00), 1.518 (0.16), 1.527 (0.19), 1.549 (0.46), 1.557 (0.49), 1.579 (0.53), 1.588 (0.47), 1.610 (0.21), 1.620 (0.17), 1.975 (0.68), 2.005 (0.59), 2.871 (0.27), 3.381 (0.18), 3.409 (0.27), 3.438 (0.15), 4.081 (0.44), 4.110 (0.42), 4.329 (3.20), 6.139 (0.15), 7.400 (0.30), 7.424 (5.31), 7.447 (0.31), 8.360 (0.49), 12.011 (0.12).

Example 356A

Tert-butyl 4-{5-oxo-3-[5-(pyridin-2-ylmethyl)-1,3,4-oxadiazol-2-yl]-4,5-dihydropyrazolo[1,5-a]pyrimidin-7-yl}piperidine-1-carboxylate

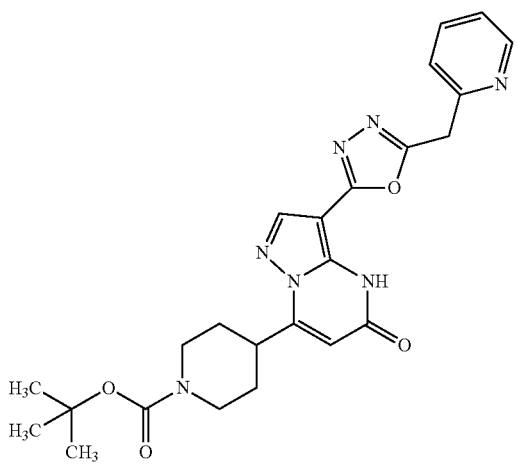 [SMILES: CC(C)(C)OC(=O)N1CCC(c2cc(=O)[nH]c3c(-c4nnc(Cc5ccccn5)o4)cnn23)CC1]

tert-butyl 4-[3-({2-[(4-chlorophenyl)acetyl]hydrazinyl}carbonyl)-5-oxo-4,5-dihydropyrazolo[1,5-a]pyrimidin-7-yl]piperidine-1-carboxylate (73.2 mg, 148 µmol) was dissolved in THF (2.5 ml, 31 mmol) and stirred with Burgess-Reagent (49.3 mg, 207 µmol) for 16 h at RT. Purification via reverse phase chromatography (Method: Reprosil C18; 10 µm; 125×30 mm/flow: 50 ml/min/solvents: A=water (0.01% formic acid), B=acetonitrile/gradient: 0.00-5.00 min=10% B, 6.50 min=20% B, 17.0-19.75 min=100% B, 19.75.00-23.00 min=90% B) afforded the desired product after drying in vacuo.

The obtained amount was 44.2 mg (100% purity, 63% of theory).

LC-MS (Method 1B): R$_t$=0.89 min; MS (ESIpos): m/z=478 [M+H]$^+$

1H-NMR (400 MHz, DMSO-d6) delta [ppm]: 1.416 (16.00), 1.519 (0.17), 1.527 (0.20), 1.549 (0.45), 1.558 (0.48), 1.579 (0.50), 1.589 (0.46), 1.610 (0.20), 1.620 (0.16), 1.978 (0.64), 2.008 (0.54), 2.869 (0.25), 3.385 (0.22), 3.415 (0.31), 3.444 (0.16), 4.083 (0.41), 4.108 (0.38), 4.494 (3.13), 6.146 (0.29), 7.303 (0.36), 7.315 (0.41), 7.321 (0.40), 7.334 (0.37), 7.459 (0.66), 7.478 (0.74), 7.792 (0.34), 7.797 (0.36), 7.811 (0.58), 7.816 (0.59), 7.831 (0.28), 7.835 (0.28), 8.365 (0.70), 8.495 (0.48), 8.505 (0.46), 12.087 (0.06).

Example 357A

Tert-butyl 4-[3-(5-methoxy-1,3,4-oxadiazol-2-yl)-5-oxo-4,5-dihydropyrazolo[1,5-a]pyrimidin-7-yl]piperidine-1-carboxylate

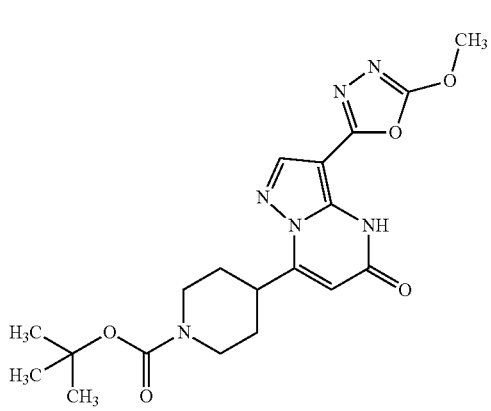 [SMILES: COc1nnc(-c2cnn3c(C4CCN(C(=O)OC(C)(C)C)CC4)cc(=O)[nH]c23)o1]

tert-butyl 4-(3-{[2-(methoxycarbonyl)hydrazinyl]carbonyl}-5-oxo-4,5-dihydropyrazolo[1,5-a]pyrimidin-7-yl)piperidine-1-carboxylate (106 mg, 244 µmol) was dissolved in THF (2.5 ml, 31 mmol) and stirred with Burgess-Reagent (81.4 mg, 342 µmol) for 16 h at RT. Purification via reverse phase chromatography (Method: Reprosil C18; 10 µm; 125×30 mm/flow: 50 ml/min/solvents: A=water (0.01% formic acid), B=acetonitrile/gradient: 0.00-5.00 min=10% B, 6.50 min=20% B, 17.0-19.75 min=100% B, 19.75.00-23.00 min=90% B) afforded the desired product after drying in vacuo.

The obtained amount was 39.8 mg (96% purity, 38% of theory).

LC-MS (Method 1B): $R_t$=0.87 min; MS (ESIpos): m/z=417 [M+H]$^+$

1H-NMR (400 MHz, DMSO-d6) delta [ppm]: 1.414 (16.00), 1.518 (0.15), 1.528 (0.18), 1.549 (0.42), 1.558 (0.43), 1.579 (0.45), 1.589 (0.41), 1.610 (0.18), 1.620 (0.14), 1.975 (0.59), 2.005 (0.50), 2.872 (0.20), 3.386 (0.31), 3.417 (0.32), 3.446 (0.18), 4.084 (0.35), 4.110 (0.34), 4.160 (5.46), 6.167 (0.18), 8.324 (0.52), 11.998 (0.07).

Example 358A

Tert-butyl 4-{5-oxo-3-[5-(thiophen-2-yl)-1,3,4-oxadiazol-2-yl]-4,5-dihydropyrazolo[1,5-a]pyrimidin-7-yl}piperidine-1-carboxylate

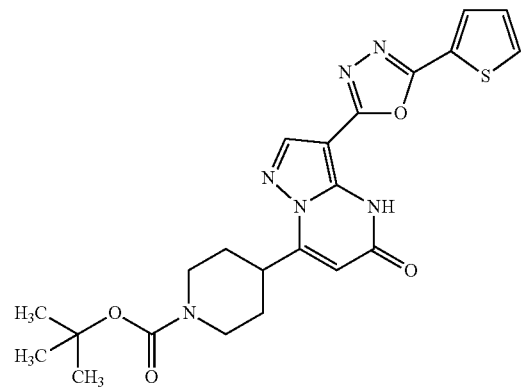 [SMILES: CC(C)(C)OC(=O)N1CCC(c2cc(=O)[nH]c3c(-c4nnc(-c5cccs5)o4)cnn23)CC1]

tert-butyl 4-(5-oxo-3-{[2-(thiophen-2-ylcarbonyl)hydrazinyl]carbonyl}-4,5-dihydropyrazolo[1,5-a]pyrimidin-7-yl)piperidine-1-carboxylate (63.0 mg, 129 µmol) was dissolved in THF (2.5 ml, 31 mmol) and stirred with Burgess-Reagent (43.2 mg, 181 µmol) for 16 h at RT. Purification via reverse phase chromatography (Method: Reprosil C18; 10 µm; 125×30 mm/flow: 50 ml/min/solvents: A=water (0.01% formic acid), B=acetonitrile/gradient: 0.00-5.00 min=10% B, 6.50 min=20% B, 17.0-19.75 min=100% B, 19.75.00-23.00 min=90% B) afforded the desired product after drying in vacuo.

The obtained amount was 50.2 mg (100% purity, 82% of theory).

LC-MS (Method 1B): $R_t$=1.06 min; MS (ESIpos): m/z=469 [M+H]$^+$

1H-NMR (400 MHz, DMSO-d6) delta [ppm]: 1.421 (16.00), 1.534 (0.18), 1.543 (0.21), 1.565 (0.52), 1.574 (0.56), 1.596 (0.55), 1.604 (0.50), 1.627 (0.21), 1.635 (0.17), 1.741 (0.07), 1.751 (0.09), 1.758 (0.14), 1.766 (0.07), 1.775 (0.04), 1.995 (0.73), 2.025 (0.62), 2.877 (0.28), 3.403 (0.20), 3.433 (0.34), 3.463 (0.17), 4.092 (0.47), 4.121 (0.43), 6.163 (0.48), 7.315 (0.52), 7.326 (0.82), 7.336 (0.49), 7.933 (0.82), 7.945 (0.76), 8.055 (0.61), 8.062 (0.60), 8.457 (0.91), 12.315 (0.11).

Example 359A

Tert-butyl 4-{5-oxo-3-[5-(2,2,2-trifluoroethyl)-1,3,4-oxadiazol-2-yl]-4,5-dihydropyrazolo[1,5-a]pyrimidin-7-yl}piperidine-1-carboxylate

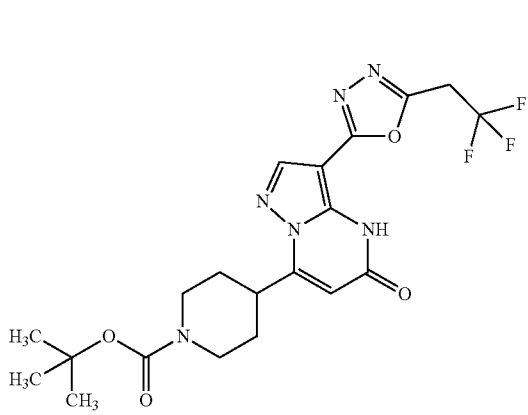 [SMILES: CC(C)(C)OC(=O)N1CCC(c2cc(=O)[nH]c3c(-c4nnc(CC(F)(F)F)o4)cnn23)CC1]

tert-butyl 4-(5-oxo-3-{[2-(3,3,3-trifluoropropanoyl)hydrazinyl]carbonyl}-4,5-dihydropyrazolo[1,5-a]pyrimidin-7-yl)piperidine-1-carboxylate (95.0 mg, 195 µmol) was dissolved in THF (2.5 ml, 31 mmol) and stirred with Burgess-Reagent (65.2 mg, 273 µmol) for 16 h at RT. Purification via reverse phase chromatography (Method: Reprosil C18; 10 µm; 125×30 mm/flow: 50 ml/min/solvents: A=water (0.01% formic acid), B=acetonitrile/gradient: 0.00-5.00 min=10% B, 6.50 min=20% B, 17.0-19.75 min=100% B, 19.75.00-23.00 min=90% B) afforded the desired product after drying in vacuo.n The obtained amount was 61 mg (62% purity, 41.6% of theory).

LC-MS (Method 1B): $R_t$=0.99 min; MS (ESIpos): m/z=469 [M+H]$^+$

1H-NMR (400 MHz, DMSO-d6) delta [ppm]: 1.157 (0.90), 1.175 (1.88), 1.193 (0.91), 1.419 (16.00), 1.537 (0.20), 1.559 (0.36), 1.568 (0.42), 1.590 (0.37), 1.600 (0.35), 1.621 (0.14), 1.986 (0.54), 2.016 (0.39), 2.877 (0.22), 3.073 (0.18), 3.092 (0.48), 3.110 (0.47), 3.128 (0.15), 3.412 (0.33), 3.440 (0.30), 3.464 (1.29), 4.089 (0.35), 4.113 (0.33), 4.288 (0.36), 4.314 (1.04), 4.341 (1.00), 4.367 (0.32), 6.158 (0.06), 8.407 (0.20), 12.009 (0.04).

Example 360A

Tert-butyl 4-{3-[5-(2-chlorophenyl)-1,3,4-oxadiazol-2-yl]-5-oxo-4,5-dihydropyrazolo[1,5-a]pyrimidin-7-yl}piperidine-1-carboxylate

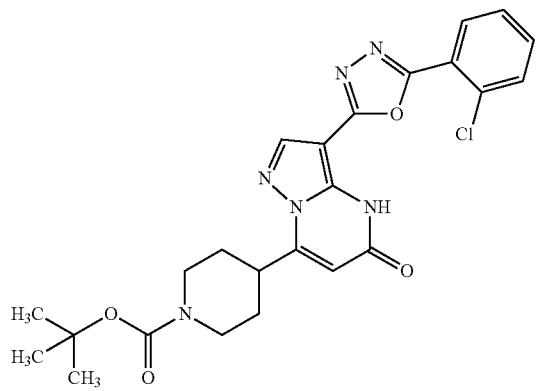

tert-butyl 4-(3-{[2-(2-chlorobenzoyl)hydrazinyl]carbonyl}-5-oxo-4,5-dihydropyrazolo[1,5-a]pyrimidin-7-yl)piperidine-1-carboxylate (119 mg, 231 µmol) was dissolved in THF (2.5 ml, 31 mmol) and stirred with Burgess-Reagent (77.1 mg, 324 µmol) for 16 h at RT. Purification via reverse phase chromatography (Method: Reprosil C18; 10 µm; 125×30 mm/flow: 50 ml/min/solvents: A=water (0.01% formic acid), B=acetonitrile/gradient: 0.00-5.00 min=10% B, 6.50 min=20% B, 17.0-19.75 min=100% B, 19.75.00-23.00 min=90% B) afforded the desired product after drying in vacuo.

The obtained amount was 78.1 mg (95% purity, 64% of theory).

LC-MS (Method 1B): $R_t$=1.11 min; MS (ESIpos): m/z=497 [M+H]$^+$

1H-NMR (400 MHz, DMSO-d6) delta [ppm]: 1.423 (16.00), 1.540 (0.11), 1.551 (0.13), 1.572 (0.33), 1.581 (0.37), 1.603 (0.36), 1.613 (0.34), 1.634 (0.15), 1.644 (0.12), 2.000 (0.43), 2.032 (0.38), 2.890 (0.16), 3.417 (0.11), 3.446 (0.20), 3.476 (0.10), 4.096 (0.27), 4.124 (0.25), 6.189 (0.20), 7.588 (0.23), 7.591 (0.24), 7.606 (0.61), 7.610 (0.59), 7.625 (0.48), 7.629 (0.47), 7.639 (0.37), 7.644 (0.39), 7.659 (0.54), 7.663 (0.57), 7.677 (0.31), 7.682 (0.28), 7.728 (0.69), 7.731 (0.63), 7.748 (0.46), 7.752 (0.39), 8.147 (0.37), 8.151 (0.37), 8.166 (0.35), 8.170 (0.33), 8.486 (0.54), 12.197 (0.06).

Example 361A

Tert-butyl 4-{5-oxo-3-[5-(piperidin-1-ylmethyl)-1,3,4-oxadiazol-2-yl]-4,5-dihydropyrazolo[1,5-a]pyrimidin-7-yl}piperidine-1-carboxylate

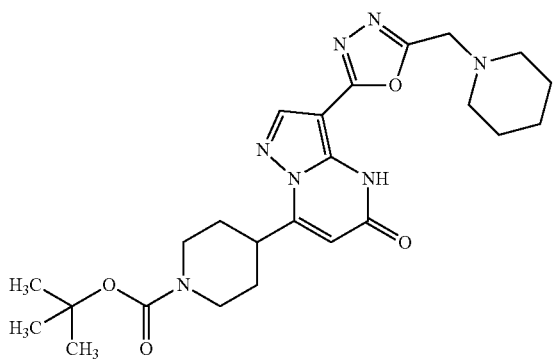 [SMILES: CC(C)(C)OC(=O)N1CCC(c2cc(=O)[nH]c3c(-c4nnc(CN5CCCCC5)o4)cnn23)CC1]

tert-butyl 4-(5-oxo-3-{[2-(piperidin-1-ylacetyl)hydrazinyl]carbonyl}-4,5-dihydropyrazolo[1,5-a]pyrimidin-7-yl)piperidine-1-carboxylate (109 mg, 217 µmol) was dissolved in THF (2.5 ml, 31 mmol) and stirred with Burgess-Reagent (72.5 mg, 304 µmol) for 16 h at RT. Purification via reverse phase chromatography (Method: Reprosil C18; 10 µm; 125×30 mm/flow: 50 ml/min/solvents: A=water (0.01% formic acid), B=acetonitrile/gradient: 0.00-5.00 min=10% B, 6.50 min=20% B, 17.0-19.75 min=100% B, 19.75.00-23.00 min=90% B) afforded the desired product after drying in vacuo.

The obtained amount was 33.5 mg (100% purity, 32% of theory).

LC-MS (Method 1B): $R_t$=0.66 min; MS (ESIpos): m/z=484 [M+H]$^+$

1H-NMR (400 MHz, DMSO-d6) delta [ppm]: 1.420 (16.00), 1.551 (0.16), 1.573 (0.35), 1.580 (0.36), 1.603 (0.39), 1.612 (0.38), 1.643 (0.29), 1.680 (0.30), 1.849 (0.18), 1.988 (0.42), 2.019 (0.36), 2.880 (0.19), 3.092 (0.17), 3.599 (0.17), 4.096 (0.28), 4.125 (0.28), 4.739 (0.19), 6.194 (0.06), 8.444 (0.25), 10.144 (0.07), 11.931 (0.02).

Example 362A

Tert-butyl 4-(5-oxo-3-{5-[(2-oxopyrrolidin-1-yl)methyl]-1,3,4-oxadiazol-2-yl}-4,5-dihydropyrazolo[1,5-a]pyrimidin-7-yl)piperidine-1-carboxylate

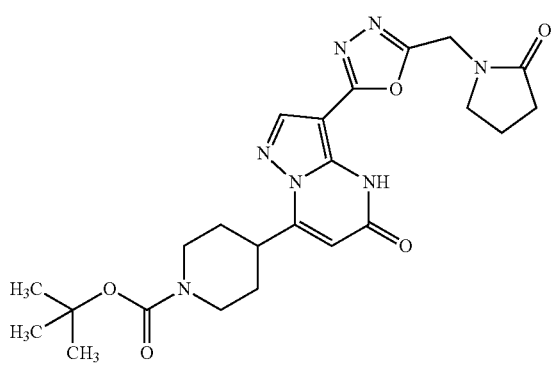 [SMILES: CC(C)(C)OC(=O)N1CCC(c2cc(=O)[nH]c3c(-c4nnc(CN5CCCC5=O)o4)cnn23)CC1]

tert-butyl 4-[5-oxo-3-({2-[(2-oxopyrrolidin-1-yl)acetyl]hydrazinyl}carbonyl)-4,5-dihydropyrazolo[1,5-a]pyrimidin-7-yl]piperidine-1-carboxylate (104 mg, 207 µmol) was dissolved in THF (2.5 ml, 31 mmol) and stirred with Burgess-Reagent (69.2 mg, 290 µmol) for 16 h at RT. Purification via reverse phase chromatography (Method: Reprosil C18; 10 µm; 125×30 mm/flow: 50 ml/min/solvents: A=water (0.01% formic acid), B=acetonitrile/gradient: 0.00-5.00 min=10% B, 6.50 min=20% B, 17.0-19.75 min=100% B, 19.75.00-23.00 min=90% B) afforded the desired product after drying in vacuo.

The obtained amount was 49.7 mg (100% purity, 50% of theory).

LC-MS (Method 1B): $R_t$=0.79 min; MS (ESIpos): m/z=484 [M+H]$^+$

1H-NMR (400 MHz, DMSO-d6) delta [ppm]: 1.419 (16.00), 1.529 (0.10), 1.536 (0.11), 1.556 (0.26), 1.565 (0.29), 1.587 (0.30), 1.596 (0.29), 1.617 (0.13), 1.627 (0.10), 1.953 (0.18), 1.973 (0.71), 1.992 (0.99), 2.011 (0.88), 2.029 (0.30), 2.281 (0.76), 2.303 (1.15), 2.322 (0.65), 2.880 (0.15), 3.414 (0.11), 3.458 (0.82), 3.476 (1.22), 3.493 (0.75), 4.086 (0.27), 4.115 (0.25), 4.710 (2.92), 6.113 (0.04), 8.376 (0.12), 12.042 (0.05).

Example 363A

Tert-butyl 4-[3-(5-cyclohexyl-1,3,4-oxadiazol-2-yl)-5-oxo-4,5-dihydropyrazolo[1,5-a]pyrimidin-7-yl]piperidine-1-carboxylate

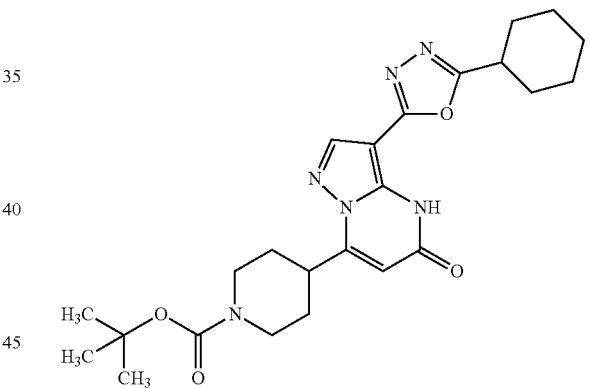

tert-butyl 4-(3-{[2-(cyclohexylcarbonyl)hydrazinyl]carbonyl}-5-oxo-4,5-dihydropyrazolo[1,5-a]pyrimidin-7-yl)piperidine-1-carboxylate (125 mg, 257 µmol) was dissolved in THF (2.5 ml, 31 mmol) and stirred with Burgess-Reagent (85.7 mg, 360 µmol) for 16 h at RT. Addition of water and Acetonitrile resulted in a precipitate that was filtered, washed with water and dried in vacuo to afford the desired product. The obtained amount was 98.8 mg (70% purity, 58% of theory).

LC-MS (Method 1B): $R_t$=1.16 min; MS (ESIpos): m/z=469 [M+H]$^+$

1H-NMR (400 MHz, DMSO-d6) delta [ppm]: 1.147 (0.15), 1.157 (0.19), 1.176 (0.34), 1.181 (0.33), 1.193 (0.20), 1.209 (0.27), 1.235 (0.35), 1.270 (0.41), 1.300 (0.38), 1.330 (0.26), 1.355 (0.50), 1.418 (16.00), 1.551 (0.70), 1.561 (0.65), 1.580 (0.95), 1.611 (0.71), 1.642 (0.40), 1.688 (0.27), 1.721 (0.64), 1.758 (1.00), 1.789 (0.43), 1.982 (0.72), 2.010 (0.48), 2.053 (0.48), 2.059 (0.47), 2.085 (0.43), 2.866 (0.32), 2.945 (0.19), 2.954 (0.25), 2.963 (0.19), 2.973 (0.25), 2.982

(0.37), 2.991 (0.22), 2.999 (0.14), 3.009 (0.18), 3.017 (0.10), 3.379 (0.19), 3.412 (0.22), 3.439 (0.12), 4.086 (0.52), 4.106 (0.48), 6.012 (0.11), 6.117 (0.12), 8.338 (0.30), 8.357 (0.36), 9.771 (0.11), 12.015 (0.07).

Example 364A

Tert-butyl 4-[3-(5-cyclobutyl-1,3,4-oxadiazol-2-yl)-5-oxo-4,5-dihydropyrazolo[1,5-a]pyrimidin-7-yl]piperidine-1-carboxylate

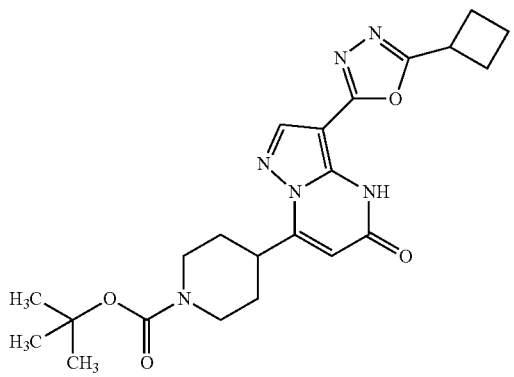 [SMILES: CC(C)(C)OC(=O)N1CCC(c2cc(=O)[nH]c3c(-c4nnc(C5CCC5)o4)cnn23)CC1]

tert-butyl 4-(3-{[2-(cyclobutylcarbonyl)hydrazinyl]carbonyl}-5-oxo-4,5-dihydropyrazolo[1,5-a]pyrimidin-7-yl)piperidine-1-carboxylate (121 mg, 263 µmol) was dissolved in THF (2.5 ml, 31 mmol) and stirred with Burgess-Reagent (87.8 mg, 369 µmol) for 16 h at RT. Purification via reverse phase chromatography (Method: Reprosil C18; 10 µm; 125×30 mm/flow: 50 ml/min/solvents: A=water (0.01% formic acid), B=acetonitrile/gradient: 0.00-5.00 min=10% B, 6.50 min=20% B, 17.0-19.75 min=100% B, 19.75.00-23.00 min=90% B) afforded the desired product after drying in vacuo.

The obtained amount was 14.7 mg (88% purity, 11% of theory).

LC-MS (Method 6B): $R_t$=3.14 min; MS (ESIpos): m/z=441 [M+H]$^+$

Example 365A

Tert-butyl 4-[3-(5-butyl-1,3,4-oxadiazol-2-yl)-5-oxo-4,5-dihydropyrazolo[1,5-a]pyrimidin-7-yl]piperidine-1-carboxylate

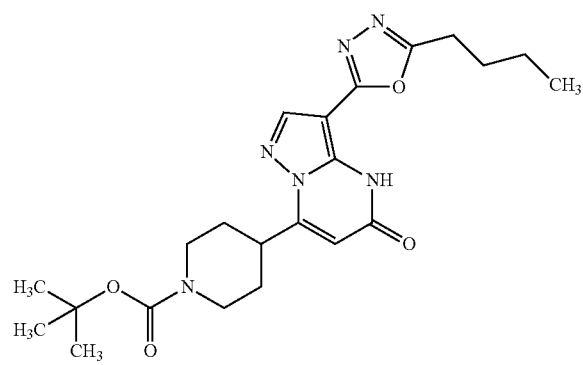 [SMILES: CCCCc1nnc(-c2cnn3c(C4CCN(C(=O)OC(C)(C)C)CC4)cc(=O)[nH]c23)o1]

tert-butyl 4-{5-oxo-3-[(2-pentanoylhydrazinyl)carbonyl]-4,5-dihydropyrazolo[1,5-a]pyrimidin-7-yl}piperidine-1-carboxylate (37.0 mg, 80.3 µmol) was dissolved in THF (2.5 ml) and stirred with Burgess-Reagent (26.8 mg, 112 µmol) for 16 h at RT. Ethyl acetate was added and the organic phase was washed with water and dried via an Extrelut NT3 filter. Solvents were removed in vacuo to afford the desired product. The obtained amount was 58.0 mg (78% purity, 127% of theory).

LC-MS (Method 1B): $R_t$=1.08 min; MS (ESIpos): m/z=443 [M+H]$^+$

1H-NMR (400 MHz, DMSO-d6) delta [ppm]: 0.906 (1.18), 0.925 (2.50), 0.943 (1.25), 1.157 (7.88), 1.175 (16.00), 1.193 (7.84), 1.418 (13.08), 1.746 (0.76), 2.870 (0.80), 2.888 (1.25), 2.907 (0.76), 3.069 (0.94), 3.086 (2.81), 3.097 (2.74), 3.104 (3.05), 3.115 (2.53), 3.133 (0.90), 3.465 (8.99), 4.119 (0.35), 8.834 (0.14).

Example 366A

Tert-butyl 4-{3-[3-(2-methoxyethyl)-1,2,4-oxadiazol-5-yl]-2-methyl-5-oxo-4,5-dihydropyrazolo[1,5-a]pyrimidin-7-yl}piperidine-1-carboxylate

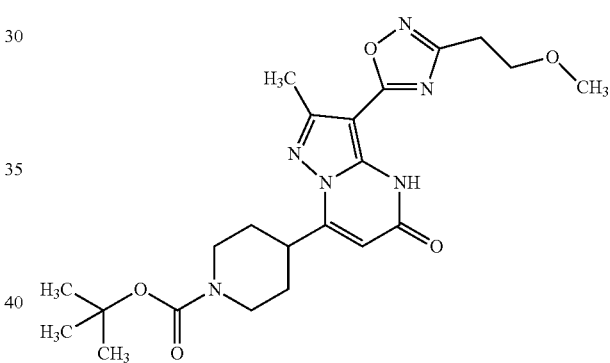

7-[1-(tert-butoxycarbonyl)piperidin-4-yl]-2-methyl-5-oxo-4,5-dihydropyrazolo[1,5-a]pyrimidine-3-carboxylic acid (150 mg, 398 µmol) was dissolved in N,N-Dimethylformamid (2 ml) and treated with N,N-Diisopropylethylamine (140 µl, 800 µmol) and 1,1'-Carboyldiimidazol (129 mg, 797 µmol). The mixture was stirred at 90° C. for 1.5 h. (1Z)-N'-hydroxy-3-methoxypropanimidamide (94.2 mg, 797 µmol) was dissolved in N,N-Dimethylformamid (1 ml) and added dropwise. The mixture was then stirred at 110° C. for 6 h. The mixture was purified via reverse phase HPLC (Method: column: Reprosil C18; 10 µm; 125×30 mm/flow: 50 ml/min/solvents: A=water (0.01% formic acid), B=acetonitrile/gradient: 0.00-5.00 min=10% B, 6.50 min=20% B, 17.0-19.75 min=100% B, 19.75.00-23.00 min=90% B) to afford the product. The obtained amount was 71.8 mg (100% purity, 39% of theory).

LC-MS (Method 1B): $R_t$=1.05 min; MS (ESIpos): m/z=459 [M+H]$^+$

Example 367A

Tert-butyl 4-[3-(5-methyl-4-phenyl-1,3-thiazol-2-yl)-5-oxo-4,5-dihydropyrazolo[1,5-a]pyrimidin-7-yl]piperidine-1-carboxylate

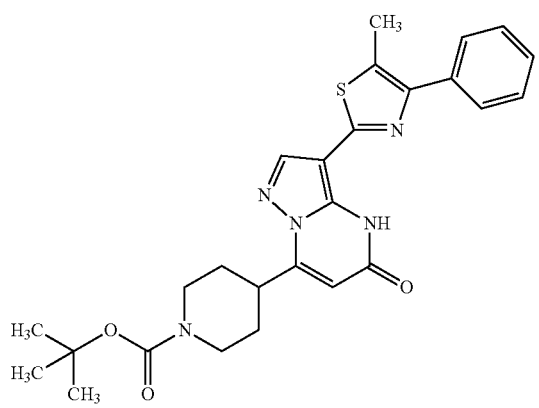 [SMILES: Cc1sc(-c2cnn3c(C4CCN(C(=O)OC(C)(C)C)CC4)cc(=O)[nH]c23)nc1-c1ccccc1]

tert-butyl 4-(3-carbamothioyl-5-oxo-4,5-dihydropyrazolo[1,5-a]pyrimidin-7-yl)piperidine-1-carboxylate (60.0 mg, 159 μmol), 2-bromo-1-phenylpropan-1-one (24 μl, 160 μmol) and N,N-Diisopropylethylamine (140 μl, 790 μmol) were dissolved in Ethanol (2.4 ml, 41 mmol) and stirred at 70° C. for 1 h. the mixture was purified via reverse phase HPLC (Method: column: Reprosil C18; 10 μm; 125×30 mm/flow: 50 ml/min/solvents: A=water (0.1% formic acid), B=acetonitrile/gradient: 0.00-4.25 min=20% B, 4.50 min=30% B, 19.00-22.50 min=100% B, 22.75-25.00 min=20% B) to afford the product. The obtained amount was 14.0 mg (100% purity, 18% of theory).

LC-MS (Method 1B): $R_t$=1.36 min; MS (ESIpos): m/z=492 [M+H]$^+$

Example 368A

Tert-butyl 4-(3-{5-[1-(4-chlorophenyl)cyclopropyl]-1,3,4-oxadiazol-2-yl}-5-oxo-4,5-dihydropyrazolo[1,5-a]pyrimidin-7-yl)piperidine-1-carboxylate

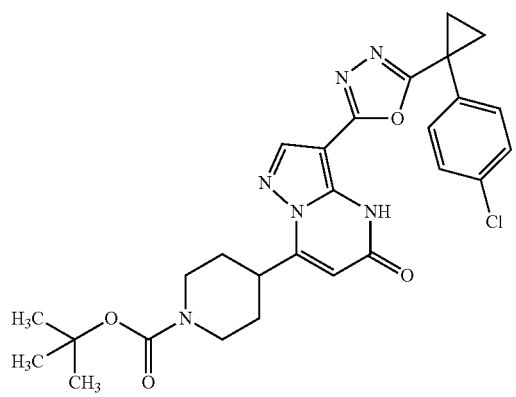 [SMILES: CC(C)(C)OC(=O)N1CCC(c2cc(=O)[nH]c3c(-c4nnc(C5(c6ccc(Cl)cc6)CC5)o4)cnn23)CC1]

tert-butyl 4-{3-[(2-{[1-(4-chlorophenyl)cyclopropyl]carbonyl}hydrazinyl)carbonyl]-5-oxo-4,5-dihydropyrazolo[1,5-a]pyrimidin-7-yl}piperidine-1-carboxylate (77.9 mg, 140 μmol) and Burgess-Reagent (46.8 mg, 196 μmol) were dissolved in THF (2.0 ml) and stirred at RT for 16 h. 1 ml of Water was added and the resulting precipitate was filtered, washed with water and dried in vacuo to afford the product. The obtained amount was 56.1 mg (100% purity, 74% of theory).

LC-MS (Method 1B): $R_t$=1.23 min; MS (ESIpos): m/z=537 [M+H]$^+$

Example 369A

Tert-butyl 4-[3-(3-tert-butyl-1,2,4-oxadiazol-5-yl)-2-methyl-5-oxo-4,5-dihydropyrazolo[1,5-a]pyrimidin-7-yl]piperidine-1-carboxylate

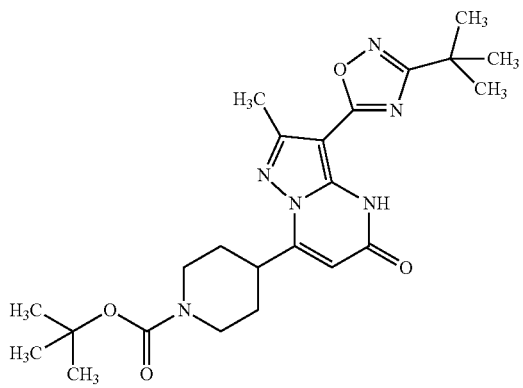 [SMILES: Cc1nn2c(C3CCN(C(=O)OC(C)(C)C)CC3)cc(=O)[nH]c2c1-c1nc(C(C)(C)C)no1]

7-[1-(tert-butoxycarbonyl)piperidin-4-yl]-2-methyl-5-oxo-4,5-dihydropyrazolo[1,5-a]pyrimidine-3-carboxylic acid (150 mg, 398 μmol) was dissolved in N,N-Dimethylformamid (2 ml) and treated with N,N-Diisopropylethylamine (140 μl, 800 μmol) and 1,1'-Carboyldiimidazol (129 mg, 797 μmol). The mixture was stirred at 90° C. for 1.5 h. (1Z)-N'-hydroxy-2,2-dimethylpropanimidamide (92.6 mg, 797 μmol) was dissolved in N,N-Dimethylformamid (1 ml) and added dropwise. The mixture was then stirred at 110° C. for 6 h. The mixture was purified via reverse phase HPLC (Method: column: Reprosil C18; 10 μm; 125×30 mm/flow: 50 ml/min/solvents: A=water (0.01% formic acid), B=acetonitrile/gradient: 0.00-5.00 min=10% B, 6.50 min=20% B, 17.0-19.75 min=100% B, 19.75.00-23.00 min=90% B) to afford the product. The obtained amount was 111 mg (100% purity, 61% of theory).

LC-MS (Method 1B): $R_t$=1.28 min; MS (ESIpos): m/z=457 [M+H]$^+$

Example 370A

Tert-butyl 4-{3-[(2-{[1-(4-chlorophenyl)cyclopropyl]carbonyl}hydrazinyl)carbonyl]-5-oxo-4,5-dihydropyrazolo[1,5-a]pyrimidin-7-yl}piperidine-1-carboxylate

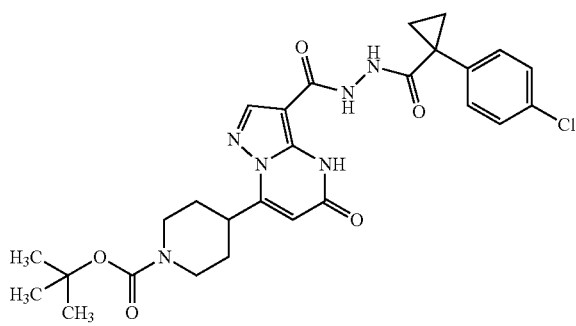 [SMILES: CC(C)(C)OC(=O)N1CCC(c2cc(=O)[nH]c3c(C(=O)NNC(=O)C4(c5ccc(Cl)cc5)CC4)cnn23)CC1]

7-[1-(tert-butoxycarbonyl)piperidin-4-yl]-5-oxo-4,5-dihydropyrazolo[1,5-a]pyrimidine-3-carboxylic acid (150 mg, 414 µmol) and 1-(4-chlorophenyl)cyclopropanecarbohydrazide (131 mg, 621 µmol) were dissolved in N,N-Dimethylformamid (1.5 ml, 19 mmol). N,N-Diisopropylethylamine (220 µl, 1.2 mmol) and HATU (266 mg, 621 µmol) were added and the mixture was stirred at RT for 16 h. Purification via revere phase HPLC (Method: Reprosil C18; 10 µm; 125×30 mm/flow: 50 ml/min/solvents: A=water (0.01% formic acid), B=acetonitrile/gradient: 0.00-5.00 min=20% B, 6.50 min=40% B, 17.0-19.75 min=100% B, 19.75.00-23.00 min=40% B) afforded the desired product after drying in vacuo.

The obtained amount was 77.9 mg (100% purity, 34% of theory).

LC-MS (Method 1B): $R_t$=1.01 min; MS (ESIpos): m/z=555 [M+H]$^+$

Example 371A

Tert-butyl 4-{3-[3-(4-fluorobenzyl)-1,2,4-oxadiazol-5-yl]-2-methyl-5-oxo-4,5-dihydropyrazolo[1,5-a]pyrimidin-7-yl}piperidine-1-carboxylate

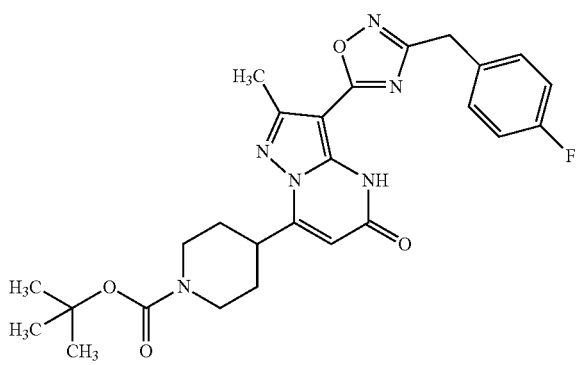 [SMILES: Cc1nn2c(C3CCN(C(=O)OC(C)(C)C)CC3)cc(=O)[nH]c2c1-c1nc(Cc2ccc(F)cc2)no1]

7-[1-(tert-butoxycarbonyl)piperidin-4-yl]-2-methyl-5-oxo-4,5-dihydropyrazolo[1,5-a]pyrimidine-3-carboxylic acid (150 mg, 398 µmol) was dissolved in N,N-Dimethylformamid (2 ml) and treated with N,N-Diisopropylethylamine (210 µl, 1.2 mmol) and 1,1'-Carboyldiimidazol (129 mg, 797 µmol). The mixture was stirred at 90° C. for 1.5 h. (1Z)-2-(4-fluorophenyl)-N'-hydroxyethanimidamide (134 mg, 797 µmol) was dissolved in N,N-Dimethylformamid (1 ml) and added dropwise. The mixture was then stirred at 110° C. for 6 h. The mixture was purified via reverse phase HPLC (Method: column: Reprosil C18; 10 µm; 125×30 mm/flow: 50 ml/min/solvents: A=water (0.01% formic acid), B=acetonitrile/gradient: 0.00-5.00 min=10% B, 6.50 min=20% B, 17.0-19.75 min=100% B, 19.75.00-23.00 min=90% B) to afford the product. The obtained amount was 93.6 mg (100% purity, 46% of theory).

LC-MS (Method 1B): $R_t$=1.20 min; MS (ESIpos): m/z=509 [M+H]$^+$

Example 372A

Tert-butyl 4-[3-(3-ethyl-1,2,4-oxadiazol-5-yl)-2-methyl-5-oxo-4,5-dihydropyrazolo[1,5-a]pyrimidin-7-yl]piperidine-1-carboxylate

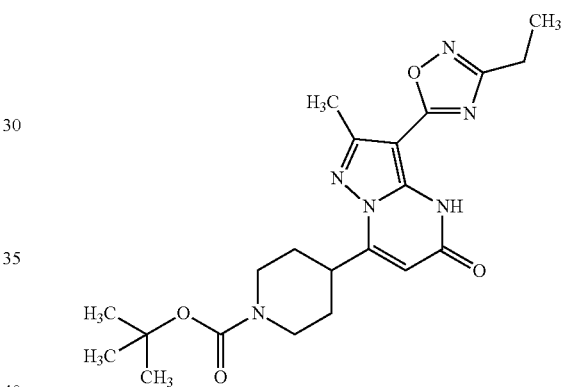

7-[1-(tert-butoxycarbonyl)piperidin-4-yl]-2-methyl-5-oxo-4,5-dihydropyrazolo[1,5-a]pyrimidine-3-carboxylic acid (150 mg, 398 µmol) was dissolved in N,N-Dimethylformamid (2 ml) and treated with N,N-Diisopropylethylamine (210 µl, 1.2 mmol) and 1,1'-Carboyldiimidazol (129 mg, 797 µmol). The mixture was stirred at 90° C. for 1.5 h. (1Z)-N'-hydroxypropanimidamide hydrochloride (1:1) (99.3 mg, 797 µmol) was dissolved in N,N-Dimethylformamid (1 ml) and added dropwise. The mixture was then stirred at 110° C. for 6 h. The mixture was purified via reverse phase HPLC (Method: column: Reprosil C18; 10 µm; 125×30 mm/flow: 50 ml/min/solvents: A=water (0.01% formic acid), B=acetonitrile/gradient: 0.00-5.00 min=10% B, 6.50 min=20% B, 17.0-19.75 min=100% B, 19.75.00-23.00 min=90% B) to afford the product. The obtained amount was 101 mg (100% purity, 59% of theory).

LC-MS (Method 11B): $R_t$=2.07 min; MS (ESIneg): m/z=427 [M−H]$^−$

Example 373A

Tert-butyl 4-{2-methyl-5-oxo-3-[3-(propan-2-yl)-1,2,4-oxadiazol-5-yl]-4,5-dihydropyrazolo[1,5-a]pyrimidin-7-yl}piperidine-1-carboxylate

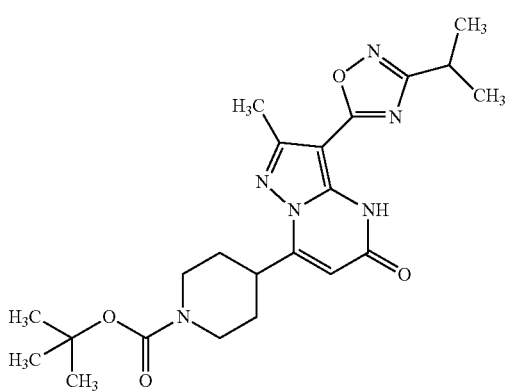 [SMILES: Cc1nn2c(C3CCN(C(=O)OC(C)(C)C)CC3)cc(=O)[nH]c2c1-c1nc(C(C)C)no1]

7-[1-(tert-butoxycarbonyl)piperidin-4-yl]-2-methyl-5-oxo-4,5-dihydropyrazolo[1,5-a]pyrimidine-3-carboxylic acid (150 mg, 398 μmol) was dissolved in N,N-Dimethylformamid (2 ml) and treated with N,N-Diisopropylethylamine (140 μl, 800 μmol) and 1,1'-Carboyldiimidazol (129 mg, 797 μmol). The mixture was stirred at 90° C. for 1.5 h. (1Z)-N'-hydroxy-2-methylpropanimidamide (81.4 mg, 797 μmol) was dissolved in N,N-Dimethylformamid (1 ml) and added dropwise. The mixture was then stirred at 110° C. for 6 h. The mixture was purified via reverse phase HPLC (Method: column: Reprosil C18; 10 μm; 125×30 mm/flow: 50 ml/min/solvents: A=water (0.01% formic acid), B=acetonitrile/gradient: 0.00-5.00 min=10% B, 6.50 min=20% B, 17.0-19.75 min=100% B, 19.75.00-23.00 min=90% B) to afford the product. The obtained amount was 80.1 mg (100% purity, 45% of theory).

LC-MS (Method 11B): $R_t$=2.22 min; MS (ESIneg): m/z=441 [M−H]⁻

Example 374A

Tert-butyl 4-{3-[3-(2-tert-butoxyethyl)-1,2,4-oxadiazol-5-yl]-2-methyl-5-oxo-4,5-dihydropyrazolo[1,5-a]pyrimidin-7-yl}piperidine-1-carboxylate

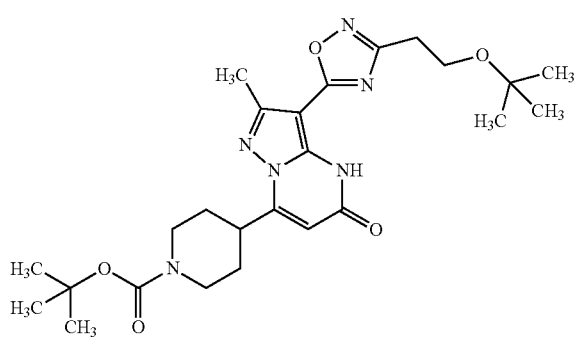 [SMILES: Cc1nn2c(C3CCN(C(=O)OC(C)(C)C)CC3)cc(=O)[nH]c2c1-c1nc(CCOC(C)(C)C)no1]

7-[1-(tert-butoxycarbonyl)piperidin-4-yl]-2-methyl-5-oxo-4,5-dihydropyrazolo[1,5-a]pyrimidine-3-carboxylic acid (150 mg, 398 μmol) was dissolved in N,N-Dimethylformamid (2 ml) and treated with N,N-Diisopropylethylamine (140 μl, 800 μmol) and 1,1'-Carboyldiimidazol (129 mg, 797 μmol). The mixture was stirred at 90° C. for 1.5 h. (1Z)-3-tert-butoxy-N'-hydroxypropanimidamide (128 mg, 797 μmol) was dissolved in N,N-Dimethylformamid (1 ml) and added dropwise. The mixture was then stirred at 110° C. for 6 h. The mixture was purified via reverse phase HPLC (Method: column: Reprosil C18; 10 μm; 125×30 mm/flow: 50 ml/min/solvents: A=water (0.01% formic acid), B=acetonitrile/gradient: 0.00-5.00 min=10% B, 6.50 min=20% B, 17.0-19.75 min=100% B, 19.75.00-23.00 min=90% B) to afford the product. The obtained amount was 55.6 mg (100% purity, 28% of theory).

LC-MS (Method 11B): $R_t$=2.27 min; MS (ESIpos): m/z=501 [M+H]⁺

Example 375A

Tert-butyl 4-[3-(3-tert-butyl-1,2,4-oxadiazol-5-yl)-5-oxo-4,5-dihydropyrazolo[1,5-a]pyrimidin-7-yl]-2-(2,2-dimethylpropyl)piperidine-1-carboxylate

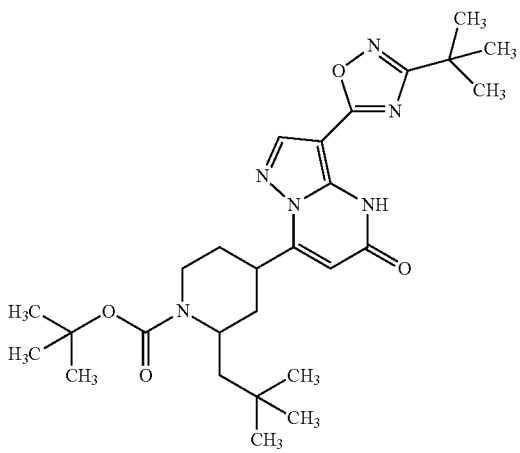 [SMILES: CC(C)(C)CC1CC(c2cc(=O)[nH]c3c(-c4nc(C(C)(C)C)no4)cnn23)CCN1C(=O)OC(C)(C)C]

7-[1-(tert-butoxycarbonyl)-2-(2,2-dimethylpropyl)piperidin-4-yl]-5-oxo-4,5-dihydropyrazolo[1,5-a]pyrimidine-3-carboxylic acid (75.0 mg, 173 μmol) was dissolved in N,N-Dimethylformamid (2 ml) and treated with N,N-Diisopropylethylamine (60 μl, 350 μmol) and 1,1'-Carboyldiimidazol (56.2 mg, 347 μmol). The mixture was stirred at 90° C. for 1.5 h. (1Z)-N'-hydroxy-3-methoxypropanimidamide (40.3 mg, 347 μmol) was dissolved in N,N-Dimethylformamid (1 ml) and added dropwise. The mixture was then stirred at 110° C. for 6 h. The mixture was purified via reverse phase HPLC (Method: column: Reprosil C18; 10 μm; 125×30 mm/flow: 50 ml/min/solvents: A=water (0.01% formic acid), B=acetonitrile/gradient: 0.00-5.00 min=10% B, 6.50 min=20% B, 17.0-19.75 min=100% B, 19.75.00-23.00 min=90% B) to afford the product. The obtained amount was 36.1 mg (100% purity, 41% of theory).

LC-MS (Method 11B): $R_t$=2.77 min; MS (ESIneg): m/z=511 [M−H]⁻

Example 376A

Tert-butyl 4-{3-[4-(3-methylbutyl)-1,3-thiazol-2-yl]-5-oxo-4,5-dihydropyrazolo[1,5-a]pyrimidin-7-yl}piperidine-1-carboxylate

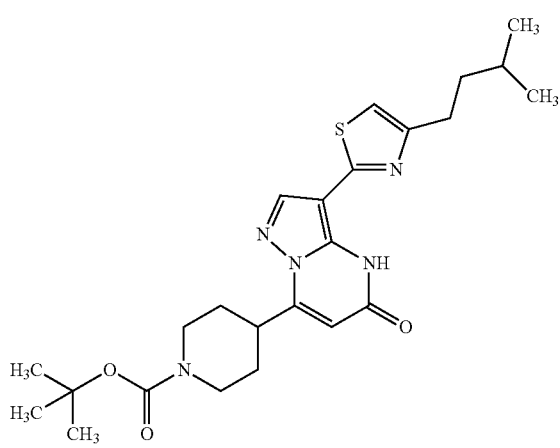 [SMILES: CC(C)CCc1csc(-c2cnn3c(C4CCN(C(=O)OC(C)(C)C)CC4)cc(=O)[nH]c23)n1]

tert-butyl 4-(3-carbamothioyl-5-oxo-4,5-dihydropyrazolo[1,5-a]pyrimidin-7-yl)piperidine-1-carboxylate (120 mg, 318 µmol), 1-bromo-5-methylhexan-2-one (61.4 mg, 318 µmol) and N,N-Diisopropylethylamine (280 µl, 1.6 mmol) were dissolved in Ethanol (4.8 ml, 82 mmol) and stirred at 70° C. for 1 h and left standing for 3 d at RT. The mixture was purified via reverse phase HPLC (Method: column: Reprosil C18; 10 µm; 125×30 mm/flow: 50 ml/min/solvents: A=water (0.1% formic acid), B=acetonitrile/gradient: 0.00-4.25 min=20% B, 4.50 min=30% B, 19.00-22.50 min=100% B, 22.75-25.00 min=20% B) to afford the product. The obtained amount was 36.7 mg (100% purity, 24% of theory).

LC-MS (Method 11B): $R_t$=2.64 min; MS (ESIpos): m/z=472 [M+H]$^+$

Example 377A

Tert-butyl 4-(3-{5-[1-(4-methoxyphenyl)cyclopropyl]-1,3,4-oxadiazol-2-yl}-5-oxo-4,5-dihydropyrazolo[1,5-a]pyrimidin-7-yl)piperidine-1-carboxylate

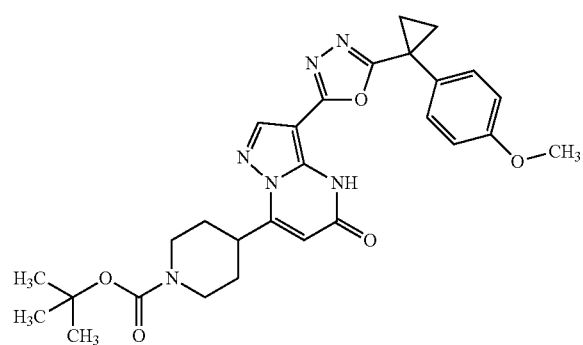 [SMILES: COc1ccc(C2(c3nnc(-c4cnn5c(C6CCN(C(=O)OC(C)(C)C)CC6)cc(=O)[nH]c45)o3)CC2)cc1]

tert-butyl 4-{3-[(2-{[1-(4-methoxyphenyl)cyclopropyl]carbonyl}hydrazinyl)carbonyl]-5-oxo-4,5-dihydropyrazolo[1,5-a]pyrimidin-7-yl}piperidine-1-carboxylate (193 mg, 351 µmol) was dissolved in THF (5.0 ml, 62 mmol) and stirred with Burgess-Reagent for 16 h at RT. Another 1.4 equivalents of Burgess-Reagent (117 mg, 491 µmol) was added and the mixture stirred for 24 h at RT. Water and the mixture purified via reverse phase chromatography (Method: Reprosil C18; 10 µm; 125×30 mm/flow: 50 ml/min/solvents: A=water (0.01% formic acid), B=acetonitrile/gradient: 0.00-5.00 min=10% B, 6.50 min=20% B, 17.0-19.75 min=100% B, 19.75.00-23.00 min=90% B) to obtain the product after removal of the solvents in vacuo. The obtained amount was 44.0 mg (91% purity, 21% of theory).

LC-MS (Method 1B): $R_t$=1.11 min; MS (ESIpos): m/z=533 [M+H]$^+$

Example 378A

Tert-butyl 4-{2-methyl-3-[3-(4-methylphenyl)-1,2,4-oxadiazol-5-yl]-5-oxo-4,5-dihydropyrazolo[1,5-a]pyrimidin-7-yl}piperidine-1-carboxylate

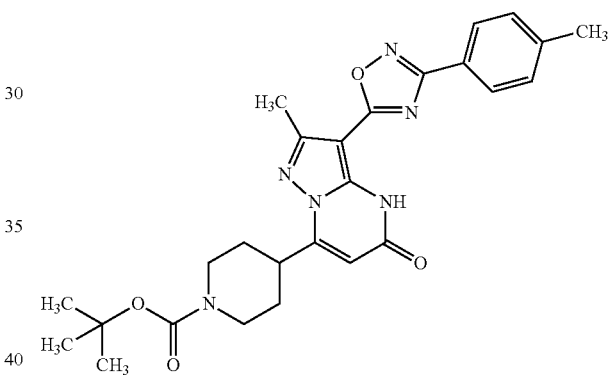

7-[1-(tert-butoxycarbonyl)piperidin-4-yl]-2-methyl-5-oxo-4,5-dihydropyrazolo[1,5-a]pyrimidine-3-carboxylic acid (150 mg, 398 µmol) was dissolved in N,N-Dimethylformamid (2 ml) and treated with N,N-Diisopropylethylamine (210 µl, 1.2 mmol) and 1,1'-Carboyldiimidazol (129 mg, 797 µmol). The mixture was stirred at 90° C. for 1.5 h N'-hydroxy-4-methylbenzenecarboximidamide (120 mg, 797 µmol) was dissolved in N,N-Dimethylformamid (1 ml) and added dropwise. The mixture was then stirred at 110° C. for 6 h. The mixture was purified via reverse phase HPLC (Method: column: Reprosil C18; 10 µm; 125×30 mm/flow: 50 ml/min/solvents: A=water (0.01% formic acid), B=acetonitrile/gradient: 0.00-5.00 min=10% B, 6.50 min=20% B, 17.0-19.75 min=100% B, 19.75.00-23.00 min=90% B) to afford the product. The obtained amount was 68.5 mg (100% purity, 35% of theory).

LC-MS (Method 11B): $R_t$=2.51 min; MS (ESIneg): m/z=489 [M−H]$^-$

Example 379A

Tert-butyl 4-{3-[4-(1,3-difluoro-2-methylpropan-2-yl)-1,3-thiazol-2-yl]-5-oxo-4,5-dihydropyrazolo[1,5-a]pyrimidin-7-yl}piperidine-1-carboxylate

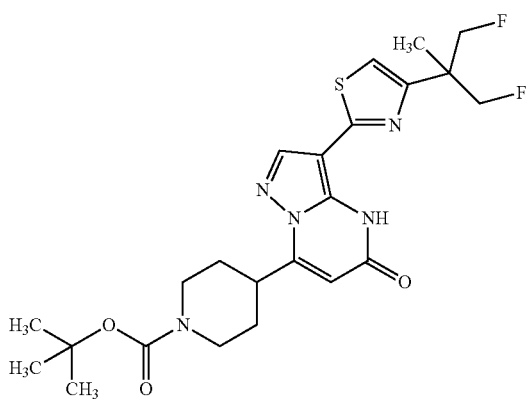 [SMILES: CC(C)(C)OC(=O)N1CCC(c2cc(=O)[nH]c3c(-c4nc(C(C)(CF)CF)cs4)cnn23)CC1]

tert-butyl 4-(3-carbamothioyl-5-oxo-4,5-dihydropyrazolo[1,5-a]pyrimidin-7-yl)piperidine-1-carboxylate (125 mg, 331 µmol), 1-bromo-4-fluoro-3-(fluoromethyl)-3-methylbutan-2-one (71.2 mg, 331 µmol) and N,N-Diisopropylethylamine (290 µl, 1.7 mmol) were dissolved in Ethanol (5.0 ml, 86 mmol) and stirred at 70° C. for 1 h and left standing for 3 d at RT. The mixture was purified via reverse phase HPLC (Method: column: Reprosil C18; 10 µm; 125×30 mm/flow: 50 ml/min/solvents: A=water (0.1% formic acid), B=acetonitrile/gradient: 0.00-4.25 min=20% B, 4.50 min=30% B, 19.00-22.50 min=100% B, 22.75-25.00 min=20% B) to afford the product. The obtained amount was 36.0 mg (100% purity, 22% of theory).

LC-MS (Method 11B): $R_t$=2.22 min; MS (ESIpos): m/z=494 [M+H]$^+$

Example 380A

Tert-butyl 4-[3-(4-ethyl-1,3-thiazol-2-yl)-5-oxo-4,5-dihydropyrazolo[1,5-a]pyrimidin-7-yl]piperidine-1-carboxylate

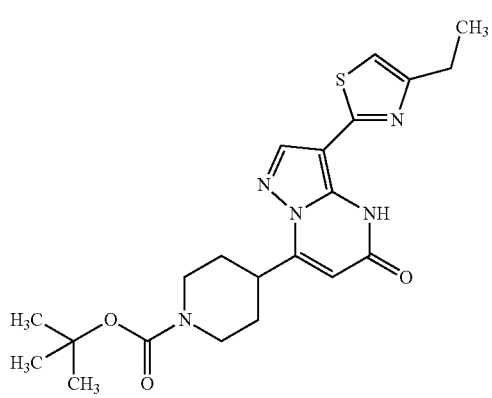 [SMILES: CCc1csc(-c2cnn3c(C4CCN(C(=O)OC(C)(C)C)CC4)cc(=O)[nH]c23)n1]

tert-butyl 4-(3-carbamothioyl-5-oxo-4,5-dihydropyrazolo[1,5-a]pyrimidin-7-yl)piperidine-1-carboxylate (120 mg, 318 µmol), 1-bromobutan-2-one (32 µl, 320 µmol) and N,N-Diisopropylethylamine (280 µl, 1.6 mmol) were dissolved in Ethanol (4.8 ml, 82 mmol) and stirred at 70° C. for 1 h and left standing for 3 d at RT. The mixture was purified via reverse phase HPLC (Method: column: Reprosil C18; 10 µm; 125×30 mm/flow: 50 ml/min/solvents: A=water (0.1% formic acid), B=acetonitrile/gradient: 0.00-4.25 min=20% B, 4.50 min=30% B, 19.00-22.50 min=100% B, 22.75-25.00 min=20% B) to afford the product. The obtained amount was 57.1 mg (100% purity, 42% of theory).

LC-MS (Method 11B): $R_t$=2.25 min; MS (ESIpos): m/z=430 [M+H]$^+$

Example 381A

Tert-butyl 4-{3-[4-(4-methylphenyl)-1,3-thiazol-2-yl]-5-oxo-4,5-dihydropyrazolo[1,5-a]pyrimidin-7-yl}piperidine-1-carboxylate

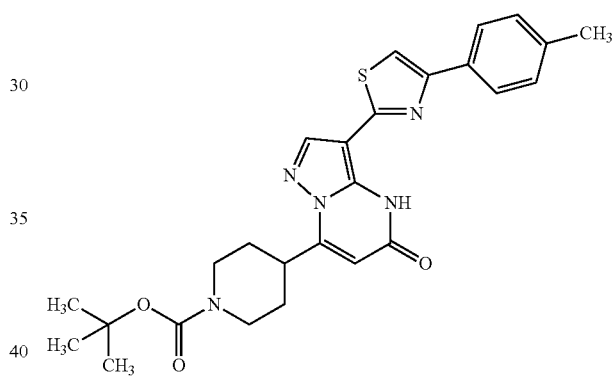

tert-butyl 4-(3-carbamothioyl-5-oxo-4,5-dihydropyrazolo[1,5-a]pyrimidin-7-yl)piperidine-1-carboxylate (120 mg, 318 µmol), 2-bromo-1-(4-methylphenyl)ethanone (67.7 mg, 318 µmol) and N,N-Diisopropylethylamine (280 µl, 1.6 mmol) were dissolved in Ethanol (4.8 ml, 82 mmol) and stirred at 70° C. for 1 h and left standing for 3 d at RT. The mixture was purified via reverse phase HPLC (Method: column: Reprosil C18; 10 µm; 125×30 mm/flow: 50 ml/min/solvents: A=water (0.1% formic acid), B=acetonitrile/gradient: 0.00-4.25 min=20% B, 4.50 min=30% B, 19.00-22.50 min=100% B, 22.75-25.00 min=20% B) to afford the product. The obtained amount was 62.2 mg (100% purity, 40% of theory).

LC-MS (Method 11B): $R_t$=2.51 min; MS (ESIpos): m/z=492 [M+H]$^+$

Example 382A

Tert-butyl 4-{5-oxo-3-[4-(propan-2-yl)-1,3-thiazol-2-yl]-4,5-dihydropyrazolo[1,5-a]pyrimidin-7-yl}piperidine-1-carboxylate

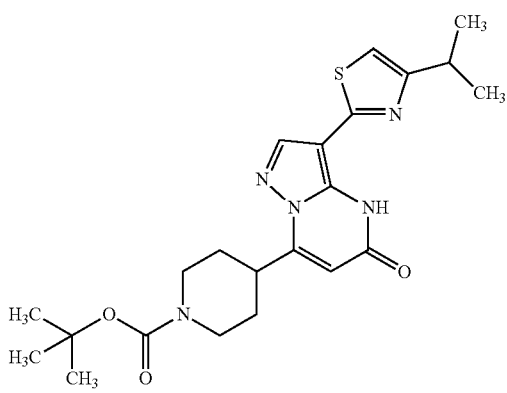 [SMILES: CC(C)c1csc(-c2cnn3c(C4CCN(C(=O)OC(C)(C)C)CC4)cc(=O)[nH]c23)n1]

tert-butyl 4-(3-carbamothioyl-5-oxo-4,5-dihydropyrazolo[1,5-a]pyrimidin-7-yl)piperidine-1-carboxylate (120 mg, 318 µmol), 1-bromo-3-methylbutan-2-one (52.5 mg, 318 µmol) and N,N-Diisopropylethylamine (280 µl, 1.6 mmol) were dissolved in Ethanol (4.8 ml, 82 mmol) and stirred at 70° C. for 1 h and left standing for 3 d at RT. The mixture was purified via reverse phase HPLC (Method: column: Reprosil C18; 10 µm; 125×30 mm/flow: 50 ml/min/solvents: A=water (0.1% formic acid), B=acetonitrile/gradient: 0.00-4.25 min=20% B, 4.50 min=30% B, 19.00-22.50 min=100% B, 22.75-25.00 min=20% B) to afford the product. The obtained amount was 56.4 mg (100% purity, 40% of theory).

LC-MS (Method 11B): $R_t$=2.41 min; MS (ESIpos): m/z=444 [M+H]$^+$

Example 383A

Tert-butyl 4-[3-(4-cyclopropyl-1,3-thiazol-2-yl)-5-oxo-4,5-dihydropyrazolo[1,5-a]pyrimidin-7-yl]piperidine-1-carboxylate

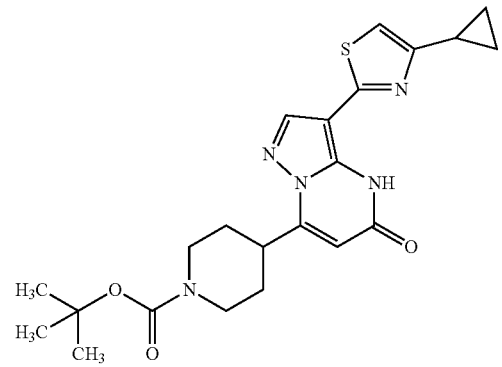 [SMILES: CC(C)(C)OC(=O)N1CCC(c2cc(=O)[nH]c3c(-c4nc(C5CC5)cs4)cnn23)CC1]

tert-butyl 4-(3-carbamothioyl-5-oxo-4,5-dihydropyrazolo[1,5-a]pyrimidin-7-yl)piperidine-1-carboxylate (120 mg, 318 µmol), 2-bromo-1-cyclopropylethanone (51.8 mg, 318 µmol) and N,N-Diisopropylethylamine (280 µl, 1.6 mmol) were dissolved in Ethanol (4.8 ml, 82 mmol) and stirred at 70° C. for 1 h and left standing for 3 d at RT. The mixture was purified via reverse phase HPLC (Method: column: Reprosil C18; 10 µm; 125×30 mm/flow: 50 ml/min/solvents: A=water (0.1% formic acid), B=acetonitrile/gradient: 0.00-4.25 min=20% B, 4.50 min=30% B, 19.00-22.50 min=100% B, 22.75-25.00 min=20% B) to afford the product. The obtained amount was 57.1 mg (100% purity, 41% of theory).

LC-MS (Method 11B): $R_t$=2.28 min; MS (ESIpos): m/z=442 [M+H]$^+$

Example 384A

Tert-butyl 4-{3-[4-(2,4-dimethylphenyl)-1,3-thiazol-2-yl]-5-oxo-4,5-dihydropyrazolo[1,5-a]pyrimidin-7-yl}piperidine-1-carboxylate

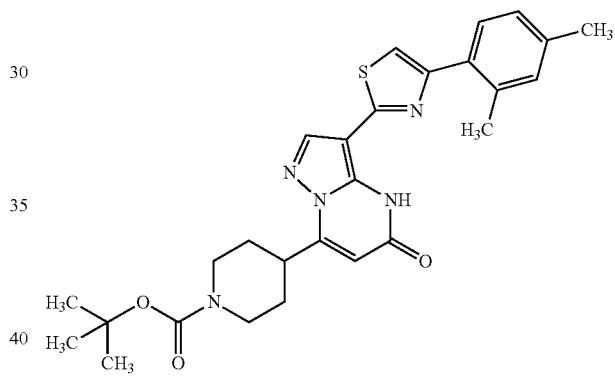

tert-butyl 4-(3-carbamothioyl-5-oxo-4,5-dihydropyrazolo[1,5-a]pyrimidin-7-yl)piperidine-1-carboxylate (120 mg, 318 µmol), 2-bromo-1-(2,4-dimethylphenyl)ethanone (72.2 mg, 318 µmol) and N,N-Diisopropylethylamine (280 µl, 1.6 mmol) were dissolved in Ethanol (4.8 ml, 82 mmol) and stirred at 70° C. for 1 h and left standing for 3 d at RT. The mixture was purified via reverse phase HPLC (Method: column: Reprosil C18; 10 µm; 125×30 mm/flow: 50 ml/min/solvents: A=water (0.1% formic acid), B=acetonitrile/gradient: 0.00-4.25 min=20% B, 4.50 min=30% B, 19.00-22.50 min=100% B, 22.75-25.00 min=20% B) to afford the product. The obtained amount was 52.2 mg (100% purity, 32% of theory).

LC-MS (Method 1B): $R_t$=1.41 min; MS (ESIpos): m/z=506 [M+H]$^+$

Example 385A

Tert-butyl 4-(3-{5-[1-(4-chlorophenyl)cyclopropyl]-1,3,4-oxadiazol-2-yl}-5-oxo-4,5-dihydropyrazolo[1,5-a]pyrimidin-7-yl)piperidine-1-carboxylate

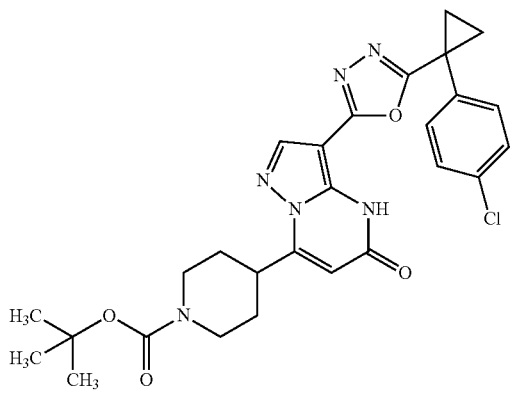 [SMILES: CC(C)(C)OC(=O)N1CCC(c2cc(=O)[nH]c3c(-c4nnc(C5(c6ccc(Cl)cc6)CC5)o4)cnn23)CC1]

tert-butyl 4-{3-[(2-{[1-(4-chlorophenyl)cyclopropyl]carbonyl}hydrazinyl)carbonyl]-5-oxo-4,5-dihydropyrazolo[1,5-a]pyrimidin-7-yl}piperidine-1-carboxylate (77.9 mg, 140 μmol) was dissolved in THF (2.0 ml) and stirred with Burgess-Reagent (46.8 mg, 196 μmol) for 16 h at RT. 1 ml of water was added, the resulting residue was filtered, washed with water and dried in vacuo to afford the product.

The obtained amount was 56 mg (100% purity, 74% of theory).

LC-MS (Method 1B): $R_t$=1.23 min; MS (ESIpos): m/z=537 [M+H]$^+$

1H-NMR (400 MHz, DMSO-d6) delta [ppm]: 1.416 (16.00), 1.477 (0.42), 1.490 (1.23), 1.496 (1.20), 1.507 (0.56), 1.523 (0.18), 1.544 (0.41), 1.554 (0.41), 1.575 (0.46), 1.585 (0.39), 1.606 (0.17), 1.617 (0.14), 1.750 (0.45), 1.761 (1.10), 1.766 (1.05), 1.779 (0.37), 1.970 (0.54), 2.001 (0.46), 2.871 (0.20), 3.379 (0.13), 3.407 (0.23), 3.438 (0.12), 4.079 (0.34), 4.111 (0.32), 6.132 (0.17), 7.412 (0.54), 7.417 (0.29), 7.434 (2.70), 7.446 (2.56), 7.461 (0.28), 7.468 (0.53), 8.315 (0.47), 12.000 (0.10).

Example 386A

Tert-butyl (4-[(2,2-dimethyl-4,6-dioxo-1,3-dioxan-5-yl)carbonyl]-2-(2,2-dimethylpropyl)piperidine-1-carboxylate

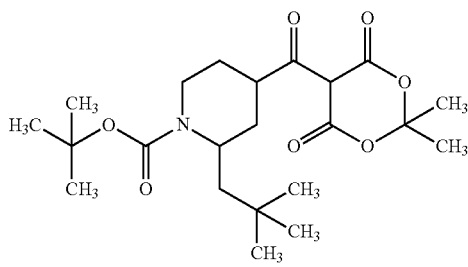 [SMILES: CC(C)(C)CC1CC(C(=O)C2C(=O)OC(C)(C)OC2=O)CCN1C(=O)OC(C)(C)C]

To a solution of 1-(tert-butoxycarbonyl)-2-(2,2-dimethylpropyl)piperidine-4-carboxylic acid (4.71 g, 15.7 mmol) and 2,2-dimethyl-1,3-dioxane-4,6-dione (2.50 g, 17.3 mmol) in dichloromethane (120 ml, 1.9 mol) was added 4-dimethylaminopyridin (2.88 g, 23.6 mmol). After cooling the mixture at 0° C., 1-(3-dimethylaminopropyl)-3-ethylcarbodiimide hydrochloride (4.22 g, 22.0 mmol) was added in portions and then the reaction mixture was stirred at RT for 16 h. The mixture was treated with water and then the layers were separated. The organic layer was washed with aqueous citric acid solution and the solvents were removed. The crude product was purified via reverse phase HPLC (Method: column: Reprosil C18; 10 μm; 125×30 mm/Flow: 50 ml/min/solvent: A=H2O (0.01% HCOOH), B=Acetonitril/gradient: 0.00-5.00 min=10% B, 6.50 min=20% B, 17.0-19.75 min=100% B, 19.75.00-23.00 min=90% B) to afford the title compound 3.87 g (94% purity, 54% of theory).

LC-MS (Method 11B): $R_t$=2.65 min; MS (ESIneg): m/z=424 [M−H]$^−$

1H-NMR (400 MHz, DMSO-d6) delta [ppm]: 0.000 (0.77), 0.865 (6.91), 0.869 (9.55), 0.882 (1.52), 0.897 (11.52), 0.907 (2.87), 1.398 (16.00), 1.415 (11.86), 1.687 (6.85), 2.086 (0.66), 2.148 (1.82), 2.300 (1.76), 3.577 (1.08), 3.582 (1.09).

Example 387A

Ethyl 7-[1-(tert-butoxycarbonyl)-2-(2,2-dimethylpropyl)piperidin-4-yl]-5-oxo-4,5-dihydropyrazolo[1,5-a]pyrimidine-3-carboxylate

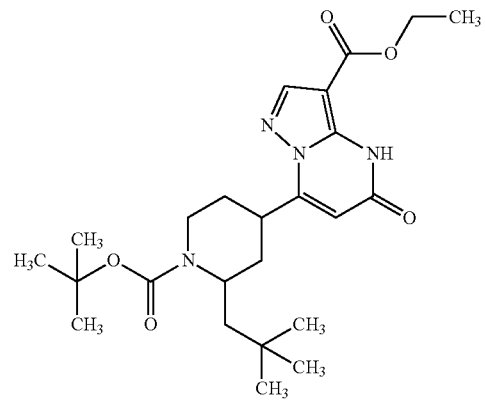 [SMILES: CCOC(=O)c1cnn2c(C3CCN(C(=O)OC(C)(C)C)C(CC(C)(C)C)C3)cc(=O)[nH]c12]

ethyl 3-amino-1H-pyrazole-4-carboxylate (117 mg, 752 μmol) and tert-butyl-4-[(2,2-dimethyl-4,6-dioxo-1,3-dioxan-5-yl)carbonyl]-2-(2,2-dimethylpropyl)piperidine-1-carboxylate (352 mg, 827 μmol) were heated in Acetonitrile (10 ml, 94 mmol) at 60° C. for 3 h. The solvents were removed and the residue dissolved in 1-Methoxy-2-propanol (10 ml, 100 mmol). Potassium triphosphat (319 mg, 1.50 mmol) was added and the mixture was heated at 100° C. for 2 h. The solvents were removed and the residue partitioned between aqueous citric acid solution (10%) and ethyl acetate. The aqueous solution was extracted two times with ethyl acetate. The organic phase was extracted with water and brine. The organic phase was treated with sodium sulfate, filtered and dried in vacuo. The residue was purified via reverse phase HPLC (Method: column: Reprosil C18; 10 μm; 125×30 mm/Flow: 50 ml/min/solvent: A=H2O (0.01% HCOOH), B=Acetonitril/gradient: 0.00-4.25 min=10% B, 4.50 min=20% B, 15.50 min=85% B, 16.00-18.50 min=100% B, 18.75.00-22.00 min=20% B) to afford the product. The obtained amount was 183 mg (95% purity, 50% of theory).

LC-MS (Method 6B): $R_t$=4.35 min; MS (ESIneg): m/z=459 [M−H]⁻

1H-NMR (400 MHz, DMSO-d6) delta [ppm]: −0.008 (1.46), 0.918 (1.81), 0.940 (2.18), 1.249 (0.81), 1.265 (0.86), 1.279 (0.74), 1.408 (2.02), 1.428 (2.62), 3.285 (1.28), 3.293 (2.58), 3.309 (16.00).

Example 388A

7-[(2S,4R)-1-(tert-butoxycarbonyl)-2-(2,2-dimethyl-propyl)piperidin-4-yl]-5-oxo-4,5-dihydropyrazolo[1,5-a]pyrimidine-3-carboxylic Acid

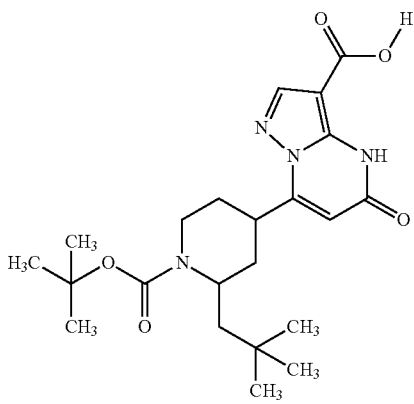 [SMILES: CC(C)(C)CC1CC(c2cc(=O)[nH]c3c(C(=O)O)cnn23)CCN1C(=O)OC(C)(C)C]

ethyl 7-[1-(tert-butoxycarbonyl)-2-(2,2-dimethylpropyl)piperidin-4-yl]-5-oxo-4,5-dihydropyrazolo[1,5-a]pyrimidine-3-carboxylate (183 mg, 397 µmol) and aqueous Lithium hydroxide-solution (790 µl, 1.0 M, 790 µmol) was stirred in THF (5.0 ml, 62 mmol) for 2 h at RT. Aqueous Lithium hydroxide-solution (1.0 M, 2 equivalents) was added and the mixture was stirred for 18 h at 70° C. Saturated ammonium chloride solution and ethyl acetate were added. The aqueous phase was extracted three times with ethyl acetate. The combined organic phases were washed with water, brine, dried with sodium sulfate and in vacuo to afford the product. The obtained amount was 165 mg (100% purity, 96% of theory).

LC-MS (Method 1B): $R_t$=1.13 min; MS (ESIneg): m/z=431 [M−H]⁻

1H-NMR (400 MHz, DMSO-d6) delta [ppm]: −0.008 (13.56), 0.008 (10.95), 0.895 (3.35), 0.918 (11.46), 0.940 (13.50), 1.169 (2.44), 1.408 (12.43), 1.428 (16.00), 2.366 (2.44), 2.709 (2.38), 3.369 (11.63).

Example 389A

Propan-2-yl 7-[1-(tert-butoxycarbonyl)piperidin-4-yl]-5-oxo-4,5-dihydropyrazolo[1,5-a]pyrimidine-3-carboxylate

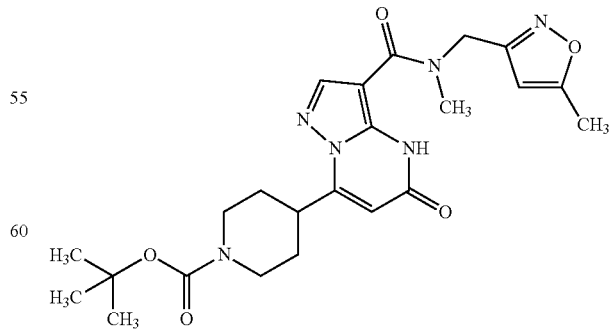

7-[1-(tert-butoxycarbonyl)piperidin-4-yl]-5-oxo-4,5-dihydropyrazolo[1,5-a]pyrimidine-3-carboxylic acid (200 mg, 552 µmol) was dissolved in tetrahydrofurane (5.0 ml, 62 mmol) and N,N'-Carbonyldiimidazole (179 mg, 1.10 mmol) was added. The mixture was heated at reflux for 1.5 h. After cooling to RT, propan-2-ol (420 µl, 5.5 mmol) and sodium hydride (60% dispersion in mineral oil) (24.3 mg, 60% purity, 607 µmol) were added and the mixture stirred at RT for 18 h. Solvents were removed and propan-2-ol (5 ml) were added. The mixture was heated at reflux for 18 h and then purified by preparative HPLC (Method: column: Reprosil C18; 10 µm; 125×30 mm/flow: 50 ml/min/solvents: A=water (0.01% formic acid), B=acetonitrile/gradient: 0.00-5.00 min=10% B, 6.50 min=20% B, 17.0-19.75 min=100% B, 19.75.00-23.00 min=90% B). Evaporation of the combined product fractions yielded the title compound (132 mg, 100% purity, 59% of theory)

LC-MS (Method 10B): $R_t$=1.90 min; MS (ESIneg): m/z=403 [M−H]⁻

Example 390A

Tert-butyl 4-(3-{methyl[(5-methyl-1,2-oxazol-3-yl)methyl]carbamoyl}-5-oxo-4,5-dihydropyrazolo[1,5-a]pyrimidin-7-yl)piperidine-1-carboxylate To a solution of 7-[1-(tert-butoxycarbonyl)piperidin-4-yl]-5-oxo-4,5-dihydropyrazolo[1,5-a]pyrimidine-3-carboxylic acid (150 mg, 414 µmol) in dimethylformamide (1.5 ml, 19 mmol) were added HATU (205 mg, 538 µmol) and N,N-Diisopropylethylamine (220 µl, 1.2 mmol). Then N-methyl-1-(5-methyl-1,2-oxazol-3-yl)methanamine (104 mg, 828 µmol) was added and the reaction mixture was stirred at RT for 16 h. More HATU (1.3 equivalents) was added and the reaction mixture was stirred at RT for 2 h. Water was added and purified by preparative HPLC (Method: column: Reprosil C18; 10 µm; 125×30 mm/flow: 50 ml/min/solvents: A=water (0.01% formic acid), B=acetonitrile/gradient: 0.00-2.00 min=20% B, 2.20 min=60% B, 8.00-12.00 min=90% B, 12.10-13.00 min=20% B). Evaporation of the combined product fractions yielded the title compound (82.8 mg, 100% purity, 43% of theory).

LC-MS (Method 1B): $R_t$=0.95 min; MS (ESIpos): m/z=471 [M+H]$^+$

Example 391A

Tert-butyl 4-[3-(ethylcarbamoyl)-2-methyl-5-oxo-4,5-dihydropyrazolo[1,5-a]pyrimidin-7-yl]piperidine-1-carboxylate

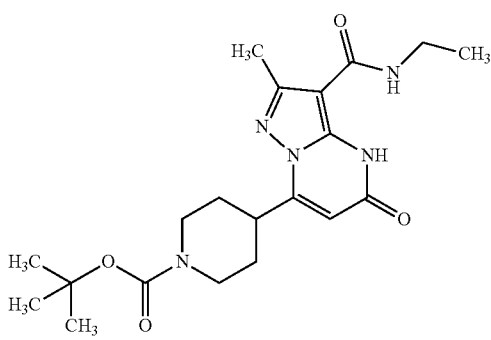 [SMILES: CCNC(=O)c1c(C)nn2c(C3CCN(C(=O)OC(C)(C)C)CC3)cc(=O)[nH]c12]

To a solution of 7-[1-(tert-butoxycarbonyl)piperidin-4-yl]-2-methyl-5-oxo-4,5-dihydropyrazolo[1,5-a]pyrimidine-3-carboxylic acid (150 mg, 398 µmol) in dimethylformamide (1.5 ml, 19 mmol) were added COMU (256 mg, 598 µmol) and N,N-Diisopropylethylamine (420 µl, 2.4 mmol). Then ethanamine hydrochloride (1:1) (130 mg, 1.59 mmol) was added and the reaction mixture was stirred at RT for 16 h. More COMU (1.5 equivalents) was added and the reaction mixture was stirred at RT for 18 h. Water was added and purified by preparative HPLC (Method: column: Reprosil C18; 10 µm; 125×30 mm/flow: 50 ml/min/solvents: A=water (0.01% formic acid), B=acetonitrile/gradient: 0.00-2.00 min=20% B, 2.20 min=60% B, 8.00-12.00 min=90% B, 12.10-13.00 min=20% B). Evaporation of the combined product fractions yielded the title compound (108 mg, 98% purity, 66% of theory).

LC-MS (Method 11B): $R_t$=1.60 min; MS (ESIneg): m/z=402 [M−H]$^-$

Example 392A

Tert-butyl 4-{3-[methyl(pyridin-3-ylmethyl)carbamoyl]-5-oxo-4,5-dihydropyrazolo[1,5-a]pyrimidin-7-yl}piperidine-1-carboxylate

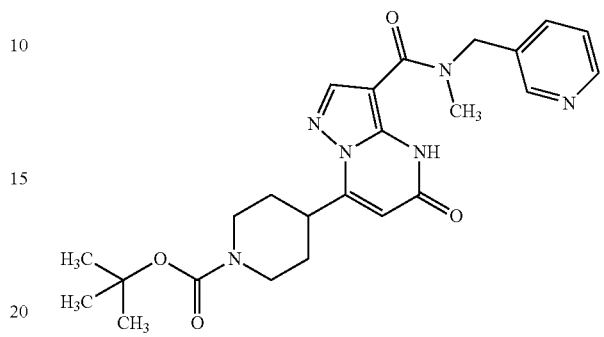

To a solution of 7-[1-(tert-butoxycarbonyl)piperidin-4-yl]-5-oxo-4,5-dihydropyrazolo[1,5-a]pyrimidine-3-carboxylic acid (150 mg, 414 µmol) in dimethylformamide (1.5 ml, 19 mmol) were added HATU (205 mg, 538 µmol) and N,N-Diisopropylethylamine (220 µl, 1.2 mmol). Then N-methyl-1-(pyridin-3-yl)methanamine (101 mg, 828 µmol) was added and the reaction mixture was stirred at RT for 16 h. More HATU (1.3 equivalents) was added and the reaction mixture was stirred at RT for 2 h. Water was added and purified by preparative HPLC (Method: column: Reprosil C18; 10 µm; 125×30 mm/flow: 50 ml/min/solvents: A=water (0.01% formic acid), B=acetonitrile/gradient: 0.00-2.00 min=20% B, 2.20 min=60% B, 8.00-12.00 min=90% B, 12.10-13.00 min=20% B). Evaporation of the combined product fractions yielded the title compound (49.6 mg, 100% purity, 26% of theory).

LC-MS (Method 1B): $R_t$=0.75 min; MS (ESIpos): m/z=467 [M+H]$^+$

Example 393A

Tert-butyl 4-[3-(dimethylcarbamoyl)-2-methyl-5-oxo-4,5-dihydropyrazolo[1,5-a]pyrimidin-7-yl]piperidine-1-carboxylate

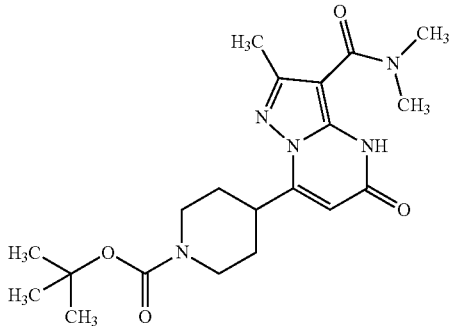 [SMILES: Cc1nn2c(C3CCN(C(=O)OC(C)(C)C)CC3)cc(=O)[nH]c2c1C(=O)N(C)C]

To a solution of 7-[1-(tert-butoxycarbonyl)piperidin-4-yl]-2-methyl-5-oxo-4,5-dihydropyrazolo[1,5-a]pyrimidine-3-carboxylic acid (150 mg, 398 µmol) were added HATU (197 mg, 518 µmol) and N,N-Diisopropylethylamine (280

μl, 1.6 mmol). Then N-methylmethanamine hydrochloride (1:1) (65.0 mg, 797 μmol) was added and the reaction mixture was stirred at RT for 16 h. More HATU (1.3 equivalents) was added and the reaction mixture was stirred at RT for 20 h. Water was added and purified by preparative HPLC (Method: column: Reprosil C18; 10 μm; 125×30 mm/flow: 50 ml/min/solvents: A=water (0.01% formic acid), B=acetonitrile/gradient: 0.00-2.00 min=20% B, 2.20 min=60% B, 8.00-12.00 min=90% B, 12.10-13.00 min=20% B). Evaporation of the combined product fractions yielded the title compound (108 mg, 85% purity, 57% of theory).

LC-MS (Method 11B): R$_t$=1.38 min; MS (ESIpos): m/z=404 [M+H]$^+$

Example 394A

Tert-butyl 4-(3-{[(3R)-3-hydroxypyrrolidin-1-yl]carbonyl}-5-oxo-4,5-dihydropyrazolo[1,5-a]pyrimidin-7-yl)piperidine-1-carboxylate

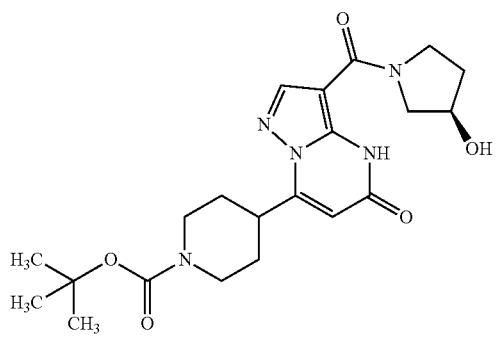 [SMILES: CC(C)(C)OC(=O)N1CCC(c2cc(=O)[nH]c3c(C(=O)N4CC[C@@H](O)C4)cnn23)CC1]

To a solution of 7-[1-(tert-butoxycarbonyl)piperidin-4-yl]-5-oxo-4,5-dihydropyrazolo[1,5-a]pyrimidine-3-carboxylic acid (150 mg, 414 μmol) in dimethylformamide (1.5 ml, 19 mmol) were added HATU (205 mg, 538 μmol) and N,N-Diisopropylethylamine (290 μl, 1.7 mmol). Then (3R)-pyrrolidin-3-ol hydrochloride (1:1) (102 mg, 828 μmol) was added and the reaction mixture was stirred at RT for 16 h. More HATU (1.3 equivalents) was added and the reaction mixture was stirred at RT for 20 h. Water was added and purified by preparative HPLC (Method: column: Reprosil C18; 10 μm; 125×30 mm/flow: 50 ml/min/solvents: A=water (0.01% formic acid), B=acetonitrile/gradient: 0.00-2.00 min=20% B, 2.20 min=60% B, 8.00-12.00 min=90% B, 12.10-13.00 min=20% B). Evaporation of the combined product fractions yielded the title compound (90.2 mg, 100% purity, 51% of theory).

LC-MS (Method 11B): R$_t$=1.30 min; MS (ESIpos): m/z=432 [M+H]$^+$

Example 395A

Tert-butyl 4-(3-{[(3R)-3-methylpyrrolidin-1-yl]carbonyl}-5-oxo-4,5-dihydropyrazolo[1,5-a]pyrimidin-7-yl)piperidine-1-carboxylate

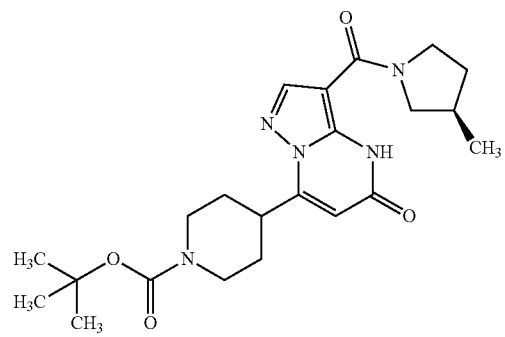 [SMILES: C[C@@H]1CCN(C(=O)c2cnn3c(C4CCN(C(=O)OC(C)(C)C)CC4)cc(=O)[nH]c23)C1]

To a solution of 7-[1-(tert-butoxycarbonyl)piperidin-4-yl]-5-oxo-4,5-dihydropyrazolo[1,5-a]pyrimidine-3-carboxylic acid (150 mg, 414 μmol) in dimethylformamide (1.5 ml, 19 mmol) were added HATU (205 mg, 538 μmol) and N,N-Diisopropylethylamine (290 μl, 1.7 mmol). Then (3R)-3-methylpyrrolidine hydrochloride (1:1) (101 mg, 828 μmol) was added and the reaction mixture was stirred at RT for 16 h. More HATU (1.3 equivalents) was added and the reaction mixture was stirred at RT for 20 h. Water was added and purified by preparative HPLC (Method: column: Reprosil C18; 10 μm; 125×30 mm/flow: 50 ml/min/solvents: A=water (0.01% formic acid), B=acetonitrile/gradient: 0.00-2.00 min=20% B, 2.20 min=60% B, 8.00-12.00 min=90% B, 12.10-13.00 min=20% B). Evaporation of the combined product fractions yielded the title compound (129 mg, 93% purity, 67% of theory).

LC-MS (Method 11B): R$_t$=1.80 min; MS (ESIpos): m/z=430 [M+H]$^+$

Example 396A

Tert-butyl 4-[5-oxo-3-(pyrrolidin-1-ylcarbonyl)-4,5-dihydropyrazolo[1,5-a]pyrimidin-7-yl]piperidine-1-carboxylate

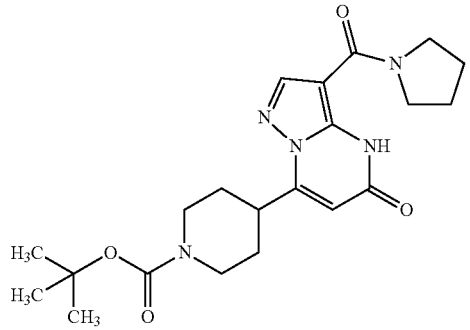 [SMILES: CC(C)(C)OC(=O)N1CCC(c2cc(=O)[nH]c3c(C(=O)N4CCCC4)cnn23)CC1]

To a solution of 7-[1-(tert-butoxycarbonyl)piperidin-4-yl]-5-oxo-4,5-dihydropyrazolo[1,5-a]pyrimidine-3-carboxylic acid (100 mg, 276 μmol) in dimethylformamide (1.5 ml, 19 mmol) were added HATU (136 mg, 359 μmol) and N,N-Diisopropylethylamine (140 µl, 830 µmol). Then pyrrolidine (39.3 mg, 552 µmol) was added and the reaction mixture was stirred at RT for 16 h. More HATU (1.3 equivalents) was added and the reaction mixture was stirred at RT for 20 h. The mixture was purified by preparative HPLC (Method: column: Reprosil C18; 10 µm; 125×30 mm/flow: 50 ml/min/solvents: A=water (0.01% formic acid), B=acetonitrile/gradient: 0.00-5.00 min=10% B, 6.50 min=20% B, 17.0-19.75 min=100% B, 19.75.00-23.00 min=90%). Evaporation of the combined product fractions yielded the title compound (31.1 mg, 100% purity, 27% of theory).

LC-MS (Method 10B): $R_t$=1.62 min; MS (ESIneg): m/z=414 [M−H]⁻

Example 397A

7-[1-(tert-butoxycarbonyl)piperidin-4-yl]-2-methyl-5-oxo-4,5-dihydropyrazolo[1,5-a]pyrimidine-3-carboxylic Acid

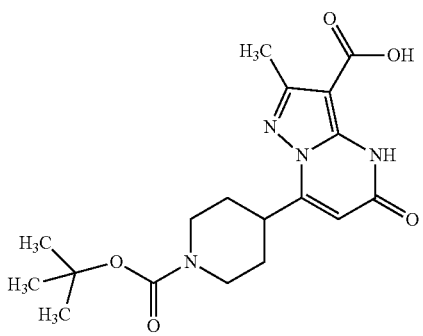 [SMILES: Cc1nn2c(C3CCN(C(=O)OC(C)(C)C)CC3)cc(=O)[nH]c2c1C(=O)O]

ethyl 7-[1-(tert-butoxycarbonyl)piperidin-4-yl]-2-methyl-5-oxo-4,5-dihydropyrazolo[1,5-a]pyrimidine-3-carboxylate (6.94 g, 17.2 mmol) was dissolved in tetrahydrofurane (30 ml, 370 mmol) and potassium hydroxide solution (30 ml, 2.0 M in water, 60 mmol) and stirred for 16 h at 65° C. Lithium hydroxide (1.23 g, 51.5 mmol) was added and the mixture was and stirred for 20 h at 65° C. Acetonitrile was added and the resulting precipitate was filtered, washed with acetonitrile and dried in vacuo. The residue was treated with water and slowly with aqueous hydrochloric acid solution until a pH value of 3 was reached. The aqueous phase was extracted several times with ethyl acetate. The combined organic phases were dried with sodium sulfate and in vacuo to yield a precipitate. This was suspended in Acetonitrile, filtered, washed with acetonitrile and dried in vacuo to afford the desired product (4.28 g, 97% purity, 65% of theory).

LC-MS (Method 11B): $R_t$=1.48 min; MS (ESIneg): m/z=375 [M−H]⁻

Example 398A

Tert-butyl 4-{3-[(3,3-dimethylpyrrolidin-1-yl)methyl]-5-oxo-4,5-dihydropyrazolo[1,5-a]pyrimidin-7-yl}piperidine-1-carboxylate

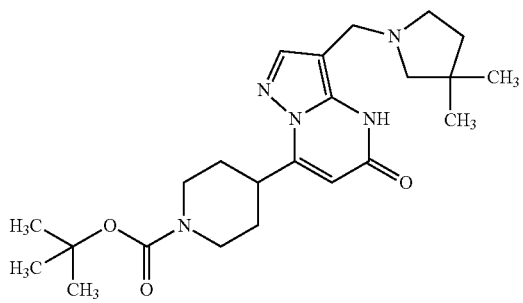 [SMILES: CC1(C)CCN(Cc2cnn3c(C4CCN(C(=O)OC(C)(C)C)CC4)cc(=O)[nH]c23)C1]

tert-butyl 4-[3-(hydroxymethyl)-5-oxo-4,5-dihydropyrazolo[1,5-a]pyrimidin-7-yl]piperidine-1-carboxylate (150 mg, 431 µmol) and Triphenylphosphine (430 µl, 1.0 M, 430 µmol) were dissolved in Tetrahydrofuran (5.0 ml, 62 mmol) and cooled to −18° C. N-Bromsuccinimide (76.6 mg, 431 µmol) was added and the mixture was stirred for 5 min at −18° C. 3,3-dimethylpyrrolidine (102 mg, 1.03 mmol) was added and stirred for 10 min at RT and then for 1 h at 80° C. Water was added and purified by preparative HPLC (Method: column: Reprosil C18; 10 µm; 125×30 mm/flow: 50 ml/min/solvents: A=water (0.01% formic acid), B=acetonitrile/gradient: 0.00-5.00 min=10% B, 6.50 min=20% B, 17.0-19.75 min=100% B, 19.75.00-23.00 min=90% B). Evaporation of the combined product fractions yielded the title compound (68.1 mg, 100% purity, 37% of theory).

LC-MS (Method 10B): $R_t$=0.66 min; MS (ESIpos): m/z=430 [M+H]⁺

Example 399A

Tert-butyl 4-(3-{[(2R)-2-methylpyrrolidin-1-yl]carbonyl}-5-oxo-4,5-dihydropyrazolo[1,5-a]pyrimidin-7-yl)piperidine-1-carboxylate

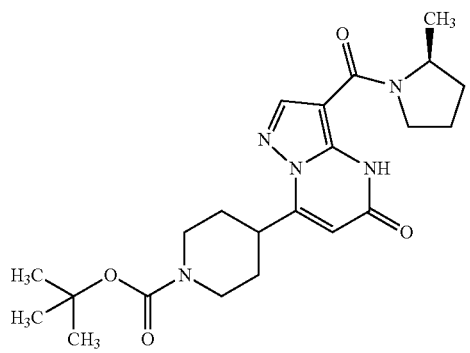 [SMILES: C[C@H]1CCCN1C(=O)c1cnn2c(C3CCN(C(=O)OC(C)(C)C)CC3)cc(=O)[nH]c12]

To a solution of 7-[1-(tert-butoxycarbonyl)piperidin-4-yl]-5-oxo-4,5-dihydropyrazolo[1,5-a]pyrimidine-3-carboxylic acid (100 mg, 276 µmol) in dimethylformamide (1.0 ml, 13 mmol) were added HATU (136 mg, 359 µmol) and N,N-Diisopropylethylamine (140 µl, 830 µmol). Then (2R)-

2-methylpyrrolidine (47.0 mg, 552 µmol) was added and the reaction mixture was stirred at RT for 16 h. More HATU (1.3 equivalents) was added and the reaction mixture was stirred at RT for 20 h. Water was added and purified by preparative HPLC (Method: column: Reprosil C18; 10 µm; 125×30 mm/flow: 50 ml/min/solvents: A=water (0.01% formic acid), B=acetonitrile/gradient: 0.00-2.00 min=20% B, 2.20 min=60% B, 8.00-12.00 min=90% B, 12.10-13.00 min=20% B). Evaporation of the combined product fractions yielded the title compound (44.0 mg, 82% purity, 30% of theory).

LC-MS (Method 11B): $R_t$=1.84 min; MS (ESIpos): m/z=430 [M+H]$^+$

Example 400A

Tert-butyl 4-{3-[(3,3-difluoroazetidin-1-yl)carbonyl]-5-oxo-4,5-dihydropyrazolo[1,5-a]pyrimidin-7-yl}piperidine-1-carboxylate

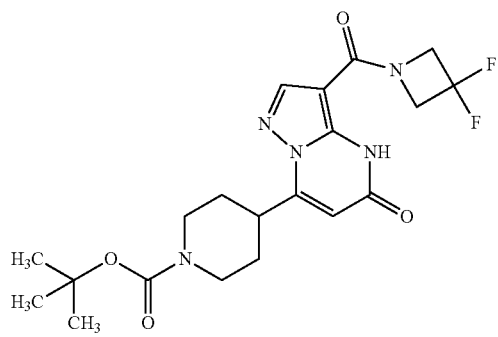 [SMILES: CC(C)(C)OC(=O)N1CCC(c2cc(=O)[nH]c3c(C(=O)N4CC(F)(F)C4)cnn23)CC1]

To a solution of 7-[1-(tert-butoxycarbonyl)piperidin-4-yl]-5-oxo-4,5-dihydropyrazolo[1,5-a]pyrimidine-3-carboxylic acid (100 mg, 276 µmol) in dimethylformamide (1.0 ml, 13 mmol) were added HATU (136 mg, 359 µmol) and N,N-Diisopropylethylamine (140 µl, 830 µmol). Then 3,3-difluoroazetidine hydrochloride (1:1) (71.5 mg, 552 µmol) was added and the reaction mixture was stirred at RT for 16 h. More HATU (1.3 equivalents) was added and the reaction mixture was stirred at RT for 20 h. Water was added, the resulting precipitate was filtered, washed with water, and dried in vacuo to afford the title compound (85.6 mg, 98% purity, 69% of theory).

LC-MS (Method 11B): $R_t$=1.65 min; MS (ESIneg): m/z=436 [M−H]$^-$

Example 401A

Tert-butyl 4-[5-oxo-3-(piperidin-1-ylcarbonyl)-4,5-dihydropyrazolo[1,5-a]pyrimidin-7-yl]piperidine-1-carboxylate

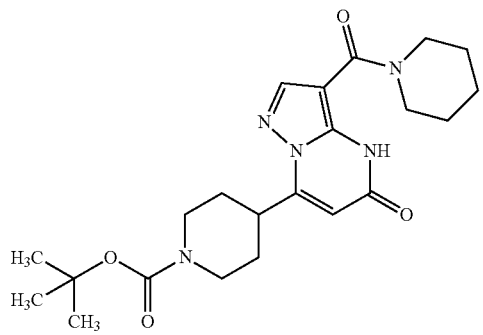 [SMILES: CC(C)(C)OC(=O)N1CCC(c2cc(=O)[nH]c3c(C(=O)N4CCCCC4)cnn23)CC1]

To a solution of 7-[1-(tert-butoxycarbonyl)piperidin-4-yl]-5-oxo-4,5-dihydropyrazolo[1,5-a]pyrimidine-3-carboxylic acid (100 mg, 276 µmol) in dimethylformamide (1.0 ml, 13 mmol) were added HATU (136 mg, 359 µmol) and N,N-Diisopropylethylamine (140 µl, 830 µmol). Then piperidine (47.0 mg, 552 µmol) was added and the reaction mixture was stirred at RT for 16 h. More HATU (1.3 equivalents) was added and the reaction mixture was stirred at RT for 20 h. Water was added and purified by preparative HPLC (Method: column: Reprosil C18; 10 µm; 125×30 mm/flow: 50 ml/min/solvents: A=water (0.01% formic acid), B=acetonitrile/gradient: 0.00-2.00 min=20% B, 2.20 min=60% B, 8.00-12.00 min=90% B, 12.10-13.00 min=20% B). Evaporation of the two product fractions yielded the title compound (33.0 mg, 90% purity, 25% yield and 36.6 mg, 87% purity, 27% of theory).

LC-MS (Method 11B): $R_t$=1.80 min; MS (ESIpos): m/z=430 [M+H]$^+$

Example 402A

Tert-butyl 4-(3-cyclopropyl-2-methyl-5-oxo-4,5-dihydropyrazolo[1,5-a]pyrimidin-7-yl)piperidine-1-carboxylate

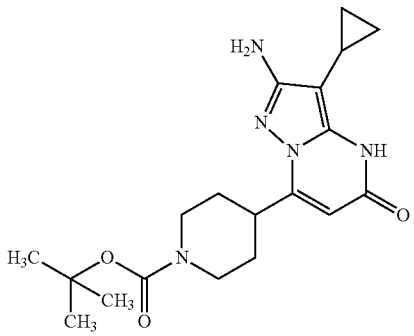 [SMILES: CC(C)(C)OC(=O)N1CCC(c2cc(=O)[nH]c3c(C4CC4)c(N)nn23)CC1]

A mixture of 4-cyclopropyl-3-methyl-1H-pyrazol-5-amine (500 mg, 3.64 mmol) and tert-butyl 4-[(2,2-dimethyl-4,6-dioxo-1,3-dioxan-5-yl)carbonyl]piperidine-1-carboxylate (1.42 g, 4.01 mmol) in acetonitrile (30 ml) was stirred under argon overnight at 60° C. and then concentrated. The 1-Methoxy-2-propanol (30 ml) and tripotassium phosphate (1.55 g, 7.29 mmol) were added, and the resulting mixture was stirred for 2 h at 110° C. before being concentrated. The recovered crude mixture was stirred overnight in a mixture of acetonitrile (25 mL) and dimethyl sulfoxide (10 mL). The resulting solid was filtered, while the filtrate was purified by preparative HPLC (gradient acetonitrile/water with 0.1% formic acid). Evaporation of the combined product fractions, which were then combined with the previously filtered solid, yielded the title compound. The obtained amount was 758 mg (100% purity, 56% of theory).

LC-MS (Method 8B): $R_t$=1.30 min; MS (ESIneg): m/z=371 [M–H]⁻

Example 403A

Tert-butyl 4-[3-(4,5-dimethyl-1,3-thiazol-2-yl)-5-oxo-4,5-dihydropyrazolo[1,5-a]pyrimidin-7-yl]piperidine-1-carboxylate

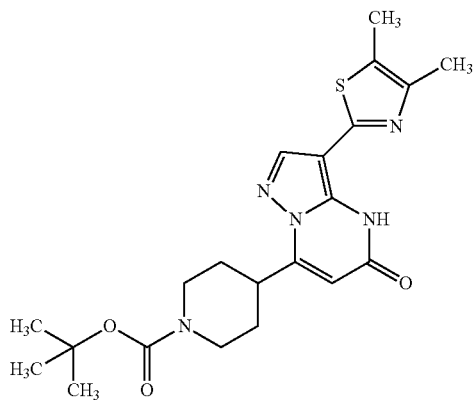 [SMILES: Cc1nc(-c2cnn3c(C4CCN(C(=O)OC(C)(C)C)CC4)cc(=O)[nH]c23)sc1C]

tert-butyl 4-(3-carbamothioyl-5-oxo-4,5-dihydropyrazolo [1,5-a]pyrimidin-7-yl)piperidine-1-carboxylate (200 mg, 530 μmol), 3-chlorobutan-2-one (54 μl, 530 μmol) and N,N-Diisopropylethylamine (460 μl, 2.6 mmol) were dissolved in Ethanol (5.0 ml, 86 mmol) and stirred at 70° C. for 1 h. The mixture was purified via reverse phase HPLC (Method: column: Reprosil C18; 10 μm; 125×30 mm/flow: 50 ml/min/solvents: A=water (0.1% formic acid), B=acetonitrile/gradient: 0.00-4.25 min=20% B, 4.50 min=30% B, 19.00-22.50 min=100% B, 22.75-25.00 min=20% B) to afford the product. The obtained amount was 84.0 mg (97% purity, 36% of theory).

LC-MS (Method 11B): $R_t$=2.26 min; MS (ESIpos): m/z=430 [M+H]⁺

Example 404A

Tert-butyl 4-{3-[4-(2,5-dimethylphenyl)-1,3-thiazol-2-yl]-5-oxo-4,5-dihydropyrazolo[1,5-a]pyrimidin-7-yl}piperidine-1-carboxylate

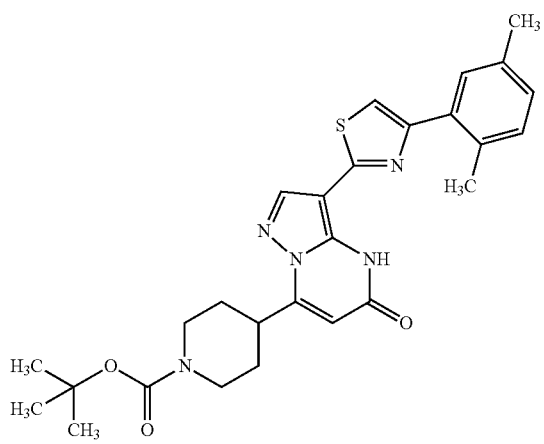 [SMILES: Cc1ccc(C)c(-c2csc(-c3cnn4c(C5CCN(C(=O)OC(C)(C)C)CC5)cc(=O)[nH]c34)n2)c1]

tert-butyl 4-(3-carbamothioyl-5-oxo-4,5-dihydropyrazolo [1,5-a]pyrimidin-7-yl)piperidine-1-carboxylate (200 mg, 530 μmol), 2-chloro-1-(2,5-dimethylphenyl)ethanone (96.8 mg, 530 μmol), N,N-Diisopropylethylamine (460 μl, 2.6 mmol), and Tetra-n-butylammoniumiodide (196 mg, 530 μmol) were dissolved in Ethanol (5.0 ml, 86 mmol) and stirred at 70° C. for 1 h. The mixture was purified via reverse phase HPLC (Method: column: Reprosil C18; 10 μm; 125× 30 mm/flow: 50 ml/min/solvents: A=water (0.1% formic acid), B=acetonitrile/gradient: 0.00-4.25 min=20% B, 4.50 min=30% B, 19.00-22.50 min=100% B, 22.75-25.00 min=20% B) to afford the product. The obtained amount was 60.0 mg (97% purity, 22% of theory).

LC-MS (Method 11B): $R_t$=2.67 min; MS (ESIpos): m/z=506 [M+H]⁺

Example 405A

Tert-butyl 4-{3-[(2,2-dimethylmorpholin-4-yl) methyl]-5-oxo-4,5-dihydropyrazolo[1,5-a]pyrimidin-7-yl}piperidine-1-carboxylate

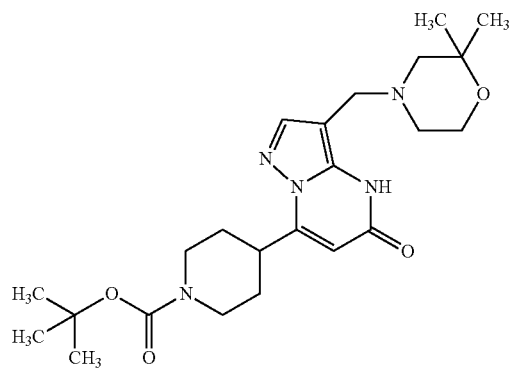 [SMILES: CC(C)(C)OC(=O)N1CCC(c2cc(=O)[nH]c3c(CN4CCOC(C)(C)C4)cnn23)CC1]

tert-butyl 4-[3-(hydroxymethyl)-5-oxo-4,5-dihydropyrazolo[1,5-a]pyrimidin-7-yl]piperidine-1-carboxylate (150 mg, 431 μmol) and Triphenylphosphine (430 μl, 1.0 M, 430 μmol) were dissolved in Tetrahydrofuran (5.0 ml, 62 mmol) and cooled to −18° C. N-Bromsuccinimide (76.6 mg, 431 μmol) was added and the mixture was stirred for 5 min at −18° C. 2,2-dimethylmorpholine (119 mg, 1.03 mmol) was added and stirred for 10 min at RT and then for 1 h at 80° C. Water was added and purified by preparative HPLC (Method: column: Reprosil C18; 10 μm; 125×30 mm/flow: 50 ml/min/solvents: A=water (0.01% formic acid), B=acetonitrile/gradient: 0.00-5.00 min=10% B, 6.50 min=20% B, 17.0-19.75 min=100% B, 19.75.00-23.00 min=90% B). Evaporation of the combined product fractions yielded the title compound (118 mg, 99% purity, 61% of theory).

LC-MS (Method 11B): $R_t$=1.02 min; MS (ESIpos): m/z=446 [M+H]$^+$

Example 406A

Tert-butyl 4-(5-oxo-3-{[2-(pyridin-3-ylacetyl)hydrazinyl]carbonyl}-4,5-dihydropyrazolo[1,5-a]pyrimidin-7-yl)piperidine-1-carboxylate

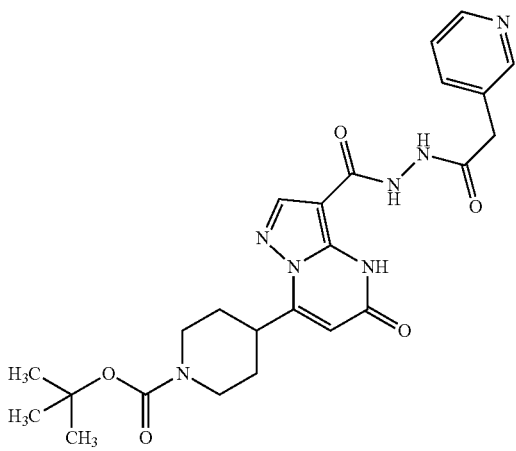 [SMILES: CC(C)(C)OC(=O)N1CCC(c2cc(=O)[nH]c3c(C(=O)NNC(=O)Cc4cccnc4)cnn23)CC1]

7-[1-(tert-butoxycarbonyl)piperidin-4-yl]-5-oxo-4,5-dihydropyrazolo[1,5-a]pyrimidine-3-carboxylic acid (150 mg, 414 μmol) and 2-(pyridin-3-yl)acetohydrazide (93.9 mg, 621 μmol) were dissolved in N,N-Dimethylformamid (1.5 ml, 19 mmol). N,N-Diisopropylethylamine (220 μl, 1.2 mmol) and HATU (266 mg, 621 μmol) were added and the mixture was stirred at RT for 16 h. Purification via revere phase HPLC (Method: Reprosil C18; 10 μm; 125×30 mm/flow: 50 ml/min/solvents: A=water (0.01% formic acid), B=acetonitrile/gradient: 0.00-5.00 min=10% B, 6.50 min=20% B, 17.0-19.75 min=100% B, 19.75.00-23.00 min=90% B) afforded the desired product after drying in vacuo. The obtained amount was 76.9 mg (100% purity, 37% of theory).

LC-MS (Method 11B): $R_t$=0.64 min; MS (ESIpos): m/z=496 [M+H]$^+$

Example 407A

Tert-butyl 4-{5-oxo-3-[5-(pyridin-3-ylmethyl)-1,3,4-oxadiazol-2-yl]-4,5-dihydropyrazolo[1,5-a]pyrimidin-7-yl}piperidine-1-carboxylate

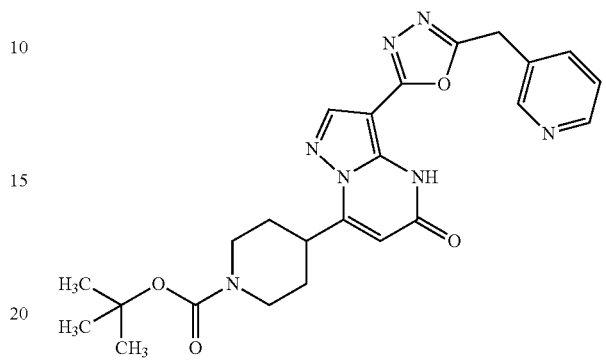

tert-butyl 4-(5-oxo-3-{[2-(pyridin-3-ylacetyl)hydrazinyl]carbonyl}-4,5-dihydropyrazolo[1,5-a]pyrimidin-7-yl)piperidine-1-carboxylate (75.0 mg, 151 μmol) was dissolved in THF (2.3 ml) and stirred with Burgess-Reagent (50.5 mg, 212 μmol) for 16 h at RT. Water and ethyl acetate were added and the organic phase was separated and dried via a filtration through an Extrelut NT3-filter. The solvent was removed and the mixture purified via reverse phase chromatography (Method: Reprosil C18; 10 μm; 125×30 mm/flow: 50 ml/min/solvents: A=water (0.01% formic acid), B=acetonitrile/gradient: 0.00-5.00 min=20% B, 6.50 min=40% B, 17.0-19.75 min=100% B, 19.75.00-23.00 min=40% B) to obtain the product after removal of the solvents in vacuo. The obtained amount was 59 mg (100% purity, 36% of theory).

LC-MS (Method 1B): $R_t$=1.04 min; MS (ESIpos): m/z=488 [M+H]$^+$

Example 408A

Tert-butyl 4-{3-[(3,3-dimethyl-2-oxobutyl)carbamoyl]-5-oxo-4,5-dihydropyrazolo[1,5-a]pyrimidin-7-yl}piperidine-1-carboxylate

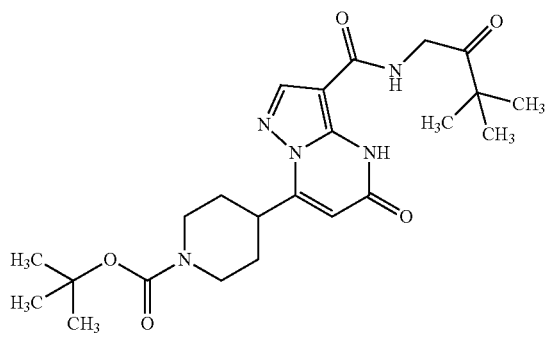 [SMILES: CC(C)(C)OC(=O)N1CCC(c2cc(=O)[nH]c3c(C(=O)NCC(=O)C(C)(C)C)cnn23)CC1]

7-[1-(tert-butoxycarbonyl)piperidin-4-yl]-5-oxo-4,5-dihydropyrazolo[1,5-a]pyrimidine-3-carboxylic acid (1.00 g, 2.76 mmol) and 1-amino-3,3-dimethylbutan-2-one hydrochloride (1:1) (1.05 g, 6.90 mmol) were dissolved in N,N-

Dimethylformamid (5.0 ml, 65 mmol). N,N-Diisopropylethylamine (2.4 ml, 14 mmol) and HATU (1.78 g, 4.69 mmol) were added and the mixture was stirred at RT for 16 h. More 1-amino-3,3-dimethylbutan-2-one hydrochloride (1:1) (2.5 equivalents), N,N-Diisopropylethylamine (5 equivalents), and HATU (1.7 equivalents) were added and the mixture was stirred at RT for 3 h. Water was added. The resulting precipitate was filtered, washed with water, and dried in vacuo. Diethylether was added and the resulting precipitate was filtered, washed with water, and dried in vacuo. The obtained amount of product was 705 mg (97% purity, 54% of theory).

LC-MS (Method 1B): $R_t$=0.93 min; MS (ESIpos): m/z=460 $[M+H]^+$

Example 409A

Tert-butyl 4-(2-oxo-1,2,7,8,9,10-hexahydropyrimido[1,2-b]indazol-4-yl)piperidine-1-carboxylate

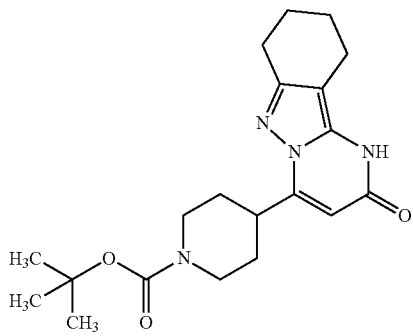 [SMILES: CC(C)(C)OC(=O)N1CCC(c2cc(=O)[nH]c3c4c(nn23)CCCC4)CC1]

4,5,6,7-tetrahydro-2H-indazol-3-amine hydrochloride (1:1) (150 mg, 864 µmol), tert-butyl 4-[(2,2-dimethyl-4,6-dioxo-1,3-dioxan-5-yl)carbonyl]piperidine-1-carboxylate (307 mg, 864 µmol), and N,N-Diisopropylethylamine (180 µl, 1.0 mmol) were heated in Acetonitrile (3.5 ml, 74 mmol) at 60° C. for 1.5 h. The solvents were removed and the residue dissolved in (3.5 ml, 36 mmol). Potassium triphosphat (367 mg, 1.73 mmol) was added and the mixture was heated at 110° C. for 1.5 h. The solvents were removed and the residue partitioned between water and ethyl acetate. The organic fraction was washed with saturated ammonium chloride solution (aqueous), water and brine. Then it was dried with sodium sulfate and in vacuo. The residue was purified via reverse phase HPLC (Method: column: Reprosil C18; 10 µm; 125×30 mm/Flow: 50 ml/min/solvent: A=H2O (0.01% HCOOH), B=Acetonitril/gradient: 0.00-5.00 min=10% B, 6.50 min=20% B, 17.0-19.75 min=100% B, 19.75.00-23.00 min=90% B) to afford the product. The obtained amount was 114 mg (100% purity, 36% of theory).

LC-MS (Method 11B): $R_t$=1.75 min; MS (ESIneg): m/z=371 $[M-H]^-$

Example 410A

Tert-butyl 4-{3-[5-methyl-4-(trifluoromethyl)-1,3-thiazol-2-yl]-5-oxo-4,5-dihydropyrazolo[1,5-a]pyrimidin-7-yl}piperidine-1-carboxylate

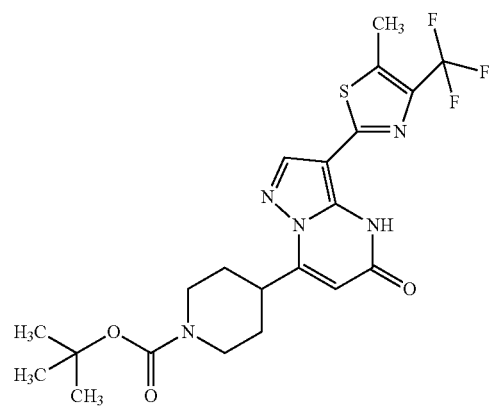 [SMILES: Cc1sc(-c2cnn3c(C4CCN(C(=O)OC(C)(C)C)CC4)cc(=O)[nH]c23)nc1C(F)(F)F]

tert-butyl 4-(3-carbamothioyl-5-oxo-4,5-dihydropyrazolo[1,5-a]pyrimidin-7-yl)piperidine-1-carboxylate (120 mg, 318 µmol), 3-bromo-1,1,1-trifluorobutan-2-one (40 µl, 320 µmol) and N,N-Diisopropylethylamine (280 µl, 1.6 mmol) were dissolved in Ethanol (4.8 ml, 82 mmol) and stirred at 70° C. for 1 h. Toluene was added and the mixture was heated at reflux for 2 h. The mixture was purified via reverse phase HPLC (Method: column: Reprosil C18; 10 µm; 125× 30 mm/flow: 50 ml/min/solvents: A=water (0.1% formic acid), B=acetonitrile/gradient: 0.00-4.25 min=20% B, 4.50 min=30% B, 19.00-22.50 min=100% B, 22.75-25.00 min=20% B) to afford the product. The obtained amount was 57.0 mg (100% purity, 36% of theory).

LC-MS (Method 1B): $R_t$=1.12 min; MS (ESIpos): m/z=502 $[M+H]^+$

Example 411A

Tert-butyl 4-[3-(4-cyclohexyl-1,3-thiazol-2-yl)-5-oxo-4,5-dihydropyrazolo[1,5-a]pyrimidin-7-yl]piperidine-1-carboxylate

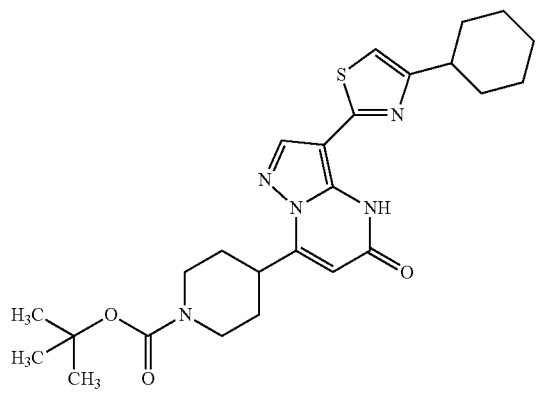 [SMILES: CC(C)(C)OC(=O)N1CCC(c2cc(=O)[nH]c3c(-c4nc(C5CCCCC5)cs4)cnn23)CC1]

tert-butyl 4-(3-carbamothioyl-5-oxo-4,5-dihydropyrazolo[1,5-a]pyrimidin-7-yl)piperidine-1-carboxylate (120 mg, 318 μmol), 2-bromo-1-cyclohexylethanone (65.2 mg, 318 μmol) and N,N-Diisopropylethylamine (280 μl, 1.6 mmol) were dissolved in Ethanol (3.0 ml, 52 mmol) and stirred at 70° C. for 1 h. Water was added, the resulting precipitate was filtered, washed with water, and dried in vacuo. The residue was treated in methanol/acetonitrile (1:1), filtered, and dried in vacuo. The obtained amount was 60.6 mg (100% purity, 39% of theory).

LC-MS (Method 10B): $R_t$=2.52 min; MS (ESIpos): m/z=484 [M+H]$^+$

Example 412A

Tert-butyl 4-{3-[4-(1-chlorocyclopropyl)-1,3-thiazol-2-yl]-5-oxo-4,5-dihydropyrazolo[1,5-a]pyrimidin-7-yl}piperidine-1-carboxylate

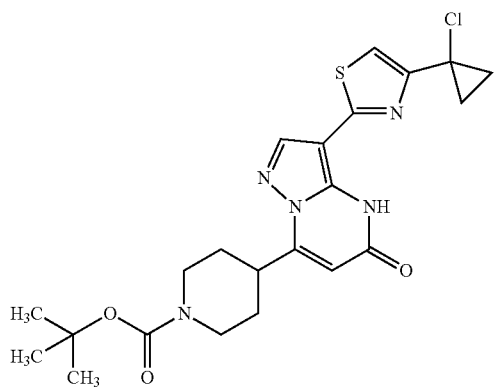 [SMILES: CC(C)(C)OC(=O)N1CCC(c2cc(=O)[nH]c3c(-c4nc(C5(Cl)CC5)cs4)cnn23)CC1]

tert-butyl 4-(3-carbamothioyl-5-oxo-4,5-dihydropyrazolo[1,5-a]pyrimidin-7-yl)piperidine-1-carboxylate (120 mg, 318 μmol), 2-chloro-1-(1-chlorocyclopropyl)ethanone (48.6 mg, 318 μmol), Tetra-n-butylammoniumiodide (117 mg, 318 μmol), and N,N-Diisopropylethylamine (280 μl, 1.6 mmol) were dissolved in Ethanol (3.0 ml, 52 mmol) and stirred at 70° C. for 1 h. The mixture was purified via reverse phase HPLC (Method: column: Reprosil C18; 10 μm; 125×30 mm/flow: 50 ml/min/solvents: A=water (0.1% formic acid), B=acetonitrile/gradient: 0.00-4.25 min=20% B, 4.50 min=30% B, 19.00-22.50 min=100% B, 22.75-25.00 min=20% B) to afford the product. The obtained amount was 46.0 mg (100% purity, 30% of theory).

LC-MS (Method 11B): $R_t$=2.38 min; MS (ESIpos): m/z=476 [M+H]$^+$

Example 413A

Tert-butyl 4-(3-{4-[2-(difluoromethoxy)phenyl]-1,3-thiazol-2-yl}-5-oxo-4,5-dihydropyrazolo[1,5-a]pyrimidin-7-yl)piperidine-1-carboxylate

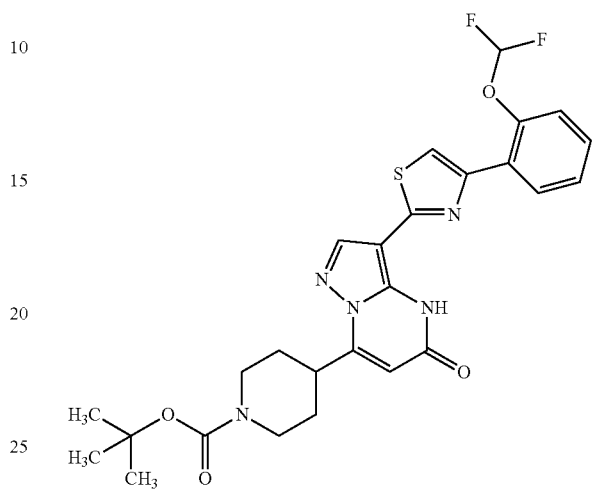

tert-butyl 4-(3-carbamothioyl-5-oxo-4,5-dihydropyrazolo[1,5-a]pyrimidin-7-yl)piperidine-1-carboxylate (120 mg, 318 μmol), 2-bromo-1-[2-(difluoromethoxy)phenyl]ethanone (84.3 mg, 318 μmol) and N,N-Diisopropylethylamine (280 μl, 1.6 mmol) were dissolved in Ethanol (3.0 ml, 52 mmol) and stirred at 70° C. for 1 h. Water was added; the resulting precipitate was filtered, washed with water, and dried in vacuo. The residue was treated in methanol/acetonitrile (1:1), filtered, and dried in vacuo. The obtained amount was 70.0 mg (100% purity, 41% of theory).

LC-MS (Method 11B): $R_t$=2.44 min; MS (ESIpos): m/z=544 [M+H]$^+$

Example 414A

Tert-butyl 4-(3-{[2-(2,2-dimethylpropanoyl)hydrazinyl]carbonyl}-2-methyl-5-oxo-4,5-dihydropyrazolo[1,5-a]pyrimidin-7-yl)piperidine-1-carboxylate

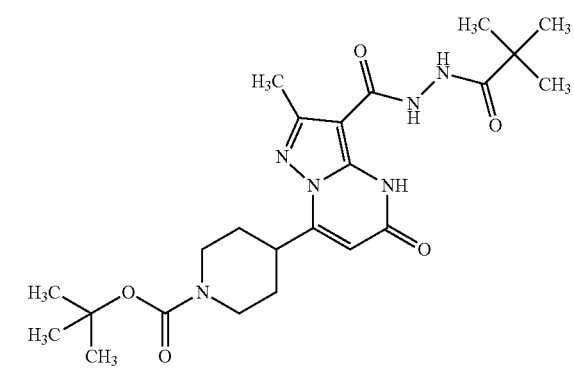 [SMILES: Cc1nn2c(C3CCN(C(=O)OC(C)(C)C)CC3)cc(=O)[nH]c2c1C(=O)NNC(=O)C(C)(C)C]

7-[1-(tert-butoxycarbonyl)piperidin-4-yl]-2-methyl-5-oxo-4,5-dihydropyrazolo[1,5-a]pyrimidine-3-carboxylic acid (150 mg, 398 μmol) and 2,2-dimethylpropanehydrazide (69.4 mg, 598 µmol) were dissolved in N,N-Dimethylformamid (1.5 ml, 19 mmol). N,N-Diisopropylethylamine (220 µl, 1.2 mmol) and HATU (227 mg, 598 µmol) were added and the mixture was stirred at RT for 16 h. Further HATU (1.5 equivalents) and 2,2-dimethylpropanehydrazide (1.5 equivalents) were added and the mixture stirred at RT for 18 h. Purification via revere phase HPLC (Method: Reprosil C18; 10 µm; 125×30 mm/flow: 50 ml/min/solvents: A=water (0.01% formic acid), B=acetonitrile/gradient: 0.00-5.00 min=20% B, 6.50 min=40% B, 17.0-19.75 min=100% B, 19.75.00-23.00 min=40% B) afforded the desired product after drying in vacuo. The obtained amount was 106 mg (100% purity, 56% of theory).

LC-MS (Method 11B): $R_t$=1.60 min; MS (ESIneg): m/z=473 [M−H]⁻

Example 415A

Tert-butyl 4-[3-(5-tert-butyl-1,3,4-oxadiazol-2-yl)-2-methyl-5-oxo-4,5-dihydropyrazolo[1,5-a]pyrimidin-7-yl]piperidine-1-carboxylate

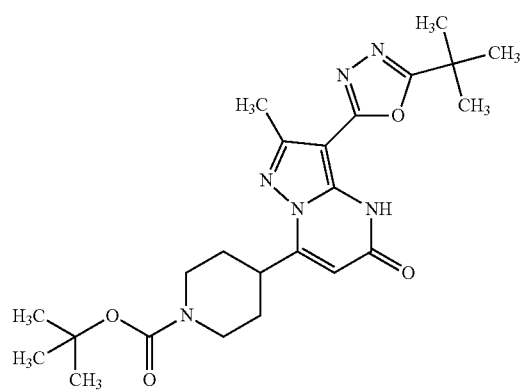 [SMILES: Cc1nn2c(C3CCN(C(=O)OC(C)(C)C)CC3)cc(=O)[nH]c2c1-c1nnc(C(C)(C)C)o1]

tert-butyl 4-(3-{[2-(2,2-dimethylpropanoyl)hydrazinyl]carbonyl}-2-methyl-5-oxo-4,5-dihydropyrazolo[1,5-a]pyrimidin-7-yl)piperidine-1-carboxylate (94.8 mg, 200 µmol) was dissolved in THF (3.1 ml, 39 mmol) and stirred with Burgess-Reagent (57.1 mg, 240 µmol) for 16 h at RT. Water was added and purified by preparative HPLC (Method: column: Reprosil C18; 10 µm; 125×30 mm/flow: 50 ml/min/solvents: A=water (0.01% formic acid), B=acetonitrile/gradient: 0.00-5.00 min=10% B, 6.50 min=20% B, 17.0-19.75 min=100% B, 19.75.00-23.00 min=90% B). Evaporation of the combined product fractions yielded the title compound (65.4 mg, 100% purity, 72% of theory).

LC-MS (Method 11B): $R_t$=2.10 min; MS (ESIpos): m/z=457 [M+H]⁺

Example 416A

Tert-butyl 4-[2-methyl-3-(3-methyl-1,2,4-oxadiazol-5-yl)-5-oxo-4,5-dihydropyrazolo[1,5-a]pyrimidin-7-yl]piperidine-1-carboxylate

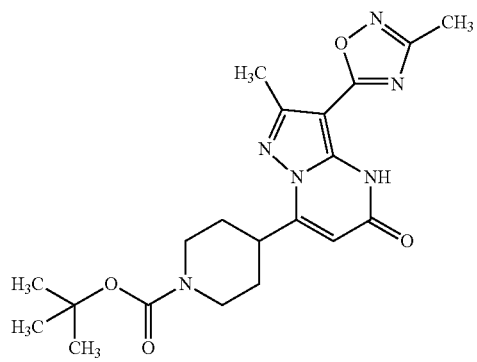 [SMILES: Cc1noc(-c2c(C)nn3c(C4CCN(C(=O)OC(C)(C)C)CC4)cc(=O)[nH]c23)n1]

7-[1-(tert-butoxycarbonyl)piperidin-4-yl]-2-methyl-5-oxo-4,5-dihydropyrazolo[1,5-a]pyrimidine-3-carboxylic acid (150 mg, 398 µmol) was dissolved in N,N-Dimethylformamid (3.0 ml, 39 mmol) and treated with N,N-Diisopropylethylamine (210 µl, 1.2 mmol) and 1,1'-Carboyldiimidazol (129 mg, 797 µmol). The mixture was stirred at 90° C. for 1.5 h (1Z)-N'-hydroxyethanimidamide hydrochloride (1:1) (88.1 mg, 797 µmol) was dissolved in N,N-Dimethylformamid (1 ml) and added dropwise. The mixture was then stirred at 110° C. for 6 h. The mixture was purified via reverse phase HPLC (Method: column: Reprosil C18; 10 µm; 125×30 mm/flow: 50 ml/min/solvents: A=water (0.01% formic acid), B=acetonitrile/gradient: 0.00-5.00 min=10% B, 6.50 min=20% B, 17.0-19.75 min=100% B, 19.75.00-23.00 min=90% B) to afford the product. The obtained amount was 40.8 mg (91% purity, 22% of theory).

LC-MS (Method 11B): $R_t$=1.97 min; MS (ESIneg): m/z=413 [M−H]⁻

Example 417A

Tert-butyl 4-(3-{[2-(cyclobutylcarbonyl)hydrazinyl]carbonyl}-2-methyl-5-oxo-4,5-dihydropyrazolo[1,5-a]pyrimidin-7-yl)piperidine-1-carboxylate

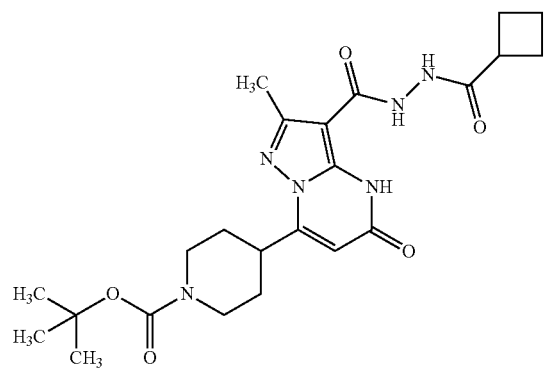 [SMILES: Cc1nn2c(C3CCN(C(=O)OC(C)(C)C)CC3)cc(=O)[nH]c2c1C(=O)NNC(=O)C1CCC1]

7-[1-(tert-butoxycarbonyl)piperidin-4-yl]-2-methyl-5-oxo-4,5-dihydropyrazolo[1,5-a]pyrimidine-3-carboxylic acid (150 mg, 398 µmol) and cyclobutanecarbohydrazide (68.2 mg, 598 µmol) were dissolved in N,N-Dimethylformamid (1.5 ml, 19 mmol). N,N-Diisopropylethylamine (220 µl, 1.2 mmol) and HATU (227 mg, 598 µmol) were added and the mixture was stirred at RT for 16 h. Further HATU (1.5 equivalents) and cyclobutanecarbohydrazide (1.5 equivalents) were added and the mixture stirred at RT for 18 h. Purification via revere phase HPLC (Method: Reprosil C18; 10 µm; 125×30 mm/flow: 50 ml/min/solvents: A=water (0.01% formic acid), B=acetonitrile/gradient: 0.00-5.00 min=20% B, 6.50 min=40% B, 17.0-19.75 min=100% B, 19.75.00-23.00 min=40% B) afforded the desired product after drying in vacuo. The obtained amount was 127 mg (68% of theory).

LC-MS (Method 11B): $R_t$=1.55 min; MS (ESIneg): m/z=471 [M−H]⁻

Example 418A

Tert-butyl 4-[3-(5-cyclobutyl-1,3,4-oxadiazol-2-yl)-2-methyl-5-oxo-4,5-dihydropyrazolo[1,5-a]pyrimidin-7-yl]piperidine-1-carboxylate

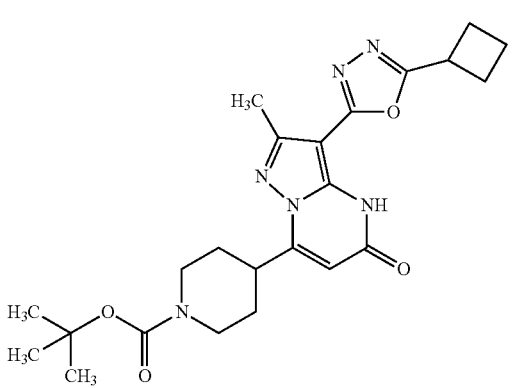 [SMILES: Cc1nn2c(C3CCN(C(=O)OC(C)(C)C)CC3)cc(=O)[nH]c2c1-c1nnc(C2CCC2)o1]

tert-butyl 4-(3-{[2-(cyclobutylcarbonyl)hydrazinyl]carbonyl}-2-methyl-5-oxo-4,5-dihydropyrazolo[1,5-a]pyrimidin-7-yl)piperidine-1-carboxylate (118 mg, 249 µmol) was dissolved in THF (2.4 ml, 29 mmol) and stirred with Burgess-Reagent (83.1 mg, 349 µmol) for 16 h at RT. Water was added and purified by preparative HPLC (Method: column: Reprosil C18; 10 µm; 125×30 mm/flow: 50 ml/min/solvents: A=water (0.01% formic acid), B=acetonitrile/gradient: 0.00-5.00 min=10% B, 6.50 min=20% B, 17.0-19.75 min=100% B, 19.75.00-23.00 min=90% B). Evaporation of the combined product fractions yielded the title compound (81.9 mg, 100% purity, 72% of theory).

LC-MS (Method 11B): $R_t$=2.02 min; MS (ESIpos): m/z=455 [M+H]⁺

Example 419A

Tert-butyl 4-{2-methyl-5-oxo-3-[3-(trifluoromethyl)-1,2,4-oxadiazol-5-yl]-4,5-dihydropyrazolo[1,5-a]pyrimidin-7-yl}piperidine-1-carboxylate

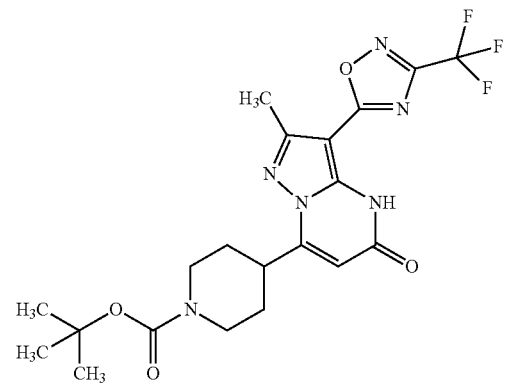 [SMILES: Cc1nn2c(C3CCN(C(=O)OC(C)(C)C)CC3)cc(=O)[nH]c2c1-c1nc(C(F)(F)F)no1]

7-[1-(tert-butoxycarbonyl)piperidin-4-yl]-2-methyl-5-oxo-4,5-dihydropyrazolo[1,5-a]pyrimidine-3-carboxylic acid (150 mg, 398 µmol) was dissolved in N,N-Dimethylformamid (3.0 ml, 39 mmol) and treated with N,N-Diisopropylethylamine (210 µl, 1.2 mmol) and 1,1'-Carboyldiimidazol (129 mg, 797 µmol). The mixture was stirred at 90° C. for 1.5 h. (1Z)-2,2,2-trifluoro-N'-hydroxyethanimidamide (102 mg, 797 µmol) was dissolved in N,N-Dimethylformamid (1 ml) and added dropwise. The mixture was then stirred at 110° C. for 6 h. The mixture was purified via reverse phase HPLC (Method: column: Reprosil C18; 10 µm; 125× 30 mm/flow: 50 ml/min/solvents: A=water (0.01% formic acid), B=acetonitrile/gradient: 0.00-5.00 min=10% B, 6.50 min=20% B, 17.0-19.75 min=100% B, 19.75.00-23.00 min=90% B) to afford the product. The obtained amount was 101 mg (100% purity, 54% of theory).

LC-MS (Method 11B): $R_t$=2.22 min; MS (ESIneg): m/z=467 [M−H]⁻

Example 420A

Tert-butyl 4-{3-[(dimethylamino)methyl]-5-oxo-4,5-dihydropyrazolo[1,5-a]pyrimidin-7-yl}piperidine-1-carboxylate

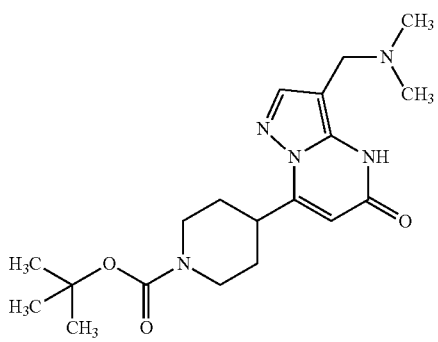 [SMILES: CN(C)Cc1cnn2c(C3CCN(C(=O)OC(C)(C)C)CC3)cc(=O)[nH]c12]

tert-butyl 4-{3-(hydroxymethyl)-5-oxo-4,5-dihydropyrazolo[1,5-a]pyrimidin-7-yl}piperidine-1-carboxylate (150 mg, 431 µmol) and Triphenylphosphine (430 µl, 1.0 M, 430 µmol) were dissolved in Tetrahydrofuran (5.0 ml, 62 mmol) and cooled to −18° C. N-Bromsuccinimide (76.6 mg, 431 µmol) was added and the mixture was stirred for 5 min at −18° C. Dimethylamine (520 µl, 2.0 M, 1.0 mmol) was added and stirred for 10 min at RT and then for 1 h at 80° C. Water was added and purified by preparative HPLC (Method: column: Reprosil C18; 10 µm; 125×30 mm/flow: 50 ml/min/solvents: A=water (0.01% formic acid), B=acetonitrile/gradient: 0.00-5.00 min=10% B, 6.50 min=20% B, 17.0-19.75 min=100% B, 19.75.00-23.00 min=90% B). Evaporation of the combined product fractions yielded the title compound (45.8 mg, 93% purity, 26% of theory).

LC-MS (Method 1B): $R_t$=0.87 min; MS (ESIneg): m/z=374 [M−H]⁻

Example 421A

Tert-butyl 4-[5-oxo-3-(pyrrolidin-1-ylmethyl)-4,5-dihydropyrazolo[1,5-a]pyrimidin-7-yl]piperidine-1-carboxylate

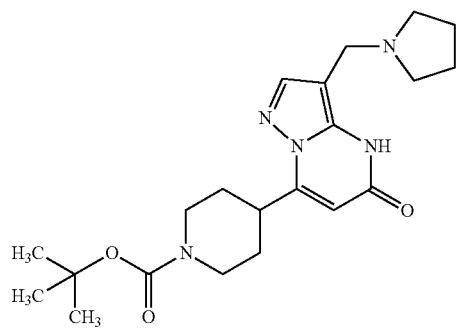 [SMILES: CC(C)(C)OC(=O)N1CCC(c2cc(=O)[nH]c3c(CN4CCCC4)cnn23)CC1]

tert-butyl 4-[3-(hydroxymethyl)-5-oxo-4,5-dihydropyrazolo[1,5-a]pyrimidin-7-yl]piperidine-1-carboxylate (150 mg, 431 µmol) and Triphenylphosphine (430 µl, 1.0 M, 430 µmol) were dissolved in Tetrahydrofuran (5.0 ml, 62 mmol) and cooled to −18° C. N-Bromsuccinimide (76.6 mg, 431 µmol) was added and the mixture was stirred for 5 min at −18° C. Pyrrolidine (86 µl, 1.0 mmol) was added and stirred for 10 min at RT and then for 1 h at 80° C. Water was added and purified by preparative HPLC (Method: column: Reprosil C18; 10 µm; 125×30 mm/flow: 50 ml/min/solvents: A=water (0.01% formic acid), B=acetonitrile/gradient: 0.00-5.00 min=10% B, 6.50 min=20% B, 17.0-19.75 min=100% B, 19.75.00-23.00 min=90% B). Evaporation of the combined product fractions yielded the title compound (58.2 mg, 100% purity, 34% of theory).

LC-MS (Method 1B): $R_t$=0.59 min; MS (ESIpos): m/z=402 [M+H]⁺

Example 422A

Tert-butyl 4-(3-cyclopropyl-5-oxo-4,5-dihydropyrazolo[1,5-a]pyrimidin-7-yl)piperidine-1-carboxylate

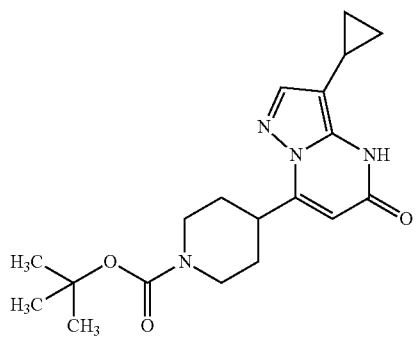 [SMILES: CC(C)(C)OC(=O)N1CCC(c2cc(=O)[nH]c3c(C4CC4)cnn23)CC1]

4-cyclopropyl-1H-pyrazol-3-amine (300 mg, 2.44 mmol) and tert-butyl 4-[(2,2-dimethyl-4,6-dioxo-1,3-dioxan-5-yl)carbonyl]piperidine-1-carboxylate (866 mg, 2.44 mmol) were heated in Acetonitrile (9.0 ml, 190 mmol) at 60° C. for 1.5 h. The solvents were removed and the residue dissolved in 1-Methoxy-2-propanol (9.0 ml, 92 mmol). Potassium triphosphat (1.03 g, 4.87 mmol) was added and the mixture was heated at 110° C. for 1.5 h. The solvents were removed and the residue partitioned between water and ethyl acetate. The organic fraction was washed with saturated ammonium chloride solution (aqueous), water and brine. Then it was dried with sodium sulfate and in vacuo. The residue was purified via reverse phase HPLC (Method: column: Reprosil C18; 10 µm; 125×30 mm/Flow: 50 ml/min/solvent: A=H2O (0.01% HCOOH), B=Acetonitril/gradient: 0.00-5.00 min=10% B, 6.50 min=20% B, 17.0-19.75 min=100% B, 19.75.00-23.00 min=90% B) to afford the product. The obtained amount was 454 mg (100% purity, 52% of theory).

LC-MS (Method 1B): $R_t$=0.91 min; MS (ESIneg): m/z=357 [M−H]⁻

Example 423A

Tert-butyl 4-{3-[(1,1-dioxidothiomorpholin-4-yl)methyl]-5-oxo-4,5-dihydropyrazolo[1,5-a]pyrimidin-7-yl}piperidine-1-carboxylate

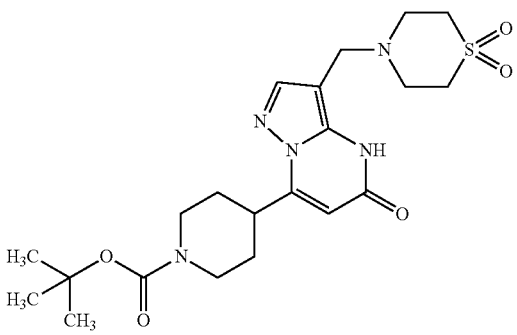 [SMILES: CC(C)(C)OC(=O)N1CCC(c2cc(=O)[nH]c3c(CN4CCS(=O)(=O)CC4)cnn23)CC1]

tert-butyl 4-[3-(hydroxymethyl)-5-oxo-4,5-dihydropyrazolo[1,5-a]pyrimidin-7-yl]piperidine-1-carboxylate (150 mg, 431 µmol) and Triphenylphosphine (430 µl, 1.0 M, 430

μmol) were dissolved in Tetrahydrofuran (5.0 ml, 62 mmol) and cooled to −18° C. N-Bromsuccinimide (76.6 mg, 431 μmol) was added and the mixture was stirred for 5 min at −18° C. Thiomorpholine1,1-dioxide (140 mg, 1.03 mmol) was added and stirred for 10 min at RT and then for 1 h at 80° C. Water was added and purified by preparative HPLC (Method: column: Reprosil C18; 10 μm; 125×30 mm/flow: 50 ml/min/solvents: A=water (0.01% formic acid), B=acetonitrile/gradient: 0.00-5.00 min=10% B, 6.50 min=20% B, 17.0-19.75 min=100% B, 19.75.00-23.00 min=90% B). Evaporation of the combined product fractions yielded the title compound (134 mg, 80% purity, 54% of theory).

LC-MS (Method 1B): $R_t$=0.73 min; MS (ESIneg): m/z=464 [M−H]⁻

Example 424A

Tert-butyl 4-{3-[3-(2,2-dimethylcyclopropyl)-1,2,4-oxadiazol-5-yl]-2-methyl-5-oxo-4,5-dihydropyrazolo[1,5-a]pyrimidin-7-yl}piperidine-1-carboxylate

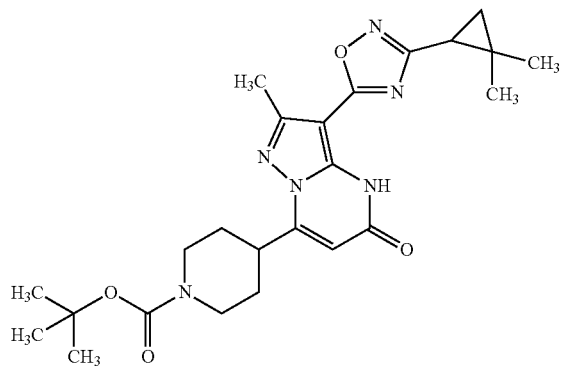 [SMILES: Cc1nn2c(C3CCN(C(=O)OC(C)(C)C)CC3)cc(=O)[nH]c2c1-c1nc(C2CC2(C)C)no1]

7-[1-(tert-butoxycarbonyl)piperidin-4-yl]-2-methyl-5-oxo-4,5-dihydropyrazolo[1,5-a]pyrimidine-3-carboxylic acid (150 mg, 398 μmol) was dissolved in N,N-Dimethylformamid (3.0 ml, 39 mmol) and treated with N,N-Diisopropylethylamine (210 μl, 1.2 mmol) and 1,1'-Carboyldiimidazol (129 mg, 797 μmol). The mixture was stirred at 90° C. for 1.5 h. N'-hydroxy-2,2-dimethylcyclopropanecarboximidamide (102 mg, 797 μmol) was dissolved in N,N-Dimethylformamid (1 ml) and added dropwise. The mixture was then stirred at 110° C. for 6 h. The mixture was purified via reverse phase HPLC (Method: column: Reprosil C18; 10 μm; 125×30 mm/flow: 50 ml/min/solvents: A=water (0.01% formic acid), B=acetonitrile/gradient: 0.00-5.00 min=10% B, 6.50 min=20% B, 17.0-19.75 min=100% B, 19.75.00-23.00 min=90% B) to afford the product. The obtained amount was 112 mg (100% purity, 60% of theory).

LC-MS (Method 11B): $R_t$=2.41 min; MS (ESIpos): m/z=469 [M+H]⁺

Example 425A

Tert-butyl 4-(2-methyl-5-oxo-3-{3-[2-(trifluoromethoxy)phenyl]-1,2,4-oxadiazol-5-yl}-4,5-dihydropyrazolo[1,5-a]pyrimidin-7-yl)piperidine-1-carboxylate

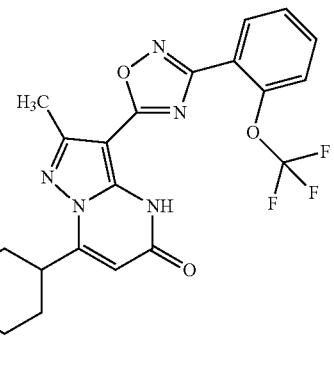

7-[1-(tert-butoxycarbonyl)piperidin-4-yl]-2-methyl-5-oxo-4,5-dihydropyrazolo[1,5-a]pyrimidine-3-carboxylic acid (150 mg, 398 μmol) was dissolved in N,N-Dimethylformamid (3.0 ml, 39 mmol) and treated with N,N-Diisopropylethylamine (210 μl, 1.2 mmol) and 1,1'-Carboyldiimidazol (129 mg, 797 μmol). The mixture was stirred at 90° C. for 1.5 h N'-hydroxy-2-(trifluoromethoxy)benzenecarboximidamide (175 mg, 797 μmol) was dissolved in N,N-Dimethylformamid (1 ml) and added dropwise. The mixture was then stirred at 110° C. for 6 h. The mixture was purified via reverse phase HPLC (Method: column: Reprosil C18; 10 μm; 125×30 mm/flow: 50 ml/min/solvents: A=water (0.01% formic acid), B=acetonitrile/gradient: 0.00-5.00 min=10% B, 6.50 min=20% B, 17.0-19.75 min=100% B, 19.75.00-23.00 min=90% B) to afford the product.

The obtained amount was 109 mg (98% purity, 48% of theory).

LC-MS (Method 11B): $R_t$=2.54 min; MS (ESIpos): m/z=561 [M+H]⁺

Example 426A

Tert-butyl 4-[3-(morpholin-4-ylmethyl)-5-oxo-4,5-dihydropyrazolo[1,5-a]pyrimidin-7-yl]piperidine-1-carboxylate

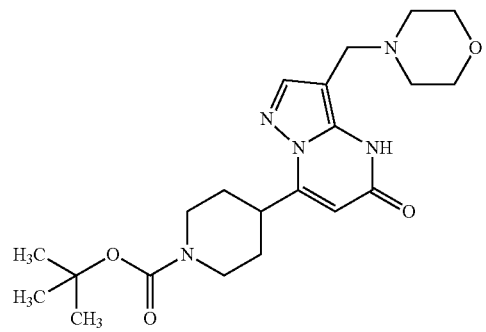 [SMILES: CC(C)(C)OC(=O)N1CCC(c2cc(=O)[nH]c3c(CN4CCOCC4)cnn23)CC1]

tert-butyl 4-[3-(hydroxymethyl)-5-oxo-4,5-dihydropyrazolo[1,5-a]pyrimidin-7-yl]piperidine-1-carboxylate (150 mg, 431 µmol) and Triphenylphosphine (430 µl, 1.0 M, 430 µmol) were dissolved in Tetrahydrofuran (5.0 ml, 62 mmol) and cooled to −18° C. N-Bromsuccinimide (76.6 mg, 431 µmol) was added and the mixture was stirred for 5 min at −18° C. Morpholine (90 µl, 1.0 mmol) was added and stirred for 10 min at RT and then for 1 h at 80° C. Water and saturated sodium carbonate solution was added until a pH value of 11 was reached. The aqueous phase was extracted three times with dichloromethane, dried with sodium sulfate and in vacuo. The obtained residue was purified by preparative HPLC (Method: column: Reprosil C18; 10 µm; 125×30 mm/flow: 50 ml/min/solvents: A=water (0.01% formic acid), B=acetonitrile/gradient: 0.00-5.00 min=10% B, 6.50 min=20% B, 17.0-19.75 min=100% B, 19.75.00-23.00 min=90% B). Evaporation of the combined product fractions yielded the title compound (117 mg, 95% purity, 62% of theory).

LC-MS (Method 11B): $R_t$=0.57 min; MS (ESIneg): m/z=416 [M−H]⁻

Example 427A

Tert-butyl (2S,4R)-2-(2,2-dimethylpropyl)-4-{3-[3-(2-fluorophenyl)-1,2,4-oxadiazol-5-yl]-5-oxo-4,5-dihydropyrazolo[1,5-a]pyrimidin-7-yl}piperidine-1-carboxylate

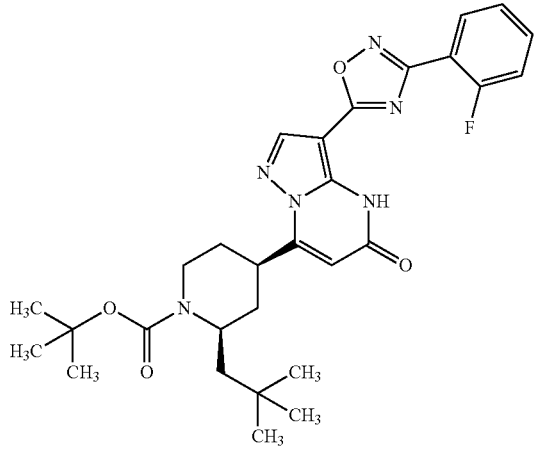 [SMILES: CC(C)(C)C[C@@H]1C[C@H](c2cc(=O)[nH]c3c(-c4nc(-c5ccccc5F)no4)cnn23)CCN1C(=O)OC(C)(C)C]

7-[(2S,4R)-1-(tert-butoxycarbonyl)-2-(2,2-dimethylpropyl)piperidin-4-yl]-5-oxo-4,5-dihydropyrazolo[1,5-a]pyrimidine-3-carboxylic acid (87.7 mg, 203 µmol) was dissolved in N,N-Dimethylformamid (2.3 ml, 30 mmol) and treated with N,N-Diisopropylethylamine (71 µl, 410 µmol) and 1,1'-Carboyldiimidazol (65.8 mg, 406 µmol). The mixture was stirred at 90° C. for 1.5 h. 2-fluoro-N'-hydroxybenzenecarboximidamide (62.5 mg, 406 µmol) was dissolved in N,N-Dimethylformamid (1 ml) and added dropwise. The mixture was then stirred at 110° C. for 6 h. The mixture was purified via reverse phase HPLC (Method: column: Reprosil C18; 10 µm; 125×30 mm/flow: 50 ml/min/solvents: A=water (0.01% formic acid), B=acetonitrile/gradient: 0.00-5.00 min=10% B, 6.50 min=20% B, 17.0-19.75 min=100% B, 19.75.00-23.00 min=90% B) to afford the product. The obtained amount was 32.6 mg (98% purity, 29% of theory).

LC-MS (Method 11B): $R_t$=2.71 min; MS (ESIneg): m/z=549 [M−H]⁻

Example 428A

Tert-butyl 4-[3-(3-cyclohexyl-1,2,4-oxadiazol-5-yl)-2-methyl-5-oxo-4,5-dihydropyrazolo[1,5-a]pyrimidin-7-yl]piperidine-1-carboxylate

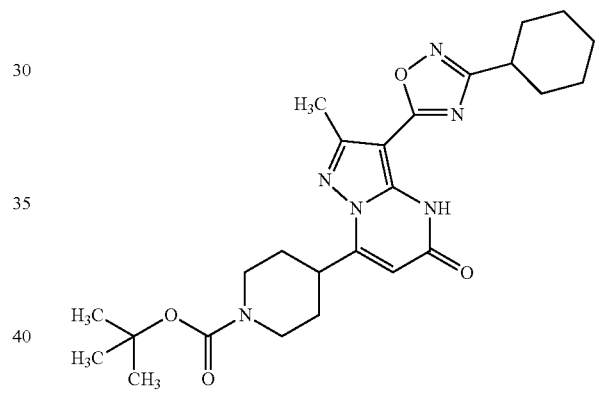

7-[1-(tert-butoxycarbonyl)piperidin-4-yl]-2-methyl-5-oxo-4,5-dihydropyrazolo[1,5-a]pyrimidine-3-carboxylic acid (150 mg, 398 µmol) was dissolved in N,N-Dimethylformamid (3.0 ml, 39 mmol) and treated with N,N-Diisopropylethylamine (210 µl, 1.2 mmol) and 1,1'-Carboyldiimidazol (129 mg, 797 µmol). The mixture was stirred at 90° C. for 1.5 h. N'-hydroxycyclohexanecarboximidamide (113 mg, 797 µmol) was dissolved in N,N-Dimethylformamid (1 ml) and added dropwise. The mixture was then stirred at 110° C. for 6 h. The mixture was purified via reverse phase HPLC (Method: column: Reprosil C18; 10 µm; 125×30 mm/flow: 50 ml/min/solvents: A=water (0.01% formic acid), B=acetonitrile/gradient: 0.00-5.00 min=10% B, 6.50 min=20% B, 17.0-19.75 min=100% B, 19.75.00-23.00 min=90% B) to afford the product. The obtained amount was 116 mg (100% purity, 60% of theory).

LC-MS (Method 1B): $R_t$=1.37 min; MS (ESIpos): m/z=483 [M+H]⁺

Example 429A

Tert-butyl 4-(5-oxo-3-{[(3,3,3-trifluoro-2-oxopropyl)sulfanyl]carbonoimidoyl}-4,5-dihydropyrazolo[1,5-a]pyrimidin-7-yl)piperidine-1-carboxylate

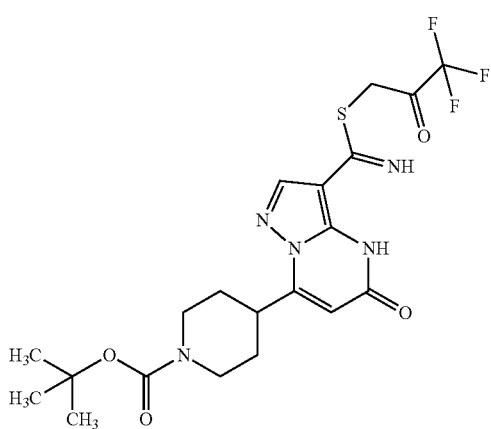 [SMILES: CC(C)(C)OC(=O)N1CCC(c2cc(=O)[nH]c3c(C(=N)SCC(=O)C(F)(F)F)cnn23)CC1]

tert-butyl 4-(3-carbamothioyl-5-oxo-4,5-dihydropyrazolo[1,5-a]pyrimidin-7-yl)piperidine-1-carboxylate (127 mg, 336 μmol), 3-bromo-1,1,1-trifluoropropan-2-one (35 μl, 340 μmol), and N,N-Diisopropylethylamine (290 μl, 1.7 mmol) were dissolved in Ethanol (5.1 ml, 87 mmol) and stirred at 70° C. for 1 h. The mixture was purified via reverse phase HPLC (Method: column: Reprosil C18; 10 μm; 125×30 mm/flow: 50 ml/min/solvents: A=water (0.1% formic acid), B=acetonitrile/gradient: 0.00-4.25 min=20% B, 4.50 min=30% B, 19.00-22.50 min=100% B, 22.75-25.00 min=20% B) to afford the product. The obtained amount was 59.0 mg (100% purity, 36% of theory).

LC-MS (Method 1B): $R_t$=1.04 min; MS (ESIpos): m/z=488 [M+H]$^+$

Example 430A

Tert-butyl 4-{5-oxo-3-[4-(trifluoromethyl)-1,3-thiazol-2-yl]-4,5-dihydropyrazolo[1,5-a]pyrimidin-7-yl}piperidine-1-carboxylate

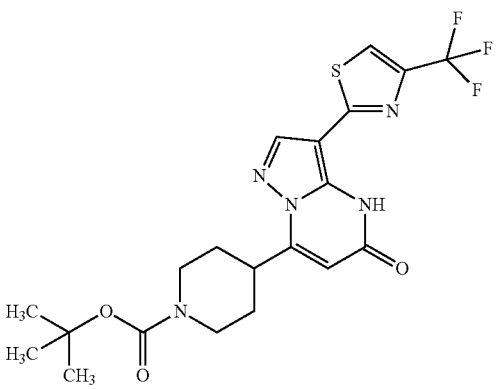 [SMILES: CC(C)(C)OC(=O)N1CCC(c2cc(=O)[nH]c3c(-c4nc(C(F)(F)F)cs4)cnn23)CC1]

tert-butyl 4-(5-oxo-3-{[(3,3,3-trifluoro-2-oxopropyl)sulfanyl]carbonoimidoyl}-4,5-dihydropyrazolo[1,5-a]pyrimidin-7-yl)piperidine-1-carboxylate (58.0 mg, 119 μmol), Burgess reagent (39.7 mg, 167 μmol) were dissolved in Tetrahydrofuran (2.6 ml, 32 mmol) and stirred at RT for 2 d. The mixture was heated to 70° C. for 1 h. More Burgess reagent (1 equivalent) was added, and the mixture was stirred at 70° C. for 20 h. The mixture was purified via reverse phase HPLC (Method: column: Reprosil C18; 10 μm; 125×30 mm/flow: 50 ml/min/solvents: A=water (0.1% formic acid), B=acetonitrile/gradient: 0.00-4.25 min=20% B, 4.50 min=30% B, 19.00-22.50 min=100% B, 22.75-25.00 min=20% B) to afford the product. The obtained amount was 35.2 mg (100% purity, 63% of theory).

LC-MS (Method 11B): $R_t$=2.15 min; MS (ESIneg): m/z=468 [M−H]$^-$

Example 431A

Tert-butyl 4-[3-(1H-imidazol-1-ylcarbonyl)-5-oxo-4,5-dihydropyrazolo[1,5-a]pyrimidin-7-yl]piperidine-1-carboxylate

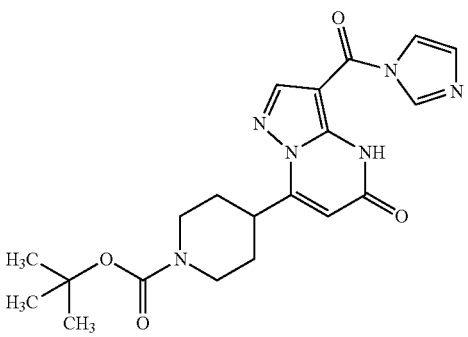 [SMILES: CC(C)(C)OC(=O)N1CCC(c2cc(=O)[nH]c3c(C(=O)n4ccnc4)cnn23)CC1]

7-[1-(tert-butoxycarbonyl)piperidin-4-yl]-5-oxo-4,5-dihydropyrazolo[1,5-a]pyrimidine-3-carboxylic acid (1.00 g, 2.76 mmol) and di-1H-imidazol-1-ylmethanone (895 mg, 5.52 mmol) were dissolved in Tetrahydrofurane (20 ml, 250 mmol). The mixture was stirred at 80° C. for 30 min. Ethyl acetate was added and the resulting precipitate was filtered, washed with Ethyl acetate and dried in vacuo to afford the title compound (746 mg, 100% purity, 66% of theory).

LC-MS (Method 11B): $R_t$=1.42 min; MS (ESIpos): m/z=413 [M+H]$^+$

Example 432A 3-fluoropropyl 7-[1-(tert-butoxycarbonyl)piperidin-4-yl]-5-oxo-4,5-dihydropyrazolo[1,5-a]pyrimidine-3-carboxylate

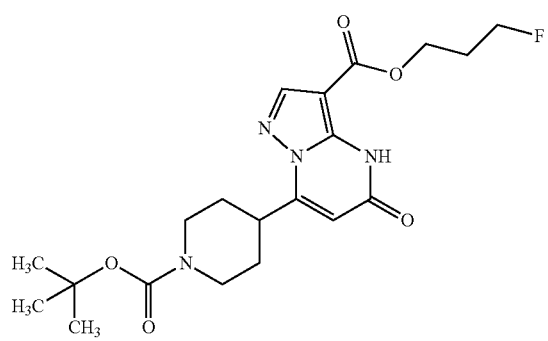 [SMILES: CC(C)(C)OC(=O)N1CCC(c2cc(=O)[nH]c3c(C(=O)OCCCF)cnn23)CC1]

tert-butyl 4-[3-(1H-imidazol-1-ylcarbonyl)-5-oxo-4,5-di-hydropyrazolo[1,5-a]pyrimidin-7-yl]piperidine-1-carboxylate (100 mg, 242 μmol) was dissolved in 3-fluoropropan-1-ol (947 mg, 12.1 mmol) and heated at 110° C. for 1 h. The solvent was removed and then Ethyl acetate and water were added. The organic phase was washed with water, dried via filtration (Extrelut NT3) and in vacuo. The obtained amount of product was 88.2 mg (100% purity, 86% of theory).

LC-MS (Method 11B): $R_t$=1.81 min; MS (ESIneg): m/z=421 [M–H]⁻

Example 433A 2,2-difluoroethyl 7-[1-(tert-butoxycarbonyl)piperidin-4-yl]-5-oxo-4,5-dihydropyrazolo[1,5-a]pyrimidine-3-carboxylate

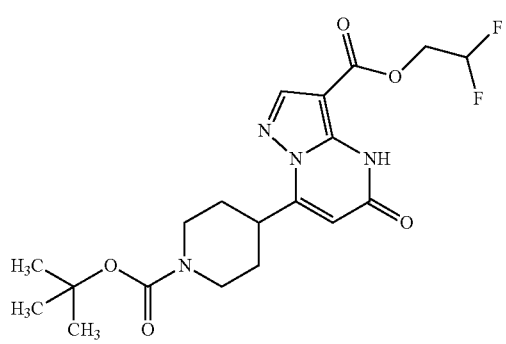 [SMILES: CC(C)(C)OC(=O)N1CCC(c2cc(=O)[nH]c3c(C(=O)OCC(F)F)cnn23)CC1]

tert-butyl 4-[3-(1H-imidazol-1-ylcarbonyl)-5-oxo-4,5-di-hydropyrazolo[1,5-a]pyrimidin-7-yl]piperidine-1-carboxylate (100 mg, 242 μmol) was dissolved in 2,2-difluoroethanol (398 mg, 4.85 mmol) and heated at reflux for 1 h. The solvent was removed and then Ethyl acetate and water were added. The organic phase was washed with water, dried via filtration (Extrelut NT3) and in vacuo. The obtained amount of product was 94.6 mg (100% purity, 92% of theory).

LC-MS (Method 11B): $R_t$=1.81 min; MS (ESIneg): m/z=425 [M–H]⁻

Example 434A 2,2,2-trifluoroethyl 7-[1-(tert-butoxycarbonyl)piperidin-4-yl]-5-oxo-4,5-dihydropyrazolo[1,5-a]pyrimidine-3-carboxylate

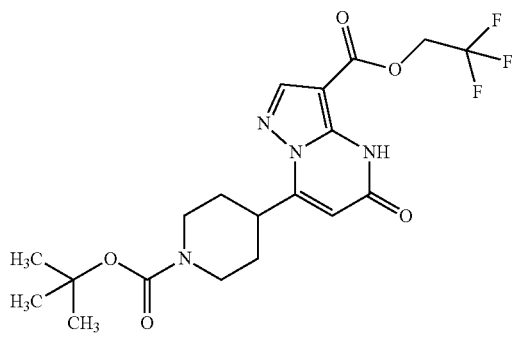 [SMILES: CC(C)(C)OC(=O)N1CCC(c2cc(=O)[nH]c3c(C(=O)OCC(F)(F)F)cnn23)CC1]

tert-butyl 4-[3-(1H-imidazol-1-ylcarbonyl)-5-oxo-4,5-di-hydropyrazolo[1,5-a]pyrimidin-7-yl]piperidine-1-carboxylate (100 mg, 242 μmol) was dissolved in 2,2,2-trifluoroethanol (485 mg, 4.85 mmol) and heated at reflux for 1 h. The solvent was removed and then Ethyl acetate and water were added. The organic phase was washed with water, dried via filtration (Extrelut NT3) and in vacuo. The obtained amount of product was 118 mg (90% purity, 99% of theory).

LC-MS (Method 11B): $R_t$=1.94 min; MS (ESIneg): m/z=443 [M–H]⁻

Example 435A 3,3,3-trifluoropropyl 7-[1-(tert-butoxycarbonyl)piperidin-4-yl]-5-oxo-4,5-dihydropyrazolo[1,5-a]pyrimidine-3-carboxylate

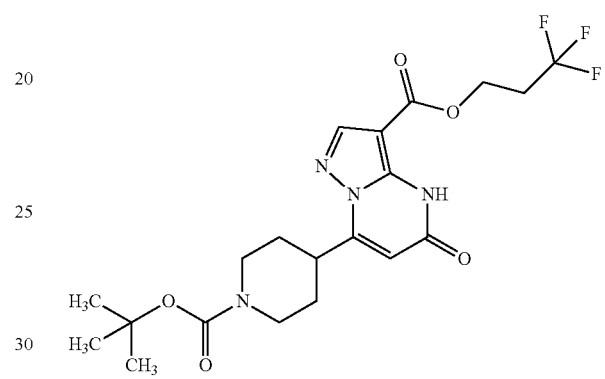

tert-butyl 4-[3-(1H-imidazol-1-ylcarbonyl)-5-oxo-4,5-di-hydropyrazolo[1,5-a]pyrimidin-7-yl]piperidine-1-carboxylate (100 mg, 242 μmol) was dissolved in 3,3,3-trifluoropropan-1-ol (553 mg, 4.85 mmol) and heated at reflux for 1 h. The solvent was removed and then Ethyl acetate and water were added. The organic phase was washed with water, dried via filtration (Extrelut NT3) and in vacuo. The obtained amount of product was 79.7 mg (100% purity, 72% of theory).

LC-MS (Method 11B): $R_t$=1.96 min; MS (ESIneg): m/z=457 [M–H]⁻

Example 436A

Cyclobutyl 7-[1-(tert-butoxycarbonyl)piperidin-4-yl]-5-oxo-4,5-dihydropyrazolo[1,5-a]pyrimidine-3-carboxylate

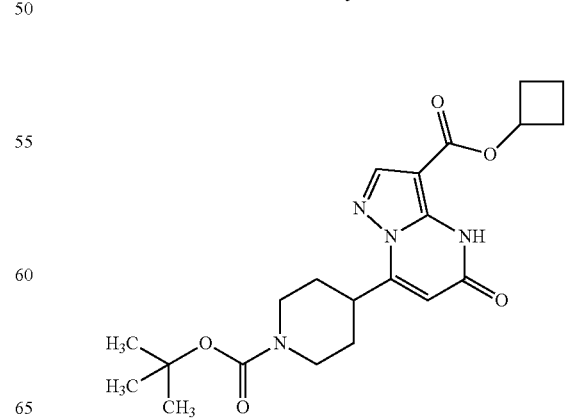

tert-butyl 4-[3-(1H-imidazol-1-ylcarbonyl)-5-oxo-4,5-dihydropyrazolo[1,5-a]pyrimidin-7-yl]piperidine-1-carboxylate (100 mg, 242 μmol) was dissolved in cyclobutanol (950 μl, 12 mmol) and heated at 110° C. for 1 h. The solvent was removed and then Ethyl acetate and water were added. The organic phase was washed with water, dried via filtration (Extrelut NT3) and in vacuo. The obtained amount of product was 131 mg (75% purity, 97% of theory).

LC-MS (Method 11B): $R_t$=2.04 min; MS (ESIneg): m/z=415 [M–H]⁻

Example 437A

Methyl 7-[1-(tert-butoxycarbonyl)piperidin-4-yl]-5-oxo-4,5-dihydropyrazolo[1,5-a]pyrimidine-3-carboxylate

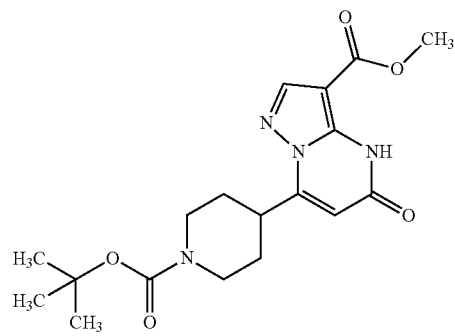

tert-butyl 4-[3-(1H-imidazol-1-ylcarbonyl)-5-oxo-4,5-dihydropyrazolo[1,5-a]pyrimidin-7-yl]piperidine-1-carboxylate (100 mg, 242 μmol) was dissolved in methanol (5.0 ml, 120 mmol) and heated at reflux for 16 h. The precipitate was filtered, washed with methanol, and dried in vacuo. The obtained amount of product was 83.7 mg (100% purity, 92% of theory).

LC-MS (Method 11B): $R_t$=1.68 min; MS (ESIneg): m/z=375 [M–H]⁻

Example 438A

Propyl 7-[1-(tert-butoxycarbonyl)piperidin-4-yl]-5-oxo-4,5-dihydropyrazolo[1,5-a]pyrimidine-3-carboxylate

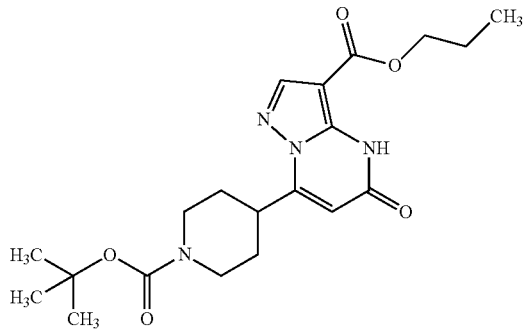 [SMILES: CCCOC(=O)c1cnn2c(C3CCN(C(=O)OC(C)(C)C)CC3)cc(=O)[nH]c12]

tert-butyl 4-[3-(1H-imidazol-1-ylcarbonyl)-5-oxo-4,5-dihydropyrazolo[1,5-a]pyrimidin-7-yl]piperidine-1-carboxylate (100 mg, 242 μmol) was dissolved in n-propanol (5.0 ml, 67 mmol) and heated at reflux for 16 h. The solvent was removed and then Ethyl acetate and water were added. The organic phase was washed with water, dried via filtration (Extrelut NT3) and in vacuo. The obtained amount of product was 97.9 mg (100% purity, 100% of theory).

LC-MS (Method 11B): $R_t$=2.00 min; MS (ESIneg): m/z=403 [M–H]⁻

Example 439A

Tert-butyl 4-[3-(7-oxa-1-azaspiro[3.5]non-1-ylcarbonyl)-5-oxo-4,5-dihydropyrazolo[1,5-a]pyrimidin-7-yl]piperidine-1-carboxylate

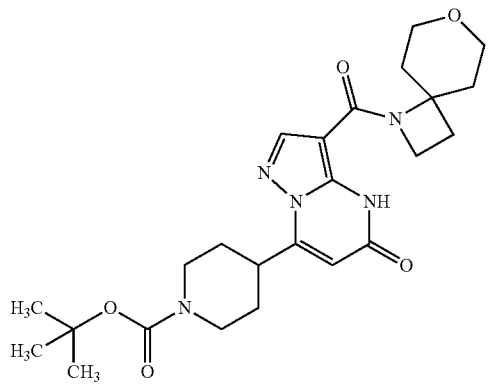 [SMILES: CC(C)(C)OC(=O)N1CCC(c2cc(=O)[nH]c3c(C(=O)N4CCC45CCOCC5)cnn23)CC1]

To a solution of 7-[1-(tert-butoxycarbonyl)piperidin-4-yl]-5-oxo-4,5-dihydropyrazolo[1,5-a]pyrimidine-3-carboxylic acid (150 mg, 414 μmol) in dimethylformamide (1.5 ml, 19 mmol) were added HATU (205 mg, 538 μmol) and N,N-Diisopropylethylamine (220 μl, 1.2 mmol). Then 7-oxa-1-azaspiro[3.5]nonane (105 mg, 828 μmol) was added and the reaction mixture was stirred at RT for 16 h. More HATU (1.3 equivalents) was added and the reaction mixture was stirred at RT for 2 h. Water was added and the mixture was purified by preparative HPLC (Method: column: Reprosil C18; 10 μm; 125×30 mm/flow: 50 ml/min/solvents: A=water (0.01% formic acid), B=acetonitrile/gradient: 0.00-2.00 min=20% B, 2.20 min=60% B, 8.00-12.00 min=90% B, 12.10-13.00 min=20% B). Evaporation of the combined product fractions yielded the title compound (66.1 mg, 98% purity, 33% of theory).

LC-MS (Method 1B): $R_t$=0.94 min; MS (ESIpos): m/z=472 [M+H]⁺

Example 440A

Tert-butyl 4-(3-{methyl[(1S)-1-phenylethyl]carbamoyl}-5-oxo-4,5-dihydropyrazolo[1,5-a]pyrimidin-7-yl)piperidine-1-carboxylate

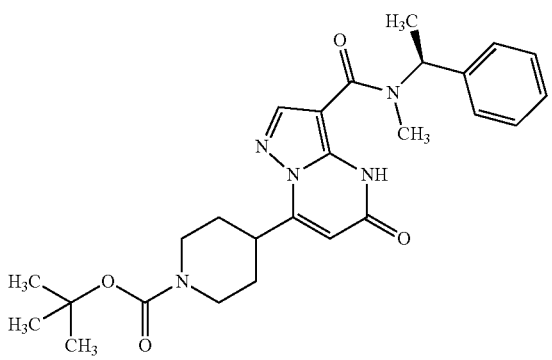 [SMILES: C[C@@H](c1ccccc1)N(C)C(=O)c1cnn2c(C3CCN(C(=O)OC(C)(C)C)CC3)cc(=O)[nH]c12]

To a solution of 7-[1-(tert-butoxycarbonyl)piperidin-4-yl]-5-oxo-4,5-dihydropyrazolo[1,5-a]pyrimidine-3-carboxylic acid (150 mg, 414 µmol) in dimethylformamide (1.5 ml, 19 mmol) were added HATU (205 mg, 538 µmol) and N,N-Diisopropylethylamine (220 µl, 1.2 mmol). Then (1S)-N-methyl-1-phenylethanamine (112 mg, 828 µmol) was added and the reaction mixture was stirred at RT for 16 h. More HATU (1.3 equivalents) was added and the reaction mixture was stirred at RT for 2 h. Water was added and the mixture was purified by preparative HPLC (Method: column: Reprosil C18; 10 µm; 125×30 mm/flow: 50 ml/min/solvents: A=water (0.01% formic acid), B=acetonitrile/gradient: 0.00-2.00 min=20% B, 2.20 min=60% B, 8.00-12.00 min=90% B, 12.10-13.00 min=20% B).

Evaporation of the combined product fractions yielded the title compound (88.3 mg, 96% purity, 43% of theory).

LC-MS (Method 1B): $R_t$=1.14 min; MS (ESIpos): m/z=480 [M+H]$^+$

Example 441A

Tert-butyl 4-{3-[methyl(pyridin-2-ylmethyl)carbamoyl]-5-oxo-4,5-dihydropyrazolo[1,5-a]pyrimidin-7-yl}piperidine-1-carboxylate

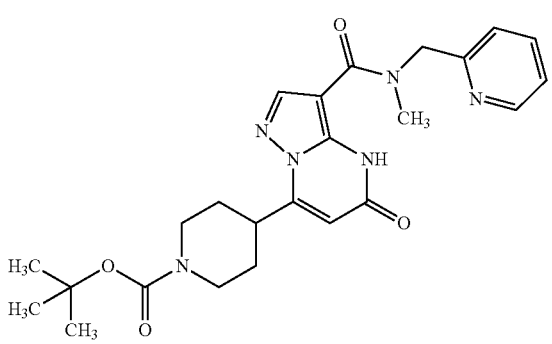

To a solution of 7-[1-(tert-butoxycarbonyl)piperidin-4-yl]-5-oxo-4,5-dihydropyrazolo[1,5-a]pyrimidine-3-carboxylic acid (150 mg, 414 µmol) in dimethylformamide (1.5 ml, 19 mmol) were added HATU (205 mg, 538 µmol) and N,N-Diisopropylethylamine (220 µl, 1.2 mmol). Then N-methyl-1-(pyridin-2-yl)methanamine (101 mg, 828 µmol) was added and the reaction mixture was stirred at RT for 16 h. More HATU (1.3 equivalents) was added and the reaction mixture was stirred at RT for 2 h. Water was added and the mixture was purified by preparative HPLC (Method: column: Reprosil C18; 10 µm; 125×30 mm/flow: 50 ml/min/solvents: A=water (0.01% formic acid), B=acetonitrile/gradient: 0.00-2.00 min=20% B, 2.20 min=60% B, 8.00-12.00 min=90% B, 12.10-13.00 min=20% B). Evaporation of the combined product fractions yielded the title compound (128 mg, 98% purity, 65% of theory).

LC-MS (Method 1B): $R_t$=0.85 min; MS (ESIpos): m/z=467 [M+H]$^+$

Example 442A

Tert-butyl 4-{3-[(4,4-difluoropiperidin-1-yl)carbonyl]-5-oxo-4,5-dihydropyrazolo[1,5-a]pyrimidin-7-yl}piperidine-1-carboxylate

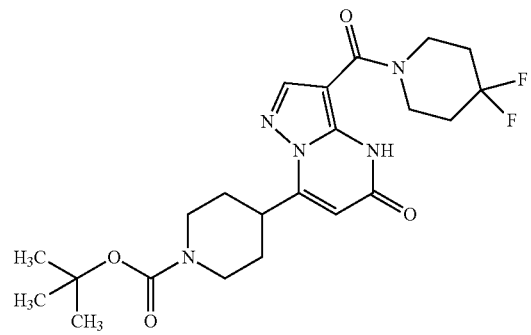 [SMILES: CC(C)(C)OC(=O)N1CCC(c2cc(=O)[nH]c3c(C(=O)N4CCC(F)(F)CC4)cnn23)CC1]

To a solution of 7-[1-(tert-butoxycarbonyl)piperidin-4-yl]-5-oxo-4,5-dihydropyrazolo[1,5-a]pyrimidine-3-carboxylic acid (150 mg, 414 µmol) in dimethylformamide (1.5 ml, 19 mmol) were added HATU (205 mg, 538 µmol) and N,N-Diisopropylethylamine (220 µl, 1.2 mmol). Then 4,4-difluoropiperidine (100 mg, 828 µmol) was added and the reaction mixture was stirred at RT for 16 h. More HATU (1.3 equivalents) was added and the reaction mixture was stirred at RT for 2 h. Water was added and the mixture was purified by preparative HPLC (Method: column: Reprosil C18; 10 µm; 125×30 mm/flow: 50 ml/min/solvents: A=water (0.01% formic acid), B=acetonitrile/gradient: 0.00-2.00 min=20% B, 2.20 min=60% B, 8.00-12.00 min=90% B, 12.10-13.00 min=20% B). Evaporation of the combined product fractions yielded the title compound (40.7 mg, 92% purity, 20% of theory).

LC-MS (Method 11B): $R_t$=1.73 min; MS (ESIneg): m/z=464 [M−H]$^-$

Example 443A

7-[1-(tert-butoxycarbonyl)piperidin-4-yl]-4-(4-methoxybenzyl)-5-oxo-4,5-dihydropyrazolo[1,5-a]pyrimidine-3-carboxylic Acid

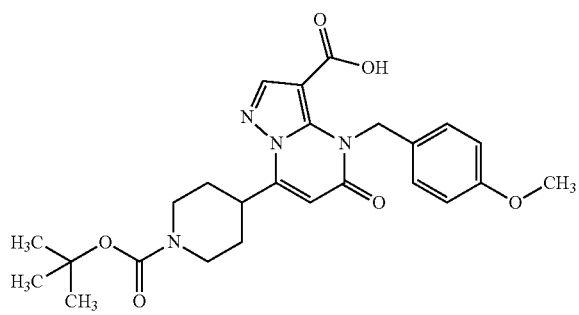 [SMILES: COc1ccc(Cn2c(=O)cc(C3CCN(C(=O)OC(C)(C)C)CC3)n3ncc(C(=O)O)c23)cc1]

ethyl 7-[1-(tert-butoxycarbonyl)piperidin-4-yl]-4-(4-methoxybenzyl)-5-oxo-4,5-dihydropyrazolo[1,5-a]pyrimidine-3-carboxylate (90.0 mg, 176 µmol) and aqueous Lithium hydroxide (350 µl, 1.0 M, 350 µmol) were suspended in Tetrahydrofuran (2.0 ml, 25 mmol). The mixture was stirred at RT for 16 h. Another 2 equivalents of the Lithium hydroxide solution were added and the mixture was stirred for 3 d. Another 2 equivalents of the Lithium hydroxide solution were added and the mixture was stirred for 16 h. Solvents were removed, then water and acetonitrile were added. The mixture was purified by preparative HPLC (Method: column: Reprosil C18; 10 µm; 125×30 mm/flow: 50 ml/min/solvents: A=water (0.01% formic acid), B=acetonitrile/gradient: 0.00-4.25 min=10% B, 4.50 min=20% B, 15.50 min=85% B, 16.00-18.50 min=100% B, 18.75.00-22.00 min=20% B). Evaporation of the combined product fractions yielded the title compound (67.0 mg, 100% purity, 79% of theory).

LC-MS (Method 1B): $R_t$=0.99 min; MS (ESIpos): m/z=483 [M+H]$^+$

Example 444A

Tert-butyl 4-(3-{[(2S)-2-methylpyrrolidin-1-yl]methyl}-5-oxo-4,5-dihydropyrazolo[1,5-a]pyrimidin-7-yl)piperidine-1-carboxylate

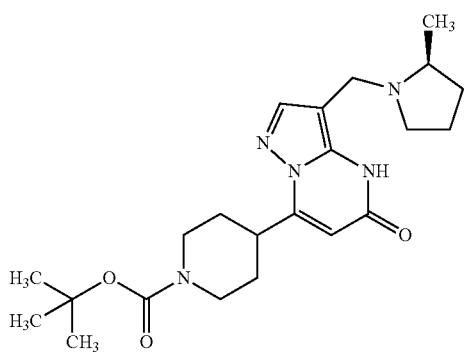 [SMILES: C[C@H]1CCCN1Cc1cnn2c(C3CCN(C(=O)OC(C)(C)C)CC3)cc(=O)[nH]c12]

tert-butyl 4-[3-(hydroxymethyl)-5-oxo-4,5-dihydropyrazolo[1,5-a]pyrimidin-7-yl]piperidine-1-carboxylate (150 mg, 431 µmol) and Triphenylphosphine (430 µl, 1.0 M, 430 µmol) were dissolved in Tetrahydrofuran (5.0 ml, 62 mmol) and cooled to −18° C. N-Bromsuccinimide (76.6 mg, 431 µmol) was added and the mixture was stirred for 5 min at −18° C. (2S)-2-methylpyrrolidine (88.0 mg, 1.03 mmol) was added and stirred for 10 min at RT and then for 1 h at 80° C. Water was added and purified by preparative HPLC (Method: column: Reprosil C18; 10 µm; 125×30 mm/flow: 50 ml/min/solvents: A=water (0.01% formic acid), B=acetonitrile/gradient: 0.00-5.00 min=10% B, 6.50 min=20% B, 17.0-19.75 min=100% B, 19.75.00-23.00 min=90% B). Evaporation of the combined product fractions yielded the title compound (9.2 mg, 100% purity, 5% of theory).

MS (Method 1B): $R_t$=0.67 min; MS (ESIpos): m/z=416 [M+H]$^+$

Example 445A

Cyclobutyl 7-[1-(tert-butoxycarbonyl)piperidin-4-yl]-2-methyl-5-oxo-4,5-dihydropyrazolo[1,5-a]pyrimidine-3-carboxylate

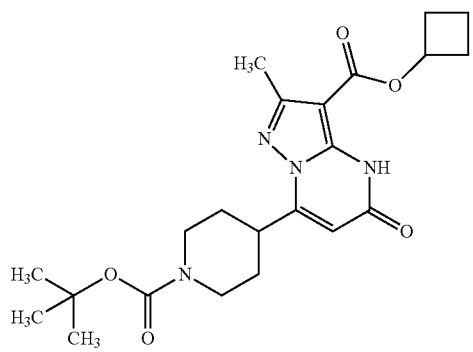 [SMILES: Cc1nn2c(C3CCN(C(=O)OC(C)(C)C)CC3)cc(=O)[nH]c2c1C(=O)OC1CCC1]

7-[1-(tert-butoxycarbonyl)piperidin-4-yl]-2-methyl-5-oxo-4,5-dihydropyrazolo[1,5-a]pyrimidine-3-carboxylic acid (100 mg, 266 µmol) was dissolved in tetrahydrofurane (5.0 ml, 62 mmol) and N,N'-Carbonyldiimidazole (86.2 mg, 531 µmol) was added. The mixture was heated at reflux for 15 min. The solvents were removed in vacuo. Cyclobutanol (95.8 mg, 1.33 mmol) was added and the mixture stirred at RT for 18 h. Solvents were removed and propan-2-ol (5 ml) were added. The mixture was heated at 105° C. for 1 h and then purified by preparative HPLC (Method: column: Reprosil C18; 10 µm; 125×30 mm/flow: 50 ml/min/solvents: A=water (0.01% formic acid), B=acetonitrile/gradient: 0.00-5.00 min=10% B, 6.50 min=20% B, 17.0-19.75 min=100% B, 19.75.00-23.00 min=90% B). Evaporation of the combined product fractions yielded the title compound (132 mg, 100% purity, 59% of theory)

LC-MS (Method 11B): $R_t$=2.20 min; MS (ESIneg): m/z=429 [M−H]$^-$

Example 446A

Propyl 7-[1-(tert-butoxycarbonyl)piperidin-4-yl]-2-methyl-5-oxo-4,5-dihydropyrazolo[1,5-a]pyrimidine-3-carboxylate

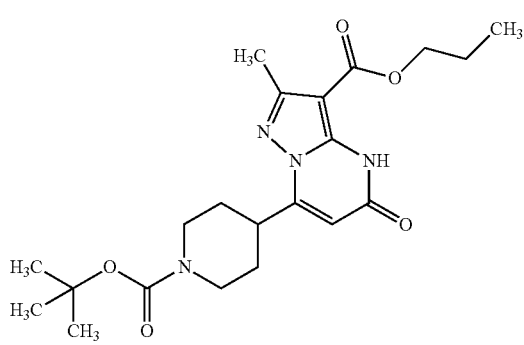 [SMILES: CCCOC(=O)c1c(C)nn2c(C3CCN(C(=O)OC(C)(C)C)CC3)cc(=O)[nH]c12]

7-[1-(tert-butoxycarbonyl)piperidin-4-yl]-2-methyl-5-oxo-4,5-dihydropyrazolo[1,5-a]pyrimidine-3-carboxylic acid (100 mg, 266 µmol) was dissolved in tetrahydrofurane (2.0 ml, 25 mmol) and N,N'-Carbonyldiimidazole (86.2 mg, 531 µmol) was added. The mixture was heated at reflux for 15 min. The solvents were removed in vacuo. Propan-1-ol (79.8 mg, 1.33 mmol) was added and the mixture stirred at RT for 18 h. Solvents were removed and propan-2-ol (5 ml) were added. The mixture was heated at 105° C. for 1 h and then purified by preparative HPLC (Method: column: Reprosil C18; 10 µm; 125×30 mm/flow: 50 ml/min/solvents: A=water (0.01% formic acid), B=acetonitrile/gradient: 0.00-5.00 min=10% B, 6.50 min=20% B, 17.0-19.75 min=100% B, 19.75.00-23.00 min=90% B). Evaporation of the combined product fractions yielded the title compound (88.2 mg, 95% purity, 75% yield of theory).

LC-MS (Method 11B): $R_t$=2.14 min; MS (ESIneg): m/z=417 [M–H]⁻

Example 447A

Propan-2-yl 7-[1-(tert-butoxycarbonyl)piperidin-4-yl]-2-methyl-5-oxo-4,5-dihydropyrazolo[1,5-a]pyrimidine-3-carboxylate

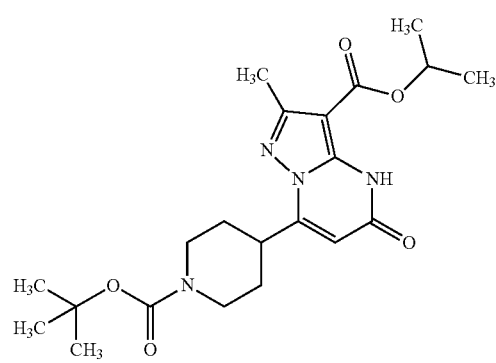 [SMILES: Cc1nn2c(C3CCN(C(=O)OC(C)(C)C)CC3)cc(=O)[nH]c2c1C(=O)OC(C)C]

tert-butyl 4-[3-(1H-imidazol-1-ylcarbonyl)-2-methyl-5-oxo-4,5-dihydropyrazolo[1,5-a]pyrimidin-7-yl]piperidine-1-carboxylate (142 mg, 332 µmol) was dissolved in propan-2-ol (510 µl, 6.6 mmol) and heated at 110° C. for 1 h. The mixture was purified by preparative HPLC (Method: column: Reprosil C18; 10 µm; 125×30 mm/flow: 50 ml/min/solvents: A=water (0.01% formic acid), B=acetonitrile/gradient: 0.00-5.00 min=10% B, 6.50 min=20% B, 17.0-19.75 min=100% B, 19.75.00-23.00 min=90% B). Evaporation of the combined product fractions yielded the title compound (72.9 mg, 100% purity, 52% of theory).

LC-MS (Method 1B): $R_t$=1.16 min; MS (ESIneg): m/z=417 [M–H]⁻

Example 448A 2,2,2-trifluoroethyl 7-[1-(tert-butoxycarbonyl)piperidin-4-yl]-2-methyl-5-oxo-4,5-dihydropyrazolo[1,5-a]pyrimidine-3-carboxylate

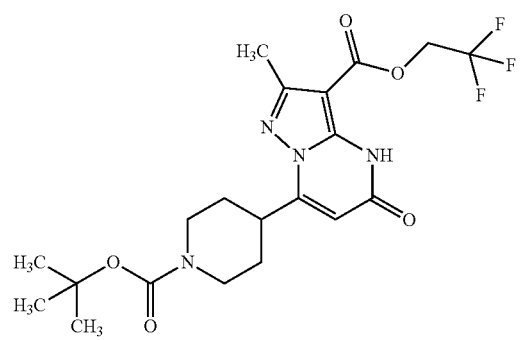 [SMILES: Cc1nn2c(C3CCN(C(=O)OC(C)(C)C)CC3)cc(=O)[nH]c2c1C(=O)OCC(F)(F)F]

tert-butyl 4-[3-(1H-imidazol-1-ylcarbonyl)-2-methyl-5-oxo-4,5-dihydropyrazolo[1,5-a]pyrimidin-7-yl]piperidine-1-carboxylate (142 mg, 332 µmol) was dissolved in 2,2,2-trifluoroethanol (500 µl, 6.6 mmol) and heated at 110° C. for 1 h. The mixture was purified by preparative HPLC (Method: column: Reprosil C18; 10 µm; 125×30 mm/flow: 50 ml/min/solvents: A=water (0.01% formic acid), B=acetonitrile/gradient: 0.00-5.00 min=10% B, 6.50 min=20% B, 17.0-19.75 min=100% B, 19.75.00-23.00 min=90% B). Evaporation of the combined product fractions yielded the title compound (116 mg, 100% purity, 76% of theory).

LC-MS (Method 1B): $R_t$=1.15 min; MS (ESIneg): m/z=457 [M–H]⁻

Example 449A

Ethyl 4-[1-(tert-butoxycarbonyl)piperidin-4-yl]-2-oxo-1,2-dihydroimidazo[1,5-a]pyrimidine-8-carboxylate

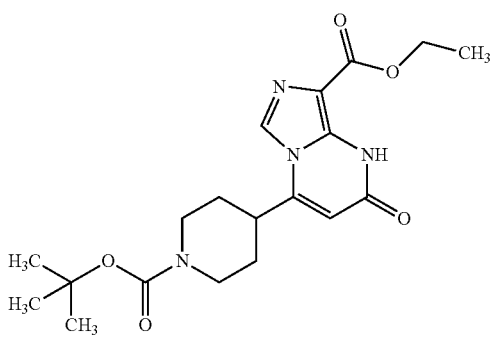 [SMILES: CCOC(=O)c1ncn2c(C3CCN(C(=O)OC(C)(C)C)CC3)cc(=O)[nH]c12]

ethyl 5-amino-1H-imidazole-4-carboxylate (808 mg, 5.21 mmol) and tert-butyl 4-[(2,2-dimethyl-4,6-dioxo-1,3-dioxan-5-yl)carbonyl]piperidine-1-carboxylate (1.85 g, 5.21 mmol) were heated in Acetonitrile (25 ml, 530 mmol) at 60° C. for 1.5 h. The solvents were removed. 1-Methoxy-2-propanol (25 ml, 260 mmol) and Potassium triphosphate (2.21 g, 10.4 mmol) were added and the mixture was heated at reflux for 2 d. Solvents were removed and the residue purified by preparative HPLC (Method: column: Reprosil C18; 10 μm; 125×30 mm/flow: 50 ml/min/solvents: A=water (0.01% formic acid), B=acetonitrile/gradient: 0.00-5.00 min=10% B, 6.50 min=20% B, 17.0-19.75 min=100% B, 19.75.00-23.00 min=90% B). Evaporation of the combined product fractions yielded the title compound (109 mg, 89% purity, 5% of theory).

LC-MS (Method 11B): $R_t$=1.42 min; MS (ESIpos): m/z=391 [M+H]$^+$

Example 450A

Tert-butyl 4-{3-[methoxy(methyl)carbamoyl]-5-oxo-4,5-dihydropyrazolo[1,5-a]pyrimidin-7-yl}piperidine-1-carboxylate

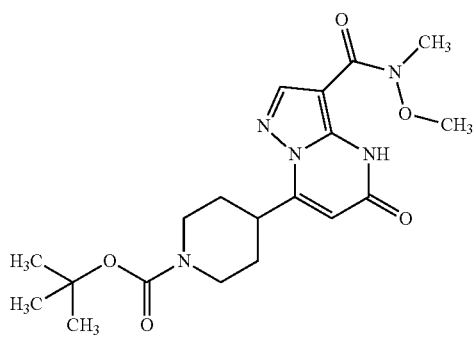 [SMILES: CON(C)C(=O)c1cnn2c(C3CCN(C(=O)OC(C)(C)C)CC3)cc(=O)[nH]c12]

To a solution of 7-[1-(tert-butoxycarbonyl)piperidin-4-yl]-5-oxo-4,5-dihydropyrazolo[1,5-a]pyrimidine-3-carboxylic acid (10.0 g, 27.6 mmol) in acetonitrile (150 mL) were added successively 4-dimethylaminopyridine (135 mg, 1.10 mmol), 1-Hydroxybenzotriazole hydrate (6.34 g, 41.4 mmol), and 1-(3-Dimethylaminopropyl)-3-ethylcarbodiimide hydrochloride (7.94 g, 41.4 mmol). The mixture was stirred 15 min at room temperature before a solution of N-methoxymethanamine hydrochloride (1:1) (6.73 g, 69.0 mmol) and ethyldiisopropylamine (14 ml, 83 mmol) in acetonitrile (20 mL) was added drop wise. The solution was stirred overnight at room temperature, concentrated and diluted with 500 mL of dichloromethane. The organic phase was washed twice with a saturated aqueous solution of sodium hydrogen carbonate and a 1N aqueous solution of hydrochloric acid, before being dried over sodium sulfate and concentrated to yield the title compound. The obtained amount was 10.5 g (91% purity, 85% of theory).

LC-MS (Method 8B): $R_t$=1.18 min; MS (ESIneg): m/z=404 [M−H]$^−$

Example 451A

Tert-butyl 4-(3-acetyl-5-oxo-4,5-dihydropyrazolo[1,5-a]pyrimidin-7-yl)piperidine-1-carboxylate

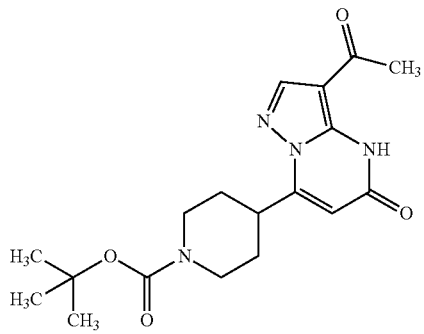

A solution of tert-butyl 4-{3-[methoxy(methyl)carbamoyl]-5-oxo-4,5-dihydropyrazolo[1,5-a]pyrimidin-7-yl}piperidine-1-carboxylate (1.00 g, 94% purity, 2.32 mmol) in THF (10 mL) was added drop wise under argon to a solution of bromo(methyl)magnesium (3.9 ml, 3.0 M in diethyl ether, 12 mmol), which had been prediluted with THF (10 mL) and precooled to 0° C. The ice bath was removed and the mixture was stirred overnight at room temperature. The crude mixture was then diluted with 200 mL of ethyl acetate. The organic phase was washed once with a 5% aqueous solution of sodium hydrogen carbonate and twice with a 1N aqueous hydrochloric acid solution, before being dried over sodium sulfate and concentrated to yield the title compound. The obtained amount was 690 mg (96% purity, 79% of theory).

LC-MS (Method 11B): $R_t$=1.52 min; MS (ESIneg): m/z=359 [M−H]$^−$

Example 452A

Tert-butyl 4-[3-(2-bromopropanoyl)-5-oxo-4,5-dihydropyrazolo[1,5-a]pyrimidin-7-yl]piperidine-1-carboxylate

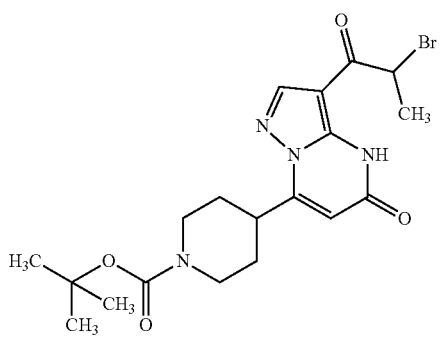 [SMILES: CC(Br)C(=O)c1cnn2c(C3CCN(C(=O)OC(C)(C)C)CC3)cc(=O)[nH]c12]

To a solution of tert-butyl 4-(5-oxo-3-propanoyl-4,5-dihydropyrazolo[1,5-a]pyrimidin-7-yl)piperidine-1-carboxylate (100 mg, 267 µmol) in tetrahydrofuran (6.0 ml) at room temperature was added pyridinium tribromide (85.4 mg, 267 µmol). The mixture was stirred 48 h at room temperature before being dissolved in acetonitrile (10 ml) and water (1.0 ml). The solution was purified by preparative HPLC (gradient acetonitrile/water with 0.1% formic acid). Evaporation of the combined product fractions yielded the title compound. The obtained amount was 44.0 mg (94% purity, 34% of theory).

LC-MS (Method 1B): $R_t$=1.00 min; MS (ESIneg): m/z=451 [M–H]⁻

Example 453A

Tert-butyl 4-(5-[(4-methoxybenzyl)oxy]-3-{4-methyl-2-[4-(trifluoromethyl)phenyl]-1,3-thiazol-5-yl}pyrazolo[1,5-a]pyrimidin-7-yl)piperidine-1-carboxylate

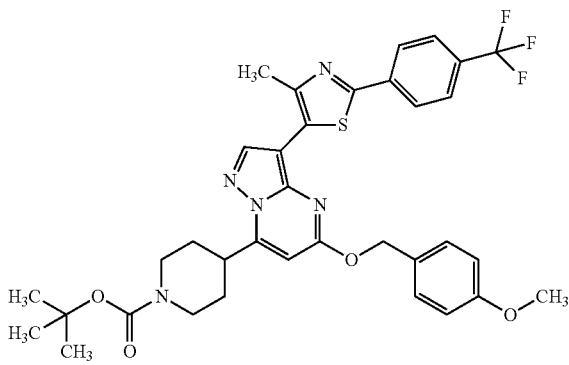 [SMILES: COc1ccc(COc2cc(C3CCN(C(=O)OC(C)(C)C)CC3)n3ncc(-c4sc(-c5ccc(C(F)(F)F)cc5)nc4C)c3n2)cc1]

To a suspension of tert-butyl 4-{3-bromo-5-[(4-methoxybenzyl)oxy]pyrazolo[1,5-a]pyrimidin-7-yl}piperidine-1-carboxylate (50.0 mg, 96.6 µmol) in 1,4-dioxan (2.0 ml) were added 4-methyl-5-(4,4,5,5-tetramethyl-1,3,2-dioxaborolan-2-yl)-2-[4-(trifluoromethyl)phenyl]-1,3-thiazole (42.8 mg, 116 µmol), tripotassium phosphate (290 µL, 1.0 M in water, 290 µmol) and XPhos Pd G3 (4.09 mg, 4.83 µmol).

The mixture was degased with argon for 2 min and stirred 1 h at 110° C. After cooling to room temperature, the mixture was purified by preparative HPLC (gradient acetonitrile/water with 0.1% formic acid). Evaporation of the combined product fractions yielded the title compound. The obtained amount was 55.8 mg (100% purity, 85% of theory).

LC-MS (Method 11B): $R_t$=3.17 min; MS (ESIpos): m/z=680 [M+H]⁺

Example 454A

Tert-butyl 4-{3-acetyl-5-[(4-methoxybenzyl)oxy]pyrazolo[1,5-a]pyrimidin-7-yl}piperidine-1-carboxylate

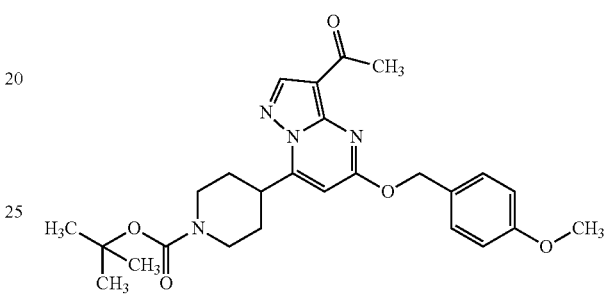

To a solution of tert-butyl 4-(3-acetyl-5-oxo-4,5-dihydropyrazolo[1,5-a]pyrimidin-7-yl)piperidine-1-carboxylate (250 mg, 694 µmol) in N,N-Dimethylformamide (25 ml) under argon were added potassium carbonate (144 mg, 1.04 mmol) and 1-(chloromethyl)-4-methoxybenzene (339 µL, 694 µmol). The mixture was stirred overnight at room temperature and filtered on a micro filter before being purified by preparative HPLC (gradient acetonitrile/water with 0.1% formic acid). Evaporation of the combined product fractions yielded the title compound. The obtained amount was 218 mg (100% purity, 65% of theory).

LC-MS (Method 11B): $R_t$=2.35 min; MS (ESIneg): m/z=479 [M–H]⁻

Example 455A

Tert-butyl 4-(5-oxo-3-propanoyl-4,5-dihydropyrazolo[1,5-a]pyrimidin-7-yl)piperidine-1-carboxylate

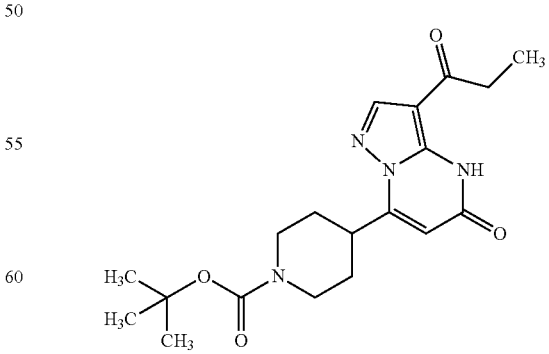

A solution of tert-butyl 4-{3-[methoxy(methyl)carbamoyl]-5-oxo-4,5-dihydropyrazolo[1,5-a]pyrimidin-7-yl}piperidine-1-carboxylate (1.00 g, 94% purity, 2.32 mmol)

in THF (10 mL) was added drop wise under argon to a solution of bromo(ethyl)magnesium (7.0 ml, 1.0 M in THF, 7.0 mmol), which had been prediluted with THF (10 mL) and precooled to 0° C. The ice bath was removed and the mixture was stirred overnight at room temperature. The mixture was cooled again to 0° C., another portion of bromo(ethyl)magnesium (2.3 ml, 1.0 M in THF, 2.3 mmol) was added drop wise and the stirring was continued at room temperature over 2 days. The crude mixture was then diluted with 200 mL of ethyl acetate. The organic phase was washed once with a 5% aqueous solution of sodium hydrogen carbonate and twice with a 1N aqueous hydrochloric acid solution, before being dried over sodium sulfate and concentrated to yield the title compound. The obtained amount was 570 mg (91% purity, 60% of theory).

LC-MS (Method 11B): $R_t$=1.74 min; MS (ESIneg): m/z=373 [M−H]⁻

Example 456A

Tert-butyl 4-{5-[(4-methoxybenzyl)oxy]-3-(2-phenyl-1,3-oxazol-4-yl)pyrazolo[1,5-a]pyrimidin-7-yl}piperidine-1-carboxylate

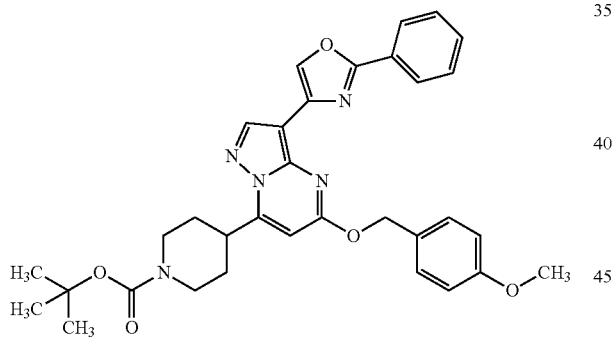

tert-butyl 4-{3-bromo-5-[(4-methoxybenzyl)oxy]pyrazolo[1,5-a]pyrimidin-7-yl}piperidine-1-carboxylate (200 mg, 387 μmol)

2-phenyl-4-(4,4,5,5-tetramethyl-1,3,2-dioxaborolan-2-yl)-1,3-oxazole (126 mg, 464 μmol) XPhos Pd G3 (16.4 mg, 19.3 μmol)

1,4-dioxan (3.5 ml) Tripotassium phosphate (1.2 ml, 1.0 M in water, 1.2 mmol)

The title compound was prepared according to the same procedure as Example 451A. The obtained amount was 146 mg (100% purity, 65% of theory).

LC-MS (Method 1B): $R_t$=1.52 min; MS (ESIpos): m/z=582 [M+H]⁺

Example 457A

Tert-butyl 4-(2-bromo-3-cyano-5-oxo-4,5-dihydropyrazolo[1,5-a]pyrimidin-7-yl)piperidine-1-carboxylate

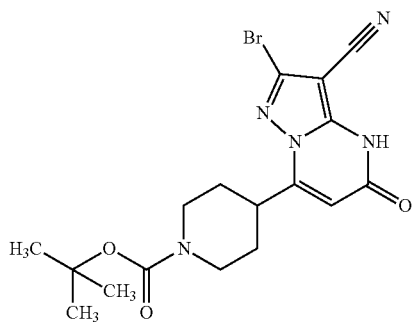 [SMILES: CC(C)(C)OC(=O)N1CCC(c2cc(=O)[nH]c3c(C#N)c(Br)nn23)CC1]

A mixture of 5-amino-3-bromo-1H-pyrazole-4-carbonitrile (3.00 g, 16.0 mmol) and tert-butyl 4-[(2,2-dimethyl-4,6-dioxo-1,3-dioxan-5-yl)carbonyl]piperidine-1-carboxylate (6.27 g, 17.6 mmol) in acetonitrile (200 ml) was stirred under argon overnight at 60° C. and then concentrated. The 1-Methoxy-2-propanol (200 ml) and tripotassium phosphate (6.81 g, 32.1 mmol) were added, and the resulting mixture was stirred for 2 h at 110° C. before being concentrated. The recovered crude mixture was diluted in a mixture of acetonitrile and dimethyl sulfoxide, and purified by preparative HPLC (gradient acetonitrile/water with 0.1% formic acid). Evaporation of the acetonitrile from the combined product fractions induced the precipitation of a solid (in the aqueous phase), which was filtered and dried under high vacuum to yield the title compound. The obtained amount was 5.35 g (100% purity, 79% of theory).

LC-MS (Method 1B): $R_t$=0.97 min; MS (ESIneg): m/z=420 [M−H]⁻

Example 458A

Tert-butyl 4-{5-[(4-methoxybenzyl)oxy]-3-(1,2-thiazol-5-yl)pyrazolo[1,5-a]pyrimidin-7-yl}piperidine-1-carboxylate

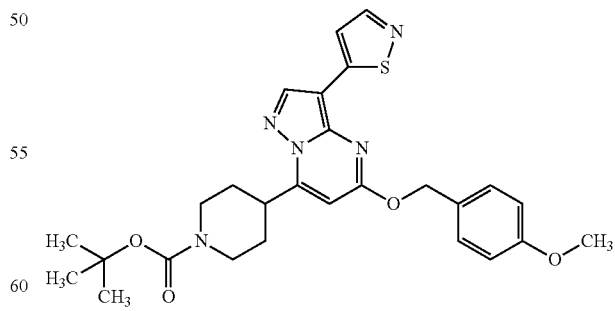

To a suspension of tert-butyl 4-{3-bromo-5-[(4-methoxybenzyl)oxy]pyrazolo[1,5-a]pyrimidin-7-yl}piperidine-1-carboxylate (100 mg, 193 μmol) in 1,4-dioxan (4.0 ml) were added 5-(4,4,5,5-tetramethyl-1,3,2-dioxaborolan-2-yl)-1,2-thiazole (81.6 mg, 387 μmol), tripotassium phosphate (970

μL, 1.0 M in water, 970 μmol) and XPhos Pd G3 (4.09 mg, 4.83 μmol). The mixture was degased with argon for 2 min and stirred overnight at 110° C. A new portion of 5-(4,4,5,5-tetramethyl-1,3,2-dioxaborolan-2-yl)-1,2-thiazole (81.6 mg, 387 μmol) and XPhos Pd G3 (4.09 mg, 4.83 μmol) was added and the mixture was stirred for 2 h at 110° C. A last portion of 5-(4,4,5,5-tetramethyl-1,3,2-dioxaborolan-2-yl)-1,2-thiazole (81.6 mg, 387 μmol) and XPhos Pd G3 (4.09 mg, 4.83 μmol) was added and the mixture was stirred overnight at 80° C. and 1 h more at 110° C. After cooling to room temperature, the mixture was purified by preparative HPLC (gradient acetonitrile/water with 0.1% formic acid). Evaporation of the combined product fractions yielded the title compound. The obtained amount was 26.0 mg (100% purity, 26% of theory).

LC-MS (Method 8B): $R_t$=1.67 min; MS (ESIpos): m/z=522 [M+H]$^+$

Example 459A

Tert-butyl 4-{5-[(4-methoxybenzyl)oxy]-3-(1-methyl-1H-pyrazol-5-yl)pyrazolo[1,5-a]pyrimidin-7-yl}piperidine-1-carboxylate

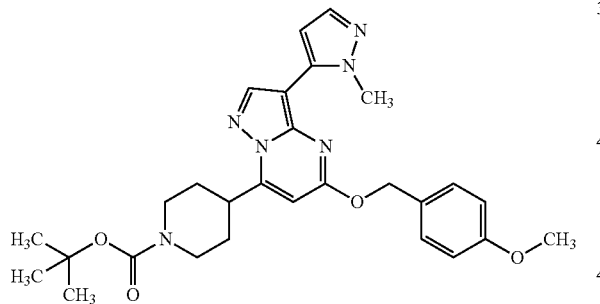

To a suspension of tert-butyl 4-{3-bromo-5-[(4-methoxybenzyl)oxy]pyrazolo[1,5-a]pyrimidin-7-yl}piperidine-1-carboxylate (300 mg, 580 μmol) in 1,4-dioxan (12 ml) were added 1-methyl-5-(4,4,5,5-tetramethyl-1,3,2-dioxaborolan-2-yl)-1H-pyrazole (145 mg, 696 μmol), tripotassium phosphate (1.7 ml, 1.0 M in water, 1.7 mmol) and XPhos Pd G3 (24.5 mg, 29.0 μmol). The mixture was degased with argon for 2 min and stirred 1 h at 100° C. After cooling to room temperature, the mixture was purified by preparative HPLC (gradient acetonitrile/water with 0.1% formic acid). Evaporation of the combined product fractions yielded the title compound. The obtained amount was 200 mg (97% purity, 65% of theory).

LC-MS (Method 8B): $R_t$=1.57 min; MS (ESIpos): m/z=519 [M+H]$^+$

Example 460A

Tert-butyl 4-{5-[(4-methoxybenzyl)oxy]-3-[2-(morpholin-4-yl)-1,3-thiazol-5-yl]pyrazolo[1,5-a]pyrimidin-7-yl}piperidine-1-carboxylate

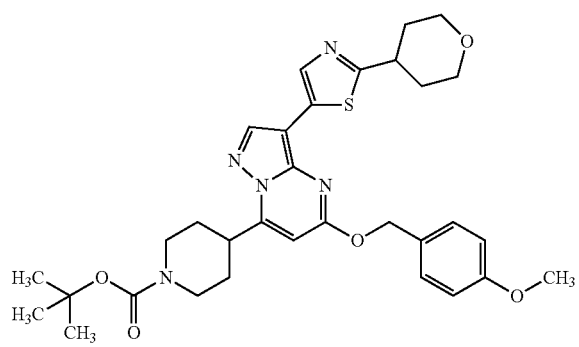 [SMILES: COc1ccc(COc2cc(C3CCN(C(=O)OC(C)(C)C)CC3)n3ncc(-c4cnc(C5CCOCC5)s4)c3n2)cc1]

tert-butyl 4-{3-bromo-5-[(4-methoxybenzyl)oxy]pyrazolo[1,5-a]pyrimidin-7-yl}piperidine-1-carboxylate (100 mg, 193 μmol)
4-[5-(4,4,5,5-tetramethyl-1,3,2-dioxaborolan-2-yl)-1,3-thiazol-2-yl]morpholine (68.7 mg, 232 μmol) XPhos Pd G3 (8.18 mg, 9.66 μmol)
1,4-dioxan (4.0 ml) Tripotassium phosphate (580 μl, 1.0 M in water, 580 μmol)

The title compound was prepared according to the same procedure as Example 457A. The obtained amount was 74.0 mg (100% purity, 63% of theory).

LC-MS (Method 1B): $R_t$=1.40 min; MS (ESIpos): m/z=607 [M+H]$^+$

Example 461A

Tert-butyl 4-[3-(2,2-dimethylbutanimidoyl)-5-oxo-4,5-dihydropyrazolo[1,5-a]pyrimidin-7-yl]piperidine-1-carboxylate

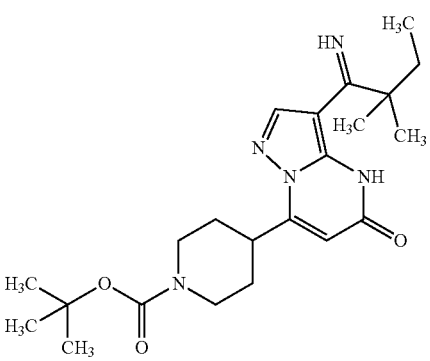 [SMILES: CCC(C)(C)C(=N)c1cnn2c(C3CCN(C(=O)OC(C)(C)C)CC3)cc(=O)[nH]c12]

A solution of tert-butyl 4-(3-cyano-5-oxo-4,5-dihydropyrazolo[1,5-a]pyrimidin-7-yl)piperidine-1-carboxylate (200 mg, 582 μmol) and chloro(2-methylbutan-2-yl)magnesium (2.9 ml, 1.0 M in diethyl ether, 2.9 mmol) in tetrahydrofuran (1.0 ml) was stirred overnight at room temperature under argon. The reaction was stirred at 40° C. one more night before being diluted and stirred with ethyl acetate and hydrochloric acid (1N solution in water). The organic phase was extracted, dried over sodium sulfate and concentrated. The mixture was purified twice by preparative HPLC (gradient acetonitrile/water with 0.1% formic acid). Fractions containing the imine (title compound) or the corresponding ketone were combined, evaporated and used in the next step (26.0 mg).

LC-MS (Method 8B): $R_t$=1.15 min; MS (ESIneg): m/z=414 [M–H]⁻

Example 462A

Tert-butyl 4-{3-[N'-hydroxy-N-(3-methylbutanoyl)carbamimidoyl]-5-oxo-4,5-dihydropyrazolo[1,5-a]pyrimidin-7-yl}piperidine-1-carboxylate

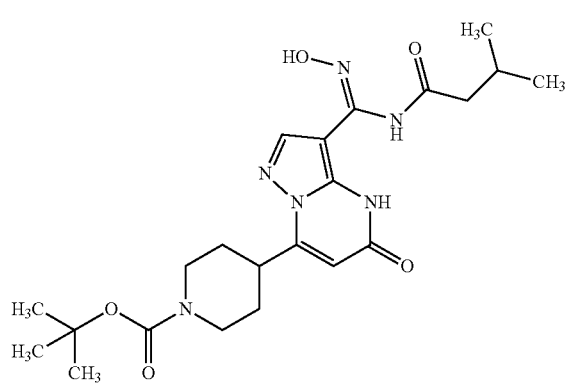 [SMILES: CC(C)CC(=O)N/C(=N/O)c1cnn2c(C3CCN(C(=O)OC(C)(C)C)CC3)cc(=O)[nH]c12]

0.2 ml (1.16 mmol) N,N-Diisopropylethylamine was added to a mixture of 0.13 ml (1.16 mmol) 3-methylbutanoic acid and 440 mg (1.16 mmol) 1-[bis(dimethylamino)methylene]-1H-1,2,3-triazolo[4,5-b]pyridinium 3-oxid hexafluorophosphate in N,N-dimethylformamide (10 ml). The mixture was stirred for 10 minutes at room temperature. 600 mg (1.05 mmol, 66%) Tert-butyl 4-[3-(N-hydroxycarbamimidoyl)-5-oxo-4,5-dihydropyrazolo[1,5-a]pyrimidin-7-yl]piperidine-1-carboxylate was added and the mixture stirred at room temperature for 16 hours. Water (25 ml) was added and the mixture was extracted with ethyl acetate (50 ml). The organic layer was washed with saturated aqueous sodium chloride, dried with sodium sulfate and concentrated yielding 640 mg (0.96 mmol; 91% of theory; purity: 69%) of the target compound.

LC-MS (Method 13B): $R_t$=1.97 min; m/z=459 (M–1)⁻

Example 463A

Tert-butyl 4-[3-(N-heptanoyl-N'-hydroxycarbamimidoyl)-5-oxo-4,5-dihydropyrazolo[1,5-a]pyrimidin-7-yl]piperidine-1-carboxylate

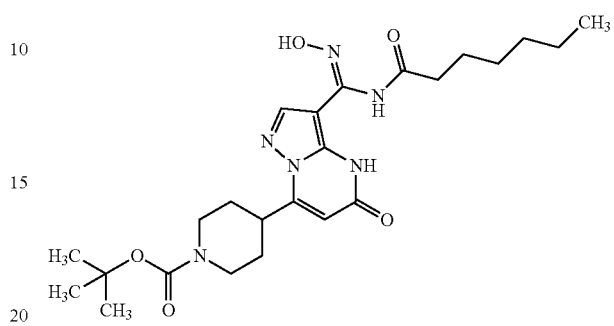

0.2 ml (1.16 mmol) N,N-Diisopropylethylamine was added to a mixture of 0.15 g (1.16 mmol) heptanoic acid and 440 mg (1.16 mmol) 1-[bis(dimethylamino)methylene]-1H-1,2,3-triazolo[4,5-b]pyridinium 3-oxid hexafluorophosphate in N,N-dimethylformamide (7 ml). The mixture was stirred for 10 minutes at room temperature. 600 mg (1.05 mmol, 66%) Tert-butyl 4-[3-(N-hydroxycarbamimidoyl)-5-oxo-4,5-dihydropyrazolo[1,5-a]pyrimidin-7-yl]piperidine-1-carboxylate was added and the mixture stirred at room temperature for 16 hours. Water (25 ml) was added and the mixture was extracted with ethyl acetate (50 ml). The organic layer was washed with saturated aqueous sodium chloride, dried with sodium sulfate and concentrated yielding 1.0 g (0.96 mmol; 105% of theory; purity: 54%) of the target compound.

LC-MS (Method 13B): $R_t$=2.10 min; m/z=487 (M–1)⁻

Example 464A

Tert-butyl 4-{3-[N-(cyclopropylcarbonyl)-N'-hydroxycarbamimidoyl]-5-oxo-4,5-dihydropyrazolo[1,5-a]pyrimidin-7-yl}piperidine-1-carboxylate

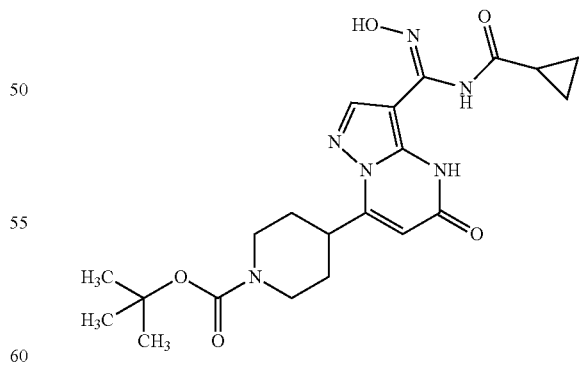

0.22 ml (1.25 mmol) N,N-Diisopropylethylamine was added to a mixture of 0.11 g (1.25 mmol) cyclopropanecarboxylic acid and 477 mg (1.25 mmol) 1-[bis(dimethylamino)methylene]-1H-1,2,3-triazolo[4,5-b]pyridinium 3-oxid hexafluorophosphate in N,N-dimethylformamide (7 ml). The mixture was stirred for 10 minutes at room temperature. 650 mg (1.14 mmol, 66%) Tert-butyl 4-[3-(N-hydroxycarbamimidoyl)-5-oxo-4,5-dihydropyrazolo[1,5-a]pyrimidin-7-yl]piperidine-1-carboxylate was added and the mixture stirred at room temperature for 16 hours. Saturated aqueous sodium hydrogen carbonate (25 ml) was added and the mixture was extracted with ethyl acetate (50 ml). The organic layer was washed with saturated aqueous sodium chloride, dried with sodium sulfate and concentrated yielding 560 mg (1.0 mmol; 88% of theory; purity: 80%) of the target compound.

LC-MS (Method 13B): $R_t$=1.88 min; m/z=443 (M−1)⁻

Example 465A

Rac-tert-butyl 4-(3-{N'-hydroxy-N-[(1-methylcyclopropyl)carbonyl]carbamimidoyl}-5-oxo-4,5-dihydropyrazolo[1,5-a]pyrimidin-7-yl)piperidine-1-carboxylate

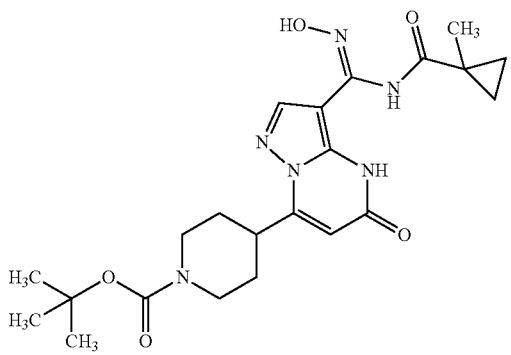 [SMILES: CC(C)(C)OC(=O)N1CCC(c2cc(=O)[nH]c3c(/C(=N\O)NC(=O)C4(C)CC4)cnn23)CC1]

0.22 ml (1.25 mmol) N,N-Diisopropylethylamine was added to a mixture of 0.13 g (1.25 mmol) rac-1-methylcyclopropanecarboxylic acid and 477 mg (1.25 mmol) 1-[bis(dimethylamino)methylene]-1H-1,2,3-triazolo[4,5-b]pyridinium 3-oxid hexafluorophosphate in N,N-dimethylformamide (7 ml). The mixture was stirred for 10 minutes at room temperature. 650 mg (1.14 mmol, 66%) Tert-butyl 4-[3-(N-hydroxycarbamimidoyl)-5-oxo-4,5-dihydropyrazolo[1,5-a]pyrimidin-7-yl]piperidine-1-carboxylate was added and the mixture stirred at room temperature for 16 hours. Saturated aqueous sodium hydrogen carbonate (25 ml) was added and the turbid mixture was extracted with ethyl acetate (50 ml). The organic layer was washed with saturated aqueous sodium chloride, dried with sodium sulfate and concentrated yielding 575 mg (0.98 mmol; 86% of theory; purity: 78%) of the target compound.

LC-MS (Method 13B): $R_t$=1.94 min; m/z=457 (M−1)⁻

Example 466A

Tert-butyl rel-4-[3-(N'-hydroxy-N-{[(1R,2S)-2-methylcyclopropyl]carbonyl}carbamimidoyl)-5-oxo-4,5-dihydropyrazolo[1,5-a]pyrimidin-7-yl]piperidine-1-carboxylate

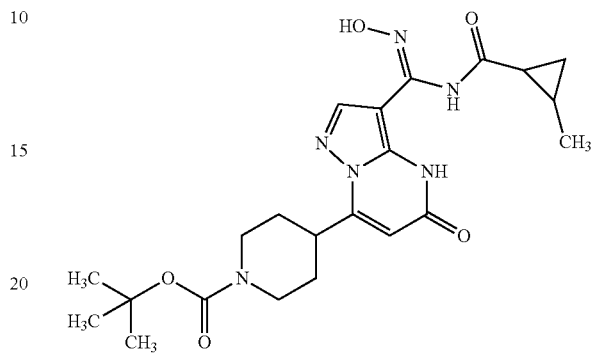

0.22 ml (1.25 mmol) N,N-Diisopropylethylamine was added to a mixture of 0.13 g (1.25 mmol) 2-methylcyclopropanecarboxylic acid and 477 mg (1.25 mmol) 1-[bis(dimethylamino)methylene]-1H-1,2,3-triazolo[4,5-b]pyridinium 3-oxid hexafluorophosphate in N,N-dimethylformamide (7 ml). The mixture was stirred for 10 minutes at room temperature. 650 mg (1.14 mmol, 66%) Tert-butyl 4-[3-(N-hydroxycarbamimidoyl)-5-oxo-4,5-dihydropyrazolo[1,5-a]pyrimidin-7-yl]piperidine-1-carboxylate was added and the mixture stirred at room temperature for 16 hours. Saturated aqueous sodium hydrogen carbonate (25 ml) was added and the turbid mixture was extracted with ethyl acetate (50 ml). The organic layer was washed with saturated aqueous sodium chloride, dried with sodium sulfate and concentrated yielding 760 mg (1.21 mmol; 106% of theory; purity: 73%) of the target compound.

LC-MS (Method 13B): $R_t$=1.94 min; m/z=459 (M+1)⁺

Example 467A

Tert-butyl 4-{3-[N'-hydroxy-N-(3-methylbut-2-enoyl)carbamimidoyl]-5-oxo-4,5-dihydropyrazolo[1,5-a]pyrimidin-7-yl}piperidine-1-carboxylate

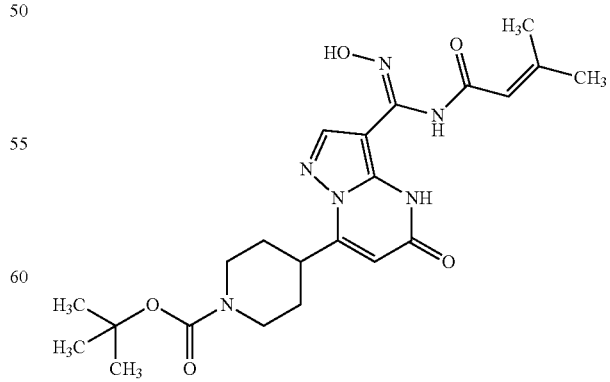

0.22 ml (1.25 mmol) N,N-Diisopropylethylamine was added to a mixture of 0.13 g (1.25 mmol) 3-methylbut-2-

443 enoic acid and 477 mg (1.25 mmol) 1-[bis(dimethylamino)methylene]-1H-1,2,3-triazolo[4,5-b]pyridinium 3-oxid hexafluorophosphate in N,N-dimethylformamide (7 ml). The mixture was stirred for 10 minutes at room temperature. 650 mg (1.14 mmol, 66%) Tert-butyl 4-[3-(N-hydroxycarbamimidoyl)-5-oxo-4,5-dihydropyrazolo[1,5-a]pyrimidin-7-yl]piperidine-1-carboxylate was added and the mixture stirred at room temperature for 16 hours. Saturated aqueous sodium hydrogen carbonate (25 ml) was added and the turbid mixture was extracted with ethyl acetate (50 ml). The organic layer was washed with saturated aqueous sodium chloride, dried with sodium sulfate and concentrated yielding 944 mg (1.44 mmol; 126% of theory; purity: 70%) of the target compound.

LC-MS (Method 13B): $R_t$=1.96 min; m/z=457 (M−1)⁻

Example 468A

Tert-butyl 4-{3-[N-(cyclopentylideneacetyl)-N'-hydroxycarbamimidoyl]-5-oxo-4,5-dihydropyrazolo[1,5-a]pyrimidin-7-yl}piperidine-1-carboxylate

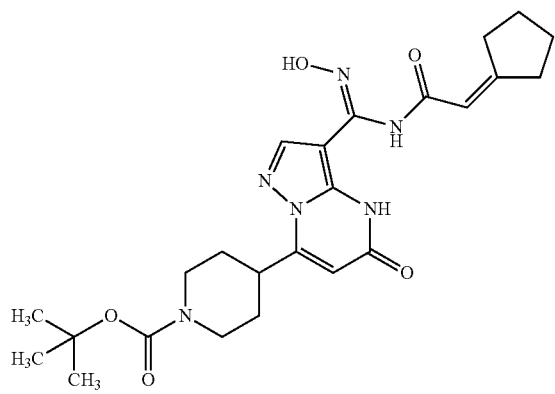 [SMILES: CC(C)(C)OC(=O)N1CCC(c2cc(=O)[nH]c3c(/C(=N\O)NC(=O)C=C4CCCC4)cnn23)CC1]

0.22 ml (1.25 mmol) N,N-Diisopropylethylamine was added to a mixture of 0.16 g (1.25 mmol) 2-cyclopentylideneacetic acid and 477 mg (1.25 mmol) 1-[bis(dimethylamino)methylene]-1H-1,2,3-triazolo[4,5-b]pyridinium 3-oxid hexafluorophosphate in N,N-dimethylformamide (7 ml). The mixture was stirred for 10 minutes at room temperature. 650 mg (1.14 mmol, 66%) Tert-butyl 4-[3-(N-hydroxycarbamimidoyl)-5-oxo-4,5-dihydropyrazolo[1,5-a]pyrimidin-7-yl]piperidine-1-carboxylate was added and the mixture stirred at room temperature for 16 hours. Saturated aqueous sodium hydrogen carbonate (25 ml) was added and the turbid mixture was extracted with ethyl acetate (50 ml). The organic layer was washed with saturated aqueous sodium chloride, dried with sodium sulfate and concentrated yielding 1.1 g (1.61 mmol; 141% of theory; purity: 71%) of the target compound.

LC-MS (Method 13B): $R_t$=2.02 min; m/z=483 (M−1)⁻

444

Example 469A

Tert-butyl 4-{3-[N-(cyclopentylcarbonyl)-N'-hydroxycarbamimidoyl]-5-oxo-4,5-dihydropyrazolo[1,5-a]pyrimidin-7-yl}piperidine-1-carboxylate

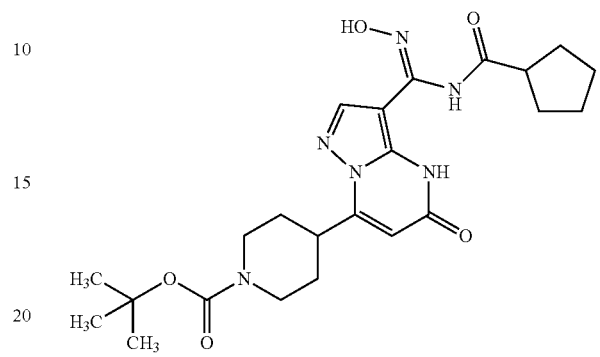

0.22 ml (1.25 mmol) N,N-Diisopropylethylamine was added to a mixture of 0.13 g (1.14 mmol) cyclopentanecarboxylic acid and 477 mg (1.25 mmol) 1-[bis(dimethylamino)methylene]-1H-1,2,3-triazolo[4,5-b]pyridinium 3-oxid hexafluorophosphate in N,N-dimethylformamide (7 ml). The mixture was stirred for 10 minutes at room temperature. 650 mg (1.14 mmol, 66%) Tert-butyl 4-[3-(N-hydroxycarbamimidoyl)-5-oxo-4,5-dihydropyrazolo[1,5-a]pyrimidin-7-yl]piperidine-1-carboxylate was added and the mixture stirred at room temperature for 16 hours. Saturated aqueous sodium hydrogen carbonate (25 ml) was added and the turbid mixture was extracted with ethyl acetate (50 ml). The organic layer was washed with saturated aqueous sodium chloride, dried with sodium sulfate and concentrated yielding 1.1 g (1.89 mmol; 165% of theory; purity: 81%) of the target compound.

LC-MS (Method 13B): $R_t$=1.99 min; m/z=471 (M−1)⁻

Example 470A

Rac-tert-butyl 4-(3-{N'-hydroxy-N-[(1-methylcyclopentyl)carbonyl]carbamimidoyl}-5-oxo-4,5-dihydropyrazolo[1,5-a]pyrimidin-7-yl)piperidine-1-carboxylate

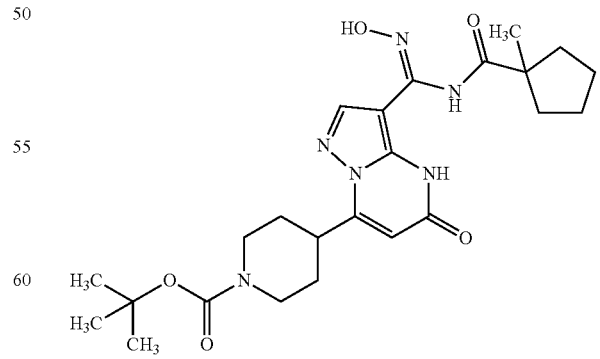

0.22 ml (1.25 mmol) N,N-Diisopropylethylamine was added to a mixture of 0.15 g (1.14 mmol) rac-1-methylcyclopentanecarboxylic acid and 477 mg (1.25 mmol) 1-[bis (dimethylamino)methylene]-1H-1,2,3-triazolo[4,5-b]pyridinium 3-oxid hexafluorophosphate in N,N-dimethylformamide (7 ml). The mixture was stirred for 10 minutes at room temperature. 650 mg (1.14 mmol, 66%) Tert-butyl 4-[3-(N-hydroxycarbamimidoyl)-5-oxo-4,5-dihydropyrazolo[1,5-a]pyrimidin-7-yl]piperidine-1-carboxylate was added and the mixture stirred at room temperature for 16 hours. Saturated aqueous sodium hydrogen carbonate (25 ml) was added and the turbid mixture was extracted with ethyl acetate (50 ml). The organic layer was washed with saturated aqueous sodium chloride, dried with sodium sulfate and concentrated yielding 930 mg (1.32 mmol; 116% of theory; purity: 69%) of the target compound.

LC-MS (Method 13B): $R_t$=2.04 min; m/z=485 (M−1)⁻

Example 471A

Tert-butyl rel-4-[3-(N'-hydroxy-N-{[(1R,2S)-2-methylcyclopentyl]carbonyl}carbamimidoyl)-5-oxo-4,5-dihydropyrazolo[1,5-a]pyrimidin-7-yl]piperidine-1-carboxylate

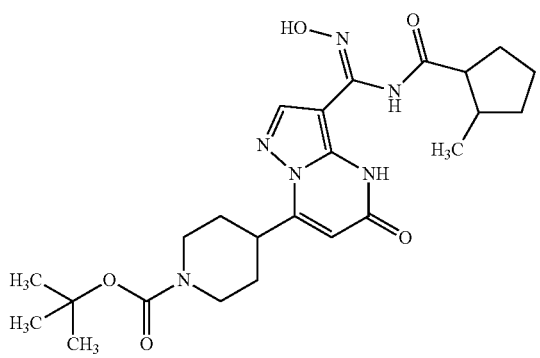 [SMILES: CC1CCCC1C(=O)N/C(=N/O)c1cnn2c(C3CCN(C(=O)OC(C)(C)C)CC3)cc(=O)[nH]c12]

0.22 ml (1.25 mmol) N,N-Diisopropylethylamine was added to a mixture of 0.15 g (1.14 mmol) 2-methylcyclopentanecarboxylic acid and 477 mg (1.25 mmol) 1-[bis(dimethylamino)methylene]-1H-1,2,3-triazolo[4,5-b]pyridinium 3-oxid hexafluorophosphate in N,N-dimethylformamide (7 ml). The mixture was stirred for 10 minutes at room temperature. 650 mg (1.14 mmol, 66%) Tert-butyl 4-[3-(N-hydroxycarbamimidoyl)-5-oxo-4,5-dihydropyrazolo[1,5-a]pyrimidin-7-yl]piperidine-1-carboxylate was added and the mixture stirred at room temperature for 16 hours. Saturated aqueous sodium hydrogen carbonate (25 ml) was added and the turbid mixture was extracted with ethyl acetate (50 ml). The organic layer was washed with saturated aqueous sodium chloride, dried with sodium sulfate and concentrated yielding 960 mg (1.48 mmol; 130% of theory; purity: 75%) of the target compound.

LC-MS (Method 13B): $R_t$=2.04 min; m/z=485 (M−1)⁻

Example 472A

Tert-butyl 4-{3-[N'-hydroxy-N-(3,3,3-trifluoropropanoyl)carbamimidoyl]-5-oxo-4,5-dihydropyrazolo[1,5-a]pyrimidin-7-yl}piperidine-1-carboxylate

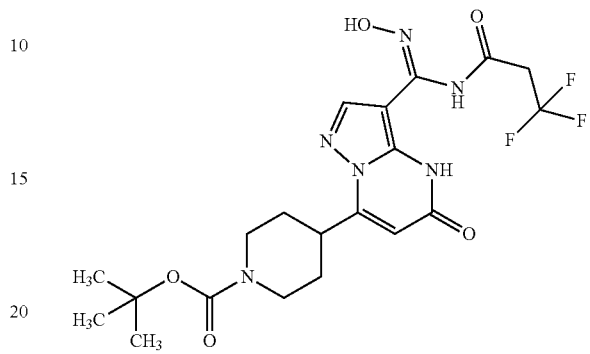

0.22 ml (1.25 mmol) N,N-Diisopropylethylamine was added to a mixture of 0.15 g (1.14 mmol) 3,3,3-trifluoropropanoic acid and 477 mg (1.25 mmol) 1-[bis(dimethylamino)methylene]-1H-1,2,3-triazolo[4,5-b]pyridinium 3-oxid hexafluorophosphate in N,N-dimethylformamide (7 ml). The mixture was stirred for 10 minutes at room temperature. 650 mg (1.14 mmol, 66%) Tert-butyl 4-[3-(N-hydroxycarbamimidoyl)-5-oxo-4,5-dihydropyrazolo[1,5-a]pyrimidin-7-yl]piperidine-1-carboxylate was added and the mixture stirred at room temperature for 16 hours. Saturated aqueous sodium hydrogen carbonate (25 ml) was added and the turbid mixture was extracted with ethyl acetate (50 ml). The organic layer was washed with saturated aqueous sodium chloride, dried with sodium sulfate and concentrated yielding 816 mg (0.87 mmol; 77% of theory; purity: 52%) of the target compound.

LC-MS (Method 13B): $R_t$=1.94 min; m/z=485 (M−1)⁻

Example 473A

Rac-tert-butyl 4-(5-oxo-3-(5-(tetrahydrofuran-2-yl)-1,2,4-oxadiazol-3-yl)-4,5-dihydropyrazolo[1,5-a]pyrimidin-7-yl)piperidine-1-carboxylate

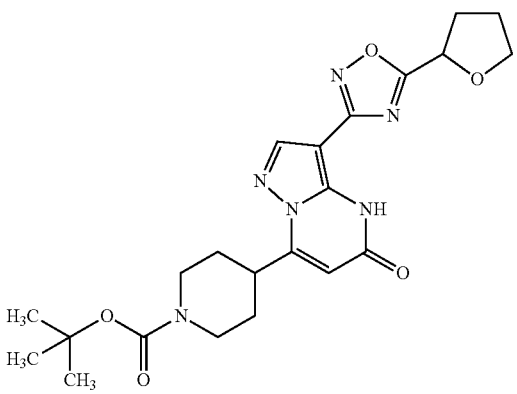 [SMILES: CC(C)(C)OC(=O)N1CCC(c2cc(=O)[nH]c3c(-c4noc(C5CCCO5)n4)cnn23)CC1]

In a 8 ml screw cap vial equipped with a stirring bar were placed 139 mg (1.200 mmol, 0.119 ml) rac-tetrahydrofuran- 2-carboxylic acid, 204 mg (1.260 mmol) 1,1'-Carbonyldiimidazole and 4 ml (dry) N-Methyl-2-pyrrolidinone. The vial was closed and the resulting solution stirred at ambient temperature for 10 minutes. Effervescence detected. To this was added 342 mg (0.600 mmol, 66%) tert-butyl 4-(3-(N-hydroxycarbamimidoyl)-5-oxo-4,5-dihydropyrazolo[1,5-a]pyrimidin-7-yl)piperidine-1-carboxylate and the resulting clear solution stirred at 80° C., for 23 hours. Volatiles were removed at the rotary evaporator (80° C./10 mbar) and the residue diluted with 100 ml of 0.5 M hydrochloric acid and 50 ml dichloromethane. The layers were separated and the aqueous one was further extracted with 2 portions of 50 ml dichloromethane. The organics were combined, washed with 100 ml brine, dried with sodium sulfate, filtered and concentrated. 713 mg of a brown oil was obtained which was purified (Method 15B; 12 g cartridge; dichloromethane, gradient, 0%-10% methanol). Fractions containing the product were pooled and concentrated. 176 mg (0.370 mmol; 61% of theory, purity: 96%) of the target compound was obtained.

LC-MS (Method 13B): $R_t$=1.96 min; m/z=455 (M−1)⁻
¹H-NMR (300 MHz, DMSO-d6) δ[ppm]=8.33 (s, 1H), 6.13 (s, 1H), 5.28 (dd, J=7.8, 5.3 Hz, 1H), 4.10 (d, J=12.7 Hz, 2H), 4.00-3.85 (m, 2H), 3.42 (t, J=12.1 Hz, 1H), 2.88 (s, 2H), 2.45-2.14 (m, 3H), 2.09-1.81 (m, 4H), 1.58 (tt, J=12.1, 6.6 Hz, 2H), 1.42 (s, 6H)

Example 474A 7-(1-(2,2,2-trifluoroacetyl)piperidin-4-yl)-3-(5-(trifluoromethyl)-1,2,4-oxadiazol-3-yl)pyrazolo[1,5-a]pyrimidin-5(4H)-one

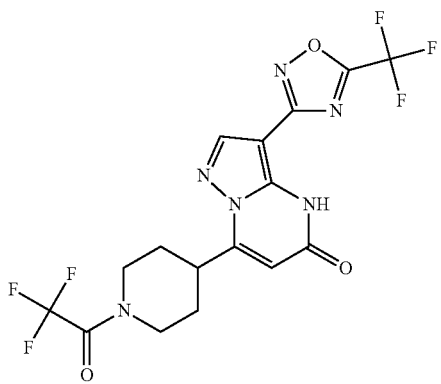 [SMILES: O=C(N1CCC(c2cc(=O)[nH]c3c(-c4noc(C(F)(F)F)n4)cnn23)CC1)C(F)(F)F]

In a 8 ml screw cap vial equipped with a stirring bar were placed 6301 mg (30.0 mmol, 4173 µl) 2,2,2-trifluoroacetic anhydride and 342 mg (0.600 mmol, 66%) tert-butyl 4-(3-(N-hydroxycarbamimidoyl)-5-oxo-4,5-dihydropyrazolo[1,5-a]pyrimidin-7-yl)piperidine-1-carboxylate. The vial was closed and the resulting reaction mixture stirred at room temperature for 23 hours. LCMS indicated that the reaction was not complete, temperature was raised to 40° C. and stirring continued for 8 hours. Volatiles were removed at the rotary evaporator (40° C./20 mbar). To the remaining yellow sticky resin was added 75 ml DCM and 100 ml saturated sodium bicarbonate. The layers were separated and the aqueous one was further extracted with 2 portions of 50 ml dichloromethane. The organics were combined, dried with sodium sulfate and concentrated. 197 mg slightly yellow solid was obtained and purified by flash column chromatography (Method 15B; 12 g cartridge; dichloromethane, gradient, 1%-4% methanol). 169 mg (0.375 mmol; 63% of theory, purity: 100%) of the target compound was obtained.

LC-MS (Method 13B): $R_t$=1.98 min; m/z=449 (M−1)⁻
¹H-NMR (300 MHz, DMSO-d6) δ[ppm]=12.25 (s, 1H), 8.49 (s, 1H), 6.29 (s, 1H), 4.47 (d, J=13.5 Hz, 2H), 4.01 (d, J=13.3 Hz, 1H), 3.68 (t, J=11.9 Hz, 1H), 3.48 (t, J=12.4 Hz, 1H), 3.08 (t, J=12.2 Hz, 1H), 2.17 (t, J=8.5 Hz, 2H), 1.77 (ddd, J=16.8, 8.5, 4.5 Hz, 2H)

Example 475A (E)-tert-butyl 4-(3-(N'-hydroxy-N-(3,3,3-trifluoro-2,2-dimethylpropanoyl)carbamimidoyl)-5-oxo-4,5-dihydropyrazolo[1,5-a]pyrimidin-7-yl)piperidine-1-carboxylate hydrochloride

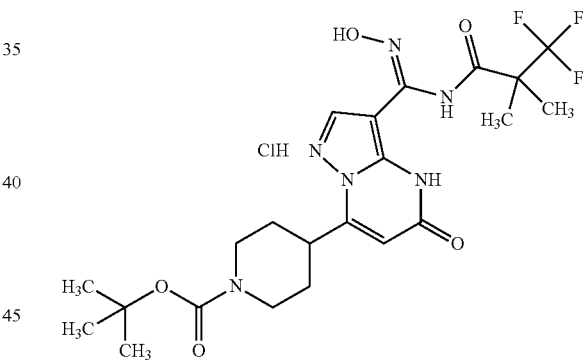

In a 8 ml screw cap vial equipped with a stirring bar were placed 188 mg (1.208 mmol) 3,3,3-trifluoro-2,2-dimethylpropanoic acid, 163 mg (1.265 mmol, 0.217 ml) N,N-Diisopropylethylamine and 481 mg (1.265 mmol) (1-[Bis(dimethylamino)methylene]-1H-1,2,3-triazolo[4,5-b]pyridinium 3-oxid hexafluorophosphate) in 2 ml (dry) N,N-Dimethylformamide. The resulting colorless solution was stirred for 10 minutes at room temperature, then 656 mg (1.150 mmol, 66%) tert-butyl 4-(3-(N-hydroxycarbamimidoyl)-5-oxo-4,5-dihydropyrazolo[1,5-a]pyrimidin-7-yl)piperidine-1-carboxylate was added and stirring continued for 20 hours. The reaction mixture was then diluted with 100 ml 0.5 M hydrochloric acid and extracted with three portions of 30 ml dichloromethane. The combined organic layers were dried with sodium sulfate, filtered and concentrated yielding 1236 mg of a yellow semi-solid material which was used as such.

Example 476A (E)-tert-butyl 4-(3-(N-(3,3-difluorocyclobutanecarbonyl)-N'-hydroxycarbamimidoyl)-5-oxo-4,5-dihydropyrazolo[1,5-a]pyrimidin-7-yl)piperidine-1-carboxylate hydrochloride

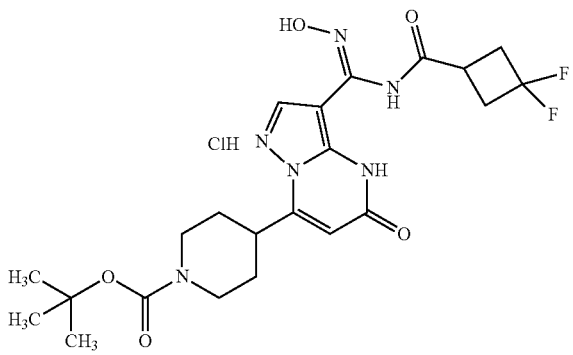 [SMILES: CC(C)(C)OC(=O)N1CCC(c2cc(=O)[nH]c3c(/C(=N\O)NC(=O)C4CC(F)(F)C4)cnn23)CC1 ; Cl]

In a 8 ml screw cap vial equipped with a stirring bar were placed 164 mg (1.208 mmol) 3,3-difluorocyclobutanecarboxylic acid, 163 mg (1.265 mmol, 0.217 ml) N,N-Diisopropylethylamine and 481 mg (1.265 mmol) (1-[Bis(dimethylamino)methylene]-1H-1,2,3-triazolo[4,5-b]pyridinium 3-oxid hexafluorophosphate) in 2 ml (dry) N,N-Dimethylformamide. The resulting colorless solution was stirred for 10 minutes at room temperature, then 656 mg (1.150 mmol, 66%) tert-butyl 4-(3-(N-hydroxycarbamimidoyl)-5-oxo-4,5-dihydropyrazolo[1,5-a]pyrimidin-7-yl)piperidine-1-carboxylate was added and the mixture stirred further for 20 hours. Diluted with 100 ml 0.5 M hydrochloric acid and extracted with 3×30 ml dichloromethane. The combined organics were dried with sodium sulfate, filtered and concentrated yielding 1188 mg of a yellow semi-solid material which was used as such.

Example 477A (E)-tert-butyl 4-(3-(N-(4,4-difluorocyclohexanecarbonyl)-N'-hydroxycarbamimidoyl)-5-oxo-4,5-dihydropyrazolo[1,5-a]pyrimidin-7-yl)piperidine-1-carboxylate hydrochloride

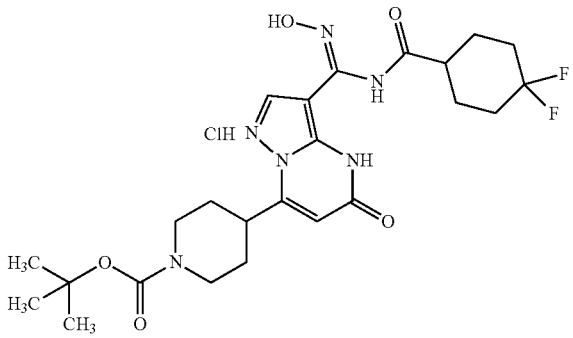 [SMILES: CC(C)(C)OC(=O)N1CCC(c2cc(=O)[nH]c3c(/C(=N\O)NC(=O)C4CCC(F)(F)CC4)cnn23)CC1 ; Cl]

In a 8 ml screw cap vial equipped with a stirring bar were placed 0.198 g (1.208 mmol) 4,4-difluorocyclohexanecarboxylic acid, 0.163 g (1.265 mmol, 0.217 ml) N,N-Diisopropylethylamine and 0.481 g (1.265 mmol) (1-[Bis(dimethylamino)methylene]-1H-1,2,3-triazolo[4,5-b]pyridinium 3-oxid hexafluorophosphate) in 2 ml (dry) N,N-Dimethylformamide. The resulting colorless solution was stirred for 10 minutes at ambient temperature, then 0.656 g (1.150 mmol, 66%) tert-butyl 4-(3-(N-hydroxycarbamimidoyl)-5-oxo-4,5-dihydropyrazolo[1,5-a]pyrimidin-7-yl)piperidine-1-carboxylate was added and the mixture stirred further for 20 hours. Diluted with 100 ml 0.5 M hydrochloric acid and extracted with 3 times with 30 ml dichloromethane. The combined organic layers were dried with sodium sulfate, filtered and concentrated yielding 1.254 g of a yellow semi-solid material which was used as such.

Example 478A (E)-tert-butyl 4-(3-(N-hydroxy-N-(2-methoxyacetyl)carbamimidoyl)-5-oxo-4,5-dihydropyrazolo[1,5-a]pyrimidin-7-yl)piperidine-1-carboxylate hydrochloride

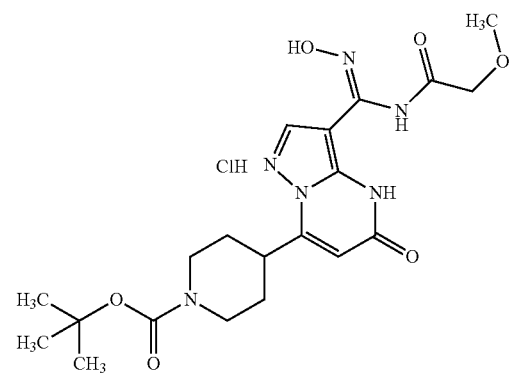 [SMILES: COCC(=O)N/C(=N/O)c1cnn2c(C3CCN(C(=O)OC(C)(C)C)CC3)cc(=O)[nH]c12 ; Cl]

In a 8 ml screw cap vial equipped with a stirring bar were placed 0.109 g (1.208 mmol) 2-methoxyacetic acid, 0.163 g (1.265 mmol, 0.217 ml) N,N-Diisopropylethylamine and 0.481 g (1.265 mmol) (1-[Bis(dimethylamino)methylene]-1H-1,2,3-triazolo[4,5-b]pyridinium 3-oxid hexafluorophosphate) in 2 ml (dry) N,N-Dimethylformamide. The resulting colorless solution was stirred for 10 minutes at room temperature, then 0.656 g (1.150 mmol, 66%) tert-butyl 4-(3-(N-hydroxycarbamimidoyl)-5-oxo-4,5-dihydropyrazolo[1,5-a]pyrimidin-7-yl)piperidine-1-carboxylate was added and the mixture stirred further for 20 hours. The reaction mixture was diluted with 100 ml 0.5 M hydrochloric acid and extracted with 3 portions of 30 ml dichloromethane. The combined organic layers were dried with sodium sulfate, filtered and concentrated yielding 1.420 g of a yellow semi-solid material which was used as such.

Example 479A (E)-tert-butyl 4-(3-(N-hydroxy-N-(4-methoxybutanoyl)carbamimidoyl)-5-oxo-4,5-dihydropyrazolo[1,5-a]pyrimidin-7-yl)piperidine-1-carboxylate hydrochloride

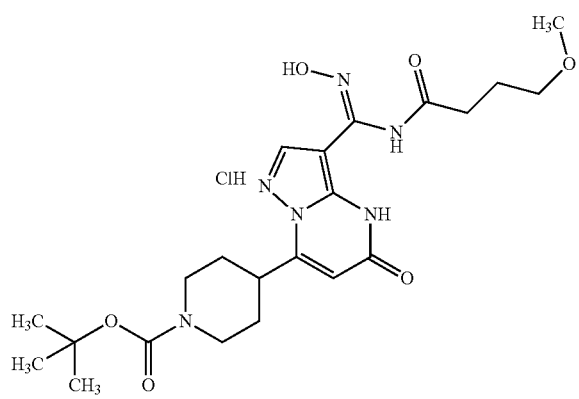 [SMILES: COCCCC(=O)N/C(=N/O)c1cnn2c(C3CCN(C(=O)OC(C)(C)C)CC3)cc(=O)[nH]c12 ; Cl]

In a 8 ml screw cap vial equipped with a stirring bar were placed 0.143 g (1.208 mmol) 4-methoxybutanoic acid, 0.163 g (1.265 mmol, 0.217 ml) N,N-Diisopropylethylamine and 0.481 g (1.265 mmol) (1-[Bis(dimethylamino)methylene]-1H-1,2,3-triazolo[4,5-b]pyridinium 3-oxid hexafluorophosphate) in 2 ml (dry) N,N-Dimethylformamide. The resulting colorless solution was stirred for 10 minutes at ambient temperature, then 0.656 g (1.150 mmol, 66%) tert-butyl 4-(3-(N-hydroxycarbamimidoyl)-5-oxo-4,5-dihydropyrazolo[1,5-a]pyrimidin-7-yl)piperidine-1-carboxylate was added and the mixture stirred further for 20 hours. The reaction mixture was diluted with 100 ml 0.5M hydrochloric acid and extracted with 3 times 30 ml dichloromethane. The combined organic layers were dried with sodium sulfate, filtered and concentrated yielding 1.100 g of a yellow semi-solid material which was used as such.

Example 480A

Tert-butyl 4-[3-(5-isobutyl-1,2,4-oxadiazol-3-yl)-5-oxo-4,5-dihydropyrazolo[1,5-a]pyrimidin-7-yl]piperidine-1-carboxylate

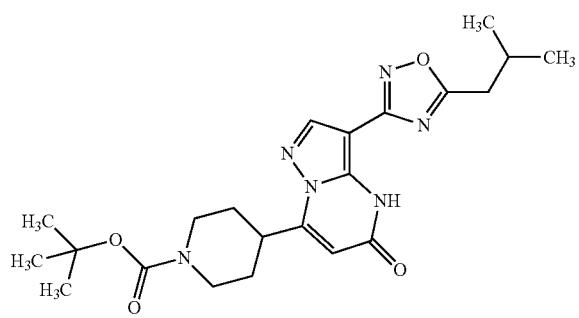 [SMILES: CC(C)Cc1nc(-c2cnn3c(C4CCN(C(=O)OC(C)(C)C)CC4)cc(=O)[nH]c23)no1]

283 mg (0.430 mmol, 69%) Tert-butyl 4-{3-[N'-hydroxy-N-(3-methylbutanoyl)carbamimidoyl]-5-oxo-4,5-dihydropyrazolo[1,5-a]pyrimidin-7-yl}piperidine-1-carboxylate was dissolved in 1,4-dioxan (8 ml). 0.03 ml (0.13 mmol) 4 M Hydrogen chloride in 1,4-dioxan was added and the mixture was heated to 100° C. for 16 hours. The organic layer was diluted with ethyl acetate, washed with saturated aqueous sodium hydrogen carbonate and saturated aqueous sodium chloride, dried with sodium sulfate and concentrated. Purification via flash column chromatography (Method 15B; 12 g cartridge; dichloromethane, gradient, 0%-3% 7 M ammonia in methanol) afforded 58 mg (0.13 mmol; 30% of theory, purity: 95%) of the target compound.

LC-MS (Method 13B): $R_t$=2.12 min; m/z=441 (M−1)⁻

$^1$H-NMR (300 MHz, Chloroform-d): δ [ppm]=9.73 (s, 1H), 8.19 (s, 1H), 5.93 (s, 1H), 4.46-4.16 (m, 2H), 3.58-3.36 (m, 1H), 2.99-2.77 (m, 4H), 2.36-2.21 (m, 1H), 2.11 (d, J=12.7 Hz, 2H), 1.69-1.56 (m, 2H), 1.48 (s, 9H), 1.04 (d, J=6.7 Hz, 6H)

Example 481A

Tert-butyl 4-[3-(5-hexyl-1,2,4-oxadiazol-3-yl)-5-oxo-4,5-dihydropyrazolo[1,5-a]pyrimidin-7-yl]piperidine-1-carboxylate

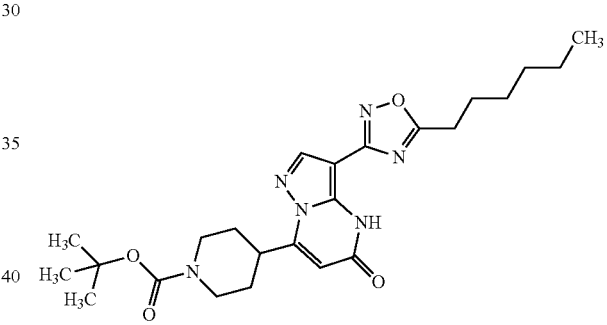

514 mg (0.57 mmol, 54%) Tert-butyl 4-[3-(N-heptanoyl-N'-hydroxycarbamimidoyl)-5-oxo-4,5-dihydropyrazolo[1,5-a]pyrimidin-7-yl]piperidine-1-carboxylate was dissolved in 1,4-dioxan (8 ml). 0.03 ml (0.11 mmol) 4 M Hydrogen chloride in 1,4-dioxan was added and the mixture was heated to 100° C. for 16 hours. The organic layer was diluted with ethyl acetate, washed with saturated aqueous sodium hydrogen carbonate and saturated aqueous sodium chloride, dried with sodium sulfate and concentrated. Purification via flash column chromatography (Method 15B; 12 g cartridge; dichloromethane, gradient, 0%-3% 7 M ammonia in methanol) afforded 166 mg (0.35 mmol; 62% of theory, purity: 99%) of the target compound.

LC-MS (Method 13B): $R_t$=2.27 min; m/z=469 (M−1)⁻

$^1$H-NMR (300 MHz, Chloroform-d): δ [ppm]=9.72 (s, 1H), 8.20 (s, 1H), 5.93 (s, 1H), 4.28 (s, 2H), 3.45 (t, J=11.9 Hz, 1H), 3.12-2.78 (m, 4H), 2.12 (d, J=12.8 Hz, 2H), 1.97-1.80 (m, 2H), 1.69-1.27 (m, 17H), 0.90 (t, 3H)

Example 482A

Tert-butyl 4-[3-(5-cyclopropyl-1,2,4-oxadiazol-3-yl)-5-oxo-4,5-dihydropyrazolo[1,5-a]pyrimidin-7-yl]piperidine-1-carboxylate

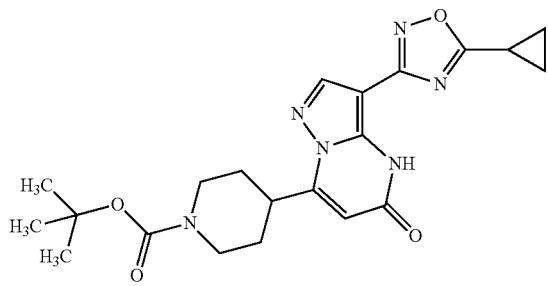 [SMILES: CC(C)(C)OC(=O)N1CCC(c2cc(=O)[nH]c3c(-c4noc(C5CC5)n4)cnn23)CC1]

560 mg (1.0 mmol, 80%) Tert-butyl 4-{3-[N-(cyclopropylcarbonyl)-N'-hydroxycarbamimidoyl]-5-oxo-4,5-dihydropyrazolo[1,5-a]pyrimidin-7-yl}piperidine-1-carboxylate was dissolved in 1,4-dioxan (8 ml). 0.05 ml (0.20 mmol) 4 M Hydrogen chloride in 1,4-dioxan was added and the mixture was heated to 90° C. for 16 hours. The organic layer was diluted with ethyl acetate, washed with saturated aqueous sodium hydrogen carbonate and saturated aqueous sodium chloride, dried with sodium sulfate and concentrated. Purification via flash column chromatography (Method 15B; 12 g cartridge; dichloromethane, gradient, 0%-3% 7 M ammonia in methanol) afforded 122 mg (0.28 mmol; 28% of theory, purity: 100%) of the target compound.

LC-MS (Method 13B): $R_t$=2.01 min; m/z=425 (M−1)⁻
¹H-NMR (300 MHz, Chloroform-d): δ [ppm]=9.67 (s, 1H), 8.17 (s, 1H), 5.93 (s, 1H), 4.32 (br. s, 2H), 3.45 (t, J=11.8 Hz, 1H), 2.90 (t, J=12.1 Hz, 2H), 2.33-2.20 (m, 1H), 2.12 (d, J=13.2 Hz, 2H), 1.70-1.56 (m, 2H), 1.49 (s, 9H), 1.38-1.26 (m, 4H)

Example 483A

Rac-tert-butyl 4-{3-[5-(1-methylcyclopropyl)-1,2,4-oxadiazol-3-yl]-5-oxo-4,5-dihydropyrazolo[1,5-a]pyrimidin-7-yl}piperidine-1-carboxylate

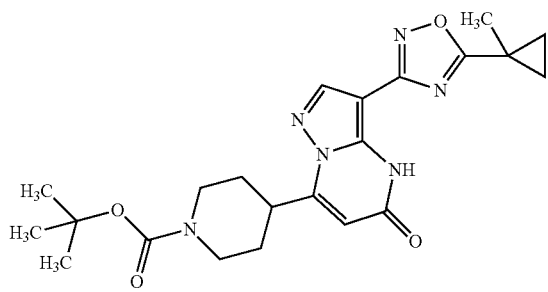 [SMILES: CC(C)(C)OC(=O)N1CCC(c2cc(=O)[nH]c3c(-c4noc(C5(C)CC5)n4)cnn23)CC1]

575 mg (0.98 mmol, 78%) rac-tert-butyl 4-(3-{N-hydroxy-N-[(1-methylcyclopropyl)carbonyl]carbamimidoyl}-5-oxo-4,5-dihydropyrazolo[1,5-a]pyrimidin-7-yl)piperidine-1-carboxylate was dissolved in 1,4-dioxan (8 ml). 0.05 ml (0.20 mmol) 4 M Hydrogen chloride in 1,4-dioxan was added and the mixture was heated to 90° C. for 16 hours. The organic layer was diluted with ethyl acetate, washed with saturated aqueous sodium hydrogen carbonate and saturated aqueous sodium chloride, dried with sodium sulfate and concentrated. Purification via flash column chromatography (Method 15B; 12 g cartridge; dichloromethane, gradient, 0%-3% 7 M ammonia in methanol) afforded 90 mg (0.20 mmol; 21% of theory, purity: 99%) of the target compound.

LC-MS (Method 13B): $R_t$=2.08 min; m/z=439 (M−1)⁻
¹H-NMR (300 MHz, Chloroform-d): δ [ppm]=9.63 (s, 1H), 8.17 (s, 1H), 5.92 (s, 1H), 4.32 (b r. s, 2H), 3.44 (t, J=12.0 Hz, 1H), 2.89 (t, J=12.2 Hz, 2H), 2.11 (d, J=10.4 Hz, 2H), 1.61 (s, 3H), 1.48 (s, 11H), 1.18-0.88 (m, 2H)

Example 484A

Tert-butyl rel-4-(3-{5-[(1R,2S)-2-methylcyclopropyl]-1,2,4-oxadiazol-3-yl}-5-oxo-4,5-dihydropyrazolo[1,5-a]pyrimidin-7-yl)piperidine-1-carboxylate

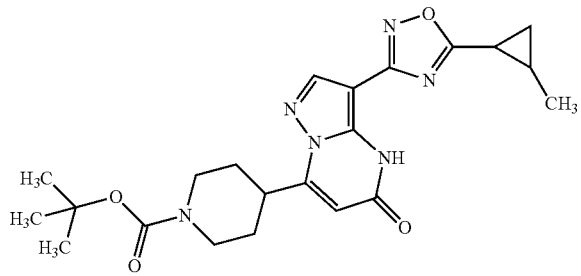 [SMILES: CC1CC1c1nc(-c2cnn3c(C4CCN(C(=O)OC(C)(C)C)CC4)cc(=O)[nH]c23)no1]

760 mg (1.21 mmol, 73%) Tert-butyl rel-4-[3-(N'-hydroxy-N-{[(1R,2S)-2-methylcyclopropyl]carbonyl}carbamimidoyl)-5-oxo-4,5-dihydropyrazolo[1,5-a]pyrimidin-7-yl]piperidine-1-carboxylate was dissolved in 1,4-dioxan (8 ml). 0.06 ml (0.24 mmol) 4 M Hydrogen chloride in 1,4-dioxan was added and the mixture was heated to 90° C. for 16 hours. The organic layer was diluted with ethyl acetate, washed with saturated aqueous sodium hydrogen carbonate and saturated aqueous sodium chloride, dried with sodium sulfate and concentrated. Purification via flash column chromatography (Method 15B; 12 g cartridge; dichloromethane, gradient, 0%-3% 7 M ammonia in methanol) afforded 84 mg (0.19 mmol; 16% of theory, purity: 99%) of the target compound.

LC-MS (Method 13B): $R_t$=2.08 min; m/z=439 (M−1)⁻
¹H-NMR (300 MHz, Chloroform-d): δ [ppm]=9.68 (s, 1H), 8.16 (s, 1H), 5.92 (s, 1H), 4.32 (s, 2H), 3.56-3.31 (m, 1H), 2.89 (t, J=12.6 Hz, 2H), 2.11 (d, J=12.9 Hz, 2H), 2.04-1.87 (m, 1H), 1.73-1.59 (m, 3H), 1.48 (s, 9H), 1.26 (d, J=6.0 Hz, 3H), 1.22-1.04 (m, 2H)

Example 485A

Tert-butyl 4-{3-[5-(2-methylprop-1-en-1-yl)-1,2,4-oxadiazol-3-yl]-5-oxo-4,5-dihydropyrazolo[1,5-a]pyrimidin-7-yl}piperidine-1-carboxylate

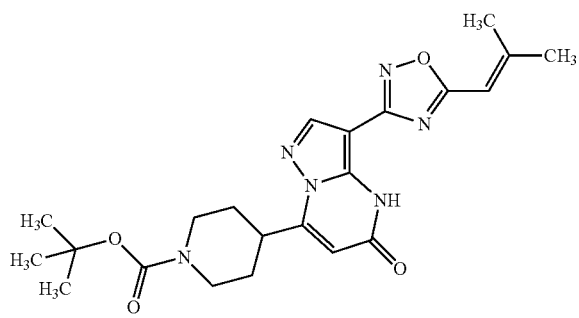 [SMILES: CC(C)=Cc1nc(-c2cnn3c(C4CCN(C(=O)OC(C)(C)C)CC4)cc(=O)[nH]c23)no1]

744 mg (1.14 mmol, 70%) Tert-butyl 4-{3-[N'-hydroxy-N-(3-methylbut-2-enoyl)carbamimidoyl]-5-oxo-4,5-dihydropyrazolo[1,5-a]pyrimidin-7-yl}piperidine-1-carboxylate was dissolved in 1,4-dioxan (8 ml). 0.06 ml (0.24 mmol) 4 M Hydrogen chloride in 1,4-dioxan was added and the mixture was heated to 90° C. for 16 hours. The organic layer was diluted with ethyl acetate, washed with saturated aqueous sodium hydrogen carbonate and saturated aqueous sodium chloride, dried with sodium sulfate and concentrated. Purification via flash column chromatography (Method 15B; 12 g cartridge; dichloromethane, gradient, 0%-3% 7 M ammonia in methanol) afforded 19 mg (0.04 mmol; 4% of theory, purity: 95%) of the target compound.

LC-MS (Method 13B): $R_t$=2.12 min; m/z=439 (M−1)⁻

$^1$H-NMR (300 MHz, Chloroform-d): δ [ppm]=9.71 (s, 1H), 8.20 (s, 1H), 6.44-6.20 (m, 1H), 5.93 (s, 1H), 4.30 (d, J=9.7 Hz, 2H), 3.56-3.38 (m, 1H), 2.97-2.80 (m, 2H), 2.34 (d, J=0.9 Hz, 3H), 2.09 (d, J=1.1 Hz, 5H), 1.70-1.56 (m, 2H), 1.48 (s, 9H)

Example 486A

Tert-butyl 4-{3-[5-(cyclopentylidenemethyl)-1,2,4-oxadiazol-3-yl]-5-oxo-4,5-dihydropyrazolo[1,5-a]pyrimidin-7-yl}piperidine-1-carboxylate

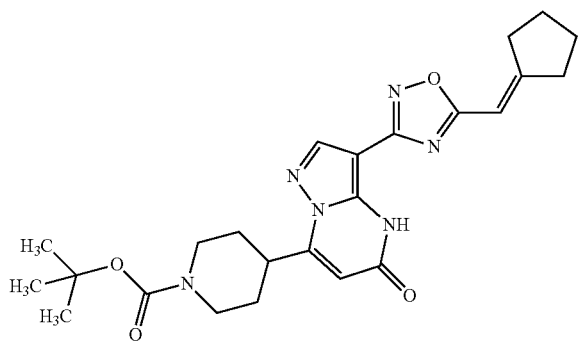 [SMILES: CC(C)(C)OC(=O)N1CCC(c2cc(=O)[nH]c3c(-c4noc(C=C5CCCC5)n4)cnn23)CC1]

770 mg (1.13 mmol, 71%) Tert-butyl 4-{3-[N-(cyclopentylideneacetyl)-N'-hydroxycarbamimidoyl]-5-oxo-4,5-dihydropyrazolo[1,5-a]pyrimidin-7-yl}piperidine-1-carboxylate was dissolved in 1,4-dioxan (8 ml). 0.06 ml (0.24 mmol) 4 M Hydrogen chloride in 1,4-dioxan was added and the mixture was heated to 90° C. for 16 hours. The organic layer was diluted with ethyl acetate, washed with saturated aqueous sodium hydrogen carbonate and saturated aqueous sodium chloride, dried with sodium sulfate and concentrated. Purification via flash column chromatography (Method 15B; 12 g cartridge; dichloromethane, gradient, 0%-3% 7 M ammonia in methanol) afforded 73 mg (0.16 mmol; 14% of theory, purity: 96%) of the target compound.

LC-MS (Method 13B): $R_t$=2.16 min; m/z=465 (M−1)⁻

$^1$H-NMR (300 MHz, Chloroform-d): δ [ppm]=9.74 (s, 1H), 8.20 (s, 1H), 5.93 (s, 1H), 5.60 (s, 1H), 4.32 (br. s, 2H), 3.75 (s, 2H), 3.64-3.29 (m, 1H), 2.90 (t, J=12.2 Hz, 2H), 2.36 (t, J=7.4 Hz, 4H), 2.11 (d, J=12.6 Hz, 2H), 2.04-1.85 (m, 2H), 1.70-1.58 (m, 2H), 1.48 (s, 9H)

Example 487A

Tert-butyl 4-[3-(5-cyclopentyl-1,2,4-oxadiazol-3-yl)-5-oxo-4,5-dihydropyrazolo[1,5-a]pyrimidin-7-yl]piperidine-1-carboxylate

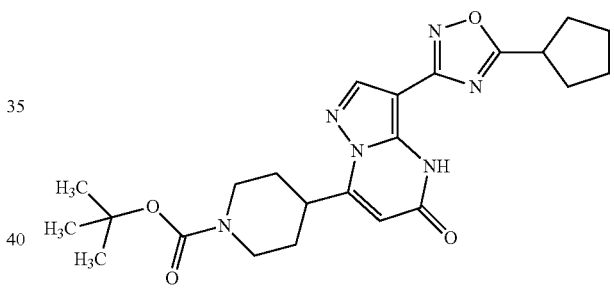

690 mg (1.18 mmol, 81%) Tert-butyl 4-{3-[N-(cyclopentylcarbonyl)-N'-hydroxycarbamimidoyl]-5-oxo-4,5-dihydropyrazolo[1,5-a]pyrimidin-7-yl}piperidine-1-carboxylate was dissolved in 1,4-dioxan (8 ml). 0.06 ml (0.24 mmol) 4 M Hydrogen chloride in 1,4-dioxan was added and the mixture was heated to 90° C. for 16 hours. The organic layer was diluted with ethyl acetate, washed with saturated aqueous sodium hydrogen carbonate and saturated aqueous sodium chloride, dried with sodium sulfate and concentrated. Purification via flash column chromatography (Method 15B; 12 g cartridge; dichloromethane, gradient, 0%-3% 7 M ammonia in methanol) afforded 147 mg (0.32 mmol; 27% of theory, purity: 100%) of the target compound.

LC-MS (Method 13B): $R_t$=2.14 min; m/z=453 (M−1)⁻

$^1$H-NMR (300 MHz, Chloroform-d): δ [ppm]=9.71 (s, 1H), 8.19 (s, 1H), 5.92 (s, 1H), 4.31 (br. s, 2H), 3.70-3.25 (m, 2H), 3.19-2.70 (m, 2H), 2.30-2.06 (m, 4H), 2.05-1.69 (m, 6H), 1.69-1.55 (m, 2H), 1.48 (s, 9H)

Example 488A

Rac-tert-butyl 4-{3-[5-(1-methylcyclopentyl)-1,2,4-oxadiazol-3-yl]-5-oxo-4,5-dihydropyrazolo[1,5-a]pyrimidin-7-yl}piperidine-1-carboxylate

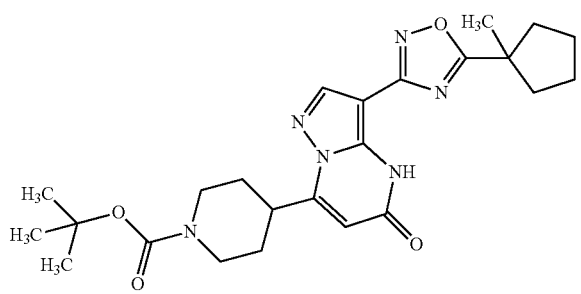 [SMILES: CC(C)(C)OC(=O)N1CCC(c2cc(=O)[nH]c3c(-c4noc(C5(C)CCCC5)n4)cnn23)CC1]

800 mg (1.13 mmol, 69%) rac-tert-butyl 4-(3-{N'-hydroxy-N-[(1-methylcyclopentyl)carbonyl]carbamimidoyl}-5-oxo-4,5-dihydropyrazolo[1,5-a]pyrimidin-7-yl)piperidine-1-carboxylate was dissolved in 1,4-dioxan (8 ml). 0.06 ml (0.24 mmol) 4 M Hydrogen chloride in 1,4-dioxan was added and the mixture was heated to 90° C. for 16 hours. The organic layer was diluted with ethyl acetate, washed with saturated aqueous sodium hydrogen carbonate and saturated aqueous sodium chloride, dried with sodium sulfate and concentrated. Purification via flash column chromatography (Method 15B; 12 g cartridge; dichloromethane, gradient, 0%-3% 7 M ammonia in methanol) afforded 111 mg (0.24 mmol; 21% of theory, purity: 100%) of the target compound.

LC-MS (Method 13B): $R_t$=2.21 min; m/z=467 (M−1)⁻

¹H-NMR (300 MHz, Chloroform-d): δ [ppm]=9.68 (s, 1H), 8.20 (s, 1H), 5.93 (s, 1H), 4.47-4.10 (m, 2H), 3.60-3.36 (m, 1H), 2.90 (t, J=12.9 Hz, 2H), 2.39-2.19 (m, 2H), 2.12 (d, J=12.9 Hz, 2H), 1.87-1.75 (m, 6H), 1.64-1.56 (m, 2H), 1.51 (s, 3H), 1.49 (s, 9H)

Example 489A

Tert-butyl rel-4-(3-{5-[(1R,2S)-2-methylcyclopentyl]-1,2,4-oxadiazol-3-yl}-5-oxo-4,5-dihydropyrazolo[1,5-a]pyrimidin-7-yl)piperidine-1-carboxylate

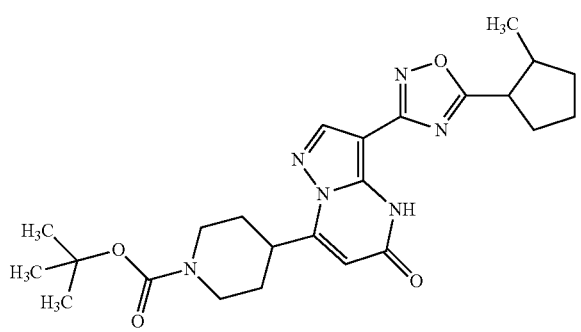 [SMILES: CC1CCCC1c1nc(-c2cnn3c(C4CCN(C(=O)OC(C)(C)C)CC4)cc(=O)[nH]c23)no1]

750 mg (1.16 mmol, 75%) Tert-butyl rel-4-[3-(N'-hydroxy-N-{[(1R,2S)-2-methylcyclopentyl]carbonyl}carbamimidoyl)-5-oxo-4,5-dihydropyrazolo[1,5-a]pyrimidin-7-yl]piperidine-1-carboxylate was dissolved in 1,4-dioxan (8 ml). 0.06 ml (0.24 mmol) 4 M Hydrogen chloride in 1,4-dioxan was added and the mixture was heated to 90° C. for 16 hours. The organic layer was diluted with ethyl acetate, washed with saturated aqueous sodium hydrogen carbonate and saturated aqueous sodium chloride, dried with sodium sulfate and concentrated. Purification via flash column chromatography (Method 15B; 12 g cartridge; dichloromethane, gradient, 0%-3% 7 M ammonia in methanol) afforded 171 mg (0.37 mmol; 32% of theory, purity: 99%) of the target compound.

LC-MS (Method 13B): $R_t$=2.21 min; m/z=467 (M−1)⁻

¹H-NMR (300 MHz, Chloroform-d): δ [ppm]=9.72 (s, 1H), 8.20 (s, 1H), 5.93 (s, 1H), 4.29 (d, J=10.8 Hz, 2H), 3.44 (s, 1H), 2.97-2.81 (m, 3H), 2.41-1.97 (m, 5H), 1.92-1.77 (m, 2H), 1.67-1.53 (m, 3H), 1.48 (s, 9H), 1.43-1.31 (m, 1H), 1.12 (d, J=6.6 Hz, 3H)

Example 490A

Tert-butyl 4-{5-oxo-3-[5-(2,2,2-trifluoroethyl)-1,2,4-oxadiazol-3-yl]-4,5-dihydropyrazolo[1,5-a]pyrimidin-7-yl}piperidine-1-carboxylate

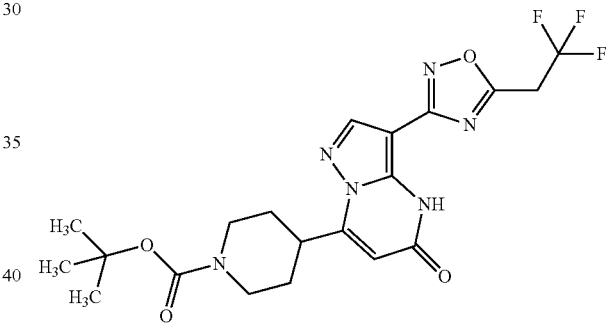

816 mg (0.87 mmol, 52%) Tert-butyl 4-{3-[N'-hydroxy-N-(3,3,3-trifluoropropanoyl)carbamimidoyl]-5-oxo-4,5-dihydropyrazolo[1,5-a]pyrimidin-7-yl}piperidine-1-carboxylate was dissolved in 1,4-dioxan (8 ml). 0.044 ml (0.17 mmol) 4 M Hydrogen chloride in 1,4-dioxan was added and the mixture was heated to 90° C. for 16 hours. The organic layer was diluted with ethyl acetate, washed with saturated aqueous sodium hydrogen carbonate and saturated aqueous sodium chloride, dried with sodium sulfate and concentrated. Purification via flash column chromatography (Method 15B; 12 g cartridge; dichloromethane, gradient, 0%-3% 7 M ammonia in methanol) afforded 120 mg (0.26 mmol; 29% of theory, purity: 98%) of the target compound.

LC-MS (Method 13B): $R_t$=2.03 min; m/z=467 (M−1)⁻

¹H-NMR (300 MHz, Chloroform-d): δ [ppm]=9.59 (s, 1H), 8.21 (s, 1H), 5.95 (s, 1H), 5.29, 4.30 (d, J=9.0 Hz, 2H), 3.85 (q, J=9.4 Hz, 2H), 3.56-3.36 (m, 1H), 3.07-2.79 (m, 2H), 2.11 (d, J=12.7 Hz, 2H), 1.70-1.60 (m, 2H), 1.48 (s, 9H)

Example 491A

Tert-butyl 4-(5-oxo-3-(5-(1,1,1-trifluoro-2-methyl-propan-2-yl)-1,2,4-oxadiazol-3-yl)-4,5-dihydropyrazolo[1,5-a]pyrimidin-7-yl)piperidine-1-carboxylate

Example 492A

Tert-butyl 4-(3-(5-(3,3-difluorocyclobutyl)-1,2,4-oxadiazol-3-yl)-5-oxo-4,5-dihydropyrazolo[1,5-a]pyrimidin-7-yl)piperidine-1-carboxylate

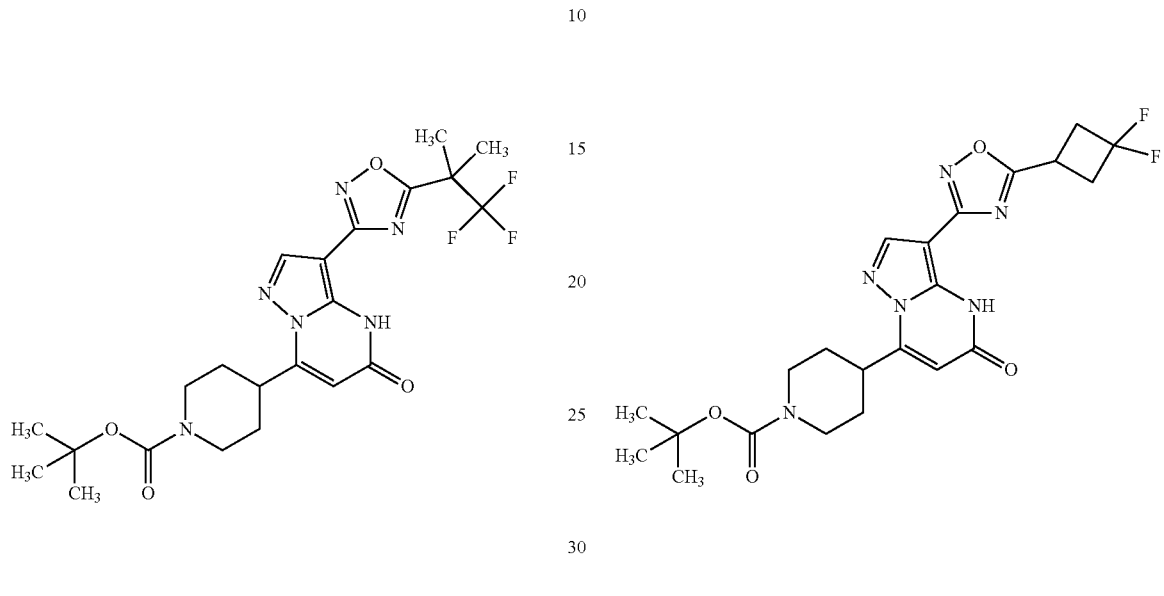

In a 8 ml screw cap vial equipped with a stirring bar was placed 1236 mg (E)-tert-butyl 4-(3-(N'-hydroxy-N-(3,3,3-trifluoro-2,2-dimethylpropanoyl)carbamimidoyl)-5-oxo-4,5-dihydropyrazolo[1,5-a]pyrimidin-7-yl)piperidine-1-carboxylate hydrochloride from Example 28A and 6 ml (dry) 1,4-dioxan. 0.04 ml (0.161 mmol) hydrochloric acid (4.0 M in dioxane) was added and the clear yellow solution stirred at 90° C. for 8 hours. The reaction mixture was diluted with 100 ml 0.5 M hydrochloric acid and extracted with dichloromethane (3×50 ml). The organic layers were combined, washed with 100 ml aqueous ammonia (15% w/w), dried with sodium sulfate, filtered and concentrated. 352 mg yellow solid was obtained and purified by flash column chromatography (Method 15B; 12 g cartridge; dichloromethane, gradient, 1%-4% methanol). Fractions containing the product were pooled, concentrated and co-evaporated with 20 ml dichloromethane. 208 mg (0.412 mmol; 36% of theory over two steps, purity: 98%) of the target compound was obtained as a white free flowing powder.

LC-MS (Method 13B): $R_t$=2.14 min; m/z=495 (M−1)⁻
¹H-NMR (300 MHz, DMSO-d6) δ[ppm]=8.20 (s, 1H), 5.97 (s, 1H), 4.08 (d, J=11.9 Hz, 2H), 3.36 (t, J=11.9 Hz, 1H), 2.89 (br. s, 2H), 2.00 (d, J=12.2 Hz, 2H), 1.70 (s, 6H), 1.50 (dd, J=12.1, 3.8 Hz, 2H), 1.41 (s, 9H)

In a 8 ml screw cap vial equipped with a stirring bar was placed 1188 mg (E)-tert-butyl 4-(3-(N-(3,3-difluorocyclobutanecarbonyl)-N'-hydroxycarbamimidoyl)-5-oxo-4,5-dihydropyrazolo[1,5-a]pyrimidin-7-yl)piperidine-1-carboxylate hydrochloride and 6 ml (dry) 1,4-dioxan. 0.04 ml (0.161 mmol) hydrochloric acid (4.0 M in dioxane) was added and the clear yellow solution heated to 90° C. for 8 hours. The reaction mixture was diluted with 100 ml 0.5 M hydrochloric acid and extracted with 3 portions of 50 ml dichloromethane. The organics layers were combined, washed with 100 ml aqueous ammonia (15% w/w), dried with sodium sulfate, filtered and concentrated: 303 mg yellow solid was obtained and purified (Method 15B; 12 g cartridge; dichloromethane, gradient, 1%-4% methanol). Fractions containing the product were pooled, concentrated and co-evaporated with 20 ml dichloromethane. 221 mg (0.444 mmol; 38% of theory over two steps, purity: 96%) of the target compound was obtained as a white free flowing powder.

LC-MS (Method 13B): $R_t$=2.05 min; m/z=475 (M−1)⁻
¹H-NMR (300 MHz, DMSO-d6) δ[ppm]=11.47 (s, 1H), 8.33 (s, 1H), 6.11 (s, 1H), 4.10 (d, J=12.4 Hz, 2H), 3.85 (td, J=8.6, 2.6 Hz, 1H), 3.42 (t, J=11.9 Hz, 1H), 3.22-3.09 (m, 4H), 2.87 (br. s, 2H), 2.00 (d, J=11.7 Hz, 2H), 1.57 (qd, J=12.3, 4.0 Hz, 2H), 1.42 (s, 9H)

Example 493A

Tert-butyl 4-(3-(5-(4,4-difluorocyclohexyl)-1,2,4-oxadiazol-3-yl)-5-oxo-4,5-dihydropyrazolo[1,5-a]pyrimidin-7-yl)piperidine-1-carboxylate

Example 494A

Tert-butyl 4-(3-(5-(methoxymethyl)-1,2,4-oxadiazol-3-yl)-5-oxo-4,5-dihydropyrazolo[1,5-a]pyrimidin-7-yl)piperidine-1-carboxylate

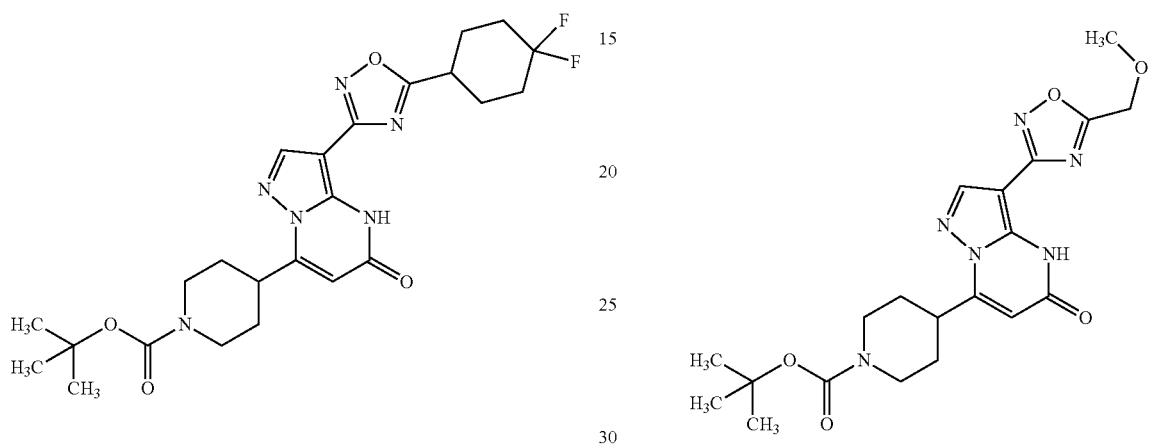

In a 8 ml screw cap vial equipped with a stirring bar was placed 1.254 g (E)-tert-butyl 4-(3-(N-(4,4-difluorocyclohexanecarbonyl)-N'-hydroxycarbamimidoyl)-5-oxo-4,5-dihydropyrazolo[1,5-a]pyrimidin-7-yl)piperidine-1-carboxylate hydrochloride from Example 32A and 6 ml (dry) 1,4-dioxan. 0.40 ml (0.161 mmol) hydrochloric acid (4.0 M in dioxane) was added and the clear yellow solution stirred for 8 hours at 90° C. The reaction mixture was diluted with 100 ml 0.5 M hydrochloric acid and extracted with 3 portions of 50 ml dichloromethane. The organic layers were combined, washed with 100 ml aqueous ammonia (15% w/w), dried with sodium sulfate, filtered and concentrated: 378 mg yellow solid was obtained and purified (Method 15B; 12 g cartridge; dichloromethane, gradient, 1%-4% methanol). Fractions containing the product were pooled, concentrated and co-evaporated with 20 ml dichloromethane. 252 mg (0.499 mmol; 43% of theory over two steps, purity: 100%) of the target compound was obtained as a white free flowing powder.

LC-MS (Method 13B): $R_f$=2.11 min; m/z=503 (M−1)⁻

¹H-NMR (300 MHz, DMSO-d6) δ 11.40 [ppm]=(br. s, 1H), 8.31 (s, 1H), 6.10 (s, 1H), 4.10 (d, J=12.6 Hz, 2H), 3.50-3.21 (m, 4H), 2.25-1.85 (m, 10H), 1.57 (qd, J=12.4, 4.1 Hz, 2H), 1.42 (s, 9H)

In a 8 ml screw cap vial equipped with a stirring bar was placed 1.420 g (E)-tert-butyl 4-(3-(N'-hydroxy-N-(2-methoxyacetyl)carbamimidoyl)-5-oxo-4,5-dihydropyrazolo[1,5-a]pyrimidin-7-yl)piperidine-1-carboxylate hydrochloride from Example 34A 6 ml (dry) 1,4-dioxan. 0.040 ml (0.161 mmol) Hydrochloric acid (4.0 M in dioxane) was added and the clear yellow solution stirred at 90° C. for 8 hours. The reaction mixture was diluted with 100 ml 0.5 M hydrochloric acid and extracted 3 times with 50 ml dichloromethane. The organic layers were combined, washed with 100 ml aqueous ammonia (15% w/w), dried with sodium sulfate, filtered and concentrated. 207 mg yellow solid was obtained and purified by flash column chromatography (Method 15B; 12 g cartridge; dichloromethane, gradient, 1%-4% methanol). Fractions containing the product were pooled, concentrated and co-evaporated with 20 ml dichloromethane. 118 mg (0.241 mmol; 15% of theory over two steps, purity: 88%) of the target compound was obtained.

LC-MS (Method 13B): $R_f$=1.91 min; m/z=429 (M−1)⁻

¹H-NMR (300 MHz, DMSO-d6) δ[ppm]=11.47 (br. s, 1H), 8.35 (s, 1H), 6.14 (s, 1H), 4.81 (s, 2H), 4.10 (d, J=12.5 Hz, 2H), 3.50-3.37 (m, 4H), 2.87 (s, 2H), 2.01 (d, J=12.5 Hz, 2H), 1.58 (qd, J=12.4, 4.1 Hz, 2H), 1.42 (s, 9H)

Example 495A

Tert-butyl 4-(3-(5-(3-methoxypropyl)-1,2,4-oxadiazol-3-yl)-5-oxo-4,5-dihydropyrazolo[1,5-a]pyrimidin-7-yl)piperidine-1-carboxylate

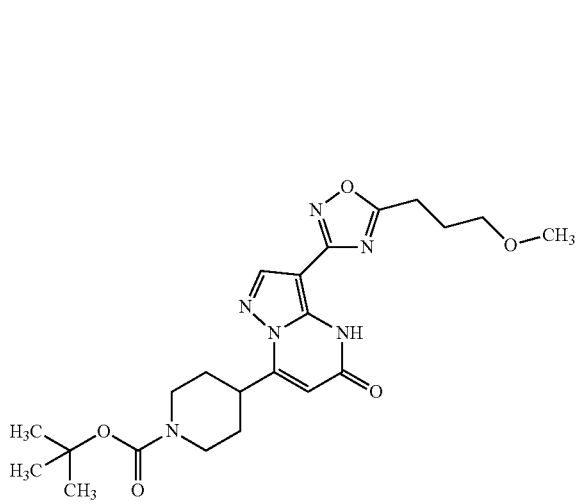 [SMILES: COCCCc1nc(-c2cnn3c(C4CCN(C(=O)OC(C)(C)C)CC4)cc(=O)[nH]c23)no1]

In a 8 ml screw cap vial equipped with a stirring bar was placed 1.100 g (E)-tert-butyl 4-(3-(N'-hydroxy-N-(4-methoxybutanoyl)carbamimidoyl)-5-oxo-4,5-dihydropyrazolo[1,5-a]pyrimidin-7-yl)piperidine-1-carboxylate hydrochloride from Example 36A and 6 ml (dry) 1,4-dioxan. 0.040 ml (0.161 mmol) hydrochloric acid (4.0 M in dioxane) was added and the clear yellow solution stirred at 90° C. for 24 hours. The reaction mixture was diluted with 100 ml 0.5 M hydrochloric acid and extracted with 3 times with 50 ml dichloromethane. The organics were combined, washed with 100 ml aqueous ammonia (15% w/w), dried with sodium sulfate, filtered and concentrated. 219 mg yellow solid remained and was purified by flash column chromatography. (Method 15B; 12 g cartridge; dichloromethane, gradient, 1%-4% methanol). Fractions containing the product were pooled, concentrated and co-evaporated with 20 ml dichloromethane. 122 mg (0.263 mmol; 22% of theory over two steps, purity: 33%) of the target compound was obtained.

LC-MS (Method 13B): $R_t$=1.96 min; m/z=457 (M−1)⁻
¹H-NMR (300 MHz, DMSO-d6) δ[ppm] 11.31 (br. s, 1H), 8.31 (s, 1H), 6.11 (s, 1H), 4.10 (d, J=12.2 Hz, 2H), 3.42 (t, J=6.2 Hz, 3H), 3.24 (s, 3H), 3.01 (t, J=7.5 Hz, 2H), 2.87 (br. s, 2H), 2.09-1.94 (m, 4H), 1.57 (qd, J=12.5, 4.1 Hz, 2H), 1.42 (s, 9H)

Example 496A

Tert-butyl 4-{3-[3-(2-methoxyphenyl)-1,2,4-oxadiazol-5-yl]-2-methyl-5-oxo-4,5-dihydropyrazolo[1,5-a]pyrimidin-7-yl}piperidine-1-carboxylate

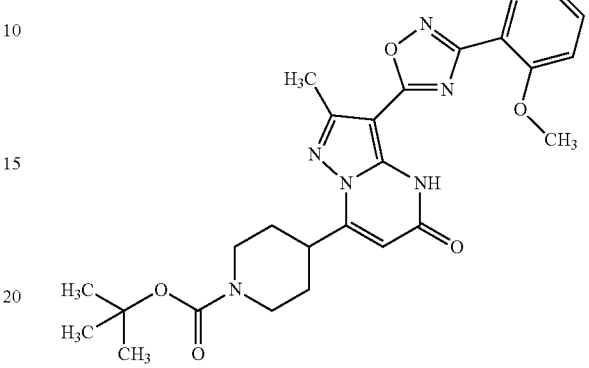

7-[1-(tert-butoxycarbonyl)piperidin-4-yl]-2-methyl-5-oxo-4,5-dihydropyrazolo[1,5-a]pyrimidine-3-carboxylic acid (150 mg, 398 µmol) was dissolved in N,N-Dimethylformamid (2 ml) and treated with N,N-Diisopropylethylamine (210 µl, 1.2 mmol) and 1,1'-Carboyldiimidazol (129 mg, 797 µmol). The mixture was stirred at 90° C. for 1.5 h. N'-hydroxy-2-methoxybenzenecarboximidamide (132 mg, 797 µmol) was dissolved in N,N-Dimethylformamid (1 ml) and added dropwise. The mixture was then stirred at 110° C. for 6 h. The mixture was purified via reverse phase HPLC (Method: column: Reprosil C18; 10 µm; 125×30 mm/flow: 50 ml/min/solvents: A=water (0.01% formic acid), B=acetonitrile/gradient: 0.00-5.00 min=10% B, 6.50 min=20% B, 17.0-19.75 min=100% B, 19.75.00-23.00 min=90% B) to afford the product. The obtained amount was 94.0 mg (96% purity, 45% of theory).

LC-MS (Method 11B): $R_t$=2.25 min; MS (ESIneg): m/z=505 [M−H]⁻

Example 497A

Tert-butyl 4-{3-[3-(2-fluorophenyl)-1,2,4-oxadiazol-5-yl]-2-methyl-5-oxo-4,5-dihydropyrazolo[1,5-a]pyrimidin-7-yl}piperidine-1-carboxylate

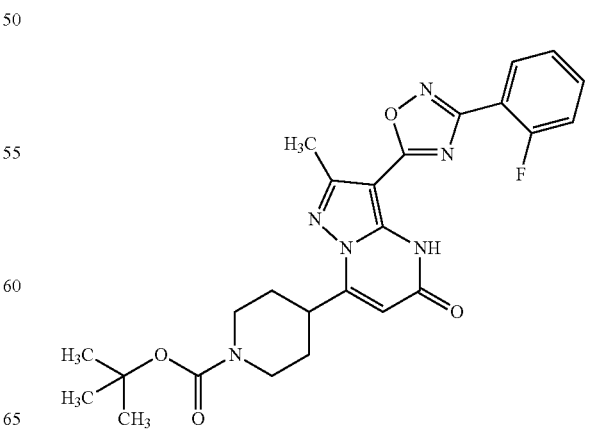

7-[1-(tert-butoxycarbonyl)piperidin-4-yl]-2-methyl-5-oxo-4,5-dihydropyrazolo[1,5-a]pyrimidine-3-carboxylic acid (150 mg, 398 μmol) was dissolved in N,N-Dimethylformamid (2 ml) and treated with N,N-Diisopropylethylamine (210 μl, 1.2 mmol) and 1,1'-Carboyldiimidazol (129 mg, 797 μmol). The mixture was stirred at 90° C. for 1.5 h. 2-fluoro-N'-hydroxybenzenecarboximidamide (123 mg, 797 μmol) was dissolved in N,N-Dimethylformamid (1 ml) and added dropwise. The mixture was then stirred at 110° C. for 6 h. The mixture was purified via reverse phase HPLC (Method: column: Reprosil C18; 10 μm; 125×30 mm/flow: 50 ml/min/solvents: A=water (0.01% formic acid), B=acetonitrile/gradient: 0.00-5.00 min=10% B, 6.50 min=20% B, 17.0-19.75 min=100% B, 19.75.00-23.00 min=90% B) to afford the product. The obtained amount was 92.7 mg (100% purity, 47% of theory).

LC-MS (Method 11B): $R_t$=2.36 min; MS (ESIpos): m/z=495 [M+H]$^+$

Example 498A

Tert-butyl 4-{3-[3-(2-chlorobenzyl)-1,2,4-oxadiazol-5-yl]-2-methyl-5-oxo-4,5-dihydropyrazolo[1,5-a]pyrimidin-7-yl}piperidine-1-carboxylate

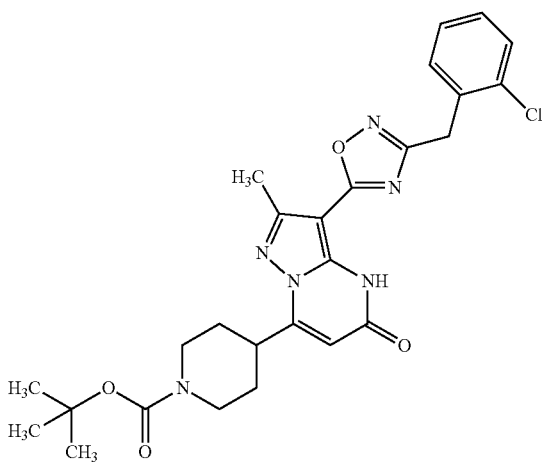 [SMILES: Cc1nn2c(C3CCN(C(=O)OC(C)(C)C)CC3)cc(=O)[nH]c2c1-c1nc(Cc2ccccc2Cl)no1]

7-[1-(tert-butoxycarbonyl)piperidin-4-yl]-2-methyl-5-oxo-4,5-dihydropyrazolo[1,5-a]pyrimidine-3-carboxylic acid (150 mg, 398 μmol) was dissolved in N,N-Dimethylformamid (2 ml) and treated with N,N-Diisopropylethylamine (210 μl, 1.2 mmol) and 1,1'-Carboyldiimidazol (129 mg, 797 μmol). The mixture was stirred at 90° C. for 1.5 h. (1Z)-2-(2-chlorophenyl)-N'-hydroxyethanimidamide (147 mg, 797 μmol) was dissolved in N,N-Dimethylformamid (1 ml) and added dropwise. The mixture was then stirred at 110° C. for 6 h. The mixture was purified via reverse phase HPLC (Method: column: Reprosil C18; 10 μm; 125×30 mm/flow: 50 ml/min/solvents: A=water (0.01% formic acid), B=acetonitrile/gradient: 0.00-5.00 min=10% B, 6.50 min=20% B, 17.0-19.75 min=100% B, 19.75.00-23.00 min=90% B) to afford the product. The obtained amount was 42.4 mg (60% purity, 12% of theory).

LC-MS (Method 11B): $R_t$=2.43 min; MS (ESIpos): m/z=525 [M+H]$^+$

Example 499A

Tert-butyl 4-{2-methyl-3-[3-(2-methylphenyl)-1,2,4-oxadiazol-5-yl]-5-oxo-4,5-dihydropyrazolo[1,5-a]pyrimidin-7-yl}piperidine-1-carboxylate

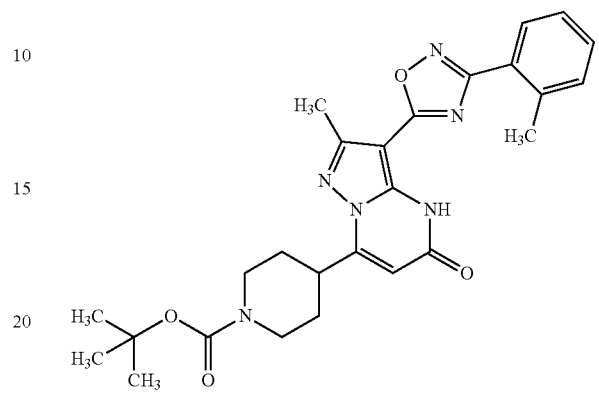

7-[1-(tert-butoxycarbonyl)piperidin-4-yl]-2-methyl-5-oxo-4,5-dihydropyrazolo[1,5-a]pyrimidine-3-carboxylic acid (150 mg, 398 μmol) was dissolved in N,N-Dimethylformamid (2 ml) and treated with N,N-Diisopropylethylamine (210 μl, 1.2 mmol) and 1,1'-Carboyldiimidazol (129 mg, 797 μmol). The mixture was stirred at 90° C. for 1.5 h. N'-hydroxy-2-methylbenzenecarboximidamide (120 mg, 797 μmol) was dissolved in N,N-Dimethylformamid (1 ml) and added dropwise. The mixture was then stirred at 110° C. for 6 h. The mixture was purified via reverse phase HPLC (Method: column: Reprosil C18; 10 μm; 125×30 mm/flow: 50 ml/min/solvents: A=water (0.01% formic acid), B=acetonitrile/gradient: 0.00-5.00 min=10% B, 6.50 min=20% B, 17.0-19.75 min=100% B, 19.75.00-23.00 min=90% B) to afford the product. The obtained amount was 111 mg (93% purity, 53% of theory).

LC-MS (Method 11B): $R_t$=2.53 min; MS (ESIpos): m/z=491 [M+H]$^+$

Example 500A

Tert-butyl 4-{3-[3-(3-chlorophenyl)-1,2,4-oxadiazol-5-yl]-2-methyl-5-oxo-4,5-dihydropyrazolo[1,5-a]pyrimidin-7-yl}piperidine-1-carboxylate

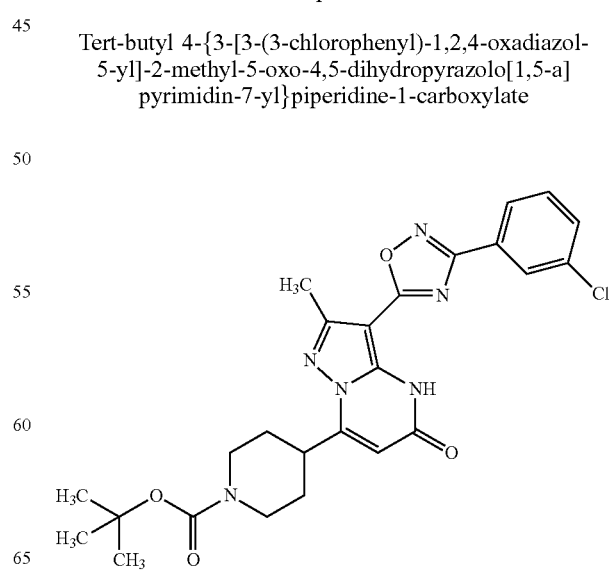

7-[1-(tert-butoxycarbonyl)piperidin-4-yl]-2-methyl-5-oxo-4,5-dihydropyrazolo[1,5-a]pyrimidine-3-carboxylic acid (150 mg, 398 µmol) was dissolved in N,N-Dimethylformamid (2 ml) and treated with N,N-Diisopropylethylamine (210 µl, 1.2 mmol) and 1,1'-Carboyldiimidazol (129 mg, 797 µmol). The mixture was stirred at 90° C. for 1.5 h. 3-chloro-N'-hydroxybenzenecarboximidamide (136 mg, 797 µmol) was dissolved in N,N-Dimethylformamid (1 ml) and added dropwise. The mixture was then stirred at 110° C. for 6 h. The mixture was purified via reverse phase HPLC (Method: column: Reprosil C18; 10 µm; 125×30 mm/flow: 50 ml/min/solvents: A=water (0.01% formic acid), B=acetonitrile/gradient: 0.00-5.00 min=10% B, 6.50 min=20% B, 17.0-19.75 min=100% B, 19.75.00-23.00 min=90% B) to afford the product. The obtained amount was 83.7 mg (100% purity, 41% of theory).

LC-MS (Method 11B): R$_t$=2.61 min; MS (ESIneg): m/z=509 [M−H]$^-$

Example 501A

Tert-butyl 4-(2-methyl-5-oxo-3-{3-[4-(trifluoromethyl)phenyl]-1,2,4-oxadiazol-5-yl}-4,5-dihydropyrazolo[1,5-a]pyrimidin-7-yl)piperidine-1-carboxylate

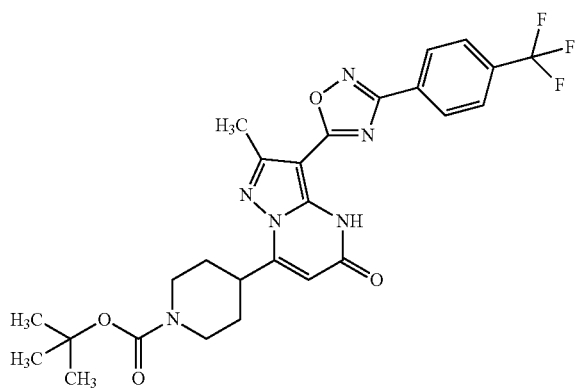 [SMILES: Cc1nn2c(C3CCN(C(=O)OC(C)(C)C)CC3)cc(=O)[nH]c2c1-c1nc(-c2ccc(C(F)(F)F)cc2)no1]

7-[1-(tert-butoxycarbonyl)piperidin-4-yl]-2-methyl-5-oxo-4,5-dihydropyrazolo[1,5-a]pyrimidine-3-carboxylic acid (150 mg, 398 µmol) was dissolved in N,N-Dimethylformamid (2 ml) and treated with N,N-Diisopropylethylamine (210 µl, 1.2 mmol) and 1,1'-Carboyldiimidazol (129 mg, 797 µmol). The mixture was stirred at 90° C. for 1.5 h. N'-hydroxy-4-(trifluoromethyl)benzenecarboximidamide (163 mg, 797 µmol) was dissolved in N,N-Dimethylformamid (1 ml) and added dropwise. The mixture was then stirred at 110° C. for 6 h. The mixture was purified via reverse phase HPLC (Method: column: Reprosil C18; 10 µm; 125×30 mm/flow: 50 ml/min/solvents: A=water (0.01% formic acid), B=acetonitrile/gradient: 0.00-5.00 min=10% B, 6.50 min=20% B, 17.0-19.75 min=100% B, 19.75.00-23.00 min=90% B) to afford the product. The obtained amount was 52.7 mg (90% purity, 22% of theory).

LC-MS (Method 11B): R$_t$=2.62 min; MS (ESIneg): m/z=543 [M−H]$^-$

Example 502A

Tert-butyl 4-{3-[4-methyl-5-(2-methylpropyl)-1,3-thiazol-2-yl]-5-oxo-4,5-dihydropyrazolo[1,5-a]pyrimidin-7-yl}piperidine-1-carboxylate

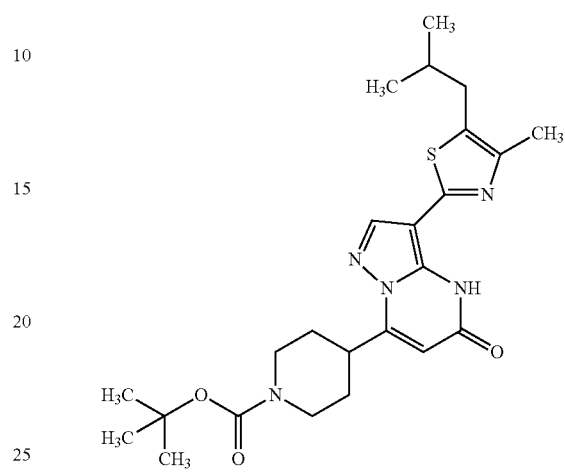

tert-butyl 4-(3-carbamothioyl-5-oxo-4,5-dihydropyrazolo[1,5-a]pyrimidin-7-yl)piperidine-1-carboxylate (120 mg, 318 µmol), 3-chloro-5-methylhexan-2-one (47.3 mg, 318 µmol) and N,N-Diisopropylethylamine (280 µl, 1.6 mmol) were dissolved in Ethanol (4.8 ml, 82 mmol) and stirred at 70° C. for 1 h. Tetra-n-butylammoniumiodide (23.5 mg, 63.6 µmol) was added and the mixture was stirred at 70° C. for 16 h. Water was added and the mixture was purified via reverse phase HPLC (Method: column: Reprosil C18; 10 µm; 125×30 mm/flow: 50 ml/min/solvents: A=water (0.1% formic acid), B=acetonitrile/gradient: 0.00-4.25 min=20% B, 4.50 min=30% B, 19.00-22.50 min=100% B, 22.75-25.00 min=20% B) to afford the product. The obtained amount was 32.0 mg (100% purity, 21% of theory).

LC-MS (Method 11B): R$_t$=2.65 min; MS (ESIpos): m/z=472 [M+H]$^+$

Example 503A

Tert-butyl 4-{3-[5-(3,5-difluoro-4-methoxybenzyl)-1,3,4-oxadiazol-2-yl]-5-oxo-4,5-dihydropyrazolo[1,5-a]pyrimidin-7-yl}piperidine-1-carboxylate

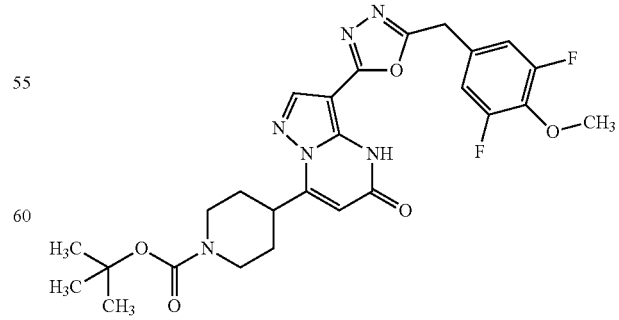

tert-butyl 4-[3-({2-[(3,5-difluoro-4-methoxyphenyl)acetyl]hydrazinyl}carbonyl)-5-oxo-4,5-dihydropyrazolo[1, 5-a]pyrimidin-7-yl]piperidine-1-carboxylate (50.0 mg, 89.2 µmol) was dissolved in THF (2.0 ml, 25 mmol) and stirred with Burgess-Reagent (29.8 mg, 125 µmol) for 16 h at RT. Water and ethyl acetate were added and the mixture purified via reverse phase chromatography (Method: Reprosil C18; 10 µm; 125×30 mm/flow: 50 ml/min/solvents: A=water (0.01% formic acid), B=acetonitrile/gradient: 0.00-5.00 min=10% B, 6.50 min=20% B, 17.0-19.75 min=100% B, 19.75.00-23.00 min=90% B) to obtain the product after removal of the solvents in vacuo. The obtained amount was 24.7 mg (100% purity, 51% of theory).

LC-MS (Method 1B): $R_t$=1.10 min; MS (ESIpos): m/z=543 [M+H]$^+$

Example 504A

Tert-butyl 4-{3-[5-(2-fluorophenyl)-1,3,4-oxadiazol-2-yl]-2-methyl-5-oxo-4,5-dihydropyrazolo[1,5-a]pyrimidin-7-yl}piperidine-1-carboxylate

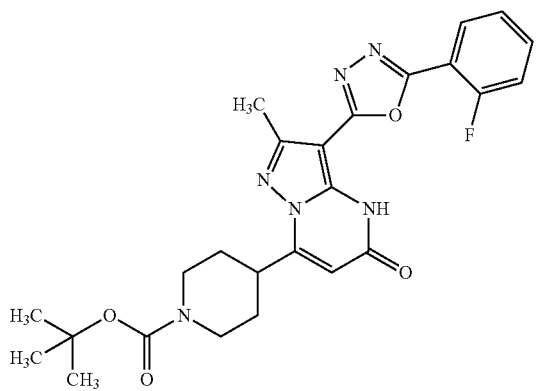 [SMILES: Cc1nn2c(C3CCN(C(=O)OC(C)(C)C)CC3)cc(=O)[nH]c2c1-c1nnc(-c2ccccc2F)o1]

tert-butyl 4-(3-{[2-(2-fluorobenzoyl)hydrazinyl]carbonyl}-2-methyl-5-oxo-4,5-dihydropyrazolo[1,5-a]pyrimidin-7-yl)piperidine-1-carboxylate (38.6 mg, 75.3 µmol) was dissolved in THF (2.0 ml, 25 mmol) and stirred with Burgess-Reagent (25.1 mg, 105 µmol) for 16 h at RT. Water and ethyl acetate were added and the mixture purified via reverse phase chromatography (Method: Reprosil C18; 10 µm; 125×30 mm/flow: 50 ml/min/solvents: A=water (0.01% formic acid), B=acetonitrile/gradient: 0.00-5.00 min=10% B, 6.50 min=20% B, 17.0-19.75 min=100% B, 19.75.00-23.00 min=90% B) to obtain the product after removal of the solvents in vacuo. The obtained amount was 29.5 mg (100% purity, 79% of theory).

LC-MS (Method 1B): $R_t$=1.12 min; MS (ESIpos): m/z=495 [M+H]$^+$

Example 505A

Tert-butyl 4-{3-[3-(4-hydroxybenzyl)-1,2,4-oxadiazol-5-yl]-2-methyl-5-oxo-4,5-dihydropyrazolo[1,5-a]pyrimidin-7-yl}piperidine-1-carboxylate

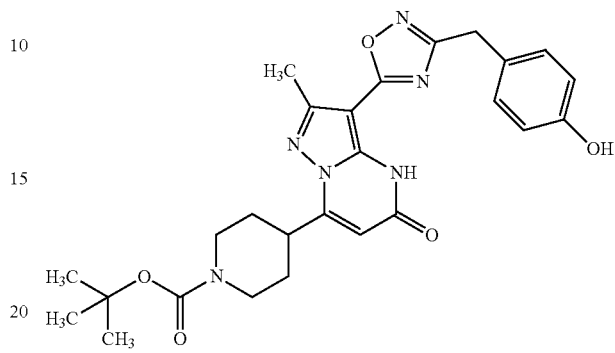

7-[1-(tert-butoxycarbonyl)piperidin-4-yl]-2-methyl-5-oxo-4,5-dihydropyrazolo[1,5-a]pyrimidine-3-carboxylic acid (150 mg, 398 µmol) was dissolved in N,N-Dimethylformamid (2 ml) and treated with N,N-Diisopropylethylamine (210 µl, 1.2 mmol) and 1,1'-Carboyldiimidazol (129 mg, 797 µmol). The mixture was stirred at 90° C. for 1.5 h. (1Z)-N'-hydroxy-2-(4-methoxyphenyl)ethanimidamide (144 mg, 797 µmol) was dissolved in N,N-Dimethylformamid (1 ml) and added dropwise. The mixture was then stirred at 110° C. for 6 h. The mixture was purified via reverse phase HPLC (Method: column: Reprosil C18; 10 µm; 125×30 mm/flow: 50 ml/min/solvents: A=water (0.01% formic acid), B=acetonitrile/gradient: 0.00-5.00 min=10% B, 6.50 min=20% B, 17.0-19.75 min=100% B, 19.75.00-23.00 min=90% B) to afford the product. The obtained amount was 84.6 mg (99% purity, 41% of theory).

LC-MS (Method 1B): $R_t$=1.33 min; MS (ESIpos): m/z=507 [M+H]$^+$

Example 506A

Tert-butyl 4-{3-[5-(3-fluoro-4-methoxybenzyl)-1,3,4-oxadiazol-2-yl]-5-oxo-4,5-dihydropyrazolo[1,5-a]pyrimidin-7-yl}piperidine-1-carboxylate

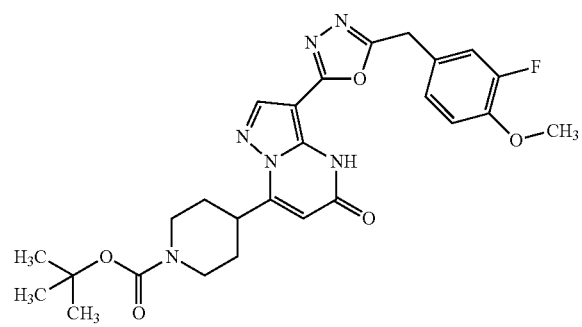 [SMILES: COc1ccc(Cc2nnc(-c3cnn4c(C5CCN(C(=O)OC(C)(C)C)CC5)cc(=O)[nH]c34)o2)cc1F]

tert-butyl 4-[3-({2-[(3-fluoro-4-methoxyphenyl)acetyl]hydrazinyl}carbonyl)-5-oxo-4,5-dihydropyrazolo[1,5-a]pyrimidin-7-yl]piperidine-1-carboxylate (34.0 mg, 62.7 µmol) was dissolved in THF (1.7 ml, 21 mmol) and stirred with Burgess-Reagent (20.9 mg, 87.7 µmol) for 16 h at RT. Water was added and the mixture purified via reverse phase chromatography (Method: Reprosil C18; 10 µm; 125×30 mm/flow: 50 ml/min/solvents: A=water (0.01% formic acid), B=acetonitrile/gradient: 0.00-5.00 min=10% B, 6.50 min=20% B, 17.0-19.75 min=100% B, 19.75.00-23.00 min=90% B) to obtain the product after removal of the solvents in vacuo. The obtained amount was 10.1 mg (100% purity, 31% of theory).

LC-MS (Method 11B): R$_t$=1.90 min; MS (ESIpos): m/z=525 [M+H]$^+$

Example 507A

Tert-butyl 4-{3-[4-(2-methylphenyl)-1,3-thiazol-2-yl]-5-oxo-4,5-dihydropyrazolo[1,5-a]pyrimidin-7-yl}piperidine-1-carboxylate

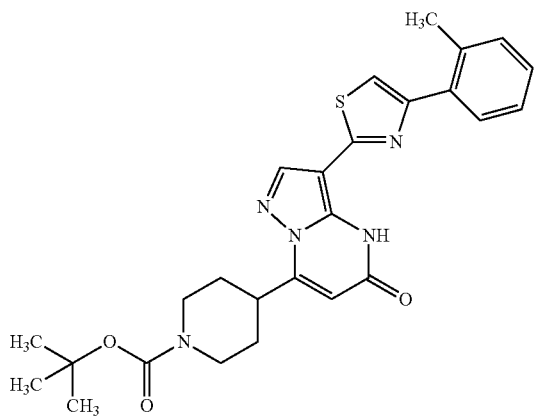 [SMILES: Cc1ccccc1-c1csc(-c2cnn3c(C4CCN(C(=O)OC(C)(C)C)CC4)cc(=O)[nH]c23)n1]

tert-butyl 4-(3-carbamothioyl-5-oxo-4,5-dihydropyrazolo[1,5-a]pyrimidin-7-yl)piperidine-1-carboxylate (100 mg, 265 µmol), and 2-bromo-1-(2-methylphenyl)ethanone (40 µl, 260 µmol) were dissolved in Ethanol (3.0 ml, 52 mmol) and stirred at 70° C. for 2 h. The solvents were removed in vacuo to afford the product. The obtained amount was 12 mg (95% purity, 22% of theory).

LC-MS (Method 1B): R$_t$=1.37 min; MS (ESIpos): m/z=492 [M+H]$^+$

Example 508A

Tert-butyl 4-[3-({2-[(3,5-difluoro-4-methoxyphenyl)acetyl]hydrazinyl}carbonyl)-5-oxo-4,5-dihydropyrazolo[1,5-a]pyrimidin-7-yl]piperidine-1-carboxylate

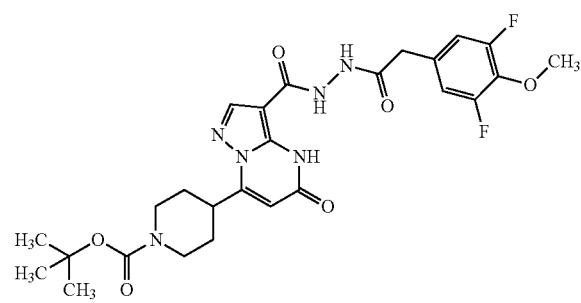 [SMILES: COc1c(F)cc(CC(=O)NNC(=O)c2cnn3c(C4CCN(C(=O)OC(C)(C)C)CC4)cc(=O)[nH]c23)cc1F]

7-[1-(tert-butoxycarbonyl)piperidin-4-yl]-5-oxo-4,5-dihydropyrazolo[1,5-a]pyrimidine-3-carboxylic acid (150 mg, 414 µmol) and 2-(3,5-difluoro-4-methoxyphenyl)acetohydrazide (134 mg, 621 µmol) were dissolved in N,N-Dimethylformamid (1.5 ml, 19 mmol). N,N-Diisopropylethylamine (220 µl, 1.2 mmol) and HATU (236 mg, 621 µmol) were added and the mixture was stirred at RT for 16 h. Purification via revere phase HPLC (Method: Reprosil C18; 10 µm; 125×30 mm/flow: 50 ml/min/solvents: A=water (0.01% trifluoroacetic acid), B=acetonitrile/gradient: 0.00-5.00 min=20% B, 6.50 min=40% B, 17.0-19.75 min=100% B, 19.75.00-23.00 min=40% B) afforded the desired product after drying in vacuo. The obtained amount was 50.1 mg (22% of theory).

LC-MS (Method 1B): R$_t$=0.91 min; MS (ESIneg): m/z=559 [M−H]$^-$

Example 509A

Tert-butyl 4-(3-{[2-(2-fluorobenzoyl)hydrazinyl]carbonyl}-2-methyl-5-oxo-4,5-dihydropyrazolo[1,5-a]pyrimidin-7-yl)piperidine-1-carboxylate

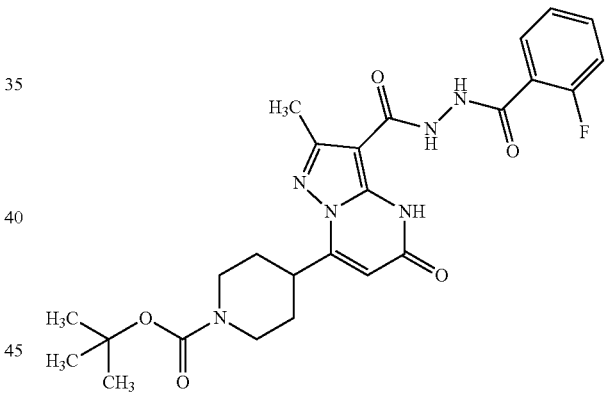

7-[1-(tert-butoxycarbonyl)piperidin-4-yl]-2-methyl-5-oxo-4,5-dihydropyrazolo[1,5-a]pyrimidine-3-carboxylic acid (150 mg, 398 µmol) and 2-fluorobenzohydrazide (92.1 mg, 598 µmol) were dissolved in N,N-Dimethylformamid (2.0 ml, 26 mmol). N,N-Diisopropylethylamine (210 µl, 1.2 mmol) and HATU (256 mg, 598 µmol) were added and the mixture was stirred at RT for 16 h. Purification via revere phase HPLC (Method: Reprosil C18; 10 µm; 125×30 mm/flow: 50 ml/min/solvents: A=water (0.01% trifluoroacetic acid), B=acetonitrile/gradient: 0.00-5.00 min=20% B, 6.50 min=40% B, 17.0-19.75 min=100% B, 19.75.00-23.00 min=40% B) afforded the desired product after drying in vacuo.

The obtained amount was 40.7 mg (100% purity, 20% of theory).

LC-MS (Method 11B): R$_t$=1.73 min; MS (ESIpos): m/z=513 [M+H]$^+$

Example 510A

Tert-butyl 4-[3-({2-[(3-fluoro-4-methoxyphenyl)acetyl]hydrazinyl}carbonyl)-5-oxo-4,5-dihydropyrazolo[1,5-a]pyrimidin-7-yl]piperidine-1-carboxylate

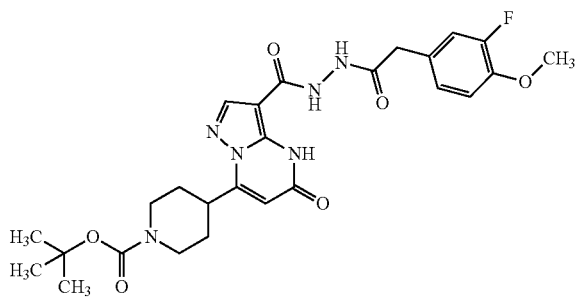 [SMILES: COc1ccc(CC(=O)NNC(=O)c2cnn3c(C4CCN(C(=O)OC(C)(C)C)CC4)cc(=O)[nH]c23)cc1F]

7-[1-(tert-butoxycarbonyl)piperidin-4-yl]-5-oxo-4,5-dihydropyrazolo[1,5-a]pyrimidine-3-carboxylic acid (150 mg, 414 µmol) and 2-(3-fluoro-4-methoxyphenyl)acetohydrazide (123 mg, 621 µmol) were dissolved in N,N-Dimethylformamid (1.5 ml, 19 mmol). N,N-Diisopropylethylamine (220 µl, 1.2 mmol) and HATU (236 mg, 621 µmol) were added and the mixture was stirred at RT for 16 h. Purification via revere phase HPLC (Method: Reprosil C18; 10 µm; 125×30 mm/flow: 50 ml/min/solvents: A=water (0.01% trifluoroacetic acid), B=acetonitrile/gradient: 0.00-5.00 min=20% B, 6.50 min=40% B, 17.0-19.75 min=100% B, 19.75.00-23.00 min=40% B) afforded the desired product after drying in vacuo. The obtained amount was 34.0 mg (73% purity, 11% of theory).

LC-MS (Method 11B): $R_t$=1.54 min; MS (ESIneg): m/z=541 [M–H]$^-$

Example 511A

Tert-butyl 4-[3-(2-hydroxypropan-2-yl)-5-oxo-4,5-dihydropyrazolo[1,5-a]pyrimidin-7-yl]piperidine-1-carboxylate

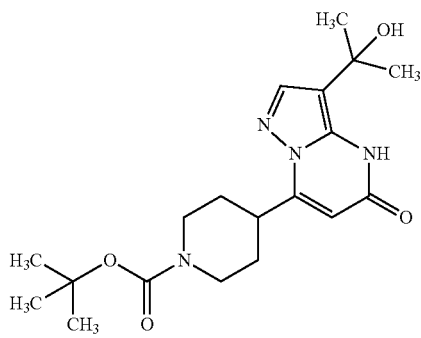 [SMILES: CC(C)(C)OC(=O)N1CCC(c2cc(=O)[nH]c3c(C(C)(C)O)cnn23)CC1]

A solution of bromo(methyl)magnesium (1.4 ml, 1.0 M in diethyl ether, 1.4 mmol) in tetrahydrofuran (2.0 ml) under argon was cooled to 0° C. before a solution of ethyl 7-[1-(tert-butoxycarbonyl)piperidin-4-yl]-5-oxo-4,5-dihydropyrazolo[1,5-a]pyrimidine-3-carboxylate (200 mg, 94% purity, 482 µmol) in tetrahydrofuran (2.0 ml) was added drop wise. The ice bath was removed and the mixture was stirred overnight at room temperature. The reaction was quenched with hydrochloric acid (1N solution in water, 1.5 ml), dissolved in water (3.0 ml) and acetonitrile (2.0 ml) before being purified by preparative HPLC (gradient acetonitrile/water with 0.1% formic acid). Evaporation of the combined product fractions, which were then lyophilized, yielded the title compound. The obtained amount was 125 mg (100% purity, 69% of theory).

LC-MS (Method 11B): $R_t$=1.52 min; MS (ESIneg): m/z=375 [M–H]$^-$

Example 512A

Tert-butyl 4-[3-(5-methyl-2-phenyl-1,3-thiazol-4-yl)-5-oxo-4,5-dihydropyrazolo[1,5-a]pyrimidin-7-yl]piperidine-1-carboxylate

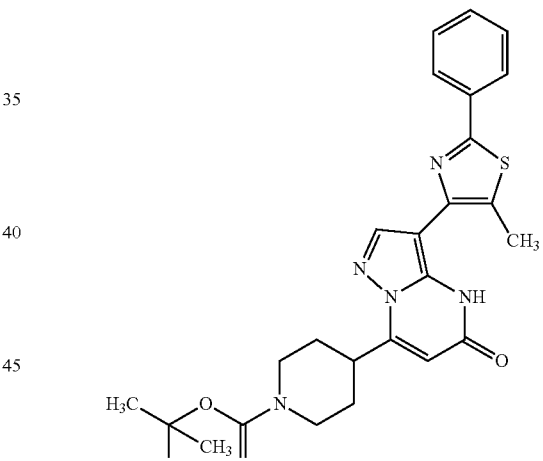

A solution of tert-butyl 4-[3-(2-bromopropanoyl)-5-oxo-4,5-dihydropyrazolo[1,5-a]pyrimidin-7-yl]piperidine-1-carboxylate (44.0 mg, 97.1 µmol), benzenecarbothioamide (13.3 mg, 97.1 µmol) and ethyldiisopropylamine (85 µl, 490 µmol) in ethanol (3.0 ml) was stirred 1 h at 70° C. The mixture was purified by preparative HPLC (gradient acetonitrile/water with 0.1% formic acid). Evaporation of the combined product fractions yielded the title compound. The obtained amount was 7.50 mg (100% purity, 16% of theory).

LC-MS (Method 1B): $R_t$=1.32 min; MS (ESIpos): m/z=492 [M+H]$^+$

Example 513A

Tert-butyl 4-[3-(cyclopentylcarbonoimidoyl)-5-oxo-4,5-dihydropyrazolo[1,5-a]pyrimidin-7-yl]piperidine-1-carboxylate

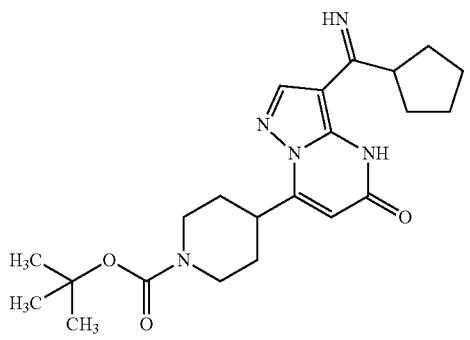 [SMILES: CC(C)(C)OC(=O)N1CCC(c2cc(=O)[nH]c3c(C(=N)C4CCCC4)cnn23)CC1]

A solution of tert-butyl 4-(3-cyano-5-oxo-4,5-dihydropyrazolo[1,5-a]pyrimidin-7-yl)piperidine-1-carboxylate (400 mg, 1.16 mmol) and bromo(cyclopentyl)magnesium (2.9 ml, 2.0 M in diethyl ether, 5.8 mmol) in tetrahydrofuran (2.0 ml) was stirred overnight at 60° C. under argon before being stirred with ethyl acetate (100 ml) and hydrochloric acid (1N solution in water, 100 ml). The organic phase was extracted, dried over sodium sulfate and concentrated. The mixture was dissolved in a mixture of acetonitrile/dimethyl sulfoxide, and purified by preparative HPLC (gradient acetonitrile/water with 0.1% formic acid). Fractions containing the imine (title compound) or the corresponding ketone were combined, evaporated and used in the next step (147 mg).

LC-MS (Method 11B): $R_t$=1.55 min; MS (ESIpos): m/z=414 [M+H]$^+$

Example 514A

Tert-butyl 4-[3-(2-methylbutanimidoyl)-5-oxo-4,5-dihydropyrazolo[1,5-a]pyrimidin-7-yl]piperidine-1-carboxylate

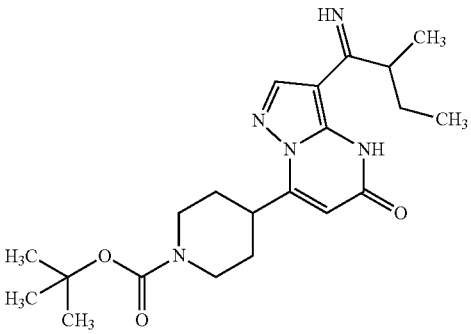 [SMILES: CCC(C)C(=N)c1cnn2c(C3CCN(C(=O)OC(C)(C)C)CC3)cc(=O)[nH]c12]

A solution of tert-butyl 4-(3-cyano-5-oxo-4,5-dihydropyrazolo[1,5-a]pyrimidin-7-yl)piperidine-1-carboxylate (50.0 mg, 146 µmol) and bromo(butan-2-yl)magnesium (730 µl, 1.0 M in tetrahydrofuran, 730 µmol) in tetrahydrofuran (1.0 ml) was stirred overnight at 60° C. under argon before being stirred with hydrochloric acid (1N solution in water). The mixture was purified by preparative HPLC (gradient acetonitrile/water with 0.1% formic acid). Fractions containing the imine (title compound) or the corresponding ketone were combined, evaporated and used in the next step (27.0 mg).

LC-MS (Method 11B): $R_t$=1.51 min; MS (ESIpos): m/z=402 [M+H]$^+$

Example 515A

Tert-butyl 4-[3-(cyclopropylcarbonyl)-5-oxo-4,5-dihydropyrazolo[1,5-a]pyrimidin-7-yl]piperidine-1-carboxylate

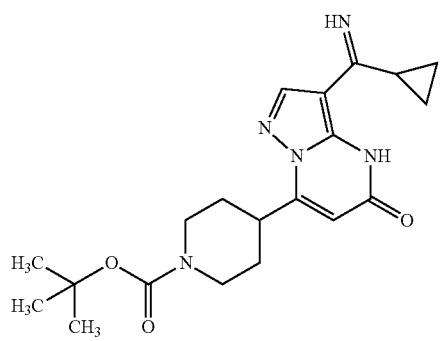 [SMILES: CC(C)(C)OC(=O)N1CCC(c2cc(=O)[nH]c3c(C(=N)C4CC4)cnn23)CC1]

A solution of tert-butyl 4-(3-cyano-5-oxo-4,5-dihydropyrazolo[1,5-a]pyrimidin-7-yl)piperidine-1-carboxylate (300 mg, 874 µmol) and bromo(cyclopropyl)magnesium (8.7 ml, 0.50 M in tetrahydrofuran, 4.4 mmol) in tetrahydrofuran (7.5 ml) was stirred overnight at 60° C. under argon before being stirred with ethyl acetate and hydrochloric acid (1N solution in water). The organic phase was extracted, dried over sodium sulfate and concentrated. The mixture was dissolved in a mixture of acetonitrile/dimethyl sulfoxide, and purified by preparative HPLC (gradient acetonitrile/water with 0.1% formic acid). Fractions containing the imine (title compound) or the corresponding ketone were combined, evaporated and used in the next step (42 mg).

LC-MS (Method 1B): $R_t$=0.79 min; MS (ESIpos): m/z=386 [M+H]$^+$

Example 516A

Methyl 7-[1-(tert-butoxycarbonyl)piperidin-4-yl]-5-oxo-2-(trifluoromethyl)-4,5-dihydropyrazolo[1,5-a]pyrimidine-3-carboxylate

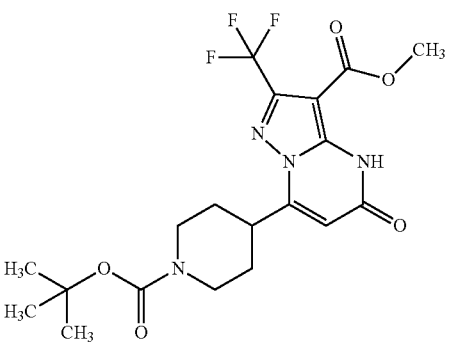 [SMILES: COC(=O)c1c(C(F)(F)F)nn2c(C3CCN(C(=O)OC(C)(C)C)CC3)cc(=O)[nH]c12]

A mixture of methyl 5-amino-3-(trifluoromethyl)-1H-pyrazole-4-carboxylate (1.32 g, 6.29 mmol) and tert-butyl 4-[(2,2-dimethyl-4,6-dioxo-1,3-dioxan-5-yl)carbonyl]piperidine-1-carboxylate (5.81 g, 16.4 mmol) in acetonitrile (65 ml) was stirred under argon for 1 h at reflux. Triethylamine (2.6 ml, 19 mmol) was added and the stirring was continued for 24 h. The mixture was diluted with 200 ml of ethyl acetate and washed three times with hydrochloric acid (1N solution in water, 200 ml). The organic phase was dried over sodium sulfate, filtered and concentrated. A 1:1 mixture of acetonitrile/water was added and the newly formed solid was filtered and dried in vacuo to yield the title product. The obtained amount was 1.34 g (96% purity, 46% of theory).

LC-MS (Method 8B): $R_t$=1.38 min; MS (ESIneg): m/z=443 [M−H]⁻

Example 517A

Ethyl 7-[1-(tert-butoxycarbonyl)piperidin-4-yl]-2-(methylsulfanyl)-5-oxo-4,5-dihydropyrazolo[1,5-a]pyrimidine-3-carboxylate

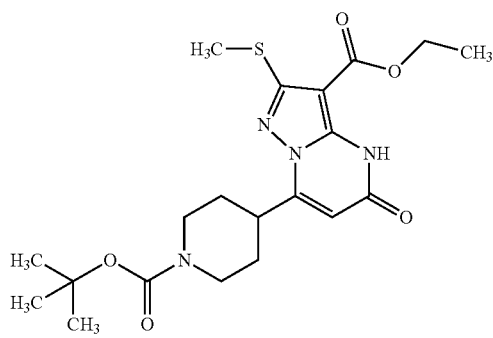 [SMILES: CCOC(=O)c1c(SC)nn2c(C3CCN(C(=O)OC(C)(C)C)CC3)cc(=O)[nH]c12]

A mixture of ethyl 5-amino-3-(methylsulfanyl)-1H-pyrazole-4-carboxylate (625 mg, 3.11 mmol) and tert-butyl 4-[(2,2-dimethyl-4,6-dioxo-1,3-dioxan-5-yl)carbonyl]piperidine-1-carboxylate (2.87 g, 8.07 mmol) in acetonitrile (24 ml) was stirred under argon overnight at reflux. Triethylamine (1.3 ml, 9.3 mmol) was added and the stirring was continued for 4 h. The mixture was acidified with hydrochloric acid (1N solution in water, 10 ml). The newly formed solid was filtered and dried in vacuo. The filtrate was concentrated, diluted with acetonitrile and water, and the resulting suspension was filtered and dried in vacuo. Both solid fractions were combined to yield the title compound. The obtained amount was 1.17 g (100% purity, 86% of theory).

LC-MS (Method 1B): $R_t$=1.16 min; MS (ESIneg): m/z=435 [M−H]⁻

Example 518A

Tert-butyl 4-[3-(2,2-dimethylpropanoyl)-5-oxo-4,5-dihydropyrazolo[1,5-a]pyrimidin-7-yl]piperidine-1-carboxylate

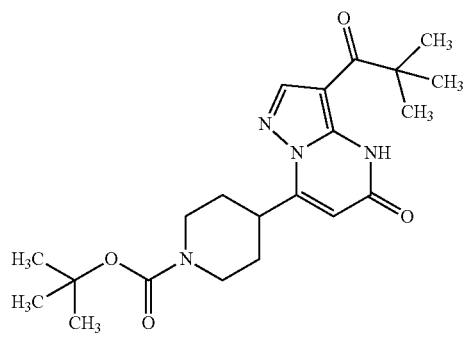 [SMILES: CC(C)(C)OC(=O)N1CCC(c2cc(=O)[nH]c3c(C(=O)C(C)(C)C)cnn23)CC1]

A solution of tert-butyl 4-(3-cyano-5-oxo-4,5-dihydropyrazolo[1,5-a]pyrimidin-7-yl)piperidine-1-carboxylate (200 mg, 582 μmol) and tert-butyl(chloro)magnesium (1.5 ml, 2.0 M, 2.9 mmol) in tetrahydrofuran (4.0 ml) was stirred overnight at 60° C. under argon before being quenched with a saturated aqueous solution of ammonium chloride and diluted with ethyl acetate. The organic phase was extracted, washed twice with a saturated aqueous solution of ammonium chloride and once with hydrochloric acid (1N solution in water) before being dried over sodium sulfate and concentrated. The recovered mixture was stirred overnight with a mixture of acetonitrile/formic acid (0.05% solution in water) and concentrated. The solid was filtered and was used as such in the next step. The obtained amount was 54.8 mg (80% purity).

LC-MS (Method 11B): $R_t$=2.04 min; MS (ESIneg): m/z=401 [M−H]⁻

Example 519A

7-[1-(tert-butoxycarbonyl)piperidin-4-yl]-5-oxo-2-(trifluoromethyl)-4,5-dihydropyrazolo[1,5-a]pyrimidine-3-carboxylic Acid

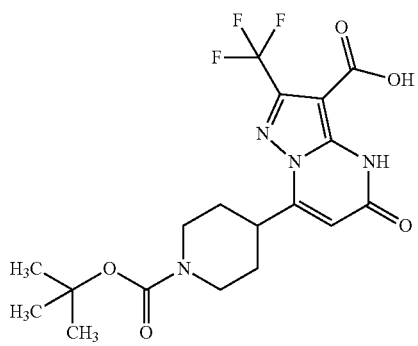 [SMILES: CC(C)(C)OC(=O)N1CCC(c2cc(=O)[nH]c3c(C(=O)O)c(C(F)(F)F)nn23)CC1]

A mixture of methyl 7-[1-(tert-butoxycarbonyl)piperidin-4-yl]-5-oxo-2-(trifluoromethyl)-4,5-dihydropyrazolo[1,5-a]pyrimidine-3-carboxylate (1.34 g, 3.02 mmol) and lithium hydroxyde (56 μl, 30 mmol) in methanol (100 ml) and water (50 ml) was stirred for three days at 45° C. The methanol was evaporated and the remaining aqueous solution was acidified with hydrochloric acid (1N solution in water). The newly formed solid was filtered and dried in vacuo to yield the title compound. The obtained amount was 1.12 g (100% purity, 86% of theory).

LC-MS (Method 11B): R$_t$=1.72 min; MS (ESIneg): m/z=429 [M–H]$^-$

Example 520A

Tert-butyl 4-[3-(1H-imidazol-1-ylcarbonyl)-5-oxo-2-(trifluoromethyl)-4,5-dihydropyrazolo[1,5-a]pyrimidin-7-yl]piperidine-1-carboxylate

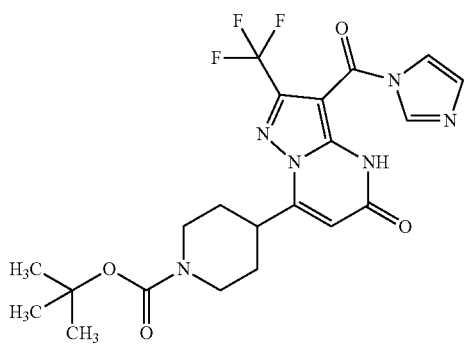 [SMILES: CC(C)(C)OC(=O)N1CCC(c2cc(=O)[nH]c3c(C(=O)n4ccnc4)c(C(F)(F)F)nn23)CC1]

Compound 7-[1-(tert-butoxycarbonyl)piperidin-4-yl]-5-oxo-2-(trifluoromethyl)-4,5-dihydropyrazolo[1,5-a]pyrimidine-3-carboxylic acid (100 mg, 232 µmol) was diluted in tetrahydrofuran (1.7 ml) before 1,1'-carbonyldiimidazole (75.4 mg, 465 µmol) was added. The mixture was stirred for 2 h at 80° C. before being concentrated and used as such in the next step.

LC-MS (Method 8B): R$_t$=1.27 min; MS (ESIneg): m/z=479 [M–H]$^-$

Example 521A

Ethyl 7-[1-(tert-butoxycarbonyl)piperidin-4-yl]-5-oxo-2-(trifluoromethyl)-4,5-dihydropyrazolo[1,5-a]pyrimidine-3-carboxylate

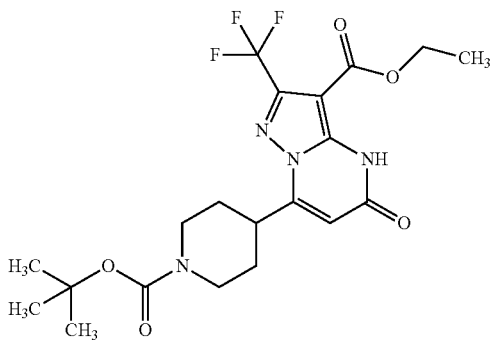 [SMILES: CCOC(=O)c1c(C(F)(F)F)nn2c(C3CCN(C(=O)OC(C)(C)C)CC3)cc(=O)[nH]c12]

Compound tert-butyl 4-[3-(1H-imidazol-1-ylcarbonyl)-5-oxo-2-(trifluoromethyl)-4,5-dihydropyrazolo[1,5-a]pyrimidin-7-yl]piperidine-1-carboxylate (111 mg, 231 µmol) was diluted in ethanol (3.0 ml, 460 µmol). The mixture was stirred for 2 h at 80° C. and purified by preparative HPLC (gradient acetonitrile/water with 0.1% formic acid). Evaporation of the combined product fractions yielded the title compound. The obtained amount was 85.0 mg (99% purity, 79% of theory).

LC-MS (Method 8B): R$_t$=1.46 min; MS (ESIneg): m/z=457 [M–H]$^-$

Example 522A

Propyl 7-[1-(tert-butoxycarbonyl)piperidin-4-yl]-5-oxo-2-(trifluoromethyl)-4,5-dihydropyrazolo[1,5-a]pyrimidine-3-carboxylate

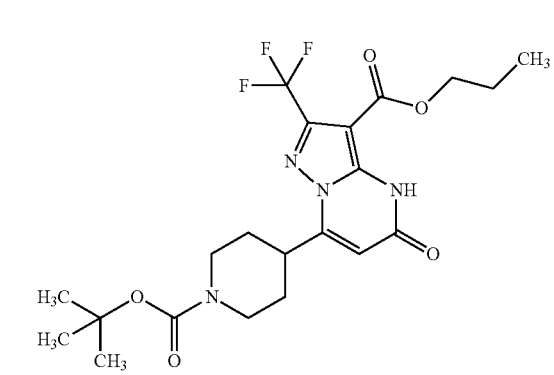 [SMILES: CCCOC(=O)c1c(C(F)(F)F)nn2c(C3CCN(C(=O)OC(C)(C)C)CC3)cc(=O)[nH]c12]

Compound tert-butyl 4-[3-(1H-imidazol-1-ylcarbonyl)-5-oxo-2-(trifluoromethyl)-4,5-dihydropyrazolo[1,5-a]pyrimidin-7-yl]piperidine-1-carboxylate (111 mg, 231 µmol) was diluted in propan-1-ol (3.0 ml, 460 µmol). The mixture was stirred for 2 h at 100° C. and purified by preparative HPLC (gradient acetonitrile/water with 0.1% formic acid). Evaporation of the combined product fractions yielded the title compound. The obtained amount was 98.0 mg (100% purity, 90% of theory).

LC-MS (Method 8B): R$_t$=1.54 min; MS (ESIneg): m/z=471 [M–H]$^-$

Example 523A

Propan-2-yl 7-[1-(tert-butoxycarbonyl)piperidin-4-yl]-5-oxo-2-(trifluoromethyl)-4,5-dihydropyrazolo[1,5-a]pyrimidine-3-carboxylate

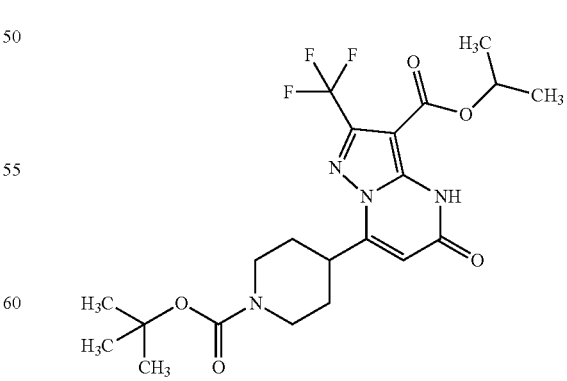

Compound tert-butyl 4-[3-(1H-imidazol-1-ylcarbonyl)-5-oxo-2-(trifluoromethyl)-4,5-dihydropyrazolo[1,5-a]pyrimidin-7-yl]piperidine-1-carboxylate (111 mg, 231 µmol) was diluted in propan-2-ol (3.0 ml, 460 µmol). The mixture was stirred for 2 h at 80° C. and purified by preparative HPLC (gradient acetonitrile/water with 0.1% formic acid). Evaporation of the combined product fractions yielded the title compound. The obtained amount was 73.0 mg (100% purity, 67% of theory).

LC-MS (Method 8B): $R_t$=1.55 min; MS (ESIneg): m/z=471 [M–H]⁻

Example 524A 2,2-difluoropropyl 7-[1-(tert-butoxycarbonyl)piperidin-4-yl]-2-methyl-5-oxo-4,5-dihydropyrazolo[1,5-a]pyrimidine-3-carboxylate

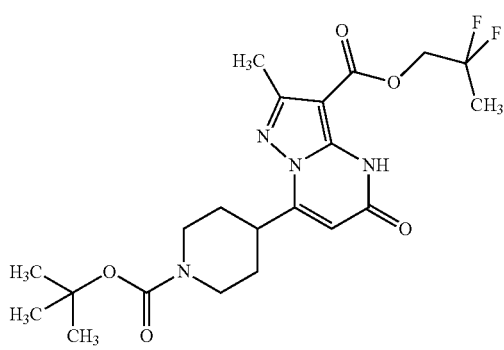 [SMILES: Cc1nn2c(C3CCN(C(=O)OC(C)(C)C)CC3)cc(=O)[nH]c2c1C(=O)OCC(C)(F)F]

7-[1-(tert-butoxycarbonyl)piperidin-4-yl]-2-methyl-5-oxo-4,5-dihydropyrazolo[1,5-a]pyrimidine-3-carboxylic acid (100 mg, 266 µmol) was dissolved in tetrahydrofurane (5.0 ml, 62 mmol) and N,N'-Carbonyldiimidazole (86.2 mg, 531 µmol) was added. The mixture was heated at reflux for 1.5 h. Solvents were removed and 2,2-difluoropropan-1-ol (3.01 g, 31.4 mmol) was added. The mixture was heated at reflux for 18 h and then purified by preparative HPLC (Method: column: Reprosil C18; 10 µm; 125×30 mm/flow: 50 ml/min/solvents: A=water (0.01% formic acid), B=acetonitrile/gradient: 0.00-5.00 min=10% B, 6.50 min=20% B, 17.0-19.75 min=100% B, 19.75.00-23.00 min=90% B). Evaporation of the combined product fractions yielded the title compound (105 mg, 99% purity, 86% of theory).

LC-MS (Method 11B): $R_t$=2.03 min; MS (ESIneg): m/z=453 [M–H]⁻

Example 525A

Tert-butyl 4-{3-[(3,3-dimethylpyrrolidin-1-yl)carbonyl]-5-oxo-4,5-dihydropyrazolo[1,5-a]pyrimidin-7-yl}piperidine-1-carboxylate

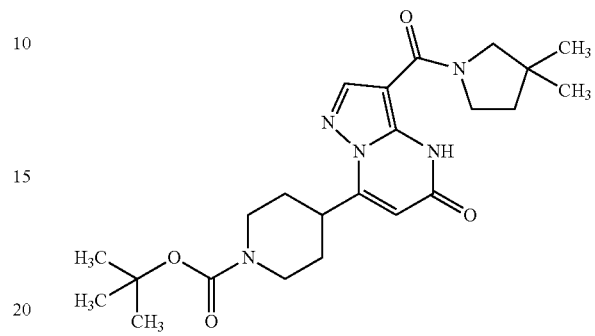

7-[1-(tert-butoxycarbonyl)piperidin-4-yl]-5-oxo-4,5-dihydropyrazolo[1,5-a]pyrimidine-3-carboxylic acid (100 mg, 276 µmol) in dimethylformamide (1.0 ml, 13 mmol) were added HATU (136 mg, 359 µmol) and N,N-Diisopropylethylamine (140 µl, 830 µmol). Then 3,3-dimethylpyrrolidine (54.7 mg, 552 µmol) was added and the reaction mixture was stirred at RT for 16 h. More HATU (1.3 equivalents) was added and the reaction mixture was stirred at RT for 24 h. Water was added and the resulting precipitate was filtered, washed with water, and dried in vacuo. The obtained amount of product was 51.0 mg (93% purity, 39% of theory).

LC-MS (Method 11B): $R_t$=1.92 min; MS (ESIpos): m/z=444 [M+H]⁺

Example 526A 2,2-difluoropropyl 7-[1-(tert-butoxycarbonyl)piperidin-4-yl]-5-oxo-4,5-dihydropyrazolo[1,5-a]pyrimidine-3-carboxylate

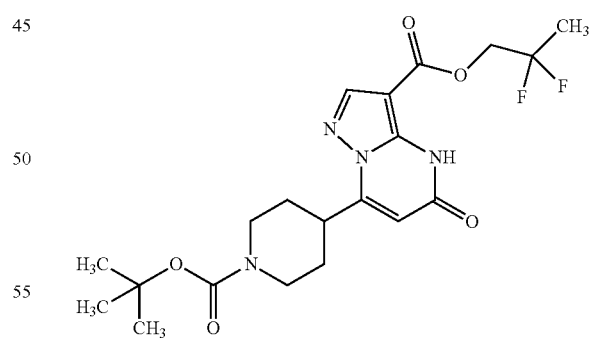

tert-butyl 4-[3-(1H-imidazol-1-ylcarbonyl)-5-oxo-4,5-dihydropyrazolo[1,5-a]pyrimidin-7-yl]piperidine-1-carboxylate (100 mg, 242 µmol) was dissolved in 2,2-difluoropropan-1-ol (466 mg, 4.85 mmol) and heated at reflux for 1 h. The solvent was removed and then Ethyl acetate and water were added. The organic phase was washed with water, dried via filtration (Extrelut NT3) and in vacuo. The residue was purified by preparative HPLC (Method: column: Reprosil C18; 10 µm; 125×30 mm/flow: 50 ml/min/solvents:

A=water (0.01% formic acid), B=acetonitrile/gradient: 0.00-5.00 min=10% B, 6.50 min=20% B, 17.0-19.75 min=100% B, 19.75.00-23.00 min=90% B). Evaporation of the combined product fractions yielded the title compound (83.0 mg, 100% purity, 78% of theory).

LC-MS (Method 1B): $R_t$=1.00 min; MS (ESIneg): m/z=439 [M−H]⁻

Example 527A 3-fluoropropyl 7-[1-(tert-butoxycarbonyl)piperidin-4-yl]-2-methyl-5-oxo-4,5-dihydropyrazolo[1,5-a]pyrimidine-3-carboxylate

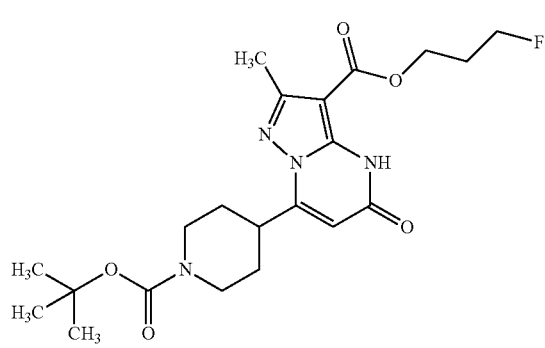 [SMILES: Cc1nn2c(C3CCN(C(=O)OC(C)(C)C)CC3)cc(=O)[nH]c2c1C(=O)OCCCF]

7-[1-(tert-butoxycarbonyl)piperidin-4-yl]-2-methyl-5-oxo-4,5-dihydropyrazolo[1,5-a]pyrimidine-3-carboxylic acid (100 mg, 266 µmol) was dissolved in tetrahydrofurane (5.0 ml, 62 mmol) and N,N'-Carbonyldiimidazole (86.2 mg, 531 µmol) was added. The mixture was heated at reflux for 1.5 h.

Solvents were removed and 3-fluoropropan-1-ol (500 µl, 1.3 mmol) was added. The mixture was heated at reflux for 18 h and then purified by preparative HPLC (Method: column: Reprosil C18; 10 µm; 125×30 mm/flow: 50 ml/min/solvents: A=water (0.01% formic acid), B=acetonitrile/gradient: 0.00-5.00 min=10% B, 6.50 min=20% B, 17.0-19.75 min=100% B, 19.75.00-23.00 min=90% B). Evaporation of the combined product fractions yielded the title compound (84.4 mg, 58% purity, 42% of theory).

LC-MS (Method 10B): $R_t$=1.86 min; MS (ESIneg): m/z=435 [M−H]⁻

Example 528A 2,2-difluoroethyl 7-[1-(tert-butoxycarbonyl)piperidin-4-yl]-2-methyl-5-oxo-4,5-dihydropyrazolo[1,5-a]pyrimidine-3-carboxylate

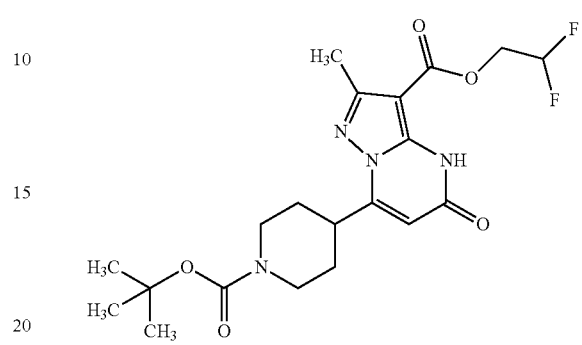

7-[1-(tert-butoxycarbonyl)piperidin-4-yl]-2-methyl-5-oxo-4,5-dihydropyrazolo[1,5-a]pyrimidine-3-carboxylic acid (100 mg, 266 µmol) was dissolved in tetrahydrofurane (5.0 ml, 62 mmol) and N,N'-Carbonyldiimidazole (86.2 mg, 531 µmol) was added. The mixture was heated at reflux for 1.5 h. Solvents were removed and 2,2-difluoroethanol (500 µl, 31 mmol) was added. The mixture was heated at reflux for 18 h and then purified by preparative HPLC (Method: column: Reprosil C18; 10 µm; 125×30 mm/flow: 50 ml/min/solvents: A=water (0.01% formic acid), B=acetonitrile/gradient: 0.00-5.00 min=10% B, 6.50 min=20% B, 17.0-19.75 min=100% B, 19.75.00-23.00 min=90% B). Evaporation of the combined product fractions yielded the title compound (93.8 mg, 100% purity, 80% of theory).

LC-MS (Method 11B): $R_t$=1.93 min; MS (ESIneg): m/z=439 [M−H]⁻

Example 529A 3,3,3-trifluoropropyl 7-[1-(tert-butoxycarbonyl)piperidin-4-yl]-2-methyl-5-oxo-4,5-dihydropyrazolo[1,5-a]pyrimidine-3-carboxylate

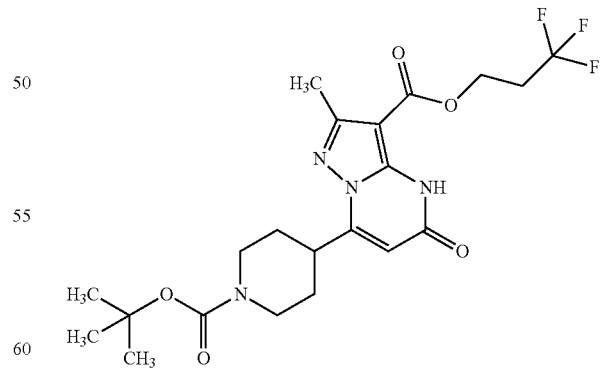

7-[1-(tert-butoxycarbonyl)piperidin-4-yl]-2-methyl-5-oxo-4,5-dihydropyrazolo[1,5-a]pyrimidine-3-carboxylic acid (100 mg, 266 µmol) was dissolved in tetrahydrofurane (5.0 ml, 62 mmol) and N,N'-Carbonyldiimidazole (86.2 mg, 531 µmol) was added. The mixture was heated at reflux for 1.5 h. Solvents were removed and 3,3,3-trifluoropropan-1-ol (500 µl, 530 µmol) was added. The mixture was heated at reflux for 18 h and then purified by preparative HPLC (Method: column: Reprosil C18; 10 µm; 125×30 mm/flow: 50 ml/min/solvents: A=water (0.01% formic acid), B=acetonitrile/gradient: 0.00-5.00 min=10% B, 6.50 min=20% B, 17.0-19.75 min=100% B, 19.75.00-23.00 min=90% B). Evaporation of the combined product fractions yielded the title compound (94.9 mg, 99% purity, 75% of theory).

LC-MS (Method 1B): $R_t$=1.12 min; MS (ESIneg): m/z=471 [M−H]⁻

Example 530A

Propyl 7-[1-(tert-butoxycarbonyl)piperidin-4-yl]-2-methyl-5-oxo-4,5-dihydropyrazolo[1,5-a]pyrimidine-3-carboxylate

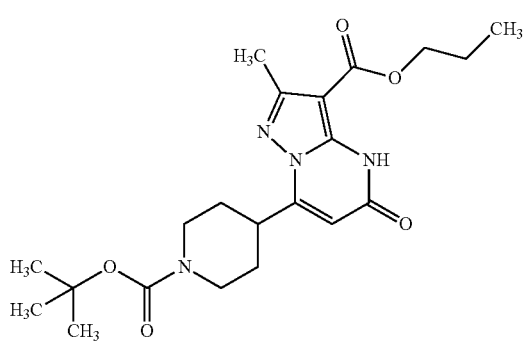 [SMILES: CCCOC(=O)c1c(C)nn2c(C3CCN(C(=O)OC(C)(C)C)CC3)cc(=O)[nH]c12]

7-[1-(tert-butoxycarbonyl)piperidin-4-yl]-2-methyl-5-oxo-4,5-dihydropyrazolo[1,5-a]pyrimidine-3-carboxylic acid (100 mg, 266 µmol) was dissolved in tetrahydrofurane (5.0 ml, 62 mmol) and N,N'-Carbonyldiimidazole (86.2 mg, 531 µmol) was added. The mixture was heated at reflux for 1.5 h. Solvents were removed propan-1-ol (79.8 mg, 1.33 mmol) was added. The mixture was heated at reflux for 18 h and then purified by preparative HPLC (Method: column: Reprosil C18; 10 µm; 125×30 mm/flow: 50 ml/min/solvents: A=water (0.01% formic acid), B=acetonitrile/gradient: 0.00-5.00 min=10% B, 6.50 min=20% B, 17.0-19.75 min=100% B, 19.75.00-23.00 min=90% B). Evaporation of the combined product fractions yielded the title compound (88.2 mg, 95% purity, 75% of theory).

LC-MS (Method 11B): $R_t$=2.14 min; MS (ESIneg): m/z=417 [M−H]⁻

Example 531A

Cyclobutyl 7-[1-(tert-butoxycarbonyl)piperidin-4-yl]-2-methyl-5-oxo-4,5-dihydropyrazolo[1,5-a]pyrimidine-3-carboxylate

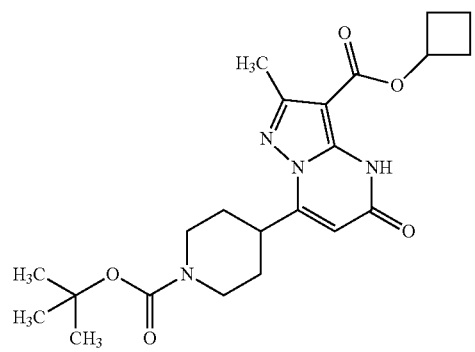 [SMILES: Cc1nn2c(C3CCN(C(=O)OC(C)(C)C)CC3)cc(=O)[nH]c2c1C(=O)OC1CCC1]

7-[1-(tert-butoxycarbonyl)piperidin-4-yl]-2-methyl-5-oxo-4,5-dihydropyrazolo[1,5-a]pyrimidine-3-carboxylic acid (100 mg, 266 µmol) was dissolved in tetrahydrofurane (5.0 ml, 62 mmol) and N,N'-Carbonyldiimidazole (86.2 mg, 531 µmol) was added. The mixture was heated at reflux for 1.5 h. Solvents were removed cyclobutanol (95.8 mg, 1.33 mmol) was added. The mixture was heated at reflux for 18 h and then purified by preparative HPLC (Method: column: Reprosil C18; 10 µm; 125×30 mm/flow: 50 ml/min/solvents: A=water (0.01% formic acid), B=acetonitrile/gradient: 0.00-5.00 min=10% B, 6.50 min=20% B, 17.0-19.75 min=100% B, 19.75.00-23.00 min=90% B). Evaporation of the combined product fractions yielded the title compound (98.7 mg, 95% purity, 82% of theory).

LC-MS (Method 11B): $R_t$=2.20 min; MS (ESIneg): m/z=429 [M−H]⁻

Example 532A

Tert-butyl 7-[1-(tert-butoxycarbonyl)piperidin-4-yl]-2-methyl-5-oxo-4,5-dihydropyrazolo[1,5-a]pyrimidine-3-carboxylate

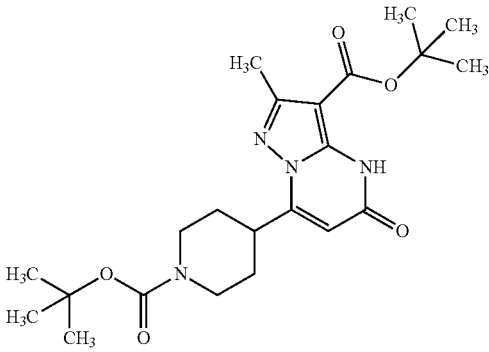 [SMILES: Cc1nn2c(C3CCN(C(=O)OC(C)(C)C)CC3)cc(=O)[nH]c2c1C(=O)OC(C)(C)C]

7-[1-(tert-butoxycarbonyl)piperidin-4-yl]-2-methyl-5-oxo-4,5-dihydropyrazolo[1,5-a]pyrimidine-3-carboxylic acid (100 mg, 266 µmol) was dissolved in Tetrahydrofuran (1.0 ml, 12 mmol), Boron trifluoride diethyl etherate (1.7 µl, 13 µmol) and then tert-butyl 2,2,2-trichloroethanimidate (116 mg, 531 µmol) were added. The mixture was stirred at RT for 18 h and then purified by preparative HPLC (Method: column: Reprosil C18; 10 µm; 125×30 mm/flow: 50 ml/min/ solvents: A=water (0.01% formic acid), B=acetonitrile/gradient: 0.00-5.00 min=10% B, 6.50 min=20% B, 17.0-19.75 min=100% B, 19.75.00-23.00 min=90% B). Evaporation of the combined product fractions yielded the title compound (87.8 mg, 96% purity, 73% of theory).

LC-MS (Method 1B): $R_t$=1.24 min; MS (ESIneg): m/z=431 [M−H]⁻

Example 433A

Ethyl 7-[1-(tert-butoxycarbonyl)piperidin-4-yl]-2-(methylsulfanyl)-5-oxo-4,5-dihydropyrazolo[1,5-a]pyrimidine-3-carboxylate

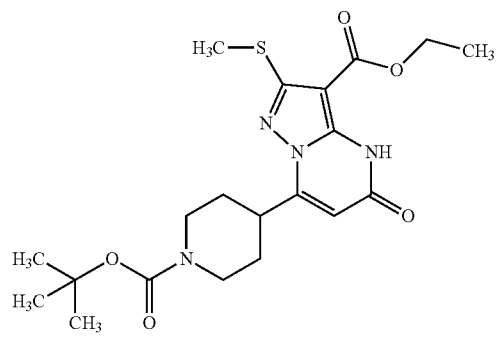 [SMILES: CCOC(=O)c1c(SC)nn2c(C3CCN(C(=O)OC(C)(C)C)CC3)cc(=O)[nH]c12]

A mixture of ethyl 5-amino-3-(methylsulfanyl)-1H-pyrazole-4-carboxylate (625 mg, 3.11 mmol) and tert-butyl 4-[(2,2-dimethyl-4,6-dioxo-1,3-dioxan-5-yl)carbonyl]piperidine-1-carboxylate (2.87 g, 8.07 mmol) in acetonitrile (24 ml) was stirred under argon overnight at reflux. Triethylamine (1.3 ml, 9.3 mmol) was added and the stirring was continued for 4 h. The mixture was acidified with hydrochloric acid (1N solution in water, 10 ml). The solid that fell off was filtered and dried in vacuo. The mother liquor was concentrated and suspended in a mixture of water and acetonitrile. The newly formed solid was filtered, dried in vacuo and combined with the previous one to yield the title product. The obtained amount was 1.17 g (100% purity, 86% of theory).

LC-MS (Method 6B): $R_t$=1.16 min; MS (ESIneg): m/z=435 [M−H]⁻

Example 434A

Methyl 5-amino-3-ethyl-1H-pyrazole-4-carboxylate

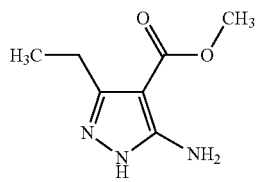

Methyl (2E)-2-cyano-3-ethoxypent-2-enoate (7.70 g, 42.0 mmol) was diluted with acetic acid (77 ml) under argon before the hydrazine hydrate (1:1) (2.5 ml, 50 mmol) was added. The mixture was stirred for 1 h at 80° C. and then concentrated. The crude material was dissolved in acetonitrile and purified by preparative HPLC (gradient acetonitrile/ water with 0.1% formic acid). Evaporation of the combined product fractions yielded the title compound. The obtained amount was 4.40 g (100% purity, 62% of theory).

LC-MS (Method 8B): $R_t$=0.65 min; MS (ESIneg): m/z=168 [M−H]⁻

Example 435A

Methyl 7-[1-(tert-butoxycarbonyl)piperidin-4-yl]-2-ethyl-5-oxo-4,5-dihydropyrazolo[1,5-a]pyrimidine-3-carboxylate

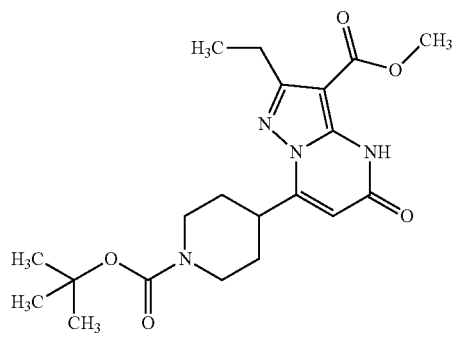 [SMILES: CCc1nn2c(C3CCN(C(=O)OC(C)(C)C)CC3)cc(=O)[nH]c2c1C(=O)OC]

A mixture of methyl 5-amino-3-ethyl-1H-pyrazole-4-carboxylate (1.00 g, 5.91 mmol) and tert-butyl 4-[(2,2-dimethyl-4,6-dioxo-1,3-dioxan-5-yl)carbonyl]piperidine-1-carboxylate (5.46 g, 15.4 mmol) in acetonitrile (61 ml) was stirred under argon for 1 h at reflux. Triethylamine (2.5 ml, 18 mmol) was added and the stirring was continued overnight. A new portion of triethylamine (2.5 ml, 18 mmol) was added and the stirring under reflux was prolonged overnight. The mixture was diluted with 200 ml of ethyl acetate and washed three times with hydrochloric acid (1N solution in water, 200 ml). The organic phase was dried over sodium sulfate, filtered and concentrated. A 1:1 mixture of acetonitrile/water was added and the newly formed solid was filtered and dried in vacuo to yield the title product. The obtained amount was 1.57 g (100% purity, 66% of theory).

LC-MS (Method 8B): $R_t$=1.38 min; MS (ESIneg): m/z=403 [M−H]⁻

Example 436A

7-[1-(tert-butoxycarbonyl)piperidin-4-yl]-2-ethyl-5-oxo-4,5-dihydropyrazolo[1,5-a]pyrimidine-3-carboxylic Acid

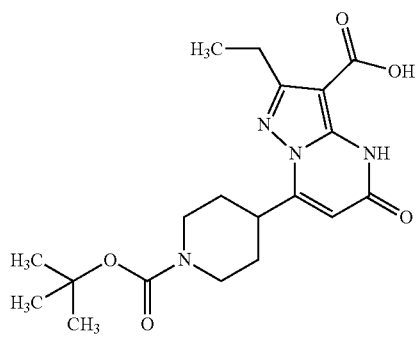 [SMILES: CCc1nn2c(C3CCN(C(=O)OC(C)(C)C)CC3)cc(=O)[nH]c2c1C(=O)O]

A mixture of methyl 7-[1-(tert-butoxycarbonyl)piperidin-4-yl]-2-ethyl-5-oxo-4,5-dihydropyrazolo[1,5-a]pyrimidine-3-carboxylate (570 mg, 1.41 mmol) and lithium hydroxyde (169 mg, 7.05 mmol) in methanol (7.0 ml) and water (7.0 ml) was stirred for two days at 50° C. The newly formed solid was filtered and stirred with hydrochloric acid (1N solution in water) before being filtered again and dried in vacuo to yield the title compound. The obtained amount was 500 mg (83% of purity, 75% of theory).

LC-MS (Method 8B): $R_t$=1.19 min; MS (ESIneg): m/z=389 [M–H]⁻

Example 437A

7-[1-(tert-butoxycarbonyl)piperidin-4-yl]-2-(methylsulfanyl)-5-oxo-4,5-dihydropyrazolo[1,5-a]pyrimidine-3-carboxylic Acid

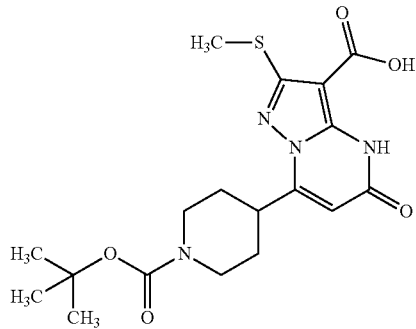 [SMILES: CSc1nn2c(C3CCN(C(=O)OC(C)(C)C)CC3)cc(=O)[nH]c2c1C(=O)O]

A mixture of ethyl 7-[1-(tert-butoxycarbonyl)piperidin-4-yl]-2-(methylsulfanyl)-5-oxo-4,5-dihydropyrazolo[1,5-a]pyrimidine-3-carboxylate (1.50 g, 3.42 mmol) and lithium hydroxyde (820 mg, 34.2 mmol) in ethanol (60 ml) and water (30 ml) was stirred overnight at 50° C. A new portion of lithium hydroxyde (410 mg, 17.1 mmol) was added and the stirring was continued for one more night at 50° C. The mixture was acidified with hydrochloric acid (1N solution in water) until it reached pH=3 and was extracted twice with ethyl acetate (150 ml). The organic phases were combined, dried over sodium sulfate, filtered (the filter was washed with a 9:1 mixture of dichloromethane and methanol) and concentrated to yield the title compound, which was stored in the freezer. The obtained amount was 1.16 g (100% purity, 82% of theory).

LC-MS (Method 8B): $R_t$=1.18 min; MS (ESIneg): m/z=407 [M–H]⁻

Example 438A

Propyl 7-[1-(tert-butoxycarbonyl)piperidin-4-yl]-2-(methylsulfanyl)-5-oxo-4,5-dihydropyrazolo[1,5-a]pyrimidine-3-carboxylate

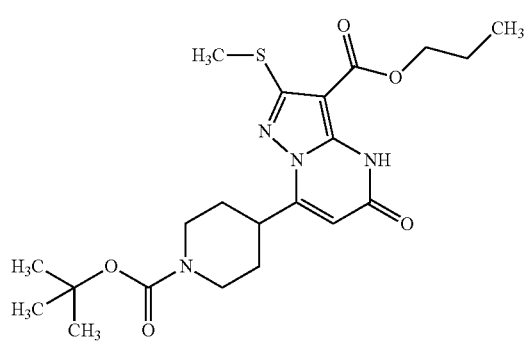 [SMILES: CCCOC(=O)c1c(SC)nn2c(C3CCN(C(=O)OC(C)(C)C)CC3)cc(=O)[nH]c12]

Compound 7-[1-(tert-butoxycarbonyl)piperidin-4-yl]-2-(methylsulfanyl)-5-oxo-4,5-dihydropyrazolo[1,5-a]pyrimidine-3-carboxylic acid (100 mg, 245 µmol) was diluted in N,N-dimethylformamide (10 ml) before 1,1'-carbonyldiimidazole (79.4 mg, 490 µmol) was added. The mixture was stirred for 1.5 h at 80° C. before propan-1-ol (10 ml, 130 mmol) was added. The stirring was continued overnight at 100° C. The mixture was then purified by preparative HPLC (gradient acetonitrile/water with 0.1% formic acid). Evaporation of the combined product fractions yielded the title compound. The obtained amount was 84.6 mg (96% purity, 74% of theory).

LC-MS (Method 8B): $R_t$=1.52 min; MS (ESIneg): m/z=449 [M–H]⁻

Example 439A

Propan-2-yl 7-[1-(tert-butoxycarbonyl)piperidin-4-yl]-2-(methylsulfanyl)-5-oxo-4,5-dihydropyrazolo[1,5-a]pyrimidine-3-carboxylate

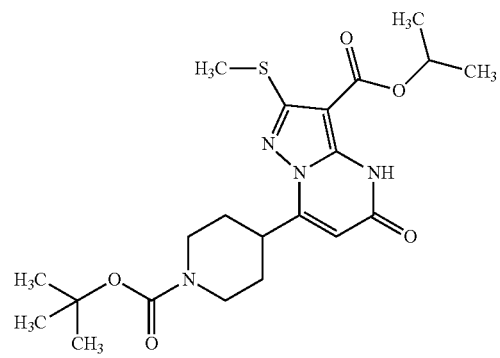 [SMILES: CSc1nn2c(C3CCN(C(=O)OC(C)(C)C)CC3)cc(=O)[nH]c2c1C(=O)OC(C)C]

Compound 7-[1-(tert-butoxycarbonyl)piperidin-4-yl]-2-(methylsulfanyl)-5-oxo-4,5-dihydropyrazolo[1,5-a]pyrimidine-3-carboxylic acid (100 mg, 245 µmol) was diluted in N,N-dimethylformamide (10 ml) before 1,1'-carbonyldiimidazole (79.4 mg, 490 µmol) was added. The mixture was stirred for 1.5 h at 80° C. before propan-1-ol (10 ml, 130 mmol) was added. The stirring was continued overnight at 80° C. The mixture was then purified by preparative HPLC (gradient acetonitrile/water with 0.1% formic acid). Evaporation of the combined product fractions yielded the title compound. The obtained amount was 43.5 mg (89% purity, 35% of theory).

LC-MS (Method 8B): $R_t$=1.52 min; MS (ESIneg): m/z=449 [M−H]−

Example 440A

Ethyl 7-[1-(tert-butoxycarbonyl)piperidin-4-yl]-2-ethyl-5-oxo-4,5-dihydropyrazolo[1,5-a]pyrimidine-3-carboxylate

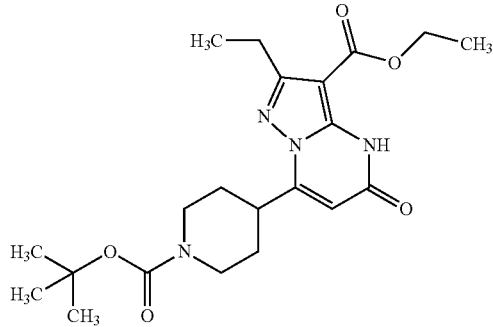

Compound 7-[1-(tert-butoxycarbonyl)piperidin-4-yl]-2-ethyl-5-oxo-4,5-dihydropyrazolo[1,5-a]pyrimidine-3-carboxylic acid (100 mg, 256 µmol) was diluted in tetrahydrofuran (2.5 ml) before 1,1'-carbonyldiimidazole (83.1 mg, 512 µmol) was added. The mixture was stirred for 2 h at 80° C. before being concentrated. The remaining material was diluted with ethanol (2.5 ml, 43 mmol) and stirred for 2 h at 80° C. The mixture was then purified by preparative HPLC (gradient acetonitrile/water with 0.1% formic acid). Evaporation of the combined product fractions yielded the title compound. The obtained amount was 43.6 mg (100% purity, 41% of theory).

LC-MS (Method 8B): $R_t$=1.47 min; MS (ESIneg): m/z=417 [M−H]

PREPARATION OF COMPOUND EXAMPLES

Example 1

3-Phenyl-7-(piperidin-4-yl)pyrazolo[1,5-a]pyrimidin-5(4H)-one hydrochloride

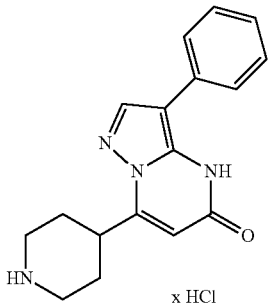 [SMILES: O=c1cc(C2CCNCC2)n2ncc(-c3ccccc3)c2[nH]1]

Tert-butyl 4-(5-oxo-3-phenyl-4,5-dihydropyrazolo[1,5-a]pyrimidin-7-yl)piperidine-1-carboxylate (12.2 mg, 0.03 mmol) was dissolved in 4N HCl in dioxane (1.3 mL) was evaporated in vacuo. The residue was dissolved in methanol (2 mL), evaporated in vacuo and again dissolved in methanol (0.5 mL) and water (2 mL). The resulting solution was lyophilized to give the title compound (9.6 mg, 92% of theory).

LC-MS (Method 1B): $R_t$=0.59 min, MS (ESIPos): m/z=295 [M+H]+

1H-NMR (400 MHz, DMSO-d6): δ=12.10 (br. s, 1H), 8.87 (br. s, 1H), 8.66 (br. s, 1H), 7.79-7.44 (m, 2H), 7.40 (t, 2H), 7.29-7.19 (m, 1H), 5.95 (br. s, 1H), 4.12-3.95 (m, 2H), 3.72-3.53 (m, 1H), 3.12 (dd-like, 2H), 2.24 (br. d, 2H), 1.90 (q-like, 2H); 1 exchangable proton not visible.

Example 2

7-(Piperidin-4-yl)-3-(pyridin-2-yl)pyrazolo[1,5-a]pyrimidin-5(4H)-one dihydrochloride

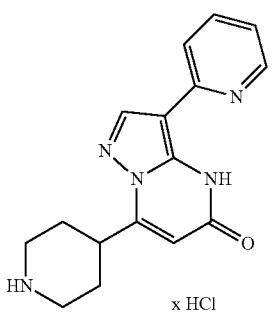 [SMILES: O=c1cc(C2CCNCC2)n2ncc(-c3ccccn3)c2[nH]1]

Tert-butyl 4-[7-oxo-3-(pyridin-2-yl)-4,7-dihydropyrazolo[1,5-a]pyrimidin-5-yl]piperidine-1-carboxylate (220 mg, 0.557 mmol) was dissolved in methanol (3 mL). 4N HCl in dioxane (3 mL) was added and the mixture was irradiated with ultrasound for 15 min at RT. The resulting suspension was filtered, washed with dioxane (2 mL) and dried for 16 h at 50° C. in vacuo to give the title compound (197 mg, 96% of theory).

LC-MS (Method 2B): $R_t$=1.41 min, MS (ESIPos): m/z=296 [M+H]$^+$ $^1$H-NMR (400 MHz, D$_2$O): δ=8.64 (d, 1H), 8.41 (s, 1H), 8.37 (t, 1H), 8.06 (d, 1H), 7.69 (dd, 1H), 6.28 (s, 1H), 3.72-3.57 (m, 3H), 3.27 (dd, 2H), 2.42 (d, 2H), 2.00 (q-like, 2H).

Example 3

2-(Methoxymethyl)-3-(4-methoxyphenyl)-7-(piperidin-4-yl)pyrazolo[1,5-a]pyrimidin-5 (4H)-one hydrochloride

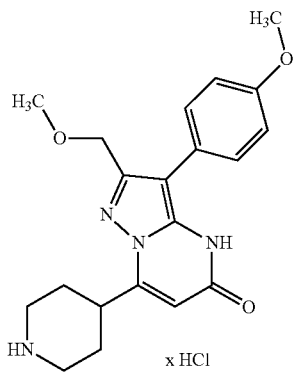 [SMILES: COCc1nn2c(C3CCNCC3)cc(=O)[nH]c2c1-c1ccc(OC)cc1]

Tert-butyl 4-[2-(methoxymethyl)-3-(4-methoxyphenyl)-5-oxo-4,5-dihydropyrazolo[1,5-a]pyrimidin-7-yl]piperidine-1-carboxylate (66 mg, 0.14 mmol) was dissolved in methanol (1.5 mL). 4N HCl in dioxane (1.5 mL) was added and the mixture was irradiated with ultrasound for 15 min at RT. The mixture was evaporated in vacuo and dioxane (2 mL) was added. The resulting suspension was filtered, washed with dioxane (2 mL) and dried for 16 h at 50° C. in vacuo to give the title compound (46 mg, 81% of theory).

LC-MS (Method 1B): $R_t$=0.55 min, MS (ESIPos): m/z=369 [M+H]$^+$ $^1$H-NMR (400 MHz, D$_2$O): δ=7.37 (d, 2H), 7.11 (d, 2H), 6.07 (s, 1H), 4.55 (s, 2H), 3.90 (s, 3H), 3.69-3.59 (m, 3H), 3.37 (s, 3H), 3.29 (dd, 2H), 2.43 (d, 2H), 1.99 (dq-like, 2H).

Example 4

3-(4-Fluorophenyl)-7-(piperidin-4-yl)pyrazolo[1,5-a]pyrimidin-5(4H)-one hydrochloride

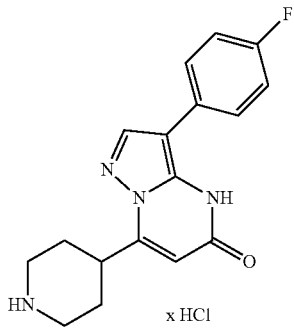 [SMILES: O=c1cc(C2CCNCC2)n2ncc(-c3ccc(F)cc3)c2[nH]1]

Tert-butyl 4-[3-(4-fluorophenyl)-7-oxo-4,7-dihydropyrazolo[1,5-a]pyrimidin-5-yl]piperidine-1-carboxylate (64 mg, 0.155 mmol) was dissolved in methanol (1.5 mL). 4N HCl in dioxane (1.5 mL) was added and the mixture was irradiated with ultrasound for 15 min at RT. The mixture was evaporated in vacuo and dioxane (2 mL) was added. The resulting suspension was filtered, washed with dioxane (2 mL) and dried for 16 h at 50° C. in vacuo to give the title compound (47 mg, 85% of theory).

LC-MS (Method 2B): $R_t$=1.57 min, MS (ESIPos): m/z=313 [M+H]$^+$ $^1$H-NMR (400 MHz, D$_2$O): δ=8.09 (s, 1H), 7.50 (dd, 2H), 7.23 (t, 2H), 5.90 (s, 1H), 3.60 (d, 2H), 3.17 (dd, 2H), 3.08 (t-like, 1H), 2.28 (d, 2H), 1.98 (dq-like, 2H).

Example 5

7-(Piperidin-4-yl)-3-(pyridin-3-yl)pyrazolo[1,5-a]pyrimidin-5 (4H)-one hydrochloride

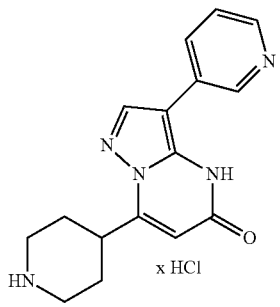 [SMILES: O=c1cc(C2CCNCC2)n2ncc(-c3cccnc3)c2[nH]1]

Tert-butyl 4-[7-oxo-3-(pyridin-3-yl)-4,7-dihydropyrazolo[1,5-a]pyrimidin-5-yl]piperidine-1-carboxylate (9.5 mg, 0.24 mmol) was dissolved in methanol (0.5 mL) and 4N HCl in dioxane (0.5 mL). The mixture was irradiated with ultrasound for 15 min at RT and evaporated in vacuo. The residue was dissolved in methanol (2 mL), evaporated in vacuo and dissolved in water (1 mL). The resulting solution was lyophilized to give the title compound (9.1 mg, 99% of theory).

LC-MS (Method 2B): $R_t$=1.22 min, MS (ESIPos): m/z=296 [M+H]$^+$ $^1$H-NMR (400 MHz, D$_2$O): δ=8.93 (s, 1H), 8.65 (d, 1H), 8.54 (d, 1H), 8.22 (s, 1H), 7.97 (dd, 1H), 6.17 (s, 1H), 3.71-3.60 (m, 3H), 3.27 (dd, 2H), 2.42 (d, 2H), 1.99 (qm-like, 2H).

Example 6

3-(2-Methoxyphenyl)-2-methyl-7-(piperidin-4-yl)pyrazolo[1,5-a]pyrimidin-5(4H)-one hydrochloride

Tert-butyl 4-[3-(2-methoxyphenyl)-2-methyl-7-oxo-4,7-dihydropyrazolo[1,5-a]pyrimidin-5-yl]piperidine-1-carboxylate (3.6 mg, 0.01 mmol) was dissolved in methanol (0.5 mL) and 4N HCl in dioxane (0.5 mL). After 3 h, the solution was evaporated in vacuo. The residue was dissolved in methanol (2 mL), evaporated in vacuo and dissolved in methanol (0.5 mL) and water (2 mL). The resulting solution was lyophilized to give the title compound (2.9 mg, 99% of theory).

LC-MS (Method 1B): $R_t$=0.60 min, MS (ESIPos): m/z=339 [M+H]$^+$ $^1$H-NMR (400 MHz, D$_2$O): δ=7.42 (t, 1H), 7.26 (d, 1H), 7.13 (d, 1H), 7.07 (t, 1H), 5.93 (s, 1H), 3.80 (s, 3H), 3.56 (dd, 2H), 3.53 (t-like, 1H), 3.22 (dd, 2H), 2.35 (d, 2H), 2.22 (s, 3H), 1.91 (dq-like, 2H).

Example 7

2-Methyl-7-(piperidin-4-yl)-3-[3-(trifluoromethyl)phenyl]pyrazolo[1,5-a]pyrimidin-5 (4H)-one hydrochloride

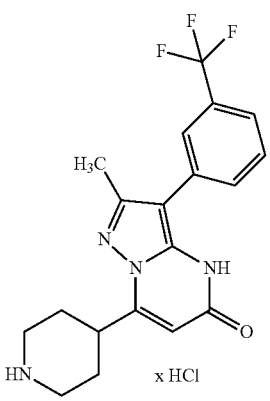 [SMILES: Cc1nn2c(C3CCNCC3)cc(=O)[nH]c2c1-c1cccc(C(F)(F)F)c1]

Tert-butyl 4-{2-methyl-5-oxo-3-[3-(trifluoromethyl)phenyl]-4,5-dihydropyrazolo[1,5-a]pyrimidin-7-yl}piperidine-1-carboxylate (0.9 mg, 0.01 mmol) was dissolved in methanol (0.5 mL) and 4N HCl in dioxane (0.5 mL). After 3 h, the solution was evaporated in vacuo. The residue was dissolved in methanol (2 mL), evaporated in vacuo and dissolved in methanol (0.5 mL) and water (2 mL). The resulting solution was lyophilized to give the title compound (0.7 mg, 99% of theory).

$^1$H-NMR (400 MHz, DMSO-d$_6$): δ=12.20 (br. s, 1H), 8.79 (br. s, 1H), 8.56 (br. s, 1H), 8.02-7.55 (m, 4H), 5.82 (br. s, 1H), 3.69-3.53 (m, 1H), 3.43 (d, 2H), 3.16 (dd, 2H), 2.40-2.17 (m, 5H), 1.88 (q-like, 2H).

Example 8

2-Methyl-5-oxo-7-(piperidin-4-yl)-4,5-dihydropyrazolo[1,5-a]pyrimidine-3-carbonitrile trifluoroacetate

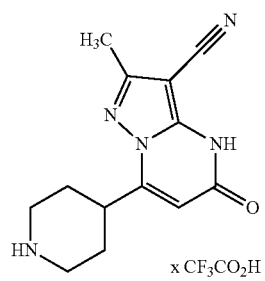

To a solution of tert-Butyl 4-(3-cyano-2-methyl-5-oxo-4,5-dihydropyrazolo[1,5-a]pyrimidin-7-yl)piperidine-1-carboxylate (47 mg, 0.13 mmol) in dichloromethane (5 mL) was added TFA (0.1 mL) and the mixture was stirred for 16 h at RT. The resulting solution was evaporated in vacuo, dissolved in water (15 mL) and lyophilized to give the title compound (49 mg, 99% of theory).

LC-MS (Method 2B): $R_t$=1.13 min, MS (ESIPos): m/z=258 [M+H]$^+$ $^1$H-NMR (400 MHz, DMSO-d$_6$): δ=13.19 (br. s, 1H), 8.75 (br. s, 1H), 8.45 (br. s, 1H), 6.10 (br. s, 1H), 3.51 (br. s, 1H), 3.40 (d, 2H), 3.11 (dd, 2H), 2.38 (s, 3H), 2.16 (d, 2H), 1.81 (q-like, 2H).

Example 9

Ethyl 2-methyl-5-oxo-7-(piperidin-4-yl)-4,5-dihydropyrazolo[1,5-a]pyrimidine-3-carboxylate trifluoroacetate

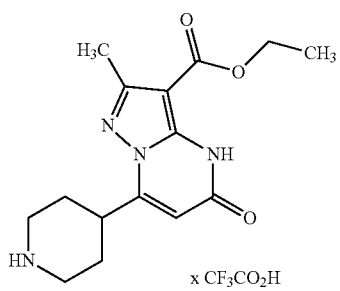 [SMILES: CCOC(=O)c1c(C)nn2c(C3CCNCC3)cc(=O)[nH]c12]

To a solution of ethyl 7-[1-(tert-butoxycarbonyl)piperidin-4-yl]-2-methyl-5-oxo-4,5-dihydropyrazolo[1,5-a]pyrimidine-3-carboxylate (47 mg, 0.13 mmol) in dichloromethane (1.3 mL) was added TFA (0.1 mL) and the mixture was stirred for 7 days at RT. The resulting solution was evaporated in vacuo, dissolved in water (15 mL) and lyophilized to give the title compound (23.2 mg, 86% of theory).

LC-MS (Method 2B): $R_t$=1.39 min, MS (ESIPos): m/z=305 [M+H]$^+$ $^1$H-NMR (400 MHz, DMSO-d$_6$): δ=11.41 (s, 1H), 8.68 (br. s, 1H), 8.36 (br. s, 1H), 5.95 (s, 1H), 4.29 (q, 2H), 3.50 (t-like, 1H), 3.11 (dd, 2H), 2.42 (s, 3H), 2.16 (d, 2H), 1.78 (dq-like, 2H), 1.28 (t, 3H); 2 protons not visible due to residual water signal.

Example 10

3-(4-Bromophenyl)-2-methyl-7-(piperidin-4-yl)pyrazolo[1,5-a]pyrimidin-5(4H)-one hydrochloride

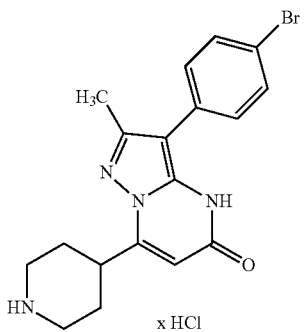 [SMILES: Cc1nn2c(C3CCNCC3)cc(=O)[nH]c2c1-c1ccc(Br)cc1]

Tert-butyl 4-(3-cyano-2-methyl-5-oxo-4,5-dihydropyrazolo[1,5-a]pyrimidin-7-yl)piperidine-1-carboxylate (111 mg, 0.222 mmol) was dissolved in methanol (0.7 mL). 4N HCl in dioxane (0.7 mL) was added. After 16 h, the mixture was irradiated with ultrasound for 10 min at RT. The mixture was evaporated in vacuo and dioxane (2 mL) was added. The resulting suspension was filtered, washed with dioxane (2 mL) and dried for 16 h at 50° C. in vacuo to give the title compound (39.6 mg, 42% of theory).

LC-MS (Method 1B): $R_t$=0.70 min, MS (ESIPos): m/z=387 [M+H]$^+$ $^1$H-NMR (400 MHz, DMSO-d$_6$): δ=11.99 (br. s, 1H), 8.78 (br. s, 1H), 8.59 (br. s, 1H), 7.61 (d, 2H), 7.35 (br. s, 2H), 5.80 (br. s, 1H), 3.56 (br. s, 1H), 3.40 (d, 2H), 3.12 (dd, 2H), 2.39-2.14 (m, 5H), 1.84 (dq-like, 2H).

Example 11

2-(Methoxymethyl)-3-phenyl-7-(piperidin-4-yl)pyrazolo[1,5-a]pyrimidin-5(4H)-one hydrochloride

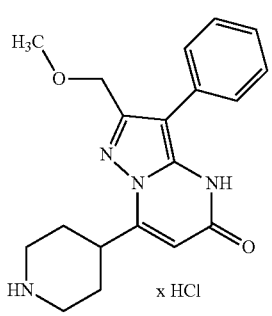 [SMILES: COCc1nn2c(C3CCNCC3)cc(=O)[nH]c2c1-c1ccccc1]

Tert-butyl 4-[2-(methoxymethyl)-5-oxo-3-phenyl-4,5-dihydropyrazolo[1,5-a]pyrimidin-7-yl]piperidine-1-carboxylate (142 mg, 0.321 mmol) was dissolved in methanol (0.9 mL). 4N HCl in dioxane (0.9 mL) was added. After 5 h, the resulting suspension was filtered, washed with methanol (0.3 mL) and dried for 16 h at 50° C. in vacuo to give the title compound (18.1 mg, 15% of theory).

LC-MS (Method 1B): $R_t$=0.58 min, MS (ESIPos): m/z=339 [M+H]$^+$

Example 12

3-[3-(Benzyloxy)phenyl]-7-(piperidin-4-yl)pyrazolo[1,5-a]pyrimidin-5(4H)-one hydrochloride

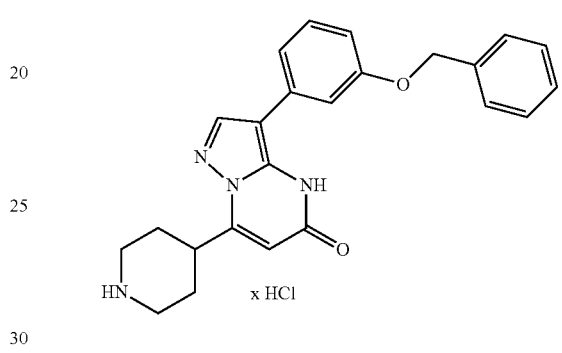

Tert-butyl 4-{3-[3-(benzyloxy)phenyl]-5-oxo-4,5-dihydropyrazolo[1,5-a]pyrimidin-7-yl}piperidine-1-carboxylate (120 mg, 0.229 mmol) was dissolved in methanol (0.7 mL). 4N HCl in dioxane (0.7 mL) was added. After 2 h, the resulting suspension was filtered, washed with methanol (0.3 mL) and dried for 16 h at 50° C. in vacuo to give the title compound (89 mg, 89% of theory).

LC-MS (Method 1B): $R_t$=0.77 min, MS (ESIPos): m/z=401 [M+H]$^+$ $^1$H-NMR (400 MHz, DMSO-d$_6$): δ=12.13 (br. s, 1H), 8.83 (br. s, 2H), 8.20 (br. s, 1H), 7.49 (d, 2H), 7.41 (dd, 2H), 7.34 (dd, 1H), 7.31 (dd, 1H), 7.31-7.04 (m, 2H), 5.91 (br. s, 1H), 6.89 (d, 1H), 5.17 (s, 2H), 3.61 (br. s, 1H), 3.41 (d, 2H), 3.11 (dd, 2H), 2.23 (d, 2H), 1.91 (q-like, 2H).

Example 13

2-Methyl-7-(piperidin-4-yl)-3-[3-(trifluoromethyl)phenyl]pyrazolo[1,5-a]pyrimidin-5(4H)-one hydrochloride

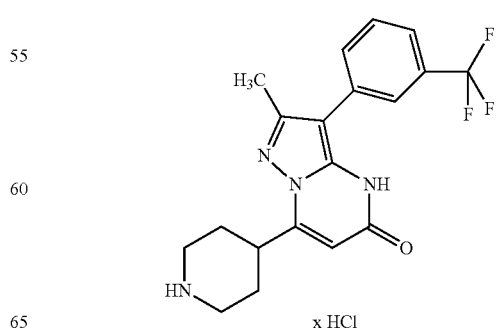

A solution of tert-Butyl 4-{2-methyl-5-oxo-3-[3-(trifluoromethyl)phenyl]-4,5-dihydropyrazolo[1,5-a]pyrimidin-7-yl}piperidine-1-carboxylate (120 mg, 0.24 mmol) in methanol (0.70 ml) was treated with HCl 4N in dioxane (0.70 ml) and the reaction mixture was left without stirring for 16 h at RT. The resulting precipitate was filtrated and dried under vacuo to yield the title compound (84 mg, quantitative).

LC-MS (Method 1B): R$_t$=0.65 min, MS (ESIPos): m/z=377 [M+H-xHCl]$^+$ $^1$H-NMR (400 MHz, DMSO-d$_6$): δ=12.21 (br. s, 1H), 8.80 (br. s, 1H), 8.58 (br. s, 1H), 7.75-7.55 (m, 4H), 5.81 (br. s, 1H), 3.58 (br. s, 1H), 3.20-3.07 (m, 2H), 2.39-2.15 (m, 4H), 1.93-1.75 (m, 2H).

Example 14

5-Oxo-7-(piperidin-4-yl)-4,5-dihydropyrazolo[1,5-a]pyrimidine-3-carboxamide hydrochloride

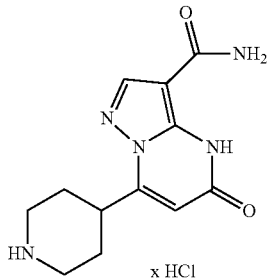 [SMILES: NC(=O)c1cnn2c(C3CCNCC3)cc(=O)[nH]c12]

A suspension of tert-Butyl 4-(3-carbamoyl-5-oxo-4,5-dihydropyrazolo[1,5-a]pyrimidin-7-yl)piperidine-1-carboxylate (38 mg, 0.11 mmol) in methanol (1.0 ml) was treated with HCl 4N in dioxane (1.0 ml). The reaction mixture was sonicated for 15 min at RT and after that 15 min at 40° C. The resulting precipitate was filtrated, washed with dioxane and dried under vacuo 16 h at 50° C. to yield the title compound (14 mg, 45% of theory).

LC-MS (Method 1B): R$_t$=0.47 min, MS (ESIPos): m/z=262 [M+H-xHCl]$^+$ $^1$H-NMR (400 MHz, D$_2$O): δ=8.22 (s, 1H), 6.16 (s, 1H), 3.65-3.56 (m, 3H), 3.25 (dd, 2H), 2.38 (d, 2H), 2.01-1.91 (dd, 2H).

Example 15

5-Oxo-7-(piperidin-4-yl)-4,5-dihydropyrazolo[1,5-a]pyrimidine-3-carbonitrile

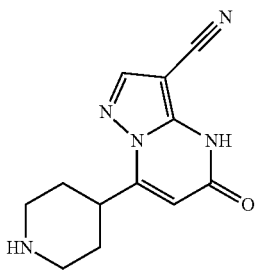 [SMILES: N#Cc1cnn2c(C3CCNCC3)cc(=O)[nH]c12]

A suspension of tert-Butyl 4-(3-cyano-5-oxo-4,5-dihydropyrazolo[1,5-a]pyrimidin-7-yl)piperidine-1-carboxylate (95 mg, 0.28 mmol) in dichloromethane (1.00 ml) was treated with trifluoroacetic acid (0.11 ml) and then the reaction mixture was stirred for 16 h at RT. After this time trifluoroacetic acid (0.11 ml) was added again and the mixture was stirred for 2 h at RT. The solvent was evaporated under vacuo and the residue was dissolved in water and treated with ammonia until pH=9 was achieved. The resulting precipitate was filtered and dried under vacuo at 50° C. overnight to yield the title compound (52 mg, 75% of theory).

LC-MS (Method 2B): R$_t$=0.95 min, MS (ESIPos): m/z=244 [M+H]$^+$ $^1$H-NMR (400 MHz, TFA): δ=8.52 (s, 1H), 7.87 (br. s, 1H), 7.43 (br. s, 1H), 6.84 (s, 1H), 4.15-4.07 (m, 3H), 3.76-3.70 (m, 2H), 2.75 (d, 2H), 2.56 (dd, 2H).

Example 16

Ethyl 5-oxo-7-(piperidin-4-yl)-4,5-dihydropyrazolo[1,5-a]pyrimidine-3-carboxylate hydrochloride

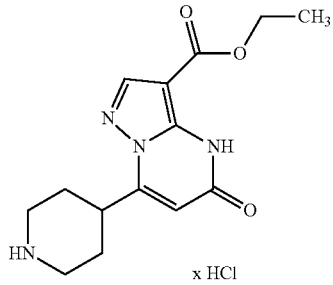 [SMILES: CCOC(=O)c1cnn2c(C3CCNCC3)cc(=O)[nH]c12]

A suspension of compound Ethyl 7-[1-(tert-butoxycarbonyl)piperidin-4-yl]-5-oxo-4,5-dihydropyrazolo[1,5-a]pyrimidine-3-carboxylate (10 mg, 0.03 mmol) in methanol (0.50 ml) was treated with HCl 4N in dioxane (0.50 ml). The reaction mixture was sonicated 15 min at RT. After the evaporation of the solvent under vacuo the resulting solid was dried under vacuo overnight to yield the title compound (9 mg, quantitative).

LC-MS (Method 1B): R$_t$=0.38 min, MS (ESIPos): m/z=291 [M+H-xHCl]$^+$ $^1$H-NMR (400 MHz, D$_2$O): δ=8.25 (s, 1H), 6.19 (s, 1H), 4.42-4.37 (q, 2H), 3.65-3.58 (m, 3H), 3.26 (dd, 2H), 2.39 (d, 2H), 1.98 (dd, 2H), 1.38 (t, 3H).

Example 17

5-Oxo-7-(piperidin-4-yl)-4,5-dihydropyrazolo[1,5-a]pyrimidine-3-carboxylic acid hydrochloride

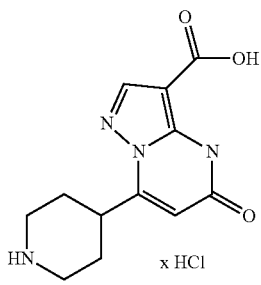 [SMILES: O=C(O)c1cnn2c(C3CCNCC3)cc(=O)[nH]c12]

A suspension of compound 7-[1-(tert-Butoxycarbonyl)piperidin-4-yl]-5-oxo-4,5-dihydropyrazolo[1,5-a]pyrimidine-3-carboxylic acid (19 mg, 0.05 mmol) in methanol (0.50 ml) was treated with HCl 4N in dioxane (0.50 ml). The reaction mixture was sonicated 15 min at RT. After the evaporation of the solvent under vacuo the residue was stirred in a dioxane/MeO 2/1 solution. The resulting precipitate was filtered, washed with 2 ml of the dioxane/methanol 2/1 solution and dried overnight under vacuo at 50° C. to yield the title compound (8 mg, 50% of theory).

LC-MS (Method 2B): $R_t$=0.25 min, MS (ESIPos): m/z=263 [M+H-xHCl]$^+$ $^1$H-NMR (400 MHz, D$_2$O): δ=8.17 (s, 1H), 6.16 (s, 1H), 3.63 (d, 2H), 3.57 (dd, 1H), 3.25 (dd, 2H), 2.38 (d, 2H), 2.00-1.92 (q, 2H).

Example 18

Benzyl 5-oxo-7-(piperidin-4-yl)-4,5-dihydropyrazolo[1,5-a]pyrimidine-3-carboxylate hydrochloride

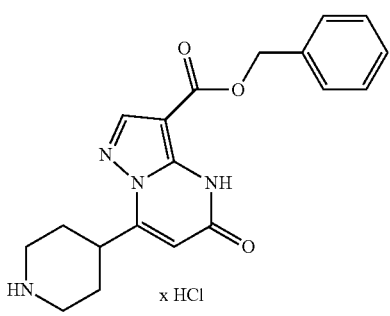 [SMILES: O=C(OCc1ccccc1)c1cnn2c(C3CCNCC3)cc(=O)[nH]c12]

A suspension of compound Benzyl 7-[1-(tert-butoxycarbonyl)piperidin-4-yl]-5-oxo-4,5-dihydropyrazolo[1,5-a]pyrimidine-3-carboxylate (38 mg, 0.09 mmol) in methanol (1.00 ml) was treated with HCl 4N in dioxane (1.00 ml). The reaction mixture sonicated 15 min at RT. After the evaporation of the solvent under vacuo the crude product was stirred in dioxane. The resulting precipitate was filtered, washed with dioxane and dried under vacuo at 50° C. to yield the title compound (27 mg, 83% of theory).

LC-MS (Method 1B): $R_t$=0.59 min, MS (ESIPos): m/z=352 [M+H-xHCl]$^+$ $^1$H-NMR (400 MHz, DMSO-d$_6$): δ=11.87 (br. s, 1H), 8.72 (br. s, 1H), 8.24 (s, 1H), 7.44 (d, 2H), 7.42-7.30 (m, 3H), 6.02 (s, 1H), 5.33 (s, 2H), 3.51 (dd, 1H), 3.38 (d, 2H), 3.08 (dd, 2H), 2.17 (d, 2H), 1.85 (dd, 2H).

Example 19

N-Ethyl-5-oxo-7-(piperidin-4-yl)-4,5-dihydropyrazolo[1,5-a]pyrimidine-3-carboxamide hydrochloride

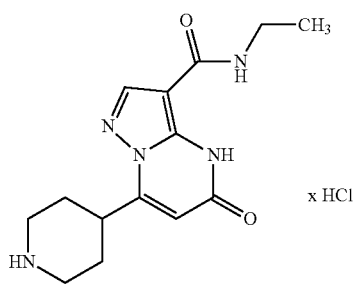 [SMILES: CCNC(=O)c1cnn2c(C3CCNCC3)cc(=O)[nH]c12]

A suspension of compound tert-Butyl 4-[3-(ethylcarbamoyl)-5-oxo-4,5-dihydropyrazolo[1,5-a]pyrimidin-7-yl]piperidine-1-carboxylate (10 mg, 0.03 mmol) in methanol (0.25 ml) was treated with HCl 4N in dioxane (0.25 ml). The reaction mixture sonicated 15 min at RT. After the evaporation of the solvent under vacuo the crude product was stirred in 1 ml of the mixture dioxane/methanol 2/1. The resulting precipitate was filtered, washed with dioxane and dried overnight under vacuo at 50° C. to yield the title compound (3 mg, 41% of theory).

LC-MS (Method 2B): $R_t$=1.05 min, MS (ESIPos): m/z=290 [M+H-xHCl]$^+$ $^1$H-NMR (400 MHz, D$_2$O): δ=8.13 (s, 1H), 6.10 (s, 1H), 3.59-3.52 (m, 3H), 3.31 (q, 2H), 3.20 (dd, 2H), 2.33 (d, 2H), 1.91 (dd, 2H), 1.15 (t, 3H).

Example 20

3-(4-Chlorophenyl)-7-(piperidin-4-yl)-2-(trifluoromethyl)pyrazolo[1,5-a]pyrimidin-5(4H)-one hydrochloride

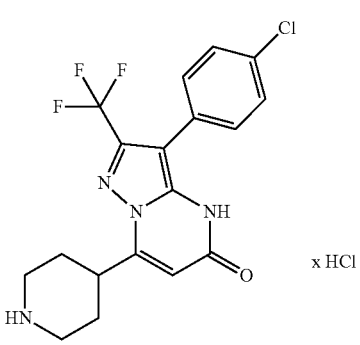 [SMILES: O=c1cc(C2CCNCC2)n2nc(C(F)(F)F)c(-c3ccc(Cl)cc3)c2[nH]1]

A suspension of compound tert-Butyl 4-[3-(ethylcarbamoyl)-5-oxo-4,5-dihydropyrazolo[1,5-a]pyrimidin-7-yl]piperidine-1-carboxylate (3.7 mg, 0.01 mmol) in methanol (0.02 ml) was treated with HCl 4N in dioxane (0.02 ml). The reaction mixture stirred for 2 h at RT. The resulting precipitate was filtered and dried under vacuo to yield the title compound. The filtrate was evaporated under vacuo to yield also the title compound. Overall yield (4 mg, quantitative).

$^1$H-NMR (400 MHz, D$_2$O): δ=7.48 (d, 4H), 6.22 (s, 1H), 3.68-3.59 (m, 3H), 3.28 (dd, 2H), 2.44 (d, 2H), 2.04-1.97 (m, 2H).

Example 21

N-Isobutyl-5-oxo-7-(piperidin-4-yl)-4,5-dihydropyrazolo[1,5-a]pyrimidine-3-carboxamide hydrochloride

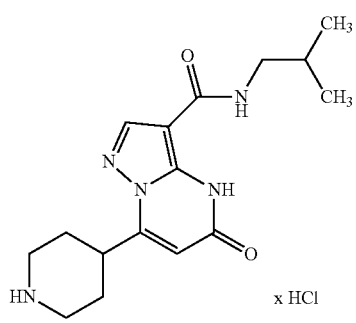 [SMILES: CC(C)CNC(=O)c1cnn2c(C3CCNCC3)cc(=O)[nH]c12]

A suspension of compound tert-Butyl 4-[3-(isobutylcarbamoyl)-5-oxo-4,5-dihydropyrazolo[1,5-a]pyrimidin-7-yl]piperidine-1-carboxylate (35 mg, 0.08 mmol) in methanol (0.50 ml) was treated with HCl 4N in dioxane (0.50 ml). The reaction mixture was sonicated 30 min at RT. After the evaporation of the solvent under vacuo the crude product was stirred in 1 ml of the mixture dioxane/methanol 2/1. The resulting precipitate was filtered, washed with dioxane and dried 2 h under vacuo at 50° C. to yield the title compound (23 mg, 76% of theory).

LC-MS (Method 1B): R$_t$=0.47 min, MS (ESIPos): m/z=318 [M+H-xHCl]$^+$ $^1$H-NMR (400 MHz, D$_2$O): δ=8.21 (s, 1H), 6.16 (s, 1H), 3.65-3.57 (m, 2H), 3.26 (dd, 3H), 3.16 (d, 2H), 2.39 (d, 2H), 2.01-1.92 (dd, 2H), 1.90-1.89 (m, 1H), 0.93 (d, 6H).

Example 22

N-Benzyl-5-oxo-7-(piperidin-4-yl)-4,5-dihydropyrazolo[1,5-a]pyrimidine-3-carboxamide hydrochloride

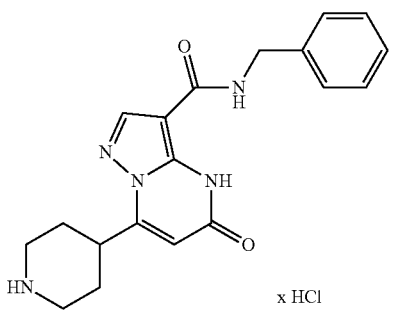 [SMILES: O=C(NCc1ccccc1)c1cnn2c(C3CCNCC3)cc(=O)[nH]c12]

A suspension of compound tert-Butyl 4-[3-(benzylcarbamoyl)-5-oxo-4,5-dihydropyrazolo[1,5-a]pyrimidin-7-yl]piperidine-1-carboxylate (42 mg, 0.09 mmol) in methanol (0.50 ml) was treated with HCl 4N in dioxane (0.50 ml). The reaction mixture sonicated 30 min at RT. After the evaporation of the solvent under vacuo the crude product was stirred with a mixture of dioxane/methanol 2/1. The resulting precipitate was filtered, washed with dioxane and dried 2 h under vacuo at 60° C. to yield the title compound (24 mg, 65% of theory).

LC-MS (Method 1B): R$_t$=0.52 min, MS (ESIPos): m/z=352 [M+H-xHCl]$^+$ $^1$H-NMR (400 MHz, D$_2$O): δ=8.23 (s, 1H), 7.41-7.32 (m, 5H), 6.15 (s, 1H), 4.55 (s, 2H), 3.62 (d, 2H), 3.56 (d, 1H), 3.24 (dd, 2H), 2.37 (d, 2H), 1.96 (dd, 2H).

Example 23

3-(Morpholin-4-ylcarbonyl)-7-(piperidin-4-yl)pyrazolo[1,5-a]pyrimidin-5(4H)-one hydrochloride

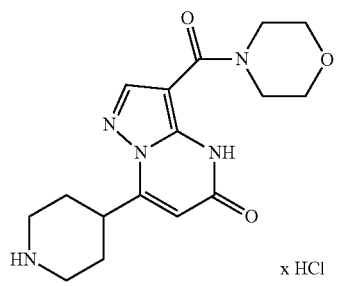 [SMILES: O=C(c1cnn2c(C3CCNCC3)cc(=O)[nH]c12)N1CCOCC1]

A suspension of compound tert-Butyl 4-[3-(morpholin-4-ylcarbonyl)-5-oxo-4,5-dihydropyrazolo[1,5-a]pyrimidin-7-yl]piperidine-1-carboxylate (26 mg, 0.06 mmol) in methanol (0.50 ml) was treated with HCl 4N in dioxane (0.50 ml). The reaction mixture sonicated 30 min at RT. The resulting precipitate was filtered, washed with dioxane and dried 2 h under vacuo at 60° C. to yield the title compound (16 mg, 69% of theory).

LC-MS (Method 1B): R$_t$=0.21 min, MS (ESIPos): m/z=331 [M+H-xHCl]$^+$ $^1$H-NMR (400 MHz, D$_2$O): δ=8.11 (s, 1H), 6.18 (s, 1H), 3.85-3.76 (m, 9H), 3.63 (d, 2H), 3.27 (dd, 2H), 2.40 (s, 2H), 2.00 (dd, 2H).

Example 24

7-(Piperidin-4-yl)-2-(trifluoromethyl)pyrazolo[1,5-a]pyrimidin-5(4H)-one hydrochloride

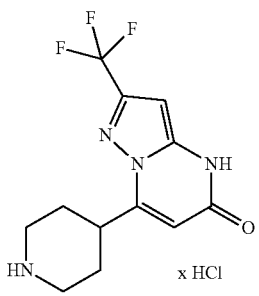 [SMILES: O=c1cc(C2CCNCC2)n2nc(C(F)(F)F)cc2[nH]1]

A suspension of compound tert-Butyl 4-[5-oxo-2-(trifluoromethyl)-4,5-dihydropyrazolo[1,5-a]pyrimidin-7-yl]piperidine-1-carboxylate (66 mg, 0.17 mmol) in methanol (0.50 ml) was treated with HCl 4N in dioxane (0.50 ml). The reaction mixture was left without stirring for 2 h at RT and then was sonicated 10 minutes at RT. The resulting precipitate was filtered and dried under vacuo to yield the title compound. Yield: 48 mg (88% of theory).

LC-MS (Method 1B): $R_t$=0.36 min, MS (ESIPos): m/z=287 [M+H-xHCl]$^+$ $^1$H-NMR (400 MHz, DMSO-d$_6$): δ=12.54 (s, 1H), 8.84 (br. s, 1H), 8.64 (br. s, 1H), 6.29 (s, 1H), 6.04 (s, 1H), 3.51 (dd, 1H), 3.37 (d, 2H), 3.14-3.05 (m, 2H), 2.15 (d, 2H), 1.84 (dd, 2H).

Example 25

7-(Piperidin-4-yl)-2-(2-thienyl)pyrazolo[1,5-a]pyrimidin-5(4H)-one hydrochloride

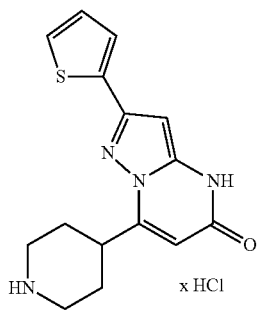 [SMILES: O=c1cc(C2CCNCC2)n2nc(-c3cccs3)cc2[nH]1]

A suspension of compound tert-Butyl 4-[5-oxo-2-(2-thienyl)-4,5-dihydropyrazolo[1,5-a]pyrimidin-7-yl]piperidine-1-carboxylate (44 mg, 0.11 mmol) in methanol (1.0 ml) was treated with HCl 4N in dioxane (1.0 ml). The reaction mixture was sonicated 15 minutes at RT. The resulting precipitate was filtered, washed with of dioxane and dried overnight at 50° C. under vacuo to yield the title compound (33 mg, 87% of theory).

LC-MS (Method 1B): $R_t$=0.49 min, MS (ESIPos): m/z=301 [M+H-xHCl]$^+$ $^1$H-NMR (400 MHz, DMSO-d$_6$): δ=12.27 (br. s, 1H), 8.90 (br. s, 1H), 8.72 (br. s, 1H), 7.64 (dd, 1H), 7.60 (dd, 1H), 7.14 (dd, 1H), 6.26 (s, 1H), 5.80 (s, 1H), 3.52 (dd, 1H), 3.41 (d, 2H), 3.14 (dd, 2H), 2.22 (d, 2H), 1.85 (dd, 2H).

Example 26

2-Cyclopropyl-7-(piperidin-4-yl)pyrazolo[1,5-a]pyrimidin-5(4H)-one hydrochloride

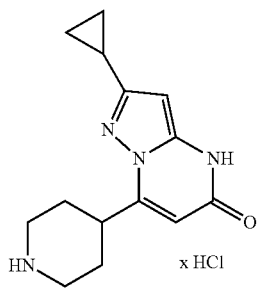 [SMILES: O=c1cc(C2CCNCC2)n2nc(C3CC3)cc2[nH]1]

A suspension of compound tert-Butyl 4-(2-cyclopropyl-5-oxo-4,5-dihydropyrazolo[1,5-a]pyrimidin-7-yl)piperidine-1-carboxylate (77 mg, 0.21 mmol) in methanol (1.0 ml) was treated with HCl 4N in dioxane (1.0 ml). The reaction mixture was sonicated 15 minutes at RT. The resulting precipitate was filtered, washed with dioxane and dried overnight at 50° C. under vacuo to yield the title compound (66 mg, 99% of theory).

LC-MS (Method 1B): $R_t$=0.30 min, MS (ESIPos): m/z=259 [M+H-xHCl]$^+$ $^1$H-NMR (400 MHz, D$_2$O): δ=5.91 (s, 1H), 5.71 (s, 1H), 3.62 (d, 2H), 3.51 (dd, 1H), 3.26 (dd, 2H), 2.36 (d, 2H), 2.02-1.97 (m, 1H), 1.93 (d, 2H), 1.09-1.05 (m, 2H), 0.80-0.77 (m, 2H).

Example 27

2-(4-Fluorophenyl)-7-(piperidin-4-yl)pyrazolo[1,5-a]pyrimidin-5(4H)-one hydrochloride

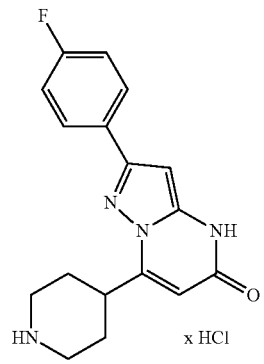 [SMILES: O=c1cc(C2CCNCC2)n2nc(-c3ccc(F)cc3)cc2[nH]1]

A suspension of compound tert-Butyl 4-[2-(4-fluorophenyl)-5-oxo-4,5-dihydropyrazolo[1,5-a]pyrimidin-7-yl]piperidine-1-carboxylate (109 mg, 0.27 mmol) in methanol (3.0 ml) was treated with HCl 4N in dioxane (3.0 ml). The reaction mixture was sonicated 15 minutes at RT. The resulting precipitate was filtered, washed with dioxane and dried overnight at 50° C. under vacuo to yield the title compound (86 mg, 93% of theory).

LC-MS (Method 1B): $R_t$=0.56 min, MS (ESIPos): m/z=313 [M+H-xHCl]$^+$ $^1$H-NMR (400 MHz, DMSO-d$_6$): δ=12.26 (s, 1H), 8.76 (br. s, 1H), 8.49 (br. s, 1H), 8.00 (dd, 2H), 7.30 (dd, 2H), 6.34 (s, 1H), 5.82 (s, 1H), 3.57 (dd, 1H), 3.42 (d, 2H), 3.20-3.07 (br. s, 2H), 2.24 (d, 2H), 1.89 (dd, 2H).

Example 28

Methyl 5-oxo-7-(piperidin-4-yl)-4,5-dihydropyrazolo[1,5-a]pyrimidine-2-carboxylate

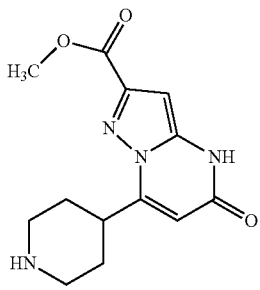 [SMILES: COC(=O)c1cc2[nH]c(=O)cc(C3CCNCC3)n2n1]

A solution of compound Methyl 7-[1-(tert-butoxycarbonyl)piperidin-4-yl]-5-oxo-4,5-dihydropyrazolo[1,5-a]pyrimidine-2-carboxylate (70 mg, 0.19 mmol) in dichloromethane (1.0 ml) was treated with trifluoroacetic acid (0.16 ml). The reaction mixture was stirred 1 h at RT. After evaporation of the solvent under vacuo the crude product was treated with water and was lyophilised overnight. Afterwards the crude product was purified by preparative HPLC (Method 2A). Yield: (40 mg, 77% of theory).

LC-MS (Method 2B): $R_t$=1.07 min, MS (ESIPos): m/z=277 [M+H]$^+$ $^1$H-NMR (400 MHz, TFA): δ=7.88 (br. s, 1H), 7.39 (br. s, 1H), 7.15 (d, 1H), 6.86 (d, 1H), 4.23-4.10 (m, 3H), 3.74 (dd, 2H), 2.85 (d, 2H), 3.64 (s, 3H), 2.60-2.50 (m, 2H).

Example 29

3-Bromo-2-phenyl-7-(piperidin-4-yl)pyrazolo[1,5-a]pyrimidin-5(4H)-one hydrochloride

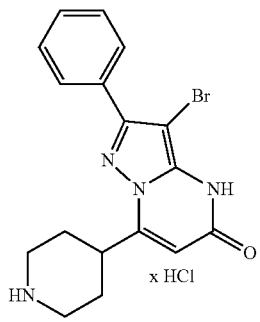 [SMILES: O=c1cc(C2CCNCC2)n2nc(-c3ccccc3)c(Br)c2[nH]1]

A suspension of compound tert-Butyl 4-(3-bromo-5-oxo-2-phenyl-4,5-dihydropyrazolo[1,5-a]pyrimidin-7-yl)piperidine-1-carboxylate (68 mg, 0.14 mmol) in methanol (1.0 ml) was treated with HCl 4N in dioxane (1.0 ml). The reaction mixture was sonicated 30 minutes at RT. The resulting precipitate was filtered, washed with dioxane and dried 2 h at 60° C. under vacuo to yield the title compound (20 mg; 34% of theory).

LC-MS (Method 1B): $R_t$=0.67 min, MS (ESIPos): m/z=373 [M+H-xHCl]$^+$ $^1$H-NMR (400 MHz, D$_2$O): δ=7.73 (d, 2H), 7.48-7.40 (m, 3H), 5.84 (s, 1H), 3.54 (d, 2H), 3.28 (dd, 1H), 3.12 (dd, 2H), 2.16 (d, 2H), 1.76 (dd, 2H).

Example 30

4-(Piperidin-4-yl)-1,7,8,9-tetrahydro-2H-cyclopenta[3,4]pyrazolo[1,5-a]pyrimidin-2-one hydrochloride

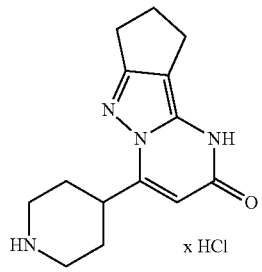

A suspension of compound tert-Butyl 4-(2-oxo-1,7,8,9-tetrahydro-2H-cyclopenta[3,4]pyrazolo[1,5-a]pyrimidin-4-yl)piperidine-1-carboxylate (41 mg, 0.12 mmol) in methanol (0.33 ml) was treated with HCl 4N in dioxane (0.33 ml). The reaction mixture was left without stirring overnight at RT. The resulting precipitate was filtered and dried under vacuo to yield the title compound (38 mg, quantitative).

LC-MS (Method 2B): $R_t$=1.30 min, MS (ESIPos): m/z=259 [M+H-xHCl]$^+$ $^1$H-NMR (400 MHz, DMSO-d$_6$): δ=9.07 (br. s, 1H), 8.94 (br. s, 1H), 5.59 (s, 1H), 3.48 (dd, 1H), 3.36 (d, 2H), 3.05 (dd, 2H), 2.68 (dd, 2H), 2.59 (dd, 2H), 2.38-2.31 (m, 2H), 2.16 (d, 2H), 1.86 (dd, 2H).

Example 31

3-Bromo-7-(piperidin-4-yl)pyrazolo[1,5-a]pyrimidin-5(4H)-one hydrochloride

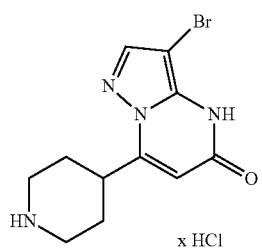 [SMILES: O=c1cc(C2CCNCC2)n2ncc(Br)c2[nH]1]

A suspension of compound tert-Butyl 4-(3-bromo-5-oxo-4,5-dihydropyrazolo[1,5-a]pyrimidin-7-yl)piperidine-1-carboxylate (118 mg, 0.12 mmol) in methanol (2.0 ml) was treated with HCl 4N in dioxane (2.0 ml). The reaction mixture was sonicated 30 minutes at RT. The resulting precipitate was filtered, washed with dioxane and dried 2 h under vacuo at 60° C. to yield the title compound (85 mg, 82% of theory).

LC-MS (Method 1B): $R_t$=0.23 min, MS (ESIPos): m/z=298 [M+H-xHCl]$^+$ $^1$H-NMR (400 MHz, D$_2$O): δ=7.88 (s, 1H), 6.05 (s, 1H), 3.63 (d, 2H), 3.55 (dd, 1H), 3.25 (dd, 2H), 2.38 (d, 2H), 1.95 (dd, 2H).

Example 32

3-(3-Methyl-1,2,4-oxadiazol-5-yl)-7-(piperidin-4-yl)pyrazolo[1,5-a]pyrimidin-5(4H)-one hydrochloride

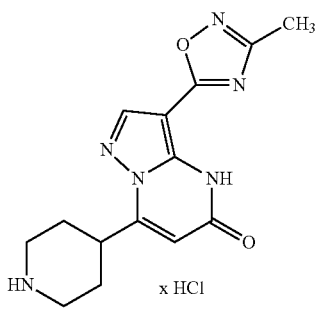 [SMILES: Cc1noc(-c2cnn3c(C4CCNCC4)cc(=O)[nH]c23)n1]

A suspension of compound tert-Butyl 4-[3-(3-methyl-1,2,4-oxadiazol-5-yl)-5-oxo-4,5-dihydropyrazolo[1,5-a]pyrimidin-7-yl]piperidine-1-carboxylate (8 mg, 0.02 mmol) in methanol (0.5 ml) was treated with HCl 4N in dioxane (0.5 ml). The reaction mixture was sonicated 30 minutes at RT. The solvent was evaporated under pressure and the crude product was dissolved in water and lyophilized overnight to yield the title compound (6 mg, 92% of theory).

LC-MS (Method 2B): $R_t$=1.20 min, MS (ESIPos): m/z=301[M+H-xHCl]$^+$ $^1$H-NMR (400 MHz, D$_2$O): δ=8.37 (s, 1H), 6.21 (s, 1H), 3.64 (d, 3H), 3.27 (dd, 2H), 2.44 (s, 3H), 2.41 (d, 2H), 1.99 (dd, 2H).

Example 33

3-(3-Isopropyl-1,2,4-oxadiazol-5-yl)-7-(piperidin-4-yl)pyrazolo[1,5-a]pyrimidin-5 (4H)-one hydrochloride

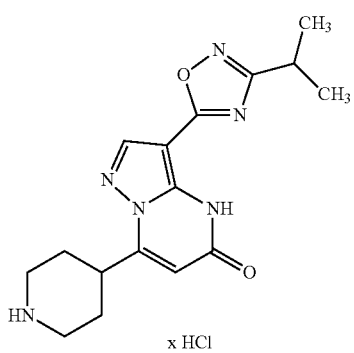 [SMILES: CC(C)c1noc(-c2cnn3c(C4CCNCC4)cc(=O)[nH]c23)n1]

A suspension of compound tert-Butyl 4-[3-(3-isopropyl-1,2,4-oxadiazol-5-yl)-5-oxo-4,5-dihydropyrazolo[1,5-a]pyrimidin-7-yl]piperidine-1-carboxylate (92 mg, 0.21 mmol) in methanol (1.0 ml) was treated with HCl 4N in dioxane (1.0 ml). The reaction mixture was sonicated 30 minutes at RT. The mixture was diluted in dioxane and the solid was filtered, washed with dioxane and dried overnight under vacuo at 60° C. to yield the title compound (67 mg, 86% of theory).

LC-MS (Method 1B): $R_t$=0.54 min, MS (ESIPos): m/z=329 [M+H-xHCl]$^+$ $^1$H-NMR (400 MHz, D$_2$O): δ=8.34 (s, 1H), 6.21 (s, 1H), 3.67-3.59 (m, 3H), 3.28 (dd, 2H), 3.19-3.13 (m, 1H), 2.42 (d, 2H), 2.00 (dd, 2H), 1.36 (d, 6H).

Example 34

7-(Piperidin-4-yl)-3-(3-propyl-1,2,4-oxadiazol-5-yl)pyrazolo[1,5-a]pyrimidin-5(4H)-one hydrochloride

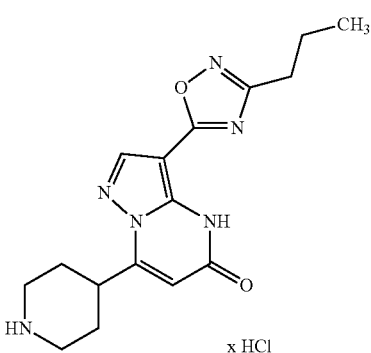 [SMILES: CCCc1noc(-c2cnn3c(C4CCNCC4)cc(=O)[nH]c23)n1]

A suspension of compound tert-Butyl4-[5-oxo-3-(3-propyl-1,2,4-oxadiazol-5-yl)-4,5-dihydropyrazolo[1,5-a]pyrimidin-7-yl]piperidine-1-carboxylate (59 mg, 0.14 mmol) in methanol (1.0 ml) was treated with HCl 4N in dioxane (1.0 ml). The reaction mixture was sonicated 30 minutes at RT. The mixture was diluted in dioxane and the solid was filtered, washed with dioxane and dried overnight under vacuo at 60° C. to yield the title compound (40 mg, 78% of theory).

LC-MS (Method 1B): $R_t$=0.54 min, MS (ESIPos): m/z=329 [M+H-xHCl]$^+$ $^1$H-NMR (400 MHz, D$_2$O): δ=8.36 (s, 1H), 6.22 (s, 1H), 3.65-3.59 (m, 3H), 3.27 (dd, 2H), 2.78 (t, 2H), 2.41 (d, 2H), 1.99 (dd, 2H), 1.82-1.75 (m, 2H), 0.97 (t, 3H).

Example 35

3-(3-Phenyl-1,2,4-oxadiazol-5-yl)-7-(piperidin-4-yl)pyrazolo[1,5-a]pyrimidin-5(4H)-one hydrochloride

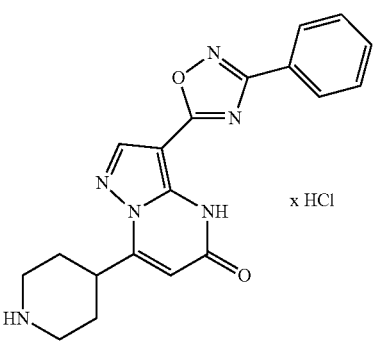 [SMILES: O=c1cc(C2CCNCC2)n2ncc(-c3nc(-c4ccccc4)no3)c2[nH]1]

A suspension of compound tert-Butyl 4-[5-oxo-3-(3-phenyl-1,2,4-oxadiazol-5-yl)-4,5-dihydropyrazolo[1,5-a]pyrimidin-7-yl]piperidine-1-carboxylate (103 mg, 0.22 mmol) in methanol (1.0 ml) was treated with HCl 4N in dioxane (1.0 ml). The reaction mixture was sonicated 30 minutes at RT. The mixture was diluted in dioxane and the solid was filtered, washed with dioxane and dried 2 h under vacuo at 70° C. to yield the title compound (85 mg, 92% of theory).

LC-MS (Method 1B): R$_t$=0.63 min, MS (ESIPos): m/z=363 [M+H-xHCl]$^+$ $^1$H-NMR (400 MHz, D$_2$O): δ=8.12 (s, 1H), 7.56 (d, 2H), 7.37-7.34 (m, 1H), 7.28-7.25 (m, 2H), 5.96 (s, 1H), 3.63 (d, 2H), 3.21 (dd, 3H), 2.25 (d, 2H), 1.88 (dd, 2H).

Example 36

N-[Methyl(4-methylphenyl)oxido-lambda$^6$-sulfanylidene]-5-oxo-7-(piperidin-4-yl)-4,5-dihydropyrazolo[1,5-a]pyrimidine-3-carboxamide hydrochloride

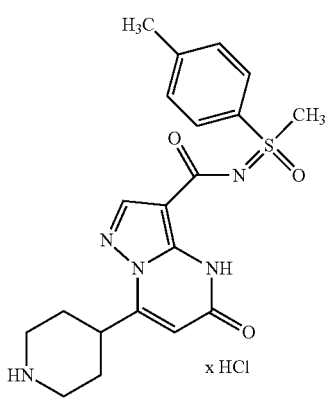 [SMILES: Cc1ccc(S(C)(=O)=NC(=O)c2cnn3c(C4CCNCC4)cc(=O)[nH]c23)cc1]

A suspension of compound tert-Butyl 4-(3-{[methyl(4-methylphenyl)oxido-lambda$^6$-sulfanylidene]carbamoyl}-5-oxo-4,5-dihydropyrazolo[1,5-a]pyrimidin-7-yl)piperidine-1-carboxylate (15 mg, 0.03 mmol) in methanol (0.5 ml) was treated with HCl 4N in dioxane (0.50 ml). The reaction mixture was sonicated 30 minutes at RT. The mixture was evaporated under vacuo and the crude product was diluted in water and lyophilized overnight to yield the title compound (11 mg, 76% of theory).

LC-MS (Method 2B): R$_t$=1.51 min, MS (ESIPos): m/z=414 [M+H-xHCl]$^+$ $^1$H-NMR (400 MHz, D$_2$O): δ=8.19 (s, 1H), 7.89 (d, 2H), 7.52 (d, 2H), 6.16 (s, 1H), 3.64-3.54 (m, 6H), 3.24 (dd, 2H), 2.45 (s, 3H), 2.38 (d, 2H), 1.96 (dd, 2H).

Example 37

N-(4-Oxido-1,4-lambda$^4$-oxathian-4-ylidene)-5-oxo-7-(piperidin-4-yl)-4,5-dihydropyrazolo[1,5-a]pyrimidine-3-carboxamide hydrochloride

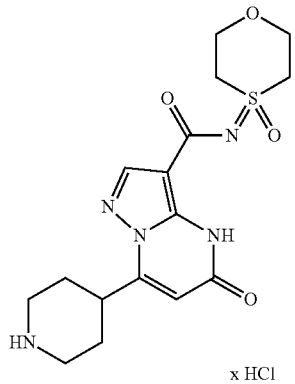 [SMILES: O=C(N=S1(=O)CCOCC1)c1cnn2c(C3CCNCC3)cc(=O)[nH]c12]

A suspension of compound tert-butyl 4-{3-[(4-oxido-1,4lambda$^4$-oxathian-4-ylidene)carbamoyl]-5-oxo-4,5-dihydropyrazolo[1,5-a]pyrimidin-7-yl}piperidine-1-carboxylate (66 mg, 0.14 mmol) in methanol (1.0 ml) was treated with HCl 4N in dioxane (1.0 ml). The reaction mixture was sonicated 30 minutes at RT. The mixture was evaporated under vacuo and the crude product was stirred in a mixture of dioxane/methanol 3/1. The resulting solid was filtered, washed with dioxane and dried at 60° C. for 16 h to yield the title compound (54 mg, 89% of theory).

LC-MS (Method 2B): R$_t$=3.79 min, MS (ESIPos): m/z=380 [M+H-xHCl]$^+$ $^1$H-NMR (400 MHz, D$_2$O): δ=8.22 (s, 1H), 6.18 (s, 1H), 4.37-4.30 (m, 2H), 4.03-3.96 (m, 2H), 3.77-3.74 (m, 2H), 3.65 (d, 1H), 3.59 (dd, 2H), 3.27 (dd, 2H), 2.39 (d, 2H), 1.98 (dd, 2H).

Example 38

Ethyl 5-oxo-2-phenyl-7-(piperidin-4-yl)-4,5-dihydropyrazolo[1,5-a]pyrimidine-3-carboxylate trifluoroacetate

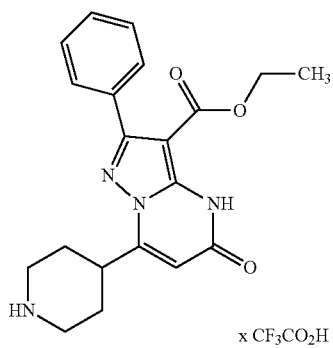 [SMILES: CCOC(=O)c1c(-c2ccccc2)nn2c(C3CCNCC3)cc(=O)[nH]c12]

A suspension of compound ethyl 7-[1-(tert-butoxycarbonyl)piperidin-4-yl]-5-oxo-2-phenyl-4,5-dihydropyrazolo[1,5-a]pyrimidine-3-carboxylate (40 mg, 0.08 mmol) in dichloromethane (0.45 ml) was treated with trifluoroacetic acid (0.07 ml). The reaction mixture was left without stirring at RT for 16 h.

The mixture was evaporated under vacuo and the crude product was stirred in dioxane. The solid was filtered, and dried under vacuo to yield the title compound (29 mg, 71% of theory).

LC-MS (Method 1B): $R_t$=0.65 min, MS (ESIPos): m/z=367 [M+H-xTFA]$^+$ $^1$H-NMR (400 MHz, DMSO-d$_6$): δ 8.67 (br. s, 1H), 8.36 (br. s, 1H), 7.71 (d, 1H), 7.70 (d, 1H), 7.47-7.44 (m, 3H), 6.06 (s, 1H), 4.26 (q, 2H), 3.56 (dd, 1H), 3.40 (d, 2H), 3.11 (dd, 2H), 2.22 (d, 2H), 1.83 (dd, 2H), 1.21 (t, 3H)

Example 39

3-[3-(4-Methylphenyl)-1,2,4-oxadiazol-5-yl]-7-(piperidin-4-yl)pyrazolo[1,5-a]pyrimidin-5 (4H)-hydrochloride

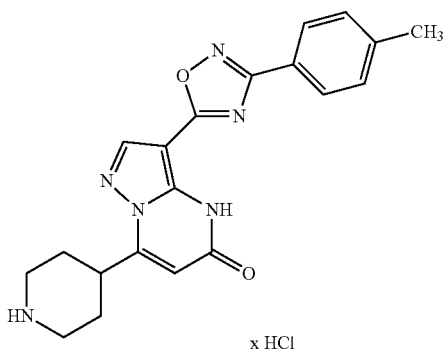 [SMILES: Cc1ccc(-c2noc(-c3cnn4c(C5CCNCC5)cc(=O)[nH]c34)n2)cc1]

A suspension of compound tert-butyl 4-{3-[3-(4-methylphenyl)-1,2,4-oxadiazol-5-yl]-5-oxo-4,5-dihydropyrazolo[1,5-a]pyrimidin-7-yl}piperidine-1-carboxylate (46 mg, 0.10 mmol) in methanol (1.0 ml) was treated with HCl 4N in dioxane (1.0 ml). The reaction mixture was sonicated 30 minutes at 40° C. The mixture was diluted in 2 ml dioxane and the resulting solid was filtered, washed with dioxane and dried at 60° C. for 16 h to yield the title compound (27 mg, 65% of theory).

LC-MS (Method 2B): $R_t$=1.76 min, MS (ESIPos): m/z=377 [M+H-xHCl]$^+$ $^1$H-NMR (400 MHz, TFA): δ 8.90 (s, 1H), 8.24 (d, 2H), 7.88 (br. s, 1H), 7.61 (d, 2H), 7.51 (br. s, 1H), 6.86 (s, 1H), 4.14-4.06 (m, 3H), 3.76-3.69 (m, 2H), 2.77 (d, 2H), 2.66 (s, 3H), 2.61-2.54 (m, 2H)

Example 40

(−)-trans-3-Chloro-7-(2-methylpiperidin-4-yl)pyrazolo[1,5-a]pyrimidin-5(4H)-one hydrochloride

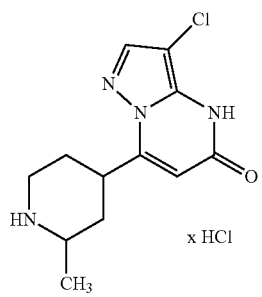

A suspension of compound tert-butyl-4-(3-chloro-5-oxo-4,5-dihydropyrazolo[1,5-a]pyrimidin-7-yl)-2-methylpiperidine-1-carboxylate (Example 51A, enantiomerically pure trans-Isomer) (337 mg, 0.90 mmol) in methanol (2.5 ml) was treated with HCl 4N in dioxane (2.5 ml). The reaction mixture was left without stirring at RT for 16 h. The resulting solid was filtered, washed with dioxane and dried under vacuo. After that the solid was diluted in water and lyophilized to yield the title compound (140 mg, 52% of theory).

LC-MS (Method 2B): $R_t$=0.27 min, MS (ESIPos): m/z=267 [M+H-xHCl]$^+$

[α]$^{20}$=−8.657 (c. 0.335, methanol) WL=589 nm $^1$H-NMR (400 MHz, DMSO-d$_6$): δ 9.09 (br. s, 1H), 8.88 (br. s, 1H), 8.00 (s, 1H), 5.96 (s, 1H), 3.66-3.62 (m, 2H), 3.26-3.12 (m, 2H), 2.12-1.99 (m, 4H), 1.35 (d, 3H)

Example 41

5-Oxo-2-phenyl-7-(piperidin-4-yl)-4,5-dihydropyrazolo[1,5-a]pyrimidine-3-carboxamide trifluoroacetate

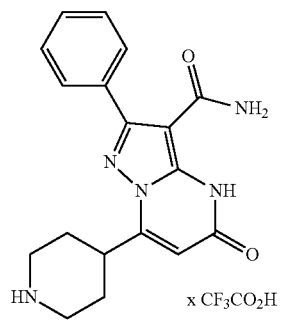 [SMILES: NC(=O)c1c(-c2ccccc2)nn2c(C3CCNCC3)cc(=O)[nH]c12]

A solution of compound tert-butyl 4-(3-carbamoyl-5-oxo-2-phenyl-4,5-dihydropyrazolo[1,5-a]pyrimidin-7-yl)piperidine-1-carboxylate (15 mg, 0.03 mmol) in dichloromethane (0.8 ml) was treated with trifluoroacetic acid (0.03 ml). The reaction mixture was stirred 6 h at RT and was left two days at RT without stirring. After that the solvent was evaporated under vacuo and the crude product was dissolved in water and lyophilized overnight to yield the title compound (15 mg, 98% of theory).

LC-MS (Method 1B): $R_t$=0.34 min, MS (ESIPos): m/z=338 [M+H-×TFA]$^+$

Example 42

N-Benzyl-5-oxo-2-phenyl-7-(piperidin-4-yl)-4,5-dihydropyrazolo[1,5-a]pyrimidine-3-carboxamide trifluoroacetate

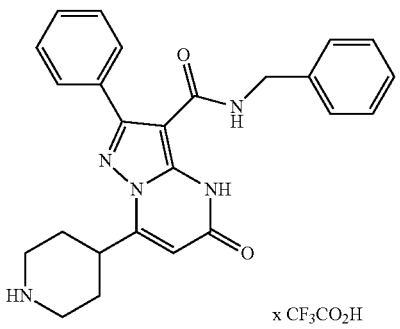 [SMILES: O=C(NCc1ccccc1)c1c(-c2ccccc2)nn2c(C3CCNCC3)cc(=O)[nH]c12]

A solution of compound tert-Butyl 4-[3-(benzylcarbamoyl)-5-oxo-2-phenyl-4,5-dihydropyrazolo[1,5-a]pyrimidin-7-yl]piperidine-1-carboxylate (15 mg, 0.03 mmol) in dichloromethane (0.7 ml) was treated with trifluoroacetic acid (0.02 ml). The reaction mixture was stirred 6 h at RT and was left two days at RT without stirring. After that the solvent was evaporated under vacuo and the crude product was dissolved in water and lyophilized overnight to yield the title compound (17 mg, quantitative).

LC-MS (Method 1B): $R_t$=0.66 min, MS (ESIPos): m/z=428 [M+H-×TFA]$^+$ $^1$H-NMR (400 MHz, DMSO-$d_6$): δ 8.72 (br. s, 1H), 8.43 (br. s, 1H), 7.75 (s, 2H), 7.49-7.37 (m, 3H), 7.37-7.22 (m, 5H), 5.98 (br. s, 1H), 4.45 (s, 2H), 3.42 (d, 3H), 3.18-3.10 (m, 2H), 2.26 (d, 2H), 1.92-1.83 (m, 2H).

Example 43

3-(Morpholin-4-ylcarbonyl)-2-phenyl-7-(piperidin-4-yl)pyrazolo[1,5-a]pyrimidin-5(4H)-one trifluoroacetate

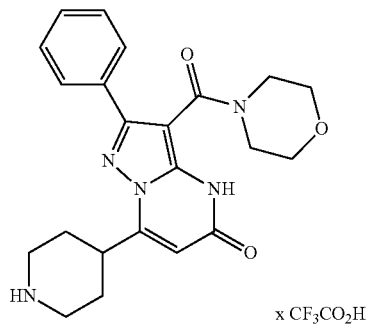 [SMILES: O=C(c1c(-c2ccccc2)nn2c(C3CCNCC3)cc(=O)[nH]c12)N1CCOCC1]

A solution of compound tert-Butyl 4-[3-(morpholin-4-ylcarbonyl)-5-oxo-2-phenyl-4,5-dihydropyrazolo[1,5-a]pyrimidin-7-yl]piperidine-1-carboxylate (12 mg, 0.02 mmol) in dichloromethane (0.5 ml) was treated with trifluoroacetic acid (0.02 ml). The reaction mixture was stirred 6 h at RT and was left two days at RT without stirring. After that the solvent was evaporated under vacuo and the crude product was dissolved in water and lyophilized overnight to yield the title compound (11 mg, 89% of theory).

LC-MS (Method 1B): $R_t$=0.47 min, MS (ESIPos): m/z=408 [M+H-×TFA]$^+$ $^1$H-NMR (400 MHz, DMSO-$d_6$): δ 12.37 (br. s, 1H), 8.73 (br. s, 1H), 8.42 (br. s, 1H), 7.70 (d, 2H), 7.50-7.44 (m, 3H), 5.92 (br. s, 1H), 3.45-3.10 (m, 11H), 2.26 (d, 2H), 1.87 (dd, 2H).

Example 44

N-(3-Methylbutyl)-5-oxo-2-phenyl-7-(piperidin-4-yl)-4,5-dihydropyrazolo[1,5-a]pyrimidine-3-carboxamide trifluoroacetate

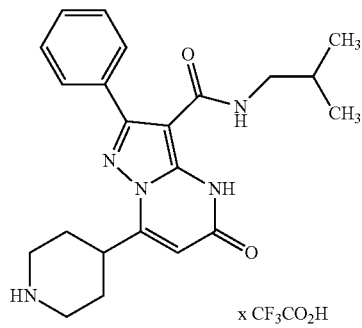 [SMILES: CC(C)CNC(=O)c1c(-c2ccccc2)nn2c(C3CCNCC3)cc(=O)[nH]c12]

A solution of compound tert-Butyl 4-[3-(isobutylcarbamoyl)-5-oxo-2-phenyl-4,5-dihydropyrazolo[1,5-a]pyrimidin-7-yl]piperidine-1-carboxylate (10 mg, 0.02 mmol) in dichloromethane (0.5 ml) was treated with trifluoroacetic acid (0.02 ml). The reaction mixture was stirred 6 h at RT and was left two days at RT without stirring. After that the solvent was evaporated under vacuo and the crude product was dissolved in water and lyophilized overnight to yield the title compound (10 mg, quantitative).

LC-MS (Method 1B): $R_t$=0.63 min, MS (ESIPos): m/z=394 [M+H-×TFA]$^+$ $^1$H-NMR (400 MHz, DMSO-$d_6$): δ 8.68 (br. s, 1H), 8.39 (br. s, 1H), 7.77 (s, 2H), 7.45 (s, 3H), 5.96 (br. s, 1H), 3.42 (d, 2H), 3.18-3.02 (m, 5H), 2.26 (d, 2H), 1.96-1.80 (m, 2H), 1.80-1.69 (m, 1H), 0.84 (d, 6H).

Example 45

3-(4-Methylphenyl)-7-(piperidin-4-yl)pyrazolo[1,5-a]pyrimidin-5(4H)-one hydrochloride

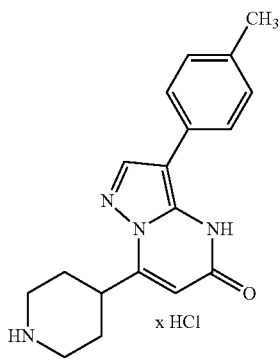 [SMILES: Cc1ccc(-c2cnn3c(C4CCNCC4)cc(=O)[nH]c23)cc1]

A suspension of compound tert-Butyl 4-[3-(4-methylphenyl)-5-oxo-4,5-dihydropyrazolo[1,5-a]pyrimidin-7-yl]piperidine-1-carboxylate (6 mg, 0.02 mmol) in methanol (0.5 ml) was treated with HCl 4N in dioxane (0.5 ml). The reaction mixture was sonicated 15 minutes at RT. The mixture was evaporated under vacuo and then the crude product was diluted in methanol and was evaporated again. The crude product was finally diluted in water and lyophilized overnight to yield the title compound (6 mg, 98% of theory).

LC-MS (Method 1B): $R_t$=0.57 min, MS (ESIPos): m/z=309 [M+H-×HCl]$^+$ $^1$H-NMR (400 MHz, DMSO-d$_6$): δ 11.99 (br. s, 1H), 8.90 (br. s, 1H), 8.23 (br. s, 1H), 7.21 (d, 4H), 5.98 (s, 1H), 3.66-3.54 (m, 1H), 3.41 (d, 2H), 3.11 (dd, 2H), 2.32 (s, 3H), 2.23 (d. 2H), 1.91 (dd, 2H):

Example 46

5-Oxo-7-(piperidin-4-yl)-4,5-dihydropyrazolo[1,5-a]pyrimidine-2-carboxylic acid hydrochloride

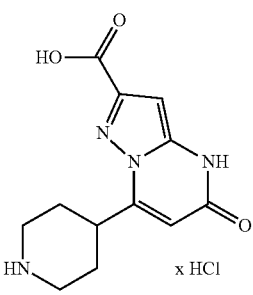 [SMILES: O=C(O)c1cc2[nH]c(=O)cc(C3CCNCC3)n2n1]

A suspension of 7-[1-(tert-Butoxycarbonyl)piperidin-4-yl]-5-oxo-4,5-dihydropyrazolo[1,5-a]pyrimidine-2-carboxylic acid (46 mg, 0.13 mmol) in methanol (0.5 ml) was treated with HCl 4N in dioxane (0.5 ml). The reaction mixture was sonicated 30 minutes at 40° C. The suspension was diluted in dioxane, filtered and then the solid was washed with dioxane and finally dried under vacuo at 60° C. overnight to yield the title compound (31 mg, 78% of theory).

LC-MS (Method 1B): $R_t$=0.16 min, MS (ESIPos): m/z=263 [M+H-×HCl]$^+$ $^1$H-NMR (400 MHz, TFA): δ 7.19 (s, 1H), 6.90 (s, 1H), 4.28-4.12 (d, 3H), 3.83-3.69 (m, 2H), 2.86 (d. 2H), 2.66-2.52 (m, 2H).

Example 47

4-[5-Oxo-7-(piperidin-4-yl)-4,5-dihydropyrazolo[1,5-a]pyrimidin-3-yl]benzonitrile trifluoroacetate

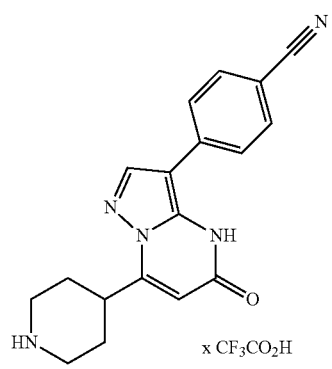 [SMILES: N#Cc1ccc(-c2cnn3c(C4CCNCC4)cc(=O)[nH]c23)cc1]

A suspension of compound tert-Butyl 4-[3-(4-cyanophenyl)-5-oxo-4,5-dihydropyrazolo[1,5-a]pyrimidin-7-yl]piperidine-1-carboxylate (42 mg, 0.10 mmol) in methanol (1.0 ml) was treated with trifluoroacetic acid (0.08 ml). The reaction mixture was left without stirring at RT for 2.5 days. The mixture was evaporated under vacuo and then the crude product was stirred with dioxane. The resulting solid was filtered and washed with dioxane and finally dried under vacuo at 70° C. for 2.5 h to yield the title compound (40 mg, 90% of theory).

LC-MS (Method 2B): $R_t$=1.46 min, MS (ESIPos): m/z=320 [M+H-×TFA]$^+$ $^1$H-NMR (400 MHz, TFA): δ 8.67 (s, 1H), 8.13 (s, 2H), 7.96 (s, 2H), 7.84 (br. s, 1H), 6.79 (s, 1H), 4.12-4.05 (m, 3H), 3.76 (s, 2H), 2.77 (s, 2H), 2.55 (s, 2H).

Example 48

3-(3-Chlorophenyl)-7-(piperidin-4-yl)pyrazolo[1,5-a]pyrimidin-5(4H)-one hydrochloride

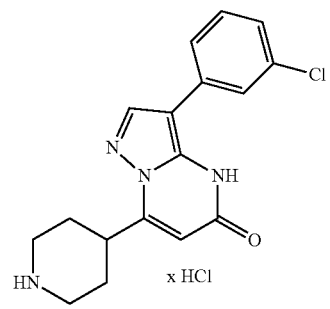 [SMILES: O=c1cc(C2CCNCC2)n2ncc(-c3cccc(Cl)c3)c2[nH]1]

A suspension of compound tert-Butyl 4-[3-(3-chlorophenyl)-5-oxo-4,5-dihydropyrazolo[1,5-a]pyrimidin-7-yl]piperidine-1-carboxylate (34 mg, 0.08 mmol) in methanol (0.5 ml) was treated with HCl 4N (0.5 ml). The reaction mixture sonicated at RT for 30 minutes. The resulting solid was filtered and washed with dioxane and finally dried under vacuo at 60° C. overnight to yield the title compound (20 mg, 66% of theory).

LC-MS (Method 1B): $R_t$=0.58 min, MS (ESIPos): m/z=329 [M+H-xHCl]$^+$ $^1$H-NMR (400 MHz, TFA): δ 8.64 (s, 1H), 7.86 (br. s, 1H), 7.71-7.65 (m, 3H), 7.60 (d, 1H), 7.57 (br. s, 1H), 6.82 (s, 1H), 4.15 (d, 2H), 4.11-4.01 (m, 1H), 3.84-3.70 (m, 2H), 2.79 (d, 2H), 2.64-2.49 (m, 2H).

Example 49

2-[5-Oxo-7-(piperidin-4-yl)-4,5-dihydropyrazolo[1,5-a]pyrimidin-3-yl]benzonitrile trifluoroacetate

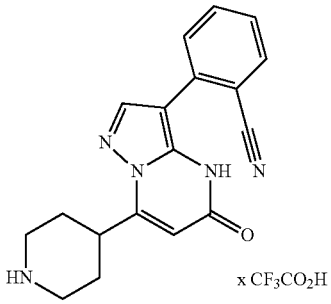 [SMILES: N#Cc1ccccc1-c1cnn2c(C3CCNCC3)cc(=O)[nH]c12]

A suspension of compound tert-Butyl 4-[3-(2-cyanophenyl)-5-oxo-4,5-dihydropyrazolo[1,5-a]pyrimidin-7-yl]piperidine-1-carboxylate (25 mg, 0.06 mmol) in methanol (0.5 ml) was treated with trifluoroacetic (0.05 ml). The reaction mixture was left without stirring for 2.5 days at RT. The mixture was evaporated under vacuo and then the crude product was stirred with dioxane. The resulting solid was filtered and washed with dioxane and finally dried under vacuo at 60° C. for 2.5 h to yield the title compound (18 mg, 67% of theory).

LC-MS (Method 2B): $R_t$=1.45 min, MS (ESIPos): m/z=320 [M+H-xTFA]$^+$ $^1$H-NMR (400 MHz, TFA): δ 8.69 (s, 1H), 8.15 (d, 1H), 8.11-8.06 (m, 1H), 7.92-7.79 (m, 2H), 6.82 (s, 1H), 4.14-4.04 (m, 3H), 3.85-3.70 (m, 2H), 2.81 (d, 2H), 2.64-2.48 (m, 2H).

Example 50

3-[5-Oxo-7-(piperidin-4-yl)-4,5-dihydropyrazolo[1,5-a]pyrimidin-3-yl]benzonitrile trifluoroacetate

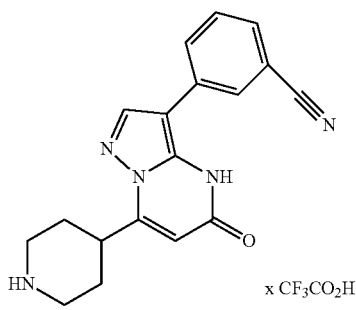 [SMILES: N#Cc1cccc(-c2cnn3c(C4CCNCC4)cc(=O)[nH]c23)c1]

A suspension of compound tert-Butyl 4-[3-(3-cyanophenyl)-5-oxo-4,5-dihydropyrazolo[1,5-a]pyrimidin-7-yl]piperidine-1-carboxylate (29 mg, 0.07 mmol) in methanol (0.5 ml) was treated with trifluoroacetic (0.05 ml). The reaction mixture was left without stirring for 2.5 days at RT. The mixture was evaporated under vacuo and then the crude product was stirred with dioxane. The resulting solid was filtered, washed with dioxane and finally dried under vacuo at 70° C. for 2.5 h to yield the title compound (20 mg, 67% of theory).

LC-MS (Method 2B): $R_t$=1.48 min, MS (ESIPos): m/z=320 [M+H-xTFA]$^+$ $^1$H-NMR (400 MHz, TFA): δ 8.65 (s, 1H), 8.16 (s, 1H), 8.09-8.03 (m, 2H), 7.99-7.89 (m, 1H), 7.85 (br. s, 1H), 6.79 (s, 1H), 4.20-3.97 (m, 3H), 3.84-3.68 (m, 2H), 2.78 (d, 2H), 2.61-2.45 (m, 2H).

Example 51

(−)-trans-7-(2-Methylpiperidin-4-yl)-5-oxo-4,5-dihydropyrazolo[1,5-a]pyrimidine-3-carboxamide trifluoroacetate

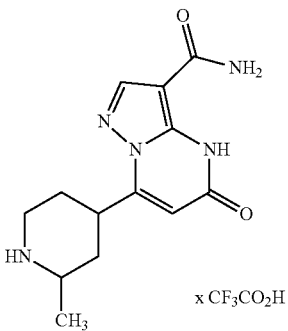 [SMILES: CC1CC(c2cc(=O)[nH]c3c(C(N)=O)cnn23)CCN1]

A solution of compound trans-tert-Butyl 4-(3-carbamoyl-5-oxo-4,5-dihydropyrazolo[1,5-a]pyrimidin-7-yl)-2-methylpiperidine-1-carboxylate (Example 64A, enantiomerically pure trans-Isomer) (100 mg, 0.27 mmol) in dichlormethane (6 ml) was treated with trifluoroacetic acid (0.2 ml). The reaction mixture was left without stirring at RT for 4 days. Methanol was evaporated and the crude product was treated with dioxane. The resulting solid was filtered, washed with dioxane and again dissolved in MeOH, evaporated and dried under vacuo to yield the title compound (98 mg, 96% of theory).

LC-MS (Method 2B): $R_t$=0.77 min, MS (ESINeg): m/z=276 [M−H-xTFA]$^-$

[α]$^{20}$=4.225 (c. 0.355, methanol) WL=546 nm $^1$H-NMR (400 MHz, DMSO-d$_6$): δ 10.72 (br. s, 1H), 8.68 (br. s, 1H), 8.51 (br. s, 1H), 8.29 (br. s, 1H), 7.78 (br. s, 1H), 7.32 (br. s, 1H), 6.08 (s, 1H), 3.34-3.15 (m, 4H), 2.18-1.89 (m, 4H), 1.34 (d, 3H).

Example 52

3-(3-Fluorophenyl)-7-(piperidin-4-yl)pyrazolo[1,5-a]pyrimidin-5(4H)-one hydrochloride

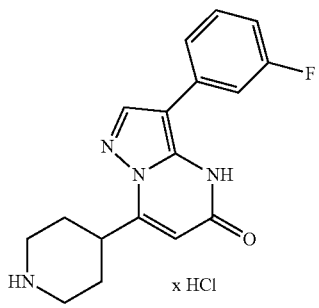 [SMILES: O=c1cc(C2CCNCC2)n2ncc(-c3cccc(F)c3)c2[nH]1]

A suspension of compound tert-Butyl 4-[3-(3-fluorophenyl)-5-oxo-4,5-dihydropyrazolo[1,5-a]pyrimidin-7-yl]piperidine-1-carboxylate (20 mg, 0.05 mmol) in methanol (0.5 ml) was treated with HCl 4N (0.5 ml). The reaction mixture was sonicated at RT for 15 minutes. The resulting solid was filtered and washed with dioxane and finally dried under vacuo at 70° C. overnight to yield the title compound (4 mg, 22% of theory).

LC-MS (Method 2B): $R_t$=1.52 min, MS (ESIPos): m/z=313 [M+H-xHCl]$^+$ $^1$H-NMR (400 MHz, D$_2$O): δ 7.97 (s, 1H), 7.42 (s, 1H), 7.21-7.05 (m, 3H), 6.01 (m, 1H), 3.69-3.59 (m, 2H), 3.52-3.41 (m, 1H), 3.31-3.19 (m, 2H), 2.39-2.29 (m, 2H), 2.00-1.86 (m, 2H)

Example 53

3-(4-Methoxyphenyl)-7-(piperidin-4-yl)pyrazolo[1,5-a]pyrimidin-5(4H)-one hydrochloride

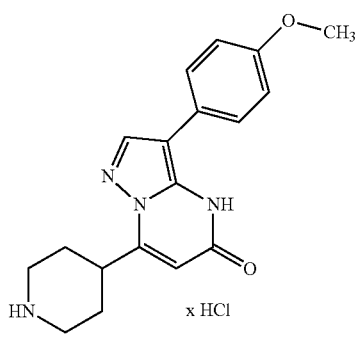 [SMILES: COc1ccc(-c2cnn3c(C4CCNCC4)cc(=O)[nH]c23)cc1]

A suspension of compound tert-Butyl 4-[3-(4-methoxyphenyl)-5-oxo-4,5-dihydropyrazolo[1,5-a]pyrimidin-7-yl]piperidine-1-carboxylate (17 mg, 0.04 mmol) in methanol (0.5 ml) was treated with HCl 4N (0.5 ml). The reaction mixture was sonicated at RT for 30 minutes. The resulting solid was filtered and washed with dioxane and finally dried under vacuo at 60° C. overnight to yield the title compound (11 mg, 78% of theory).

LC-MS (Method 1B): $R_t$=0.54 min, MS (ESIPos): m/z=325 [M+H-xHCl]$^+$ $^1$H-NMR (400 MHz, TFA): δ 8.55 (s, 1H), 7.76 (br. s, 1H), 7.63 (d, 2H), 7.52 (br. s, 1H), 7.34 (d, 2H), 6.75 (s, 1H), 3.14 (s, 3H), 4.07 (d, 2H), 4.03-3.94 (m, 1H), 3.78-3.63 (m, 2H), 2.71 (d, 2H), 2.57-2.38 (m, 2H)

Example 54

3-(3,4-Dimethoxyphenyl)-7-(piperidin-4-yl)pyrazolo[1,5-a]pyrimidin-5(4H)-one hydrochloride

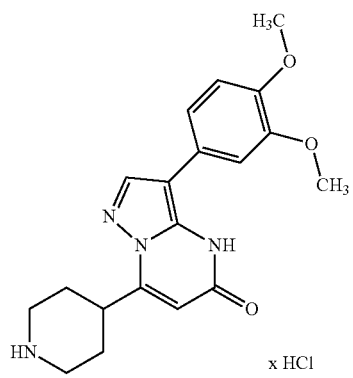 [SMILES: COc1ccc(-c2cnn3c(C4CCNCC4)cc(=O)[nH]c23)cc1OC]

A suspension of compound tert-Butyl 4-[3-(3,4-dimethoxyphenyl)-5-oxo-4,5-dihydropyrazolo[1,5-a]pyrimidin-7-yl]piperidine-1-carboxylate (29 mg, 0.06 mmol) in methanol (0.75 ml) was treated with HCl 4N (0.75 ml). The reaction mixture was sonicated at 40° C. for 30 minutes. The resulting solid was filtered and washed with dioxane and finally dried under vacuo at 60° C. overnight to yield the title compound (12 mg, 48% of theory).

LC-MS (Method 1B): $R_t$=0.50 min, MS (ESIPos): m/z=355 [M+H-xHCl]$^+$ $^1$H-NMR (400 MHz, TFA): δ 8.61 (s, 1H), 7.77 (br. s, 1H), 7.63 (br. s, 1H), 7.30 (d, 3H), 6.79 (s, 1H), 4.18 (s, 3H), 4.17 (s, 3H), 4.13-3.97 (m, 3H), 3.83-3.68 (m, 2H), 2.77-2.69 (m, 2H), 2.59-2.45 (m, 2H)

Example 55

3-[4-(Methylsulfonyl)phenyl]-7-(piperidin-4-yl)pyrazolo[1,5-a]pyrimidin-5(4H)-one hydrochloride

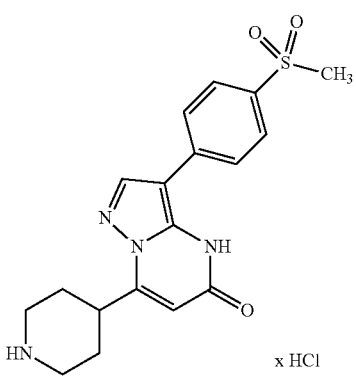 [SMILES: CS(=O)(=O)c1ccc(-c2cnn3c(C4CCNCC4)cc(=O)[nH]c23)cc1]

A suspension of compound tert-Butyl 4-{3-[4-(methylsulfonyl)phenyl]-5-oxo-4,5-dihydropyrazolo[1,5-a]pyrimidin-7-yl}piperidine-1-carboxylate (53 mg, 0.11 mmol) in methanol (1.0 ml) was treated with HCl 4N (1.0 ml). The reaction mixture was sonicated at 40° C. for 30 minutes. The resulting solid was filtered, washed with dioxane and finally dried under vacuo at 60° C. overnight to yield the title compound (27 mg, 57% of theory).

LC-MS (Method 1B): $R_t$=0.41 min, MS (ESIPos): m/z=373 [M+H-xHCl]$^+$ $^1$H-NMR (400 MHz, TFA): δ 8.64 (s, 1H), 8.33 (d, 2H), 8.02 (d, 2H), 7.81 (br. s, 1H), 7.55 (br. s, 1H), 6.76 (s, 1H), 4.18-3.96 (m, 3H), 3.78-3.63 (m, 2H), 3.49 (s, 3H), 2.81-2.68 (m, 2H), 2.60-2.46 (m, 2H)

Example 56

3-(2-Fluorophenyl)-7-(piperidin-4-yl)pyrazolo[1,5-a]pyrimidin-5(4H)-one hydrochloride

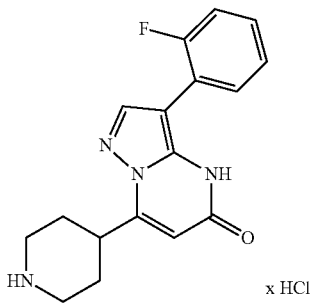 [SMILES: O=c1cc(C2CCNCC2)n2ncc(-c3ccccc3F)c2[nH]1]

A suspension of compound tert-Butyl 4-[3-(2-fluorophenyl)-5-oxo-4,5-dihydropyrazolo[1,5-a]pyrimidin-7-yl]piperidine-1-carboxylate (35 mg, 0.06 mmol) in methanol (0.5 ml) was treated with HCl 4N (0.5 ml). The reaction mixture was sonicated at RT for 15 minutes. The resulting solid was filtered, washed with dioxane and finally dried under vacuo at 760° C. overnight to yield the title compound (10 mg, 51% of theory).

LC-MS (Method 2B): $R_t$=1.53 min, MS (ESIPos): m/z=313 [M+H-xHCl]$^+$ $^1$H-NMR (400 MHz, D$_2$O): δ 7.90 (s, 1H), 7.44-7.35 (m, 2H), 7.30-7.18 (m, 2H), 6.03 (s, 1H), 3.64 (d, 2H), 3.51 (dd, 1H), 3.25 (dd, 2H), 2.33 (d, 2H), 1.96-1.89 (m, 2H)

Example 57

7-(Piperidin-4-yl)-3-[4-(trifluoromethyl)phenyl]pyrazolo[1,5-a]pyrimidin-5(4H)-one hydrochloride

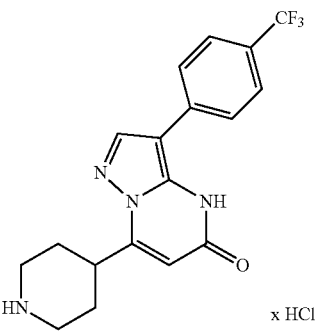 [SMILES: O=c1cc(C2CCNCC2)n2ncc(-c3ccc(C(F)(F)F)cc3)c2[nH]1]

A suspension of compound tert-Butyl 4-{5-oxo-3-[4-(trifluoromethyl)phenyl]-4,5-dihydropyrazolo[1,5-a]pyrimidin-7-yl}piperidine-1-carboxylate (38 mg, 0.08 mmol) in methanol (1.5 ml) was treated with HCl 4N (0.38 ml). The reaction mixture was sonicated at RT for 15 minutes. The mixture was evaporated and the crude product was stirred in dioxane. The resulting solid was filtered, washed with dioxane and finally dried under vacuo at 70° C. overnight to yield the title compound (21 mg, 64% of theory).

LC-MS (Method 1B): $R_t$=0.69 min, MS (ESIPos): m/z=363 [M+H-xHCl]$^+$

Example 58

7-(Piperidin-4-yl)-3-[3-(trifluoromethyl)phenyl]pyrazolo[1,5-a]pyrimidin-5(4H)-one hydrochloride

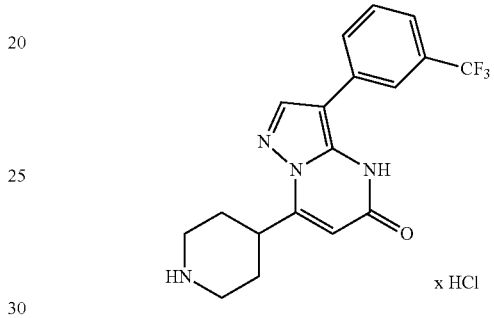

A suspension of tert-Butyl 4-{5-oxo-3-[3-(trifluoromethyl)phenyl]-4,5-dihydropyrazolo[1,5-a]pyrimidin-7-yl}piperidine-1-carboxylate (63 mg, 0.14 mmol) in methanol (1.0 ml) was treated with HCl 4N (1.0 ml). The reaction mixture was sonicated at RT for 30 minutes. The mixture was evaporated and the crude product was stirred in a mixture dioxane/methanol (4/1). The resulting solid was filtered, washed with dioxane and finally dried under vacuo at 60° C. overnight to yield the title compound (48 mg, 86% of theory).

LC-MS (Method 2B): $R_t$=1.74 min, MS (ESIPos): m/z=363 [M+H-xHCl]$^+$ $^1$H-NMR (400 MHz, TFA): δ 8.58 (s, 1H), 7.91-7.86 (m, 2H), 7.85-7.79 (m, 2H), 7.77 (br. s, 1H), 7.50 (br. s, 1H), 6.73 (s, 1H), 4.11-4.03 (m, 2H), 4.04-3.94 (m, 1H), 3.74-3.61 (m, 2H), 2.74-2.66 (m, 2H), 2.54-2.43 (m, 2H).

Example 59

7-(Piperidin-4-yl)-3-(2-thienyl)pyrazolo[1,5-a]pyrimidin-5(4H)-one hydrochloride

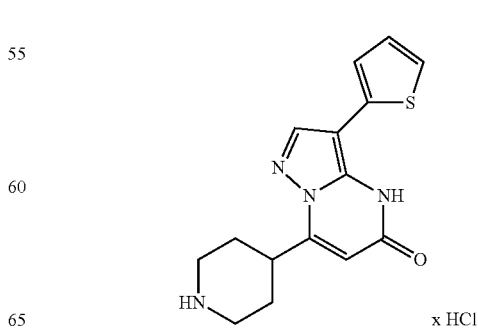

A suspension of tert-Butyl 4-[5-oxo-3-(2-thienyl)-4,5-dihydropyrazolo[1,5-a]pyrimidin-7-yl]piperidine-1-carboxylate (23 mg, 0.06 mmol) in methanol (0.5 ml) was treated with HCl 4N (0.5 ml). The reaction mixture was sonicated at RT for 30 minutes. The mixture was diluted in dioxane and the resulting solid was filtered, washed with dioxane and finally dried under vacuo at 60° C. overnight to yield the title compound (5 mg, 24% of theory).

LC-MS (Method 2B): $R_t$=1.41 min, MS (ESIPos): m/z=301 [M+H-xHCl]$^+$ $^1$H-NMR (400 MHz, D$_2$O): δ 7.97 (s, 1H), 7.48-7.42 (m, 1H), 7.17 (d, 2H), 6.02 (s, 1H), 3.63 (d, 2H), 3.50 (dd, 1H), 3.24 (dd, 2H), 2.35 (d, 2H), 1.94 (dd, 2H).

Example 60

3-(3-Methoxyphenyl)-7-(piperidin-4-yl)pyrazolo[1,5-a]pyrimidin-5(4H)-one hydrochloride

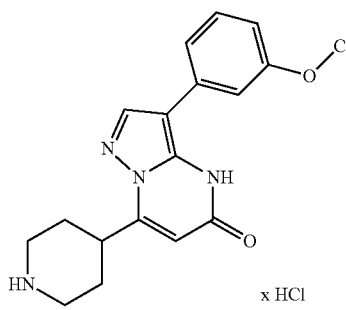

A suspension of compound tert-Butyl 4-[3-(3-methoxyphenyl)-5-oxo-4,5-dihydropyrazolo[1,5-a]pyrimidin-7-yl]piperidine-1-carboxylate (38 mg, 0.09 mmol) in methanol (0.5 ml) was treated with HCl 4N (0.5 ml). The reaction mixture was sonicated at RT for 30 minutes. The suspension was diluted in dioxane and the resulting solid was filtered, washed with dioxane and finally dried under vacuo at 60° C. overnight to yield the title compound (23 mg, 71% of theory).

LC-MS (Method 2B): $R_t$=1.51 min, MS (ESIPos): m/z=325 [M+H-xHCl]$^+$ $^1$H-NMR (400 MHz, TFA): δ 8.61 (s, 1H), 7.79 (br. s, 1H), 7.71-7.68 (m, 1H), 7.53 (br. s, 1H), 7.41-7.34 (m, 2H), 7.32 (d, 1H), 6.78 (s, 1H), 4.17-3.94 (m, 3H), 3.80-3.65 (m, 2H), 2.81-2.64 (m, 2H), 2.62-2.42 (m, 2H).

Example 61

3-(2,3-Dihydro-1,4-benzodioxin-6-yl)-7-(piperidin-4-yl)pyrazolo[1,5-a]pyrimidin-5 (4H)-one hydrochloride

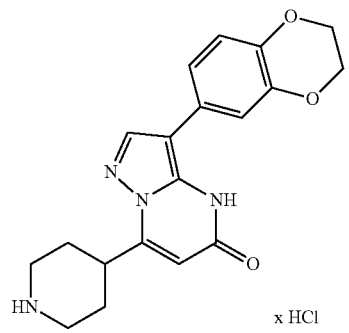 [SMILES: O=c1cc(C2CCNCC2)n2ncc(-c3ccc4c(c3)OCCO4)c2[nH]1]

A suspension of tert-Butyl 4-[3-(2,3-dihydro-1,4-benzodioxin-6-yl)-5-oxo-4,5-dihydropyrazolo[1,5-a]pyrimidin-7-yl]piperidine-1-carboxylate (13 mg, 0.03 mmol) in methanol (0.48 ml) was treated with HCl 4N (0.48 ml). The reaction mixture was sonicated at RT for 30 minutes. The suspension was diluted in dioxane and the resulting solid was filtered, washed with dioxane and finally dried under vacuo at 60° C. overnight to yield the title compound (7 mg, 60% of theory).

LC-MS (Method 2B): $R_t$=1.49 min, MS (ESIPos): m/z=353 [M+H-xHCl]$^+$ $^1$H-NMR (400 MHz, TFA): δ 8.55 (s, 1H), 7.77 (br. s, 1H), 7.45 (br. s, 1H), 7.36-7.11 (m, 3H), 6.78 (s, 1H), 4.63 (s, 4H), 4.18-3.94 (m, 3H), 3.86-3.64 (m, 2H), 2.85-2.64 (m, 2H), 2.61-2.42 (m, 2H).

Example 62

3-(2,5-Dimethoxyphenyl)-7-(piperidin-4-yl)pyrazolo[1,5-a]pyrimidin-5(4H)-one hydrochloride

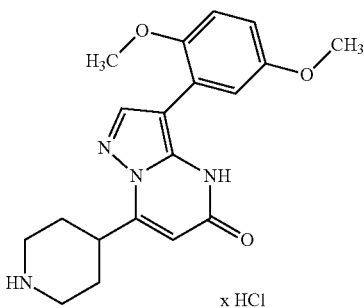 [SMILES: COc1ccc(OC)c(-c2cnn3c(C4CCNCC4)cc(=O)[nH]c23)c1]

A suspension of tert-Butyl 4-[3-(2,5-dimethoxyphenyl)-5-oxo-4,5-dihydropyrazolo[1,5-a]pyrimidin-7-yl]piperidine-1-carboxylate (20 mg, 0.04 mmol) in methanol (0.50 ml) was treated with HCl 4N (0.50 ml). The reaction mixture was sonicated at RT for 30 minutes. The suspension was diluted in dioxane and the resulting solid was filtered, washed with dioxane and finally dried under vacuo at 60° C. overnight to yield the title compound (16 mg, 94% of theory).

LC-MS (Method 2B): $R_t$=1.66 min, MS (ESIPos): m/z=355 [M+H-xHCl]$^+$ $^1$H-NMR (400 MHz, TFA): δ 8.71 (s, 1H), 7.84 (br. s, 1H), 7.55 (br. s, 1H), 7.43-7.35 (m, 3H), 6.85 (s, 1H), 4.26 (s, 3H), 4.17 (s, 3H), 4.16-4.05 (m, 3H), 3.86-3.72 (m, 2H), 2.86-2.75 (m, 2H), 2.66-2.49 (m, 2H).

Example 63

7-(Piperidin-4-yl)-3-[2-(trifluoromethyl)phenyl]pyrazolo[1,5-a]pyrimidin-5(4H)-one hydrochloride

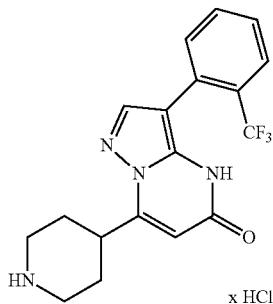 [SMILES: O=c1cc(C2CCNCC2)n2ncc(-c3ccccc3C(F)(F)F)c2[nH]1]

A suspension of compound tert-Butyl 4-{5-oxo-3-[2-(trifluoromethyl)phenyl]-4,5-dihydropyrazolo[1,5-a]pyrimidin-7-yl}piperidine-1-carboxylate (15 mg, 0.03 mmol) in methanol (0.50 ml) was treated with HCl 4N (0.50 ml). The reaction mixture was sonicated at RT for 30 minutes. The mixture was evaporated and the crude product was stirred in a mixture of dioxane/methanol 4/1. The resulting solid was filtered, washed with dioxane and finally dried under vacuo at 60° C. overnight to yield the title compound (8 mg, 58% of theory).

LC-MS (Method 2B): $R_t$=1.69 min, MS (ESIPos): m/z=363 [M+H-xHCl]$^+$ $^1$H-NMR (400 MHz, D$_2$O): δ 7.94 (s, 1H), 7.91 (d, 1H), 7.74-7.71 (m, 1H), 7.66-7.63 (m, 1H), 7.47 (d, 1H), 6.09 (s, 1H), 3.70-3.61 (m, 3H), 3.29 (dd, 2H), 2.43 (d, 2H), 2.00 (dd, 2H).

Example 64

3-(4-Fluorophenyl)-2-phenyl-7-(piperidin-4-yl)pyrazolo[1,5-a]pyrimidin-5(4H)-one hydrochloride

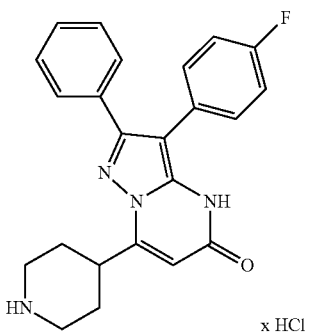 [SMILES: O=c1cc(C2CCNCC2)n2nc(-c3ccccc3)c(-c3ccc(F)cc3)c2[nH]1]

A suspension of tert-Butyl 4-[3-(4-fluorophenyl)-5-oxo-2-phenyl-4,5-dihydropyrazolo[1,5-a]pyrimidin-7-yl]piperidine-1-carboxylate (29 mg, 0.063 mmol) in methanol (1.5 ml) was treated with HCl 4N (0.37 ml). The reaction mixture was sonicated at RT for 15 minutes. The resulting solid was filtered, washed with dioxane and finally dried under vacuo at 70° C. overnight to yield the title compound (9 mg, 38% of theory).

LC-MS (Method 1B): $R_t$=0.74 min, MS (ESIPos): m/z=389 [M+H-xHCl]$^+$ $^1$H-NMR (400 MHz, DMSO-d$_6$): δ 8.84 (br. s, 1H), 8.62 (br. s, 1H), 7.46-7.38 (m, 2H), 7.38-7.32 (m, 3H), 7.31-7.24 (m, 2H), 7.24-7.17 (m, 2H), 5.88 (br. s, 1H), 3.71-3.56 (m, 1H), 3.42 (d, 2H), 3.15 (dd, 2H), 2.29 (d, 2H), 1.92 (dd, 2H).

Example 65

(−)-trans-7-(2-Methylpiperidin-4-yl)-5-oxo-4,5-dihydropyrazolo[1,5-a]pyrimidine-3-carbonitrile trifluoroacetate

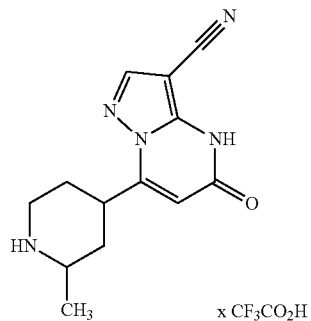 [SMILES: CC1CC(c2cc(=O)[nH]c3c(C#N)cnn23)CCN1]

A solution of tert-Butyl 4-(3-cyano-5-oxo-4,5-dihydropyrazolo[1,5-a]pyrimidin-7-yl)-2-methylpiperidine-1-carboxylate (Example 78A, enantiomerically pure trans-Isomer) (200 mg, 0.56 mmol) in dichloromethane (12.94 ml) was treated with trifluoroacetic acid (0.43 ml). The reaction mixture left without stirring one day at RT. The mixture was evaporated and the crude product was treated with dioxane. The resulting solid was filtered, washed with dioxane and finally dried under vacuo. After that the crude product was dissolved in water and lyophilized to yield the title compound (139 mg, 67% of theory).

LC-MS (Method 1B): $R_t$=0.19 min, MS (ESIPos): m/z=258 [M+H-xTFA]$^+$ $[α]^{20}$=−6.00 (c. 0.350, methanol) WL=578 nm $^1$H-NMR (400 MHz, DMSO-d$_6$): δ=8.68 (br. s, 1H), 8.51 (br. s, 1H), 8.43 (s, 1H), 6.27 (br. s, 1H), 3.79-3.60 (m, 2H), 3.29-3.10 (m, 2H), 2.16-1.90 (m, 4H), 1.33 (d, 3H).

Example 66

3-(4-Methyl-2-thienyl)-7-(piperidin-4-yl)pyrazolo[1,5-a]pyrimidin-5(4H)-one hydrochloride

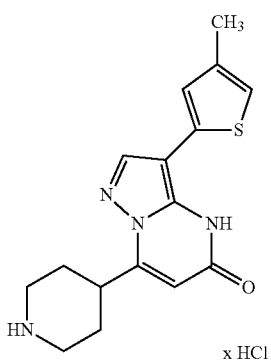 [SMILES: Cc1csc(-c2cnn3c(C4CCNCC4)cc(=O)[nH]c23)c1]

x HCl

A suspension of tert-Butyl 4-[3-(4-methyl-2-thienyl)-5-oxo-4,5-dihydropyrazolo[1,5-a]pyrimidin-7-yl]piperidine-1-carboxylate (25 mg, 0.06 mmol) in methanol (0.34 ml) was treated with HCl 4N (0.34 ml). The reaction mixture was sonicated at RT for 30 minutes. The suspension was diluted in dioxane and the solid was filtered, washed with dioxane and finally dried under vacuo at 60° C. overnight to yield the title compound (7 mg, 34% of theory).

LC-MS (Method 2B): $R_t$=1.56 min, MS (ESIPos): m/z=315 [M+H-xHCl]$^+$ $^1$H-NMR (400 MHz, D$_2$O): 7.89 (s, 1H), 6.98 (s, 1H), 6.94 (s, 1H), 5.99 (s, 1H), 3.68-3.57 (m, 2H), 3.53-3.41 (m, 1H), 3.28-3.17 (m, 2H), 2.35-2.29 (m, 2H), 2.26 (s, 3H), 1.99-1.82 (m, 2H).

Example 67

3-(2-Methoxyphenyl)-7-(piperidin-4-yl)pyrazolo[1,5-a]pyrimidin-5(4H)-one hydrochloride

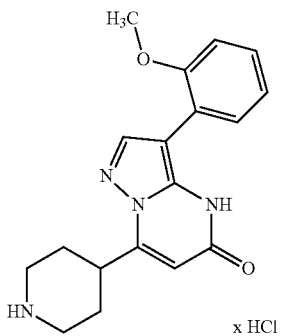 [SMILES: COc1ccccc1-c1cnn2c(C3CCNCC3)cc(=O)[nH]c12]

x HCl

A suspension of tert-Butyl 4-[3-(2-methoxyphenyl)-5-oxo-4,5-dihydropyrazolo[1,5-a]pyrimidin-7-yl]piperidine-1-carboxylate (44 mg, 0.10 mmol) in methanol (1.0 ml) was treated with HCl 4N (1.0 ml).

The reaction mixture was sonicated at RT for 30 minutes. The suspension was diluted in dioxane and the solid was filtered, washed with dioxane and finally dried under vacuo at 60° C. overnight to yield the title compound (26 mg, 70% of theory).

LC-MS (Method 2B): $R_t$=1.68 min, MS (ESIPos): m/z=325 [M+H-xHCl]$^+$ $^1$H-NMR (400 MHz, D$_2$O): 7.96 (s, 1H), 7.39 (dd, 1H), 7.33 (d, 1H), 7.12 (d, 1H), 7.05 (dd, 1H), 6.00 (s, 1H), 3.07 (s, 3H), 3.62 (d, 2H), 3.49 (dd, 1H), 3.24 (dd, 2H), 2.33 (d, 2H), 1.92 (dd, 2H).

Example 68

5-[5-Oxo-7-(piperidin-4-yl)-4,5-dihydropyrazolo[1,5-a]pyrimidin-3-yl]thiophene-3-carbonitrile trifluoroacetate

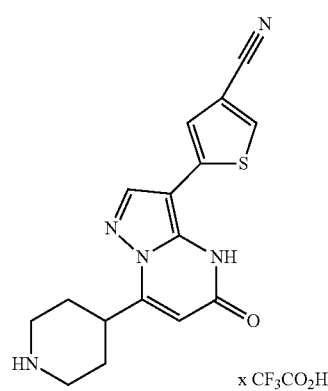 [SMILES: N#Cc1csc(-c2cnn3c(C4CCNCC4)cc(=O)[nH]c23)c1]

x CF$_3$CO$_2$H

A suspension of tert-Butyl 4-[3-(4-cyano-2-thienyl)-5-oxo-4,5-dihydropyrazolo[1,5-a]pyrimidin-7-yl]piperidine-1-carboxylate (4 mg, 0.01 mmol) in dichlormethane (0.67 ml) was treated with trifluoroacetic acid (0.01 ml). The reaction mixture was sonicated at 40° C. for 30 minutes. The mixture was evaporated under vacuo and then the crude product was diluted in water and lyophilized overnight to yield the title compound (4 mg, 89% of theory).

LC-MS (Method 2B): $R_t$=0.45 min, MS (ESIPos): m/z=326 [M+H-xTFA]$^+$ $^1$H-NMR (400 MHz, D$_2$O): 8.20 (s, 1H), 8.03 (s, 1H), 7.39 (s, 1H), 6.09 (s, 1H), 3.69-3.51 (m, 3H), 3.26 (dd, 2H), 2.40 (d, 2H), 1.96 (dd, 2H).

Example 69

3-(6-Methoxypyridin-3-yl)-7-(piperidin-4-yl)pyrazolo[1,5-a]pyrimidin-5 (4H)-one

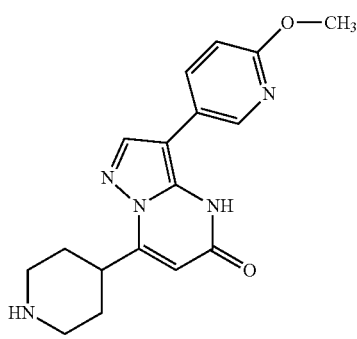 [SMILES: COc1ccc(-c2cnn3c(C4CCNCC4)cc(=O)[nH]c23)cn1]

A suspension of tert-Butyl 4-[3-(6-methoxypyridin-3-yl)-5-oxo-4,5-dihydropyrazolo[1,5-a]pyrimidin-7-yl]piperidine-1-carboxylate (42 mg, 0.10 mmol) in methanol (1.0 ml) was treated with HCl 4N (1.0 ml). The reaction mixture was sonicated at RT for 30 minutes. The reaction mixture was diluted in dioxane, and the resulting salt was filtered, washed with dioxane and dried overnight under vacuo. The residue was purified by preparative HPLC (Method 2A). After evaporating acetonitrile from the combined product fractions the aqueous fraction was lyophilized overnight to yield the title compound (12 mg, 37% of theory).

LC-MS (Method 1B): $R_t$=0.42 min, MS (ESIPos): m/z=326 [M+H]$^+$ $^1$H-NMR (400 MHz, TFA): 8.87 (d, 1H), 8.73 (s, 1H), 8.60 (s, 1H), 7.80 (d, 1H), 6.75 (s, 1H), 4.43 (s, 3H), 4.07 (d, 2H), 4.02 (dd, 1H), 3.70 (dd, 2H), 2.72 (d, 2H), 2.50 (dd, 2H).

Example 70

7-(Piperidin-4-yl)-3-[3-(trifluoromethoxy)phenyl]pyrazolo[1,5-a]pyrimidin-5(4H)-one hydrochloride

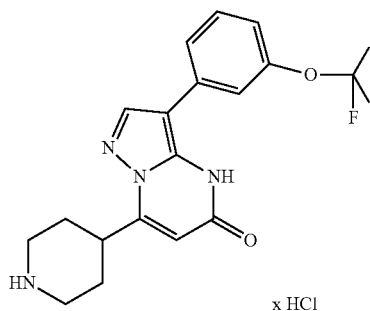

A suspension of tert-butyl 4-{5-oxo-3-[3-(trifluoromethoxy)phenyl]-4,5-dihydropyrazolo[1,5-a]pyrimidin-7-yl}piperidine-1-carboxylate (43 mg, 0.10 mmol) in methanol (1.0 ml) was treated with HCl 4N (1.0 ml). The reaction mixture was sonicated at RT for 15 minutes. The reaction mixture was evaporated and the residue was dissolved in dioxane and again evaporated to yield the title compound (37 mg, 98% of theory).

LC-MS (Method 1B): $R_t$=0.71 min, MS (ESIPos): m/z=379 [M+H-xHCl]$^+$ $^1$H-NMR (400 MHz, DMSO-d$_6$): 12.25 (s, 1H), 8.93 (br. s, 1H), 8.76 (br. s, 1H), 7.53 (t, 1H), 7.25-7.15 (m, 1H), 3.71-3.58 (m, 1H), 3.42 (d, 2H), 3.21-3.03 (m, 2H), 2.22 (d, 2H), 1.99-1.83 (m, 2H)

Example 71

7-(Piperidin-4-yl)-3-[2-(trifluoromethoxy)phenyl]pyrazolo[1,5-a]pyrimidin-5(4H)-one hydrochloride

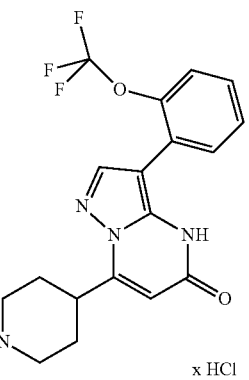

A suspension of tert-butyl 4-{5-oxo-3-[2-(trifluoromethoxy)phenyl]-4,5-dihydropyrazolo[1,5-a]pyrimidin-7-yl}piperidine-1-carboxylate (44 mg, 0.10 mmol) in methanol (1.0 ml) was treated with HCl 4N (1.0 ml). The reaction mixture was sonicated at RT for 15 minutes. The reaction mixture was evaporated and the residue was dissolved in dioxane and then the salt was filtered and dried overnight at 70° C. to yield the title compound (32 mg, 81% of theory).

LC-MS (Method 1B): $R_t$=0.65 min, MS (ESIPos): m/z=379 [M+H-xHCl]$^+$ $^1$H-NMR (400 MHz, DMSO-d$_6$): 12.08 (s, 1H), 8.90 (br. s, 1H), 8.72 (br. s, 1H), 7.99 (br. s, 1H), 7.56 (br. s, 1H), 7.45 (s, 3H), 5.88 (s, 1H), 3.45-3.37 (m, 2H), 3.18-3.02 (m, 2H), 2.30-2.16 (d, 2H), 2.00-1.77 (m, 2H).

Example 72

3-(3-Chloro-4-fluorophenyl)-7-(piperidin-4-yl)pyrazolo[1,5-a]pyrimidin-5(4H)-one hydrochloride

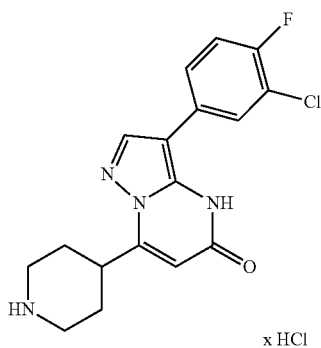 [SMILES: O=c1cc(C2CCNCC2)n2ncc(-c3ccc(F)c(Cl)c3)c2[nH]1]

A suspension of tert-butyl 4-[3-(3-chloro-4-fluorophenyl)-5-oxo-4,5-dihydropyrazolo[1,5-a]pyrimidin-7-yl]piperidine-1-carboxylate (29 mg, 0.07 mmol) in methanol (0.50 ml) was treated with HCl 4N (0.50 ml). The reaction mixture was sonicated at RT for 30 minutes. The suspension was diluted in dioxane and the solid was filtered, washed with dioxane and finally dried under vacuo at 60° C. overnight to yield the title compound (10 mg, 41% of theory).

LC-MS (Method 1B): $R_t$=0.60 min, MS (ESIPos): m/z=347 [M+H-xHCl]$^+$ $^1$H-NMR (400 MHz, D$_2$O): 7.94 (s, 1H), 7.46 (s, 1H), 7.32 (s, 1H), 7.23 (s, 1H), 6.06 (br. s, 1H), 3.75-3.60 (m, 2H), 3.60-3.44 (m, 1H), 3.38-3.17 (m, 2H), 2.47-2.25 (m, 2H), 2.05-1.78 (m, 2H).

Example 73

3-(Phenylsulfonyl)-7-(piperidin-4-yl)pyrazolo[1,5-a]pyrimidin-5(4H)-one hydrochloride

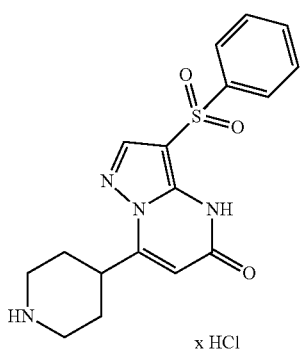 [SMILES: O=c1cc(C2CCNCC2)n2ncc(S(=O)(=O)c3ccccc3)c2[nH]1]

x HCl

Tert-butyl 4-[5-oxo-3-(phenylsulfonyl)-4,5-dihydropyrazolo[1,5-a]pyrimidin-7-yl]piperidine-1-carboxylate (0.82 g, 1.78 mmol) was dissolved in 1,4-dioxan and treated with hydrochloric acid (4 M solution in 1,4-dioxan, 4.4 mL, 17.8 mmol). The mixture was stirred at RT for 16 h. The resulting solid was filtered and washed with 1,4-dioxan and diethyl ether to afford the title compound (640 mg, 83% of theory).

LC-MS (Method 3B): $R_t$=1.36 min, MS (ESIPos): m/z=359 [M+H-xHCl]$^+$ $^1$H-NMR (400 MHz, DMSO-d$_6$): δ=12.66 (br. s, 1H), 8.90 (br. s., 1H), 8.69 (br. s., 1H), 8.39 (br. s., 1H), 8.12 (d, 1H), 7.72-7.53 (m, 4H), 6.30 (br. s, 1H), 3.37 (d, 3H), 3.07 (q, 2H), 2.14 (d, 2H), 1.95-1.77 (m, 2H)

Example 74

3-[(2,4-Dichlorophenyl)sulfonyl]-7-(piperidin-4-yl)pyrazolo[1,5-a]pyrimidin-5(4H)-one hydrochloride

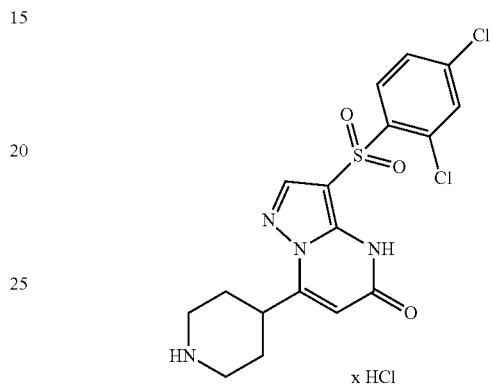

x HCl

Tert-butyl 4-{3-[(2,4-dichlorophenyl)sulfonyl]-5-oxo-4,5-dihydropyrazolo[1,5-a]pyrimidin-7-yl}piperidine-1-carboxylate (0.61 g, 1.16 mmol) was dissolved in 1,4-dioxan (12 mL) and treated with hydrochloric acid (4 M solution in 1,4-dioxan, 2.9 mL, 11.6 mmol). The mixture was stirred at RT for 16 h. The resulting solid was filtered and washed with 1,4-dioxan to afford the title compound (540 mg, 93% of theory).

LC-MS (Method 1B): $R_t$=0.62 min, MS (ESIPos): m/z=427 [M+H-xHCl]$^+$ $^1$H-NMR (500 MHz, D$_2$O): δ=8.35-8.13 (m, 2H), 7.72-7.53 (m, 2H), 6.23 (s, 1H), 3.69-3.48 (m, 3H), 3.31-3.12 (m, 2H), 2.46-2.22 (m, 2H), 2.03-1.82 (m, 2H).

TABLE 1

Examples 75-81, prepared according to General Procedure 3A

| Example | Structure | Name | Yield | LC-MS data |
|---|---|---|---|---|
| Example 75 | 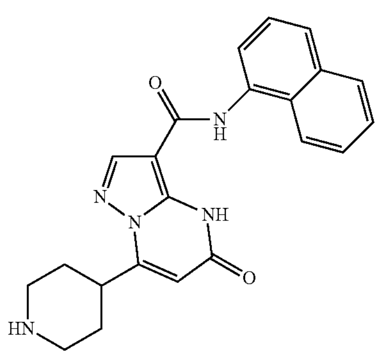 [SMILES: O=C(Nc1cccc2ccccc12)c1cnn2c(C3CCNCC3)cc(=O)[nH]c12] | N-(naphthalen-1-yl)-5-oxo-7-(piperidin-4-yl)-4,5-dihydropyrazolo[1,5-a]pyrimidine-3-carboxamide | 4.2 mg, (11% of theory) | LC-MS (Method 4B): $R_t$ = 0.65 min, MS (ESIPos): m/z = 388 [M + H]$^+$ purity: 100% |

TABLE 1-continued

Examples 75-81, prepared according to General Procedure 3A

| Example | Structure | Name | Yield | LC-MS data |
| --- | --- | --- | --- | --- |
| Example 76 | 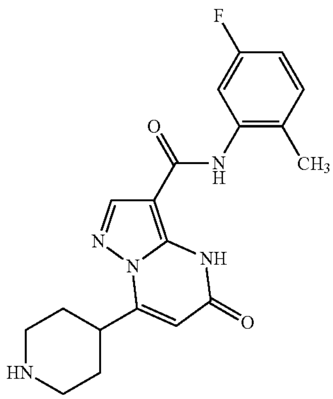 [SMILES: Cc1ccc(F)cc1NC(=O)c1cnn2c(C3CCNCC3)cc(=O)[nH]c12] | N-(5-fluoro-2-methylphenyl)-5-oxo-7-(piperidin-4-yl)-4,5-dihydropyrazolo[1,5-a]pyrimidine-3-carboxamide | 3.6 mg (8% of theory) | LC-MS (Method 4B): $R_t$ = 0.63 min, MS (ESIPos): m/z = 370 $[M + H]^+$ purity: 82% |
| Example 77 | 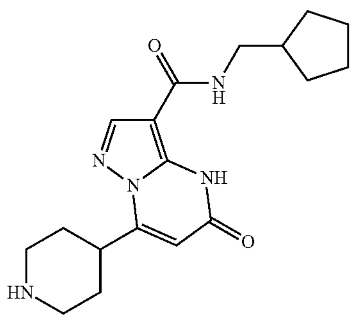 [SMILES: O=C(NCC1CCCC1)c1cnn2c(C3CCNCC3)cc(=O)[nH]c12] | N-cyclopentylmethyl)-5-oxo-7-(piperidin-4-yl)-4,5-dihydropyrazolo[1,5-a]pyrimidine-3-carboxamide | 5.6 mg (14% of theory) | LC-MS (Method 4B): $R_t$ = 0.65 min, MS (ESIPos): m/z = 344 $[M + H]^+$ purity: 86% |
| Example 78 | 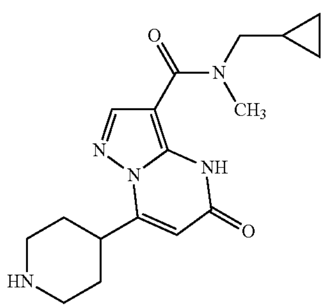 [SMILES: CN(CC1CC1)C(=O)c1cnn2c(C3CCNCC3)cc(=O)[nH]c12] | N-(cyclopropylmethyl)-N-methyl-5-oxo-7-(piperidin-4-yl)-4,5-dihydropyrazolo[1,5-a]pyrimidine-3-carboxamide | 4.4 mg (14% of theory) | LC-MS (Method 4B): $R_t$ = 0.59 min, MS (ESIPos): m/z = 330 $[M + H]^+$ purity: 100% |
| Example 79 | 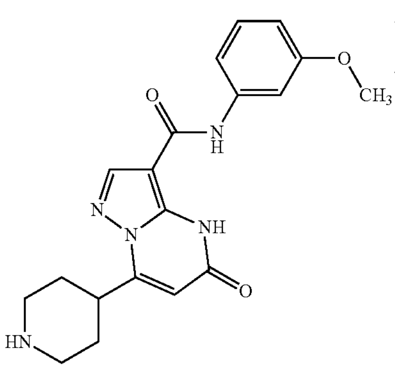 [SMILES: COc1cccc(NC(=O)c2cnn3c(C4CCNCC4)cc(=O)[nH]c23)c1] | N-(3-methoxyphenyl)-5-oxo-7-(piperidin-4-yl)-4,5-dihydropyrazolo[1,5-a]pyrimidine-3-carboxamide | 0.6 mg (1% of theory) | LC-MS (Method 4B): $R_t$ = 0.63 min, MS (ESIPos): m/z = 368 $[M + H]^+$ purity: 89% |

TABLE 1-continued

Examples 75-81, prepared according to General Procedure 3A

| Example | Structure | Name | Yield | LC-MS data |
| --- | --- | --- | --- | --- |
| Example 80 | 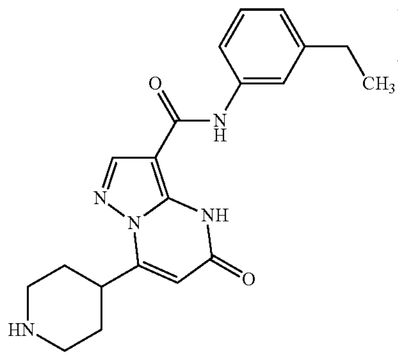 | N-(3-ethylphenyl)-5-oxo-7-(piperidin-4-yl)-4,5-dihydropyrazolo[1,5-a]pyrimidine-3-carboxamide | 1.8 mg (5% of theory) | LC-MS (Method 4B): $R_t$ = 0.69 min, MS (ESIPos): m/z = 366 $[M + H]^+$ purity: 100% |
| Example 81 | 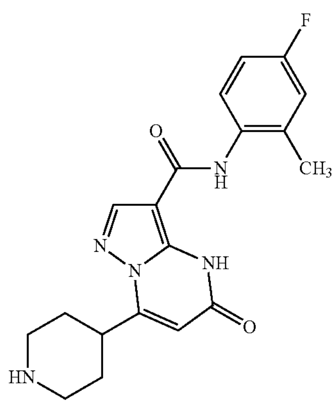 [SMILES: Cc1cc(F)ccc1NC(=O)c1cnn2c(C3CCNCC3)cc(=O)[nH]c12] | N-(4-fluoro-2-methylphenyl)-5-oxo-7-(piperidin-4-yl)-4,5-dihydropyrazolo[1,5-a]pyrimidine-3-carboxamide | 1.9 mg (5% of theory) | LC-MS (Method 4B): $R_t$ = 0.62 min, MS (ESIPos): m/z = 370 $[M + H]^+$ purity: 90% |

TABLE 2

Examples 82-104, prepared according to General Procedure 4A

| Example | Structure | Name | Yield | LC-MS data |
| --- | --- | --- | --- | --- |
| Example 82 | 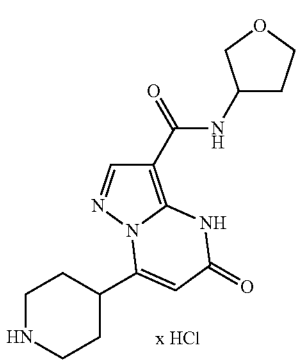 [SMILES: O=C(NC1CCOC1)c1cnn2c(C3CCNCC3)cc(=O)[nH]c12] | 5-oxo-7-(piperidin-4-yl)-N-(tetrahydrofuran-3-yl)-4,5-dihydropyrazolo[1,5-a]pyrimidine-3-carboxamide hydrochloride | 16.7 mg (36% of theory) | LC-MS (Method 4B): $R_t$ = 0.49 min, MS (ESIPos): m/z = 352 $[M + H - xHCl]^+$ purity: 78% |

TABLE 2-continued

Examples 82-104, prepared according to General Procedure 4A

| Example | Structure | Name | Yield | LC-MS data |
|---|---|---|---|---|
| Example 83 | 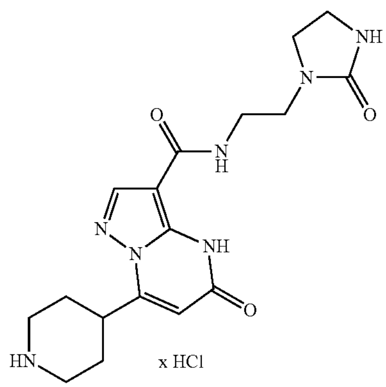 [SMILES: O=C(NCCN1CCNC1=O)c1cnn2c(C3CCNCC3)cc(=O)[nH]c12] | 5-oxo-N-[2-(2-oxoimidazolidin-1-yl)ethyl]-7-(piperidin-4-yl)-4,5-dihydropyrazolo[1,5-a]pyrimidine-3-carboxamide hydrochloride | 15.5 mg (38% of theory) | LC-MS (Method 4B): $R_t$ = 0.51 min, MS (ESIPos): m/z = 332 [M + H − xHCl]$^+$ purity: 100% |
| Example 84 | 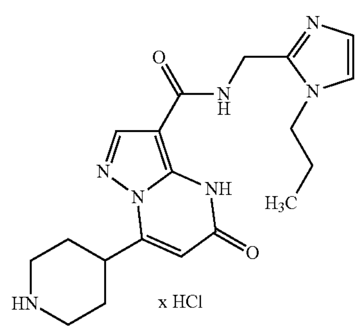 | 5-oxo-7-(piperidin-4-yl)-N-[(1-propyl-1H-imidazol-2-yl)methyl]-4,5-dihydropyrazolo[1,5-a]pyrimidine-3-carboxamide hydrochloride | 23.8 mg (57% of theory) | LC-MS (Method 4B): $R_t$ = 0.50 min, MS (ESIPos): m/z = 374 [M + H − xHCl]$^+$ purity: 100% |
| Example 85 | 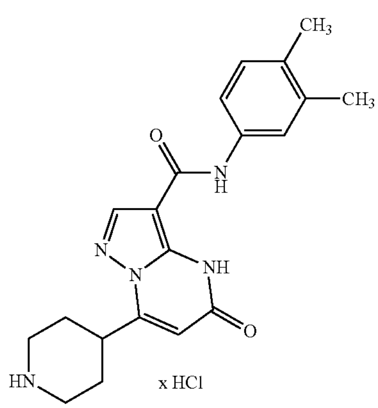 [SMILES: Cc1ccc(NC(=O)c2cnn3c(C4CCNCC4)cc(=O)[nH]c23)cc1C] | N-(3,4-dimethylphenyl)-5-oxo-7-(piperidin-4-yl)-4,5-dihydropyrazolo[1,5-a]pyrimidine-3-carboxamide hydrochloride | 3.0 mg (7% of theory) | LC-MS (Method 4B): $R_t$ = 0.68 min, MS (ESIPos): m/z = 366 [M + H − xHCl]$^+$ purity: 100% |
| Example 86 | 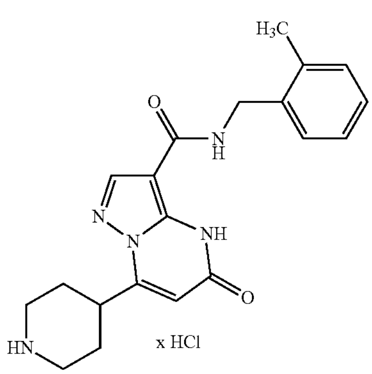 [SMILES: Cc1ccccc1CNC(=O)c1cnn2c(C3CCNCC3)cc(=O)[nH]c12] | N-(2-methylbenzyl)-5-oxo-7-(piperidin-4-yl)-4,5-dihydropyrazolo[1,5-a]pyrimidine-3-carboxamide hydrochloride | 5.6 mg (13% of theory) | LC-MS (Method 4B): $R_t$ = 0.64 min, MS (ESIPos): m/z = 366 [M + H − xHCl]$^+$ purity: 91% |

TABLE 2-continued

Examples 82-104, prepared according to General Procedure 4A

| Example | Structure | Name | Yield | LC-MS data |
| --- | --- | --- | --- | --- |
| Example 87 | 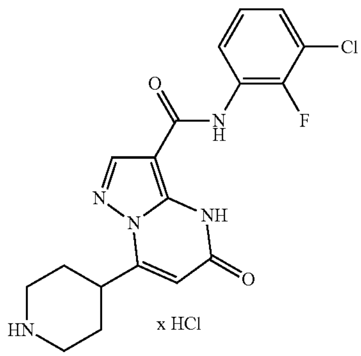 [SMILES: O=C(Nc1cccc(Cl)c1F)c1cnn2c(C3CCNCC3)cc(=O)[nH]c12] | N-(3-chloro-2-fluorophenyl)-5-oxo-7-(piperidin-4-yl)-4,5-dihydropyrazolo[1,5-a]pyrimidine-3-carboxamide hydrochloride | 9.3 mg (22% of theory) | LC-MS (Method 4B): $R_t$ = 0.66 min, MS (ESIPos): m/z = 390 [M + H − xHCl]$^+$ purity: 100% |
| Example 88 | 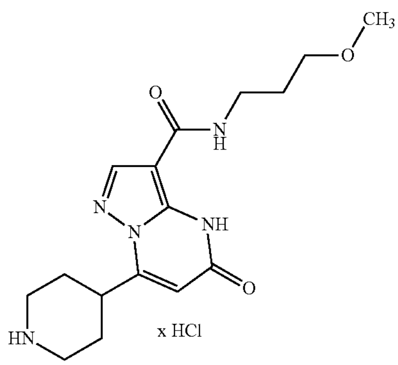 [SMILES: COCCCNC(=O)c1cnn2c(C3CCNCC3)cc(=O)[nH]c12] | N-(3-methoxypropyl)-5-oxo-7-(piperidin-4-yl)-4,5-dihydropyrazolo[1,5-a]pyrimidine-3-carboxamide hydrochloride | 11.1 mg (26% of theory) | LC-MS (Method 4B): $R_t$ = 0.53 min, MS (ESIPos): m/z = 334 [M + H − xHCl]$^+$ purity: 87% |
| Example 89 | 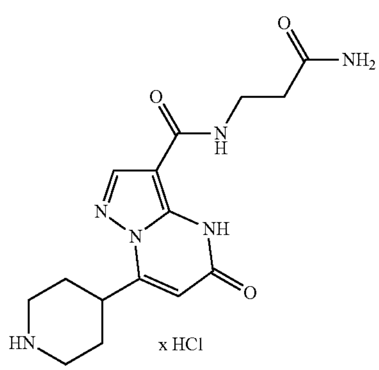 [SMILES: NC(=O)CCNC(=O)c1cnn2c(C3CCNCC3)cc(=O)[nH]c12] | N-(3-amino-3-oxopropyl)-5-oxo-7-(piperidin-4-yl)-4,5-dihydropyrazolo[1,5-a]pyrimidine-3-carboxamide hydrochloride | 7.9 mg (19% of theory) | LC-MS (Method 4B): $R_t$ = 0.48 min, MS (ESIPos): m/z = 333 [M + H − xHCl]$^+$ purity: 90% |
| Example 90 | 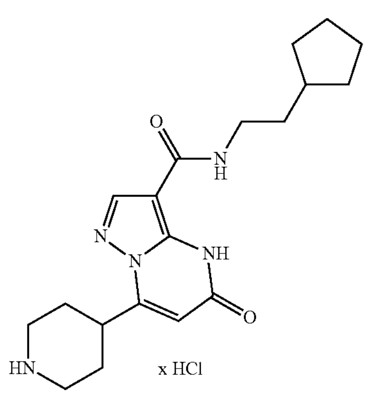 [SMILES: O=C(NCCC1CCCC1)c1cnn2c(C3CCNCC3)cc(=O)[nH]c12] | N-(2-cyclopentylethyl)-5-oxo-7-(piperidin-4-yl)-4,5-dihydropyrazolo[1,5-a]pyrimidine-3-carboxamide hydrochloride | 4.8 mg (11% of theory) | LC-MS (Method 4B): $R_t$ = 0.68 min, MS (ESIPos): m/z = 357 [M + H − xHCl]$^+$ purity: 94% |

TABLE 2-continued

Examples 82-104, prepared according to General Procedure 4A

| Example | Structure | Name | Yield | LC-MS data |
|---|---|---|---|---|
| Example 91 | 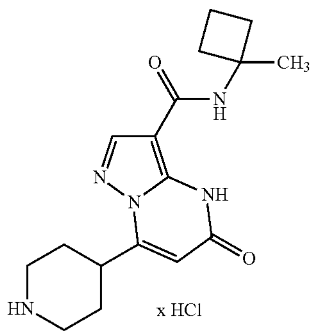 [SMILES: CC1(NC(=O)c2cnn3c(C4CCNCC4)cc(=O)[nH]c23)CCC1] | N-(1-methylcyclobutyl)-5-oxo-7-(piperidin-4-yl)-4,5-dihydropyrazolo[1,5-a]pyrimidine-3-carboxamide hydrochloride | 6.2 mg (14% of theory) | LC-MS (Method 4B): $R_t$ = 0.59 min, MS (ESIPos): m/z = 330 [M + H − xHCl]$^+$ purity: 83% |
| Example 92 | 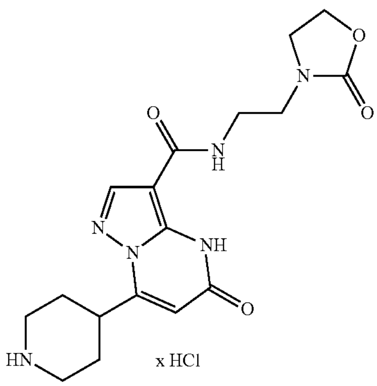 [SMILES: O=C(NCCN1CCOC1=O)c1cnn2c(C3CCNCC3)cc(=O)[nH]c12] | 5-oxo-N-[2-(2-oxo-1,3-oxazolidin-3-yl)ethyl]-7-(piperidin-4-yl)-4,5-dihydropyrazolo[1,5-a]pyrimidine-3-carboxamide hydrochloride | 11.2 mg (26% of theory) | LC-MS (Method 4B): $R_t$ = 0.50 min, MS (ESIPos): m/z = 375 [M + H − xHCl]$^+$ purity: 95% |
| Example 93 | 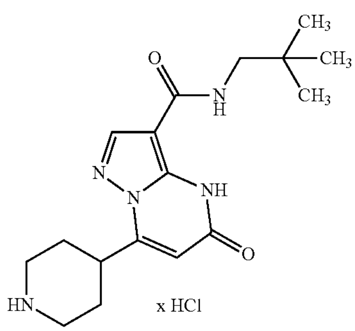 [SMILES: CC(C)(C)CNC(=O)c1cnn2c(C3CCNCC3)cc(=O)[nH]c12] | N-(2,2-dimethylpropyl)-5-oxo-7-(piperidin-4-yl)-4,5-dihydropyrazolo[1,5-a]pyrimidine-3-carboxamide hydrochloride | 8.6 mg (20% of theory) | LC-MS (Method 4B): $R_t$ = 0.61 min, MS (ESIPos): m/z = 332 [M + H − xHCl]$^+$ purity: 88% |
| Example 94 | 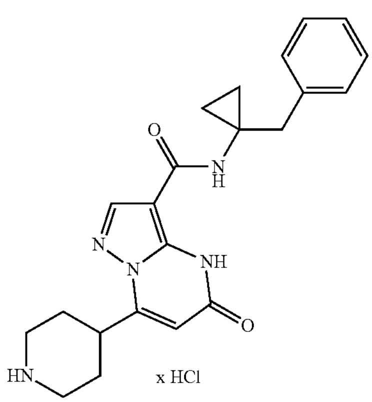 [SMILES: O=C(NC1(Cc2ccccc2)CC1)c1cnn2c(C3CCNCC3)cc(=O)[nH]c12] | N-(1-benzylcyclopropyl)-5-oxo-7-(piperidin-4-yl)-4,5-dihydropyrazolo[1,5-a]pyrimidine-3-carboxamide hydrochloride | 11.9 mg (26% of theory) | LC-MS (Method 4B): $R_t$ = 0.65 min, MS (ESIPos): m/z = 392 [M + H − xHCl]$^+$ purity: 94% |

TABLE 2-continued

Examples 82-104, prepared according to General Procedure 4A

| Example | Structure | Name | Yield | LC-MS data |
|---|---|---|---|---|
| Example 95 | 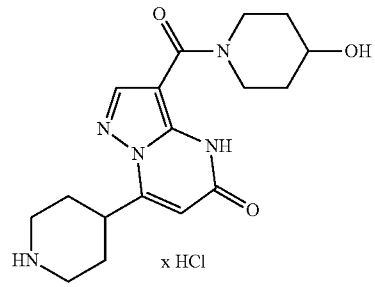 [SMILES: O=C(c1cnn2c(C3CCNCC3)cc(=O)[nH]c12)N1CCC(O)CC1] | 3-[(4-hydroxypiperidin-1-yl)carbonyl]-7-(piperidin-4-yl)pyrazolo[1,5-a]pyrimidin-5(4H)-one hydrochloride | 6.4 mg (15% of theory) | LC-MS (Method 4B): $R_t$ = 0.49 min, MS (ESIPos): m/z = 346 [M + H − xHCl]$^+$ purity: 87% |
| Example 96 | 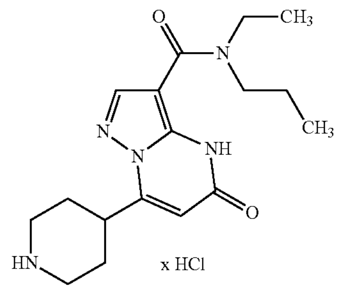 [SMILES: CCCN(CC)C(=O)c1cnn2c(C3CCNCC3)cc(=O)[nH]c12] | N-ethyl-5-oxo-7-(piperidin-4-yl)-N-propyl-4,5-dihydropyrazolo[1,5-a]pyrimidine-3-carboxamide hydrochloride | 12.1 mg (27% of theory) | LC-MS (Method 4B): $R_t$ = 0.60 min, MS (ESIPos): m/z = 332 [M + H − xHCl]$^+$ purity: 83% |
| Example 97 | 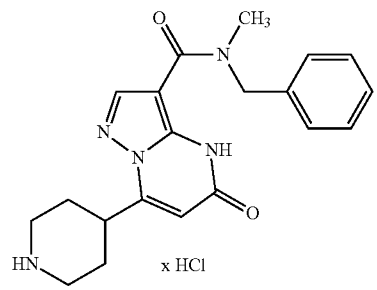 [SMILES: CN(Cc1ccccc1)C(=O)c1cnn2c(C3CCNCC3)cc(=O)[nH]c12] | N-benzyl-N-methyl-5-oxo-7-(piperidin-4-yl)-4,5-dihydropyrazolo[1,5-a]pyrimidine-3-carboxamide hydrochloride | 4.6 mg (11% of theory) | LC-MS (Method 4B): $R_t$ = 0.63 min, MS (ESIPos): m/z = 366 [M + H − xHCl]$^+$ purity: 97% |
| Example 98 | 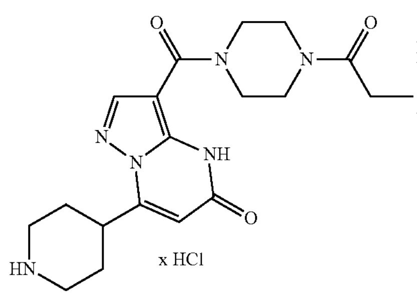 [SMILES: CCC(=O)N1CCN(C(=O)c2cnn3c(C4CCNCC4)cc(=O)[nH]c23)CC1] | 7-(piperidin-4-yl)-3-[(4-propanoylpiperazin-1-yl)carbonyl]pyrazolo[1,5-a]pyrimidin-5(4H)-one hydrochloride | 10.5 mg (22% of theory) | LC-MS (Method 4B): $R_t$ = 0.53 min, MS (ESIPos): m/z = 387 [M + H − xHCl]$^+$ purity: 88% |
| Example 99 | 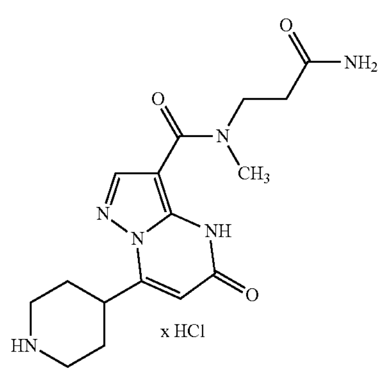 [SMILES: CN(CCC(N)=O)C(=O)c1cnn2c(C3CCNCC3)cc(=O)[nH]c12] | N-(3-amino-3-oxopropyl)-N-methyl-5-oxo-7-(piperidin-4-yl)-4,5-dihydropyrazolo[1,5-a]pyrimidine-3-carboxamide hydrochloride | 4.4 mg (9% of theory) | LC-MS (Method 4B): $R_t$ = 0.49 min, MS (ESIPos): m/z = 347 [M + H − xHCl]$^+$ purity: 82% |

TABLE 2-continued

Examples 82-104, prepared according to General Procedure 4A

| Example | Structure | Name | Yield | LC-MS data |
|---|---|---|---|---|
| Example 100 | 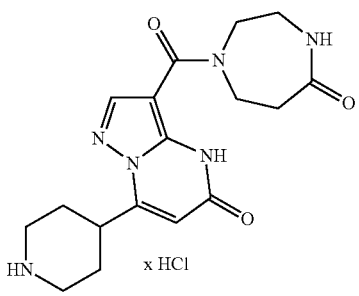 [SMILES: O=C1CCN(C(=O)c2cnn3c(C4CCNCC4)cc(=O)[nH]c23)CCN1] | 3-[(5-oxo-1,4-diazepan-1-yl)carbonyl]-7-(piperidin-4-yl)pyrazolo[1,5-a]pyrimidin-5(4H)-one hydrochloride | 5.5 mg (13% of theory) | LC-MS (Method 4B): $R_t$ = 0.48 min, MS (ESIPos): m/z = 359 [M + H − xHCl]$^+$ purity: 97% |
| Example 101 | 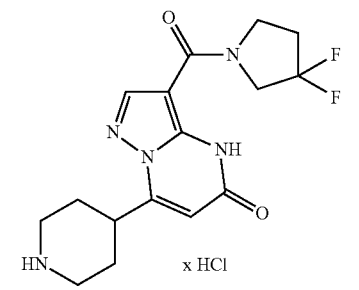 [SMILES: O=C(c1cnn2c(C3CCNCC3)cc(=O)[nH]c12)N1CCC(F)(F)C1] | 3-[(3,3-difluoropyrrolidin-1-yl)carbonyl]-7-(piperidin-4-yl)pyrazolo[1,5-a]pyrimidin-5(4H)-one hydrochloride | 1.8 mg (5% of theory) | LC-MS (Method 4B): $R_t$ = 0.56 min, MS (ESIPos): m/z = 352 [M + H − xHCl]$^+$ purity: 100% |
| Example 102 | 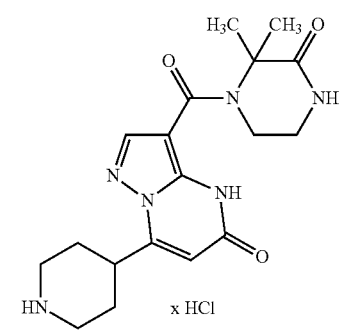 [SMILES: CC1(C)C(=O)NCCN1C(=O)c1cnn2c(C3CCNCC3)cc(=O)[nH]c12] | 3-[(2,2-dimethyl-3-oxopiperazin-1-yl)carbonyl]-7-(piperidin-4-yl)pyrazolo[1,5-a]pyrimidin-5(4H)-one hydrochloride | 0.9 mg (2% of theory) | LC-MS (Method 4B): $R_t$ = 0.31 min, MS (ESIPos): m/z = 373 [M + H − xHCl]$^+$ purity: 100% |
| Example 103 | 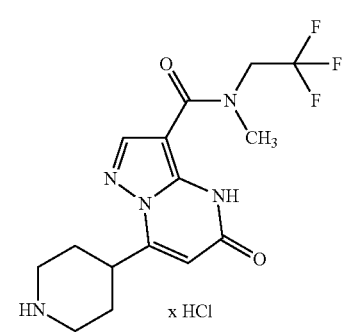 [SMILES: CN(CC(F)(F)F)C(=O)c1cnn2c(C3CCNCC3)cc(=O)[nH]c12] | N-methyl-5-oxo-7-(piperidin-4-yl)-N-(2,2,2-trifluoroethyl)-4,5-dihydropyrazolo[1,5-a]pyrimidine-3-carboxamide hydrochloride | 4.2 mg (10% of theory) | LC-MS (Method 4B): $R_t$ = 0.57 min, MS (ESIPos): m/z = 358 [M + H − xHCl]$^+$ purity: 96% |

TABLE 2-continued

Examples 82-104, prepared according to General Procedure 4A

| Example | Structure | Name | Yield | LC-MS data |
| --- | --- | --- | --- | --- |
| Example 104 | 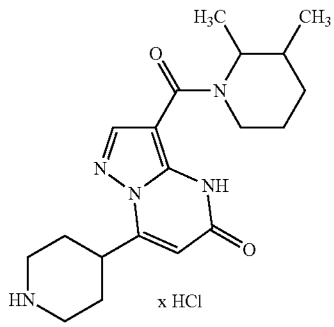 [SMILES: CC1CCCN(C(=O)c2cnn3c(C4CCNCC4)cc(=O)[nH]c23)C1C] | 3-[(2,3-dimethylpiperidin-1-yl)carbonyl]-7-(piperidin-4-yl)pyrazolo[1,5-a]pyrimidin-5(4H)-one hydrochloride | 2.2 mg (5% of theory) | LC-MS (Method 4B): $R_t$ = 0.63 min, MS (ESIPos): m/z = 358 [M + H − xHCl]$^+$ purity: 94% |

TABLE 3

Examples 105-110, prepared according to General Procedure 5A

| Example | Structure | Name | yield | LC-MS data |
| --- | --- | --- | --- | --- |
| Example 105 | 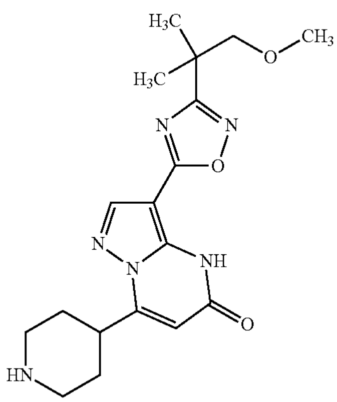 [SMILES: COCC(C)(C)c1noc(-c2cnn3c(C4CCNCC4)cc(=O)[nH]c23)n1] | 3-[3-(1-methoxy-2-methylpropan-2-yl)-1,2,4-oxadiazol-5-yl]-7-(piperidin-4-yl)pyrazolo[1,5-a]pyrimidin-5(4H)-one | 8.1 mg (22% of theory) | LC-MS (Method 4B): $R_t$ = 0.62 min, MS (ESIPos): m/z = 373 [M + H]$^+$ purity: 100% |
| Example 106 | 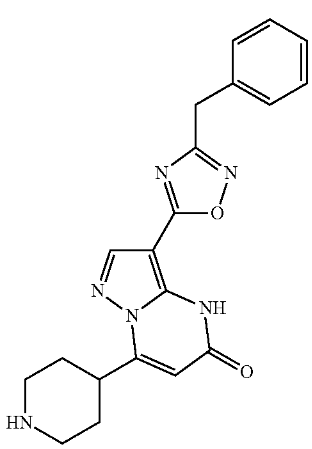 [SMILES: O=c1cc(C2CCNCC2)n2ncc(-c3nc(Cc4ccccc4)no3)c2[nH]1] | 3-(3-benzyl-1,2,4-oxadiazol-5-yl)-7-(piperidin-4-yl)pyrazolo[1,5-a]pyrimidin-5(4H)-one | 2.0 mg (5% of theory) | LC-MS (Method 4B): $R_t$ = 0.67 min, MS (ESIPos): m/z = 377 [M + H]$^+$ purity: 91% |

TABLE 3-continued

Examples 105-110, prepared according to General Procedure 5A

| Example | Structure | Name | yield | LC-MS data |
| --- | --- | --- | --- | --- |
| Example 107 | 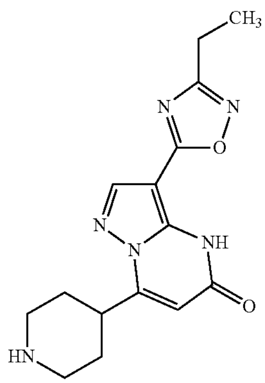 [SMILES: CCc1noc(-c2cnn3c(C4CCNCC4)cc(=O)[nH]c23)n1] | 3-(3-ethyl-1,2,4-oxadiazol-5-yl)-7-(piperidin-4-yl)pyrazolo[1,5-a]pyrimidin-5(4H)-one | 2.6 mg (8% of theory) | LC-MS (Method 4B): $R_t$ = 0.57 min, MS (ESIPos): m/z = 315 [M + H]$^+$ purity: 100% |
| Example 108 | 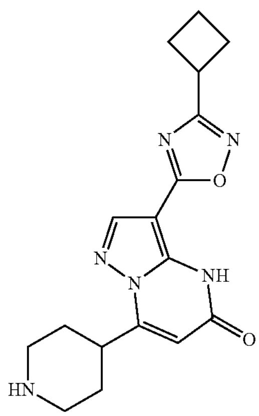 [SMILES: O=c1cc(C2CCNCC2)n2ncc(-c3nc(C4CCC4)no3)c2[nH]1] | 3-(3-cyclobutyl-1,2,4-oxadiazol-5-yl)-7-(piperidin-4-yl)pyrazolo[1,5-a]pyrimidin-5(4H)-one | 5.4 mg (14% of theory) | LC-MS (Method 4B): $R_t$ = 0.63 min, MS (ESIPos): m/z = 341 [M + H]$^+$ purity: 90% |
| Example 109 | 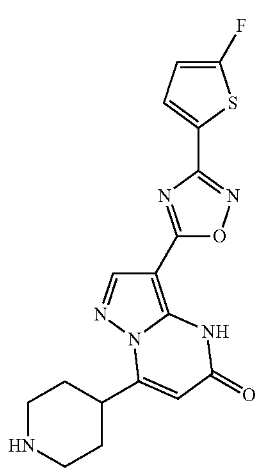 [SMILES: O=c1cc(C2CCNCC2)n2ncc(-c3nc(-c4ccc(F)s4)no3)c2[nH]1] | 3-[3-(5-fluorothiophen-2-yl)-1,2,4-oxadiazol-5-yl]-7-(piperidin-4-yl)pyrazolo[1,5-a]pyrimidin-5(4H)-one | 2.4 mg (6% of theory) | LC-MS (Method 4B): $R_t$ = 0.70 min, MS (ESIPos): m/z = 387 [M + H]$^+$ purity: 100% |

TABLE 3-continued

Examples 105-110, prepared according to General Procedure 5A

| Example | Structure | Name | yield | LC-MS data |
|---|---|---|---|---|
| Example 110 | 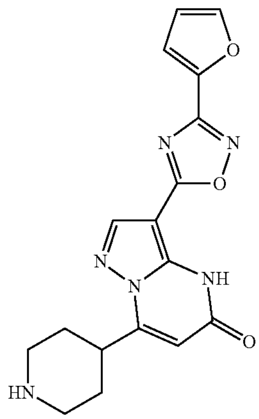 [SMILES: O=c1cc(C2CCNCC2)n2ncc(-c3nc(-c4ccco4)no3)c2[nH]1] | 3-[3-(furan-2-yl)-1,2,4-oxadiazol-5-yl]-7-(piperidin-4-yl)pyrazolo[1,5-a]pyrimidin-5(4H)-one | 3.2 mg (9% of theory) | LC-MS (Method 4B): $R_t$ = 0.63 min, MS (ESIPos): m/z = 353 [M + H]$^+$ purity: 94% |

Example 111

7-(Piperidin-4-yl)-3-{3-[3-(trifluoromethyl)phenyl]-1,2,4-oxadiazol-5-yl}pyrazolo[1,5-a]pyrimidin-5(4H)-one hydrochloride

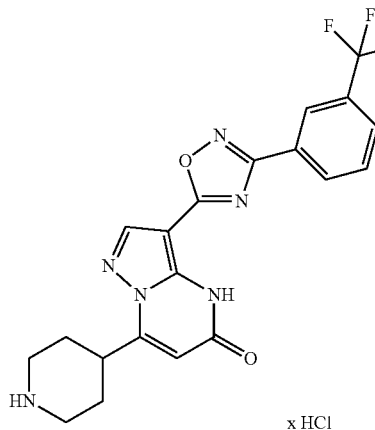

x HCl

A suspension of tert-butyl 4-(5-oxo-3-{3-[3-(trifluoromethyl)phenyl]-1,2,4-oxadiazol-5-yl}-4,5-dihydropyrazolo[1,5-a]pyrimidin-7-yl)piperidine-1-carboxylate (55 mg, 0.10 mmol) in methanol (0.5 ml) was treated with HCl 4N in dioxane (0.5 ml). The reaction mixture was stirred 30 minutes at 40° C. The mixture was diluted in 2 ml dioxane and the solid was filtered, washed with dioxane and dried under vacuum for 16 h to yield the title compound (47 mg, 96% of theory).

LC-MS (method 1B): RT=0.76 min, m/z=431 (M+H-HCl)$^+$ $^1$H-NMR (400 MHz, MeOD): δ 8.53 (bs, 1H), 8.51 (s, 1H), 8.48 (d, 1H), 7.92 (d, 1H), 7.80 (dd, 1H), 6.21 (s, 1H), 3.74 (dd, 1H), 3.61 (d, 2H), 3.28 (dd, 2H), 2.46 (d, 2H), 2.05 (dd, 2H).

Example 112

3-[3-(3-Fluorophenyl)-1,2,4-oxadiazol-5-yl]-7-(piperidin-4-yl)pyrazolo[1,5-a]pyrimidin-5 (4H)-one hydrochloride

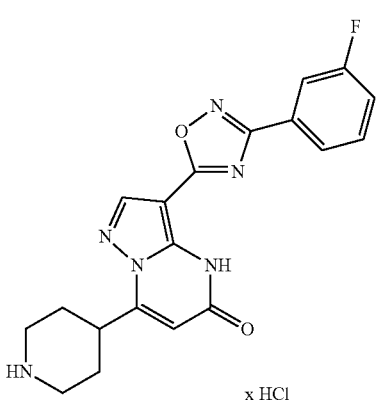 [SMILES: O=c1cc(C2CCNCC2)n2ncc(-c3nc(-c4cccc(F)c4)no3)c2[nH]1]

x HCl

A suspension of tert-butyl 4-{3-[3-(3-fluorophenyl)-1,2,4-oxadiazol-5-yl]-5-oxo-4,5-dihydropyrazolo[1,5-a]pyrimidin-7-yl}piperidine-1-carboxylate (82 mg, 0.17 mmol) in methanol (0.8 ml) was treated with HCl 4N in dioxane (0.8 ml). The reaction mixture was stirred 30 minutes at 40° C. The mixture was diluted in 2 ml dioxane and the solid was filtered, washed with dioxane and dried under vacuum for 16 h to yield the title compound (70 mg, 99% of theory).

LC-MS (method 1B): RT=0.67 min, m/z=381 (M+H-HCl)$^+$ $^1$H-NMR (400 MHz, MeOD): δ 7.18 (s, 1H), 6.73 (d, 1H), 6.65 (d, 1H), 6.28 (dd, 1H), 6.04 (dd, 1H), 4.89 (s, 1H), 2.42 (dd, 1H), 2.30 (d, 2H), 1.97 (dd, 2H), 1.14 (d, 2H), 0.73 (dd, 2H).

Example 113

7-(Piperidin-4-yl)-3-{3-[4-(trifluoromethyl)phenyl]-1,2,4-oxadiazol-5-yl}pyrazolo[1,5-a]pyrimidin-5(4H)-one hydrochloride

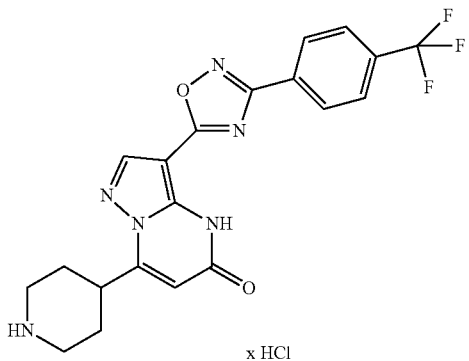 [SMILES: O=c1cc(C2CCNCC2)n2ncc(-c3nc(-c4ccc(C(F)(F)F)cc4)no3)c2[nH]1]

x HCl

A suspension of compound tert-butyl 4-(5-oxo-3-{3-[4-(trifluoromethyl)phenyl]-1,2,4-oxadiazol-5-yl}-4,5-dihydropyrazolo[1,5-a]pyrimidin-7-yl)piperidine-1-carboxylate (258 mg, 0.49 mmol) in methanol (2.4 ml) was treated with HCl 4N in dioxane (2.4 ml). The reaction mixture was stirred 30 minutes at 40° C. The mixture was diluted in 2 ml dioxane and the solid was filtered, washed with dioxane and dried under vacuum for 16 h to yield the title compound (189 mg, 83% of theory).

LC-MS (method 1B): RT=0.76 min, m/z=431 (M+H-HCl)+

$^1$H-NMR (400 MHz, MeOD): δ 8.38 (s, 1H), 8.30 (d, 2H), 7.78 (d, 2H), 6.09 (s, 1H), 3.62 (dd, 1H), 3.48 (d, 2H), 3.18 (dd, 2H), 2.33 (d, 2H), 1.93 (dd, 2H)

Example 114

3-[3-(4-Benzylphenyl)-1,2,4-oxadiazol-5-yl]-7-(piperidin-4-yl)pyrazolo[1,5-a]pyrimidin-5(4H)-one hydrochloride

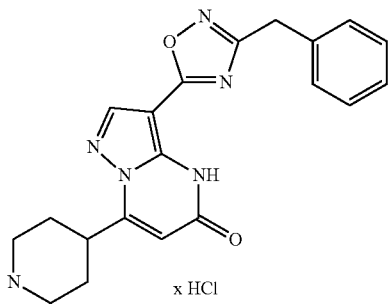 [SMILES: O=c1cc(C2CCNCC2)n2ncc(-c3nc(Cc4ccccc4)no3)c2[nH]1]

x HCl

A suspension of tert-butyl 4-{3-[3-(4-benzylphenyl)-1,2,4-oxadiazol-5-yl]-5-oxo-4,5-dihydropyrazolo[1,5-a]pyrimidin-7-yl}piperidine-1-carboxylate (14 mg, 0.03 mmol) in methanol (0.14 ml) was treated with HCl 4N in dioxane (0.14 ml). The reaction mixture was stirred 30 minutes at room temperature. The mixture was diluted in 2 ml dioxane and the resulting solid was filtered, washed with dioxane and dried under vacuum for 16 h to yield the title compound (9 mg, 73% of theory).

LC-MS (method 1B): RT=0.61 min, m/z=377 (M+H-HCl)+

Example 115

7-(Piperidin-4-yl)-3-{3-[4-(trifluoromethoxy)phenyl]-1,2,4-oxadiazol-5-yl}pyrazolo[1,5-a]pyrimidin-5(4H)-one hydrochloride

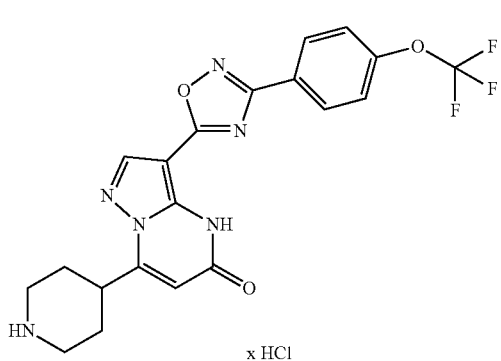 [SMILES: O=c1cc(C2CCNCC2)n2ncc(-c3nc(-c4ccc(OC(F)(F)F)cc4)no3)c2[nH]1]

x HCl

A suspension of tert-butyl 4-(5-oxo-3-{3-[4-(trifluoromethoxy)phenyl]-1,2,4-oxadiazol-5-yl}-4,5-dihydropyrazolo[1,5-a]pyrimidin-7-yl)piperidine-1-carboxylate (104 mg, 0.20 mmol) in methanol (0.9 ml) was treated with HCl 4N in dioxane (1.0 ml). The reaction mixture was stirred 30 minutes at 40° C. The mixture was diluted in 2 ml dioxane and the solid was filtered, washed with dioxane and dried under vacuum for 16 h to yield the title compound (73 mg, 79% of theory).

LC-MS (method 1B): RT=0.77 min, m/z=447 (M+H-HCl)+

$^1$H-NMR (400 MHz, MeOD): δ 8.36 (s, 1H), 8.21 (d, 2H), 7.38 (d, 2H), 6.08 (s, 1H), 3.61 (dd, 1H), 3.48 (d, 2H), 3.15 (dd, 2H), 2.32 (d, 2H), 1.93 (dd, 2H)

Example 116

3-[3-(3-Methoxy-4-methylphenyl)-1,2,4-oxadiazol-5-yl]-7-(piperidin-4-yl)pyrazolo[1,5-a]pyrimidin-5(4H)-one hydrochloride

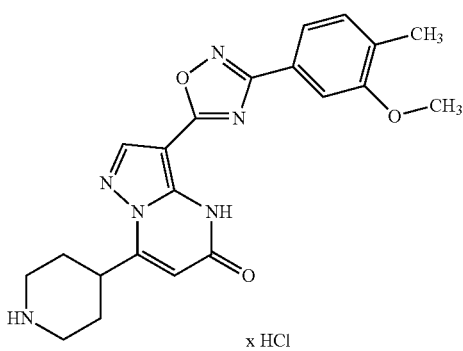 [SMILES: COc1cc(-c2noc(-c3cnn4c(C5CCNCC5)cc(=O)[nH]c34)n2)ccc1C]

x HCl

A suspension of tert-butyl 4-{3-[3-(3-methoxy-4-methylphenyl)-1,2,4-oxadiazol-5-yl]-5-oxo-4,5-dihydropyrazolo[1,5-a]pyrimidin-7-yl}piperidine-1-carboxylate (21 mg, 0.04 mmol) in methanol (0.20 ml) was treated with HCl 4N in dioxane (0.20 ml). The reaction mixture was stirred 30 minutes at 40° C. The mixture was diluted in 2 ml dioxane and the solid was filtered, washed with dioxane and dried under vacuum for 16 h. Finally the product was stirred in methanol and filtered to yield the title compound (10 mg, 50% of theory).

LC-MS (method 1B): RT=0.74 min, m/z=407 (M+H-HCl)+

$^1$H-NMR (400 MHz, MeOD): δ 8.36 (s, 1H), 8.08 (d, 1H), 7.58 (s, 1H), 7.20 (s, 1H), 6.07 (s, 1H), 3.66-3.63 (m, 1H), 3.56 (s, 3H), 3.48 (d, 2H), 2.34 (d, 2H), 2.17 (s, 2H), 1.93 (2H), 1.19 (s, 3H)

Example 117

3-[3-(3-Fluoro-4-methylphenyl)-1,2,4-oxadiazol-5-yl]-7-(piperidin-4-yl)pyrazolo[1,5-a]pyrimidin-5(4H)-one hydrochloride

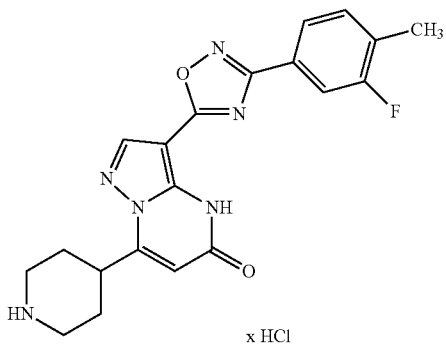 [SMILES: Cc1ccc(-c2noc(-c3cnn4c(C5CCNCC5)cc(=O)[nH]c34)n2)cc1F]

A suspension of tert-butyl 4-{3-[3-(3-fluoro-4-methylphenyl)-1,2,4-oxadiazol-5-yl]-5-oxo-4,5-dihydropyrazolo[1,5-a]pyrimidin-7-yl}piperidine-1-carboxylate (74 mg, 0.15 mmol) in methanol (0.7 ml) was treated with HCl 4N in dioxane (0.7 ml). The reaction mixture was stirred 30 minutes at 40° C. The mixture was diluted in 2 ml dioxane and the solid was filtered, washed with dioxane and dried under vacuum for 16 h to yield the title compound (62 mg, 95% of theory).

LC-MS (method 1B): RT=0.72 min, m/z=395 (M+H-HCl)+

$^1$H-NMR (400 MHz, MeOD): δ 8.36 (s, 1H), 7.79 (d, 1H), 7.75 (d, 1H), 7.33 (dd, 1H), 6.08 (s, 1H), 3.65 (dd, 1H), 3.48 (d, 2H), 3.15 (dd, 2H), 2.32 (d, 2H), 1.92 (dd, 2H), 1.19 (s, 3H)

Example 118

3-{3-[4-Methyl-3-(trifluoromethyl)phenyl]-1,2,4-oxadiazol-5-yl}-7-(piperidin-4-yl)pyrazolo[1,5-a]pyrimidin-5(4H)-one hydrochloride

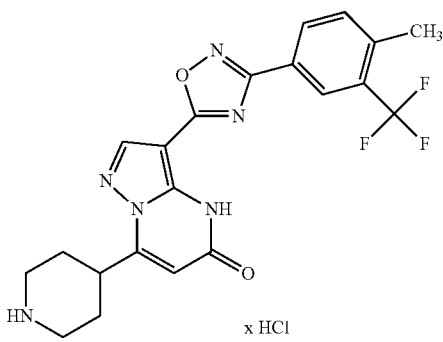 [SMILES: Cc1ccc(-c2noc(-c3cnn4c(C5CCNCC5)cc(=O)[nH]c34)n2)cc1C(F)(F)F]

A suspension of tert-butyl 4-(3-{3-[4-methyl-3-(trifluoromethyl)phenyl]-1,2,4-oxadiazol-5-yl}-5-oxo-4,5-dihydropyrazolo[1,5-a]pyrimidin-7-yl)piperidine-1-carboxylate (110 mg, 0.20 mmol) in methanol (0.9 ml) was treated with HCl 4N in dioxane (1.0 ml). The reaction mixture was stirred 30 minutes at 40° C. The mixture was diluted in 2 ml dioxane and the solid was filtered, washed with dioxane and dried under vacuum for 16 h to yield the title compound (85 mg, 88% of theory).

LC-MS (method 1B): RT=0.78 min, m/z=446 (M+H-HCl)+

$^1$H-NMR (400 MHz, MeOD): δ 8.49 (s, 1H), 8.46 (s, 1H), 8.32 (d, 1H), 7.61 (d, 1H), 6.20 (s, 1H), 3.73 (dd, 1H), 3.60 (d, 2H), 3.28 (dd, 2H), 2.60 (s, 3H), 2.45 (d, 2H), 2.05 (dd, 2H)

Example 119

3-[3-(2-Methylphenyl)-1,2,4-oxadiazol-5-yl]-7-(piperidin-4-yl)pyrazolo[1,5-a]pyrimidin-5 (4H)-one hydrochloride

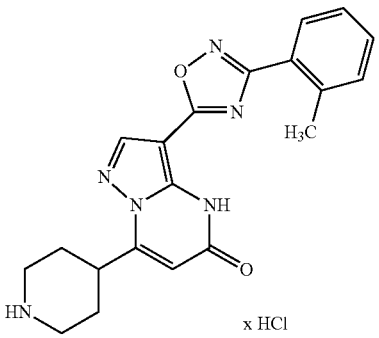 [SMILES: Cc1ccccc1-c1noc(-c2cnn3c(C4CCNCC4)cc(=O)[nH]c23)n1]

A suspension of tert-butyl 4-{3-[3-(2-methylphenyl)-1,2,4-oxadiazol-5-yl]-5-oxo-4,5-dihydropyrazolo[1,5-a]pyrimidin-7-yl}piperidine-1-carboxylate (94 mg, 0.20 mmol) in methanol (1.0 ml) was treated with HCl 4N in dioxane (1.0 ml). The reaction mixture was stirred 30 minutes at room temperature. The mixture was diluted in 2 ml dioxane and the solid was filtered, washed with dioxane and dried under vacuum for 16 h to yield the title compound (85 mg, 97% of theory).

LC-MS (method 1B): RT=0.69 min, m/z=377 (M+H-HCl)$^+$ $^1$H-NMR (400 MHz, DMSO-d$_6$): δ 8.75 (bs, 1H), 8.61 (bs, 1H), 8.50 (bs, 1H), 8.20 (bs, 1H), 7.49 (dd, 2H), 7.42 (d, 2H), 6.21 (bs, 1H), 3.68-3.57 (m, 1H), 3.43 (d, 2H), 3.13 (dd, 2H), 2.61 (s, 3H), 2.23 (d, 2H), 1.90 (dd, 2H)

Example 120

3-[3-(3-Methylphenyl)-1,2,4-oxadiazol-5-yl]-7-(piperidin-4-yl)pyrazolo[1,5-a]pyrimidin-5 (4H)-one hydrochloride

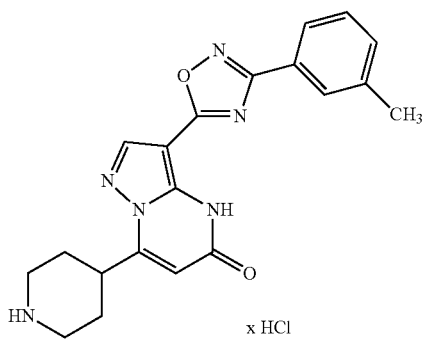 [SMILES: Cc1cccc(-c2noc(-c3cnn4c(C5CCNCC5)cc(=O)[nH]c34)n2)c1]

A suspension of tert-butyl 4-{3-[3-(3-methylphenyl)-1,2,4-oxadiazol-5-yl]-5-oxo-4,5-dihydropyrazolo[1,5-a]pyrimidin-7-yl}piperidine-1-carboxylate (54 mg, 0.11 mmol) in methanol (0.5 ml) was treated with HCl 4N in dioxane (0.5 ml). The reaction mixture was stirred 30 minutes at room temperature. The mixture was diluted in 2 ml dioxane and the solid was filtered, washed with dioxane and dried under vacuum to yield the title compound (43 mg, 88% of theory).

LC-MS (method 1B): RT=0.70 min, m/z=377 (M+H-HCl)$^+$ $^1$H-NMR (400 MHz, DMSO-d$_6$): δ 8.84 (bs, 1H), 8.63 (bs, 1H), 7.98 (s, 2H), 7.50-7.42 (m, 2H), 6.22 (bs, 1H), 3.68-3.57 (m, 1H), 3.42 (m, 2H), 3.19-3.05 (m, 2H), 2.43 (s, 3H), 2.23 (d, 2H), 1.91 (dd, 2H)

Example 121

3-[3-(2-Chlorophenyl)-1,2,4-oxadiazol-5-yl]-7-(piperidin-4-yl)pyrazolo[1,5-a]pyrimidin-5(4H)-one hydrochloride

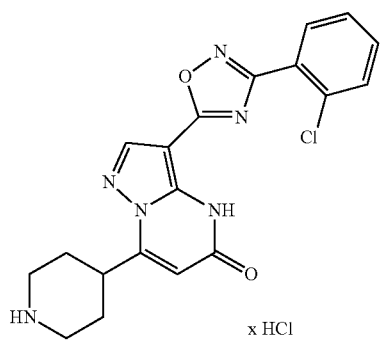 [SMILES: O=c1cc(C2CCNCC2)n2ncc(-c3nc(-c4ccccc4Cl)no3)c2[nH]1]

A suspension tert-butyl 4-{3-[3-(2-chlorophenyl)-1,2,4-oxadiazol-5-yl]-5-oxo-4,5-dihydropyrazolo[1,5-a]pyrimidin-7-yl}piperidine-1-carboxylate (89 mg, 0.18 mmol) in methanol (0.9 ml) was treated with HCl 4N in dioxane (0.9 ml). The reaction mixture was stirred 30 minutes at room temperature. The mixture was diluted in 2 ml dioxane and the solid was filtered, washed with dioxane and dried under vacuum for 16 h to yield the title compound (81 mg, 97% of theory).

LC-MS (method 1B): RT=0.67 min, m/z=397 (M+H-HCl)$^+$ $^1$H-NMR (400 MHz, DMSO-d$_6$): δ 8.76 (bs, 1H), 8.63 (bs, 1H), 8.51 (bs, 1H), 8.20 (bs, 1H), 7.70 (d, 1H), 7.65-7.56 (m, 2H), 6.25 (bs, 1H), 3.70-3.57 (m, 1H), 3.42 (d, 2H), 3.13 (dd, 2H), 2.23 (d, 2H), 1.90 (dd, 2H)

Example 122

3-[3-(3-Fluoro-4-methoxyphenyl)-1,2,4-oxadiazol-5-yl]-7-(piperidin-4-yl)pyrazolo[1,5-a]pyrimidin-5 (4H)-one hydrochloride

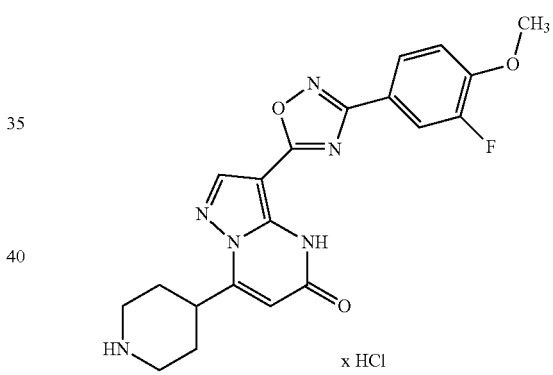

A suspension of tert-butyl 4-{3-[3-(3-fluoro-4-methoxyphenyl)-1,2,4-oxadiazol-5-yl]-5-oxo-4,5-dihydropyrazolo[1,5-a]pyrimidin-7-yl}piperidine-1-carboxylate (69 mg, 0.14 mmol) in methanol (0.7 ml) was treated with HCl 4N in dioxane (0.7 ml). The reaction mixture was 30 minutes at room temperature. The mixture was diluted in 2 ml dioxane and the solid was filtered, washed with dioxane and dried under vacuum for 16 h to yield the title compound (65 mg, quantitative).

LC-MS (method 1B): RT=0.67 min, m/z=411 (M+H-HCl)$^+$ $^1$H-NMR (400 MHz, DMSO-d$_6$): δ 8.79 (bs, 1H), 8.61 (s, 1H), 8.09 (bs, 1H), 8.00 (d, 1H), 7.37 (dd, 1H), 6.19 (bs, 1H), 3.94 (s, 3H), 3.67-3.56 (m, 1H), 3.42 (d, 2H), 3.12 (dd, 2H), 2.23 (d, 2H), 1.90 (dd, 2H)

Example 123

3-[3-(3-Chloro-4-methylphenyl)-1,2,4-oxadiazol-5-yl]-7-(piperidin-4-yl)pyrazolo[1,5-a]pyrimidin-5(4H)-one hydrochloride

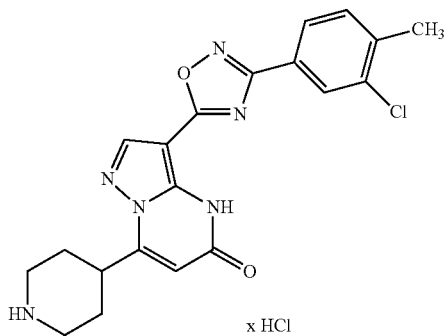 [SMILES: Cc1ccc(-c2noc(-c3cnn4c(C5CCNCC5)cc(=O)[nH]c34)n2)cc1Cl]

A suspension of tert-butyl 4-{3-[3-(3-chloro-4-methylphenyl)-1,2,4-oxadiazol-5-yl]-5-oxo-4,5-dihydropyrazolo[1,5-a]pyrimidin-7-yl}piperidine-1-carboxylate (70 mg, 0.14 mmol) in methanol (0.7 ml) was treated with HCl 4N in dioxane (0.7 ml). The reaction mixture was stirred 30 minutes at room temperature. The mixture was diluted in 2 ml dioxane and the solid was filtered, washed with dioxane and dried under vacuum for 16 h to yield the title compound (61 mg, 98% of theory).

LC-MS (method 1B): RT=0.75 min, m/z=411 (M+H-HCl)+

$^1$H-NMR (400 MHz, DMSO-d$_6$): δ 8.86 (bs, 1H), 8.63 (s, 1H), 8.23 (s, 1H), 8.04 (d, 1H), 7.59 (d, 1H), 6.22 (bs, 1H), 3.66-3.58 (m, 1H), 3.42 (d, 2H), 3.12 (dd, 2H), 2.22 (d, 2H), 1.91 (dd, 2H)

Example 124

7-(Piperidin-4-yl)-3-{3-[3-(trifluoromethoxy)phenyl]-1,2,4-oxadiazol-5-yl}pyrazolo[1,5-a]pyrimidin-5(4H)-one hydrochloride

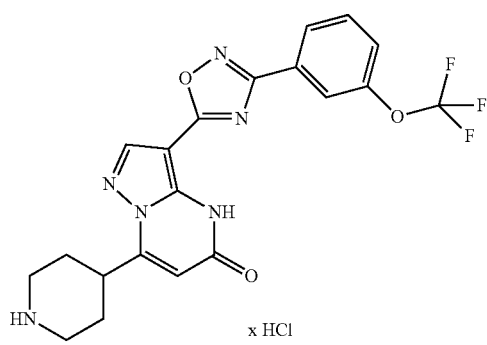 [SMILES: O=c1cc(C2CCNCC2)n2ncc(-c3nc(-c4cccc(OC(F)(F)F)c4)no3)c2[nH]1]

A suspension of tert-butyl 4-(5-oxo-3-{3-[3-(trifluoromethoxy)phenyl]-1,2,4-oxadiazol-5-yl}-4,5-dihydropyrazolo[1,5-a]pyrimidin-7-yl)piperidine-1-carboxylate (53 mg, 0.10 mmol) in methanol (0.5 ml) was treated with HCl 4N in dioxane (0.5 ml). The reaction mixture was stirred 30 minutes at room temperature. The mixture was diluted in 2 ml dioxane and the solid was filtered, washed with dioxane and dried under vacuum for 16 h to yield the title compound (45 mg, 96% of theory).

LC-MS (method 1B): RT=0.75 min, m/z=447 (M+H-HCl)+

$^1$H-NMR (400 MHz, DMSO-d$_6$): δ 8.65 (bs, 1H), 8.43 (bs, 1H), 8.22 (bs, 1H), 7.76 (dd, 1H), 7.65 (d, 1H), 6.18 (bs, 1H), 3.67-3.57 (m, 1H), 3.43 (d, 2H), 3.13 (dd, 2H), 2.23 (d, 2H), 1.89 (dd, 2H)

Example 125

3-[3-(3-Methoxyphenyl)-1,2,4-oxadiazol-5-yl]-7-(piperidin-4-yl)pyrazolo[1,5-a]pyrimidin-5(4H)-one hydrochloride

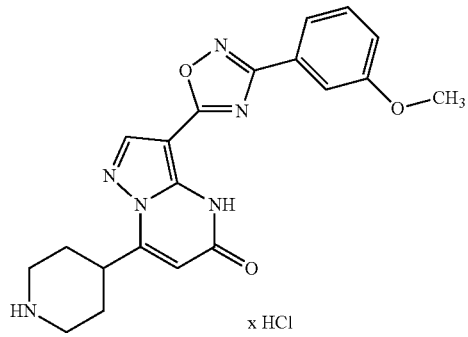 [SMILES: COc1cccc(-c2noc(-c3cnn4c(C5CCNCC5)cc(=O)[nH]c34)n2)c1]

A suspension of tert-butyl 4-{3-[3-(3-methoxyphenyl)-1,2,4-oxadiazol-5-yl]-5-oxo-4,5-dihydropyrazolo[1,5-a]pyrimidin-7-yl}piperidine-1-carboxylate (60 mg, 0.12 mmol) in methanol (0.6 ml) was treated with HCl 4N in dioxane (0.6 ml). The reaction mixture was stirred 30 minutes at room temperature. The mixture was diluted in 2 ml dioxane and the solid was filtered, washed with dioxane and dried under vacuum for 16 h to yield the title compound (43 mg, 83% of theory).

LC-MS (method 1B): RT=0-65 min, m/z=393 (M+H-HCl)+

$^1$H-NMR (400 MHz, DMSO-d$_6$): δ 8.82 (bs, 1H), 8.63 (bs, 2H), 7.78 (d, 1H), 7.70 (s, 1H), 7.51 (dd, 1H), 7.20 (dd, 1H), 6.21 (bs 1H), 3.87 (s, 3H), 3.66-3.57 (m, 1H), 3.42 (d, 2H), 3.12 (dd, 2H), 2.23 (d, 2H), 1.90 (dd, 2H)

Example 126

3-[3-(4-Fluorophenyl)-1,2,4-oxadiazol-5-yl]-7-(piperidin-4-yl)pyrazolo[1,5-a]pyrimidin-5 (4H)-one hydrochloride

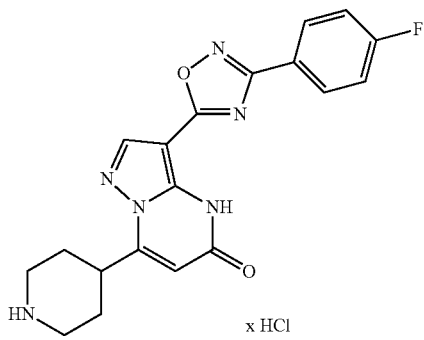 [SMILES: O=c1cc(C2CCNCC2)n2ncc(-c3nc(-c4ccc(F)cc4)no3)c2[nH]1]

x HCl

A suspension of tert-butyl 4-{3-[3-(4-fluorophenyl)-1,2,4-oxadiazol-5-yl]-5-oxo-4,5-dihydropyrazolo[1,5-a]pyrimidin-7-yl}piperidine-1-carboxylate (27 mg, 0.06 mmol) in methanol (0.3 ml) was treated with HCl 4N in dioxane (0.3 ml). The reaction mixture was stirred 30 minutes at room temperature. The mixture was diluted in 2 ml dioxane and the solid was filtered, washed with dioxane and dried under vacuum for 16 h to yield the title compound (20 mg, 87% of theory).

LC-MS (method 1B): RT=0.65 min, m/z=381 (M+H-HCl)$^+$ $^1$H-NMR (400 MHz, DMSO-d$_6$): δ 8.78 (bs, 1H), 8.54 (bs, 1H), 7.35 (dd, 3H), 7.29-7.24 (m, 1H), 6.24 (bs, 1H), 3.66-3.58 (m, 1H), 3.40 (d, 2H), 3.11 (dd, 2H), 2.20 (d, 2H), 1.88 (dd, 2H)

Example 127

3-[3-(2,4-Dimethylphenyl)-1,2,4-oxadiazol-5-yl]-7-(piperidin-4-yl)pyrazolo[1,5-a]pyrimidin-5(4H)-one hydrochloride

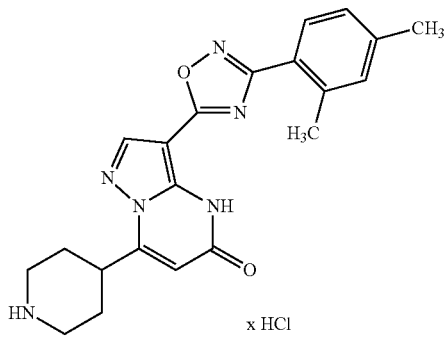 [SMILES: Cc1ccc(-c2noc(-c3cnn4c(C5CCNCC5)cc(=O)[nH]c34)n2)c(C)c1]

x HCl

A suspension of tert-butyl 4-{3-[3-(2,4-dimethylphenyl)-1,2,4-oxadiazol-5-yl]-5-oxo-4,5-dihydropyrazolo[1,5-a]pyrimidin-7-yl}piperidine-1-carboxylate (39 mg, 0.08 mmol) in methanol (0.4 ml) was treated with HCl 4N in dioxane (0.4 ml). The reaction mixture was stirred 30 minutes at room temperature. The mixture was diluted in 2 ml dioxane and the solid was filtered, washed with dioxane and dried under vacuum for 16 h to yield the title compound (32 mg, 94% of theory).

LC-MS (method 2B): RT=0.72 min, m/z=391 (M+H-HCl)$^+$ $^1$H-NMR (400 MHz, DMSO-d$_6$): δ 8.60 (bs, 1H), 8.41 (bs, 1H), 8.13 (bs, 1H), 7.23 (d, 2H), 3.68-3.55 (m, 1H), 3.43 (d, 2H), 3.13 (dd, 2H), 2.58 (s, 3H), 2.37 (s, 3H), 2.23 (d, 2H), 1.88 (dd, 2H)

Example 128

3-{3-[4-Methyl-2-(trifluoromethyl)phenyl]-1,2,4-oxadiazol-5-yl}-7-(piperidin-4-yl)pyrazolo[1,5-a]pyrimidin-5(4H)-one hydrochloride

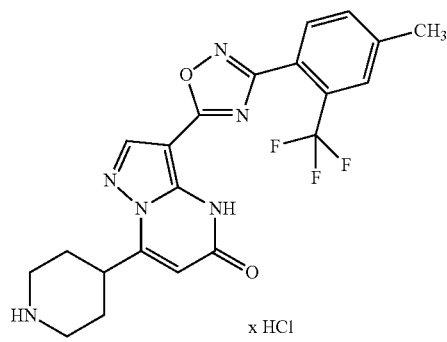 [SMILES: Cc1ccc(-c2noc(-c3cnn4c(C5CCNCC5)cc(=O)[nH]c34)n2)c(C(F)(F)F)c1]

x HCl

A suspension of tert-butyl 4-(3-{3-[4-methyl-2-(trifluoromethyl)phenyl]-1,2,4-oxadiazol-5-yl}-5-oxo-4,5-dihydropyrazolo[1,5-a]pyrimidin-7-yl)piperidine-1-carboxylate (47 mg, 0.09 mmol) in methanol (0.4 ml) was treated with HCl 4N in dioxane (0.4 ml). The reaction mixture was stirred 30 minutes at room temperature. The mixture was diluted in 2 ml dioxane and the solid was filtered, washed with dioxane and dried under vacuum for 16 h to yield the title compound (37 mg, 89% of theory).

LC-MS (method 1B): RT=0.73 min, m/z=445 (M+H-HCl)$^+$ $^1$H-NMR (400 MHz, DMSO-d$_6$): δ 8.82 (bs, 1H), 8.61 (bs, 1H), 7.91 (bs, 1H), 7.82 (s, 1H), 7.70 (d, 1H), 6.26 (bs, 1H), 3.68-3.59 (m, 1H), 3.43 (d, 2H), 3.13 (dd, 2H), 2.24 (d, 2H), 1.90 (dd, 2H)

Example 129

3-[3-(3,4-Dimethylphenyl)-1,2,4-oxadiazol-5-yl]-7-(piperidin-4-yl)pyrazolo[1,5-a]pyrimidin-5(4H)-one hydrochloride

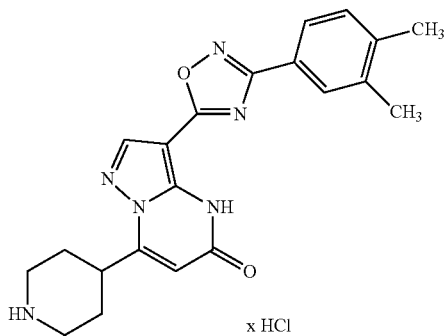 [SMILES: Cc1ccc(-c2noc(-c3cnn4c(C5CCNCC5)cc(=O)[nH]c34)n2)cc1C]

A suspension of tert-butyl 4-{3-[3-(3,4-dimethylphenyl)-1,2,4-oxadiazol-5-yl]-5-oxo-4,5-dihydropyrazolo[1,5-a]pyrimidin-7-yl}piperidine-1-carboxylate (22 mg, 0.05 mmol) in methanol (0.2 ml) was treated with HCl 4N in dioxane (0.2 ml). The reaction mixture was stirred 30 minutes at room temperature. The mixture was diluted in 2 ml dioxane and the solid was filtered, washed with dioxane and dried under vacuum for 16 h to yield the title compound (18 mg, 97% of theory).

LC-MS (method 2B): RT=0.72 min, m/z=391 (M+H-HCl)+

$^1$H-NMR (400 MHz, DMSO-$d_6$): δ 8.79 (bs, 1H), 8.62 (bs, 1H), 8.55 (bs, 1H), 7.93 (s, 2H), 7.35 (dd, 1H), 6.20 (bs, 1H), 3.66-3.58 (m, 1H), 3.42 (d, 2H), 3.13 (dd, 2H), 2.34 (s, 3H), 2.32 (s, 3H), 2.24 (d, 2H), 1.90 (m, 2H)

Example 130

3-[3-(2-Chloro-4-methylphenyl)-1,2,4-oxadiazol-5-yl]-7-(piperidin-4-yl)pyrazolo[1,5-a]pyrimidin-5(4H)-one hydrochloride

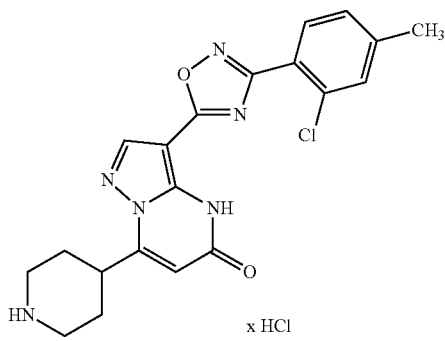 [SMILES: Cc1ccc(-c2noc(-c3cnn4c(C5CCNCC5)cc(=O)[nH]c34)n2)c(Cl)c1]

A suspension of tert-butyl 4-{3-[3-(2-chloro-4-methylphenyl)-1,2,4-oxadiazol-5-yl]-5-oxo-4,5-dihydropyrazolo[1,5-a]pyrimidin-7-yl}piperidine-1-carboxylate (110 mg, 0.21 mmol) in methanol (1.0 ml) was treated with HCl 4N in dioxane (2.1 ml). The reaction mixture was stirred 30 minutes at room temperature. The mixture was diluted in 2 ml dioxane and the solid was filtered, washed with dioxane and dried under vacuum for 16 h to yield the title compound (92 mg, 95% of theory).

LC-MS (method 2B): RT=0.71 min, m/z=411 (M+H-HCl)+

$^1$H-NMR (400 MHz, DMSO-$d_6$): δ 8.75 (bs, 1H), 8.62 (bs, 1H), 8.49 (bs, 1H), 8.12 (bs, 1H), 7.54 (s, 1H), 7.39 (d, 1H), 6.25 (bs, 1H), 3.68-3.55 (m, 1H), 3.43 (d, 2H), 3.13 (d, 2H), 2.41 (s, 3H), 2.23 (d, 2H), 1.90 (dd, 2H)

Example 131

3-[3-(2-Fluoro-4-methylphenyl)-1,2,4-oxadiazol-5-yl]-7-(piperidin-4-yl)pyrazolo[1,5-a]pyrimidin-5(4H)-one hydrochloride

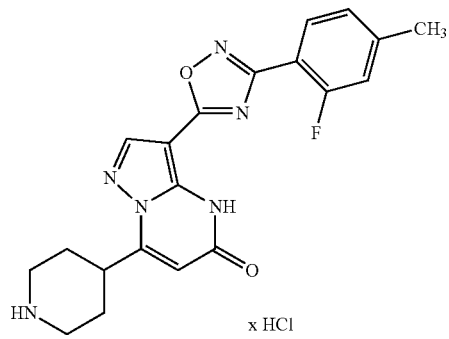 [SMILES: Cc1ccc(-c2noc(-c3cnn4c(C5CCNCC5)cc(=O)[nH]c34)n2)c(F)c1]

A suspension of tert-butyl 4-{3-[3-(2-fluoro-4-methylphenyl)-1,2,4-oxadiazol-5-yl]-5-oxo-4,5-dihydropyrazolo[1,5-a]pyrimidin-7-yl}piperidine-1-carboxylate (102 mg, 0.21 mmol) in methanol (1.0 ml) was treated with HCl 4N in dioxane (2.1 ml). The reaction mixture was stirred 30 minutes at room temperature. The mixture was diluted in 2 ml dioxane and the solid was filtered, washed with dioxane and dried under vacuum for 16 h to yield the title compound (86 mg, 97% of theory).

LC-MS (method 1B): RT=0.67 min, m/z=395 (M+H-HCl)+

$^1$H-NMR (400 MHz, DMSO-$d_6$): δ 8.82 (bs, 1H), 8.62 (bs, 1H), 8.25 (bs, 1H), 7.28 (dd, 2H), 6.22 (bs, 1H), 3.68-3.58 (m, 1H), 3.42 (d, 2H), 3.13 (dd, 2H), 2.43 (s, 3H), 2.23 (d, 2H), 1.90 (dd, 2H)

Example 132

3-[3-(3-Chloro-2-fluorophenyl)-1,2,4-oxadiazol-5-yl]-7-(piperidin-4-yl)pyrazolo[1,5-a]pyrimidin-5(4H)-one hydrochloride

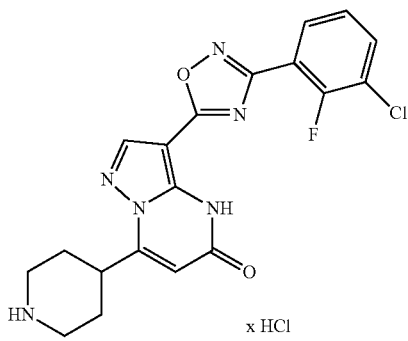

A suspension of tert-butyl 4-{3-[3-(3-chloro-2-fluorophenyl)-1,2,4-oxadiazol-5-yl]-5-oxo-4,5-dihydropyrazolo[1,5-a]pyrimidin-7-yl}piperidine-1-carboxylate (82 mg, 0.16 mmol) in methanol (0.8 ml) was treated with HCl 4N in dioxane (0.8 ml). The reaction mixture was stirred 30 minutes at room temperature. The mixture was diluted in 2 ml dioxane and the solid was filtered, washed with dioxane and dried under vacuum for 16 h to yield the title compound (66 mg, 92% of theory).

LC-MS (method 1B): RT=0.72 min, m/z=415 (M+H-HCl)$^+$ $^1$H-NMR (400 MHz, DMSO-d$_6$): δ 8.64 (s, 1H), 8.36 (bs, 1H), 7.87 (dd, 1H), 7.49 (dd, 1H), 6.23 (bs, 1H), 3.66-3.56 (m, 1H), 3.42 (d, 2H), 3.13 (dd, 2H), 2.23 (d, 2H), 1.90 (dd, 2H)

Example 133

3-[3-(6-Chloropyridin-2-yl)-1,2,4-oxadiazol-5-yl]-7-(piperidin-4-yl)pyrazolo[1,5-a]pyrimidin-5(4H)-one hydrochloride

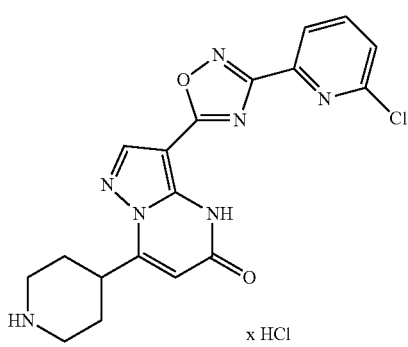 [SMILES: O=c1cc(C2CCNCC2)n2ncc(-c3nc(-c4cccc(Cl)n4)no3)c2[nH]1]

A suspension of tert-butyl 4-{3-[3-(6-chloropyridin-2-yl)-1,2,4-oxadiazol-5-yl]-5-oxo-4,5-dihydropyrazolo[1,5-a]pyrimidin-7-yl}piperidine-1-carboxylate (29 mg, 0.06 mmol) in dioxane (0.28 ml) was treated with HCl 4N in dioxane (0.14 ml). The reaction mixture was stirred 7 h at room temperature. The mixture was filtered and the solid was filtered, washed with dioxane to yield the title compound (23 mg, 86% of theory).

LC-MS (method 1B): RT=0.59 min, m/z=398 (M+H-2.HCl)$^+$ $^1$H-NMR (400 MHz, MeOD): δ 8.46 (s, 1H), 8.25 (d, 1H), 8.06 (dd, 1H), 7.71 (d, 1H), 6.16 (s, 1H), 3.75.3.67 (m, 1H), 3.58 (d, 2H), 3.25 (dd, 2H), 2.43 (d, 2H), 2.01 (dd, 2H)

Example 134

3-{3-[3-Fluoro-4-(trifluoromethyl)phenyl]-1,2,4-oxadiazol-5-yl}-7-(piperidin-4-yl)pyrazolo[1,5-a]pyrimidin-5(4H)-one hydrochloride

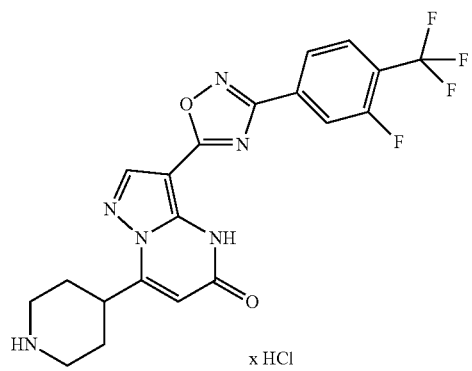 [SMILES: O=c1cc(C2CCNCC2)n2ncc(-c3nc(-c4ccc(C(F)(F)F)c(F)c4)no3)c2[nH]1]

A suspension of tert-butyl 4-(3-{3-[3-fluoro-4-(trifluoromethyl)phenyl]-1,2,4-oxadiazol-5-yl}-5-oxo-4,5-dihydropyrazolo[1,5-a]pyrimidin-7-yl)piperidine-1-carboxylate (26 mg, 0.05 mmol) in dioxane (0.4 ml) was treated with HCl 4N in dioxane (0.1 ml). The reaction mixture was stirred at room temperature overnight. The suspension was filtered and the solid washed with dioxane and dried under vacuum for 16 h to yield the title compound (14 mg, 56% of theory).

LC-MS (method 1B): RT=0.79 min, m/z=449 (M+H-HCl)$^+$ $^1$H-NMR (400 MHz, MeOD): δ 8.50 (s, 1H), 8.21 (d, 2H), 7.93 (dd, 1H), 6.21 (s, 1H), 3.73 (dd, 1H), 3.60 (d, 2H), 3.27 (dd, 2H), 2.45 (d, 2H), 2.04 (dd, 2H)

Example 135

3-{3-[2-Fluoro-4-(trifluoromethyl)phenyl]-1,2,4-oxadiazol-5-yl}-7-(piperidin-4-yl)pyrazolo[1,5-a]pyrimidin-5(4H)-one hydrochloride

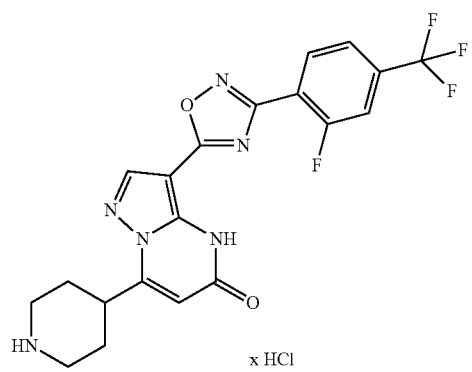 [SMILES: O=c1cc(C2CCNCC2)n2ncc(-c3nc(-c4ccc(C(F)(F)F)cc4F)no3)c2[nH]1]

A suspension of tert-butyl 4-(3-{3-[2-fluoro-4-(trifluoromethyl)phenyl]-1,2,4-oxadiazol-5-yl}-5-oxo-4,5-dihydropyrazolo[1,5-a]pyrimidin-7-yl)piperidine-1-carboxylate (22 mg, 0.04 mmol) in dioxane (0.4 ml) was treated with HCl 4N in dioxane (0.1 ml). The reaction mixture was stirred at room temperature overnight. The suspension was filtered and the solid washed with dioxane and dried under vacuum for 16 h to yield the title compound (10 mg, 44% of theory).

LC-MS (method 1B): RT=0.76 min, m/z=448 (M+H-2.HCl)$^+$ $^1$H-NMR (400 MHz, MeOD): δ 8.54-8.48 (m, 2H), 7.75 (d, 2H), 6.21 (s, 1H), 3.73 (dd, 1H), 3.60 (d, 2H), 3.27 (dd, 2H), 2.44 (d, 2H), 2.03 (dd, 2H)

Example 136

3-{3-[2-Chloro-4-(trifluoromethyl)phenyl]-1,2,4-oxadiazol-5-yl}-7-(piperidin-4-yl)pyrazolo[1,5-a]pyrimidin-5(4H)-one hydrochloride

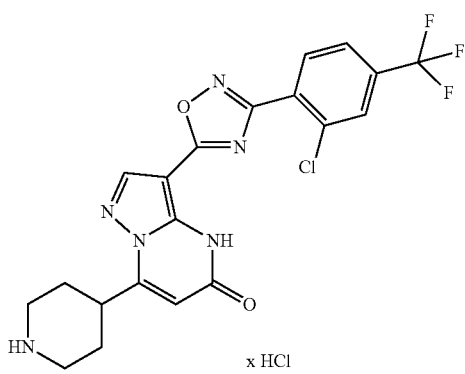 [SMILES: O=c1cc(C2CCNCC2)n2ncc(-c3nc(-c4ccc(C(F)(F)F)cc4Cl)no3)c2[nH]1]

A suspension of tert-butyl 4-(3-{3-[2-chloro-4-(trifluoromethyl)phenyl]-1,2,4-oxadiazol-5-yl}-5-oxo-4,5-dihydropyrazolo[1,5-a]pyrimidin-7-yl)piperidine-1-carboxylate (56 mg, 0.10 mmol) in dioxane (0.9 ml) was treated with HCl 4N in dioxane (0.25 ml). The reaction mixture was stirred at room temperature overnight. The suspension was filtered and the solid was washed with dioxane and dried under vacuum for 16 h to yield the title compound (36 mg, 71% of theory).

LC-MS (method 1B): RT=0.79 min, m/z=465 (M+H-HCl)$^+$ $^1$H-NMR (400 MHz, MeOD): δ 8.51 (s, 1H), 8.34 (d, 1H), 8.00 (s, 1H), 7.86 (d, 1H), 6.21 (s, 1H), 3.73 (dd, 1H), 3.60 (d, 2H), 3.27 (dd, 2H), 2.44 (d, 2H), 2.04 (dd, 2H)

Example 137

3-[3-(5-Chloro-2-fluorophenyl)-1,2,4-oxadiazol-5-yl]-7-(piperidin-4-yl)pyrazolo[1,5-a]pyrimidin-5(4H)-one hydrochloride

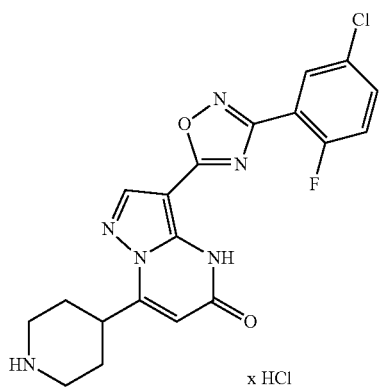 [SMILES: O=c1cc(C2CCNCC2)n2ncc(-c3nc(-c4cc(Cl)ccc4F)no3)c2[nH]1]

A suspension of compound tert-butyl 4-{3-[3-(5-chloro-2-fluorophenyl)-1,2,4-oxadiazol-5-yl]-5-oxo-4,5-dihydropyrazolo[1,5-a]pyrimidin-7-yl}piperidine-1-carboxylate (19 mg, 0.04 mmol) in dioxane (0.3 ml) was treated with HCl 4N in dioxane (0.09 ml). The reaction mixture was stirred at room temperature overnight. The suspension was filtered and the solid washed with dioxane and dried under vacuum for 16 h to yield the title compound (5 mg, 30% of theory).

LC-MS (method 1B): RT=0.76 min, m/z=415 (M+H-HCl)$^+$ $^1$H-NMR (400 MHz, MeOD): δ 7.18 (s, 1H), 6.80 (s, 1H), 6.63 (s, 1H), 6.17 (s, 1H), 4.90 (s, 1H), 2.43 (dd, 1H), 2.29 (d, 2H), 1.96 (dd, 2H), 1.14 (d, 2H), 0.73 (dd, 2H)

Example 138

3-[3-(3-Chloro-5-fluorophenyl)-1,2,4-oxadiazol-5-yl]-7-(piperidin-4-yl)pyrazolo[1,5-a]pyrimidin-5(4H)-one hydrochloride

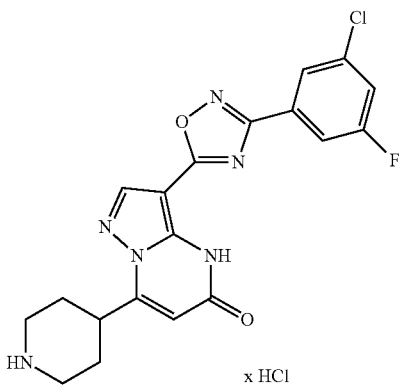 [SMILES: O=c1cc(C2CCNCC2)n2ncc(-c3nc(-c4cc(F)cc(Cl)c4)no3)c2[nH]1]

A suspension of compound tert-butyl 4-{3-[3-(3-chloro-5-fluorophenyl)-1,2,4-oxadiazol-5-yl]-5-oxo-4,5-dihydropyrazolo[1,5-a]pyrimidin-7-yl}piperidine-1-carboxylate (24 mg, 0.05 mmol) in dioxane (0.4 ml) was treated with HCl 4N in dioxane (0.1 ml). The reaction mixture was stirred at room

Example 139

3-{3-[2-Methyl-4-(trifluoromethyl)phenyl]-1,2,4-oxadiazol-5-yl}-7-(piperidin-4-yl)pyrazolo[1,5-a]pyrimidin-5(4H)-one hydrochloride

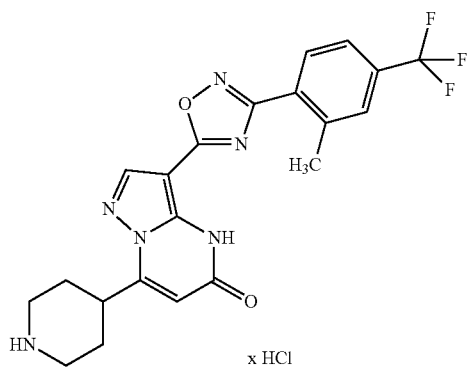 [SMILES: Cc1cc(C(F)(F)F)ccc1-c1noc(-c2cnn3c(C4CCNCC4)cc(=O)[nH]c23)n1]

A suspension of tert-butyl 4-(3-{3-[2-methyl-4-(trifluoromethyl)phenyl]-1,2,4-oxadiazol-5-yl}-5-oxo-4,5-dihydropyrazolo[1,5-a]pyrimidin-7-yl)piperidine-1-carboxylate (53 mg, 0.10 mmol) in dioxane (0.9 ml) was treated with HCl 4N in dioxane (0.2 ml). The reaction mixture was stirred at room temperature overnight. The suspension was filtered and the solid was washed with dioxane and dried under vacuum for 16 h. Purification via preparative HPLC afforded the title compound (10 mg, 21% of theory).

LC-MS (method 1B): RT=0.76 min, m/z=445 (M+H-2.HCl)⁺

¹H-NMR (400 MHz, MeOD): δ 8.47 (s, 1H), 8.34 (d, 1H), 8.14 (s, 1H), 7.73-7.66 (m, 1H), 7.68 (d, 1H), 6.17 (s, 1H), 3.71 (dd, 1H), 3.57 (d, 2H), 3.25 (dd, 2H), 2.74 (s, 3H), 2.42 (d, 2H), 2.01 (dd, 2H)

temperature overnight. The suspension was filtered and the solid was washed with dioxane and dried under vacuum for 16 h to yield the title compound (15 mg, 66% of theory).

LC-MS (method 2B): RT=0.70 min, m/z=415 (M+H-HCl)⁺

¹H-NMR (400 MHz, MeOD): δ 8.50 (s, 1H), 8.41-8.32 (m, 1H), 7.68-7.59 (m, 1H), 7.38 (dd, 1H), 6.21 (s, 1H), 3.73 (dd, 1H), 3.60 (d, 2H), 3.27 (dd, 2H), 2.44 (d, 2H), 2.05 (dd, 2H)

Example 140

3-[3-(3-Chloro-2-methylphenyl)-1,2,4-oxadiazol-5-yl]-7-(piperidin-4-yl)pyrazolo[1,5-a]pyrimidin-5(4H)-one hydrochloride

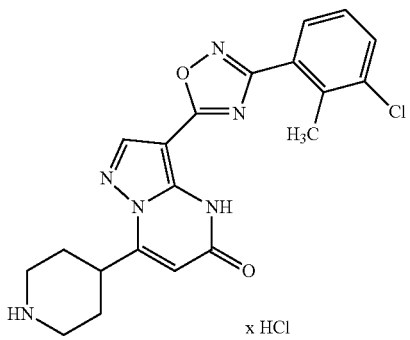 [SMILES: Cc1c(Cl)cccc1-c1noc(-c2cnn3c(C4CCNCC4)cc(=O)[nH]c23)n1]

A suspension of tert-butyl 4-{3-[3-(3-chloro-2-methylphenyl)-1,2,4-oxadiazol-5-yl]-5-oxo-4,5-dihydropyrazolo[1,5-a]pyrimidin-7-yl}piperidine-1-carboxylate (101 mg, 0.20 mmol) in dioxane (1.8 ml) was treated with HCl 4N in dioxane (0.5 ml). The reaction mixture was stirred at room temperature overnight. After that HCl 4N in dioxane (0.5 ml) was added again and the mixture was stirred at room temperature for 5 h. The suspension was filtered and the solid washed with dioxane and dried under vacuum for 16 h to yield the title compound (66 mg, 73% of theory).

LC-MS (method 1B): RT=0.72 min, m/z=411 (M+H-HCl)⁺

¹H-NMR (400 MHz, MeOD): δ 8.46 (s, 1H), 7.93 (d, 1H), 7.60 (d, 1H), 7.36 (dd, 1H), 6.17 (s, 1H), 3.71 (dd, 1H), 3.58 (d, 2H), 3.25 (dd, 2H), 2.42 (d, 2H), 2.02 (dd, 2H)

Example 141

3-[3-(5-Chloro-2-methylphenyl)-1,2,4-oxadiazol-5-yl]-7-(piperidin-4-yl)pyrazolo[1,5-a]pyrimidin-5(4H)-one hydrochloride

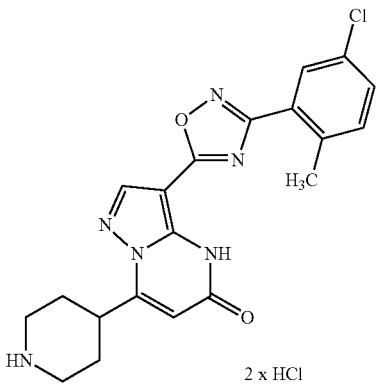 [SMILES: Cc1ccc(Cl)cc1-c1noc(-c2cnn3c(C4CCNCC4)cc(=O)[nH]c23)n1]

A suspension of tert-butyl 4-{3-[3-(5-chloro-2-methylphenyl)-1,2,4-oxadiazol-5-yl]-5-oxo-4,5-dihydropyrazolo[1,5-a]pyrimidin-7-yl}piperidine-1-carboxylate (45 mg, 0.09 mmol) in dioxane (0.8 ml) was treated with HCl 4N in dioxane (0.2 ml). The reaction mixture was stirred at room temperature overnight. The suspension was filtered and the solid was washed with dioxane and dried under vacuum for 16 h to yield the title compound (49 mg, quantitative).

LC-MS (method 1B): RT=0.73 min, m/z=411 (M+H-2.HCl)+

$^1$H-NMR (400 MHz, MeOD): δ 8.46 (s, 1H), 8.20 (d, 1H), 7.45 (d, 1H), 7.39 (d, 1H), 6.17 (s, 1H), 3.71 (dd, 1H), 3.58 (d, 2H), 3.25 (dd, 2H), 2.64 (s, 3H), 2.42 (d, 2H), 2.01 (dd, 2H)

Example 142

3-[3-(3-Chloro-4-methoxyphenyl)-1,2,4-oxadiazol-5-yl]-7-(piperidin-4-yl)pyrazolo[1,5-a]pyrimidin-5(4H)-one hydrochloride

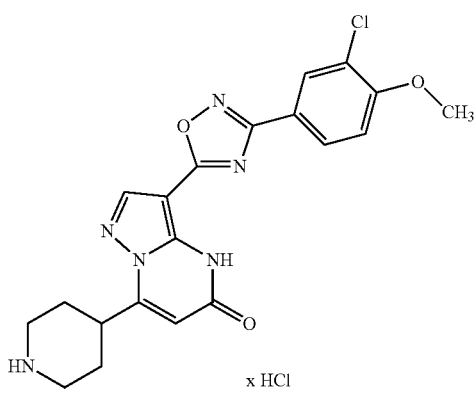 [SMILES: COc1ccc(-c2noc(-c3cnn4c(C5CCNCC5)cc(=O)[nH]c34)n2)cc1Cl]

A suspension of tert-butyl 4-{3-[3-(3-chloro-4-methoxyphenyl)-1,2,4-oxadiazol-5-yl]-5-oxo-4,5-dihydropyrazolo[1,5-a]pyrimidin-7-yl}piperidine-1-carboxylate (34 mg, 0.07 mmol) in dioxane (0.30 ml) was treated with HCl 4N in dioxane (0.16 ml). The reaction mixture was stirred at room temperature overnight. The suspension was filtered and the solid was washed with dioxane and dried under vacuum for 16 h to yield the title compound (25 mg, 84% of theory).

LC-MS (method 1B): RT=0.72 min, m/z=427 (M+H-HCl)+

$^1$H-NMR (400 MHz, MeOD): 8.35 (s, 1H), 8.10 (s, 1H), 8.01 (d, 1H), 7.15 (d, 1H), 6.07 (s, 1H), 3.89 (s, 3H), 3.61 (dd, 1H), 3.48 (d, 2H), 3.15 (dd, 2H), 2.33 (d, 2H), 1.91 (dd, 2H)

Example 143

3-[3-(2,3-Dichlorophenyl)-1,2,4-oxadiazol-5-yl]-7-(piperidin-4-yl)pyrazolo[1,5-a]pyrimidin-5(4H)-one hydrochloride

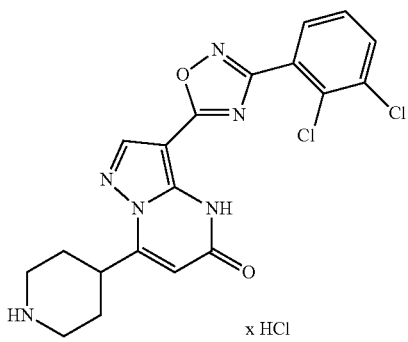 [SMILES: O=c1cc(C2CCNCC2)n2ncc(-c3nc(-c4cccc(Cl)c4Cl)no3)c2[nH]1]

A suspension of tert-butyl 4-{3-[3-(2,3-dichlorophenyl)-1,2,4-oxadiazol-5-yl]-5-oxo-4,5-dihydropyrazolo[1,5-a]pyrimidin-7-yl}piperidine-1-carboxylate (63 mg, 0.12 mmol) in dioxane (0.6 ml) was treated with HCl 4N in dioxane (0.3 ml). The reaction mixture was stirred at room temperature overnight. The suspension was filtered and the solid was washed with dioxane to yield the title compound (55 mg, 99% of theory).

LC-MS (method 1B): RT=0.75 min, m/z=431 (M+H-HCl)+

$^1$H-NMR (400 MHz, MeOD): δ 8.38 (s, 1H), 7.86 (d, 1H), 7.69 (d, 1H), 7.40 8dd, 1H), 6.08 (s, 1H), 3.61 (dd, 1H), 3.47 (d, 2H), 3.15 (dd, 2H), 2.32 (d, 2H), 1.91 (dd, 2H)

Example 144

3-[3-(3-Chloro-4-fluorophenyl)-1,2,4-oxadiazol-5-yl]-7-(piperidin-4-yl)pyrazolo[1,5-a]pyrimidin-5(4H)-one hydrochloride

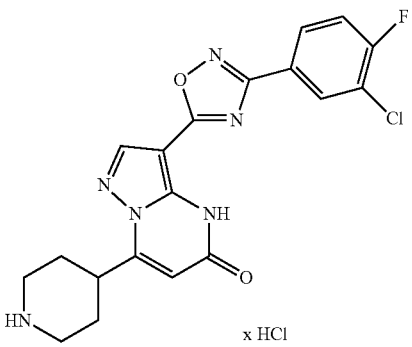 [SMILES: O=c1cc(C2CCNCC2)n2ncc(-c3nc(-c4ccc(F)c(Cl)c4)no3)c2[nH]1]

A suspension of tert-butyl 4-{3-[3-(3-chloro-4-fluorophenyl)-1,2,4-oxadiazol-5-yl]-5-oxo-4,5-dihydropyrazolo[1,5-a]pyrimidin-7-yl}piperidine-1-carboxylate (68 mg, 0.13 mmol) in dioxane (1.2 ml) was treated with HCl 4N in dioxane (0.3 ml). The reaction mixture was stirred at room temperature overnight. After that HCl 4N in dioxane (0.3 ml) was added again and the mixture was further stirred 5 h. The suspension was filtered and the solid was washed with dioxane and dried under vacuum for 16 h to yield the title compound (60 mg, 60% of theory).

LC-MS (method 1B): RT=0.71 min, m/z=414 (M+H-HCl)+

$^1$H-NMR (400 MHz, MeOD): δ 8.46 (s, 1H), 8.36 (d, 2H), 8.18-8.15 (m, 1H), 7.45 (dd, 1H), 6.17 (s, 1H), 3.71 (dd, 1H), 3.57 (d, 2H), 3.25 (dd, 2H), 3.42 (d, 2H), 2.01 (dd, 2H)

Example 145

3-{3-[5-Chloro-2-(trifluoromethyl)phenyl]-1,2,4-oxadiazol-5-yl}-7-(piperidin-4-yl)pyrazolo[1,5-a]pyrimidin-5(4H)-one hydrochloride

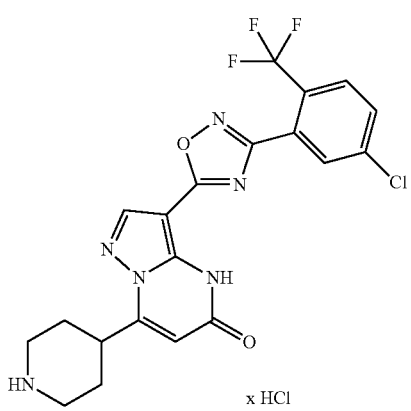 [SMILES: O=c1cc(C2CCNCC2)n2ncc(-c3nc(-c4cc(Cl)ccc4C(F)(F)F)no3)c2[nH]1]

A suspension of tert-butyl 4-(3-{3-[5-chloro-2-(trifluoromethyl)phenyl]-1,2,4-oxadiazol-5-yl}-5-oxo-4,5-dihydropyrazolo[1,5-a]pyrimidin-7-yl)piperidine-1-carboxylate (54 mg, 0.10 mmol) in dioxane (0.8 ml) was treated with HCl 4N in dioxane (0.2 ml). The reaction mixture was stirred at room temperature overnight. After that HCl 4N in dioxane (0.2 ml) was added again and the mixture was further stirred 3 h. The suspension was filtered and the solid was washed with dioxane and dried under vacuum for 16 h to yield the title compound (34 mg, 71% of theory).

LC-MS (method 1B): RT=0.77 min, m/z=465 (M+H-HCl)+

$^1$H-NMR (400 MHz, MeOD): δ 8.47 (s, 1H), 8.00 (d, 2H), 7.88 (dd, 1H), 6.19 (s, 1H), 3.72 (dd, 1H), 3.60 (d, 2H), 3.26 (dd, 2H), 2.43 (d, 2H), 2.04 (dd, 2H)

Example 146

7-(Piperidin-4-yl)-3-{3-[6-(trifluoromethyl)pyridin-2-yl]-1,2,4-oxadiazol-5-yl}pyrazolo[1,5-a]pyrimidin-5(4H)-one hydrochloride

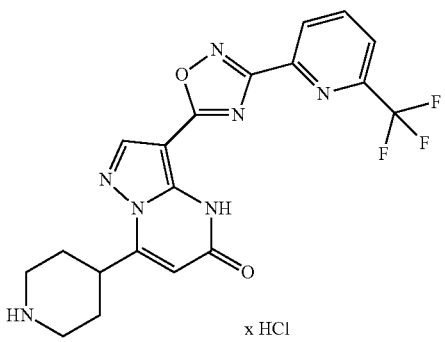 [SMILES: O=c1cc(C2CCNCC2)n2ncc(-c3nc(-c4cccc(C(F)(F)F)n4)no3)c2[nH]1]

A suspension of tert-butyl 4-(5-oxo-3-{3-[6-(trifluoromethyl)pyridin-2-yl]-1,2,4-oxadiazol-5-yl}-4,5-dihydropyrazolo[1,5-a]pyrimidin-7-yl)piperidine-1-carboxylate (106 mg, 0.2 mmol) in dioxane (1.8 ml) was treated with HCl 4N in dioxane (0.5 ml). The reaction mixture was stirred at room temperature overnight. After that HCl 4N in dioxane (0.5 ml) was added again and the mixture was sonicated 1 h at 45° C. The suspension was filtered and the resulting solid was washed with dioxane and dried under vacuum for 16 h to yield the title compound (90 mg, 93% of theory).

LC-MS (method 1B): RT=0.61 min, m/z=432 (M+H-HCl)+

$^1$H-NMR (400 MHz, MeOD): δ 8.54 (d, 1H), 8.49 (s, 1H), 8.30 (dd, 1H), 8.06 (d, 1H), 6.17 (s, 1H), 3.71 (dd, 1H), 3.58 (d, 2H), 3.25 (dd, 2H), 2.42 (d, 2H), 2.001 (dd, 2H)

Example 147

7-(piperidin-4-yl)-3-{3-[4-(trifluoromethyl)pyridin-2-yl]-1,2,4-oxadiazol-5-yl}pyrazolo[1,5-a]pyrimidin-5(4H)-one hydrochloride

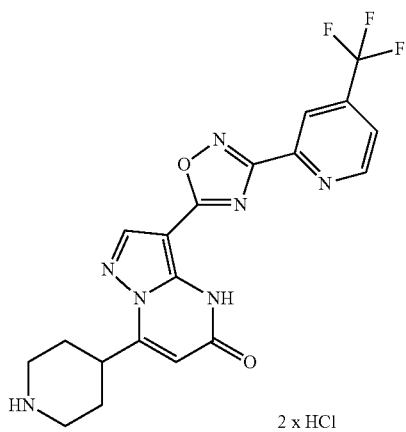 [SMILES: O=c1cc(C2CCNCC2)n2ncc(-c3nc(-c4cc(C(F)(F)F)ccn4)no3)c2[nH]1]

A suspension of tert-butyl 4-(5-oxo-3-{3-[4-(trifluoromethyl)pyridin-2-yl]-1,2,4-oxadiazol-5-yl}-4,5-dihydropyrazolo[1,5-a]pyrimidin-7-yl)piperidine-1-carboxylate (104 mg, 0.2 mmol) in dioxane (1.8 ml) was treated with HCl 4N in dioxane (0.5 ml). The reaction mixture was stirred at room temperature overnight After that HCl 4N in dioxane (0.5 ml) was added again and the mixture was stirred 1 h. The suspension was filtered and the solid was washed with dioxane and dried under vacuum for 16 h to yield the title compound (107 mg, quantitative).

LC-MS (method 1B): RT=0.66 min, m/z=432 (M+H-2.HCl)+

$^1$H-NMR (400 MHz, MeOD): δ 9.05 (d, 1H), 8.59 (s, 1H), 8.50 (s, 1H), 7.97 (d, 1H), 6.19 (s, 1H), 3.73 (dd, 1H), 3.60 (d, 2H), 3.27 (dd, 2H), 2.44 (s, 2H), 2.04 (dd, 2H)

Example 148

3-[3-(2-Chloropyridin-3-yl)-1,2,4-oxadiazol-5-yl]-7-(piperidin-4-yl)pyrazolo[1,5-a]pyrimidin-5(4H)-one hydrochloride

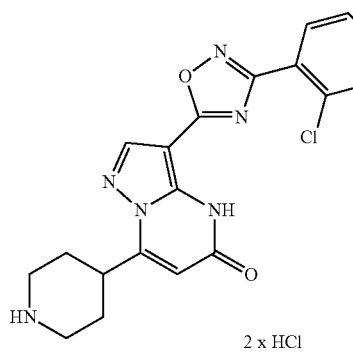

2 x HCl

A suspension of tert-butyl 4-{3-[3-(2-chloropyridin-3-yl)-1,2,4-oxadiazol-5-yl]-5-oxo-4,5-dihydropyrazolo[1,5-a]pyrimidin-7-yl}piperidine-1-carboxylate (37 mg, 0.1 mmol) in dioxane (0.6 ml) was treated with HCl 4N in dioxane (0.2 ml). The reaction mixture was stirred at room temperature overnight. The suspension was filtered and the solid was washed with dioxane and dried under vacuum for 16 h to yield the title compound (33 mg, quantitative).

LC-MS (method 1B): RT=0.53 min, m/z=398 (M+H-2.HCl)+

$^1$H-NMR (400 MHz, DMSO-d$_6$): δ 8.94 (bs, 1H), 8.75 (bs, 1H), 8.65 (dd, 1H), 7.70 (dd, 1H), 6.24 (bs, 1H), 3.62 (dd, 1H), 3.12 (dd, 2H), 2.23 (d, 2H), 1.93 (dd, 2H)

Example 149

3-{3-[3-Chloro-4-(trifluoromethoxy)phenyl]-1,2,4-oxadiazol-5-yl}-7-(piperidin-4-yl)pyrazolo[1,5-a]pyrimidin-5(4H)-one hydrochloride

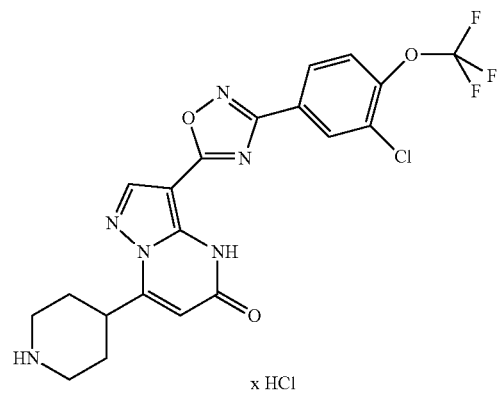 [SMILES: O=c1cc(C2CCNCC2)n2ncc(-c3nc(-c4ccc(OC(F)(F)F)c(Cl)c4)no3)c2[nH]1]

x HCl

A suspension of tert-butyl 4-(3-{3-[3-chloro-4-(trifluoromethoxy)phenyl]-1,2,4-oxadiazol-5-yl}-5-oxo-4,5-dihydropyrazolo[1,5-a]pyrimidin-7-yl)piperidine-1-carboxylate (56 mg, 0.1 mmol) in dioxane (0.8 ml) was treated with HCl 4N in dioxane (0.2 ml). The reaction mixture was stirred at room temperature overnight. The suspension was filtered and the solid was washed with dioxane and dried under vacuum for 16 h to yield the title compound (14 mg, 27% of theory).

LC-MS (Method 1B): RT=0.84 min, m/z=481 (M+H-HCl)+

$^1$H-NMR (400 MHz, MeOD): δ 8.45 (s, 1H), 8.43 (d, 1H), 8.22 (dd, 1H), 7.63 (dd, 1H), 6.18 (s, 1H), 3.71 (dd, 1H), 3.58 (d, 2H), 3.25 (dd, 2H), 2.42 (d, 2H), 2.02 (dd, 2H)

Example 150

3-{3-[2,6-Dichloro-4-(trifluoromethyl)phenyl]-1,2,4-oxadiazol-5-yl}-7-(piperidin-4-yl)pyrazolo[1,5-a]pyrimidin-5(4H)-one hydrochloride

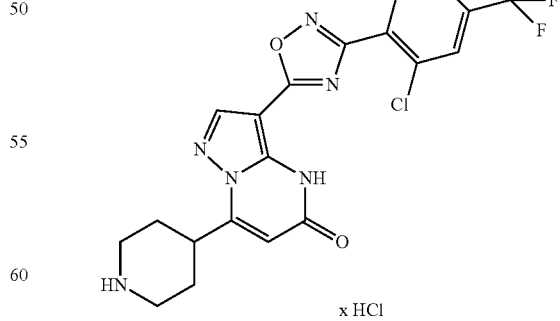

x HCl

A suspension of tert-butyl 4-(3-{3-[2,6-dichloro-4-(trifluoromethyl)phenyl]-1,2,4-oxadiazol-5-yl}-5-oxo-4,5-dihydropyrazolo[1,5-a]pyrimidin-7-yl)piperidine-1-carboxylate (10 mg, 0.02 mmol) in dioxane (0.1 ml) was treated with HCl 4N in dioxane (0.04 ml). The reaction mixture was stirred at room temperature overnight. The suspension was filtered and the resulting solid was washed with dioxane and dried under vacuum for 16 h to yield the title compound (6 mg, 66% of theory).

LC-MS (method 1B): RT=0.77 min, m/z=499 (M+H-HCl)+

Example 151

3-[3-(3,5-Dichlorophenyl)-1,2,4-oxadiazol-5-yl]-7-(piperidin-4-yl)pyrazolo[1,5-a]pyrimidin-5 (4H)-one hydrochloride

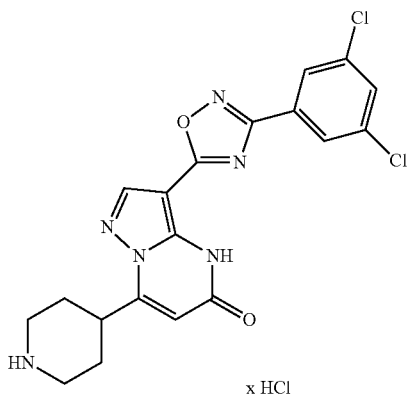 [SMILES: O=c1cc(C2CCNCC2)n2ncc(-c3nc(-c4cc(Cl)cc(Cl)c4)no3)c2[nH]1]

A suspension of tert-butyl 4-{3-[3-(3,5-dichlorophenyl)-1,2,4-oxadiazol-5-yl]-5-oxo-4,5-dihydropyrazolo[1,5-a]pyrimidin-7-yl}piperidine-1-carboxylate (16 mg, 0.03 mmol) in dioxane (0.3 ml) was treated with HCl 4N in dioxane (0.08 ml). The reaction mixture was stirred at room temperature overnight, then was sonicated 1 h and finally stirred at room temperature for 16 h additionally. The suspension was filtered and the resulting solid was washed with dioxane and dried under vacuum for 16 h to yield the title compound (13 mg, 88% of theory).

LC-MS (method 1B): RT=0.81 min, m/z=431 (M+H-HCl)+

1H-NMR (400 MHz, MeOD): δ 8.41 (s, 1H), 8.26 (s, 3H), 8.22 (dd, 1H), 7.85 (s, 1H), 7.54 (s, 1H), 6.24 (s, 1H), 3.69-3.54 (m, 3H), 3.34-3.22 (m, 2H), 2.47-2.37 (m, 2H), 2.06-1.92 (m, 2H)

Example 152

3-{3-[2,4-Bis(trifluoromethyl)phenyl]-1,2,4-oxadiazol-5-yl}-7-(piperidin-4-yl)pyrazolo[1,5-a]pyrimidin-5(4H)-one hydrochloride

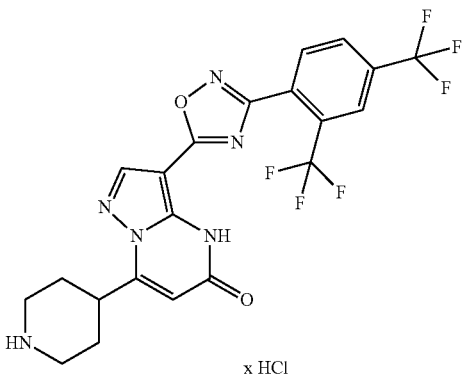 [SMILES: O=c1cc(C2CCNCC2)n2ncc(-c3nc(-c4ccc(C(F)(F)F)cc4C(F)(F)F)no3)c2[nH]1]

A suspension of tert-butyl 4-(3-{3-[2,4-bis(trifluoromethyl)phenyl}-1,2,4-oxadiazol-5-yl]-5-oxo-4,5-dihydropyrazolo[1,5-a]pyrimidin-7-yl)piperidine-1-carboxylate (21 mg, 0.04 mmol) in dioxane (0.3 ml) was treated with HCl 4N in dioxane (0.09 ml) and the reaction mixture was stirred at room temperature overnight. After that 0.09 ml HCl 4N in dioxane was added again and the mixture was stirred additionally 16 h. The suspension was filtered and the resulting solid was washed with dioxane and dried under vacuum for 16 h to yield the title compound (15 mg, 81% of theory).

LC-MS (method 1B): RT=0.77 min, m/z=499 (M+H-HCl)+

1H-NMR (400 MHz, D2O): δ 8.48 (s, 1H), 8.33 (s, 3H), 8.16 (d, 1H), 8.05 (d, 1H), 6.25 (s, 1H), 3.69-3.59 (m, 3H), 3.26 (dd, 2H), 2.40 (d, 2H), 1.99 (dd, 2H).

Example 153

3-[3-(3-chlorophenyl)-1,2,4-oxadiazol-5-yl]-7-(piperidin-4-yl)pyrazolo[1,5-a]pyrimidin-5(4H)-one hydrochloride

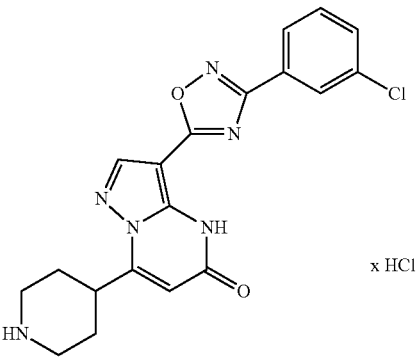 [SMILES: O=c1cc(C2CCNCC2)n2ncc(-c3nc(-c4cccc(Cl)c4)no3)c2[nH]1]

Tert-butyl 4-{3-[3-(3-chlorophenyl)-1,2,4-oxadiazol-5-yl]-5-oxo-4,5-dihydropyrazolo[1,5-a]pyrimidin-7-yl}piperidine-1-carboxylate (57.3 mg, 0.12 mmol) was dissolved in dioxane (1 mL) and treated with hydrochloric acid (4 M in dioxane, 2 mL) for 16 h at RT. Evaporation of the solvent yielded the title compound (40 mg, 74% of theory).

LC-MS (Method 5B): Rt=0.94 min, MS (ESIPos): m/z=397 [M+H-xHCl]+

$^1$H-NMR (500 MHz, D$_2$O): d [ppm]=8.29 (s, 1H), 7.72 (m, 2H), 7.45-7.33 (m, 2H), 6.15 (s, 1H), 3.66 (d, 2H), 3.46 (t, 1H), 3.26 (t, 2H), 2.38 (d, 2H), 1.97 (dd, 2H)

Example 154

3-[3-(4-methoxy-2-methylphenyl)-1,2,4-oxadiazol-5-yl]-7-(piperidin-4-yl)pyrazolo[1,5-a]pyrimidin-5(4H)-one hydrochloride

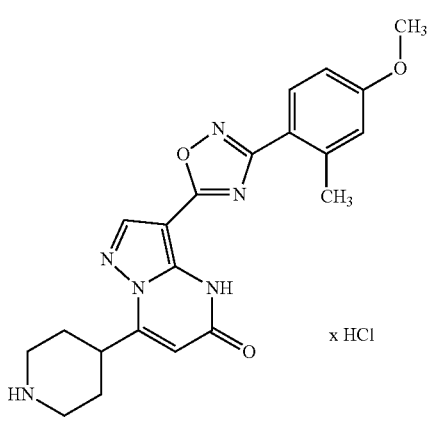 [SMILES: COc1ccc(-c2noc(-c3cnn4c(C5CCNCC5)cc(=O)[nH]c34)n2)c(C)c1]

Tert-butyl 4-{3-[3-(4-methoxy-2-methylphenyl)-1,2,4-oxadiazol-5-yl]-5-oxo-4,5-dihydropyrazolo[1,5-a]pyrimidin-7-yl}piperidine-1-carboxylate (55.8 mg, 0.12 mmol) was dissolved in dioxane (1 mL) and treated with hydrochlorid acid (4 M in dioxane, 2 mL) for 16 h at RT. Evaporation of the solvent yielded the title compound (47 mg, 89% of theory).

LC-MS (Method 1B): Rt=0.72 min, MS (ESIPos): m/z=407 [M+H-xHCl]+

$^1$H-NMR (500 MHz, D$_2$O): d [ppm]=8.27 (s, 1H), 7.70 (d, 1H), 6.77-6.69 (m, 1H), 6.58 (s, 1H), 6.12 (s, 1H), 3.79 (s, 3H), 3.70-3.62 (m, 1H), 3.47-3.36 (m, 2H), 3.26 (dd, 2H), 2.39-2.31 (m, 2H), 2.28 (s, 3H), 1.96 (dd, 2H)

Example 155

7-(piperidin-4-yl)-3-{3-[2-(trifluoromethoxy)phenyl]-1,2,4-oxadiazol-5-yl}pyrazolo[1,5-a]pyrimidin-5(4H)-one hydrochloride

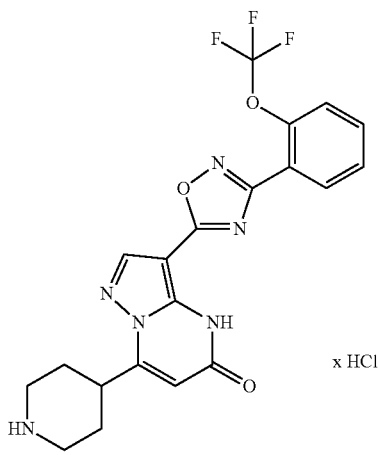 [SMILES: O=c1cc(C2CCNCC2)n2ncc(-c3nc(-c4ccccc4OC(F)(F)F)no3)c2[nH]1]

Tert-butyl 4-(5-oxo-3-{3-[2-(trifluoromethoxy)phenyl]-1,2,4-oxadiazol-5-yl}-4,5-dihydropyrazolo[1,5-a]pyrimidin-7-yl)piperidine-1-carboxylate (49.7 mg, 0.09 mmol) was dissolved in dioxane (1 mL) and treated with hydrochloric acid (4 M in dioxane, 2 mL) for 16 h at RT. Evaporation of the solvent yielded the title compound (47 mg, 99% of theory).

LC-MS (Method 5B): Rt=0.94 min, MS (ESIPos): m/z=447 [M+H-xHCl]+

$^1$H-NMR (500 MHz, D$_2$O): d [ppm]=8.30 (s, 1H), 7.96 (d, 1H), 7.64-7.59 (m, 1H), 7.46 (br. s., 2H), 6.16 (s, 1H), 3.48 (t, 1H), 3.25 (t, 2H), 3.65 (d, 2H), 3.65 (d, 2H), 2.01-1.92 (m, 2H)

Example 156

3-[3-(4-methoxyphenyl)-1,2,4-oxadiazol-5-yl]-7-(piperidin-4-yl)pyrazolo[1,5-a]pyrimidin-5(4H)-one hydrochloride

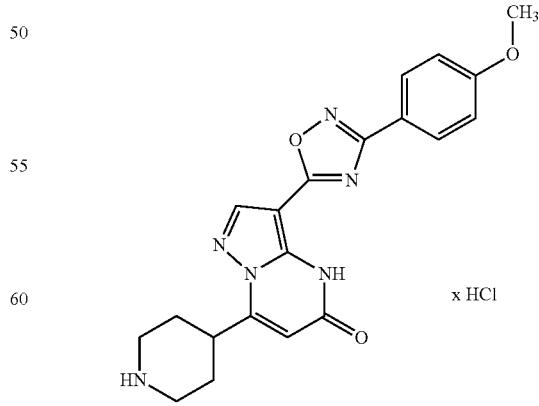

Tert-butyl 4-{3-[3-(4-methoxyphenyl)-1,2,4-oxadiazol-5-yl]-5-oxo-4,5-dihydropyrazolo[1,5-a]pyrimidin-7- yl}piperidine-1-carboxylate (37.4 mg, 0.08 mmol) was dissolved in dioxane (1 mL) and treated with hydrochloric acid (4 M in dioxane, 2 mL) for 16 h at RT. Evaporation of the solvent yielded the title compound (35 mg, 98% of theory).

LC-MS (Method 5B): Rt=0.86 min, MS (ESIPos): m/z=393 [M+H-xHCl]$^+$ $^1$H-NMR (500 MHz, D$_2$O): d [ppm]=8.18 (s, 1H), 7.49 (d, 2H), 6.72 (d, 2H), 6.05 (s, 1H), 3.79-3.73 (m, 3H), 3.66 (d, 2H), 3.36 (t, 1H), 3.25 (t, 2H), 2.33 (d, 2H), 1.93 (q, 2H)

Example 157

3-[3-(4-chlorophenyl)-1,2,4-oxadiazol-5-yl]-7-(piperidin-4-yl)pyrazolo[1,5-a]pyrimidin-5 (4H)-one hydrochloride

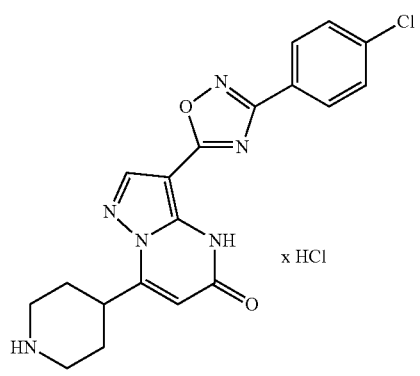 [SMILES: O=c1cc(C2CCNCC2)n2ncc(-c3nc(-c4ccc(Cl)cc4)no3)c2[nH]1]

Tert-butyl 4-{3-[3-(4-chlorophenyl)-1,2,4-oxadiazol-5-yl]-5-oxo-4,5-dihydropyrazolo[1,5-a]pyrimidin-7-yl}piperidine-1-carboxylate (49.0 mg, 0.10 mmol) was dissolved in dioxane (1 mL) and treated with hydrochloric acid (4 M in dioxane, 2 mL) for 16 h at RT. Evaporation of the solvent yielded the title compound (19 mg, 37% of theory).

LC-MS (Method 1B): Rt=0.72 min, MS (ESIPos): m/z=397 [M+H-xHCl]$^+$ $^1$H-NMR (400 MHz, DMSO-d6): d [ppm]=12.31 (br. s., 1H), 9.05-8.68 (m, 2H), 8.68-8.55 (m, 1H), 8.22 (d, 2H), 7.73-7.61 (m, 2H), 6.22 (br. s., 1H), 3.66-3.58 (m, 1H), 3.42 (d, 2H), 3.20-3.02 (m, 2H), 2.22 (d, 2H), 2.02-1.82 (m, 2H)

Example 158

3-[3-(2,4-difluorophenyl)-1,2,4-oxadiazol-5-yl]-7-(piperidin-4-yl)pyrazolo[1,5-a]pyrimidin-5(4H)-one hydrochloride

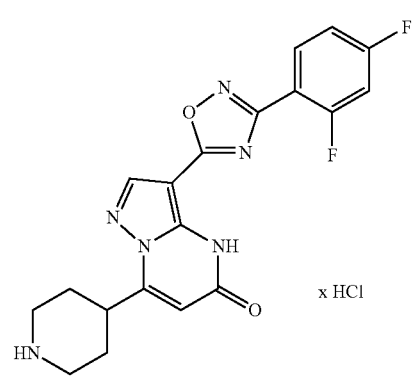 [SMILES: O=c1cc(C2CCNCC2)n2ncc(-c3nc(-c4ccc(F)cc4F)no3)c2[nH]1]

Tert-butyl 4-{3-[3-(2,4-difluorophenyl)-1,2,4-oxadiazol-5-yl]-5-oxo-4,5-dihydropyrazolo[1,5-a]pyrimidin-7-yl}piperidine-1-carboxylate (36.2 mg, 0.07 mmol) was dissolved in dioxane (1 mL) and treated with hydrochloric acid (4 M in dioxane, 2 mL) for 16 h at RT. Evaporation of the solvent yielded the title compound (34 mg, 98% of theory).

LC-MS (Method 5B): Rt=0.85 min, MS (ESIPos): m/z=399 [M+H-xHCl]$^+$ $^1$H-NMR (500 MHz, D$_2$O): d [ppm]=8.36 (br. s., 1H), 7.98 (d, 1H), 7.12-7.06 (m, 2H), 6.18 (s, 1H), 3.66 (d, 2H), 3.53 (t, 1H), 3.27 (t, 2H), 2.39 (d, 2H), 2.03-1.93 (m, 2H)

Example 159

3-[3-(2-fluorophenyl)-1,2,4-oxadiazol-5-yl]-7-(piperidin-4-yl)pyrazolo[1,5-a]pyrimidin-5(4H)-one hydrochloride

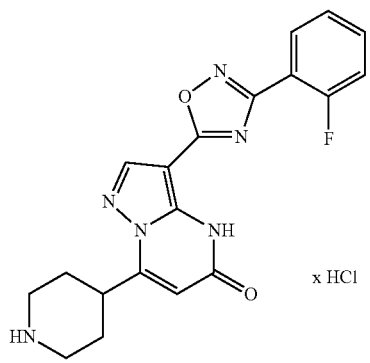 [SMILES: O=c1cc(C2CCNCC2)n2ncc(-c3nc(-c4ccccc4F)no3)c2[nH]1]

Tert-butyl 4-{3-[3-(2-fluorophenyl)-1,2,4-oxadiazol-5-yl]-5-oxo-4,5-dihydropyrazolo[1,5-a]pyrimidin-7-yl}piperidine-1-carboxylate (52.9 mg, 0.11 mmol) was dissolved in dioxane (1 mL) and treated with hydrochloric acid (4 M in dioxane, 2 mL) for 16 h at RT. Evaporation of the solvent yielded the title compound (45 mg, 89% of theory).

LC-MS (Method 5B): Rt=0.82 min, MS (ESIPos): m/z=381 [M+H-xHCl]$^+$ $^1$H-NMR (500 MHz, D$_2$O): d [ppm]=8.30 (s, 1H), 7.88 (t, 1H), 7.55-7.50 (m, 1H), 7.29-7.25 (m, 1H), 7.22-7.17 (m, 1H), 6.09 (s, 1H), 3.65 (d, 2H), 3.41 (t, 1H), 3.25 (t, 2H), 2.34 (d, 2H), 1.99-1.90 (m, 2H)

Example 160

3-[3-(2-methoxyphenyl)-1,2,4-oxadiazol-5-yl]-7-(piperidin-4-yl)pyrazolo[1,5-a]pyrimidin-5(4H)-one hydrochloride

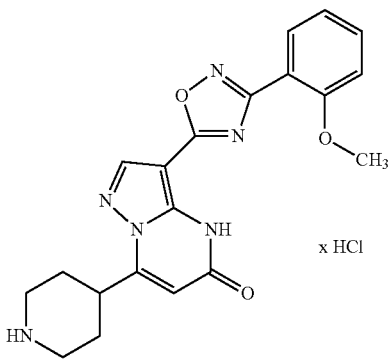 [SMILES: COc1ccccc1-c1noc(-c2cnn3c(C4CCNCC4)cc(=O)[nH]c23)n1]

Tert-butyl 4-{3-[3-(2-methoxyphenyl)-1,2,4-oxadiazol-5-yl]-5-oxo-4,5-dihydropyrazolo[1,5-a]pyrimidin-7-yl}piperidine-1-carboxylate (54.5 mg, 0.11 mmol) was dissolved in dioxane (1 mL) and treated with hydrochloric acid (4 M in dioxane, 2 mL) for 16 h at RT. Evaporation of the solvent yielded the title compound (51 mg, 98% of theory).

LC-MS (Method 5B): Rt=0.8 min, MS (ESIPos): m/z=393 [M+H-xHCl]$^+$ $^1$H-NMR (500 MHz, D$_2$O): d [ppm]=8.20 (s, 1H), 7.71 (d, 1H), 7.33 (t, 1H), 6.94-6.89 (m, 2H), 6.05 (s, 1H), 3.82 (s, 3H), 3.69-3.62 (m, 2H), 3.34-3.20 (m, 2H), 2.31 (d, 2H), 1.97-1.88 (m, 2H)

Example 161

7-(piperidin-4-yl)-3-[4'-(trifluoromethyl)biphenyl-4-yl]pyrazolo[1,5-a]pyrimidin-5(4H)-one hydrochloride

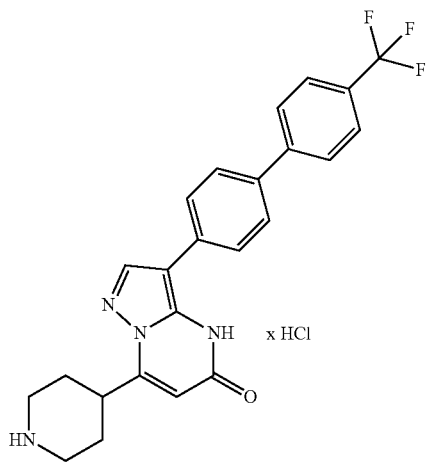 [SMILES: O=c1cc(C2CCNCC2)n2ncc(-c3ccc(-c4ccc(C(F)(F)F)cc4)cc3)c2[nH]1]

Tert-butyl 4-{5-oxo-3-[4'-(trifluoromethyl)biphenyl-4-yl]-4,5-dihydropyrazolo[1,5-a]pyrimidin-7-yl}piperidine-1-carboxylate (34.0 mg, 0.06 mmol) was dissolved in dichloromethane and treated with hydrochloric acid (4 M in dioxane, 2 mL) for 16 h at RT. The resulting solid was washed with dichloromethane and subjected to preparative HPLC (method 1A). The product fractions were treated with hydrochloric acid (4 M in dioxane). Evaporation of the solvent yielded the title compound (20 mg, 64% of theory).

LC-MS (Method 1B): Rt=0.79 min, MS (ESIPos): m/z=439 [M+H-xHCl]$^+$

Example 162

7-(piperidin-4-yl)-3-[4'-(trifluoromethyl)biphenyl-3-yl]pyrazolo[1,5-a]pyrimidin-5(4H)-one hydrochloride

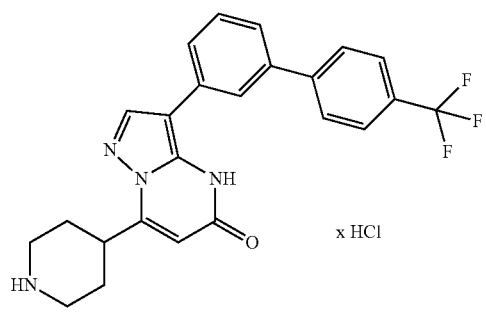 [SMILES: O=c1cc(C2CCNCC2)n2ncc(-c3cccc(-c4ccc(C(F)(F)F)cc4)c3)c2[nH]1]

Tert-butyl 4-{5-oxo-3-[4'-(trifluoromethyl)biphenyl-3-yl]-4,5-dihydropyrazolo[1,5-a]pyrimidin-7-yl}piperidine-1-carboxylate (155.0 mg, 0.29 mmol) was dissolved in dichloromethane and treated with hydrochloric acid (4 M in dioxane, 4 mL) for 16 h at RT. The resulting solid was washed with dichloromethane and subjected to preparative HPLC (method 1A). The product fractions were treated with hydrochloric acid (4 M in dioxane). Evaporation of the solvent yielded the title compound (132 mg, 92% of theory).

LC-MS (Method 1B): Rt=0.77 min, MS (ESIPos): m/z=439 [M+H-xHCl]$^+$

Example 163

3-[4-(3-chlorophenyl)-1,3-thiazol-2-yl]-7-(piperidin-4-yl)pyrazolo[1,5-a]pyrimidin-5 (4H)-one hydrochloride

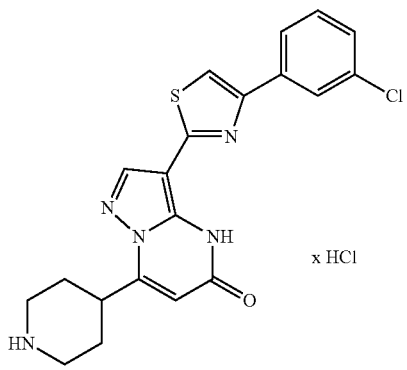 [SMILES: O=c1cc(C2CCNCC2)n2ncc(-c3nc(-c4cccc(Cl)c4)cs3)c2[nH]1]

Tert-butyl 4-{3-[4-(3-chlorophenyl)-1,3-thiazol-2-yl]-5-oxo-4,5-dihydropyrazolo[1,5-a]pyrimidin-7-yl}piperidine-1-carboxylate (120.0 mg, 0.23 mmol) was dissolved in dichloromethane and treated with hydrochloric acid (4 M in dioxane, 2 mL) for 16 h at RT. Evaporation of the solvent yielded the title compound (115 mg, quantitative).

LC-MS (Method 1B): Rt=0.76 min, MS (ESIPos): m/z=412 [M+H-xHCl]$^+$ $^1$H-NMR (400 MHz, DMSO-d6): d [ppm]=8.88 (br. s., 1H), 8.67 (br. s., 1H), 8.54 (br. s., 1H), 8.25-8.13 (m, 2H), 8.05 (d, 1H), 7.51 (t, 1H), 7.43 (dd, 1H), 6.24 (br. s, 1H), 3.57 (s, 1H), 3.53-3.38 (m, 2H), 3.19-3.07 (m, 2H), 2.25 (d, 2H), 1.99-1.87 (m, 2H)

Example 164

7-(piperidin-4-yl)-3-{4-[4-(trifluoromethyl)phenyl]-1,3-thiazol-2-yl}pyrazolo[1,5-a]pyrimidin-5(4H)-one hydrochloride

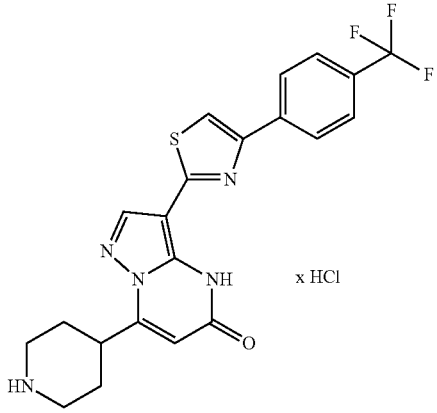 [SMILES: O=c1cc(C2CCNCC2)n2ncc(-c3nc(-c4ccc(C(F)(F)F)cc4)cs3)c2[nH]1]

Tert-butyl 4-(5-oxo-3-{4-[4-(trifluoromethyl)phenyl]-1,3-thiazol-2-yl}-4,5-dihydropyrazolo[1,5-a]pyrimidin-7-yl)piperidine-1-carboxylate (50.0 mg, 0.09 mmol) was dissolved in dichloromethane and treated with hydrochloric acid (4 M in dioxane, 2 mL) for 16 h at RT. Evaporation of the solvent yielded the title compound (46 mg, 98% of theory).

LC-MS (Method 1B): Rt=0.79 min, MS (ESIPos): m/z=446 [M+H-xHCl]$^+$ $^1$H-NMR (400 MHz, DMSO-d6): d [ppm]=8.88 (br. s., 1H), 8.69 (br. s., 1H), 8.56 (br. s., 1H), 8.32 (d, 2H), 8.26 (s, 1H), 7.84 (d, 2H), 6.25 (br. s., 1H), 3.57 (s, 1H), 3.52-3.39 (m, 2H), 3.20-3.07 (m, 2H), 2.25 (d, 2H), 1.99-1.87 (m, 2H)

Example 165

3-(5-tert-butyl-1,3,4-oxadiazol-2-yl)-7-(piperidin-4-yl)pyrazolo[1,5-a]pyrimidin-5 (4H)-one hydrochloride

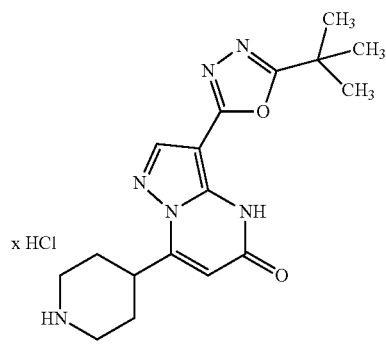 [SMILES: CC(C)(C)c1nnc(-c2cnn3c(C4CCNCC4)cc(=O)[nH]c23)o1]

tert-butyl 4-[3-(5-tert-butyl-1,3,4-oxadiazol-2-yl)-5-oxo-4,5-dihydropyrazolo[1,5-a]pyrimidin-7-yl]piperidine-1-carboxylate (145.6 mg, 0.11 mmol) was dissolved in 1,4-dioxan (5 mL) and treated with hydrochloric acid (4 M solution in 1,4-dioxan, 1.65 mL, 6.6 mmol) for 2 h at RT. More hydrochloric acid (4 M solution in 1,4-dioxan, 1.65 mL, 6.6 mmol) was added and left for 6 d at RT. The resulting solid was filtered and washed with acetonitrile to afford the title compound (77.6 mg, 59% of theory).

LC-MS (Method 5B): R$_t$=0.50 min, MS (ESIPos): m/z=343 [M+H-xHCl]$^+$ $^1$H-NMR (400 MHz, DMSO-d$_6$): δ=ppm 8.78 (br. s, 1H), 8.53 (br. s, 1H), 8.37 (s, 1H), 5.94-6.26 (m, 1H), 3.42 (br. s, 1H), 2.99-3.19 (m, 3H), 2.11-2.28 (m, 2H), 1.75-1.98 (m, 2H), 1.43 (s, 9H).

Example 166

7-(piperidin-4-yl)-3-{5-[4-(trifluoromethyl)phenyl]-1,3,4-oxadiazol-2-yl}pyrazolo[1,5-a]pyrimidin-5 (4H)-one hydrochloride

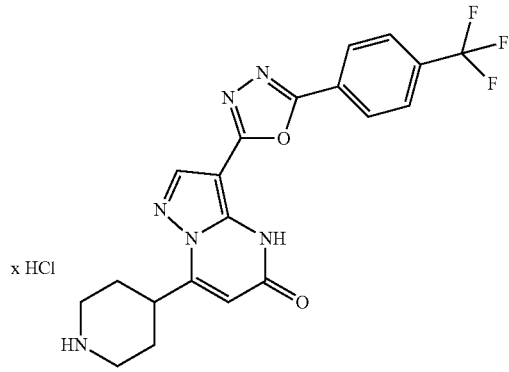 [SMILES: O=c1cc(C2CCNCC2)n2ncc(-c3nnc(-c4ccc(C(F)(F)F)cc4)o3)c2[nH]1]

tert-butyl 4-(5-oxo-3-{5-[4-(trifluoromethyl)phenyl]-1,3,4-oxadiazol-2-yl}-4,5-dihydropyrazolo[1,5-a]pyrimidin-7-yl)piperidine-1-carboxylate (109 mg, 0.21 mmol) was dissolved in 1,4-dioxan (2 mL) and treated with hydrochloric acid (4 M solution in 1,4-dioxan, 0.77 mL, 3.1 mmol) for 16

589 h at RT. The mixture was purified via reverse phase HPLC (gradient acetonitrile/water with 0.01% formic acid). The resulting residue was treated with 1,4-dioxan (2 mL) and hydrochloric acid (4 M solution in 1,4-dioxan, 0.77 mL, 3.1 mmol). The solvent was removed in vacuo which afforded the title compound (37.3 mg, 37% of theory).

LC-MS (Method 5B): $R_t$=0.66 min, MS (ESIPos): m/z=431 [M+H-xHCl]$^+$ $^1$H-NMR (400 MHz, DMSO-d$_6$): δ=ppm 12.58 (br. s, 1H), 8.83 (br. s, 1H), 8.63 (br. s, 1H), 8.54 (s, 1H), 8.37-8.47 (m, 2H), 7.99-8.06 (m, 2H), 6.15 (br. s, 1H), 3.56-3.67 (m, 1H), 3.38-3.48 (m, 2H), 3.06-3.20 (m, 2H), 2.11-2.31 (m, 2H), 1.77-2.03 (m, 2H).

Example 167

4-{5-[5-oxo-7-(piperidin-4-yl)-4,5-dihydropyrazolo[1,5-a]pyrimidin-3-yl]-1,3,4-oxadiazol-2-yl}benzonitrile hydrochloride

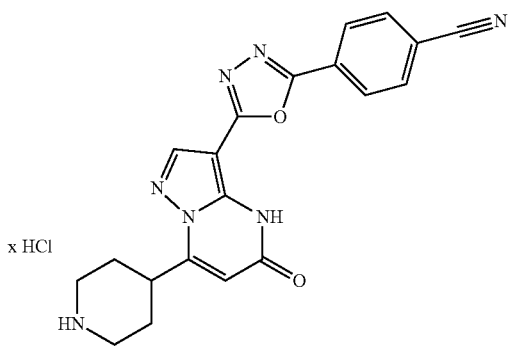 [SMILES: N#Cc1ccc(-c2nnc(-c3cnn4c(C5CCNCC5)cc(=O)[nH]c34)o2)cc1]

tert-butyl 4-{3-[5-(4-cyanophenyl)-1,3,4-oxadiazol-2-yl]-5-oxo-4,5-dihydropyrazolo[1,5-a]pyrimidin-7-yl}piperidine-1-carboxylate (72 mg, 0.21 mmol) was dissolved in 1,4-dioxan (2 mL) and treated with hydrochloric acid (4 M solution in 1,4-dioxan, 0.55 mL, 2.2 mmol) for 16 h at RT. Acetonitrile was added to the mixture and the resulting residue was filtered, washed with acetonitrile and dried. The residue was purified via reverse phase HPLC (gradient acetonitrile/water with 0.01% formic acid). The resulting residue was treated with 1,4-dioxan (2 mL) and hydrochloric acid (4 M solution in 1,4-dioxan, 0.77 mL, 3.1 mmol). The solvent was removed in vacuo which afforded the title compound (32 mg, 51% of theory).

LC-MS (Method 5B): $R_t$=0.50 min, MS (ESIPos): m/z=388.2 [M+H-xHCl]$^+$ $^1$H-NMR (400 MHz, DMSO-d$_6$): δ=ppm 9.04 (br. s, 2H), 8.82 (br. s, 1H), 8.55 (s, 1H), 8.40 (d, 2H), 8.13 (d, 2H), 6.14 (br. s., 1H), 3.58-3.65 (m, 1H), 3.32-3.45 (m, 2H), 3.12 (dd, 2H), 2.22 (m, 2H), 1.93 (m, 3H).

590

Example 168

3-[5-(1-methyl-1H-imidazol-5-yl)-1,3,4-oxadiazol-2-yl]-7-(piperidin-4-yl)pyrazolo[1,5-a]pyrimidin-5(4H)-one hydrochloride

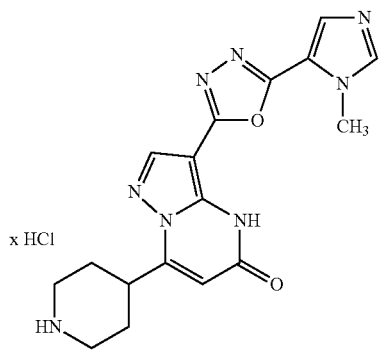 [SMILES: Cn1cncc1-c1nnc(-c2cnn3c(C4CCNCC4)cc(=O)[nH]c23)o1]

tert-butyl 4-{3-[5-(1-methyl-1H-imidazol-5-yl)-1,3,4-oxadiazol-2-yl]-5-oxo-4,5-dihydropyrazolo[1,5-a]pyrimidin-7-yl}piperidine-1-carboxylate (39 mg, 0.08 mmol) was dissolved in 1,4-dioxan (2 mL) and treated with hydrochloric acid (4 M solution in 1,4-dioxan, 0.313 mL, 1.3 mmol) for 16 h at RT. Acetonitrile was added to the mixture and the resulting residue was filtered, washed with acetonitrile and dried to afford the title compound (25 mg, 67% of theory).

LC-MS (Method 7B): $R_t$=1.25 min, MS (ESIPos): m/z=367.1 [M+H-xHCl]$^+$ $^1$H-NMR (500 MHz, D$_2$O) δ=ppm 9.06 (s, 1H), 8.43 (s, 1H), 8.36 (s, 1H), 6.25 (s, 1H), 4.28 (s, 3H), 3.61-3.71 (m, 3H), 3.21-3.32 (m, 2H), 2.38-2.47 (m, 2H), 1.94-2.07 (m, 2H).

Example 169

3-[5-(3-chlorophenyl)-1,3,4-oxadiazol-2-yl]-7-(piperidin-4-yl)pyrazolo[1,5-a]pyrimidin-5(4H)-one hydrochloride

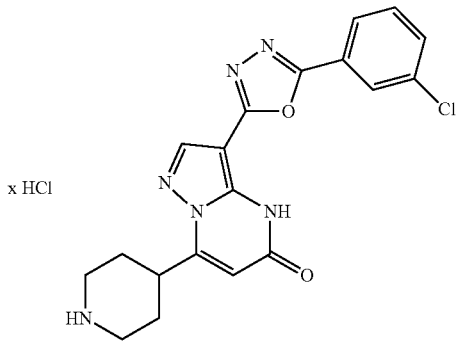 [SMILES: O=c1cc(C2CCNCC2)n2ncc(-c3nnc(-c4cccc(Cl)c4)o3)c2[nH]1]

tert-butyl 4-{3-[5-(3-chlorophenyl)-1,3,4-oxadiazol-2-yl]-5-oxo-4,5-dihydropyrazolo[1,5-a]pyrimidin-7-yl}piperidine-1-carboxylate (150 mg, 0.3 mmol) was dissolved in 1,4-dioxan (2.5 mL) and treated with hydrochloric acid (4 M solution in 1,4-dioxan, 1.13 mL, 4.5 mmol) for 16 h at RT. Acetonitrile was added to the mixture and the resulting residue was filtered, washed with acetonitrile and dried to afford the title compound (25 mg, 67% of theory).

LC-MS (Method 5B): $R_t$=0.61 min, MS (ESIPos): m/z=397.3 [M+H-xHCl]$^+$ $^1$H-NMR (400 MHz, DMSO-d$_6$) δ=ppm 9.15 (br. s., 1H), 8.99 (br. s, 1H), 8.54 (s, 1H), 8.27 (s, 1H), 8.17 (d, 1H), 7.63-7.75 (m, 2H), 6.13 (s, 1H), 3.55-3.64 (m, 1H), 3.41 (m, 2H), 2.99-3.18 (m, 2H), 2.22 (m, 2H), 1.81-2.03 (m, 2H).

Example 170

3-[5-(4-methylphenyl)-1,3,4-oxadiazol-2-yl]-7-(piperidin-4-yl)pyrazolo[1,5-a]pyrimidin-5 (4H)-one hydrochloride

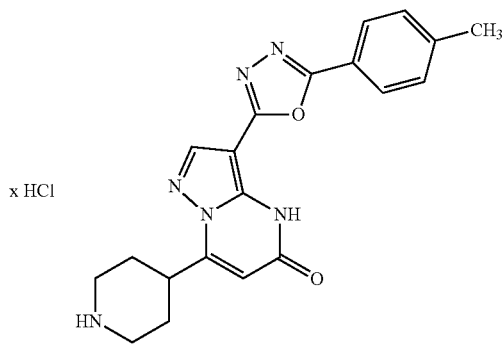 [SMILES: Cc1ccc(-c2nnc(-c3cnn4c(C5CCNCC5)cc(=O)[nH]c34)o2)cc1]

tert-butyl 4-(3-{[2-(4-methylbenzoyl)hydrazino]carbonyl}-5-oxo-4,5-dihydropyrazolo[1,5-a]pyrimidin-7-yl)piperidine-1-carboxylate (100 mg, 0.2 mmol) were dissolved in tetrahydrofurane (2.5 ml) and treated with Methyl N-(triethylammoniosulfonyl)carbamate (67.6 mg, 0.28 mmol) for 16 h at RT. More Methyl N-(triethylammoniosulfonyl)carbamate (67.6 mg, 0.28 mmol) was added and stirred for 1 h at RT. Hydrochloric acid (4 M solution in 1,4-dioxan, 0.76 mL, 3.0 mmol) was added and the mixture was stirred for 16 h at RT. The mixture was purified via reverse phase HPLC (gradient acetonitrile/water with 0.01% formic acid). The resulting residue was treated with 1,4-dioxan (2 mL) and hydrochloric acid (4 M solution in 1,4-dioxan, 1 mL). The solvent was removed in vacuo which afforded the title compound (8 mg, 10% of theory).

LC-MS (Method 5B): $R_t$=0.60 min, MS (ESIPos): m/z=377.3 [M+H-xHCl]$^+$ $^1$H-NMR (400 MHz, DMSO-d$_6$) δ=ppm 12.50 (br. s, 1H), 8.86 (br. s, 1H), 8.64 (br. s, 1H), 8.50 (s, 1H), 8.09 (d, 2H), 7.41 (d, 2H), 6.11 (br. s, 1H), 3.54-3.65 (m, 1H), 3.38-3.46 (m, 2H), 3.03-3.19 (m, 2H), 2.42 (s, 3H), 2.18-2.27 (m, 2H), 1.81-1.99 (m, 2H).

Example 171

3-[5-(2-methylphenyl)-1,3,4-oxadiazol-2-yl]-7-(piperidin-4-yl)pyrazolo[1,5-a]pyrimidin-5(4H)-one hydrochloride

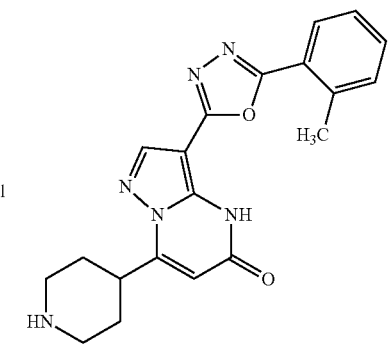

tert-butyl 4-(3-{[2-(2-methylbenzoyl)hydrazino]carbonyl}-5-oxo-4,5-dihydropyrazolo[1,5-a]pyrimidin-7-yl)piperidine-1-carboxylate (112 mg, 0.23 mmol) were dissolved in tetrahydrofurane (2.5 ml) and treated with Methyl N-(triethylammoniosulfonyl)carbamate (75.8 mg, 0.32 mmol) for 16 h at RT. More Methyl N-(triethylammoniosulfonyl)carbamate (75.8 mg, 0.32 mmol) was added and stirred for 1 h at RT. Hydrochloric acid (4 M solution in 1,4-dioxan, 0.85 mL, 3.4 mmol) was added and the mixture was stirred for 16 h at RT. The mixture was purified via reverse phase HPLC (gradient acetonitrile/water with 0.01% formic acid). The resulting residue was treated with 1,4-dioxan (2 mL) and hydrochloric acid (4 M solution in 1,4-dioxan, 1 mL). The solvent was removed in vacuo which afforded the title compound (46 mg, 49% of theory).

LC-MS (Method 5B): $R_t$=0.58 min, MS (ESIPos): m/z=377.2 [M+H-xHCl]$^+$ $^1$H-NMR (400 MHz, DMSO-d6) δ=ppm 8.98 (s, 1H), 8.78 (br. s, 1H), 8.52 (s, 1H), 8.09-8.19 (m, 1H), 7.38-7.58 (m, 3H), 6.15 (br. s, 1H), 3.36-3.45 (m, 3H), 3.04-3.16 (m, 2H), 2.68 (s, 3H), 2.16-2.27 (m, 2H), 1.83-2.01 (m, 2H).

Example 172

7-(piperidin-4-yl)-3-{5-[2-(trifluoromethyl)phenyl]-1,3,4-oxadiazol-2-yl}pyrazolo[1,5-a]pyrimidin-5 (4H)-one hydrochloride

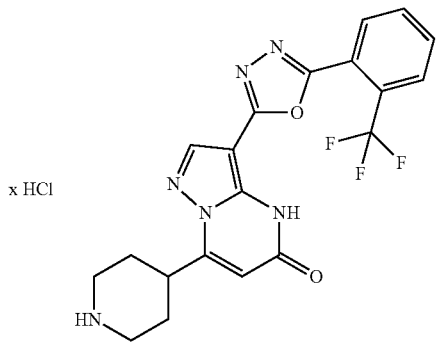 [SMILES: O=c1cc(C2CCNCC2)n2ncc(-c3nnc(-c4ccccc4C(F)(F)F)o3)c2[nH]1]

tert-butyl 4-[5-oxo-3-({2-[2-(trifluoromethyl)benzoyl]hydrazino}carbonyl)-4,5-dihydropyrazolo[1,5-a]pyrimidin-7-yl]piperidine-1-carboxylate (106 mg, 0.2 mmol) were dissolved in tetrahydrofurane (5 ml) and treated with Methyl N-(triethylammoniosulfonyl)carbamate (55.2 mg, 0.23 mmol) for 16 h at RT. More Methyl N-(triethylammoniosulfonyl)carbamate (55.2 mg, 0.23 mmol) was added and stirred for 1 h at RT. Hydrochloric acid (4 M solution in 1,4-dioxan, 0.72 mL, 2.9 mmol) was added and the mixture was stirred for 16 h at RT. The mixture was purified via reverse phase HPLC (gradient acetonitrile/water with 0.01% formic acid). The resulting residue was treated with 1,4-dioxan (2 mL) and hydrochloric acid (4 M solution in 1,4-dioxan, 1 mL). The solvent was removed in vacuo which afforded the title compound (45 mg, 50% of theory).

LC-MS (Method 5B): $R_t$=0.59 min, MS (ESIPos): m/z=431.2 [M+H-xHCl]$^+$ $^1$H-NMR (400 MHz, DMSO-$d_6$) δ=ppm 8.68 (br. s, 1H), 8.48 (s, 1H), 8.37 (br. s, 1H), 8.17 (d, 1H), 8.04 (d, 1H), 7.86-8.00 (m, 2H), 6.18 (s, 1H), 3.61-3.67 (m, 1H), 3.38-3.48 (m, 2H), 3.06-3.20 (m, 2H), 2.18-2.28 (m, 2H), 1.80-1.96 (m, 2H).

Example 173

3-[5-(methoxymethyl)-1,3,4-oxadiazol-2-yl]-7-(piperidin-4-yl)pyrazolo[1,5-a]pyrimidin-5(4H)-one hydrochloride

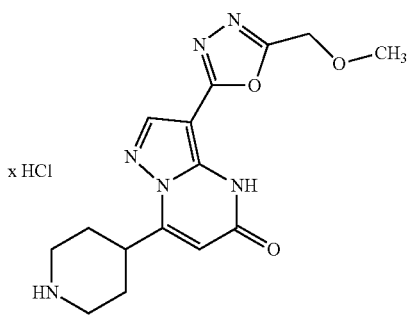 [SMILES: COCc1nnc(-c2cnn3c(C4CCNCC4)cc(=O)[nH]c23)o1]

tert-butyl 4-{3-[5-(methoxymethyl)-1,3,4-oxadiazol-2-yl]-5-oxo-4,5-dihydropyrazolo[1,5-a]pyrimidin-7-yl}piperidine-1-carboxylate (35 mg, 0.08 mmol) was dissolved in 1,4-dioxan (2.5 mL) and treated with hydrochloric acid (4 M solution in 1,4-dioxan, 0.3 mL, 1.2 mmol) for 16 h at RT. Acetonitrile was added to the mixture and the resulting residue was filtered, washed with acetonitrile and dried to afford the title compound (24 mg, 75% of theory).

LC-MS (Method 5B): $R_t$=0.21 min, MS (ESIPos): m/z=331.3 [M+H-xHCl]$^+$ $^1$H-NMR (400 MHz, DMSO-$d_6$) δ=ppm 9.03 (br. s, 1H), 8.78 (br. s, 1H), 8.46 (s, 1H), 6.16 (br. s, 1H), 4.70 (s, 2H), 3.52-3.64 (m, 4H), 3.32-3.40 (m, 2H), 2.98-3.17 (m, 2H), 2.13-2.27 (m, 2H), 1.80-1.98 (m, 2H).

Example 174

3-(5-cyclopropyl-1,3,4-oxadiazol-2-yl)-7-(piperidin-4-yl)pyrazolo[1,5-a]pyrimidin-5 (4H)-one hydrochloride

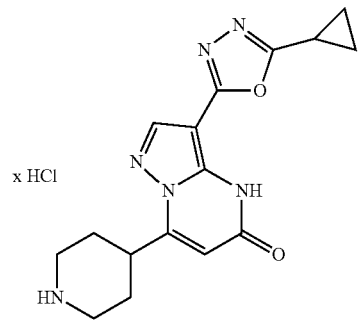 [SMILES: O=c1cc(C2CCNCC2)n2ncc(-c3nnc(C4CC4)o3)c2[nH]1]

tert-butyl 4-[3-(5-cyclopropyl-1,3,4-oxadiazol-2-yl)-5-oxo-4,5-dihydropyrazolo[1,5-a]pyrimidin-7-yl]piperidine-1-carboxylate (43 mg, 0.08 mmol) was dissolved in 1,4-dioxan (2.5 mL) and treated with hydrochloric acid (4 M solution in 1,4-dioxan, 0.38 mL, 1.5 mmol) for 16 h at RT. Acetonitrile was added to the mixture and the resulting residue was filtered, washed with acetonitrile and dried to afford the title compound (33 mg, 86% of theory).

LC-MS (Method 5B): $R_t$=0.37 min, MS (ESIPos): m/z=327.3 [M+H-xHCl]$^+$ $^1$H-NMR (400 MHz, DMSO-d6) δ=ppm 8.86-9.32 (m, 2H), 8.37 (s, 1H), 6.09 (br. s, 1H), 3.51-3.65 (m, 1H), 3.39 (m, 2H), 3.09 (m, 2H), 2.24-2.31 (m, 1H), 2.19 (m, 2H), 1.94 (m, 2H), 1.08-1.18 (m, 4H).

Example 175

7-(piperidin-4-yl)-3-{5-[3-(trifluoromethyl)phenyl]-1,3,4-oxadiazol-2-yl}pyrazolo[1,5-a]pyrimidin-5 (4H)-one hydrochloride

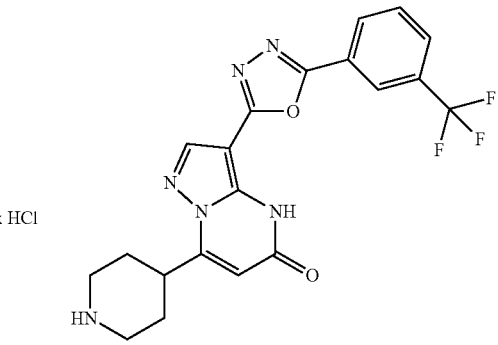

tert-butyl 4-(5-oxo-3-{5-[3-(trifluoromethyl)phenyl]-1,3,4-oxadiazol-2-yl}-4,5-dihydropyrazolo[1,5-a]pyrimidin-7-yl)piperidine-1-carboxylate (113.5 mg, 0.21 mmol) was dissolved in 1,4-dioxan (2.5 mL) and treated with hydrochloric acid (4 M solution in 1,4-dioxan, 1.07 mL, 4.3 mmol) for 2 h at RT. More hydrochloric acid (4 M solution in 1,4-dioxan, 1.07 mL, 4.3 mmol) was added and stirred for 4 h at RT. Solvents were removed in vacuo and the resulting residue washed with acetonitrile and dried to afford the title compound (50 mg, 47% of theory).

LC-MS (Method 5B): R$_t$=0.63 min, MS (ESIPos): m/z=431.2 [M+H-xHCl]$^+$ $^1$H-NMR (400 MHz, DMSO-d6) δ=ppm 9.16 (br. s, 1H), 8.97 (br. s, 1H), 8.42-8.59 (m, 3H), 8.03 (d, 1H), 7.84-7.95 (m, 1H), 6.13 (br. s., 1H), 3.60 (t, 1H), 3.41 (m, 2H), 3.11 (m, 2H), 2.22 (m, 2H), 1.95 (m, 2H).

Example 176

3-[5-(4-methoxybenzyl)-1,3,4-oxadiazol-2-yl]-7-(piperidin-4-yl)pyrazolo[1,5-a]pyrimidin-5(4H)-one hydrochloride

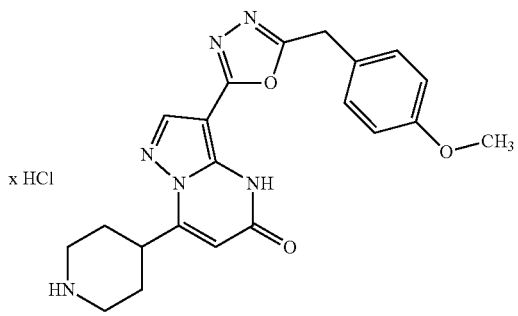 [SMILES: COc1ccc(Cc2nnc(-c3cnn4c(C5CCNCC5)cc(=O)[nH]c34)o2)cc1]

tert-butyl 4-{3-[5-(4-methoxybenzyl)-1,3,4-oxadiazol-2-yl]-5-oxo-4,5-dihydropyrazolo[1,5-a]pyrimidin-7-yl}piperidine-1-carboxylate (190 mg, 0.38 mmol) was dissolved in 1,4-dioxan (2.5 mL) and treated with hydrochloric acid (4 M solution in 1,4-dioxan, 1.41 mL, 5.6 mmol) for 16 h at RT. Acetonitrile was added to the mixture and the resulting residue was filtered, washed with acetonitrile and dried to afford the title compound (34 mg, 18% of theory).

LC-MS (Method 5B): R$_t$=0.54 min, MS (ESIPos): m/z=407.4 [M+H-xHCl]$^+$ $^1$H-NMR (500 MHz, D$_2$O) δ=ppm 8.01 (s, 1H), 7.14 (d, 2H), 6.74 (d, 2H), 6.16 (s, 1H), 4.07 (s, 1H), 3.61-3.76 (m, 5H), 3.46-3.58 (m, 1H), 3.21-3.36 (m, 2H), 2.39 (m, 2H), 1.92-2.10 (m, 2H).

Example 177

3-(5-cyclopentyl-1,3,4-oxadiazol-2-yl)-7-(piperidin-4-yl)pyrazolo[1,5-a]pyrimidin-5(4H)-one hydrochloride

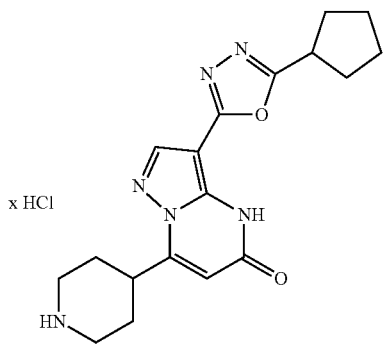 [SMILES: O=c1cc(C2CCNCC2)n2ncc(-c3nnc(C4CCCC4)o3)c2[nH]1]

tert-butyl 4-[3-(5-cyclopentyl-1,3,4-oxadiazol-2-yl)-5-oxo-4,5-dihydropyrazolo[1,5-a]pyrimidin-7-yl]piperidine-1-carboxylate (170 mg, 0.37 mmol) was dissolved in 1,4-dioxan (2.5 mL) and treated with hydrochloric acid (4 M solution in 1,4-dioxan, 1.4 mL, 4.3 mmol) for 2 h at RT. Acetonitrile was added to the mixture and the resulting residue was filtered, washed with acetonitrile and dried to afford the title compound (34 mg, 18% of theory).

LC-MS (Method 5B): R$_t$=0.52 min, MS (ESIPos): m/z=355.3 [M+H-xHCl]$^+$ $^1$H-NMR (500 MHz, D$_2$O) δ=ppm 8.19 (s, 1H), 6.18 (s, 1H), 3.71 (m, 2H), 3.52-3.62 (m, 1H), 3.37-3.45 (m, 1H), 3.31 (m, 2H), 2.84-3.11 (m, 1H), 2.43 (m, 2H), 2.14-2.24 (m, 2H), 2.03 (m, 2H), 1.72-1.95 (m, 6H).

Example 178

3-[5-(2-furyl)-1,3,4-oxadiazol-2-yl]-7-(piperidin-4-yl)pyrazolo[1,5-a]pyrimidin-5 (4H)-one hydrochloride

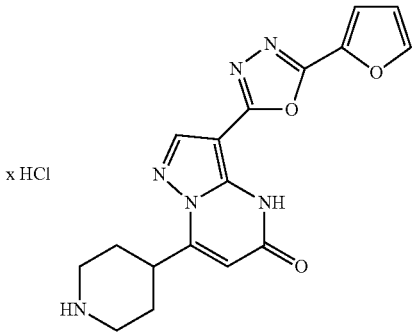 [SMILES: O=c1cc(C2CCNCC2)n2ncc(-c3nnc(-c4ccco4)o3)c2[nH]1]

tert-butyl 4-{3-[5-(2-furyl)-1,3,4-oxadiazol-2-yl]-5-oxo-4,5-dihydropyrazolo[1,5-a]pyrimidin-7-yl}piperidine-1-carboxylate (90 mg, 0.20 mmol) was dissolved in 1,4-dioxan (2.5 mL) and treated with hydrochloric acid (4 M solution in 1,4-dioxan, 0.75 mL, 2.9 mmol) for 16 h at RT. Acetonitrile was added to the mixture and the resulting residue was filtered, washed with acetonitrile and dried to afford the title compound (38 mg, 45% of theory).

LC-MS (Method 5B): R$_t$=0.44 min, MS (ESIPos): m/z=353.3 [M+H-xHCl]$^+$ $^1$H-NMR (500 MHz, D$_2$O) δ=ppm 9.11 (br. s, 1H), 8.87 (br. s, 1H), 8.49 (s, 1H), 8.08 (d, 1H), 7.49 (d, 1H), 6.83 (dd, 1H), 6.15 (br. s., 1H), 3.58 (m, 1H), 3.41 (m, 2H), 3.11 (m, 2H), 2.22 (m, 2H), 1.93 (m, 2H).

Example 179

3-[5-(4-tert-butylphenyl)-1,3,4-oxadiazol-2-yl]-7-(piperidin-4-yl)pyrazolo[1,5-a]pyrimidin-5 (4H)-one hydrochloride

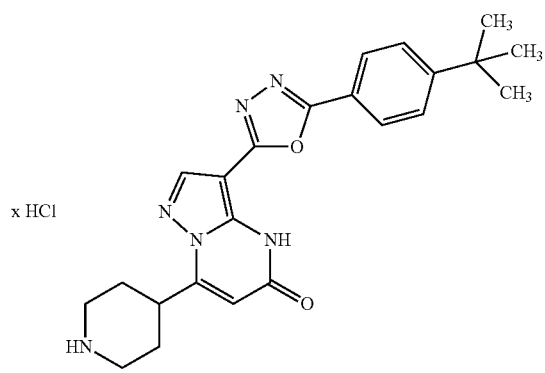 [SMILES: CC(C)(C)c1ccc(-c2nnc(-c3cnn4c(C5CCNCC5)cc(=O)[nH]c34)o2)cc1]

tert-butyl 4-{3-[5-(4-tert-butylphenyl)-1,3,4-oxadiazol-2-yl]-5-oxo-4,5-dihydropyrazolo[1,5-a]pyrimidin-7-yl}piperidine-1-carboxylate (160 mg, 0.31 mmol) was dissolved in 1,4-dioxan (2.5 mL) and treated with hydrochloric acid (4 M solution in 1,4-dioxan, 1.16 mL, 4.6 mmol) for 16 h at RT.
More hydrochloric acid (4 M solution in 1,4-dioxan, 1.16 mL, 4.6 mmol) was added and stirred for 4 h at RT. Acetonitrile was added to the mixture and the resulting residue was filtered, washed with acetonitrile and dried to afford the title compound (86.7 mg, 62% of theory).

LC-MS (Method 5B): $R_t$=0.72 min, MS (ESIPos): m/z=419.3 [M+H-xHCl]$^+$ $^1$H-NMR (500 MHz, D$_2$O) δ=ppm 9.16 (br. s, 1H), 8.94 (br. s, 1H), 8.51 (s, 1H), 8.11 (d, 2H), 7.65 (d, 2H), 6.12 (br. s., 1H), 3.57-3.64 (m, 1H), 3.41 (m, 2H), 3.11 (m, 3H), 2.22 (m, 2H), 1.95 (m, 2H), 1.33 (s, 9H).

Example 180

3-(5-benzyl-1,3,4-oxadiazol-2-yl)-7-(piperidin-4-yl)pyrazolo[1,5-a]pyrimidin-5(4H)-one hydrochloride

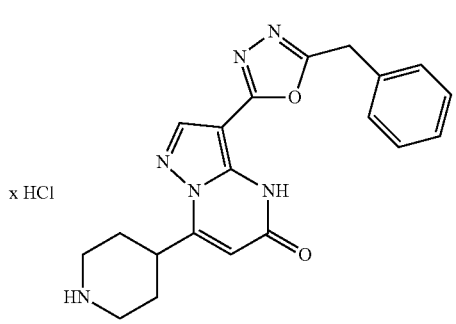 [SMILES: O=c1cc(C2CCNCC2)n2ncc(-c3nnc(Cc4ccccc4)o3)c2[nH]1]

tert-butyl 4-[3-(5-benzyl-1,3,4-oxadiazol-2-yl)-5-oxo-4,5-dihydropyrazolo[1,5-a]pyrimidin-7-yl]piperidine-1-carboxylate (100 mg, 0.21 mmol) was dissolved in 1,4-dioxan (2.5 mL) and treated with hydrochloric acid (4 M solution in 1,4-dioxan, 0.79 mL, 3.2 mmol) for 16 h at RT. More hydrochloric acid (4 M solution in 1,4-dioxan, 0.79 mL, 3.2 mmol) was added and stirred for 20 h at RT. Acetonitrile was added to the mixture and the resulting residue was filtered, washed with acetonitrile and dried to afford the title compound (40 mg, 42% of theory).

LC-MS (Method 5B): $R_t$=0.51 min, MS (ESIPos): m/z=377.2 [M+H-xHCl]$^+$ $^1$H-NMR (500 MHz, D$_2$O) δ=ppm 9.09 (br. s., 1H), 8.92 (br. s, 1H), 8.39 (s, 1H), 7.25-7.43 (m, 5H), 6.11 (br. s, 1H), 4.32 (s, 2H), 3.51-3.63 (m, 1H), 3.39 (m, 2H), 3.00-3.19 (m, 2H), 2.19 (m, 2H), 1.82-2.01 (m, 2H).

Example 181

3-[5-(4-chlorophenyl)-1,3,4-oxadiazol-2-yl]-7-(piperidin-4-yl)pyrazolo[1,5-a]pyrimidin-5(4H)-one hydrochloride

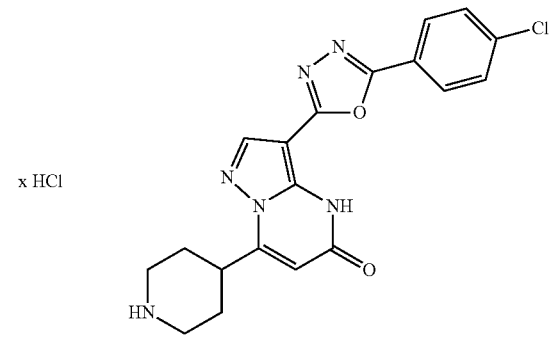 [SMILES: O=c1cc(C2CCNCC2)n2ncc(-c3nnc(-c4ccc(Cl)cc4)o3)c2[nH]1]

tert-butyl 4-{3-[5-(4-chlorophenyl)-1,3,4-oxadiazol-2-yl]-5-oxo-4,5-dihydropyrazolo[1,5-a]pyrimidin-7-yl}piperidine-1-carboxylate (70 mg, 0.14 mmol) was dissolved in 1,4-dioxan (2.5 mL) and treated with hydrochloric acid (4 M solution in 1,4-dioxan, 0.53 mL, 2.1 mmol) for 16 h at RT. Acetonitrile was added to the mixture and the resulting residue was filtered, washed with acetonitrile and dried to afford the title compound (25 mg, 37% of theory).

LC-MS (Method 5B): $R_t$=0.60 min, MS (ESIPos): m/z=397.3 [M+H-xHCl]$^+$ $^1$H-NMR (400 MHz, DMSO-d$_6$) δ=ppm 8.99 (br. s, 1H), 8.77 (br. s, 1H), 8.52 (s, 1H), 8.23 (d, 2H), 7.72 (d, 2H), 6.13 (s, 1H), 3.53-3.65 (m, 1H), 3.36-3.45 (m, 2H), 3.02-3.17 (m, 2H), 2.22 (m, 2H), 1.78-2.00 (m, 2H).

Example 182

3-[5-(cyclohexylmethyl)-1,3,4-oxadiazol-2-yl]-7-(piperidin-4-yl)pyrazolo[1,5-a]pyrimidin-5 (4H)-one hydrochloride

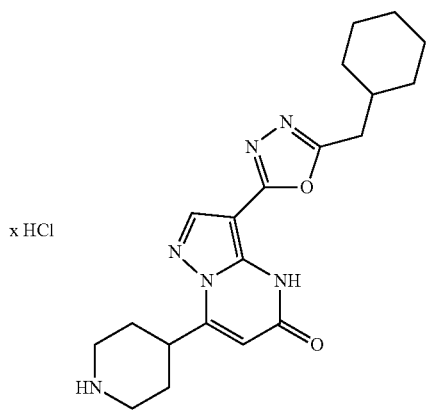 [SMILES: O=c1cc(C2CCNCC2)n2ncc(-c3nnc(CC4CCCCC4)o3)c2[nH]1]

tert-butyl 4-{3-[5-(cyclohexylmethyl)-1,3,4-oxadiazol-2-yl]-5-oxo-4,5-dihydropyrazolo[1,5-a]pyrimidin-7-yl}piperidine-1-carboxylate (96 mg, 0.20 mmol) was dissolved in 1,4-dioxan (2.5 mL) and treated with hydrochloric acid (4 M solution in 1,4-dioxan, 0.74 mL, 2.9 mmol) for 16 h at RT. Acetonitrile was added to the mixture and the resulting residue was filtered, washed with acetonitrile and dried to afford the title compound (82 mg, 99% of theory).

LC-MS (Method 5B): $R_t$=0.63 min, MS (ESIPos): m/z=383.4 [M+H-xHCl]$^+$ $^1$H-NMR (500 MHz, DMSO-d$_6$) δ=ppm 9.14 (m, 1H), 9.01 (m, 1H), 8.39 (s, 1H), 6.09 (br. s., 1H), 3.53-3.63 (m, 1H), 3.39 (d, 2H), 3.02-3.14 (m, 2H), 2.79 (d, 2H), 2.20 (m, 2H), 1.78-2.01 (m, 3H), 1.57-1.74 (m, 5H), 1.10-1.27 (m, 3H), 0.98-1.09 (m, 2H).

Example 183

3-[5-(2-methylpyridin-4-yl)-1,3,4-oxadiazol-2-yl]-7-(piperidin-4-yl)pyrazolo[1,5-a]pyrimidin-5(4H)-one hydrochloride

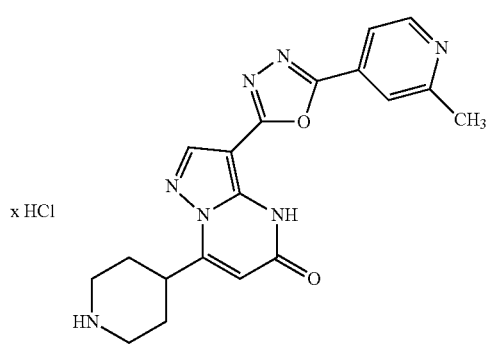 [SMILES: Cc1cc(-c2nnc(-c3cnn4c(C5CCNCC5)cc(=O)[nH]c34)o2)ccn1]

tert-butyl 4-{3-[5-(2-methylpyridin-4-yl)-1,3,4-oxadiazol-2-yl]-5-oxo-4,5-dihydropyrazolo[1,5-a]pyrimidin-7-yl}piperidine-1-carboxylate (21 mg, 0.04 mmol) was dissolved in 1,4-dioxan (1 mL) and treated with hydrochloric acid (4 M solution in 1,4-dioxan, 0.02 mL, 0.65 mmol) for 16 h at RT. Acetonitrile was added to the mixture and the resulting residue was filtered, washed with acetonitrile and dried to afford the title compound (20 mg, 99% of theory).

LC-MS (Method 5B): $R_t$=0.39 min, MS (ESIPos): m/z=378.3 [M+H-xHCl]$^+$ $^1$H-NMR (500 MHz, DMSO-d6) δ=ppm 11.99-12.39 (m, 1H), 9.00-9.12 (m, 1H), 8.89-8.98 (m, 1H), 8.86 (d, 1H), 8.59 (s, 1H), 8.19-8.32 (m, 2H), 6.17 (br. s., 1H), 3.59 (m, 1H), 3.34-3.44 (m, 2H), 3.00-3.17 (m, 2H), 2.73 (s, 3H), 2.22 (d, 2H), 1.94 (m, 2H).

Example 184

3-[5-(2-methoxyphenyl)-1,3,4-oxadiazol-2-yl]-7-(piperidin-4-yl)pyrazolo[1,5-a]pyrimidin-5(4H)-one hydrochloride

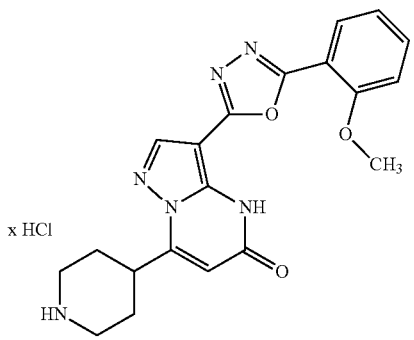 [SMILES: COc1ccccc1-c1nnc(-c2cnn3c(C4CCNCC4)cc(=O)[nH]c23)o1]

tert-butyl 4-{3-[5-(2-methoxyphenyl)-1,3,4-oxadiazol-2-yl]-5-oxo-4,5-dihydropyrazolo[1,5-a]pyrimidin-7-yl}piperidine-1-carboxylate (52 mg, 0.11 mmol) was dissolved in 1,4-dioxan (2.5 mL) and treated with hydrochloric acid (4 M solution in 1,4-dioxan, 0.39 mL, 1.58 mmol) for 16 h at RT. Acetonitrile was added to the mixture and the resulting residue was filtered, washed with acetonitrile and dried to afford the title compound (46 mg, quantitative).

LC-MS (Method 5B): $R_t$=0.53 min, MS (ESIPos): m/z=393.3 [M+H-xHCl]$^+$ $^1$H-NMR (500 MHz, DMSO-d$_6$) δ=ppm 9.19 (m, 1H), 9.06 (m, 1H), 8.48 (s, 1H), 7.97 (dd, 1H), 7.62 (ddd, 1H), 7.29 (d, 1H), 7.13-7.20 (m, 1H), 6.14 (s, 1H), 3.92 (s, 3H), 3.55-3.65 (m, 1H), 3.40 (m, 2H), 3.04-3.16 (m, 2H), 2.22 (m, 2H), 1.89-2.01 (m, 2H).

Example 185

7-(piperidin-4-yl)-3-[5-(pyridin-4-yl)-1,3,4-oxadiazol-2-yl]pyrazolo[1,5-a]pyrimidin-5 (4H)-one hydrochloride

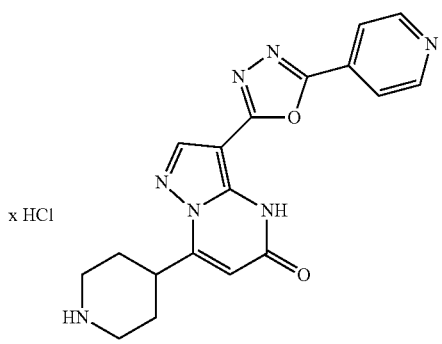 [SMILES: O=c1cc(C2CCNCC2)n2ncc(-c3nnc(-c4ccncc4)o3)c2[nH]1]

tert-butyl 4-{5-oxo-3-[5-(pyridin-4-yl)-1,3,4-oxadiazol-2-yl]-4,5-dihydropyrazolo[1,5-a]pyrimidin-7-yl}piperidine-1-carboxylate (63 mg, 0.14 mmol) was dissolved in 1,4-dioxan (2.5 mL) and treated with hydrochloric acid (4 M solution in 1,4-dioxan, 0.51 mL, 2.03 mmol) for 16 h at RT. Acetonitrile was added to the mixture and the resulting residue was filtered, washed with acetonitrile and dried to afford the title compound (54 mg, 94% of theory).

LC-MS (Method 5B): $R_t$=0.39 min, MS (ESIPos): m/z=364.3 [M+H-xHCl]$^+$ $^1$H-NMR (500 MHz, DMSO-d6) δ=ppm 9.01-9.11 (m, 1H), 8.96 (d, 2H), 8.81-8.94 (m, 1H), 8.58 (s, 1H), 8.33 (d, 2H), 6.16 (br. s., 1H), 3.58 (m, 1H), 3.41 (m, 2H), 3.11 (m, 2H), 2.22 (m, 2H), 1.94 (m, 2H).

Example 186

3-[5-(2-fluorophenyl)-1,3,4-oxadiazol-2-yl]-7-(piperidin-4-yl)pyrazolo[1,5-a]pyrimidin-5(4H)-one hydrochloride

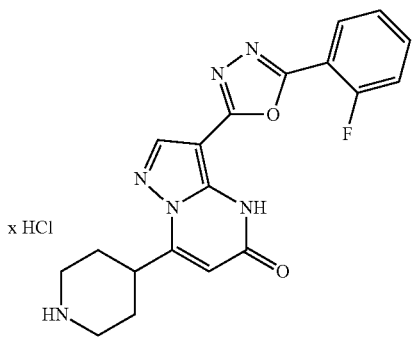 [SMILES: O=c1cc(C2CCNCC2)n2ncc(-c3nnc(-c4ccccc4F)o3)c2[nH]1]

tert-butyl 4-{3-[5-(2-fluorophenyl)-1,3,4-oxadiazol-2-yl]-5-oxo-4,5-dihydropyrazolo[1,5-a]pyrimidin-7-yl}piperidine-1-carboxylate (74 mg, 0.15 mmol) was dissolved in 1,4-dioxan (2.5 mL) and treated with hydrochloric acid (4 M solution in 1,4-dioxan, 0.58 mL, 2.3 mmol) for 16 h at RT. Acetonitrile was added to the mixture and the resulting residue was filtered, washed with acetonitrile and dried to afford the title compound (56 mg, 87% of theory).

LC-MS (Method 5B): $R_t$=0.53 min, MS (ESIPos): m/z=381.3 [M+H-xHCl]$^+$ $^1$H-NMR (500 MHz, DMSO-d6) δ=ppm 9.00 (m, 1H), 8.83 (m, 1H), 8.51 (s, 1H), 8.23 (t, 1H), 7.63-7.76 (m, 1H), 7.40-7.56 (m, 2H), 6.15 (br. s., 1H), 3.56-3.65 (m, 1H), 3.03-3.17 (m, 2H), 2.22 (m, 2H), 1.86-1.99 (m, 2H) (one signal hidden below solvent peak).

Example 187

3-(4-methyl-2-phenyl-1,3-thiazol-5-yl)-7-(piperidin-4-yl)pyrazolo[1,5-a]pyrimidin-5(4H)-one hydrochloride

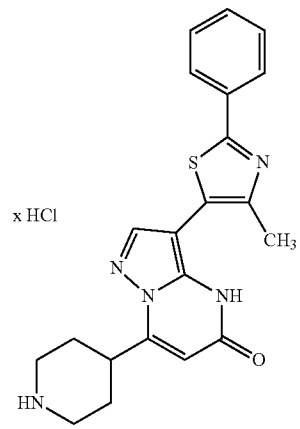 [SMILES: Cc1nc(-c2ccccc2)sc1-c1cnn2c(C3CCNCC3)cc(=O)[nH]c12]

tert-butyl 4-[3-(4-methyl-2-phenyl-1,3-thiazol-5-yl)-5-oxo-4,5-dihydropyrazolo[1,5-a]pyrimidin-7-yl]piperidine-1-carboxylate (45 mg, 0.09 mmol) was dissolved in 1,4-dioxan (2 mL) and treated with hydrochloric acid (4 M solution in 1,4-dioxan, 0.46 mL, 1.8 mmol) for 16 h at RT. Solvents were removed in vacuo to afford the title compound (44 mg, 98% of theory).

LC-MS (Method 5B): $R_t$=0.61 min, MS (ESIPos): m/z=392.3 [M+H-xHCl]$^+$ $^1$H-NMR (400 MHz, D20-d6) δ=ppm 7.90-8.00 (m, 1H), 7.78-7.86 (m, 2H), 7.44-7.64 (m, 3H), 5.95-6.12 (m, 1H), 3.55-3.69 (m, 2H), 3.41-3.51 (m, 1H), 3.12-3.29 (m, 2H), 2.27-2.38 (m, 5H), 1.75-2.03 (m, 2H).

Example 188

7-(piperidin-4-yl)-3-{3-[6-(trifluoromethyl)pyridin-3-yl]-1,2,4-oxadiazol-5-yl}pyrazolo[1,5-a]pyrimidin-5(4H)-one hydrochloride

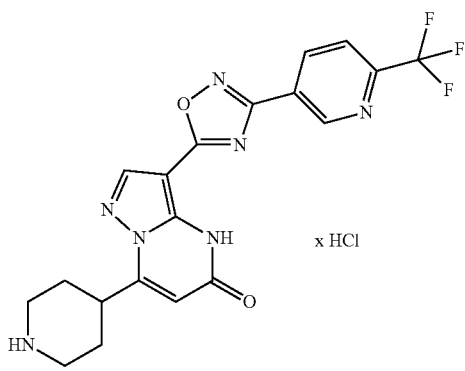 [SMILES: O=c1cc(C2CCNCC2)n2ncc(-c3nc(-c4ccc(C(F)(F)F)nc4)no3)c2[nH]1]

A suspension of compound tert-butyl 4-(5-oxo-3-{3-[6-(trifluoromethyl)pyridin-3-yl]-1,2,4-oxadiazol-5-yl}-4,5-dihydropyrazolo[1,5-a]pyrimidin-7-yl)piperidine-1-carboxylate (200 mg, 0.38 mmol) in 1,4-dioxan (2.0 ml) was treated with HCl 4N in 1,4-dioxan (4.0 ml). The reaction mixture was stirred overnight at RT. The suspension was filtered, washed with methanol (2.0 ml) and dried in vacuo overnight to yield the title compound (125 mg, 94% purity, 67% of theory).

LC-MS (Method 8B): $R_t$=0.82 min, MS (ESINeg): m/z=430 [M−H−xHCl]⁻

¹H-NMR (400 MHz, DMSO): δ=12.44 (bs, 1H), 9.56 (s, 1H), 8.94-8.81 (m, 1H), 8.75 (bs, 1H), 8.67 (s, 1H), 8.50 (bs, 1H), 8.17 (d, 1H), 6.23 (bs, 1H), 3.68-3.54 (m, 1H), 3.43 (d, 2H), 3.13 (t, 2H), 2.23 (d, 2H), 1.90 (q, 2H).

Example 189

7-(piperidin-4-yl)-3-{3-[4-(trifluoromethyl)pyridin-3-yl]-1,2,4-oxadiazol-5-yl}pyrazolo[1,5-a]pyrimidin-5(4H)-one hydrochloride

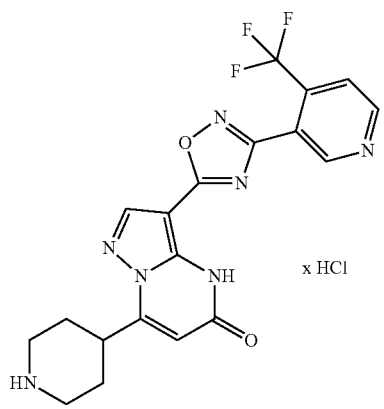 [SMILES: O=c1cc(C2CCNCC2)n2ncc(-c3nc(-c4cnccc4C(F)(F)F)no3)c2[nH]1]

A suspension of compound tert-butyl 4-(5-oxo-3-{3-[4-(trifluoromethyl)pyridin-3-yl]-1,2,4-oxadiazol-5-yl}-4,5-dihydropyrazolo[1,5-a]pyrimidin-7-yl)piperidine-1-carboxylate (110 mg, 0.21 mmol) in 1,4-dioxan (2.0 ml) was treated with HCl 4N in 1,4-dioxan (4.0 ml). The reaction mixture was stirred overnight at RT. The suspension was filtered, washed with diethylether (5.0 ml) and dried in vacuo overnight to yield the title compound (80 mg, 82% of theory).

LC-MS (Method 8B): $R_t$=0.77 min, MS (ESINeg): m/z=430 [M−H−xHCl]⁻

¹H-NMR (400 MHz, DMSO): δ=12.37 (bs, 1H), 9.39 (bs, 1H), 9.11 (d, 1H), 8.85 (bs, 1H), 8.72-8.51 (m, 2H), 8.05 (d, 1H), 6.28 (bs, 1H), 3.74-3.56 (m, 1H), 3.54-3.29 (m, 2H), 3.13 (q, 2H), 2.23 (d, 2H), 1.91 (q, 2H).

Example 190

7-(piperidin-4-yl)-3-[3-(2,4,5-trifluorophenyl)-1,2,4-oxadiazol-5-yl]pyrazolo[1,5-a]pyrimidin-5(4H)-one hydrochloride

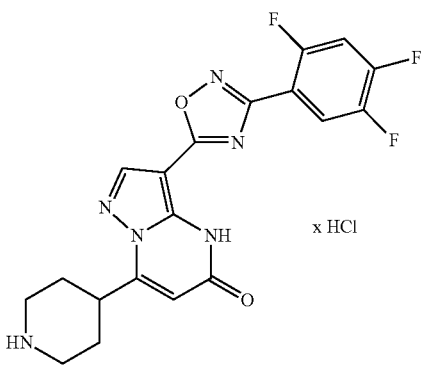 [SMILES: O=c1cc(C2CCNCC2)n2ncc(-c3nc(-c4cc(F)c(F)cc4F)no3)c2[nH]1]

A suspension of compound tert-tert-butyl 4-{5-oxo-3-[3-(2,4,5-trifluorophenyl)-1,2,4-oxadiazol-5-yl]-4,5-dihydropyrazolo[1,5-a]pyrimidin-7-yl}piperidine-1-carboxylate (65 mg, 0.13 mmol) in 1,4-dioxan (2.0 ml) was treated with HCl 4N in 1,4-dioxan (3.0 ml). The reaction mixture was stirred overnight at RT. The suspension was filtered, washed with diethylether (5.0 ml) and dried in vacuo overnight to yield the title compound (46 mg, 81% of theory).

LC-MS (Method 8B): $R_t$=0.87 min, MS (ESINeg): m/z=415 [M−H−xHCl]⁻

¹H-NMR (400 MHz, DMSO): δ=12.29 (bs, 1H), 8.90-8.43 (m, 4H), 7.86 (dt, 1H), 6.19 (bs, 1H), 3.65-3.53 (m, 1H), 3.42 (d, 2H), 3.13 (q, 2H), 2.22 (d, 2H), 1.89 (q, 2H).

Example 191

3-{3-[(methylsulfonyl)methyl]-1,2,4-oxadiazol-5-yl}-7-(piperidin-4-yl)pyrazolo[1,5-a]pyrimidin-5(4H)-one hydrochloride

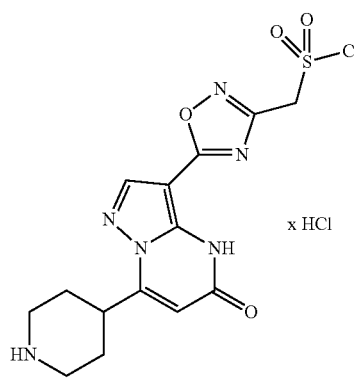

A suspension of compound tert-butyl 4-(3-{3-[(methylsulfonyl)methyl]-1,2,4-oxadiazol-5-yl}-5-oxo-4,5-dihydropyrazolo[1,5-a]pyrimidin-7-yl)piperidine-1-carboxylate (40 mg, 0.08 mmol) in 1,4-dioxan (2.0 ml) was treated with HCl 4N in 1,4-dioxan (4.0 ml). The reaction mixture was stirred overnight at RT. The suspension was concentrated, dissolved in water and lyophilized to yield the title compound (34 mg, 95% of theory).

LC-MS (Method 8B): $R_t$=0.22 min, MS (ESINeg): m/z=377 [M−H−xHCl]⁻

¹H-NMR (400 MHz, DMSO): δ=8.86 (bs, 1H), 8.62 (bs, 2H), 6.31 (bs, 1H), 4.86 (s, 2H), 3.74-3.53 (m, 1H), 3.42 (d, 2H), 3.25 (s, 3H), 3.12 (q, 2H), 2.22 (d, 2H), 1.91 (q, 2H).

Example 192

7-(piperidin-4-yl)-3-[3-(4,4,4-trifluorobutyl)-1,2,4-oxadiazol-5-yl]pyrazolo[1,5-a]pyrimidin-5(4H)-one hydrochloride

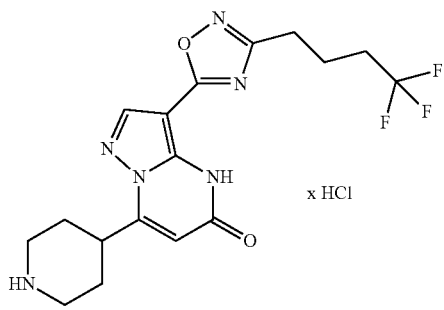 [SMILES: O=c1cc(C2CCNCC2)n2ncc(-c3nc(CCCC(F)(F)F)no3)c2[nH]1]

A suspension of compound Tert-butyl 4-{5-oxo-3-[3-(4,4,4-trifluorobutyl)-1,2,4-oxadiazol-5-yl]-4,5-dihydropyrazolo[1,5-a]pyrimidin-7-yl}piperidine-1-carboxylate (170 mg, 0.34 mmol) in 1,4-dioxan (2.0 ml) was treated with HCl 4N in 1,4-dioxan (4.0 ml). The reaction mixture was stirred overnight at RT. The suspension was concentrated, dissolved in water and lyophilized to yield the title compound (148 mg, 100% of theory).

LC-MS (Method 8B): $R_t$=0.77 min, MS (ESINeg): m/z=395 [M−H−xHCl]⁻

¹H-NMR (400 MHz, DMSO): δ=13.46-11.54 (m, 1H), 9.06 (bs, 1H), 8.91 (bs, 1H), 8.56 (s, 1H), 6.24 (bs, 1H), 3.61 (d, 1H), 3.52-3.28 (m, 2H), 3.10 (q, 2H), 2.86 (t, 2H), 2.47-2.33 (m, 2H), 2.21 (d, 2H), 2.01-1.86 (m, 4H).

Example 193

3-[3-(1-cyclopropylpiperidin-4-yl)-1,2,4-oxadiazol-5-yl]-7-(piperidin-4-yl)pyrazolo[1,5-a]pyrimidin-5(4H)-one hydrochloride

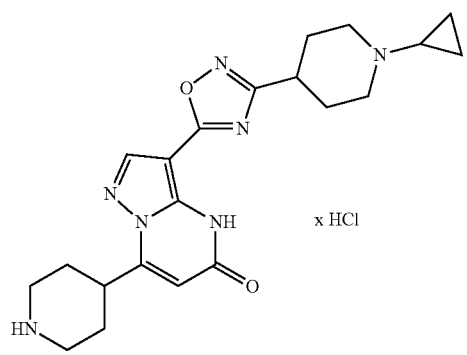 [SMILES: O=c1cc(C2CCNCC2)n2ncc(-c3nc(C4CCN(C5CC5)CC4)no3)c2[nH]1]

A suspension of compound tert-butyl 4-{3-[3-(1-cyclopropylpiperidin-4-yl)-1,2,4-oxadiazol-5-yl]-5-oxo-4,5-dihydropyrazolo[1,5-a]pyrimidin-7-yl}piperidine-1-carboxylate trifluoroacetate salt (148 mg, 0.29 mmol) in 1,4-dioxan (2.0 ml) was treated with HCl 4N in 1,4-dioxan (4.0 ml). The reaction mixture was stirred overnight at RT. The suspension was concentrated, dissolved in water and lyophilized to yield the title compound (101 mg, 72% of theory).

LC-MS (Method 7B): $R_t$=1.58 min, MS (ESINeg): m/z=408 [M−H−xHCl]⁻

¹H-NMR (400 MHz, DMSO): δ=13.29-11.66 (m, 1H), 10.57 (bs, 1H), 9.03 (bs, 1H), 8.88 (bs, 1H), 8.65-8.49 (m, 1H), 6.22 (bs, 1H), 3.65-3.33 (m, 6H), 3.21-3.03 (m, 3H), 2.79 (bs, 1H), 2.40-2.03 (m, 6H), 1.93 (q, 2H), 1.15 (bs, 2H), 0.95-0.74 (m, 2H).

Example 194

3-(3-tert-butyl-1,2,4-oxadiazol-5-yl)-7-(piperidin-4-yl)pyrazolo[1,5-a]pyrimidin-5(4H)-one hydrochloride

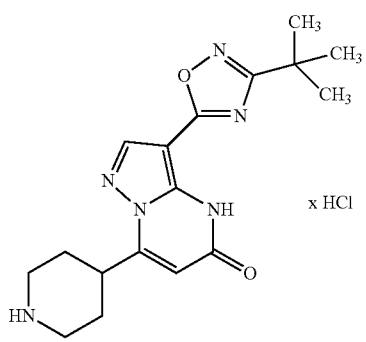 [SMILES: CC(C)(C)c1noc(-c2cnn3c(C4CCNCC4)cc(=O)[nH]c23)n1]

A suspension of compound tert-butyl 4-[3-(3-tert-butyl-1,2,4-oxadiazol-5-yl)-5-oxo-4,5-dihydropyrazolo[1,5-a]pyrimidin-7-yl]piperidine-1-carboxylate (173 mg, 0.39 mmol) in 1,4-dioxan (2.0 ml) was treated with HCl 4N in 1,4-dioxan (4.6 ml). The reaction mixture was stirred overnight at RT. The suspension was concentrated, dissolved in water and lyophilized to yield the title compound (138 mg, 93% of theory).

LC-MS (Method 8B): R$_t$=0.74 min, MS (ESINeg): m/z=341 [M−H−xHCl]$^-$ $^1$H-NMR (400 MHz, DMSO): δ=13.30-11.65 (m, 1H), 9.04 (bs, 1H), 8.89 (bs, 1H), 8.52 (s, 1H), 6.20 (bs, 1H), 3.60 (t, 1H), 3.40 (d, 2H), 3.10 (q, 2H), 2.21 (d, 2H), 1.93 (q, 2H), 1.37 (s, 9H).

Example 195

3-[3-(2-chloro-4-fluorobenzyl)-1,2,4-oxadiazol-5-yl]-7-(piperidin-4-yl)pyrazolo[1,5-a]pyrimidin-5(4H)-one hydrochloride

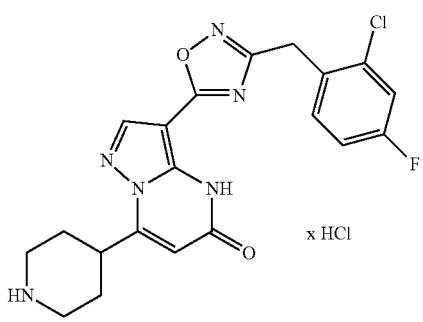 [SMILES: O=c1cc(C2CCNCC2)n2ncc(-c3nc(Cc4ccc(F)cc4Cl)no3)c2[nH]1]

A suspension of compound tert-butyl 4-{3-[3-(2-chloro-4-fluorobenzyl)-1,2,4-oxadiazol-5-yl]-5-oxo-4,5-dihydropyrazolo[1,5-a]pyrimidin-7-yl}piperidine-1-carboxylate (158 mg, 0.30 mmol) in 1,4-dioxan (2.0 ml) was treated with HCl 4N in 1,4-dioxan (3.5 ml). The reaction mixture was stirred overnight at RT. The suspension was concentrated, dissolved in water and lyophilized to yield the title compound (109 mg, 79% of theory).

LC-MS (Method 8B): R$_t$=0.90 min, MS (ESINeg): m/z=427 [M−H−xHCl]$^-$ $^1$H-NMR (400 MHz, DMSO): δ=13.28-11.68 (m, 1H), 8.98-8.84 (m, 1H), 8.78-8.64 (m, 1H), 8.54 (s, 1H), 7.55 (dd, 1H), 7.50 (dd, 1H), 7.26 (dt, 1H), 6.26 (bs, 1H), 4.24 (s, 2H), 3.67-3.53 (m, 1H), 3.41 (d, 2H), 3.10 (q, 2H), 2.21 (d, 2H), 1.90 (q, 2H).

Example 196

3-[3-(4-tert-butylphenyl)-1,2,4-oxadiazol-5-yl]-7-(piperidin-4-yl)pyrazolo[1,5-a]pyrimidin-5(4H)-one hydrochloride

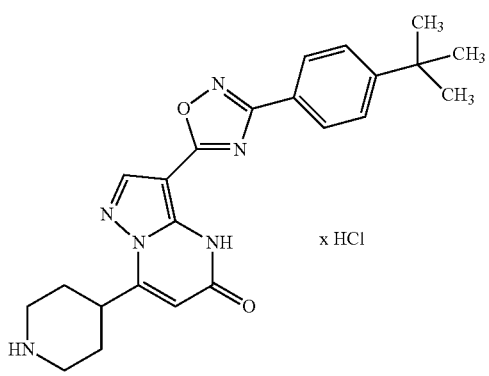 [SMILES: CC(C)(C)c1ccc(-c2noc(-c3cnn4c(C5CCNCC5)cc(=O)[nH]c34)n2)cc1]

A suspension of compound tert-butyl 4-{3-[3-(4-tert-butylphenyl)-1,2,4-oxadiazol-5-yl]-5-oxo-4,5-dihydropyrazolo[1,5-a]pyrimidin-7-yl}piperidine-1-carboxylate (110 mg, 0.21 mmol) in 1,4-dioxan (2.0 ml) was treated with HCl 4N in 1,4-dioxan (2.5 ml). The reaction mixture was stirred overnight at RT. The suspension was concentrated, dissolved in water and lyophilized to yield the title compound (78 mg, 82% of theory).

LC-MS (Method 8B): R$_t$=1.03 min, MS (ESINeg): m/z=417 [M−H−xHCl]$^-$ $^1$H-NMR (400 MHz, DMSO): δ=13.30-11.88 (m, 1H), 9.12-8.67 (m, 2H), 8.62 (s, 1H), 8.10 (d, 2H), 7.61 (d, 2H), 6.22 (bs, 1H), 3.62 (t, 1H), 3.42 (d, 2H), 3.12 (t, 2H), 2.23 (d, 2H), 1.93 (q, 2H), 1.34 (s, 9H).

Example 197

3-{3-[4-(dimethylamino)-3-fluorophenyl]-1,2,4-oxadiazol-5-yl}-7-(piperidin-4-yl)pyrazolo[1,5-a]pyrimidin-5(4H)-one hydrochloride

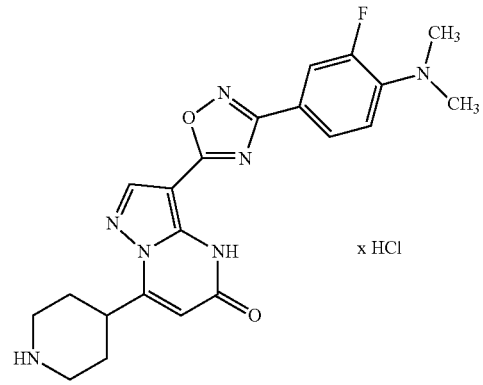 [SMILES: CN(C)c1ccc(-c2noc(-c3cnn4c(C5CCNCC5)cc(=O)[nH]c34)n2)cc1F]

A suspension of compound tert-butyl 4-(3-{3-[4-(dimethylamino)-3-fluorophenyl]-1,2,4-oxadiazol-5-yl}-5-oxo-4,5-dihydro pyrazolo[1,5-a]pyrimidin-7-yl)piperidine-1-carboxylate (65 mg, 0.12 mmol) in 1,4-dioxan (2.0 ml) was treated with HCl 4N in 1,4-dioxan (1.5 ml). The reaction mixture was stirred overnight at RT. The suspension was concentrated, dissolved in water and lyophilized to yield the title compound (56 mg, quantitative).

LC-MS (Method 8B): $R_t$=0.90 min, MS (ESINeg): m/z=422 [M−H−xHCl]⁻

¹H-NMR (400 MHz, DMSO): δ=12.19 (bs, 1H), 9.04 (bs, 1H), 8.85 (bs, 1H), 8.60 (s, 1H), 7.92 (d, 1H), 7.85 (d, 1H), 7.07 (t, 1H), 6.20 (bs, 1H), 3.70-3.53 (m, 1H), 3.41 (d, 2H), 3.11 (q, 2H), 2.93 (s, 6H), 2.22 (d, 2H), 1.93 (q, 2H).

Example 198

3-[3-(2-methylbenzyl)-1,2,4-oxadiazol-5-yl]-7-(piperidin-4-yl)pyrazolo[1,5-a]pyrimidin-5(4H)-one hydrochloride

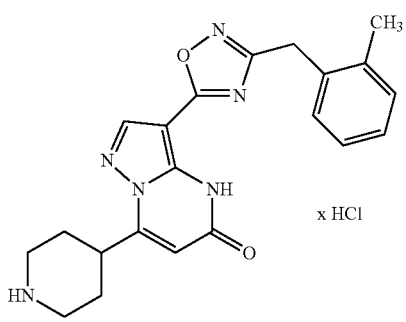 [SMILES: Cc1ccccc1Cc1noc(-c2cnn3c(C4CCNCC4)cc(=O)[nH]c23)n1]

A suspension of compound tert-butyl 4-{3-[3-(2-methylbenzyl)-1,2,4-oxadiazol-5-yl]-5-oxo-4,5-dihydropyrazolo[1,5-a]pyrimidin-7-yl}piperidine-1-carboxylate (155 mg, 0.31 mmol) in 1,4-dioxan (2.0 ml) was treated with HCl 4N in 1,4-dioxan (3.7 ml). The reaction mixture was stirred overnight at RT. The suspension was concentrated, dissolved in water and lyophilized to yield the title compound (118 mg, 86% of theory).

LC-MS (Method 8B): $R_t$=0.85 min, MS (ESINeg): m/z=389 [M−H−xHCl]⁻

¹H-NMR (400 MHz, DMSO): δ=13.43-11.47 (m, 1H), 9.04 (bs, 1H), 8.99 (bs, 1H), 8.82 (bs, 1H), 8.52 (s, 1H), 7.27-7.11 (m, 4H), 6.24 (bs, 1H), 4.11 (s, 2H), 3.60 (t, 1H), 3.40 (d, 2H), 3.10 (q, 2H), 2.33 (s, 3H), 2.20 (d, 2H), 1.91 (q, 2H).

Example 199

3-(3-ethyl-1,2,4-oxadiazol-5-yl)-7-(piperidin-4-yl)pyrazolo[1,5-a]pyrimidin-5(4H)-one hydrochloride

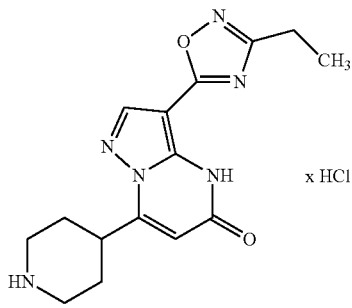 [SMILES: CCc1noc(-c2cnn3c(C4CCNCC4)cc(=O)[nH]c23)n1]

A suspension of compound tert-butyl 4-[3-(3-ethyl-1,2,4-oxadiazol-5-yl)-5-oxo-4,5-dihydropyrazolo[1,5-a]pyrimidin-7-yl]piperidine-1-carboxylate (101 mg, 0.24 mmol) in 1,4-dioxan (2.0 ml) was treated with HCl 4N in 1,4-dioxan (4.0 ml). The reaction mixture was stirred overnight at RT. The reaction mixture was concentrated, dissolved in water and lyophilized to yield the title compound (80 mg, 94% of theory).

LC-MS (Method 8B): $R_t$=0.53 min, MS (ESINeg): m/z=313 [M−H−xHCl]⁻

¹H-NMR (400 MHz, DMSO): δ=11.95 (bs, 1H), 8.80 (bs, 1H), 8.55 (bs, 2H), 6.23 (bs, 1H), 3.61 (bs, 1H), 3.42 (d, 2H), 3.11 (q, 2H), 2.76 (q, 2H), 2.22 (d, 2H), 1.89 (q, 2H), 1.29 (t, 3H).

Example 200

5-[5-oxo-7-(piperidin-4-yl)-4,5-dihydropyrazolo[1,5-a]pyrimidin-3-yl]-1,2,4-oxadiazole-3-carboxamide hydrochloride

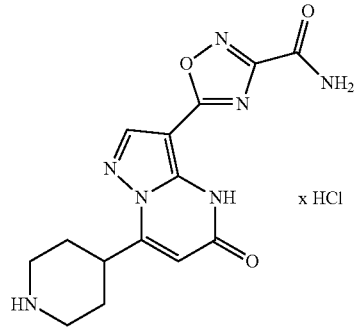 [SMILES: NC(=O)c1noc(-c2cnn3c(C4CCNCC4)cc(=O)[nH]c23)n1]

A suspension of compound tert-butyl 4-[3-(3-carbamoyl-1,2,4-oxadiazol-5-yl)-5-oxo-4,5-dihydropyrazolo[1,5-a]pyrimidin-7-yl]piperidine-1-carboxylate (120 mg, 94% purity, 0.26 mmol) in 1,4-dioxan (2.0 ml) was treated with HCl 4N in 1,4-dioxan (4.0 ml). The reaction mixture was stirred overnight at RT. The reaction mixture was concentrated, dissolved in water and lyophilized to yield the title compound (86 mg, 90% purity, 81% of theory).

LC-MS (Method 9B): $R_t$=3.44 min, MS (ESIPos): m/z=330 [M+H−xHCl]⁺

¹H-NMR (400 MHz, DMSO): δ=11.96 (bs, 1H), 9.02 (bs, 1H), 8.94-8.68 (m, 2H), 8.60 (s, 1H), 8.20 (s, 1H), 6.15 (bs, 1H), 3.57 (t, 1H), 3.40 (d, 2H), 3.10 (q, 2H), 2.21 (d, 2H), 1.92 (q, 2H).

Example 201

3-{3-[(isopropylsulfonyl)methyl]-1,2,4-oxadiazol-5-yl}-7-(piperidin-4-yl)pyrazolo[1,5-a]pyrimidin-5(4H)-one hydrochloride

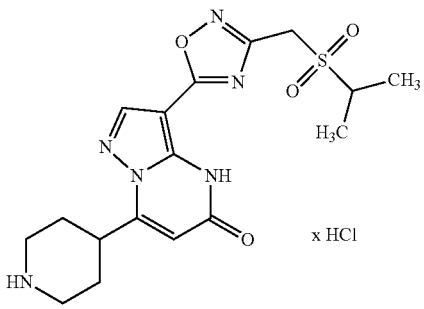 [SMILES: CC(C)S(=O)(=O)Cc1noc(-c2cnn3c(C4CCNCC4)cc(=O)[nH]c23)n1]

x HCl

A suspension of compound tert-butyl 4-(3-{3-[(isopropylsulfonyl)methyl]-1,2,4-oxadiazol-5-yl}-5-oxo-4,5-dihydropyrazolo[1,5-a]pyrimidin-7-yl)piperidine-1-carboxylate (24 mg, 93% purity, 0.044 mmol) in 1,4-dioxan (2.0 ml) was treated with HCl 4N in 1,4-dioxan (4.0 ml). The reaction mixture was stirred overnight at RT. The reaction mixture was concentrated, dissolved in water and lyophilized to yield the title compound (20 mg, 93% purity, quantitative).

LC-MS (Method 8B): $R_t$=0.51 min, MS (ESINeg): m/z=405 [M–H–xHCl]⁻

¹H-NMR (400 MHz, DMSO): δ=8.88 (bs, 1H), 8.77-8.54 (m, 2H), 6.32 (bs, 1H), 4.83 (s, 2H), 3.74-3.29 (m, 4H), 3.12 (q, 2H), 2.22 (d, 2H), 1.91 (q, 2H), 1.34 (d, 6H).

Example 202

3-[3-(3,5-difluoropyridin-2-yl)-1,2,4-oxadiazol-5-yl]-7-(piperidin-4-yl)pyrazolo[1,5-a]pyrimidin-5(4H)-one hydrochloride

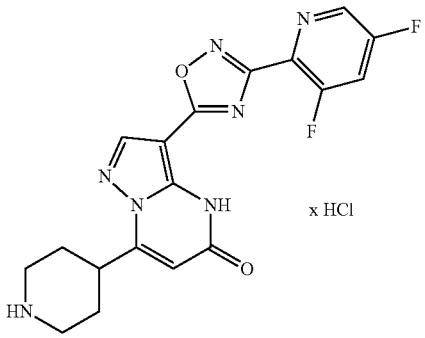 [SMILES: O=c1cc(C2CCNCC2)n2ncc(-c3nc(-c4ncc(F)cc4F)no3)c2[nH]1]

x HCl

A suspension of compound tert-butyl 4-{3-[3-(3,5-difluoropyridin-2-yl)-1,2,4-oxadiazol-5-yl]-5-oxo-4,5-dihydropyrazolo[1,5-a]pyrimidin-7-yl}piperidine-1-carboxylate (25 mg, 0.050 mmol) in 1,4-dioxan (2.0 ml) was treated with HCl 4N in 1,4-dioxan (4.0 ml). The reaction mixture was stirred overnight at RT. The reaction mixture was concentrated, dissolved in water and lyophilized to yield the title compound (22 mg, quantitative).

LC-MS (Method 8B): $R_t$=0.70 min, MS (ESINeg): m/z=398 [M–H–xHCl]⁻

¹H-NMR (400 MHz, DMSO): δ=8.94 (bs, 1H), 8.78 (d, 1H), 8.82-8.63 (m, 1H), 8.69 (s, 1H), 8.30-8.23 (m, 1H), 6.33 (bs, 1H), 4.01-3.56 (m, 1H), 3.42 (d, 2H), 3.12 (q, 2H), 2.24 (d, 2H), 1.94 (q, 2H).

Example 203

3-{3-[(1-methylpiperidin-4-yl)methyl]-1,2,4-oxadiazol-5-yl}-7-(piperidin-4-yl)pyrazolo[1,5-a]pyrimidin-5(4H)-one hydrochloride

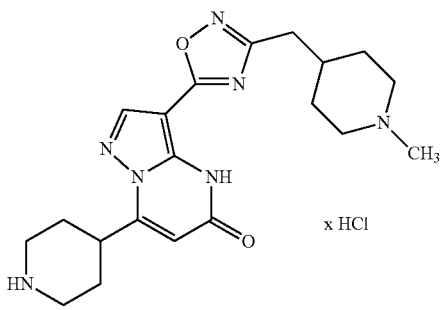 [SMILES: CN1CCC(Cc2noc(-c3cnn4c(C5CCNCC5)cc(=O)[nH]c34)n2)CC1]

x HCl

A suspension of compound tert-butyl 4-(3-{3-[(1-methylpiperidin-4-yl)methyl]-1,2,4-oxadiazol-5-yl}-5-oxo-4,5-dihydropyrazolo[1,5-a]pyrimidin-7-yl)piperidine-1-carboxylate (281 mg, 91% purity, 0.51 mmol) in 1,4-dioxan (2.0 ml) was treated with HCl 4N in 1,4-dioxan (4.0 ml). The reaction mixture was stirred overnight at RT. The reaction mixture was concentrated, dissolved in water and lyophilized to yield the title compound (189 mg, 90% purity, 70% of theory).

LC-MS (Method 9B): $R_t$=3.47 min, MS (ESIPos): m/z=398 [M+H–xHCl]⁺

¹H-NMR (400 MHz, DMSO): δ=10.61-10.25 (m, 1H), 9.14 (bs, 1H), 9.03 (bs, 1H), 8.55 (s, 1H), 6.26 (bs, 1H), 3.61 (t, 1H), 3.39 (t, 4H), 3.10 (q, 2H), 2.98-2.86 (m, 2H), 2.72 (d, 2H), 2.69 (d, 3H), 2.21 (d, 2H), 1.95 (q, 2H), 1.86 (d, 2H), 1.60 (q, 2H). One proton is missing, it is believed to be below the water signal.

Example 204

Methyl 4-{5-[5-oxo-7-(piperidin-4-yl)-4,5-dihydropyrazolo[1,5-a]pyrimidin-3-yl]-1,2,4-oxadiazol-3-yl}benzoate hydrochloride

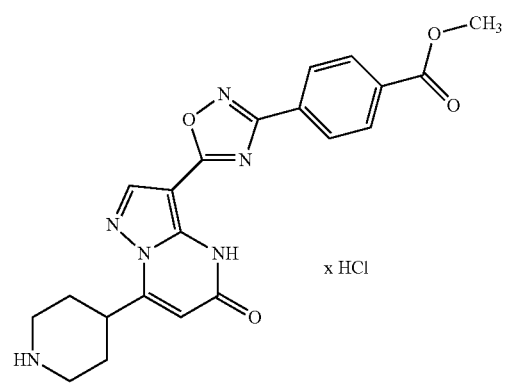 [SMILES: COC(=O)c1ccc(-c2noc(-c3cnn4c(C5CCNCC5)cc(=O)[nH]c34)n2)cc1]

x HCl

A suspension of compound tert-butyl 4-(3-{3-[4-(methoxycarbonyl)phenyl]-1,2,4-oxadiazol-5-yl}-5-oxo-4,5-dihydropyrazolo[1,5-a]pyrimidin-7-yl)piperidine-1-carboxylate (41 mg, 0.079 mmol) in 1,4-dioxan (2.0 ml) was treated with HCl 4N in 1,4-dioxan (4.0 ml). The reaction mixture was stirred overnight at RT. The reaction mixture was concentrated and the title compound was obtained by crystallization in a mixture of water and acetonitrile (10 mg, 92% purity, 26% of theory).

LC-MS (Method 8B): $R_t$=0.85 min, MS (ESINeg): m/z=419 [M–H–xHCl]$^-$ $^1$H-NMR (400 MHz, DMSO): δ=12.40 (bs, 1H), 8.79 (bs, 1H), 8.65 (s, 1H), 8.54 (bs, 1H), 8.38-8.31 (m, 2H), 8.29-8.14 (m, 2H), 6.24 (bs, 1H), 3.91 (s, 3H), 3.74-3.57 (m, 1H), 3.43 (d, 2H), 3.13 (q, 2H), 2.24 (d, 2H), 1.90 (q, 2H).

Example 205

3-[3-(3-nitrophenyl)-1,2,4-oxadiazol-5-yl]-7-(piperidin-4-yl)pyrazolo[1,5-a]pyrimidin-5(4H)-one hydrochloride

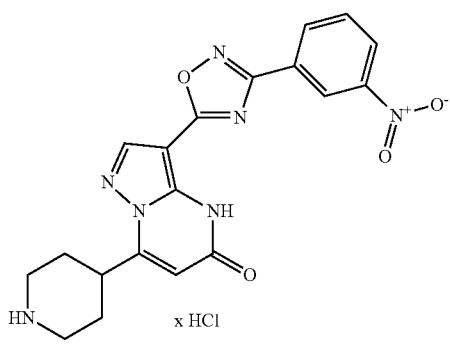 [SMILES: O=c1cc(C2CCNCC2)n2ncc(-c3nc(-c4cccc([N+](=O)[O-])c4)no3)c2[nH]1]

A suspension of compound tert-butyl 4-{3-[3-(3-nitrophenyl)-1,2,4-oxadiazol-5-yl]-5-oxo-4,5-dihydropyrazolo[1,5-a]pyrimidin-7-yl}piperidine-1-carboxylate (59 mg, 0.11 mmol) in 1,4-dioxan (2.0 ml) was treated with HCl 4N in 1,4-dioxan (4.0 ml). The reaction mixture was stirred overnight at RT. The reaction mixture was concentrated, dissolved in water and lyophilized to yield the title compound (45 mg, 89% of theory).

LC-MS (Method 8B): $R_t$=0.79 min, MS (ESINeg): m/z=406 [M–H–xHCl]$^-$ $^1$H-NMR (400 MHz, DMSO): δ=12.47 (bs, 1H), 8.98-8.81 (m, 2H), 8.76-8.57 (m, 3H), 8.47 (d, 1H), 7.92 (t, 1H), 6.25 (bs, 1H), 3.67-3.56 (m, 1H), 3.43 (d, 2H), 3.13 (q, 2H), 2.24 (d, 2H), 1.92 (q, 2H).

Example 206

3-[3-(2-methoxyethyl)-1,2,4-oxadiazol-5-yl]-7-(piperidin-4-yl)pyrazolo[1,5-a]pyrimidin-5(4H)-one hydrochloride

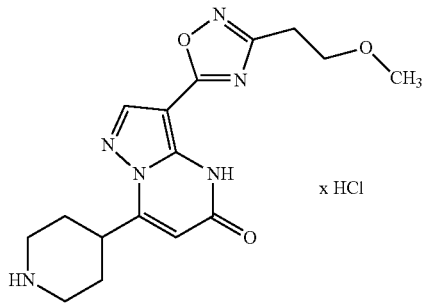 [SMILES: COCCc1noc(-c2cnn3c(C4CCNCC4)cc(=O)[nH]c23)n1]

A suspension of compound tert-butyl 4-{3-[3-(2-methoxyethyl)-1,2,4-oxadiazol-5-yl]-5-oxo-4,5-dihydropyrazolo[1,5-a]pyrimidin-7-yl}piperidine-1-carboxylate (100 mg, 93% purity, 0.21 mmol) in 1,4-dioxan (2.0 ml) was treated with HCl 4N in 1,4-dioxan (4.0 ml). The reaction mixture was stirred overnight at RT. The reaction mixture was concentrated, dissolved in water and lyophilized to yield the title compound (77 mg, 94% of theory).

LC-MS (Method 8B): $R_t$=0.52 min, MS (ESINeg): m/z=343 [M–H–xHCl]$^-$ $^1$H-NMR (400 MHz, DMSO): δ=13.35-11.52 (m, 1H), 8.96 (bs, 1H), 8.77 (bs, 1H), 8.55 (s, 1H), 6.24 (bs, 1H), 3.75 (t, 2H), 3.66-3.55 (m, 1H), 3.41 (d, 2H), 3.26 (s, 3H), 3.11 (q, 2H), 2.98 (t, 2H), 2.22 (d, 2H), 1.92 (q, 2H).

Example 207

7-(piperidin-4-yl)-3-[3-(pyridin-4-yl)-1,2,4-oxadiazol-5-yl]pyrazolo[1,5-a]pyrimidin-5(4H)-one hydrochloride

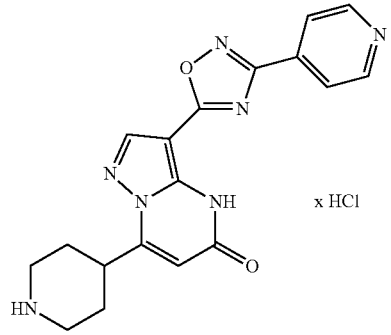 [SMILES: O=c1cc(C2CCNCC2)n2ncc(-c3nc(-c4ccncc4)no3)c2[nH]1]

A suspension of compound tert-butyl 4-{5-oxo-3-[3-(pyridin-4-yl)-1,2,4-oxadiazol-5-yl]-4,5-dihydropyrazolo[1,5-a]pyrimidin-7-yl}piperidine-1-carboxylate (170 mg, 0.35 mmol) in 1,4-dioxan (2.0 ml) was treated with HCl 4N in 1,4-dioxan (4.0 ml). The reaction mixture was stirred overnight at RT. The reaction mixture was concentrated, dissolved in water and lyophilized to yield the title compound (109 mg, 87% purity, 62% of theory).

LC-MS (Method 9B): R$_t$=3.57 min, MS (ESIPos): m/z=364 [M+H−xHCl]$^+$ $^1$H-NMR (400 MHz, DMSO): δ=9.11-8.72 (m, 2H), 8.91 (bs, 2H), 8.67 (s, 1H), 8.28 (bs, 2H), 6.25 (bs, 1H), 3.83-3.46 (m, 1H), 3.45-3.34 (m, 2H), 3.18-3.02 (m, 2H), 2.27-2.13 (m, 2H), 2.01-1.81 (q, 2H).

Example 208

3-[3-(3-aminophenyl)-1,2,4-oxadiazol-5-yl]-7-(piperidin-4-yl)pyrazolo[1,5-a]pyrimidin-5 (4H)-one hydrochloride

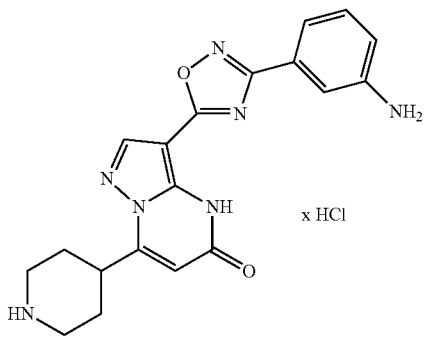 [SMILES: Nc1cccc(-c2noc(-c3cnn4c(C5CCNCC5)cc(=O)[nH]c34)n2)c1]

A suspension of compound tert-butyl 4-{3-[3-(3-aminophenyl)-1,2,4-oxadiazol-5-yl]-5-oxo-4,5-dihydropyrazolo[1,5-a]pyrimidin-7-yl}piperidine-1-carboxylate (173 mg, 88% purity, 0.32 mmol) in 1,4-dioxan (2.0 ml) was treated with HCl 4N in 1,4-dioxan (4.0 ml). The reaction mixture was stirred overnight at RT. The reaction mixture was concentrated, dissolved in water and lyophilized to yield the title compound (98 mg, 74% of theory).

LC-MS (Method 8B): R$_t$=0.66 min, MS (ESINeg): m/z=376 [M−H−xHCl]$^-$ $^1$H-NMR (400 MHz, DMSO): δ=9.25-8.89 (m, 2H), 8.63 (s, 1H), 8.00-7.78 (m, 2H), 7.59-7.49 (m, 1H), 7.35 (bs, 1H), 6.25 (s, 1H), 3.62 (t, 1H), 3.41 (d, 2H), 3.11 (q, 2H), 2.22 (d, 2H), 1.96 (q, 2H).

Example 209

3-[3-(2-chlorobenzyl)-1,2,4-oxadiazol-5-yl]-7-(piperidin-4-yl)pyrazolo[1,5-a]pyrimidin-5(4H)-one hydrochloride

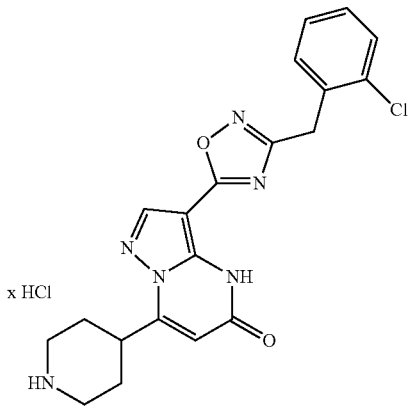 [SMILES: O=c1cc(C2CCNCC2)n2ncc(-c3nc(Cc4ccccc4Cl)no3)c2[nH]1]

Compound tert-butyl 4-{3-[3-(2-chlorobenzyl)-1,2,4-oxadiazol-5-yl]-5-oxo-4,5-dihydropyrazolo[1,5-a]pyrimidin-7-yl}piperidine-1-carboxylate (128 mg, 92% purity, 230 μmol) was dissolved in 1,4-dioxan (2.0 ml) and stirred overnight at RT with hydrochloric acid 4N in 1,4-dioxan (4.0 ml). The suspension was filtered, washed with diethyl ether (2.0 ml) and dried in vacuo to yield the title compound.

The obtained amount was 71.0 mg (99% purity, 68% of theory).

LC-MS (Method 8B): R$_t$=0.84 min; MS (ESIpos): m/z=411 [M+H−xHCl]$^+$ $^1$H-NMR (500 MHz, DMSO-d6) delta [ppm]: −0.007 (0.49), −0.000 (10.25), 1.890 (0.58), 1.898 (0.71), 1.918 (1.87), 1.924 (1.85), 1.942 (2.02), 1.950 (1.89), 1.968 (0.90), 1.977 (0.70), 2.185 (2.67), 2.187 (2.77), 2.214 (2.35), 3.057 (0.78), 3.077 (1.72), 3.083 (2.09), 3.104 (2.17), 3.109 (1.88), 3.130 (0.89), 3.381 (2.75), 3.407 (2.38), 3.568 (6.73), 3.584 (0.88), 3.608 (1.45), 3.631 (0.94), 4.255 (16.00), 6.254 (0.84), 7.327 (0.70), 7.336 (3.25), 7.339 (3.87), 7.341 (3.25), 7.347 (6.25), 7.352 (3.49), 7.355 (4.73), 7.357 (4.79), 7.367 (0.91), 7.457 (0.42), 7.463 (2.78), 7.468 (1.69), 7.474 (2.32), 7.477 (2.11), 7.483 (5.07), 7.488 (2.16), 7.491 (2.39), 7.493 (1.97), 7.497 (1.62), 7.502 (2.60), 8.537 (3.69), 8.936 (0.73), 8.960 (0.78), 9.084 (1.00), 9.109 (0.81).

Example 210

3-[3-(4-chlorobenzyl)-1,2,4-oxadiazol-5-yl]-7-(piperidin-4-yl)pyrazolo[1,5-a]pyrimidin-5(4H)-one hydrochloride

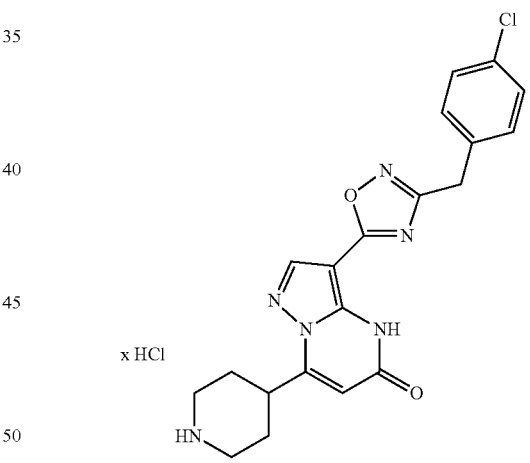

Compound tert-butyl 4-{3-[3-(4-chlorobenzyl)-1,2,4-oxadiazol-5-yl]-5-oxo-4,5-dihydropyrazolo[1,5-a]pyrimidin-7-yl}piperidine-1-carboxylate (117 mg, 95% purity, 218 μmol) was dissolved in 1,4-dioxan (2.0 ml) and stirred 2 h at RT with hydrochloric acid 4N in 1,4-dioxan (4.0 ml). The suspension was filtered, washed with diethyl ether (2.0 ml) and dried in vacuo to yield the title compound.

The obtained amount was 45.0 mg (98% purity, 45% of theory).

LC-MS (Method 8B): R$_t$=0.85 min; MS (ESIpos): m/z=411 [M+H−xHCl]$^+$ $^1$H-NMR (500 MHz, DMSO-d6) delta [ppm]: 0.007 (0.70), 1.148 (0.26), 1.235 (0.39), 1.885 (1.20), 1.908 (1.27), 1.932 (0.55), 2.192 (1.81), 2.219 (1.53), 2.363 (0.30), 2.637 (0.30), 3.068 (0.52), 3.093 (1.42), 3.115 (1.44), 3.140 (0.57), 3.394 (2.18), 3.418 (1.79), 3.568 (16.00), 4.141 (11.14), 6.290 (0.17), 7.377 (1.48), 7.395 (6.91), 7.403 (11.33), 7.416 (1.20), 7.421 (2.03), 8.540 (0.57), 8.657 (0.54), 8.857 (0.68).

Example 211

Ethyl 5-[5-oxo-7-(piperidin-4-yl)-4,5-dihydropyrazolo[1,5-a]pyrimidin-3-yl]-1,2,4-oxadiazole-3-carboxylate hydrochloride

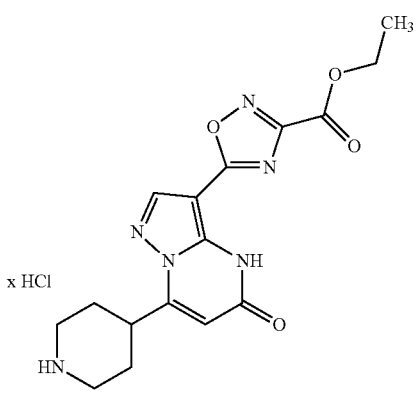 [SMILES: CCOC(=O)c1noc(-c2cnn3c(C4CCNCC4)cc(=O)[nH]c23)n1]

tert-butyl 4-{3-[3-(ethoxycarbonyl)-1,2,4-oxadiazol-5-yl]-5-oxo-4,5-dihydropyrazolo[1,5-a]pyrimidin-7-yl}piperidine-1-carboxylate (107 mg, 100% purity, 233 µmol)
hydrochloric acid 4N in 1,4-dioxan (4.0 ml)
1,4-dioxan (2.0 ml)

The title compound was prepared according to the same procedure as Example 210.

The obtained amount was 56.0 mg (100% purity, 61% of theory).

LC-MS (Method 8B): $R_t$=0.64 min; MS (ESIpos): m/z=359 [M+H-xHCl]$^+$ $^1$H-NMR (400 MHz, DMSO-d6) delta [ppm]: 0.000 (0.74), 0.016 (0.68), 1.197 (0.17), 1.345 (3.59), 1.362 (7.71), 1.380 (3.67), 1.894 (0.26), 1.924 (0.70), 1.949 (0.77), 1.981 (0.33), 2.218 (1.09), 2.251 (0.88), 3.114 (0.75), 3.144 (0.79), 3.411 (1.15), 3.442 (0.93), 3.576 (16.00), 3.656 (0.40), 4.419 (1.02), 4.437 (3.24), 4.455 (3.21), 4.473 (1.00), 6.388 (0.19), 8.712 (0.81), 8.907 (0.34).

Example 212

3-[3-(aminomethyl)-1,2,4-oxadiazol-5-yl]-7-(piperidin-4-yl)pyrazolo[1,5-a]pyrimidin-5 (4H)-one hydrochloride

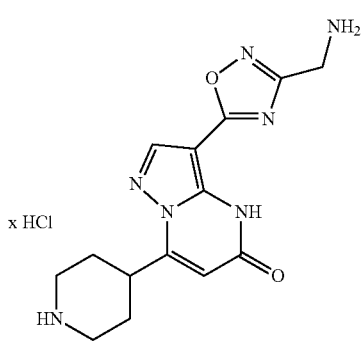 [SMILES: NCc1noc(-c2cnn3c(C4CCNCC4)cc(=O)[nH]c23)n1]

tert-butyl 4-[3-(3-{[(tert-butoxycarbonyl)amino]methyl}-1,2,4-oxadiazol-5-yl)-5-oxo-4,5-dihydropyrazolo[1,5-a]pyrimidin-7-yl]piperidine-1-carboxylate (158 mg, 98% purity, 300 µmol) hydrochloric acid 4N in 1,4-dioxan (6.0 ml)

1,4-dioxan (2.0 ml)

The title compound was prepared according to the same procedure as Example 209.

The obtained amount was 89.0 mg (98% purity, 83% of theory).

LC-MS (Method 9B): $R_t$=3.15 min; MS (ESIpos): m/z=316 [M+H-xHCl]$^+$ $^1$H-NMR (500 MHz, DMSO-d6) delta [ppm]: −0.007 (0.65), 0.000 (16.00), 0.006 (0.54), 1.927 (0.96), 1.934 (1.16), 1.953 (3.02), 1.959 (3.08), 1.979 (3.35), 1.984 (3.21), 2.004 (1.43), 2.011 (1.22), 2.188 (4.59), 2.214 (3.66), 3.055 (1.27), 3.080 (3.40), 3.102 (3.44), 3.127 (1.36), 3.381 (4.45), 3.406 (3.76), 3.568 (12.09), 3.596 (1.81), 3.618 (1.01), 4.057 (4.56), 4.126 (2.56), 4.305 (2.54), 4.317 (6.94), 4.328 (6.74), 4.339 (2.32), 6.249 (0.73), 8.597 (7.90), 8.854 (6.55), 9.166 (1.22), 9.186 (1.39), 9.246 (1.84).

Example 213

3-[3-(3,4-dichlorobenzyl)-1,2,4-oxadiazol-5-yl]-7-(piperidin-4-yl)pyrazolo[1,5-a]pyrimidin-5 (4H)-one hydrochloride

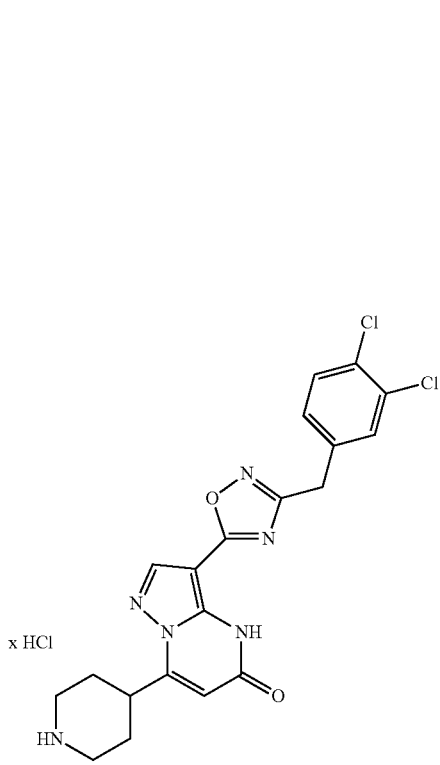 [SMILES: O=c1cc(C2CCNCC2)n2ncc(-c3nc(Cc4ccc(Cl)c(Cl)c4)no3)c2[nH]1]

tert-butyl 4-{3-[3-(3,4-dichlorobenzyl)-1,2,4-oxadiazol-5-yl]-5-oxo-4,5-dihydropyrazolo[1,5-a]pyrimidin-7-yl}piperidine-1-carboxylate (163 mg, 100% purity, 299 µmol) hydrochloric acid 4N in 1,4-dioxan (4.0 ml)

1,4-dioxan (2.0 ml)

The title compound was prepared according to the same procedure as Example 210.

The obtained amount was 102 mg (100% purity, 71% of theory).

LC-MS (Method 8B): $R_t$=0.91 min; MS (ESIpos): m/z=445 [M+H-xHCl]$^+$ $^1$H-NMR (400 MHz, DMSO-d6) delta [ppm]: 1.893 (1.30), 1.923 (1.41), 2.189 (2.00), 2.222 (1.62), 3.088 (1.48), 3.117 (1.54), 3.568 (16.00), 4.181 (9.99), 7.364 (1.55), 7.385 (1.81), 7.608 (4.43), 7.629 (3.79), 7.673 (2.99), 8.547 (0.97), 8.740 (0.51), 8.936 (0.63).

Example 214

3-[3-(4-methylbenzyl)-1,2,4-oxadiazol-5-yl]-7-(piperidin-4-yl)pyrazolo[1,5-a]pyrimidin-5(4H)-one hydrochloride

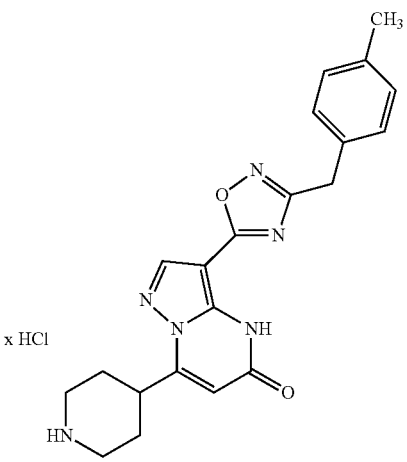 [SMILES: Cc1ccc(Cc2noc(-c3cnn4c(C5CCNCC5)cc(=O)[nH]c34)n2)cc1]

tert-butyl 4-{3-[3-(4-methylbenzyl)-1,2,4-oxadiazol-5-yl]-5-oxo-4,5-dihydropyrazolo[1,5-a]pyrimidin-7-yl}piperidine-1-carboxylate (130 mg, 100% purity, 265 µmol) hydrochloric acid 4N in 1,4-dioxan (4.0 ml)

1,4-dioxan (2.0 ml)

The title compound was prepared according to the same procedure as Example 210.

The obtained amount was 75.0 mg (100% purity, 66% of theory).

LC-MS (Method 8B): $R_t$=0.85 min; MS (ESIpos): m/z=391 [M+H-xHCl]$^+$ $^1$H-NMR (400 MHz, DMSO-d6) delta [ppm]: −0.008 (1.29), 0.008 (1.26), 1.875 (1.07), 1.905 (1.17), 2.189 (1.69), 2.222 (1.39), 2.272 (16.00), 3.089 (1.23), 3.118 (1.29), 3.390 (1.94), 3.422 (1.53), 3.568 (2.83), 4.065 (8.86), 7.133 (3.33), 7.153 (5.41), 7.217 (4.61), 7.237 (2.96), 8.535 (0.55), 8.851 (0.48).

Example 215

3-[3-(1-phenylethyl)-1,2,4-oxadiazol-5-yl]-7-(piperidin-4-yl)pyrazolo[1,5-a]pyrimidin-5(4H)-one hydrochloride

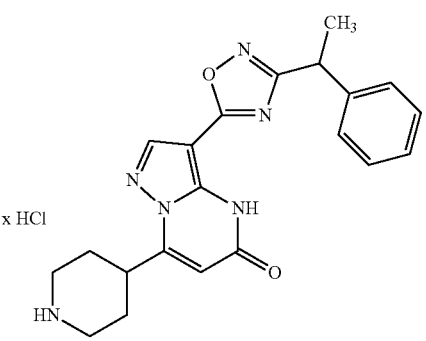 [SMILES: CC(c1ccccc1)c1noc(-c2cnn3c(C4CCNCC4)cc(=O)[nH]c23)n1]

tert-butyl 4-{5-oxo-3-[3-(1-phenylethyl)-1,2,4-oxadiazol-5-yl]-4,5-dihydropyrazolo[1,5-a]pyrimidin-7-yl}piperidine-1-carboxylate (56.0 mg, 100% purity, 114 µmol) hydrochloric acid 4N in 1,4-dioxan (4.0 ml)

1,4-dioxan (2.0 ml)

The title compound was prepared according to the same procedure as Example 210.

The obtained amount was 36.0 mg (97% purity, 72% of theory).

LC-MS (Method 8B): $R_t$=0.82 min; MS (ESIpos): m/z=391 [M+H-xHCl]$^+$ $^1$H-NMR (400 MHz, DMSO-d6) delta [ppm]: −0.008 (0.41), 0.008 (0.44), 1.416 (0.32), 1.596 (0.16), 1.644 (1.89), 1.662 (1.91), 1.846 (0.10), 1.878 (0.29), 1.909 (0.31), 1.936 (0.13), 2.185 (0.44), 2.218 (0.36), 3.057 (0.12), 3.087 (0.33), 3.115 (0.34), 3.146 (0.15), 3.388 (0.58), 3.568 (16.00), 4.342 (0.15), 4.360 (0.53), 4.378 (0.52), 4.396 (0.15), 6.232 (0.06), 7.234 (0.17), 7.251 (0.49), 7.269 (0.38), 7.320 (0.51), 7.340 (1.19), 7.358 (0.88), 7.376 (0.99), 7.394 (0.45), 8.530 (0.19), 8.661 (0.10), 8.869 (0.13).

Example 216

3-[5-(2-fluorophenyl)-1,2,4-oxadiazol-3-yl]-7-(piperidin-4-yl)pyrazolo[1,5-a]pyrimidin-5 (4H)-one hydrochloride

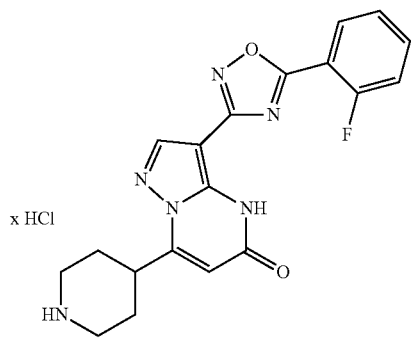 [SMILES: O=c1cc(C2CCNCC2)n2ncc(-c3noc(-c4ccccc4F)n3)c2[nH]1]

Compound tert-butyl 4-{3-[5-(2-fluorophenyl)-1,2,4-oxadiazol-3-yl]-5-oxo-4,5-dihydropyrazolo[1,5-a]pyrimidin-7-yl}piperidine-1-carboxylate (345 mg, 53% purity, 381 µmol) was dissolved in 1,4-dioxan (4.0 ml) and stirred overnight at RT with hydrochloric acid 4N in 1,4-dioxan (4.0 ml). The suspension was filtered, washed with diethyl ether (2.0 ml), crystallized from a mixture of methanol and diethyl ether, filtered and dried in vacuo to yield the title compound.

The obtained amount was 50.0 mg (100% purity, 32% of theory).

LC-MS (Method 8B): $R_t$=0.81 min; MS (ESIpos): m/z=381 [M+H-xHCl]$^+$ $^1$H-NMR (400 MHz, DMSO-d6) delta [ppm]: −0.008 (10.47), 0.008 (9.50), 1.892 (6.96), 1.924 (7.51), 2.137 (4.55), 2.216 (10.29), 2.249 (8.49), 3.103 (7.73), 3.132 (7.82), 3.200 (2.35), 3.248 (2.35), 3.403 (13.16), 3.435 (9.80), 3.600 (4.76), 6.102 (3.42), 7.497 (6.87), 7.515 (14.38), 7.534 (9.19), 7.549 (8.24), 7.577 (7.51), 7.785 (3.11), 7.799 (5.74), 7.819 (5.59), 7.833 (2.72), 8.441 (16.00), 8.680 (2.05), 8.894 (2.60).

Example 217

3-[5-(3-chlorobenzyl)-1,2,4-oxadiazol-3-yl]-7-(piperidin-4-yl)pyrazolo[1,5-a]pyrimidin-5(4H)-one hydrochloride

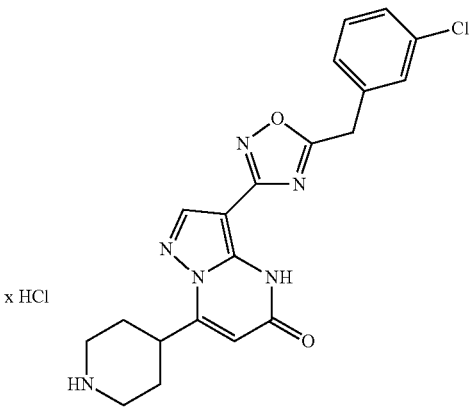 [SMILES: O=c1cc(C2CCNCC2)n2ncc(-c3noc(Cc4cccc(Cl)c4)n3)c2[nH]1]

tert-butyl 4-{3-[5-(3-chlorobenzyl)-1,2,4-oxadiazol-3-yl]-5-oxo-4,5-dihydropyrazolo[1,5-a]pyrimidin-7-yl}piperidine-1-carboxylate (52.0 mg, 92% purity, 93.6 µmol) hydrochloric acid 4N in 1,4-dioxan (2.0 ml)

1,4-dioxan (2.0 ml)

The title compound was prepared according to the same procedure as Example 209.

The obtained amount was 35.0 mg (89% purity, 74% of theory).

LC-MS (Method 8B): $R_t$=0.83 min; MS (ESIneg): m/z=409 [M−H-xHCl]$^-$ $^1$H-NMR (400 MHz, DMSO-d6) delta [ppm]: 0.854 (1.22), 1.235 (12.31), 1.356 (2.66), 1.868 (2.20), 1.898 (2.35), 2.192 (3.40), 2.226 (2.70), 2.671 (0.60), 3.112 (2.06), 3.389 (3.92), 3.420 (3.15), 3.474 (0.87), 3.594 (2.21), 3.681 (1.36), 3.701 (1.56), 3.916 (4.15), 4.469 (16.00), 5.755 (0.69), 6.081 (0.47), 7.149 (0.76), 7.264 (1.22), 7.317 (1.27), 7.335 (0.96), 7.400 (6.99), 7.406 (7.40), 7.410 (7.95), 7.427 (2.31), 7.447 (1.13), 7.520 (5.21), 8.339 (2.08), 8.610 (0.70), 8.839 (0.87), 11.295 (0.55).

Example 218

3-[5-(3-chloro-2-fluorophenyl)-1,2,4-oxadiazol-3-yl]-7-(piperidin-4-yl)pyrazolo[1,5-a]pyrimidin-5 (4H)-one hydrochloride

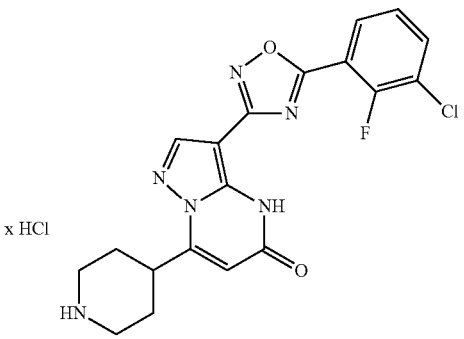 [SMILES: O=c1cc(C2CCNCC2)n2ncc(-c3noc(-c4cccc(Cl)c4F)n3)c2[nH]1]

tert-butyl 4-{3-[5-(3-chloro-2-fluorophenyl)-1,2,4-oxadiazol-3-yl]-5-oxo-4,5-dihydropyrazolo[1,5-a]pyrimidin-7-yl}piperidine-1-carboxylate (80.0 mg, 100% purity, 155 µmol)

hydrochloric acid 4N in 1,4-dioxan (2.0 ml)

1,4-dioxan (2.0 ml)

The title compound was prepared according to the same procedure as Example 209.

The obtained amount was 61.0 mg (100% purity, 87% of theory).

LC-MS (Method 8B): $R_t$=0.87 min; MS (ESIneg): m/z=413 [M−H−xHCl]⁻

¹H-NMR (400 MHz, DMSO-d6) delta [ppm]: −0.141 (0.06), 0.000 (0.55), 0.016 (0.50), 0.154 (0.06), 1.118 (0.12), 1.604 (0.07), 1.890 (0.17), 1.921 (0.18), 2.226 (0.27), 2.259 (0.22), 2.336 (0.06), 2.678 (0.06), 3.116 (0.18), 3.144 (0.19), 3.416 (0.28), 3.445 (0.23), 3.576 (16.00), 6.111 (0.05), 7.526 (0.20), 7.546 (0.41), 7.566 (0.22), 7.985 (0.15), 7.989 (0.17), 8.007 (0.27), 8.023 (0.15), 8.027 (0.14), 8.456 (0.26), 8.822 (0.07), 11.646 (0.06).

Example 219

3-[5-(2-methoxyphenyl)-1,2,4-oxadiazol-3-yl]-7-(piperidin-4-yl)pyrazolo[1,5-a]pyrimidin-5(4H)-one hydrochloride

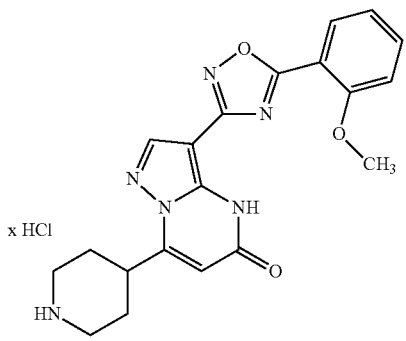 [SMILES: COc1ccccc1-c1nc(-c2cnn3c(C4CCNCC4)cc(=O)[nH]c23)no1]

tert-butyl 4-{3-[5-(2-methoxyphenyl)-1,2,4-oxadiazol-3-yl]-5-oxo-4,5-dihydropyrazolo[1,5-a]pyrimidin-7-yl}piperidine-1-carboxylate (37.0 mg, 100% purity, 75.1 µmol)

hydrochloric acid 4N in 1,4-dioxan (2.0 ml)

1,4-dioxan (2.0 ml)

The title compound was prepared according to the same procedure as Example 209.

The obtained amount was 22.0 mg (99% purity, 68% of theory).

LC-MS (Method 8B): $R_t$=0.81 min; MS (ESIneg): m/z=391 [M−H−xHCl]⁻

¹H-NMR (400 MHz, DMSO-d6) delta [ppm]: −0.149 (0.08), 0.000 (16.00), 0.008 (0.56), 1.882 (0.16), 1.913 (0.17), 2.215 (0.25), 2.247 (0.20), 2.328 (0.08), 2.670 (0.09), 3.104 (0.19), 3.131 (0.19), 3.968 (2.52), 6.078 (0.09), 7.178 (0.17), 7.197 (0.34), 7.216 (0.18), 7.319 (0.32), 7.340 (0.36), 7.679 (0.16), 7.701 (0.24), 7.719 (0.13), 8.263 (0.10), 8.409 (0.32), 8.605 (0.05), 8.830 (0.07).

Example 220

3-[5-(4-methylphenyl)-1,2,4-oxadiazol-3-yl]-7-(piperidin-4-yl)pyrazolo[1,5-a]pyrimidin-5 (4H)-one hydrochloride

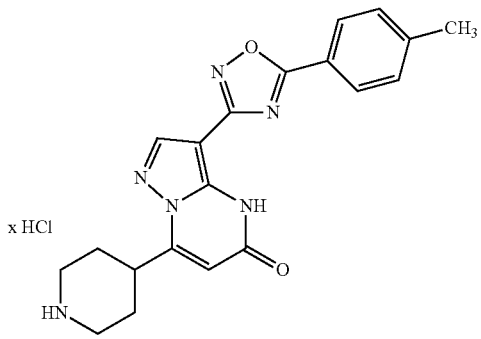 [SMILES: Cc1ccc(-c2nc(-c3cnn4c(C5CCNCC5)cc(=O)[nH]c34)no2)cc1]

tert-butyl 4-{3-[5-(4-methylphenyl)-1,2,4-oxadiazol-3-yl]-5-oxo-4,5-dihydropyrazolo[1,5-a]pyrimidin-7-yl}piperidine-1-carboxylate (37.0 mg, 94% purity, 73.0 µmol)

hydrochloric acid 4N in 1,4-dioxan (2.0 ml)

1,4-dioxan (2.0 ml)

The title compound was prepared according to the same procedure as Example 209.

The obtained amount was 25.0 mg (96% purity, 80% of theory).

LC-MS (Method 8B): $R_t$=0.91 min; MS (ESIpos): m/z=377 [M+H−xHCl]⁺

¹H-NMR (400 MHz, DMSO-d6) delta [ppm]: 1.880 (1.51), 1.912 (1.60), 2.216 (2.35), 2.248 (2.07), 2.444 (16.00), 3.105 (1.78), 3.133 (1.94), 3.245 (2.30), 3.568 (4.79), 6.090 (0.62), 7.473 (4.96), 7.494 (5.27), 8.180 (3.27), 8.199 (3.07), 8.426 (2.38), 8.593 (0.52), 8.822 (0.59).

Example 221

5-[5-oxo-7-(piperidin-4-yl)-4,5-dihydropyrazolo[1,5-a]pyrimidin-3-yl]-1,2,4-oxadiazole-3-carboxylic acid hydrochloride

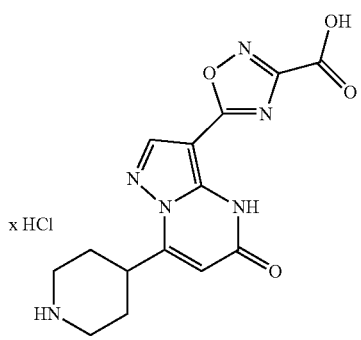 [SMILES: O=C(O)c1noc(-c2cnn3c(C4CCNCC4)cc(=O)[nH]c23)n1]

5-{7-[1-(tert-butoxycarbonyl)piperidin-4-yl]-5-oxo-4,5-dihydropyrazolo[1,5-a]pyrimidin-3-yl}-1,2,4-oxadiazole-3-carboxylic acid (36.0 mg, 99% purity, 82.8 µmol)

hydrochloric acid 4N in 1,4-dioxan (2.0 ml)

1,4-dioxan (2.0 ml)

The title compound was prepared according to the same procedure as Example 209.

The obtained amount was 27.0 mg (94% purity, 84% of theory).

LC-MS (Method 1B): $R_t$=0.16 min; MS (ESIpos): m/z=331 [M+H-xHCl]$^+$ $^1$H-NMR (400 MHz, DMSO-d6) delta [ppm]: 1.073 (1.11), 1.091 (2.23), 1.108 (1.13), 1.884 (0.64), 1.915 (1.09), 1.945 (1.10), 2.208 (1.56), 2.242 (1.23), 3.101 (1.37), 3.128 (1.40), 3.375 (3.69), 3.393 (4.73), 3.568 (16.00), 3.639 (0.68), 6.054 (0.37), 6.350 (0.34), 8.669 (1.25), 8.937 (0.45).

Example 222

7-(piperidin-4-yl)-3-{3-[3-(trifluoromethyl)benzyl]-1,2,4-oxadiazol-5-yl}pyrazolo[1,5-a]pyrimidin-5(4H)-one hydrochloride

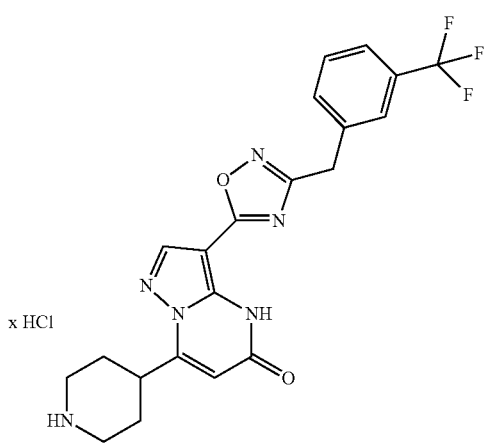 [SMILES: O=c1cc(C2CCNCC2)n2ncc(-c3nc(Cc4cccc(C(F)(F)F)c4)no3)c2[nH]1]

Compound tert-butyl 4-(5-oxo-3-{3-[3-(trifluoromethyl)benzyl]-1,2,4-oxadiazol-5-yl}-4,5-dihydropyrazolo[1,5-a]pyrimidin-7-yl)piperidine-1-carboxylate (41.0 mg, 100% purity, 75.3 μmol) was dissolved in 1,4-dioxan (2.0 ml) and stirred overnight at RT with hydrochloric acid 4N in 1,4-dioxan (2.0 ml). The suspension was concentrated, dissolved in water and lyophilized to yield the title compound.

The obtained amount was 38.0 mg (95% purity, quantitative)

LC-MS (Method 8B): $R_t$=0.90 min; MS (ESIpos): m/z=445 [M+H-xHCl]$^+$ $^1$H-NMR (400 MHz, DMSO-d6) delta [ppm]: −0.149 (0.09), −0.008 (0.90), 0.000 (16.00), 0.008 (0.41), 0.146 (0.07), 1.870 (0.08), 1.901 (0.08), 2.189 (0.11), 2.223 (0.09), 3.094 (0.09), 3.123 (0.09), 4.278 (0.60), 7.577 (0.05), 7.597 (0.15), 7.616 (0.15), 7.646 (0.15), 7.673 (0.12), 7.692 (0.09), 7.752 (0.18), 8.546 (0.06), 8.804 (0.04).

Example 223

3-[3-(2-phenylpropan-2-yl)-1,2,4-oxadiazol-5-yl]-7-(piperidin-4-yl)pyrazolo[1,5-a]pyrimidin-5(4H)-one hydrochloride

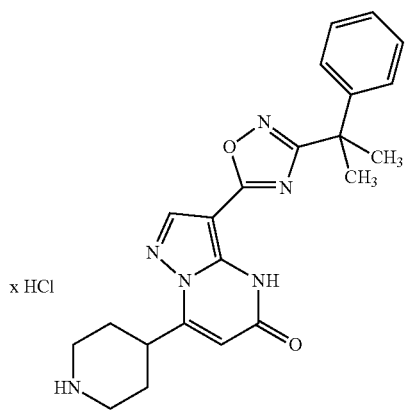 [SMILES: CC(C)(c1ccccc1)c1noc(-c2cnn3c(C4CCNCC4)cc(=O)[nH]c23)n1]

tert-butyl 4-{5-oxo-3-[3-(2-phenylpropan-2-yl)-1,2,4-oxadiazol-5-yl]-4,5-dihydropyrazolo[1,5-a]pyrimidin-7-yl}piperidine-1-carboxylate (10.0 mg, 100% purity, 19.8 μmol)

hydrochloric acid 4N in 1,4-dioxan (2.0 ml)

1,4-dioxan (2.0 ml)

The title compound was prepared according to the same procedure as Example 222.

The obtained amount was 8.00 mg (100% purity, 92% of theory).

LC-MS (Method 8B): $R_t$=0.89 min; MS (ESIpos): m/z=405 [M+H-xHCl]$^+$ $^1$H-NMR (400 MHz, DMSO-d6) delta [ppm]: −0.149 (0.25), −0.008 (2.46), 0.008 (2.07), 0.146 (0.25), 1.235 (0.33), 1.752 (16.00), 1.874 (0.71), 1.906 (0.81), 2.179 (1.16), 2.212 (0.94), 3.083 (0.85), 3.112 (0.89), 3.390 (4.59), 3.492 (0.53), 3.508 (0.45), 3.593 (0.44), 3.699 (0.23), 4.020 (0.27), 4.318 (0.21), 6.222 (0.13), 7.230 (0.91), 7.245 (0.74), 7.251 (0.54), 7.305 (0.72), 7.326 (3.37), 7.341 (6.91), 8.507 (0.57), 8.708 (0.21), 8.904 (0.29).

Example 224

3-[3-(4-fluorobenzyl)-1,2,4-oxadiazol-5-yl]-7-(piperidin-4-yl)pyrazolo[1,5-a]pyrimidin-5(4H)-one hydrochloride

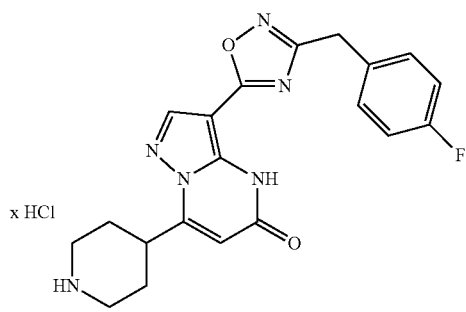 [SMILES: O=c1cc(C2CCNCC2)n2ncc(-c3nc(Cc4ccc(F)cc4)no3)c2[nH]1]

tert-butyl 4-{3-[3-(4-fluorobenzyl)-1,2,4-oxadiazol-5-yl]-5-oxo-4,5-dihydropyrazolo[1,5-a]pyrimidin-7-yl}piperidine-1-carboxylate (96.0 mg, 98% purity, 190 µmol)

hydrochloric acid 4N in 1,4-dioxan (2.0 ml)

1,4-dioxan (2.0 ml)

The title compound was prepared according to the same procedure as Example 222.

The obtained amount was 67.0 mg (99% purity, 81% of theory).

LC-MS (Method 8B): R$_t$=0.78 min; MS (ESIpos): m/z=395 [M+H-xHCl]$^+$ $^1$H-NMR (400 MHz, DMSO-d6) delta [ppm]: −0.149 (0.59), −0.008 (5.80), 0.008 (4.56), 0.146 (0.58), 1.091 (0.34), 1.861 (0.78), 1.892 (2.08), 1.919 (2.25), 1.948 (0.97), 2.188 (3.20), 2.221 (2.60), 2.367 (0.36), 2.711 (0.39), 3.087 (2.27), 3.115 (2.36), 3.387 (3.58), 3.419 (2.79), 3.568 (6.33), 3.601 (1.01), 4.128 (16.00), 6.244 (0.34), 7.149 (4.64), 7.171 (9.88), 7.194 (5.65), 7.384 (3.75), 7.398 (4.47), 7.405 (4.02), 7.419 (3.18), 8.541 (1.24), 8.734 (0.84), 8.917 (1.04).

Example 225

3-[5-(2-methylphenyl)-1,2,4-oxadiazol-3-yl]-7-(piperidin-4-yl)pyrazolo[1,5-a]pyrimidin-5(4H)-one hydrochloride

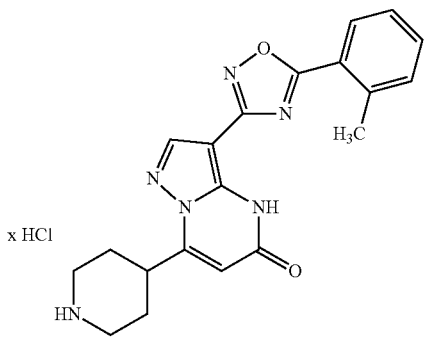 [SMILES: Cc1ccccc1-c1nc(-c2cnn3c(C4CCNCC4)cc(=O)[nH]c23)no1]

tert-butyl 4-{3-[5-(2-methylphenyl)-1,2,4-oxadiazol-3-yl]-5-oxo-4,5-dihydropyrazolo[1,5-a]pyrimidin-7-yl}piperidine-1-carboxylate (56.0 mg, 100% purity, 118 µmol)

hydrochloric acid 4N in 1,4-dioxan (2.0 ml)

1,4-dioxan (2.0 ml)

The title compound was prepared according to the same procedure as Example 209.

The obtained amount was 44.0 mg (100% purity, 91% of theory).

LC-MS (Method 8B): R$_t$=0.89 min; MS (ESIpos): m/z=377 [M+H-xHCl]$^+$ $^1$H-NMR (400 MHz, DMSO-d6) delta [ppm]: −0.008 (1.63), 0.008 (1.70), 1.894 (1.15), 1.925 (1.27), 2.216 (1.87), 2.250 (1.53), 2.328 (0.22), 2.443 (0.59), 2.671 (0.23), 2.716 (16.00), 3.105 (1.28), 3.134 (1.35), 3.403 (2.01), 3.433 (1.61), 3.601 (0.91), 6.097 (0.92), 7.456 (0.90), 7.475 (2.15), 7.495 (2.77), 7.515 (2.41), 7.591 (1.37), 7.608 (1.89), 7.626 (0.74), 8.221 (1.41), 8.239 (1.36), 8.425 (2.77), 8.665 (0.24), 8.880 (0.31), 11.483 (0.31).

Example 226

3-[5-(3-chlorophenyl)-1,2,4-oxadiazol-3-yl]-7-(piperidin-4-yl)pyrazolo[1,5-a]pyrimidin-5 (4H)-one hydrochloride

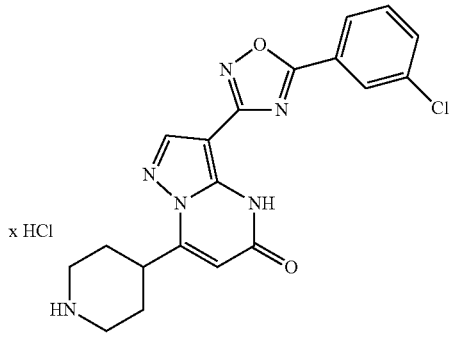 [SMILES: O=c1cc(C2CCNCC2)n2ncc(-c3noc(-c4cccc(Cl)c4)n3)c2[nH]1]

Compound tert-butyl 4-{3-[5-(3-chlorophenyl)-1,2,4-oxadiazol-3-yl]-5-oxo-4,5-dihydropyrazolo[1,5-a]pyrimidin-7-yl}piperidine-1-carboxylate (649 mg, 24% purity, 313 µmol) was dissolved in 1,4-dioxan (4.0 ml) and stirred overnight at RT with hydrochloric acid 4N in 1,4-dioxan (4.0 ml). The suspension was filtered, washed with diethyl ether (4.0 ml), crystallized from a mixture of methanol and diethyl ether, dissolved in water/acetonitrile and purified by preparative HPLC (gradient acetonitrile/water with 0.1% trifluoroacetic acid). Evaporation of the combined product fractions yielded the title compound.

The obtained amount was 12.0 mg (100% purity, 9% of theory).

LC-MS (Method 8B): R$_t$=0.96 min; MS (ESIpos): m/z=397 [M+H-xHCl]$^+$ $^1$H-NMR (400 MHz, DMSO-d6) delta [ppm]: 1.881 (7.46), 1.912 (8.18), 2.215 (11.39), 2.249 (9.49), 3.104 (8.41), 3.133 (8.50), 3.405 (13.38), 3.436 (10.67), 3.592 (4.97), 6.087 (3.44), 7.686 (7.05), 7.706 (16.00), 7.726 (10.40), 7.816 (10.67), 7.833 (7.77), 8.239 (8.05), 8.258 (7.64), 8.447 (11.98), 8.838 (3.53), 11.716 (2.12).

Example 227

7-(piperidin-4-yl)-3-{5-[3-(trifluoromethyl)phenyl]-1,2,4-oxadiazol-3-yl}pyrazolo[1,5-a]pyrimidin-5 (4H)-one hydrochloride

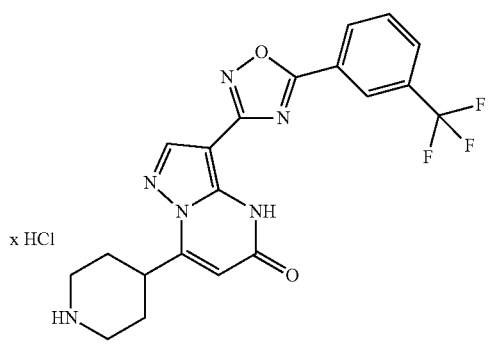 [SMILES: O=c1cc(C2CCNCC2)n2ncc(-c3noc(-c4cccc(C(F)(F)F)c4)n3)c2[nH]1]

tert-butyl 4-(5-oxo-3-{5-[3-(trifluoromethyl)phenyl]-1,2,4-oxadiazol-3-yl}-4,5-dihydropyrazolo[1,5-a]pyrimidin-7-yl)piperidine-1-carboxylate (51.0 mg, 99% purity, 95.2 μmol)

hydrochloric acid 4N in 1,4-dioxan (2.0 ml)
1,4-dioxan (2.0 ml)

The title compound was prepared according to the same procedure as Example 209.

The obtained amount was 31.0 mg (100% purity, 70% of theory).

LC-MS (Method 8B): $R_t$=0.98 min; MS (ESIpos): m/z=431 [M+H-xHCl]$^+$ $^1$H-NMR (400 MHz, DMSO-d6) delta [ppm]: 0.008 (13.57), 1.091 (4.58), 1.886 (7.73), 1.920 (8.36), 2.219 (12.67), 2.252 (10.61), 3.104 (8.36), 3.133 (8.63), 3.407 (13.48), 3.437 (11.06), 3.568 (7.91), 3.597 (5.03), 6.093 (2.88), 7.912 (7.19), 7.931 (16.00), 7.951 (9.35), 8.122 (12.31), 8.141 (10.52), 8.469 (8.81), 8.591 (9.35), 8.612 (13.66), 8.855 (2.34), 11.737 (3.15).

Example 228

3-(5-benzyl-1,2,4-oxadiazol-3-yl)-7-(piperidin-4-yl)pyrazolo[1,5-a]pyrimidin-5(4H)-one hydrochloride

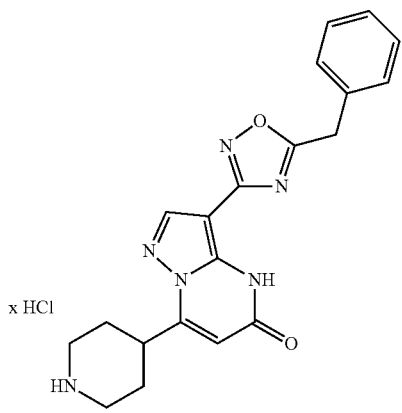 [SMILES: O=c1cc(C2CCNCC2)n2ncc(-c3noc(Cc4ccccc4)n3)c2[nH]1]

tert-butyl 4-[3-(5-benzyl-1,2,4-oxadiazol-3-yl)-5-oxo-4,5-dihydropyrazolo[1,5-a]pyrimidin-7-yl]piperidine-1-carboxylate (116 mg, 86% purity, 209 μmol)

hydrochloric acid 4N in 1,4-dioxan (3.0 ml)
1,4-dioxan (3.0 ml)

The title compound was prepared according to the same procedure as Example 209.

The obtained amount was 89.0 mg (97% purity, quantitative)

LC-MS (Method 8B): $R_t$=0.80 min; MS (ESIpos): m/z=377 [M+H-xHCl]$^+$ $^1$H-NMR (400 MHz, DMSO-d6) delta [ppm]: −0.008 (0.82), 0.000 (16.00), 0.008 (0.74), 1.091 (0.16), 1.417 (0.18), 1.596 (0.23), 1.730 (0.17), 1.876 (0.41), 1.906 (0.44), 2.137 (0.50), 2.191 (0.65), 2.224 (0.52), 2.671 (0.11), 3.081 (0.49), 3.110 (0.49), 3.205 (0.37), 3.414 (0.70), 3.568 (3.27), 4.427 (3.81), 6.075 (0.13), 7.298 (0.26), 7.314 (0.52), 7.322 (0.39), 7.330 (0.51), 7.335 (0.38), 7.361 (0.54), 7.381 (1.86), 7.393 (1.96), 7.398 (3.75), 7.413 (0.35), 8.341 (0.49), 8.721 (0.11), 8.908 (0.13), 11.261 (0.07).

Example 229

3-[5-(3-chloro-2-methylphenyl)-1,2,4-oxadiazol-3-yl]-7-(piperidin-4-yl)pyrazolo[1,5-a]pyrimidin-5(4H)-one hydrochloride

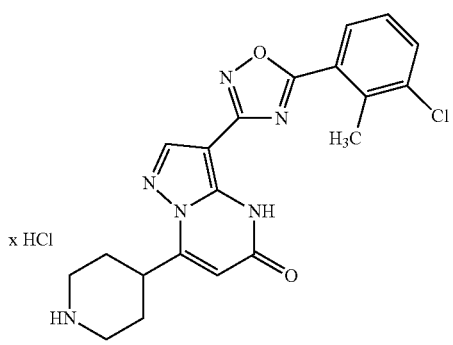 [SMILES: Cc1c(Cl)cccc1-c1nc(-c2cnn3c(C4CCNCC4)cc(=O)[nH]c23)no1]

tert-butyl 4-{3-[5-(3-chloro-2-methylphenyl)-1,2,4-oxadiazol-3-yl]-5-oxo-4,5-dihydropyrazolo[1,5-a]pyrimidin-7-yl}piperidine-1-carboxylate (36.0 mg, 100% purity, 70.5 μmol)

hydrochloric acid 4N in 1,4-dioxan (2.0 ml)
1,4-dioxan (2.0 ml)

The title compound was prepared according to the same procedure as Example 209.

The obtained amount was 31.0 mg (99% purity, 97% of theory).

LC-MS (Method 8B): $R_t$=0.96 min; MS (ESIpos): m/z=411 [M+H-xHCl]$^+$ $^1$H-NMR (400 MHz, DMSO-d6) delta [ppm]: 1.885 (1.16), 1.918 (1.25), 2.216 (1.88), 2.251 (1.61), 2.328 (0.43), 2.367 (0.39), 2.670 (0.40), 2.709 (0.50), 2.730 (16.00), 3.081 (0.51), 3.104 (1.33), 3.138 (1.43), 3.163 (0.59), 3.402 (2.42), 3.434 (1.76), 3.567 (10.80), 3.602 (0.83), 6.110 (0.67), 7.486 (1.24), 7.505 (2.64), 7.525 (1.44), 7.801 (2.34), 7.821 (2.12), 8.130 (1.33), 8.148 (1.33), 8.433 (2.37), 8.837 (0.39), 11.577 (0.35).

Example 230

3-[5-(5-chloro-2-methylphenyl)-1,2,4-oxadiazol-3-yl]-7-(piperidin-4-yl)pyrazolo[1,5-a]pyrimidin-5(4H)-one hydrochloride

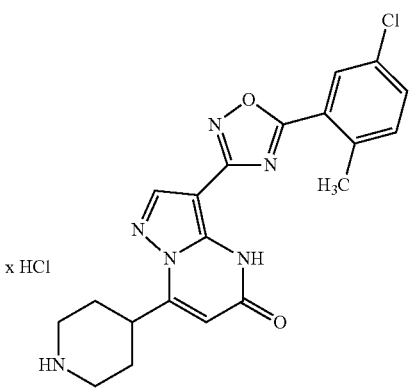 [SMILES: Cc1ccc(Cl)cc1-c1nc(-c2cnn3c(C4CCNCC4)cc(=O)[nH]c23)no1]

tert-butyl 4-{3-[5-(5-chloro-2-methylphenyl)-1,2,4-oxadiazol-3-yl]-5-oxo-4,5-dihydropyrazolo[1,5-a]pyrimidin-7-yl}piperidine-1-carboxylate (50.0 mg, 100% purity, 97.9 μmol)

hydrochloric acid 4N in 1,4-dioxan (2.0 ml)

1,4-dioxan (2.0 ml)

The title compound was prepared according to the same procedure as Example 209.

The obtained amount was 26.0 mg (100% purity, 59% of theory).

LC-MS (Method 8B): R$_t$=0.97 min; MS (ESIpos): m/z=411 [M+H−xHCl]$^+$ $^1$H-NMR (400 MHz, DMSO-d6) delta [ppm]: −0.149 (0.40), 0.008 (3.26), 0.146 (0.41), 1.894 (1.29), 1.926 (1.41), 2.215 (1.96), 2.248 (1.59), 2.686 (16.00), 3.103 (1.43), 3.131 (1.45), 3.425 (6.89), 3.568 (5.03), 3.599 (1.01), 6.101 (1.06), 7.532 (2.22), 7.553 (2.96), 7.665 (1.94), 7.670 (1.95), 7.685 (1.43), 7.691 (1.44), 8.342 (1.45), 8.438 (3.05), 8.714 (0.42), 8.919 (0.56), 11.634 (0.23).

Example 231

7-(piperidin-4-yl)-3-{5-[4-(trifluoromethyl)phenyl]-1,2,4-oxadiazol-3-yl}pyrazolo[1,5-a]pyrimidin-5(4H)-one hydrochloride

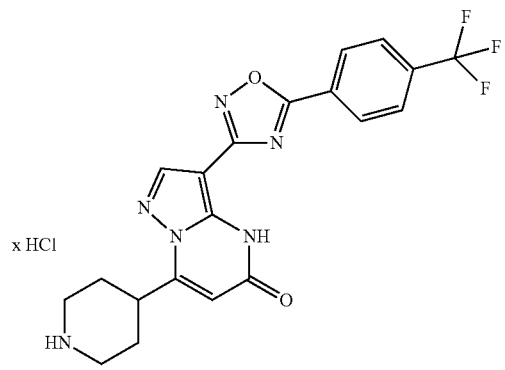 [SMILES: O=c1cc(C2CCNCC2)n2ncc(-c3noc(-c4ccc(C(F)(F)F)cc4)n3)c2[nH]1]

tert-butyl 4-(5-oxo-3-{5-[4-(trifluoromethyl)phenyl]-1,2,4-oxadiazol-3-yl}-4,5-dihydropyrazolo[1,5-a]pyrimidin-7-yl)piperidine-1-carboxylate (57.0 mg, 100% purity, 107 μmol)

hydrochloric acid 4N in 1,4-dioxan (2.0 ml)

1,4-dioxan (2.0 ml)

The title compound was prepared according to the same procedure as Example 209.

The obtained amount was 38.0 mg (98% purity, 74% of theory).

LC-MS (Method 8B): R$_t$=0.91 min; MS (ESIneg): m/z=429 [M−H−xHCl]$^-$ $^1$H-NMR (400 MHz, DMSO-d6) delta [ppm]: −0.149 (0.11), 0.146 (0.12), 1.909 (0.71), 1.941 (0.79), 1.971 (0.32), 2.215 (1.17), 2.248 (0.95), 3.100 (0.76), 3.128 (0.79), 3.400 (1.19), 3.431 (0.95), 3.568 (16.00), 3.598 (0.56), 6.098 (0.51), 8.044 (2.11), 8.064 (2.33), 8.457 (1.41), 8.520 (1.61), 8.540 (1.49), 8.827 (0.18), 8.994 (0.23), 11.738 (0.26).

Example 232

3-{5-[2-chloro-4-(trifluoromethyl)phenyl]-1,2,4-oxadiazol-3-yl}-7-(piperidin-4-yl)pyrazolo[1,5-a]pyrimidin-5(4H)-one hydrochloride

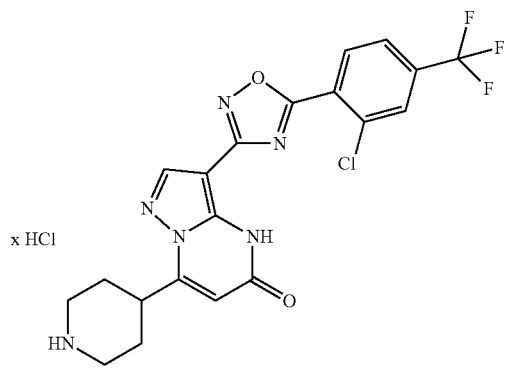 [SMILES: O=c1cc(C2CCNCC2)n2ncc(-c3noc(-c4ccc(C(F)(F)F)cc4Cl)n3)c2[nH]1]

tert-butyl 4-(3-{5-[2-chloro-4-(trifluoromethyl)phenyl]-1,2,4-oxadiazol-3-yl}-5-oxo-4,5-dihydropyrazolo[1,5-a]pyrimidin-7-yl)piperidine-1-carboxylate (51.0 mg, 99% purity, 89.4 μmol)

hydrochloric acid 4N in 1,4-dioxan (2.0 ml)

1,4-dioxan (2.0 ml)

The title compound was prepared according to the same procedure as Example 209.

The obtained amount was 32.0 mg (98% purity, 70% of theory).

LC-MS (Method 8B): R$_t$=0.98 min; MS (ESIpos): m/z=465 [M+H−xHCl]$^+$ $^1$H-NMR (400 MHz, DMSO-d6) delta [ppm]: −0.008 (1.00), 0.000 (16.00), 0.008 (0.55), 1.426 (0.18), 1.868 (0.10), 1.894 (0.26), 1.926 (0.28), 1.957 (0.12), 2.215 (0.40), 2.248 (0.32), 3.072 (0.12), 3.101 (0.29), 3.131 (0.29), 3.160 (0.12), 3.375 (0.16), 3.404 (0.43), 3.434 (0.33), 3.568 (5.27), 3.593 (0.17), 6.096 (0.11), 8.154 (0.54), 8.175 (0.61), 8.431 (0.27), 8.451 (0.26), 8.470 (0.36), 8.694 (0.23), 8.912 (0.12), 11.773 (0.09).

Example 233

3-[5-(4-chlorophenyl)-1,2,4-oxadiazol-3-yl]-7-(piperidin-4-yl)pyrazolo[1,5-a]pyrimidin-5(4H)-one hydrochloride

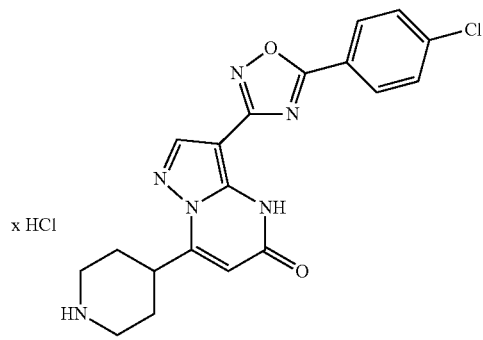 [SMILES: O=c1cc(C2CCNCC2)n2ncc(-c3noc(-c4ccc(Cl)cc4)n3)c2[nH]1]

tert-butyl 4-{3-[5-(4-chlorophenyl)-1,2,4-oxadiazol-3-yl]-5-oxo-4,5-dihydropyrazolo[1,5-a]pyrimidin-7-yl}piperidine-1-carboxylate (41.0 mg, 96% purity, 79.2 μmol)

hydrochloric acid 4N in 1,4-dioxan (2.0 ml)

1,4-dioxan (2.0 ml)

The title compound was prepared according to the same procedure as Example 209.

The obtained amount was 27.0 mg (96% purity, 76% of theory).

LC-MS (Method 8B): $R_t$=0.93 min; MS (ESIpos): m/z=397 [M+H-xHCl]$^+$ $^1$H-NMR (400 MHz, DMSO-d6) delta [ppm]: −0.149 (0.08), −0.008 (1.00), 0.000 (16.00), 0.008 (0.55), 0.146 (0.07), 1.091 (0.08), 1.426 (0.18), 1.596 (0.08), 1.894 (0.26), 1.926 (0.28), 1.957 (0.12), 2.215 (0.40), 2.248 (0.32), 3.101 (0.29), 3.131 (0.29), 3.404 (0.43), 3.434 (0.33), 3.568 (5.27), 3.593 (0.17), 6.096 (0.11), 8.154 (0.54), 8.175 (0.61), 8.431 (0.27), 8.451 (0.26), 8.470 (0.36), 8.694 (0.23), 8.912 (0.12), 11.773 (0.09).

Example 234

3-[5-(3,5-dichlorophenyl)-1,2,4-oxadiazol-3-yl]-7-(piperidin-4-yl)pyrazolo[1,5-a]pyrimidin-5(4H)-one hydrochloride

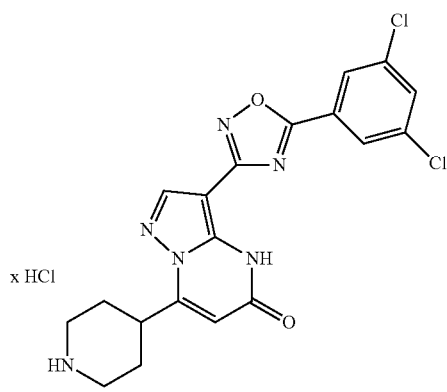 [SMILES: O=c1cc(C2CCNCC2)n2ncc(-c3noc(-c4cc(Cl)cc(Cl)c4)n3)c2[nH]1]

tert-butyl 4-{3-[5-(3,5-dichlorophenyl)-1,2,4-oxadiazol-3-yl]-5-oxo-4,5-dihydropyrazolo[1,5-a]pyrimidin-7-yl}piperidine-1-carboxylate (25.0 mg, 77% purity, 36.2 μmol)

hydrochloric acid 4N in 1,4-dioxan (2.0 ml)

1,4-dioxan (2.0 ml)

The title compound was prepared according to the same procedure as Example 209.

The obtained amount was 18.2 mg (93% purity, quantitative)

LC-MS (Method 8B): $R_t$=1.00 min; MS (ESIpos): m/z=431 [M+H-xHCl]$^+$ $^1$H-NMR (400 MHz, DMSO-d6) delta [ppm]: −0.149 (0.47), 0.008 (4.34), 0.146 (0.48), 1.425 (0.35), 1.884 (1.06), 1.915 (1.16), 2.214 (1.66), 2.248 (1.37), 3.102 (1.20), 3.130 (1.28), 3.403 (1.90), 3.434 (1.48), 3.568 (16.00), 6.079 (0.42), 8.037 (2.25), 8.387 (1.22), 8.454 (1.20), 8.642 (0.30), 8.859 (0.39), 11.742 (0.42).

Example 235

3-[5-(5-chloro-2-fluorophenyl)-1,2,4-oxadiazol-3-yl]-7-(piperidin-4-yl)pyrazolo[1,5-c]pyrimidin-5(4H)-one hydrochloride

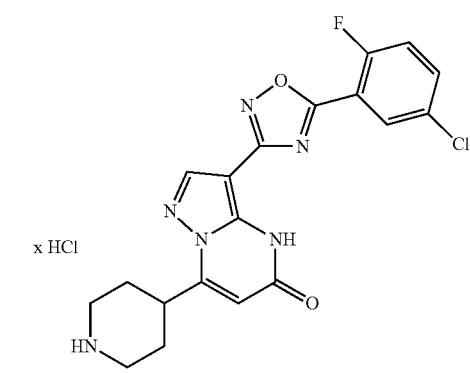 [SMILES: O=c1cc(C2CCNCC2)n2ncc(-c3noc(-c4cc(Cl)ccc4F)n3)c2[nH]1]

Compound tert-butyl 4-{3-[5-(5-chloro-2-fluorophenyl)-1,2,4-oxadiazol-3-yl]-5-oxo-4,5-dihydropyrazolo[1,5-a]pyrimidin-7-yl}piperidine-1-carboxylate (27.0 mg, 87% purity, 45.6 μmol) was dissolved in 1,4-dioxan (2.0 ml) and stirred overnight at RT with hydrochloric acid 4N in 1,4-dioxan (2.0 ml). The suspension was filtered and washed with diethyl ether (2.0 ml). The recovered solid was diluted with acetonitrile (2.0 mL), the suspension was filtered and the filtrate concentrated to yield the title compound.

The obtained amount was 12.0 mg (90% purity, 52% of theory).

LC-MS (Method 8B): $R_t$=0.87 min; MS (ESIneg): m/z=413 [M−H-xHCl]$^-$ $^1$H-NMR (400 MHz, DMSO-d6) delta [ppm]: 1.892 (5.22), 1.925 (5.58), 2.074 (9.05), 2.214 (7.82), 2.246 (6.29), 2.739 (15.79), 3.101 (5.89), 3.130 (5.85), 3.402 (10.12), 3.483 (16.00), 6.099 (2.93), 7.598 (4.35), 7.621 (6.87), 7.646 (5.04), 7.861 (4.09), 7.883 (3.52), 8.455 (8.59), 8.585 (2.05), 8.910 (2.45), 11.686 (0.87).

Example 236

7-(piperidin-4-yl)-3-{5-[2-(trifluoromethoxy)phe-nyl]-1,2,4-oxadiazol-3-yl}pyrazolo[1,5-c]pyrimidin-5(4H)-one hydrochloride

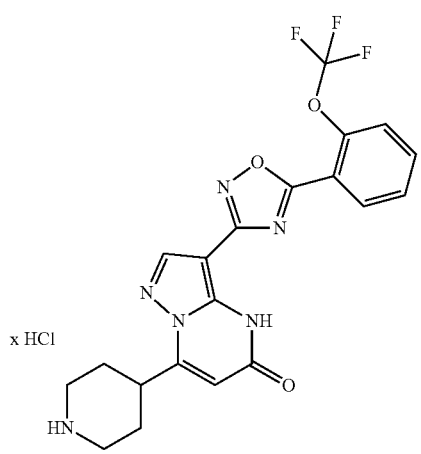 [SMILES: O=c1cc(C2CCNCC2)n2ncc(-c3noc(-c4ccccc4OC(F)(F)F)n3)c2[nH]1]

tert-butyl 4-(5-oxo-3-{5-[2-(trifluoromethoxy)phenyl]-1,2,4-oxadiazol-3-yl}-4,5-dihydropyrazolo[1,5-a]pyrimidin-7-yl)piperidine-1-carboxylate (45.0 mg, 93% purity, 76.6 μmol)

hydrochloric acid 4N in 1,4-dioxan (2.0 ml)

1,4-dioxan (2.0 ml)

The title compound was prepared according to the same procedure as Example 209.

The obtained amount was 34.0 mg (100% purity, 92% of theory).

LC-MS (Method 8B): $R_t$=0.90 min; MS (ESIpos): m/z=447 [M+H-xHCl]$^+$ $^1$H-NMR (400 MHz, DMSO-d6) delta [ppm]: 1.893 (0.80), 1.923 (0.89), 2.215 (1.26), 2.249 (1.05), 3.103 (0.84), 3.132 (0.88), 3.402 (1.30), 3.433 (1.06), 3.568 (16.00), 3.597 (0.53), 6.098 (0.32), 7.712 (1.70), 7.731 (3.17), 7.750 (1.09), 7.875 (0.93), 7.880 (0.93), 7.896 (1.24), 7.915 (0.62), 7.919 (0.61), 8.429 (1.56), 8.553 (0.45), 8.690 (0.25), 8.893 (0.31), 11.539 (0.32).

Example 237

3-[5-(3-chloro-4-methoxyphenyl)-1,2,4-oxadiazol-3-yl]-7-(piperidin-4-yl)pyrazolo[1,5-c]pyrimidin-5(4H)-one hydrochloride

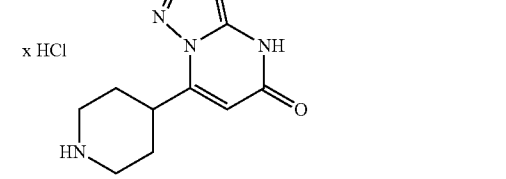

tert-butyl 4-{3-[5-(3-chloro-4-methoxyphenyl)-1,2,4-oxadiazol-3-yl]-5-oxo-4,5-dihydropyrazolo[1,5-a]pyrimidin-7-yl}piperidine-1-carboxylate (10.0 mg, 72% purity, 13.7 μmol)

hydrochloric acid 4N in 1,4-dioxan (2.0 ml)

1,4-dioxan (2.0 ml)

The title compound was prepared according to the same procedure as Example 209.

The obtained amount was 5.00 mg (100% purity, 79% of theory).

LC-MS (Method 8B): $R_t$=0.89 min; MS (ESIpos): m/z=427 [M+H-xHCl]$^+$ $^1$H-NMR (400 MHz, DMSO-d6) delta [ppm]: 1.885 (1.19), 1.911 (1.28), 2.213 (1.80), 2.247 (1.47), 3.102 (1.25), 3.130 (1.29), 3.402 (1.87), 3.433 (1.50), 3.585 (0.74), 4.004 (16.00), 6.076 (0.50), 7.407 (2.74), 7.429 (2.94), 8.225 (1.17), 8.247 (1.12), 8.425 (2.45), 8.631 (0.45), 8.843 (0.52), 11.656 (0.54).

Example 238

3-{3-[hydroxy(phenyl)methyl]-1,2,4-oxadiazol-5-yl}-7-(piperidin-4-yl)pyrazolo[1,5-a]pyrimidin-5(4H)-one hydrochloride

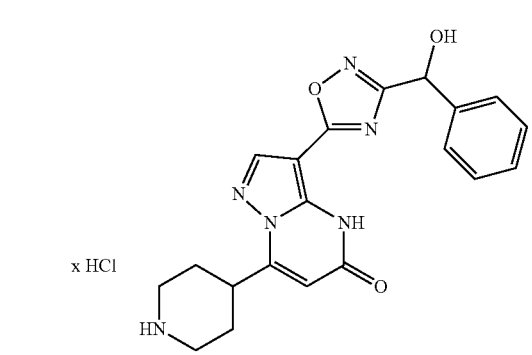 [SMILES: O=c1cc(C2CCNCC2)n2ncc(-c3nc(C(O)c4ccccc4)no3)c2[nH]1]

tert-butyl 4-(3-{3-[hydroxy(phenyl)methyl]-1,2,4-oxadiazol-5-yl}-5-oxo-4,5-dihydropyrazolo[1,5-a]pyrimidin-7-yl)piperidine-1-carboxylate (25.0 mg, 85% purity, 43.1 μmol)

hydrochloric acid 4N in 1,4-dioxan (2.0 ml)
1,4-dioxan (2.0 ml)

The title compound was prepared according to the same procedure as Example 222.

The obtained amount was 15.0 mg (92% purity, 75% of theory).

LC-MS (Method 8B): R$_t$=0.67 min; MS (ESIpos): m/z=393 [M+H-xHCl]$^+$ $^1$H-NMR (400 MHz, DMSO-d6) delta [ppm]: −0.149 (0.08), 0.000 (16.00), 0.146 (0.08), 1.898 (0.09), 2.188 (0.13), 2.220 (0.11), 3.089 (0.11), 3.119 (0.11), 3.568 (0.08), 5.900 (0.34), 6.418 (0.03), 7.282 (0.06), 7.300 (0.18), 7.319 (0.14), 7.355 (0.24), 7.374 (0.40), 7.392 (0.19), 7.485 (0.28), 7.503 (0.22), 8.543 (0.06), 8.811 (0.04).

Example 239

7-(piperidin-4-yl)-3-{5-[4-(trifluoromethoxy)benzyl]-1,2,4-oxadiazol-3-yl}pyrazolo[1,5-c]pyrimidin-5(4H)-one hydrochloride

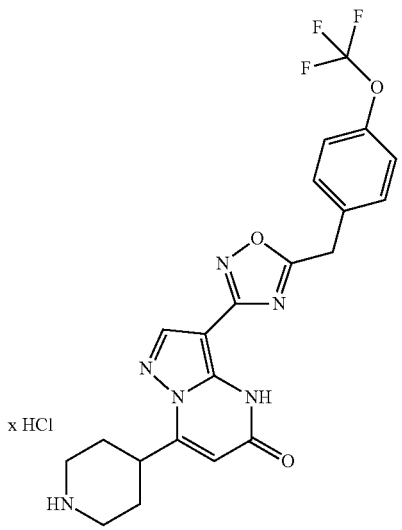 [SMILES: O=c1cc(C2CCNCC2)n2ncc(-c3noc(Cc4ccc(OC(F)(F)F)cc4)n3)c2[nH]1]

tert-butyl 4-(5-oxo-3-{5-[4-(trifluoromethoxy)benzyl]-1,2,4-oxadiazol-3-yl}-4,5-dihydropyrazolo[1,5-a]pyrimidin-7-yl)piperidine-1-carboxylate (64.0 mg, 97% purity, 111 μmol)

hydrochloric acid 4N in 1,4-dioxan (4.0 ml)
1,4-dioxan (2.0 ml)

The title compound was prepared according to the same procedure as Example 222.

The obtained amount was 58.0 mg (95% purity, quantitative)

LC-MS (Method 8B): R$_t$=0.95 min; MS (ESIpos): m/z=461 [M+H-xHCl]$^+$ $^1$H-NMR (400 MHz, DMSO-d6) delta [ppm]: −0.149 (0.36), −0.008 (3.62), 0.008 (3.43), 0.146 (0.39), 1.235 (1.98), 1.861 (0.72), 1.893 (2.00), 1.918 (2.21), 1.950 (1.02), 2.137 (1.00), 2.188 (3.09), 2.221 (2.51), 2.712 (0.34), 3.080 (2.10), 3.108 (2.19), 3.380 (3.94), 3.413 (2.85), 3.577 (1.30), 3.595 (1.22), 3.633 (0.65), 3.682 (0.37), 3.701 (0.44), 3.949 (0.60), 4.494 (16.00), 6.084 (0.75), 7.295 (1.08), 7.379 (5.58), 7.399 (6.97), 7.545 (9.17), 7.567 (7.16), 8.338 (3.66), 8.804 (0.71), 8.986 (0.88), 11.286 (0.44).

Example 240

3-[5-(3,5-difluoro-4-methoxybenzyl)-1,2,4-oxadiazol-3-yl]-7-(piperidin-4-yl)pyrazolo[1,5-c]pyrimidin-5(4H)-one hydrochloride

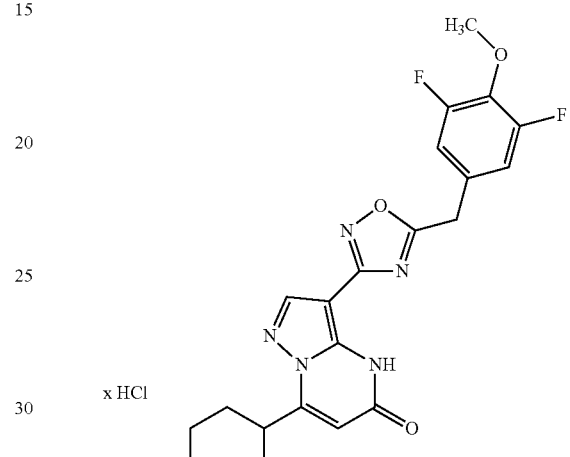

tert-butyl 4-{3-[5-(3,5-difluoro-4-methoxybenzyl)-1,2,4-oxadiazol-3-yl]-5-oxo-4,5-dihydropyrazolo[1,5-a]pyrimidin-7-yl}piperidine-1-carboxylate (58.0 mg, 100% purity, 107 μmol)

hydrochloric acid 4N in 1,4-dioxan (4.0 ml)
1,4-dioxan (2.0 ml)

The title compound was prepared according to the same procedure as Example 222.

The obtained amount was 53.0 mg (96% purity, 99% of theory).

LC-MS (Method 8B): R$_t$=0.85 min; MS (ESIpos): m/z=443 [M+H-xHCl]$^+$ $^1$H-NMR (400 MHz, DMSO-d6) delta [ppm]: −0.149 (0.07), 0.000 (16.00), 0.146 (0.09), 0.853 (0.08), 1.171 (0.09), 1.234 (0.78), 1.469 (0.10), 1.874 (0.28), 1.903 (0.77), 1.932 (0.84), 1.962 (0.37), 2.137 (0.12), 2.188 (1.19), 2.221 (0.93), 2.370 (0.06), 2.674 (0.07), 2.714 (0.07), 3.078 (0.83), 3.106 (0.85), 3.136 (0.36), 3.412 (1.12), 3.476 (0.43), 3.493 (0.42), 3.548 (0.47), 3.577 (0.72), 3.595 (0.50), 3.682 (0.16), 3.702 (0.18), 3.857 (0.10), 3.894 (0.38), 3.918 (8.91), 4.099 (0.06), 4.420 (5.00), 4.648 (0.06), 6.081 (0.44), 7.240 (0.42), 7.254 (2.33), 7.277 (2.32), 7.291 (0.33), 8.340 (1.72), 8.896 (0.27), 9.056 (0.36), 11.300 (0.09).

Example 241

3-{5-[rac-1-(4-methoxyphenyl)propyl]-1,2,4-oxadiazol-3-yl}-7-(piperidin-4-yl)pyrazolo[1,5-a]pyrimidin-5(4H)-one hydrochloride

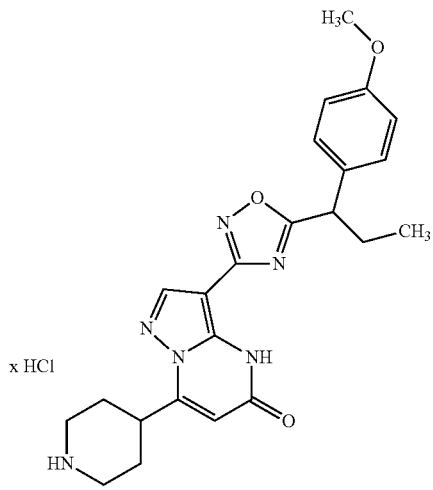 [SMILES: CCC(c1ccc(OC)cc1)c1nc(-c2cnn3c(C4CCNCC4)cc(=O)[nH]c23)no1]

tert-butyl 4-(3-{5-[rac-1-(4-methoxyphenyl)propyl]-1,2,4-oxadiazol-3-yl}-5-oxo-4,5-dihydropyrazolo[1,5-a]pyrimidin-7-yl)piperidine-1-carboxylate (41.0 mg, 93% purity, 71.3 µmol)

hydrochloric acid 4N in 1,4-dioxan (4.0 ml)

1,4-dioxan (2.0 ml)

The title compound was prepared according to the same procedure as Example 222.

The obtained amount was 34.0 mg (92% purity, 93% of theory).

LC-MS (Method 8B): $R_t$=0.93 min; MS (ESIpos): m/z=435 [M+H-xHCl]$^+$ $^1$H-NMR (400 MHz, DMSO-d6) delta [ppm]: −0.149 (0.08), −0.008 (0.84), 0.000 (16.00), 0.146 (0.07), 0.788 (0.07), 0.806 (0.16), 0.824 (0.08), 0.858 (0.87), 0.877 (1.93), 0.895 (0.90), 1.148 (0.05), 1.235 (0.43), 1.625 (0.05), 1.880 (0.29), 1.910 (0.32), 1.940 (0.17), 2.004 (0.12), 2.023 (0.20), 2.038 (0.21), 2.057 (0.24), 2.076 (0.15), 2.137 (0.41), 2.190 (0.45), 2.226 (0.50), 2.245 (0.29), 2.263 (0.24), 2.279 (0.20), 2.297 (0.12), 2.368 (0.04), 2.674 (0.06), 2.712 (0.05), 3.085 (0.31), 3.113 (0.32), 3.415 (0.50), 3.463 (0.11), 3.474 (0.11), 3.492 (0.10), 3.574 (0.18), 3.594 (0.23), 3.681 (0.09), 3.701 (0.11), 3.727 (0.59), 3.736 (5.47), 4.313 (0.29), 4.332 (0.60), 4.352 (0.27), 4.647 (0.04), 6.068 (0.09), 6.866 (0.08), 6.888 (0.09), 6.919 (1.16), 6.941 (1.28), 7.181 (0.10), 7.202 (0.08), 7.329 (1.10), 7.350 (0.99), 7.968 (0.06), 8.343 (0.32), 8.739 (0.08), 8.955 (0.15), 11.349 (0.07).

Example 242

3-{5-[2-(4-methoxyphenyl)propan-2-yl]-1,2,4-oxadiazol-3-yl}-7-(piperidin-4-yl)pyrazolo[1,5-a]pyrimidin-5(4H)-one hydrochloride

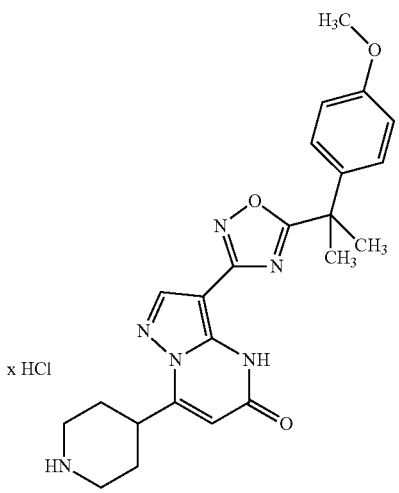 [SMILES: COc1ccc(C(C)(C)c2nc(-c3cnn4c(C5CCNCC5)cc(=O)[nH]c34)no2)cc1]

tert-butyl 4-(3-{5-[2-(4-methoxyphenyl)propan-2-yl]-1,2,4-oxadiazol-3-yl}-5-oxo-4,5-dihydropyrazolo[1,5-a]pyrimidin-7-yl)piperidine-1-carboxylate (30.0 mg, 96% purity, 53.9 µmol)

hydrochloric acid 4N in 1,4-dioxan (4.0 ml)

1,4-dioxan (2.0 ml)

The title compound was prepared according to the same procedure as Example 222.

The obtained amount was 26.0 mg (99% purity, quantitative)

LC-MS (Method 8B): $R_t$=0.97 min; MS (ESIpos): m/z=435 [M+H-xHCl]$^+$ $^1$H-NMR (400 MHz, DMSO-d6) delta [ppm]: −0.149 (0.17), −0.008 (1.72), 0.008 (1.64), 0.146 (0.17), 1.239 (0.22), 1.254 (0.17), 1.440 (1.52), 1.815 (15.65), 1.884 (0.81), 1.913 (0.87), 1.942 (0.46), 1.975 (0.17), 2.137 (1.08), 2.193 (1.19), 2.227 (0.97), 3.057 (0.30), 3.086 (0.83), 3.115 (0.86), 3.145 (0.37), 3.258 (0.17), 3.418 (1.15), 3.463 (0.25), 3.474 (0.27), 3.491 (0.24), 3.503 (0.21), 3.551 (0.37), 3.579 (0.52), 3.593 (0.65), 3.667 (0.17), 3.671 (0.18), 3.681 (0.22), 3.701 (0.27), 3.713 (0.24), 3.729 (2.04), 3.734 (16.00), 6.065 (0.31), 6.868 (0.22), 6.890 (0.32), 6.895 (0.38), 6.903 (3.29), 6.908 (1.21), 6.920 (1.23), 6.925 (3.76), 6.933 (0.48), 7.243 (0.27), 7.265 (0.27), 7.285 (3.17), 7.307 (2.94), 8.339 (1.03), 8.748 (0.25), 8.955 (0.39), 11.394 (0.20).

Example 243

7-(piperidin-4-yl)-3-[5-(tetrahydro-2H-pyran-4-yl)-1,2,4-oxadiazol-3-yl]pyrazolo[1,5-c]pyrimidin-5(4H)-one hydrochloride

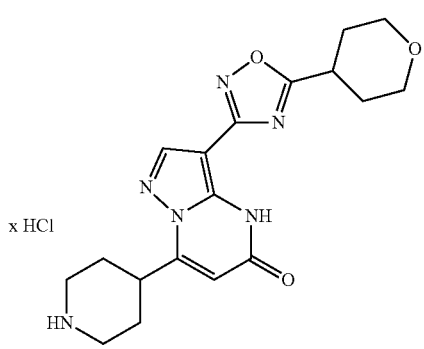 [SMILES: O=c1cc(C2CCNCC2)n2ncc(-c3noc(C4CCOCC4)n3)c2[nH]1]

tert-butyl 4-{5-oxo-3-[5-(tetrahydro-2H-pyran-4-yl)-1,2,4-oxadiazol-3-yl]-4,5-dihydropyrazolo[1,5-a]pyrimidin-7-yl}piperidine-1-carboxylate (58.0 mg, 94% purity, 116 µmol)

hydrochloric acid 4N in 1,4-dioxan (4.0 ml)

1,4-dioxan (2.0 ml)

The title compound was prepared according to the same procedure as Example 222.

The obtained amount was 46.0 mg (100% purity, 98% of theory).

LC-MS (Method 1B): $R_t$=0.46 min; MS (ESIpos): m/z=371 [M+H-xHCl]$^+$ $^1$H-NMR (400 MHz, DMSO-d6) delta [ppm]: −0.008 (13.67), 0.008 (12.31), 1.806 (2.33), 1.817 (2.64), 1.840 (6.22), 1.845 (7.62), 1.868 (9.69), 1.879 (11.11), 1.895 (7.76), 1.907 (6.85), 1.918 (6.39), 1.947 (2.76), 1.999 (9.63), 2.004 (9.83), 2.031 (6.79), 2.037 (6.48), 2.137 (1.53), 2.195 (8.84), 2.229 (7.22), 3.055 (2.30), 3.085 (6.34), 3.113 (6.54), 3.143 (2.67), 3.357 (2.30), 3.367 (4.80), 3.385 (12.02), 3.395 (14.10), 3.405 (7.87), 3.413 (8.47), 3.422 (10.06), 3.470 (7.25), 3.475 (9.35), 3.498 (15.80), 3.504 (16.00), 3.527 (9.46), 3.532 (8.44), 3.548 (3.61), 3.578 (5.94), 3.608 (5.31), 3.656 (5.83), 3.667 (6.37), 3.681 (6.42), 3.699 (5.91), 3.709 (5.09), 3.713 (5.09), 3.899 (6.85), 3.907 (10.74), 3.915 (8.27), 3.927 (7.22), 3.935 (9.32), 3.944 (6.00), 6.076 (3.75), 8.346 (13.10), 8.761 (1.56), 8.952 (1.99), 11.331 (0.40).

Example 244

3-{5-[4-(difluoromethoxy)benzyl]-1,2,4-oxadiazol-3-yl}-7-(piperidin-4-yl)pyrazolo[1,5-c]pyrimidin-5(4H)-one hydrochloride

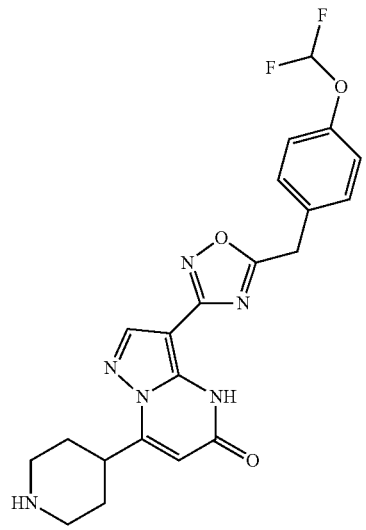

tert-butyl 4-(3-{5-[4-(difluoromethoxy)benzyl]-1,2,4-oxadiazol-3-yl}-5-oxo-4,5-dihydropyrazolo[1,5-a]pyrimidin-7-yl)piperidine-1-carboxylate (38.0 mg, 98% purity, 68.6 µmol)

hydrochloric acid 4N in 1,4-dioxan (4.0 ml)

1,4-dioxan (2.0 ml)

The title compound was prepared according to the same procedure as Example 222.

The obtained amount was 33.0 mg (100% purity, quantitative)

LC-MS (Method 8B): $R_t$=0.90 min; MS (ESIpos): m/z=443 [M+H-xHCl]$^+$ $^1$H-NMR (400 MHz, DMSO-d6) delta [ppm]: 1.860 (0.81), 1.890 (2.36), 1.920 (2.66), 1.949 (1.20), 2.189 (3.56), 2.222 (3.05), 3.051 (0.93), 3.078 (2.55), 3.108 (2.74), 3.125 (1.75), 3.137 (1.27), 3.410 (4.85), 3.463 (0.71), 3.475 (0.68), 3.492 (0.61), 3.503 (0.52), 3.546 (0.95), 3.575 (1.57), 3.595 (1.67), 3.682 (0.51), 3.701 (0.56), 4.439 (16.00), 6.083 (0.84), 7.049 (2.89), 7.182 (7.15), 7.203 (8.62), 7.234 (5.86), 7.419 (2.92), 7.460 (8.12), 7.482 (7.25), 8.336 (2.89), 8.802 (0.73), 8.988 (0.98), 11.284 (0.36).

Example 245

3-{5-[1-(4-methoxyphenyl)cyclopropyl]-1,2,4-oxadiazol-3-yl}-7-(piperidin-4-yl)pyrazolo[1,5-a]pyrimidin-5(4H)-one hydrochloride

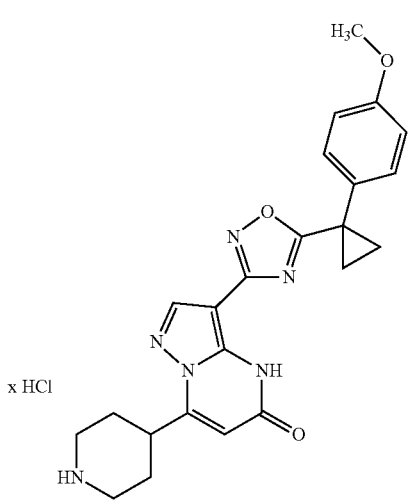 [SMILES: COc1ccc(C2(c3nc(-c4cnn5c(C6CCNCC6)cc(=O)[nH]c45)no3)CC2)cc1]

tert-butyl 4-(3-{5-[1-(4-methoxyphenyl)cyclopropyl]-1,2,4-oxadiazol-3-yl}-5-oxo-4,5-dihydropyrazolo[1,5-a]pyrimidin-7-yl)piperidine-1-carboxylate (41.0 mg, 100% purity, 77.0 µmol)

hydrochloric acid 4N in 1,4-dioxan (4.0 ml)

1,4-dioxan (2.0 ml)

The title compound was prepared according to the same procedure as Example 222.

The obtained amount was 36.0 mg (100% purity, quantitative)

LC-MS (Method 8B): $R_t$=0.95 min; MS (ESIpos): m/z=433 [M+H-xHCl]$^+$ $^1$H-NMR (400 MHz, DMSO-d6) delta [ppm]: −0.008 (0.81), 0.000 (16.00), 0.008 (0.74), 1.531 (0.64), 1.543 (1.77), 1.549 (1.76), 1.560 (0.78), 1.820 (0.67), 1.830 (1.59), 1.836 (1.55), 1.847 (0.76), 1.876 (0.58), 1.882 (0.59), 1.908 (0.63), 1.939 (0.29), 1.946 (0.24), 2.179 (0.87), 2.212 (0.71), 3.046 (0.21), 3.074 (0.57), 3.103 (0.60), 3.131 (0.25), 3.378 (0.94), 3.409 (0.74), 3.531 (0.23), 3.560 (0.42), 3.593 (0.41), 3.775 (10.71), 6.044 (0.46), 6.937 (0.28), 6.945 (2.32), 6.961 (0.90), 6.966 (2.58), 6.974 (0.33), 7.392 (0.32), 7.399 (2.59), 7.403 (0.91), 7.416 (0.85), 7.421 (2.35), 7.428 (0.30), 8.270 (1.48), 8.801 (0.19), 8.955 (0.22), 8.971 (0.25), 11.288 (0.21).

Example 246

3-[5-(2-fluoro-4-methoxybenzyl)-1,2,4-oxadiazol-3-yl]-7-(piperidin-4-yl)pyrazolo[1,5-c]pyrimidin-5(4H)-one hydrochloride

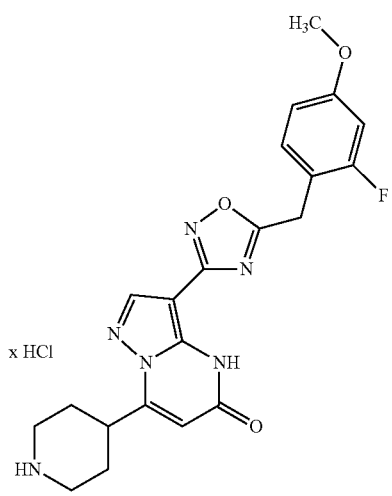 [SMILES: COc1ccc(Cc2nc(-c3cnn4c(C5CCNCC5)cc(=O)[nH]c34)no2)c(F)c1]

Compound tert-butyl 4-{3-[5-(2-fluoro-4-methoxybenzyl)-1,2,4-oxadiazol-3-yl]-5-oxo-4,5-dihydropyrazolo[1,5-a]pyrimidin-7-yl}piperidine-1-carboxylate (63.0 mg, 100% purity, 120 µmol) was dissolved in 1,4-dioxan (2.0 ml) and stirred overnight at RT with hydrochloric acid 4N in 1,4-dioxan (4.0 ml). The suspension was concentrated, dissolved in water and purified by preparative HPLC (gradient acetonitrile/water with 1.0% aqueous hydrochloric acid 1N). Lyophilization of the combined product fractions yielded the title compound.

The obtained amount was 36.0 mg (100% purity, 65% of theory).

LC-MS (Method 8B): $R_t$=0.82 min; MS (ESIpos): m/z=425 [M+H-xHCl]$^+$ $^1$H-NMR (400 MHz, DMSO-d6) delta [ppm]: −0.008 (0.54), 0.008 (0.48), 1.841 (0.22), 1.872 (0.62), 1.903 (0.68), 1.934 (0.28), 2.188 (1.07), 2.222 (0.88), 2.524 (0.30), 3.052 (0.28), 3.082 (0.76), 3.111 (0.80), 3.141 (0.33), 3.573 (0.39), 3.591 (0.31), 3.774 (16.00), 4.374 (4.72), 6.079 (0.18), 6.807 (0.90), 6.813 (1.02), 6.828 (0.95), 6.834 (1.12), 6.872 (1.16), 6.878 (0.94), 6.902 (1.13), 6.909 (0.98), 7.385 (0.90), 7.407 (1.64), 7.429 (0.85), 8.326 (0.63), 8.642 (0.14), 8.872 (0.18), 11.242 (0.12).

Example 247

3-[5-(3-fluoro-4-methoxybenzyl)-1,2,4-oxadiazol-3-yl]-7-(piperidin-4-yl)pyrazolo[1,5-c]pyrimidin-5(4H)-one hydrochloride

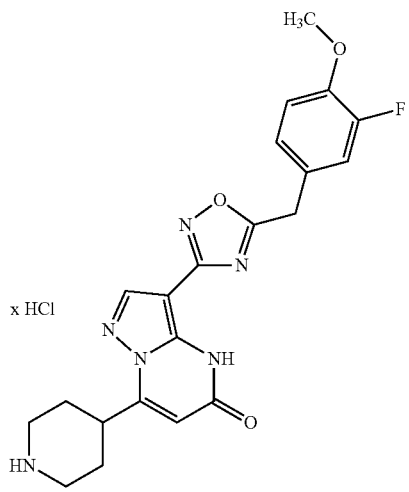 [SMILES: COc1ccc(Cc2nc(-c3cnn4c(C5CCNCC5)cc(=O)[nH]c34)no2)cc1F]

tert-butyl 4-{3-[5-(3-fluoro-4-methoxybenzyl)-1,2,4-oxadiazol-3-yl]-5-oxo-4,5-dihydropyrazolo[1,5-a]pyrimidin-7-yl}piperidine-1-carboxylate (71.0 mg, 97% purity, 131 µmol)

hydrochloric acid 4N in 1,4-dioxan (4.0 ml)

1,4-dioxan (2.0 ml)

The title compound was prepared according to the same procedure as Example 246.

The obtained amount was 42.0 mg (100% purity, 69% of theory).

LC-MS (Method 8B): $R_t$=0.79 min; MS (ESIpos): m/z=425 [M+H-xHCl]$^+$ $^1$H-NMR (400 MHz, DMSO-d6) delta [ppm]: 1.891 (1.71), 1.923 (1.86), 2.188 (2.74), 2.221 (2.19), 3.077 (1.90), 3.105 (1.98), 3.381 (2.64), 3.412 (2.14), 3.574 (1.30), 4.371 (16.00), 6.083 (1.40), 7.141 (1.11), 7.162 (4.02), 7.180 (8.75), 7.286 (2.62), 7.319 (2.99), 8.336 (5.38), 8.801 (0.46), 8.995 (0.57).

Example 248

3-[5-(3-chloro-4-methylphenyl)-1,2,4-oxadiazol-3-yl]-7-(piperidin-4-yl)pyrazolo[1,5-c]pyrimidin-5(4H)-one hydrochloride

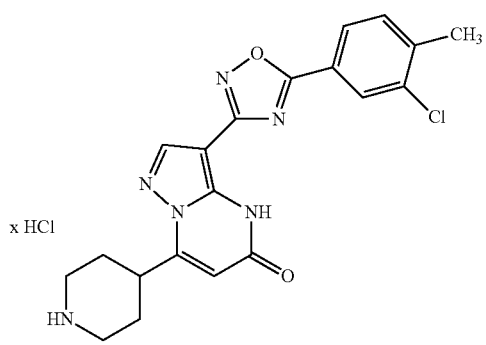 [SMILES: Cc1ccc(-c2nc(-c3cnn4c(C5CCNCC5)cc(=O)[nH]c34)no2)cc1Cl]

tert-butyl 4-{3-[5-(3-chloro-4-methylphenyl)-1,2,4-oxadiazol-3-yl]-5-oxo-4,5-dihydropyrazolo[1,5-a]pyrimidin-7-yl}piperidine-1-carboxylate (82.0 mg, 93% purity, 149 µmol)

hydrochloric acid 4N in 1,4-dioxan (4.0 ml)

1,4-dioxan (2.0 ml)

The title compound was prepared according to the same procedure as Example 209.

The obtained amount was 51.0 mg (94% purity, 72% of theory).

LC-MS (Method 8B): $R_t$=0.96 min; MS (ESIpos): m/z=411 [M+H-xHCl]$^+$ $^1$H-NMR (400 MHz, DMSO-d6) delta [ppm]: −0.008 (3.19), 0.008 (4.10), 1.899 (2.14), 1.926 (2.38), 1.956 (1.33), 2.213 (2.92), 2.246 (2.46), 2.465 (16.00), 2.525 (2.09), 3.099 (2.38), 3.129 (2.53), 3.156 (1.43), 3.399 (3.41), 3.429 (2.99), 3.509 (1.45), 3.585 (8.32), 3.733 (1.65), 3.744 (1.49), 4.003 (1.22), 6.086 (1.15), 7.651 (2.85), 7.671 (3.27), 8.139 (1.84), 8.159 (1.79), 8.378 (1.97), 8.435 (3.27), 8.742 (0.68), 8.938 (1.05).

Example 249

3-{5-[4-methyl-2-(trifluoromethyl)phenyl]-1,2,4-oxadiazol-3-yl}-7-(piperidin-4-yl)pyrazolo[1,5-c]pyrimidin-5(4H)-one hydrochloride

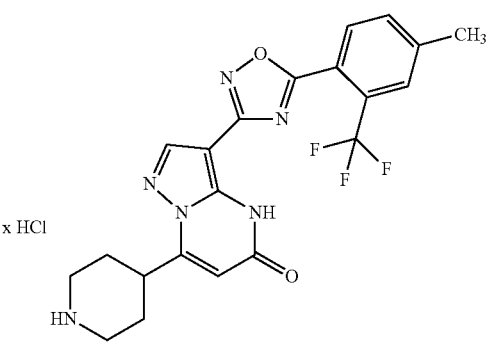 [SMILES: Cc1ccc(-c2nc(-c3cnn4c(C5CCNCC5)cc(=O)[nH]c34)no2)c(C(F)(F)F)c1]

tert-butyl 4-(3-{5-[4-methyl-2-(trifluoromethyl)phenyl]-1,2,4-oxadiazol-3-yl}-5-oxo-4,5-dihydropyrazolo[1,5-a]pyrimidin-7-yl)piperidine-1-carboxylate (33.0 mg, 98% purity, 59.4 µmol)

hydrochloric acid 4N in 1,4-dioxan (11 ml)

1,4-dioxan (2.0 ml)

The title compound was prepared according to the same procedure as Example 209.

The obtained amount was 28.0 mg (100% purity, 98% of theory).

LC-MS (Method 8B): $R_t$=0.96 min; MS (ESIpos): m/z=445 [M+H-xHCl]$^+$ $^1$H-NMR (400 MHz, DMSO-d6) delta [ppm]: −0.008 (7.75), 0.008 (8.06), 1.861 (1.91), 1.890 (5.50), 1.921 (6.11), 1.952 (2.63), 2.138 (2.18), 2.214 (8.48), 2.248 (6.99), 3.074 (2.29), 3.103 (6.11), 3.133 (6.30), 3.161 (2.71), 3.401 (9.39), 3.433 (7.60), 3.568 (15.96), 3.598 (3.36), 6.099 (1.72), 7.783 (7.45), 7.802 (8.21), 7.912 (16.00), 8.231 (2.86), 8.247 (2.83), 8.432 (6.87), 8.671 (1.72), 8.883 (2.25), 11.485 (1.49).

Example 250

3-(2,4-dimethyl-1,3-thiazol-5-yl)-7-(piperidin-4-yl)pyrazolo[1,5-c]pyrimidin-5(4H)-one hydrochloride

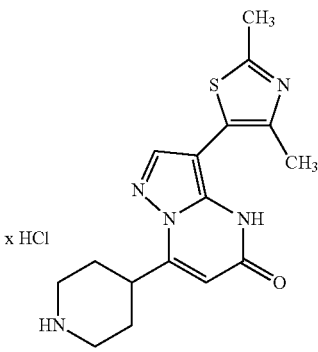 [SMILES: Cc1nc(C)c(-c2cnn3c(C4CCNCC4)cc(=O)[nH]c23)s1]

tert-butyl 4-{3-(2,4-dimethyl-1,3-thiazol-5-yl)-5-[(4-methoxybenzyl)oxy]pyrazolo[1,5-a]pyrimidin-7-yl}piperidine-1-carboxylate (18.0 mg, 98% purity, 32.1 μmol)

hydrochloric acid 4N in 1,4-dioxan (2.0 ml)

The title compound was prepared according to the same procedure as Example 222.

The obtained amount was 13.0 mg (89% purity, quantitative)

LC-MS (Method 8B): $R_t$=0.42 min; MS (ESIpos): m/z=330 [M+H-xHCl]$^+$ $^1$H-NMR (400 MHz, DMSO-d6) delta [ppm]: -0.149 (0.68), -0.008 (6.30), 0.008 (5.46), 0.146 (0.66), 1.907 (3.27), 1.939 (3.66), 1.969 (1.49), 2.193 (5.54), 2.226 (4.67), 2.271 (9.72), 2.368 (0.93), 2.696 (16.00), 3.080 (3.84), 3.109 (3.87), 3.138 (1.59), 3.378 (5.17), 3.409 (4.20), 3.578 (2.21), 5.783 (1.36), 6.018 (1.63), 8.033 (1.55), 8.928 (0.99), 9.066 (1.36).

Example 251

3-{5-[(6-methoxypyridin-3-yl)methyl]-1,2,4-oxadiazol-3-yl}-7-(piperidin-4-yl)pyrazolo[1,5-a]pyrimidin-5(4H)-one hydrochloride

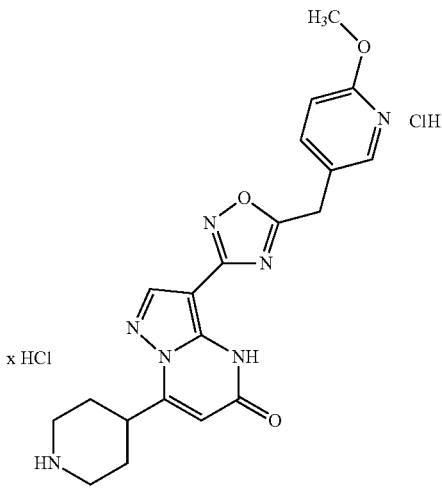 [SMILES: COc1ccc(Cc2nc(-c3cnn4c(C5CCNCC5)cc(=O)[nH]c34)no2)cn1 ; Cl]

tert-butyl 4-(3-{5-[(6-methoxypyridin-3-yl)methyl]-1,2,4-oxadiazol-3-yl}-5-oxo-4,5-dihydropyrazolo[1,5-a]pyrimidin-7-yl)piperidine-1-carboxylate (46.0 mg, 100% purity, 90.6 μmol)

hydrochloric acid 4N in 1,4-dioxan (4.0 ml)

1,4-dioxan (2.0 ml)

The title compound was prepared according to the same procedure as Example 222.

The obtained amount was 44.0 mg (100% purity, quantitative)

LC-MS (Method 7B): $R_t$=1.06 min; MS (ESIpos): m/z=408 [M+H-xHCl]$^+$ $^1$H-NMR (400 MHz, DMSO-d6) delta [ppm]: 1.873 (0.69), 1.901 (1.93), 1.932 (2.13), 1.962 (0.88), 2.183 (3.08), 2.216 (2.44), 3.041 (0.78), 3.070 (2.13), 3.100 (2.18), 3.130 (0.89), 3.374 (2.90), 3.389 (2.74), 3.405 (2.41), 3.463 (0.85), 3.475 (1.08), 3.492 (1.17), 3.503 (0.94), 3.545 (0.90), 3.574 (1.62), 3.604 (0.79), 3.667 (0.87), 3.681 (1.02), 3.701 (0.99), 3.713 (0.77), 4.392 (16.00), 5.011 (1.45), 6.078 (2.79), 6.846 (4.79), 6.868 (5.08), 7.761 (3.05), 7.768 (3.14), 7.783 (2.95), 7.789 (3.02), 8.237 (4.14), 8.243 (4.06), 8.328 (5.91), 8.934 (0.57), 9.085 (0.75).

Example 252

7-(piperidin-4-yl)-3-{5-[4-(propan-2-yloxy)benzyl]-1,2,4-oxadiazol-3-yl}pyrazolo[1,5-a]pyrimidin-5(4H)-one hydrochloride

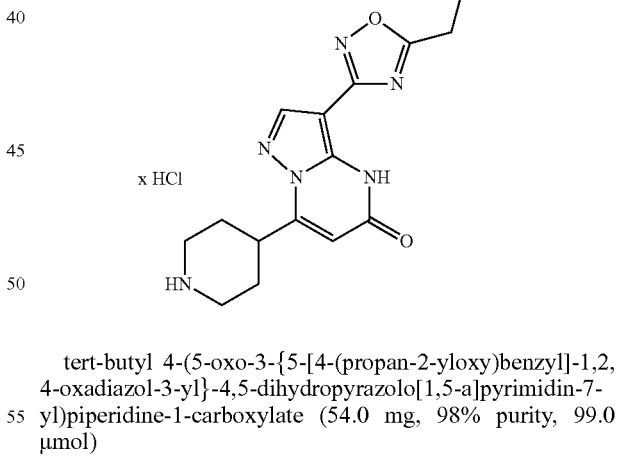

tert-butyl 4-(5-oxo-3-{5-[4-(propan-2-yloxy)benzyl]-1,2,4-oxadiazol-3-yl}-4,5-dihydropyrazolo[1,5-a]pyrimidin-7-yl)piperidine-1-carboxylate (54.0 mg, 98% purity, 99.0 μmol)

hydrochloric acid 4N in 1,4-dioxan (4.0 ml)

1,4-dioxan (2.0 ml)

The title compound was prepared according to the same procedure as Example 246.

The obtained amount was 32.0 mg (100% purity, 69% of theory).

LC-MS (Method 8B): $R_t$=0.93 min; MS (ESIpos): m/z=435 [M+H-xHCl]$^+$ $^1$H-NMR (400 MHz, DMSO-d6) delta [ppm]: 1.240 (15.93), 1.255 (16.00), 1.881 (0.95), 1.913 (1.03), 2.189 (1.54), 2.222 (1.25), 3.079 (1.06), 3.108 (1.12), 3.138 (0.45), 3.351 (3.16), 3.573 (0.62), 4.327 (7.17), 4.555 (0.47), 4.570 (1.17), 4.585 (1.55), 4.600 (1.14), 4.615 (0.45), 6.076 (0.35), 6.892 (3.69), 6.914 (4.07), 7.277 (3.74), 7.298 (3.37), 8.338 (1.14), 8.759 (0.20), 8.945 (0.26), 11.260 (0.19).

Example 253

3-(2-methyl-1,3-thiazol-5-yl)-7-(piperidin-4-yl)pyrazolo[1,5-c]pyrimidin-5(4H)-one hydrochloride

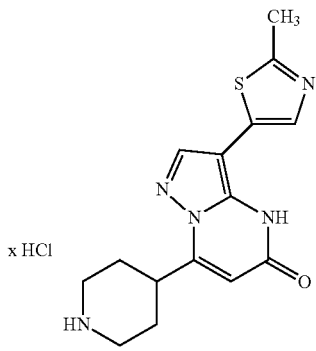 [SMILES: Cc1ncc(-c2cnn3c(C4CCNCC4)cc(=O)[nH]c23)s1]

Compound tert-butyl 4-{5-[(4-methoxybenzyl)oxy]-3-(2-methyl-1,3-thiazol-5-yl)pyrazolo[1,5-a]pyrimidin-7-yl}piperidine-1-carboxylate (33.0 mg, 100% purity, 61.6 μmol) was stirred overnight at RT with hydrochloric acid 4N in 1,4-dioxan (4.0 ml). The solution was concentrated, dissolved in water and lyophilized to yield the title compound.

The obtained amount was 22.8 mg (95% purity, quantitative)

LC-MS (Method 8B): $R_t$=0.40 min; MS (ESIpos): m/z=316 [M+H-xHCl]$^+$ $^1$H-NMR (400 MHz, DMSO-d6) delta [ppm]: −0.008 (1.21), 0.008 (1.16), 1.876 (0.52), 1.906 (1.43), 1.936 (1.56), 1.964 (0.64), 2.196 (2.24), 2.228 (1.80), 2.681 (16.00), 3.060 (0.63), 3.089 (1.64), 3.118 (1.66), 3.148 (0.65), 3.415 (1.80), 3.576 (0.56), 3.594 (1.51), 3.604 (1.00), 3.729 (0.82), 4.406 (1.63), 4.646 (0.88), 6.127 (0.37), 7.945 (1.61), 8.226 (0.37), 8.849 (0.46), 9.006 (0.62).

Example 254

N-[5-oxo-7-(piperidin-4-yl)-4,5-dihydropyrazolo[1,5-c]pyrimidin-3-yl]benzamide hydrochloride

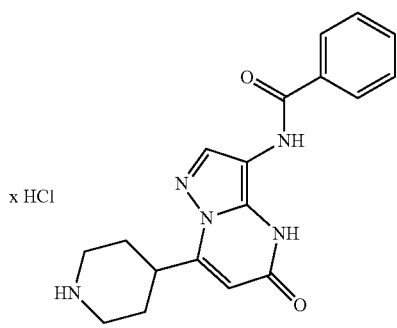 [SMILES: O=C(Nc1cnn2c(C3CCNCC3)cc(=O)[nH]c12)c1ccccc1]

Compound tert-butyl 4-{3-(benzoylamino)-5-[(4-methoxybenzyl)oxy]pyrazolo[1,5-a]pyrimidin-7-yl}piperidine-1-carboxylate (43.0 mg, 100% purity, 77.1 μmol) was stirred overnight at RT with hydrochloric acid 4N in 1,4-dioxan (4.0 ml). The solution was concentrated and purified by preparative HPLC (gradient acetonitrile/water with 1.0% aqueous hydrochloric acid 1N). Evaporation of the combined product fractions yielded the title compound.

The obtained amount was 20.0 mg (100% purity, 69% of theory).

LC-MS (Method 8B): $R_t$=0.52 min; MS (ESIpos): m/z=338 [M+H-xHCl]$^+$ $^1$H-NMR (500 MHz, DMSO-d6) delta [ppm]: 0.000 (12.41), 1.915 (7.55), 2.183 (9.71), 3.080 (8.15), 5.802 (7.88), 7.528 (13.84), 7.588 (7.39), 8.030 (16.00), 8.176 (13.58), 8.920 (3.40), 9.074 (3.91), 10.075 (13.43), 12.097 (4.51).

Example 255

3-{3-[2-(4-fluorophenyl)propan-2-yl]-1,2,4-oxadiazol-5-yl}-7-(piperidin-4-yl)pyrazolo[1,5-a]pyrimidin-5(4H)-one hydrochloride

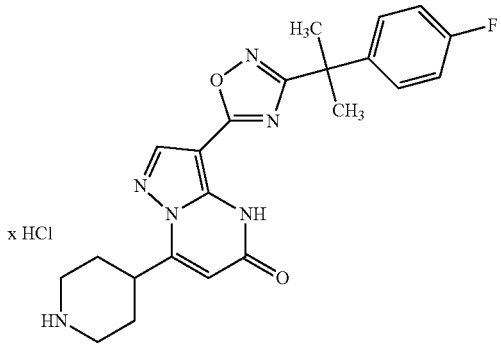 [SMILES: CC(C)(c1ccc(F)cc1)c1noc(-c2cnn3c(C4CCNCC4)cc(=O)[nH]c23)n1]

Compound tert-butyl 4-(3-{3-[2-(4-fluorophenyl)propan-2-yl]-1,2,4-oxadiazol-5-yl}-5-oxo-4,5-dihydropyrazolo[1,5-a]pyrimidin-7-yl)piperidine-1-carboxylate (600 mg, 1.15 mmol) was dissolved in 1,4-dioxan (4.0 ml) and stirred overnight at RT with hydrochloric acid 4N in 1,4-dioxan (10 ml). The solution was concentrated to yield the title compound.

The obtained amount was 480 mg (100% purity, 91% of theory).

LC-MS (Method 8B): $R_t$=0.91 min; MS (ESIpos): m/z=423 [M+H-xHCl]$^+$ $^1$H-NMR (400 MHz, DMSO-d6) delta [ppm]: 0.000 (4.73), 1.750 (16.00), 1.882 (0.30), 1.910 (0.92), 1.942 (0.95), 1.972 (0.39), 2.177 (1.39), 2.209 (1.09), 3.047 (0.35), 3.077 (0.95), 3.106 (0.98), 3.135 (0.40), 3.377 (1.35), 3.392 (1.04), 3.408 (1.11), 3.565 (0.41), 3.594 (0.67), 3.623 (0.41), 6.212 (0.38), 7.125 (1.47), 7.147 (3.21), 7.169 (1.77), 7.377 (1.64), 7.391 (1.87), 7.399 (1.70), 7.413 (1.39), 8.506 (1.40), 8.969 (0.23), 9.111 (0.31).

Example 256

7-(piperidin-4-yl)-3-[5-(propan-2-yl)-1,2,4-oxadiazol-3-yl]pyrazolo[1,5-a]pyrimidin-5(4H)-one hydrochloride

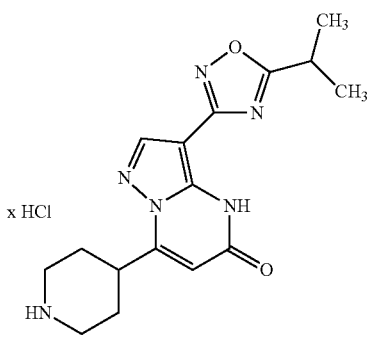 [SMILES: CC(C)c1nc(-c2cnn3c(C4CCNCC4)cc(=O)[nH]c23)no1]

Compound tert-butyl 4-{5-oxo-3-[5-(propan-2-yl)-1,2,4-oxadiazol-3-yl]-4,5-dihydropyrazolo[1,5-a]pyrimidin-7-yl}piperidine-1-carboxylate (48.0 mg, 112 µmol) was dissolved in 1,4-dioxan (2.0 ml) and stirred overnight at RT with hydrochloric acid 4N in 1,4-dioxan (2.0 ml). The solution was concentrated, dried in vacuo, dissolved in water and lyophilized to yield the title compound.

The obtained amount was 41 mg (100% purity, quantitative)

LC-MS (Method 11B): $R_t$=0.75 min; MS (ESIpos): m/z=329 [M+H-xHCl]$^+$ $^1$H-NMR (400 MHz, DMSO-d6) delta [ppm]: 1.210 (3.63), 1.226 (3.56), 1.377 (16.00), 1.395 (15.91), 1.840 (0.30), 1.875 (0.88), 1.905 (0.91), 1.935 (0.41), 2.197 (1.33), 2.232 (1.01), 3.060 (0.41), 3.089 (0.98), 3.118 (1.06), 3.148 (0.44), 3.362 (1.82), 3.392 (1.69), 3.423 (1.33), 3.482 (0.44), 3.550 (0.67), 3.568 (1.06), 6.069 (0.27), 8.344 (1.12), 8.641 (0.30), 8.860 (0.35), 11.277 (0.18).

Example 257

3-(5-tert-butyl-1,2,4-oxadiazol-3-yl)-7-(piperidin-4-yl)pyrazolo[1,5-a]pyrimidin-5(4H)-one hydrochloride

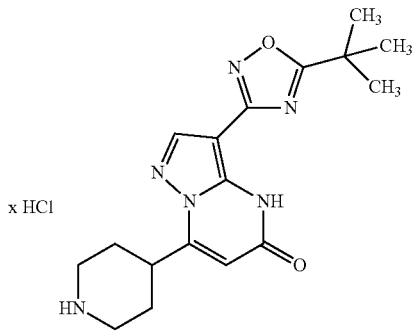 [SMILES: CC(C)(C)c1nc(-c2cnn3c(C4CCNCC4)cc(=O)[nH]c23)no1]

tert-butyl 4-[3-(5-tert-butyl-1,2,4-oxadiazol-3-yl)-5-oxo-4,5-dihydropyrazolo[1,5-a]pyrimidin-7-yl]piperidine-1-carboxylate (35.0 mg, 79.1 µmol)

hydrochloric acid 4N in 1,4-dioxan (2.0 ml)

1,4-dioxan (2.0 ml)

The title compound was prepared according to the same procedure as Example 256.

The obtained amount was 28.5 mg (100% purity, 95% of theory).

LC-MS (Method 11B): $R_t$=0.89 min; MS (ESIpos): m/z=343 [M+H-xHCl]$^+$ $^1$H-NMR (400 MHz, DMSO-d6) delta [ppm]: 1.091 (0.13), 1.450 (16.00), 1.856 (0.12), 1.887 (0.33), 1.914 (0.36), 1.944 (0.16), 1.953 (0.14), 2.195 (0.51), 2.228 (0.42), 3.086 (0.31), 3.113 (0.33), 3.168 (0.14), 3.392 (0.56), 3.419 (0.44), 3.548 (0.13), 3.578 (0.23), 3.606 (0.12), 6.067 (0.22), 8.333 (0.83), 8.763 (0.11), 8.941 (0.14), 11.311 (0.12).

Example 258

3-(2-ethyl-4-methyl-1,3-thiazol-5-yl)-7-(piperidin-4-yl)pyrazolo[1,5-a]pyrimidin-5(4H)-one hydrochloride

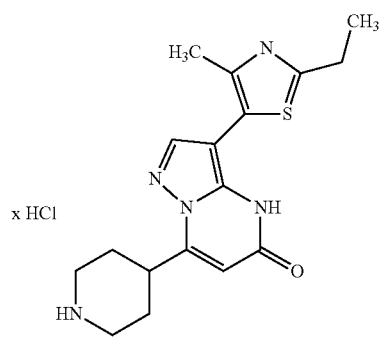

Compound tert-butyl 4-{3-(2-ethyl-4-methyl-1,3-thiazol-5-yl)-5-[(4-methoxybenzyl)oxy]pyrazolo[1,5-a]pyrimidin-7-yl}piperidine-1-carboxylate (114 mg, 202 µmol) was stirred overnight at RT with hydrochloric acid 4N in 1,4-dioxan (3.0 ml). The solution was concentrated, dissolved in water/acetonitrile and lyophilized, before being stirred with a 1/2 mixture of methanol/diethyl ether. The suspension was then filtered and dried in vacuo to yield the title compound.

The obtained amount was 73.5 mg (100% purity, 96% of theory).

LC-MS (Method 10B): $R_t$=0.96 min; MS (ESIpos): m/z=344 [M+H-xHCl]$^+$ $^1$H-NMR (400 MHz, DMSO-d6) delta [ppm]: 0.008 (1.70), 1.291 (7.55), 1.310 (16.00), 1.329 (7.76), 1.865 (0.67), 1.895 (1.79), 1.920 (1.94), 1.952 (0.85), 2.198 (2.97), 2.245 (5.62), 2.944 (2.01), 2.962 (5.99), 2.981 (5.84), 3.000 (1.90), 3.052 (0.70), 3.082 (1.94), 3.110 (2.01), 3.142 (0.86), 3.383 (2.71), 3.413 (2.25), 3.544 (0.58), 3.571 (1.03), 3.601 (0.57), 4.516 (1.63), 5.979 (0.42), 7.995 (0.71), 8.810 (0.64), 8.968 (0.86).

Example 259

3-[4-methyl-2-(propan-2-yl)-1,3-thiazol-5-yl]-7-(piperidin-4-yl)pyrazolo[1,5-a]pyrimidin-5(4H)-one hydrochloride

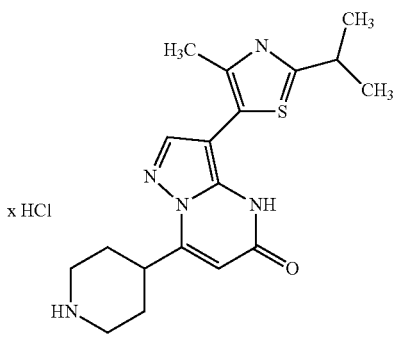

x HCl tert-butyl 4-{5-[(4-methoxybenzyl)oxy]-3-[4-methyl-2-(propan-2-yl)-1,3-thiazol-5-yl]pyrazolo[1,5-a]pyrimidin-7-yl}piperidine-1-carboxylate (110 mg, 190 µmol) hydrochloric acid 4N in 1,4-dioxan (3.0 ml)

The title compound was prepared according to the same procedure as Example 258.

The obtained amount was 57.0 mg (98% purity, 74% of theory).

LC-MS (Method 10B): $R_t$=1.07 min; MS (ESIpos): m/z=358 [M+H-xHCl]$^+$ $^1$H-NMR (400 MHz, DMSO-d6) delta [ppm]: 1.326 (15.73), 1.344 (16.00), 1.842 (0.29), 1.878 (0.86), 1.908 (0.91), 1.939 (0.37), 2.204 (1.69), 2.234 (2.97), 3.055 (0.36), 3.086 (0.93), 3.115 (0.99), 3.142 (0.40), 3.208 (0.44), 3.225 (1.08), 3.243 (1.45), 3.260 (1.03), 3.277 (0.40), 3.387 (1.37), 3.419 (1.11), 3.531 (0.23), 3.565 (0.44), 3.593 (0.26), 5.947 (0.17), 7.983 (0.26), 8.665 (0.29), 8.882 (0.37).

Example 260

7-(piperidin-4-yl)-3-{3-[2-(trifluoromethyl)phenyl]-1,2,4-oxadiazol-5-yl}pyrazolo[1,5-c]pyrimidin-5(4H)-one hydrochloride

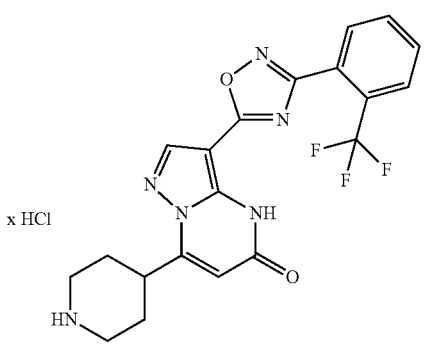 [SMILES: O=c1cc(C2CCNCC2)n2ncc(-c3nc(-c4ccccc4C(F)(F)F)no3)c2[nH]1]

x HCl

Compound tert-butyl 4-(5-oxo-3-{3-[2-(trifluoromethyl)phenyl]-1,2,4-oxadiazol-5-yl}-4,5-dihydropyrazolo[1,5-a]pyrimidin-7-yl)piperidine-1-carboxylate (300 mg, 565 µmol) was stirred overnight at RT with hydrochloric acid 4N in 1,4-dioxan (5.0 ml). The solution was concentrated, dissolved in water/acetonitrile and lyophilized to yield the title compound.

The obtained amount was 262 mg (100% purity, 99% of theory).

LC-MS (Method 8B): $R_t$=0.87 min; MS (ESIpos): m/z=431 [M+H-xHCl]$^+$ $^1$H-NMR (400 MHz, DMSO-d6) delta [ppm]: −0.008 (9.20), 0.008 (8.86), 1.855 (2.15), 1.866 (2.67), 1.897 (7.40), 1.923 (8.00), 1.952 (3.44), 1.962 (2.84), 2.216 (11.44), 2.249 (9.38), 3.098 (4.47), 3.125 (8.09), 3.156 (4.90), 3.409 (13.08), 3.441 (10.67), 3.601 (2.41), 3.628 (3.53), 3.657 (2.15), 6.276 (1.12), 7.838 (3.70), 7.857 (10.75), 7.876 (9.98), 7.888 (8.86), 7.906 (12.22), 7.923 (5.16), 7.994 (16.00), 8.012 (14.37), 8.633 (5.85), 8.826 (2.49).

Example 261

3-[5-(bicyclo[2.2.2]oct-1-yl)-1,2,4-oxadiazol-3-yl]-7-(piperidin-4-yl)pyrazolo[1,5-a]pyrimidin-5(4H)-one hydrochloride

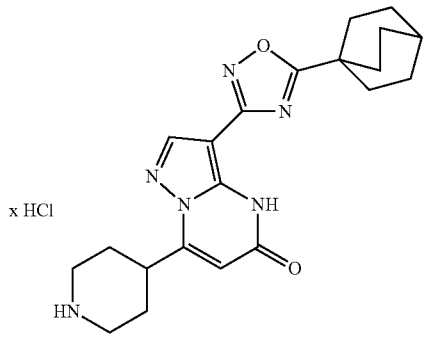 [SMILES: O=c1cc(C2CCNCC2)n2ncc(-c3noc(C45CCC(CC4)CC5)n3)c2[nH]1]

x HCl

Compound tert-butyl 4-{3-[5-(bicyclo[2.2.2]oct-1-yl)-1,2,4-oxadiazol-3-yl]-5-oxo-4,5-dihydropyrazolo[1,5-a]pyrimidin-7-yl}piperidine-1-carboxylate (65.0 mg, 131 µmol) was stirred overnight at RT with hydrochloric acid 4N in 1,4-dioxan (2.0 ml). The mixture was diluted with diethyl ether and was stirred 10 min at RT. The suspension was filtered, dried in vacuo, dissolved in water/acetonitrile and lyophilized to yield the title compound.

The obtained amount was 47.0 mg (100% purity, 83% of theory).

LC-MS (Method 8B): $R_t$=0.95 min; MS (ESIpos): m/z=395 [M+H-xHCl]$^+$ $^1$H-NMR (400 MHz, DMSO-d6) delta [ppm]: −0.149 (1.96), 0.008 (16.00), 0.146 (1.96), 1.652 (6.16), 1.672 (8.65), 1.707 (3.22), 1.714 (2.86), 1.722 (1.67), 1.809 (0.69), 1.843 (1.96), 1.876 (2.20), 1.916 (10.90), 1.927 (7.84), 1.937 (9.63), 1.955 (7.67), 2.195 (2.90), 2.229 (2.41), 3.076 (1.22), 3.106 (2.41), 3.140 (1.31), 3.396 (3.47), 3.429 (2.90), 3.565 (0.98), 6.026 (0.61), 8.313 (1.55), 8.481 (0.53), 8.703 (0.53), 11.269 (0.45).

Example 262

3-(5-ethyl-1,2,4-oxadiazol-3-yl)-7-(piperidin-4-yl)pyrazolo[1,5-a]pyrimidin-5(4H)-one hydrochloride

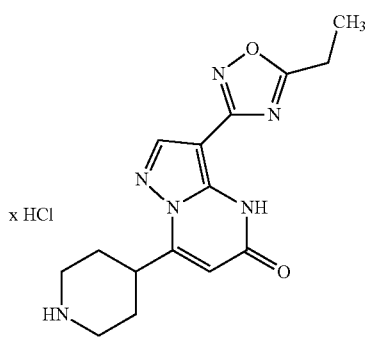 [SMILES: CCc1nc(-c2cnn3c(C4CCNCC4)cc(=O)[nH]c23)no1]

Compound tert-butyl 4-[3-(5-ethyl-1,2,4-oxadiazol-3-yl)-5-oxo-4,5-dihydropyrazolo[1,5-a]pyrimidin-7-yl]piperidine-1-carboxylate (180 mg, 434 µmol) was stirred overnight at RT with hydrochloric acid 4N in 1,4-dioxan (3.0 ml). The mixture was kept for 5 min into the ultrasonic bath before being filtered. The solid was then washed with diethyl ether and dried in vacuo to yield the title compound.

The obtained amount was 146 mg (92% purity, 88% of theory).

LC-MS (Method 8B): $R_t$=0.60 min; MS (ESIpos): m/z=315 [M+H-xHCl]$^+$ $^1$H-NMR (400 MHz, DMSO-d6) delta [ppm]: 0.000 (16.00), 0.008 (0.66), 1.330 (0.35), 1.349 (0.73), 1.368 (0.35), 1.827 (0.03), 1.857 (0.08), 1.890 (0.09), 1.920 (0.04), 2.201 (0.12), 2.234 (0.10), 2.976 (0.11), 2.995 (0.30), 3.013 (0.29), 3.032 (0.09), 3.063 (0.04), 3.094 (0.09), 3.121 (0.09), 3.149 (0.04), 3.392 (0.15), 3.429 (0.10), 3.568 (0.26), 6.052 (0.02), 8.348 (0.06), 8.497 (0.03), 8.740 (0.06), 11.249 (0.04).

Example 263

3-(3-phenyl-1,2-oxazol-5-yl)-7-(piperidin-4-yl)pyrazolo[1,5-a]pyrimidin-5(4H)-one hydrochloride

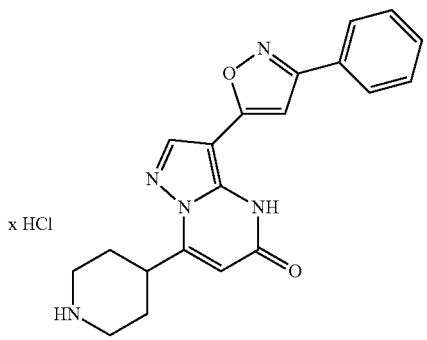 [SMILES: O=c1cc(C2CCNCC2)n2ncc(-c3cc(-c4ccccc4)no3)c2[nH]1]

Compound tert-butyl 4-{5-[(4-methoxybenzyl)oxy]-3-(3-phenyl-1,2-oxazol-5-yl)pyrazolo[1,5-a]pyrimidin-7-yl}piperidine-1-carboxylate (60.0 mg, 103 µmol) was stirred for 4 h at RT with hydrochloric acid 4N in 1,4-dioxan (2.6 ml). The mixture was diluted with 150 mL of diethyl ether and the stirring was continued for 30 min. The resulting solid was filtered, dissolved in water/acetonitrile and lyophilized to yield the title compound.

The obtained amount was 39 mg (100% purity, 95% of theory).

LC-MS (Method 11B): $R_t$=0.95 min; MS (ESIpos): m/z=362 [M+H-xHCl]$^+$ $^1$H-NMR (400 MHz, DMSO-d6) delta [ppm]: 1.859 (0.20), 1.889 (0.58), 1.919 (0.62), 1.949 (0.26), 2.207 (0.88), 2.240 (0.73), 2.502 (16.00), 3.073 (0.24), 3.103 (0.67), 3.132 (0.70), 3.162 (0.30), 3.400 (1.04), 3.431 (0.83), 3.600 (0.30), 6.043 (0.11), 7.533 (0.66), 7.548 (2.89), 7.567 (1.97), 7.868 (1.85), 7.883 (1.55), 8.414 (0.31), 8.662 (0.22), 8.883 (0.28), 12.364 (0.16).

Example 264

7-(piperidin-4-yl)-3-{3-[1-(propan-2-yl)piperidin-4-yl]-1,2,4-oxadiazol-5-yl}pyrazolo[1,5-a]pyrimidin-5(4H)-one hydrochloride

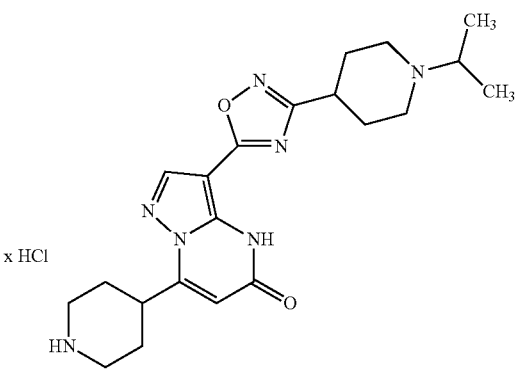 [SMILES: CC(C)N1CCC(c2noc(-c3cnn4c(C5CCNCC5)cc(=O)[nH]c34)n2)CC1]

Compound tert-butyl 4-(5-oxo-3-{3-[1-(propan-2-yl)piperidin-4-yl]-1,2,4-oxadiazol-5-yl}-4,5-dihydropyrazolo[1,5-a]pyrimidin-7-yl)piperidine-1-carboxylate (174 mg, 99% purity, 337 µmol) was dissolved in 1,4-dioxan (2.0 ml) and stirred overnight at RT with hydrochloric acid 4N in 1,4-dioxan (4.0 ml). The suspension was concentrated, dissolved in water, lyophilized and purified [Column: Kinetex, 5 µm C18, 100×21.2 mm, Eluent: 95 to 50% water/0 to 45% acetonitrile/5% (acetonitrile/water 80/20+2% formic acid), Flow: 60 ml/min, Detection: 210 nm]. The combined product fractions were concentrated, dissolved with aqueous 2N HCl/acetonitrile and lyophilized to yield the title compound.

The obtained amount was 14.0 mg (95% purity, 9% of theory).

LC-MS (Method 9B): $R_t$=3.45 min; MS (ESIpos): m/z=412 [M+H-xHCl]$^+$ $^1$H-NMR (400 MHz, DMSO-d6) delta [ppm]: 1.431 (15.77), 1.447 (16.00), 1.754 (3.38), 1.888 (2.02), 1.919 (2.23), 1.995 (2.91), 2.161 (5.69), 2.191 (3.95), 3.038 (0.92), 3.067 (2.33), 3.098 (2.45), 3.128 (1.11), 3.252 (1.45), 3.289 (2.96), 3.317 (1.66), 3.383 (3.60), 3.410 (3.35), 3.566 (10.22), 3.897 (3.28), 3.927 (2.93), 3.943 (2.33), 3.961 (1.79), 4.045 (1.27), 6.086 (0.34), 8.614 (3.16), 8.860 (0.75), 9.001 (1.00).

Example 265

3-ethyl-7-(piperidin-4-yl)pyrazolo[1,5-a]pyrimidin-5(4H)-one hydrochloride

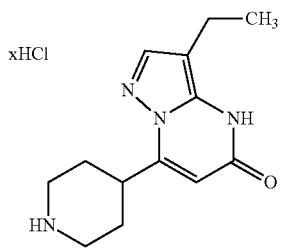 [SMILES: CCc1cnn2c(C3CCNCC3)cc(=O)[nH]c12]

tert-butyl 4-(3-ethyl-5-oxo-4,5-dihydropyrazolo[1,5-a]pyrimidin-7-yl)piperidine-1-carboxylate (335 mg, 967 µmol) was dissolved in 1,4-dioxan (5.0 ml, 58 mmol) and treated with hydrochloric acid in 1,4-dioxan (3.6 ml, 4.0 M, 15 mmol) at RT for 16 h. Acetonitrile was added and the resulting participate was filtered and washed with acetonitrile. Drying in vacuo afforded the product. The obtained amount was 280 mg (97% purity, 99% of theory).

LC-MS (Method 11B): $R_t$=0.49 min; MS (ESIpos): m/z=247 [M+H]$^+$

1H-NMR (400 MHz, DMSO-d6) delta [ppm]: 1.086 (7.25), 1.105 (16.00), 1.123 (7.56), 1.860 (0.56), 1.869 (0.68), 1.893 (1.85), 1.901 (1.89), 1.925 (2.14), 1.933 (2.08), 1.957 (0.96), 1.966 (0.83), 2.128 (3.00), 2.161 (2.26), 2.449 (2.14), 2.992 (0.72), 3.023 (2.03), 3.050 (2.08), 3.081 (0.84), 3.356 (2.28), 3.459 (0.89), 3.489 (1.67), 3.519 (0.80), 3.559 (5.70), 5.697 (8.00), 7.709 (8.93), 9.261 (0.81), 9.315 (1.11).

Example 266

3-(4-phenyl-1,3-thiazol-2-yl)-7-(piperidin-4-yl)pyrazolo[1,5-c]pyrimidin-5(4H)-one hydrochloride

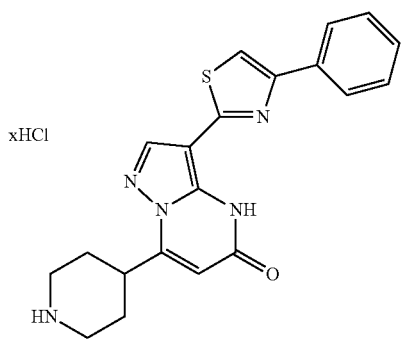 [SMILES: O=c1cc(C2CCNCC2)n2ncc(-c3nc(-c4ccccc4)cs3)c2[nH]1]

tert-butyl 4-[5-oxo-3-(4-phenyl-1,3-thiazol-2-yl)-4,5-dihydropyrazolo[1,5-a]pyrimidin-7-yl]piperidine-1-carboxylate (57.0 mg, 119 µmol) was dissolved in 1,4-dioxan (2.3 ml) and treated with hydrochloric acid in 1,4-dioxan (600 µl, 4.0 M, 2.4 mmol) at RT for 16 h. Drying in vacuo afforded the product. The obtained amount was 53.5 mg (90% purity, 90% of theory).

LC-MS (Method 7B): $R_t$=1.31 min; MS (ESIpos): m/z=378 [M+H]$^+$

1H-NMR (400 MHz, DMSO-d6) delta [ppm]: 1.927 (1.11), 1.952 (2.82), 1.959 (2.89), 1.983 (3.16), 1.991 (3.00), 2.015 (1.37), 2.215 (4.38), 2.248 (3.49), 3.059 (1.09), 3.092 (3.01), 3.120 (3.11), 3.150 (1.26), 3.385 (4.36), 3.417 (3.38), 3.561 (8.02), 3.612 (1.11), 3.641 (1.97), 3.671 (1.06), 6.225 (1.91), 7.326 (2.11), 7.346 (2.58), 7.365 (4.94), 7.383 (3.43), 7.456 (6.70), 7.474 (10.60), 7.493 (5.21), 7.616 (1.36), 7.648 (1.47), 7.667 (1.24), 7.984 (1.22), 8.017 (16.00), 8.065 (9.27), 8.083 (8.26), 8.535 (5.82), 9.066 (1.08), 9.091 (1.24), 9.175 (1.69), 9.199 (1.22).

Example 267

3-[4-(2-fluorophenyl)-1,3-thiazol-2-yl]-7-(piperidin-4-yl)pyrazolo[1,5-c]pyrimidin-5(4H)-one hydrochloride

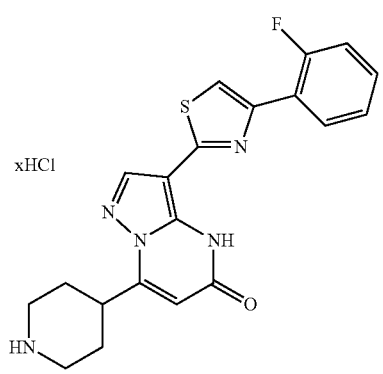 [SMILES: O=c1cc(C2CCNCC2)n2ncc(-c3nc(-c4ccccc4F)cs3)c2[nH]1]

tert-butyl 4-{3-[4-(2-fluorophenyl)-1,3-thiazol-2-yl]-5-oxo-4,5-dihydropyrazolo[1,5-a]pyrimidin-7-yl}piperidine-1-carboxylate (58.0 mg, 117 µmol) was dissolved in 1,4-dioxan (2.3 ml) and treated with hydrochloric acid in 1,4-dioxan (590 µl, 4.0 M, 2.3 mmol) at RT for 16 h. Drying in vacuo afforded the product. The obtained amount was 54.0 mg (100% purity, 99% of theory).

LC-MS (Method 1B): $R_t$=0.70 min; MS (ESIpos): m/z=396 [M+H]$^+$

1H-NMR (400 MHz, DMSO-d6) delta [ppm]: 1.907 (0.82), 1.916 (0.94), 1.940 (2.40), 1.947 (2.49), 1.972 (2.69), 1.978 (2.62), 2.004 (1.14), 2.010 (0.97), 2.223 (3.79), 2.256 (2.98), 3.072 (0.98), 3.103 (2.73), 3.132 (2.81), 3.161 (1.11), 3.397 (3.77), 3.429 (3.05), 3.565 (16.00), 3.619 (0.82), 3.648 (1.38), 3.676 (0.82), 6.237 (0.65), 7.321 (1.67), 7.324 (1.82), 7.344 (5.06), 7.351 (2.23), 7.354 (2.40), 7.362 (4.73), 7.374 (3.72), 7.379 (4.30), 7.407 (1.60), 7.412 (1.79), 7.420 (1.86), 7.425 (2.86), 7.431 (1.96), 7.437 (1.46), 7.444 (2.17), 7.458 (0.78), 7.463 (0.69), 7.918 (8.35), 7.924 (8.25), 8.327 (1.38), 8.345 (2.62), 8.363 (1.34), 8.557 (2.38), 8.951 (0.92), 9.084 (1.20).

Example 268

3-[5-(3-chloro-2-fluorophenyl)-1,3,4-oxadiazol-2-yl]-7-(piperidin-4-yl)pyrazolo[1,5-c]pyrimidin-5(4H)-one hydrochloride

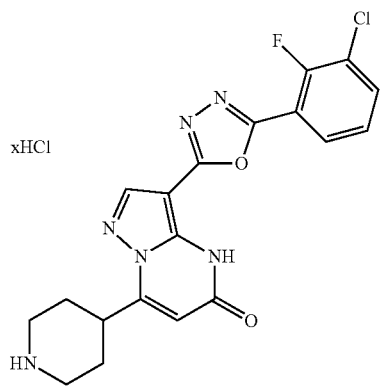 [SMILES: O=c1cc(C2CCNCC2)n2ncc(-c3nnc(-c4cccc(Cl)c4F)o3)c2[nH]1]

tert-butyl 4-{3-[5-(3-chloro-2-fluorophenyl)-1,3,4-oxadiazol-2-yl]-5-oxo-4,5-dihydropyrazolo[1,5-a]pyrimidin-7-yl}piperidine-1-carboxylate (31.9 mg, 61.9 μmol) was dissolved in 1,4-dioxan (2.0 ml, 23 mmol) and treated with hydrochloric acid in 1,4-dioxan (230 μl, 4.0 M, 930 μmol) at RT for 16 h. Acetonitrile was added and the resulting participate was filtered and washed with acetonitrile. Drying in vacuo afforded the product. The obtained amount was 22.9 mg (98% purity, 80% of theory).

LC-MS (Method 1B): R$_t$=0.58 min; MS (ESIpos): m/z=415 [M+H]$^+$

1H-NMR (400 MHz, DMSO-d6) delta [ppm]: 1.880 (3.68), 1.911 (9.44), 1.942 (9.96), 1.968 (4.23), 2.208 (13.67), 2.241 (10.95), 2.712 (1.34), 3.073 (4.06), 3.101 (10.02), 3.130 (10.21), 3.160 (4.39), 3.428 (16.00), 3.568 (9.69), 3.604 (6.12), 3.634 (3.21), 6.157 (4.34), 7.495 (6.28), 7.514 (12.79), 7.534 (7.03), 7.884 (5.85), 7.902 (10.32), 7.920 (5.35), 8.207 (4.53), 8.223 (7.57), 8.240 (4.45), 8.526 (14.00), 8.795 (3.13), 8.970 (4.17), 12.369 (0.85).

Example 269

3-{5-[4-(difluoromethoxy)benzyl]-1,3,4-oxadiazol-2-yl}-7-(piperidin-4-yl)pyrazolo[1,5-c]pyrimidin-5(4H)-one hydrochloride

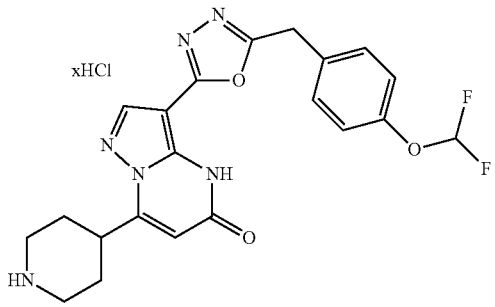 [SMILES: O=c1cc(C2CCNCC2)n2ncc(-c3nnc(Cc4ccc(OC(F)F)cc4)o3)c2[nH]1]

tert-butyl 4-(3-{5-[4-(difluoromethoxy)benzyl]-1,3,4-oxadiazol-2-yl}-5-oxo-4,5-dihydropyrazolo[1,5-a]pyrimidin-7-yl)piperidine-1-carboxylate (49.4 mg, 91.1 μmol) was dissolved in 1,4-dioxan (2.0 ml, 23 mmol) and treated with hydrochloric acid in 1,4-dioxan (340 μl, 4.0 M, 1.4 mmol) at RT for 16 h. Acetonitrile was added and the resulting participate was filtered and washed with acetonitrile. Drying in vacuo afforded the product. The obtained amount was 35.0 mg (97% purity, 78% of theory).

LC-MS (Method 1B): R$_t$=0.58 min; MS (ESIpos): m/z=443 [M+H]$^+$

1H-NMR (400 MHz, DMSO-d6) delta [ppm]: 1.862 (0.76), 1.890 (2.04), 1.922 (2.25), 1.950 (0.94), 2.177 (3.24), 2.209 (2.61), 3.043 (0.87), 3.075 (2.32), 3.104 (2.38), 3.134 (1.00), 3.377 (4.25), 3.539 (1.12), 3.566 (2.98), 3.599 (0.80), 4.325 (16.00), 6.101 (0.72), 7.166 (8.12), 7.187 (9.35), 7.218 (8.17), 7.403 (3.99), 7.432 (9.38), 7.453 (7.88), 8.388 (2.97), 8.865 (0.67), 9.021 (0.86), 12.123 (0.12).

Example 270

7-(piperidin-4-yl)-3-{5-[4-(trifluoromethoxy)benzyl]-1,3,4-oxadiazol-2-yl}pyrazolo[1,5-c]pyrimidin-5(4H)-one hydrochloride

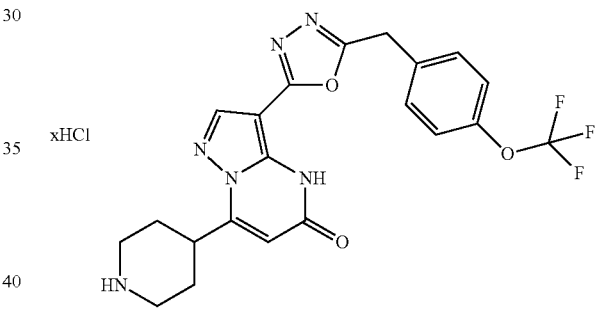

tert-butyl 4-(5-oxo-3-{5-[4-(trifluoromethoxy)benzyl]-1,3,4-oxadiazol-2-yl}-4,5-dihydropyrazolo[1,5-a]pyrimidin-7-yl)piperidine-1-carboxylate (34.3 mg, 61.2 μmol) was dissolved in 1,4-dioxan (2.0 ml, 23 mmol) and treated with hydrochloric acid in 1,4-dioxan (230 μl, 4.0 M, 920 μmol) at RT for 16 h. Acetonitrile was added and the resulting participate was filtered and washed with acetonitrile. Drying in vacuo afforded the product. The obtained amount was 28.7 mg (92% purity, 87% of theory).

LC-MS (Method 1B): R$_t$=0.66 min; MS (ESIpos): m/z=461 [M+H]$^+$

1H-NMR (400 MHz, DMSO-d6) delta [ppm]: 1.872 (0.88), 1.900 (2.39), 1.931 (2.59), 1.962 (1.11), 2.175 (3.73), 2.208 (3.01), 3.042 (1.05), 3.072 (2.66), 3.101 (2.79), 3.130 (1.28), 3.371 (4.14), 3.388 (2.66), 3.405 (3.36), 3.539 (1.13), 3.565 (10.68), 3.596 (1.20), 4.377 (16.00), 6.105 (1.81), 7.361 (5.73), 7.381 (7.23), 7.515 (9.45), 7.536 (7.23), 8.394 (5.98), 8.935 (0.83), 9.079 (1.08).

Example 271

3-(4-tert-butyl-1,3-thiazol-2-yl)-7-(piperidin-4-yl)pyrazolo[1,5-c]pyrimidin-5(4H)-one hydrochloride

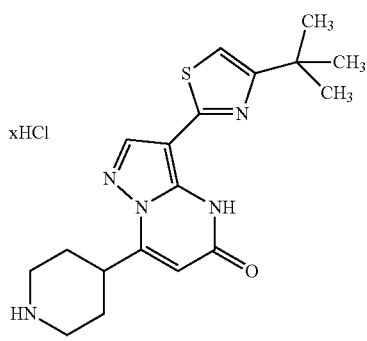 [SMILES: CC(C)(C)c1csc(-c2cnn3c(C4CCNCC4)cc(=O)[nH]c23)n1]

tert-butyl 4-[3-(4-tert-butyl-1,3-thiazol-2-yl)-5-oxo-4,5-dihydropyrazolo[1,5-a]pyrimidin-7-yl]piperidine-1-carboxylate (14.5 mg, 31.7 µmol) was dissolved in 1,4-dioxan (620 µl) and treated with hydrochloric acid in 1,4-dioxan (160 µl, 4.0 M, 630 µmol) at RT for 16 h. The solvent was removed in vacuo to afford the product. The obtained amount was 14.0 mg (100% purity, 103% of theory).

LC-MS (Method 7B): $R_t$=1.41 min; MS (ESIpos): m/z=358 [M+H]$^+$

1H-NMR (400 MHz, DMSO-d6) delta [ppm]: 1.359 (16.00), 1.882 (0.12), 1.908 (0.34), 1.940 (0.36), 1.971 (0.16), 2.202 (0.51), 2.234 (0.41), 3.067 (0.15), 3.096 (0.37), 3.123 (0.37), 3.154 (0.15), 3.390 (0.52), 3.422 (0.41), 3.613 (0.18), 6.169 (0.08), 7.185 (0.96), 8.475 (0.16), 8.831 (0.07), 8.996 (0.11).

Example 272

3-(5-methyl-4-phenyl-1,3-thiazol-2-yl)-7-(piperidin-4-yl)pyrazolo[1,5-c]pyrimidin-5(4H)-one hydrochloride

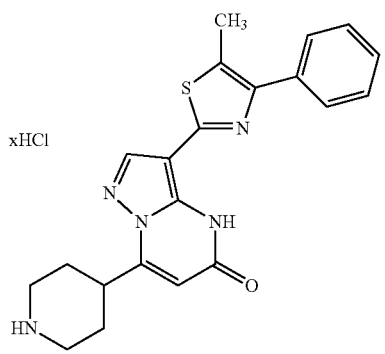 [SMILES: Cc1sc(-c2cnn3c(C4CCNCC4)cc(=O)[nH]c23)nc1-c1ccccc1]

tert-butyl 4-[3-(5-methyl-4-phenyl-1,3-thiazol-2-yl)-5-oxo-4,5-dihydropyrazolo[1,5-a]pyrimidin-7-yl]piperidine-1-carboxylate (13.5 mg, 27.5 µmol) was dissolved in 1,4-dioxan (540 µl) and treated with hydrochloric acid in 1,4-dioxan (140 µl, 4.0 M, 550 µmol) at RT for 16 h. The solvent was removed in vacuo to afford the product. The obtained amount was 12.7 mg (100% purity, 100% of theory).

LC-MS (Method 1B): $R_t$=0.73 min; MS (ESIpos): m/z=392 [M+H]$^+$

1H-NMR (400 MHz, DMSO-d6) delta [ppm]: 1.885 (0.37), 1.917 (1.06), 1.943 (1.14), 1.974 (0.49), 2.217 (1.63), 2.250 (1.32), 2.584 (16.00), 3.072 (0.43), 3.102 (1.19), 3.130 (1.23), 3.160 (0.51), 3.398 (1.69), 3.428 (1.36), 3.592 (0.42), 3.623 (0.66), 3.652 (0.38), 6.199 (0.28), 7.381 (0.75), 7.400 (2.13), 7.418 (1.53), 7.483 (2.69), 7.503 (4.41), 7.521 (2.09), 7.767 (3.35), 7.785 (2.90), 8.457 (0.85), 8.762 (0.36), 8.949 (0.47).

Example 273

3-[4-(2-methylphenyl)-1,3-thiazol-2-yl]-7-(piperidin-4-yl)pyrazolo[1,5-c]pyrimidin-5(4H)-one hydrochloride

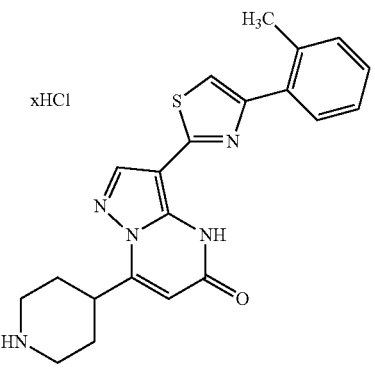 [SMILES: Cc1ccccc1-c1csc(-c2cnn3c(C4CCNCC4)cc(=O)[nH]c23)n1]

tert-butyl 4-{3-[4-(2-methylphenyl)-1,3-thiazol-2-yl]-5-oxo-4,5-dihydropyrazolo[1,5-a]pyrimidin-7-yl}piperidine-1-carboxylate (11.5 mg, 23.4 µmol) was dissolved in 1,4-dioxan (460 µl) and treated with hydrochloric acid in 1,4-dioxan (120 µl, 4.0 M, 470 µmol) at RT for 16 h. The solvent was removed in vacuo to afford the product. The obtained amount was 10.8 mg (100% purity, 99% of theory).

LC-MS (Method 1B): $R_t$=0.71 min; MS (ESIpos): m/z=392 [M+H]$^+$

1H-NMR (400 MHz, DMSO-d6) delta [ppm]: 1.892 (0.37), 1.924 (1.00), 1.950 (1.11), 1.982 (0.49), 2.222 (1.59), 2.255 (1.27), 2.469 (16.00), 3.079 (0.40), 3.106 (1.11), 3.135 (1.17), 3.165 (0.49), 3.401 (1.57), 3.431 (1.29), 3.607 (0.38), 3.636 (0.61), 3.665 (0.39), 6.211 (0.21), 7.283 (0.38), 7.292 (1.54), 7.299 (1.69), 7.309 (2.73), 7.315 (4.77), 7.321 (3.22), 7.335 (0.95), 7.347 (0.31), 7.683 (5.70), 7.699 (1.18), 7.708 (1.35), 7.721 (1.06), 8.521 (1.41), 8.780 (0.38), 8.956 (0.48).

Example 274

3-[5-(3-chlorobenzyl)-1,3,4-oxadiazol-2-yl]-7-(piperidin-4-yl)pyrazolo[1,5-c]pyrimidin-5(4H)-one hydrochloride

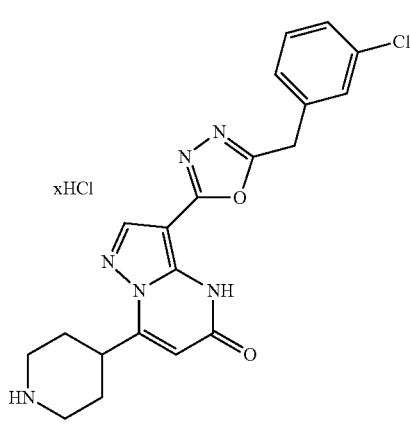 [SMILES: O=c1cc(C2CCNCC2)n2ncc(-c3nnc(Cc4cccc(Cl)c4)o3)c2[nH]1]

tert-butyl 4-{3-[5-(3-chlorobenzyl)-1,3,4-oxadiazol-2-yl]-5-oxo-4,5-dihydropyrazolo[1,5-a]pyrimidin-7-yl}piperidine-1-carboxylate (27.8 mg, 54.4 µmol) was dissolved in 1,4-dioxan (1.3 ml, 16 mmol) and treated with hydrochloric acid in 1,4-dioxan (200 µl, 4.0 M, 820 µmol) at RT for 16 h. Acetonitrile was added and the resulting participate was filtered and washed with acetonitrile. Drying in vacuo afforded the product. The obtained amount was 24.5 mg (97% purity, 97% of theory).

LC-MS (Method 1B): $R_t$=0.60 min; MS (ESIpos): m/z=411 [M+H]$^+$

1H-NMR (400 MHz, DMSO-d6) delta [ppm]: 1.844 (0.29), 1.875 (0.71), 1.903 (0.74), 1.933 (0.31), 2.182 (1.09), 2.215 (0.83), 3.059 (0.31), 3.084 (0.73), 3.111 (0.74), 3.141 (0.31), 3.388 (1.32), 3.415 (0.93), 3.566 (16.00), 4.355 (5.55), 6.090 (0.15), 7.347 (0.68), 7.365 (1.59), 7.378 (1.29), 7.382 (1.81), 7.392 (2.09), 7.410 (1.11), 7.428 (0.39), 7.497 (1.48), 8.396 (0.47), 8.691 (0.24), 8.897 (0.31), 12.134 (0.09).

Example 275

7-(piperidin-4-yl)-3-{5-[2-(1H-1,2,4-triazol-1-yl)propan-2-yl]-1,3,4-oxadiazol-2-yl}pyrazolo[1,5-a]pyrimidin-5(4H)-one hydrochloride

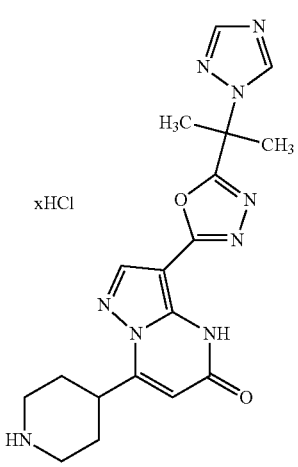 [SMILES: CC(C)(c1nnc(-c2cnn3c(C4CCNCC4)cc(=O)[nH]c23)o1)n1cncn1]

tert-butyl 4-(5-oxo-3-{5-[2-(1H-1,2,4-triazol-1-yl)propan-2-yl]-1,3,4-oxadiazol-2-yl}-4,5-dihydropyrazolo[1,5-a]pyrimidin-7-yl)piperidine-1-carboxylate (46.8 mg, 94.4 µmol) was dissolved in 1,4-dioxan (2.0 ml, 23 mmol) and treated with hydrochloric acid in 1,4-dioxan (350 µl, 4.0 M, 1.4 mmol) at RT for 16 h. Acetonitrile was added and the resulting participate was filtered and washed with acetonitrile. Drying in vacuo afforded the product. The obtained amount was 42.5 mg (100% purity, 104% of theory).

LC-MS (Method 1B): $R_t$=0.30 min; MS (ESIpos): m/z=396 [M+H]$^+$

1H-NMR (400 MHz, DMSO-d6) delta [ppm]: 1.844 (0.30), 1.853 (0.30), 1.883 (0.75), 1.914 (0.81), 1.941 (0.35), 1.950 (0.35), 2.117 (16.00), 2.168 (1.23), 2.200 (0.94), 3.044 (0.32), 3.075 (0.85), 3.102 (0.85), 3.132 (0.34), 3.373 (1.19), 3.404 (0.93), 6.109 (0.49), 8.028 (3.80), 8.385 (1.88), 8.895 (3.75), 9.013 (0.34).

Example 276

3-[5-(2-chlorobenzyl)-1,3,4-oxadiazol-2-yl]-7-(piperidin-4-yl)pyrazolo[1,5-a]pyrimidin-5(4H)-one hydrochloride

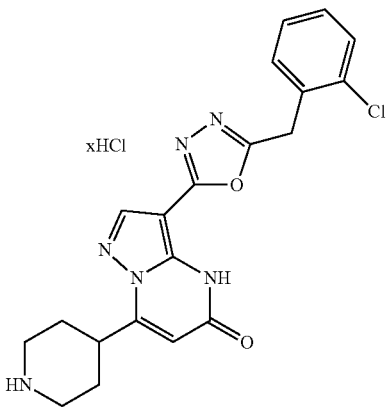 [SMILES: O=c1cc(C2CCNCC2)n2ncc(-c3nnc(Cc4ccccc4Cl)o3)c2[nH]1]

tert-butyl 4-{3-[5-(2-chlorobenzyl)-1,3,4-oxadiazol-2-yl]-5-oxo-4,5-dihydropyrazolo[1,5-a]pyrimidin-7-yl}piperidine-1-carboxylate (41.5 mg, 81.2 µmol) was dissolved in 1,4-dioxan (2.0 ml, 23 mmol) and treated with hydrochloric acid in 1,4-dioxan (300 µl, 4.0 M, 1.2 mmol) at RT for 16 h. Acetonitrile was added and the resulting participate was filtered and washed with acetonitrile. Drying in vacuo afforded the product. The obtained amount was 36.1 mg (100% purity, 99% of theory).

LC-MS (Method 1B): $R_t$=0.57 min; MS (ESIpos): m/z=411 [M+H]$^+$

1H-NMR (400 MHz, DMSO-d6) delta [ppm]: 1.878 (0.52), 1.887 (0.65), 1.912 (1.73), 1.918 (1.79), 1.943 (1.96), 1.950 (1.92), 1.974 (0.87), 1.983 (0.75), 2.174 (2.80), 2.207 (2.18), 3.037 (0.69), 3.068 (1.94), 3.096 (2.00), 3.126 (0.80), 3.399 (2.18), 3.542 (0.80), 3.549 (0.67), 3.564 (9.79), 3.595 (0.55), 3.601 (0.70), 4.426 (16.00), 6.104 (2.82), 7.348 (0.69), 7.358 (5.06), 7.367 (4.65), 7.373 (4.82), 7.382 (6.84), 7.391 (1.05), 7.480 (0.52), 7.489 (3.17), 7.502 (4.86), 7.511 (3.96), 7.524 (2.35), 7.533 (0.34), 8.389 (7.21), 9.049 (0.66), 9.164 (0.86).

Example 277

3-{5-[(5-methyl-1,3-thiazol-2-yl)methyl]-1,3,4-oxadiazol-2-yl}-7-(piperidin-4-yl)pyrazolo[1,5-a]pyrimidin-5(4H)-one hydrochloride

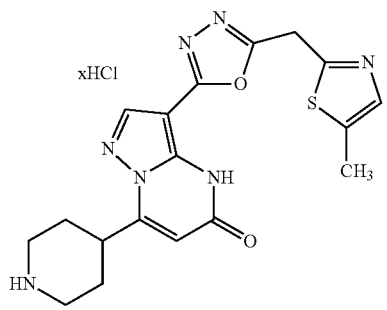 [SMILES: Cc1cnc(Cc2nnc(-c3cnn4c(C5CCNCC5)cc(=O)[nH]c34)o2)s1]

tert-butyl 4-(3-{5-[(5-methyl-1,3-thiazol-2-yl)methyl]-1,3,4-oxadiazol-2-yl}-5-oxo-4,5-dihydropyrazolo[1,5-a]pyrimidin-7-yl)piperidine-1-carboxylate (43.0 mg, 86.4 µmol) was dissolved in 1,4-dioxan (1.8 ml, 21 mmol) and treated with hydrochloric acid in 1,4-dioxan (320 µl, 4.0 M, 1.3 mmol) at RT for 16 h. Acetonitrile was added and the resulting participate was filtered and washed with acetonitrile. Drying in vacuo afforded the product. The obtained amount was 37.4 mg (100% purity, 100% of theory).

LC-MS (Method 1B): $R_t$=0.43 min; MS (ESIpos): m/z=398 [M+H]$^+$

1H-NMR (400 MHz, DMSO-d6) delta [ppm]: 1.894 (0.60), 1.925 (1.49), 1.956 (1.56), 1.981 (0.72), 2.175 (2.25), 2.207 (1.76), 2.330 (15.16), 2.332 (16.00), 2.350 (1.63), 3.041 (0.60), 3.067 (1.58), 3.095 (1.63), 3.124 (0.70), 3.369 (2.60), 3.386 (1.94), 3.397 (1.88), 3.545 (0.74), 3.562 (11.51), 3.574 (1.25), 3.604 (0.53), 4.741 (10.90), 6.114 (1.98), 7.264 (3.46), 7.266 (3.66), 8.415 (4.71), 9.091 (0.55), 9.204 (0.76).

Example 278

3-{5-[1-(4-chlorophenyl)cyclopropyl]-1,3,4-oxadiazol-2-yl}-7-(piperidin-4-yl)pyrazolo[1,5-a]pyrimidin-5(4H)-one hydrochloride

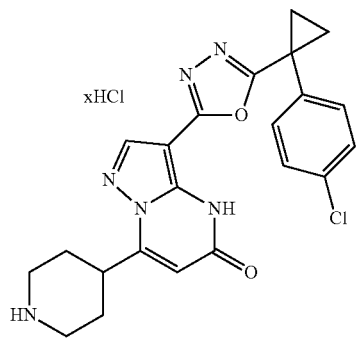 [SMILES: O=c1cc(C2CCNCC2)n2ncc(-c3nnc(C4(c5ccc(Cl)cc5)CC4)o3)c2[nH]1]

tert-butyl 4-(3-{5-[1-(4-chlorophenyl)cyclopropyl]-1,3,4-oxadiazol-2-yl}-5-oxo-4,5-dihydropyrazolo[1,5-a]pyrimidin-7-yl)piperidine-1-carboxylate (56.1 mg, 104 µmol) was dissolved in 1,4-dioxan (2.0 ml) and treated with hydrochloric acid in 1,4-dioxan (390 µl, 4.0 M, 1.6 mmol) at RT for 16 h. Acetonitrile was added and the resulting participate was filtered and washed with acetonitrile. Drying in vacuo afforded the product. The obtained amount was 38.5 mg (96% purity, 75% of theory).

LC-MS (Method 1B): $R_t$=0.66 min; MS (ESIpos): m/z=437 [M+H]$^+$

1H-NMR (400 MHz, DMSO-d6) delta [ppm]: −0.001 (16.00), 1.485 (0.64), 1.497 (1.91), 1.503 (1.85), 1.514 (0.83), 1.748 (0.71), 1.759 (1.74), 1.764 (1.69), 1.776 (0.67), 1.843 (0.22), 1.873 (0.58), 1.903 (0.63), 1.931 (0.28), 2.174 (0.94), 2.207 (0.77), 3.055 (0.26), 3.081 (0.61), 3.108 (0.63), 3.138 (0.28), 3.356 (0.47), 3.373 (1.34), 3.391 (1.16), 3.408 (0.97), 3.536 (0.23), 3.566 (0.83), 3.595 (0.21), 6.095 (0.22), 7.414 (0.99), 7.421 (0.53), 7.437 (4.24), 7.447 (4.00), 7.463 (0.54), 7.468 (0.79), 8.343 (0.60), 8.726 (0.14), 8.917 (0.18), 12.110 (0.10).

Example 279

3-[5-(2-chloro-6-fluorobenzyl)-1,3,4-oxadiazol-2-yl]-7-(piperidin-4-yl)pyrazolo[1,5-a]pyrimidin-5(4H)-one hydrochloride tert-butyl 4-{3-[5-(2-chloro-6-fluorobenzyl)-1,3,4-oxadiazol-2-yl]-5-oxo-4,5-dihydropyrazolo[1,5-a]pyrimidin-7-yl}piperidine-1-carboxylate (31.6 mg, 59.7 µmol) was dissolved in 1,4-dioxan (2.0 ml) and treated with hydrochloric acid in 1,4-dioxan (220 µl, 4.0 M, 900 µmol) at RT for 16 h. Acetonitrile was added and the resulting participate was filtered and washed with acetonitrile. Drying in vacuo afforded the product. The obtained amount was 19.8 mg (100% purity, 71% of theory).

LC-MS (Method 1B): $R_t$=0.58 min; MS (ESIpos): m/z=429 [M+H]$^+$

1H-NMR (400 MHz, DMSO-d6) delta [ppm]: 1.856 (1.00), 1.885 (2.83), 1.917 (3.07), 1.946 (1.35), 2.186 (4.29), 2.218 (3.50), 3.087 (2.66), 3.106 (2.72), 3.373 (3.97), 3.390 (5.54), 3.415 (3.97), 3.566 (13.60), 4.436 (16.00), 6.104 (0.75), 7.306 (1.75), 7.310 (1.84), 7.330 (4.28), 7.351 (2.83), 7.353 (2.83), 7.415 (2.42), 7.432 (7.91), 7.453 (3.64), 7.458 (3.40), 7.473 (3.41), 7.493 (1.18), 8.382 (3.11), 8.777 (0.85), 8.958 (1.09), 12.131 (0.38).

Example 280

3-[5-(2-methoxybenzyl)-1,3,4-oxadiazol-2-yl]-7-(piperidin-4-yl)pyrazolo[1,5-a]pyrimidin-5(4H)-one hydrochloride tert-butyl 4-{3-[5-(2-methoxybenzyl)-1,3,4-oxadiazol-2-yl]-5-oxo-4,5-dihydropyrazolo[1,5-a]pyrimidin-7-yl}piperidine-1-carboxylate (66.2 mg, 131 µmol) was dissolved in 1,4-dioxan (2.1 ml) and treated with hydrochloric acid in 1,4-dioxan (490 µl, 4.0 M, 2.0 mmol) at RT for 16 h. Acetonitrile was added and the resulting participate was filtered and washed with acetonitrile. Drying in vacuo afforded the product. The obtained amount was 61.3 mg (85% purity, 90% of theory).

LC-MS (Method 1B): $R_t$=0.57 min; MS (ESIpos): m/z=407 [M+H]$^+$

1H-NMR (400 MHz, DMSO-d6) delta [ppm]: 1.874 (0.43), 1.907 (1.00), 1.934 (1.01), 1.963 (0.42), 2.174 (1.47), 2.207 (1.12), 3.040 (0.42), 3.070 (1.05), 3.097 (1.04), 3.125 (0.41), 3.372 (1.51), 3.400 (1.22), 3.785 (16.00), 4.226 (6.46), 6.102 (1.08), 6.894 (0.26), 6.920 (0.83), 6.938 (1.73), 6.957 (1.19), 6.977 (0.28), 7.028 (1.54), 7.049 (1.80), 7.237 (0.33), 7.244 (1.31), 7.248 (1.53), 7.263 (1.36), 7.266 (1.43), 7.279 (1.04), 7.283 (0.90), 7.300 (1.26), 7.318 (0.65), 7.322 (0.56), 8.375 (3.01), 8.961 (0.33), 9.098 (0.45).

Example 281

3-{5-[1-(morpholin-4-yl)propan-2-yl]-1,3,4-oxadiazol-2-yl}-7-(piperidin-4-yl)pyrazolo[1,5-a]pyrimidin-5(4H)-one hydrochloride

Example 282

3-{5-[2-(morpholin-4-yl)ethyl]-1,3,4-oxadiazol-2-yl}-7-(piperidin-4-yl)pyrazolo[1,5-a]pyrimidin-5(4H)-one hydrochloride

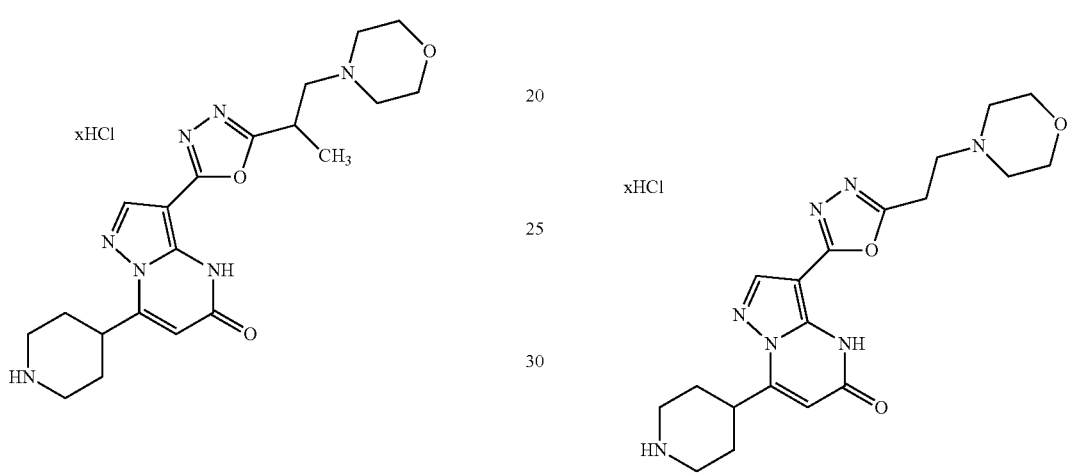

tert-butyl 4-(3-{5-[−1-(morpholin-4-yl)propan-2-yl]-1,3,4-oxadiazol-2-yl}-5-oxo-4,5-dihydropyrazolo[1,5-a]pyrimidin-7-yl)piperidine-1-carboxylate (24.1 mg, 46.9 µmol) was dissolved in 1,4-dioxan (1.0 ml, 12 mmol) and treated with hydrochloric acid in 1,4-dioxan (180 µl, 4.0 M, 700 µmol) at RT for 16 h. Acetonitrile was added and the resulting participate was filtered and washed with acetonitrile. The residue was purified via reverse phase chromatography (Method: Reprosil C18; 10 µm; 125×30 mm/flow: 50 ml/min/solvents: A=water (0.01% formic acid), B=acetonitrile/gradient: 0.00-5.00 min=10% B, 6.50 min=20% B, 17.0-19.75 min=100% B, 19.75.00-23.00 min=90% B). The solvents were removed and the residue was treated with hydrochloric acid in 1,4-dioxan (4M, 0.5 mL) and the solvent was removed in vacuo to afford the product. The obtained amount was 5.80 mg (100% purity, 25% of theory).

LC-MS (Method 7B): $R_t$=0.83 min; MS (ESIpos): m/z=414 [M+H]$^+$

1H-NMR (400 MHz, DMSO-d6) delta [ppm]: 1.455 (0.40), 1.471 (0.39), 1.858 (0.07), 1.886 (0.17), 1.914 (0.18), 1.944 (0.07), 2.187 (0.26), 2.220 (0.19), 3.062 (0.09), 3.087 (0.23), 3.116 (0.26), 3.146 (0.17), 3.566 (16.00), 3.807 (0.18), 3.835 (0.15), 3.928 (0.10), 3.958 (0.13), 3.990 (0.08), 6.079 (0.03), 8.429 (0.09), 8.777 (0.06), 8.923 (0.08), 10.734 (0.03).

tert-butyl 4-(3-{5-[2-(morpholin-4-yl)ethyl]-1,3,4-oxadiazol-2-yl}-5-oxo-4,5-dihydropyrazolo[1,5-a]pyrimidin-7-yl)piperidine-1-carboxylate (13.4 mg, 26.8 µmol) was dissolved in 1,4-dioxan (1.0 ml, 12 mmol) and treated with hydrochloric acid in 1,4-dioxan (100 µl, 4.0 M, 400 µmol) at RT for 16 h. Acetonitrile was added and the resulting participate was filtered and washed with acetonitrile. Drying in vacuo afforded the product. The obtained amount was 13.2 mg (95% purity, 99% of theory).

LC-MS (Method 7B): $R_t$=0.75 min; MS (ESIpos): m/z=400 [M+H]$^+$

1H-NMR (400 MHz, DMSO-d6) delta [ppm]: 1.861 (1.77), 1.870 (2.27), 1.901 (5.32), 1.927 (5.51), 1.958 (2.31), 1.965 (1.93), 2.188 (7.90), 2.221 (5.94), 3.054 (3.01), 3.083 (6.67), 3.111 (6.94), 3.150 (4.90), 3.182 (4.47), 3.387 (10.60), 3.416 (7.44), 3.501 (9.56), 3.529 (16.00), 3.548 (14.27), 3.613 (7.79), 3.630 (7.67), 3.650 (5.24), 3.796 (4.28), 3.827 (8.02), 3.858 (5.59), 3.983 (9.14), 4.017 (6.40), 6.132 (3.62), 8.429 (11.14), 8.851 (1.97), 8.992 (2.54), 11.553 (1.50).

Example 283

3-[5-(2-phenylethyl)-1,3,4-oxadiazol-2-yl]-7-(piperidin-4-yl)pyrazolo[1,5-a]pyrimidin-5(4H)-one hydrochloride

Example 284

3-[5-(4-chlorobenzyl)-1,3,4-oxadiazol-2-yl]-7-(piperidin-4-yl)pyrazolo[1,5-a]pyrimidin-5(4H)-one hydrochloride

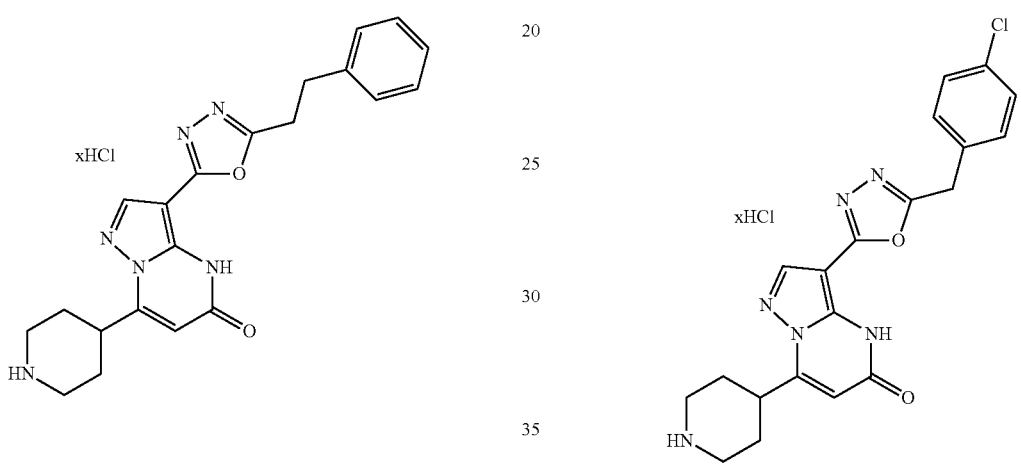

tert-butyl 4-{5-oxo-3-[5-(2-phenylethyl)-1,3,4-oxadiazol-2-yl]-4,5-dihydropyrazolo[1,5-a]pyrimidin-7-yl}piperidine-1-carboxylate (35.6 mg, 72.6 µmol) was dissolved in 1,4-dioxan (1.0 ml, 12 mmol) and treated with hydrochloric acid in 1,4-dioxan (270 µl, 4.0 M, 1.1 mmol) at RT for 16 h. Acetonitrile was added and the resulting participate was filtered and washed with acetonitrile. Drying in vacuo afforded the product. The obtained amount was 34.6 mg (95% purity, 106% of theory).

LC-MS (Method 1B): $R_t$=0.57 min; MS (ESIpos): m/z=391 [M+H]$^+$

1H-NMR (400 MHz, DMSO-d6) delta [ppm]: 1.846 (0.38), 1.855 (0.45), 1.879 (1.14), 1.886 (1.16), 1.911 (1.25), 1.917 (1.20), 1.942 (0.53), 1.951 (0.44), 2.188 (1.79), 2.221 (1.38), 3.053 (0.52), 3.085 (1.36), 3.103 (1.88), 3.120 (3.97), 3.139 (3.25), 3.203 (2.91), 3.222 (3.19), 3.239 (1.22), 3.387 (1.88), 3.418 (1.45), 6.099 (0.52), 7.175 (0.18), 7.183 (0.35), 7.191 (0.65), 7.200 (0.81), 7.205 (1.17), 7.209 (0.98), 7.213 (0.96), 7.219 (1.08), 7.226 (0.99), 7.239 (0.25), 7.250 (0.25), 7.272 (1.14), 7.285 (16.00), 7.293 (4.93), 7.299 (4.81), 7.318 (0.47), 8.388 (2.07), 8.745 (0.43), 8.933 (0.54).

tert-butyl 4-{3-[5-(4-chlorobenzyl)-1,3,4-oxadiazol-2-yl]-5-oxo-4,5-dihydropyrazolo[1,5-a]pyrimidin-7-yl}piperidine-1-carboxylate (34.3 mg, 67.1 µmol) was dissolved in 1,4-dioxan (1.0 ml, 12 mmol) and treated with hydrochloric acid in 1,4-dioxan (250 µl, 4.0 M, 1.0 mmol) at RT for 16 h. Acetonitrile was added and the resulting participate was filtered and washed with acetonitrile. Drying in vacuo afforded the product. The obtained amount was 31.7 mg (95% purity, 100% of theory).

LC-MS (Method 1B): $R_t$=0.61 min; MS (ESIpos): m/z=411 [M+H]$^+$

1H-NMR (400 MHz, DMSO-d6) delta [ppm]: 1.831 (0.62), 1.859 (1.65), 1.889 (1.76), 1.921 (0.70), 2.177 (2.52), 2.210 (2.01), 3.052 (0.73), 3.080 (1.94), 3.108 (1.93), 3.139 (0.78), 3.383 (3.14), 3.414 (3.02), 3.468 (2.81), 4.328 (14.38), 6.090 (0.39), 7.397 (1.78), 7.404 (1.32), 7.419 (15.34), 7.424 (16.00), 7.439 (0.99), 7.446 (1.43), 8.384 (1.23), 8.621 (0.54), 8.845 (0.68).

Example 285

7-(piperidin-4-yl)-3-[5-(pyridin-2-ylmethyl)-1,3,4-oxadiazol-2-yl]pyrazolo[1,5-a]pyrimidin-5 (4H)-one trihydrochloride

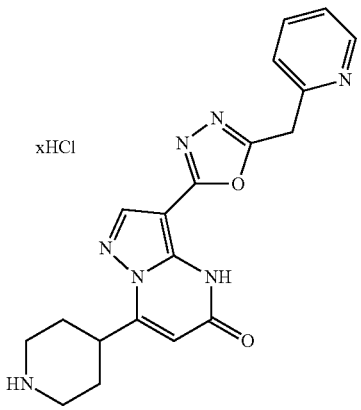 [SMILES: O=c1cc(C2CCNCC2)n2ncc(-c3nnc(Cc4ccccn4)o3)c2[nH]1]

tert-butyl 4-{3-[5-(4-chlorobenzyl)-1,3,4-oxadiazol-2-yl]-5-oxo-4,5-dihydropyrazolo[1,5-a]pyrimidin-7-yl}piperidine-1-carboxylate (37.2 mg, 77.9 µmol) was dissolved in 1,4-dioxan (1.0 ml, 12 mmol) and treated with hydrochloric acid in 1,4-dioxan (290 µl, 4.0 M, 1.2 mmol) at RT for 16 h. Acetonitrile was added and the resulting participate was filtered and washed with acetonitrile. Drying in vacuo afforded the product. The obtained amount was 39.9 mg (95% purity, 100% of theory).

LC-MS (Method 1B): $R_t$=0.34 min; MS (ESIneg): m/z=376 [M−H]⁻

1H-NMR (400 MHz, DMSO-d6) delta [ppm]: 1.866 (2.08), 1.898 (5.66), 1.928 (6.03), 1.959 (2.42), 2.180 (9.02), 2.212 (6.85), 3.045 (2.37), 3.075 (6.40), 3.105 (6.50), 3.135 (2.56), 3.378 (8.57), 3.408 (6.92), 4.620 (10.69), 6.118 (6.28), 7.539 (2.87), 7.672 (3.22), 8.055 (2.58), 8.413 (16.00), 8.638 (4.54), 8.885 (1.59), 9.042 (2.09).

Example 286

3-(5-hydroxy-1,3,4-oxadiazol-2-yl)-7-(piperidin-4-yl)pyrazolo[1,5-a]pyrimidin-5(4H)-one hydrochloride

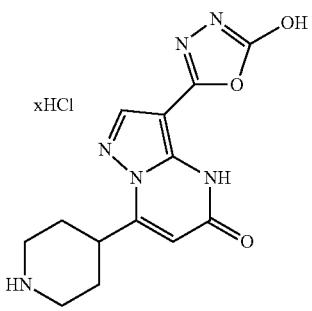 [SMILES: O=c1cc(C2CCNCC2)n2ncc(-c3nnc(O)o3)c2[nH]1]

tert-butyl 4-{3-[5-(4-chlorobenzyl)-1,3,4-oxadiazol-2-yl]-5-oxo-4,5-dihydropyrazolo[1,5-a]pyrimidin-7-yl}piperidine-1-carboxylate (38.9 mg, 93.4 µmol) was dissolved in 1,4-dioxan (1.0 ml, 12 mmol) and treated with hydrochloric acid in 1,4-dioxan (350 µl, 4.0 M, 1.4 mmol) at RT for 16 h. Acetonitrile was added and the resulting participate was filtered and washed with acetonitrile. Drying in vacuo afforded the product. The obtained amount was 32.5 mg (95% purity, 98% of theory).

LC-MS (Method 1B): $R_t$=0.17 min; MS (ESIpos): m/z=303 [M+H]⁺

¹H NMR (400 MHz, DMSO-d₆) ppm=12.42 (s, 1H), 9.02 (br. s., 1H), 8.85 (br. s., 1H), 8.29 (s, 1H), 6.14 (br. s., 1H), 3.51-3.63 (m, 1H), 3.36-3.42 (m, 2H), 3.09 (q, 2H), 2.20 (d, 2H), 1.91 (q, 2H).

Example 287

5-oxo-7-(piperidin-4-yl)-4,5-dihydropyrazolo[1,5-a]pyrimidine-3-carbothioamide hydrochloride

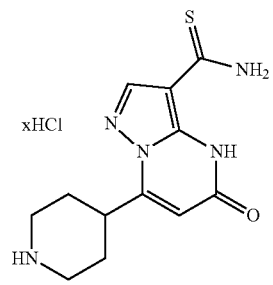 [SMILES: NC(=S)c1cnn2c(C3CCNCC3)cc(=O)[nH]c12]

tert-butyl 4-(3-carbamothioyl-5-oxo-4,5-dihydropyrazolo[1,5-a]pyrimidin-7-yl)piperidine-1-carboxylate (50.0 mg, 132 µmol) was dissolved in 1,4-dioxan (2.6 ml) and treated with hydrochloric acid in 1,4-dioxan (660 µl, 4.0 M, 2.6 mmol) at RT for 16 h. Drying in vacuo afforded the product. The obtained amount was 42.5 mg (90% purity, 82% of theory).

LC-MS (Method 7B): $R_t$=0.61 min; MS (ESIpos): m/z=278 [M+H]⁺

1H-NMR (400 MHz, DMSO-d6) delta [ppm]: 1.544 (0.22), 1.555 (0.24), 1.576 (0.51), 1.583 (0.65), 1.610 (0.82), 1.619 (0.59), 1.639 (0.33), 1.649 (0.32), 1.834 (0.53), 1.862 (1.44), 1.892 (1.59), 1.936 (1.10), 1.975 (0.83), 1.981 (0.79), 2.135 (10.31), 2.153 (2.26), 2.185 (1.77), 2.839 (0.28), 2.869 (0.73), 2.896 (0.76), 2.926 (0.36), 3.037 (0.62), 3.066 (1.73), 3.095 (1.79), 3.125 (0.76), 3.226 (0.89), 3.259 (0.88), 3.401 (2.60), 3.513 (0.86), 3.566 (16.00), 6.058 (0.76), 8.499 (5.89), 8.711 (0.53), 8.916 (0.73), 9.435 (0.67), 9.497 (2.10), 11.857 (0.59).

Example 288

7-(piperidin-4-yl)-3-[5-(thiophen-2-yl)-1,3,4-oxadiazol-2-yl]pyrazolo[1,5-a]pyrimidin-5 (4H)-one hydrochloride

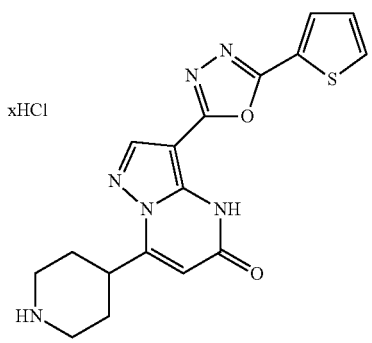 [SMILES: O=c1cc(C2CCNCC2)n2ncc(-c3nnc(-c4cccs4)o3)c2[nH]1]

tert-butyl 4-{5-oxo-3-[5-(thiophen-2-yl)-1,3,4-oxadiazol-2-yl]-4,5-dihydropyrazolo[1,5-a]pyrimidin-7-yl}piperidine-1-carboxylate (49.0 mg, 105 µmol) was dissolved in 1,4-dioxan (2.0 ml, 23 mmol) and treated with hydrochloric acid in 1,4-dioxan (390 µl, 4.0 M, 1.6 mmol) at RT for 16 h. Acetonitrile was added and the resulting participate was filtered and washed with acetonitrile. Drying in vacuo afforded the product. The obtained amount was 40.3 mg (100% purity, 95% of theory).

LC-MS (Method 1B): $R_t$=0.50 min; MS (ESIpos): m/z=369 [M+H]$^+$ $^1$H NMR (400 MHz, DMSO-d$_6$) ppm=9.09 (br. s, 1H), 8.91 (br. s, 1H), 8.49 (s, 1H), 8.06 (d, 1H), 7.95 (dd, 1H), 7.33 (dd, 1H), 6.13 (br. s., 2H), 3.52-3.65 (m, 1H), 3.40 (m, 2H), 3.11 (m, 2H), 2.22 (m, 2H), 1.82-2.00 (m, 2H).

Example 289

7-(piperidin-4-yl)-3-[5-(2,2,2-trifluoroethyl)-1,3,4-oxadiazol-2-yl]pyrazolo[1,5-a]pyrimidin-5(4H)-one hydrochloride

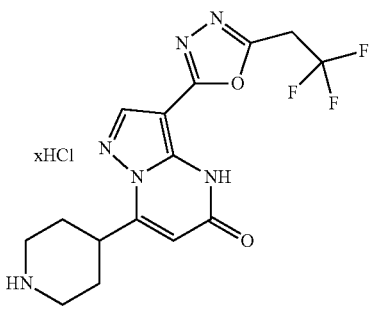 [SMILES: O=c1cc(C2CCNCC2)n2ncc(-c3nnc(CC(F)(F)F)o3)c2[nH]1]

tert-butyl 4-{5-oxo-3-[5-(2,2,2-trifluoroethyl)-1,3,4-oxadiazol-2-yl]-4,5-dihydropyrazolo[1,5-a]pyrimidin-7-yl}piperidine-1-carboxylate (70.0 mg, 149 µmol) was dissolved in 1,4-dioxan (2.0 ml, 23 mmol) and treated with hydrochloric acid in 1,4-dioxan (560 µl, 4.0 M, 2.2 mmol) at RT for 16 h. Acetonitrile was added and the resulting participate was filtered and washed with acetonitrile. Drying in vacuo afforded the product. The obtained amount was 41.2 mg (98% purity, 67% of theory).

LC-MS (Method 1B): $R_t$=0.43 min; MS (ESIpos): m/z=369 [M+H]$^+$

1H-NMR (400 MHz, DMSO-d6) delta [ppm]: 1.870 (2.19), 1.901 (5.23), 1.931 (5.25), 1.961 (2.08), 2.188 (7.77), 2.220 (5.86), 3.056 (2.46), 3.083 (5.57), 3.111 (5.44), 3.140 (2.22), 3.382 (9.75), 3.414 (7.22), 3.565 (8.77), 3.582 (2.75), 4.294 (5.43), 4.320 (16.00), 4.347 (15.39), 4.373 (4.85), 6.139 (1.22), 8.435 (5.14), 8.865 (1.54), 9.023 (2.08), 12.129 (0.35).

Example 290

3-[5-(2-chlorophenyl)-1,3,4-oxadiazol-2-yl]-7-(piperidin-4-yl)pyrazolo[1,5-a]pyrimidin-5(4H)-one hydrochloride

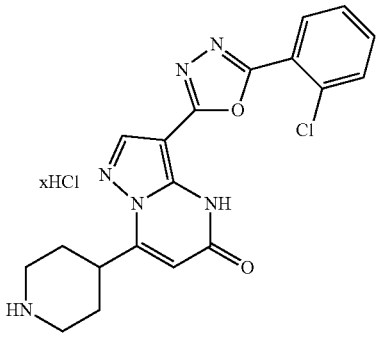 [SMILES: O=c1cc(C2CCNCC2)n2ncc(-c3nnc(-c4ccccc4Cl)o3)c2[nH]1]

tert-butyl 4-{3-[5-(2-chlorophenyl)-1,3,4-oxadiazol-2-yl]-5-oxo-4,5-dihydropyrazolo[1,5-a]pyrimidin-7-yl}piperidine-1-carboxylate (76.3 mg, 154 µmol) was dissolved in 1,4-dioxan (2.0 ml, 23 mmol) and treated with hydrochloric acid in 1,4-dioxan (580 µl, 4.0 M, 2.3 mmol) at RT for 16 h. Acetonitrile was added and the resulting participate was filtered and washed with acetonitrile. Drying in vacuo afforded the product. The obtained amount was 60.8 mg (100% purity, 91% of theory).

LC-MS (Method 1B): $R_t$=0.58 min; MS (ESIpos): m/z=397 [M+H]$^+$

1H-NMR (400 MHz, DMSO-d6) delta [ppm]: 1.892 (1.63), 1.901 (1.98), 1.926 (5.17), 1.933 (5.20), 1.957 (5.77), 1.964 (5.41), 1.989 (2.46), 1.997 (2.04), 2.199 (7.99), 2.232 (6.14), 3.061 (2.05), 3.090 (4.96), 3.117 (4.97), 3.146 (2.14), 3.386 (8.32), 3.416 (6.38), 3.564 (4.14), 3.573 (2.32), 3.603 (4.01), 3.633 (1.90), 6.147 (5.71), 7.589 (3.61), 7.592 (3.90), 7.607 (9.24), 7.611 (9.20), 7.626 (7.29), 7.630 (7.30), 7.640 (5.60), 7.645 (5.92), 7.660 (8.35), 7.664 (8.70), 7.679 (4.74), 7.683 (4.16), 7.728 (11.20), 7.730 (10.67), 7.748 (7.08), 7.751 (6.34), 8.145 (7.74), 8.149 (7.79), 8.164 (6.97), 8.168 (6.60), 8.510 (16.00), 8.999 (1.80), 9.122 (2.34).

Example 291

7-(piperidin-4-yl)-3-[5-(piperidin-1-ylmethyl)-1,3,4-oxadiazol-2-yl]pyrazolo[1,5-a]pyrimidin-5(4H)-one hydrochloride

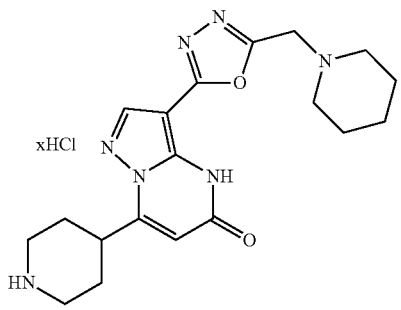 [SMILES: O=c1cc(C2CCNCC2)n2ncc(-c3nnc(CN4CCCCC4)o3)c2[nH]1]

tert-butyl 4-{5-oxo-3-[5-(piperidin-1-ylmethyl)-1,3,4-oxadiazol-2-yl]-4,5-dihydropyrazolo[1,5-a]pyrimidin-7-yl}piperidine-1-carboxylate (33.3 mg, 68.9 µmol) was dissolved in 1,4-dioxan (2.0 ml, 23 mmol) and treated with hydrochloric acid in 1,4-dioxan (260 µl, 4.0 M, 1.0 mmol) at RT for 16 h. Acetonitrile was added and the resulting participate was filtered and washed with acetonitrile. Drying in vacuo afforded the product. The obtained amount was 31.9 mg (95% purity, 96% of theory).

LC-MS (Method 7B): $R_t$=0.92 min; MS (ESIpos): m/z=384 [M+H]$^+$

1H-NMR (400 MHz, DMSO-d6) delta [ppm]: 1.512 (0.46), 1.776 (1.77), 1.789 (2.04), 1.801 (1.37), 1.878 (0.33), 1.900 (0.82), 1.934 (0.78), 1.964 (0.34), 2.072 (16.00), 2.184 (1.08), 2.217 (0.79), 3.053 (0.50), 3.082 (0.93), 3.110 (0.93), 3.140 (0.56), 3.387 (1.43), 3.413 (0.89), 3.566 (3.46), 3.581 (0.66), 4.610 (0.98), 6.148 (1.76), 8.468 (3.23), 8.915 (0.24), 9.042 (0.32).

Example 292

3-{5-[(2-oxopyrrolidin-1-yl)methyl]-1,3,4-oxadiazol-2-yl}-7-(piperidin-4-yl)pyrazolo[1,5-a]pyrimidin-5(4H)-one hydrochloride

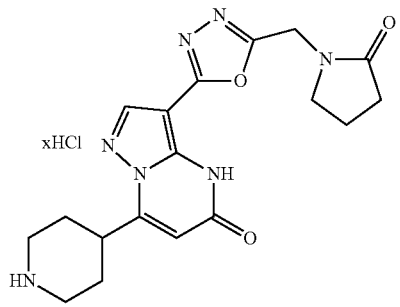 [SMILES: O=C1CCCN1Cc1nnc(-c2cnn3c(C4CCNCC4)cc(=O)[nH]c23)o1]

tert-butyl 4-(5-oxo-3-{5-[(2-oxopyrrolidin-1-yl)methyl]-1,3,4-oxadiazol-2-yl}-4,5-dihydropyrazolo[1,5-a]pyrimidin-7-yl)piperidine-1-carboxylate (48.2 mg, 99.7 µmol) was dissolved in 1,4-dioxan (2.0 ml, 23 mmol) and treated with hydrochloric acid in 1,4-dioxan (370 µl, 4.0 M, 1.5 mmol) at RT for 16 h. Acetonitrile was added and the resulting participate was filtered and washed with acetonitrile. Drying in vacuo afforded the product. The obtained amount was 42.2 mg (95% purity, 96% of theory).

LC-MS (Method 7B): $R_t$=0.71 min; MS (ESIpos): m/z=384 [M+H]$^+$

1H-NMR (400 MHz, DMSO-d6) delta [ppm]: 1.859 (0.62), 1.890 (1.66), 1.922 (1.82), 1.956 (1.60), 1.975 (2.78), 1.994 (3.98), 2.013 (3.00), 2.031 (1.09), 2.072 (12.56), 2.186 (2.65), 2.219 (2.10), 2.283 (4.13), 2.303 (6.18), 2.323 (3.24), 3.056 (0.75), 3.083 (1.86), 3.112 (1.90), 3.141 (0.76), 3.387 (2.66), 3.414 (2.25), 3.461 (4.21), 3.478 (6.67), 3.496 (4.07), 3.566 (3.79), 4.714 (16.00), 6.120 (0.80), 8.411 (2.43), 8.770 (0.37), 8.963 (0.47).

Example 293

3-(5-cyclohexyl-1,3,4-oxadiazol-2-yl)-7-(piperidin-4-yl)pyrazolo[1,5-a]pyrimidin-5 (4H)-one hydrochloride

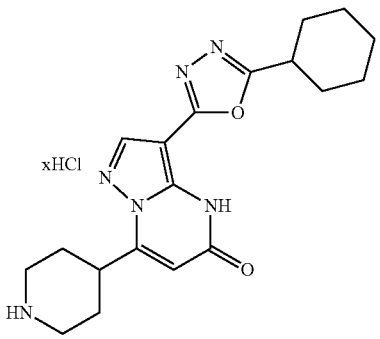 [SMILES: O=c1cc(C2CCNCC2)n2ncc(-c3nnc(C4CCCCC4)o3)c2[nH]1]

tert-butyl 4-[3-(5-cyclohexyl-1,3,4-oxadiazol-2-yl)-5-oxo-4,5-dihydropyrazolo[1,5-a]pyrimidin-7-yl]piperidine-1-carboxylate (98.8 mg, 211 µmol) was dissolved in 1,4-dioxan (2.0 ml, 23 mmol) and treated with hydrochloric acid in 1,4-dioxan (790 µl, 4.0 M, 3.2 mmol) at RT for 16 h. Acetonitrile was added and the resulting participate was filtered and washed with acetonitrile. The residue was dissolved in acetonitrile water and purified via reverse phase chromatography (Method: Reprosil C18; 10 µm; 125×30 mm/flow: 50 ml/min/solvents: A=water (0.01% formic acid), B=acetonitrile/gradient: 0.00-5.00 min=10% B, 6.50 min=20% B, 17.0-19.75 min=100% B, 19.75.00-23.00 min=90% B). The solvents were removed and 1 ml hydrochloric acid in 1,4-dioxan (4M) was added. Drying in vacuo afforded the product. The obtained amount was 45.5 mg (96% purity, 51% of theory).

LC-MS (Method 1B): $R_t$=0.56 min; MS (ESIpos): m/z=369 [M+H]$^+$

1H-NMR (400 MHz, DMSO-d6) delta [ppm]: 1.229 (1.20), 1.238 (1.13), 1.247 (0.81), 1.261 (1.69), 1.268 (2.91), 1.277 (1.70), 1.291 (2.26), 1.298 (3.97), 1.305 (2.24), 1.320 (1.65), 1.328 (2.65), 1.348 (2.21), 1.354 (2.96), 1.361 (2.07), 1.384 (6.36), 1.415 (6.22), 1.436 (1.52), 1.444 (2.57), 1.542 (2.55), 1.550 (2.63), 1.574 (6.11), 1.578 (6.20), 1.602 (6.02), 1.609 (5.81), 1.632 (2.59), 1.639 (3.25), 1.655 (3.35), 1.664 (2.71), 1.676 (2.39), 1.687 (2.93), 1.747 (5.30), 1.755 (7.00), 1.764 (5.49), 1.778 (4.95), 1.787 (5.65), 1.796 (3.79), 1.886 (1.77), 1.911 (4.83), 1.943 (5.36), 1.974 (2.22), 2.051 (6.53), 2.058 (6.52), 2.070 (3.87), 2.083 (5.81), 2.090 (5.41), 2.176 (7.55), 2.209 (5.83), 2.945 (1.47), 2.954 (2.82), 2.963 (1.77), 2.973 (3.01), 2.981 (5.35), 2.991 (2.85), 3.000 (1.70), 3.009

(2.65), 3.018 (1.44), 3.039 (1.93), 3.069 (5.22), 3.097 (5.31), 3.128 (2.08), 3.370 (7.17), 3.400 (5.78), 6.083 (9.31), 8.384 (16.00), 9.046 (1.57), 9.161 (2.07).

Example 294

3-(5-cyclobutyl-1,3,4-oxadiazol-2-yl)-7-(piperidin-4-yl)pyrazolo[1,5-a]pyrimidin-5 (4H)-one hydrochloride

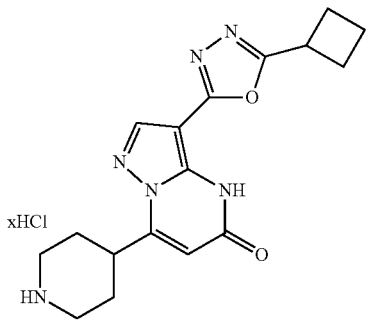 [SMILES: O=c1cc(C2CCNCC2)n2ncc(-c3nnc(C4CCC4)o3)c2[nH]1]

tert-butyl 4-[3-(5-cyclobutyl-1,3,4-oxadiazol-2-yl)-5-oxo-4,5-dihydropyrazolo[1,5-a]pyrimidin-7-yl]piperidine-1-carboxylate (14.7 mg, 33.4 μmol) was dissolved in 1,4-dioxan (1.0 ml) and treated with hydrochloric acid in 1,4-dioxan (130 μl, 4.0 M, 500 μmol) at RT for 16 h. Acetonitrile was added and the resulting participate was filtered and washed with acetonitrile. Drying in vacuo afforded the product.

The obtained amount was 13.1 mg (90% purity, 94% of theory).

LC-MS (Method 1B): $R_t$=0.48 min; MS (ESIpos): m/z=341 [M+H]$^+$

1H-NMR (400 MHz, DMSO-d6) delta [ppm]: 1.844 (1.96), 1.853 (2.23), 1.878 (4.85), 1.883 (4.73), 1.909 (5.15), 1.917 (4.97), 1.942 (3.65), 1.951 (4.34), 1.972 (3.27), 1.979 (3.36), 1.992 (2.58), 2.000 (2.05), 2.012 (1.04), 2.015 (1.03), 2.031 (1.12), 2.053 (3.52), 2.074 (5.93), 2.081 (3.29), 2.097 (5.20), 2.102 (4.99), 2.118 (2.74), 2.125 (4.07), 2.146 (2.12), 2.187 (6.35), 2.221 (6.09), 2.373 (5.82), 2.379 (8.48), 2.387 (8.11), 2.400 (11.82), 2.407 (13.08), 2.417 (5.91), 2.426 (9.88), 2.448 (3.31), 3.055 (1.96), 3.085 (4.83), 3.113 (5.29), 3.143 (2.74), 3.420 (12.50), 3.460 (13.58), 3.566 (16.00), 3.763 (1.61), 3.782 (4.62), 3.784 (4.42), 3.803 (6.42), 3.806 (6.04), 3.824 (4.07), 3.827 (3.91), 3.846 (1.17), 6.101 (1.72), 8.399 (5.56), 8.740 (1.52), 8.919 (2.27).

Example 295

3-(5-butyl-1,3,4-oxadiazol-2-yl)-7-(piperidin-4-yl)pyrazolo[1,5-a]pyrimidin-5(4H)-one hydrochloride

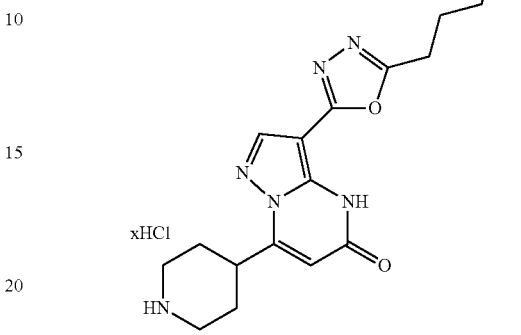

tert-butyl 4-[3-(5-butyl-1,3,4-oxadiazol-2-yl)-5-oxo-4,5-dihydropyrazolo[1,5-a]pyrimidin-7-yl]piperidine-1-carboxylate (35.6 mg, 80.3 μmol) was dissolved in 1,4-dioxan (2.0 ml) and treated with hydrochloric acid in 1,4-dioxan (300 μl, 4.0 M, 1.2 mmol) at RT for 16 h. Acetonitrile was added and the resulting participate was filtered and washed with acetonitrile. Drying in vacuo afforded the product.

The obtained amount was 17.0 mg (95% purity, 53% of theory).

LC-MS (Method 1B): $R_t$=0.52 min; MS (ESIpos): m/z=343 [M+H]$^+$

1H-NMR (400 MHz, DMSO-d6) delta [ppm]: 0.906 (7.17), 0.924 (16.00), 0.943 (7.94), 1.348 (0.65), 1.367 (2.26), 1.385 (3.79), 1.404 (3.77), 1.423 (2.26), 1.441 (0.60), 1.709 (1.20), 1.728 (3.10), 1.747 (4.12), 1.766 (2.98), 1.784 (1.03), 1.869 (0.54), 1.877 (0.69), 1.903 (1.63), 1.908 (1.72), 1.934 (1.80), 1.940 (1.75), 1.965 (0.78), 1.973 (0.66), 2.182 (2.78), 2.214 (1.98), 2.872 (4.28), 2.891 (7.08), 2.909 (4.03), 3.049 (0.78), 3.075 (1.85), 3.104 (1.88), 3.132 (0.85), 3.407 (2.66), 3.542 (0.91), 3.565 (6.26), 3.601 (0.73), 6.092 (1.34), 8.390 (4.31), 8.943 (0.58), 9.088 (0.78).

Example 296

3-(3-tert-butyl-1,2,4-oxadiazol-5-yl)-2-methyl-7-(piperidin-4-yl)pyrazolo[1,5-a]pyrimidin-5(4H)-one hydrochloride

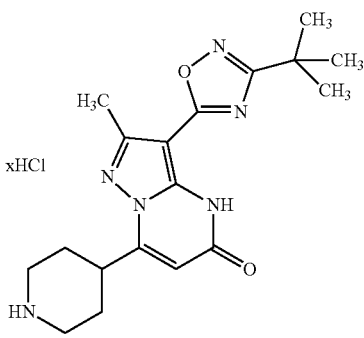 [SMILES: Cc1nn2c(C3CCNCC3)cc(=O)[nH]c2c1-c1nc(C(C)(C)C)no1]

tert-butyl 4-[3-(3-tert-butyl-1,2,4-oxadiazol-5-yl)-2-methyl-5-oxo-4,5-dihydropyrazolo[1,5-a]pyrimidin-7-yl]piperidine-1-carboxylate (104 mg, 228 µmol) was dissolved in 1,4-dioxan (3.9 ml, 46 mmol) and treated with hydrochloric acid in 1,4-dioxan (860 µl, 4.0 M, 3.4 mmol) at RT for 16 h. Acetonitrile was added and the resulting participate was filtered and washed with acetonitrile. Drying in vacuo afforded the product. The obtained amount was 90.3 mg (100% purity, 101% of theory).

LC-MS (Method 11B): $R_t$=0.99 min; MS (ESIpos): m/z=357 [M+H]$^+$

1H-NMR (400 MHz, DMSO-d6) delta [ppm]: 1.376 (16.00), 1.835 (0.10), 1.844 (0.11), 1.868 (0.32), 1.875 (0.32), 1.900 (0.35), 1.906 (0.34), 1.931 (0.15), 1.940 (0.13), 2.177 (0.50), 2.210 (0.40), 2.566 (2.49), 3.082 (0.18), 3.112 (0.35), 3.141 (0.21), 3.313 (3.03), 3.379 (0.54), 3.411 (0.43), 6.098 (0.12), 8.820 (0.08), 8.938 (0.10), 11.555 (0.04).

Example 297

3-[3-(2-methoxyethyl)-1,2,4-oxadiazol-5-yl]-2-methyl-7-(piperidin-4-yl)pyrazolo[1,5-a]pyrimidin-5(4H)-one hydrochloride

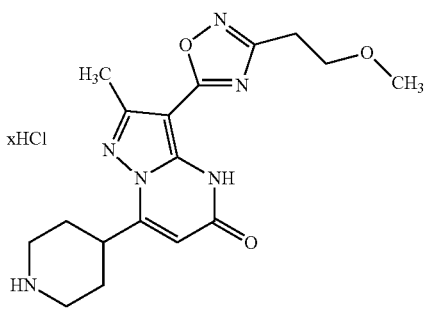 [SMILES: COCCc1noc(-c2c(C)nn3c(C4CCNCC4)cc(=O)[nH]c23)n1]

tert-butyl 4-{3-[3-(2-methoxyethyl)-1,2,4-oxadiazol-5-yl]-2-methyl-5-oxo-4,5-dihydropyrazolo[1,5-a]pyrimidin-7-yl}piperidine-1-carboxylate (66.9 mg, 146 µmol) was dissolved in 1,4-dioxan (2.5 ml, 29 mmol) and treated with hydrochloric acid in 1,4-dioxan (550 µl, 4.0 M, 2.2 mmol) at RT for 16 h. Acetonitrile was added and the resulting participate was filtered and washed with acetonitrile. Drying in vacuo afforded the product. The obtained amount was 47.8 mg (100% purity, 83% of theory).

LC-MS (Method 11B): $R_t$=0.65 min; MS (ESIpos): m/z=359 [M+H]$^+$

1H-NMR (400 MHz, DMSO-d6) delta [ppm]: 1.833 (0.24), 1.866 (0.64), 1.896 (0.70), 1.927 (0.28), 2.184 (1.09), 2.215 (0.88), 2.576 (4.24), 2.966 (1.62), 2.983 (3.50), 2.998 (1.77), 3.083 (0.45), 3.120 (0.79), 3.151 (0.46), 3.260 (16.00), 3.391 (1.23), 3.416 (0.98), 3.566 (1.84), 3.743 (1.69), 3.759 (3.44), 3.775 (1.57), 6.139 (0.13), 8.714 (0.13), 8.881 (0.19), 11.546 (0.06).

Example 298

Ethyl 2-methyl-5-oxo-7-(piperidin-4-yl)-4,5-dihydropyrazolo[1,5-a]pyrimidine-3-carboxylate hydrochloride

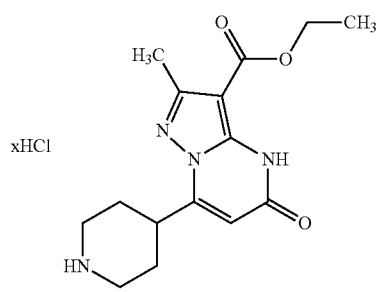 [SMILES: CCOC(=O)c1c(C)nn2c(C3CCNCC3)cc(=O)[nH]c12]

ethyl 7-[1-(tert-butoxycarbonyl)piperidin-4-yl]-2-methyl-5-oxo-4,5-dihydropyrazolo[1,5-a]pyrimidine-3-carboxylate (75.0 mg, 185 µmol) was dissolved in 1,4-dioxan (2.0 ml, 23 mmol) and treated with hydrochloric acid in 1,4-dioxan (700 µl, 4.0 M, 2.8 mmol) at RT for 16 h. Acetonitrile was added and the resulting participate was filtered and washed with acetonitrile. Drying in vacuo afforded the product.

The obtained amount was 43.0 mg (100% purity, 68% of theory).

LC-MS (Method 1B): $R_t$=0.45 min; MS (ESIpos): m/z=305 [M+H]$^+$

1H-NMR (400 MHz, DMSO-d6) delta [ppm]: 1.263 (4.62), 1.281 (10.09), 1.298 (4.73), 1.825 (0.35), 1.857 (1.07), 1.889 (1.19), 1.921 (0.48), 2.131 (1.83), 2.161 (1.38), 2.421 (16.00), 3.031 (0.41), 3.059 (1.06), 3.086 (1.09), 3.113 (0.47), 3.378 (1.42), 3.467 (0.52), 3.474 (0.37), 3.490 (0.62), 3.496 (0.97), 3.503 (0.61), 3.519 (0.35), 3.526 (0.47), 4.258 (1.33), 4.276 (4.18), 4.293 (4.12), 4.311 (1.28), 5.910 (2.79), 9.071 (0.51), 11.348 (0.88).

Example 299

3-[3-(4-fluorobenzyl)-1,2,4-oxadiazol-5-yl]-2-methyl-7-(piperidin-4-yl)pyrazolo[1,5-a]pyrimidin-5(4H)-one hydrochloride

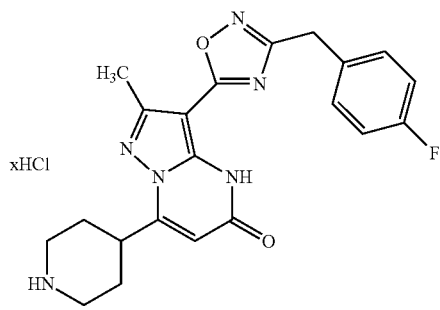 [SMILES: Cc1nn2c(C3CCNCC3)cc(=O)[nH]c2c1-c1nc(Cc2ccc(F)cc2)no1]

tert-butyl 4-{3-[3-(4-fluorobenzyl)-1,2,4-oxadiazol-5-yl]-2-methyl-5-oxo-4,5-dihydropyrazolo[1,5-a]pyrimidin-7-yl}piperidine-1-carboxylate (80.3 mg, 158 µmol) was dissolved in 1,4-dioxan (2.5 ml, 29 mmol) and treated with hydrochloric acid in 1,4-dioxan (590 µl, 4.0 M, 2.4 mmol) at RT for 16 h. Acetonitrile was added and the resulting participate was filtered and washed with acetonitrile. Drying in vacuo afforded the product. The obtained amount was 50.1 mg (100% purity, 71% of theory).

LC-MS (Method 7B): R$_t$=1.27 min; MS (ESIpos): m/z=409 [M+H]$^+$

1H-NMR (400 MHz, DMSO-d6) delta [ppm]: 1.837 (0.74), 1.867 (2.17), 1.898 (2.37), 1.931 (0.95), 2.171 (3.59), 2.204 (2.90), 3.067 (0.91), 3.097 (2.24), 3.123 (2.30), 3.152 (1.04), 3.376 (3.85), 3.407 (3.02), 3.566 (12.82), 4.139 (16.00), 6.149 (0.56), 7.147 (4.21), 7.169 (8.81), 7.192 (4.98), 7.403 (4.45), 7.417 (5.27), 7.424 (4.75), 7.439 (3.76), 8.791 (0.56), 8.931 (0.77).

Example 300

3-(3-ethyl-1,2,4-oxadiazol-5-yl)-2-methyl-7-(piperidin-4-yl)pyrazolo[1,5-a]pyrimidin-5(4H)-one hydrochloride

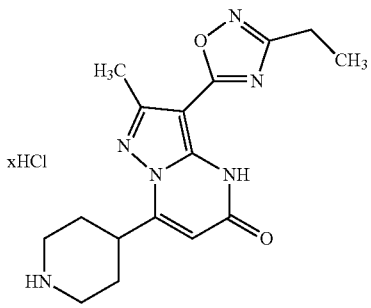 [SMILES: CCc1noc(-c2c(C)nn3c(C4CCNCC4)cc(=O)[nH]c23)n1]

tert-butyl 4-[3-(3-ethyl-1,2,4-oxadiazol-5-yl)-2-methyl-5-oxo-4,5-dihydropyrazolo[1,5-a]pyrimidin-7-yl]piperidine-1-carboxylate (91.1 mg, 213 µmol) was dissolved in 1,4-dioxan (2.5 ml, 29 mmol) and treated with hydrochloric acid in 1,4-dioxan (800 µl, 4.0 M, 3.2 mmol) at RT for 16 h. Acetonitrile was added and the resulting participate was filtered and washed with acetonitrile. Drying in vacuo afforded the product. The obtained amount was 58.3 mg (100% purity, 75% of theory).

LC-MS (Method 7B): R$_t$=0.99 min; MS (ESIpos): m/z=329 [M+H]$^+$

1H-NMR (400 MHz, DMSO-d6) delta [ppm]: 1.271 (6.97), 1.290 (14.47), 1.309 (6.93), 1.850 (0.68), 1.876 (1.72), 1.906 (1.85), 1.938 (0.75), 2.180 (2.66), 2.213 (2.09), 2.575 (14.12), 2.737 (2.42), 2.756 (6.61), 2.775 (6.32), 2.794 (1.97), 3.087 (1.08), 3.115 (1.85), 3.144 (1.08), 3.380 (2.84), 3.411 (2.19), 3.566 (16.00), 3.591 (1.09), 3.618 (0.55), 6.137 (0.75), 8.811 (0.45), 8.936 (0.57).

Example 301

2-methyl-7-(piperidin-4-yl)-3-[3-(propan-2-yl)-1,2,4-oxadiazol-5-yl]pyrazolo[1,5-a]pyrimidin-5(4H)-one hydrochloride

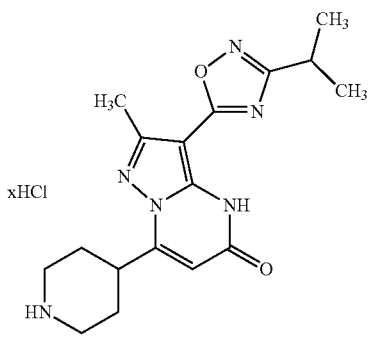 [SMILES: Cc1nn2c(C3CCNCC3)cc(=O)[nH]c2c1-c1nc(C(C)C)no1]

tert-butyl 4-{2-methyl-5-oxo-3-[3-(propan-2-yl)-1,2,4-oxadiazol-5-yl]-4,5-dihydropyrazolo[1,5-a]pyrimidin-7-yl}piperidine-1-carboxylate (71.6 mg, 162 µmol) was dissolved in 1,4-dioxan (2.5 ml, 29 mmol) and treated with hydrochloric acid in 1,4-dioxan (610 µl, 4.0 M, 2.4 mmol) at RT for 16 h. Acetonitrile was added and the resulting participate was filtered and washed with acetonitrile. Drying in vacuo afforded the product. The obtained amount was 51.3 mg (100% purity, 84% of theory).

LC-MS (Method 7B): R$_t$=1.12 min; MS (ESIpos): m/z=343 [M+H]$^+$

1H-NMR (400 MHz, DMSO-d6) delta [ppm]: 1.315 (16.00), 1.333 (16.00), 1.858 (0.36), 1.889 (0.94), 1.916 (1.01), 1.946 (0.41), 2.176 (1.46), 2.209 (1.12), 2.570 (8.28), 3.071 (0.94), 3.089 (1.68), 3.106 (2.44), 3.123 (1.66), 3.140 (0.97), 3.376 (1.54), 3.408 (1.19), 3.556 (0.37), 3.585 (0.61), 3.615 (0.30), 6.120 (0.50), 8.909 (0.26), 8.995 (0.34).

Example 302

3-[3-(2-tert-butoxyethyl)-1,2,4-oxadiazol-5-yl]-2-methyl-7-(piperidin-4-yl)pyrazolo[1,5-a]pyrimidin-5(4H)-one hydrochloride

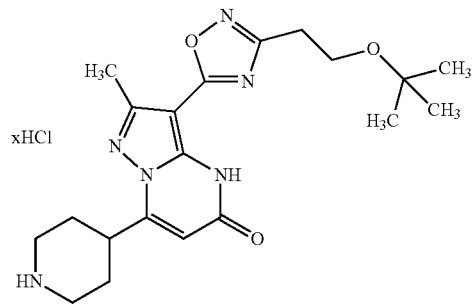 [SMILES: Cc1nn2c(C3CCNCC3)cc(=O)[nH]c2c1-c1nc(CCOC(C)(C)C)no1]

tert-butyl 4-{3-[3-(2-tert-butoxyethyl)-1,2,4-oxadiazol-5-yl]-2-methyl-5-oxo-4,5-dihydropyrazolo[1,5-a]pyrimidin-7-yl}piperidine-1-carboxylate (42.0 mg, 83.9 µmol) was dissolved in 1,4-dioxan (2.0 ml, 23 mmol) and treated with hydrochloric acid in 1,4-dioxan (310 µl, 4.0 M, 1.3 mmol) at RT for 16 h. Acetonitrile was added and the resulting participate was filtered and washed with acetonitrile. Drying in vacuo afforded the product. The obtained amount was 30.6 mg (100% purity, 83% of theory).

LC-MS (Method 7B): $R_t$=1.19 min; MS (ESIpos): m/z=401 $[M+H]^+$

1H-NMR (400 MHz, DMSO-d6) delta [ppm]: 1.113 (16.00), 1.837 (0.12), 1.864 (0.32), 1.896 (0.35), 1.927 (0.14), 2.181 (0.50), 2.215 (0.40), 2.578 (1.82), 2.878 (0.64), 2.895 (1.26), 2.910 (0.61), 3.122 (0.32), 3.383 (0.55), 3.414 (0.43), 3.587 (0.16), 3.720 (0.65), 3.736 (1.27), 3.752 (0.58), 6.131 (0.07), 8.708 (0.09), 8.879 (0.12).

Example 303

3-(3-tert-butyl-1,2,4-oxadiazol-5-yl)-7-[2-(2,2-dimethylpropyl)piperidin-4-yl]pyrazolo[1,5-a]pyrimidin-5(4H)-one hydrochloride

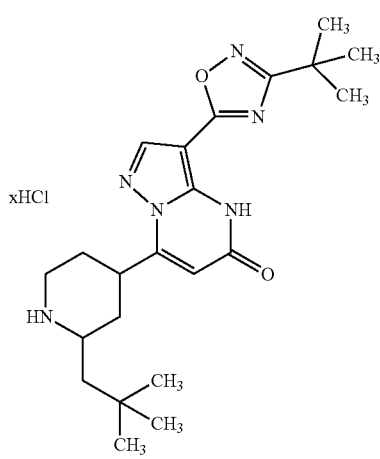 [SMILES: CC(C)(C)CC1CC(c2cc(=O)[nH]c3c(-c4nc(C(C)(C)C)no4)cnn23)CCN1]

tert-butyl 4-[3-(3-tert-butyl-1,2,4-oxadiazol-5-yl)-5-oxo-4,5-dihydropyrazolo[1,5-a]pyrimidin-7-yl]-2-(2,2-dimethylpropyl)piperidine-1-carboxylate (36.1 mg, 70.4 µmol) was dissolved in 1,4-dioxan (2.1 ml, 24 mmol) and treated with hydrochloric acid in 1,4-dioxan (260 µl, 4.0 M, 1.1 mmol) at RT for 16 h. The mixture was treated for 1 h at RT in a supersonic bath. The solvent was removed in vacuo to afford the product. The obtained amount was 29.7 mg (97% purity, 91% of theory).

LC-MS (Method 11B): $R_t$=1.24 min; MS (ESIneg): m/z=411 $[M-H]^-$

1H-NMR (400 MHz, DMSO-d6) delta [ppm]: 0.947 (10.09), 1.369 (16.00), 1.525 (0.29), 1.558 (0.28), 1.796 (0.19), 1.817 (0.21), 1.831 (0.17), 1.853 (0.16), 1.961 (0.05), 1.986 (0.12), 2.013 (0.14), 2.041 (0.07), 2.115 (0.45), 2.128 (0.44), 3.186 (0.13), 3.231 (0.23), 3.264 (0.12), 3.566 (7.38), 3.743 (0.13), 6.208 (0.05), 8.513 (0.23), 8.718 (0.09), 8.936 (0.07).

Example 304

3-[4-(3-methylbutyl)-1,3-thiazol-2-yl]-7-(piperidin-4-yl)pyrazolo[1,5-a]pyrimidin-5 (4H)-one hydrochloride

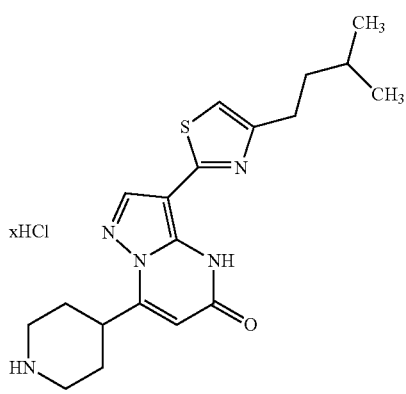 [SMILES: CC(C)CCc1csc(-c2cnn3c(C4CCNCC4)cc(=O)[nH]c23)n1]

tert-butyl 4-{3-[4-(3-methylbutyl)-1,3-thiazol-2-yl]-5-oxo-4,5-dihydropyrazolo[1,5-a]pyrimidin-7-yl}piperidine-1-carboxylate (35.0 mg, 74.2 µmol) was dissolved in 1,4-dioxan (1.5 ml) and treated with hydrochloric acid in 1,4-dioxan (370 µl, 4.0 M, 1.5 mmol) at RT for 16 h. Solvents were removed in vacuo. The residue was purified via reverse phase chromatography (Method: Reprosil C18; 10 µm; 125×30 mm/flow: 50 ml/min/solvents: A=water (0.01% formic acid), B=acetonitrile/gradient: 0.00-4.25 min=10% B, 4.50 min=20% B, 15.50 min=85% B, 16.00-18.50 min=100% B, 18.75.00-22.00 min=20% B). The solvents were removed and the residue was treated with hydrochloric acid in 1,4-dioxan (4M, 0.5 mL) and the solvent was removed in vacuo to afford the product. The obtained amount was 24.0 mg (70% purity, 51% of theory).

LC-MS (Method 11B): $R_t$=1.28 min; MS (ESIneg): m/z=370 $[M-H]^-$

1H-NMR (400 MHz, DMSO-d6) delta [ppm]: 0.931 (16.00), 0.944 (14.71), 0.948 (10.95), 1.584 (1.98), 1.599 (3.34), 1.613 (1.85), 1.886 (0.55), 1.918 (1.58), 1.950 (1.70), 1.975 (0.71), 2.205 (2.39), 2.238 (1.93), 2.349 (6.44), 2.656 (1.86), 2.674 (1.95), 2.756 (1.53), 2.774 (2.06), 2.792 (1.50), 3.063 (0.60), 3.094 (1.70), 3.123 (1.77), 3.152 (0.73), 3.393 (2.37), 3.424 (1.96), 3.621 (1.01), 6.213 (0.44), 6.259 (0.33), 7.224 (2.94), 8.526 (0.60), 8.581 (0.24), 8.828 (0.55), 8.976 (0.73).

Example 305

3-{5-[1-(4-methoxyphenyl)cyclopropyl]-1,3,4-oxadiazol-2-yl}-7-(piperidin-4-yl)pyrazolo[1,5-a]pyrimidin-5(4H)-one hydrochloride

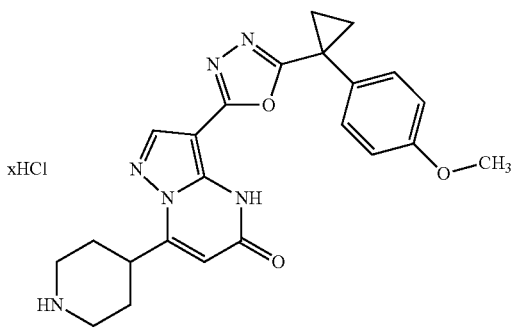 [SMILES: COc1ccc(C2(c3nnc(-c4cnn5c(C6CCNCC6)cc(=O)[nH]c45)o3)CC2)cc1]

tert-butyl 4-(3-{5-[1-(4-methoxyphenyl)cyclopropyl]-1,3,4-oxadiazol-2-yl}-5-oxo-4,5-dihydropyrazolo[1,5-a]pyrimidin-7-yl)piperidine-1-carboxylate (42.0 mg, 78.9 μmol) was dissolved in 1,4-dioxan (2.0 ml, 23 mmol) and treated with hydrochloric acid in 1,4-dioxan (300 μl, 4.0 M, 1.2 mmol) at RT for 16 h. Acetonitrile was added and the resulting participate was filtered and washed with acetonitrile. Drying in vacuo afforded the product. The obtained amount was 30.6 mg (100% purity, 83% of theory).

LC-MS (Method 11B): $R_t$=1.05 min; MS (ESIpos): m/z=433 [M+H]$^+$

1H-NMR (400 MHz, DMSO-d6) delta [ppm]: 1.399 (3.75), 1.412 (11.44), 1.418 (10.99), 1.429 (4.65), 1.681 (4.48), 1.691 (11.29), 1.698 (10.60), 1.709 (4.06), 1.876 (1.20), 1.908 (3.41), 1.934 (3.87), 1.965 (1.84), 2.165 (5.19), 2.197 (4.38), 3.035 (1.28), 3.065 (3.64), 3.093 (3.85), 3.122 (1.66), 3.364 (4.98), 3.395 (4.20), 3.534 (1.47), 3.564 (3.96), 3.594 (1.62), 6.086 (6.17), 6.905 (14.25), 6.927 (15.88), 7.345 (16.00), 7.367 (14.42), 8.323 (12.39), 9.029 (1.13), 9.144 (1.56).

Example 306

2-methyl-3-[3-(4-methylphenyl)-1,2,4-oxadiazol-5-yl]-7-(piperidin-4-yl)pyrazolo[1,5-a]pyrimidin-5(4H)-one hydrochloride

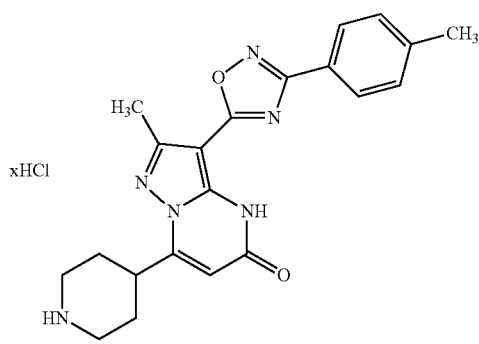 [SMILES: Cc1ccc(-c2noc(-c3c(C)nn4c(C5CCNCC5)cc(=O)[nH]c34)n2)cc1]

tert-butyl 4-{2-methyl-3-[3-(4-methylphenyl)-1,2,4-oxadiazol-5-yl]-5-oxo-4,5-dihydropyrazolo[1,5-a]pyrimidin-7-yl}piperidine-1-carboxylate (60.7 mg, 124 μmol) was dissolved in 1,4-dioxan (2.5 ml, 29 mmol) and treated with hydrochloric acid in 1,4-dioxan (460 μl, 4.0 M, 1.9 mmol) at RT for 16 h. Acetonitrile was added and the resulting participate was filtered and washed with acetonitrile. Drying in vacuo afforded the product. The obtained amount was 44.9 mg (100% purity, 85% of theory).

LC-MS (Method 7B): $R_t$=1.38 min; MS (ESIpos): m/z=391 [M+H]$^+$

1H-NMR (400 MHz, DMSO-d6) delta [ppm]: 1.855 (0.51), 1.887 (1.42), 1.918 (1.53), 1.950 (0.61), 2.195 (2.34), 2.227 (1.87), 2.406 (16.00), 2.638 (14.14), 3.085 (0.64), 3.114 (1.36), 3.132 (1.37), 3.165 (0.67), 3.389 (2.63), 3.420 (2.00), 3.566 (3.67), 3.595 (1.10), 3.625 (0.54), 6.132 (1.21), 7.388 (4.79), 7.408 (4.95), 8.074 (4.16), 8.094 (3.81), 8.794 (0.32), 8.930 (0.47).

Example 307

3-[4-(1,3-difluoro-2-methylpropan-2-yl)-1,3-thiazol-2-yl]-7-(piperidin-4-yl)pyrazolo[1,5-a]pyrimidin-5(4H)-one hydrochloride

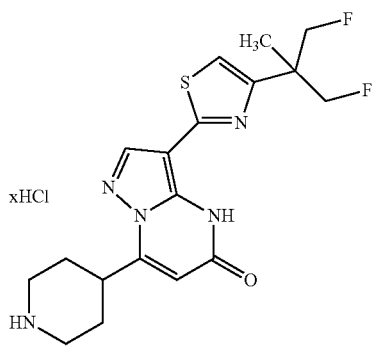 [SMILES: CC(CF)(CF)c1csc(-c2cnn3c(C4CCNCC4)cc(=O)[nH]c23)n1]

tert-butyl 4-{3-[4-(1,3-difluoro-2-methylpropan-2-yl)-1,3-thiazol-2-yl]-5-oxo-4,5-dihydropyrazolo[1,5-a]pyrimidin-7-yl}piperidine-1-carboxylate (35.5 mg, 71.9 μmol) was dissolved in 1,4-dioxan (1.4 ml) and treated with hydrochloric acid (360 μl, 4.0 M, 1.4 mmol) in 1,4-dioxan at RT for 16 h. The solvent was removed in vacuo to afford the product. The obtained amount was 33.5 mg (100% purity, 100% of theory).

LC-MS (Method 11B): $R_t$=1.05 min; MS (ESIpos): m/z=394 [M+H]$^+$

1H-NMR (400 MHz, DMSO-d6) delta [ppm]: 1.407 (16.00), 1.857 (0.86), 1.888 (2.12), 1.919 (2.21), 1.950 (0.94), 2.202 (3.20), 2.235 (2.50), 3.065 (1.03), 3.097 (2.52), 3.126 (2.50), 3.156 (1.00), 3.393 (3.68), 3.422 (3.01), 4.674 (1.59), 4.699 (4.38), 4.709 (4.60), 4.730 (1.30), 4.797 (1.58), 4.817 (4.24), 4.827 (4.49), 4.849 (1.15), 7.425 (13.81), 8.423 (1.15), 8.728 (0.74), 8.918 (1.00).

Example 308

3-(4-ethyl-1,3-thiazol-2-yl)-7-(piperidin-4-yl)pyrazolo[1,5-a]pyrimidin-5(4H)-one hydrochloride

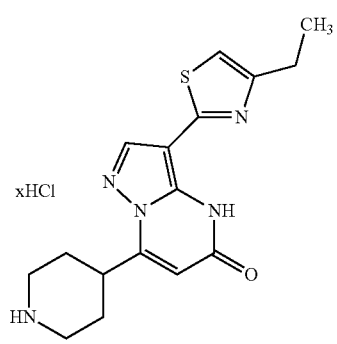 [SMILES: CCc1csc(-c2cnn3c(C4CCNCC4)cc(=O)[nH]c23)n1]

tert-butyl 4-[3-(4-ethyl-1,3-thiazol-2-yl)-5-oxo-4,5-dihydropyrazolo[1,5-a]pyrimidin-7-yl]piperidine-1-carboxylate (54.0 mg, 126 µmol) was dissolved in 1,4-dioxan (2.5 ml) and treated with hydrochloric acid in 1,4-dioxan (630 µl, 4.0 M, 2.5 mmol) at RT for 16 h. The solvent was removed in vacuo to afford the product. The obtained amount was 50.5 mg (100% purity, 100% of theory).

LC-MS (Method 11B): $R_t$=0.95 min; MS (ESIpos): m/z=330 [M+H]$^+$

1H-NMR (400 MHz, DMSO-d6) delta [ppm]: 1.261 (7.76), 1.280 (16.00), 1.299 (7.64), 1.898 (0.78), 1.925 (1.93), 1.957 (2.07), 1.986 (0.86), 2.206 (3.04), 2.239 (2.31), 2.772 (1.99), 2.791 (5.11), 2.809 (4.88), 2.828 (1.60), 3.065 (0.89), 3.094 (2.13), 3.123 (2.14), 3.150 (0.84), 3.389 (2.96), 3.422 (2.32), 3.601 (0.76), 3.629 (1.31), 3.656 (0.68), 6.250 (0.97), 7.245 (3.34), 8.590 (0.96), 8.902 (0.68), 9.029 (0.86).

Example 309

3-[4-(4-methylphenyl)-1,3-thiazol-2-yl]-7-(piperidin-4-yl)pyrazolo[1,5-a]pyrimidin-5(4H)-one hydrochloride

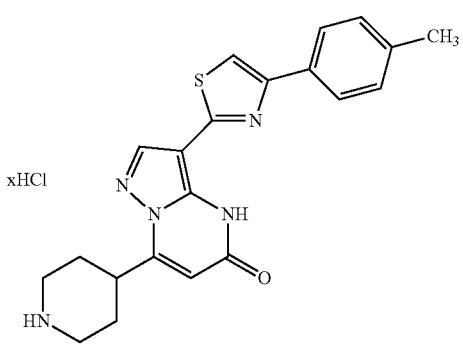 [SMILES: Cc1ccc(-c2csc(-c3cnn4c(C5CCNCC5)cc(=O)[nH]c34)n2)cc1]

tert-butyl 4-{3-[4-(4-methylphenyl)-1,3-thiazol-2-yl]-5-oxo-4,5-dihydropyrazolo[1,5-a]pyrimidin-7-yl}piperidine-1-carboxylate (57.6 mg, 117 µmol) was dissolved in 1,4-dioxan (2.3 ml) and treated with hydrochloric acid in 1,4-dioxan (590 µl, 4.0 M, 2.3 mmol) at RT for 16 h. The solvent was removed in vacuo to afford the product. The obtained amount was 57.2 mg (95% purity, 100% of theory).

LC-MS (Method 1B): $R_t$=0.76 min; MS (ESIpos): m/z=392 [M+H]$^+$

1H-NMR (400 MHz, DMSO-d6) delta [ppm]: 1.894 (0.57), 1.925 (1.52), 1.956 (1.60), 1.985 (0.62), 2.224 (2.40), 2.258 (1.94), 2.354 (16.00), 3.078 (0.69), 3.109 (1.67), 3.135 (1.73), 3.165 (0.70), 3.404 (2.38), 3.433 (1.87), 3.641 (0.80), 6.217 (0.36), 7.274 (4.86), 7.295 (5.05), 7.942 (8.80), 7.956 (5.19), 7.976 (4.67), 8.529 (1.05), 8.785 (0.36), 8.954 (0.44).

Example 310

7-(piperidin-4-yl)-3-[4-(propan-2-yl)-1,3-thiazol-2-yl]pyrazolo[1,5-a]pyrimidin-5 (4H)-one hydrochloride

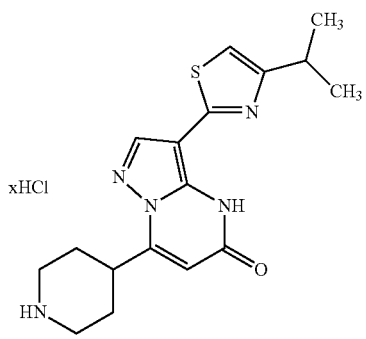 [SMILES: CC(C)c1csc(-c2cnn3c(C4CCNCC4)cc(=O)[nH]c23)n1]

tert-butyl 4-{5-oxo-3-[4-(propan-2-yl)-1,3-thiazol-2-yl]-4,5-dihydropyrazolo[1,5-a]pyrimidin-7-yl}piperidine-1-carboxylate (49.5 mg, 112 µmol) was dissolved in 1,4-dioxan (2.2 ml) and treated with hydrochloric acid in 1,4-dioxan (560 µl, 4.0 M, 2.2 mmol) at RT for 16 h. The solvent was removed in vacuo to afford the product. The obtained amount was 46.4 mg (100% purity, 100% of theory).

LC-MS (Method 1B): $R_t$=0.67 min; MS (ESIpos): m/z=343 [M+H]$^+$

1H-NMR (400 MHz, DMSO-d6) delta [ppm]: 1.299 (16.00), 1.316 (15.66), 1.897 (0.39), 1.924 (0.98), 1.954 (1.06), 1.985 (0.44), 2.203 (1.54), 2.236 (1.18), 3.069 (0.48), 3.091 (1.34), 3.105 (1.36), 3.122 (2.00), 3.139 (0.98), 3.155 (0.63), 3.387 (1.54), 3.419 (1.18), 3.595 (0.41), 3.625 (0.65), 3.654 (0.33), 6.230 (0.43), 7.220 (1.73), 8.573 (0.37), 8.906 (0.34), 9.039 (0.44).

Example 311

3-(4-cyclopropyl-1,3-thiazol-2-yl)-7-(piperidin-4-yl)pyrazolo[1,5-a]pyrimidin-5(4H)-one hydrochloride

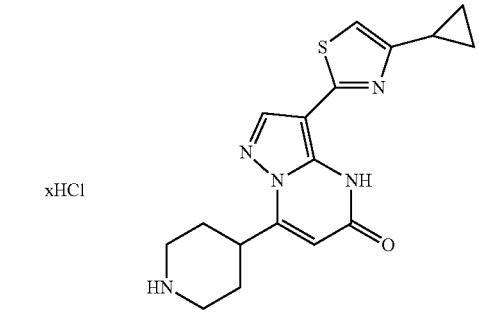 [SMILES: O=c1cc(C2CCNCC2)n2ncc(-c3nc(C4CC4)cs3)c2[nH]1]

tert-butyl 4-[3-(4-cyclopropyl-1,3-thiazol-2-yl)-5-oxo-4,5-dihydropyrazolo[1,5-a]pyrimidin-7-yl]piperidine-1-carboxylate (51.0 mg, 116 µmol) was dissolved in 1,4-dioxan (2.3 ml) and treated with hydrochloric acid in 1,4-dioxan (580 µl, 4.0 M, 2.3 mmol) at RT for 16 h. The solvent was removed in vacuo to afford the product. The obtained amount was 47.8 mg (100% purity, 100% of theory).

LC-MS (Method 1B): $R_t$=0.62 min; MS (ESIpos): m/z=342 [M+H]$^+$

1H-NMR (400 MHz, DMSO-d6) delta [ppm]: 0.916 (14.53), 0.936 (8.94), 1.872 (1.11), 1.906 (2.95), 1.930 (3.19), 1.963 (1.27), 2.100 (1.05), 2.119 (2.00), 2.133 (3.37), 2.147 (1.90), 2.166 (1.10), 2.198 (4.41), 2.232 (3.42), 3.062 (1.24), 3.092 (3.06), 3.121 (3.17), 3.151 (1.22), 3.388 (4.37), 3.420 (3.38), 3.579 (1.14), 3.606 (1.74), 3.636 (0.89), 6.171 (0.97), 7.164 (16.00), 8.431 (2.87), 8.786 (1.02), 8.962 (1.22).

Example 312

3-[4-(2,4-dimethylphenyl)-1,3-thiazol-2-yl]-7-(piperidin-4-yl)pyrazolo[1,5-a]pyrimidin-5(4H)-one hydrochloride

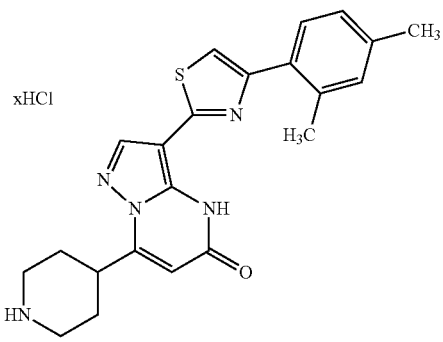 [SMILES: Cc1ccc(-c2csc(-c3cnn4c(C5CCNCC5)cc(=O)[nH]c34)n2)c(C)c1]

tert-butyl 4-{3-[4-(2,4-dimethylphenyl)-1,3-thiazol-2-yl]-5-oxo-4,5-dihydropyrazolo[1,5-a]pyrimidin-7-yl}piperidine-1-carboxylate (47.7 mg, 94.3 µmol) was dissolved in 1,4-dioxan (1.9 ml) and treated with hydrochloric acid in 1,4-dioxan (470 µl, 4.0 M, 1.9 mmol) at RT for 16 h. The solvent was removed in vacuo to afford the product. The obtained amount was 46.0 mg (100% purity, 102% of theory).

LC-MS (Method 7B): $R_t$=1.52 min; MS (ESIpos): m/z=406 [M+H]$^+$

1H-NMR (400 MHz, DMSO-d6) delta [ppm]: 1.899 (0.43), 1.930 (1.20), 1.956 (1.32), 1.987 (0.58), 2.217 (1.86), 2.250 (1.53), 2.325 (13.28), 2.437 (16.00), 3.072 (0.46), 3.101 (1.30), 3.130 (1.35), 3.160 (0.55), 3.397 (1.85), 3.427 (1.49), 3.602 (0.40), 3.633 (0.68), 3.664 (0.38), 6.208 (0.34), 7.099 (1.59), 7.119 (1.78), 7.141 (3.23), 7.604 (2.67), 7.623 (8.66), 8.516 (1.61), 8.838 (0.41), 8.862 (0.44), 9.006 (0.61), 9.029 (0.50).

Example 313

3-(3-tert-butyl-1,2,4-oxadiazol-5-yl)-7-(piperidin-4-yl)pyrazolo[1,5-a]pyrimidin-5 (4H)-one

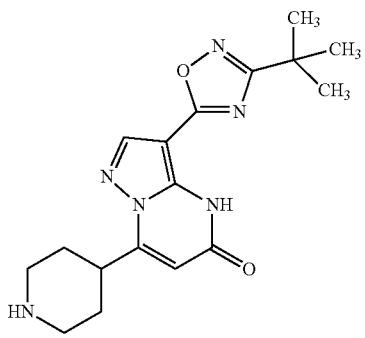 [SMILES: CC(C)(C)c1noc(-c2cnn3c(C4CCNCC4)cc(=O)[nH]c23)n1]

3-(3-tert-butyl-1,2,4-oxadiazol-5-yl)-7-(piperidin-4-yl)pyrazolo[1,5-a]pyrimidin-5 (4H)-one dihydrochloride (7.70 g, 18.5 mmol) was dissolved in water (45 ml). Aqueous sodium hydroxide solution (30 ml, 1.0 M, 30 mmol) was added until a pH of about 9 was reached. The resulting precipitate was filtered, washed with water and dried in vacuo. The obtained amount was 5.98 g (100% purity, 94% of theory).

LC-MS (Method 10B): $R_t$=1.10 min; MS (ESIpos): m/z=343 [M+H]$^+$ $^1$H-NMR (400 MHz, DMSO-d6) delta [ppm]: −0.150 (0.13), −0.009 (1.27), 0.007 (1.04), 0.145 (0.11), 1.147 (0.19), 1.172 (0.08), 1.333 (16.00), 1.694 (0.12), 1.727 (0.32), 1.763 (0.36), 1.791 (0.15), 2.124 (0.50), 2.156 (0.43), 2.327 (0.18), 2.366 (0.16), 2.669 (0.16), 2.709 (0.18), 2.969 (0.25), 3.002 (0.48), 3.034 (0.25), 3.376 (0.78), 3.567 (0.06), 5.718 (0.51), 8.160 (1.11), 8.509 (0.06), 8.588 (0.07).

Example 314

Ethyl 2-methyl-5-oxo-7-(piperidin-4-yl)-4,5-dihydropyrazolo[1,5-a]pyrimidine-3-carboxylate

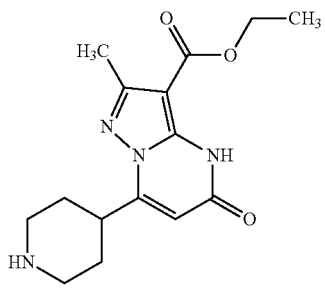 [SMILES: CCOC(=O)c1c(C)nn2c(C3CCNCC3)cc(=O)[nH]c12]

ethyl 2-methyl-5-oxo-7-(piperidin-4-yl)-4,5-dihydropyrazolo[1,5-a]pyrimidine-3-carboxylate hydrochloride (100 mg, 293 µmol) was dissolved in water (1 ml). Aqueous sodium hydroxide solution (500 µl, 1.0 M, 500 µmol) was added until a pH of about 9 was reached. The resulting precipitate was filtered, washed with water and dried in vacuo. The obtained amount was 62.0 mg (100% purity, 69% of theory).

LC-MS (Method 10B): $R_t$=0.95 min; MS (ESIpos): m/z=305 [M+H]$^+$ $^1$H-NMR (500 MHz, DMSO-d6) delta [ppm]: −0.120 (1.12), −0.007 (10.41), 0.006 (9.29), 0.116 (1.12), 0.854 (0.22), 1.147 (2.01), 1.235 (1.34), 1.259 (1.79), 1.273 (3.80), 1.287 (1.68), 1.455 (0.22), 1.480 (0.45), 1.499 (0.45), 1.505 (0.45), 1.876 (0.56), 1.901 (0.56), 2.357 (1.34), 2.361 (1.79), 2.365 (1.34), 2.401 (5.59), 2.601 (0.45), 2.631 (1.57), 2.635 (1.90), 2.638 (1.45), 3.030 (0.56), 3.053 (0.56), 3.223 (0.45), 3.286 (16.00), 3.567 (0.90), 4.233 (0.45), 4.247 (1.12), 4.261 (1.12), 4.275 (0.34), 5.824 (0.34).

Example 315

Propan-2-yl 5-oxo-7-(piperidin-4-yl)-4,5-dihydropyrazolo[1,5-a]pyrimidine-3-carboxylate hydrochloride

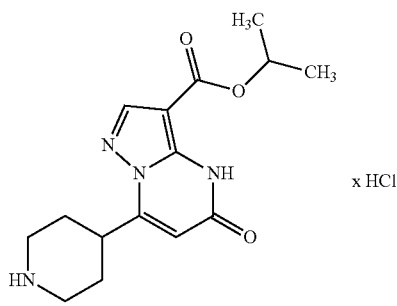 [SMILES: CC(C)OC(=O)c1cnn2c(C3CCNCC3)cc(=O)[nH]c12]

propan-2-yl 7-[1-(tert-butoxycarbonyl)piperidin-4-yl]-5-oxo-4,5-dihydropyrazolo[1,5-a]pyrimidine-3-carboxylate (127 mg, 313 μmol) was dissolved in 1,4-dioxan (2.0 ml, 23 mmol) and treated with hydrochloric acid in 1,4-dioxan (1.2 ml, 4.0 M, 4.7 mmol) at RT for 3 h. Acetonitrile was added and the resulting participate was filtered and washed with acetonitrile. Drying in vacuo afforded the product.

The obtained amount was 51.9 mg (100% purity, 49% of theory).

LC-MS (Method 10B): $R_t$=1.02 min; MS (ESIpos): m/z=305 [M+H]$^+$ $^1$H-NMR (500 MHz, DMSO-d6) delta [ppm]: −0.122 (0.08), −0.009 (0.81), 0.114 (0.08), 1.146 (0.09), 1.177 (0.08), 1.189 (0.08), 1.233 (0.08), 1.305 (16.00), 1.317 (15.98), 1.430 (0.07), 1.442 (0.08), 1.825 (0.32), 1.832 (0.38), 1.851 (1.00), 1.857 (1.02), 1.877 (1.09), 1.883 (1.07), 1.902 (0.47), 1.909 (0.41), 2.072 (0.43), 2.146 (1.51), 2.172 (1.26), 2.361 (0.07), 2.635 (0.08), 3.048 (0.59), 3.072 (1.14), 3.096 (0.64), 3.365 (1.60), 3.390 (1.35), 3.486 (0.39), 3.510 (0.73), 3.534 (0.37), 3.566 (4.43), 5.085 (0.07), 5.097 (0.44), 5.110 (1.18), 5.122 (1.61), 5.135 (1.17), 5.147 (0.44), 5.160 (0.07), 6.006 (0.99), 8.168 (3.13), 8.814 (0.21), 8.980 (0.26), 11.495 (0.24).

Example 316

N-methyl-N-[(5-methyl-1,2-oxazol-3-yl)methyl]-5-oxo-7-(piperidin-4-yl)-4,5-dihydropyrazolo[1,5-a]pyrimidine-3-carboxamide hydrochloride

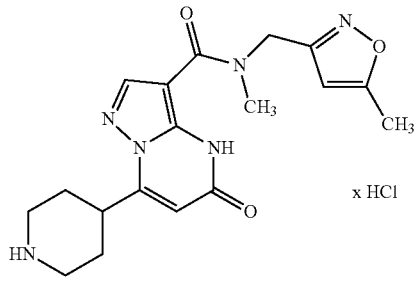 [SMILES: Cc1cc(CN(C)C(=O)c2cnn3c(C4CCNCC4)cc(=O)[nH]c23)no1]

tert-butyl 4-(3-{methyl[(5-methyl-1,2-oxazol-3-yl)methyl]carbamoyl}-5-oxo-4,5-dihydropyrazolo[1,5-a]pyrimidin-7-yl)piperidine-1-carboxylate (74.0 mg, 157 μmol) was dissolved in 1,4-dioxan (2.0 ml, 23 mmol) and treated with hydrochloric acid in 1,4-(590 μl, 4.0 M, 2.4 mmol) at RT for 16 h. Solvents were removed, acetonitrile was added and the resulting participate was filtered and washed with acetonitrile. Drying in vacuo afforded the product. The obtained amount was 49.2 mg (100% purity, 77% of theory).

LC-MS (Method 10B): $R_t$=0.89 min; MS (ESIpos): m/z=371 [M+H]$^+$ $^1$H-NMR (400 MHz, DMSO-d6) delta [ppm]: 1.860 (0.67), 1.891 (0.73), 1.921 (0.36), 2.069 (0.31), 2.077 (0.28), 2.161 (1.03), 2.193 (0.86), 2.378 (3.76), 2.384 (3.54), 2.706 (0.34), 3.121 (1.46), 3.314 (16.00), 3.321 (14.49), 3.367 (1.42), 3.399 (1.11), 3.517 (0.56), 3.563 (2.43), 3.570 (2.23), 4.648 (1.25), 5.978 (0.56), 6.235 (0.98), 7.960 (0.06), 8.167 (0.40), 8.759 (0.26), 8.949 (0.29), 11.380 (0.31).

Example 317

N-ethyl-2-methyl-5-oxo-7-(piperidin-4-yl)-4,5-dihydropyrazolo[1,5-a]pyrimidine-3-carboxamide hydrochloride

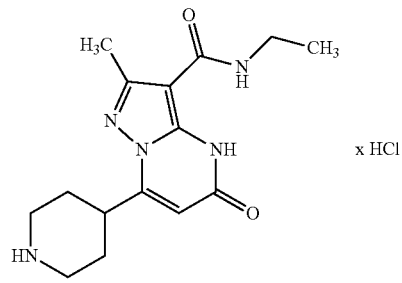 [SMILES: CCNC(=O)c1c(C)nn2c(C3CCNCC3)cc(=O)[nH]c12]

tert-butyl 4-[3-(ethylcarbamoyl)-2-methyl-5-oxo-4,5-dihydropyrazolo[1,5-a]pyrimidin-7-yl]piperidine-1-carboxylate (95.8 mg, 237 μmol) was dissolved in 1,4-dioxan (2.0 ml, 23 mmol) and treated with hydrochloric acid in 1,4-dioxan (890 μl, 4.0 M, 3.6 mmol) at RT for 16 h. Solvents were removed, acetonitrile was added and the resulting participate was filtered and washed with acetonitrile. Drying in vacuo afforded the product. The obtained amount was 76.2 mg (100% purity, 94% of theory).

LC-MS (Method 10B): $R_t$=0.69 min; MS (ESIpos): m/z=304 [M+H]$^+$ $^1$H-NMR (400 MHz, DMSO-d6) delta [ppm]: −0.152 (0.12), −0.010 (1.16), 0.005 (0.96), 0.143 (0.11), 0.974 (0.09), 1.116 (7.30), 1.134 (16.00), 1.152 (7.56), 1.754 (0.15), 1.844 (0.58), 1.874 (1.65), 1.905 (1.79), 1.935 (0.74), 2.072 (0.53), 2.166 (2.76), 2.199 (2.17), 2.327 (0.17), 2.365 (0.22), 2.411 (0.72), 2.668 (0.16), 2.709 (0.20), 3.062 (0.73), 3.090 (1.93), 3.119 (1.98), 3.148 (0.82), 3.264 (0.92), 3.281 (2.74), 3.298 (3.40), 3.313 (2.63), 3.331 (0.94), 3.369 (2.88), 3.400 (2.38), 3.566 (15.00), 3.604 (4.27), 4.054 (0.11), 5.904 (0.13), 6.146 (0.28), 7.795 (0.35), 8.966 (0.74).

Example 318

N-methyl-5-oxo-7-(piperidin-4-yl)-N-(pyridin-3-ylmethyl)-4,5-dihydropyrazolo[1,5-a]pyrimidine-3-carboxamide hydrochloride

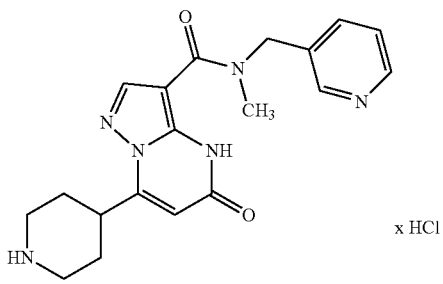 [SMILES: CN(Cc1cccnc1)C(=O)c1cnn2c(C3CCNCC3)cc(=O)[nH]c12]

x HCl tert-butyl 4-{3-[methyl(pyridin-3-ylmethyl)carbamoyl]-5-oxo-4,5-dihydropyrazolo[1,5-a]pyrimidin-7-yl}piperidine-1-carboxylate (45.8 mg, 98.2 μmol) was dissolved in 1,4-dioxan (2.0 ml, 23 mmol) and treated with hydrochloric acid in 1,4-dioxan (370 μl, 4.0 M, 1.5 mmol) at RT for 16 h. Solvents were removed, acetonitrile was added and the resulting participate was filtered and washed with acetonitrile. Drying in vacuo afforded the product. The obtained amount was 39.7 mg (100% purity, 92% of theory).

LC-MS (Method 10B): $R_t$=0.82 min; MS (ESIpos): m/z=367 [M+H]$^+$ $^1$H-NMR (400 MHz, DMSO-d6) delta [ppm]: −0.152 (0.35), 0.005 (2.72), 0.143 (0.35), 1.593 (0.20), 1.857 (1.88), 1.890 (5.24), 1.920 (5.74), 1.946 (2.26), 2.072 (7.82), 2.153 (8.29), 2.186 (6.42), 2.326 (0.51), 2.366 (0.60), 2.411 (1.23), 2.670 (0.45), 2.709 (0.68), 3.027 (2.64), 3.058 (6.25), 3.086 (6.69), 3.117 (3.84), 3.177 (6.85), 3.361 (8.73), 3.391 (7.33), 3.492 (3.32), 3.522 (5.11), 3.729 (2.02), 4.346 (0.64), 4.462 (0.47), 4.510 (0.43), 4.809 (16.00), 5.985 (9.81), 7.891 (3.42), 8.205 (2.22), 8.361 (1.85), 8.776 (6.18), 8.818 (4.58), 8.972 (1.52), 9.117 (1.97), 11.449 (0.44).

Example 319

N,N,2-trimethyl-5-oxo-7-(piperidin-4-yl)-4,5-dihydropyrazolo[1,5-a]pyrimidine-3-carboxamide hydrochloride

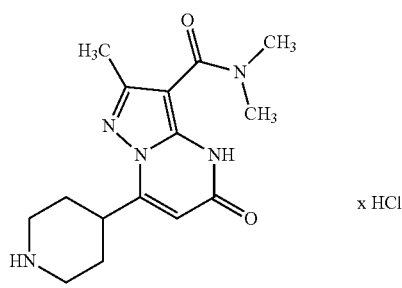 [SMILES: Cc1nn2c(C3CCNCC3)cc(=O)[nH]c2c1C(=O)N(C)C]

x HCl tert-butyl 4-[3-(dimethylcarbamoyl)-2-methyl-5-oxo-4,5-dihydropyrazolo[1,5-a]pyrimidin-7-yl]piperidine-1-carboxylate (100 mg, 249 μmol) was dissolved in 1,4-dioxan (2.0 ml, 23 mmol) and treated with hydrochloric acid in 1,4-dioxan (930 μl, 4.0 M, 3.7 mmol) at RT for 16 h. Solvents were removed, acetonitrile was added and the resulting participate was filtered and washed with acetonitrile. Drying in vacuo afforded the product. The obtained amount was 63.2 mg (100% purity, 75% of theory).

LC-MS (Method 10B): $R_t$=0.69 min; MS (ESIpos): m/z=304 [M+H]$^+$ $^1$H-NMR (400 MHz, DMSO-d6) delta [ppm]: 1.144 (0.04), 1.758 (0.14), 1.840 (0.28), 1.871 (0.73), 1.899 (0.79), 1.928 (0.31), 2.066 (0.08), 2.142 (1.15), 2.175 (0.93), 2.228 (7.88), 2.326 (0.04), 2.365 (0.05), 2.386 (0.05), 2.449 (0.18), 2.709 (0.04), 2.740 (0.08), 2.914 (16.00), 3.033 (0.31), 3.063 (0.78), 3.090 (0.80), 3.121 (0.33), 3.158 (0.08), 3.348 (1.08), 3.379 (0.86), 3.480 (0.33), 3.511 (0.61), 3.540 (0.38), 5.128 (0.19), 5.665 (0.05), 5.797 (1.50), 9.079 (0.40).

Example 320

3-{[(3R)-3-hydroxypyrrolidin-1-yl]carbonyl}-7-(piperidin-4-yl)pyrazolo[1,5-a]pyrimidin-5(4H)-one hydrochloride

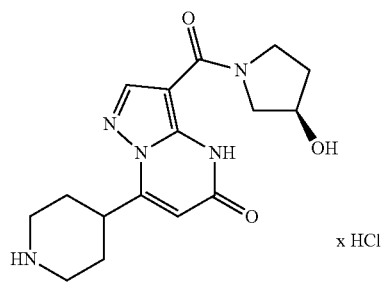 [SMILES: O=C(c1cnn2c(C3CCNCC3)cc(=O)[nH]c12)N1CC[C@@H](O)C1]

x HCl tert-butyl 4-(3-{[(3R)-3-hydroxypyrrolidin-1-yl]carbonyl}-5-oxo-4,5-dihydropyrazolo[1,5-a]pyrimidin-7-yl)piperidine-1-carboxylate (85.1 mg, 197 μmol) was dissolved in 1,4-dioxan (2.0 ml, 23 mmol) and treated with hydrochloric acid in 1,4-dioxan (740 μl, 4.0 M, 3.0 mmol) at RT for 16 h. Solvents were removed, acetonitrile was added and the resulting participate was filtered and washed with acetonitrile. Drying in vacuo afforded the product. The obtained amount was 63.3 mg (100% purity, 87% of theory).

LC-MS (Method 10B): R$_t$=0.67 min; MS (ESIpos): m/z=332 [M+H]$^+$ $^1$H-NMR (400 MHz, DMSO-d6) delta [ppm]: 1.146 (0.89), 1.752 (0.87), 1.833 (5.90), 1.865 (10.78), 1.896 (13.04), 1.927 (7.89), 2.009 (2.57), 2.072 (2.80), 2.165 (14.75), 2.199 (11.71), 2.327 (0.80), 2.365 (0.89), 2.669 (0.75), 2.710 (0.93), 2.916 (0.69), 3.045 (3.99), 3.069 (9.73), 3.098 (10.00), 3.125 (4.24), 3.160 (1.03), 3.371 (16.00), 3.403 (12.56), 3.497 (8.75), 3.528 (12.20), 3.555 (10.07), 3.566 (15.86), 3.813 (6.02), 4.310 (4.13), 4.395 (3.65), 4.938 (0.46), 5.021 (2.19), 5.066 (2.23), 5.997 (13.86), 8.214 (5.93), 8.274 (6.09), 8.782 (2.60), 9.000 (3.21), 10.908 (3.62).

Example 321

3-{[(3R)-3-methylpyrrolidin-1-yl]carbonyl}-7-(piperidin-4-yl)pyrazolo[1,5-a]pyrimidin-5(4H)-one hydrochloride

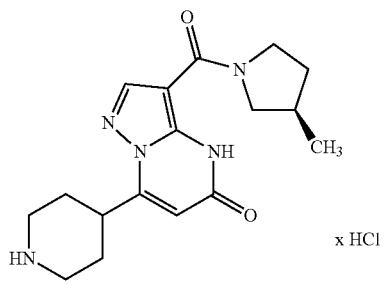 [SMILES: C[C@@H]1CCN(C(=O)c2cnn3c(C4CCNCC4)cc(=O)[nH]c23)C1]

tert-butyl 4-(3-{[(3R)-3-methylpyrrolidin-1-yl]carbonyl}-5-oxo-4,5-dihydropyrazolo[1,5-a]pyrimidin-7-yl)piperidine-1-carboxylate (112 mg, 260 µmol) was dissolved in 1,4-dioxan (2.0 ml, 23 mmol) and treated with hydrochloric acid in 1,4-dioxan (970 µl, 4.0 M, 3.9 mmol) at RT for 16 h. Solvents were removed, acetonitrile was added and the resulting participate was filtered and washed with acetonitrile. Drying in vacuo afforded the product. The obtained amount was 69.6 mg (92% purity, 67% of theory).

LC-MS (Method 10B): R$_t$=0.97 min; MS (ESIpos): m/z=330 [M+H]$^+$ $^1$H-NMR (400 MHz, DMSO-d6) delta [ppm]: 1.055 (5.51), 1.066 (5.75), 1.149 (0.42), 1.478 (0.56), 1.502 (0.56), 1.609 (0.53), 1.820 (0.79), 1.851 (2.10), 1.877 (2.32), 1.909 (0.97), 2.006 (0.62), 2.108 (0.61), 2.167 (3.27), 2.200 (2.81), 2.328 (0.77), 2.671 (0.42), 2.690 (0.42), 2.711 (0.38), 3.005 (0.81), 3.080 (2.28), 3.107 (2.25), 3.260 (1.21), 3.377 (3.71), 3.409 (3.27), 3.497 (1.05), 3.528 (1.67), 3.568 (16.00), 3.696 (1.24), 3.712 (1.09), 3.806 (0.81), 3.843 (0.76), 3.862 (0.86), 6.003 (3.20), 8.143 (0.59), 8.228 (4.86), 8.648 (0.75), 8.881 (0.92), 10.948 (1.02).

Example 322

7-(piperidin-4-yl)-3-(pyrrolidin-1-ylcarbonyl)pyrazolo[1,5-a]pyrimidin-5(4H)-one hydrochloride

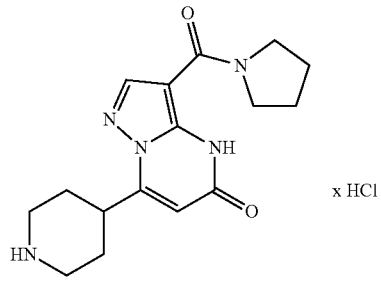 [SMILES: O=C(c1cnn2c(C3CCNCC3)cc(=O)[nH]c12)N1CCCC1]

tert-butyl 4-[5-oxo-3-(pyrrolidin-1-ylcarbonyl)-4,5-dihydropyrazolo[1,5-a]pyrimidin-7-yl]piperidine-1-carboxylate (28.0 mg, 67.4 µmol) was dissolved in 1,4-dioxan (1.0 ml, 12 mmol) and treated with hydrochloric acid in 1,4-dioxan (250 µl, 4.0 M, 1.0 mmol) at RT for 16 h. Solvents were removed, acetonitrile was added and the resulting participate was filtered and washed with acetonitrile. Drying in vacuo afforded the product. The obtained amount was 24.9 mg (95% purity, 100% of theory).

LC-MS (Method 10B): R$_t$=0.86 min; MS (ESIpos): m/z=316 [M+H]$^+$ $^1$H-NMR (400 MHz, DMSO-d6) delta [ppm]: 1.235 (0.93), 1.853 (11.26), 1.877 (7.64), 1.911 (3.68), 1.967 (6.37), 2.166 (7.84), 2.199 (6.39), 3.074 (5.34), 3.102 (5.38), 3.377 (8.68), 3.406 (7.03), 3.480 (9.00), 3.524 (4.87), 3.567 (11.52), 3.701 (8.04), 6.002 (7.69), 8.233 (16.00), 8.659 (1.94), 8.888 (2.31), 10.942 (4.92).

Example 323

2-methyl-5-oxo-7-(piperidin-4-yl)-4,5-dihydropyrazolo[1,5-a]pyrimidine-3-carboxylic acid hydrochloride

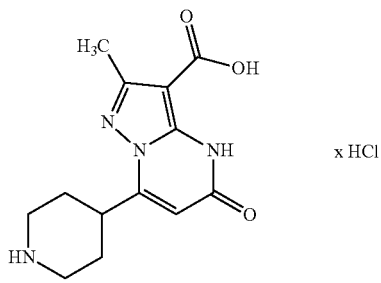 [SMILES: Cc1nn2c(C3CCNCC3)cc(=O)[nH]c2c1C(=O)O]

7-[1-(tert-butoxycarbonyl)piperidin-4-yl]-2-methyl-5-oxo-4,5-dihydropyrazolo[1,5-a]pyrimidine-3-carboxylic acid (100 mg, 267 µmol) was dissolved in 1,4-dioxan (2.0 ml, 23 mmol) and treated with hydrochloric acid in 1,4-dioxan (1.0 ml, 4.0 M, 4.0 mmol) at RT for 16 h. Solvents were removed, acetonitrile was added and the resulting participate was filtered and washed with acetonitrile. Drying in vacuo afforded the product. The obtained amount was 83.2 mg (100% purity, 100% of theory).

LC-MS (Method 10B): R$_t$=0.31 min; MS (ESIpos): m/z=277 [M+H]$^+$ $^1$H-NMR (400 MHz, DMSO-d6) delta [ppm]: −0.150 (0.26), 0.145 (0.25), 1.109 (0.46), 1.147 (0.34), 1.233 (0.63), 1.282 (0.18), 1.355 (0.26), 1.595 (1.06), 1.783 (0.59), 1.813 (1.59), 1.840 (1.81), 1.870 (0.76), 2.145 (2.43), 2.178 (2.05), 2.326 (0.26), 2.366 (0.56), 2.413 (16.00), 2.669 (0.33), 2.709 (0.60), 3.047 (0.64), 3.079 (1.73), 3.108 (1.83), 3.136 (0.78), 3.388 (2.73), 3.462 (0.93), 3.472 (1.17), 3.500 (1.60), 3.529 (0.72), 3.567 (15.15), 3.666 (0.35), 3.679 (0.47), 3.699 (0.43), 3.711 (0.37), 5.917 (2.10), 8.623 (0.64), 8.820 (0.77), 10.836 (0.96), 12.793 (0.30).

Example 324

3-[(3,3-dimethylpyrrolidin-1-yl)methyl]-7-(piperidin-4-yl)pyrazolo[1,5-a]pyrimidin-5(4H)-one hydrochloride

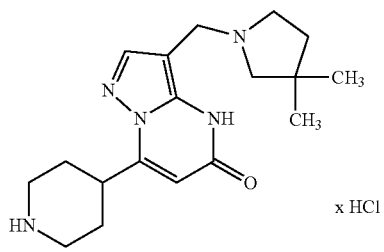 [SMILES: CC1(C)CCN(Cc2cnn3c(C4CCNCC4)cc(=O)[nH]c23)C1]

tert-butyl 4-{3-[(3,3-dimethylpyrrolidin-1-yl)methyl]-5-oxo-4,5-dihydropyrazolo[1,5-a]pyrimidin-7-yl}piperidine-1-carboxylate (66.6 mg, 155 µmol) was dissolved in 1,4-dioxan (2.0 ml, 23 mmol) and treated with hydrochloric acid in 1,4-dioxan (580 µl, 4.0 M, 2.3 mmol) at RT for 16 h. Solvents were removed, acetonitrile was added and the resulting participate was filtered and washed with acetonitrile. Drying in vacuo afforded the product. The obtained amount was 30.3 mg (100% purity, 53% of theory).

LC-MS (Method 10B): R$_t$=0.62 min; MS (ESIneg): m/z=328 [M-H]$^-$ $^1$H-NMR (400 MHz, DMSO-d6) delta [ppm]: 1.272 (0.64), 1.303 (16.00), 1.335 (0.56), 1.525 (0.35), 1.566 (15.21), 1.798 (0.97), 1.818 (0.93), 1.845 (0.60), 1.930 (2.73), 1.954 (5.08), 2.141 (2.48), 2.175 (1.92), 3.020 (0.61), 3.049 (1.67), 3.079 (1.75), 3.108 (0.71), 3.248 (2.08), 3.353 (2.29), 3.383 (1.92), 3.479 (0.71), 3.509 (1.37), 3.539 (0.71), 3.565 (12.15), 4.056 (0.61), 4.086 (0.98), 4.113 (0.83), 4.312 (1.76), 4.344 (1.41), 4.989 (0.39), 5.856 (2.51), 8.112 (3.43), 9.149 (0.68), 10.470 (0.41).

Example 325

3-{[(2R)-2-methylpyrrolidin-1-yl]carbonyl}-7-(piperidin-4-yl)pyrazolo[1,5-a]pyrimidin-5(4H)-one hydrochloride

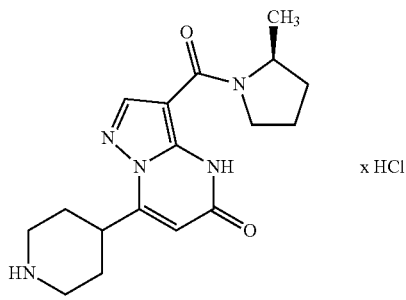 [SMILES: C[C@H]1CCCN1C(=O)c1cnn2c(C3CCNCC3)cc(=O)[nH]c12]

tert-butyl 4-(3-{[(2R)-2-methylpyrrolidin-1-yl]carbonyl}-5-oxo-4,5-dihydropyrazolo[1,5-a]pyrimidin-7-yl)piperidine-1-carboxylate (44.0 mg, 102 µmol) was dissolved in 1,4-dioxan (2.0 ml, 23 mmol) and treated with hydrochloric acid in 1,4-dioxan (380 µl, 4.0 M, 1.5 mmol) at RT for 16 h. Solvents were removed, acetonitrile was added and the resulting participate was filtered and washed with acetonitrile. Drying in vacuo afforded the product. The obtained amount was 31.3 mg (100% purity, 84% of theory).

LC-MS (Method 10B): R$_t$=0.93 min; MS (ESIpos): m/z=330 [M+H]$^+$ $^1$H-NMR (400 MHz, DMSO-d6) delta [ppm]: −0.011 (2.13), 1.186 (8.99), 1.200 (8.74), 1.577 (1.26), 1.881 (5.01), 1.910 (5.33), 1.941 (2.39), 2.012 (2.51), 2.072 (1.61), 2.155 (5.53), 2.190 (4.44), 2.709 (0.47), 3.029 (1.82), 3.057 (3.89), 3.087 (4.09), 3.117 (1.73), 3.361 (5.35), 3.393 (4.57), 3.492 (1.93), 3.522 (3.61), 3.551 (1.93), 3.565 (6.32), 3.636 (1.32), 3.802 (1.26), 4.224 (1.28), 4.783 (1.46), 5.983 (11.52), 8.153 (0.97), 8.212 (16.00), 8.477 (0.44), 8.964 (1.06), 9.128 (1.40).

Example 326

3-[(3,3-difluoroazetidin-1-yl)carbonyl]-7-(piperidin-4-yl)pyrazolo[1,5-a]pyrimidin-5 (4H)-one hydrochloride

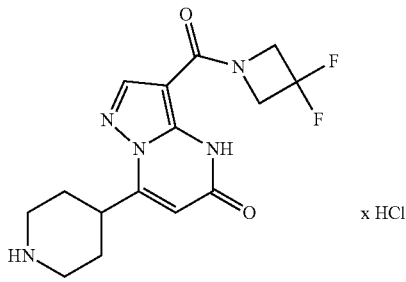 [SMILES: O=C(c1cnn2c(C3CCNCC3)cc(=O)[nH]c12)N1CC(F)(F)C1]

tert-butyl 4-{3-[(3,3-difluoroazetidin-1-yl)carbonyl]-5-oxo-4,5-dihydropyrazolo[1,5-a]pyrimidin-7-yl}piperidine-1-carboxylate (63.8 mg, 146 µmol) was dissolved in 1,4-dioxan (2.0 ml, 23 mmol) and treated with hydrochloric acid in 1,4-dioxan (550 µl, 4.0 M, 2.2 mmol) at RT for 16 h.

Solvents were removed, acetonitrile was added and the resulting participate was filtered and washed with acetonitrile. Drying in vacuo afforded the product. The obtained amount was 52.7 mg (100% purity, 97% of theory).

LC-MS (Method 10B): $R_t$=0.79 min; MS (ESIpos): m/z=338 [M+H]$^+$ $^1$H-NMR (400 MHz, DMSO-d6) delta [ppm]: −0.150 (1.84), −0.038 (0.68), −0.009 (16.00), 0.007 (13.28), 0.145 (1.84), 1.146 (2.33), 1.234 (0.39), 1.414 (0.39), 1.595 (0.29), 1.818 (1.84), 1.853 (2.04), 2.072 (1.26), 2.163 (2.91), 2.195 (2.52), 2.322 (1.26), 2.327 (1.75), 2.331 (1.26), 2.365 (2.62), 2.523 (3.98), 2.579 (0.58), 2.664 (1.36), 2.669 (1.84), 2.674 (1.45), 2.689 (0.48), 2.709 (2.72), 3.069 (1.36), 3.098 (2.52), 3.131 (1.55), 3.275 (2.33), 3.352 (1.16), 3.386 (3.68), 3.416 (2.91), 3.508 (1.16), 3.567 (12.51), 4.705 (1.07), 6.031 (1.55), 8.132 (1.75), 8.438 (0.58), 8.688 (0.58), 11.011 (0.48).

Example 327

7-(piperidin-4-yl)-3-(piperidin-1-ylcarbonyl)pyrazolo[1,5-a]pyrimidin-5(4H)-one hydrochloride

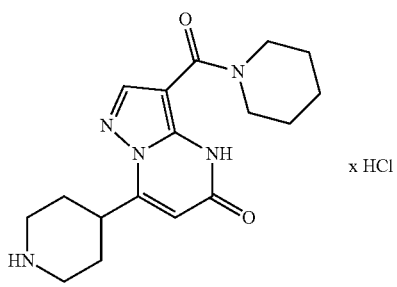 [SMILES: O=C(c1cnn2c(C3CCNCC3)cc(=O)[nH]c12)N1CCCCC1]

tert-butyl 4-[5-oxo-3-(piperidin-1-ylcarbonyl)-4,5-dihydropyrazolo[1,5-a]pyrimidin-7-yl]piperidine-1-carboxylate (60.6 mg, 141 µmol) was dissolved in 1,4-dioxan (2.0 ml, 23 mmol) and treated with hydrochloric acid in 1,4-dioxan (530 µl, 4.0 M, 2.1 mmol) at RT for 16 h. Solvents were removed, acetonitrile was added and the resulting participate was filtered and washed with acetonitrile. Drying in vacuo afforded the product. The obtained amount was 46.5 mg (91% purity, 82% of theory).

LC-MS (Method 10B): $R_t$=0.88 min; MS (ESIpos): m/z=330 [M+H]$^+$ $^1$H-NMR (400 MHz, DMSO-d6) delta [ppm]: −0.010 (0.76), 0.006 (0.65), 1.513 (1.65), 1.523 (1.42), 1.612 (0.81), 1.624 (0.80), 1.839 (0.22), 1.862 (0.58), 1.893 (0.67), 1.924 (0.27), 2.072 (6.73), 2.160 (0.90), 2.194 (0.71), 2.365 (0.13), 3.027 (0.30), 3.059 (0.73), 3.087 (0.72), 3.117 (0.30), 3.364 (0.90), 3.393 (0.73), 3.482 (0.34), 3.517 (2.09), 3.530 (2.43), 3.544 (1.91), 3.566 (16.00), 4.417 (0.57), 5.930 (1.67), 5.960 (0.16), 8.031 (3.50), 8.142 (0.29), 8.832 (0.23), 9.021 (0.26).

Example 328

3-(4,5-dimethyl-1,3-thiazol-2-yl)-7-(piperidin-4-yl)pyrazolo[1,5-a]pyrimidin-5(4H)-one hydrochloride

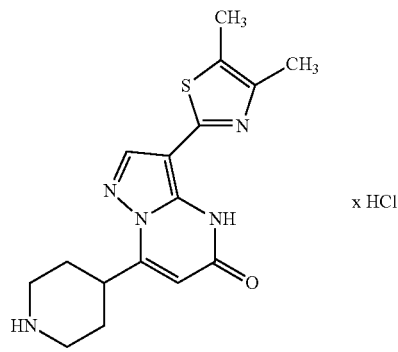 [SMILES: Cc1nc(-c2cnn3c(C4CCNCC4)cc(=O)[nH]c23)sc1C]

tert-butyl 4-[3-(4,5-dimethyl-1,3-thiazol-2-yl)-5-oxo-4,5-dihydropyrazolo[1,5-a]pyrimidin-7-yl]piperidine-1-carboxylate (83.0 mg, 193 µmol) was dissolved in 1,4-dioxan (2.0 ml, 23 mmol) and treated with hydrochloric acid in 1,4-dioxan (720 µl, 4.0 M, 2.9 mmol) at RT for 16 h. Solvents were removed, acetonitrile was added and the resulting participate was filtered and washed with acetonitrile. Drying in vacuo afforded the product. The obtained amount was 81.5 mg (95% purity, 100% of theory).

LC-MS (Method 10B): $R_t$=1.08 min; MS (ESIpos): m/z=330 [M+H]$^+$ $^1$H-NMR (400 MHz, DMSO-d6) delta [ppm]: −0.011 (1.32), 1.573 (0.78), 1.591 (0.78), 1.907 (0.71), 1.939 (1.64), 1.970 (1.84), 2.000 (0.85), 2.200 (2.72), 2.233 (2.29), 2.279 (0.39), 2.314 (1.80), 2.354 (12.88), 2.387 (16.00), 2.719 (0.93), 3.061 (0.72), 3.092 (1.94), 3.120 (2.04), 3.150 (0.87), 3.387 (2.85), 3.418 (2.21), 3.488 (0.34), 3.565 (8.88), 3.606 (0.72), 3.636 (1.22), 3.664 (0.80), 3.697 (0.33), 4.017 (0.51), 4.234 (0.51), 4.321 (0.55), 4.327 (0.54), 6.343 (0.66), 6.737 (0.34), 8.712 (0.38), 8.983 (0.53), 9.092 (0.72), 10.087 (0.39).

Example 329

3-[4-(2,5-dimethylphenyl)-1,3-thiazol-2-yl]-7-(piperidin-4-yl)pyrazolo[1,5-a]pyrimidin-5(4H)-one hydrochloride

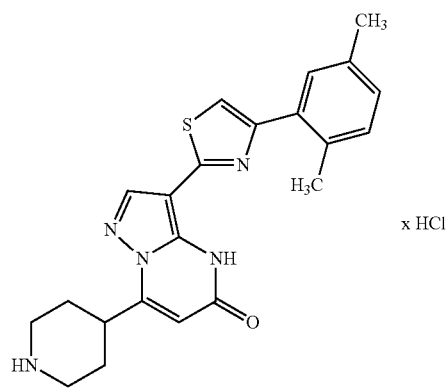 [SMILES: Cc1ccc(C)c(-c2csc(-c3cnn4c(C5CCNCC5)cc(=O)[nH]c34)n2)c1]

tert-butyl 4-{3-[4-(2,5-dimethylphenyl)-1,3-thiazol-2-yl]-5-oxo-4,5-dihydropyrazolo[1,5-a]pyrimidin-7-yl}piperidine-1-carboxylate (59.0 mg, 117 µmol) was dissolved in 1,4-dioxan (3.0 ml) and treated with hydrochloric acid in 1,4-dioxan (440 µl, 4.0 M, 1.8 mmol) at RT for 16 h. Solvents were removed. Drying in vacuo afforded the product. The obtained amount was 59.0 mg (96% purity, 100% of theory).

LC-MS (Method 11B): R$_t$=1.32 min; MS (ESIpos): m/z=406 [M+H]$^+$ $^1$H-NMR (400 MHz, DMSO-d6) delta [ppm]: −0.151 (0.43), −0.009 (3.47), 0.007 (3.31), 0.145 (0.40), 1.146 (0.44), 1.233 (0.32), 1.885 (0.44), 1.910 (1.12), 1.945 (1.26), 1.973 (0.52), 2.057 (0.41), 2.095 (0.16), 2.170 (0.24), 2.223 (2.36), 2.251 (1.92), 2.296 (0.61), 2.313 (0.69), 2.332 (15.59), 2.365 (0.59), 2.410 (16.00), 2.664 (0.33), 2.669 (0.39), 2.709 (0.49), 3.080 (0.47), 3.110 (1.30), 3.141 (1.33), 3.168 (0.57), 3.404 (1.84), 3.435 (1.52), 3.473 (0.23), 3.490 (0.20), 3.501 (0.23), 3.637 (0.68), 3.665 (0.53), 3.698 (0.32), 3.711 (0.28), 3.980 (2.66), 6.213 (0.25), 7.092 (0.17), 7.112 (1.30), 7.131 (2.06), 7.154 (0.24), 7.198 (3.38), 7.217 (2.18), 7.293 (0.17), 7.496 (3.25), 7.653 (7.91), 8.521 (1.37), 8.712 (0.41), 8.897 (0.52).

Example 330

3-[(2,2-dimethylmorpholin-4-yl)methyl]-7-(piperidin-4-yl)pyrazolo[1,5-a]pyrimidin-5(4H)-one hydrochloride

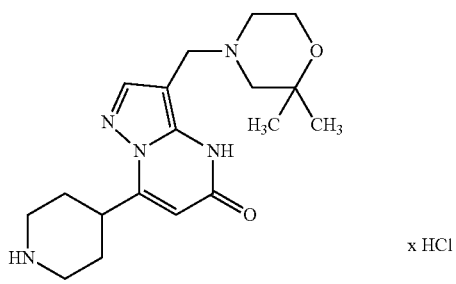 [SMILES: CC1(C)CN(Cc2cnn3c(C4CCNCC4)cc(=O)[nH]c23)CCO1]

tert-butyl 4-{3-[(2,2-dimethylmorpholin-4-yl)methyl]-5-oxo-4,5-dihydropyrazolo[1,5-a]pyrimidin-7-yl}piperidine-1-carboxylate (107 mg, 240 µmol) was dissolved in 1,4-dioxan (4.0 ml, 47 mmol) and treated with hydrochloric acid in 1,4-dioxan (900 µl, 4.0 M, 3.6 mmol) at RT for 16 h. Solvents were removed, acetonitrile was added and the resulting participate was filtered and washed with acetonitrile. Drying in vacuo afforded the product. The obtained amount was 72.9 mg (100% purity, 79% of theory).

LC-MS (Method 10B): R$_t$=0.82 min; MS (ESIneg): m/z=344 [M−H]$^-$ $^1$H-NMR (400 MHz, DMSO-d6) delta [ppm]: −0.152 (0.11), −0.011 (1.00), 0.005 (0.93), 0.143 (0.12), 1.145 (0.24), 1.182 (16.00), 1.240 (0.14), 1.250 (0.15), 1.322 (0.17), 1.339 (0.13), 1.400 (14.79), 1.428 (0.40), 1.557 (0.13), 1.862 (0.65), 1.886 (1.60), 1.917 (1.77), 1.950 (0.71), 2.072 (2.50), 2.144 (2.53), 2.176 (1.98), 2.327 (0.10), 2.366 (0.16), 2.523 (0.22), 2.669 (0.11), 2.709 (0.21), 2.750 (0.91), 2.778 (1.64), 2.807 (1.12), 2.830 (0.46), 2.850 (0.85), 2.880 (0.84), 2.904 (0.42), 2.914 (0.34), 3.030 (0.65), 3.060 (1.78), 3.089 (1.86), 3.118 (0.77), 3.170 (0.14), 3.232 (1.77), 3.261 (2.99), 3.290 (1.37), 3.359 (2.50), 3.389 (2.09), 3.478 (0.94), 3.508 (1.84), 3.538 (2.12), 3.730 (0.12), 3.742 (0.12), 3.753 (0.13), 3.779 (0.70), 3.788 (0.86), 3.811 (1.89), 3.821 (1.70), 3.842 (1.39), 3.871 (1.55), 3.902 (0.55), 4.255 (0.27), 4.266 (0.35), 4.299 (3.35), 4.329 (0.32), 4.342 (0.26), 5.877 (2.01), 7.616 (0.13), 8.075 (3.52), 8.137 (0.30), 8.990 (0.57), 9.105 (0.75), 10.786 (0.59), 12.457 (1.07).

Example 331

7-(piperidin-4-yl)-3-[5-(pyridin-3-ylmethyl)-1,3,4-oxadiazol-2-yl]pyrazolo[1,5-a]pyrimidin-5 (4H)-one hydrochloride

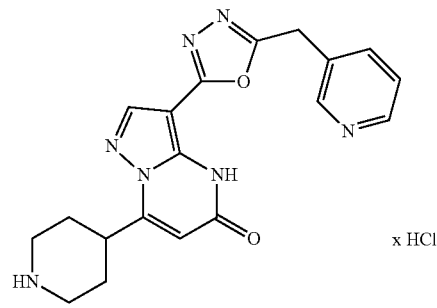 [SMILES: O=c1cc(C2CCNCC2)n2ncc(-c3nnc(Cc4cccnc4)o3)c2[nH]1]

tert-butyl 4-{5-oxo-3-[5-(pyridin-3-ylmethyl)-1,3,4-oxadiazol-2-yl]-4,5-dihydropyrazolo[1,5-a]pyrimidin-7-yl}piperidine-1-carboxylate (18.6 mg, 39.0 µmol) was dissolved in 1,4-dioxan (1.0 ml) and treated with hydrochloric acid in 1,4-dioxan (49 µl, 4.0 M, 190 µmol) at RT for 16 h. Solvents were removed, acetonitrile was added and the resulting participate was filtered and washed with acetonitrile. Drying in vacuo afforded the product. The obtained amount was 72.9 mg (100% purity, 79% of theory).

LC-MS (Method 10B): R$_t$=0.78 min; MS (ESIneg): m/z=376 [M−H]$^-$ $^1$H-NMR (400 MHz, DMSO-d6) delta [ppm]: −0.012 (1.63), 1.416 (0.28), 1.889 (0.97), 1.914 (2.49), 1.921 (2.57), 1.946 (2.79), 1.952 (2.70), 1.977 (1.22), 1.985 (1.03), 2.072 (1.50), 2.177 (3.95), 2.209 (3.05), 2.365 (0.21), 2.709 (0.22), 3.040 (1.00), 3.071 (2.78), 3.099 (2.84), 3.129 (1.17), 3.373 (3.81), 3.403 (3.12), 3.544 (1.21), 3.573 (2.57), 3.603 (1.02), 3.872 (0.41), 4.556 (16.00), 6.120 (4.66), 7.879 (1.51), 7.897 (2.24), 7.912 (1.67), 8.407 (2.42), 8.420 (11.29), 8.789 (3.28), 8.802 (3.29), 8.943 (4.89), 9.054 (0.93), 9.143 (1.32).

Example 332

3-(5-tert-butyl-1,3-oxazol-2-yl)-7-(piperidin-4-yl)pyrazolo[1,5-a]pyrimidin-5 (4H)-one hydrochloride

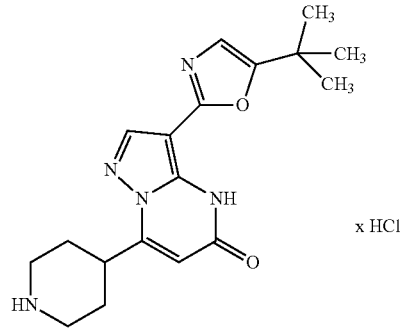 [SMILES: CC(C)(C)c1cnc(-c2cnn3c(C4CCNCC4)cc(=O)[nH]c23)o1]

tert-butyl 4-{3-[(3,3-dimethyl-2-oxobutyl)carbamoyl]-5-oxo-4,5-dihydropyrazolo[1,5-a]pyrimidin-7-yl}piperidine-1-carboxylate (200 mg, 435 µmol) was dissolved in toluene (5.0 ml, 47 mmol) and treated with phosphoryl chloride (160 µl, 1.7 mmol) at reflux for 4 h. Water was added carefully, solvents were removed. The precipitate was purified via reverse phase HPLC (Method: column: Reprosil C18; 10 µm; 125×30 mm/flow: 50 ml/min/solvents: A=water (0.1% formic acid), B=acetonitrile/gradient: 0.00-5.00 min=10% B, 6.50 min=20% B, 17.0-19.75 min=100% B, 19.75.00-23.00 min=90% B) to afford the product, after addition of hydrochloric acid in 1,4-dioxan. The obtained amount was 73.2 mg (100% purity, 45% of theory).

LC-MS (Method 11B): $R_t$=0.97 min; MS (ESIpos): m/z=342 [M+H]$^+$ $^1$H-NMR (400 MHz, DMSO-d6) delta [ppm]: 1.138 (0.03), 1.161 (0.08), 1.173 (0.04), 1.227 (0.03), 1.322 (16.00), 1.478 (0.07), 1.883 (0.14), 1.911 (0.40), 1.942 (0.44), 1.973 (0.18), 2.172 (0.63), 2.204 (0.49), 3.035 (0.16), 3.065 (0.44), 3.093 (0.45), 3.123 (0.18), 3.365 (0.60), 3.396 (0.49), 3.442 (0.02), 3.447 (0.02), 3.459 (0.04), 3.470 (0.05), 3.487 (0.06), 3.498 (0.05), 3.528 (0.19), 3.563 (0.83), 3.588 (0.16), 3.663 (0.04), 3.676 (0.06), 3.696 (0.06), 3.705 (0.04), 5.753 (0.03), 6.008 (1.23), 6.926 (1.52), 7.439 (0.02), 8.140 (0.07), 8.308 (1.43), 9.072 (0.13), 9.186 (0.17).

Example 333

4-(piperidin-4-yl)-7,8,9,10-tetrahydropyrimido[1,2-b]indazol-2(1H)-one hydrochloride

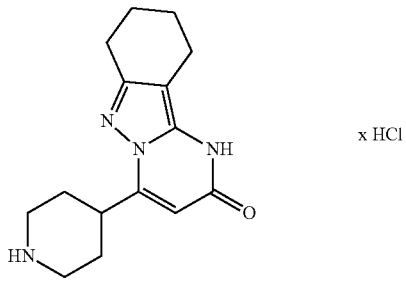 [SMILES: O=c1cc(C2CCNCC2)n2nc3c(c2[nH]1)CCCC3]

tert-butyl 4-(2-oxo-1,2,7,8,9,10-hexahydropyrimido[1,2-b]indazol-4-yl)piperidine-1-carboxylate (106 mg, 284 µmol) was dissolved in 1,4-dioxan (3.0 ml, 35 mmol) and treated with hydrochloric acid in 1,4-dioxan (1.1 ml, 4.0 M, 4.3 mmol) at RT for 16 h. Solvents were removed, acetonitrile was added and the resulting participate was filtered and washed with acetonitrile. Drying in vacuo afforded the product.

The obtained amount was 72.7 mg (100% purity, 83% of theory).

LC-MS (Method 10B): $R_t$=0.88 min; MS (ESIpos): m/z=273 [M+H]$^+$ $^1$H-NMR (400 MHz, DMSO-d6) delta [ppm]: −0.010 (5.43), 0.006 (3.04), 1.108 (0.53), 1.145 (0.61), 1.594 (0.95), 1.672 (6.92), 1.688 (7.91), 1.735 (7.78), 1.751 (7.16), 1.816 (4.94), 1.849 (5.32), 1.881 (2.15), 2.129 (7.80), 2.163 (6.21), 2.327 (0.62), 2.365 (0.73), 2.428 (7.55), 2.597 (8.05), 2.613 (14.14), 2.628 (6.47), 2.669 (0.69), 2.709 (0.62), 3.029 (2.06), 3.058 (5.36), 3.088 (5.44), 3.117 (2.20), 3.346 (7.81), 3.376 (7.10), 3.444 (16.00), 3.492 (13.40), 5.631 (8.86), 8.879 (1.45), 12.009 (2.74).

Example 334

3-[5-methyl-4-(trifluoromethyl)-1,3-thiazol-2-yl]-7-(piperidin-4-yl)pyrazolo[1,5-a]pyrimidin-5(4H)-one hydrochloride

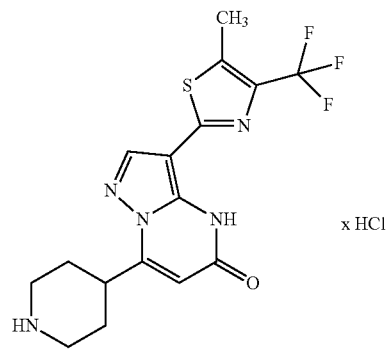 [SMILES: Cc1sc(-c2cnn3c(C4CCNCC4)cc(=O)[nH]c23)nc1C(F)(F)F]

tert-butyl 4-{3-[5-methyl-4-(trifluoromethyl)-1,3-thiazol-2-yl]-5-oxo-4,5-dihydropyrazolo[1,5-a]pyrimidin-7-yl}piperidine-1-carboxylate (4.90 mg, 10.1 µmol) was dissolved in 1,4-dioxan (1.0 ml, 12 mmol) and treated with hydrochloric acid in 1,4-dioxan (38 µl, 4.0 M, 150 µmol) at RT for 16 h. Solvents were removed, acetonitrile was added and the resulting participate was filtered and washed with acetonitrile. Drying in vacuo afforded the product. The obtained amount was 3.30 mg (100% purity, 71% of theory).

LC-MS (Method 11B): $R_t$=1.01 min; MS (ESIneg): m/z=382 [M−H]$^−$ $^1$H-NMR (500 MHz, DMSO-d6) delta [ppm]: −0.064 (0.13), 0.836 (0.28), 0.853 (1.37), 1.145 (0.31), 1.166 (0.19), 1.177 (0.23), 1.191 (0.28), 1.228 (2.35), 1.352 (5.69), 1.383 (1.80), 1.391 (1.42), 1.420 (16.00), 1.544 (0.15), 1.589 (0.44), 1.608 (0.46), 1.632 (0.21), 1.862 (0.14), 1.919 (1.20), 1.944 (3.18), 1.966 (3.46), 1.989 (1.60), 2.040 (0.57), 2.107 (0.63), 2.133 (0.15), 2.180 (0.94), 2.218 (4.79), 2.244 (4.01), 2.361 (0.23), 2.726 (0.19), 2.905 (0.22), 3.115 (3.56), 3.137 (2.12), 3.399 (5.37), 3.424 (4.54), 3.506 (0.50), 3.565 (0.77), 3.628 (0.92), 3.666 (1.75), 3.863 (0.15), 4.109 (0.39), 6.386 (0.75), 6.632 (0.35), 6.867 (0.52), 8.521 (3.33), 8.732 (0.12), 8.897 (0.88), 9.017 (1.12), 9.120 (0.15), 12.577 (0.18).

Example 335

3-(4-cyclohexyl-1,3-thiazol-2-yl)-7-(piperidin-4-yl)pyrazolo[1,5-a]pyrimidin-5(4H)-one hydrochloride

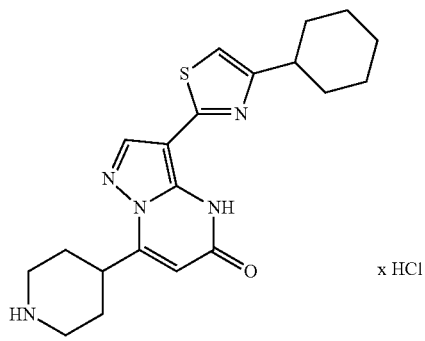 [SMILES: O=c1cc(C2CCNCC2)n2ncc(-c3nc(C4CCCCC4)cs3)c2[nH]1]

tert-butyl 4-[3-(4-cyclohexyl-1,3-thiazol-2-yl)-5-oxo-4,5-dihydropyrazolo[1,5-a]pyrimidin-7-yl]piperidine-1-carboxylate (54.0 mg, 112 µmol) was dissolved in 1,4-dioxan (2.5 ml) and treated with hydrochloric acid in 1,4-dioxan (420 µl, 4.0 M, 1.7 mmol) at RT for 16 h. Solvents were removed, acetonitrile was added and the resulting participate was filtered and washed with acetonitrile. Drying in vacuo afforded the product. The obtained amount was 50.9 mg (100% purity, 100% of theory).

LC-MS (Method 10B): $R_t$=1.51 min; MS (ESIpos): m/z=384 [M+H]$^+$ $^1$H-NMR (400 MHz, DMSO-d6) delta [ppm]: −0.010 (5.84), 1.230 (2.91), 1.259 (3.40), 1.268 (2.91), 1.282 (2.02), 1.290 (1.99), 1.298 (1.83), 1.342 (2.35), 1.373 (5.78), 1.405 (12.05), 1.434 (12.41), 1.465 (5.78), 1.495 (1.89), 1.698 (3.76), 1.728 (3.56), 1.782 (6.37), 1.806 (6.79), 1.812 (7.41), 1.882 (2.02), 1.913 (5.00), 1.939 (5.36), 1.945 (5.32), 1.970 (2.42), 2.045 (8.62), 2.071 (5.94), 2.205 (7.44), 2.237 (6.01), 2.365 (1.44), 2.709 (1.44), 2.756 (1.83), 2.783 (3.62), 2.803 (1.89), 2.811 (1.86), 3.064 (1.99), 3.094 (5.36), 3.123 (5.55), 3.153 (2.22), 3.388 (7.77), 3.422 (6.04), 3.566 (8.00), 3.591 (2.35), 3.615 (3.04), 3.644 (1.57), 4.321 (1.47), 4.516 (2.42), 4.637 (1.76), 4.654 (1.86), 6.194 (1.63), 7.181 (16.00), 8.513 (2.48), 8.795 (1.76), 8.818 (1.86), 8.964 (2.48).

Example 336

3-[4-(1-chlorocyclopropyl)-1,3-thiazol-2-yl]-7-(piperidin-4-yl)pyrazolo[1,5-a]pyrimidin-5(4H)-one hydrochloride

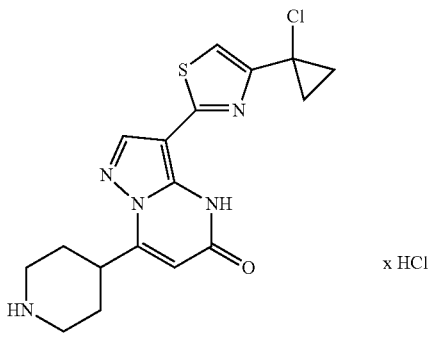 [SMILES: O=c1cc(C2CCNCC2)n2ncc(-c3nc(C4(Cl)CC4)cs3)c2[nH]1]

tert-butyl 4-{3-[4-(1-chlorocyclopropyl)-1,3-thiazol-2-yl]-5-oxo-4,5-dihydropyrazolo[1,5-a]pyrimidin-7-yl}piperidine-1-carboxylate (45.0 mg, 94.5 µmol) was dissolved in 1,4-dioxan (3.1 ml) and treated with hydrochloric acid in 1,4-dioxan (350 µl, 4.0 M, 1.4 mmol) at RT for 16 h. Solvents were removed. Drying in vacuo afforded the product. The obtained amount was 45.0 mg (100% purity, 106% of theory).

LC-MS (Method 10B): $R_t$=1.22 min; MS (ESIpos): m/z=376 [M+H]$^+$ $^1$H-NMR (400 MHz, DMSO-d6) delta [ppm]: −0.156 (0.36), −0.014 (3.34), 0.140 (0.39), 1.141 (0.64), 1.229 (0.52), 1.248 (0.27), 1.264 (0.23), 1.275 (0.20), 1.325 (0.34), 1.341 (0.20), 1.423 (0.23), 1.441 (0.32), 1.462 (3.55), 1.476 (9.77), 1.482 (9.41), 1.495 (4.73), 1.536 (0.59), 1.570 (0.50), 1.584 (0.48), 1.591 (0.64), 1.598 (0.59), 1.668 (3.00), 1.729 (0.61), 1.736 (0.57), 1.750 (0.34), 1.779 (0.27), 1.793 (0.39), 1.800 (0.36), 1.814 (0.20), 1.867 (0.93), 1.898 (2.45), 1.925 (2.64), 1.956 (1.14), 2.198 (3.75), 2.231 (3.00), 2.322 (0.43), 2.361 (0.89), 2.561 (0.20), 2.665 (0.43), 2.669 (0.36), 2.705 (0.91), 3.063 (1.00), 3.093 (2.77), 3.121 (2.89), 3.151 (1.16), 3.389 (4.00), 3.419 (3.18), 3.468 (0.23), 3.484 (0.25), 3.496 (0.20), 3.581 (1.05), 3.614 (1.16), 3.674 (0.36), 3.693 (0.25), 3.727 (0.30), 3.738 (0.27), 3.749 (0.27), 4.324 (3.11), 4.487 (0.57), 4.665 (0.20), 6.216 (0.34), 7.524 (16.00), 8.114 (0.48), 8.432 (1.82), 8.759 (0.93), 8.914 (1.30).

Example 337

3-{4-[2-(difluoromethoxy)phenyl]-1,3-thiazol-2-yl}-7-(piperidin-4-yl)pyrazolo[1,5-a]pyrimidin-5(4H)-one hydrochloride

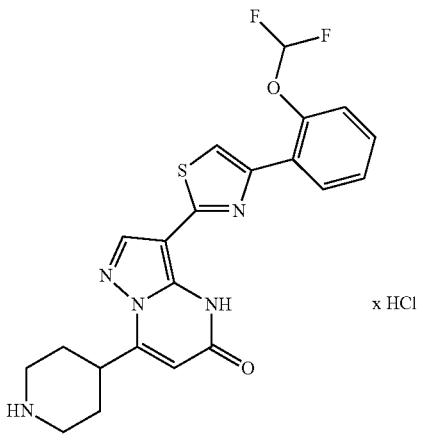 [SMILES: O=c1cc(C2CCNCC2)n2ncc(-c3nc(-c4ccccc4OC(F)F)cs3)c2[nH]1]

tert-butyl 4-(3-{4-[2-(difluoromethoxy)phenyl]-1,3-thiazol-2-yl}-5-oxo-4,5-dihydropyrazolo[1,5-a]pyrimidin-7-yl)piperidine-1-carboxylate (66.0 mg, 121 µmol) was dissolved in 1,4-dioxan (3.0 ml) and treated with hydrochloric acid in 1,4-dioxan (460 µl, 4.0 M, 1.8 mmol) at RT for 16 h. Solvents were removed. Drying in vacuo afforded the product. The obtained amount was 62.5 mg (100% purity, 100% of theory).

LC-MS (Method 10B): $R_t$=1.39 min; MS (ESIpos): m/z=444 [M+H]$^+$ $^1$H-NMR (400 MHz, DMSO-d6) delta [ppm]: −0.010 (2.46), 1.145 (0.42), 1.904 (0.99), 1.934 (2.62), 1.960 (2.85), 1.992 (1.22), 2.226 (4.03), 2.258 (3.24), 2.327 (0.35), 2.365 (0.59), 2.669 (0.34), 2.709 (0.59), 3.076 (1.03), 3.106 (2.87), 3.135 (2.98), 3.165 (1.23), 3.401 (4.04), 3.432 (3.26), 3.566 (1.90), 3.647 (1.34), 4.923 (0.91), 6.225 (0.56), 7.178 (3.97), 7.313 (3.96), 7.333 (5.30), 7.362 (8.11), 7.384 (2.01), 7.401 (4.62), 7.420 (3.40), 7.441 (3.16), 7.446 (3.45), 7.461 (3.50), 7.465 (3.71), 7.480 (1.51), 7.484 (1.41), 7.547 (3.85), 7.911 (16.00), 8.317 (3.44), 8.321 (3.72), 8.336 (3.43), 8.340 (3.44), 8.549 (1.93), 8.852 (0.95), 8.998 (1.26).

Example 338

3-(5-tert-butyl-1,3,4-oxadiazol-2-yl)-2-methyl-7-(piperidin-4-yl)pyrazolo[1,5-a]pyrimidin-5(4H)-one hydrochloride

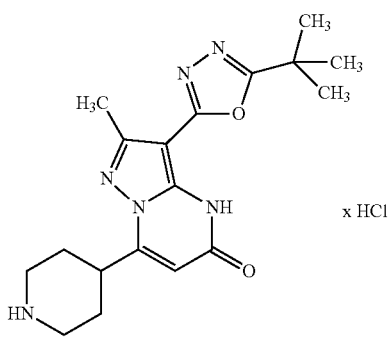 [SMILES: Cc1nn2c(C3CCNCC3)cc(=O)[nH]c2c1-c1nnc(C(C)(C)C)o1]

tert-butyl 4-[3-(5-tert-butyl-1,3,4-oxadiazol-2-yl)-2-methyl-5-oxo-4,5-dihydropyrazolo[1,5-a]pyrimidin-7-yl]piperidine-1-carboxylate (61.1 mg, 134 µmol) was dissolved in 1,4-dioxan (2.0 ml, 23 mmol) and treated with hydrochloric acid in 1,4-dioxan (500 µl, 4.0 M, 2.0 mmol) at RT for 16 h. Solvents were removed. Drying in vacuo afforded the product. The obtained amount was 49.4 mg (100% purity, 94% of theory).

LC-MS (Method 10B): $R_t$=1.06 min; MS (ESIpos): m/z=357 [M+H]$^+$ $^1$H-NMR (400 MHz, DMSO-d6) delta [ppm]: −0.156 (0.02), −0.014 (0.21), 0.140 (0.02), 1.142 (0.03), 1.178 (0.06), 1.189 (0.03), 1.208 (0.03), 1.263 (0.07), 1.425 (16.00), 1.582 (0.07), 1.818 (0.09), 1.826 (0.11), 1.851 (0.28), 1.858 (0.29), 1.883 (0.32), 1.889 (0.31), 1.914 (0.14), 1.923 (0.12), 2.169 (0.44), 2.202 (0.36), 2.322 (0.03), 2.327 (0.03), 2.361 (0.04), 2.385 (0.02), 2.407 (0.02), 2.424 (0.02), 2.570 (0.03), 2.655 (0.02), 2.665 (0.03), 2.705 (0.04), 3.106 (0.28), 3.373 (0.48), 3.405 (0.38), 3.458 (0.02), 3.468 (0.02), 3.528 (0.10), 3.562 (1.48), 3.583 (0.10), 3.661 (0.01), 3.674 (0.02), 3.693 (0.02), 3.706 (0.01), 5.990 (0.11), 8.776 (0.08), 8.917 (0.10), 11.913 (0.05), 12.008 (0.02).

Example 339

2-methyl-3-(3-methyl-1,2,4-oxadiazol-5-yl)-7-(piperidin-4-yl)pyrazolo[1,5-a]pyrimidin-5(4H)-one hydrochloride

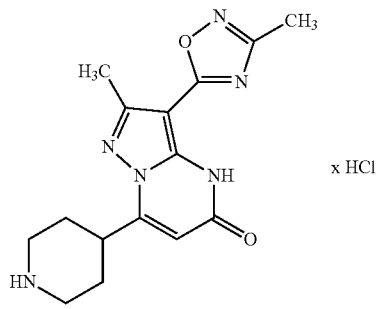 [SMILES: Cc1noc(-c2c(C)nn3c(C4CCNCC4)cc(=O)[nH]c23)n1]

tert-butyl 4-[2-methyl-3-(3-methyl-1,2,4-oxadiazol-5-yl)-5-oxo-4,5-dihydropyrazolo[1,5-a]pyrimidin-7-yl]piperidine-1-carboxylate (40.8 mg, 98.4 µmol) was dissolved in 1,4-dioxan (2.0 ml, 23 mmol) and treated with hydrochloric acid in 1,4-dioxan (370 µl, 4.0 M, 1.5 mmol) at RT for 16 h. Solvents were removed. Drying in vacuo afforded the product. The obtained amount was 36.1 mg (90% purity, 94% of theory).

LC-MS (Method 10B): $R_t$=0.84 min; MS (ESIpos): m/z=315 [M+H]$^+$ $^1$H-NMR (400 MHz, DMSO-d6) delta [ppm]: 1.145 (0.07), 1.176 (0.07), 1.194 (0.14), 1.212 (0.08), 1.229 (0.10), 1.263 (0.39), 1.281 (0.84), 1.298 (0.40), 1.353 (0.10), 1.371 (0.09), 1.388 (0.05), 1.418 (0.88), 1.428 (0.22), 1.821 (0.04), 1.875 (0.46), 1.906 (1.12), 1.932 (1.21), 1.963 (0.53), 2.129 (0.18), 2.174 (1.80), 2.207 (1.39), 2.254 (0.07), 2.327 (0.08), 2.387 (16.00), 2.420 (1.43), 2.572 (11.76), 2.669 (0.08), 2.709 (0.09), 2.731 (0.07), 3.108 (1.11), 3.373 (1.95), 3.404 (1.49), 3.460 (0.16), 3.470 (0.19), 3.489 (0.16), 3.498 (0.16), 3.565 (13.11), 3.594 (0.81), 3.624 (0.40), 3.665 (0.11), 3.678 (0.13), 3.697 (0.13), 3.710 (0.10), 3.721 (0.05), 4.258 (0.11), 4.275 (0.34), 4.293 (0.34), 4.310 (0.11), 4.327 (0.04), 4.450 (0.04), 5.913 (0.29), 6.148 (0.80), 9.047 (0.51), 11.491 (0.07), 12.759 (0.04).

Example 340

3-(5-cyclobutyl-1,3,4-oxadiazol-2-yl)-2-methyl-7-(piperidin-4-yl)pyrazolo[1,5-a]pyrimidin-5 (4H)-one hydrochloride

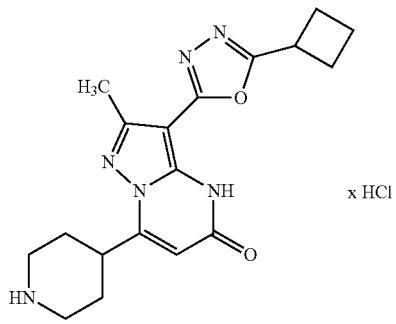 [SMILES: Cc1nn2c(C3CCNCC3)cc(=O)[nH]c2c1-c1nnc(C2CCC2)o1]

tert-butyl 4-[3-(5-cyclobutyl-1,3,4-oxadiazol-2-yl)-2-methyl-5-oxo-4,5-dihydropyrazolo[1,5-a]pyrimidin-7-yl]piperidine-1-carboxylate (77.3 mg, 170 µmol) was dissolved in 1,4-dioxan (2.5 ml) and treated with hydrochloric acid in 1,4-dioxan (640 µl, 4.0 M, 2.6 mmol) at RT for 16 h. Solvents were removed, acetonitrile was added and the resulting participate was filtered and washed with acetonitrile. Drying in vacuo afforded the product. The obtained amount was 40.6 mg (100% purity, 61% of theory).

LC-MS (Method 10B): $R_t$=1.00 min; MS (ESIpos): m/z=355 [M+H]$^+$ $^1$H-NMR (400 MHz, DMSO-d6) delta [ppm]: −0.078 (0.03), 0.071 (5.45), 0.217 (0.03), 1.219 (0.07), 1.491 (0.02), 1.914 (0.24), 1.939 (0.68), 1.971 (0.77), 2.005 (0.42), 2.027 (0.33), 2.054 (0.42), 2.066 (0.32), 2.075 (0.24), 2.088 (0.13), 2.099 (0.11), 2.121 (0.37), 2.143 (0.68), 2.166 (0.55), 2.192 (0.32), 2.214 (0.15), 2.245 (1.06), 2.277 (0.86), 2.401 (0.07), 2.424 (0.10), 2.453 (1.11), 2.478 (1.99), 2.522 (0.54), 2.575 (11.88), 2.612 (16.00), 2.737 (0.06), 2.782 (0.08), 3.135 (0.27), 3.164 (0.73), 3.194 (0.77), 3.221 (0.32), 3.447 (1.04), 3.477 (0.85), 3.603 (0.30), 3.640 (3.52), 3.662 (0.30), 3.840 (0.40), 3.861 (0.90), 3.882 (1.23), 3.903 (0.99), 3.924 (0.60), 6.068 (0.55), 8.928 (0.22), 9.044 (0.31), 9.445 (0.03), 9.888 (0.02).

Example 341

2-methyl-7-(piperidin-4-yl)-3-[3-(trifluoromethyl)-1,2,4-oxadiazol-5-yl]pyrazolo[1,5-a]pyrimidin-5(4H)-one hydrochloride

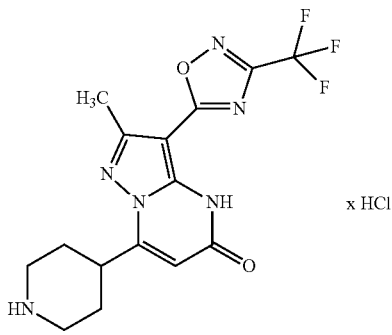 [SMILES: Cc1nn2c(C3CCNCC3)cc(=O)[nH]c2c1-c1nc(C(F)(F)F)no1]

tert-butyl 4-{2-methyl-5-oxo-3-[3-(trifluoromethyl)-1,2,4-oxadiazol-5-yl]-4,5-dihydropyrazolo[1,5-a]pyrimidin-7-yl}piperidine-1-carboxylate (99.5 mg, 212 µmol) was dissolved in 1,4-dioxan (2.0 ml, 23 mmol) and treated with hydrochloric acid in 1,4-dioxan (800 µl, 4.0 M, 3.2 mmol) at RT for 16 h. Solvents were removed, acetonitrile was added and the resulting participate was filtered and washed with acetonitrile. Drying in vacuo afforded the product. The obtained amount was 86.1 mg (100% purity, 100% of theory).

LC-MS (Method 10B): R$_t$=1.12 min; MS (ESIpos): m/z=369 [M+H]$^+$ $^1$H-NMR (400 MHz, DMSO-d6) delta [ppm]: −0.152 (0.09), 0.143 (0.10), 1.147 (0.13), 1.229 (0.09), 1.421 (0.76), 1.875 (0.48), 1.908 (1.46), 1.940 (1.62), 1.970 (0.67), 2.191 (2.42), 2.225 (1.94), 2.327 (0.11), 2.366 (0.17), 2.457 (0.08), 2.590 (0.24), 2.622 (13.14), 2.669 (0.21), 2.709 (0.20), 2.781 (0.09), 3.132 (1.41), 3.388 (2.53), 3.419 (2.01), 3.461 (0.14), 3.471 (0.14), 3.488 (0.10), 3.566 (16.00), 3.618 (0.55), 3.647 (0.93), 3.665 (0.52), 3.676 (0.54), 3.706 (0.11), 6.337 (0.54), 8.969 (0.50), 12.850 (0.09).

Example 342

3-[(dimethylamino)methyl]-7-(piperidin-4-yl)pyrazolo[1,5-a]pyrimidin-5(4H)-one hydrochloride

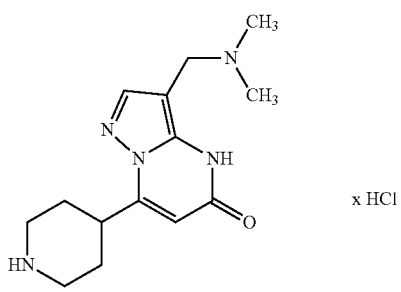 [SMILES: CN(C)Cc1cnn2c(C3CCNCC3)cc(=O)[nH]c12]

tert-butyl 4-{3-[(dimethylamino)methyl]-5-oxo-4,5-dihydropyrazolo[1,5-a]pyrimidin-7-yl}piperidine-1-carboxylate (45.8 mg, 122 µmol) was dissolved in 1,4-dioxan (2.0 ml, 23 mmol) and treated with hydrochloric acid in 1,4-dioxan (460 µl, 4.0 M, 1.8 mmol) at RT for 16 h. Solvents were removed, acetonitrile was added and the resulting participate was filtered and washed with acetonitrile. Drying in vacuo afforded the product. The obtained amount was 40.5 mg (100% purity, 95% of theory).

$^1$H-NMR (400 MHz, DMSO-d6) delta [ppm]: −0.151 (0.06), 0.007 (0.52), 0.145 (0.06), 1.145 (0.08), 1.413 (0.06), 1.594 (1.78), 1.838 (0.18), 1.869 (0.46), 1.895 (0.49), 1.926 (0.22), 2.149 (0.68), 2.182 (0.54), 2.365 (0.11), 2.610 (0.12), 2.645 (0.39), 2.656 (0.46), 2.663 (0.44), 2.689 (4.63), 2.701 (4.61), 2.795 (0.19), 2.842 (0.11), 2.942 (0.10), 2.955 (0.16), 3.032 (0.19), 3.061 (0.49), 3.091 (0.53), 3.121 (0.21), 3.245 (0.07), 3.367 (0.82), 3.507 (0.45), 3.566 (16.00), 3.678 (0.06), 4.088 (0.06), 4.099 (0.06), 4.244 (1.29), 4.256 (1.28), 5.887 (0.59), 7.535 (0.18), 7.564 (0.05), 7.596 (0.05), 7.614 (0.06), 7.625 (0.07), 7.985 (0.90), 8.851 (0.18), 8.874 (0.19), 8.994 (0.24), 10.313 (0.26), 11.087 (0.09), 12.478 (0.40).

Example 343

7-(piperidin-4-yl)-3-(pyrrolidin-1-ylmethyl)pyrazolo[1,5-a]pyrimidin-5(4H)-one hydrochloride

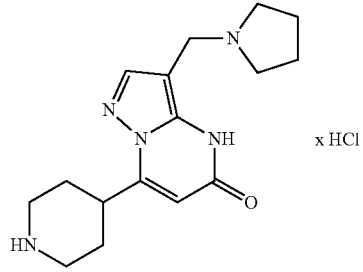 [SMILES: O=c1cc(C2CCNCC2)n2ncc(CN3CCCC3)c2[nH]1]

tert-butyl 4-[5-oxo-3-(pyrrolidin-1-ylmethyl)-4,5-dihydropyrazolo[1,5-a]pyrimidin-7-yl]piperidine-1-carboxylate (58.2 mg, 145 µmol) was dissolved in 1,4-dioxan (2.0 ml, 23 mmol) and treated with hydrochloric acid in 1,4-dioxan (540 µl, 4.0 M, 2.2 mmol) at RT for 16 h. Solvents were removed, acetonitrile was added and the resulting participate was filtered and washed with acetonitrile. Drying in vacuo afforded the product. The obtained amount was 54.2 mg (100% purity, 100% of theory).

$^1$H-NMR (400 MHz, DMSO-d6) delta [ppm]: 0.144 (0.19), 1.146 (0.31), 1.387 (0.19), 1.413 (4.33), 1.434 (0.19), 1.536 (0.31), 1.566 (0.59), 1.594 (11.04), 1.702 (0.28), 1.732 (0.25), 1.777 (0.25), 1.867 (4.08), 1.885 (3.03), 1.922 (1.12), 1.984 (2.20), 2.002 (2.57), 2.146 (2.39), 2.179 (1.90), 2.327 (0.21), 2.366 (0.36), 2.604 (0.38), 2.645 (0.40), 2.669 (0.32), 2.689 (0.22), 2.709 (0.51), 2.790 (0.39), 2.814 (0.41), 2.899 (0.23), 3.032 (2.43), 3.053 (2.63), 3.091 (2.14), 3.116 (1.04), 3.166 (0.21), 3.247 (0.59), 3.369 (4.86), 3.386 (4.46), 3.397 (4.88), 3.438 (16.00), 3.504 (1.75), 3.614 (0.37), 3.678 (0.27), 3.698 (0.24), 3.732 (0.31), 3.743 (0.30), 3.753 (0.24), 4.126 (0.20), 4.138 (0.22), 4.159 (0.40), 4.173 (0.36), 4.194 (0.36), 4.208 (0.37), 4.228 (0.23), 4.242 (0.20), 4.319 (4.38), 4.332 (4.27), 4.394 (0.34), 5.878 (1.83), 5.931 (0.18), 7.572 (1.29), 8.003 (0.29), 8.035 (3.05), 8.844 (0.70), 8.985 (0.83), 10.597 (0.85), 11.099 (0.67), 12.487 (1.21).

Example 344

3-cyclopropyl-7-(piperidin-4-yl)pyrazolo[1,5-a]py-rimidin-5(4H)-one hydrochloride

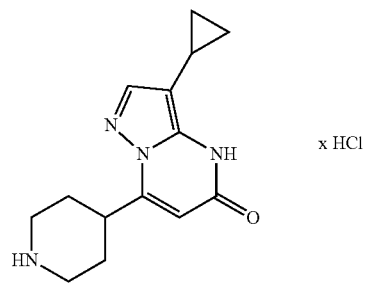 [SMILES: O=c1cc(C2CCNCC2)n2ncc(C3CC3)c2[nH]1]

x HCl tert-butyl 4-(3-cyclopropyl-5-oxo-4,5-dihydropyrazolo[1,5-a]pyrimidin-7-yl)piperidine-1-carboxylate (443 mg, 1.24 mmol) was dissolved in 1,4-dioxan (15 ml, 180 mmol) and treated with hydrochloric acid in 1,4-dioxan (4.6 ml, 4.0 M, 19 mmol) at RT for 16 h. Solvents were removed, acetonitrile was added and the resulting participate was filtered and washed with acetonitrile. Drying in vacuo afforded the product. The obtained amount was 350 mg (90% purity, 86% of theory).

LC-MS (Method 10B): $R_t$=0.84 min; MS (ESIpos): m/z=259 [M+H]$^+$ $^1$H-NMR (500 MHz, DEUTERIUM OXIDE) delta [ppm]: −0.056 (4.69), 0.451 (0.24), 0.471 (2.71), 0.480 (8.84), 0.483 (8.41), 0.490 (8.41), 0.493 (8.53), 0.501 (2.64), 0.521 (0.21), 0.795 (0.21), 0.812 (0.38), 0.825 (2.80), 0.833 (7.40), 0.837 (7.52), 0.841 (4.12), 0.846 (4.01), 0.850 (7.63), 0.854 (7.38), 0.862 (2.40), 1.193 (0.33), 1.206 (0.45), 1.522 (1.15), 1.532 (2.24), 1.538 (2.43), 1.548 (4.08), 1.558 (2.26), 1.565 (1.98), 1.575 (0.92), 1.684 (0.28), 1.689 (0.21), 1.706 (0.35), 1.712 (0.47), 1.736 (0.54), 1.744 (0.45), 1.759 (0.28), 1.767 (0.28), 1.841 (1.34), 1.849 (1.48), 1.869 (3.56), 1.875 (3.58), 1.894 (3.82), 1.900 (3.68), 1.920 (1.70), 1.928 (1.53), 2.132 (0.52), 2.155 (0.49), 2.233 (6.10), 2.282 (5.37), 2.311 (4.62), 2.825 (0.21), 2.840 (0.24), 2.847 (0.42), 2.855 (0.21), 2.870 (0.21), 3.023 (0.33), 3.048 (0.68), 3.072 (0.38), 3.174 (2.78), 3.178 (3.04), 3.200 (5.87), 3.204 (5.87), 3.226 (3.20), 3.230 (2.95), 3.342 (0.75), 3.400 (0.99), 3.406 (1.74), 3.412 (1.18), 3.424 (2.33), 3.430 (3.96), 3.436 (2.36), 3.448 (1.46), 3.454 (2.19), 3.520 (0.24), 3.530 (0.28), 3.573 (5.75), 3.599 (5.00), 3.719 (1.30), 5.913 (15.01), 7.571 (16.00).

Example 345

3-[(1,1-dioxidothiomorpholin-4-yl)methyl]-7-(piperidin-4-yl)pyrazolo[1,5-a]pyrimidin-5 (4H)-one hydrochloride

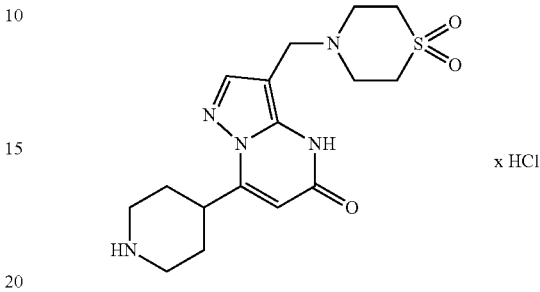

x HCl tert-butyl 4-{3-[(1,1-dioxidothiomorpholin-4-yl)methyl]-5-oxo-4,5-dihydropyrazolo[1,5-a]pyrimidin-7-yl}piperidine-1-carboxylate (134 mg, 288 μmol) was dissolved in 1,4-dioxan (3.0 ml, 35 mmol) and treated with hydrochloric acid in 1,4-dioxan (1.1 ml, 4.0 M, 4.3 mmol) at RT for 16 h. The mixture was purified via reverse phase HPLC (Method: column: Reprosil C18; 10 μm; 125×30 mm/flow: 50 ml/min/solvents: A=water (0.1% formic acid), B=acetonitrile/gradient: 0.00-5.00 min=10% B, 6.50 min=20% B, 17.0-19.75 min=100% B, 19.75.00-23.00 min=90% B) to afford the product, after addition of hydrochloric acid in 1,4-dioxan. The obtained amount was 105 mg (100% purity, 83% of theory).

LC-MS (Method 10B): $R_t$=0.67 min; MS (ESIpos): m/z=366 [M+H]$^+$ $^1$H-NMR (400 MHz, DMSO-d6) delta [ppm]: −0.152 (0.68), 0.144 (0.74), 1.146 (0.68), 1.235 (0.42), 1.257 (1.44), 1.274 (1.56), 1.290 (1.06), 1.305 (0.94), 1.570 (0.56), 1.609 (0.38), 1.718 (0.40), 1.744 (0.34), 1.851 (2.36), 1.879 (5.53), 1.910 (5.75), 1.940 (2.44), 2.044 (0.40), 2.145 (8.45), 2.177 (6.61), 2.327 (0.48), 2.365 (0.76), 2.563 (2.98), 2.603 (0.84), 2.642 (1.34), 2.669 (0.86), 2.710 (1.22), 2.781 (0.66), 2.873 (0.40), 3.033 (2.76), 3.061 (6.23), 3.090 (6.35), 3.115 (2.86), 3.153 (0.62), 3.239 (0.96), 3.358 (8.47), 3.387 (7.73), 3.478 (4.39), 3.507 (6.77), 3.555 (8.99), 3.565 (5.79), 3.622 (5.39), 3.678 (5.03), 3.697 (4.83), 3.723 (5.71), 4.189 (4.03), 4.414 (10.97), 4.534 (0.84), 4.863 (1.84), 5.268 (0.30), 5.301 (0.30), 5.751 (1.58), 5.851 (0.48), 5.889 (8.35), 7.555 (1.30), 7.668 (0.48), 7.687 (1.06), 7.706 (0.92), 7.716 (1.24), 7.734 (0.72), 7.752 (3.68), 7.790 (0.74), 7.809 (0.42), 7.851 (0.30), 7.870 (0.42), 7.947 (0.68), 7.989 (16.00), 8.054 (0.42), 8.942 (1.50), 9.065 (2.18), 11.015 (0.40), 12.370 (1.12).

Example 346

3-[3-(2,2-dimethylcyclopropyl)-1,2,4-oxadiazol-5-yl]-2-methyl-7-(piperidin-4-yl)pyrazolo[1,5-a]pyrimidin-5(4H)-one hydrochloride

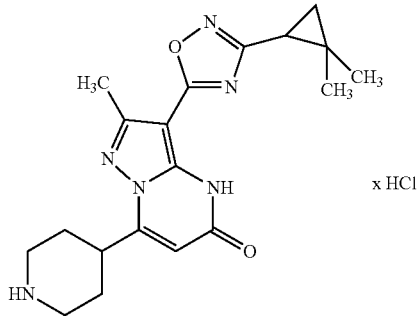 [SMILES: Cc1nn2c(C3CCNCC3)cc(=O)[nH]c2c1-c1nc(C2CC2(C)C)no1]

tert-butyl 4-{3-[3-(2,2-dimethylcyclopropyl)-1,2,4-oxadiazol-5-yl]-2-methyl-5-oxo-4,5-dihydropyrazolo[1,5-a]pyrimidin-7-yl}piperidine-1-carboxylate (102 mg, 218 µmol) was dissolved in 1,4-dioxan (2.0 ml, 23 mmol) and treated with hydrochloric acid in 1,4-dioxan (820 µl, 4.0 M, 3.3 mmol) at RT for 16 h. Solvents were removed, acetonitrile was added and the resulting participate was filtered and washed with acetonitrile. Drying in vacuo afforded the product. The obtained amount was 63.1 mg (100% purity, 71% of theory).

LC-MS (Method 11B): $R_t$=1.05 min; MS (ESIpos): m/z=369 [M+H]$^+$ $^1$H-NMR (400 MHz, DMSO-d6) delta [ppm]: −0.152 (0.06), −0.011 (0.56), 0.005 (0.49), 0.143 (0.06), 0.947 (0.08), 1.030 (1.07), 1.040 (1.37), 1.051 (1.25), 1.061 (1.29), 1.074 (0.16), 1.106 (16.00), 1.145 (0.13), 1.197 (0.74), 1.208 (1.17), 1.233 (14.12), 1.262 (0.15), 1.388 (0.07), 1.417 (0.07), 1.849 (0.31), 1.878 (0.93), 1.908 (1.03), 1.938 (0.43), 1.960 (1.45), 1.974 (1.54), 1.981 (1.53), 1.995 (1.26), 2.173 (1.50), 2.206 (1.21), 2.322 (0.06), 2.327 (0.07), 2.365 (0.14), 2.396 (0.05), 2.669 (0.09), 2.709 (0.16), 2.719 (0.05), 3.081 (0.57), 3.109 (1.11), 3.141 (0.65), 3.376 (1.62), 3.407 (1.30), 3.566 (11.93), 3.583 (0.61), 3.610 (0.31), 6.125 (0.32), 8.861 (0.24), 8.961 (0.30), 11.579 (0.09), 11.695 (0.04), 12.820 (0.04).

Example 347

2-methyl-7-(piperidin-4-yl)-3-{3-[2-(trifluoromethoxy)phenyl]-1,2,4-oxadiazol-5-yl}pyrazolo[1,5-a]pyrimidin-5(4H)-one hydrochloride

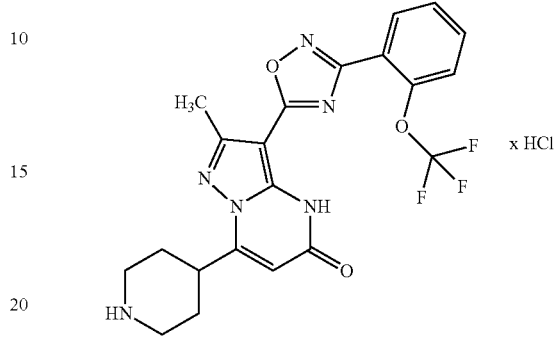

tert-butyl 4-(2-methyl-5-oxo-3-{3-[2-(trifluoromethoxy)phenyl]-1,2,4-oxadiazol-5-yl}-4,5-dihydropyrazolo[1,5-a]pyrimidin-7-yl)piperidine-1-carboxylate (100 mg, 179 µmol) was dissolved in 1,4-dioxan (2.0 ml, 23 mmol) and treated with hydrochloric acid in 1,4-dioxan (670 µl, 4.0 M, 2.7 mmol) at RT for 16 h. Solvents were removed, acetonitrile was added and the resulting participate was filtered and washed with acetonitrile. Drying in vacuo afforded the product. The obtained amount was 46.2 mg (100% purity, 52% of theory).

LC-MS (Method 11B): $R_t$=1.25 min; MS (ESIpos): m/z=461 [M+H]$^+$ $^1$H-NMR (400 MHz, DMSO-d6) delta [ppm]: −0.152 (0.09), 0.143 (0.08), 1.145 (0.16), 1.875 (0.56), 1.899 (1.68), 1.931 (1.87), 1.963 (0.75), 2.195 (2.78), 2.228 (2.25), 2.327 (0.13), 2.365 (0.24), 2.643 (16.00), 2.709 (0.27), 2.803 (0.11), 3.097 (1.05), 3.125 (2.02), 3.154 (1.18), 3.389 (2.89), 3.420 (2.33), 3.566 (2.31), 3.577 (0.68), 3.607 (1.18), 3.636 (0.61), 6.160 (0.91), 7.616 (1.97), 7.640 (2.94), 7.662 (3.25), 7.681 (2.05), 7.745 (1.76), 7.749 (2.00), 7.768 (2.56), 7.784 (1.00), 7.787 (1.05), 8.424 (0.98), 8.976 (0.54), 11.934 (0.15).

Example 348

3-(morpholin-4-ylmethyl)-7-(piperidin-4-yl)pyrazolo[1,5-a]pyrimidin-5(4H)-one hydrochloride

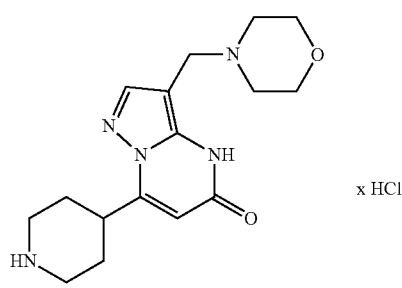 [SMILES: O=c1cc(C2CCNCC2)n2ncc(CN3CCOCC3)c2[nH]1]

tert-butyl 4-[3-(morpholin-4-ylmethyl)-5-oxo-4,5-dihydropyrazolo[1,5-a]pyrimidin-7-yl]piperidine-1-carboxylate (117 mg, 280 µmol) was dissolved in 1,4-dioxan (10 ml, 120 mmol) and treated with hydrochloric acid in 1,4-dioxan (1.0 ml, 4.0 M, 4.2 mmol) at RT for 1 h. Solvents were removed. Drying in vacuo afforded the product. The obtained amount was 108 mg (100% purity, 99% of theory).

LC-MS (Method 10B): $R_t$=0.67 min; MS (ESIneg): m/z=316 [M−H]⁻

¹H-NMR (400 MHz, DMSO-d6) delta [ppm]: −0.009 (4.31), 0.007 (3.73), 1.146 (0.71), 1.236 (0.81), 1.253 (0.97), 1.270 (0.92), 1.280 (0.89), 1.296 (0.81), 1.414 (0.92), 1.594 (12.37), 1.834 (1.26), 1.865 (3.36), 1.890 (3.49), 1.922 (1.52), 2.145 (4.86), 2.178 (3.94), 2.365 (1.02), 2.709 (1.02), 2.982 (1.44), 3.003 (3.26), 3.034 (4.60), 3.066 (4.62), 3.094 (3.76), 3.124 (1.94), 3.308 (6.15), 3.338 (5.57), 3.369 (7.51), 3.400 (16.00), 3.474 (2.08), 3.506 (3.02), 3.537 (1.73), 3.599 (0.81), 3.607 (0.74), 3.692 (3.23), 3.720 (6.07), 3.750 (3.63), 3.947 (5.89), 3.975 (4.52), 4.306 (7.67), 4.317 (7.41), 5.893 (4.05), 7.549 (1.50), 7.994 (7.36), 8.135 (2.86), 8.802 (1.23), 8.824 (1.23), 8.956 (1.58), 10.929 (1.52), 11.063 (0.71), 12.443 (2.18).

Example 349

7-[(2S,4R)-2-(2,2-dimethylpropyl)piperidin-4-yl]-3-[3-(2-fluorophenyl)-1,2,4-oxadiazol-5-yl]pyrazolo[1,5-a]pyrimidin-5(4H)-one hydrochloride

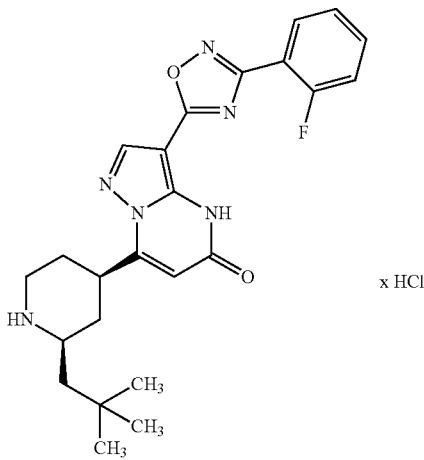 [SMILES: CC(C)(C)C[C@@H]1C[C@H](c2cc(=O)[nH]c3c(-c4nc(-c5ccccc5F)no4)cnn23)CCN1]

tert-butyl (2S,4R)-2-(2,2-dimethylpropyl)-4-{3-[3-(2-fluorophenyl)-1,2,4-oxadiazol-5-yl]-5-oxo-4,5-dihydropyrazolo[1,5-a]pyrimidin-7-yl}piperidine-1-carboxylate (36.1 mg, 65.6 μmol) was dissolved in 1,4-dioxan (1.9 ml, 22 mmol) and treated with hydrochloric acid in 1,4-dioxan (250 μl, 4.0 M, 980 μmol) at RT for 3 d. Solvents were removed. Drying in vacuo afforded the product. The obtained amount was 30.7 mg (100% purity, 96% of theory).

LC-MS (Method 11B): $R_t$=1.31 min; MS (ESIneg): m/z=449 [M−H]⁻

¹H-NMR (400 MHz, DMSO-d6) delta [ppm]: −0.151 (0.13), 0.007 (1.03), 0.145 (0.13), 0.802 (0.07), 0.960 (16.00), 1.114 (0.09), 1.145 (0.20), 1.232 (0.17), 1.517 (0.49), 1.552 (0.50), 1.815 (0.35), 1.836 (0.38), 1.851 (0.31), 1.871 (0.28), 1.995 (0.22), 2.021 (0.24), 2.129 (0.83), 2.327 (0.14), 2.365 (0.27), 2.669 (0.18), 2.709 (0.29), 3.204 (0.31), 3.255 (0.66), 3.567 (1.07), 3.618 (0.39), 3.756 (0.24), 6.226 (0.09), 7.436 (1.07), 7.456 (1.57), 7.475 (0.65), 7.484 (0.58), 7.651 (0.25), 7.655 (0.26), 7.668 (0.45), 7.689 (0.41), 7.703 (0.19), 7.707 (0.19), 8.401 (0.10), 8.627 (0.45), 8.770 (0.19), 12.290 (0.06).

Example 350

3-(3-cyclohexyl-1,2,4-oxadiazol-5-yl)-2-methyl-7-(piperidin-4-yl)pyrazolo[1,5-a]pyrimidin-5(4H)-one hydrochloride

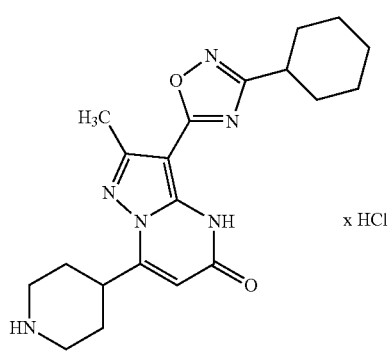 [SMILES: Cc1nn2c(C3CCNCC3)cc(=O)[nH]c2c1-c1nc(C2CCCCC2)no1]

tert-butyl 4-[3-(3-cyclohexyl-1,2,4-oxadiazol-5-yl)-2-methyl-5-oxo-4,5-dihydropyrazolo[1,5-a]pyrimidin-7-yl]piperidine-1-carboxylate (106 mg, 220 μmol) was dissolved in 1,4-dioxan (2.5 ml) and treated with hydrochloric acid in 1,4-dioxan (830 μl, 4.0 M, 3.3 mmol) at RT for 16 h. Solvents were removed, acetonitrile was added and the resulting participate was filtered and washed with acetonitrile. Drying in vacuo afforded the product. The obtained amount was 38.7 mg (100% purity, 42% of theory).

LC-MS (Method 1B): $R_t$=0.70 min; MS (ESIpos): m/z=383 [M+H]⁺

¹H-NMR (400 MHz, DMSO-d6) delta [ppm]: −0.156 (0.08), −0.015 (0.75), −0.006 (16.00), 0.140 (0.07), 1.141 (0.18), 1.221 (0.15), 1.230 (0.27), 1.238 (0.19), 1.252 (0.47), 1.260 (0.86), 1.268 (0.46), 1.282 (0.64), 1.290 (1.18), 1.298 (0.62), 1.312 (0.46), 1.320 (0.75), 1.349 (0.82), 1.356 (0.57), 1.379 (1.93), 1.387 (1.24), 1.410 (1.92), 1.432 (0.48), 1.440 (0.79), 1.448 (0.47), 1.517 (0.73), 1.525 (0.76), 1.549 (1.81), 1.554 (1.77), 1.578 (1.72), 1.584 (1.69), 1.607 (0.64), 1.615 (0.65), 1.667 (0.98), 1.687 (0.69), 1.697 (0.90), 1.747 (1.55), 1.754 (2.05), 1.763 (1.59), 1.777 (1.47), 1.786 (1.72), 1.795 (1.18), 1.835 (0.53), 1.866 (1.39), 1.892 (1.52), 1.923 (0.67), 1.974 (1.94), 1.980 (1.94), 2.006 (1.71), 2.068 (0.06), 2.173 (2.14), 2.206 (1.73), 2.322 (0.15), 2.361 (0.20), 2.398 (0.08), 2.560 (10.95), 2.665 (0.17), 2.705 (0.23), 2.718 (0.08), 2.787 (0.45), 2.796 (0.86), 2.805 (0.53), 2.815 (0.93), 2.824 (1.65), 2.833 (0.86), 2.843 (0.51), 2.852 (0.80), 2.860 (0.36), 3.080 (0.85), 3.109 (1.66), 3.139 (0.97), 3.375 (2.38), 3.406 (1.88), 3.562 (13.87), 3.605 (0.45), 3.739 (0.04), 6.109 (0.47), 8.773 (0.31), 8.912 (0.39), 11.327 (0.03), 11.507 (0.12), 12.721 (0.04).

Example 351

7-(piperidin-4-yl)-3-[4-(trifluoromethyl)-1,3-thiazol-2-yl]pyrazolo[1,5-a]pyrimidin-5 (4H)-one hydrochloride

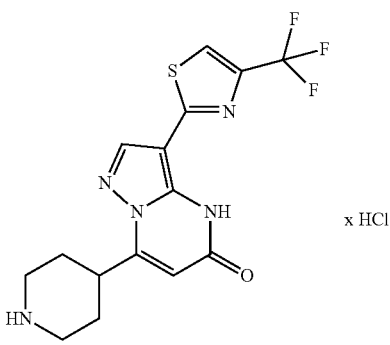 [SMILES: O=c1cc(C2CCNCC2)n2ncc(-c3nc(C(F)(F)F)cs3)c2[nH]1]

tert-butyl 4-{5-oxo-3-[4-(trifluoromethyl)-1,3-thiazol-2-yl]-4,5-dihydropyrazolo[1,5-a]pyrimidin-7-yl}piperidine-1-carboxylate (34.5 mg, 73.5 µmol) was dissolved in 1,4-dioxan (3 ml) and treated with hydrochloric acid in 1,4-dioxan (180 µl, 4.0 M, 730 µmol)) at RT for 16 h. Solvents were removed. Drying in vacuo afforded the product. The obtained amount was 35.0 mg (100% purity, 108% of theory).

LC-MS (Method 10B): $R_t$=1.07 min; MS (ESIpos): m/z=370 [M+H]⁺

¹H-NMR (400 MHz, DMSO-d6) delta [ppm]: 1.146 (0.70), 1.230 (1.37), 1.945 (8.44), 1.972 (9.26), 2.222 (12.83), 2.252 (10.78), 2.327 (1.23), 2.365 (1.26), 2.666 (1.26), 2.710 (1.03), 3.106 (9.23), 3.131 (9.61), 3.400 (13.57), 3.427 (11.87), 6.411 (2.68), 8.369 (16.00), 8.599 (10.97), 8.874 (3.72), 9.011 (4.64), 12.650 (0.63).

Example 352

3-fluoropropyl 5-oxo-7-(piperidin-4-yl)-4,5-dihydropyrazolo[1,5-a]pyrimidine-3-carboxylate hydrochloride

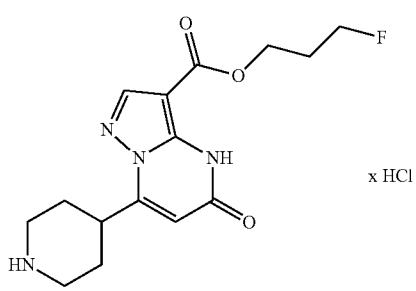 [SMILES: O=C(OCCCF)c1cnn2c(C3CCNCC3)cc(=O)[nH]c12]

3-fluoropropyl 7-[1-(tert-butoxycarbonyl)piperidin-4-yl]-5-oxo-4,5-dihydropyrazolo[1,5-a]pyrimidine-3-carboxylate (88.0 mg, 208 µmol) was dissolved in 1,4-dioxan (2.0 ml, 23 mmol) and treated with hydrochloric acid in 1,4-dioxan (780 µl, 4.0 M, 3.1 mmol) at RT for 3 h. Solvents were removed, acetonitrile was added and the resulting participate was filtered and washed with acetonitrile. Drying in vacuo afforded the product. The obtained amount was 65.8 mg (100% purity, 88% of theory).

LC-MS (Method 10B): $R_t$=0.86 min; MS (ESIpos): m/z=323 [M+H]⁺

1H-NMR (400 MHz, DMSO-d6) delta [ppm]: −0.150 (0.65), −0.009 (5.54), 0.007 (5.13), 0.145 (0.67), 1.109 (0.14), 1.146 (0.53), 1.236 (0.14), 1.412 (0.65), 1.594 (1.13), 1.752 (0.14), 1.839 (2.80), 1.871 (3.06), 1.901 (1.25), 2.030 (1.11), 2.045 (3.88), 2.060 (5.98), 2.075 (4.07), 2.091 (1.37), 2.096 (1.30), 2.112 (3.98), 2.127 (6.27), 2.142 (7.88), 2.181 (4.07), 2.327 (0.43), 2.366 (0.84), 2.523 (1.18), 2.584 (0.14), 2.664 (0.36), 2.669 (0.46), 2.674 (0.36), 2.709 (0.87), 3.065 (2.92), 3.091 (3.06), 3.370 (4.99), 3.401 (4.02), 3.481 (1.28), 3.512 (2.24), 3.541 (1.16), 3.566 (8.65), 4.324 (7.76), 4.340 (16.00), 4.356 (7.57), 4.502 (5.08), 4.517 (9.78), 4.531 (4.84), 4.620 (4.99), 4.635 (9.78), 4.650 (4.92), 6.014 (2.72), 8.234 (5.88), 8.707 (0.60), 8.911 (0.75), 11.696 (1.45).

Example 353

2,2-difluoroethyl 5-oxo-7-(piperidin-4-yl)-4,5-dihydropyrazolo[1,5-a]pyrimidine-3-carboxylate hydrochloride

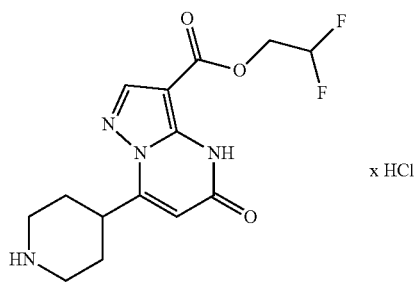 [SMILES: O=C(OCC(F)F)c1cnn2c(C3CCNCC3)cc(=O)[nH]c12]

2,2-difluoroethyl 7-[1-(tert-butoxycarbonyl)piperidin-4-yl]-5-oxo-4,5-dihydropyrazolo[1,5-a]pyrimidine-3-carboxylate (83.3 mg, 195 µmol) was dissolved in 1,4-dioxan (2.0 ml, 23 mmol) and treated with hydrochloric acid in 1,4-dioxan (730 µl, 4.0 M, 2.9 mmol) at RT for 3 h. Solvents were removed, acetonitrile was added and the resulting participate was filtered and washed with acetonitrile. Drying in vacuo afforded the product. The obtained amount was 68.7 mg (100% purity, 97% of theory).

LC-MS (Method 11B): $R_t$=0.57 min; MS (ESIpos): m/z=327 [M+H]⁺

¹H-NMR (400 MHz, DMSO-d6) delta [ppm]: −0.155 (0.16), −0.013 (1.49), 0.141 (0.15), 1.143 (0.22), 1.591 (0.48), 1.876 (1.48), 1.902 (4.25), 1.908 (4.27), 1.934 (4.87), 1.964 (2.12), 2.134 (7.11), 2.167 (5.38), 2.327 (0.21), 2.331 (0.16), 2.365 (0.35), 2.585 (0.09), 2.664 (0.14), 2.669 (0.19), 2.673 (0.13), 2.709 (0.36), 3.040 (4.00), 3.067 (4.13), 3.092 (1.91), 3.160 (0.14), 3.372 (7.91), 3.486 (1.91), 3.516 (3.40), 3.545 (1.74), 3.563 (7.31), 4.487 (5.26), 4.496 (5.79), 4.524 (10.87), 4.533 (11.27), 4.561 (5.40), 4.570 (5.13), 6.017 (3.95), 6.246 (1.63), 6.255 (3.37), 6.264 (1.58), 6.383 (3.15), 6.392 (6.75), 6.401 (3.23), 6.520 (1.43), 6.529 (3.07), 6.538 (1.55), 7.676 (15.12), 7.679 (16.00), 7.927 (0.08), 8.258 (12.93), 8.497 (0.09), 9.115 (6.78), 9.221 (1.43), 9.288 (1.91), 11.918 (0.16), 14.592 (0.21).

Example 354

2,2,2-trifluoroethyl 5-oxo-7-(piperidin-4-yl)-4,5-dihydropyrazolo[1,5-a]pyrimidine-3-carboxylate hydrochloride

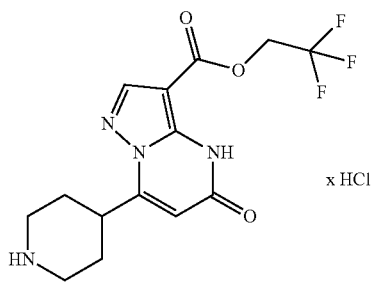 [SMILES: O=C(OCC(F)(F)F)c1cnn2c(C3CCNCC3)cc(=O)[nH]c12]

2,2,2-trifluoroethyl 7-[1-(tert-butoxycarbonyl)piperidin-4-yl]-5-oxo-4,5-dihydropyrazolo[1,5-a]pyrimidine-3-carboxylate (110 mg, 247 µmol) was dissolved in 1,4-dioxan (2.0 ml, 23 mmol) and treated with hydrochloric acid in 1,4-dioxan (930 µl, 4.0 M, 3.7 mmol) at RT for 16 h. Solvents were removed, acetonitrile was added and the resulting participate was filtered and washed with acetonitrile. Drying in vacuo afforded the product. The obtained amount was 86.2 mg (100% purity, 92% of theory).

LC-MS (Method 11B): $R_t$=0.68 min; MS (ESIpos): m/z=345 [M+H]$^+$ $^1$H-NMR (400 MHz, DMSO-d6) delta [ppm]: −0.153 (0.04), 0.143 (0.05), 1.070 (0.02), 1.088 (0.04), 1.105 (0.02), 1.145 (0.06), 1.593 (0.11), 1.859 (0.26), 1.885 (0.76), 1.916 (0.84), 1.948 (0.34), 2.072 (0.13), 2.141 (1.24), 2.173 (0.95), 2.327 (0.05), 2.365 (0.08), 2.590 (0.02), 2.669 (0.06), 2.709 (0.09), 3.035 (0.59), 3.065 (1.12), 3.096 (0.63), 3.353 (1.53), 3.385 (1.10), 3.492 (0.33), 3.522 (0.60), 3.565 (16.00), 3.640 (0.02), 3.730 (0.04), 3.741 (0.03), 3.774 (0.05), 4.885 (0.90), 4.908 (2.53), 4.930 (2.39), 4.953 (0.73), 6.054 (0.44), 7.434 (0.02), 8.288 (1.57), 8.851 (0.03), 9.101 (0.21), 12.050 (0.06).

Example 355

3,3,3-trifluoropropyl 5-oxo-7-(piperidin-4-yl)-4,5-dihydropyrazolo[1,5-a]pyrimidine-3-carboxylate hydrochloride

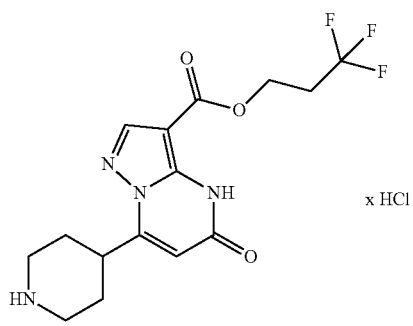 [SMILES: O=C(OCCC(F)(F)F)c1cnn2c(C3CCNCC3)cc(=O)[nH]c12]

3,3,3-trifluoropropyl 7-[1-(tert-butoxycarbonyl)piperidin-4-yl]-5-oxo-4,5-dihydropyrazolo[1,5-a]pyrimidine-3-carboxylate (72.1 mg, 157 µmol) was dissolved in 1,4-dioxan (1.5 ml, 18 mmol) and treated with hydrochloric acid in 1,4-dioxan (590 µl, 4.0 M, 2.4 mmol) at RT for 16 h. Solvents were removed, acetonitrile was added and the resulting participate was filtered and washed with acetonitrile. Drying in vacuo afforded the product. The obtained amount was 59.2 mg (100% purity, 95% of theory).

LC-MS (Method 11B): $R_t$=0.72 min; MS (ESIpos): m/z=359 [M+H]$^+$ $^1$H-NMR (400 MHz, DMSO-d6) delta [ppm]: −0.153 (0.12), −0.012 (1.15), 0.143 (0.14), 0.918 (0.15), 1.070 (0.41), 1.088 (0.86), 1.105 (0.43), 1.145 (0.16), 1.753 (0.39), 1.833 (1.01), 1.842 (1.24), 1.867 (3.34), 1.874 (3.43), 1.898 (3.79), 1.906 (3.70), 1.930 (1.68), 1.939 (1.43), 2.142 (5.35), 2.175 (4.23), 2.327 (0.16), 2.366 (0.20), 2.669 (0.17), 2.674 (0.13), 2.710 (0.22), 2.776 (0.93), 2.791 (1.90), 2.804 (3.33), 2.819 (5.53), 2.834 (4.86), 2.848 (5.42), 2.863 (3.42), 2.876 (1.82), 2.892 (0.95), 3.065 (3.47), 3.093 (2.04), 3.174 (0.08), 3.356 (5.72), 3.371 (2.40), 3.389 (4.98), 3.479 (1.45), 3.509 (2.65), 3.538 (1.33), 3.565 (4.45), 3.590 (0.10), 4.269 (0.08), 4.445 (8.23), 4.461 (16.00), 4.476 (7.98), 4.646 (0.08), 6.013 (4.22), 8.214 (14.71), 8.948 (0.93), 9.079 (1.14), 11.729 (1.15).

Example 356

Cyclobutyl 5-oxo-7-(piperidin-4-yl)-4,5-dihydropyrazolo[1,5-a]pyrimidine-3-carboxylate hydrochloride

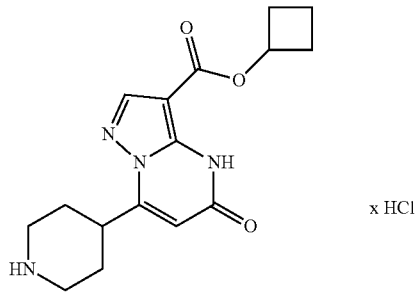 [SMILES: O=C(OC1CCC1)c1cnn2c(C3CCNCC3)cc(=O)[nH]c12]

cyclobutyl 7-[1-(tert-butoxycarbonyl)piperidin-4-yl]-5-oxo-4,5-dihydropyrazolo[1,5-a]pyrimidine-3-carboxylate (120 mg, 288 µmol) was dissolved in 1,4-dioxan (2.0 ml, 23 mmol) and treated with hydrochloric acid in 1,4-dioxan (1.1 ml, 4.0 M, 4.3 mmol) at RT for 16 h. Solvents were removed, acetonitrile was added and the resulting participate was filtered and washed with acetonitrile. Drying in vacuo afforded the product. The obtained amount was 70.7 mg (100% purity, 70% of theory).

LC-MS (Method 11B): $R_t$=0.75 min; MS (ESIpos): m/z=317 [M+H]$^+$ $^1$H-NMR (400 MHz, DMSO-d6) delta [ppm]: −0.151 (0.61), −0.010 (5.64), 0.006 (6.12), 0.144 (0.69), 0.344 (0.26), 0.359 (0.29), 0.516 (0.24), 0.536 (0.21), 1.146 (0.71), 1.567 (0.58), 1.594 (2.19), 1.613 (4.24), 1.639 (4.88), 1.660 (2.77), 1.665 (2.19), 1.685 (1.08), 1.738 (1.42), 1.744 (1.08), 1.763 (3.82), 1.787 (3.69), 1.805 (2.27), 1.813 (2.69), 1.837 (4.85), 1.869 (5.38), 1.901 (2.24), 2.072 (0.55), 2.147 (7.70), 2.180 (6.27), 2.219 (3.87), 2.224 (3.95), 2.244 (6.75), 2.249 (6.38), 2.269 (7.12), 2.274 (7.01), 2.281 (5.25), 2.294 (7.96), 2.299 (8.28), 2.313 (4.88), 2.320 (5.98), 2.343 (1.71), 2.366 (1.03), 2.664 (0.50), 2.669 (0.61), 2.674 (0.47), 2.709 (0.98), 3.065 (4.27), 3.086 (4.40), 3.368 (7.93), 3.399 (6.48), 3.480

(2.06), 3.509 (3.74), 3.538 (1.92), 3.566 (16.00), 4.074 (0.45), 4.092 (0.47), 4.292 (0.21), 5.076 (1.24), 5.095 (4.72), 5.114 (6.93), 5.133 (4.61), 5.151 (1.19), 5.793 (0.21), 5.867 (0.18), 6.015 (5.11), 7.800 (0.21), 8.194 (12.02), 8.718 (1.13), 8.904 (1.40), 11.656 (1.98).

Example 357

Methyl 5-oxo-7-(piperidin-4-yl)-4,5-dihydropyrazolo[1,5-a]pyrimidine-3-carboxylate hydrochloride

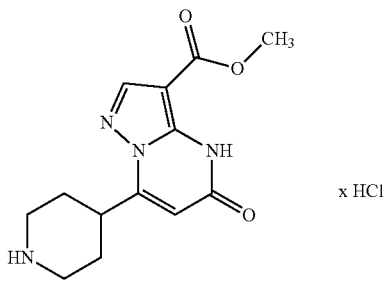 [SMILES: COC(=O)c1cnn2c(C3CCNCC3)cc(=O)[nH]c12]

methyl 7-[1-(tert-butoxycarbonyl)piperidin-4-yl]-5-oxo-4,5-dihydropyrazolo[1,5-a]pyrimidine-3-carboxylate (127 mg, 336 µmol) was dissolved in 1,4-dioxan (2.1 ml, 25 mmol) and treated with hydrochloric acid in 1,4-dioxan (1.3 ml, 4.0 M, 5.0 mmol) at RT for 16 h. Solvents were removed, acetonitrile was added and the resulting participate was filtered and washed with acetonitrile. Drying in vacuo afforded the product. The obtained amount was 56.8 mg (100% purity, 54% of theory).

LC-MS (Method 10B): $R_t$=0.71 min; MS (ESIpos): m/z=277 [M+H]$^+$ $^1$H-NMR (500 MHz, DMSO-d6) delta [ppm]: −0.122 (0.03), −0.009 (0.26), 0.114 (0.03), 1.089 (0.02), 1.146 (0.08), 1.176 (0.02), 1.191 (0.05), 1.206 (0.02), 1.232 (0.08), 1.829 (0.30), 1.836 (0.36), 1.856 (0.93), 1.862 (0.94), 1.881 (1.02), 1.887 (0.98), 1.907 (0.44), 1.914 (0.37), 2.012 (0.01), 2.150 (1.39), 2.176 (1.16), 2.358 (0.05), 2.361 (0.07), 2.635 (0.07), 2.638 (0.05), 3.032 (0.36), 3.057 (1.00), 3.079 (1.05), 3.104 (0.40), 3.365 (1.63), 3.387 (1.68), 3.448 (0.05), 3.460 (0.08), 3.483 (0.38), 3.506 (0.68), 3.530 (0.34), 3.625 (0.09), 3.653 (0.02), 3.665 (0.04), 3.668 (0.03), 3.677 (0.04), 3.700 (0.04), 3.710 (0.04), 3.722 (0.02), 3.775 (16.00), 3.826 (0.02), 3.920 (0.08), 4.018 (0.03), 6.002 (0.76), 8.227 (2.42), 8.804 (0.32), 8.822 (0.33), 8.983 (0.42), 9.000 (0.36), 11.798 (0.45).

Example 358

Propyl 5-oxo-7-(piperidin-4-yl)-4,5-dihydropyrazolo[1,5-a]pyrimidine-3-carboxylate hydrochloride

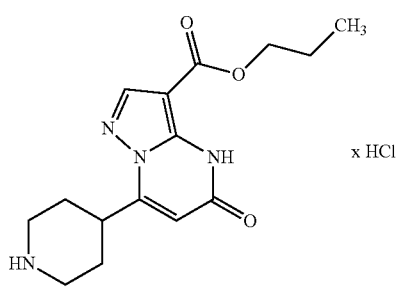 [SMILES: CCCOC(=O)c1cnn2c(C3CCNCC3)cc(=O)[nH]c12]

propyl 7-[1-(tert-butoxycarbonyl)piperidin-4-yl]-5-oxo-4,5-dihydropyrazolo[1,5-a]pyrimidine-3-carboxylate (84.0 mg, 208 µmol) was dissolved in 1,4-dioxan (2.0 ml, 23 mmol) and treated with hydrochloric acid in 1,4-dioxan (780 µl, 4.0 M, 3.1 mmol) at RT for 16 h. Solvents were removed, acetonitrile was added and the resulting participate was filtered and washed with acetonitrile. Drying in vacuo afforded the product. The obtained amount was 68.8 mg (100% purity, 97% of theory).

LC-MS (Method 1B): $R_t$=0.46 min; MS (ESIpos): m/z=305 [M+H]$^+$ $^1$H-NMR (500 MHz, DMSO-d6) delta [ppm]: −0.121 (0.04), −0.008 (0.38), 0.115 (0.04), 0.777 (0.02), 0.792 (0.03), 0.807 (0.02), 0.853 (0.02), 0.870 (0.02), 0.905 (2.87), 0.920 (6.40), 0.935 (3.09), 1.028 (0.02), 1.043 (0.03), 1.058 (0.02), 1.089 (0.02), 1.146 (0.13), 1.234 (0.11), 1.412 (0.02), 1.663 (0.25), 1.678 (1.05), 1.692 (2.02), 1.706 (2.02), 1.721 (0.97), 1.735 (0.22), 1.753 (0.04), 1.813 (0.22), 1.820 (0.26), 1.840 (0.69), 1.846 (0.70), 1.865 (0.74), 1.871 (0.72), 1.890 (0.32), 1.898 (0.27), 1.934 (0.02), 2.002 (0.02), 2.018 (0.02), 2.072 (2.05), 2.152 (1.02), 2.179 (0.87), 2.321 (0.05), 2.343 (0.03), 2.358 (0.08), 2.361 (0.12), 2.365 (0.08), 2.631 (0.09), 2.635 (0.12), 2.639 (0.09), 3.067 (0.60), 3.088 (0.62), 3.110 (0.28), 3.218 (0.04), 3.372 (1.08), 3.397 (0.90), 3.430 (0.06), 3.486 (0.26), 3.510 (0.45), 3.534 (0.25), 3.566 (16.00), 3.698 (0.02), 3.707 (0.02), 3.715 (0.02), 3.737 (0.02), 4.018 (0.04), 4.045 (0.02), 4.142 (0.02), 4.180 (1.68), 4.194 (3.49), 4.208 (1.65), 4.274 (0.02), 4.339 (0.02), 6.011 (0.49), 6.167 (0.02), 7.061 (0.02), 7.163 (0.02), 7.267 (0.02), 7.669 (0.48), 8.209 (1.53), 8.680 (0.21), 8.884 (0.26), 9.045 (0.17), 11.662 (0.11).

Example 359

3-(7-oxa-1-azaspiro[3.5]non-1-ylcarbonyl)-7-(piperidin-4-yl)pyrazolo[1,5-a]pyrimidin-5(4H)-one trifluoroacetate

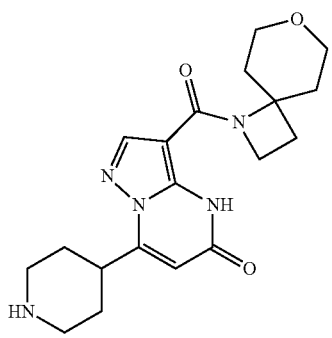

tert-butyl 4-[3-(7-oxa-1-azaspiro[3.5]non-1-ylcarbonyl)-5-oxo-4,5-dihydropyrazolo[1,5-a]pyrimidin-7-yl]piperidine-1-carboxylate (57.9 mg, 123 µmol) was dissolved in Dichloromethane (1.0 ml) and treated with trifluoroacetic acid (47 µl, 610 µmol) at RT for 16 h. Another 250 µl trifluoroacetic acid was added and the mixture stirred at RT for 6 h. The mixture was purified via reverse phase HPLC (Method: column: Reprosil C18; 10 µm; 125×30 mm/flow: 50 ml/min/solvents: A=water (0.1% formic acid), B=acetonitrile/gradient: 0.00-5.00 min=10% B, 6.50 min=20% B, 17.0-19.75 min=100% B, 19.75.00-23.00 min=90% B). The residue was dissolved in Dichloromethane (1.0 ml) and 250 µl trifluoroacetic acid were added.

Solvents were removed in vacuo to afford the product. The obtained amount was 14.3 mg (90% purity, 22% of theory).

LC-MS (Method 10B): R$_t$=0.80 min; MS (ESIpos): m/z=372 [M+H]$^+$ $^1$H-NMR (500 MHz, DMSO-d6) delta [ppm]: −0.121 (1.15), −0.008 (10.23), 0.006 (10.60), 0.116 (1.15), 0.853 (0.32), 1.146 (1.36), 1.235 (2.35), 1.258 (1.02), 1.298 (0.37), 1.351 (0.80), 1.602 (0.37), 1.814 (1.39), 1.821 (1.74), 1.840 (4.49), 1.847 (4.91), 1.853 (4.09), 1.865 (7.13), 1.873 (7.51), 1.882 (7.16), 1.891 (6.06), 1.901 (5.53), 1.910 (3.74), 2.013 (5.16), 2.041 (3.77), 2.182 (9.75), 2.196 (11.99), 2.207 (10.20), 2.358 (0.83), 2.361 (1.18), 2.365 (0.85), 2.635 (1.50), 2.638 (1.23), 2.890 (0.32), 3.087 (2.11), 3.112 (5.13), 3.134 (5.29), 3.160 (2.43), 3.415 (7.99), 3.440 (7.35), 3.582 (6.54), 3.606 (8.31), 3.629 (6.94), 3.679 (11.35), 3.691 (16.00), 3.703 (11.06), 3.718 (7.67), 3.726 (10.07), 3.741 (9.22), 3.750 (12.13), 3.758 (7.99), 3.810 (7.37), 3.814 (8.04), 3.833 (10.18), 3.852 (5.56), 3.857 (5.26), 4.376 (0.43), 5.753 (14.80), 6.385 (3.63), 8.439 (1.55), 8.458 (1.68), 8.590 (6.46), 8.727 (2.06), 8.750 (1.90).

Example 360

N-methyl-5-oxo-N-[(1S)-1-phenylethyl]-7-(piperidin-4-yl)-4,5-dihydropyrazolo[1,5-a]pyrimidine-3-carboxamide hydrochloride

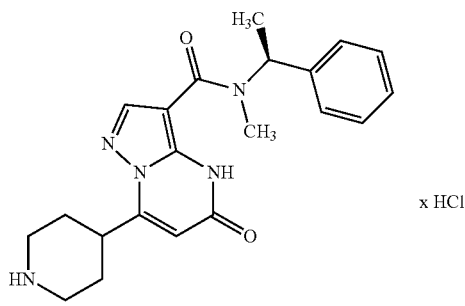 [SMILES: C[C@@H](c1ccccc1)N(C)C(=O)c1cnn2c(C3CCNCC3)cc(=O)[nH]c12]

tert-butyl 4-(3-{methyl[(1S)-1-phenylethyl]carbamoyl}-5-oxo-4,5-dihydropyrazolo[1,5-a]pyrimidin-7-yl)piperidine-1-carboxylate (79.7 mg, 166 μmol) was dissolved in 1,4-dioxan (2.0 ml, 23 mmol) and treated with hydrochloric acid in 1,4-dioxan (620 μl, 4.0 M, 2.5 mmol) at RT for 16 h. Solvents were removed, acetonitrile was added and the resulting participate was filtered and washed with acetonitrile. Drying in vacuo afforded the product. The obtained amount was 15.1 mg (95% purity, 21% of theory).

LC-MS (Method 1B): R$_t$=0.57 min; MS (ESIpos): m/z=380 [M+H]$^+$ $^1$H-NMR (400 MHz, DMSO-d6) delta [ppm]: −1.264 (0.07), −0.150 (0.75), −0.023 (0.14), −0.020 (0.27), −0.015 (0.75), −0.009 (6.58), 0.007 (6.92), 0.015 (0.88), 0.018 (0.61), 0.021 (0.47), 0.026 (0.34), 0.030 (0.27), 0.052 (0.20), 0.145 (0.81), 0.212 (0.07), 0.885 (0.27), 1.127 (0.27), 1.146 (1.02), 1.234 (0.54), 1.355 (5.83), 1.563 (7.73), 1.579 (7.86), 1.751 (0.14), 1.834 (2.64), 1.865 (2.92), 1.897 (1.22), 2.169 (4.14), 2.202 (3.46), 2.322 (0.54), 2.327 (0.75), 2.331 (0.54), 2.366 (1.29), 2.522 (2.17), 2.524 (2.03), 2.560 (0.95), 2.567 (0.68), 2.578 (0.47), 2.582 (0.47), 2.665 (0.75), 2.669 (0.95), 2.674 (0.75), 2.709 (1.49), 2.847 (4.34), 3.075 (2.64), 3.104 (2.85), 3.202 (0.07), 3.263 (0.27), 3.359 (1.63), 3.379 (5.15), 3.410 (4.34), 3.445 (0.75), 3.450 (0.81), 3.455 (0.81), 3.461 (1.90), 3.473 (2.44), 3.489 (2.51), 3.514 (2.37), 3.544 (1.15), 3.567 (4.88), 3.624 (0.27), 3.640 (0.47), 3.650 (0.54), 3.654 (0.75), 3.661 (0.81), 3.666 (1.63), 3.670 (1.29), 3.677 (1.76), 3.680 (2.10), 3.698 (1.97), 3.700 (1.83), 3.707 (1.22), 3.711 (1.63), 3.716 (0.81), 3.723 (0.75), 3.728 (0.47), 3.810 (0.20), 3.838 (0.20), 3.860 (0.20), 4.018 (1.15), 4.141 (0.14), 4.187 (0.20), 4.208 (0.14), 4.233 (0.14), 4.310 (0.14), 4.436 (0.14), 4.608 (0.27), 5.415 (0.07), 5.561 (0.14), 5.682 (0.20), 5.835 (0.41), 5.923 (0.27), 5.989 (5.08), 6.348 (0.27), 6.632 (0.27), 6.869 (0.41), 7.150 (0.07), 7.271 (1.42), 7.288 (4.14), 7.305 (2.92), 7.309 (2.64), 7.333 (3.46), 7.350 (11.80), 7.357 (16.00), 7.374 (9.22), 7.394 (2.58), 7.565 (0.07), 8.147 (0.81), 8.537 (0.88), 8.794 (1.08), 11.389 (0.61), 17.644 (0.07).

Example 361

N-methyl-5-oxo-7-(piperidin-4-yl)-N-(pyridin-2-ylmethyl)-4,5-dihydropyrazolo[1,5-a]pyrimidine-3-carboxamide hydrochloride

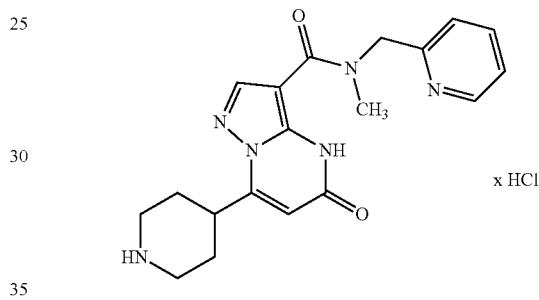

tert-butyl 4-{3-[methyl(pyridin-2-ylmethyl)carbamoyl]-5-oxo-4,5-dihydropyrazolo[1,5-a]pyrimidin-7-yl}piperidine-1-carboxylate (111 mg, 239 μmol) was dissolved in 1,4-dioxan (2.0 ml, 23 mmol) and treated with hydrochloric acid in 1,4-dioxan (900 μl, 4.0 M, 3.6 mmol) at RT for 16 h. Solvents were removed, acetonitrile was added and the resulting participate was filtered and washed with acetonitrile. Drying in vacuo afforded the product. The obtained amount was 20.2 mg (95% purity, 18% of theory).

LC-MS (Method 10B): R$_t$=0.82 min; MS (ESIpos): m/z=367 [M+H]$^+$ $^1$H-NMR (400 MHz, DMSO-d6) delta [ppm]: −0.010 (0.26), 0.006 (0.41), 1.146 (0.23), 1.234 (0.24), 1.354 (1.90), 1.833 (0.39), 1.865 (1.10), 1.891 (1.22), 1.922 (0.52), 1.986 (0.10), 2.001 (0.07), 2.158 (1.70), 2.190 (1.40), 2.327 (0.19), 2.365 (0.26), 2.669 (0.25), 2.709 (0.31), 2.737 (0.07), 3.036 (0.66), 3.058 (1.63), 3.063 (1.56), 3.090 (1.56), 3.123 (0.88), 3.166 (4.32), 3.297 (0.51), 3.368 (2.45), 3.387 (2.58), 3.400 (2.49), 3.449 (2.59), 3.460 (3.55), 3.473 (4.61), 3.491 (6.45), 3.501 (7.48), 3.544 (10.54), 3.566 (16.00), 3.645 (2.78), 3.654 (2.39), 3.660 (2.17), 3.665 (2.39), 3.669 (2.15), 3.679 (2.26), 3.697 (1.90), 3.699 (1.86), 3.706 (1.50), 3.711 (1.61), 3.715 (1.21), 3.722 (1.11), 3.727 (1.00), 3.839 (0.52), 3.858 (0.51), 4.018 (0.21), 4.131 (0.33), 4.186 (0.31), 4.207 (0.28), 4.327 (0.09), 4.851 (4.29), 5.966 (0.46), 5.985 (3.56), 6.346 (0.31), 6.868 (0.15), 7.565 (0.95), 8.061 (0.56), 8.141 (0.93), 8.163 (1.48), 8.665 (1.24), 8.677 (1.16), 8.770 (0.37), 8.956 (0.46).

Example 362

3-[(4,4-difluoropiperidin-1-yl)carbonyl]-7-(piperidin-4-yl)pyrazolo[1,5-a]pyrimidin-5 (4H)-one hydrochloride

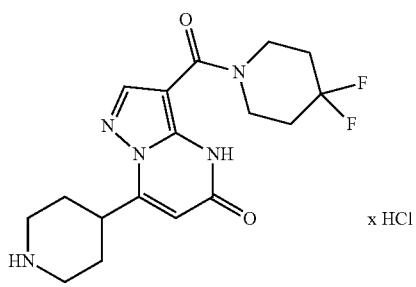 [SMILES: O=C(c1cnn2c(C3CCNCC3)cc(=O)[nH]c12)N1CCC(F)(F)CC1]

tert-butyl 4-{3-[(4,4-difluoropiperidin-1-yl)carbonyl]-5-oxo-4,5-dihydropyrazolo[1,5-a]pyrimidin-7-yl}piperidine-1-carboxylate (39.0 mg, 83.8 µmol) was dissolved in 1,4-dioxan (1.0 ml, 12 mmol) and treated with hydrochloric acid in 1,4-dioxan (310 µl, 4.0 M, 1.3 mmol) at RT for 16 h. Acetonitrile was added and the resulting participate was filtered and washed with acetonitrile. Drying in vacuo afforded the product. The obtained amount was 5.60 mg (100% purity, 17% of theory).

LC-MS (Method 11B): $R_t$=0.62 min; MS (ESIpos): m/z=366 [M+H]$^+$ $^1$H-NMR (400 MHz, DMSO-d6) delta [ppm]: −0.009 (2.41), 0.007 (1.75), 0.145 (0.22), 1.146 (1.32), 1.234 (0.66), 1.801 (0.66), 1.830 (1.97), 1.856 (2.19), 1.888 (1.10), 2.000 (2.41), 2.018 (3.51), 2.033 (4.38), 2.048 (3.51), 2.068 (2.41), 2.167 (3.29), 2.201 (2.85), 2.248 (0.22), 2.327 (1.10), 2.331 (0.88), 2.366 (1.75), 2.405 (0.22), 2.523 (2.19), 2.569 (0.44), 2.575 (0.44), 2.586 (0.22), 2.660 (0.44), 2.669 (1.10), 2.673 (0.88), 2.709 (1.53), 3.064 (1.75), 3.091 (3.29), 3.125 (1.97), 3.194 (0.22), 3.234 (0.44), 3.262 (0.66), 3.272 (1.53), 3.294 (10.30), 3.363 (1.97), 3.382 (4.60), 3.414 (3.51), 3.510 (1.32), 3.566 (16.00), 3.592 (1.10), 3.635 (6.14), 3.649 (8.77), 3.663 (6.14), 3.699 (0.66), 4.645 (0.44), 5.941 (1.97), 8.054 (2.41), 8.683 (0.44), 11.773 (0.44).

Example 363

3-{[(2S)-2-methylpyrrolidin-1-yl]methyl}-7-(piperidin-4-yl)pyrazolo[1,5-a]pyrimidin-5(4H)-one hydrochloride

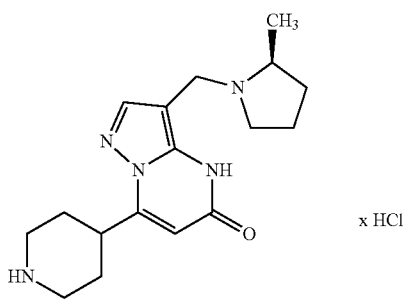 [SMILES: C[C@H]1CCCN1Cc1cnn2c(C3CCNCC3)cc(=O)[nH]c12]

tert-butyl 4-(3-{[(2S)-2-methylpyrrolidin-1-yl]methyl}-5-oxo-4,5-dihydropyrazolo[1,5-a]pyrimidin-7-yl)piperidine-1-carboxylate (12.8 mg, 30.8 µmol) was dissolved in 1,4-dioxan (2.0 ml, 23 mmol) and treated with hydrochloric acid in 1,4-dioxan (120 µl, 4.0 M, 460 µmol). Solvents were removed in vacuo to afford the product. The obtained amount was 9.30 mg (95% purity, 82% of theory).

LC-MS (Method 10B): $R_t$=0.55 min; MS (ESIpos): m/z=316 [M+H]$^+$ $^1$H-NMR (400 MHz, DMSO-d6) delta [ppm]: −0.150 (0.10), −0.009 (0.97), 0.007 (0.71), 0.145 (0.09), 1.146 (0.18), 1.235 (0.12), 1.266 (0.07), 1.293 (0.24), 1.310 (0.24), 1.362 (0.23), 1.389 (2.06), 1.405 (2.06), 1.436 (0.09), 1.505 (0.05), 1.571 (0.13), 1.595 (0.30), 1.605 (0.20), 1.614 (0.29), 1.626 (0.27), 1.637 (0.20), 1.646 (0.28), 1.669 (0.14), 1.820 (0.29), 1.851 (0.73), 1.873 (0.72), 1.883 (0.74), 1.906 (0.50), 2.064 (0.07), 2.150 (0.68), 2.185 (0.63), 2.206 (0.33), 2.225 (0.27), 2.239 (0.18), 2.327 (0.16), 2.365 (0.21), 2.669 (0.12), 2.674 (0.09), 2.709 (0.16), 2.796 (0.06), 2.825 (0.06), 3.065 (0.62), 3.093 (0.74), 3.375 (0.81), 3.400 (0.80), 3.473 (0.21), 3.504 (0.33), 3.534 (0.18), 3.567 (16.00), 3.666 (0.04), 3.679 (0.06), 3.698 (0.06), 4.139 (0.24), 4.156 (0.27), 4.174 (0.31), 4.191 (0.30), 4.304 (0.04), 4.347 (0.05), 4.449 (0.33), 4.457 (0.33), 4.483 (0.28), 4.492 (0.26), 5.889 (0.67), 7.571 (0.09), 7.583 (0.08), 8.036 (0.83), 8.734 (0.15), 8.903 (0.17), 10.165 (0.10), 11.106 (0.05), 12.468 (0.06), 12.518 (0.50).

Example 364

Cyclobutyl 2-methyl-5-oxo-7-(piperidin-4-yl)-4,5-dihydropyrazolo[1,5-a]pyrimidine-3-carboxylate hydrochloride

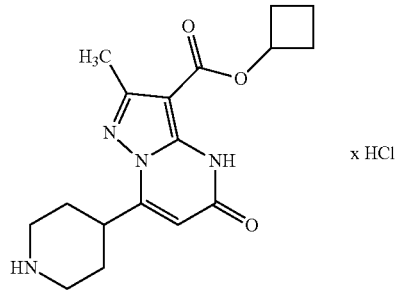 [SMILES: Cc1nn2c(C3CCNCC3)cc(=O)[nH]c2c1C(=O)OC1CCC1]

cyclobutyl 7-[1-(tert-butoxycarbonyl)piperidin-4-yl]-2-methyl-5-oxo-4,5-dihydropyrazolo[1,5-a]pyrimidine-3-carboxylate (92.7 mg, 215 µmol) was dissolved in 1,4-dioxan (2.0 ml, 23 mmol) and treated with hydrochloric acid in 1,4-dioxan (810 µl, 4.0 M, 3.2 mmol) at RT for 16 h. Acetonitrile was added and the resulting participate was filtered and washed with acetonitrile. Drying in vacuo afforded the product. The obtained amount was 61.1 mg (100% purity, 77% of theory).

LC-MS (Method 11B): $R_t$=0.88 min; MS (ESIpos): m/z=331 [M+H]$^+$ $^1$H-NMR (400 MHz, DMSO-d6) delta [ppm]: −0.151 (0.15), −0.010 (1.41), 0.006 (1.24), 0.144 (0.15), 0.349 (0.05), 0.353 (0.04), 0.362 (0.05), 0.506 (0.04), 0.530 (0.04), 0.924 (0.06), 1.146 (0.09), 1.569 (0.12), 1.594 (0.41), 1.616 (0.92), 1.642 (1.00), 1.663 (0.60), 1.688 (0.22), 1.712 (0.04), 1.735 (0.16), 1.742 (0.31), 1.758 (0.38), 1.767 (0.76), 1.774 (0.57), 1.791 (0.87), 1.831 (0.92), 1.861 (0.99), 1.893 (0.39), 2.072 (0.83), 2.133 (1.64), 2.166 (1.33), 2.213 (0.22), 2.218

(0.20), 2.237 (0.81), 2.242 (0.86), 2.261 (1.71), 2.266 (1.63), 2.281 (1.88), 2.286 (2.35), 2.294 (2.03), 2.299 (1.81), 2.303 (1.78), 2.312 (1.37), 2.321 (1.24), 2.365 (0.15), 2.422 (16.00), 2.436 (0.55), 2.582 (0.12), 2.664 (0.07), 2.669 (0.09), 2.709 (0.13), 3.051 (0.70), 3.081 (1.43), 3.113 (0.81), 3.356 (1.77), 3.388 (1.40), 3.466 (0.49), 3.496 (0.90), 3.526 (0.44), 3.566 (1.75), 4.078 (0.08), 4.097 (0.08), 5.076 (0.26), 5.095 (1.03), 5.114 (1.53), 5.132 (1.01), 5.151 (0.25), 5.933 (1.90), 8.922 (0.25), 11.211 (0.17).

Example 365

Propyl 2-methyl-5-oxo-7-(piperidin-4-yl)-4,5-dihydropyrazolo[1,5-a]pyrimidine-3-carboxylate hydrochloride

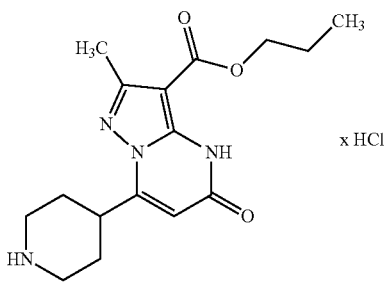 [SMILES: CCCOC(=O)c1c(C)nn2c(C3CCNCC3)cc(=O)[nH]c12]

propyl 7-[1-(tert-butoxycarbonyl)piperidin-4-yl]-2-methyl-5-oxo-4,5-dihydropyrazolo[1,5-a]pyrimidine-3-carboxylate (78.3 mg, 187 µmol) was dissolved in 1,4-dioxan (2.0 ml, 23 mmol) and treated with hydrochloric acid in 1,4-dioxan (700 µl, 4.0 M, 2.8 mmol) at RT for 16 h. Acetonitrile was added and the resulting participate was filtered and washed with acetonitrile. Drying in vacuo afforded the product.

The obtained amount was 49.2 mg (100% purity, 74% of theory).

LC-MS (Method 11B): $R_t$=0.85 min; MS (ESIpos): m/z=319 [M+H]$^+$ $^1$H-NMR (400 MHz, DMSO-d6) delta [ppm]: −0.151 (0.21), −0.010 (1.79), 0.006 (1.69), 0.144 (0.22), 0.765 (0.05), 0.906 (4.55), 0.924 (10.38), 0.943 (5.04), 1.072 (0.14), 1.079 (0.06), 1.089 (0.27), 1.107 (0.13), 1.146 (0.13), 1.412 (0.05), 1.594 (0.05), 1.658 (0.38), 1.676 (1.60), 1.693 (3.17), 1.712 (3.10), 1.729 (1.51), 1.747 (0.35), 1.827 (0.82), 1.856 (0.88), 1.887 (0.35), 2.072 (0.06), 2.137 (1.59), 2.170 (1.29), 2.263 (0.08), 2.327 (0.11), 2.331 (0.08), 2.365 (0.17), 2.427 (16.00), 2.523 (0.26), 2.525 (0.27), 2.570 (0.09), 2.579 (0.08), 2.585 (0.13), 2.664 (0.09), 2.669 (0.12), 2.673 (0.09), 2.709 (0.18), 3.054 (0.73), 3.085 (1.52), 3.117 (0.85), 3.358 (1.72), 3.391 (1.50), 3.469 (0.48), 3.498 (0.87), 3.528 (0.44), 3.566 (1.60), 4.184 (2.58), 4.201 (5.36), 4.217 (2.53), 5.929 (1.63), 8.857 (0.20), 11.258 (0.10).

Example 366

Propan-2-yl 2-methyl-5-oxo-7-(piperidin-4-yl)-4,5-dihydropyrazolo[1,5-a]pyrimidine-3-carboxylate hydrochloride

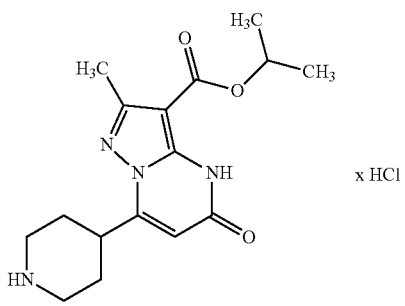 [SMILES: Cc1nn2c(C3CCNCC3)cc(=O)[nH]c2c1C(=O)OC(C)C]

propan-2-yl 7-[1-(tert-butoxycarbonyl)piperidin-4-yl]-2-methyl-5-oxo-4,5-dihydropyrazolo[1,5-a]pyrimidine-3-carboxylate (66.8 mg, 160 µmol) was dissolved in 1,4-dioxan (2.0 ml, 23 mmol) and treated with hydrochloric acid in 1,4-dioxan (600 µl, 4.0 M, 2.4 mmol) at RT for 3 h. Solvents were removed, acetonitrile was added and the resulting participate was filtered and washed with acetonitrile. Drying in vacuo afforded the product. The obtained amount was 55.1 mg (100% purity, 97% of theory).

LC-MS (Method 11B): $R_t$=0.79 min; MS (ESIpos): m/z=319 [M+H]$^+$ $^1$H-NMR (400 MHz, DMSO-d6) delta [ppm]: −0.010 (0.48), 0.006 (0.50), 1.315 (15.80), 1.330 (16.00), 1.796 (0.25), 1.827 (0.81), 1.859 (0.89), 1.890 (0.36), 2.072 (0.95), 2.134 (1.35), 2.168 (1.09), 2.366 (0.14), 2.419 (14.50), 2.578 (0.12), 2.709 (0.14), 3.038 (0.33), 3.068 (0.90), 3.098 (0.94), 3.126 (0.39), 3.387 (1.15), 3.467 (0.41), 3.497 (0.76), 3.526 (0.37), 5.084 (0.43), 5.100 (1.14), 5.116 (1.55), 5.131 (1.13), 5.147 (0.41), 5.931 (1.74), 8.790 (0.22), 8.936 (0.29), 11.027 (0.75).

Example 367

2,2,2-trifluoroethyl 2-methyl-5-oxo-7-(piperidin-4-yl)-4,5-dihydropyrazolo[1,5-a]pyrimidine-3-carboxylate hydrochloride

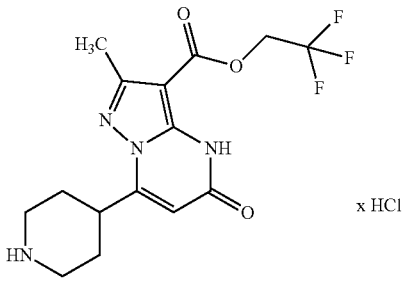 [SMILES: Cc1nn2c(C3CCNCC3)cc(=O)[nH]c2c1C(=O)OCC(F)(F)F]

2,2,2-trifluoroethyl 7-[1-(tert-butoxycarbonyl)piperidin-4-yl]-2-methyl-5-oxo-4,5-dihydropyrazolo[1,5-a]pyrimidine-3-carboxylate (109 mg, 237 µmol) was dissolved in 1,4-dioxan (2.4 ml, 28 mmol) and treated with hydrochloric acid in 1,4-dioxan (890 µl, 4.0 M, 3.6 mmol) at RT for 3 h.

Solvents were removed, acetonitrile was added and the resulting participate was filtered and washed with acetonitrile. Drying in vacuo afforded the product. The obtained amount was 93.4 mg (100% purity, 100% of theory).

LC-MS (Method 11B): $R_t$=0.80 min; MS (ESIpos): m/z=359 [M+H]$^+$ $^1$H-NMR (400 MHz, DMSO-d6) delta [ppm]: −0.010 (1.33), 0.006 (0.78), 1.145 (0.14), 1.832 (1.31), 1.863 (1.37), 2.072 (0.27), 2.136 (2.31), 2.170 (1.81), 2.327 (0.15), 2.366 (0.27), 2.431 (16.00), 2.518 (0.83), 2.709 (0.19), 3.073 (1.48), 3.101 (1.47), 3.129 (0.62), 3.360 (2.37), 3.390 (1.80), 3.474 (0.59), 3.503 (0.98), 3.532 (0.52), 3.566 (3.73), 4.884 (1.79), 4.907 (4.96), 4.929 (4.62), 4.952 (1.39), 5.976 (1.08), 8.754 (0.30), 8.912 (0.43), 11.645 (0.94).

Example 368

3-cyclopropyl-2-methyl-7-(piperidin-4-yl)pyrazolo[1,5-a]pyrimidin-5(4H)-one hydrochloride

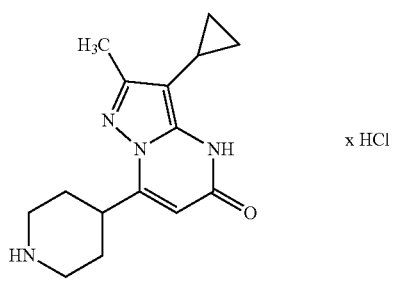 [SMILES: Cc1nn2c(C3CCNCC3)cc(=O)[nH]c2c1C1CC1]

Compound tert-butyl 4-(3-cyclopropyl-2-methyl-5-oxo-4,5-dihydropyrazolo[1,5-a]pyrimidin-7-yl)piperidine-1-carboxylate (758 mg, 2.04 mmol) was stirred overnight at room temperature with hydrochloric acid (4N solution in 1,4-dioxan, 15 ml). The mixture was diluted with diethyl ether (15 mL) and filtered. The recovered solid was dissolved in water and lyophilized to yield the title compound. The obtained amount was 639 mg (98% purity, 100% of theory).

LC-MS (Method 8B): $R_t$=0.53 min; MS (ESIneg): m/z=271 [M−H−xHCl]$^-$ $^1$H-NMR (400 MHz, DMSO-d6) delta [ppm]: 0.447 (0.60), 0.458 (2.19), 0.462 (2.16), 0.471 (2.34), 0.474 (2.20), 0.485 (0.72), 0.778 (0.82), 0.789 (2.21), 0.793 (2.18), 0.799 (1.14), 0.804 (1.14), 0.809 (2.33), 0.814 (2.17), 0.825 (0.78), 1.450 (0.33), 1.463 (0.67), 1.470 (0.70), 1.475 (0.47), 1.483 (1.25), 1.491 (0.45), 1.496 (0.65), 1.504 (0.61), 1.517 (0.28), 1.805 (0.30), 1.831 (0.90), 1.862 (1.02), 1.892 (0.41), 2.115 (1.45), 2.146 (1.16), 2.229 (16.00), 3.020 (0.36), 3.051 (1.00), 3.078 (1.03), 3.110 (0.41), 3.336 (1.39), 3.366 (1.13), 3.440 (0.25), 3.446 (0.45), 3.453 (0.31), 3.469 (0.53), 3.476 (0.87), 3.484 (0.51), 3.498 (0.31), 3.506 (0.43), 3.514 (0.25), 5.635 (3.30), 8.969 (0.33), 9.030 (0.46), 11.774 (0.04).

Example 369

3-{4-methyl-2-[4-(trifluoromethyl)phenyl]-1,3-thiazol-5-yl}-7-(piperidin-4-yl)pyrazolo[1,5-a]pyrimidin-5(4H)-one hydrochloride

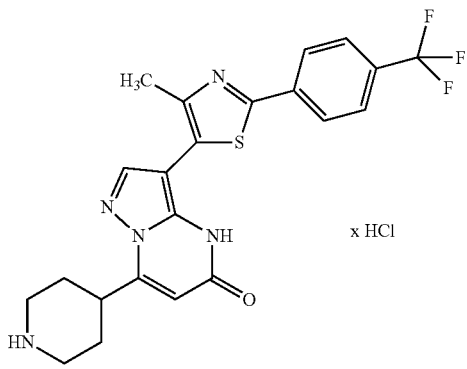 [SMILES: Cc1nc(-c2ccc(C(F)(F)F)cc2)sc1-c1cnn2c(C3CCNCC3)cc(=O)[nH]c12]

Compound tert-butyl 4-(5-[(4-methoxybenzyl)oxy]-3-{4-methyl-2-[4-(trifluoromethyl)phenyl]-1,3-thiazol-5-yl}pyrazolo[1,5-a]pyrimidin-7-yl)piperidine-1-carboxylate (115 mg, 169 µmol) was stirred overnight at room temperature with hydrochloric acid (4N solution in 1,4-dioxan, 4.0 ml). Another portion of hydrochloric acid (4N solution in 1,4-dioxan, 4.0 ml) was added and stirring was continued. The mixture was diluted with diethyl ether (16 mL) and filtered. The recovered solid was stirred overnight with a 1/2 mixture of methanol/diethyl ether and filtered again before being dissolved in water and lyophilized to yield the title compound. The obtained amount was 58.9 mg (100% purity, 70% of theory).

LC-MS (Method 8B): $R_t$=0.96 min; MS (ESIpos): m/z=460 [M+H−xHCl]$^+$ $^1$H-NMR (400 MHz, DMSO-d6) delta [ppm]: 1.844 (1.46), 1.881 (3.92), 1.912 (4.51), 1.941 (2.12), 2.224 (5.84), 2.256 (5.31), 3.081 (1.86), 3.111 (4.71), 3.138 (4.91), 3.170 (2.32), 3.572 (2.12), 5.921 (1.13), 7.864 (14.01), 7.885 (16.00), 8.123 (14.87), 8.144 (12.22), 8.522 (1.86), 8.787 (2.32), 12.222 (1.33).

Example 370

3-acetyl-7-(piperidin-4-yl)pyrazolo[1,5-a]pyrimidin-5(4H)-one hydrochloride

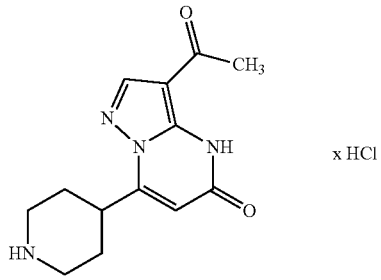 [SMILES: CC(=O)c1cnn2c(C3CCNCC3)cc(=O)[nH]c12]

Compound tert-butyl 4-{3-acetyl-5-[(4-methoxybenzyl)oxy]pyrazolo[1,5-a]pyrimidin-7-yl}piperidine-1-carboxylate (72.0 mg, 150 µmol) was stirred overnight at room

Example 371

7-(piperidin-4-yl)-3-propanoylpyrazolo[1,5-a]pyrimidin-5(4H)-one hydrochloride

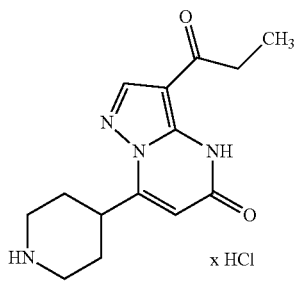 [SMILES: CCC(=O)c1cnn2c(C3CCNCC3)cc(=O)[nH]c12]

Compound tert-butyl 4-(5-oxo-3-propanoyl-4,5-dihydropyrazolo[1,5-a]pyrimidin-7-yl)piperidine-1-carboxylate (85.0 mg, 227 μmol) was stirred overnight at room temperature with hydrochloric acid (4N solution in 1,4-dioxan, 2.0 ml). The mixture was diluted and stirred with diethyl ether (10 mL) and methanol (1.0 mL) before being filtered. The recovered solid was dried in vacuo to yield the title compound. The obtained amount was 39.0 mg (100% purity, 88% of theory).

LC-MS (Method 10B): $R_t$=0.64 min; MS (ESIpos): m/z=261 [M+H-xHCl]$^+$ $^1$H-NMR (400 MHz, DMSO-d6) delta [ppm]: 1.800 (0.73), 1.833 (2.43), 1.866 (2.57), 1.898 (1.22), 2.157 (3.90), 2.193 (3.06), 2.435 (8.77), 3.048 (0.83), 3.080 (2.78), 3.110 (2.78), 3.135 (1.25), 3.380 (4.28), 3.410 (3.34), 3.524 (1.29), 6.049 (1.22), 8.431 (16.00), 8.542 (0.83), 8.782 (1.08), 11.413 (0.97).

Example 371

7-(piperidin-4-yl)-3-propanoylpyrazolo[1,5-a]pyrimidin-5(4H)-one hydrochloride

Compound tert-butyl 4-(5-oxo-3-propanoyl-4,5-dihydropyrazolo[1,5-a]pyrimidin-7-yl)piperidine-1-carboxylate (85.0 mg, 227 μmol) was stirred overnight at room temperature with hydrochloric acid (4N solution in 1,4-dioxan, 4.3 ml). The mixture was diluted and stirred for 30 min with diethyl ether (30 mL) and methanol (1.0 mL) before being filtered. The recovered solid was dried in vacuo to yield the title compound. The obtained amount was 66.0 mg (99% purity, 93% of theory).

LC-MS (Method 10B): $R_t$=0.75 min; MS (ESIpos): m/z=275 [M+H-xHCl]$^+$ $^1$H-NMR (500 MHz, DMSO-d6) delta [ppm]: 1.062 (7.32), 1.077 (16.00), 1.092 (7.76), 1.821 (0.54), 1.828 (0.66), 1.848 (1.67), 1.853 (1.74), 1.873 (1.86), 1.878 (1.80), 1.897 (0.79), 1.904 (0.69), 2.159 (2.43), 2.185 (2.15), 2.851 (1.39), 3.090 (1.80), 3.113 (1.10), 3.377 (3.22), 3.403 (2.62), 3.500 (0.60), 3.522 (0.92), 3.541 (0.57), 6.029 (0.88), 8.439 (10.64), 8.626 (0.50), 8.864 (0.60), 11.389 (0.28).

Example 372

3-(2-phenyl-1,3-oxazol-4-yl)-7-(piperidin-4-yl)pyrazolo[1,5-a]pyrimidin-5(4H)-one hydrochloride

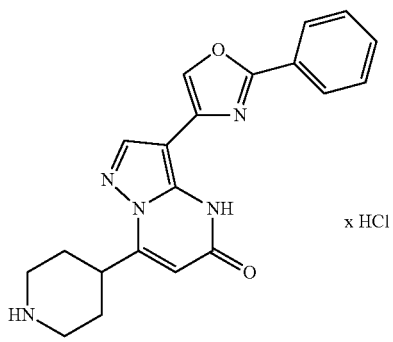 [SMILES: O=c1cc(C2CCNCC2)n2ncc(-c3coc(-c4ccccc4)n3)c2[nH]1]

Compound tert-butyl 4-{5-[(4-methoxybenzyl)oxy]-3-(2-phenyl-1,3-oxazol-4-yl)pyrazolo[1,5-a]pyrimidin-7-yl}piperidine-1-carboxylate (168 mg, 289 μmol) was stirred overnight at room temperature with hydrochloric acid (4N solution in 1,4-dioxan, 5.0 ml). The mixture was diluted with diethyl ether (16 mL) and filtered. The recovered solid was dried in vacuo to yield the title compound.

The obtained amount was 91.3 mg (100% purity, 79% of theory).

LC-MS (Method 8B): $R_t$=0.84 min; MS (ESIpos): m/z=362 [M+H-xHCl]$^+$ $^1$H-NMR (400 MHz, DMSO-d6) delta [ppm]: 1.832 (1.07), 1.864 (2.90), 1.896 (3.09), 1.929 (1.26), 2.210 (4.28), 2.240 (3.09), 3.071 (1.45), 3.103 (3.40), 3.134 (3.21), 3.161 (1.32), 3.401 (5.17), 3.433 (4.54), 5.945 (1.32), 7.551 (2.77), 7.560 (16.00), 7.566 (14.80), 7.574 (9.26), 7.578 (9.39), 7.587 (2.77), 8.081 (6.55), 8.086 (7.24), 8.095 (6.80), 8.097 (5.86), 8.105 (5.80), 8.259 (3.34), 8.549 (1.20), 8.648 (1.64), 8.779 (1.39), 11.755 (0.63).

Example 373

7-(piperidin-4-yl)-3-(1,2-thiazol-5-yl)pyrazolo[1,5-a]pyrimidin-5(4H)-one hydrochloride

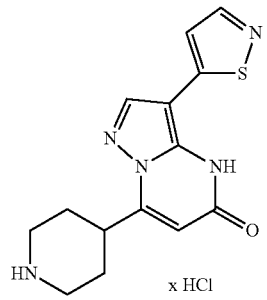 [SMILES: O=c1cc(C2CCNCC2)n2ncc(-c3ccns3)c2[nH]1]

tert-butyl 4-{5-[(4-methoxybenzyl)oxy]-3-(1,2-thiazol-5-yl)pyrazolo[1,5-a]pyrimidin-7-yl}piperidine-1-carboxylate (58.0 mg, 111 μmol)

Hydrochloric acid (4N solution in 1,4-dioxan, 2.1 ml)

The title compound was prepared according to the same procedure as Example 371. The obtained amount was 36.0 mg (100% purity, 96% of theory).

LC-MS (Method 10B): R$_t$=0.75 min; MS (ESIpos): m/z=302 [M+H-xHCl]$^+$ $^1$H-NMR (400 MHz, DMSO-d6) delta [ppm]: 1.856 (3.26), 1.886 (7.34), 1.917 (7.78), 1.948 (3.42), 2.176 (10.59), 2.208 (8.48), 3.032 (3.43), 3.064 (7.81), 3.092 (7.88), 3.123 (4.39), 3.356 (10.71), 3.384 (8.69), 3.594 (3.22), 3.630 (3.95), 3.650 (2.95), 6.276 (2.66), 7.708 (13.45), 8.468 (16.00), 8.807 (3.03), 8.954 (3.78).

Example 374

2-bromo-5-oxo-7-(piperidin-4-yl)-4,5-dihydropyrazolo[1,5-a]pyrimidine-3-carbonitrile hydrochloride

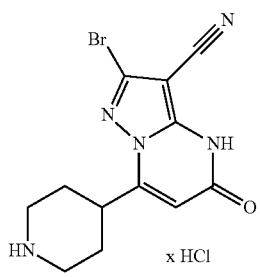 [SMILES: N#Cc1c(Br)nn2c(C3CCNCC3)cc(=O)[nH]c12]

tert-butyl 4-(2-bromo-3-cyano-5-oxo-4,5-dihydropyrazolo[1,5-a]pyrimidin-7-yl)piperidine-1-carboxylate (200 mg, 474 μmol) Hydrochloric acid (4N solution in 1,4-dioxan, 1.2 ml)

The title compound was prepared according to the same procedure as Example 373. The obtained amount was 169 mg (99% purity, 98% of theory).

LC-MS (Method 8B): R$_t$=0.25 min; MS (ESIpos): m/z=322 [M+H-xHCl]$^+$ $^1$H-NMR (400 MHz, DMSO-d6) delta [ppm]: 1.789 (3.04), 1.818 (8.83), 1.851 (9.63), 1.881 (4.05), 2.118 (14.19), 2.149 (11.37), 3.062 (3.62), 3.095 (9.27), 3.122 (10.21), 3.150 (4.27), 3.369 (16.00), 3.399 (12.52), 3.482 (3.55), 3.510 (6.08), 3.543 (4.34), 6.284 (3.26), 8.544 (2.90), 8.793 (4.42), 13.455 (2.97).

Example 375

3-(1-methyl-1H-pyrazol-5-yl)-7-(piperidin-4-yl) pyrazolo[1,5-a]pyrimidin-5(4H)-one hydrochloride

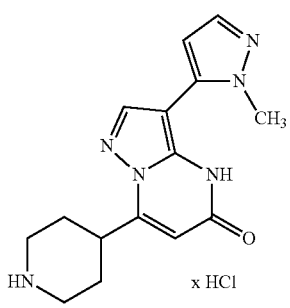 [SMILES: Cn1nccc1-c1cnn2c(C3CCNCC3)cc(=O)[nH]c12]

Compound tert-butyl 4-{5-[(4-methoxybenzyl)oxy]-3-(1-methyl-1H-pyrazol-5-yl)pyrazolo[1,5-a]pyrimidin-7-yl}piperidine-1-carboxylate (210 mg, 405 μmol) was stirred overnight at room temperature with hydrochloric acid (4N solution in 1,4-dioxan, 9.6 ml) and 1,4-dioxan (5.0 ml). The mixture was diluted with diethyl ether (16 mL), stirred and filtered. The recovered solid was dried in vacuo to yield the title compound. The obtained amount was 148 mg (86% purity, 93% of theory).

LC-MS (Method 1B): R$_t$=0.22 min; MS (ESIpos): m/z=299 [M+H-xHCl]$^+$ $^1$H-NMR (400 MHz, DMSO-d6) delta [ppm]: 1.903 (0.33), 1.912 (0.43), 1.936 (1.07), 1.944 (1.11), 1.968 (1.22), 1.975 (1.19), 2.000 (0.55), 2.008 (0.47), 2.188 (1.75), 2.221 (1.33), 3.039 (0.46), 3.070 (1.22), 3.098 (1.23), 3.129 (0.49), 3.365 (1.65), 3.396 (1.34), 3.577 (0.73), 3.584 (0.98), 3.607 (0.34), 3.614 (0.46), 3.772 (16.00), 5.983 (1.76), 6.405 (2.80), 7.506 (3.25), 8.062 (3.45), 9.161 (0.43), 9.255 (0.54).

Example 376

3-[2-(morpholin-4-yl)-1,3-thiazol-5-yl]-7-(piperidin-4-yl)pyrazolo[1,5-a]pyrimidin-5 (4H)-one hydrochloride

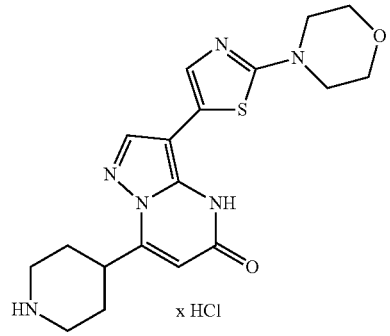 [SMILES: O=c1cc(C2CCNCC2)n2ncc(-c3cnc(N4CCOCC4)s3)c2[nH]1]

Compound tert-butyl 4-{5-[(4-methoxybenzyl)oxy]-3-[2-(morpholin-4-yl)-1,3-thiazol-5-yl]pyrazolo[1,5-a]pyrimidin-7-yl}piperidine-1-carboxylate (139 mg, 229 μmol) was stirred overnight at room temperature with hydrochloric acid (4N solution in 1,4-dioxan, 4.0 ml). Another portion of hydrochloric acid (4N solution in 1,4-dioxan, 4.0 ml) was added and stirring was continued. The mixture was diluted with diethyl ether (16 mL) and filtered. The recovered solid was dissolved in water and lyophilized to yield the title compound. The obtained amount was 103 mg (93% purity, 99% of theory).

LC-MS (Method 8B): R$_t$=0.58 min; MS (ESIneg): m/z=385 [M–H-xHCl]$^-$ $^1$H-NMR (400 MHz, DMSO-d6) delta [ppm]: 1.836 (1.00), 1.868 (3.03), 1.900 (3.00), 1.933 (1.17), 2.185 (4.00), 2.217 (3.47), 3.058 (1.10), 3.086 (3.27), 3.116 (3.53), 3.142 (1.40), 3.384 (5.00), 3.422 (12.17), 3.431 (13.40), 3.445 (10.30), 3.566 (3.17), 3.728 (12.70), 3.741 (16.00), 3.752 (10.63), 6.045 (0.80), 7.485 (2.00), 8.058 (0.87), 8.665 (1.17), 8.859 (1.80).

Example 377

3-(2,2-dimethylbutanoyl)-7-(piperidin-4-yl)pyrazolo[1,5-a]pyrimidin-5(4H)-one hydrochloride

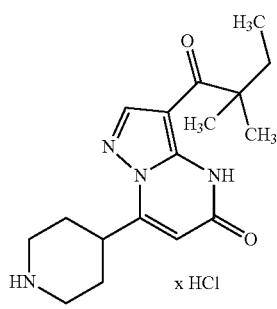 [SMILES: CCC(C)(C)C(=O)c1cnn2c(C3CCNCC3)cc(=O)[nH]c12]

A mixture of tert-butyl 4-[3-(2,2-dimethylbutanimidoyl)-5-oxo-4,5-dihydropyrazolo[1,5-a]pyrimidin-7-yl]piperidine-1-carboxylate (26.0 mg, 62.6 µmol), hydrochloric acid (1N solution in water, 130 µl) and acetonitrile (520 µl) was stirred overnight at 40° C. The reaction mixture was purified by preparative HPLC (gradient acetonitrile/water with 0.1% formic acid). The combined product fraction were concentrated, diluted with hydrochloric acid (1N solution in water, 1.0 ml) and lyophilized. Due to the presence of ammonium chloride, the material was diluted in water, brought to pH=7 with a saturated solution of sodium hydrogen carbonate in water, and purified again by preparative HPLC (gradient acetonitrile/water with 0.1% formic acid). The combined product fractions were evaporated, dissolved in hydrochloric acid (4N solution in 1,4-dioxan, 50 µl) and lyophilized to yield the title compound. The obtained amount was 15.0 mg (100% purity, 68% of theory).

LC-MS (Method 1B): $R_t$=0.57 min; MS (ESIpos): m/z=317 [M+H-xHCl]$^+$ $^1$H-NMR (400 MHz, DMSO-d6) delta [ppm]: 11.02 (bs, 1H), 8.88 (bs, 1H), 8.67 (bs, 1H), 8.58 (s, 1H), 6.05 (s, 1H), 3.51 (t, 1H), 3.39 (d, 2H), 3.09 (t, 2H), 2.17 (d, 2H), 1.93-1.83 (m, 2H), 1.79 (q, 2H), 1.23 (s, 6H), 0.75 (t, 3H).

Example 378

3-(5-Isobutyl-1,2,4-oxadiazol-3-yl)-7-(piperidin-4-yl)pyrazolo[1,5-a]pyrimidin-5(4H)-one hydrochloride

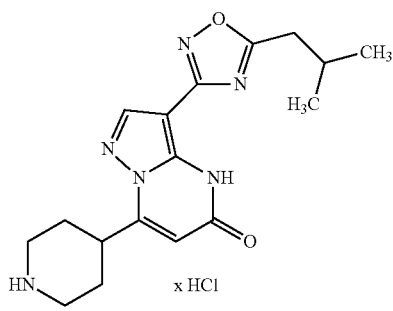 [SMILES: CC(C)Cc1nc(-c2cnn3c(C4CCNCC4)cc(=O)[nH]c23)no1]

65 mg (0.15 mmol) Tert-butyl 4-[3-(5-isobutyl-1,2,4-oxadiazol-3-yl)-5-oxo-4,5-dihydropyrazolo[1,5-a]pyrimidin-7-yl]piperidine-1-carboxylate was treated with 3 ml (12.0 mmol) 4 M hydrogen chloride in 1,4-dioxan. The reaction mixture was stirred for 4 days at room temperature. The solids were filtered off, rinsed with diethyl ether and air dried to afford 45 mg (0.12 mmol; 81% of theory, purity: 98%) of the target compound.

LC-MS (Method 14B): $R_t$=2.24 min; m/z=343 (M+1)$^+$ $^1$H-NMR (300 MHz, DMSO-d$_6$): δ [ppm]=8.35 (s, 1H), 6.08 (s, 1H), 3.68-3.50 (m, 1H), 3.41 (d, J=12.1 Hz, 2H), 3.10 (t, J=12.3 Hz, 2H), 2.89 (d, J=6.9 Hz, 2H), 2.29-2.10 (m, 3H), 1.89 (d, J=11.7 Hz, 2H), 0.99 (d, J=6.4 Hz, 6H).

Example 379

3-(5-Hexyl-1,2,4-oxadiazol-3-yl)-7-(piperidin-4-yl)pyrazolo[1,5-a]pyrimidin-5(4H)-one hydrochloride

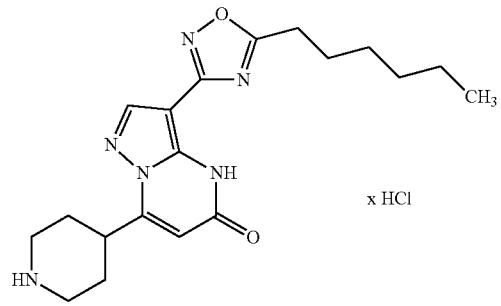 [SMILES: CCCCCCc1nc(-c2cnn3c(C4CCNCC4)cc(=O)[nH]c23)no1]

166 mg (0.35 mmol) Tert-butyl 4-[3-(5-hexyl-1,2,4-oxadiazol-3-yl)-5-oxo-4,5-dihydropyrazolo[1,5-a]pyrimidin-7-yl]piperidine-1-carboxylate was treated with 8 ml (32.0 mmol) 4 M hydrogen chloride in 1,4-dioxan. The reaction mixture was stirred for 4 days at room temperature. The solids were filtered off, rinsed with diethyl ether and air dried to afford 93 mg (0.23 mmol; 65% of theory, purity: 100%) of the target compound.

LC-MS (Method 14B): $R_t$=2.60 min; m/z=371 (M+1)$^+$ $^1$H-NMR (300 MHz, DMSO-d$_6$): δ [ppm]=9.32 (s, 2H), 8.32 (s, 1H), 6.06 (s, 1H), 3.55 (t, J=11.4 Hz, 1H), 3.38 (d, J=12.5 Hz, 2H), 3.09 (d, J=12.9 Hz, 2H), 2.96 (t, J=7.5 Hz, 2H), 2.19 (d, J=12.5 Hz, 2H), 1.99-1.58 (m, 4H), 1.42-1.20 (m, 6H), 0.86 (t, 3H).

Example 380

3-(5-Cyclopropyl-1,2,4-oxadiazol-3-yl)-7-(piperidin-4-yl)pyrazolo[1,5-a]pyrimidin-5(4H)-one hydrochloride

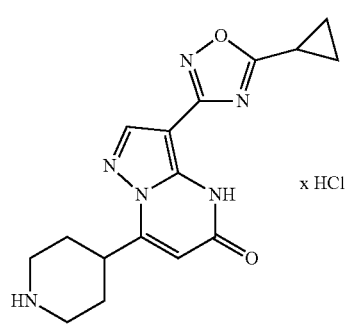 [SMILES: O=c1cc(C2CCNCC2)n2ncc(-c3noc(C4CC4)n3)c2[nH]1]

122 mg (0.29 mmol) Tert-butyl 4-[3-(5-cyclopropyl-1,2,4-oxadiazol-3-yl)-5-oxo-4,5-dihydropyrazolo[1,5-a]pyrimidin-7-yl]piperidine-1-carboxylate was treated with 6 ml (24.0 mmol) 4 M hydrogen chloride in 1,4-dioxan. The reaction mixture was stirred for 16 hours at room temperature. The solids were filtered off, rinsed with diethyl ether and dried in a vacuum oven at 40° C. for 16 hours to afford 95 mg (0.26 mmol; 92% of theory, purity: 98%) of the target compound.

LC-MS (Method 14B): $R_t$=1.92 min; m/z=327 (M+1)$^+$ $^1$H-NMR (300 MHz, DMSO-d$_6$): δ [ppm]=9.26 (br. s, 2H), 8.30 (s, 1H), 6.05 (s, 1H), 3.57 (t, J=11.8 Hz, 1H), 3.39 (d, J=12.6 Hz, 2H), 3.09 (t, J=12.0 Hz, 2H), 2.45-2.32 (m, 1H), 2.20 (d, J=13.7 Hz, 2H), 2.03-1.81 (m, 2H), 1.36-1.18 (m, 4H).

Example 381

Rac-3-[5-(1-Methylcyclopropyl)-1,2,4-oxadiazol-3-yl]-7-(piperidin-4-yl)pyrazolo[1,5-a]pyrimidin-5(4H)-one hydrochloride

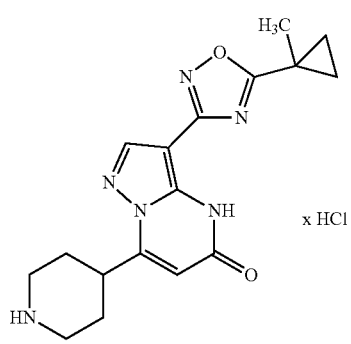 [SMILES: CC1(c2nc(-c3cnn4c(C5CCNCC5)cc(=O)[nH]c34)no2)CC1]

90 mg (0.20 mmol) rac-tert-butyl 4-{3-[5-(1-methylcyclopropyl)-1,2,4-oxadiazol-3-yl]-5-oxo-4,5-dihydropyrazolo[1,5-a]pyrimidin-7-yl}piperidine-1-carboxylate was treated with 5 ml (20.0 mmol) 4 M hydrogen chloride in 1,4-dioxan. The reaction mixture was stirred for 16 hours at room temperature. The solids were filtered off, rinsed with diethyl ether and dried in a vacuum oven at 40° C. for 16 hours to afford 60 mg (0.16 mmol; 78% of theory, purity: 99%) of the target compound.

LC-MS (Method 14B): $R_t$=2.15 min; m/z=341 (M+1)$^+$ $^1$H-NMR (300 MHz, DMSO-d$_6$): δ [ppm]=9.59 (br. s, 2H), 8.30 (s, 1H), 6.04 (s, 1H), 3.57 (t, J=11.9 Hz, 1H), 3.39 (d, J=13.1 Hz, 2H), 3.09 (t, J=11.7 Hz, 2H), 2.20 (d, J=12.6 Hz, 2H), 2.03-1.79 (m, 2H), 1.56 (s, 3H), 1.52-1.33 (m, 2H), 1.27-0.99 (m, 2H).

Example 382

Rel-3-{5-[(1R,2S)-2-methylcyclopropyl]-1,2,4-oxadiazol-3-yl}-7-(piperidin-4-yl)pyrazolo[1,5-a]pyrimidin-5(4H)-one hydrochloride

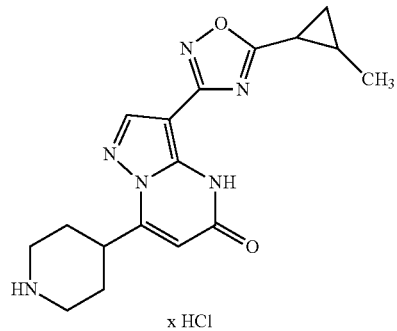 [SMILES: CC1CC1c1nc(-c2cnn3c(C4CCNCC4)cc(=O)[nH]c23)no1]

84 mg (0.19 mmol) Tert-butyl rel-4-(3-{5-[(1R,2S)-2-methylcyclopropyl]-1,2,4-oxadiazol-3-yl}-5-oxo-4,5-dihydropyrazolo[1,5-a]pyrimidin-7-yl)piperidine-1-carboxylate was treated with 5 ml (20.0 mmol) 4 M hydrogen chloride in 1,4-dioxan. The reaction mixture was stirred for 16 hours at room temperature. The solids were filtered off, rinsed with diethyl ether and dried in a vacuum oven at 40° C. for 16 hours to afford 56 mg (0.15 mmol; 78% of theory, purity: 99%) of the target compound.

LC-MS (Method 14B): $R_t$=2.15 min; m/z=341 (M+1)$^+$ $^1$H-NMR (300 MHz, DMSO-d$_6$): δ [ppm]=9.37 (br. s, 2H), 8.60-8.07 (m, 1H), 6.04 (s, 1H), 3.65-3.49 (m, 1H), 3.39 (d, J=12.6 Hz, 2H), 3.09 (t, J=12.0 Hz, 2H), 2.29-2.07 (m, 3H), 2.06-1.79 (m, 2H), 1.78-1.58 (m, 1H), 1.51-1.35 (m, 1H), 1.21 (d, J=6.0 Hz, 3H), 1.17-1.08 (m, 1H).

Example 383

3-[5-(2-Methylprop-1-en-1-yl)-1,2,4-oxadiazol-3-yl]-7-(piperidin-4-yl)pyrazolo[1,5-a]pyrimidin-5(4H)-one hydrochloride

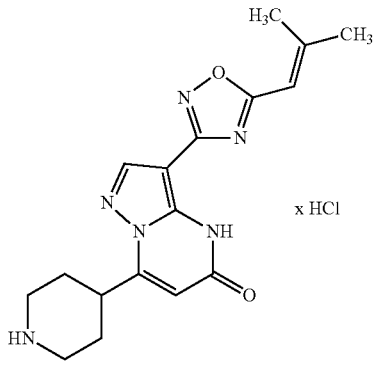 [SMILES: CC(C)=Cc1nc(-c2cnn3c(C4CCNCC4)cc(=O)[nH]c23)no1]

19 mg (0.04 mmol) Tert-butyl 4-{3-[5-(2-methylprop-1-en-1-yl)-1,2,4-oxadiazol-3-yl]-5-oxo-4,5-dihydropyrazolo[1,5-a]pyrimidin-7-yl}piperidine-1-carboxylate was treated with 1 ml (4.0 mmol) 4 M hydrogen chloride in 1,4-dioxan. The reaction mixture was stirred for 16 hours at room temperature. The solids were filtered off, rinsed with diethyl

Example 384

3-[5-(Cyclopentylidenemethyl)-1,2,4-oxadiazol-3-yl]-7-(piperidin-4-yl)pyrazolo[1,5-a]pyrimidin-5(4H)-one hydrochloride

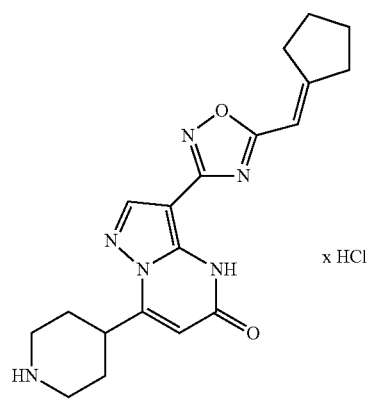 [SMILES: O=c1cc(C2CCNCC2)n2ncc(-c3noc(C=C4CCCC4)n3)c2[nH]1]

73 mg (0.16 mmol) tert-butyl 4-{3-[5-(cyclopentylidenemethyl)-1,2,4-oxadiazol-3-yl]-5-oxo-4,5-dihydropyrazolo[1,5-a]pyrimidin-7-yl}piperidine-1-carboxylate was treated with 5 ml (20.0 mmol) 4 M hydrogen chloride in 1,4-dioxan. The reaction mixture was stirred for 16 hours at room temperature. The solids were filtered off, triturated with dichloromethane (4 ml) and hot methanol (3 ml), filtered off, rinsed with diethyl ether and air dried to afford 43 mg (0.11 mmol; 68% of theory, purity: 96%) of the target compound.

LC-MS (Method 14B): $R_t$=2.40 min; m/z=367 (M+1)$^+$ $^1$H-NMR (300 MHz, DMSO-d$_6$): δ [ppm]=9.48 (br. s, 2H), 8.35 (s, 1H), 6.08 (s, 1H), 5.60 (s, 1H), 3.86 (s, 2H), 3.71-3.49 (m, 1H), 3.40 (d, J=12.2 Hz, 2H), 3.10 (t, J=11.9 Hz, 2H), 2.32 (t, J=7.4 Hz, 4H), 2.21 (d, J=14.3 Hz, 2H), 2.04-1.76 (m, 4H).

Example 385

3-(5-Cyclopentyl-1,2,4-oxadiazol-3-yl)-7-(piperidin-4-yl)pyrazolo[1,5-a]pyrimidin-5(4H)-one hydrochloride

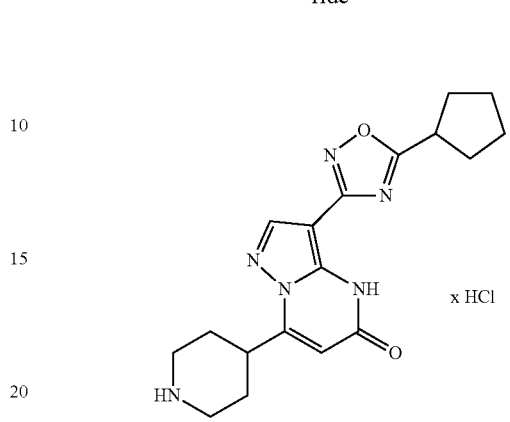

147 mg (0.32 mmol) Tert-butyl 4-[3-(5-cyclopentyl-1,2,4-oxadiazol-3-yl)-5-oxo-4,5-dihydropyrazolo[1,5-a]pyrimidin-7-yl]piperidine-1-carboxylate was treated with 6 ml (24.0 mmol) 4 M hydrogen chloride in 1,4-dioxan. The reaction mixture was stirred for 16 hours at room temperature. The solids were filtered off, rinsed with diethyl ether and dried in a vacuum oven at 40° C. for 16 hours to afford 109 mg (0.28 mmol; 86% of theory, purity: 99%) of the target compound.

LC-MS (Method 14B): $R_t$=2.40 min; m/z=355 (M+1)$^+$ $^1$H-NMR (300 MHz, DMSO-d$_6$): δ [ppm]=9.48 (br. s, 2H), 8.33 (s, 1H), 6.07 (s, 1H), 3.65-3.37 (m, 4H), 3.09 (t, J=11.8 Hz, 2H), 2.29-2.04 (m, 4H), 2.02-1.83 (m, 4H), 1.83-1.60 (m, 4H).

Example 386

Rac-3-[5-(1-Methylcyclopentyl)-1,2,4-oxadiazol-3-yl]-7-(piperidin-4-yl)pyrazolo[1,5-a]pyrimidin-5(4H)-one hydrochloride

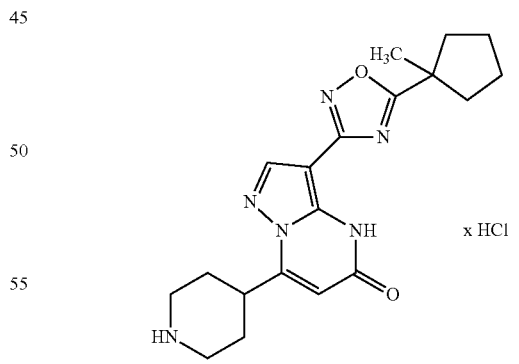

112 mg (0.24 mmol) rac-tert-butyl 4-{3-[5-(1-methylcyclopentyl)-1,2,4-oxadiazol-3-yl]-5-oxo-4,5-dihydropyrazolo[1,5-a]pyrimidin-7-yl}piperidine-1-carboxylate was treated with 5 ml (20.0 mmol) 4 M hydrogen chloride in 1,4-dioxan. The reaction mixture was stirred for 16 hours at room temperature. The solids were filtered off, rinsed with diethyl ether and dried in a vacuum oven at 40° C. for 16 hours. The solids were suspended in acetonitrile (3 ml) and

---

(from previous page continuation:)

ether and dried in a vacuum oven at 40° C. for 16 hours to afford 12 mg (0.03 mmol; 74% of theory, purity: 99%) of the target compound.

LC-MS (Method 14B): $R_t$=2.24 min; m/z=341 (M+1)$^+$ $^1$H-NMR (300 MHz, DMSO-d$_6$): δ [ppm]=9.56 (br. s, 2H), 8.34 (s, 1H), 6.44 (s, 1H), 6.07 (s, 1H), 3.75-3.51 (m, 1H), 3.40 (d, J=12.2 Hz, 2H), 3.10 (t, J=11.9 Hz, 2H), 2.32 (s, 3H), 2.21 (d, J=12.8 Hz, 2H), 2.07 (s, 3H), 2.04-1.76 (m, 2H).

water (5 ml) was added, a clear solution was obtained which was lyophilized for 20 hours to afford 79 mg (0.20 mmol; 82% of theory, purity: 100%) of the target compound.

LC-MS (Method 14B): $R_t$=2.43 min; m/z=369 (M+1)$^+$ $^1$H-NMR (300 MHz, DMSO-d$_6$): δ [ppm]=9.58 (s, 2H), 8.33 (s, 1H), 6.06 (s, 1H), 3.64-3.50 (m, 1H), 3.40 (d, J=12.5 Hz, 2H), 3.19-3.01 (m, 2H), 2.35-2.12 (m, 4H), 2.00-1.83 (m, 2H), 1.83-1.70 (m, 6H), 1.47 (s, 3H).

Example 387

Rel-3-{5-[(1R,2S)-2-methylcyclopentyl]-1,2,4-oxadiazol-3-yl}-7-(piperidin-4-yl)pyrazolo[1,5-a]pyrimidin-5(4H)-one hydrochloride

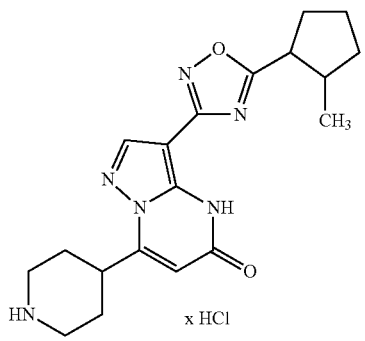 [SMILES: CC1CCCC1c1nc(-c2cnn3c(C4CCNCC4)cc(=O)[nH]c23)no1]

171 mg (0.37 mmol) Tert-butyl rel-4-(3-{5-[(1R,2S)-2-methylcyclopentyl]-1,2,4-oxadiazol-3-yl}-5-oxo-4,5-dihydropyrazolo[1,5-a]pyrimidin-7-yl)piperidine-1-carboxylate was treated with 8 ml (32.0 mmol) 4 M hydrogen chloride in 1,4-dioxan. The reaction mixture was stirred for 16 hours at room temperature. The solids were filtered off, rinsed with diethyl ether and dried in a vacuum oven at 40° C. for 16 hours to afford 133 mg (0.33 mmol; 90% of theory, purity: 99%) of the target compound.

LC-MS (Method 14B): $R_t$=2.45 min; m/z=369 (M+1)$^+$ $^1$H-NMR (300 MHz, DMSO-d$_6$): δ [ppm]=9.58 (br. s, 2H), 8.34 (s, 1H), 6.07 (s, 1H), 3.69-3.50 (m, 1H), 3.40 (d, J=12.3 Hz, 2H), 3.17-2.94 (m, 3H), 2.39-2.10 (m, 4H), 2.08-1.84 (m, 4H), 1.83-1.69 (m, 2H), 1.45-1.22 (m, 1H), 1.09 (d, J=6.6 Hz, 3H).

Example 388

7-(Piperidin-4-yl)-3-[5-(2,2,2-trifluoroethyl)-1,2,4-oxadiazol-3-yl]pyrazolo[1,5-a]pyrimidin-5(4H)-one hydrochloride

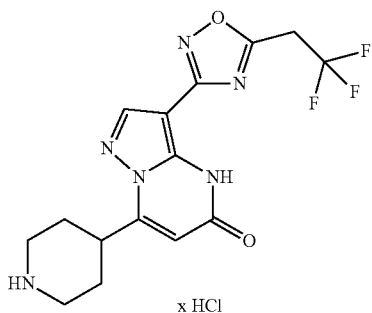 [SMILES: O=c1cc(C2CCNCC2)n2ncc(-c3noc(CC(F)(F)F)n3)c2[nH]1]

120 mg (0.26 mmol) Tert-butyl 4-{5-oxo-3-[5-(2,2,2-trifluoroethyl)-1,2,4-oxadiazol-3-yl]-4,5-dihydropyrazolo[1,5-a]pyrimidin-7-yl}piperidine-1-carboxylate was treated with 5 ml (20.0 mmol) 4 M hydrogen chloride in 1,4-dioxan. The reaction mixture was stirred for 16 hours at room temperature. The solids were filtered off, rinsed with diethyl ether and dried in a vacuum oven at 40° C. for 16 hours to afford 91 mg (0.23 mmol; 88% of theory, purity: 100%) of the target compound.

LC-MS (Method 14B): $R_t$=1.99 min; m/z=369 (M+1)$^+$ $^1$H-NMR (300 MHz, DMSO-d$_6$): δ [ppm]=9.01 (br. s, 2H), 8.39 (s, 1H), 6.14 (s, 1H), 4.52 (q, J=10.7 Hz, 2H), 3.72-3.52 (m, 1H), 3.40 (d, J=12.4 Hz, 2H), 3.10 (t, J=11.8 Hz, 2H), 2.22 (d, J=13.0 Hz, 2H), 2.05-1.80 (m, 2H).

Example 389

Rac-7-(piperidin-4-yl)-3-(5-(tetrahydrofuran-2-yl)-1,2,4-oxadiazol-3-yl)pyrazolo[1,5-a]pyrimidin-5(4H)-one hydrochloride

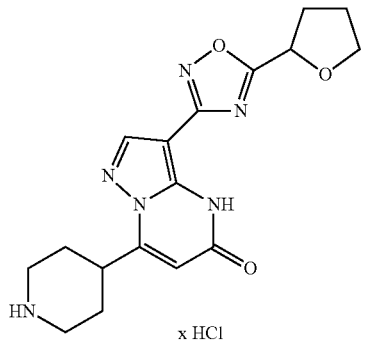 [SMILES: O=c1cc(C2CCNCC2)n2ncc(-c3noc(C4CCCO4)n3)c2[nH]1]

In a 8 ml screw cap vial equipped with a stirring bar were placed 169 mg (0.370 mmol) rac-tert-butyl 4-(5-oxo-3-(5-(tetrahydrofuran-2-yl)-1,2,4-oxadiazol-3-yl)-4,5-dihydropyrazolo[1,5-a]pyrimidin-7-yl)piperidine-1-carboxylate and 4625 µl (18.50 mmol) hydrochloric acid (4.0 M in dioxane). The vial was closed and the resulting suspension stirred at room temperature for 3 hours. The precipitate was collected on a glass filter (Pore 3) and dried for 18 hours in a vacuum oven (40° C./20 mbar). 101 mg (0.247 mmol, 66% of theory, purity: 96%) of the title compound was isolated as a slightly yellow powder.

LC-MS (Method 16B): $R_t$=2.15 min; m/z=357 (M+1)$^+$ $^1$H-NMR (300 MHz, DMSO-d6) δ[ppm]=9.19 (br. s, 2H), 8.35 (s, 1H), 6.08 (s, 1H), 5.28 (dd, J=7.9, 5.3 Hz, 1H), 4.06-3.81 (m, 2H), 3.65-3.52 (m, 2H), 3.44-3.28 (m, 2H), 3.16-3.00 (m, 2H), 2.46-2.14 (m, 4H), 2.13-1.85 (m, 4H).

Example 390

7-(piperidin-4-yl)-3-(5-(trifluoromethyl)-1,2,4-oxadiazol-3-yl)pyrazolo[1,5-a]pyrimidin-5(4H)-one hydrochloride

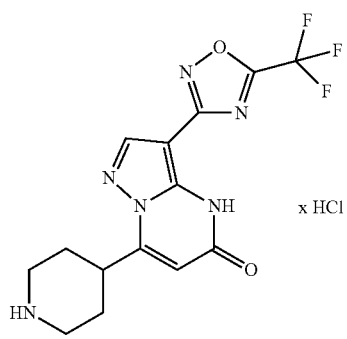 [SMILES: O=c1cc(C2CCNCC2)n2ncc(-c3noc(C(F)(F)F)n3)c2[nH]1]

In a 8 ml screw cap vial equipped with a stirring bar were placed 135 mg (0.3 mmol) 7-(1-(2,2,2-trifluoroacetyl)piperidin-4-yl)-3-(5-(trifluoromethyl)-1,2,4-oxadiazol-3-yl)pyrazolo[1,5-a]pyrimidin-5(4H)-one and 7500 µl (30.0 mmol) hydrochloric acid (4.0 M in dioxane). The vial was closed and the colorless solution stirred at 80° C. for 19 hours. Upon cooling to RT crystallization/precipitation occurred.

The reaction mixture was diluted with 30 ml diethyl ether and stirred for 30 minutes. The precipitate was collected on a glass filter (pore 3) and dried for 3 hours in a vacuum oven (40° C./20 mbar). 114 mg (0.292 mmol, 97% of theory, purity: 100%) of the title compound was obtained as a white free flowing powder.

LC-MS (Method 16B): $R_t$=2.41 min; m/z=355 (M+1)$^+$ $^1$H-NMR (300 MHz, DMSO-d6) δ[ppm]=12.30 (br. s, 1H), 9.17 (br. s, 2H), 8.50 (s, 1H), 6.23 (s, 1H), 3.62 (t, J=11.9 Hz, 1H), 3.40 (d, J=12.5 Hz, 2H), 3.10 (t, J=12.0 Hz, 2H), 2.22 (d, J=13.1 Hz, 2H), 1.96 (qd, J=13.2, 3.6 Hz, 2H).

Example 391

7-(piperidin-4-yl)-3-(5-(1,1,1-trifluoro-2-methylpropan-2-yl)-1,2,4-oxadiazol-3-yl)pyrazolo[1,5-a]pyrimidin-5(4H)-one hydrochloride

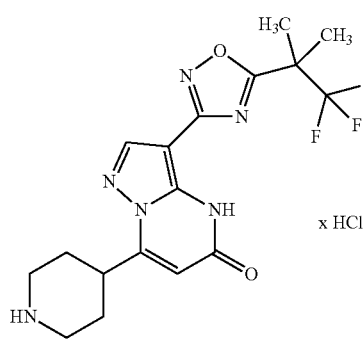

In a 8 ml screw cap vial equipped with a stirring bar were placed 199 mg (0.400 mmol) tert-butyl 4-(5-oxo-3-(5-(1,1,1-trifluoro-2-methylpropan-2-yl)-1,2,4-oxadiazol-3-yl)-4,5-dihydropyrazolo[1,5-a]pyrimidin-7-yl)piperidine-1-carboxylate and 5 ml (20.00 mmol) hydrochloric acid (4.0 M in dioxane). The vial was closed and the resulting suspension stirred at ambient temperature for 2.5 hours. 4 ml diethylether was added to the reaction mixture then which was stirred for an additional 2 hours. The precipitate was collected on a glass filter (pore 31), washed two times with 5 ml diethylether and dried in a vacuum oven for 48 hours (40° C./15 mbar). 171 mg (0.395 mmol; 99% of theory, purity: 100%) of the title compound was obtained as a white powder.

LC-MS (Method 16B): $R_t$=2.66 min; m/z=397 (M+1)$^+$ $^1$H-NMR (300 MHz, DMSO-d6) δ[ppm]=9.48-9.12 (m, 2H), 8.37 (s, 1H), 6.09 (s, 1H), 3.65-3.57 (m, 1H), 3.38 (d, J=12.3 Hz, 2H), 3.08 (q, J=12.4 Hz, 2H), 2.20 (d, J=12.6 Hz, 2H), 2.05-1.88 (m, 2H), 1.72 (s, 6H).

Example 392

3-(5-(3,3-difluorocyclobutyl)-1,2,4-oxadiazol-3-yl)-7-(piperidin-4-yl)pyrazolo[1,5-a]pyrimidin-5(4H)-one hydrochloride

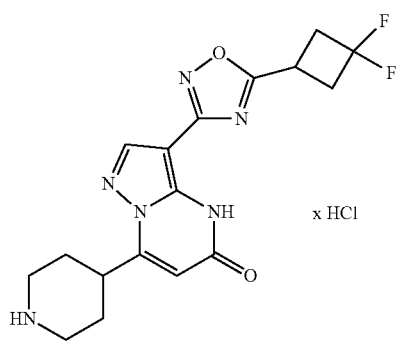 [SMILES: O=c1cc(C2CCNCC2)n2ncc(-c3noc(C4CC(F)(F)C4)n3)c2[nH]1]

In a 8 ml screw cap vial equipped with a stirring bar were placed 233 mg (0.490 mmol) tert-butyl 4-(3-(5-(3,3-difluorocyclobutyl)-1,2,4-oxadiazol-3-yl)-5-oxo-4,5-dihydropyrazolo[1,5-a]pyrimidin-7-yl)piperidine-1-carboxylate and 6125 µl (24.50 mmol) hydrochloric acid (40M in dioxane). The vial was closed and the resulting suspension stirred at room temperature for 2.5 hours. 4 ml diethylether was added and stirring continued for 2 hours. The precipitate was then collected on a glass filter (pore 31), washed two times with 5 ml diethylether and dried in a vacuum oven for 48 hours (40° C./15 mbar). 166 mg (0.398 mmol; 81% of theory, purity: 99%) of the title compound was isolated as a white powder.

LC-MS (Method 16B): $R_t$=2.39 min; m/z=377 (M+1)$^+$ $^1$H-NMR (300 MHz, DMSO-d6) δ[ppm]=11.42 (br. s, 1H), 9.19 (br. s, 2H), 8.35 (s, 1H), 6.06 (s, 1H), 3.85 (pd, J=8.3, 2.3 Hz, 1H), 3.56 (s, 1H), 3.39 (d, J=12.8 Hz, 2H), 3.25-3.00 (m, 6H), 2.20 (d, J=13.2 Hz, 2H), 1.94 (qd, J=13.2, 3.6 Hz, 2H).

Example 393

3-(5-(4,4-difluorocyclohexyl)-1,2,4-oxadiazol-3-yl)-7-(piperidin-4-yl)pyrazolo[1,5-a]pyrimidin-5(4H)-one hydrochloride

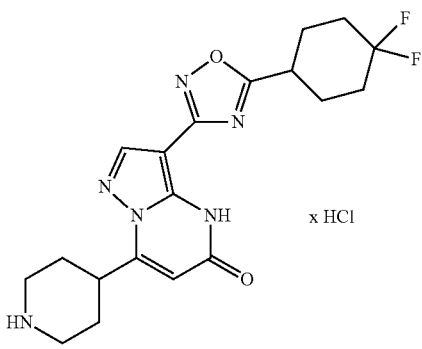 [SMILES: O=c1cc(C2CCNCC2)n2ncc(-c3noc(C4CCC(F)(F)CC4)n3)c2[nH]1]

In a 8 ml screw cap vial equipped with a stirring bar were placed 247 mg (0.490 mmol) tert-butyl 4-(3-(5-(4,4-difluorocyclohexyl)-1,2,4-oxadiazol-3-yl)-5-oxo-4,5-dihydropyrazolo[1,5-a]pyrimidin-7-yl)piperidine-1-carboxylate and 6125 µl (24.50 mmol) hydrochloric acid (4.0 M in dioxane). The vial was closed and the resulting suspension stirred at ambient temperature for 2.5 hours. 4 ml diethylether was added to the reaction mixture and stirring continued for 2 hours. The precipitate was collected on a glass filter (pore 3), washed two times with 5 ml diethyl ether and dried in a vacuum oven for 48 hours (40° C./15 mbar). 187 mg (0.416 mmol, 85% of theory, purity: 98%) of the title compound was isolated as a white powder.

LC-MS (Method 16B): $R_t$=2.61 min; m/z=405 (M+1)$^+$ $^1$H-NMR (300 MHz, DMSO-d6) δ[ppm] 11.35 (br. s, 1H), 9.15 (br. s, 2H), 8.33 (s, 1H), 6.06 (s, 1H), 3.65-3.51 (m, 1H), 3.44-3.27 (m, 3H), 3.08 (t, J=11.7 Hz, 2H), 2.26-1.82 (m, 12H).

Example 394

3-(5-(methoxymethyl)-1,2,4-oxadiazol-3-yl)-7-(piperidin-4-yl)pyrazolo[1,5-a]pyrimidin-5(4H)-one hydrochloride

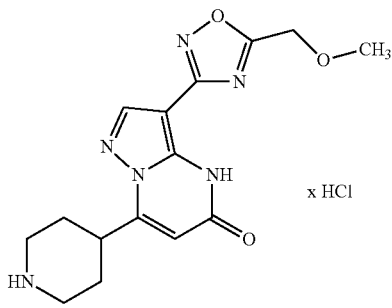 [SMILES: COCc1nc(-c2cnn3c(C4CCNCC4)cc(=O)[nH]c23)no1]

In a 8 ml screw cap vial equipped with a stirring bar were placed 99 mg (0.230 mmol) tert-butyl 4-(3-(5-(methoxymethyl)-1,2,4-oxadiazol-3-yl)-5-oxo-4,5-dihydropyrazolo[1,5-a]pyrimidin-7-yl)piperidine-1-carboxylate and 2875 µl (11.50 mmol) hydrochloric acid (4.0 M in dioxane). The vial was closed and the resulting suspension stirred at room temperature for 2.5 hours. 4 ml diethylether was added to the reaction mixture and stirring was continued for 2 hours. The precipitate was collected on a glass filter (pore 31), washed two times with 5 ml diethylether and dried in a vacuum oven for 48 hours (40° C./15 mbar). 85 mg (0.225 mmol; 98% of theory, purity: 97%) of the title compound was obtained as a white powder.

LC-MS (Method 16B): $R_t$=1.91 min; m/z=331 (M+1)$^+$ $^1$H-NMR (300 MHz, DMSO-d6) δ[ppm]=9.29 (br. s, 3H), 8.38 (s, 1H), 6.10 (s, 1H), 4.82 (s, 2H), 3.57 (d, J=7.1 Hz, 1H), 3.47-3.28 (m, 5H), 3.16-3.01 (m, 2H), 2.21 (d, J=13.3 Hz, 2H), 2.05-1.83 (m, 2H).

Example 395

3-(5-(3-methoxypropyl)-1,2,4-oxadiazol-3-yl)-7-(piperidin-4-yl)pyrazolo[1,5-a]pyrimidin-5(4H)-one hydrochloride

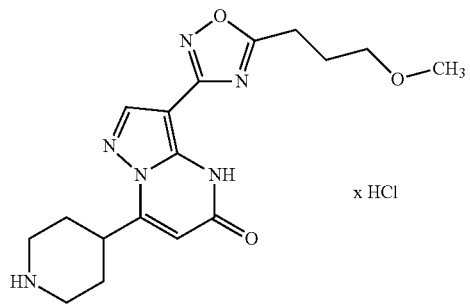 [SMILES: COCCCc1nc(-c2cnn3c(C4CCNCC4)cc(=O)[nH]c23)no1]

In a 8 ml screw cap vial equipped with a stirring bar were placed tert-butyl 105 mg (0.230 mmol) 4-(3-(5-(3-methoxypropyl)-1,2,4-oxadiazol-3-yl)-5-oxo-4,5-dihydropyrazolo[1,5-a]pyrimidin-7-yl)piperidine-1-carboxylate and 2875 µl (11.50 mmol) hydrochloric acid (4.0 M in dioxane). The vial was closed and the resulting suspension stirred at ambient temperature for 2.5 hours. 4 ml diethylether was added and stirring continued for 2 more hours. The precipitate was then collected on a glass filter (pore 3), washed two times with 5 ml diethylether and dried in a vacuum oven for 48 hours (40° C./15 mbar). 88 mg (0.221 mmol; 96% of theory, purity: 99%) of the title compound was obtained as a white powder.

LC-MS (Method 16B): $R_t$=2.17 min; m/z=359 (M+1)$^+$ $^1$H-NMR (300 MHz, DMSO-d6) δ[ppm]=9.30 (br. s, 3H), 8.34 (s, 1H), 6.06 (s, 1H), 3.66-3.51 (m, 1H), 3.47-3.28 (m, 5H), 3.24 (s, 3H), 3.15-2.96 (m, 4H), 2.20 (d, J=12.8 Hz, 2H), 2.10-1.85 (m, 4H).

Example 396

Ethyl 2-methyl-5-oxo-7-(piperidin-4-yl)-4,5-dihydropyrazolo[1,5-a]pyrimidine-3-carboxylate hydrochloride

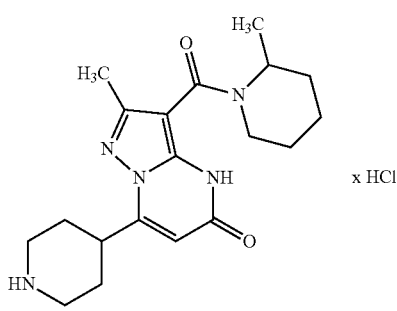 [SMILES: Cc1nn2c(C3CCNCC3)cc(=O)[nH]c2c1C(=O)N1CCCCC1C]

x HCl

7-[1-(tert-butoxycarbonyl)piperidin-4-yl]-2-methyl-5-oxo-4,5-dihydropyrazolo[1,5-a]pyrimidine-3-carboxylic acid (37.6 mg, 0.1 mmol) was dissolved in 0.4 ml DMF and added to 1 eq. of 2-methylpiperidine (9.9 mg, 0.1 mmol) in a 96 deep well plate followed by a solution of HATU (57.0 mg, 0.15 mmol) in 0.4 ml DMF and 4-Methylmorpholine (46.0 mg, 0.46 mmol). The plate was sealed and shaken at 40° C. overnight and then evaporated to dryness. The residue was treated with 0.6 ml TFA and shaken at RT overnight. The mixture was evaporated to dryness and the crude product was treated with 0.6 ml DMF, filtered off and the filtrate was purified by LC-MS via Method 5A.

The product containing fractions were treated with 100 µl aq. HCl (36%) and evaporated in vacuo with a centrifugal dryer, dissolved in 0.6 ml DMSO then pooled and evaporated again to give the final product.

The obtained amount was 6.9 mg (89% purity, 16% of theory).

In analogy the examples shown in Table 4 were synthesized.

TABLE 4

Examples 397 to 437, prepared in analogy to Example 397

| Example | Structure | Name | % of theory | LC-MS data |
|---|---|---|---|---|
| Example 397 | 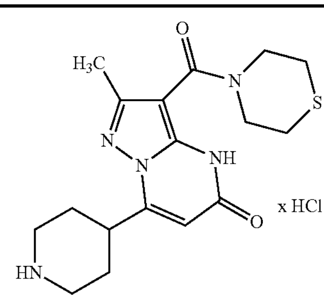 | 2-methyl-7-(piperidin-4-yl)-3-(thiomorpholin-4-ylcarbonyl)pyrazolo[1,5-a]pyrimidin-5(4H)-one hydrochloride | 3.3 mg, (7%) | LC/MS (Method 12B): $R_t$ = 0.54 min MS (ESIpos): m/z = 362 (M + H)+ purity: 89% |
| Example 398 | 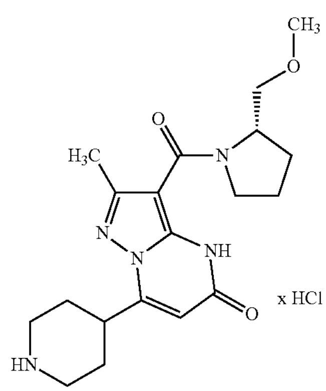 [SMILES: COC[C@@H]1CCCN1C(=O)c1c(C)nn2c(C3CCNCC3)cc(=O)[nH]c12] | 3-{[(2S)-2-(methoxymethyl)pyrrolidin-1-yl]carbonyl}-2-methyl-7-(piperidin-4-yl)pyrazolo[1,5-a]pyrimidin-5(4H)-one hydrochloride | 1.4 mg (3%) | LC/MS (Method 12B): $R_t$ = 0.55 min MS (ESIpos): m/z = 374 (M + H)+ purity: 100% |
| Example 399 | 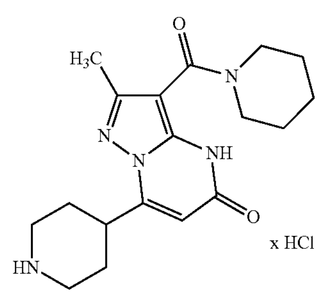 [SMILES: Cc1nn2c(C3CCNCC3)cc(=O)[nH]c2c1C(=O)N1CCCCC1] | 2-methyl-7-(piperidin-4-yl)-3-(piperidin-1-ylcarbonyl)pyrazolo[1,5-a]pyrimidin-5(4H)-one hydrochloride | 1.6 mg (4%) | LC/MS (Method 12B): $R_t$ = 0.55 min MS (ESIpos): m/z = 344 (M + H)+ purity: 100% |

TABLE 4-continued

Examples 397 to 437, prepared in analogy to Example 397

| Example | Structure | Name | % of theory | LC-MS data |
|---|---|---|---|---|
| Example 400 | 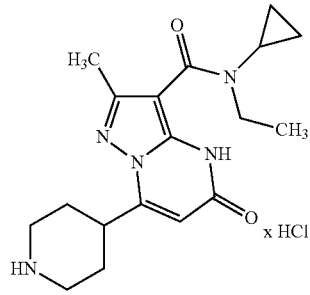 [SMILES: CCN(C(=O)c1c(C)nn2c(C3CCNCC3)cc(=O)[nH]c12)C1CC1] | N-cyclopropyl-N-ethyl-2-methyl-5-oxo-7-(piperidin-4-yl)-4,5-dihydro-pyrazolo[1,5-a]pyrimidine-3-carboxamide hydrochloride | 1.1 mg (3%) | LC/MS (Method 12B): $R_t$ = 0.55 min MS (ESIpos): m/z = 344 (M + H)$^+$ purity: 100% |
| Example 401 | 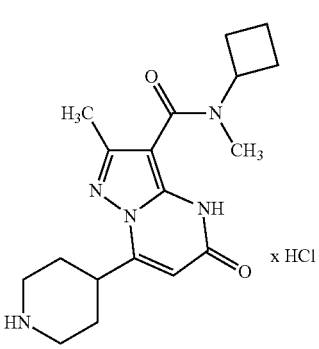 [SMILES: Cc1nn2c(C3CCNCC3)cc(=O)[nH]c2c1C(=O)N(C)C1CCC1] | N-cyclobutyl-N,2-dimethyl-5-oxo-7-(piperidin-4-yl)-4,5-dihydro-pyrazolo[1,5-a]pyrimidine-3-carboxamide hydrochloride | 7.3 mg (19%) | LC/MS (Method 12B): $R_t$ = 0.55 min MS (ESIpos): m/z = 344 (M + H)$^+$ purity: 100% |
| Example 402 | 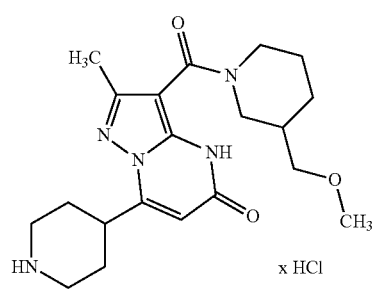 [SMILES: COCC1CCCN(C(=O)c2c(C)nn3c(C4CCNCC4)cc(=O)[nH]c23)C1] | 3-{[3-(methoxymethyl)piperidin-1-yl]carbonyl}-2-methyl-7-(piperidin-4-yl)pyrazolo[1,5-a]pyrimidin-5(4H)-one hydrochloride | 4.9 mg (11%) | LC/MS (Method 12B): $R_t$ = 0.56 min MS (ESIpos): m/z = 388 (M + H)$^+$ purity: 100% |
| Example 403 | 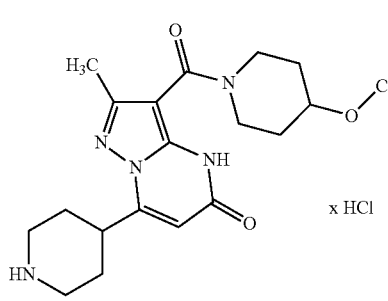 | 3-[(4-methoxypiperidin-1-yl)carbonyl]-2-methyl-7-(piperidin-4-yl)pyrazolo[1,5-a]pyrimidin-5(4H)-one hydrochloride | 1.1 mg (3%) | LC/MS (Method 12B): $R_t$ = 0.53 min MS (ESIpos): m/z = 374 (M + H)$^+$ purity: 100% |
| Example 404 | 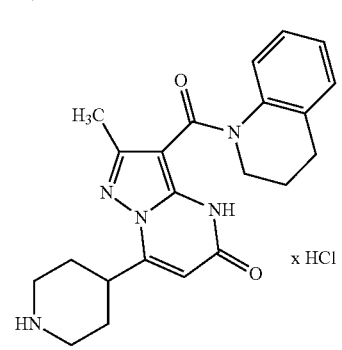 [SMILES: Cc1nn2c(C3CCNCC3)cc(=O)[nH]c2c1C(=O)N1CCCc2ccccc21] | 3-(3,4-dihydroquinolin-1(2H)-ylcarbonyl)-2-methyl-7-(piperidin-4-yl)pyrazolo[1,5-a]pyrimidin-5(4H)-one hydrochloride | 1.1 mg (2%) | LC/MS (Method 12B): $R_t$ = 0.62 min MS (ESIpos): m/z = 392 (M + H)$^+$ purity: 95% |

TABLE 4-continued

Examples 397 to 437, prepared in analogy to Example 397

| Example | Structure | Name | % of theory | LC-MS data |
|---|---|---|---|---|
| Example 405 | 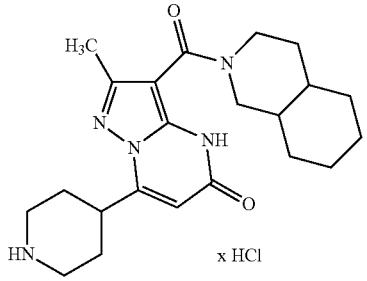 [SMILES: Cc1nn2c(C3CCNCC3)cc(=O)[nH]c2c1C(=O)N1CCC2CCCCC2C1] | 2-methyl-3-(octahydro-isoquinolin-2(1H)-ylcarbonyl)-7-(piperidin-4-yl)pyrazolo[1,5-a]pyrimidin-5(4H)-one hydrochloride | 8.3 mg (18%) | LC/MS (Method 12B):<br>$R_t$ = 0.65 min<br>MS (ESIpos):<br>m/z = 398 (M + H)$^+$<br>purity: 93% |
| Example 406 | 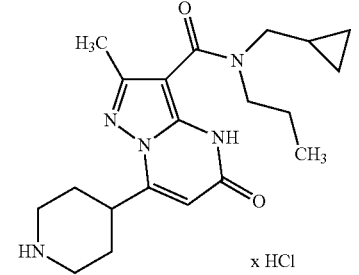 [SMILES: CCCN(CC1CC1)C(=O)c1c(C)nn2c(C3CCNCC3)cc(=O)[nH]c12] | N-(cyclopropyl-methyl)-2-methyl-5-oxo-7-(piperidin-4-yl)-N-propyl-4,5-dihydropyrazolo[1,5-a]pyrimidine-3-carboxamide hydrochloride | 1.1 mg (3%) | LC/MS (Method 12B):<br>$R_t$ = 0.66 min<br>MS (ESIpos):<br>m/z = 372 (M + H)$^+$<br>purity: 93% |
| Example 407 | 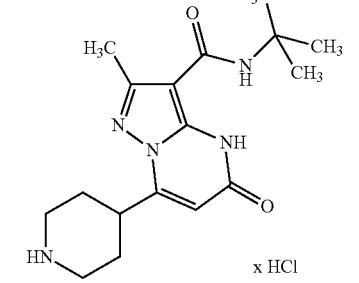 | N-tert-butyl-2-methyl-5-oxo-7-(piperidin-4-yl)-4,5-dihydropyrazolo[1,5-a]pyrimidine-3-carboxamide hydrochloride | 0.6 mg (2%) | LC/MS (Method 12B):<br>$R_t$ = 0.65 min<br>MS (ESIpos):<br>m/z = 344 (M + H)$^+$<br>purity: 100% |
| Example 408 | 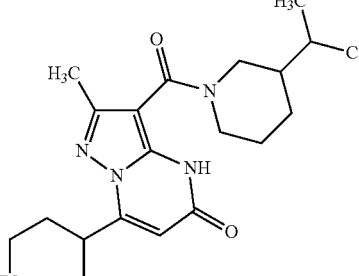 | 3-[(3-isopropyl-piperidin-1-yl)carbonyl]-2-methyl-7-(piperidin-4-yl)pyrazolo[1,5-a]pyrimidin-5(4H)-one hydrochloride | 14.6 mg (33%) | LC/MS (Method 12B):<br>$R_t$ = 0.69 min<br>MS (ESIpos):<br>m/z = 386 (M + H)$^+$<br>purity: 96% |
| Example 409 | 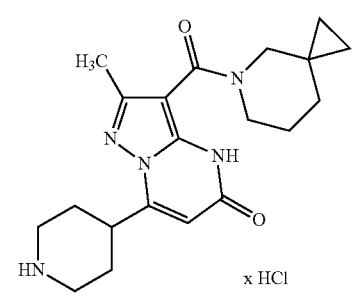 [SMILES: Cc1nn2c(C3CCNCC3)cc(=O)[nH]c2c1C(=O)N1CCCC2(CC2)C1] | 3-(5-azaspiro[2.5]oct-5-ylcarbonyl)-2-methyl-7-(piperidin-4-yl)pyrazolo[1,5-a]pyrimidin-5(4H)-one hydrochloride | 14.0 mg (30%) | LC/MS (Method 12B):<br>$R_t$ = 0.63 min<br>MS (ESIpos):<br>m/z = 370 (M + H)$^+$<br>purity: 86% |

TABLE 4-continued

Examples 397 to 437, prepared in analogy to Example 397

| Example | Structure | Name | % of theory | LC-MS data |
|---|---|---|---|---|
| Example 410 | 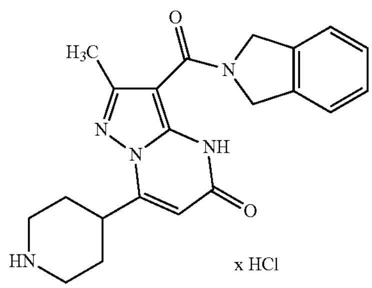 [SMILES: Cc1nn2c(C3CCNCC3)cc(=O)[nH]c2c1C(=O)N1Cc2ccccc2C1] | 3-(1,3-dihydro-2H-isoindol-2-ylcarbonyl)-2-methyl-7-(piperidin-4-yl)pyrazolo[1,5-a]pyrimidin-5(4H)-one hydrochloride | 5.0 mg (10%) | LC/MS (Method 12B): R$_t$ = 0.64 min MS (ESIpos): m/z = 378 (M + H)$^+$ purity: 85% |
| Example 411 | 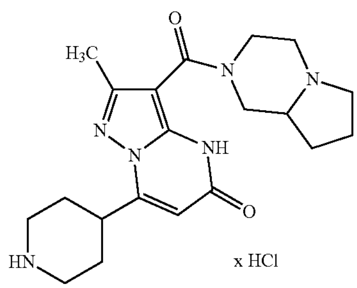 [SMILES: Cc1nn2c(C3CCNCC3)cc(=O)[nH]c2c1C(=O)N1CCN2CCCC2C1] | 3-(hexahydropyrrolo[1,2-a]pyrazin-2(1H)-ylcarbonyl)-2-methyl-7-(piperidin-4-yl)pyrazolo[1,5-a]pyrimidin-5(4H)-one hydrochloride | 1.5 mg (3%) | LC/MS (Method 12B): R$_t$ = 0.68 min MS (ESIpos): m/z = 385 (M + H)$^+$ purity: 95% |
| Example 412 | 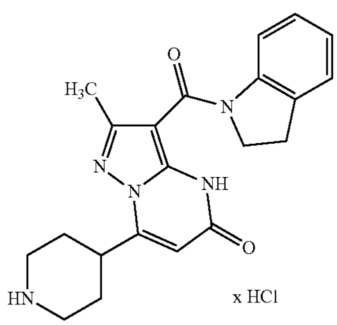 [SMILES: Cc1nn2c(C3CCNCC3)cc(=O)[nH]c2c1C(=O)N1CCc2ccccc21] | 3-(2,3-dihydro-1H-indol-1-ylcarbonyl)-2-methyl-7-(piperidin-4-yl)pyrazolo[1,5-a]pyrimidin-5(4H)-one hydrochloride | 18.8 mg (42%) | LC/MS (Method 12B): R$_t$ = 0.65 min MS (ESIpos): m/z = 378 (M + H)$^+$ purity: 93% |
| Example 413 | 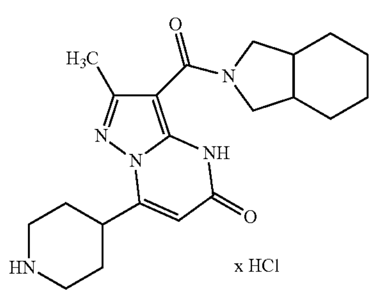 [SMILES: Cc1nn2c(C3CCNCC3)cc(=O)[nH]c2c1C(=O)N1CC2CCCCC2C1] | 2-methyl-3-(octahydro-2H-isoindol-2-ylcarbonyl)-7-(piperidin-4-yl)pyrazolo[1,5-a]pyrimidin-5(4H)-one hydrochloride | 11.0 mg (25%) | LC/MS (Method 12B): R$_t$ = 0.65 min MS (ESIpos): m/z = 384 (M + H)$^+$ purity: 94% |
| Example 414 | 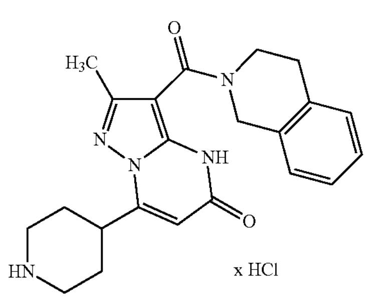 [SMILES: Cc1nn2c(C3CCNCC3)cc(=O)[nH]c2c1C(=O)N1CCc2ccccc2C1] | 3-(3,4-dihydroisoquinolin-2(1H)-ylcarbonyl)-2-methyl-7-(piperidin-4-yl)pyrazolo[1,5-a]pyrimidin-5(4H)-one hydrochloride | 5.5 mg (13%) | LC/MS (Method 12B): R$_t$ = 0.66 min MS (ESIpos): m/z = 392 (M + H)$^+$ purity: 100% |

TABLE 4-continued

Examples 397 to 437, prepared in analogy to Example 397

| Example | Structure | Name | % of theory | LC-MS data |
|---|---|---|---|---|
| Example 415 | 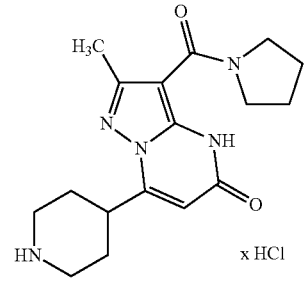 [SMILES: Cc1nn2c(C3CCNCC3)cc(=O)[nH]c2c1C(=O)N1CCCC1] | 2-methyl-7-(piperidin-4-yl)-3-(pyrrolidin-1-ylcarbonyl)pyrazolo[1,5-a]pyrimidin-5(4H)-one hydrochloride | 10.7 mg (27%) | LC/MS (Method 12B): $R_t$ = 0.52 min MS (ESIpos): m/z = 330 (M + H)$^+$ purity: 92% |
| Example 416 | 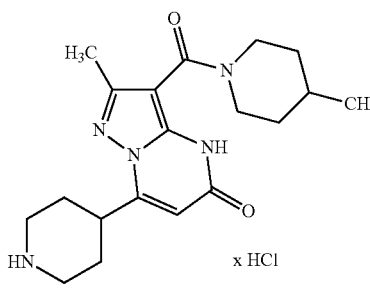 | 2-methyl-3-[(4-methyl-piperidin-1-yl)carbonyl]-7-(piperidin-4-yl)pyrazolo[1,5-a]pyrimidin-5(4H)-one hydrochloride | 1.0 mg (3%) | LC/MS (Method 12B): $R_t$ = 0.59 min MS (ESIpos): m/z = 358 (M + H)$^+$ purity: 100% |
| Example 417 | 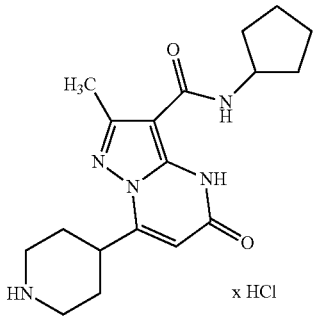 [SMILES: Cc1nn2c(C3CCNCC3)cc(=O)[nH]c2c1C(=O)NC1CCCC1] | N-cyclopentyl-2-methyl-5-oxo-7-(piperidin-4-yl)-4,5-dihydro-pyrazolo[1,5-a]pyrimidine-3-carboxamide hydrochloride | 1.2 mg (3%) | LC/MS (Method 12B): $R_t$ = 0.61 min MS (ESIpos): m/z = 344 (M + H)$^+$ purity: 100% |
| Example 418 | 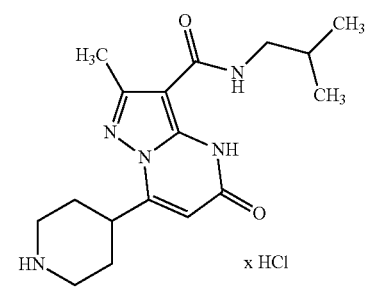 [SMILES: Cc1nn2c(C3CCNCC3)cc(=O)[nH]c2c1C(=O)NCC(C)C] | N-isobutyl-2-methyl-5-oxo-7-(piperidin-4-yl)-4,5-dihydro-pyrazolo[1,5-a]pyrimidine-3-carboxamide hydrochloride | 0.8 mg (2%) | LC/MS (Method 12B): $R_t$ = 0.60 min MS (ESIpos): m/z = 332 (M + H)$^+$ purity: 90% |
| Example 419 | 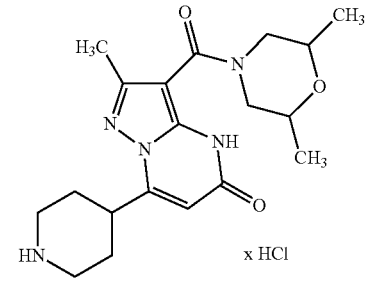 [SMILES: Cc1nn2c(C3CCNCC3)cc(=O)[nH]c2c1C(=O)N1CC(C)OC(C)C1] | 3-[(2,6-dimethyl-morpholin-4-yl)carbonyl]-2-methyl-7-(piperidin-4-yl)pyrazolo[1,5-a]pyrimidin-5(4H)-one hydrochloride | 3.9 mg (10%) | LC/MS (Method 12B): $R_t$ = 0.54 min MS (ESIpos): m/z = 374 (M + H)$^+$ purity: 100% |

TABLE 4-continued

Examples 397 to 437, prepared in analogy to Example 397

| Example | Structure | Name | % of theory | LC-MS data |
|---|---|---|---|---|
| Example 420 | 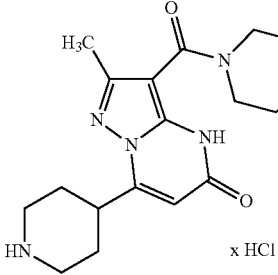 | 3-[(3,3-dimethyl-piperidin-1-yl)carbonyl]-2-methyl-7-(piperidin-4-yl)pyrazolo[1,5-a]pyrimidin-5(4H)-one hydrochloride | 2.1 mg (5%) | LC/MS (Method 12B): $R_t$ = 0.61 min MS (ESIpos): m/z = 372 (M + H)⁺ purity: 100% |
| Example 421 | 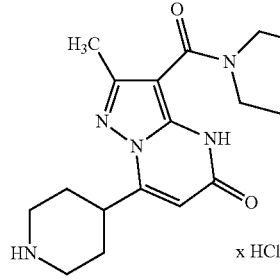 | 3-[(3,5-dimethyl-piperidin-1-yl)carbonyl]-2-methyl-7-(piperidin-4-yl)pyrazolo[1,5-a]pyrimidin-5(4H)-one hydrochloride | 0.8 mg (2%) | LC/MS (Method 12B): $R_t$ = 0.63 min MS (ESIpos): m/z = 372 (M + H)⁺ purity: 100% |
| Example 422 | 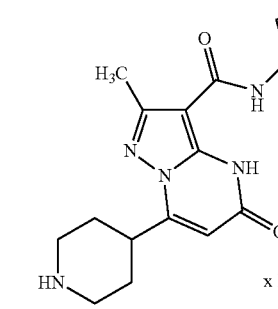 | N-cyclobutyl-2-methyl-5-oxo-7-(piperidin-4-yl)-4,5-dihydro-pyrazolo[1,5-a]pyrimidine-3-carboxamide hydrochloride | 4.3 mg (11%) | LC/MS (Method 12B): $R_t$ = 0.58 min MS (ESIpos): m/z = 330 (M + H)⁺ purity: 94% |
| Example 423 | 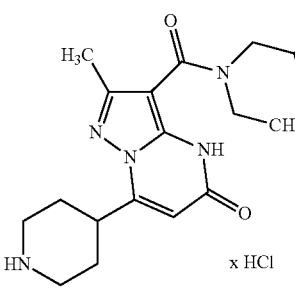 | N-benzyl-N-ethyl-2-methyl-5-oxo-7-(piperidin-4-yl)-4,5-dihydro-pyrazolo[1,5-a]pyrimidine-3-carboxamide hydrochloride | 4.8 mg (11%) | LC/MS (Method 12B): $R_t$ = 0.62 min MS (ESIpos): m/z = 394 (M + H)⁺ purity: 100% |
| Example 424 | 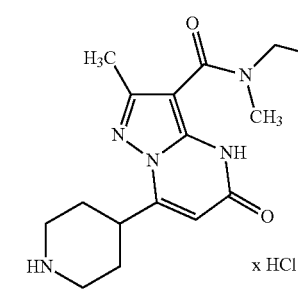 | N-ethyl-N,2-dimethyl-5-oxo-7-(piperidin-4-yl)-4,5-dihydro-pyrazolo[1,5-a]pyrimidine-3-carboxamide hydrochloride | 9.6 mg (24%) | LC/MS (Method 12B): $R_t$ = 0.52 min MS (ESIpos): m/z = 318 (M + H)⁺ purity: 90% |

TABLE 4-continued

Examples 397 to 437, prepared in analogy to Example 397

| Example | Structure | Name | % of theory | LC-MS data |
|---|---|---|---|---|
| Example 425 | 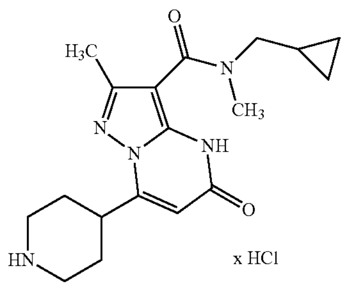 [SMILES: Cc1nn2c(C3CCNCC3)cc(=O)[nH]c2c1C(=O)N(C)CC1CC1] | N-(cyclopropyl-methyl)-N,2-dimethyl-5-oxo-7-(piperidin-4-yl)-4,5-dihydro-pyrazolo[1,5-a]pyrimidine-3-carboxamide hydrochloride | 9.7 mg (24%) | LC/MS (Method 12B): $R_t$ = 0.55 min MS (ESIpos): m/z = 344 (M + H)$^+$ purity: 92% |
| Example 426 | 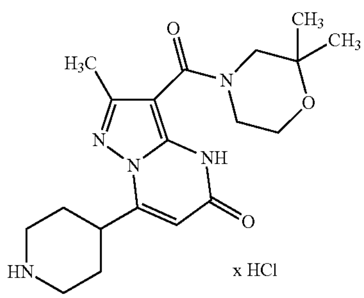 [SMILES: Cc1nn2c(C3CCNCC3)cc(=O)[nH]c2c1C(=O)N1CCOC(C)(C)C1] | 3-[(2,2-dimethyl-morpholin-4-yl)carbonyl]-2-methyl-7-(piperidin-4-yl)pyrazolo[1,5-a]pyrimidin-5(4H)-one hydrochloride | 8.3 mg (19%) | LC/MS (Method 12B): $R_t$ = 0.53 min MS (ESIpos): m/z = 374 (M + H)$^+$ purity: 95% |
| Example 427 | 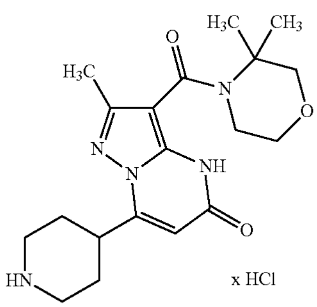 [SMILES: Cc1nn2c(C3CCNCC3)cc(=O)[nH]c2c1C(=O)N1CCOCC1(C)C] | 3-[(3,3-dimethyl-morpholin-4-yl)carbonyl]-2-methyl-7-(piperidin-4-yl)pyrazolo[1,5-a]pyrimidin-5(4H)-one hydrochloride | 0.6 mg (1%) | LC/MS (Method 12B): $R_t$ = 0.56 min MS (ESIpos): m/z = 374 (M + H)$^+$ purity: 100% |
| Example 428 | 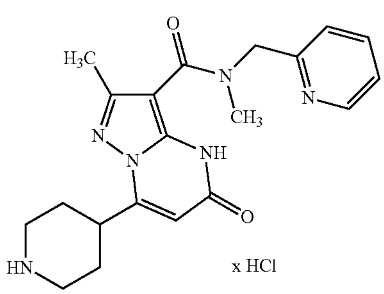 [SMILES: Cc1nn2c(C3CCNCC3)cc(=O)[nH]c2c1C(=O)N(C)Cc1ccccn1] | N,2-dimethyl-5-oxo-7-(piperidin-4-yl)-N-(pyridin-2-ylmethyl)-4,5-dihydro-pyrazolo[1,5-a]pyrimidine-3-carboxamide hydrochloride | 0.6 mg (1%) | LC/MS (Method 12B): $R_t$ = 0.55 min MS (ESIpos): m/z = 381 (M + H)$^+$ purity: 100% |
| Example 429 | 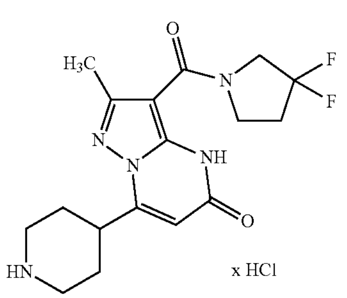 [SMILES: Cc1nn2c(C3CCNCC3)cc(=O)[nH]c2c1C(=O)N1CCC(F)(F)C1] | 3-[(3,3-difluoro-pyrrolidin-1-yl)carbonyl]-2-methyl-7-(piperidin-4-yl)pyrazolo[1,5-a]pyrimidin-5(4H)-one hydrochloride | 7.8 mg (19%) | LC/MS (Method 12B): $R_t$ = 0.53 min MS (ESIpos): m/z = 366 (M + H)$^+$ purity: 100% |

TABLE 4-continued

Examples 397 to 437, prepared in analogy to Example 397

| Example | Structure | Name | % of theory | LC-MS data |
|---|---|---|---|---|
| Example 430 | 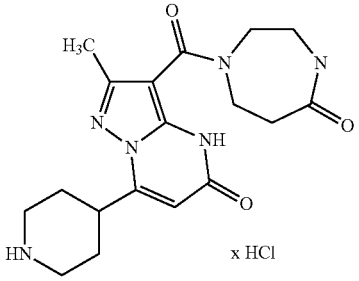 [SMILES: Cc1nn2c(C3CCNCC3)cc(=O)[nH]c2c1C(=O)N1CCNC(=O)CC1] | 2-methyl-3-[(5-oxo-1,4-diazepan-1-yl)carbonyl]-7-(piperidin-4-yl)pyrazolo[1,5-a]pyrimidin-5(4H)-one hydrochloride | 0.7 mg (2%) | LC/MS (Method 12B):<br>$R_t$ = 0.50 min<br>3 min<br>MS (ESIpos):<br>m/z = 373 (M + H)$^+$<br>purity: 90% |
| Example 431 | 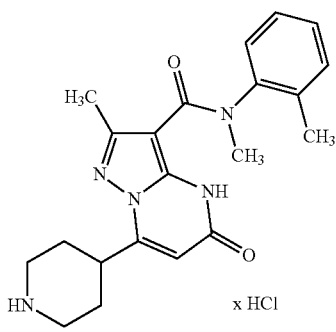 [SMILES: Cc1ccccc1N(C)C(=O)c1c(C)nn2c(C3CCNCC3)cc(=O)[nH]c12] | N,2-dimethyl-N-(2-methylphenyl)-5-oxo-7-(piperidin-4-yl)-4,5-dihydropyrazolo[1,5-a]pyrimidine-3-carboxamide hydrochloride | 0.5 mg (1%) | LC/MS (Method 12B):<br>$R_t$ = 0.61 min<br>3 min<br>MS (ESIpos):<br>m/z = 380 (M + H)$^+$<br>purity: 100% |
| Example 432 | 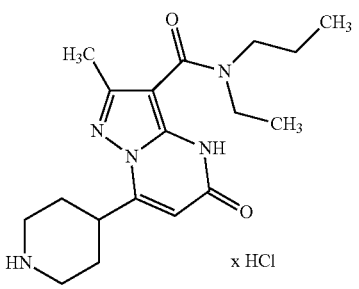 [SMILES: CCCN(CC)C(=O)c1c(C)nn2c(C3CCNCC3)cc(=O)[nH]c12] | N-ethyl-2-methyl-5-oxo-7-(piperidin-4-yl)-N-propyl-4,5-dihydropyrazolo[1,5-a]pyrimidine-3-carboxamide hydrochloride | 4.0 mg (10%) | LC/MS (Method 12B):<br>$R_t$ = 0.53 min<br>MS (ESIpos):<br>m/z = 346 (M + H)$^+$<br>purity: 100% |
| Example 433 | 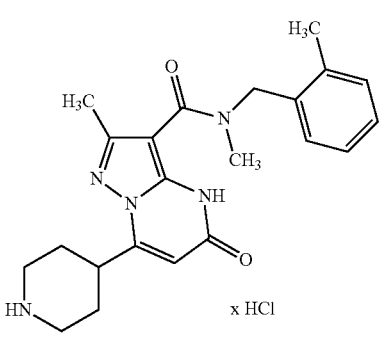 [SMILES: Cc1ccccc1CN(C)C(=O)c1c(C)nn2c(C3CCNCC3)cc(=O)[nH]c12] | N,2-dimethyl-N-(2-methylbenzyl)-5-oxo-7-(piperidin-4-yl)-4,5-dihydropyrazolo[1,5-a]pyrimidine-3-carboxamide hydrochloride | 5.4 mg (11%) | LC/MS (Method 12B):<br>$R_t$ = 0.67 min<br>MS (ESIpos):<br>m/z = 394 (M + H)$^+$<br>purity: 88% |
| Example 434 | 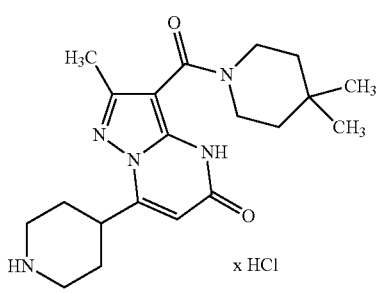 [SMILES: Cc1nn2c(C3CCNCC3)cc(=O)[nH]c2c1C(=O)N1CCC(C)(C)CC1] | 3-[(4,4-dimethylpiperidin-1-yl)carbonyl]-2-methyl-7-(piperidin-4-yl)pyrazolo[1,5-a]pyrimidin-5(4H)-one hydrochloride | 22.1 mg (51%) | LC/MS (Method 12B):<br>$R_t$ = 0.65 min<br>MS (ESIpos):<br>m/z = 372 (M + H)$^+$<br>purity: 95% |

TABLE 4-continued

Examples 397 to 437, prepared in analogy to Example 397

| Example | Structure | Name | % of theory | LC-MS data |
|---|---|---|---|---|
| Example 435 | 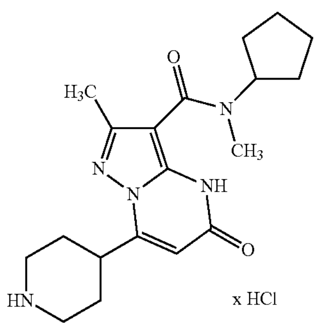 | N-cyclopentyl-N,2-dimethyl-5-oxo-7-(piperidin-4-yl)-4,5-dihydro-pyrazolo[1,5-a]pyrimidine-3-carboxamide hydrochloride | 2.5 mg (5%) | LC/MS (Method 12B): $R_t$ = 0.62 min MS (ESIpos): m/z = 372 (M + H)$^+$ purity: 86% |
| Example 436 | 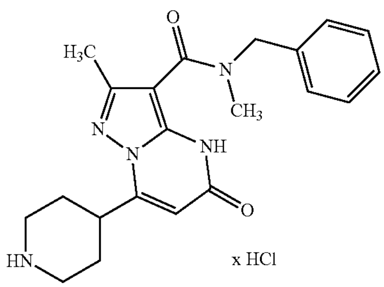 [SMILES: Cc1nn2c(C3CCNCC3)cc(=O)[nH]c2c1C(=O)N(C)Cc1ccccc1] | N-benzyl-N,2-dimethyl-5-oxo-7-(piperidin-4-yl)-4,5-dihydro-pyrazolo[1,5-a]pyrimidine-3-carboxamide hydrochloride | 22.4 mg (47%) | LC/MS (Method 12B): $R_t$ = 0.63 min MS (ESIpos): m/z = 380 (M + H)$^+$ purity: 88% |

Example 437

3-[3-(2-methoxyphenyl)-1,2,4-oxadiazol-5-yl]-2-methyl-7-(piperidin-4-yl)pyrazolo[1,5-a]pyrimidin-5(4H)-one hydrochloride

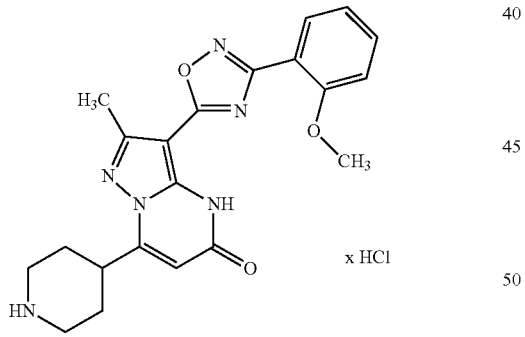

tert-butyl 4-{3-[3-(2-methoxyphenyl)-1,2,4-oxadiazol-5-yl]-2-methyl-5-oxo-4,5-dihydropyrazolo[1,5-a]pyrimidin-7-yl}piperidine-1-carboxylate (89.9 mg, 177 µmol) was dissolved in 1,4-dioxan (2.0 ml, 23 mmol) and treated with hydrochloric acid in 1,4-dioxan (670 µl, 4.0 M, 2.7 mmol) at RT for 16 h. Solvents were removed, acetonitrile was added and the resulting participate was filtered and washed with acetonitrile. Drying in vacuo afforded the product. The obtained amount was 82.8 mg (100% purity, 105% of theory).

LC-MS (Method 1B): $R_t$=0.60 min; MS (ESIpos): m/z=407 [M+H]$^+$ $^1$H-NMR (400 MHz, DMSO-d6) delta [ppm]: 1.145 (0.13), 1.867 (0.31), 1.899 (0.94), 1.931 (1.03), 1.963 (0.42), 2.072 (0.18), 2.191 (1.50), 2.224 (1.19), 2.322 (0.08), 2.327 (0.11), 2.365 (0.20), 2.461 (0.12), 2.591 (0.10), 2.624 (10.69), 2.664 (0.10), 2.669 (0.12), 2.709 (0.18), 3.074 (0.37), 3.104 (1.00), 3.132 (1.05), 3.161 (0.43), 3.384 (1.52), 3.414 (1.16), 3.596 (0.75), 3.626 (0.38), 3.710 (0.14), 3.730 (0.15), 3.742 (0.15), 3.753 (0.13), 3.828 (0.15), 3.838 (0.15), 3.894 (16.00), 4.073 (1.04), 4.115 (1.06), 6.120 (0.94), 7.081 (0.06), 7.125 (1.01), 7.144 (2.07), 7.163 (1.14), 7.229 (1.88), 7.250 (2.14), 7.551 (0.78), 7.555 (0.81), 7.573 (1.36), 7.591 (0.65), 7.594 (0.65), 8.131 (0.72), 8.149 (0.70), 9.027 (0.34).

Example 438

3-[3-(2-fluorophenyl)-1,2,4-oxadiazol-5-yl]-2-methyl-7-(piperidin-4-yl)pyrazolo[1,5-a]pyrimidin-5(4H)-one hydrochloride

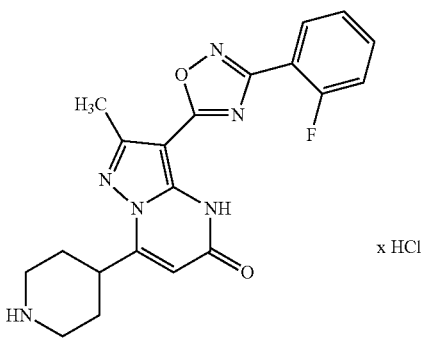 [SMILES: Cc1nn2c(C3CCNCC3)cc(=O)[nH]c2c1-c1nc(-c2ccccc2F)no1]

tert-butyl 4-{3-[3-(2-fluorophenyl)-1,2,4-oxadiazol-5-yl]-2-methyl-5-oxo-4,5-dihydropyrazolo[1,5-a]pyrimidin- 7-yl}piperidine-1-carboxylate (88.5 mg, 179 μmol) was dissolved in 1,4-dioxan (2.0 ml, 23 mmol) and treated with hydrochloric acid in 1,4-dioxan (670 μl, 4.0 M, 2.7 mmol) at RT for 16 h. Solvents were removed, acetonitrile was added and the resulting participate was filtered and washed with acetonitrile. Drying in vacuo afforded the product. The obtained amount was 70.3 mg (100% purity, 91% of theory).

LC-MS (Method 1B): $R_t$=0.61 min; MS (ESIpos): m/z=395 [M+H]$^+$ $^1$H-NMR (400 MHz, DMSO-d6) delta [ppm]: −0.153 (0.03), −0.012 (0.32), 0.142 (0.03), 1.145 (0.05), 1.193 (0.06), 1.227 (0.04), 1.352 (0.05), 1.423 (0.13), 1.871 (0.25), 1.880 (0.31), 1.905 (0.82), 1.912 (0.84), 1.936 (0.92), 1.944 (0.89), 1.968 (0.40), 1.977 (0.34), 2.072 (1.97), 2.192 (1.28), 2.225 (1.02), 2.326 (0.04), 2.366 (0.07), 2.475 (0.10), 2.638 (10.34), 2.709 (0.08), 2.798 (0.06), 3.109 (0.73), 3.133 (0.75), 3.386 (1.33), 3.417 (1.05), 3.472 (0.04), 3.490 (0.03), 3.565 (16.00), 3.598 (0.65), 3.628 (0.32), 3.664 (0.03), 3.679 (0.03), 3.730 (0.03), 6.144 (0.98), 7.429 (1.85), 7.449 (3.10), 7.469 (1.14), 7.476 (1.03), 7.642 (0.41), 7.647 (0.45), 7.655 (0.49), 7.661 (0.75), 7.667 (0.65), 7.677 (0.66), 7.681 (0.70), 7.686 (0.38), 7.694 (0.33), 7.699 (0.30), 8.346 (0.40), 8.364 (0.70), 8.382 (0.39), 8.952 (0.29), 9.031 (0.40), 11.933 (0.09).

Example 439

3-[3-(2-chlorobenzyl)-1,2,4-oxadiazol-5-yl]-2-methyl-7-(piperidin-4-yl)pyrazolo[1,5-a]pyrimidin-5 (4H)-one hydrochloride

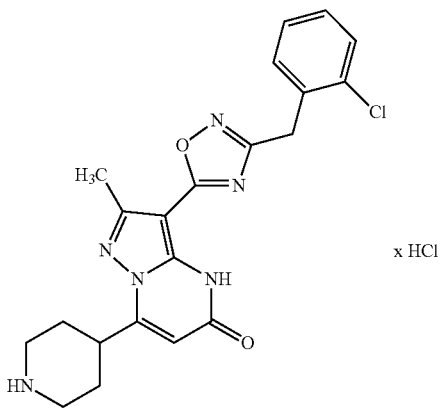 [SMILES: Cc1nn2c(C3CCNCC3)cc(=O)[nH]c2c1-c1nc(Cc2ccccc2Cl)no1]

tert-butyl 4-{3-[3-(2-chlorobenzyl)-1,2,4-oxadiazol-5-yl]-2-methyl-5-oxo-4,5-dihydropyrazolo[1,5-a]pyrimidin-7-yl}piperidine-1-carboxylate (44.2 mg, 84.2 μmol) was dissolved in 1,4-dioxan (2.0 ml, 23 mmol) and treated with hydrochloric acid in 1,4-dioxan (320 μl, 4.0 M, 1.3 mmol) at RT for 16 h. Solvents were removed, acetonitrile was added and the resulting participate was filtered and washed with acetonitrile. Drying in vacuo afforded the product. The obtained amount was 32.3 mg (95% purity, 79% of theory).

LC-MS (Method 11B): $R_t$=1.15 min; MS (ESIpos): m/z=425 [M+H]$^+$ $^1$H-NMR (400 MHz, DMSO-d6) delta [ppm]: −0.151 (0.13), −0.009 (1.72), 0.007 (1.23), 0.145 (0.15), 1.146 (0.32), 1.234 (0.16), 1.753 (0.54), 1.827 (0.84), 1.858 (1.98), 1.883 (2.08), 1.915 (0.87), 2.175 (2.95), 2.207 (2.29), 2.276 (0.11), 2.327 (0.29), 2.366 (0.55), 2.409 (1.43), 2.639 (0.25), 2.664 (0.27), 2.669 (0.28), 2.709 (0.55), 3.114 (1.89), 3.379 (3.22), 3.410 (2.48), 3.462 (0.23), 3.474 (0.25), 3.566 (1.97), 3.585 (0.92), 3.665 (0.20), 3.678 (0.20), 3.697 (0.19), 3.711 (0.16), 4.261 (16.00), 4.425 (0.08), 5.411 (0.71), 5.962 (0.20), 6.145 (0.39), 7.312 (0.46), 7.319 (0.88), 7.331 (4.86), 7.337 (3.40), 7.342 (5.15), 7.348 (3.85), 7.354 (6.03), 7.367 (1.10), 7.373 (0.39), 7.382 (0.34), 7.473 (3.27), 7.483 (4.97), 7.490 (3.18), 7.494 (4.13), 7.506 (2.61), 7.519 (0.24), 8.679 (0.60), 8.859 (0.76), 11.500 (0.16).

Example 440

2-methyl-3-[3-(2-methylphenyl)-1,2,4-oxadiazol-5-yl]-7-(piperidin-4-yl)pyrazolo[1,5-a]pyrimidin-5 (4H)-one hydrochloride

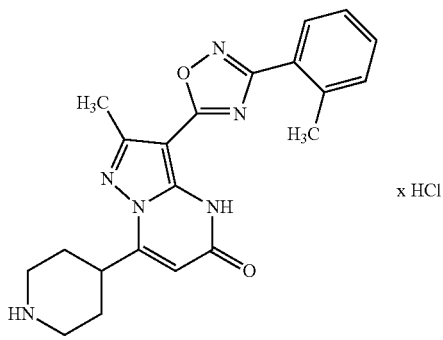 [SMILES: Cc1ccccc1-c1noc(-c2c(C)nn3c(C4CCNCC4)cc(=O)[nH]c23)n1]

tert-butyl 4-{2-methyl-3-[3-(2-methylphenyl)-1,2,4-oxadiazol-5-yl]-5-oxo-4,5-dihydropyrazolo[1,5-a]pyrimidin-7-yl}piperidine-1-carboxylate (104 mg, 211 μmol) was dissolved in 1,4-dioxan (2.0 ml, 23 mmol) and treated with hydrochloric acid in 1,4-dioxan (790 μl, 4.0 M, 3.2 mmol) at RT for 16 h. Solvents were removed, acetonitrile was added and the resulting participate was filtered and washed with acetonitrile. Drying in vacuo afforded the product. The obtained amount was 81.1 mg (98% purity, 88% of theory).

LC-MS (Method 1B): $R_t$=0.68 min; MS (ESIpos): m/z=391 [M+H]$^+$ $^1$H-NMR (400 MHz, DMSO-d6) delta [ppm]: −0.152 (0.06), −0.011 (0.52), 0.005 (0.49), 0.144 (0.06), 1.108 (0.13), 1.146 (0.10), 1.228 (0.05), 1.424 (0.78), 1.593 (0.10), 1.859 (0.35), 1.868 (0.43), 1.892 (1.11), 1.900 (1.15), 1.924 (1.25), 1.931 (1.20), 1.956 (0.55), 1.965 (0.46), 2.072 (0.08), 2.197 (1.73), 2.230 (1.39), 2.322 (0.06), 2.327 (0.08), 2.331 (0.06), 2.365 (0.16), 2.455 (0.10), 2.616 (16.00), 2.644 (13.66), 2.669 (0.20), 2.709 (0.16), 2.774 (0.09), 2.803 (0.08), 3.125 (1.04), 3.390 (1.80), 3.421 (1.44), 3.566 (2.20), 3.575 (0.46), 3.605 (0.82), 3.635 (0.40), 6.150 (0.99), 7.393 (0.74), 7.413 (2.74), 7.432 (3.41), 7.468 (1.66), 7.472 (1.73), 7.487 (1.76), 7.505 (0.61), 7.509 (0.59), 8.171 (1.01), 8.189 (1.01), 8.847 (0.33), 8.968 (0.42), 11.869 (0.11).

Example 441

3-[3-(3-chlorophenyl)-1,2,4-oxadiazol-5-yl]-2-methyl-7-(piperidin-4-yl)pyrazolo[1,5-a]pyrimidin-5(4H)-one hydrochloride

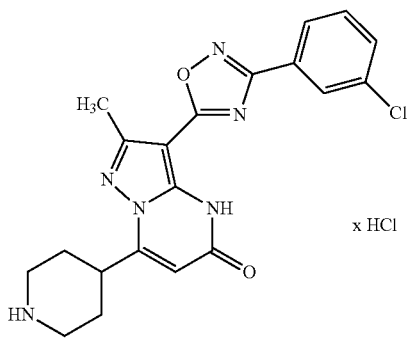 [SMILES: Cc1nn2c(C3CCNCC3)cc(=O)[nH]c2c1-c1nc(-c2cccc(Cl)c2)no1]

tert-butyl 4-{3-[3-(3-chlorophenyl)-1,2,4-oxadiazol-5-yl]-2-methyl-5-oxo-4,5-dihydropyrazolo[1,5-a]pyrimidin-7-yl}piperidine-1-carboxylate (76.6 mg, 150 μmol) was dissolved in 1,4-dioxan (2.0 ml, 23 mmol) and treated with hydrochloric acid in 1,4-dioxan (560 μl, 4.0 M, 2.2 mmol) at RT for 16 h. Solvents were removed, acetonitrile was added and the resulting participate was filtered and washed with acetonitrile. Drying in vacuo afforded the product. The obtained amount was 56.9 mg (97% purity, 82% of theory).

LC-MS (Method 1B): $R_t$=0.72 min; MS (ESIpos): m/z=411 [M+H]$^+$ $^1$H-NMR (400 MHz, DMSO-d6) delta [ppm]: −0.151 (0.17), −0.010 (1.46), 0.006 (1.44), 0.144 (0.20), 1.146 (0.25), 1.229 (0.09), 1.424 (2.84), 1.594 (0.23), 1.855 (0.65), 1.885 (1.81), 1.912 (1.99), 1.944 (0.83), 2.015 (0.09), 2.072 (2.28), 2.195 (2.85), 2.229 (2.31), 2.327 (0.24), 2.366 (0.38), 2.522 (0.53), 2.524 (0.50), 2.574 (0.13), 2.639 (16.00), 2.668 (0.42), 2.709 (0.39), 2.799 (0.09), 3.139 (1.63), 3.392 (2.93), 3.424 (2.37), 3.566 (3.29), 3.592 (1.19), 3.622 (0.60), 6.140 (1.00), 7.610 (2.21), 7.630 (5.28), 7.649 (4.10), 7.682 (2.66), 7.684 (3.31), 7.686 (3.23), 7.690 (2.87), 7.702 (1.51), 7.707 (1.82), 7.710 (1.47), 8.142 (2.46), 8.161 (2.27), 8.273 (1.85), 8.769 (0.55), 8.917 (0.70), 12.007 (0.25).

Example 442

2-methyl-7-(piperidin-4-yl)-3-{3-[4-(trifluoromethyl)phenyl]-1,2,4-oxadiazol-5-yl}pyrazolo[1,5-a]pyrimidin-5(4H)-one hydrochloride

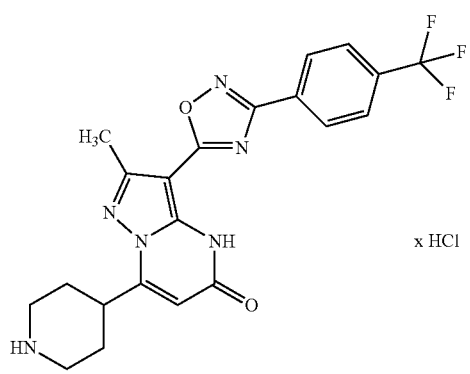 [SMILES: Cc1nn2c(C3CCNCC3)cc(=O)[nH]c2c1-c1nc(-c2ccc(C(F)(F)F)cc2)no1]

tert-butyl 4-(2-methyl-5-oxo-3-{3-[4-(trifluoromethyl)phenyl]-1,2,4-oxadiazol-5-yl}-4,5-dihydropyrazolo[1,5-a]pyrimidin-7-yl)piperidine-1-carboxylate (48.5 mg, 89.1 μmol) was dissolved in 1,4-dioxan (2.0 ml, 23 mmol) and treated with hydrochloric acid in 1,4-dioxan (330 μl, 4.0 M, 1.3 mmol) at RT for 16 h. Solvents were removed, acetonitrile was added and the resulting participate was filtered and washed with acetonitrile. Drying in vacuo afforded the product. The obtained amount was 39.5 mg (93% purity, 86% of theory).

LC-MS (Method 1B): $R_t$=0.75 min; MS (ESIpos): m/z=445 [M+H]$^+$ $^1$H-NMR (400 MHz, DMSO-d6) delta [ppm]: −0.011 (0.89), 1.145 (0.18), 1.424 (8.00), 1.577 (0.17), 1.593 (0.23), 1.870 (0.60), 1.903 (1.65), 1.927 (1.81), 1.958 (0.80), 1.968 (0.71), 2.011 (0.22), 2.072 (0.73), 2.195 (2.56), 2.228 (2.07), 2.327 (0.15), 2.365 (0.23), 2.650 (16.00), 2.709 (0.28), 3.113 (1.47), 3.138 (1.51), 3.392 (2.65), 3.422 (2.15), 3.566 (1.24), 3.599 (1.17), 3.628 (0.58), 4.089 (0.16), 4.122 (0.15), 6.152 (1.21), 6.205 (0.27), 7.962 (5.43), 7.983 (5.89), 8.416 (4.11), 8.436 (3.74), 8.865 (0.56), 8.980 (0.72), 12.022 (0.19).

Example 443

3-[4-methyl-5-(2-methylpropyl)-1,3-thiazol-2-yl]-7-(piperidin-4-yl)pyrazolo[1,5-a]pyrimidin-5(4H)-one hydrochloride

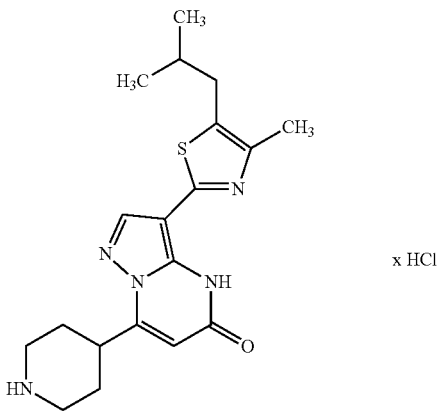 [SMILES: Cc1nc(-c2cnn3c(C4CCNCC4)cc(=O)[nH]c23)sc1CC(C)C]

tert-butyl 4-{3-[4-methyl-5-(2-methylpropyl)-1,3-thiazol-2-yl]-5-oxo-4,5-dihydropyrazolo[1,5-a]pyrimidin-7-yl}piperidine-1-carboxylate (31.5 mg, 66.8 μmol) was dissolved in 1,4-dioxan (2.0 ml, 23 mmol) and treated with hydrochloric acid in 1,4-dioxan (330 μl, 4.0 M, 1.3 mmol) at RT for 16 h. The mixture was purified via reverse phase HPLC (Method: column: Reprosil C18; 10 μm; 125×30 mm/flow: 45 ml/min/solvents: A=water (0.1% formic acid), B=acetonitrile/gradient: 0.00-4.25 min=10% B, 4.50 min=20% B, 15.50 min=85% B, 16.00-18.50 min=100% B, 18.75.00-22.00 min=20% B) to afford the product, after addition of hydrochloric acid in 1,4-dioxan. The obtained amount was 16.5 mg (95% purity, 53% of theory).

LC-MS (Method 10B): $R_t$=1.46 min; MS (ESIpos): m/z=372 [M+H]$^+$ $^1$H-NMR (400 MHz, DMSO-d6) delta [ppm]: −0.152 (0.18), −0.010 (1.98), 0.006 (1.72), 0.144 (0.18), 0.805 (0.20), 0.822 (0.20), 0.832 (0.16), 0.849 (0.16), 0.933 (15.68), 0.949 (16.00), 0.987 (0.17), 1.045 (0.18), 1.062 (0.18), 1.149 (0.62), 1.166 (0.53), 1.780 (0.14), 1.796 (0.45), 1.812 (0.87), 1.829 (1.10), 1.846 (0.86), 1.863 (0.45), 1.897 (0.45), 1.929 (1.20), 1.954 (1.32), 1.985 (0.56), 2.203 (1.81), 2.237 (1.42), 2.356 (13.27), 2.382 (0.27), 2.401 (0.46), 2.660 (3.71), 2.678 (3.57), 2.692 (0.60), 2.709 (0.26), 3.063 (0.45), 3.092 (1.27), 3.121 (1.30), 3.150 (0.54), 3.390 (1.78), 3.421 (1.44), 3.566 (2.55), 3.599 (0.48), 3.629 (0.81), 3.656 (0.45), 3.699 (0.15), 6.288 (0.53), 8.594 (0.23), 8.628 (0.44), 8.908 (0.43), 9.023 (0.59).

Example 444

3-[5-(3,5-difluoro-4-methoxybenzyl)-1,3,4-oxadiazol-2-yl]-7-(piperidin-4-yl)pyrazolo[1,5-a]pyrimidin-5(4H)-one hydrochloride

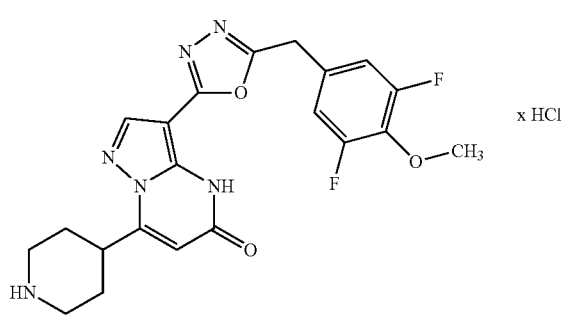 [SMILES: COc1c(F)cc(Cc2nnc(-c3cnn4c(C5CCNCC5)cc(=O)[nH]c34)o2)cc1F]

tert-butyl 4-{3-[5-(3,5-difluoro-4-methoxybenzyl)-1,3,4-oxadiazol-2-yl]-5-oxo-4,5-dihydropyrazolo[1,5-a]pyrimidin-7-yl}piperidine-1-carboxylate (24.0 mg, 44.2 µmol) was dissolved in 1,4-dioxan (10 ml, 120 mmol) and treated with hydrochloric acid in 1,4-dioxan (170 µl, 4.0 M, 660 µmol) at RT for 1 h. Solvents were removed. Drying in vacuo afforded the product. The obtained amount was 14.0 mg (100% purity, 66% of theory).

LC-MS (Method 10B): $R_t$=1.13 min; MS (ESIpos): m/z=443 [M+H]$^+$ $^1$H-NMR (400 MHz, DMSO-d6) delta [ppm]: −0.151 (0.39), −0.009 (3.50), 0.007 (3.24), 0.145 (0.39), 1.146 (0.33), 1.233 (0.26), 1.417 (0.32), 1.843 (0.44), 1.876 (1.18), 1.905 (1.24), 1.937 (0.51), 2.184 (1.79), 2.217 (1.39), 2.327 (0.29), 2.365 (0.33), 2.669 (0.25), 2.709 (0.36), 3.054 (0.47), 3.084 (1.25), 3.112 (1.29), 3.142 (0.54), 3.387 (1.83), 3.417 (1.46), 3.541 (0.52), 3.566 (1.28), 3.600 (0.53), 3.711 (0.37), 3.882 (0.82), 3.905 (16.00), 3.994 (0.86), 4.085 (0.68), 4.306 (9.65), 6.109 (0.56), 7.193 (0.27), 7.201 (0.53), 7.215 (4.08), 7.238 (4.25), 7.252 (0.52), 7.260 (0.31), 8.405 (2.12), 8.696 (0.31), 8.902 (0.41).

Example 445

3-[5-(2-fluorophenyl)-1,3,4-oxadiazol-2-yl]-2-methyl-7-(piperidin-4-yl)pyrazolo[1,5-a]pyrimidin-5(4H)-one hydrochloride

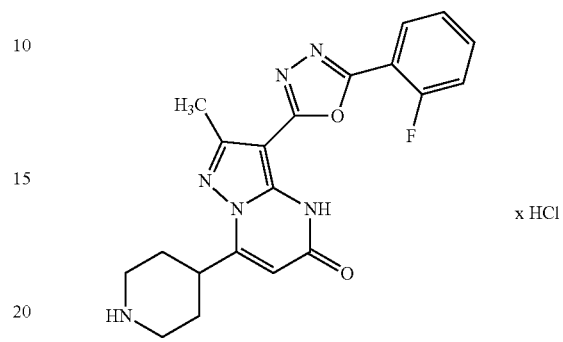

tert-butyl 4-{3-[5-(2-fluorophenyl)-1,3,4-oxadiazol-2-yl]-2-methyl-5-oxo-4,5-dihydropyrazolo[1,5-a]pyrimidin-7-yl}piperidine-1-carboxylate (29.5 mg, 59.7 µmol) was dissolved in 1,4-dioxan (2.0 ml, 23 mmol) and treated with hydrochloric acid in 1,4-dioxan (220 µl, 4.0 M, 890 µmol) at RT for 16 h. Solvents were removed, acetonitrile was added and the resulting participate was filtered and washed with acetonitrile. Drying in vacuo afforded the product. The obtained amount was 16.3 mg (99% purity, 62% of theory).

LC-MS (Method 1B): $R_t$=0.55 min; MS (ESIpos): m/z=395 [M+H]$^+$ $^1$H-NMR (400 MHz, DMSO-d6) delta [ppm]: 1.862 (0.39), 1.894 (1.19), 1.926 (1.32), 1.957 (0.55), 2.190 (1.89), 2.222 (1.49), 2.365 (0.21), 2.574 (16.00), 2.709 (0.21), 3.073 (0.47), 3.102 (1.28), 3.132 (1.31), 3.161 (0.54), 3.384 (1.84), 3.413 (1.47), 3.565 (5.51), 3.585 (1.01), 3.616 (0.49), 4.510 (0.33), 6.048 (2.05), 7.461 (1.25), 7.481 (2.84), 7.499 (1.77), 7.506 (1.59), 7.512 (1.27), 7.534 (1.36), 7.683 (0.61), 7.697 (1.06), 7.717 (0.98), 7.731 (0.44), 7.735 (0.41), 8.180 (0.85), 8.184 (0.88), 8.199 (1.67), 8.202 (1.70), 8.218 (0.88), 8.222 (0.84), 8.921 (0.34), 9.019 (0.48).

Example 446

3-[3-(4-hydroxybenzyl)-1,2,4-oxadiazol-5-yl]-2-methyl-7-(piperidin-4-yl)pyrazolo[1,5-a]pyrimidin-5(4H)-one hydrochloride

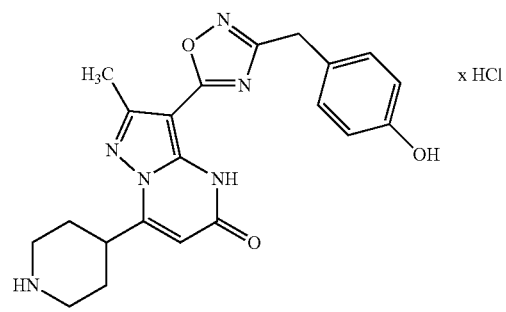 [SMILES: Cc1nn2c(C3CCNCC3)cc(=O)[nH]c2c1-c1nc(Cc2ccc(O)cc2)no1]

tert-butyl 4-{3-[3-(4-hydroxybenzyl)-1,2,4-oxadiazol-5-yl]-2-methyl-5-oxo-4,5-dihydropyrazolo[1,5-a]pyrimidin- 7-yl}piperidine-1-carboxylate (74.8 mg, 148 μmol) was dissolved in 1,4-dioxan (2.0 ml, 23 mmol) and treated with hydrochloric acid in 1,4-dioxan (550 μl, 4.0 M, 2.2 mmol) at RT for 16 h. The mixture was purified via reverse phase HPLC (Method: column: Reprosil C18; 10 μm; 125×30 mm/flow: 50 ml/min/solvents: A=water (0.1% formic acid), B=acetonitrile/gradient: 0.00-5.00 min=10% B, 6.50 min=20% B, 17.0-19.75 min=100% B, 19.75.00-23.00 min=90% B) to afford the product, after addition of hydrochloric acid in 1,4-dioxan. The obtained amount was 31.5 mg (100% purity, 48% of theory).

LC-MS (Method 1B): $R_t$=0.67 min; MS (ESIpos): m/z=407 [M+H]$^+$ $^1$H-NMR (400 MHz, DMSO-d6) delta [ppm]: −0.152 (0.05), −0.010 (0.48), 0.006 (0.48), 0.144 (0.05), 1.146 (0.08), 1.861 (0.30), 1.891 (0.84), 1.917 (0.90), 1.948 (0.39), 2.193 (1.28), 2.226 (1.03), 2.327 (0.07), 2.366 (0.11), 2.633 (8.03), 2.709 (0.13), 3.093 (0.53), 3.124 (1.03), 3.154 (0.60), 3.388 (1.38), 3.420 (1.11), 3.564 (0.32), 3.592 (0.59), 3.622 (0.29), 3.670 (0.08), 3.739 (0.06), 3.853 (16.00), 4.032 (0.07), 5.753 (1.12), 6.124 (0.63), 7.116 (3.63), 7.139 (3.78), 8.119 (2.40), 8.141 (2.26), 8.937 (0.24), 11.871 (0.07).

Example 447

3-[5-(3-fluoro-4-methoxybenzyl)-1,3,4-oxadiazol-2-yl]-7-(piperidin-4-yl)pyrazolo[1,5-a]pyrimidin-5(4H)-one hydrochloride

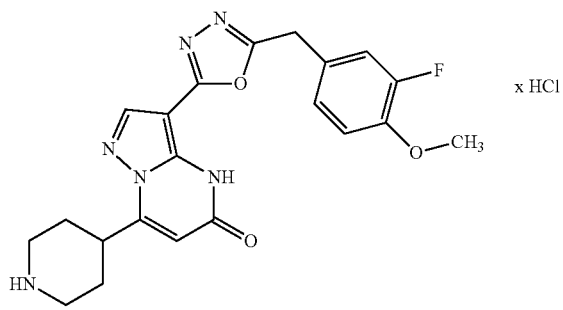 [SMILES: COc1ccc(Cc2nnc(-c3cnn4c(C5CCNCC5)cc(=O)[nH]c34)o2)cc1F]

tert-butyl 4-{3-[5-(3-fluoro-4-methoxybenzyl)-1,3,4-oxadiazol-2-yl]-5-oxo-4,5-dihydropyrazolo[1,5-a]pyrimidin-7-yl}piperidine-1-carboxylate (10.5 mg, 20.0 μmol) was dissolved in 1,4-dioxan (2.0 ml, 23 mmol) and treated with hydrochloric acid in 1,4-dioxan (75 μl, 4.0 M, 300 μmol) at RT for 16 h. Solvents were removed, acetonitrile was added and the resulting participate was filtered and washed with acetonitrile. Drying in vacuo afforded the product. The obtained amount was 9.80 mg (92% purity, 98% of theory).

LC-MS (Method 11B): $R_t$=0.91 min; MS (ESIpos): m/z=425 [M+H]$^+$ $^1$H-NMR (400 MHz, DMSO-d6) delta [ppm]: −0.150 (0.55), −0.009 (5.23), 0.007 (4.36), 0.145 (0.58), 1.146 (0.78), 1.234 (0.58), 1.250 (0.41), 1.266 (0.44), 1.416 (11.24), 1.833 (0.73), 1.862 (1.86), 1.893 (1.95), 1.922 (0.84), 1.977 (0.38), 2.183 (2.82), 2.215 (2.24), 2.322 (0.44), 2.327 (0.61), 2.331 (0.44), 2.365 (1.02), 2.523 (1.54), 2.665 (0.55), 2.669 (0.67), 2.709 (1.07), 3.056 (0.75), 3.086 (2.00), 3.114 (2.09), 3.145 (0.93), 3.387 (3.22), 3.419 (2.47), 3.480 (0.64), 3.567 (1.83), 3.599 (1.60), 3.707 (7.23), 3.732 (6.94), 3.998 (0.41), 4.090 (0.38), 4.236 (0.41), 4.261 (16.00), 6.113 (0.67), 7.124 (0.61), 7.145 (5.98), 7.153 (5.58), 7.158 (7.67), 7.173 (0.52), 7.254 (2.70), 7.287 (2.82), 8.361 (0.44), 8.389 (1.92), 8.615 (0.64), 8.830 (0.84).

Example 448

3-[4-(2-methylphenyl)-1,3-thiazol-2-yl]-7-(piperidin-4-yl)pyrazolo[1,5-a]pyrimidin-5(4H)-one acetate

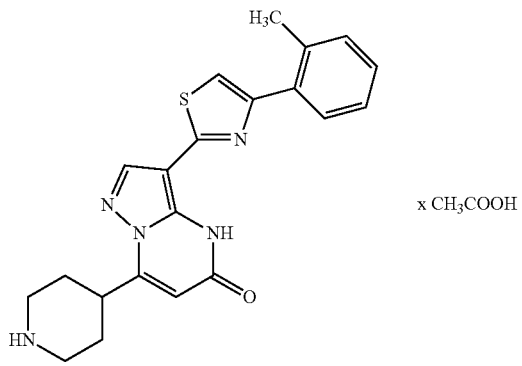 [SMILES: Cc1ccccc1-c1csc(-c2cnn3c(C4CCNCC4)cc(=O)[nH]c23)n1]

tert-butyl 4-{3-[4-(2-methylphenyl)-1,3-thiazol-2-yl]-5-oxo-4,5-dihydropyrazolo[1,5-a]pyrimidin-7-yl}piperidine-1-carboxylate (140 mg, 285 μmol) was dissolved in 1,4-dioxan (5.6 ml, and treated with hydrobromic acid in water (32 μl, 48%, 280 μmol) at RT for 16 h. The mixture was purified via reverse phase HPLC (Method: column: Reprosil C18; 10 μm; 125×30 mm/flow: 45 ml/min/solvents: A=water (0.1% formic acid), B=acetonitrile/gradient: 0.00-4.25 min=10% B, 4.50 min=20% B, 15.50 min=85% B, 16.00-18.50 min=100% B, 18.75.00-22.00 min=20% B) to afford the product, after addition of acetic acid and removal of the solvents. The obtained amount was 47.4 mg (100% purity, 37% of theory).

LC-MS (Method 11B): $R_t$=1.18 min; MS (ESIpos): m/z=392 [M+H]$^+$ $^1$H-NMR (400 MHz, DMSO-d6) delta [ppm]: 1.147 (0.27), 1.813 (0.56), 1.842 (1.39), 1.869 (1.60), 1.908 (12.50), 2.072 (0.20), 2.208 (2.06), 2.240 (1.69), 2.327 (0.28), 2.365 (0.44), 2.464 (16.00), 2.669 (0.30), 2.709 (0.37), 3.072 (1.35), 3.101 (2.41), 3.132 (1.55), 3.309 (3.65), 3.397 (3.25), 3.430 (2.44), 3.513 (0.87), 3.542 (1.23), 3.570 (0.67), 5.995 (2.28), 7.269 (2.15), 7.278 (2.71), 7.284 (3.25), 7.292 (5.23), 7.300 (3.60), 7.559 (4.38), 7.681 (1.49), 7.690 (1.63), 7.703 (1.28), 8.180 (2.13), 8.369 (3.50).

Example 449

7-(piperidin-4-yl)-3-(prop-1-en-2-yl)pyrazolo[1,5-a]pyrimidin-5 (4H)-one hydrochloride

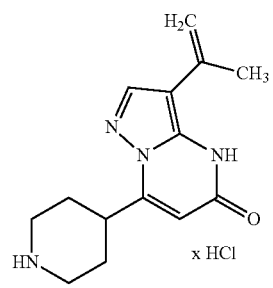 [SMILES: C=C(C)c1cnn2c(C3CCNCC3)cc(=O)[nH]c12]

Compound tert-butyl 4-[3-(2-hydroxypropan-2-yl)-5-oxo-4,5-dihydropyrazolo[1,5-a]pyrimidin-7-yl]piperidine-1-carboxylate (124 mg, 329 μmol) was stirred overnight at room temperature with hydrochloric acid (4N solution in 1,4-dioxan, 2.1 ml). The mixture was stirred with diethyl ether (10 ml) and methanol (0.5 ml) before being filtered. The recovered solid yielded the title compound. The obtained amount was 71.3 mg (100% purity, 73% of theory).

LC-MS (Method 11B): $R_t$=0.57 min; MS (ESIpos): m/z=259 [M+H-xHCl]$^+$ $^1$H-NMR (400 MHz, DMSO-d6) delta [ppm]: 11.88 (bs, 1H), 8.93 (bs, 1H), 8.84-8.66 (m, 1H), (7.85, 7.61, s×2, 1H), (5.76, 5.64, s×2, 1H), 3.59-3.25 (m, 3H), 3.17-3.01 (m, 2H), 2.26-1.76 (m×2, 6H), (1.37, 1.11, s×2, 3H).

Example 450

3-(5-methyl-2-phenyl-1,3-thiazol-4-yl)-7-(piperidin-4-yl)pyrazolo[1,5-a]pyrimidin-5 (4H)-one hydrochloride

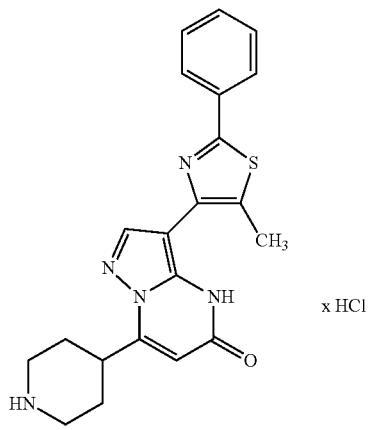 [SMILES: Cc1sc(-c2ccccc2)nc1-c1cnn2c(C3CCNCC3)cc(=O)[nH]c12]

Compound tert-butyl 4-[3-(5-methyl-2-phenyl-1,3-thiazol-4-yl)-5-oxo-4,5-dihydropyrazolo[1,5-a]pyrimidin-7-yl]piperidine-1-carboxylate (7.50 mg, 15.3 μmol) was stirred for 2 h at room temperature with hydrochloric acid (4N solution in 1,4-dioxan, 2.0 ml). The mixture was diluted with water and lyophilized to yield the title compound. The obtained amount was 7.00 mg (95% purity, quantitative).

LC-MS (Method 1B): $R_t$=0.72 min; MS (ESIpos): m/z=392 [M+H-xHCl]$^+$ $^1$H-NMR (400 MHz, DMSO-d6) delta [ppm]: 11.33 (s, 1H), 8.80-8.69 (m, 1H), 8.55-8.41 (m, 1H), 8.21 (s, 1H), 7.96-7.92 (m, 2H), 7.56-7.47 (m, 3H), 5.95 (s, 1H), 3.59 (t, 1H), 3.43 (d, 2H), 3.13 (q, 2H), 2.56 (s, 3H), 2.25 (d, 2H), 1.89 (q, 2H).

Example 451

3-(cyclopentylcarbonyl)-7-(piperidin-4-yl)pyrazolo[1,5-a]pyrimidin-5(4H)-one hydrochloride

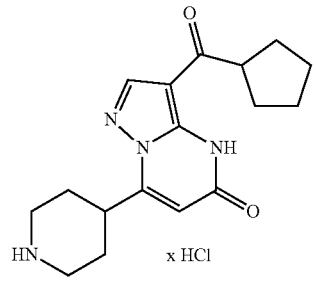 [SMILES: O=C(c1cnn2c(C3CCNCC3)cc(=O)[nH]c12)C1CCCC1]

A mixture of tert-butyl 4-[3-(cyclopentylcarbonoimidoyl)-5-oxo-4,5-dihydropyrazolo[1,5-a]pyrimidin-7-yl]piperidine-1-carboxylate (147 mg, 355 μmol) and hydrochloric acid (1N solution in water, 23 ml) in acetonitrile (23 ml) was stirred overnight at 40° C. The reaction mixture was then frozen and lyophilized. Due to the presence of ammonium chloride, the material was dissolved in water and purified by preparative HPLC (gradient acetonitrile/water with 0.1% formic acid). The combined product fractions were evaporated, dissolved in hydrochloric acid (1N solution in water, 3.0 ml) and lyophilized to yield the title compound. The obtained amount was 109 mg (100% purity, 87% of theory).

LC-MS (Method 1B): $R_t$=0.50 min; MS (ESIpos): m/z=315 [M+H-xHCl]$^+$ $^1$H-NMR (400 MHz, DMSO-d6) delta [ppm]: 11.33 (bs, 1H), 8.98 (bs, 1H), 8.80 (bs, 1H), 8.48 (s, 1H), 6.03 (s, 1H), 3.61-3.46 (m, 2H), 3.38 (d, 2H), 3.08 (t, 2H), 2.17 (d, 2H), 1.95-1.82 (m, 4H), 1.80-1.69 (m, 2H), 1.68-1.56 (m, 4H).

Example 452

3-(2-methylbutanoyl)-7-(piperidin-4-yl)pyrazolo[1,5-a]pyrimidin-5 (4H)-one hydrochloride

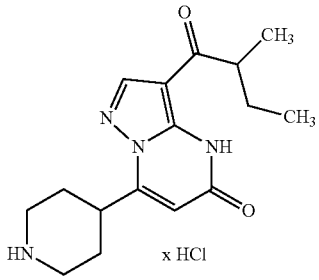 [SMILES: CCC(C)C(=O)c1cnn2c(C3CCNCC3)cc(=O)[nH]c12]

A mixture of tert-butyl 4-[3-(2-methylbutanimidoyl)-5-oxo-4,5-dihydropyrazolo[1,5-a]pyrimidin-7-yl]piperidine-1-carboxylate (144 mg, 359 μmol) and hydrochloric acid (1N solution in water, 11 ml) in acetonitrile (11 ml) was stirred overnight at 40° C. The reaction mixture was then frozen and lyophilized. Due to the presence of ammonium chloride, the material was dissolved in water and purified by preparative HPLC (gradient acetonitrile/water with 0.1% formic acid). The combined product fractions were evaporated, dissolved in hydrochloric acid (1N solution in water, 3.0 ml) and lyophilized to yield the title compound. The obtained amount was 105 mg (100% purity, 86% of theory).

LC-MS (Method 1B): $R_t$=0.47 min; MS (ESIpos): m/z=303 [M+H-xHCl]$^+$ $^1$H-NMR (400 MHz, DMSO-d6) delta [ppm]: 11.35 (bs, 1H), 8.87 (bs, 1H), 8.67 (bs, 1H), 8.50 (s, 1H), 6.04 (bs, 1H), 3.58-3.46 (m, 1H), 3.39 (d, 2H), 3.24-3.03 (m, 1H), 3.09 (t, 2H), 2.17 (d, 2H), 1.87 (q, 2H), 1.75-1.62 (m, 1H), 1.42 (sept, 1H), 1.08 (d, 3H), 0.86 (t, 3H).

Example 453

3-(cyclopropylcarbonyl)-7-(piperidin-4-yl)pyrazolo[1,5-a]pyrimidin-5(4H)-one hydrochloride

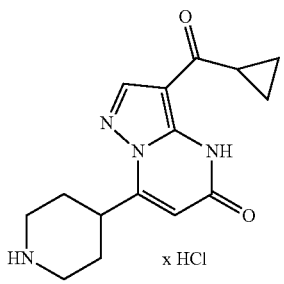 [SMILES: O=C(c1cnn2c(C3CCNCC3)cc(=O)[nH]c12)C1CC1]

A mixture of tert-butyl 4-[3-(cyclopropylcarbonoimidoyl)-5-oxo-4,5-dihydropyrazolo[1,5-a]pyrimidin-7-yl]piperidine-1-carboxylate (44.0 mg, 114 μmol) and hydrochloric acid (1N solution in water, 3.4 ml) in acetonitrile (3.4 ml) was stirred overnight at 40° C. The reaction mixture was then purified by preparative HPLC (gradient acetonitrile/water with 0.1% formic acid). The combined product fractions were evaporated, dissolved in hydrochloric acid (1N solution in water, 2.0 ml) and lyophilized to yield the title compound. The obtained amount was 32.0 mg (93% purity, 81% of theory).

LC-MS (Method 11B): $R_t$=0.51 min; MS (ESIpos): m/z=287 [M+H-xHCl]$^+$ $^1$H-NMR (400 MHz, DMSO-d6) delta [ppm]: 11.29 (bs, 1H), 8.88 (bs, 1H), 8.79-8.53 (m, 1H), 8.64 (s, 1H), 6.05 (bs, 1H), 3.54 (t, 1H), 3.45-3.29 (d, 2H, under water signal), 3.09 (q, 2H), 2.75-2.59 (m, 1H), 2.18 (d, 2H), 1.87 (q, 2H), 1.03-0.95 (m, 4H).

Example 454

Methyl 5-oxo-7-(piperidin-4-yl)-2-(trifluoromethyl)-4,5-dihydropyrazolo[1,5-a]pyrimidine-3-carboxylate hydrochloride

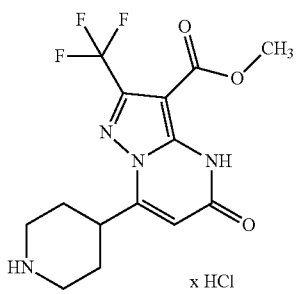 [SMILES: COC(=O)c1c(C(F)(F)F)nn2c(C3CCNCC3)cc(=O)[nH]c12]

To a solution of methyl 7-[1-(tert-butoxycarbonyl)piperidin-4-yl]-5-oxo-2-(trifluoromethyl)-4,5-dihydropyrazolo[1,5-a]pyrimidine-3-carboxylate (50.0 mg, 113 μmol) in acetonitrile (5.0 ml) was added hydrochloric acid (1N solution in water, 5.0 ml). The mixture was stirred overnight at 40° C. The material was purified by preparative HPLC (gradient acetonitrile/water with 0.1% formic acid). Evaporation of the combined product fractions yielded the title compound. The obtained amount was 36.0 mg (95% purity, 80% of theory).

LC-MS (Method 8B): $R_t$=0.65 min; MS (ESIpos): m/z=345 [M+H-xHCl]$^+$ $^1$H-NMR (400 MHz, DMSO-d6) delta [ppm]: −0.009 (5.09), 0.007 (4.66), 1.776 (0.28), 1.813 (0.76), 1.843 (0.88), 1.871 (0.38), 2.129 (1.35), 2.165 (1.09), 3.073 (0.31), 3.102 (0.88), 3.132 (0.90), 3.160 (0.38), 3.371 (1.49), 3.402 (1.14), 3.455 (0.36), 3.485 (0.62), 3.515 (0.33), 3.817 (16.00), 6.188 (0.76), 8.547 (0.19), 8.792 (0.28), 12.008 (0.26).

Example 455

Ethyl 2-(methylsulfanyl)-5-oxo-7-(piperidin-4-yl)-4,5-dihydropyrazolo[1,5-a]pyrimidine-3-carboxylate hydrochloride

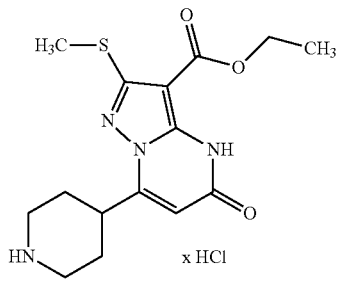 [SMILES: CCOC(=O)c1c(SC)nn2c(C3CCNCC3)cc(=O)[nH]c12]

To a solution of ethyl 7-[1-(tert-butoxycarbonyl)piperidin-4-yl]-2-(methylsulfanyl)-5-oxo-4,5-dihydropyrazolo[1,5-a]pyrimidine-3-carboxylate (50.0 mg, 115 μmol) in acetonitrile (2.0 ml) was added hydrochloric acid (1N solution in water, 1.0 ml). The mixture was stirred overnight at 40° C. before being lyophilized. The material was then purified by preparative HPLC (gradient acetonitrile/water with 0.1% formic acid) and the combined product fractions were lyophilized to yield the title compound. The obtained amount was 23.6 mg (100% purity, 55% of theory).

LC-MS (Method 8B): $R_t$=0.72 min; MS (ESIpos): m/z=337 [M+H-xHCl]$^+$ $^1$H-NMR (400 MHz, DMSO-d6) delta [ppm]: −0.009 (1.10), 0.007 (0.99), 1.253 (3.77), 1.271 (8.60), 1.289 (3.90), 1.798 (0.25), 1.831 (0.77), 1.863 (0.83), 1.894 (0.33), 2.167 (1.18), 2.200 (0.97), 2.512 (16.00), 3.025 (0.27), 3.054 (0.71), 3.081 (0.74), 3.109 (0.32), 3.372 (1.25), 3.404 (1.05), 3.450 (0.61), 3.472 (0.30), 3.480 (0.31), 4.246 (1.01), 4.264 (3.30), 4.281 (3.26), 4.299 (0.99), 5.917 (0.77), 8.641 (0.19), 8.895 (0.24), 11.512 (0.43).

Example 456

3-(2,2-dimethylpropanoyl)-7-(piperidin-4-yl)pyrazolo[1,5-a]pyrimidin-5(4H)-one hydrochloride

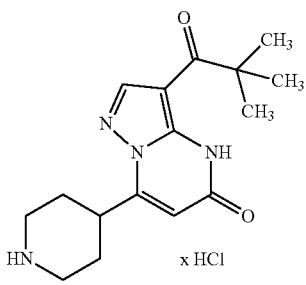 [SMILES: CC(C)(C)C(=O)c1cnn2c(C3CCNCC3)cc(=O)[nH]c12]

A mixture of tert-butyl 4-[3-(2,2-dimethylpropanoyl)-5-oxo-4,5-dihydropyrazolo[1,5-a]pyrimidin-7-yl]piperidine-1-carboxylate (68.5 mg, 81% purity, 137 µmol) and hydrochloric acid (4N solution in 1,4-dioxan, 340 µl) was stirred overnight at room temperature. The reaction mixture was dissolved in water/acetonitrile and purified by preparative HPLC (gradient acetonitrile/water with 0.1% formic acid). The combined product fractions were evaporated to yield the title compound. The obtained amount was 16.3 mg (100% purity, 35% of theory).

LC-MS (Method 11B): $R_t$=0.76 min; MS (ESIpos): m/z=303 [M+H-xHCl]$^+$ $^1$H-NMR (400 MHz, DMSO-d6) delta [ppm]: −0.009 (1.41), 0.007 (0.86), 1.292 (16.00), 1.617 (0.09), 1.650 (0.29), 1.653 (0.29), 1.681 (0.32), 1.714 (0.13), 2.006 (0.43), 2.037 (0.36), 2.798 (0.24), 2.829 (0.47), 2.860 (0.27), 3.189 (0.66), 3.220 (0.73), 5.971 (1.17), 8.236 (0.62), 8.501 (1.44). One proton is not visible and is thought to be below the water peak.

Example 457

5-oxo-7-(piperidin-4-yl)-2-(trifluoromethyl)-4,5-dihydropyrazolo[1,5-a]pyrimidine-3-carboxylic acid hydrochloride

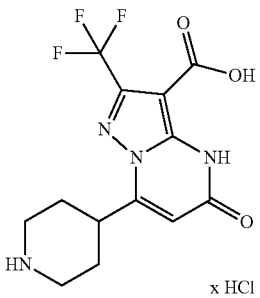 [SMILES: O=C(O)c1c(C(F)(F)F)nn2c(C3CCNCC3)cc(=O)[nH]c12]

A mixture of 7-[1-(tert-butoxycarbonyl)piperidin-4-yl]-5-oxo-2-(trifluoromethyl)-4,5-dihydropyrazolo[1,5-a]pyrimidine-3-carboxylic acid (50.0 mg, 116 µmol) and hydrochloric acid (4N solution in 1,4-dioxan, 500 µl) in 1,4-dioxan (1.0 ml) was stirred overnight at room temperature. The reaction mixture was diluted with water (5.0 ml) and lyophilized to yield the title compound. The obtained amount was 42.0 mg (100% purity, 99% of theory).

LC-MS (Method 8B): $R_t$=0.25 min; MS (ESIpos): m/z=331 [M+H-xHCl]$^+$ $^1$H-NMR (400 MHz, DMSO-d6) delta [ppm]: 0.007 (6.07), 1.787 (2.71), 1.796 (3.04), 1.827 (8.53), 1.855 (9.27), 1.885 (3.94), 1.893 (3.45), 2.132 (13.21), 2.165 (10.58), 3.071 (3.20), 3.098 (8.45), 3.127 (9.11), 3.157 (4.02), 3.367 (16.00), 3.400 (11.73), 3.459 (3.53), 3.488 (6.15), 3.517 (3.28), 6.171 (6.97), 8.631 (2.87), 8.840 (3.53), 11.369 (1.39), 13.354 (1.23).

Example 458

Ethyl 5-oxo-7-(piperidin-4-yl)-2-(trifluoromethyl)-4,5-dihydropyrazolo[1,5-a]pyrimidine-3-carboxylate hydrochloride

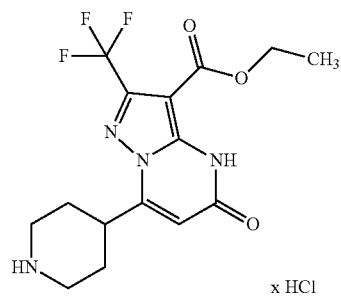 [SMILES: CCOC(=O)c1c(C(F)(F)F)nn2c(C3CCNCC3)cc(=O)[nH]c12]

A mixture of ethyl 7-[1-(tert-butoxycarbonyl)piperidin-4-yl]-5-oxo-2-(trifluoromethyl)-4,5-dihydropyrazolo[1,5-a]pyrimidine-3-carboxylate (85.0 mg, 185 µmol) and hydrochloric acid (4N solution in 1,4-dioxan, 1.0 ml) in 1,4-dioxan (1.0 ml) was stirred for 2 h at room temperature. The reaction mixture was lyophilized to yield the title compound. The obtained amount was 74.0 mg (95% purity, 96% of theory).

LC-MS (Method 8B): $R_t$=0.74 min; MS (ESIneg): m/z=357 [M−H-xHCl]$^-$ $^1$H-NMR (400 MHz, DMSO-d6) delta [ppm]: 1.265 (7.13), 1.282 (16.00), 1.300 (7.28), 1.804 (0.48), 1.836 (1.46), 1.868 (1.59), 1.901 (0.64), 2.123 (2.30), 2.156 (1.82), 3.064 (0.54), 3.093 (1.51), 3.122 (1.59), 3.151 (0.68), 3.364 (2.70), 3.395 (1.96), 3.457 (0.68), 3.487 (1.22), 3.507 (0.85), 4.298 (1.89), 4.315 (6.23), 4.333 (6.15), 4.351 (1.89), 6.183 (1.51), 8.738 (0.37), 8.907 (0.62), 11.876 (0.32).

Example 459

Propyl 5-oxo-7-(piperidin-4-yl)-2-(trifluoromethyl)-4,5-dihydropyrazolo[1,5-a]pyrimidine-3-carboxylate hydrochloride

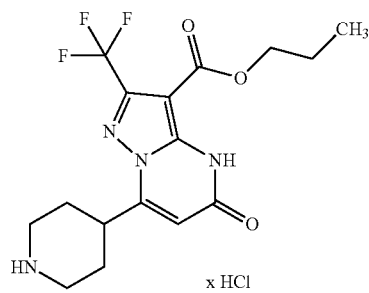 [SMILES: CCCOC(=O)c1c(C(F)(F)F)nn2c(C3CCNCC3)cc(=O)[nH]c12]

A mixture of propyl 7-[1-(tert-butoxycarbonyl)piperidin-4-yl]-5-oxo-2-(trifluoromethyl)-4,5-dihydropyrazolo[1,5-a]pyrimidine-3-carboxylate (98.0 mg, 207 µmol) and hydrochloric acid (4N solution in 1,4-dioxan, 1.0 ml) in 1,4-dioxan (1.0 ml) was stirred for 2 h at room temperature. The reaction mixture was lyophilized to yield the title compound. The obtained amount was 85.0 mg (99% purity, 99% of theory).

LC-MS (Method 8B): $R_t$=0.82 min; MS (ESIneg): m/z=371 [M−H−xHCl]⁻

¹H-NMR (400 MHz, DMSO-d6) delta [ppm]: 0.902 (6.97), 0.920 (16.00), 0.939 (7.64), 1.652 (0.57), 1.669 (2.36), 1.687 (4.68), 1.705 (4.60), 1.722 (2.20), 1.740 (0.51), 1.803 (0.45), 1.813 (0.55), 1.845 (1.54), 1.869 (1.68), 1.901 (0.72), 1.909 (0.63), 2.124 (2.39), 2.157 (1.89), 3.064 (0.55), 3.092 (1.51), 3.121 (1.59), 3.147 (0.68), 3.364 (2.67), 3.394 (2.00), 3.461 (0.93), 3.473 (0.81), 3.489 (1.46), 3.517 (0.67), 4.221 (3.95), 4.238 (8.36), 4.255 (3.86), 6.188 (1.51), 8.766 (0.51), 8.909 (0.68), 11.802 (0.34).

Example 460

Propan-2-yl 5-oxo-7-(piperidin-4-yl)-2-(trifluoromethyl)-4,5-dihydropyrazolo[1,5-a]pyrimidine-3-carboxylate hydrochloride

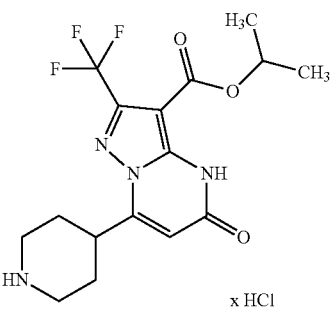 [SMILES: CC(C)OC(=O)c1c(C(F)(F)F)nn2c(C3CCNCC3)cc(=O)[nH]c12]

A mixture of propan-2-yl 7-[1-(tert-butoxycarbonyl)piperidin-4-yl]-5-oxo-2-(trifluoromethyl)-4,5-dihydropyrazolo[1,5-a]pyrimidine-3-carboxylate (73.0 mg, 155 µmol) and hydrochloric acid (4N solution in 1,4-dioxan, 1.0 ml) in 1,4-dioxan (1.0 ml) was stirred for 2 h at room temperature. The reaction mixture was lyophilized to yield the title compound. The obtained amount was 63.0 mg (98% purity, 98% of theory).

LC-MS (Method 8B): $R_t$=0.82 min; MS (ESIneg): m/z=371 [M−H−xHCl]⁻

¹H-NMR (400 MHz, DMSO-d6) delta [ppm]: −0.010 (0.37), 0.006 (0.34), 1.303 (15.90), 1.318 (16.00), 1.796 (0.23), 1.804 (0.29), 1.829 (0.77), 1.835 (0.80), 1.860 (0.88), 1.867 (0.86), 1.892 (0.38), 1.901 (0.33), 2.123 (1.25), 2.156 (1.00), 3.064 (0.30), 3.093 (0.78), 3.121 (0.83), 3.150 (0.36), 3.364 (1.36), 3.396 (1.05), 3.459 (0.35), 3.488 (0.62), 3.507 (0.31), 3.517 (0.30), 5.087 (0.06), 5.103 (0.40), 5.118 (1.07), 5.134 (1.47), 5.150 (1.06), 5.165 (0.39), 5.180 (0.07), 6.194 (0.77), 8.733 (0.26), 8.889 (0.37), 11.640 (0.14).

Example 461

2,2-difluoropropyl 2-methyl-5-oxo-7-(piperidin-4-yl)-4,5-dihydropyrazolo[1,5-a]pyrimidine-3-carboxylate hydrochloride

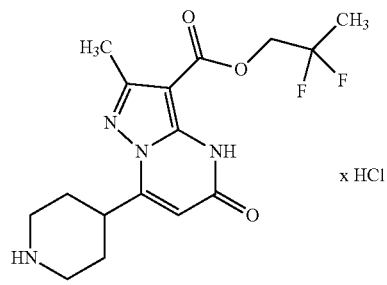 [SMILES: Cc1nn2c(C3CCNCC3)cc(=O)[nH]c2c1C(=O)OCC(C)(F)F]

2,2-difluoropropyl 7-[1-(tert-butoxycarbonyl)piperidin-4-yl]-2-methyl-5-oxo-4,5-dihydropyrazolo[1,5-a]pyrimidine-3-carboxylate (83.5 mg, 184 µmol) was added to 1,4-dioxan (160 µl, 1.9 mmol) and treated with hydrochloric acid in 1,4-dioxan (690 µl, 4.0 M, 2.8 mmol) at RT for 16 h. Solvents were removed, acetonitrile was added and the resulting participate was filtered and washed with Acetonitrile. Drying in vacuo afforded the product. The obtained amount was 72.3 mg (100% purity, 101% of theory).

LC-MS (Method 1B): $R_t$=0.51 min; MS (ESIpos): m/z=355 [M+H]⁺

¹H-NMR (400 MHz, DMSO-d6) delta [ppm]: −0.151 (0.12), −0.009 (1.03), 0.006 (1.01), 0.145 (0.11), 1.146 (0.20), 1.664 (4.34), 1.712 (8.68), 1.760 (3.97), 1.830 (1.18), 1.861 (1.27), 2.072 (0.29), 2.140 (2.19), 2.174 (1.79), 2.327 (0.18), 2.365 (0.30), 2.437 (16.00), 2.597 (0.15), 2.669 (0.18), 2.709 (0.30), 3.095 (1.35), 3.363 (2.34), 3.394 (1.85), 3.475 (0.58), 3.505 (1.01), 3.536 (0.54), 3.566 (3.33), 4.521 (2.38), 4.555 (4.72), 4.588 (2.22), 4.852 (0.21), 4.869 (0.14), 4.887 (0.24), 5.970 (1.17), 8.899 (0.32), 11.332 (0.61).

Example 462

3-[(3,3-dimethylpyrrolidin-1-yl)carbonyl]-7-(piperidin-4-yl)pyrazolo[1,5-a]pyrimidin-5 (4H)-one hydrochloride

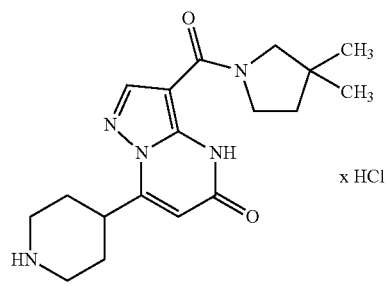 [SMILES: CC1(C)CCN(C(=O)c2cnn3c(C4CCNCC4)cc(=O)[nH]c23)C1]

tert-butyl 4-{3-[(3,3-dimethylpyrrolidin-1-yl)carbonyl]-5-oxo-4,5-dihydropyrazolo[1,5-a]pyrimidin-7-yl}piperidine-1-carboxylate (35.5 mg, 80.0 µmol) was added to 1,4-dioxan (72 µl, 840 µmol) and treated with hydrochloric acid in 1,4-dioxan (300 µl, 4.0 M, 1.2 mmol) at RT for 16 h. Solvents were removed, acetonitrile was added and the resulting participate was filtered and washed with Acetonitrile. Drying in vacuo afforded the product. The obtained amount was 30.2 mg (100% purity, 99% of theory).

LC-MS (Method 1B): R$_t$=0.49 min; MS (ESIpos): m/z=344 [M+H]$^+$ $^1$H-NMR (400 MHz, DMSO-d6) delta [ppm]: −0.151 (0.06), −0.010 (0.63), 0.006 (0.63), 0.145 (0.08), 0.922 (0.08), 1.081 (16.00), 1.146 (0.13), 1.236 (0.11), 1.414 (0.06), 1.594 (0.12), 1.653 (0.49), 1.671 (0.91), 1.688 (0.53), 1.777 (0.48), 1.794 (0.87), 1.812 (0.55), 1.858 (0.82), 1.890 (0.89), 1.920 (0.36), 2.072 (0.06), 2.161 (1.34), 2.194 (1.08), 2.327 (0.09), 2.365 (0.18), 2.669 (0.10), 2.709 (0.19), 3.060 (0.59), 3.087 (1.04), 3.119 (0.59), 3.259 (1.95), 3.372 (1.44), 3.404 (1.19), 3.460 (1.53), 3.495 (0.42), 3.524 (0.74), 3.542 (0.70), 3.558 (1.16), 3.566 (2.39), 3.576 (0.55), 3.797 (0.49), 3.815 (0.86), 3.832 (0.48), 5.995 (0.97), 8.141 (0.31), 8.198 (1.11), 8.255 (1.17), 8.752 (0.17), 8.944 (0.19), 10.913 (0.19), 10.945 (0.18).

Example 463

2,2-difluoropropyl 5-oxo-7-(piperidin-4-yl)-4,5-dihydropyrazolo[1,5-a]pyrimidine-3-carboxylate hydrochloride

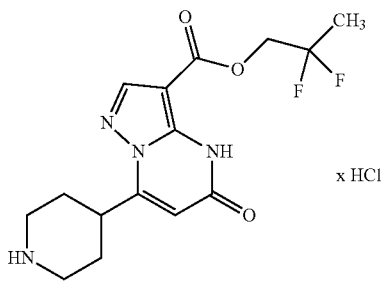 [SMILES: CC(F)(F)COC(=O)c1cnn2c(C3CCNCC3)cc(=O)[nH]c12]

2,2-difluoropropyl 7-[1-(tert-butoxycarbonyl)piperidin-4-yl]-5-oxo-4,5-dihydropyrazolo[1,5-a]pyrimidine-3-carboxylate (70.3 mg, 160 μmol) was added to 1,4-dioxan (140 μl, 1.7 mmol) and treated with hydrochloric acid in 1,4-dioxan (600 μl, 4.0 M, 2.4 mmol) at RT for 16 h. Solvents were removed, acetonitrile was added and the resulting participate was filtered and washed with Acetonitrile. Drying in vacuo afforded the product. The obtained amount was 58.3 mg (100% purity, 97% of theory).

LC-MS (Method 1B): R$_t$=0.45 min; MS (ESIpos): m/z=341 [M+H]$^+$ $^1$H-NMR (400 MHz, DMSO-d6) delta [ppm]: −0.151 (0.31), −0.010 (2.53), 0.007 (2.43), 0.144 (0.27), 1.147 (0.43), 1.413 (0.16), 1.670 (7.97), 1.718 (16.00), 1.766 (7.25), 1.813 (0.82), 1.846 (2.35), 1.877 (2.66), 1.908 (1.08), 2.072 (1.29), 2.153 (3.84), 2.187 (3.11), 2.322 (0.29), 2.327 (0.35), 2.332 (0.31), 2.365 (0.72), 2.669 (0.39), 2.709 (0.74), 3.057 (1.45), 3.085 (2.82), 3.114 (1.63), 3.373 (4.11), 3.404 (3.33), 3.495 (0.88), 3.523 (1.45), 3.548 (0.86), 3.566 (6.48), 4.507 (4.37), 4.541 (8.70), 4.574 (4.01), 4.847 (0.45), 4.883 (0.49), 4.902 (0.18), 4.921 (0.22), 6.047 (1.19), 8.276 (3.27), 8.707 (0.49), 8.894 (0.57), 11.764 (0.55).

Example 464

3-fluoropropyl 2-methyl-5-oxo-7-(piperidin-4-yl)-4,5-dihydropyrazolo[1,5-a]pyrimidine-3-carboxylate hydrochloride

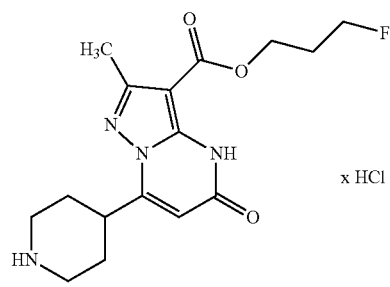 [SMILES: Cc1nn2c(C3CCNCC3)cc(=O)[nH]c2c1C(=O)OCCCF]

3-fluoropropyl 7-[1-(tert-butoxycarbonyl)piperidin-4-yl]-2-methyl-5-oxo-4,5-dihydropyrazolo[1,5-a]pyrimidine-3-carboxylate (83.5 mg, 191 μmol) was added to 1,4-dioxan (170 μl, 2.0 mmol) and treated with hydrochloric acid in 1,4-dioxan (720 μl, 4.0 M, 2.9 mmol) at RT for 16 h. Solvents were removed, acetonitrile was added and the resulting participate was filtered and washed with Acetonitrile. Drying in vacuo afforded the product. The obtained amount was 58.2 mg (100% purity, 82% of theory).

LC-MS (Method 10B): R$_t$=0.99 min; MS (ESIpos): m/z=337 [M+H]$^+$ $^1$H-NMR (400 MHz, DMSO-d6) delta [ppm]: −0.150 (0.40), −0.009 (3.41), 0.007 (3.23), 0.145 (0.42), 1.147 (0.34), 1.282 (0.21), 1.595 (0.24), 1.769 (0.35), 1.801 (1.01), 1.833 (1.12), 2.036 (0.37), 2.051 (1.36), 2.066 (2.11), 2.081 (1.42), 2.097 (0.45), 2.103 (0.44), 2.118 (1.46), 2.133 (3.28), 2.148 (2.68), 2.175 (1.49), 2.322 (0.20), 2.327 (0.30), 2.331 (0.21), 2.366 (0.41), 2.427 (16.00), 2.523 (0.61), 2.587 (0.17), 2.665 (0.23), 2.669 (0.30), 2.674 (0.23), 2.709 (0.41), 3.097 (1.12), 3.366 (1.90), 3.397 (1.50), 3.470 (0.48), 3.500 (0.89), 3.530 (0.44), 3.567 (1.94), 4.333 (2.72), 4.349 (5.66), 4.365 (2.68), 4.500 (1.76), 4.514 (3.40), 4.529 (1.70), 4.618 (1.74), 4.633 (3.38), 4.647 (1.68), 5.940 (1.55), 8.577 (0.22), 8.786 (0.29), 11.328 (0.65).

Example 465

2,2-difluoroethyl 2-methyl-5-oxo-7-(piperidin-4-yl)-4,5-dihydropyrazolo[1,5-a]pyrimidine-3-carboxylate hydrochloride

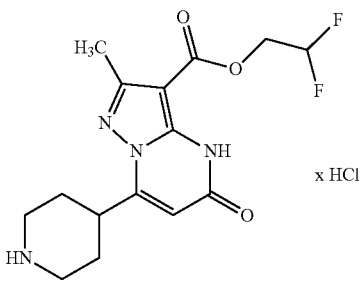 [SMILES: Cc1nn2c(C3CCNCC3)cc(=O)[nH]c2c1C(=O)OCC(F)F]

2,2-difluoroethyl 7-[1-(tert-butoxycarbonyl)piperidin-4-yl]-2-methyl-5-oxo-4,5-dihydropyrazolo[1,5-a]pyrimidine- 3-carboxylate (86.0 mg, 195 µmol) was added to 1,4-dioxan (2.4 ml, 28 mmol) and treated with hydrochloric acid in 1,4-dioxan (730 µl, 4.0 M, 2.9 mmol) at RT for 16 h. Solvents were removed, acetonitrile was added and the resulting participate was filtered and washed with Acetonitrile. Drying in vacuo afforded the product. The obtained amount was 72.8 mg (100% purity, 99% of theory).

LC-MS (Method 10B): $R_t$=0.98 min; MS (ESIpos): m/z=341 [M+H]$^+$ $^1$H-NMR (400 MHz, DMSO-d6) delta [ppm]: −0.152 (0.15), −0.011 (1.25), 0.005 (1.14), 0.143 (0.14), 1.281 (0.17), 1.299 (0.08), 1.412 (0.35), 1.593 (0.41), 1.677 (0.22), 1.680 (0.40), 1.683 (0.23), 1.805 (0.31), 1.814 (0.38), 1.839 (1.03), 1.846 (1.05), 1.870 (1.16), 1.878 (1.12), 1.902 (0.49), 1.911 (0.42), 2.133 (1.64), 2.166 (1.32), 2.267 (0.09), 2.327 (0.08), 2.366 (0.12), 2.431 (16.00), 2.590 (0.10), 2.709 (0.10), 3.081 (0.99), 3.356 (1.76), 3.387 (1.39), 3.473 (0.46), 3.503 (0.82), 3.532 (0.41), 3.566 (7.39), 4.489 (1.24), 4.498 (1.34), 4.526 (2.55), 4.535 (2.62), 4.563 (1.26), 4.572 (1.17), 4.647 (0.08), 5.954 (1.37), 6.258 (0.39), 6.267 (0.81), 6.276 (0.36), 6.395 (0.75), 6.404 (1.63), 6.413 (0.76), 6.533 (0.34), 6.542 (0.73), 6.551 (0.36), 8.877 (0.31), 8.980 (0.39), 11.543 (0.46).

Example 466

3,3,3-trifluoropropyl 2-methyl-5-oxo-7-(piperidin-4-yl)-4,5-dihydropyrazolo[1,5-a]pyrimidine-3-carboxylate hydrochloride

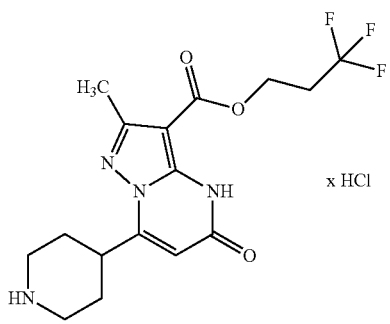 [SMILES: Cc1nn2c(C3CCNCC3)cc(=O)[nH]c2c1C(=O)OCCC(F)(F)F]

3,3,3-trifluoropropyl 7-[1-(tert-butoxycarbonyl)piperidin-4-yl]-2-methyl-5-oxo-4,5-dihydropyrazolo[1,5-a]pyrimidine-3-carboxylate (75.0 mg, 159 µmol) was added to 1,4-dioxan (1.9 ml, 22 mmol) and treated with hydrochloric acid in 1,4-dioxan (600 µl, 4.0 M, 2.4 mmol) at RT for 16 h. Solvents were removed, acetonitrile was added and the resulting participate was filtered and washed with Acetonitrile. Drying in vacuo afforded the product. The obtained amount was 57.0 mg (100% purity, 88% of theory).

LC-MS (Method 10B): $R_t$=1.12 min; MS (ESIpos): m/z=373 [M+H]$^+$ $^1$H-NMR (400 MHz, DMSO-d6) delta [ppm]: −0.152 (0.12), −0.011 (1.03), 0.143 (0.11), 1.146 (0.06), 1.264 (0.03), 1.281 (0.07), 1.299 (0.03), 1.593 (0.04), 1.816 (0.32), 1.847 (0.94), 1.875 (1.03), 1.905 (0.42), 2.072 (0.04), 2.131 (1.52), 2.164 (1.22), 2.258 (0.08), 2.327 (0.06), 2.366 (0.10), 2.422 (16.00), 2.582 (0.10), 2.669 (0.06), 2.710 (0.09), 2.780 (0.27), 2.795 (0.57), 2.808 (0.99), 2.823 (1.64), 2.838 (1.43), 2.852 (1.60), 2.867 (1.00), 2.880 (0.53), 2.895 (0.28), 3.048 (0.78), 3.075 (1.52), 3.080 (1.51), 3.108 (0.89), 3.352 (1.71), 3.384 (1.36), 3.468 (0.45), 3.497 (0.83), 3.527 (0.41), 3.566 (2.74), 4.277 (0.03), 4.294 (0.03), 4.445 (2.34), 4.460 (4.57), 4.475 (2.28), 5.937 (2.16), 8.958 (0.23), 11.379 (0.08).

Example 467

Propyl 2-methyl-5-oxo-7-(piperidin-4-yl)-4,5-dihydropyrazolo[1,5-a]pyrimidine-3-carboxylate hydrochloride

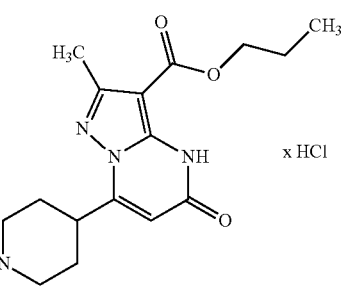

3 propyl 7-[1-(tert-butoxycarbonyl)piperidin-4-yl]-2-methyl-5-oxo-4,5-dihydropyrazolo[1,5-a]pyrimidine-3-carboxylate (78.3 mg, 187 µmol) was added to 1,4-dioxan (2.0 ml, 23 mmol) and treated with hydrochloric acid in 1,4-dioxan (700 µl, 4.0 M, 2.8 mmol) at RT for 16 h. Solvents were removed, acetonitrile was added and the resulting participate was filtered and washed with acetonitrile. Drying in vacuo afforded the product. The obtained amount was 49.2 mg (100% purity, 74% of theory).

LC-MS (Method 11B): $R_t$=0.85 min; MS (ESIpos): m/z=319 [M+H]$^+$ $^1$H-NMR (400 MHz, DMSO-d6) delta [ppm]: −0.151 (0.21), −0.010 (1.79), 0.006 (1.69), 0.144 (0.22), 0.765 (0.05), 0.906 (4.55), 0.924 (10.38), 0.943 (5.04), 1.072 (0.14), 1.079 (0.06), 1.089 (0.27), 1.107 (0.13), 1.146 (0.13), 1.412 (0.05), 1.594 (0.05), 1.658 (0.38), 1.676 (1.60), 1.693 (3.17), 1.712 (3.10), 1.729 (1.51), 1.747 (0.35), 1.827 (0.82), 1.856 (0.88), 1.887 (0.35), 2.072 (0.06), 2.137 (1.59), 2.170 (1.29), 2.263 (0.08), 2.327 (0.11), 2.331 (0.08), 2.365 (0.17), 2.427 (16.00), 2.523 (0.26), 2.525 (0.27), 2.570 (0.09), 2.579 (0.08), 2.585 (0.13), 2.664 (0.09), 2.669 (0.12), 2.673 (0.09), 2.709 (0.18), 3.054 (0.73), 3.085 (1.52), 3.117 (0.85), 3.358 (1.72), 3.391 (1.50), 3.469 (0.48), 3.498 (0.87), 3.528 (0.44), 3.566 (1.60), 4.184 (2.58), 4.201 (5.36), 4.217 (2.53), 5.929 (1.63), 8.857 (0.20), 11.258 (0.10).

Example 468

Tert-butyl 2-methyl-5-oxo-7-(piperidin-4-yl)-4,5-dihydropyrazolo[1,5-a]pyrimidine-3-carboxylate hydrochloride

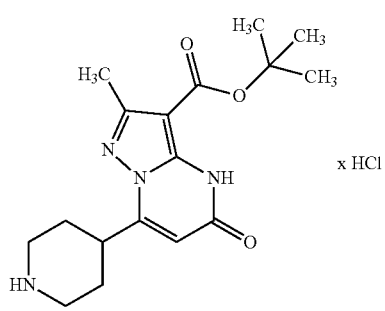 [SMILES: Cc1nn2c(C3CCNCC3)cc(=O)[nH]c2c1C(=O)OC(C)(C)C]

tert-butyl 7-[1-(tert-butoxycarbonyl)piperidin-4-yl]-2-methyl-5-oxo-4,5-dihydropyrazolo[1,5-a]pyrimidine-3-carboxylate (82.5 mg, 191 µmol) was added to 1,4-dioxan (2.0 ml, 23 mmol) and treated with hydrochloric acid in 1,4-dioxan (720 µl, 4.0 M, 2.9 mmol) at RT for 16 h. Solvents were removed, acetonitrile was added and the resulting participate was filtered and washed with Acetonitrile. After drying in vacuo the residue was dissolved in Methanol, filtered through a PL-HCO3 MP-column, and dried in vacuo. The residue was added to 1,4-dioxan (5.0 ml) and treated with hydrochloric acid in 1,4-dioxan (200 µl, 4.0 M). Drying in vacuo afforded the product. The obtained amount was 25.8 mg (95% purity, 35% of theory).

LC-MS (Method 10B): $R_t$=1.22 min; MS (ESIpos): m/z=333 [M+H]$^+$ $^1$H-NMR (400 MHz, DMSO-d6) delta [ppm]: −0.151 (0.09), −0.010 (0.79), 0.007 (0.76), 0.145 (0.09), 0.853 (0.01), 1.146 (0.05), 1.234 (0.11), 1.384 (0.06), 1.412 (0.02), 1.545 (16.00), 1.701 (0.06), 1.778 (0.11), 1.810 (0.32), 1.841 (0.34), 1.868 (0.14), 2.135 (0.50), 2.168 (0.41), 2.235 (0.03), 2.323 (0.03), 2.327 (0.04), 2.331 (0.03), 2.366 (0.06), 2.398 (5.62), 2.523 (0.11), 2.525 (0.11), 2.586 (0.02), 2.664 (0.04), 2.669 (0.05), 2.673 (0.03), 2.709 (0.06), 3.056 (0.22), 3.087 (0.45), 3.117 (0.26), 3.361 (0.57), 3.393 (0.47), 3.461 (0.17), 3.490 (0.28), 3.520 (0.14), 3.566 (10.63), 3.665 (0.03), 3.669 (0.02), 3.680 (0.03), 3.698 (0.03), 3.707 (0.02), 3.712 (0.03), 3.732 (0.02), 3.743 (0.02), 3.754 (0.02), 4.328 (0.02), 5.929 (0.72), 7.481 (0.04), 7.500 (0.08), 7.519 (0.06), 7.605 (0.03), 7.608 (0.02), 7.623 (0.04), 7.642 (0.01), 7.932 (0.07), 7.935 (0.08), 7.953 (0.07), 8.683 (0.05), 8.825 (0.06), 10.658 (0.06).

Example 469

2-(methylsulfanyl)-5-oxo-7-(piperidin-4-yl)-4,5-dihydropyrazolo[1,5-a]pyrimidine-3-carboxylic acid hydrochloride

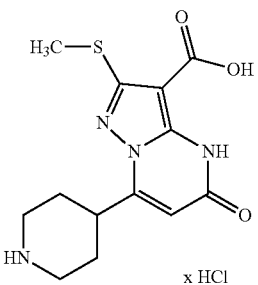 [SMILES: CSc1nn2c(C3CCNCC3)cc(=O)[nH]c2c1C(=O)O]

A mixture of 7-[1-(tert-butoxycarbonyl)piperidin-4-yl]-2-(methylsulfanyl)-5-oxo-4,5-dihydropyrazolo[1,5-a]pyrimidine-3-carboxylic acid (50.0 mg, 122 µmol) and hydrochloric acid (4N solution in 1,4-dioxane, 2.0 ml) in 1,4-dioxane (1.0 ml) was stirred overnight at room temperature. The reaction mixture was concentrated and suspended in diethyl ether. The solid was filtered and then lyophilized to yield the title compound. The obtained amount was 35.6 mg (100% purity, 84% of theory).

LC-MS (Method 8B): $R_t$=0.21 min; MS (ESIpos): m/z=309 [M+H-xHCl]$^+$ $^1$H-NMR (500 MHz, DEUTERIUM OXIDE) delta [ppm]: −0.014 (2.48), 1.874 (0.68), 1.899 (2.03), 1.923 (2.03), 1.946 (0.90), 2.393 (2.70), 2.421 (2.48), 2.502 (16.00), 3.196 (1.58), 3.221 (2.93), 3.246 (1.58), 3.503 (0.90), 3.527 (1.35), 3.550 (0.90), 3.587 (2.93), 3.612 (2.70), 4.576 (0.68), 4.579 (0.68), 4.600 (0.68), 4.610 (0.90), 4.621 (0.90), 4.872 (1.13), 4.874 (1.13), 4.895 (0.68), 4.902 (0.68), 4.910 (0.68), 6.004 (5.18).

Example 470

Propyl 2-(methylsulfanyl)-5-oxo-7-(piperidin-4-yl)-4,5-dihydropyrazolo[1,5-a]pyrimidine-3-carboxylate hydrochloride

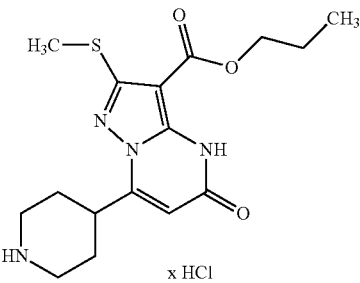 [SMILES: CCCOC(=O)c1c(SC)nn2c(C3CCNCC3)cc(=O)[nH]c12]

A mixture of propyl 7-[1-(tert-butoxycarbonyl)piperidin-4-yl]-2-(methylsulfanyl)-5-oxo-4,5-dihydropyrazolo[1,5-a] pyrimidine-3-carboxylate (84.6 mg, 188 µmol) and hydrochloric acid (4N solution in 1,4-dioxane, 1.0 ml) in 1,4-dioxane (1.0 ml) was stirred 4 h at room temperature. The reaction mixture was concentrated and suspended in diethyl ether. The solid was filtered and then lyophilized to yield the title compound. The obtained amount was 26.9 mg (100% purity, 37% of theory).

LC-MS (Method 8B): $R_t$=0.80 min; MS (ESIpos): m/z=351 [M+H-xHCl]$^+$ $^1$H-NMR (400 MHz, DMSO-d6) delta [ppm]: 0.912 (3.28), 0.931 (6.89), 0.949 (3.70), 1.648 (0.42), 1.665 (1.45), 1.682 (2.70), 1.700 (2.69), 1.718 (1.40), 1.734 (0.39), 1.814 (0.53), 1.846 (1.46), 1.878 (1.58), 1.906 (0.69), 2.137 (0.49), 2.168 (2.22), 2.200 (1.85), 2.519 (16.00), 2.617 (0.29), 3.068 (1.64), 3.371 (2.43), 3.402 (2.07), 3.452 (1.14), 3.471 (0.56), 3.480 (0.62), 4.172 (2.26), 4.188 (4.27), 4.205 (2.20), 5.924 (1.56), 8.669 (0.29), 8.691 (0.36), 8.700 (0.35), 8.705 (0.36), 8.708 (0.35), 8.710 (0.35), 8.722 (0.35), 8.727 (0.35), 8.729 (0.34), 8.742 (0.32), 8.750 (0.31), 8.905 (0.35), 8.925 (0.45), 8.931 (0.44), 8.942 (0.42), 8.953 (0.41), 8.962 (0.38), 8.971 (0.34), 8.978 (0.30), 11.410 (0.32), 11.414 (0.34), 11.422 (0.33), 11.428 (0.34), 11.438 (0.32), 11.451 (0.28).

Example 471

Propan-2-yl 2-(methylsulfanyl)-5-oxo-7-(piperidin-4-yl)-4,5-dihydropyrazolo[1,5-a]pyrimidine-3-carboxylate hydrochloride

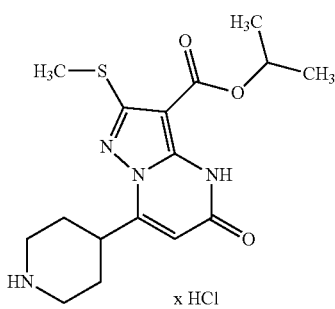 [SMILES: CSc1nn2c(C3CCNCC3)cc(=O)[nH]c2c1C(=O)OC(C)C]

A mixture of propan-2-yl 7-[1-(tert-butoxycarbonyl)piperidin-4-yl]-2-(methylsulfanyl)-5-oxo-4,5-dihydropyrazolo[1,5-a]pyrimidine-3-carboxylate (35.1 mg, 77.9 µmol) and hydrochloric acid (4N solution in 1,4-dioxane, 1.0 ml) in 1,4-dioxane (1.0 ml) was stirred overnight at room temperature. The reaction mixture was concentrated and suspended in diethyl ether. The solid was filtered and purified by preparative HPLC (gradient acetonitrile/water with 0.1% formic acid). The product containing fractions were combined, diluted with hydrochloric acid (1N solution in water) and concentrated to yield the title compound. The obtained amount was 14.9 mg (100% purity, 49% of theory).

LC-MS (Method 8B): $R_t$=0.79 min; MS (ESIpos): m/z=351 [M+H-xHCl]$^+$ $^1$H-NMR (400 MHz, DMSO-d6) delta [ppm]: 1.304 (15.93), 1.319 (16.00), 1.853 (0.96), 1.884 (1.04), 1.916 (0.42), 2.158 (1.48), 2.191 (1.21), 3.028 (0.71), 3.058 (1.43), 3.089 (0.81), 3.363 (1.66), 3.394 (1.35), 3.450 (0.81), 3.480 (0.40), 5.073 (0.43), 5.089 (1.16), 5.104 (1.59), 5.120 (1.15), 5.136 (0.43), 5.918 (1.52), 8.979 (0.17).

Example 472

Ethyl 2-ethyl-5-oxo-7-(piperidin-4-yl)-4,5-dihydropyrazolo[1,5-a]pyrimidine-3-carboxylate hydrochloride

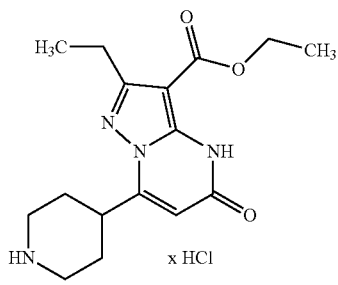 [SMILES: CCOC(=O)c1c(CC)nn2c(C3CCNCC3)cc(=O)[nH]c12]

A mixture of ethyl 7-[1-(tert-butoxycarbonyl)piperidin-4-yl]-2-ethyl-5-oxo-4,5-dihydropyrazolo[1,5-a]pyrimidine-3-carboxylate (43.0 mg, 103 µmol) and hydrochloric acid (4N solution in 1,4-dioxane, 2.0 ml) in 1,4-dioxane (2.0 ml) was stirred overnight at room temperature. The reaction mixture was concentrated, dissolved in water and lyophilized to yield the title compound. The obtained amount was 38.0 mg (95% purity, 99% of theory).

LC-MS (Method 8B): $R_t$=0.70 min; MS (ESIpos): m/z=319 [M+H-xHCl]$^+$ $^1$H-NMR (400 MHz, DMSO-d6) delta [ppm]: −0.009 (1.65), 0.007 (1.30), 1.146 (0.26), 1.191 (6.98), 1.210 (15.99), 1.229 (7.34), 1.265 (7.02), 1.283 (16.00), 1.300 (7.19), 1.787 (0.53), 1.820 (1.44), 1.843 (1.57), 1.875 (0.68), 2.150 (2.19), 2.183 (1.80), 2.366 (0.45), 2.710 (0.45), 2.821 (1.79), 2.839 (5.50), 2.858 (5.39), 2.877 (1.66), 3.067 (1.07), 3.095 (2.06), 3.126 (1.21), 3.366 (2.51), 3.397 (2.02), 3.461 (0.69), 3.491 (1.29), 3.566 (0.58), 3.592 (1.09), 3.684 (0.31), 3.699 (0.30), 3.732 (0.35), 4.018 (0.21), 4.266 (1.93), 4.284 (6.30), 4.302 (6.25), 4.319 (1.93), 4.645 (0.42), 5.933 (2.86), 8.778 (0.27).

B. ASSESSMENT OF THE PHARMACOLOGICAL ACTIVITY

The following abbreviations are used:
Brij polyoxyethylene lauryl ether
$CaCl_2$ calciumchloride
CFT clot formation time
CM5 carboxymethylated dextran biosensor chips
CT clotting time
DMSO dimethylsulfoxide
EDC N-ethyl-N'-(3-dimethylaminopropyl)-carbodiimide hydrochloride
FVIII factor eight
HEPES hydroxyethyl-piperazineethanesulfonic acid
HCl hydrochloric acid
IC50 half-maximal inhibitory concentration
$K_D$ dissociation constant
MCF maximum clot firmness
ML maximum lysis
NaCl sodium chloride
NHS N-hydroxysuccinimide
OD optical density
PBS phosphate buffered saline
P-20 hybond P20
Rmax response at saturation RU response units
SPR surface plasmon resonance
TF tissue factor
tPA tissue plasminogen activator
v/v volume/volume The pharmacological effect of the compounds of formula (I-A) or (I-B) according to the invention can be shown in the following assays:

B-1. Biacore Assay
Assay Description Surface Plasmon Resonance Plasminogen Inh.

Definitions

The term "surface plasmon resonance", as used herein, refers to an optical phenomenon that allows for the analysis of the reversible associations of biological molecules in real time within a biosensor matrix, for example using the Biacore® system (GE Healthcare Biosciences, Uppsala, Sweden). Biacore® uses the optical properties of surface plasmon resonance (SPR) to detect alterations in the refractive index of a buffer, which changes as molecules in solution interact with the target immobilized on the surface. In brief, proteins are covalently bound to the dextran matrix at a known concentration and a ligand for the protein is injected through the dextran matrix. Near infrared light, directed onto the opposite side of the sensor chip surface is reflected and also induces an evanescent wave in the gold film, which in turn, causes an intensity dip in the reflected light at a particular angle known as the resonance angle. If the refractive index of the sensor chip surface is altered (e.g. by compound binding to the protein bound to the surface) a shift occurs in the resonance angle. This angle shift can be measured. These changes are displayed with respect to time along the y-axis of a sensorgram, which depicts the association and dissociation of any biological reaction. For further descriptions see Jönsson U et al., 1993 Ann Biol Clin.; 51(1):19-26.; Johnsson B et al, Anal Biochem. 1991; 198(2):268-77.; Day Y et al, Protein Science, 2002; 11, 1017-1025; Myskza D G, Anal Biochem., 2004; 329, 316-323 The term "$K_D$", as used herein, is intended to refer to the dissociation constant of a particular compound/target protein complex.

Biological Activity

The biological activity (e.g. as inhibitors of plasminogen) of the compounds of the invention can be measured using the assays set forth in the examples below, for example the surface plasmon resonance (SPR) experiments described in Example 1. The level of activity exhibited by a given compound in the SPR assay can be defined in terms of the $K_D$ value.

Example 1

The ability of the compounds of the invention to bind human plasminogen protein may be determined using surface plasmon resonance (SPR). $K_D$ values may be measured using a Biacore® T200 or Biacore® 4000 instrument (GE Healthcare, Uppsala, Sweden).

Cloning, expression, and purification of recombinant human plasminogen kringle 1 domain protein is performed according to a protocol based on published methods (Menhart et al, Biochemistry, 1991, 30, 1948-1957) with modifications as follows: Briefly, an E. coli expression construct coding for the amino acid sequence MKYLLPTAAAGLLL-LAAQPAMAHHHHHHHHHHMDYDIPTTENLYFQG followed by the human plasminogen kringle 1 domain protein sequence amino acids 101 to 181 (numbering based on Uniprot acc no P00747) and a stop codon is synthesized (GeneArt, Regensburg, Germany) and cloned into a modified pET22b vector (Novagen, Darmstadt, Germany), allowing for periplasmatic expression in E. coli and immobilized metal ion affinity chromatography employing a deca-histidine tag. E. coli BL21DE3 cells (Novagen) are transformed, grown and harvested and their periplasmatic fraction released using a buffer comprising 50 mM Tris pH 8 and 500 mM sucrose (modified from Menhart et al, Biochemistry, 1991, 30, 1948-1957). The periplasmatic fraction is then sequentially filtered using 8 µm, 3 µm and 1.2 µm cellulose nitrate filters (Sartorius Stedim, Göttingen, Germany) and the filtrate subjected to Ni-Sepharose HP chromatography (GE Healthcare) according to the manufacturer's instructions. The resulting eluate is then subjected to a Desalting Hi Prep 26/10 column (GE Healthcare) equilibrated in buffer (100 mM sodium phosphate pH 8, 300 mM NaCl) followed by a lysine sepharose 4B (GE Healthcare) chromatography step according to the manufacturer's instructions. The resulting fractions of highly purified protein at concentrations of approximately 0.5 mg/ml are buffer exchanged against buffer (100 mM sodium phosphate pH 8, 300 mM NaCl) and stored at −80° C.

For SPR measurements, recombinant human plasminogen kringle 1 protein is immobilized using standard amine coupling (Johnsson B et al, Anal Biochem. 1991 Nov. 1; 198(2):268-77). Briefly, carboxymethylated dextran biosensor chips (CM5, GE Healthcare) are activated with N-ethyl-N'-(3-dimethylaminopropyl)-carbodiimide hydrochloride (EDC) and N-hydroxysuccinimide (NHS) according to the supplier's instructions. Purified recombinant human plasminogen kringle 1 protein is diluted in 10 mM sodium acetate pH 4.5 into 10 µg/ml and injected on the activated chip surface. Subsequently, 1 M ethanolamine-HCl (GE Healthcare) is injected to block unreacted groups, resulting in approximately 400 response units (RU) of immobilized protein. A reference surface is generated by treatment with NHS-EDC and ethanolamine-HCl. Compounds are dissolved in an aqueous 1% v/v acetic acid solution to a concentration of 20 mM, followed by addition of 1 vol of 100% dimethylsulfoxide (DMSO, Sigma-Aldrich, Germany) resulting in a compound concentration of 10 mM and subsequently diluted in running buffer (PBS pH 7.4, 0.05% v/v Surfactant P-20 (GE Healthcare), 1% v/v DMSO). For affinity measurements, five-fold serial dilutions of compound (0.64 nM to 10 µM) are injected over immobilized protein. The resulting sensorgrams are double-referenced against the reference surface as well as against blank injections. The double-referenced steady state responses are plotted against the test compound concentration and a fit using the equation Response=Rmax*[compound]/([compound]+$K_D$)+offset is generated. Parameters Rmax (response at saturation), $K_D$ (dissociation constant) and the offset parameter are calculated using a nonlinear least squares fit as implemented in the Biacore® evaluation software (GE Healthcare).

B-2. Plasma-based Clot Lysis Assay (5%)

The clot-lysis test system configures the kinetics of clot formation and degradation in vitro and allows quantifying modulation of the process by selected test compounds.

The test compounds were dissolved in 1% acetic acid and further complemented with an equal volume of DMSO. The resulting stock solutions were serially diluted in 0.5% acetic acid/50% DMSO. 1 µL aliquots of these solutions were placed into 384 well microplates (Greiner, black, transparent bottom), followed by 30 µL of diluted human citrated plasma (platelet-poor, final concentration: 5%; supplemented with fibrinogen, final concentration: 3 μM; dilution buffer: 20 mM HEPES, 150 mM NaCl, 0.01% Brij (pH 7)). The reactions were started by addition of 20 μL of $CaCl_2$ (final concentration: 10 mM), and tPA (tissue plasminogen activator, final concentration: 0.2 nM) in dilution buffer, followed by an additional volume of 20 μL dilution buffer for improved mixing. The reactions were incubated at 37° C. Clot formation and degradation was monitored spectrophotometrically by kinetic optical density measurements at 405 nm. IC50 values were determined by comparing the resulting time courses with the time course of a blank control reaction.

Results B-2.

| Example | IC50 (nM) | Example | IC50 (nM) | Example | IC50 (nM) |
|---|---|---|---|---|---|
| 1 | 38 | 2 | 39 | 3 | 33 |
| 4 | 40 | 5 | 32 | 6 | 170 |
| 7 | 31 | 8 | 29 | 9 | 33 |
| 10 | 110 | 11 | 57 | 12 | 30 |
| 13 | 21 | 14 | 24 | 15 | 19 |
| 16 | 11 | 17 | 46 | 18 | 15 |
| 19 | 15 | 20 | 420 | 21 | 14 |
| 22 | 13 | 23 | 14 | 24 | 59 |
| 25 | 160 | 26 | 310 | 27 | 170 |
| 28 | 110 | 29 | 20 | 30 | 200 |
| 31 | 18 | 32 | 15 | 33 | 13 |
| 34 | 12 | 35 | 15 | 36 | 28 |
| 37 | 29 | 38 | 18 | 39 | 27 |
| 40 | 14 | 41 | 19 | 42 | 18 |
| 43 | 27 | 44 | 23 | 45 | 23 |
| 46 | 69 | 47 | 13 | 48 | 14 |
| 49 | 16 | 50 | 24 | 51 | 16 |
| 52 | 24 | 53 | 15 | 54 | 18 |
| 55 | 19 | 56 | 770 | 57 | 21 |
| 58 | 16 | 59 | 15 | 60 | 13 |
| 61 | 34 | 62 | 34 | 63 | 40 |
| 64 | 39 | 65 | 12 | 66 | 17 |
| 67 | 97 | 68 | 11 | 69 | 19 |
| 70 | 14 | 71 | 34 | 72 | 64 |
| 73 | 12 | 74 | 18 | 75 | 40 |
| 76 | 29 | 77 | 62 | 78 | 48 |
| 80 | 33 | 81 | 81 | 82 | 29 |
| 83 | 30 | 84 | 34 | 85 | 32 |
| 86 | 17 | 87 | 30 | 88 | 49 |
| 89 | 140 | 90 | 28 | 91 | 19 |
| 92 | 33 | 93 | 22 | 94 | 30 |
| 95 | 43 | 96 | 33 | 97 | 24 |
| 98 | 90 | 99 | 49 | 100 | 110 |
| 101 | 34 | 103 | 35 | 104 | 31 |
| 105 | 95 | 106 | 63 | 107 | 49 |
| 108 | 76 | 109 | 120 | 110 | 82 |
| 111 | 32 | 112 | 29 | 113 | 44 |
| 114 | 23 | 115 | 27 | 116 | 39 |
| 117 | 38 | 118 | 45 | 119 | 79 |
| 120 | 35 | 121 | 40 | 122 | 35 |
| 123 | 47 | 124 | 38 | 125 | 40 |
| 126 | 47 | 127 | 62 | 128 | 110 |
| 129 | 38 | 130 | 41 | 131 | 63 |
| 132 | 35 | 133 | 39 | 134 | 43 |
| 135 | 40 | 136 | 43 | 137 | 31 |
| 138 | 39 | 139 | 41 | 140 | 130 |
| 141 | 74 | 142 | 41 | 143 | 41 |
| 144 | 87 | 145 | 28 | 146 | 35 |
| 147 | 38 | 148 | 43 | 149 | 100 |
| 150 | 45 | 151 | 44 | 152 | 43 |
| 153 | 31 | 154 | 24 | 155 | 14 |
| 156 | 16 | 157 | 56 | 158 | 38 |
| 159 | 23 | 160 | 73 | 161 | 330 |
| 162 | 140 | 163 | 40 | 164 | — |
| 165 | 34 | 166 | 8.7 | 167 | 34 |
| 168 | 33 | 169 | 34 | 170 | 34 |
| 171 | 35 | 172 | 59 | 173 | 34 |
| 174 | 34 | 175 | 35 | 176 | 38 |
| 177 | 40 | 178 | 34 | 179 | 37 |
| 180 | 35 | 181 | 28 | 182 | 35 |
| 183 | 50 | 184 | 36 | 185 | 38 |
| 186 | 34 | 187 | 35 | 188 | 35 |
| 189 | 38 | 190 | 34 | 191 | 34 |
| 192 | 34 | 193 | 32 | 194 | 29 |
| 195 | 35 | 196 | 75 | 197 | 35 |
| 198 | 34 | 199 | 34 | 200 | 34 |
| 201 | 34 | 202 | 37 | 203 | 34 |
| 204 | 35 | 205 | 35 | 206 | 20 |
| 207 | 93 | 208 | 55 | 209 | 36 |
| 210 | 34 | 211 | 34 | 212 | 58 |
| 213 | 30 | 214 | 32 | 215 | 34 |
| 216 | 34 | 217 | 36 | 218 | 54 |
| 219 | 35 | 220 | 15 | 221 | 48 |
| 222 | 37 | 223 | 31 | 224 | 9.7 |
| 225 | 34 | 226 | 35 | 227 | 34 |
| 228 | 33 | 229 | 36 | 230 | 36 |
| 231 | 34 | 232 | 71 | 233 | 36 |
| 234 | 35 | 235 | 30 | 236 | 27 |
| 237 | 20 | 238 | 28 | 239 | 30 |
| 240 | 20 | 241 | 21 | 242 | 20 |
| 243 | 29 | 244 | 21 | 245 | 29 |
| 246 | 28 | 247 | 28 | 248 | 47 |
| 249 | 12 | 250 | 34 | 251 | 31 |
| 252 | 24 | 253 | 8.2 | 254 | 100 |
| 255 | 17 | 256 | 28 | 257 | 34 |
| 258 | 21 | 259 | 19 | 260 | 31 |
| 261 | 24 | 262 | 23 | 263 | 28 |
| 264 | 200 | 265 | 340 | 266 | 29 |
| 267 | 15 | 268 | 24 | 269 | 33 |
| 270 | 24 | 271 | 25 | 272 | 13 |
| 273 | 27 | 274 | 11 | 275 | 20 |
| 276 | 14 | 277 | 17 | 278 | 19 |
| 279 | 25 | 280 | 29 | 281 | 90 |
| 282 | 34 | 283 | 10 | 284 | 20 |
| 285 | 28 | 286 | 33 | 287 | 37 |
| 288 | 27 | 289 | 27 | 290 | 26 |
| 291 | 85 | 292 | 34 | 293 | 31 |
| 294 | 37 | 295 | 35 | 296 | 23 |
| 297 | 27 | 298 | 35 | 299 | 25 |
| 300 | 16 | 301 | 30 | 302 | 6 |
| 303 | 38 | 304 | 24 | 305 | 20 |
| 306 | 11 | 307 | 20 | 308 | 11 |
| 309 | 41 | 310 | 25 | 311 | 18 |
| 312 | 22 | 313 | nd | 314 | nd |
| 315 | 36 | 316 | 27 | 317 | 29 |
| 318 | 45 | 319 | 75 | 320 | 82 |
| 321 | 82 | 322 | 36 | 323 | 460 |
| 324 | 150 | 325 | 18 | 326 | 12 |
| 327 | 9 | 328 | 21 | 329 | 54 |
| 330 | 110 | 331 | 24 | 332 | 26 |
| 333 | 370 | 334 | 30 | 335 | 9 |
| 336 | 25 | 337 | 30 | 338 | 11 |
| 339 | 28 | 340 | 28 | 341 | 34 |
| 342 | 170 | 343 | 130 | 344 | 120 |
| 345 | 120 | 346 | 17 | 347 | 28 |
| 348 | 160 | 349 | 21 | 350 | 20 |
| 351 | 26 | 352 | 44 | 353 | 28 |
| 354 | 27 | 355 | 27 | 356 | 23 |
| 357 | 14 | 358 | 24 | 359 | 120 |
| 360 | 52 | 361 | 32 | 362 | 21 |
| 363 | 130 | 364 | 11 | 365 | 38 |
| 366 | 27 | 367 | 25 | 368 | 390 |
| 369 | 39 | 370 | 36 | 371 | 30 |
| 372 | 22 | 373 | 11 | 374 | 34 |
| 375 | 30 | 376 | 32 | 377 | 25 |
| 378 | 32 | 379 | 22 | 380 | 14 |
| 381 | 29 | 382 | 28 | 383 | 15 |
| 384 | 26 | 385 | 14 | 386 | 28 |
| 387 | 10 | 388 | 30 | 389 | 30 |
| 390 | 34 | 391 | 30 | 392 | 27 |
| 393 | 30 | 394 | 29 | 395 | 27 |
| 396 | 40 | 397 | 36 | 398 | 34 |
| 399 | 42 | 400 | 32 | 401 | 34 |
| 402 | 40 | 403 | 36 | 404 | 30 |

-continued

Results B-2.

| Example | IC50 (nM) | Example | IC50 (nM) | Example | IC50 (nM) |
|---|---|---|---|---|---|
| 405 | 37 | 406 | 37 | 407 | 34 |
| 408 | 34 | 409 | 46 | 410 | 45 |
| 411 | 540 | 412 | 33 | 413 | 35 |
| 414 | 35 | 415 | 61 | 416 | 31 |
| 417 | 24 | 418 | 31 | 419 | 35 |
| 420 | 47 | 421 | 30 | 422 | 23 |
| 423 | 33 | 424 | 78 | 425 | 37 |
| 426 | 56 | 427 | 23 | 428 | 29 |
| 429 | 30 | 430 | 120 | 431 | 28 |
| 432 | 120 | 433 | 31 | 434 | 32 |
| 435 | 42 | 436 | 39 | 437 | 10 |
| 438 | 12 | 439 | 26 | 440 | 23 |
| 441 | 29 | 442 | 27 | 443 | 23 |
| 444 | 17 | 445 | 56 | 446 | 10 |
| 447 | 14 | 448 | 30 | 449 | 55 |
| 450 | 360 | 451 | 11 | 452 | 8 |
| 453 | 8 | 454 | 34 | 455 | 36 |
| 456 | 39 | 457 | 85 | 458 | 130 |
| 459 | 83 | 460 | 59 | 461 | 61 |
| 462 | 34 | 463 | 51 | 464 | 130 |
| 465 | 40 | 466 | 85 | 467 | 38 |
| 468 | 39 | 469 | 160 | 470 | 25 |

B-3. Plasma-Based Clot Lysis Assay (85%)

For induction of clot formation and subsequent clot lysis (fibrinolysis) a mixture of tissue factor (1 pM) and tissue plasminogen activator (tPA, 0.04 µM) was added to human plasma (final concentration 85%). The test compounds or saline controls were added simultaneously to TF and tPA. The functional activity is triggered with $CaCl_2$ (12.5 mM) and was monitored by measuring the optical density at 405 nM ($OD_{405}$). Fibrinolysis was evaluated as a relative decrease of OD after maximal clot formation. (Sperzel M, Huetter J, 2007, J Thromb Haemost 5(10): 2113-2118).

B-4. Thrombelastometry

Whole blood Thrombelastometry measurements are performed to confirm the potency of the compounds in inhibiting fibrinolysis and improving firmness of the clots (as seen in plasma based assays), for example using the ROTEM® system (Tem International GmbH, Munich, Germany). The ROTEM® system is a diagnostic (viscoelastic) technique which provides information on hemostasis. It includes a four-channel instrument, a computer, activators and disposable cups and pins. Kinetic changes in the blood sample are detected optically (light reflection) and data obtained from the reflected light is then processed into a graphical output by an integrated computer. Characteristic curves and numeric paremeters are generated. Thrombelastographic parameters of ROTEM® hemostatic systems include: Clotting Time (CT), which reflects the reaction time (the time required to obtain 2 mm amplitude following the initiation of data collection) to initiate blood clotting; Clot Formation Time (CFT), provides information about the kinetics of clot formation; the alpha angle to reflect clotting propagation. Maximum Clot Firmness (MCF) is defined as maximum amplitude which reflects the firmness of the clot (clot quality) and Maximum Lysis (ML) indicates fibrinolysis. For induction of clot formation and subsequent clot lysis a mixture of tissue factor (TF) and tissue plasminogen activator (tPA) is added to 300 µL freshly drawn citrated whole blood. Blood from patients with coagulation disorders and antibodies against coagulation factors (e.g. to neutralize FVIII activity and render the blood hemophilic) may be used. TF and tPA concentrations are adjusted dependent on the different conditions and species the whole blood is drawn from. Data are collected for 2 hours using a computer-controlled ROTEM® system.

For induction of clot formation and subsequent clot lysis in human whole blood or human Factor VIII depleted whole blood, a mixture of tissue factor (final concentration 0.5 pM) and tissue plasminogen activator (tPA, final concentration 10 nM) is added to 300 µL citrated human whole blood. The test compounds or controls are added simultaneously to TF and tPA.

For induction of clot formation and subsequent clot lysis (fibrinolysis) in rat whole blood, a mixture of tissue factor (final concentration 1 pM) and tissue plasminogen activator (tPA, final concentration 50 nM) is added to 300 µL citrated rat whole blood. The test compounds or controls are added simultaneously to TF and tPA. Or in the case of ex vivo experiments the test compounds are dosed to the animal, blood is drawn at different time points after administration and added to the test cup.

For induction of clot formation and subsequent clot lysis (fibrinolysis) in hemophilia A dog plasma or whole blood, a mixture of tissue factor (TF) and tissue plasminogen activator (tPA) is added to 300 µL citrated hemophilia A whole blood or plasma. TF and tPA concentrations are titrated and adjusted according to the current needs and technical requirements. Different concentrations of rFVIII are added to the test system in vitro (1-100%). The test compounds or controls are added simultaneously to TF and tPA. In the case of ex vivo experiments the test compounds are dosed to the animal, blood is drawn at different time points after administration and added to the test cup.

B-5. In Vivo Assays

To determine the protective effect of compounds on clot stability and blood loss in vivo, different bleeding models in different species are employed. Animals may be anticoagulated with different anticoagulants to induce a bleeding tendency. Genetically modified animals to mimick blood coagulation disorders may be used or antibodies to neutralize activity of different coagulation factors may be administered. Compounds of the invention are administered orally or parenterally at various indicated doses, at varying time courses prior to the injury. Injuries and endpoints may vary dependent on the mimicked disease condition.

B-5.1 Tail Bleeding in Hyperfibrinolytic Rats

In anaesthetized rats hyperfibrinolysis is induced by a continuous infusion of tPA (8 mg/kg/h) for twenty-five minutes via the right jugular vein. The right jugular vein is exposed and cannulated with saline-filled polyethylene catheters. The catheter is connected to a syringe pump (Braun, Melsungen, Germany) for the infusion of tPA. Hemostatic efficacy is evaluated in a rat bleeding model, where 8 mg/kg/h tPA is continuously infused to prolong bleeding time beyond control values. Test compounds or vehicle are administered by oral gavage at different time points before induction of anesthesia or intravenously through a second catheter in the contralateral jugular vein starting ten minutes after initiating tPA infusion. All infusions are stopped twenty-five minutes after onset of tPA administration. Twenty five minutes after starting the tPA infusion, the rat tail is fully transected 2 mm from the tip of the tail. The tail is submerged in 37° C. physiological saline and bleeding is observed for 30 minutes. The time of bleeding is defined as the interval between the initial transection and the visual cessation of bleeding. A value of 30 minutes is assigned to those animals where bleeding does not stop during the entire observation period.

B-5.2 Tail Bleeding in Dabigatran-Anticoagulated Rats

Animals are treated orally at different time points prior to induction of bleeding. In anaesthetized, anticoagulated rats bleeding is induced by a bolus and continuous infusion (jugular vein) of the thrombin-inhibitor Dabigatran (bolus 1 mg/kg followed by an infusion of 0.3 mg/kg/ml/h) for 15 minutes. 15 minutes after Dabigatran infusion the rat tail is fully transected 2 mm from the tip of the tail. Bleeding is observed for 30 minutes after the tail is submerged in 37° C. physiological saline. Blood loss is evaluated visually in 30 second intervals utilizing a scoring system (0=no blood flow; 1=weak, breaking to no blood flow; 2=reduced blood flow; 3=continuous blood flow; 4=strong, continuous blood flow). Initial bleeding time until the first visual cessation of bleeding as well as cumulative bleeding time over the entire observation period of 30 minutes is evaluated.

C. EXEMPLARY EMBODIMENTS OF PHARMACEUTICAL COMPOSITIONS

The compounds of formula (I-A) or (I-B) according to the invention can be converted into pharmaceutical preparations in the following ways:

Tablet:
Composition:
100 mg of the compound according to the invention, 50 mg of lactose (monohydrate), 50 mg of maize starch (native), 10 mg of polyvinylpyrrolidone (PVP 25) (from BASF, Ludwigshafen, Germany) and 2 mg of magnesium stearate.

Tablet weight 212 mg, diameter 8 mm, radius of curvature 12 mm.

Production:
The mixture of compound according to the invention, lactose and starch is granulated with a 5% strength solution (m/m) of the PVP in water. The granules are dried and then mixed with the magnesium stearate for 5 minutes. This mixture is compressed in a conventional tablet press (see above for format of the tablet). A guideline compressive force for the compression is 15 kN.

Suspension which can be Administered Orally:
Composition:
1000 mg of the compound according to the invention, 1000 mg of ethanol (96%), 400 mg of Rhodigel® (xanthan gum from FMC, Pa., USA) and 99 g of water.

10 ml of oral suspension correspond to a single dose of 100 mg of the compound according to the invention.

Production:
The Rhodigel is suspended in ethanol, and the compound according to the invention is added to the suspension. The water is added while stirring. The mixture is stirred for about 6 h until the swelling of the Rhodigel is complete.

Solution which can be Administered Orally:
Composition:
500 mg of the compound according to the invention, 2.5 g of polysorbate and 97 g of polyethylene glycol 400. 20 g of oral solution correspond to a single dose of 100 mg of the compound according to the invention.

Production:
The compound according to the invention is suspended in the mixture of polyethylene glycol and polysorbate with stirring. The stirring process is continued until the compound according to the invention has completely dissolved.

i.v. solution:
The compound according to the invention is dissolved in a concentration below the saturation solubility in a physiologically tolerated solvent (e.g. isotonic saline, 5% glucose solution and/or 30% PEG 400 solution). The solution obtained is sterilized by filtration and used to fill sterile and pyrogen-free injection containers.

The invention claimed is:
1. Compound of formula (I-A)

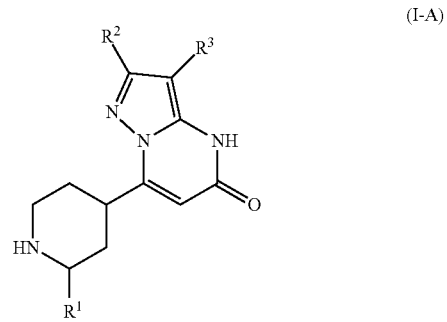

(I-A)

in which $R^1$ is selected from the group consisting of hydrogen and $C_1$-$C_5$ alkyl;

$R^2$ is selected from the group consisting of hydrogen, $C_1$-$C_4$ alkyl, $C_3$-$C_6$ cycloalkyl, $C_1$-$C_4$ haloalkyl, carboxyl, $C_1$-$C_4$ alkylester, $C_1$-$C_4$ alkoxy-$C_1$-$C_4$ alkyl, halogen, methylsulfanyl, phenyl, the phenyl being optionally substituted with halogen, and 5 membered heteroaryl;

$R^3$ is selected from the group consisting of hydrogen, halogen, cyano, $C_1$-$C_4$ alkyl, the alkyl being optionally substituted with di-$C_1$-$C_4$ alkylamino, $C_1$-$C_4$ alkenyl, $C_1$-$C_4$ alkylester, the $C_1$-$C_4$ alkylester being optionally substituted with one, two, three, four, or five halogen substituents, $C_3$-$C_4$ cycloalkylester, $C_3$-$C_4$ cycloalkyl, carboxyl, carboxamide, benzylester, —NH—CO-phenyl, —CS—NH$_2$, phenylsulfonyl, the phenylsulfonyl being optionally substituted with one, two, or three halogen substituents, phenyl,
  the phenyl being optionally substituted with one, two, or three substituents selected from the group consisting of halogen and $C_1$-$C_4$ alkoxy, where two adjacent methoxy groups may optionally form a dioxane ring,
  or the phenyl being optionally substituted with one or two substituents selected from the group consisting of $C_1$-$C_4$ alkyl, $C_1$-$C_4$ haloalkyl, $C_1$-$C_4$ haloalkoxy, cyano, benzyloxy, methylsulfonyl, and phenyl, the phenyl being optionally substituted with $C_1$-$C_4$ haloalkyl, 5-6 membered heterocyclyl-$C_1$-$C_4$ alkyl, the 5-6 membered heterocyclyl-moiety being optionally substituted with one, two, or three substituents selected from the group consisting of $C_1$-$C_4$ alkyl and oxo, 5-6 membered heteroaryl,
  the 5-6 membered heteroaryl being optionally substituted with one, two, or three substituents selected from the group consisting of $C_1$-$C_6$ alkyl, $C_2$-$C_6$ alkenyl, $C_1$-$C_6$ haloalkyl, $C_1$-$C_4$ aminoalkyl, $C_1$-$C_4$ alkylester, $C_1$-$C_4$ alkoxy, $C_1$-$C_4$ haloalkoxy, $C_1$-$C_4$ alkoxy-$C_1$-$C_4$ alkyl, cyano, hydroxyl, carboxyl, $C_1$-$C_4$ alkyl-SO$_2$—$C_1$-$C_4$ alkyl, and —CO—NH$_2$,
  or the 5-6 membered heteroaryl being optionally substituted with one $C_3$-$C_6$ cycloalkyl substituent, the $C_3$-$C_6$ cycloalkyl optionally being substituted with one, two, or three halogen or methyl substituents, or with phenyl, the phenyl being optionally substituted with $C_1$-$C_4$ alkoxy or halogen,
or the 5-6 membered heteroaryl being optionally substituted with one substituent selected from the group consisting of fused or bridged $C_5$-$C_{12}$ bi- or tricycloalkyl, $C_3$-$C_6$ cycloalkyl-$C_1$-$C_4$ alkyl, $C_3$-$C_6$ cycloalkyl-$C_1$-$C_4$ alkenyl,
phenyl, the phenyl optionally being substituted with one, two, or three substituents selected from the group consisting of $C_1$-$C_4$ alkyl, halogen, $C_1$-$C_4$ haloalkyl, $C_1$-$C_4$ alkoxy, $C_1$-$C_4$ haloalkoxy, $C_1$-$C_4$-alkylester, nitro, amino, di-$C_1$-$C_4$ alkylamine, and cyano,
phenyl-$C_1$-$C_4$ alkyl,
the phenyl moiety optionally being substituted with one, two, or three substituents selected from the group consisting of halogen, $C_1$-$C_4$ alkyl, $C_1$-$C_4$ haloalkyl, $C_1$-$C_4$ alkoxy, $C_1$-$C_4$ haloalkoxy, and hydroxyl,
the alkyl moiety optionally being substituted with one or two substituents selected from the group consisting of $C_1$-$C_4$ alkyl and hydroxyl,
5-6 membered heterocycloalkyl, the 5-6 membered heterocycloalkyl being optionally substituted with $C_3$-$C_6$ cycloalkyl or $C_1$-$C_4$ alkyl,
5-6 membered heterocycloalkyl-$C_1$-$C_4$ alkyl,
the 5-6 membered heterocycloalkyl moiety being optionally substituted with $C_1$-$C_4$ alkyl or oxo,
the $C_1$-$C_4$ alkyl moiety being optionally substituted with $C_1$-$C_4$ alkyl,
5-6 membered heteroaryl, the 5-6 membered heteroaryl being optionally substituted with one, two, or three substituents selected from the group consisting of halogen, $C_1$-$C_4$ alkyl, and $C_1$-$C_4$ haloalkyl,
and 5-6 membered heteroaryl-$C_1$-$C_4$ alkyl,
the 5-6 membered heteroaryl-moiety being optionally substituted with one or two substituents selected from the group consisting of $C_1$-$C_4$ alkoxy and $C_1$-$C_4$ alkyl,
the $C_1$-$C_4$ alkyl-moiety being optionally substituted with one or two methyl substituents,
—CO—$R^4$, with $R^4$ being selected from the group consisting of $C_1$-$C_4$ alkyl, wherein the $C_1$-$C_4$ alkyl is optionally substituted with one or two methyl, and $C_3$-$C_6$ cycloalkyl,
—CO—N($R^5R^7$), with
$R^5$ being selected from the group consisting of hydrogen and $C_1$-$C_4$ alkyl,
$R^7$ being selected from the group consisting of hydrogen, $C_1$-$C_6$ alkyl, $C_1$-$C_6$ haloalkyl, $C_1$-$C_4$-alkoxy-$C_1$-$C_4$ alkyl, amino-oxo-$C_1$-$C_4$ alkyl, naphthyl,
$C_3$-$C_6$ cycloalkyl, the $C_3$-$C_6$ cycloalkyl being optionally substituted with one or two $C_1$-$C_4$ alkyl substituents,
$C_3$-$C_6$ cycloalkyl-$C_1$-$C_4$ alkyl,
5-6 membered heterocyclyl,
oxazolidinyl-$C_1$-$C_4$ alkyl,
benzyl,
the phenyl moiety of the benzyl being optionally substituted with one, two, or three $C_1$-$C_4$ alkyl substituents,
the methyl moiety of the benzyl optionally being substituted with $C_1$-$C_4$ alkyl,
benzyl-$C_3$-$C_6$ cycloalkyl,
imidazolyl-$C_1$-$C_4$ alkyl, the imidazolyl-$C_1$-$C_4$ alkyl being optionally substituted with one, two, or three $C_1$-$C_4$ alkyl substituents,
oxazolyl-$C_1$-$C_4$ alkyl, the oxazolyl-$C_1$-$C_4$ alkyl being optionally substituted with one, two, or three $C_1$-$C_4$ alkyl substituents,
oxazolidinone-$C_1$-$C_4$ alkyl,
pyridinyl-$C_1$-$C_4$ alkyl,
and phenyl, the phenyl being optionally substituted with one, two, or three substituents selected from the group consisting of $C_1$-$C_4$ alkyl, halogen, and $C_1$-$C_4$ alkoxy,
or —N($R^5R^7$) being selected from the group consisting of 5-7 membered cyclic amines which contain one or two ring nitrogen atoms, zero or one ring oxygen atom, and zero or one ring sulfur atom, and are attached via a ring nitrogen atom, the 5 to 7 membered cyclic amines being optionally substituted with one, two, or three substituents selected from the group consisting of $C_1$-$C_4$ alkoxy, $C_1$-$C_4$ alkoxy $C_1$-$C_4$ alkyl, oxo, hydroxyl, halogen, and $C_1$-$C_4$ alkyl,
or —N($R^5R^7$) being selected from the group consisting of two annelated, aromatic, partially saturated or saturated rings which are each 5-7 membered and each contain one or two ring nitrogen atoms and are attached via a ring nitrogen atom,
and —N($R^5R^7$) being selected from the group consisting of bicyclic azaspiro compounds, the azaspiro compounds being optionally substituted with oxo;
or $R^2$ and $R^3$ together form a $C_5$-$C_6$ cycloalkyl ring;
or a salt of the compound, or a solvate of the compound, or a solvate of the salt thereof.

2. Compound of formula (I-B)

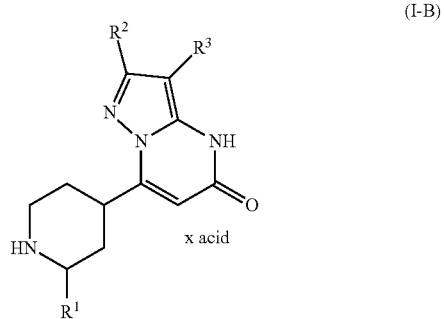

(I-B)

in which
$R^1$ is selected from the group consisting of hydrogen, and $C_1$-$C_5$ alkyl;
$R^2$ is selected from the group consisting of hydrogen, $C_1$-$C_4$ alkyl, $C_3$-$C_6$ cycloalkyl, $C_1$-$C_4$ haloalkyl, carboxyl, $C_1$-$C_4$ alkylester, $C_1$-$C_4$ alkoxy-$C_1$-$C_4$ alkyl, halogen, methylsulfanyl, phenyl, the phenyl being optionally substituted with halogen, and 5 membered heteroaryl;
$R^3$ is selected from the group consisting of hydrogen, halogen, cyano, $C_1$-$C_4$ alkyl, the alkyl being optionally substituted with di-$C_1$-$C_4$ alkylamino, $C_1$-$C_4$ alkenyl, $C_1$-$C_4$ alkylester, the $C_1$-$C_4$ alkylester being optionally substituted with one, two, three, four, or five halogen substituents, $C_3$-$C_4$ cycloalkylester, $C_3$-$C_4$ cycloalkyl, carboxyl, carboxamide, benzylester, —NH—CO-phenyl, —CS—NH$_2$, phenylsulfonyl, the phenylsulfonyl being optionally substituted with one, two, or three halogen substituents, phenyl,
　the phenyl being optionally substituted with one, two, or three substituents selected from the group consisting of halogen and $C_1$-$C_4$ alkoxy, where two adjacent methoxy groups may optionally form a dioxane ring,
　or the phenyl being optionally substituted with one or two substituents selected from the group consisting of $C_1$-$C_4$ alkyl, $C_1$-$C_4$ haloalkyl, $C_1$-$C_4$ haloalkoxy, cyano, benzyloxy, methylsulfonyl, and phenyl, the phenyl being optionally substituted with $C_1$-$C_4$ haloalkyl, 5-6 membered heterocyclyl-$C_1$-$C_4$ alkyl, the 5-6 membered heterocyclyl-moiety being optionally substituted with one, two, or three substituents selected from the group consisting of $C_1$-$C_4$ alkyl and oxo, 5-6 membered heteroaryl,
　the 5-6 membered heteroaryl being optionally substituted with one, two, or three substituents selected from the group consisting of $C_1$-$C_6$ alkyl, $C_2$-$C_6$ alkenyl, $C_1$-$C_6$ haloalkyl, $C_1$-$C_4$ aminoalkyl, $C_1$-$C_4$ alkylester, $C_1$-$C_4$ alkoxy, $C_1$-$C_4$ haloalkoxy, $C_1$-$C_4$ alkoxy-$C_1$-$C_4$ alkyl, cyano, hydroxyl, carboxyl, $C_1$-$C_4$ alkyl-SO$_2$—$C_1$-$C_4$ alkyl, and —CO—NH$_2$,
　or the 5-6 membered heteroaryl being optionally substituted with one $C_3$-$C_6$ cycloalkyl substituent, the $C_3$-$C_6$ cycloalkyl optionally being substituted with one, two, or three halogen or methyl substituents, or with phenyl, the phenyl being optionally substituted with $C_1$-$C_4$ alkoxy or halogen,
　or the 5-6 membered heteroaryl being optionally substituted with one substituent selected from the group consisting of fused or bridged $C_5$-$C_{12}$ bi- or tricycloalkyl, $C_3$-$C_6$ cycloalkyl-$C_1$-$C_4$ alkyl, $C_3$-$C_6$ cycloalkyl-$C_1$-$C_4$ alkenyl, phenyl, the phenyl optionally being substituted with one, two, or three substituents selected from the group consisting of $C_1$-$C_4$ alkyl, halogen, $C_1$-$C_4$ haloalkyl, $C_1$-$C_4$ alkoxy, $C_1$-$C_4$ haloalkoxy, $C_1$-$C_4$-alkylester, nitro, amino, di-$C_1$-$C_4$ alkylamine, and cyano, phenyl-$C_1$-$C_4$ alkyl,
　the phenyl moiety optionally being substituted with one, two, or three substituents selected from the group consisting of halogen, $C_1$-$C_4$ alkyl, $C_1$-$C_4$ haloalkyl, $C_1$-$C_4$ alkoxy, $C_1$-$C_4$ haloalkoxy, and hydroxyl,
　the alkyl moiety optionally being substituted with one or two substituents selected from the group consisting of $C_1$-$C_4$ alkyl and hydroxyl, 5-6 membered heterocycloalkyl, the 5-6 membered heterocycloalkyl being optionally substituted with $C_3$-$C_6$ cycloalkyl or $C_1$-$C_4$ alkyl, 5-6 membered heterocycloalkyl-$C_1$-$C_4$ alkyl,
　the 5-6 membered heterocycloalkyl moiety being optionally substituted with $C_1$-$C_4$ alkyl or oxo, the $C_1$-$C_4$ alkyl moiety being optionally substituted with $C_1$-$C_4$ alkyl, 5-6 membered heteroaryl, the 5-6 membered heteroaryl being optionally substituted with one, two, or three substituents selected from the group consisting of halogen, $C_1$-$C_4$ alkyl, and $C_1$-$C_4$ haloalkyl, and 5-6 membered heteroaryl-$C_1$-$C_4$ alkyl,
　the 5-6 membered heteroaryl-moiety being optionally substituted with one or two substituents selected from the group consisting of $C_1$-$C_4$ alkoxy and $C_1$-$C_4$ alkyl,
　the $C_1$-$C_4$ alkyl-moiety being optionally substituted with one or two methyl substituents, —CO—R$^4$, with R$^4$ being selected from the group consisting of $C_1$-$C_4$ alkyl, wherein the $C_1$-$C_4$ alkyl is optionally substituted with one or two methyl, and $C_3$-$C_6$ cycloalkyl, —CO—N(R$^5$R$^7$), with
　R$^5$ being selected from the group consisting of hydrogen and $C_1$-$C_4$ alkyl,
　R$^7$ being selected from the group consisting of hydrogen, $C_1$-$C_6$ alkyl, $C_1$-$C_6$ haloalkyl, $C_1$-$C_4$-alkoxy-$C_1$-$C_4$ alkyl, amino-oxo-$C_1$-$C_4$ alkyl, naphthyl,
　　$C_3$-$C_6$ cycloalkyl, the $C_3$-$C_6$ cycloalkyl being optionally substituted with one or two $C_1$-$C_4$ alkyl substituents,
　　$C_3$-$C_6$ cycloalkyl-$C_1$-$C_4$ alkyl,
　　5-6 membered heterocyclyl,
　　oxazolidinyl-$C_1$-$C_4$ alkyl,
　　benzyl,
　　　the phenyl moiety of the benzyl being optionally substituted with one, two, or three $C_1$-$C_4$ alkyl substituents,
　　　the methyl moiety of the benzyl optionally being substituted with $C_1$-$C_4$ alkyl,
　　benzyl-$C_3$-$C_6$ cycloalkyl,
　　imidazolyl-$C_1$-$C_4$ alkyl, the imidazolyl-$C_1$-$C_4$ alkyl being optionally substituted with one, two, or three $C_1$-$C_4$ alkyl substituents,
　　oxazolyl-$C_1$-$C_4$ alkyl, the oxazolyl-$C_1$-$C_4$ alkyl being optionally substituted with one, two, or three $C_1$-$C_4$ alkyl substituents,
　　oxazolidinone-$C_1$-$C_4$ alkyl,
　　pyridinyl-$C_1$-$C_4$ alkyl,
　　and phenyl, the phenyl being optionally substituted with one, two, or three substituents selected from the group consisting of $C_1$-$C_4$ alkyl, halogen, and $C_1$-$C_4$ alkoxy,
　or —N(R$^5$R$^7$) being selected from the group consisting of 5-7 membered cyclic amines which contain one or two ring nitrogen atoms, zero or one ring oxygen atom, and zero or one ring sulfur atom, and are attached via a ring nitrogen atom, the 5 to 7 membered cyclic amines being optionally substituted with one, two, or three substituents selected from the group consisting of $C_1$-$C_4$ alkoxy, $C_1$-$C_4$ alkoxy $C_1$-$C_4$ alkyl, oxo, hydroxyl, halogen, and $C_1$-$C_4$ alkyl,
　or —N(R$^5$R$^7$) being selected from the group consisting of two annelated, aromatic, partially saturated or saturated rings which are each 5-7 membered and each contain one or two ring nitrogen atoms and are attached via a ring nitrogen atom,
　and —N(R$^5$R$^7$) being selected from the group consisting of bicyclic azaspiro compounds, the azaspiro compounds being optionally substituted with oxo;

or R$^2$ and R$^3$ together form a $C_5$-$C_6$ cycloalkyl ring;

or a salt of the compound, or a solvate of the compound, or a solvate of the salt thereof.

3. Compound of formula (I-A) as defined in claim 1 or formula (I-B) as defined in claim 2 in which $R^1$ is selected from the group consisting of hydrogen and $C_1$-$C_5$ alkyl;

$R^2$ is selected from the group consisting of hydrogen, $C_1$-$C_2$ alkyl, $C_3$-$C_4$ cycloalkyl, $C_1$-$C_2$ haloalkyl, carboxyl, $C_1$-$C_2$ alkylester, $C_1$-$C_2$ alkoxy-$C_1$-$C_2$ alkyl, halogen, methylsulfanyl, phenyl, the phenyl being optionally substituted with a substituent selected from the group consisting of fluorine and chlorine, and 5-6 membered heteroaryl;

$R^3$ is selected from the group consisting of hydrogen, bromine, chlorine, cyano, methyl, the methyl being optionally substituted with di-$C_1$-$C_4$ alkylamino, ethyl, $C_1$-$C_4$ alkenyl, $C_1$-$C_4$ alkylester, the $C_1$-$C_4$ alkylester being optionally substituted with one, two, or three fluorine substituents, $C_3$-$C_4$ cycloalkylester, $C_3$-$C_4$ cycloalkyl, carboxyl, carboxamide, benzylester, —NH—CO-phenyl, —CS—NH$_2$, phenylsulfonyl, the phenylsulfonyl being optionally substituted with one or two substituents selected from the group consisting of chlorine and fluorine, phenyl, the phenyl being optionally substituted with one, two, or three substituents selected from the group consisting of bromine, chlorine, fluorine, ethoxy, and methoxy, where two adjacent methoxy groups may optionally form a dioxane ring, or the phenyl being optionally substituted with one or two substituents selected from the group consisting of $C_1$-$C_2$ alkyl, $C_1$-$C_2$ fluoroalkyl, $C_1$-$C_2$ fluoroalkoxy, and cyano, or the phenyl being optionally substituted with one substituent selected from the group consisting of benzyloxy, methylsulfonyl, and phenyl, the phenyl being optionally substituted with $C_1$-$C_2$ fluoroalkyl, 5-6 membered heterocyclyl-$C_1$-$C_2$ alkyl, the 5-6 membered heterocyclyl-moiety being optionally substituted with one, two, or three substituents selected from the group consisting of $C_1$-$C_2$ alkyl and oxo, 5-6 membered heteroaryl, the 5-6 membered heteroaryl being optionally substituted with one or two substituents selected from the group consisting of $C_1$-$C_6$ alkyl, $C_2$-$C_6$ alkenyl, $C_1$-$C_4$ haloalkyl, $C_1$-$C_2$ aminoalkyl, $C_1$-$C_2$ alkylester, $C_1$-$C_2$ alkoxy, $C_1$-$C_2$ haloalkoxy, $C_1$-$C_2$ alkoxy-$C_1$-$C_4$ alkyl, cyano, hydroxyl, carboxyl, $C_1$-$C_2$ alkyl-SO$_2$—$C_1$-$C_2$ alkyl, and —CO—NH$_2$, or the 5-6 membered heteroaryl being optionally substituted with one $C_3$-$C_6$ cycloalkyl substituent, the $C_3$-$C_6$ cycloalkyl optionally being substituted with one, two, or three chlorine, fluorine, or methyl substituents, or with phenyl, the phenyl being optionally substituted with $C_1$-$C_2$ alkoxy, chlorine, or fluorine, bridged bi- or tricycloalkyl $C_3$-$C_6$ cycloalkyl-$C_1$-$C_2$ alkyl, $C_3$-$C_6$ cycloalkyl-$C_1$-$C_4$ alkenyl, phenyl, the phenyl optionally being substituted with one, two, or three substituents selected from the group consisting of $C_1$-$C_4$ alkyl, chlorine, fluorine, $C_1$-$C_2$ fluoroalkyl, $C_1$-$C_2$ alkoxy, $C_1$-$C_2$ fluoroalkoxy, $C_1$-$C_2$-alkylester, nitro, amino, di-$C_1$-$C_2$ alkylamino, and cyano, phenyl-$C_1$-$C_2$ alkyl, the phenyl moiety optionally being substituted with one, two, or three substituents selected from the group consisting of fluorine, chlorine, $C_1$-$C_2$ alkyl, $C_1$-$C_2$ fluoroalkyl, $C_1$-$C_2$ alkoxy, $C_1$-$C_2$ fluoroalkoxy, and hydroxyl, the alkyl moiety optionally being substituted with one or two substituents selected from the group consisting of $C_1$-$C_2$ alkyl and hydroxyl, 5-6 membered heterocycloalkyl, the 5-6 membered heterocycloalkyl being optionally substituted with $C_3$-$C_5$ cycloalkyl or $C_1$-$C_3$ alkyl, 5-6 membered heterocycloalkyl-$C_1$-$C_2$ alkyl, the 5-6 membered heterocycloalkyl moiety being optionally substituted with $C_1$-$C_2$ alkyl or oxo, the $C_1$-$C_2$ alkyl moiety being optionally substituted with $C_1$-$C_2$ alkyl, 5-6 membered heteroaryl, the 5-6 membered heteroaryl being optionally substituted with one, two, or three substituents selected from the group consisting of fluorine, chlorine, $C_1$-$C_3$ alkyl, and $C_1$-$C_2$ fluoroalkyl, and 5-6 membered heteroaryl-$C_1$-$C_4$ alkyl, the 5-6 membered heteroaryl-moiety being optionally substituted with one or two substituents selected from the group consisting of $C_1$-$C_2$ alkoxy and $C_1$-$C_2$ alkyl, the $C_1$-$C_2$ alkyl-moiety being optionally substituted with one or two methyl substituents, CO—$R^4$, with $R^4$ being selected from the group consisting of $C_1$-$C_4$ alkyl, wherein the $C_1$-$C_4$ alkyl is optionally substituted with one or two methyl substituents, and $C_3$-$C_6$ cycloalkyl, and CO—N($R^5R^7$), with $R^5$ being selected from the group consisting of hydrogen and $C_1$-$C_4$ alkyl, $R^7$ being selected from the group consisting of $C_1$-$C_4$ alkyl, $C_1$-$C_4$ haloalkyl, $C_1$-$C_2$-alkoxy-$C_1$-$C_4$ alkyl, amino-oxo-$C_1$-$C_4$ alkyl, naphthyl, $C_3$-$C_6$ cycloalkyl, the $C_3$-$C_6$ cycloalkyl being optionally substituted with one or two $C_1$-$C_2$ alkyl substituents, $C_3$-$C_6$ cycloalkyl-$C_1$-$C_2$ alkyl, 5-6 membered heterocyclyl, oxazolidinyl-$C_1$-$C_2$ alkyl, benzyl, the phenyl moiety of the benzyl being optionally substituted with one, two, or three $C_1$-$C_2$ alkyl substituents, the methyl moiety of the benzyl being optionally substituted with $C_1$-$C_2$ alkyl, benzyl-$C_3$-$C_4$ cycloalkyl, imidazolyl-$C_1$-$C_2$ alkyl, the imidazolyl-$C_1$-$C_2$ alkyl being optionally substituted with one, two, or three $C_1$-$C_2$ alkyl substituents, oxazolyl-$C_1$-$C_2$ alkyl, the oxazolyl-$C_1$-$C_2$ alkyl being optionally substituted with one, two, or three $C_1$-$C_2$ alkyl substituents, pyridinyl-$C_1$-$C_2$ alkyl, and phenyl, the phenyl being optionally substituted with one, two, or three substituents selected from the group consisting of $C_1$-$C_2$ alkyl, halogen, and $C_1$-$C_2$ alkoxy, or —N($R^5R^7$) being selected from the group consisting of 5 to 7 membered cyclic amines which contain one or two ring nitrogen atoms, zero or one ring oxygen atom, and zero or one ring sulfur atom, and are attached via a ring nitrogen atom, the 5 to 7 membered cyclic amines being optionally substituted with one, two, or three substituents selected from the group consisting of $C_1$-$C_4$ alkoxy, $C_1$-$C_2$ alkoxy $C_1$-$C_2$ alkyl, oxo, hydroxyl, halogen, and $C_1$-$C_3$ alkyl, or —N($R^5R^7$) being selected from the group consisting of two annelated, aromatic, partially saturated or saturated rings which are each 5-7 membered and each contain one or two ring nitrogen atoms and are attached via a ring nitrogen atom, or —N($R^5R^7$) being selected from the group consisting of azaspiro[2.5] oct-5-yl and oxa-azaspiro[3.5] non-1-yl, the azaspiro compounds being optionally substituted with oxo;

or $R^2$ and $R^3$ together form a $C_5$-$C_6$ cycloalkyl ring;

or a salt of the compound, or a solvate of the compound, or a solvate of the salt thereof.

4. Compound of formula (I-A) as defined in claim 1 or formula (I-B) as defined in claim 2 in which $R^1$ is selected from the group consisting of hydrogen and $C_1$-$C_5$ alkyl;

$R^2$ is selected from the group consisting of hydrogen, methyl, ethyl, trifluoromethyl, and methylsulfanyl;

$R^3$ is selected from the group consisting of $C_1$-$C_4$ alkylester, the alkylester being optionally substituted with one, two, or three fluorine substituents, $C_3$-$C_4$ cycloalkylester, $C_3$-$C_4$ cycloalkyl, 5 membered heteroaryl, the 5 membered heteroaryl being optionally substituted with one or two substituents selected from the group consisting of $C_1$-$C_6$ alkyl, $C_2$-$C_6$ alkenyl, $C_1$-$C_4$ haloalkyl, $C_1$-$C_2$ aminoalkyl, $C_1$-$C_2$ alkylester, $C_1$-$C_2$ alkoxy, $C_1$-$C_2$ haloalkoxy, $C_1$-$C_2$ alkoxy-$C_1$-$C_4$ alkyl, cyano, hydroxyl, carboxyl, $C_1$-$C_2$ alkyl-$SO_2$—$C_1$-$C_2$ alkyl, and —CO—$NH_2$, or the 5 membered heteroaryl being optionally substituted with one $C_3$-$C_6$ cycloalkyl, the $C_3$-$C_6$ cycloalkyl optionally being substituted with one, two, or three chlorine, fluorine, or methyl substituents, or one or two methyl substituents, or with phenyl, the phenyl being optionally substituted with $C_1$-$C_2$ alkoxy, chlorine, or fluorine, bridged bi- or tricycloalkyl, $C_3$-$C_6$ cycloalkyl-$C_1$-$C_2$ alkyl, $C_3$-$C_6$ cycloalkyl-$C_1$-$C_4$ alkenyl, phenyl, the phenyl optionally being substituted with one, two, or three substituents selected from the group consisting of $C_1$-$C_4$ alkyl, chlorine, fluorine, $C_1$-$C_2$ fluoroalkyl, $C_1$-$C_2$ alkoxy, $C_1$-$C_2$ fluoroalkoxy, $C_1$-$C_2$-alkylester, nitro, amino, di-$C_1$-$C_2$ alkylamino, and cyano, phenyl-$C_1$-$C_2$ alkyl, the phenyl moiety optionally being substituted with one, two, or three substituents selected from the group consisting of fluorine, chlorine, $C_1$-$C_2$ alkyl, $C_1$-$C_2$ fluoroalkyl, $C_1$-$C_2$ alkoxy, $C_1$-$C_2$ fluoroalkoxy, and hydroxyl, the alkyl moiety optionally being substituted with one or two substituents selected from the group consisting of $C_1$-$C_2$ alkyl and hydroxyl, 5-6 membered heterocycloalkyl, the 5-6 membered heterocycloalkyl being optionally substituted with $C_3$-$C_5$ cycloalkyl or $C_1$-$C_3$ alkyl, 5-6 membered heterocycloalkyl-$C_1$-$C_2$ alkyl, the 5-6 membered heterocycloalkyl moiety being optionally substituted with $C_1$-$C_2$ alkyl or oxo, the $C_1$-$C_2$ alkyl moiety being optionally substituted with $C_1$-$C_2$ alkyl, 5-6 membered heteroaryl, the 5-6 membered heteroaryl being optionally substituted with one, two, or three substituents selected from the group consisting of fluorine, chlorine, $C_1$-$C_3$ alkyl, and $C_1$-$C_2$ fluoroalkyl, and 5-6 membered heteroaryl-$C_1$-$C_4$ alkyl, the 5-6 membered heteroaryl-moiety being optionally substituted with one or two substituents selected from the group consisting of $C_1$-$C_2$ alkoxy and $C_1$-$C_2$ alkyl, the $C_1$-$C_2$ alkyl-moiety being optionally substituted with one or two methyl substituents;

or $R^2$ and $R^3$ together form a $C_5$-$C_6$ cycloalkyl ring;

or a salt of the compound, or a solvate of the compound, or a solvate of the salt thereof.

5. Compound of formula (I-A) as defined in claim 1 or formula (I-B) as defined in claim 2 in which $R^1$ is hydrogen;

$R^2$ is hydrogen;

$R^3$ is selected from the group consisting of 1,2,4 oxadiazol-5-yl of formula

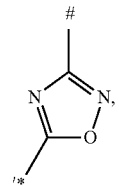

1,3,4 oxadiazol-5-yl of formula

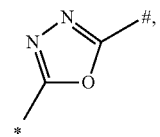

and 1,2,4 oxadiazol-3-yl of formula

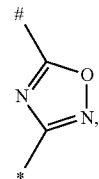

wherein * indicates the position of binding to the pyrazolopyrimidone and # denotes the optional binding to a further substituent, the oxadiazolyl being substituted with a substituent selected from the group consisting of $C_1$-$C_6$ alkyl, $C_2$-$C_6$ alkenyl, $C_1$-$C_4$ fluoroalkyl, $C_1$-$C_2$ fluoroalkoxy, methoxy-$C_1$-$C_4$ alkyl, tert-butoxy-ethyl, $C_1$-$C_2$ alkylester, $C_3$-$C_6$ cycloalkyl, the $C_3$-$C_6$ cycloalkyl optionally being substituted with chlorine, fluorine, methyl, or phenyl, the phenyl optionally being substituted with chlorine or methoxy, oxanyl, oxopyrrolidinyl-methyl, piperidinyl, the piperidinyl being substituted with cyclopropyl or iso-propyl, piperidinyl-methyl, the piperidinylmethyl being optionally substituted with methyl, morpholinyl-ethyl, the ethyl moiety being optionally substituted with methyl, tetrahydrofuranyl, phenyl, the phenyl optionally being substituted with one, two, or three substituents selected from the group consisting of $C_1$-$C_4$ alkyl, fluorine, chlorine, trifluoromethyl, methoxy, trifluoromethoxy, methylester, nitro, amino, di-methylamino, and cyano, and benzyl,
  the phenyl moiety of the benzyl being optionally substituted with one or two fluorine or one methoxy substituent,
  or the phenyl moiety of the benzyl being optionally substituted with one or two substituents selected from the group consisting of fluorine, chlorine, methoxy, and hydroxyl,
  or the phenyl moiety being optionally substituted with one substituent selected from the group consisting of fluorine, chlorine, methyl, trifluoromethyl, methoxy, isopropyloxy, trifluoromethoxy, and difluoromethoxy,
  the methyl moiety of the benzyl being optionally substituted with hydroxyl, ethyl, or one or two methyl substituents, 1,2 oxazolyl, the 1,2 oxazolyl being substituted with phenyl, thiophen-yl, the thiophen-yl being optionally substituted with a substituent selected from the group consisting of methyl and cyano, 1,3 thiazolyl,
  the 1,3 thiazolyl being optionally substituted with one substituent selected from the group consisting of $C_1$-$C_5$ alkyl, $C_1$-$C_4$ haloalkyl, cyclopropyl, and phenyl, the phenyl being optionally substituted with one or two substituents selected from the group consisting of fluorine, chlorine, methyl, and trifluoromethyl,
  or the 1,3 thiazolyl being optionally substituted with two substituents selected from the group consisting of methyl, ethyl, and iso-propyl substituents, or the thiazolyl being optionally substituted with phenyl and methyl, and pyridinyl, the pyridinyl being optionally substituted with one or two substituents selected from the group consisting of fluorine, chlorine, methyl, and trifluoromethyl;

or a salt of the compound, or a solvate of the compound, or a solvate of the salt thereof.

6. Compound of formula (I-A) as defined in claim 1 or formula (I-B) as defined in claim 2 in which $R^1$ is hydrogen;

$R^2$ is hydrogen;

$R^3$ is selected from the group consisting of 1,2,4 oxadiazol-5-yl of formula

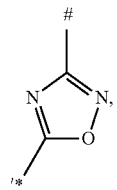

1,3,4 oxadiazol-5-yl of formula

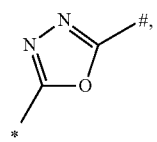

and 1,2,4 oxadiazol-3-yl of formula

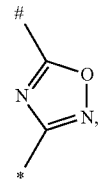

wherein * indicates the position of binding to the pyrazolopyrimidone and # denotes the optional binding to a further substituent, the oxadiazolyl being optionally substituted with one substituent selected from the group consisting of methyl, ethyl, propyl, isopropyl, tert-butyl, hexyl, trifluoromethyl, trifluoroethyl, trifluorobutyl, methoxymethyl, methoxypropyl, methoxyisobutyl, ethylester, $C_3$-$C_6$ cycloalkyl, benzyl, the phenyl moiety of the benzyl being optionally substituted with one or two substituents selected from the group consisting of methyl, methoxy, isopropyloxy, fluorine, chlorine, trifluoromethyl, trifluoromethoxy, and difluoromethoxy, and pyridinyl, the pyridinyl being optionally substituted with chlorine, fluorine, methyl, or trifluoromethyl;

or a salt of the compound, or a solvate of the compound, or a solvate of the salt thereof.

7. Compound of formula (I-A) as defined in claim 1 or formula (I-B) as defined in claim 2 in which $R^1$ is hydrogen;

$R^2$ is hydrogen;

$R^3$ is 1,2,4-oxadiazol-5-yl of formula

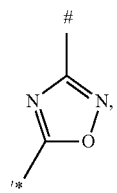

wherein * indicates the position of binding to the pyrazolopyrimidone and # denotes the optional binding to a further substituent, the oxadiazolyl being substituted with tert-butyl;
or a salt of the compound, or a solvate of the compound, or a solvate of the salt thereof.

8. Compound of formula (I-A) as defined in claim 1 or formula (I-B) as defined in claim 2 in which
$R^1$ is hydrogen;
$R^2$ is methyl;
$R^3$ is selected from the group consisting of 1,2,4 oxadiazol-5-yl of formula

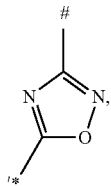

1,3,4 oxadiazol-5-yl of formula

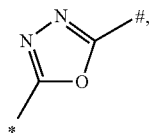

and 1,2,4 oxadiazol-3-yl of formula

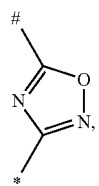

wherein * indicates the position of binding to the pyrazolopyrimidone and # denotes the optional binding to a further substituent, the oxadiazolyl being optionally substituted with one substituent selected from the group consisting of methyl, ethyl, isopropyl, tert-butyl, trifluoromethyl, methoxyethyl, tert-butoxyethyl,
$C_3$-$C_6$ cycloalkyl, the $C_3$-$C_6$ cycloalkyl being optionally substituted with one or two methyl substituents, cyclobutyl,
benzyl, the phenyl moiety of the benzyl being optionally substituted with a substituent selected from the group consisting of fluorine, chlorine, and hydroxyl, and phenyl, the phenyl being optionally substituted with a substituent selected from the group consisting of methyl, fluorine, chlorine, methoxy, trifluoromethyl, and trifluoromethoxy;
or a salt of the compound, or a solvate of the compound, or a solvate of the salt thereof.

9. Compound of formula (I-A) as defined in claim 1 or formula (I-B) as defined in claim 2 in which
$R^1$ is hydrogen;
$R^2$ is hydrogen;
$R^3$ is selected from the group consisting of methylester, ethylester, propylester, isopropylester, the ethylester and the propylester being optionally substituted with one, two, or three fluorine substituents, and cyclobutylester;
or a salt of the compound, or a solvate of the compound, or a solvate of the salt thereof.

10. Compound of formula (I-A) as defined in claim 1 or formula (I-B) as defined in claim 2 in which
$R^1$ is hydrogen;
$R^2$ is methyl;
$R^3$ is selected from the group consisting of ethylester, propylester, isopropylester, tert-butylester, the ethylester and the propylester being optionally substituted with one, two, or three fluorine substituents, and cyclobutylester;
or a salt of the compound, or a solvate of the compound, or a solvate of the salt thereof.

11. Compound of formula (I-A) as defined in claim 1 or formula (I-B) as defined in claim 2 in which
$R^1$ is hydrogen;
$R^2$ is methyl;
$R^3$ is ethylester;
or a salt of the compound, or a solvate of the compound, or a solvate of the salt thereof.

12. Compound of formula (I-A) as defined in claim 1 or formula (I-B) as defined in claim 2 in which
$R^1$ is hydrogen;
$R^2$ is selected from the group consisting of trifluoromethyl, ethyl, and methylsulfanyl;
$R^3$ is selected from the group consisting of $C_1$-$C_4$ alkylester, the $C_4$ alkylester being optionally substituted with one, two, or three fluorine substituents, and $C_3$-$C_4$ cycloalkylester;
or a salt of the compound, or a solvate of the compound, or a solvate of the salt thereof.

13. Compound of formula (I-B) as defined in claim 2 in which
$R^1$ is hydrogen;
$R^2$ is hydrogen;
$R^3$ is 1,2,4 oxadiazol-5-yl of formula

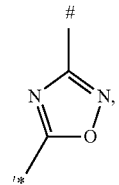

wherein * indicates the position of binding to the pyrazolopyrimidone and # indicates the position of binding to a phenyl substituent, the phenyl being optionally substituted with a substituent selected from the group consisting of methyl, trifluoromethyl, chloro, and fluoro;
wherein the acid is hydrochloric acid.

14. Compound of formula (I-B) as defined in claim 13 in which
$R^1$ is hydrogen;
$R^2$ is hydrogen;

R³ is 1,2,4 oxadiazol-5-yl of formula

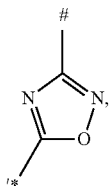

wherein * indicates the position of binding to the pyrazolopyrimidone and # indicates the position of binding to a phenyl substituent;
wherein the acid is hydrochloric acid.

15. Compound of formula (I-B) as defined in claim 13 in which
R¹ is hydrogen;
R² is hydrogen;
R³ is 1,2,4 oxadiazol-5-yl of formula

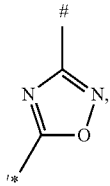

wherein * indicates the position of binding to the pyrazolopyrimidone and # indicates the position of binding to a phenyl substituent, the phenyl being substituted by methyl in para position;
wherein the acid is hydrochloric acid.

16. Compound of formula (I-B) as defined in claim 13 in which
R¹ is hydrogen;
R² is hydrogen;
R³ is 1,2,4 oxadiazol-5-yl of formula

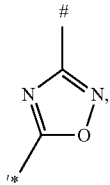

wherein * indicates the position of binding to the pyrazolopyrimidone and # indicates the position of binding to a phenyl substituent, the phenyl being substituted by trifluoromethyl in para position;
wherein the acid is hydrochloric acid.

17. Compound of formula (I-B) as defined in claim 13 in which
R¹ is hydrogen;
R² is hydrogen;
R³ is 1,2,4 oxadiazol-5-yl of formula

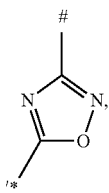

wherein * indicates the position of binding to the pyrazolopyrimidone and # indicates the position of binding to a phenyl substituent, the phenyl being substituted by chloro in meta position;
wherein the acid is hydrochloric acid.

18. Medicament, comprising a compound of formula (I-A) as defined in claim 1 or formula (I-B) as defined in claim 2; in combination with an inert, non-toxic, pharmaceutically suitable auxiliary.

19. Medicament, comprising a compound of formula (I-A) as defined in claim 1 or formula (I-B) as defined in claim 2; in combination with a further active compound selected from the group consisting of Factor VIII, Factor IX, Factor VIIa, activated prothrombin complex concentrates (aPCC) or prothrombin complex concentrates (PCCs), ε-aminocaproic acid, ethamsylate, paraaminobutyl benzoic acid, tranexamic acid, desmopressin, danazol, combined oral contraceptive pills (COCPs), progestin intrauterine system, glucocorticoid receptor agonists, analgesics, and non-steroidal anti-inflammatory drugs (NSAIDs).

* * * * *